(12) United States Patent
Helgadottir

(10) Patent No.: US 7,507,531 B2
(45) Date of Patent: Mar. 24, 2009

(54) USE OF 5-LIPOXYGENASE ACTIVATING PROTEIN (FLAP) GENE TO ASSESS SUSCEPTIBILITY FOR MYOCARDIAL INFARCTION

(75) Inventor: Anna Helgadottir, Reykjavik (IS)

(73) Assignee: deCODE Genetics chf., Reykjavik (IS)

( * ) Notice: Subject to any disclaimer, the term of this patent is extended or adjusted under 35 U.S.C. 154(b) by 0 days.

(21) Appl. No.: 10/829,674

(22) Filed: Apr. 22, 2004

(65) Prior Publication Data

US 2005/0112611 A1    May 26, 2005

Related U.S. Application Data

(63) Continuation-in-part of application No. 10/769,542, filed on Jan. 30, 2004, now abandoned, which is a continuation-in-part of application No. PCT/US03/32805, filed on Oct. 16, 2003.

(60) Provisional application No. 60/419,432, filed on Oct. 17, 2002.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 4,970,215 | A | 11/1990 | Mohrs et al. |
| 5,059,609 | A | 10/1991 | Eggler et al. |
| 5,298,512 | A | 3/1994 | Eggler et al. |
| 5,306,820 | A | 4/1994 | Decker et al. |
| 5,527,827 | A | 6/1996 | Delorme et al. |
| 5,559,134 | A | 9/1996 | Buchmann et al. |
| 5,576,338 | A | 11/1996 | Friesen et al. |
| 5,641,789 | A | 6/1997 | Marfat |
| 5,939,529 | A | 8/1999 | Potempa |
| 5,981,559 | A | 11/1999 | Nagaoka et al. |
| 5,990,148 | A | 11/1999 | Isakson et al. |
| 6,040,147 | A | 3/2000 | Ridker et al. |
| 6,166,031 | A | 12/2000 | Eggler et al. |
| 6,436,924 | B2 | 8/2002 | Poppe et al. |
| 6,521,747 | B2 | 2/2003 | Anastasio et al. |
| 6,531,279 | B1 | 3/2003 | Blumenfeld et al. |
| 6,797,475 | B2 | 9/2004 | Barnes et al. |
| 2002/0107276 | A1 | 8/2002 | Isakson et al. |
| 2003/0092019 | A1* | 5/2003 | Meyer et al. .................. 435/6 |
| 2003/0194721 | A1 | 10/2003 | Mikita et al. |
| 2003/0225155 | A1 | 12/2003 | Fernandez-Pol et al. |
| 2004/0014759 | A1 | 1/2004 | Picard et al. |
| 2004/0053983 | A1 | 3/2004 | Barvian et al. |

FOREIGN PATENT DOCUMENTS

| | | |
|---|---|---|
| CA | 2337571 | 8/2002 |
| DE | 4118014 | 12/1992 |
| DE | 4118173 | 12/1992 |
| DE | 4127842 | 2/1993 |
| DE | 100 07203 | 8/2001 |
| EP | 0 360 246 | 3/1990 |
| EP | 0 518 819 A2 | 12/1992 |
| EP | 0 344 519 B1 | 4/1993 |
| EP | 0 509 359 B1 | 2/1996 |
| EP | 0 703 216 | 3/1996 |
| EP | 0 870 762 | 10/1998 |
| EP | 0 947 502 | 10/1999 |
| JP | 03227922 | 10/1991 |
| JP | 06072947 | 3/1994 |
| JP | 00355551 | 12/2000 |
| JP | 2003238407 | 8/2003 |
| WO | WO 94/00420 | 1/1994 |
| WO | WO 95/18610 | 7/1995 |
| WO | WO 96/11192 | 4/1996 |
| WO | WO 96/27585 | 9/1996 |
| WO | WO 96/41625 | 12/1996 |
| WO | WO 97/29774 | 8/1997 |
| WO | WO 97/29775 | 8/1997 |
| WO | WO 98/09943 | 3/1998 |
| WO | WO 98/13347 | 4/1998 |
| WO | WO 98/40354 | 9/1998 |
| WO | WO 98/40364 | 9/1998 |
| WO | WO 98/40370 | 9/1998 |
| WO | WO 98/42345 | 10/1998 |
| WO | WO 98/43954 | 10/1998 |
| WO | WO 00/43001 | 7/2000 |

(Continued)

OTHER PUBLICATIONS

Helgadottir et al. Nature Genetics, vol. 38, No. 1, pp. 68-74, Jan. 2006.*

(Continued)

*Primary Examiner*—Jeanine A Goldberg
(74) *Attorney, Agent, or Firm*—Marshall, Gerstein & Borun LLP

(57) ABSTRACT

Linkage of Myocardial Infarction (MI) to a locus on chromosome 13q12-13 is disclosed. In particular, the FLAP gene within this locus is shown by association analysis to be a susceptibility gene for MI and stroke. Pathway targeting for drug delivery and diagnosis applications in identifying those at risk of developing MI or stroke, in particular are described.

4 Claims, 129 Drawing Sheets

FOREIGN PATENT DOCUMENTS

| | | |
|---|---|---|
| WO | WO 00/50577 | 8/2000 |
| WO | WO 00/59864 | 10/2000 |
| WO | WO 01/34199 | 5/2001 |
| WO | WO 01/57025 | 8/2001 |
| WO | WO 01/96347 | 12/2001 |
| WO | WO 02/05825 | 1/2002 |
| WO | WO 02/060378 | 8/2002 |
| WO | WO 03/035670 | 5/2003 |
| WO | WO 03/037349 | 5/2003 |
| WO | WO 03/063781 | 8/2003 |
| WO | WO 03/082191 | 10/2003 |
| WO | WO 03/086282 | 10/2003 |
| WO | WO 03/103602 | 12/2003 |
| WO | WO 2004/002409 | 1/2004 |
| WO | WO 2004/012686 | 2/2004 |
| WO | WO 2004/024186 | 3/2004 |
| WO | WO 2004/035741 | 4/2004 |
| WO | WO 2004/047648 | 6/2004 |
| WO | WO 2004/052839 | 6/2004 |
| WO | WO 2004/055520 | 7/2004 |

OTHER PUBLICATIONS

Meschia et al. (Ann Neurology, vol. 58, pp. 351-361, 2005).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Koch et al. (Genetics in Medicine, vol. 9, No. 2, pp. 123-129, 2007).*
International Preliminary Report on Patentability for International Application No. PCT/US2004/030582 dated Dec. 8, 2005.
Morgan et al., Nonvalidation of Reported Genetic Risk Factors for Acute Coronary Syndrome in a Large-Scale Replication Study, *J. Amer. Med. Assoc.*, 297: 1551-1561 (Apr. 11, 2007).
Ahmed et al., Serial Intravascular Ultrasound Assessment of the Efficacy of Intracoronary γ-Radiation Therapy for Preventing Recurrence in Very Long, Diffuse, In-Stent Restenosis Lesions, *Circ.*, 104:856-859 (2001).
Aiello et al., Leukotriene B4 Receptor Antagonism Reduces Monocytic Foam Cells in Mice, *Arterioscler. Thromb. Vasc. Biol.*, 22: 443-449 (2002).
Allen et al., Enhanced Excretion of Urinary Leukotriene $E_4$ in Coronary Artery Disease and After Coronary Artery Bypass Surgery, Coronary Artery Disease, 4: 899-904 (1993).
Allen et al., Differential Leukotriene Constrictor Responses in Human Atherosclerotic Coronary Arteries, *Circulation*, 97:2406-2413 (1998).
Andresdottir et al., Fifteen Percent of Myocardial Infarctions and Coronary Revascularizations Explained by Family History Unrelated to Conventional Risk Factors, *European Heart Journal*, 23:1655-1663 (2002).
Askonas et al., Pharmacological Characterization of SC-57461A (3-[Methyl[3-[4-(Phenylmethyl)Phenoxy]Propyl]Amino]Propanoic Acid HCl), a Potent and Selective Inhibitor of Leukotriene $A_4$ Hydrolase I: In Vitro Studies, *JPET*, 300:577-582 (2002).
Bakr et al., 5-Lipoxygenase and Leukotriene $A_4$ Hydrolase Expression in Primary Nephrotic Syndrome, *Pediatr Nephrol*, 19:396-399 (2004).
Barone et al., Time-Related Changes in Myeloperoxidase Activity and Leukotriene $B_4$ Receptor Binding Reflect Leukocyte Influx in Cerebral Focal Stroke, *Mol. Chem. Neuropathol.*, 24:13-30 (1995).
Barth, J., Which Tools are in your Cardiac Workshop? Carotid Ultrasound, Endothelial Function, and Magnetic Resonance Imaging, *Am. J. Cardiol.*, 87(suppl) 8A-14A (2001).
Bermudez et al, Interrelationships Among Circulating Interleukin-6, C-Reactive Protein, and Traditional Cardiovascular Risk Factors in Women, *Arterioscler Thromb Vasc Biol.*, 22:1668-1673 (2002).
Birke et al., In Vitro and in Vivo Pharmacological Characterization of BIIL 284, a Novel and Potent Leukotriene $B_4$ Receptor Antagonist, *JPET*, 297:458-466 (2001).
Blackie et al., The Identification of Clinical Candidate SB-480848: A Potent Inhibitor of Lipoprotein-Associated Phospholipase $A_2$, *Bioorganic Med. Chem. Lett.*, 13:1067-1070 (2003).
Blake et al, C-Reactive Protein, Subclinical Atherosclerosis, and Risk of Cardiovascular Events, *Arterioscler. Thromb. Vasc Biol.*, 22:1512-1513 (2002).
Blake et al., Projected Life-Expectancy Gains With Statin Therapy for Individuals With Elevated C-Reactive Protein Levels, *JACC*, 40:49-55 (2002).
Boyd et al., N-1 Substituted Pyrimidin-4-Ones: Novel, Orally Active Inhibitors of Lipoprotein-Associated Phospholipase $A_2$, *Bioorganic Med. Chem. Lett.*, 10:2557-2561 (2000).
Brennan et al., Prognostic Value of Myeloperoxidase in Patients with Chest Pain, *N. Eng J. Med.*, 349:1595-1604 (2003).
Buffon et al., Widespread Coronary Inflammation in Unstable Angina, *N. Engl. J. Med.*, 1:5-12 (2002).
Byrum et al., Determination of the Contribution of Cysteinyl Leukotrienes and Leukotriene $B_4$ in Acute Inflammatory Responses Using 5-Lipoxygenase- and Leukotriene $A_4$ Hydrolase-Deficient Mice, *J. Immunol.*, 163:6810-6819 (1999).
Carry et al., Increased Urinary Leukotriene Excretion in Patients with Cardiac Ischemia; In vivo Evidence for 5-Lipoxygenase Activation, *Circulation*, 85: 232-236 (1992).
Caslake et al., Lipoprotein-Associated Phospholipase $A_2$ (Platelet-Activating Factor Acetylhydrolase) and Cardiovascular Disease, *Curr. Opin. Lipidol.*, 14:347-352 (2003).
Chang et al., C-Reactive Protein Binds to Both Oxidized LDL and Apoptotic Cells Through Recognition of a Common Ligand: Phosphorylcholine of Oxidized Phospholipids, *PNAS*, 99:13043-13048 (2002).
Chen et al., Leukotriene $A_4$ Hydrolase in Rat and Human Esophageal Adenocarcinomas and Inhibitory Effects of Bestatin, *J. of the Natl. Cancer Institute*, 95:1053-1060 (2003).
Collins et al., Effects of Cholesterol-Lowering with Simvastatin on Stroke and Other Major Vascular Events in 20 536 People with Cerebrovascular Disease or Other High-Risk Conditions, *Lancet*, 363:757-767 (2004).
Cyrus et al., Effect of Low-Dose Aspirin on Vascular Inflammation, Plaque Stability, and Artherogenesis in Low-Density Lipoprotein Receptor-Deficient Mice, *Circ.*, 106:1282-1287 (2002).
Dahlen et al., Inhibition of Allergen-Induced Airway Obstruction and Leukotriene Generation in Atopic Asthmatic Subjects by the Leukotriene Biosynthesis Inhibitor BAYx 10005, *Thorax*, 52: 342-347 (1997).
Danesh et al., C-Reactive Protein and Other Circulating Markers of Inflammation in the Prediction of Coronary Heart Disease, *N. Engl. J. Med.*, 350:1387-1397 (2004).
Davidson, M., Introduction: Utilization of Surrogate Markers of Atherosclerosis for the Clinical Development of Pharmaceutical Agents, *Am. J. Cardiol.*, 87(suppl): 1A-7A (2001).
De Caterina et al., Leukotriene B4 Production in Human Atherosclerotic Plaques, *Biomed. Biochim. Acta*, 47: S182-85 (1988).
Devillier et al., Leukotrienes, Leukotriene Receptor Antagonists and Leukotriene Synthesis Inhibitors in Asthma: An Update. Part II: Clinical Studies with Leukotriene Receptor Antagonists and Leukotriene Synthesis Inhibitors in Asthma, *Pharmacol. Res.*, 40:15-29 (1999).
Doggen et al., C-Reactive Protein, Cardiovascular Risk Factors and the Association With Myocardial Infarction in Men, *J. Intern. Med.*, 248:406-414 (2000).
Drazen et al., Pharmacogenetic Association Between *ALOX5* Promoter Genotype and the Response to Anti-Asthma Treatment, *Nat. Genet.*, 22:168-170 (1999).
Dwyer et al., Arachidonate 5-Lipoxygenase Promoter Genotype, Dietary Arachidonic Acid, and Atherosclerosis, *N. Eng. J. Med.*, 350:29-37 (2004).
Eberhard et al., Leukotriene $A_4$-Hydrolase Expression and Leukotriene $B_4$ Levels in Chronic Inflammation of Bacterial Orgin; Immunohistochemistry and Reverse-Phase High-Performance Liquid Chromatography Analysis of Oral Mucosal Epithelium, *Virchows Arch*, 440:627-634 (2002).
Fauler et al., Cardiovascular Effects of Leukotrienes, *Cardiovasc. Drugs Ther.*, 3:499-505 (1989).

Feltenmark et al., Diverse Expression of Cytosolic Phospholipase $A_2$, 5-Lipoxygenase and Prostaglandin H Synthase 2 in Acute Pre-B-Lymphocytic Leukaemia Cells, *British J. of Haematology*, 90:585-594 (1995).
Fischer et al., Effect of a Novel 5-Lipoxygenase Activating Protein Inhibitor, BAYx 1005, on Asthma Induced by Cold Dry Air, *Thorax*, 52:1074-1077 (1997).
Folcik et al., Lipoxygenase Contributes to the Oxidation of Lipids in Human Atherosclerotic Plaques, J. Clin. Invest., 96:504-510 (1995).
Folco et al., Leukotrienes in Cardiovascular Diseases, *Am. J. Respir. Crit. Care Med.*, 161:S112-S116 (2000).
Frenette et al., Substituted Indoles as Potent and Orally Active 5-Lipoxygenase Activating Protein (Flap) Inhibitors, *Bioorg. Med. Chem. Lett.*, 9:2391-2396 (1999).
Friedrich et al., Mechanisms of Leukotriene $B_4$—Triggered Monocyte Adhesion, *Arterioscler. Thromb. Vasc. Biol.*, 23:1761 (2003).
Funk, C., Prostaglandins and Leukotrienes: Advances in Eicosanoid Biology, *Science*, 294:1871-1875 (2001).
Funk et al., Molecular Cloning and Amino Acid Sequence of Leukotriene $A_4$ Hydrolase, *Proc. Natl. Acad. Sci.*, 84:6677-6681 (1987).
Gompertz et al., A Randomized, Placebo-Controlled Trial of a Leukotriene Synthesis Inhibitor in Patients with COPD, *Chest.*, 122:289-94 (2002).
Hagenaars et al., Rationale and Design for the SARIS Trial; Effect of Statin on Atherosclerosis and Vascular Remodeling Assessed with Intravascular Sonography, *Cardiovasc. Drugs Ther.*, 15:339-343 (2001).
Heinzmann et al., Studies on Linkage and Association of Atopy with the Chromosomal Region 12q13-24, *Clin. Exp. Allergy*, 30:1554-1561 (2000).
Helgadottir et al., Familial Clustering of Myocardial Infarction in the Icelandic Population: Evidence for Genetic Compoents, *Am. J. Human Gen.*, 84:A205: 1128 (1999).
Helgadottir et al., The Gene Encoding 5-Lipoxygenase Activating Protein Confers Risk of Myocardial Infarction and Stroke, *Nat. Genet.*, 36:233-239 (2004).
In et al., Naturally Occurring Mutations in the Human 5-Lipoxygenase Gene Promoter that Modify Transcription Factor Binding and Reporter Gene Transcription, *J. Clin. Invest.*, 99:1130-1137 (1997).
Ishizaka et al., Increased Leukotriene $A_4$ Hydrolase Expression in the Heart of Angiotensin II-Induced Hypertensive Rat, *FEBS Letters*, 463:155-159 (1999).
Jonsdottir et al., Incidence and Prevalence of Recognised and Unrecognised Myocardial Infarction in Women, *Eur. Heart J.*, 19:1011-1018 (1998).
Kachur et al., Pharmacological Characterization of SC-57461A (3-[Methyl[3-[4-(Phenylmethyl)Phenoxy]Propyl]Amino]Propanoic Acid HCl), a Potent and Selective Inhibitor of Leukotriene $A_4$ Hydrolase II: In Vivo Studies, *JPET*, 300:583-587 (2002).
Kaiser et al., Proteomics Applied to the Clinical Follow-up of Patients After Allogeneic Hematopoietic Stem Cell Transplantation, *Blood*, 104:340-349 (2004).
Kanayama et al., A New Prostacyclin Analog, KP-10614, Inhibits Platelet-Polymorphonuclear Leukocyte Interaction and Limits Experimental Infarct Size in Rat Heart, *J. Pharmacol. Exp. Ther.*, 266:344-349 (1993).
Keaney, Jr. et al., The Value of Inflammation for Predicting Unstable Angina, *N. Engl. J. Med.*, 347:55-57 (2002).
Kolasa et al., Synthesis of Indolylalkoxyiminoalkylcarboxylates as Leukotriene Biosynthesis Inhibitors, *Bioorg. Med. Chem.*, 5:507-514 (1997).
Kristjansson et al., Improved One-Year Survival After Acute Myocardial Infarction in Iceland Between 1986 and 1996, *Cardiology*, 91:210-214 (1999).
Kuhn et al., Amino Acids Differences in the Deduced 5-Lipoxygenase Sequence of CAST Atherosclerosis-Resistance Mice Confer Impaired Activity when Introduced Into the Human Ortholog, *Arterioscler. Thromb. Vasc. Biol.*, 23:1072-1076 (2003).

Kuribayashi et al., Inhibitory Effects of a Phosphate Diester of α-Tocopherol and Ascorbic Acid (EPC-$K_1$) on Myocardial Infarction in Rats, *Int. J. Tiss. Reac.*, 18:73-79 (1996).
Lam et al., Leukotriene $C_4$ Uses a Probenecid-Sensitive Export Carrier That Does Not Recognize Leukotriene $B_4$, *PNAS USA*, 89:11598-11602 (1992).
Lehr et al., Involvement of 5-Lipoxygenase Products in Cigarette Smoke-Induced Leukocyte/Endothelium Interaction in Hamsters, *Int. J. Microcirc.: Clin. Exp.*, 12:61-73 (1993).
Magee et al., An Integrated Pharmacokinetic/Pharmacodynamic (PK/PD) Model for SB-480848 Inhibition of Plasma Lipoprotein-Associated Phospholipase A2 (LP-PLA2) Enzyme Activity in Human, *American Society for Clinical Pharm. and Ther. Abstract PIII-87* (2003).
Mehrabian, et al., Identification of 5-Lipoxygenase as a Major Gene Contributing to Atherosclerosis Susceptibility in Mice, *Circ. Res.*, 91:120-126 (2002).
Menegatti et al., Gene Expression of 5-Lipoxygenase and $LTA_4$ Hydrolase in Renal Tissue of Nephrotic Syndrome Patients, *Clin. Exp. Immunol*, 116:347-353 (1999).
Okano-Mitani et al. Leukotriene $A_4$ Hydrolase in Peripheral Leukocytes of Patients with Atopic Dermatitis, *Arch Dermatol Res.*, 288:168-172 (1996).
Montero et al., LTA4 Hydrolase Expression During Glomerular Inflammation: Correlation of Immunohistochemical Localization with Cytokine Regulation, *Adv. Exp. Med. Biol.*, 449-454 (1999).
Mueller et al., Leukotriene $A_4$ Hydrolase, Mutation of Tyrosine 378 Allows Conversiion of Leukotriene $A_4$ into an Isomer of Leukotriene $B_4$, *J. Biol. Chem.*, 271:24345-24348 (1996).
Muller-Peddinghaus et al., BAY X1005, A New Inhibitor of Leukotriene Synthesis: in Vivo Inflammation Pharmacology and Pharmacokinetics, *J. Pharmacol. Exp. Ther.*, 267:51-57 (1993).
Muller-Peddinghaus et al., BAY X1005, A New Selective Inhibitor of Leukotriene Synthesis: Pharmacology and Pharmacokinetics, *J. Lipid. Mediat.*, 6:245-248 (1993).
Muller-Peddinghaus, R., Potential Anti-Inflammatory Effects of 5-Lipoxygenase Inhibition—Examplified by the Leukotriene Synthesis Inhibitor Bay X 1005, *J. Phys. Pharmacol.*, 48:529-536 (1997).
Nissen, S., Coronary Angiography and Intravascular Ultrasound, *Am. J. Cardiol.*, 87(suppl):15A-20A (2001).
Oestvang et al., Role of Secretory and Cystolic Phospholipase $A_2$ Enzymes in Lysophosphatidylcholine-Stimulated Monocyte Arachidonic Acid Release, *FEBS Lett.*, 555:257-262 (2003).
Ozaki et al., Functional SNPs in the Lymphotoxin-α Gene that are Associated with Susceptibility to Myocardial Infarction, *Nat. Genet.*, Published online: Nov. 11, 2002, doi:10.1038/ng1047, pp. 1-5 (2002).
Packard, et al., Lipoprotein-Associated Phospholipase $A_2$ as an Independent Predictor of Coronary Heart Disease, *N. Engl. J. Med.*, 343:1148-1155 (2000).
Paterniti, Jr., J., Investigational New Drug Applications: The Role of the Preclinical Dossier, *Am. J. Cardiol.*, 81(suppl):10F-12F (1998).
Penning et al., Inhibitors of Leukotriene $A_4$ ($LTA_4$) Hydrolase as Potential Anti-Inflammatory Agents, *Current Pharmaceutical Design*, 7:163-179 (2001).
Penning et al., Pyrrolidine and Piperidine Analogues of SC-57461A as Potent, Orally Active Inhibitors of Leukotriene $A_4$ Hydrolase, *Bioorg. Med. Chem. Lett.*, 12:3383-3386 (2002).
Penning et al., Structure-Activity Relationship Studies on 1-[2(4-Phenylphenoxy)Ethyl]Pyrrolidine (SC-22716), a Potent Inhibitor of Leukotriene $A_4$ ($LTA_4$) Hydrolase, *J. Med. Chem.*, 43:721-735 (2000).
Penning et al., Synthesis of Imidazopyridines and Purines as Potent Inhibitors of Leukotriene $A_4$ Hydrolase, *Bioorg. Med. Chem. Lett.*, 13:1137-1139 (2003).
Penning et al., Synthesis of Potent Leukotriene $A_4$ Hydrolase Inhibitors. Identification of 3-[Methyl[3-[4-Phenylmethyl)Phenoxy]Propyl]Amino]Propanoic Acid, *J. Med. Chem.*, 45:3482-3490 (2002).
Pitt et al., Aggressive Lipid-Lowering Therapy Compared with Angioplasty in Stable Coronary Artery Disease, *N. Eng. J. Med.*, 341:70-76 (1999).

Potempa et al., Stimulatory Effects of the C-Reactive Protein Subunit on Monocyte Function, Including Release of IL-1, *Biol. Fluids* 34: 287-290, 1986.

Radmark, O., 5-Lipoxygenase-Derived Leukotrienes. Mediators Also of Atherosclerotic Inflammation, *Arterioscler. Thromb. Vasc. Biol.*, 23:1140-1142 (2003).

Raggi, P., Coronary Calcium on Electron Beam Tomography Imaging as a Surrogate Marker of Coronary Artery Disease, *Am. J. Cardiol.*, 87(suppl):27A-34A (2001).

Retterstol et al., C-Reactive Protein Predicts Death in Patients With Previous Premature Myocardial Infarction—A 10 Year Follow-Up Study, *Atherosclerosis*, 160:433-440 (2002).

Ridker et al, Comparison of C-Reactive Protein and Low-Density Lipoprotein Cholesterol Levels in the Prediction of First Cardiovascular Events, *N. Engl. J. Med.*, 347:1557-1565 (2002).

Ridker et al., C-Reactive Protein and Other Markers of Inflammation in the Prediction of Cardiovascular Disease in Women, *N. Engl. J. Med.*, 342:836-843 (2000).

Ridker et al., Inflammation, Pravastatin, and the Risk of Coronary Events After Myocardial Infarction in Patients with Average Cholesterol Levels, *Circulation*, 98:839-844 (1998).

Rosenfeld, M., Leukocyte Recruitment Into Developing Atherosclerotic Lesions. The Complex Interaction Between Multiple Molecules Keeps Getting More Complex, *Arterioscler. Thromb. Vasc. Biol.*, 22:361-363 (2002).

Ross, R., Atherosclerosis—An Inflammatory Disease, *N. Eng. J. Med.*, 340:115-126 (1999).

Rossoni et al., Myocardial Protection by the Leukotriene Synthesis Inhibitor BAY X1005: Importance of Transcellular Biosynthesis of Cysteinyl-Leukotrienes, *J. Pharmacol. Exp. Therapeutics*, 276:335-341 (1996).

Rybina et al., Alteration of Human Leukotriene $A_4$ Hydrolase Activity After Site-Directed Mutagenesis: Serine-415 is a Regulatory Residue, *Biochim. Biophys. ACTA*, 1438:199-203 (1999).

Sala et al., Leukotrienes: Lipid Bioeffectors of Inflammatory Reactions, *Biochemistry*, 63:84-92 (1998).

Sala et al., Monoclonal Anti-CD18 Antibody Prevents Transcellular Biosynthesis of Cysteinyl Leukotrienes In Vitro and In Vivo and Protects Against Leukotriene-Dependent Increase in Coronary Vascular Resistance and Myocardial Stiffness, *Circulation*, 101:1436-1440 (2000).

Sampson, Leukotrienes in Cardiovascular Disease, *Clinical and Experimental Allergy Review*, 1:170-174 (2001).

Shepherd, J., Economics of Lipid Lowering in Primary Prevention: Lessons from the West of Scotland Coronary Prevention Study, *Am. J. Cardiol.*, 87 (suppl):19B-22B (2001).

Showell et al., The Preclinical Pharmacological Profile of the Potent and Selective Leukotriene $B_4$ Antagonist CP-195543, *JPET*, 285:946-954 (1998).

Sigurdsson et al., Long-Term Prognosis of Different Forms of Coronary Heart Disease: The Reykjavik Study, *Int. J. Epidem.*, 24-58-68 (1995).

Sigurdsson et al., Silent ST-T Changes in an Epidemiologic Cohort Study—A Marker of Hypertension or Coronary Heart Disease, or Both: The Reykjavik Study, *J. Am. Coll. Cardiol.*, 27:1140-1147 (1996).

Smilde et al., Effect of Aggressive Versus Conventional Lipid Lowering on Atherosclerosis Progression in Familial Hypercholesterolaemia (ASAP): A Prospective, Randomised, Double-Blind Trial, *Lancet*, 357:577-581 (2001).

Spanbroek et al., Expanding Expression of the 5-Lipoxygenase Pathway within the arterial Wall During Human Atherogenesis, *PNAS USA* 100:1238-1243 (2003).

Stein E., Laboratory Surrogates for Anti-Atherosclerotic Drug Development, *Am. J. Cardio.*, 87:21A-26A (2001).

Steinhilber, D., 5-Lipoxygenase: A Target for Antiinflammatory Drugs Revisited, *Curr. Med. Chem.*, 5:71-85 (1999).

Subbarao et al., Role of Leukotriene $B_4$ Receptors in the Development of Atherosclerosis: Potential Mechanisms, *Arterioscler. Thromb. Vasc. Biol.*, 24:369 (2003).

Takase, Change of Plasma Leukotriene C4 During Myocardial Ischemia in Humans, *Clin. Cardiol.*, 19:198-204 (1996).

Taubes G., Does Inflammation Cut to the Heart of the Matter?, *Science*, 296:242-245 (2002).

Thunnissen et al., Crystal Structure of Human Leukotriene $A_4$ Hydrolase, a Bifunctional Enzyme in Inflammation, *Nat. Struct. Biol.*, 8:131-135 (2001).

Thunnissen et al., Crystal Structures of Leukotriene $A_4$ Hydrolase in Complex with Captopril and Two Competitive Tight-Binding Inhibitors, *FASEB Journal*, 16:1648-1650 (2002).

Tracy, Inflammation of Cardiovascular Disease. Cart, Horse or Both Revisited, *Arterioscler. Thromb. Vasc. Biol.*, 22:1514-1515 (2002).

Tselepis et al., Inflammation, Bioactive Lipids and Atherosclerosis: Potential Roles of a Lipoprotein-Associated Phospholipase A2, Platelet Activating Factor-Acetylhydrolase, *Artheroscler. Suppl.*, 3:57-68 (2002).

Verma et al., A Self-Fulfilling Prophecy. C-Reactive Protein Attenuates Nitric Oxide Production and Inhibits Angiogenesis, *Circulation*, 106:913-919 (2002).

Walter et al., Benefits of Immediate Initiation of Statin Therapy Following Successful Coronary Stent Implantation in Patients with Stable and Unstable Angina Pectoris and Q-Wave Acute Myocardial Infarction, *Am. J. Cardiol.*, 89:1-6 (2002).

Wang et al., Association of C-Reactive Protein With Carotid Atherosclerosis in Men and Women: The Framingham Heart Study, *Arterioscler. Thromb. Vasc. Biol.*, 22:1662-1667 (2002).

Waters et al., Effects of Atorvastatin on Stroke in Patients with Unstable Angina or Non-Q-Wave Myocardial Infarction. A Myocardial Ischemia Reduction with Aggressive Cholesterol Lowering (MIRACL) Substudy, *Circulation*, 106:1690-1695 (2002).

Wetterholm et al., Leukotriene $A_4$ Hydrolase: Abrogation of the Peptidase Activity by Mutation of Glutamic Acid-296, *Proc. Natl. Acad. Sci.*, 89:9141-9145, (1992).

Willerson et al., Protection of the Myocardium During Myocardial Infarction: Pharmacologic Protection During Thrombolytic Therapy, *Am. J. Cardio.*, 65: 35 I-41 I (1990).

Yamada et al., Prediction of the Risk of Myocardial Infarction from Polymorphisms in Candidate Genes, *N. Eng. J. Med:*, 347:1916-1923 (2002).

Yokomizo et al., cDNA Cloning, Expression, and Mutagenesis Study of Leukotriene $B_4$ 12-Hydroxydehydrogenase, *J. Biol. Chem.*, 271: 2844-2850 (1996).

Zhang et al., Association Between Myeloperoxidase Levels and Risk of Coronary Artery Disease, *JAMA*, 286:2136-2142 (2001).

Zhao et al., The 5-Lipoxygenase Pathway Promotes Pathogenesis of Hyperlipidemia-Dependent Aortic Aneurysm, *Nat. Med.*, 10:966-973 (2004).

The SNP Consortium Ltd., SNP Report for TSC0806241, Gene sequence, (rs1323898), Oct. 10, 2000.

International Search Report for PCT/US2003/32805 dated Jan. 14, 2005.

International Search Report for PCT/US2004/030582 dated Feb. 28, 2005.

International Search Report for International Application No. PCT/US2004/030582 dated May 23, 2005.

Written Opinion of the International Searching Authority for International Application No. PCT/US2004/030582, dated Aug. 15, 2005.

\* cited by examiner

Amino acid sequence of FLAP ( >alox5ap_protein translation NM_01629)
MDQETVGNVVLLAIVTLISVVQNGFFAHKVEHESRTQN
GRSFQRTGTLAFERVYTANQNCVDAYPTFLAVLWSAGL
LCSQVPAAFAGLMYLFVRQKYFVGYLGERTQSTPGYIFGK
RIILFLFLMSVAGIFNYYLIFFFGSDFENYIKTISTTISPLLLIP
(SEQ ID NO: 2)

MRNA of FLAP (NM_001629_mRNA)

Acttccccttcctgtacagggcaggttgtgcagctggaggcagagcagtcctctctggggagcctgaagcaaacatgg
atcaagaaactgtaggcaatgttgtcctgttggccatcgtcaccctcatcagcgtggtccagaatggattctttgcccataa
agtggagcacgaaagcaggacccagaatggggaggagcttccagaggaccggaacacttgcctttgagcgggtctaca
ctgccaaccagaactgtgtagatgcgtaccccactttcctcgctgtgctctggtctgcggggctactttgcagccaagttcc
tgctgcgtttgctggactgatgtacttgtttgtgaggcaaaagtactttgtcggttacctaggagagagaacgcagagcacc
cctggctacatatttgggaaacgcatcatactcttcctgttcctcatgtccgttgctggcatattcaactattacctcatcttctt
tttcggaagtgactttgaaaactacataaagacgatctccaccaccatctcccctctacttctcattccctaactctctgctga
atatggggttggtgttctcatctaatcaatacctacaagtcatcataattcagctcttgagagcattctgctcttctttagatgg
ctgtaaatctattggccatctgggcttcacagcttgagttaaccttgcttttccgggaacaaaatgatgtcatgtcagctccg
ccccttgaacatgaccgtggccccaaatttgctattcccatgcattttgtttgtttcttcacttatcctgttctctgaagatgtttt
gtgaccaggtttgtgttttcttaaaataaaatgcagagacatgtttt (SEQ ID NO: 3)

FIG. 4

ID CHROMOSOME 13: 28932001-29146000BP in NCBI build 34.

SQ  Sequence 214000 BP

```
GACTAAGATG AATATGCATT CATTCACCAA AATCTCATAT TCCCAAAAAG CAGGAAAGGT      60
AGTACAGTGA GATGGATGAT GCCTTCACAT GACTCAGATG TCACGTGTTT CTCACCATTG     120
AGACCCCCAA GGCACCCCCT CCCAGCATTT ACCAGAATGT GTGTGTAACT ATTTACAGTG     180
ATTTGTGTAA TTATTTGATT GTTTCTCTTG TATCCTGTAG CAATGAGGGT AGAGATTATA    240
TCCCACCTAC CACTGCAGCT CCAGGATCCA GCTTCACAAA CATTTGTTGA ATGAATGAAT    300
AAGAAAAGAG GACACCCCCA AAGAGGCTGC AAGGGAAAAA GCTACAAAGA CAGAAGCACC    360
AGGAAAAAGT AGGGTCATGT AAGTCAAAGC AGGAAAAAAG TTCCATGGTG GGGTGGTCAG    420
CAGTGTCTAA TGCCACGAAG GCACAAAGTA GGATAAAGGT TAAAAATCAG CCTTTGGTTT    480
TGGCAAATAT GAAGCTTATC GGTAGCCTTA GCGAGAACAA TTCCATCAGG GAGCAGAAGC    540
TAACTGCAGT GGGTTGAGTC ATCAAGCAGG CATAAGGAAG TAGGGATACC CCATTATAAG    600
CTACTCTTTC AAGAAGCTCA AATCTGAAGG TTAGGAGAAT TAGGTCAGTA GCTAGAAGGA    660
AATGTGGAGT CGAGGGGCTG TTTTTCCTCC CAAGGAGTAT AAAGGTGTAA CGTTGCATGA    720
AACCACTTCA GACAAAGGCC GATATCAATA GAGAAGTTAA AACGCACGCC TCAAGATTTG    780
GGAAGGCTTG GGGTTGGGCT TAAAGAGGTA GGAGCATATT TCCTATCCTA GGACAGAGAA    840
TAAAGAAGAA AGGATAGGTT CCCATGGAGA TAAATTTCTA AGTGTTAAAG AAGAGGCTCA    900
GAAAATTCTA GCATGATAGG CTCACTTTTT TCTTTTTCCA TGAAGGAGAT GGCAAAGTCA    960
ACTGACATGA GAAAGGTGAC AATACTGATG GGTTGAAGAG CGATGGACAT TTGAAATAAC   1020
TTCTTAGACC AGTAGAGGCT GGAGTTCATA AATCAGAACT GGCTACAGGT TATATATGTT   1080
TTTTTTTTTT TCTCCAACAG CATAAGATAA CAGAGCGAAG TCTGTAGAAA TGAAAGAAGA   1140
GTCAGATGAG GATAGCTGGA GCTAGTGCAA GGAGGGAAGC ACCACGGTGG GAGCCAGGTA   1200
CCCCCTGGAT TTATAATTCA TACTGAATTC CAACAACAGA AGGGCTCTAA GCAGGAGAGT   1260
GACAGATTTC AGAAGACTGA GACACATTTG GTAAAAAAAA GTAGGAGGAA AACCTGATTC   1320
TGGAATTAGG GCAGCCAATA GACGGCAGTA TTTTCAGAAA GGAGGGAATG GTCAACAGTG   1380
ACTTTCTAGT CTGGAGCTCA GGAGGAAGAG GCAACTCTAC CTGATGGTAT TAAGATCATG   1440
GAGGTAGCTG AGATCACCTA GCTTGTGTGT GTCAAATGAG AAAAGAAGAA AGAATAGGAG   1500
AAGTTCCCCA GGAACACAGA CATTAAGTGG GGCTGTGGTG ACAACACAAG AAGAGAGGCT   1560
TGCAAAGGAG CCTGAGCAGC TGTCATGAGA GAGGTAGGAT GGTGGACTCG AGAAGAGGC    1620
AGAAGATGTT CTTAAAGGAA GGACACTGCT GCCAAGTAGT CAGCCAATTG GTGACAAAGA   1680
AAGACCCTGT TGCGAGAAAA AAAGTCAGTG AAGTAGTAGG AACGATGACA GATGACACTG   1740
GGTTGAAGAC TGAGGAGAGA GAAGTGTAAG AGTGGAAGCA GAGGGCAGAC CACTCTTCTG   1800
AGACACTGAA GAGGCATAGT TAGAAATAAA GGGGAGTCGC CAGAAAGGAA TTTGTGGCTA   1860
AGCAAGAGGT TTTCTTTAAG ACTGAAATAC ATAAGCATGA TTTAAATGCT GCTGGGATGG   1920
AGTTCACAGA CCTGGAAGAC AGAAGACAAA GCGGATCATC AAGATAGTGG AATTTACTGA   1980
AATGAGAGAG GAAAATCCCA TCCACAGGAA ATGCAGACAT GAGGGAGGGG CCAGAAGGAC   2040
AGTGAAAACA TCAGCAACTG GTCCCCCAAC TTCTGAGTGA ATGTGGAGAT ATAATCAGGT   2100
AAAGGACTGC ATCATCTCCC TGGTTAATGA TGGAGTCAGA GAAAAGAGTG TCTTATACAG   2160
AAGTTGTGAT ATACTTGGCC GGGCGCAGTG GCTCACGCCT GTAATCTAAG CACTTTGGGA   2220
GGCCAAGGCA GGCGGATCAC CTGAGGTCAG GAGTTCATGA CTGGCCTGGT CAACATGGCA   2280
AAATCCCACC TCTACTAAAA ACAAAAGCCT GTAATCCCAG CTACTAGGGA GGCTGAGGCA   2340
GGAGAATCGC TTGAACCCAG GAGGCAGAGG TTGCAGTGAG CCAAGGTCGC ACCACTGTAC   2400
TCCAGCCTGG GCAACAGAGC TAGACTCAGT CTCAAAAAAA AAAAAAAAAG ATGTATTTAT   2460
```

FIG. 6.1

```
TCTCACTGTA TAAATTTCTG TGTAAGAAAT ACTCTCTCAT ATAGAAGTAA ATTTATATAT    2520
AAAATTATAT AGAACCACTA TAAAATACTC AGGTTTATAA AATTTATATA TAAACTTGTT    2580
GACATATAAA ATTCCATGTA AATGACTATA AAGTACTCTT ATATGAAAAG TATATGAATT    2640
AAATTATATA TCAACTTACT TTTATATTAC AGTATTTTTG TTATACAGAA GTTTATATAG    2700
TGACAATAAA TATTTCTCAA GAACGATTTC ACATAATAGA AGTATAAATT ATCCATTTCC    2760
AATAGTGAAA AAGAAAAGCA GTTCCACACC AGTGACAGGG CTACGAATCT AAGAGGTACA    2820
AAGACTTCAT TCTTAGAGAC ACTGAGGTCA GGGCATGGCC AACACATCTG AAGCTGATAG    2880
AATTGGCGCT GGGTTGGTTG GAGACGGTAC GGTATTACTA TTACAATGGC AGACGCTTGG    2940
CCTTGATAAC TAGCCAATCA GGGGGAAAGA TTCTGGTTTC CTCTGTTATT ATCTGAACTA    3000
GTGTGTTCCC AAAGGGTTAA GATGGTTTAT GGAAGGCACA AGATCAGCAA ACCATAAAGG    3060
ATTAGCACTA AGAAGGAAGG AAGTAGACCA AGTGTTAATG GCGATGCCAT GTAAGAGCCA    3120
GGTCTGCGAT GTATGTTCTA CATGGTTTGG GGGGTAAAAA AAATGTCAGC TCCAGAGCA    3180
CAGGGCTTTA AGCCTCAAGT ACTGTTAACA GTAGAGTTTA CTAGTCTACA GCAGGAATTA    3240
CAACCAGTAA TTCTAAGGCC AATTACTCAG GCAAGTTTTA CTAGAACAAG GAAGCTCTGC    3300
TTCGAGGTCA AATCGATTTC TGCATTTATA GAAGCATCTA GATGTTCTCT GTTCAAACAA    3360
TGGGGTAAAA TCCCCACACA TTTTATTTCT GACAGAGTGT TCCCTATATT GCCTGGCCAG    3420
GAGTGATAAC ATTGCTTGGC TATTATTAAT AAAACATTGC TGTGGCTGGG CGCAGTGGCT    3480
CACACCTGTA ATCCTGGCAC TTTGGGAGGC TGAGGCAGGA GGATCACTTA ACTCCAGGAG    3540
TTTGACAGCA GCCTGGGCAA CATAGCAAGA TCCCATCTCT CTAAAAAATT TTAAAATTAG    3600
CTGGGTGTGG TGGCAGACAC CTGTAGTCCC AGCTCCTCAG GAAGCTGAGG TGGGAGGATC    3660
ACTTGAGCCC AAGCAGGTTG AGGCTGCAGC GTGCTGTGAC TGTGCCACTG CACTCCAGCC    3720
TGCGCAACAC ACTGAGAGAG ACTCTGTCTC AAAAAAATAC ATCAAATAAA AATTAAAAGC    3780
CCATTTCTTT CTTTTGGTAC ATTACAGCCA TGCACTTCAA AGGCTAGCAC AATTATTTTT    3840
CTGCAGTTCT ATATTTAGAT TCTAGTTAGA AGTAACCTAG GACCTTCATG TTAGAGGTGT    3900
CTTTGGCAAA ACTGTTATGT GAGTGAAACG TTTAATCAAT TGAGGATAAA GATGCCTCAT    3960
TGCTAATGAA GATGTGGTTT AAGGATTTTA TGCACCCAGT TCATTTATTA ACAACTTGTT    4020
TAAGCTTTAT TAGCTGGGTC TCTACTTTAT AACTGTGTTC TTTAATTTAC AAGACAATAA    4080
AAATTAAAAT GGTAAATGGG AAACCTATCT TGCTTTTCAA TAAATAATTT ATTTTAATAA    4140
CTTCGTGGGC ATGGTGGCCA AAACATTTTA GCTGTGAAAA TAATTTCAAT TCATATTTTT    4200
TTGGAATCAA TATTAAAAGG TGATATATTC TCAAATGAAA AGTGGACAAA TGATCAGTTA    4260
TAGGACATGA TTAAGAAACT AACCATGAGC CACGTGCAGT GGCTCATGCC TGTAATCCCA    4320
GCACTCTGGG AGGCCGCGGT GAGCGGATTG CTTGAGCCCA GGAGTTCAAG ACCAGGCTGG    4380
GCAACATGGC AAAAACCCGG CTCTACTAAA AATGCAAAAA AAAAAAAAAA AAAAAAATT    4440
TAGCTGGGTT TTGGTGGCTT ATGCCTGCAG TCCCAGCTAC TCGGGAGGCT GACTCGGGAG    4500
GCTGAGGCAC AAGAATCATT TGAACCCAGG AGGCAGAGGT TGCAATGAGC TGAGAATACA    4560
CCACTGCACT CCAGCCTGGG CAACAGAGAG AGAGAGACTC AGTCTCAAAA AACAAACAAA    4620
CAAACAAACA AACCGCTGCC CTGTGCTTGG AGAGATCTGT TTACCTTTAC CACTAAAGAC    4680
TGTTGGAAGT AAATTTTAGA AGGTTTATAA TACCTAAAAG TAATCACTTC TGTCTTATGA    4740
AAGGTTCTGC TGAGATTTTT CTATTGTGGC CACTAGTGGC AATATTCCAG AAGTCATATT    4800
TAAAGAATAT CTTTAGTGGA TTCAGCAGTT TTTCAAATAT GTACTTTTAT CTCTCCAACA    4860
TTCATGATTG CAATTTTTCA AATTAACCTC ATGATATAAA CAACTGTACT CTATGATGCC    4920
TCATAGTACA GAAACTGGAG GCAGAAAGAG AAGTTGAATG TCTAAGAATC GGTAATTCTA    4980
AAACTCAACA TAGACCATTC AGCATTAGTG GTTCTAACAA TCCCACTGCA AAATGAGTTG    5040
ATAATGTGTA ACACTTTAGT GAACTAAAGC ATAAAGAACC ATGGTCTCCT AATGCAGCAA    5100
```

FIG. 6.2

```
ATTAAAACAC ATGATAGCTA CAATTAATGA AGTACATAGT CCTGGCTGGG CACTATGGTA    5160
CGTCCTTTAC ATAGATTATC TCTTAAATTA TTAACCCCGT TTTAGAGATG AGAACATTCG    5220
GGCTCAGGAA GGTTATGTAA GTTATATAAA AATCACAAAA TAAGAGACAG AGCTAAGATT    5280
TGAATCCAAG TGTGACCAGG TTCATATCAA GCTTCCATTT TTGAATTTAT ATTAGAGGTC    5340
AATAACTCAC CTTTGTCCTT TTAAAATAAT TTTTGGCTCT GTGACCTACA CAGGCAAGCT    5400
GTTATTTACA AACAACCCAC ACATCTAGAT GGTCACTGTC TCACCGCCCA CTTTTACCAT    5460
CAGGACTCCT AGTGAGCTGT CAAGGGGAAT GCTATAATTT TGGAGGTTCT AAATCTGAGG    5520
GCTTAAGAAA GAAAGAAATT GTAAAAAGCA GGCATTACTC AGGGGCATAG ATTGTCAGGC    5580
AGATCTGTCA TGCTTATAGG TAACCTCCCA GGGCCAAAAA TATATGTGCC CAAACTGCCT    5640
AAATATTTCC TGTCACTTCA TAATACTGCC TGAAATCCTG CCAAATTAGA ACTTCATTTG    5700
TGTTGCTTGT CAATTTTTAA CGCATAAGCA AATCACCTGG AGATCTTGTT AAAATGCAAA    5760
TTCTGATTAG GTTAGGTCTG GGTCTGCATG TCTGATATGC TTCCAGAGGG CACTGATGCT    5820
GCTGGTCCAT GGACCACACT TAAAGAAGCA AAAAAGATGT CTGATATTTA CTCTCTGGCT    5880
GCCTAGGAGT GCTTCTCATT TAAGTGAGAT CTCTTTGTGC ATCATAATGG GAGGGATGAG    5940
CTGAAAAGCA GCAAATTAAG AGTGAGTTAA GTGTCTACCT CACTTCCCTA CTATCTGTAA    6000
CAAGCAGGTT TGGGCACTGT GGTCAACCAG AAAATTCTTT CCAGGACCAC AACCCTTGAG    6060
ATTATGTTGC AAAGATGCAA GGACAACTTA GAAATAATTT CCAGCACTGG TGGCACTGGA    6120
TGTCTGTCAG TGGTGCTGGT GGCAGGGTCC TATTCAGACT GTGGTTTACC TGCCTGGCCC    6180
GTTTGGTTAT GGGCCATTTT CTGAGTACCA TGGAGCATCG CCCAGCTGAC AAGGGCTTGT    6240
ACTCCACCCT TGGTGCGCAG AAGGGAAGCT TGGCTGCTAC TAAGTTTGGT GCAAAGTAAT    6300
TGTGGTTTTG CCATTAATAT TTGATACAGT GAGTCCCTAC TTTCCTCAGG TGAAACTAGA    6360
ACTTAAGGGG ACACGCTCAA GTTCTCATTA TACAGTACTA AGTTTCAAAA ATCAGCAATT    6420
TTATCAAACA CATGCTCTAC AGCAGTGGTC GGCAAACTTT TTCTGTAAGG GGCCAGAGAG    6480
TAAATGTTTT AGAGTTTCTG GGCCACATAT GGTTTCTGTT CCAGCTATAA ACTCTGCCAC    6540
TGTAGGGCAA AAGCAACCCT CCACAATACA TACATGAATA GGTGTGTTCC AAAAAAACTT    6600
TATTTGTGGA CCCTGAAATT TGAATTTCAT AAACTTTTCA TGTGTCATGA AATATTCTTT    6660
TGATTTTTTC CCAACCTTTT AAAGATGTAA CAACCATTTT TAGCCTGTAG GCCATATAGA    6720
AACAGGCAGT GGGCTGGGTT TGCTGACCCT TGCTCTGAAG CAATGATATC TCGATCCAAT    6780
TTATACCCAC AAATTTTTCT CCTTGAAACC ATGCATTTAA TTCTCATCTC TTCTTACCAT    6840
GACAATAAGA AGTTATTCTA TATAACAAAG AGATTGTACC CACCCAAGCC AGCATTTAGA    6900
TCATGTCATT TGCTTCCTCA AAATTTTGGT CTTTATAAAA ATCAATTAAA GCACCTTAAA    6960
AGGTAAGCAG TGATGAAATA TTTGAAATAA TTGGCTAATT AAACATCACC TAAATAGAAA    7020
CTGTGATAAG AACCACAAAT GCGAAAAGGA ATCATGTAGT AACTAATGTG GAGGATATCT    7080
TGGTTTAGAG ATTTGATGAA CACGAGTTTT GATTTAAAAA AATTTGTGCA ATACTCACTG    7140
CTTTGGTGGG GAGCTTGCTA TGCAAGTTGG TAGAAAAATT TATCCTAAAG TCACAGTTCT    7200
CTACCACTCT GGATTTTCTC GAGCTAACTA CCATTCCAAA CTATTTTAGG CACAGTTACT    7260
AGTTTCAAGA ATCAGGCAAA TTGCCCTGGT ATTAGCACTG TTCTTTCTGT GGTCACAAGT    7320
CAAACTACTG TGGTGAATAA AATTAGATGA TTTCTTTAGT CTTTCCTTTT TCAGCCCCTG    7380
TAGTCAATTT CCAGTGCTCC ATTCAAAGAA AAACCAAAAA TGTCCAGAAT ATAACCTTAT    7440
TTTAAAACTT GTTAACCACT GATTTCACTT GTTAACCAAA TTTTTTTTTT TTTTTTTTTG    7500
AGAATGAATC TCACTCTGTC ACCAGGCTGG AGTGCAGTGG CATGATCTTG GTTCACTGCA    7560
ACCTCCGCCT CCTGGGTACT GGTTCAAGCA ATTCTCCTGC CTCAGTCTCC CGAGTAGCTG    7620
GGATTACAGG TGTGCACCCC CACACCCAGC TAATTTTTTT GTACTTTTAG TAGAGATGGG    7680
GTTTCACCAT GTTGGCCGGG CTAGTCTTAA ACTCCTGACC TCGTGATCCG CCCGCCTCGG    7740
```

FIG. 6.3

```
CCTCCCAAAG TGCTGGGATT GCAGGCATGA ACCACTGCGC CCAGCCTGTT AACCAAATTT    7800
CTAATCACAC ACACTTGAGG CCCAGTAAAT GCCTGCTGAA AAGAGGGTGC TGGTGGTGAG    7860
GCAACTGAGG GGCTAACATA CTGATAGCTG CTGAAATCTT CTACAGCTCT TTCTTGTTAG    7920
AACACTCCAT CACGGCTCCC AGGCCCACAC CACATGAAGG AACTTCTAGC TCTCTTGCTT    7980
GCTCTTTACC CAAATGTAGT TAGCAAGTCC TGGGAACTAA ACAGCATTGA CACACTTGAA    8040
GAAGACAATT AGGCAAATCC CAACTGCTGT GCTCCTGCAG CTAAAGATGA AGACTCGTCC    8100
ATTGGGCAGT TGATTAATTG TACCTAGAAA ATTAATTTCA ATGGTCCCAT GACAACATAC    8160
GGGCAGTGAA GCTCTAGTGT TCCCCCTGGG TGGAATCTTC CAGGATGTAT AGTCTCCCAT    8220
ACCAGCTCAT CCTCCCATTT TTCCAGATTC TGGTTCTTCT CTCTTACCTA GTGTGTAGTG    8280
GGCCAAATGG TGGTCCCCCA AAAAGATATG TCCATGTGTT AACCCTGGAA ACTGTGGATG    8340
TAACCTTATT TGGAAAAATG GGGCCAGGTG CAGTGGTGTG CATGTGTAGT CCCAGAACTT    8400
TGAGAAGCCA AGGTGGGAGA ATCGTTGGAG CCCAGGAGTT CAAGAACAGC CCAGGCAACA    8460
TATTGAGACC CCCGTCTCTA TAAGCAATAA AAAATTAGCT AGGTGTGGTG GCATGCACCT    8520
GAAGTTCCAG CTACTTGAGA GGCTGAGGCA GAAGGACTGC TCAAGCCCAA GGAGTTCAAG    8580
GCTGCAGTGA GCTATGATCA TGTCACCCCA CTCCAGCCTG GTGACAGAG TCAGACTCCC     8640
TGTCTCAGGA GAAAAGAAAA AAAGGTCTTT GTAAATGTAA TAAAGAATCT TGAGATAAGA    8700
TCATCCTGAT TTAGGATGGA CCCTAAATCC AATGACATTT GTCCTTACAA AAGAAAGGTA    8760
GAGGGAACTG TGAGACAGAC ACAGAGGGGA GGGCCTTGTG AAGCAGGAAG CATAGATGCA    8820
GTTACAAGTC AAGGAATGCC AAGGACTGTC TACAACCAGA AGCCAGGAGA GATGCATGGG    8880
ATGATTTCTC CCTCACAGCC TCCAGAACTT CTGGCCTCCA GGACTGTGAA GAATCAATTT    8940
CTGTTGTTTT AAGCCACCAA GTTTGTGTGT CATTTGTTAT GGCAATGGCA GTATTAGGAC    9000
TCTAATACAC AGTATAAAAA AATAAAAATA GGGCCAGGCG TGGTGGCTCA GACCTATAAC    9060
CCCAGCACTT TGGGAGGCTA AGGCGGGGAG ATCACTTGAG GTCAGGAGTT TGAGACCAAC    9120
CAGGCCAACA TGGTGAAACC CCATCTCTAT TAAAAATAAA AATTAGTTGG GCATGGTGGT    9180
GTGCATCTGT AATCCCAGTT ACTCAGGAGG CTGAGGCAGA AGAATCGCTT GAACCCAGGA    9240
AGTGGAGGTT GTAGTGAATG CCACTGCACT CCAGCCTGGG TGACAGAGCT AGACTCCTTC    9300
ATCCTAGGAC ACAGCCAAGT CTTACGTAGC AAAAAGAAGT TGTTAAAGGT CTGTAGTTCT    9360
GCATTAAGCA ACACAGGCAT GTACCTATGA ATTATATGAT TATAAAAGTG CTCGGACAGG    9420
CCCATTTCAA ACTTGGCCTC TTTCCACCAA CTGTGTACTG TTTCTCATTC CATAACTAGA    9480
GATTATGTCT TTATATCCTG TCAAAAAAGT GAATTTTTGT GGGCTAAGAC ATTATCCCTG    9540
TGTTAAATGC ACCAGTCTTA GTGTAAACAA GCCTAGTTCC TTTTTCATTT TGGCTGTCTA    9600
GTATGCATTT GTATATGCTA GGCAGTGTAC TAGGCACCTT AAATACATTA CCTTGTTTAA    9660
CCTCTACAGG ATTCTGGGAG GTAGGCATTA TCCCCATTTT ATAGATGAGA ACACTGAGAA    9720
GACAATGTTC ATAAGTGCGT CACTTGTCTG AGATGACATA TTTACTAAGT AGCAGAACCA    9780
GGCCTCGAGC TACTCAGTCT GATTTCCAAA GCCCTGCTC TTAATCACAT CAACTTCTTT     9840
CCTATATCAC CTTTCCCAGA GTGCGCTCTC ATGGATAAAG AGCAGAAGTA TAAGTTACTA    9900
GGCAGCAGAA AACTGTAGAG GTGGGAAGAT TAGATAAAAA ATGTAAATAA GAAGGCTTTA    9960
AGACACCAAA ATCAAATGTA AATACTTTAT AACCTGAATC AGTGCTTGTG TTCATGAGGC   10020
TAGAGGTCGT GCATTTTATC TCTAGGTCTG GTGATGCCAA TCCTGATCTA CAGCCAGCAG   10080
CAACAGTTCC CTAGCCTGCC TAGAAGTTTG TAAATGCATG GGCTTTGGTA GGAGGAAGAC   10140
GAGAGAAAGC AGAACAGATT ATTACAAACC CAGTGCATTC CCCCTTGATG GGTCAACAGC   10200
GATTTCTTTG TAAGTGAAGG ACAGCACACT GGTTTTGATG ACTCACGAGA GAGTAGGAGG   10260
GAAAAAGAAG TCTGAGGCAT TGCCTGGAAG CCTCGCTCTG CTTAAACAAG TACACTAATG   10320
GCTCATGCCT GTTACTCCCA GCACTTTGGA AGGCCAAGAT GGGTGGATCA CTTGAGGCCA   10380
```

FIG. 6.4

```
GGAGTTTAAG CCCAGCCTGG TCAACATAGC GAGACCTTTT CTCTATTAAA AATAAAGAAG    10440
AAAGAAAGTA ATAATGATTC AAGTTCTCAT TCTCTACAAA ATTCACTTAT GACTTTCCAA    10500
ATGCTAGTGA AAACTTTTAG GTATTGCAAA ACTGCCTTAA TGCATAACGG GATTCTCATT    10560
TTACTTAGTC TAAGATGACT TTTTCACTTT GAACTTCTGC ATCTTTATGA TCGCTTAGCT    10620
TTCTGACAAG CAATTTCAGT AAGTGTTTAT CAATTTGCAT CCACACGCTG ACACATAGGG    10680
GTCTACTTAC ATATCCTTCA TGTAATTGAG CTTTTGTAAA TCATCTTTCT ACATGGTACA    10740
CTTCTGATTT TGTGTGCAGC TTTCTTGTTT AAGCACTGTA TTAAATGCTC TGCTTCCTAC    10800
ACCCTTAGGA ACAATGAGAA TAAAAGCGTA ATGTTGGTTA CTTCTTCATA TCAAAGGAAG    10860
TTCATCTCCT GGTTATTAAA AGCTATTATT AAATGGCCAT CTTTTTGTGC CCCTGTGTTA    10920
AGCACTCTAC CAAGATACCA TTAAATAGAT AAGGGCCACA CTCCATAGAG ATGATGGTTC    10980
TATATTCTGT ATTTTCTGGG GGAGTTCTAA TTTCATGCAA TTCCTTCTTC TTAAATAAAG    11040
GCAATTCTCT AAATATATTA CCTAATGTGC TTTCACTTTC ATATTCTTGT AAGATTTTTC    11100
ACATAAATCA ATTCTCAAAA AATAGTATCA TAGGCCTTTT AAAAATAGTC ATGTTCAAAA    11160
GTCAGGCTCA TGAATAAATG TGTGCATTCA TTACATATAT TTTCATAAAT TCAAATTTAA    11220
AAGAATAAGA GTAGCTAGAA GGTGGAAGAA AAATCTTATT CTGATTAGGA ATGCACAATC    11280
ACAAGAAAAT TTGTGATATA TATAGTCATT TTATTCTGTA TTGTTTTATT TTGATTTTGG    11340
TAAGACAAGA AACAATGTAG AAAGTTTGAC AACTTAAAAA AGTAATATGA GTGTGAGAAA    11400
GTCCTCTTCC AGGATTAGCA AAAAAATGGT TTTTTTTTTT TTTTTTTCCG AGATGGAGTC    11460
TCGCTCTCTC GCCCAGGCTG GAGTGCAGTG GCGCAATCTT GGCTCACTGC AACCTCCGCC    11520
TCCCGGGTTC AGGTGATTCT CTTGCCTCAG CCTCCCAAGT AGCTGGGACT ACAGGCATGT    11580
GCCACCATGC CCGGCTAATT TTTTTTATTT TTAGTAGAGA CGGGGTTTCA CCATGCTGGC    11640
CAGGCTGGTC TTGAACTCCT GACCTTGTGA TCTGCCCGCC TTAGCCTCCC AAAGTGCTGG    11700
GATTACAGGC GTGAGCCACC GTACCCAGCC TAAATGGCCA AGTTTTATTA TGGACAATTA    11760
AGCTGTAGAA TAAAAATCTA CTTTTAATAG CTGGCATAGT GCCTAGTGGT TTTGAAGCCA    11820
CAAGCAGGTT TACAAAAAAC ATTTAAATCC ATCTGAATCT ACAGAAAACT AAGATTACCT    11880
AAGCAGAAAA TGAAAATAGT TCAGGATTAA GGAAGATTAA CAAATGAAGA GTATATGTAT    11940
TTTAGAAGTA TTACTTTATA TTTTTATAGT ATAATAATAA TATTTACGTT CCTACACTTA    12000
TAATGAGTTT CGTATATATA TTAAAATAAT TTAATGGATT AGTATGTTTA TATTTGCTTT    12060
TAGTAAATTT GGTGTATGAT AAACTCAGTT GTCTACATTG TGAGACTACA CCTGAGGCAA    12120
TTTCTGTGTT GATATATACC TGAATAGCAG ATATTACTTG GAGCAAATA AAATAGCTTC    12180
AGGCCTAATT TTGCAAGTTC ATGATGGGAG AGTAAGCATG ACTTCAAAGA ACTGACTTTG    12240
AGTTAAAACT TGAAGAATGA ATGTGACAAC AGCAAGTATA AAACAATGCC AGGCAGAGGT    12300
GGGACTGTTC ATGGGTATCA GGGTAAGTGT GTTGATAAAT GCTCAAAGTA GGAAATACCT    12360
TTCTTCCCCC ACACATGTCA GAAAATAACT GCAATAGAAT GCAACGACAT CTCAGAGATA    12420
AAGTGTTCAA CTTAGCTCTC AGAGACCGTT CAGTTACATT TTGTAATGAC ATTGGAATTG    12480
ATTGCATTTT GAAGGCAATT CTAAATGCAA AGTCTTCATT TTGTTGATAG AAGCTGGGTT    12540
ATTTATTATG AAATTTCAAA AATTAAGTAA AATATCTAAT TAGGATTATA CCAGCAAAGG    12600
CAAATTTAGA ATTCAAGACT TCATGATCCA TGGTAAGATT ATTTTAATGC AACTCTGCTA    12660
ATTAACTGAA ATTTCCTTTA ACTCTCACAT CTGCCTTTTA CTTCTTAAGA CATTTTTCTA    12720
GTATTTCACC AGAGCAAGAT ATCAGAAGGG TAAATCTCTT ACCAATGAAC TTTGCTAATT    12780
CTTAGTGACT CCGTTGACCC TGGTGTAAGG ATCAGGAACA AAGTGAATGA AATACATTTT    12840
AATACATTTC TGCTTTCTCT AATTCCAAAG ACCACTCTAA AGAATAAGTT ATTTGTGGGT    12900
ATTATCTGAA ACTTGGGATT AAAAGAGACC GTGATTACCC TTCAGGGATT TTGGCAAAAC    12960
TTAAGCCATT TCATCTGAAG AGCAAAGCAA GCCTCCCACA CTCTTGGCTT ATTCTCACAA    13020
```

FIG. 6.5

```
TTATCTAGAT ATCTAGCAAC AAAACTCTTG AGTAGTTTGT TAACTACAGA TGCCAAGGGC    13080
TGACAGTTTC ACTTTCAGTT TTCAGAATAT CTTTTGTTTC AGTGGTGTAA GCACACCATC    13140
AGAATCTCTA CTATTTAAAA TAATTAAGTT ATAATTGTAA CTTCCATTAG ATGTAGTACT    13200
TAAAGGAATC TAGAAGACAC AACTCATTAA TTATAGGAAT TTGACTGCAA ATTCTTCTGG    13260
GGGGTCTGAA TTGCAAAGGA GGCATCTTTG TAAGTCAGAC TCAACTCATT ACTCTGTGAT    13320
GCAGGCTCCT CCAAATGGCA GCAGAAACGT ATTACTCTCT AGAAACACTA CAGTAGTGCT    13380
ACAATTTCAG GGTTCTGTAG AGATAAGGAC AAATTGACAG AAACACATTC TTAGAAGGAC    13440
AGTATCATTT AAAATAAAAA TACTGTCATA ATTGTACACC AGGATAGCTT CTCCATAATA    13500
AATTCTTTAT GATTTTCTGA TTTTTAGAAA TCAGAATTGA ACTTTTTAAT GTGAAAAAAA    13560
TGAGAGAATT GTTTCAAAAT AGGACCACAT TTCTGTGTAT AATTTTAAAA GTTTAAAAAT    13620
ATTTGATTAG TAGACTGATA AACTGAAACA TTTTTGATAA GCTTTCATT ACATACAAAC     13680
CATATAATTT GTAAAAAATT GGAAATTATT CAAAACTTCA CATAACTAAA GTGACCAAAT    13740
AAATACTGGA GAGGAAAGAA AAGGAGTCAA ATGAATCTAG CATTTTCTTT TTTTTTTTT     13800
TTTTGGAGAA AGGGTCTCAC TGTGCCACCC AGGTGGGAGT GCAATGGCAC GATCATGGCT    13860
CACTGCAGCC TCAACTTTAT GGGCTTAGGT GATCCTCCCA CCTCGGCCTC CCAAGTAGCA    13920
GGGACTACAG GCATGCGCCA ACACGTCCAG CTAATTTTTT TGGTATTTTT TGCAGAGACG    13980
AGGTTTCACC AGGTTGCCGT GGCTGATCTG GAACTCCTGG TCTCAAGTGA TCTACCCAAC    14040
TCAGCCTCCC AAAGTGCTGG GATTACAGGC GTGAGCCACC GCACCCGGCC TAATCTAGCA    14100
TTTTCTAAAA GGAAGGACCC AGCAGTGAAC GGCAATATCA ATAATCATGT TCAAGACTAT    14160
CAGACATGCA AGCTGGGGAT GAATGGGTGG AAGGGGAAAA TGATGAATAA ATGATGAACA    14220
CAAGTATAGA CCCAGTGGAT TTGAGATGCC CAAGATGCCA GTGAGATATT CAAAGTTTAA    14280
CTCAAAAGCC ACTTCCCATA TGAAATCCTG ACAAACACTC CTACGTCCAA CTGGAATTAA    14340
TTTCTCTTCT GGGCTCCCAC AGCACTCTGT ATTTTTCTAA TAGCATAACA CTATTTTGTT    14400
TGTAGATATT TCTCTGATAG CATTACTATC TTTCCTCTTT ATCACAACTG TTTGAAGTTC    14460
TTTTGCCTCT TGCATCCACT GTTGCCCAAT CCCACTGCTG GAAGGCTCAT CTTATTAAGT    14520
TCTGTATTCC TAGTGCTAAC ACACTGTCTA CCATAGATGA TGTTCAATAA ATGGTTGCTA    14580
AATGAATTCT CTTGTGATAA TAGCACTATG GCAACATAAT CGACGGTAAA AATTTCTTCT    14640
CAATGTTTAC TTTTAGCAGA ATGCATTCAT TTATCAACTT TCATTGAGAA TATGCTAATT    14700
TCCATGACCC TGCTAGGAAA TAGGAAAATA AAGATGAATG TAATAAGGTG CTCATTCTAC    14760
TGAAAGTCTT GACTAGTGGA GAATTATGGA TCCAACTTTT CATGAAATGC CTTCAGTGGT    14820
AAGAATTCTC ATATTTGGAA TAAAAAATGT TATGGGTTGT GCCAAGATAC CTACATACTT    14880
CATAATTTTG TAGAGGGCTG TCCTTACTGC AGAAATGTAT ACTACTATAG TCATATGTGG    14940
AAATTCTTTT TATGATGCTA ACTGCATGCT AACCAGACTT TTTAATTTAA TACTTGCATT    15000
AAATAAACCA TGCTAGGAAT CCAGGAATCT AGCTTGGTTT ATTTTCCATA CAATGTACTC    15060
TTTGTAATAT GCATATACTA CATAAAAATT CTATTAATGG CCTCGTACTA AAGATGTGTC    15120
TGTTGGGGAA TCAGTTATTC TGTATAATTT TATCTTAATT GATATATTAA AATCTACCAA    15180
AAATATAAAC TCCGAGTAAA AGTATCTGCA TGGTGTGCAT ATGTTTATTA TTTTAAGTGT    15240
CAGCGTATAC ATTTTCATGC CATAAAGTTA TAAAATGAAA AATAGTAGC CTTTTATATT     15300
AAGTTCATGC TTATGTAGTT AGTAAAAACA AGAAAGCAAT TAACATACAA ACCATGATGG    15360
TGGTTAAACT TGCTTCAGTT TGTGTTTTTT AAAATTTGAA AGTGAGAAAT ACAGCTCGAA    15420
GTCAGCTCAT ATTTTCAGTA AGTACTGATG AGGATGTACT GGCCCTATTG ACTACGCTGA    15480
CCCCATTAAA ATATTTGTGA GTCTAAAGGT TCATATGACG CTGTTCCTTC ACTCTAGCAA    15540
CAGGCCATAC ATGTCTTACA TAGGGACTCT GTTCAATTCA TTAATACCTC CTGAAGTGCT    15600
CAACATCGTG GTTCATTTAT AGTAGATACT CAATACATAC TCCATTAACT GAATTCTAAG    15660
```

FIG. 6.6

```
ATAAACTGTC TGTTACTGAC AGAAATTTTC ACTTAAGGGA GTCTCCGTGG CTGAAGGCAA   15720
TTTTGAAATC CTGTAAAAGA ACCCACTCCT CTCCCCAAGT AATGAAGTTT GTCAGTTTCA   15780
AGCCTGTAAT AAGGTACTGA CTTAAAATTA ATTTTCTAAT AATACAGTAC TGCTATGTAT   15840
CTAATGTGGG GTTAGTCAAT GATAGGAAAA AAACATAAGA CAGAGTCACA TTTAAAAATG   15900
TGTGCTTAGG TGCATGGTGA CACCTGCCTG TAGTCCAGCT ATTCCAGGGG CTGAGGCAGG   15960
AAGATCCCTT GAGCTCACGA GTTTGAGGCT GCAGTAAGCC ACTGCACTCA GCCTGGGCAA   16020
CAGAGTGAGA CCCTGTCTCT AAAAAAAATT CGTTTTAAGT GTGCTCAGGA CATAACAGGA   16080
GCCGCTGGTA ACATGCCATT TCCACTGTGA ATATGGTAAG GACAGAATCC CTGTCTCTAG   16140
GCCCTCTTCC ACTAGTCAAT CTCATCATCA CCATCAAGGC CAACATTGGT ATTCTCTCCT   16200
CTGAGACAAA GTCTTTGACA TTTTCTATAC TATACTATGT CTTCCTCTCC CAAATGCAT    16260
ATACAAATAA AATTTGAATG CTTCTTTCTC CATTTAGTGT AATTTTTTTT ATAACATAGA   16320
CCCAATTTTC AAACCCCACA ATGGTGGATT TTATTTGATG TATTGTAAAA AGCGCTGGAT   16380
TGAAGTCAAA TGGCTTGGGA GACCTAAATT CTACTCCTGC CTGTACCATG AAAGAGACAA   16440
ATCCCAAGGC TTTGCAGGGC TTCAGCTTCC TTGTTTGTAG AATAAAGAAT TATAAAATCA   16500
TCTCTTTTGG TCCTACTGGG CAATAAAAAG CTATGATTCT AAGCCTGTTC CCTTTCTCA    16560
CCTAAGAATA CAAATTTGAT ACAAAGAGGC CGCAGAATGT GTCAAACACT CCCTGTTGCC   16620
TGGAATTCTC TCTTCCTTTG GGTTCAGGGA TAAAGGTATG TTATTTCTTA AGTCTCCCTT   16680
TGCTTTCTTC TGCTTGCCTC GTAAATATTT TTCCATCTTG GCAGTCCTAC ATGTCTTCTC   16740
ACTCTACATG TTTTCCCTAG GTGATGTGAC CCAGCCTGTG GCTTCCACTG CCATCCACAC   16800
ACGTCGCTGC CTCTCTCCAC ATCAGCATCG CAACTATCTC CTGGAAGCTT TCCAAGTGCT   16860
GAACTACAGT AACCTCAACC GAACTGCTGT TCATTCACCC CACAGGCTTG CCCCTCCTCT   16920
GCATCTTTGT GAGAACCTGA GAGTCATCCT AAACTCCTCC TTCCACCTCA CTCCCCACAT   16980
CAAATCGATT ACCAACTTGT GCTGATTTTA TCTTCAAATA CTCTCCAGAA TTGTCGCTGT   17040
CATGGACTGA ATATTTGTGT TCCCCCAAAT TCATATGTCC TAATCCCTGA TGTGACTGTA   17100
TTTAGAGACG TGACCTCTAA GGAGTAATTA AGGTTCAGTG AGGTCAAAGG TGGAGCCCTG   17160
ATCTGATAGG ATCAGTGTCC TTATAAGAAG AGACTAGAGC TGGGCACAGG GGCTCACACC   17220
TGTAATCCCA GTATTTTGGG AGGCTGAGGT GGGAAGATCA CTCAAGGAGA GGAGTCTGAG   17280
ACCAGCCTGG GCAACAGAGT GAGACTCCAT CTCTACAAGA AAATAAAATA GTCAGACACA   17340
GTGGTACACA CCTGTGGTCC CAGCTCCTCA GGAGGCTGAG GCAGGAGGAT GGCTTGAGCC   17400
CAGGAATTTG AGGCTGCAGC AAGCTATGAT CACACCTCTG CACTCCAGCC TGGGTGACAG   17460
CATGAGACCC AGTCTCTTTA AAAAAAAAAA AAAAAAAGGC CATATATAGC CCAGAAGAGC   17520
GTCCTCACCA AAACCCAATC CTGATAGCAC CTGGAGGACT TCCAGCCTCC AGAGCTGTGA   17580
GAAAATTTCT GTTGCTTGCA CCGCCCAGTC TGTGGTATTT TGCTGTGGCA GCCCAAGCTG   17640
ACTCATCAGT GACCTTCTCT CTGTTACCGC AGAGTAGCTC ATCATCCTCT CTTCCCTAGA   17700
GTCCAGCCAC TCTCTCACAT CTACCTACCT AGCAGTATCA CTGTGGGTTA GAGTCAGATC   17760
ACTGCGGATT AAGTCCTCAT TCTGCCACTG CCTGTGTAAA TCTGAGCAAG TTACTTAATC   17820
TCTCTGTGTG TCAGTAACCT CCCTGTGAAA TGAGGCTAAT AATAGCAGGG TTGTTTCAAC   17880
AAGGCGATAC ATGCATAATG CTTACAACAC AGCTTGGCAC ATTATAAGCA TTCAACGAAA   17940
AGTGAGCTAC TATTATCTCA TCCGTTATCA GAATAAACCA CCTAAGCCAC AAGGCTGCCC   18000
ACATCATCCT CATGTTTTAA AACACTTCAG TGGGCTCCCC ACCATCAACA GGATAAAGTC   18060
CAAGCTTCCT TAGCATTTCT TAGAGGCTCC ATATGAATCC CCAAGTTCCA CTACAGGAAC   18120
ACAGGTGAAC TTTCCACTCC AACCTCAGGC TCCTTCGTGT CACTCCTCAT CCACATGGAG   18180
GTAAGCAGCA AGAGACTCCG TGCAGTTCCT GGTGGTTCCC TGACCCTCAG GCAGACTCTC   18240
CCCAGCCCTC TGCCTGCAAC GTCCTTGCCC TTTGCTTCCC TTGGCCAGCT CCCATTCATT   18300
```

FIG. 6.7

```
CTCCTTGATT CTGCTTGGAA GTTTCCCTCT CAGGAAGGCT TTATGAACCT TAGTGTAGGT   18360
TATGAACCCA TCTTTGCTCC TTTCATACCT TTTGCAAGCC TTTATTTATT ATGACACTTA   18420
ACCATTATCA TACTGAAGTG ACCTGTTGGT GTGTCTTTGT TCCCCACTAG ACAGAAAACT   18480
CAAGATCAGA GACCAGTTCT TGTTCTTTTT TTTTTTTTTT TTTTTTTTTT TTGTATCACA   18540
GTGTTTAGCA GCCTGCTATA TGGTAAATGT CAGTAAATGT TCCACAAACT GAATGGAATT   18600
GAGCTCTGGA ATCTAGACCA TCTTTTCCAT ACCCATCACT CCTGTCTTAG TTGAAGTCCT   18660
TATTTCCCAT TTGAAGCAAT GCAAAGGATT TCCTAACTCT AATCTCTCTT TTCTTCACAC   18720
CATCCTTTAA ACAGCCGACA GAATGGTCAT CCTAAAGCAC ATATATCCTA TCTTACATAT   18780
CCTAGATTCG GAACCTCTCT GGGCTTCTCA CCATATAAGA AGAAAGTCTA ACCTCCTTAG   18840
CAAGGTGCAT AGGTCTTCAA TGGGCTCCAC CTCACTTCTC TATATATACC TATACTCTTG   18900
CTACACTAAA CTTCTTTCTT ACTGTTGCTG GAACAAGTTC AACGCTTTCA AACCTCCCTG   18960
ACTTTGCATA TGCAGTTCAT TCTGTCAGGA ATGCCCTTCT CTCTTATGCC TGGGATATTC   19020
TCATTCATTC CATATGACCT ATTTCATAAG TCACTCCTTA ATGAAGCCTT TCTTAGATAT   19080
CCACTGGGGC AATCAGCTGC TTGCTCCTGT TTCCACAGCA CATTGTTCAC ACAGATAGCA   19140
CAGGACTTAC CACAAGTTAT TATAATTTTG TCTGTCTTGC CCATTTGAAT CCAAGGGCAA   19200
GGACGGAATC ATTCTCATCT TTGTATGTCC TGGGAACTAG AACTGTACCT GAGACATAAT   19260
AAACACTTGA TATGTTTGTA ATTTTTAAAT AAGTTAATGA ACGGAATGGC TAGAAAAGT    19320
GAGAAGAAAC TCTGGCTTAC TGTATATCAT ACTGTCATAC TAAAAATATA TACTGAAGAC   19380
AGAATCACAT TATATCATCA CTTTTCACGC TATAGGCCAT GATCCATTAT GAAAAGAGG    19440
ATAGTAAAAA AATCACAGGG CACAATTTTT GTTTCTGTCA CACACATGTG TACCTGTATA   19500
TTGGACTGGA ATGTAAAACG CATGTTCCAT TGTAGAACGT GGTTTTAAAA GAGGCTTGGA   19560
AAACACTGCA TATGGTCATT TCTTAGTTTA GTACAATTTA TTATTTTCGT AATAACCTCA   19620
GCTATAATAT AAGTCTACCA TGAAGCATTT TGGGGAGATT AAATGAGATG TGAAAAGTAA   19680
ATGTGTTAGA TAGACTGAAT TCATATCATA GCTTGCTCTG ATACTTTACA AACATTTAA    19740
CCTTACCCAC AAGTTTTAGT TTCCTCACTA AAGTCACCCT GAGGACAGTA ATGGGATCTT   19800
CCTCACAGAG TATTGTGAGG AATACATAAG AGAACGTACG TAAATGCCTG GCACTTAGTA   19860
TTTATTCAAT AAATCTTAGC AATGATGATG ATAACAACAT GGTACCTGGC ACATAAGAGA   19920
GTTAAAAATT AGTTTCTTCA GTCAAATGTG CTTACATTGA TAGTTGATAC TAACTGGGGT   19980
TAAAAGGTCA TTGCTGGCAT CTCAGAAAGA TAGATTACAG TGAAATAAAA AATGACTACT   20040
GCTTAAAATG AATGAAGACT TATTTACAAA GTCATGTTCA TCTGGTACAA TAATGAAGTC   20100
GCTCAATTGG GAGAAAATGA CAAATAATAC AAGTGAATAT ACAATCTTAC TTAAGACGAA   20160
AGAAATAGGA CACCAGGCTA ACTATCAGTC TCCTAAACCA CAACTTTATT TCTGATACAA   20220
AGAGACAGTG AGACAATCAG GGCTTCCCTC AAATAAATTA CTTAATCTCT CTTCAATTCA   20280
GTTTTGCATC TGTAAATATA AATAACTACA ATTTCACAGT ATTTCCATTT AAAAAGTTCT   20340
AGTGCAACAT CAGAAACAAG AACTTAGTAG GTGTTCAAAA AGAAATATAA GTTCTGCTTT   20400
GTTAGCCAGC AAATAGTTGC CTGTTTCTAG CCCTCACTTC TTTTCTCCTA AATCCCTATA   20460
TTGCATTTAT TTAACTTAAA GTGCTGGATG TGGCACTACG AGAAAGAAAA AGATATTTGG   20520
TAATCTTGTT AAAATCATTA GACATCCCAG GCTATCTGGA ATCACCTTGG GCTCACAGTT   20580
AGACATCAGC TATGGCTTGT TTTATTTAAA AATTCATCCA CTGATGCATG ATAATGGAAT   20640
TCACAGGAGA GCAATTTACC AAAAAAAAGA AATTTATTGA TTTATAATGT GAGATATTAA   20700
TTTAGCCACA AATATTTATT GAGCATCTCC TACATGCCAG GGAATGGACT ATATATGGCA   20760
GGAAAACAGA TACCAATCAT TTATATCAGG CATTTTTTTC TAATAGAAGG ATATTCGCAG   20820
GAGACAATGC ATAGCACCAT GCCTTGCACG TAACAGACAT TTAATAACTA TTAGTTGAAT   20880
AAAATTGGAG ACTAGAATGA TACATAAAGA GGCAAGAAAG AGCAAAGATA AGCCTTTCTG   20940
```

FIG. 6.8

```
AGAATTTCTA TCATGTTTTG CTCAATAGCT TGTCTTTATC CACTGCTTGT ATTTTTCCAT   21000
GTAGCTAATC CTCATTGGTC GTTAGAATTG AGACACCCTT TCCTTGAAAT CAGGAGCTAT   21060
AGGAGGCCAT TCTTCCTACT GGGCATTTTC TTTCTGGGAC AGGGTCTCAC TCTGTCACCT   21120
AGGCTGGAGT GCATCATAGC TCACTATAAC CTTGAAGTCC TGGGCTCAAG GAATCCTCTT   21180
GCCAAAGAGG TGGGATTACA GGCATGAGTC ACCATGCCAG CCTATTTGGC ATTTCTACTG   21240
TAGACAAAGC AGACTTACAG CAGTAGGTCT ACCTGCCTAA TACAAAAAGA AAAAAAAGAA   21300
TTTTAACAAA CAAATGAGGG AATCAGATCC AGAAAGTGAT TCTTATAACT TAGATTACTT   21360
AGAGTAGATC TATAATCTGC TCTAGATCCA CTGCATACAG TGGGCCCTTC TTATCATATT   21420
CCATAAATAG CACTTTTCTC AGCCCAGCTT TTGATGATAG CTGAACAGAC TAACAGTTTG   21480
TCTAACAAAG GCTAGAGAAG GGGATAGCAA ATAATGGCCC ACAGGCTGAA TCCTGCCTGC   21540
TGCTCATTTT TGCAAAGTTT TATTAGAATA CGGTCATTTC CACTCATTTT CACACTGTCA   21600
ATGGCTGCTT TTGCGCTACA GCAGCAGAGC TGGGTGGTTG GGGCAGGGGT CACATGGCTA   21660
ACAAAGACTA AAATACTTAT CATCTGACCT TTTACAGAAA GTTTGCTGAT CCTTGGAGTG   21720
TACAAGTATT CTATATTGTT GATTAAGAAC AGAACCACAA GTATTAGAAG TTAGACCAGC   21780
AGGTGGTAAA GCTGATCATC TACTAATATA ATGGAAATTG GGGTTCCCAA TCAGGACTCT   21840
TGCTTTGATA GAAGGCCATC TTAACGAGGA GGGAGACACC TGCAGGCAAA GTCAGAATTT   21900
TCTGCAGGAA AAGTTTTGAG TCCATTTCCC CTTGTGAACA AGTGCTCAGC TATGCATTTC   21960
ATCTTTAGTA ACCATGCTTC TATACCTGGT TCTCCTTGGC AAAGATTTCT TTCTTCAGTA   22020
AGTCTCAAGA CTTTCTGGGA AGGTAGGGAG ATATGGGGGT AAAAGTGTCC CAGGACTTAC   22080
TGAAGGAAGT GTTTTATGAT TATCTGATAG AATCACTGTA TCATGGTAGA GAAGGCAAAC   22140
AGAATATAAT CTGAAAATAG AGGTGAGGGT GAACAAATGG GCACTAAAAG TGAACTCAGC   22200
ATCAGGAAGG TAGCAAAACA AGACATCAGT CAAAGATATG GGGTGATTCA GACCTAAGGA   22260
AGATTTAATG TGGGATGTTT CCGTGTGCCA GGAGCTGGAC ACTTAAGCAA GAGGAGATCC   22320
AGGAATGTTG CTAAAACCAT GGCCTCCATA CTTTATTGGA ATTAGCACAA CTTATCCTTG   22380
TTTCTTTCAT TTTGCAATCA AAATCTTTAA AAACACATTA TTTAAAAATA CATTATTTTA   22440
AAAGCTAGAA TGAAAATTAT GATATCATTT AGGTGGTTTA AAAAACATCC ACCAGCCGGG   22500
CGTGGTGGCT CATGCCTGTA ATCCCAGCAC TTTGGGAGTC CGAGGCGGGC AGATCACGAG   22560
GTCAGGAGAT TGAGACCATC CTGGCTGACA CGGTGAAACC CCGTCTCCAC TAAAAATACA   22620
AAAAATTAAC CGGGCGTGGT GGCGGGTGCC TGTGGTCCCA GCTACTCGGG AGGCTGAGGC   22680
CGGAGAATGG CATGAACCCG GGAGGTGGAG GTTGCAGTGA GCTGAGATCG TGCCACTGCA   22740
CTCCAGCCTG GGTGACAGAG CAAGACTCCA TCTAAAAAAA AAAAACAAAA ACCATCCACC   22800
AAAATGGGAA GAAGTGATGA AAAATTACAG TCCAAGAAGA AGGGCCATAG CTGTTTAAAT   22860
CAATTGGTAT ATTTGTTATC TAATATAACC CCACGTAACG ACAGGTATTT AACAAATGTT   22920
TCTGCTGAAT TTGACGATTC CATTTCCCTT ACATCCCATA TGCAATCCAT CAGCACCCCA   22980
CATCCAACCC ATCAGTACAT CCTGTCAGCA TTGGCTCCCA AATATAACCT AAATCTAACA   23040
CATATCCTAC TATCTCTGCT GCTACAACTT TAGTCTGAAA TCTCATAATC TCCCACTTGT   23100
ACTACTGTAG ATGACTCTGA ATGAGTCTTC TTGCTTCCAT TCCACACAGC ATCCATACTG   23160
ATCTATTTTT TTTTTCAATT TTTTGTAGAG ACGGGGTCTT GCCATGTTGC CCAGGCTGGT   23220
CTTGAACTCC TGGCTTCAAG GGATCCTCCC ACCTCAACCT CCCAAAGTGA TAGGATTTCA   23280
AGTATGAGCC ACTGTGCCTA ACCCTGACTG ATCTTTCTAA GCATAAATCT AATAATGCCC   23340
CTTCCTTGAT TAAACCCTTC AATGAATTCA CATTAAGCAA ACAACCTGGC CAGGTGTGAT   23400
GGTTCATGCC TGTAATCTCA GCACTTTGGG AGACCAAGAT GGGAGGATCA CTTGAGGCCA   23460
GGAGCTCAAC ATCAGCTTAG ACAACATGGT GAAACTACAT CTCTACAAAA AATACAAGAA   23520
TTAGCTGGGC ATGGTGGTGC ACCTATAGTC CCAGCTACTC GGGCGGCTGA GCTGGGAGGA   23580
```

FIG. 6.9

TCACTTGAGC CCTGGAGGTC AAGGCAGCAG TGAGCTGTGA TTATGCCACT ACACTTCAGC  23640
CTGGATGAAG TGAGACCTGG TCTCCAAAAA AAAAAAAAAA AAAAAAAAGA AGCAGGGCAA  23700
GGTGGCTCAC ACCTGTAATC CCATCACTTT GGGAGGCCAA GGCAGGCCTC CTGGATCATG  23760
AGGTCAAGAG ATCGAGACCA TCCTGGCCAA CATGGTGAAA CCCCATCTCT ACTAAAAATA  23820
CAAAAATTAG CTGGGCATGG TGGCATGCAC CTGTAGTCTC AGGTACTTGG GAGGCTGAGG  23880
CAGGAGAATT GCTTGAACCC GGGAGGCGAA GGTTGCAGTG AGCCAAGATT GCCTGGTGAC  23940
AGAGCGAGCG AGACTCTGTC TCAAAAAAAA AAAAAAAAAG AAAGAAAGAA AGAAAGAAAG  24000
AAAGAAGAAA TCCTTAGTCC TGTCTTAACT ACTTGAGAGG CTGAGGGAGG AGGATCACTT  24060
GAACCTAGGA ATTTGAGGCT CCAGTGAGCT ATGACAGCAC CACGGTGCTC TGGTCTGGAG  24120
AGAGTGAGAC CTTGTCTCTA AAGAAGAGAA AAGAAAAGAA TGAATGAATG AACAAAAAGA  24180
AAGAAGGAAA GGAAAAGAAG AGAGAGAGAG AGAGAGGAAG AAAGGAAGGA AGGAAACAAA  24240
ATAAAATAAA ATAATAAATA AATAAACCCA AATCCAACTT CTTTACCCTA ATCAACAAGG  24300
CTCAAATAAT CTCATGCCAA CTAAGTCTCT GAACAGCTCC TTCCATTCTA TTGCCAGATT  24360
ACTCCATCTT TCAGCCACAA GACCTTTTTA TCTTCCTTTT ACCAGCCAAA CACAATCCTA  24420
CCTCAGAACA TGTGCACTTT TTCTTTTCTC TGACTTGAAT CTCCTCCACC CATTATATAA  24480
TCTTAGCTCA AAGAGGCTTT TCTTGACAAC TTAGCGAAAG TATTTATCCC AGTCATTCTC  24540
TGCTACATTA TTCCAATTTA TTTTCTCCAT AGTACATTTC AGCACATAAA GATTTCCTTA  24600
GTATGTGCTT GTTGCCTTTC CCCAACCTCC TAAAATGTCA GCATTCCTTG AGGGCAGAGA  24660
CTGTTTCATT CCTGTATCAT CAGCACCTAA GACAGTTCCT GGAACATACC AAGTACTTAA  24720
TAAAAATTTG TTTATTGACT AGCTATGACA CATTTTACTT ATATAATTTC ATTTTCTCAG  24780
CAAAATGAAC ACTTTGAAAT GTAATTAATT ACTGATTTTT GCAGTATTTT CTAATTATTT  24840
AAATAAAATA TTTACTATTT TGGTCAACCA GAATTCTTAC ATTGTTTTAG CACCCAGATA  24900
GCTTCTAAAA ATGCTTACAA TTAACACAAT TTTATCTAGC AATATGTATT TATCACTAGA  24960
CAGAATGCAC TGAACTCTTC TTCATTAATA AAAAGCAATC CAGGCTGGGT GCAGTGGTTC  25020
ACGCCTGTAA TCCTAGCATA GTGGAAGGCC GAGGAGGGAG GATCACTTGA TACCAGGAAT  25080
TCGAGACCAG CCTGGCCAAC ATGGCAAAAC CCCATCTCTA TAAAAAACAC AAAAATTAGC  25140
TGGGTATAAT AGCAGACATC TATAGTCCCA GCTACTCAGG AGGCTGAGAG GTGGGAGGAC  25200
TGCTTGACCC CAGGAGATTG AGGTTGCAGT GAGCCGTGAT TGTGTCACTG CACTCCAGCC  25260
TGGGCTACAG AATGATACCT CATCTAAAAA AAAAAAAAAA TTAGCCAGGC ATGGTGGCAT  25320
GCACCTGTAG TCCCAGCTAC TCAGGAGGCT AAGGTGGGAG GGTCACCTGA GCCTGGAAGG  25380
TAGAGACTGC AGTGAGCCCT GGGTAGCCCG CGCCACTGCA CTCCAGCCCT GAGTGACAGA  25440
GACCCAGTTT CAAAAAAACA CAAAAAACAG AAAACAAAAC AAACAAACAA AAAACCCAA  25500
TGCATTGCTG AAATGTTAAA TCCATTATAA AGAAAAGTAC AGGGGTGGGC ATGGTGGTTC  25560
ATGCTTGTAA TCCCAGCACT TTGGGAGGCC AAGGTGGGCA GATCACTTAA GGTCAGGAAT  25620
TCAAGAACAG CCTGGCTAAC ACAGTGAAAA ATGCAAAATA CAAAATAAGC CGGGAGTGGT  25680
GGCGCATGCC TGTAATCCCA GCTACTCGGG AGGCTGAGGG GGGAGAATCG CTTGAACCTG  25740
GGAGGTGGAG GTTGCAGTCA GCCAAGATCG AACTCCAGCC TGGGTAACAG AGACTCCATC  25800
TCAAAAAAAA AAAGTAAAAA GTATATAGTT GATTCTGCAG GGACTTAAAA AAGTATAAAT  25860
ATCTTTTTTA ACATCACAAA GCTCTGATAT CTGCAGGTTT ATGACTAACT ACTAGCTCAC  25920
TCCCATGAAT ACACGTATGT AAACAGGCTC TATACAATCT ACAATCCCAG ACTAAGGGGA  25980
AAAAACTGTC CTGTCACTGT GGTCTCCAAC CCTTGGCCCA TTTCTTTCCT CTTGACCACA  26040
AAACTTCTCA GGAGTTGCTT GTTTCCTCTT GATCCACTTA TCTTTAGCCC ACTCCAATCT  26100
GGCATCGGTT CTCAGTACTC TCCACTAAAA CTGCTTTTAT GAAGGCCATC AATGACGTTC  26160
ATGCTGCCAA ATCCAGCAGA CACCTCCTGT TTTCTAATTT TTTTTATTGT TATTTTTTAA  26220

FIG. 6.10

```
GAGACTGGGT CTTGCTCTGT CACCCAGGCT GGAATGCAGT GATGCCATCA TAGCTCACTG    26280
CAGCCTTAAC CTCCCTGAGT TCAAGAGATC CTTCTACCTC AGCTGGGACT ACAGGCATGC    26340
ACAGCTATGC CTGGCTAATT ACTCAATCTT AACATAGCT GATAATTCCC TCCTTGAAAC     26400
ACTCTCAACT TTTAAGAAAC CCTGTTATTT TCCTCCTACA TTTTTAGCCA GTTCTTCTAT    26460
CAGCTTCTCC TTATCTGACC TCTAAATGTT AAGAACATTA ACAAAGACTG AACCTAGTTT    26520
TTTTCTCCCC TTACTGTACT GCTCCTGGGC GATGTCAATC AGTCCCATTG CTTTAGATAC    26580
TATCTGTTGA AACACTGAAA TCACTGGTTT TTTTTGTTTT TTTTTTTTTT TTTTTTTTTT    26640
TTGAGATGGA GTTTCGCTCT GTTGCCCAGG CTGGAGTGCA GTGGTGCAAT CTCGGCTCAC    26700
TGCAAGTTCC ACCTCCTGGG CTCAAGCAAT TTTCCTGCCT CAGTCTCCCG AGTACTGGGA    26760
TTACAGGTGT GTGCCACCAT ACCCAGCTAA TTTTTCTATT TTAGTAGAGA TGGGGTTTCA    26820
CCATGTGTCC AGGCTGGTCT TAAACTCCTG ACCTCAGGTG ATCTGCCCAC CTTGGCCTCC    26880
CAAAGGTTGG GAAAAGATAT CCCAATCTTT TTCCTATGAT TTCTTAATTG ATCTACTTGA    26940
CATATCCACT TGGACTTTTA ATAGGCATCT CAAACTTAAT GTGTTCAAAA TAAACCTCGT    27000
GACTTTCCCT CCCAAACCTG TCCCTACCTC CCTCAATAAC TAATATTATC ATTCTTATAT    27060
TCATATATTG AATAAATGTT TGTTCCCCCA AGTATTTGTT GCTATAAATT TATGAAGAAT    27120
TCTTTTCTCA CTAGTTATTA TAATTAAAAT GTAATATTTA TTTTCTTTAA AAACTTTACT    27180
TTGTAGGATT ATTATTTTTT AAACAGGGAC CAACAATAAA TAACTTCTCT ACTTGATTAA    27240
AACTAGGGCT TCCTCTTGTG CTCCCTCAGG ACTATTTCTT TGTAAAAACA ATAGGCTAAA    27300
TCAGTACTGG TGTCAAAGAA ATCATAATCT CACAACTTTA TAAATACAGC ATGTGGCAAG    27360
GGATTTTCCC ATCTTATATA GTAATAAAAT TTTCAGCTGT GCCATGGCTA AAAGTTTACC    27420
ATCAAAGTTG GAATTTTAAA TTAGAGGTAG TCATCTTTCT TTCTTTTTAA AGAAATGGAG    27480
TCTCACTATG TTGCCCAGGC TGGAGTGCAG TGGCTATTTG CAGGCATGAC CACAGCACGC    27540
TACAGCATCC TGGCCTCAAG CAATTCTCCT GCCTCAGCTT GCCAAGTAGC TGGGACTACA    27600
GGTCCCTGCC ACCACACCCA GCAGAAATAT TTAGCTTTCT GAATTTCTCA AGTGTGTGTA    27660
TGAATGAGAC TAGTGGGGTC CTTAACCAAG ATTCACAGGA TTTTTAGTGA TTTATTAAAT    27720
AACTTGGATT TGTATCTACC AGCATGTTCT TTGAGGTACA GGTATGTCTT TTATATCTCC    27780
TAATATAGTT CATTACAATG CTAAATACTA AGATGTGATG CTCACACACT ACAGAATAGC    27840
CAAGCAAATG AACTACTTAT TCTCATAGGG CTATTATAAT TAACAAATTC TTGTATCACC    27900
CCATCATTAT CAACAACAAC ATGATAGGAT TTCCTTTTAT CTTGAAGAGT CTGGAAAAAG    27960
GGTAACAGAG AGATATTTCT GAGGAACAAA CTGGTAATGA GGGAGCTACT GTGTCCATTA    28020
CAATACTCCT TCTAGAAGCT CAATACATAA TGACTAATCT CTGGAAAAAA GCAAGTGTGA    28080
GAATGGAAGG CTCTTCTTCA AACTATGCAA AATGAATCAA TCAGCAGTGA ACAAATTTAT    28140
GAGCCAAACA AATTCCTACA AAAATTACCA TCATATGCTG TCATGCATGT CTGCCAGTCT    28200
ATTTATCATA TTATTTAAGA AACAAACATT TATTGAAGAT TTATCATGTG CTCAGCACTG    28260
CCAAAGAGGA AATAAAGAGC ATAATATCTA TTCTTAGAAA ATAACATTAA CACAAATAGA    28320
AAACAAGAAA CCATAATGTT AAAAATATTA CATAGTAACA CAGAAAGACA ATGTATAATT    28380
ATACATACGC ACTAAAGCAA AGATAACATA ATTTATAAAT TATGAGGTAC AGAATAGTTA    28440
GATTCTGAAA ATTAAAATAA TCAGGAAAAA CTTCATGAAG ATGAGATCTG GCTGGATCC    28500
CAAAGGATAG GCAGGTGGAT CATGTAGAAC AGGGGAAAGG AGTTCCTGAT CGGGGATACA    28560
ATATATGTAA AAACTCGGAG ACAGGACTGA GCGTGAAATG TTAATGGGAC AGTAAAGAAA    28620
TCTTCCTCTG CAGCGGGGGA AAAAACAGAA TAATGGGAAA CTGCATGGTT AAAAGGTTTG    28680
ATGTTAAGAT AGTGCTTGGA CACAAAAGAT CTTAAAGTTG AGTCAAAAGA GTACAATGAA    28740
AGCATTAGAA ATAGAAGATA AAACACAATT AGGCCGGGTG CAGCGGCTCA TGCCTGTAAT    28800
CCCAGCACTT TGGGAGGCCA AGGTGGGTAG ATCACTTGAG GTCAAGAGTT TGAGACCAGC    28860
```

FIG. 6.11

```
CTGGCCAACA TGGTGAAACC CCGTCTCTAC TAAAAATACA GAAATTAGCC GTGAATGATG   28920
GCTCGTGCCT GTAGTCCCAG CTATTTGGGA GGCTGAGGCA GGAGACTCGC TTGAATCTGG   28980
GAGGCGGAGG TTGCAGTGAG CCGACATCGC GCCACTGCAC TCCAGCCTGG GTGACAGAGC   29040
AAGCCTCTGT TTAAAAAAAA ACGGTAAAAA TAAATAACAT TTACTATTGT TTTCTGATGA   29100
TATATATGGC CTCTAATTGT AAAGCTGAAT GCCTAGTTTA CCACTTTTTT TTTTTTTTTG   29160
AGACGGAGTC TTGCTCTTGT TGCCCAGGCT GGAGGGCAAT GGCACGATCT TGGCTCACCA   29220
CAACCTCTGT CTCCCAGGTT TAAGCGATTC TCCAGCCTCA GCCTCCCGAG TAGCTGGGAT   29280
TACAGGCATG TGCCATCATG CTCAGCTAAT TTTGTATTTT TAGTAGAGAT GGGGTTTCTC   29340
CATGTTGGTC AGGCTGGTCT CAAACTCCCA ACCTCAGGTG ATCCACCCGC CTCAGCCTCC   29400
CAAAGGGCTG GGATTACAGG CGTGAACCAC CGCGCCCGGC CTATCATTCT TATTTTATGC   29460
ATTAGGAAAC TAAGGCTCAA CAAGATTAAA GCTGTCTAGG GTCACAAAGA TTGTAAGTGG   29520
AGGGGCTAGA ATTCAAAATG AGACCTGCTT GACTCCTAAG CCTGTACCAT TTCTACTATA   29580
TTTAGAGTGA AGTAGATGGG TTGAAGAAAT ATTTAGGAGG TGAAATTTCA AAAGTGTACA   29640
GTCAGAAGAG AAGACATATA TGGAAACCTA AATTTTCACA CAGTAAAGTG TCAATAATAA   29700
AGGCATAATG CCAAAATGAC AGAGGCTGTG CATGGTGGCT CATGCCTGTA ATCCCAGCAC   29760
TCTGGGAGGC TGAGGCAGGA AGATCACTTG AGCCCAGGAG TTTGACACCA ACCTGGCCAA   29820
CACAGCGAAA CCCCATCTCT ACTAAAAATA CAAAAAATTA GCTGGTAATG GTGGTACACA   29880
CCTGTAATCC CAGCTACTCA GGAGGCTGAG GCATTAGAGT CACTTGAACC TGGGAGGCAG   29940
AGGTTGCCAT GAGCCAAGAT TGTGCCACTG CACTCTAGCC TGGGCAACAG AGTGAGACTC   30000
TGTCTCAAAA AAAAAAAAAG GAAGACTCGA GGGCTAGAAC CCTGAAATTG GAATGAACA    30060
GGACTGGCTG AAAATGTTTC TTGCACCTGA TAAAAATCTT GAAGAAGAAT GCTTTAAATA   30120
GATAAGAAAG GAGAGAGAGA GGTGGGCAGT GAGAGGAGAC CACCCTAAGT AATCAGAGAT   30180
TACTTACGTT GGTTACTCAG GCTGGTCTCT GAATCTGATT ATAAATGAAA TAGAGATTAC   30240
TTAAAACAAA GGGCTGTAAG GTAGCACTGT CCAGCAGCAC TTTCTATGAT GGAAATCTTC   30300
TATATCTGCA CTGTCCAATA AGGTGTAGCT GCTAGCACAT GTGGCCACTG AGTACTTAGA   30360
ATATAGCTAC GACAACCGAG AGGCTGAATT TTAAATTTAA TTTAATGAAT TCAAACAAAT   30420
TTATTTTTAA TACAGCACTT TAAATTTTAT TTTTAAATTT TAATCTATTA TTTATTTAGA   30480
GACTGGGTTA TGAGACTGGC TAATTTTTGT ATTTTTGGTA GAGACGGCGT TTCACCATGT   30540
TGCCCAAGTT AGTCTCAAAC TCCCGGGCTC AAGTGATCCA CCTGCCTTGG CCTCCCCGCA   30600
AAGTGCTGAG AATACAGGTG TGAGTCACCA CGCCCGGCCT AAACTTAAAT TTAAATAGCC   30660
ACGTGCGGGT AGTGGCTACC ATACTGCACA TGCAACTGTA AGATGTAGAA GTCAGATGTG   30720
AGCAAAGAAA TGACAAGCCG TTCAATGCTG TTAGAGAATG AAATTCAAGG TTCCAATGAT   30780
CTGAACTTGT GTCCCCTCAA ATTCGTATGT TGAAATCTTA ATCCTCAATG CAACAGTATT   30840
AAGAATTTGG GGCTTTAGGA GGTAATTTGG TTTTGAGGGT GGAGCCCTCA TGAATAGGAT   30900
GAGCACCTGA GGTAGCCTCT TTGACCCTTC CACCATGTGA GGACACACCA CGAAGGCACC   30960
ATGTTGGAAG CAGAGAGTGA GCACTCCCAA GACACTGAAT CTGCCACATC TTGATTTTGG   31020
GCTTCTCAGC CTACAGAACT GTGAGCAATA AATATCTGCT GTTTATAAAT TATCCAGTGT   31080
AAAGTATTTT GTTATAGCAG CCTGAATAGA CTAAGACAAA GGTGGACTAA GCAGGATAA    31140
CAGGTTAGAA AAGGAGGCAG GGCCTTTTTT TTTTTTTTTT TTTTTTGAG ACAAAGCCTC    31200
ACTCTCACCC AGGCTGGAGT GCAATGGCAT GATCTTGGCT CACTGCAACC TCCACCTCCA   31260
GGGTTCAAGC AATTCTCCTG TCTCAGCCTC CCAAGTAGCT GGGATTACAG GTGTGCACCA   31320
TCACACCCAG CTAATCTTTT GTATTTTTAG TAGAGACGGG GTTTCACTAT GTTGGCCAGG   31380
CTAGTCTTGA ACTCTTGACC TTAAATGATC CACCCGCCTC GGCCTCCCAA AGTGCTGGGA   31440
TTACAGGTGT GAACCATCGC GCCTGGCCGA GGCACAGTGT TTTTACAGAG AAGCCTGTTT   31500
```

FIG. 6.12

```
AAGGTTTAAT CATATAAAAT GTATGATATC CAGTAAGTTT TGATATAAAA AAGAAACACC    31560
TGGCGATTTT ATATAATATA TTGTGCTAAG GAATTTTAAG CACTCTACAT TCTGCTCTCT    31620
AAGCTCTGTA AAGAGCACCA GGGATTTTTT TTTTTTTTTT CTTTTTGAAC AGGGTCTTGC    31680
TCTGTCAGCC AGGCTGGAGT GCAGTGGCAC AATCTTGGCT CACTGCAACC TCTGCCTCTC    31740
GGGCTCAGCG ATTCTCCCAC CTCAGCCTCC TGAGTGGTTG GGACCACAGG CGCATGCCAC    31800
TACATCTGGC TAATTTTTTG TAGAGATGGG GTTTTGCCAT GTTGCCCAGG CTGGTCTTTA    31860
ACTCCTGGGC TCAAGCGATC CTCCCACCTT GGCCTACCAC GCATGCCTGG CCACAACAGG    31920
GATTTTTAAA TGTAAGACTA CCTAGTCAAC TCTTATTCTA TATTAACAAT ATAGACAAGA    31980
AATAACCTCT AAGTAATCTC TATTTCATTT ATAATCAGAT TCAGAGGTTC TCTTATGCTT    32040
TACAATATTG TCCTACTGTG GGTAGCGCAA TAACTAAGGT AATCTGAAAG ACCAGTTATA    32100
TTATATACTA TAGTTAAATG CATTTCAACT GCATGGGAGA AAGCAACTGT GTTCTTTCCT    32160
CTCAATTTTA ACAGAAGGAA AATTGTCAAA ATTAGCTTAT TTAGAATGTC CTATCAGAGA    32220
ATTATTTTGA TTAAAATATA TTTTTAATCA ATAAAATATT TCTCTTTGGT CAATACTTGT    32280
CAATATAGAA TAATATCTAG CCACAAAATT AAAAAAAAAA CATTTTCCCC TATATTACAT    32340
TCATGGATCT TCTTGAATTT CTGTTATCTA GGTGCTTTTA AAAGTCATAT TTCTGATAAT    32400
ATGAAATCAC AGCTCCTTTT CTTTGGCATA TTTAGTTACT GTATTAAGAA AATGTACAAC    32460
ACATAATTTA GAATGGGTAA TTATTATATT CTCTTTATTC TTATATTGAA AATGACATGA    32520
AAATTACCAG TCTTCCCAGG TAATATAATT TAAGTTAAAG AACATCTACA TACTACAACC    32580
AATACCCATT CCCCTATGTT ATGTTTGGAA AAACATAGAA GTATCTTTAG TAGTACTCTT    32640
AGAAATTATC CCAGGTTCAG CATATTGGTA TTTTATTTCC AGGTTTAAGT TACAGTATTT    32700
TGGGCACCCC AAGTTTAATA AACTATTCCC TGCAGAAACC TGACAAGTGA AGTTGTGGCT    32760
GGGAATATGT TAGTCTTCAG ATAAAATGAA TTGTTTAAGA ATTTGCTAAA GATCTCAAAG    32820
CATCTTTCTT AAATCTAAAG AAAGTCAGGA ACAAAGCCAC AACCAGGACC ATAGCATCAG    32880
AAGATGGAAA GTTGCTTTGT CTTCAAACTT AAAAAACATT TTCCATTTTA AAATAATTTT    32940
ACTATTTACC TGTGATACTG TTGAAAATTA TGAAAAAACA GATAATTTAA AATTTAGTGC    33000
TTTTTTTTAA AAAAAAAAAA AAAGCGAATC CCTGGGACAC TTCATATAGT GCAAAACAAC    33060
AATTCAAGAA TTCAAGCATT GAAAGAAATA ATCTCTTATC CCCCAGTCTC TGAAAGGGAT    33120
TGCCTTTACT ACTGTTCCCA TCTTTATGTC CATATGTACC TAAGGCTTAT CTCCCACTTA    33180
CAAGTGAGAA ACTATTCAGT ATGGCTTAGT CATTTTTAAT GCAAGAGAAT AGGTAAAAAT    33240
GCCAAGCACC AGCCAGAGTT TTTTCTTTGC AGATAGATGT GACTCTTACA GGAGCAGCAG    33300
GGATTTCCCA CTTTGGGCGG AAAGCAGCAT TTAGGTATTC CCCCTCCAGT GCAGTTACAG    33360
ACCACCCCCC CGTAGAAGCT GCTCCTGTCC TCTGTGGCAT GTCAGCCTCT GATTATCTTT    33420
TAATAAACAA TATGGCATAT TAAGTCTCTT TTATGCCCTT CTTTGTATTC CCAGGTACCA    33480
CCTCCATGTC AGGATAACAA GAATTTGGTA ATGTTTGTTG AATAAATTTA GCAGAAGTTG    33540
AAAGAAAAAT CCTGTTTCTA CAGAAAGATA CCACTGGCTT TTGGGGAGCC CGAGTTCATG    33600
ATGAAACTAA AGAAAGCCAC AAAAGTTCAC CTCAATGCCA AGACATTTCT TGATTTTTGA    33660
AAACCCAGTT GTCGAACCAC CCATCTATAG AAACTTGAAA GACTAAAAAC TATCTTACTC    33720
TAAACATTTT CTAGGAAGTT GATTCTACAA CACATTTGG TTTTCCAATT TGGCTTCTAA    33780
TAATTATTTC AAAGTTTCTG TGGCCTAAAT TTTGTTTTAC ATTGATCCTT TGAATGGACT    33840
ACTGTTTCCA CATTTTAGAA CATTTAAAAA GATATCTACA ACCCGAGTCT AATCATAAAA    33900
AAAATCAGAC AGATCCAAAA TGTGGAACAT TCCACTAAAA AAGGAGTGGG GAGAGGTCTT    33960
TATTCTTCCA AAAATATCAA TGCCATAAAA GACAAGACG GCTATGGAAA TGTTACAGAT    34020
TGAAGGAGAC TAAAGTTAAA TGCAAGAAAG GAAAAAATGG CATATAGGAC AGTATTGAAT    34080
TGACTGACAA AACTGGATTA CAATAGTAGA GTATCAATGT TAAACTTGCT GAAGTTGCTA    34140
```

FIG. 6.13

```
ACTGTATTTC TTAGGAATTA TTCACCTAAG AATTTAGGCA CACAGATATG ATGTATGTAA   34200
GTTACCCTTA AATGGCTTAG AAAAAAATGT GTGTATATTC ATTTACATAC GTATCTACAC   34260
ACACGTGTAT TAGCGGAAGA GAGCAAGGCA CACATGTGCA TAAGTGATAA AGCAAATGAG   34320
ATGAAATCTT TATTTTTAAA TTTAATTTTG TAAGTTTCAG CTTTTTAAAA TTTTAGATTC   34380
CGGGGATACA CGTGCAGTTA TTACTTGGGT ATATTGTGTG AAGCTGAGGT TTGGACCTCT   34440
AATGTTCCTG TTGCCACAAC AGTGAACACA GTACCCAGCA CGCAGTTTTT CAGCCCTTGC   34500
CCCCTCCCTC CCGCTCTCCC TCCTTGCTTT TGGAGTTCCC AGTGTCTACT GTTCCCATCT   34560
TTATGTCCAT GTGTACCCAA GACTTATCTC CCACTTACAA GTGAGAGCAT GCAGTATTTA   34620
GTTTTCTTGT TCTGCGTTAG TTCCGTTAGG ATAATTGCCT CCAGTTACAT TCATGTCACT   34680
GCAAAGGATT TGATTTCATT CTTTTTAATG GCTGTGTAGT ATTCCATGTT GTATAGGTAA   34740
CACATTTTCT TTATCCACTC ATCAATTAAT GGGCACTTAC ATTGATTTCA TGTGTTTGCT   34800
ATTGTGAACG GTGCTGCAAT GAACATCTGA GCGCAGGTGT CTTTCTGGCA GAATGATTTA   34860
TTTTCCTGTG GTATATACC CAGTAATGGG ATTGCTAGCT CAGATAAGTA TTTCTATTTT   34920
TAGTTGCTCT CCACAGGGGT AGAACTAATT TGCATTCCCA CCAACGGCGT GTAAGTGTTC   34980
CCTTTTCTCC ACGGCCTCGC CAACATACGT TCTTTTCTGA TTTTTAATAG TAGCCATTTT   35040
GAACTGGTAA GAGATGGTGT CTCATTGTAG TTTGGCTTTG CATCCAAATG AGACAAAATC   35100
TTAATGACAG GTGAATCTAG GTAAAAGGCA TACAGACGTT CTTTGTGTTG TTTTTTTAAC   35160
TTACATTTGA AGTTATTTTC AAATGAAAAA TAAAAGCAAG CAAAAAAAGG TCATTCTTCA   35220
TCTAGTAAAC TCTTCAAAGA TTACCACCCC CTTCAACAGT TTTTCCTGGT TCTAGTGAGT   35280
CTTCTCCCAT TTGTTTAGAT CTTTGTTGAA ATGTAGTCTC AGATAAAAAA TTGTATTTTT   35340
ATTTCTTTTA CATATTTCAA ACAATCTAAA TTCTTTTTAA ATGAAACTCA TTAAAAATAC   35400
TGCATTTGTT TCTAAATAAA ATGGTAGAGG TAATTTGCAC CTTTCCAAAC AGAAGCAATA   35460
GGAGCAACCC AGATGTTCTA GCCACGATCC AAGTCAACCA CATTCAATCT AAGAAGTAAT   35520
TGAAGGCTGT AACGACTTCT GTAAGGCCTA CAAAAATGAG TTCAGACACA AGCTCTGCTC   35580
AGTAAAAATC TAGTGGCAGA TGATATATAC AATGATCTGA GAAAAAGGCA GAATCAACAA   35640
AGGTTGTATT TTTATCTATT GCTGCGTAGC ATATTTCCTT AACTTTAGTA GCTTGAAACA   35700
ATAAACATTT ATTATTTCAT AAAGTTTCTG TGGTCAGAAA TCCAGGAGCA GCTTAACTGG   35760
GTGGATCTGG CTCAGCTGTA GACAAGATGT CGGCTGGGAC GGCCATCCTT TGAGGGCTCT   35820
GAGGGCTTTG AGGGCTGCAC GATCCAATTG CAAGGTGGCT CACTCACATA CTAGGCAAGT   35880
TACTGCTGGG TGCTGGGAGG AGACCTTAGT TTCTTATCAC ATGGACCTCT CCACAGGGCT   35940
GCTGGAATGT CCTCATGACC TTCCCCATAG TGAGTATTCC AAGACAGGAA AGTGGAAGCC   36000
ACAATGTCTT TCATGACCTA GCCTCAAAAG TGACATACTG TCATTTACAC AATATTCTAC   36060
TGGCTGTACA AGTTAATCCT ATTTAGTCTG GGAGGGGACT GCATAAGGGC ATGAGTAACA   36120
AGAGGCAAGA ATCCTTGGGG GCCATCTTGG AAGCTGGCTA CACAGAAGAG AAAACACCAG   36180
GGGAGTGCGA AGAAGGTGCA ATTAAACTCA ATTCCTTGGT ATGCCAATGG TAAGAAATAT   36240
TAGGTGATCT CTGGGGTGTA ACCTTTTTAA TTTAGTTCTT CACTGAATAA TCTGGCCAGT   36300
AATTGTAATA CAAAATACGG CACTCTGACA ATATTCTCTC CCTTTATAAT CAATTACACA   36360
CCAGAATATA TATAAAGAAA GACTTACAAA GTCACAAGTA ATTGTTTGGT ATTATTTTTA   36420
TAATCACATA CTAGGGCCCT ACAATTAGCA TTCACAAACA TCACTCCATG TTGGCCAGAT   36480
AAGTCTGTCT TTATAGTGGT TTACCATACG CGCCTTAGCA TGAAGTTACA TGTGGTTTCC   36540
TTAGCCATCA GATGCTCCAA ATGCAAAAAA TGTCTCACCA CAGTCACAGA ATCATGGAAT   36600
CCTAAAGTTA CCTGGGGTTT CTGAAAATCT CATGGGAACA ACTCACGAGA ATTAAGGCTT   36660
AAGAAAGTGA TTTATCAAAG AACAAAACCA GCAAGACTTG AGTTTAGAAC TCGCAGCAGA   36720
GTTGTGACTA GAACCTGTTG AAATAGGCAA TGTAGAAACC CAGACTAAGG CACATTCTCT   36780
```

FIG. 6.14

```
ACAACTTTAC TATGCAAGTA TGCTTAGATA CTCCTTAGCA AACAGCAGGC CTTGAGTAAA   36840
TTCTTTCAGA ACTGAATACA CAAAGGATAC AGAACGGAAT ACACTAACAA TAGTGCATGA   36900
TGTGCTCATT TCTGTAATAG AAATGAATTA ATTCTGATCC ATCTATAATT TATTATTGCT   36960
CCATGATTAA CGGAAGGCAT AGGAAAGATG ACTGGAATAG TGTAACTAGT ACAAACAAGT   37020
ATTACACTTG ACTGAACCTC ATTACACTGC AATTGCATAT TATATAGTAT GTAGGTGAAC   37080
AAATACTGGG TTAGTCAGTG GACCTACATT TGAATACTGG TTCTGCTCCT AGACAGCTGT   37140
ATGATTTGAA TGACTTCTTT ATACTTTCAT AGTTTCTCTG TTCTTCTCTG TAAAACAAAG   37200
GCTTAGAAGA TATTATGGGT TAGATTATGC CCCTTACAAA AGATGCTGAA GTCCTAAACT   37260
ACAATACCTG TGAATGTGAC TTTATTTGGA AATAGGGTCT TTGCAAGTGA TAAAGAAGAG   37320
GTCATGGAGT GACCTAATCC AATACGACCA GTGTCCTTAT AAAAAAAAGG AAATTTGGAT   37380
ACAGATACAC ACAAACAAGG AGAATATCAA ATGAACATGA AGGCAGAGAC CGGGGCGGTA   37440
CATCTACAAG CCAAGGGACA CCAAAGATTT TCAGCAAATC ACCAGAAGTT AGGAAGAGTC   37500
ATGGGACAGG TTCTCACAGT CCTCAGAAGA AACCCACCAT GTCAATACAT CATTTTGGAC   37560
TTCTAGTCTT CAGAACCGTA AGAAAATAAA TTTTTGTTGT TCAAGCTACC CAATTTGTGG   37620
TACTTTGTTA CAGCAGTCCT AGCAAACTAA TACAAATGAG CTCTTAACAC TGGTCTAAAA   37680
TAGGATAATC CTATGAAATG CTACAAATGT TTGGGAAGAT TTCTCATACT CAACTGTTTA   37740
CAGTATACCA CAAGCCTGTC AGTTGAAGAT ACAAACAGAC CCTCTATAAT CCTCTATACT   37800
TATATGCAAG GAACAGCACA CTTTTTCTGC AAAAGGTCAG ATAGTAAACA TTTTAGGCTT   37860
TGTGGGCCAA ACAAGGTTTC TGTTACATTT TTTTTTTATA ACTCCTTAAA AATGTAAAAA   37920
TCACCCTCAT CCCAACGGAC TACAGGAACA GACCTCAGGT CACATTTGAC TCATAGCCTG   37980
ACCCCTGGTG TGTAGGGTTA ACAAGCCTCC TTTCCCTGGG CTCCTTTTTC TTTCAGCATT   38040
CCAAGCCAAA GGAAACTATC TTTTTCAAAT CATTTTCTCT CCTAGGTGGG ACATCTTACA   38100
CCAGCCCAGG CATGCTTCCG ATAGCCTTAG AGTAGCTGTC CCTTCCTCAG AATTACTGTC   38160
TAATTGGCTA GAAGTTAGCA ACTTTTTACA TTTTTCCTTC AATTCCTTTC CATTAAGAAG   38220
AAGGCATGCA CCGGCAAATT ACTTGTGACT ATCAATGACA TACTCTCAGA AGCACCAGTA   38280
CCCCTGTGTT GTTTCTAAAC CCATTCTAAT AGACACATAC CCCAAGGTTA TGCTGTTTGT   38340
CATCTCACAA AATGACTTAC ATCTAGAGAT TTAAATAATT AATGTACTTT TCATAACTAC   38400
CAGGTACAGT AGATCTGATA ATGGCAGAGC TAAGCACATA TACAGAAAGT AGGGCAAGGG   38460
CCAGAGACTC ATTTTAAAGC AATGTTACAA GATCGTCACT GTTGCTTTTC ATTTTTCTAA   38520
ATGTGGCCAC TGCTGTTTTC TCACTAAAGG AAATGTTTTA TGTAAAGTGA ATAACAGTAC   38580
CTGGCATAAA ATAAGTGCTC AATAAATGTT AAGGCCTTCT CTCCCTCTTC AACTGGCCTC   38640
CTCATTTTTC ACAAAGTGAA ATAGAAAAAC AACATGGAAG ATAATCCTGT TGCTTAGGAA   38700
AAATAACTAA AGCTTGCTAG ACAAAATACA CCTGAAAATA TAGGAAGTGA GCTATAGCTG   38760
GCCTATATGC ATGTATGTTG GAACAGGACA AGATAGTGTA GGGTGGGGTG AAGAGGACAG   38820
AGAAATGGAA GGAAAGGGGC TACAGCCTTG GTGGCAAAAT AAAGGATAAG ACGACTCTTT   38880
TAAAATGGTC TATTTCAAAT GCTGGGTTGT GAAACTTAAT TTGATTACTT CATGAGAAAC   38940
AGCATCTATA ATCCATCCCT GATTTTTCTA CAACAAAAAT TTATTATTTA TTTTATGTTT   39000
GTGTGTAGAT CTTTTATATA TATACATGTA CACACGTATA TGTATATATT ATATATGCAT   39060
ATGCATATAT ATGTGTATAT ACATATATAA TATATTGTGT GTGTATGTGT GTGTATATAT   39120
AATTTTTTTA AAGGAATGGG GTCTCACTAT GTTGCCCAGG CTGGACTTGA ACTCCTGGGC   39180
TCAAGCAATC CTCCACCTCA GCCTCCCAAG TAGCAACCAA CAGTTTTAGT TTTGAAAAAA   39240
TAACAAATAT TAAACACCCA TGTGTAAGGG TTGGTACTGG GCCCTGTGTT AGTTGCATG   39300
GGCTGTCGTA ACGTAACACT ACAGGCCGGG CACAACGGCT CACGCCTGTA ATCCCAGTAC   39360
TTTATGAGGC CAAGGTGGGC GGATCACCTG AGGTCAGGAG TTTGAGACCA GTCTGACCAA   39420
```

FIG. 6.15

CATGGAGAAA CCCCGTCTCT ACTAAAAATA CAAAATTAGC CATGTGTGGT GGCTCATGCC  39480
TGTAATCCCA GCTACTTGGG AGACTGAGGC AGGAGAATCG CTTGAACCTG GGAGGCGGAG  39540
GTTGTGATGA GCTGAGATCA GGCCATTGTA CTCCAGCCTG GGCAACAAGA GCAAAACTCT  39600
GTCTCAAAAA CAAAAAAACA AAAACAAAAA AACCCTGATA ACACTACAGA CTGGGTAGCT  39660
GGACCAACAG AAATTTATTT TCTCACAGTT CTGGAGGCTG GAAATCTAAG ATAAAGTTGT  39720
TGGCTGGTTT GGTTTCTGAG GCCTCTCTCC TTAACTTGCA GATGGCTGCT TTCTTGAAAT  39780
GTCCTCACAT AGCTGTCCCT CTGTCTGTTT CTGGTGTCTC CCCACGTATC CAAATTTCCT  39840
CTTCTTATAA AGATACTAGT CATATTGGAT TAGGGTCCAC CATAAAGACC TCATTTAAAC  39900
TTAATCACCT TTTTACGGCC CTGTGTCCAA ATACAGTCAC ATTCCGAGTT CCAGGGGATT  39960
AGGGCTTCAA CCTATGAATT GGGGGTGGGG CACAATTCAG CCCGTAACAG GCCTAGACCT  40020
TAATTTGTCA ACACTACAGT TAGATTTATA GTATAGTAAC TGCATCTGTG CTCATCTAAA  40080
TGTCATACCC AAATGAAATA ATATAGCATG ATGATCTGAA TTTATTAAAG GCAATTTTTC  40140
CTATAGAAAC CCAAATCTAT AAATTATATA CAAACTGTGG TAAGTTACTC GATACCTTGC  40200
CAGGACTCAT CTATGGTGGT AGATAGACCA CAAAGAGTAC CACTGAAAGA TCCCTTTCCT  40260
AATCACAGTT TCCTCACTGG CTTGCCACAA AACCTAAAAT TCTTCTATTC TTTCATTGGC  40320
AATTTATTTC CCCTGAAAAT GTAAATAATC TCTGGCAGAG CAATCTATTA AGTGATCATC  40380
AGCCACTAAC ACCTTAGGGT AGAACAGCTC AGATCACAGT CTTAAAATAA ATTCCATCAG  40440
TATGAAATTT TCTTTATTAC TGCTCCGCTA CTGGAATGTT AGATCACTGT CTGCTTTAAT  40500
AATAATTCTG GTGTAGGTCA TTCAAATTTT GTTTAAGATA ATAAGACAAA TAGCAGGTAT  40560
AAAAACATTC CGTCATCTAA TAAAGCAACC CGAGAACAGT AAGAAGAACG TGATGAAATT  40620
AACATTTTTG AGTACCTGCT AGGAATCAAG TATTCTGCTA GATATTTTAG AAATCATCTC  40680
AATTCAATCC TAAAAATTAT TCTGTATAAT AGTATAGGTT GAGTATTCCT AATCCAAAAA  40740
TCTGAAGCTT TTTTTTTCCT GAGACGGAGT TTTGCTCTTG TTGACCAGGC TGGAGTGCAA  40800
TGGCGCAATC CTGACTCACT GCAACCTCCG CCTCCTGGGT TCAAGTGATT AGGGATACTC  40860
AACTGGCTAA ATATAATGCA AATATTTCAA AATCTGAAAA AACCCAAATC TGAAACACTT  40920
CTGGTCCCAA ACATTTCAGG CAAGGGACAC TCAAGTTGTA TTAATCCCAT TTTACAGAAG  40980
AAGAAACAGG CTCAGATAAA TGAACATCTC AGAGCTTGTT GATAGCAAAG GAGAGATTGA  41040
AACTGTCAGG CCTCTGATCC CAAGCCAAGC CATCACTTCC CCTGTGACTT GCATGTATAC  41100
ATCCAGATGG CCTGAAGTAA CTGAAGATCC ACAAAAGAAG TAAAAATAAC CTTAACTAAT  41160
GACATTCTAC CACTGTGATT TGTTTCTGCC CCACCCTCAC TGATCAATGT ACTTTGTAAT  41220
CTCCGCCACC CTTAAGAAGG TTCTTTATAA TTTCCCCCAC CCTTAAGAAG GTTCTTTGTA  41280
ATTCTCCCCA CCCTTGAGAA TGTAATTTGT GAGATCCACC GCTGCCCGCA AAACATTGCT  41340
CTTAACTTCA CCACCTATCC CAAAACCTAT AAGAAGTAAT GATAATCCAC CACCCTTTGC  41400
TGACTCTCTT TTCTGACTCA GCCCGCCTGC ACCCAGGTGA AATAAATAGC CATGTTGCTC  41460
ACACAAAGCC TGTTTGGTGT CTCTTCACAT GGACACGCAT GAAAGAAACC CTACCTGGTT  41520
CTGTGTCTTA CCTGTTGGGG GCCTGTGGTC AAACTACTAG TACGGAGTTT TAGTGTCCTC  41580
ACTTTAAAAA TGAGGGTTGT GGCCGGGCGC GGTGGCTCAC GCCTGTAATC CCAGCACTTT  41640
GGGAGGCCGA GGCGGGCGGA TCACGAGGTC AAGAGATCGA GACCATCCCG GCTAAAACGG  41700
TGAAACCCCG TCTCTACTAA AAATACAAAA AAATTAGCCG GGCGTAGTGG CGGGCGCCTG  41760
TAGTCCCAGC TACTTGGGAG GCTGAGGCAG GAGAATGGCG TGAACCCGGG AGGCGGAGCT  41820
TGCAGTGAGC CGAGATCCCG CCACTGCACT CCAGCCTGGG CGACAGAGCG AGACTCCGTC  41880
TCAAAAAAAA AAAAAAAAAA AAAAAAAAAA AAAAAAAAAA AAAAATGAGG GTTGTAAGGT  41940
AACTACCTAC TTTTTATAGC ATTGTAGTGA AGTTGAAATG AATTAATCCA CATATATTAT  42000
AGTGTGGTAG AATGCAGCAG AACTGATGAT GTATGACTTC TAAGACTAGT CCTTAAGAGA  42060

FIG. 6.16

CCTGCAGTTT TTGCTTTTGC CCTCTTGGAA CACTCCTGTT GCCATGTTAA GAAAAACTCT 42120
GGGGAGACTA TGAAGGAAGA GAGCATACTC GGGGCAGGGG GGTGAACAGG ACGTGCACAT 42180
GTACGAGCGT ACAAGCCAGG TGACACCAGT ACCACAGCCT CAGACATGTC ACCGGGGATA 42240
CCAGCACCAC AGCCTCAGAC ATGTCACCGG GGACACCAGC ACCACAGCCT CAGACATGTC 42300
ACCGGGGACA CCAGCACCAC GGCCTCAGAC ATGTCACCCA GGGACACCAG CACCAGCACC 42360
ACAGCCTCAG ACATGTCATC GGGGACACCA GCCCCATGGT CTCAGACATG TCCCTGAGGC 42420
CCACTTAGAC CCTTCAACCC CAGCCCAGCT GCTAACTGAC TACAGCCACA TGAACAGAAC 42480
CAGGTGAGAC CAGAGGAAAC TTCCAGTCAC CTACCAGATC ATGACAAATA ATAAACGATG 42540
TTTTTTAAAC CACAAAGATT TGGAGCAGCA TTTGTTACAC AAAATTAGAC AACTATTACA 42600
GTTCGACTAA AAACATGTTC ATTTACAATA CTAAATTAGA AGTGTAAGAA TGGGAGAAAA 42660
ACTTCATACT TTAAAAGTCA TTTTTTCCTC CAAAAACTTC CAACTTTGAA AAACTGATTT 42720
TTATAATGCA TAAAAATTAA AATAACCTTA GAATTTATAT GAGTAGCATA GCCAGCTGGC 42780
TTTATTATCT GTTGTACTCA ACACTTCAAT AATCACTGAT GTTTAGAAC TCTTCAGATT 42840
TAGAACTCTT GCCCTTGCTT TAGTCTGGTT TAAGCTAAAT AATTGTTCTT CCTCAAGAAC 42900
AAATGACCTT ACCTCGTTTT GTTTTCCTTG TCTGAGAGAA ACACATTAGC AGTCTCCCAT 42960
CTTGTTTTTC CTTTTCCTGT CACCCAGGAC AGAGGGCAGT GGTGTGATCA CAGCTCTGCA 43020
GCACGACTTC CCCAGGTTCA GGTGATCCTC CCACCTCAGC CTCCCAAGGA GCTGGGACCA 43080
CAGGCACATG CCACCACGTC CAGCTTAATT TTGTATTTTT TTGGTAGAGA TCAGGTTTTG 43140
CCTTATTGCC CCAAGCTGAT CTTGAATTCC TGGGCTGAAG CAATCTGCCT GCCCTGGCCT 43200
CTCCAAGTGT TAGGATTACA GGTATAAGCC ACCGTGCAGC CTTATATTTT GTTTTAAATT 43260
TTCCTCTGTA TTTTTCTCTC TGGCAAATTG TTTAGGGAGT TTCTTTAGTT TATCAGACTA 43320
AATTTCAAGG CTTTCCTTCC AATTTTGACA TGTAAACAGT CCCTCATTTC TGCTTATCTA 43380
GTGATTATTC CCAAATCTGT GTTACAGTC TAGCTGTCTC TCCTGAGATT AAGACTTGTT 43440
TCTCTAACTA CCTGACGGCA GAATCTCCTC TTGGAAGTAT CAAGGAGGCA GTTCAAAACT 43500
GAACTGGGCA TTGGCTCCAC TCCTTCTCCT TCTCTTTACT ATTAATACCC TTTCTCTCCT 43560
TCTATATGAC CACACTAAGT CTTATTTAGG CATCGTTTCT TCTGGGAGAC CTTTGTAGAA 43620
TCTCTGAGGT TATGTTAACA TGCTAAGGTT TTCTTGACAT TCTCAGATTG GGTTAGGTGA 43680
ACTTTTAGCA ACTTATCTTT TTACTAAAAA GTCATCCCTC AGTATCTGTG GGGAATTGGT 43740
TCTAGGACTC CCTAAGGATA TCAAAATCTG CATGAGCAGC CCAGGTGAGA CCAGCAGAAG 43800
CACTTTACAG TCACCTACAG GATCATGACA ATAATAAAT CATGTTTAAG CCACAAAGTC 43860
CTTTACATAA AATGGTATAG TATTTGCATA TAACCTACAC ATCTTCCTGT ATCCTTTAAA 43920
TCATCTCTAG TTTATAATAC CTCATACGAT GAAAATACTA CGTAAATAGT TGTTATACTG 43980
TATTGTTTAG GGAATAATGA CAAGGAAAAA AGTCCACGCG TGTTCAGAAT AGATGCTTTT 44040
TTTTCTCGTC TAATATTATG GATCCACAGT TGGTTGAATC CACAGATGTG GAATCCATGG 44100
ATACCAAGGA ACGACTGTAT GCATTTTGAC AATTATACTT CTCATCTTAC CATGCATTCA 44160
ACAAACAGAA CATGTAAAGC GGTGATAATG CTGTGATGAA AAATAAAGCA GGGGAAGAGG 44220
CTGCATCCAT CTAGTGGAAA CGATGCCCTT TTCAATCTGC ACAAAGAGAA AAAGCTGCTC 44280
TCCAAGTTGG GGGTGGGTG GGTCAGGTAT GTAAATTGGT CAGGAAGGGA TCTGTAGGCA 44340
CTTACAGATT TGACGCTAAT GAGATGGGAA GCCACAGGAA GGTTGTGAAG AAAAGACAAG 44400
ACATGATCTG ATTCATGTTT TGATCTGATA CACTGGTTGC TAGATGGAGA ATAAGCTGCA 44460
TGGCGGTGAG AGGAAGCAGA AACAATAGGA GGGTAATGCT ATAATCCAGT GGTCCATAAT 44520
CCAATATCCC CCCAAGGAAC AGTTCGGCAA TGTCTGGTGA CATTTCTGGC TGTCACAACT 44580
GTTGGGGCGG AGTGCTACTT GCATCTAGCA GGTAGAAGCT AGGGATGCTA CTAAACATCC 44640
TACAATGCAC AAGACAGCCC TTCCCCCAAC ATTGCTGGCC CAAAACGTTG ATAGTACCAA 44700

FIG. 6.17

```
GGCTGAGAAA CTCTGTTATA ATCTGTCCTA GAATGTAGCT TGGATTGAGA TGGCAGTGGT   44760
AAGAGCTGGA GAAGTGCTTA GCTTCCCAAT GTTTTTTTGT TTGTTTGTTT TTGAGACGGA   44820
GTCTCGCTCT GTCGCCCGGG CTGGAGTGCA GTGGCGTGAT CTCGGCTCAC TGCAAGCTCT   44880
GCCTCCTGGG TTCACGCCAT TCTCCCACCT CAGCCTCCCG AGTAGCTGGG ACTACGGGCG   44940
CGTGCCACCA CACCCAGCTA ATTTTTTTGT ATTTTTAGTA CAGACAGGGT TTCACCATGT   45000
TAGCCAGGAT GGTCTCCATC TCCTGATCCC GTGATCCACC CACCTCGGCC TCCCAAAGTG   45060
CTGGGATTGC AGGCGTGAGC CACCGCGCCC GGCCTGAATG TTTTTAAAGT ACTGGTGACC   45120
ATATTCGCTG AGGGATTAAA TGTAAGGTAT GAGGGGAAAA TAGGAATCAG ACACCAGGGT   45180
TTACTGCCTG AGCAATGAGA AGAACGACGT TCCTCATACG GAGATGAGGA AGAATGTGGA   45240
ATAGCAGGTA AATAGCATGT GCTTGCTTTG TTTGGGGCTG TGCAGAAGAG ACTGATGGGA   45300
CCAACGTGCT CAGTTCTGGA TATATTAAAC TTGGAATGCC TATTTGGCAC CAAGTGAATG   45360
TATCAGGTAG GCAGATGGAT AAATGAGTCT GAAGTTCAGG GGAGAGGCTG GGGTGGCAAT   45420
ATGAACTTGG GAGTCTCCAC ATCTGAATAG TATTTAAAGC TATACAACAG GATAAGGTGA   45480
TTTAGGAACT AAACACAAAT TGAGACGAGA TCCGAGCCCA GAGGCACTCC GATGTTTAAA   45540
AAAGAGGAGG AACCATCAAA AGATACTAAG GAGAAGCCAA GAAGTAGGAG AACTGAGAGT   45600
CTGAGAGAAT CATTATACTC ATTTGATCGA CTGCAACAAA TGCTGCTTAG AGGTCAAGCA   45660
AAATGAGGAC TAAGCAAGGA CCACCAGGTC TGGCAACATG GAGGCCAATG CCGACGTGGA   45720
AATGAGAGTT TTGGTGGGAA GACAGGAATA AAAGTCTCAC AGGTCTGAAT TCAAGAGAGA   45780
GAACAGCAGA AGAAGGGTAG AGGTGGTAGC CATAAACAAT GATACATTCT CTTGAGGCCT   45840
TTTCTTGCAA AGCTCAGTGA AGAAACATGG TTCCAGAGAG GGATTTTTTT TTCTCTCATT   45900
TTACATATGC AAACATATAA AAAAGCTGAA AGAATTGTTT GACAACCACC CTTATTCTTA   45960
CCACAGATTC AACATTTAAT GCCATATGTT TTCCCTGTAT GTACTGTGTA TTGTTTGAGG   46020
ATAACTTCCC CTCTAAATAT ACCTCGGATG TATCTCCTAA AATAAGTCCA TTCTCCTACA   46080
TAGCCATAGT AACCATGAAC ACACCTAGGA AAATTAAAAA TATATTCTCA AATATATTAT   46140
ATAGCTGGGT ATATTACAAT TTCCCCAATA TGTGATTTGC AAACCAGGAT CAAGTCAAAG   46200
TCCATGCACA GCATTTGGTT GTCATGTGTC TTTGGTCTCT ATTAATAATG ATGACTGTTT   46260
GAAAAGACCT GTCCTATAGA ATAAATTTGA CTGATTATGT CATGCCATTG AACTTGTTTT   46320
TCTATTCTAG AAGGATAGTT TTTTAGGGTA GTGAATACAT TTATTACTCT TGGCACAATA   46380
GTCTAACATT TCCCAATTTC CTTATATCTC TGCCCTTTCA TTTTCAGAAA ATCAATTATT   46440
CCAAGATTTG TTTTTCATTT ATCATCACTT ATTAGCTCTG AAGACTCAAC TGAGCAACTT   46500
TCAGGGTTTA TATACCCTAT ATTCAGAAAA AAACTACTAC CATCTCTCAT TTACCCTAAG   46560
AATTCATAGG AGAGCATGTC TTAAAGCTGA TCAATAACCA AACCAAACAT TTTATTGATC   46620
ATATTACATT TGGAAAGCAA AATGAATTTC CTAAAATTTC TTCCCTGATT AGCAAAATAG   46680
TGCCTCCGAA CACTTGAGGG TGAAAGTTGT TGTCAAATAT GCCTACATGA CTGGAAATTA   46740
TGACATCCAA ATGAGTTCAC TGGGTCTGAT AATAATATGC TCTACATGCT TATGTCTATG   46800
TAATAAACAG CTTACATCTG GATGAGAAAA TTGATTATAC AAATATTTGG GCTTCTACAA   46860
CTGGTCACTC ATCTGTAAGT ACTTAAAGCA ACTTAAAATG CAAACTGACC TAACAATGCT   46920
TATGGTTAGA ATTCCAAAGA ATGTTTAGGC ATTGTCAGGT TATGTTAAAA CATCTTCTGC   46980
CACAATCTTC AAGTGATTTA TCTTTTCTGT TGTGTTGAAT AGCTATAGAA GACAAATGAA   47040
TTCTGCACTC CTGAATTCAA TGAACATTTC AAGTTTCCTC ACTTACACTG TAAGATTACG   47100
TAGCATATTT TAAGAAATAA ATTATAATCA TTTTATTTCA CTTATTGAAC TTCTTTTAAG   47160
CTTTGGCATT AGAATTTTAA TCAAAGCACT GCCACTTGCT TACAGTGATG GTTTTTAGGC   47220
TCTTTGGGCC TATGGACTAT TTCAATGACC TTCACTAGCC ATCTAGTCCA CCTTATCCTA   47280
ATTATTACCA CTGCAAAAGA AACCCTCACT TGAATAAATC AGTAGATGGG CATGAGGCAC   47340
```

FIG. 6.18

CTCCCAGGAG ACTATAATTA TTAACTCATA CTAAAATCAA AATTGTAGCT ATTATCACTC   47400
ATATGGTTTG GCTCTGTGTC TCCACCCAAA TCTCATCTTG AATTGTAATC CCCACGTGTC   47460
AAAGGAGAAG CCTGGTGCGA AAGGACTGGA TCATGGGGGC GGCCTTCCCC CTTGCTGTTC   47520
TTGTGAAAGA GTTCTCCGAT GGTTTAAACG CATGGGACTT CCTCCTACTT GCTCGCTCTC   47580
TTCTGCCACC ATGTAAGATG TGCCTTGCTT CCCCTTTGCC TTCTGCCATG ATTTTAAGTT   47640
TCCTGAGGCC TCCCCAGCCA TGCAGAAATG TGAGTCAATT AAACCTCTTT TCTTTGTAAA   47700
TTACCCAGTC TCAGGTAGTT CTTTACAGCA GTGTGAAAAT AGACTAATAC AATCACCTTA   47760
TGGTAAGTCT GTCTATAAAT CACCTGAACT TTCACAGACT ATCTAGAAGA ACATGTAACC   47820
AGAGTAGTTC TTGATCATGC TATATAAATT ACTGATACAG AAATAGAGCT AGACAGGAAG   47880
GGGCTGGTAG TAGAGAATCA TCCTCTGGAC ATATTCTCAC AGCCTAATCT CTAGCTAGCA   47940
AATTTTATAA TATATATAAA AATACAATTA TTTCACAAAA TTACCATGAA ACGATTTTAT   48000
TGGGATATTA GACATTACTG AATTACTTGT TCTGTGAGGT ATACAGTGAA ATTAACATGT   48060
TATAAAATTG TGGTAGCCGG CCCCCAAGAT GGCCTCCAAT GAATCCTTCA CCTCTTGGTA   48120
TTCATACCTT TGTGTAGGTA GGTCTGTGTA ACCCATAGAA TACAGCACAG TGACAGTAGG   48180
TCACTTCCGA GGTTAGGTTG TGAAAGACAC TGTGGTTTCT GCCTCTCTCT CAGATCACGT   48240
GCTCTGGGGG AAAAGCCAGG TGTCATTTTG TGAAGACACT CAAGCAGCCT TTAGATGACT   48300
GCAACCACAT AAGAGGCTCC GAACTGGAGC CACTCAGCTA AACCACTCCC AGATTCCTGA   48360
CCATGTATCA TTTCATACAC AATGTATGAA ATGACAAATG TCTGTTGTTT TAAGCTGTTT   48420
GGGGAATAAT TTGTTACATA ACAAAATATA ACTAATACAA TAATACATAC TGATTTAACT   48480
GAAGTTGTAA CTTCATAACT TATTTAGGTA CTAAAAATCA CAGCAACCCG ATGCAAAGTA   48540
CTAAAAAAAA AATCCATTAA TACCTATTGA GTACTGTTGA GGGCATGAGG AAAGCTCTTT   48600
CATACTCCAC ATAAAACTTC CTTACCGTAA TATTCATGGC TGACCTCTAC TCTTAACTCC   48660
TTTCTAGGAT AGGAGGGGCT AACTGATCTG ACAGCAAGTT TGGGAGAAAA AATTCTGAGG   48720
CTCGGCCAAC TTCCTCTCTT CTTTCCATTT GGGATTTGGC TGACTGAAGA GGGTCATTTG   48780
TTTTGGCCTG CTCTCTTACA CAGTAAATGT AGTGGGACAA GCTCTATTCT TGTTGATAGA   48840
AAAACTCGAA TTTTAAATCT GCCTAGTTCT TTGCAGCTCG TTGTTGCTCC AAATCTCAGC   48900
TACCTTTTGA AACAACTTTT TTCAGTAAAC TTAATTTCAA TCTTCATGTG ATTTAACTGG   48960
ATCCAAACAC AGGCAGATAA AAAAGGTGGG GCATTACTTA TCAACCTCTA AACTAAGTTT   49020
AATTTTGTGC CCTCATGGAG TTTATAGTAT ATTTGAGGTT TAAACTAAAA CACCTGGTTT   49080
TAAACAGAAA CTATAAAAAA CACGATTAAT AGGTGAGGCC GGGCGCGGCG GCTCACGCCT   49140
GTAATCCCAG CACTTGGGGA GGCCAAGGCG GGTGGATCAC GAGGTCAGGA GATCAAGACC   49200
ATCCTGGCTA ACACGGTGTG AAACCCCGTC TCTACTAAAA ATACAAAAAA TTAGCCCGGC   49260
GTAGTGGTGG GAGCCTGTAG TCCCAGCTAC TCAGGACGCT GAGGCAGGAG AATGGCGTGA   49320
ACCCGGAAGG CGGAGCTTGC AGTGAGCCAT GCGCCACTG CACTCCAGCC TGGGTGACAG   49380
AGCCAGACTC CGTCTCAAAA AAACAAACAA ACAAAAAACA AATAGGTGAA AGGCCGTGAT   49440
CATTGGTAAG CGTAAGAAAA TCTGAGGGAG AAAAAAATAT AGATGCCCAG GCCCCATGCC   49500
AAACTCATGG AATCATGCAT GAAACCCAAG CAGCTGCAGT TTTAACAAGT TCCCAATATA   49560
TAGTTGACCC CTGAACAATG CAGGTTTGAA CTGCCTGGGT CCACTTATAA AATGGATTTG   49620
ATTTTTTTCA ATAAAAGTTA CACCGAGTGT GCCTGCCTCT CCTCCCTCCC TCCCTACATG   49680
CTCCTGCTCT TAAGCCTCTG CCATGAGGCT TAAGACAGCA AGAACAACCC GTCCTGTTTA   49740
TTTCAATAGT TTTGGGGGGT GCAGGTGGTT TTTGGTTACA TGGATAAGTT CTTTAGTGGT   49800
GATTTCTGAG ATTTTAGTGC AACTGTCACC TGAGCAGTGT ACACTGTATC CAACATGTAG   49860
TCTTTTAACC CCCATCCAAC CTTCTTCCCC AACCCGAATC CCCAAAGTCC ACTGTATGAT   49920
TCTTATGCCT CTGTGTTTTT ATAGCTTAGC TCCCACTTTT AAGTGAGAAC ATACCATTTT   49980

FIG. 6.19

```
TGGTTTCCCA TTCCTGAGCT ACTTCACTTA GAATACTGGC CTCCAGCTCC ATCCAAATTG    50040
CTGCAAAAGA TATTATTTCG TTCCTTTGTA TGGATGAATA GTATTCCACG ATGTACATAA    50100
ACATTTTCTT TATCCACTCA GCTCCTCTTC AGTCTACTCA ATGTGAAGGT GACAAGGACG    50160
AAGATCTTTA TGATGATCCA TTTCCACTTA ATGATTAGTA AATATACTTA CTTTTCCTTA    50220
TGATTTTCTT AGTAACTTTT TTTCTCTAAC TTACTTTATT GTAAGAATAC AGTATATAAC    50280
ACATATGACA TACAAAATAC GTTAGTCAAC AATATATGCT ATCAGTAAAC TTCCAGTCAT    50340
CAGTGGGCTA TTAGCAGCTA CGTTTTTTGG GCAGTCAAAA GCATGGGGAA GGAGAGGGTG    50400
GTCCCTAACC CCTGTGTTGC TCAAGGGTCA ATTGTAATAA TACCCATTTA AGAATCCATG    50460
GTATATATGG TAAGTGCAAC AACTCTAGAA GAGAGTGCTA GGAGTTGGAA AAGGAAAGAG    50520
AAAACAGAAT TTAAAGCAAT CTGTAAAGGA CATGCAGGGT TTAGATGAGG TGGAAGGGTG    50580
AGGGAAAACC AACATCTGCT GTGAGGGCAT ATTAACTGCC AGACATTGTT CTATGTCTTA    50640
CCTCATTTAA GAGAATTTCA TTTCACACAT GGAAAAACTG AAGCCCAGAG AGGTTAAATA    50700
ATTTGCCTGA GGCCAAAATT AGTTAAATAA CAGAAGTGGG ATTAGTAGAT GTTTTCATTT    50760
TATCAGTGAA ACTGAGCCTC AGGGAGGTTA AATATTTTGT ATGAAGTAAC AAAACTGAGA    50820
TTAATATATG GCCAAGTTTA AATGAGATCT GTAAATCTAA TGCCTACACT AAAACAAAAA    50880
AAAAAAAGTG GAAGAAAAG GTCTATATTG CTTAGCAAAA CAGAGGTAGG GAAGCAAAAA      50940
TAAACTTACA AAATCAGATT AGACCACCAA AAAACAGTCC CCATTTTAAC TTATGTGGTG    51000
AGAACCATAT ATTAAAGACC ACCAGTGGCT TAAAAATCTT TTTAAAAAAT GAATCTGTTT    51060
TCATTATTCA TTAGTTTTTA TCTAATGAAT AATGTATCTT AACTGATACA TTTACTAAAC    51120
AATTACCAGC TCCAATTAGC ACTCAGTTAC AATTCAATCA TTAAACTGAC CCTCAATTTA    51180
GCTGTCAACC TAGTCAAAAC AGTTAAGTGA TTTTACGGTC ATCCTCAGTT GCAGAAGTAT    51240
AATGTTTATG GCTGGAGTCA TTTTATTTTT AACTAACATT TTTTAAAAAG ATTGCTTTGT    51300
AACAATGTGT TATGAGTCCT TTGTGGTAAA TACTGCTTTT TTTTTGAGAC GCAGTCTCGC    51360
TTTATTGCCC AGGCTGGAGT GCAGTGGTGC GATCTTGGAT CTGAGGCTCC TGCCTCAGCC    51420
TCCTGAGTAG CTGGGACTAC AGGCATGCGC CAACGTGCCC AGCTAATTTT TTGTTTTTTT    51480
AGTAGAGATG GGGTTTCACC ATGCTGGCCA GGCTGGTCTC GAACTCCTGA CCTCGTGATC    51540
TGCCCACCTC GGCCTTCCAA AGTGCTGGGA TTACAGCTAT TTTAAGGACT TTTTAAAAAG    51600
TGAAGCTAAA CATTTATTCA TCCCTATTCC TCATCTATAG GGACTTGTGC TCTATTTTTC    51660
TTTGAAGACT GAAGTAAAAA TTCACCTTTG TGAGGGTCTT CCTATAATTA AAATTAATCA    51720
TTTTTTCCTC CATAGCTTCT ACAAAACATT GCCTGTACAA CTCTATTTAG CACTTATTTC    51780
ATCCCGCCTT GTATGAAAAC TATTTGTTTA CAAACGTTTC TACTTCTCTT TAGGAATAAG    51840
GACTATGCAT TATTCACTGT TGTATTCTCC CTGCATTTAT GGCAGTCCTT TGCACATTAA    51900
ATACAAGCTT TTTGGCTCTG TGCATCTCTT CATCTGGCTG TTCATCTGTA CCCTTTAAAA    51960
CATCCTTTAT TAAAAAAACA GTAAATGTAA AAAAAAAAAA AAGCCATTGA TGAAAAAGTT    52020
AATAGCTTTC TCAATAAGAA AAGAGTATCA ATTATGCATA CGTCTGAACT AACAAACATG    52080
AATGAAATAG GCTATTTAAT ACATTCTGTT TTAAAAGTAG GTTGGTCAG CCATGTAAAT      52140
TGAAAATTGG GAGCCACCAA GATAACTCAT CAACAAATAT GCACTATGTA CTAGGCACTA    52200
TATAGATGAT GGTGAACCAA ACAGATGTAA TCCTTGCTCT TACAGATCTC ACAACCTACT    52260
ATGGGGCCAA AAATATATGT GTATGTGTGT GTGTTATACA TATATACACA CACATACATG    52320
TATATATACA TATACACATA CACATATATA CATACGCACA CATCACACATA TATACACACA   52380
CATACATATG CTATGAGGAA AACAAACAGG TGGTGAGAAA GAATTAGAGT AGGGGTAGAG    52440
GACAGAGGGC TCCTCAAATA GGGTGGACAG CTTGACACAA GACACTCGAG CTAAGACTCC    52500
AAGGATGAGA AGACAGTTAT GTAAAGAAAA GGGGACTAGC ATTGTCAGCA GGTAGCTAAG    52560
GCCTTAAAGC AGACAGTCAT GTGCTGCAAT GCCAGCTTCA AGCGAATACA GTTACTAAAG    52620
```

FIG. 6.20

```
CATATCTAAC CTTCTATGTG AATGTAGTTA CTAAAGCATA TCCTCCAACT TTCCATTTTT    52680
CTTTTGCTAT TGTTTCTACC ACTTCTCCTT TTCTGTTGAC AATTATTTTA AATTTCCTGG    52740
CTAAATTAAA TGATGGCATG AACTCTGGGG AAAGTAAGAC TACCTATGTC CAAATAATCC    52800
TAAATTCCTT CTAGTCCTTA TGACTGATCA ATTCACCCTG AAGTGACAAC TATGTCCCAA    52860
TTAGGAAAGA GTGTTTCTTT ATCTGCACTT AATTTTTTGA TTTGGAGGCT TCCTGATTGC    52920
TAATCAACAT GTTGTGTGAT TACTTCAACA AGTACTTATA GAACGTTATT TTGTCACTGG    52980
AAAAACGTTC TGCTGCTTTC TGAACTTTAG GTTGCTCTAG AGTCTAGGAA GAGTGACTGT    53040
ACCTAAAGCA GTTCCTAATT ACTGGACATT CTCAGATCTG CTAGAGCTAC ATGTCCAATT    53100
ACGAGAATAT ACTGGAAAAA GCCCTGGATT AGAAATGAGA GGATGTAGGT TTTAGTACCA    53160
GGTCAGCCAC CTTGTTAATG CAAATTTGAG TAAATTGTTA CTTCTTTTAG GCCTTGTTTT    53220
TGCTGTTTTG TTTTTCTGAC AGTATGGTCT CTGTGGTCCA GGCTGGAGTG CAGAGGCACA    53280
ATATCAGGTC CCTGCAGTCT CTACCTCCCA GGATCAAGCC ATTTTCATGC CTCATCCTCC    53340
TGAGTAGCTG GGATTACAGG CATGTGCCAC CACACCCTCG AACTCCTGAC CTCAAGTGAT    53400
CTGCTTGCCT CAGCCTCCCA AAGTGCTGGG ATTAGAGGTG TGAGCCACTG TGCCTAGCCT    53460
TACACATTGT TTTCTTACTG GTAAAGTGGG AATATCTAGA AGTTGCATGC TACATAAATT    53520
CAACCATATA TTATTGGCAA AAAATTTTAA AGAAAAACAT CAGCTTAAGA GTACTAATTG    53580
AGTACATGCC TTGGAATGAG CATGAGCTGG AAAGAACAAA CCTGTTGTTA CATCACTCAT    53640
TGCTGTTTTC ATATGCTGCT CATTGTAAAT CTTGCTCAGT GGCATGATTT TAGTGTTTAA    53700
AGATTTATTT GTTTGTTTGT TTAGGACAAA GTCTCTACAC ATAATCTACT TGCTTCATAT    53760
ATACATACTT ATGCATATTA TGTATGTACA TACATGCTCT CAGGGCTCAC ATGAAAAAAC    53820
AGCCATTCAG GTGATGTGAT TTATCTCATA TGCTTACTTT AGAGTCAACA GGGTGTTGAC    53880
TCCACTATAC AATACTGGCA TGGAGAACAC ATAAGTCAAA GTAGACAGGA CCCAGCCGTA    53940
CCATTGGCTA GGGCACAAAT ATATTCACAT ATGTGGAGAA TGATGTACGT AGAAAGGTCT    54000
TCATTGCACA ATGCTCTTTA ATAAAGATCT GGAAAAAAAA AACACCTAAA TGTTCAAAAG    54060
GATAGGGTAG ATGAAATAAT GGTACATTAT AAAATGGAAG ATTATGCAGC CATAAAAATA    54120
AGGAAATACC TTAAATAATA ACAGAACAAC TTTTAAGGTA AGTGAACAAA TAAGGTACAT    54180
AATCACTATG CATAGTATGT ACCATTTACA TAGAAAAAGG GAAGAAAAAT AAAATATATA    54240
TAGTAATTTA TTTGTTCTTA CATGTGTAAA ATTTTTCTGA AAAATATACC AGAAACTGGT    54300
AGCACTGGTT GCTTCCTAGG CAGAAAATGA CTGAGTATCC TTTTGTACCT TTTGAATTTT    54360
GAACCACGTG AATGAATGTG TTACCTATGA ACAAAATGAC AAGTTTAGAT CAGCAAGACA    54420
GCAGTTTGAG ATGAAATGGG ATTACACCCT TAGTAGGAAA AACTTTTTAA AGCAGGTGGT    54480
ACTTCTAAGA GCAAATACCT GCACATGGAA TGTTGAAACT ATAAGGAACT CTCCTTAAGA    54540
GATCCATCTA TTCCAAACTT CTCATTTTAT AGATCTGTAA ACTGAGACCT TAAAAATTCA    54600
GTGACTTGCA TAAGGTCACA CAGCAGAAGA GATGGGATTA GATGCTAGAT ATTCCAATAT    54660
CAAGTTTAGA CTATTAAAAA TTCAGTGACT TGTGTAAGGT CACACAGCAG AAGAGATGGG    54720
ATTAGATGTC AGATATTCCA GTATCAACTT TAGACTATTA TCACACCATC TTCTCATTTT    54780
CTGGGGGCAA AACAGAACCA AGTAAGTTTG GGCTACATTA CGAGTTGTCA TGTTTTTGTT    54840
TTTGTTTTTT TGAGATGGAG TCTTGCTCTG TCGCTCAGGC TGGAGTGCAG TGGTGTAATC    54900
TCAGCTCATT GCAATCTCTG ACCCCGGGG TTCAAGCAAT CTCCCTGCC TTAGCCTCCC    54960
GAGTAGCTGG GTTTACAGGC GCCTCCCACC GCGCCCGGTT AATTTTTGTA TTTTTTTTTT    55020
TTTTTTTAG TAGAGACGGG GTTTCACCAT CTTGGCCAGG CTGGTCTTGA ACTCCTGACC    55080
TCGTGATCCA CCCACCTCAG CCTCCCAAAG TGCTGGGATT ACAGGTGTGA GCCACCACGC    55140
CCGGCCGAGT TGTCATGTTT TATCTAAATT TTAGAGTCTA ATGTATAAAT TAACCTTAAG    55200
CCCTGAAACT ACTAATTTCT TGTTTGGATC ACTATACGGC TACACTTAAA AATATGCTGT    55260
```

FIG. 6.21

GCATACCTCT ATCATTGCAT GTATACAATA TGATAGATGC ATGATATGAC AGACACACAA 55320
TATGATACAC GTATTTTTTT CTATCCTAAC ACATCTGAAT TTACTGAAAT AACTAAAATG 55380
TCTTAAGTTA CTTTTTTAAA TATACACATG CATAGCACAA GCGTGTTGCC AAAAATATGA 55440
ATACAGGTTT ACAATTCCTT AACTAAAACC CAAGGGTTGG ATGTGTTTTA GAAATAAGAA 55500
TTTCATACAA TTTTTAAGTG TTACAGGGTA TATAAACCAT TATATAACAC ATACCAGGGG 55560
CCAAGGGCAG CACCCCATAA TCAAACATAT TAATATAGTT TCAGCAAAAC ACATGGGATA 55620
AAGACTATAT ACAGCTTCTC AATAGTTCAG GTCATATTTT GCTACCAAAT GAATTTTGTT 55680
GCCAAGCTTA AGAAGTTTTT GGTTTTCACC GCTTTCTGAA TGTTAGATTG AGATGTGGGA 55740
TTACAGACTG TACTCATAGA GTGCTTCTAG AAAGCAGTCA GTCACTTCAA CTCTCATTTT 55800
TTTTTTATGA GACTAAAAAA GAAATCATAG CAAGTAGCTT TTATATCCCA GGTTTGGGCC 55860
AAAGACTTGT ATTGTGGTTA AGGAATCTAA CTTAGTAGAA GGTGCACGAG CTGACATCGT 55920
GAGTGGCTAA AATGAGAGAA AAAAAGAGAA ATCCTAATC ATACAGAAGC ACTGAACTAC 55980
TGCAGCTGTT CGTTAGTTAT TAATTTAATA AAAGCTTCCT CCCTTTAAAT CATGTGAGTT 56040
TATAACTGGA AATAGGTCAA TAAAATTTCT GTCCCACACT GCTGACAAGC GATGGACGCA 56100
ATTAGCTTTA ATCCCACTGG AAGGTACTGC ACTCTCTCTG GACCAGGAT ATGTAGAAAA 56160
AAGCATTTCA ATATATAGG AATAACCAGA AATGTATACA GTATTCTCAA CTTGGGACCG 56220
TTACTCTATA ATATAAACGA AAGGGGTTTT CTAGTCAATC TCTGCTGATC TCCTGTACCA 56280
AAGTTCTTCC CTTTATAAGT CTTGTACTAC CTTTTACAAG AGGAAAAAGC TCTAGAGCGA 56340
AAACACAGAA CACACTAAAA TCCCTTCCTT TCTCTTTACA ACTCAAGCCC CGCCTCCATT 56400
TTGTTTCTGT TACTAATTTT TCTTCTGAAA AAATACCAAA TTTACACTGA AAGACTAAAA 56460
TTCAACTTTG CAGACAACGT TTTAAAAAAT ACAATTCAGT TTGGTGATGT TGTTTTGCAG 56520
TCTTACAATT TTAGCTACAT TTTAACTGAA CCAATTGTTT TGTTCAATTT ATGAGTTAAT 56580
ACTCAGCAAG TTTGTTTTTT ACAAATAGTG TATTCCATTC TAAAAATGGA AGTAGCAGTG 56640
GTGAACAAGA AAACAACCCT CTGAGTTTTG TCTATTTCAG GAGGAAGTAC TACTTTCTCC 56700
AATTTTAATC ACAATTCATA AAAAAGAAAA ACCTAACTAG CTAGATCTTA AATATACAAA 56760
TACATTAACA ATCTAGTAAA GCAACAGAAA AAGGTAAACA AACTAACCAG CCTATTTTTG 56820
TCTGGAGAAA CCCCAACAAA CTGCTGGATT CCTTGGCCAT TTGCATTCAG AAGTACCAAA 56880
AACTAAAATC CTTTTTACTA AATAATTTCT TCTACACGAG ACTTGTTTCC TCCACACCAC 56940
CCTATCCAAA TTGTCAGCAT TATTCCAGAA TATAATCATT TAGTTTGAGA CCACTAAAAA 57000
ACCCCGCAGT CCAAAATACC AATTGTGGTT TTTCTGTAAA GAAATGGTCA GAAACTACAA 57060
ATTGTTATCC TAGGACACAG AACCAATCGA CCAAAAGGAC TTCTGGAATA TGCTGCCCCC 57120
AAGATTTAGA ATGCACAGGC AGAAATAGCA TACGCGGTCA CGATGTCCCT TAAGCCACAT 57180
GACCTTCCTA CGAAAGCAAA GGCTTAAACT TATCAAATGA GAACTCCCCC TTTCTCTGAA 57240
GTTAAAACAA GGCAGGGCAG CTGGAATTAG AGCAGCAGGG ACAGATCGGC TGTTGACTAG 57300
TCAGAACGGG TCGTGGAATG CAAAGTCCCT GCGCTTTCGC TGCTCCCCTT ACCGTGAGAA 57360
GATCTGGGAG GGAGGAAAGG AGGAGAAACA CCCCAGAATC CTGGTAGAAA AGCCCCTGGC 57420
CTCGAAGATG GGCTCTAGGG AGACAGGGAG GGGCAGCTCC GTGTGTGATG ACCCTTTGTG 57480
AACATGCACT CTGTGGCAGC TTCAGCTCCA CCGAGGCTTT GGGAGAGCGG ACTACGGATG 57540
CCCGGCGCGG CCCAGCTGTG AAGGCCGCGC CGGCGGAGAG GGTCCATGGC ACCCCCGCCG 57600
GCTTCGGAAG CCCTTCCCTC TCCCACCTCC GCGGGTCACC CCAGGAACCA GCGGCTCCCG 57660
ACCACGCTCG CGCGGACCAC GGAACAGCGA CGCGCAAGCA GGTCTCTTTC GTCAGCGTAA 57720
TCCCTCCGCA GAAAGCCGCG CACTAGTTTT AATCACGCCC CACCCCCTGG CCGCTGGCGC 57780
CACCTCCGCC ACTCGGGCGC TTTCCAGCAG CTTCCAGAAA CGTCGCCTCC CCAAACCCAG 57840
CCACTCACAC ATGGCGGGCT CAGCAGCCAC CGGCCCGCC CTCCTCGTC GCCGCAGTCG 57900

FIG. 6.22

```
CAACTGCGTC TGCGGCCACA GGGCGGACAG CCACGCCTCT GCGGAGGGCG ACCGGAAGTG    57960
CTCACGTCTT CACCTTCCCC GCCACGCCAC CGTCCTTTCA GGCCCAGCGT GCAGCAGGAA    58020
GGAGGACTCT TTTGCCGCGG ACTCAAGCCG GAAGCCGCCT TCCTAGTGGA GACGCGAGTG    58080
GGGGAGGAGC AGTCCGAGGG GAACGTGGGT TGAACGTTGC AACTAGGGTG GAGATCAAGC    58140
TGGAACAGGA GTTCCGATCG ACCCGGTACC AAGAAGGGGA GTGCCCGCGG CAGGTAAGGG    58200
AGAAGAGGGA GGGGTTTCTT TCCGCTCTCG AAATTGGGAA AAGAGACAGA GCTGGGATGA    58260
CCTATGGGGT AGTCGGCGCG CTGAAAGGAT GGGCTGGGCT GGGACGGGGT TCAAGTGGGA    58320
AAGGTTGATG ATTAAGGTAT AGAGTTGGAC TTACAGATCC GTTTGGGCGC AGAGAGGTGA    58380
ACGCTGAAGA GAAACCAGAG TTTGTTTTCG TTTTCCAAGG AGCGTGGAGA TGGGCAGGGT    58440
TAACGGACCC TGCGCCTCCT TCGGCTTCTT AGTTTGGGTG TTGAAACTCA CCTCCTTTGG    58500
TCCTGTTCGT CTCTGATTCA AGACAGTTGG GTTTGGTACC TGACAGGGCT GGGTGCAGAA    58560
AGCTGACCCT GTTCCTCGGC TTCCAGGTCG GTTGTGGCCT CGCTTTTGAC AGTTCACGTG    58620
CCGAGCCTAC TCGCTCTCGG AGGGCGAGCT CAAATGGGTG GGTTTAAGGC CCCCTCTTCG    58680
AACAGCTGTT TCCCTGGGTT TCTCCATTTT GCACACAGGA GTGTGAATTA AGTTTAATTG    58740
AATACTTTTT GCGATTCCCA GGGCCACCTT GACACGTTCA TTGTGCTATC TAACTGGGTT    58800
CATGCTGGGC TAATAATTCA CATTAAGGCT TCTGGAGTAT AAGTGGTTCA CAGAAGTATG    58860
AAAAGGGGAT GTTAGAAGAA AGATGCTGGG GGTGAAGTAG AGTTGAGGAA GACAGAACTG    58920
GAAAGCTAGG TTGGTTTCAC AGTACAATGA GCTTTAGGTC ATAATACTAC CTTTAGGTTA    58980
TATTGGGCTG TTTGGACGGA GTTTGCTGTA ATCAGGCTAG AGTAAATAGA GAATTTTAAA    59040
CTAAGCATTG ACAGGCTCAG ACTTGTAGAG GCATCATTTT GACAGTGATA TGGAAGGGAA    59100
AGAGGTAGAG ATTTGAGACC TTTCCAAAGA ACTGTCCACA GAATTTGGTG ACTTACTGTG    59160
CGAAGAGGGA AATAAAGAAT AGGGAACAAC TCAAGACTTT CTAGTCTGTG TGTTTGGAAG    59220
GATGGAGACG CCCACATTTA AGTGAGATAT GGGAAGGAGG AGCAGATTGT TTTTGAAGGG    59280
AGGAAGAGCA GTTACTTAGG GTCAAATTAA GTTGTAAAAT CCCCCCCGGG ATTTTGTATG    59340
TAAGTCAAAG TGAATTGTAT TTGGAAGAAG AACTGGGGAG CCCACCTCTG GTATTTTTTT    59400
TATGTCCCTC ATATGGACAA ATAAACCTCT GGTATTAAAT GAATTTTCTT TTGGGGGATT    59460
CTATATATTC GGGATTTCAA CCACCAACCT ATCTGGTTTT TCCCGCTGAA ATGTTGGGTG    59520
ATGGAATCAG GAGAGCAGAT TTGGAGACTC TTTATATTTT ATAATTGAGA GAGACAAAGA    59580
GAAAACCGTT TGATTTGAAA AAGTTTTCTA GGTTCCCTCA GGTAGATGGA AATTTTCATC    59640
AAAAACAGTT TATTCAAGGT ACATAGCCTA CTAGTTTCCC ATTTGAGAGT ACCGCAGAAT    59700
GATACGACGT GTACTGCTTC TCTACGCAGA ATGAAGTATA AAATTAGCAC CAAATAGTAA    59760
CTTTAATTTG TCAGGTGCTA AACTTTTTAC ATGCTTTATC TCATTTAATT CTTAGAAGAA    59820
ACTAATTTTA CAAGTAAGTG TCTGGACCAA CATCTGCAGG TACAAAGCCT GAAAAGCGTA    59880
AGTTTGACTC CTACATAGTT CTCTTTTGTA AGTAGATTAT AAATAGAACC AGCCAAAGGT    59940
AATAAGTTGT CTGTGCCTAA AAAGAAAGAA AAAAGTTAGC ATCAGTAGTT CTCACCAGAA    60000
GGGGTGATTT TGCTTACCAG GGGACATTTG GCAAGTCAGG AAACTTTTGG CTGTTGGATC    60060
TAGAGGGTAA AGGTCAGTGA CGCTGCTAAA CATCGTCAGT GCATAGAACA GCCTTCACAA    60120
ACAATTATTT GGTCAAAGAT ATTTGTAGTG CTGCAGTTGA GAAATTTCTG TCTTATGGTT    60180
ATTTCTTCAG GAATAGGAAA TTAAGATTCG CCGATACTTT CTTTAAAAAG CAGTTTTATT    60240
TTTGAAATTA TTCCTTGGCT TGAAAGGTTT GTGAAGTTTA TATAGCCGAA CCAGAATAGC    60300
GTAATTAGAT TTTAAAGTGA ATTGTGAGCC ATCGATTCCC AGGAGATGGG TGTCATAGAA    60360
TCATGGATTC TTGGATTTGG GAAAGACTTA TGCCTAGAAT TATTTTACAA CATTTCTGCT    60420
AAGTGGTAAT TCTCCTCTGC CCTAAAGGTC TCCTGTATTT GATTTTCCTA TCATTGTGAA    60480
CCCACAATTA AAATGCTCTT AATTATTTTT TGCTTACACT GAGCTCCGGT CTCTTGTAAT    60540
```

FIG. 6.23

```
TTTTACTCTG TTAAATGTGG TTCTGCACCA TAGGACTGCA CTCAAAACAA GCTTGCCACA  60600
TATGTAATTT GTACTAGGAC AGTGTTTATA TTTTTGTTCA GATAACAAAA TAAGTTAAAT  60660
GTGGTGTAAA TTAGATCATT TACAAATAAT AATTTGTTAG CAGCTTTTAA TAAGTAGTAT  60720
TTTTCCCAAC TGGTGAAGTA TTAATGTTGG TAGTTGAAAA CAATAGGAAT GTATGGAATA  60780
TATGGTTCAC TGGTTCTTTT GTTCCTGTCA AATAGTGGCA CAATGGATCT GGGGTTTTTC  60840
TCAGTATAAT GCTGGCATAT TTGTTTCAAA TTGTACATAG ACTCTAAAAA GTTAGGCTTT  60900
CAAATTCTGG TCAATATAGT TTGCTTTAAA TAGTAGCTGC CTCTACTACA AGTTTTATTT  60960
AATTTGTTGA CAAATGAGTC TGCTATGAAA ACCGGTCCTG TTGCCAGTCA CTACCCTCTG  61020
TTCACAAATT TGCTGGGTTT ATAAATATAG GTATCATTTT CACTTCAAGA TTATAATTTT  61080
AGAATATGTT TATTCTAGGA CATATAGCCC TCAAAATCTG CTTACTATAT ACGTCTTATA  61140
AAATAGCATG GTTCTTTTTT ATAGTAAATA GAATTTTTAT TTAATTGTCT ATTGACTTTT  61200
TTTTTCCAGG GTTCATTGAA AAAATCCTTA GTGATATTGA CATGTCTCAA GTGACATAAA  61260
TTAGCCAATG ACTCGGAATG ATGGATTCTC CGAAGATTGG AAATGGTTTG CCAGTGATTG  61320
GACCAGGGAC TGATATAGGG ATATCTTCAC TCCACATGGT GGGGTATTTG GGAAAAGTTA  61380
GTGAACTTAT TTTTTGCCTG AGTGCAAAGT TTTTTTTTTT TCTCTATTTT TGAGACTTAA  61440
ATTCAATTTT GATGTTACCA GTTAACTTCT AAAAAATTGT GTCTTCCACG GAAATCTTAC  61500
AGTAATGGCG AAAGATTGTT TTAATGTGTT TACCTTTCTG TGTTTTATTG ATACATGAAA  61560
GTGGAAATAA AACATAGACC TTATGATTTA CTGTTCTTTG AAAATATGGT ACATAAATTC  61620
TCCCGGGTAA TTGATGTTAC TTTTTTCCTT GCAAATAAAA TTGATACTAT TCTTAACACA  61680
TAAAATTTAA TATTTAAAAC TATAACATAA TTCTTTTTGG AATAATAGCT GTATTTAAAG  61740
GCTTATATGC ATTTCTTTTG TTTGCCATGT TTAAAATACC TTGTCAGGAT ACTTGTAATT  61800
GAAAATTATA ATTTTTTCTG GTTACCTTTC CATTTAACTT TTAATATTTT GATATATTCT  61860
AGGAATGTCT ATATTTTAAT TTGCTTTATT TCTCTTTTAG AATTTTGATT CAGCTAAAGT  61920
TCCATCAGAT GAGTATTGCC CTGCTTGTAG AGAGAAGGGA AAGTTAAAAG CCTTAAAGAC  61980
TTACCGAATT AGTTTTCAAG AATCTATCTT TTTGTGTGAG GATCTGCAGG TAAAGTATTA  62040
ATCTTATATA GTATATATAA GATTTTTCTT TTTTCTTTTG CTTTTTTATT AATTGTTTTA  62100
AAAGTTTACT CATTTTTTGT TTTTTAGACT AGATTTTTAA TATGTAATCT CAGTTTGTAA  62160
GTCTGTCTGG TATACAATGT TATTTTTCCA CCTACCTTTA CTTGGTTGCG TAAAGATGTT  62220
CGTTTTTATT GCCATTTGAT TTGCGAGAGG AGAAAATACA TTTCAAGGTT TTTTTCTTTT  62280
TTTTTAACCT TTTGGAGGTC CTTGTTAGCT ATTAGCATAT AGTAGTTACT CTCTCATCTC  62340
TTTGGTTTAT CTTTGCAACT GATGGGAAAA GTTATGAATT TCTAATGTAC CTGGAAGAGT  62400
ATTTTGGAAA TTGGTTAGTC CAAAACCAGT ATATATACTC TGAACTAAAG AGAGTATAGA  62460
ATCTTGTAAA TTCTAAAAGA TCCTTTTAGA AGCTCTAAAT CGCTTTTAGA ATTATAGTAA  62520
TTTGTACCGA CTGGTACGGC TTTTATATAG CAGCTCATTA AATTCTGTAA TACTCCACAT  62580
TTTATTGTAT TTGACAGTTT ATGAGACTGT CTCATACACT TTTAATTCTC AGAACTTTGC  62640
AAGATTTGTA TTCCTATTTC ATGAATAAGA AAATAAATTG ATTTCAGAGG GTTTGGGAAC  62700
ATAAGATCCT GATACAGTGG CAGAGCTGTG GTTGGAATAC AGACTTCTAA TTTCAGATCT  62760
GTTTATTCCA GCAAAAAATT AGCAGTTCAT CAGAATTACC TGGAGTGCTT TTAATAAATT  62820
TCTGAGTATC ACCCCCAGAT GCTGATTCAA TAGAGTTGGC CCAGAATTCT GTGGTTTTGT  62880
AACATTTGAG GATGAGTCTG ATCATCATCA GCCAGGTTTG GAAAATACTA GACTAAATCA  62940
CATGGTTGTT AATAGATACT TATGCTGGGT ATAATTTGAA GTAAAGTAAT CCCAGGCGTG  63000
TCTACAAATA TAAATTTCTT TATGTTTATA TTCAGTAATT TTTTTTATGA GTGTCACTGT  63060
TTGGCACTGT TGCAGATACA ATGTTAGGAT ACAATAATAA AACAAAAATT TCTTGCCCTT  63120
AAGGAAGTTA TGTCATAGAG TGGGAAAGAC AGTGAACAAG TATGTGTTTT TCTGTCAGGT  63180
```

FIG. 6.24

```
GATAAAAAGT GCTGTGGAGA AAAATAAGGC AGTAGGGACT GGAATGCCAA AGTAGGGGGA   63240
GTTTGCAATT TTAAATAGGA TGGTGAGGGG AACGCTTCAA TGAAAAGTGC AATTCGAGCA   63300
AAAGCCTGAA AGAGGTGAAG AGCAGTGAGC TTTCTAGGCA GGGGAAGCAA GTTCCAGGAA   63360
GGCCCTGAGA GAATGGAGGC TGCCTGTCAT GTTTGTGCTA CTGCAATGAA AGCAGCAGAG   63420
CGATAGAAGG TGGATCAGAA AAATAATGGG GGAGCTGGAC CAAGTAGGGT CTTATAAGCC   63480
ATTGTAAGCT TTCTGGCTTT TACTATGGGT GAAACCAGGA ACCATGGCAG AGATGTTGGC   63540
AGAGGAGTGA CATAAGTTGA CTTCAGTGTT AAAAGCATTA CTGTGGCTGC ACTGTTGAAA   63600
ATATATGTAA TGGGCAAGAC CTGAAGCAGG GAGATTAGTT ATAGTATAAT ATGAATTATA   63660
TTTGGTCCTT GTCTATGGTT TCCGTTACAG AGCTAAAAGT CTTGGAATTT CCTGAATGAT   63720
AAGAGTGTCC TGTTATTCAG AATGAGCCTG TTTGCTAACA CCGGGGTTCA TACTATTGTG   63780
GTGACTTAGG ATGGAGCCGT AGATAGCCTC AGATGGGGCA GTAGCTGGA AAGACCACAT    63840
GATTAGAGAA TTAACGGGTT AGAACTTTTA GCCCCACGTA CAGGCCTCCA GGAAAGGAGT   63900
GGAGGGGCTG GAGATCAAGC TGTATAAAAA TATCAAGATT TGGATTTAAT GAGTGGGTTG   63960
CTGGGGGCTG GTGCCGTGTA GGAGGTGGTA TGCTTAGAGG AAGTGGAAGC TTCATACCTC   64020
TTCTGTCCCA TACCTTGCCC TACTCATTTC TTCATCTATA CCCTTTATAA TATCCTTTAG   64080
GATAAACCAA TAAACATAAG TAAGTGTTTG TTTGAGTTCT GCGAGCTGTC CTTGCAAACT   64140
AGTTATGCCC AAGAAGGGGG AGTGGGAACC TTTGTAGCCA GTCAGTCAGA TGTACTGGTG   64200
GCCTGGATGT GGGATTGGCA TCTGAAGTGG AGGGAGTCAT GGGACTGAGC CCTCAACCTG   64260
TAGGATCTGA CATGGTCTCT AGGTAGATAA CATCCAAATG GAATTGGATT ATAGGATACC   64320
CATTTGGTGT CCTCTGGAGA ATTGCTTGGT GTGGGGAAAA AGCCCCCACA CATCTGGTCA   64380
CAAAAGTGTG CTGGGAGGAT AGAATATGTG AAAATTGTCA TAATCAAAAT GGAGTCACTT   64440
GTGTTAAAAA AGAAAAAAAA ATCCTGACTG GCCAGGCACA GTGGCTGACA ACTGTAATCC   64500
CAACACTTTG GGAGGCTGAG GCAGGAGGAT TGCTTGATCC CAGGAATTGG AGACCAGCCC   64560
ATGCAACATA GTGTGGCCTT GTCTCTACAA AAAAAAAAAT TTAAATTAGC TGGGCATGGT   64620
GGTGTGAGTC TGTAGCCCCA GCTACCCGGG AGGGGGACTA CGGGTGCACG GCACCATGCC   64680
CAGGAGGTCC AGGCTGCAGT GAGCTGTGAT TGTGCCACTG CATTCCAGTC AGGATGACAG   64740
AGTGTGAGAC CCTGTCTCTA TTAAAAGAAA AAAAAAGAC AAATAGATCC AGGAAAGGCT    64800
ATGAAGAGAG AGCTTTCATG CATAAATACC AAAATATCTC AAAAGACTCT GCAAAAACCA   64860
CACCCTTGCA CAAAGGCCAT CATGAAATAC TTCTGAAATA CACAGAAAAT ACATCATGAA   64920
ATAAATACAC AGAAAATACT TCTGCAAGGA CATCTGCCCA GCAACTGCCT GGTCCATCTG   64980
TGGACGGGTG TCATCCTTGT TATTGATCCT TGTAGCCAAG GTAATTATC TCAAAACAAG    65040
TATGTGATCC TCCTTATTTT CCTTTAAAAA CCTTTTGTCT TCCCTTACCT CCCTGAACAC   65100
ACACAGTTTA CTATGGCATG TGTATTCCCA TTGGAATACT TTATTCCTGA ATAAATGTCA   65160
CTTTCTTTTT AGAAGCTTCT CTTTTCTTTT TATTTAGATT GATAAGTAGA AAGGAAAAAA   65220
AGCTTTTTTC CCTTTGGACT AGTTGAAGGC AGTTGCAGTA TTCTGGGGGA GAGGGTGGTG   65280
GCAGAGGTGT TGAGGCATGG TTGGAGTTTA TTTATACTTT GAAGGTAAAG CCAACAGGAT   65340
TTGCTGAAAG ATTGGGATAT GGGGTTGGAA AGAGGAATCA AGGATAGTTC CAAGATTTTT   65400
GGCTTGAAAA ATTAGAAGAA TGGAATCGTG AATTACTGAG CTGGGAAGAC TTGGAAGAGC   65460
AAGGTTTTGG GGAGAAGATC AGGACTGTAA GAATAGAGAA GTCCTTGTCC CCAGGAGTTA   65520
GGTTTTTGGC TATTAAAGTT AGATGTACTA CATAGATTTT TAGTTGGTTT TTGTTTTTT    65580
GTTTTTTTTT TTTTTTTTTT TGAGACGGAG TCTCGCTCTG TCACGAGGCT GGAGTGCAGT   65640
GGTGCGATCT CGGCTCACCG CAACCTCCGA CTCCCTGGTT CAAGGGATTC TCCTGCCTCA   65700
GCCTCCTCAG TAGGTGAGAT TACAGGCATG TGCCACCCAG CCCAGCTAAT TTTTGTATTT   65760
TTAGTAGAGA CGGGGTTTCA CTATGGCCAG GATGGGCTTG ATTTCCTGAC CTCAGGTGAT   65820
```

FIG. 6.25

```
CCACCCACCT CGGCCTCCCA AAATGCTGGG GTTACAGGTG TGAGCCACCA CGCCCAGCCC    65880
GGAGTTTTGG TTTTTGAAGC ATTCTTTTTC AAGTGATAAA GCAAAAAATA TATAATCAAG    65940
AATTTTAAGT ATATACTTTG GAAATGTTAA AAAGGAACAT GAGTAATTTA TTATTATTTT    66000
TTTAATTTCT AGTCAGCAAT GAGAGCCCAG TGTACTTTAT GAAGTAGATT GGTTTACACC    66060
AGGAGTGAGC AGACATTTTG TATGATGCAC AAACAAGGAA TGATTTTTTT GTTTTTTAAA    66120
TGGTTAGGAA AATATCAAAA TAAAAAATGC CAGAAAAAAT CAAAAGAAGG GCCAGGTGCA    66180
GTGTTTCACA CCTGTAATCC CAGCACTTTG GGAGGCCAAG GTGGGTGGAT TCTCTTGAGG    66240
TCAGGAGTTC GAGACCAGCC TGGCCAACAT GGTGAAAACC TGTCTCTACT AAAAATACAA    66300
AATAGCCGGG TGTGGTGGCA TATGCCTGTA ATCCCAGCTA CTTGGGAGGC TGAGGCAGGA    66360
GAGTCGCTTG AAGCCAGTGG CAGAAGTTGC AGTGAGCCAA GATTTGAGCC ACTGCACTCC    66420
AGCCTGGGCG ACAGAGGAGA CTCTATCTCA AAATAAATAA ATAAATAAAT AAATAAATAA    66480
ATAAATCAAA AGAAGAATAC CCTTTCATAA TATGTGAAAA TTAAATGAAA TTCAAATTTC    66540
AGTGTTCATA AATAAAGTTT TACCGGAACA TAGCCATGCT CAATCATTTA TGTATTGTTC    66600
ATGGCTTCTT TTGCATACAA CAACAGAGTT GGGTAGTTGT GACAGACTAT GTAGCTCATA    66660
AAATCTAAAT ATTTATTATC TAGCCCTTTA TCAGTAAACT TTGCTGATCC CTGTATAAGT    66720
CCTCTGAATC AAATTATTTC CAAAGAGTTC CGTTATAAAA TTTGGAGTTT ACTCTGCTGT    66780
AAATTGCAAA GAACCATTTG GAAAACCTCT TTTAGTCAGG TATTTACATT AAAATGTTCC    66840
TTGATTTGTA AACACTAATA TTCAAGACTG GTCCAAAATT ATACCAAATT GAAACTCTCA    66900
AGTGTTTTTA AACAGTAGGA AGTTTTAACT TTTTTTTTTT CGTGGAGTAG TCTATCATTC    66960
AGCGTTTACT TTGGAACATT TAATTAGTCT TTTTTAAAAA CCCATGAAAT TTATAATAAA    67020
AATTTTAAAT CATTAATGTT GAGTAATCAA AGAAAACTTT TTTTGTTTTC TCCATTTGTA    67080
AAATGAGTAC ATTATTATTA TAATTTGTCT TTGGCCATAC CTTGTTGATA ATTACTTATA    67140
CAAGTATAAG AAGACATGGT ATGTTTTCCT TTTTCCTATT TCACAAGAAT AAGTACAGGA    67200
ATTTACTTAA GCTGCTCCAA AACTCAGTGA AAGAGACAGG ATTAGGTTTT TTTCAGCATT    67260
GGATTTTAAA TGATACTAGA TGGTTGCGCT GGGCTAAAAT ACTAATGCTT TGTGTATATT    67320
TTTATGACTT TTTTGAAGAC AGCTTAAAAG CTTTATTCTA GTTATAAAAA TGATACATGT    67380
TCACTGTAAA TAGAAACAAG TCAGGTATAC AGAGATACAA ATATTTAGAA CATGTGGAAA    67440
GAGGCAACAA AATTTTATAA AAAGAAAAAA GATAAAAATC TGAAATCATT AATTTATAAG    67500
GGAAAAATCA GGGCAAGGAC AAATTATATT ACAGATTGGC CTATGGTGGG AGCACAGATT    67560
ATATAGAGAA AAGTCAGTGA AGACACTTGC GAAGAGTGTG GGTGGAAATC ACTAAGTTTT    67620
GCAGTCCCGG GGCCTCTTAT GGTTATTAC TGTTTTGTTC TTTTTTTTTT TTTAATATGC    67680
ATTCCTTTGG AACCAAGGGT TTATTATGTT TTGAATAAAG TAGAGGTGTA AGTAGGATGC    67740
ATATACCATG ATCTTGACTA CTTGAGATTC ACAAAGGGTT TTCGTCTCAG GATTTTTTTT    67800
TCTCTTAAAA AAATTTGTAT TAATTTTTAA ATTGTAAAAA AATTCATCAA CTTAACCATT    67860
TTTATGTATA GAGTTCAGGA GTATTAGGTA TATTCACTTG TGCAGCAGAT CTCTAGAACT    67920
TTTTTCATCT TGCAAAACTG AAACTCTGTA CCCATTAAAC AACCACTTCC CATTTTCCTC    67980
TCCCCCAGCT TCTGGCAACC ATTCTAGTTT CTGTTTCTTT TCTTTTTTTT TCTTTTGAGA    68040
TGGAGTCTCT GTCGCCCAGG CTGGAGTGTA GTGGCATGAT CTCGGCTCGC TGCAACTTCT    68100
GCCTGCGGGT TCAAGCAGTT CTCCTCCCTC AGCCTCCTGA GTAGCTGGGA CTACAGGGGT    68160
GCACCACCAT GCCTGGCTAA TTTTTTTTTT TTTTTTTTTT TTTGTATTTT TAGTAGAGAC    68220
GGGGGTTTCA CCATGTTGGC CAGGCTGGTC TCGAACTCCT GACCTCAGGT GTTCTGCCTG    68280
CCTCAGCCTC CCAAAGTGCT GGGATTACAG GCTTGAGCCA CTGTACCCGG CCTCTAGTTT    68340
ATGTTTCTAT GAATCAGACT CAGTACCTCA TATAAACGGA ATCATACAGT ATTTGCCTTT    68400
TTTGTGACTG GCTTATTTCA CTTGGCATAA TGGCCTCAAG ATTCATCCAT GTTGTAGCAT    68460
```

FIG. 6.26

```
GGATGAATAT ACAGTTAGGA GTTCCTTTTC TTTTTTAAGT CTTAATCTCC AGTTTATTTC   68520
TGTTTATTTA TTTATTTTAT TATACTTTAA GTTCTGGGAT ACATGTGCAG AACGTGCAGG   68580
CTTGTTACAT AGGTATACAC GTGCCATGGT GGTTTGTTGC ACCTGTCAGC CTGTCATCTA   68640
CGTTAGGTAT TTCTCCTAAT GCTATCCCTC CCCTAGCCCC CTACCCGCCG ACAGGCCCCG   68700
GTGTGTGATG TTCCCCTCTC TGTGTCCGTG TGTTCTCATT GTTCAGCTCC CACTTACGAG   68760
TGAGAACATG CGGTGTTTGG TTTTCTGTTC CTGTGTTAGT TTGCTGAGAA TGATGGTTTC   68820
CAGCTTCATC CATGTCTCTG CAAAGGACAT GAGGAGTTTC TTACTTTTAA GGTTGAGTAA   68880
TATTCCACAT TATGTGTATG CCACATTTTC TTTATCCATT CACCTATCTG CAGATGTTTG   68940
AGTTGCTTTC ACTTTTTGGG AATTGTGAAT AATGCTGCAG TGAATGTGGG TGTGCAGGTA   69000
CCTTTTCAAG ATTCTGCTTT TGAGTTTTTT TTGGATACGT ACCTTTTTAT GATGCTTTAA   69060
ATACATATAT GCTATTTTTA AAGGATTCTC AGTTTTCTGA CATATGATAG GACTTAGGAA   69120
GTAATCTCAA AGCATCATGT TGACAGGTTG TTAGTTGATG GTGACTGCAG CTAGTTGGAA   69180
AGTCAGAAGA ATCTAGAACT TGTCCATTTA TACTAAAGAA TTTCATAGTA AGTGCAGTAT   69240
TATGAGTGTA ATGTTCAATT GGTAGAAGAG GCTATCTGAG GGGATTTAGT GCATTTCAGT   69300
TATCTGTTGG TGTGAAACGA ATCACCTTGA AACTTAGTCG CTCAAAAATT TTAATGGTGG   69360
CTGGGCATGG TGGCTCACAT CTGGAACTCC AGCACTTTGG GAGGCCGAGG CAGGCAGATT   69420
GCTTGAACCC AGGAGTTTGA GAGCAGCCTG GGCAACGTGG TGAAACCTTG TCTCTACAGA   69480
AAATACCGTG GCAGGCGCCT TTAGCACCAG CTACTTGGGA GGCTAAGGTT GTAGGATCTC   69540
TTGATCCCAG GAGGCAGAGG TTGCAGTGAG CTGGGATCGT GCCACTATAC TCCAGCCTGG   69600
ATAACAGAGC CAGACCCTGT CTCAAAAAAA AATTTTAATG GCTCCATTTA TTATTTCACA   69660
TGATTATGTG AGTTGACTAG GGAATTCTTA CACATCACAC CATGTCAGCT GGGACAGCTG   69720
AAATGTCCAC ATGGCTGGCA GTTGGTACTA GCTGCTAGCT GGAAGTTGAG TTCAAATAGT   69780
CAGCCAGGGG TCTCAGTTAT TTTCCATGAG GTTCTCTCCA TGAGGCCAGC TGGGCTCTTC   69840
ACAGTGTGAT AGCTGGGACT AAGAAGGAGT GTTCCAGAAG AAGGGCTTGT CCTCTTGAGC   69900
CAGTGCTTAT CAGGCCTCTA TGTATATCAT GTGTGCTAAT GTTCCATCAA AGCTAGTCAC   69960
AGGGCCAAGC CAACTCTGTA CAGTGTAGGG ACTGGCTGCA GGAGGGCATG AATTACCAGG   70020
AGGTGTAGTT CTCTAGTTCA TAGGGAGGGC CATCAAGATA GTAGTCTACC ATACTTGTGT   70080
AAAAGAAGGC ATTAATTAAC TATTATTATT ATTATTATTA TTATTTTAGA GACAGGGTCT   70140
TGCTCTGTTG CCCAGGCTGG AGCAGTAGAG TGGGGCAATC ATAGCTCATT GCAGCCTCCA   70200
ACTCCTGGGC TTAAGCAATC CTCCCATCTC AGCCTCCCAA GTAGCTGGGA ATACGGGAGT   70260
GTACTGCCAT GCCCACCTGA AAAAGAAGGC ATATTTAAAA AGCAGACCTT TAGTGTAGAG   70320
GGTTCTTGAA TTTGTTATTT AAAATATTCT GGTAGTTTTT AAACTTAGGA AAGACCCACT   70380
GATTCTTTTA GTGATATGTT TACATTGTTG TTATTTGGCA TAAATTGTGT TAATGCACAG   70440
TAAGATTTCA TGAAGTCATT AAAATTCAGC CACTTGGACT CTAAACCCAA TAAAGATGTA   70500
AAACAGCAGT GCTATGAGAT GCATATTCAG TTTCAAAATA TAGGAAACAC AGAAATTACT   70560
CTGTGCACTT TTAATTTGAA AATACTTTTA AAATGTGTAG TATAATGTAG TGTCTGTCCC   70620
AAAAGAGTAA CATTCATTAT AGTGTTTCTT TACGTTGTTG AAAATTTTAA ATTCACTTAA   70680
CATTAGATTT TTATTAAAGC AAAAATATGT TTTCCTTATT AGCTTACCCT TTTGTAACTC   70740
AGATTAAACC CTTGATTGTT CAAATTAACC TGAAAAAAAT TATTCTTTTG GAGGCCAAAC   70800
TTTTGATTAA GTAGTTGTTT GTCTCTAATT TTTTCAAATT TATGTGTATA AATATAACCT   70860
GTCATCAAAT CAATGCTAAC ATTCTATACA TGTTTTTCAT GATATGAAAA CTATAAAACA   70920
TGAAGTTATT TGAATTTGTG TAGTTTTTAT CATTTTATTT TTACTTTCCA GTGCATCTAT   70980
CCTTTGGGCT CTAAATCACT TAATAACCTA ATTTCTCCTG ATTTGGAAGA ATGTCACACT   71040
CCACATAAGC CTCAGAAAAG GAAGAGCTTA GAAAGCAGCT ATAAGGATTC ACTTCTTTTA   71100
```

FIG. 6.27

| | |
|---|---|
| GCAAATTCCA AAAAGACTAG AAATTATATT GCTATTGACG GTGGAAAAGT TTTGAACAGC | 71160 |
| AAACATAATG GAGAAGTATA TGACGAAACC TCGTCAAACT TACCTGATAG TAGTGGTCAA | 71220 |
| CAGAATCCAA TTAGGACAGC TGATTCCTTG GAGCGGAATG AGATTTTGGA AGCTGATACT | 71280 |
| GTTGACATGG CTACTACAAA AGATCCTGCT ACAGTTGATG TCTCTGGAAC TGGCAGACCT | 71340 |
| TCCCCTCAAA ATGAAGGATG TACATCTAAA CTGGAAATGC CACTGGAGAG CAAATGTACA | 71400 |
| TCATTTCCCC AGGCTTTATG TGTCCAGTGG AAAAATGCTT ATGCTCTCTG TTGGTTAGAC | 71460 |
| TGTATCCTGT CAGCTTTGGT GCACTCGGAA GAGTTAAAGA ACACCGTGAC TGGACTGTGC | 71520 |
| TCGAAGGAGG AATCTATATT CTGGCGGTTG CTTACAAAAT ATAATCAAGC AAATACACTT | 71580 |
| CTATATACCA GTCAATTGAG TGGTGTTAAA GGTTGGTACT AATATTTTAT TTTTATTTAC | 71640 |
| TTATTTATTC ATCTGGAGTC AGGGTCTCAT TCTGTCACCC AGGCTGGAGT GCAGTGGCAT | 71700 |
| GATCATGTCT CCTTGCAGCC TTGACTTCCC TGGCTCAGGT GGGCCTCCCA CCTCAGTCTC | 71760 |
| CCAAGTAGCT GGAACTACAG TCGTGCACCA CCATAGCCAG CTAAGATAGT GAGATGGTGG | 71820 |
| CCCCACTGTC TTGCCCAGGC TGGACTCGAT TTCCTGGGTG CAAGCACCCT TCCCGCCTCA | 71880 |
| GCCTCCCAAA GTGCTGGGAT TACAGGCATG AGTCACCATT CCAGCCTACT TGTCTTTAAT | 71940 |
| TCTTAAAAAT ATTAATGTTG AGTTTGTCT CCCAGCATGT GGGAAAGATG TCATCCATTG | 72000 |
| CTTCTGTTTC CTGGAGGCCT GGGAGCAAGG AGCCCAGGAA CAGTATCACG AAGCTTGAGA | 72060 |
| TAATACCAGT TACATTATCC TGACTGCCCA AAAGGCAGTT TTTTTGTTTT TTTTTTTTAT | 72120 |
| ACTTTAAGTT CTGGGGTACA TGTGCAGAAC GTGCAGTTTT GTTACATAGG TATACGTGTG | 72180 |
| CCATGGTGGT TTGTTGCACC CATCAACCCG TCACCTATAT TAGGTATTTC TCCTAATGCT | 72240 |
| GTCCTTCCCC AACCCCTCCA TTCCCCATCA GGCCCCAGTG TGTGATGTTC CCCTCCCTGT | 72300 |
| GTCCATGTGT TCTCATTGTT CAACTGTCAC TTATGAGTGA GAATATATGG TGTTTGGTTT | 72360 |
| TTTGTTCTTG TGTTAGTTTG CTGAGAATGA TGGTTTCCAG CTTTATCCAT GTCCCTGCAA | 72420 |
| AGGACATGAA CTCATCCTTT TTTATGGCTG CATAGTATTC TATGGTGTAT ATGTGCCACA | 72480 |
| TTTTCTTTAT CCAGTCTATC ATTGATGGGC ATTTGGGTTG GTTCCAAGTC TTTGCTATTG | 72540 |
| TGATTTTTTT TTTTTTTTTT TTTTTTTTAA GACAGAGCCT CACTCTGTTG CCCAGGCTGG | 72600 |
| AGTGCGATGG CATGATCTCA GCTCACTGCA ACCTCCGCCT CTCAGGTTCA AGCAATTCTT | 72660 |
| CTGCCTCAGC CTCCCAAGTA GCTGGGACTA CAGGCGCCCA CCACCAGGCC CAGCTAATTT | 72720 |
| TTGTATTTTT AGTAGAGACA GGGTTTCACC ATGTTGGTCA GGCTGGTCTT GAACTCCAGA | 72780 |
| CCTCATGATC TGCCTGCCTT GGCCTCCCAA AGTGCTGAAA TTACAGGTGT GAGCCACCAT | 72840 |
| ACCTGGCCTA GGCAGTCTTT TTCAAAACTC TAAGACTGTG CTTGTGTCTC AGGGTGTCAG | 72900 |
| GATAATAGTG GTTAGTTTTA AGTGTTTAAA CTACTGAAAA GCAGAATGAA GAAGTGAGTA | 72960 |
| AAAATCACCC ATAATCACAC AACCTCCTAA GATCTCTTGG CACAATAAGG GATATGTTTT | 73020 |
| TCATTTTATT CTCTGTAAAA TAGGATACTT ATGAACCCAC CTCCCAACAC AGGAAGAATT | 73080 |
| AAAACATTCC CAATAACTTA CATTTACCTA TGCGTTTCCT CCCATCCCAT TCTCTACCTC | 73140 |
| CCCCCCATAA GTAATCATTA TCTGAAATGT GTTTCATCAT TCCATCTTTT CTTAGTTTTT | 73200 |
| CTTACATGTG TTTATCTAAA CAGTATACAG TAGTCTCCCC TTATTGTAGT TGTACTTTTC | 73260 |
| TTGGTTTCAT TTAACCCGAG GTCTGAAAGT AGATGAGTAT AGTACAGTAA TATATTTTGA | 73320 |
| GAGAGAGGGA GACCACATTC ACATAACTTT CATTACAGCA TATTGTTATA ATTGTTGTAT | 73380 |
| TTTATTATTA GTTTTAATCT TACTATGCCT AATTATAAAA CTTGATCATA GGTATGTAGT | 73440 |
| TATAGGAAAA AGCATAATAT ATAAAATGTT TAGTTACTAT CCAAGGTTTT AGGCATCCAC | 73500 |
| TGGGGTCTTG GAAGGTATCC CTCTCAGATA ATGGGGGATG GATGGTACTG AACCCTGTAT | 73560 |
| ATACAATGTT TTTCCCTATA CATACATAAT TATGATCAAG TTTAATTAAG AGTAAATTAA | 73620 |
| ATGTGGGCCA GGTGCAGTGG CTCACATCTG TAATCCCAGC ACTTTAGGAA GCTGAAGCGG | 73680 |
| GCAGATCTCA TGAGGTCAAG AGTTCGAGAC CAGCCTGGCC AACATGGTGA AACCCCATCT | 73740 |

FIG. 6.28

```
CTACTAAAAA ATACAAAAAT TGGCTGGCTA TGGTGGCACA CGCCTGTAGT CACAGCTACT   73800
CTGGGAGGTT GAGGCAGGAG AATTGCTTGA ACCCAGGAGG TGGAAGTTGA ACAATCACTT   73860
GAACCTGGGA TCACGCCACT GCACTCCAAC CTGCCTGGGT GATAGAATGA GACTCTGTCT   73920
CAAAAAAAAA AAAAAAAAAA AAAAAGTAAA GTAAATGTGG CTCAACATGT TGCTGTCAGT   73980
TGGAACATTT GTTTCTGATC GTGTCTTCCA CCCACAAATT GAATGCTTTT TCCATCTTAA   74040
CACTTATCAG GCACTGTGGC CATAACTTGA GCAGTTGAGA TGCAACAGCA AAATTAGCAC   74100
AAATTTCTTT TTCTTTCTTC GCAGTTTCAT GGATAAGAGA TTTGTTCTTA GATCTCAGCA   74160
ACCTCAGCAT ATGATTTTTT TCTTTAAGTT GAGAACTTTG ACCTTTTTAC TTAGAGAAGC   74220
ATTTTACAGC TTCTCTTTGG CATATCTGAA TTGCCAGCAT TACTATGCTC GTGCTTTGGG   74280
GCCATTATTA AGTCAAATAA GGGTTGCTTG AACACAAGCA CTGCAATACC ATGGCAATAG   74340
ATCGCATCAC CAAGATGGCT GCTAAGTGAA CCACAGGCAG GAGTGTAGAC AGCATGGACA   74400
CATTAGACGA AGGGAAGATT CACGTTGCCA GTGGAACACA GCAGGACAGC AAGAGAGTTC   74460
ATGATGCTAC TCAGAATGGC ATGAAATTTA AAGCTTATAA ATTGTTTCTG GAATTTTCCG   74520
CTTAATATTT TCAGACCACG GTTGAGTTCA GGTAACTGAA ACCATAGGAA GCAAAACACG   74580
GATGAAGAGG GACCACTTCG TATTGCCTAA TTTAGTTTGT TTTGATCTTC TGGGACCTTT   74640
TTTTCTTGTT GTAAAAATTT ATGGGGCTGT TTATAGTTGT GGCTCATTGA TTTTTCATTG   74700
CTACATAATA CTTCCATTTT GTAAATATAA CAGAATATTC ATCTACCTGT CAGTGGACAG   74760
TGGGGTTTTT TTGCCATTAT AAATGCTGCT GCTGTGACCA TTTGGGGGGC AAGTCTCCTG   74820
GGGCACAGTA TGAGTTTCCC TTCTGTATAA CAAAGGAATG GAAAATTATA GACTTTCGTG   74880
TCCAAATTTA CAAGATAATG ACAATTGTTT CCAAAGTGG TTGTACCAAG CAATTCTCCC   74940
ATTAATAGTG TATATAAGAG GTCTTCCTGA TCCATATATT CTTCTTGGTT TATTTTCACA   75000
CTTTTGAGAT TTTTGCTATT TGAGTGGTAT AAAATGGTCT GTGATCTTGA TTTGCCGTTT   75060
CCACATTTTG AAGAGGTTGT CGGCTCTATG TGTATATATT GCTCATATTT GTTCCCTCTT   75120
CTGTGAAATG CCTTTTGTAT CTTATCCCTA TTTGTTCTGT TCTGTTGATT GTCACGTTTT   75180
AATTGATTTG TATGAGTTTG TTCCTTGTAT CATTGTTGCT AGAGTTACAT CAGATGTGTT   75240
GCTGAATCTG CTCCCAGTTT GCAGCTTGTG TTTTTACTTT TTAAAAACTG TCTTGATTTA   75300
TAGGGAAGTC TTTATCTTTT CATTTGGAGC TAGTAATGTT TGTGGCTTTT TAAAGAAATT   75360
ATTACTATTC CCAAGGTCAG AAAATCATTC ACCTATATTT TAACTGAAAA GTTATAAAGT   75420
TTTGCTTTTG ACATTGAAAT TTCTCATTCA GTTGGAATTC ATATTGATGT GTGGTATGAG   75480
GTAAGGATCC ATTTTTTTCC CATTTGCATA GCCAGTTTTT GTAGCTCCAC TTTATTTTCT   75540
CACTTGATCT GCCATGCCAC CTCTAGCATG TATCAACATA TCATGTATGT GTGCAGCTGT   75600
TCCTTAACTC TCAATTTTAT TCTCTTGGTT ACTTGTCTA ACCCAGCACT CATACTTTTT   75660
AAATTATTAT GGCTACCTTG TAGGGCAAGA ATCCTCACTT TTATTCAACT TCTTTTGAAG   75720
TGTCTTGATG CATATTTTTT CTGATCTTAC TTGGCCATAT ATATTTTGGG GACAGATGTG   75780
ACATCATACC AAGCTTTCTT TGCTTGACAT TGTAGATATT TTCTTATTCA TTAATGTGCT   75840
AAAAATTTTG AGTTGGTCA TACAGTCTTT TATATGGATC TTATACATCG TTTCCCTCTT   75900
GTTAACCATT CAGGCTGTTA CTAGTTTTTG CTGTTGTGAA TTAACACCAG GACAAATATC   75960
CATATATCTT TTGAATTAAT TACTGACTAG TTTCCTAGGA AAGATATTAG AATATGAATA   76020
TTAAAGGTCT TGCTGAATAC AGTTTCAGA ATGGTTGTAC CAATATATAA TTCCATTTTC   76080
ATTATGTAGA AAAAATACCT CAGTGTTTTC TAACCACCTT TGGTTAGAAC ATTCAAGACG   76140
TTATGGTTTT GTTAGGTAAG AAATATTTTG TTTCAGTGTA GGTTTTCTTT GAGACTGAAC   76200
TTTTTTGTGT GTGTCAGTCA TTTACAGTTT TTTGCAATTT TTAAAATTCA GTTCTCACA    76260
AGCATTTTGC CTTTGACTTT TCTTCTATTT CTGCTTTCTC TAATTACAGA AACCCCAGTG   76320
TTAAGTAGGT GACAGTTCAG TTGTTTGCTG CAGAAGAGCA GCAGTTCAAT ATTGGAATTA   76380
```

FIG. 6.29

```
ACTTTAATTT TATGTTTTTA ATCTGTTACT AATTTTTTAC AGAATAATTG TAGTTTTTAT    76440
AATCTGGTTA ATTATATGTT TGAGCTGCAT TACTTTGCAA TGTAAGTTTT TTTTTTTGGC    76500
ATGGTCAAAT AACAAAAATT CTGGTTAATG CTTATTTCAT ATTACAGGAG AATCCAGATA    76560
TTTCATTAGG GAAACATATA AGCAGAGTGT GATCAGGCTG TATGAATTAT TTATAAGAGA    76620
TGTGAGTGAA AAGATCTATT TGTAGCTTAA GAGTAAGTAG AGTCAGATGC ATGTAGAGTC    76680
TTTTATTCAA AATAATTTTC TTATTAATCT TGGATAGTTT CTTGTCACAG TAATTCCATT    76740
TTGAAGATAA TAAATATTAC CATAAAGAAG TGATCAAAAA CATAGATATG TGTGCCCAAA    76800
GGTATTTATC ACAATAGTAT TTATAATAGT GAAAAAAGAA ACAACTAAAA TGTCTGGCAA    76860
TAGGAGAATG ATTAATAAAG CGATGTTTCA GCTGAATATA GTGGCATGCG CCTGTAAGCC    76920
CAGCTACTCA GGAGGTTGAG GCTGCAAGAT GGCTTGAGCC CAGGAGTTAA TGACCAGCCC    76980
AGGCAACATA GCAAGACCCT GTCTCCAAAC ACACAAACAC ACACACAAGT GCTATGTTTC    77040
AGTCACTGTA TAATAACTAG CCAGATTTTT TGTTGTTGTT GTTTTGTTTT TGTTTTTGTT    77100
TTTTGAGAGA GCATCTCACT TGCCCAGGCT GGAGTGCAGT AGTACAATCA CAGCTCACTG    77160
CAGCTTGTAG AACCCTAACC CTCCTGGGCT CAAATGATCC TCCCACCTCA GCCTCCTGAG    77220
TAGCTGGGAC TACGGGTGGG TACCACCATA CCCAGCTTTT TTTCTAAGAG ATAGGGGTTT    77280
CACTATGTTG CCCAGGCTGG TCAGTTTTTA ATGAAGCACA TTTGTGTAGA CAAAGCAGGA    77340
TGTGGAACCG GATAAACACT ATGTTGCCAC TGAAGACCCC TTCAAACCCC TCAAAAATGA    77400
CATAGAAGGG AAATATGAGA TATTAGTTTG GGAAATAATT GTAACTTTAT TAAGACTCCT    77460
TATAAATTTA TCTGTTCCTA TGACCTGGCT AAGTTCAATA AAAGTTACAC AGAGTGGAAT    77520
AAATGGTTAG ACATCATTTG TAGTATAAGT AATTGCACAT AAGGAGGTAA CTTTAGCTGT    77580
TTTAGAGATA GACATAGTAT CTGAAAGGTT AGTTATTTTA CTAGACCTGT GATTATTTGG    77640
GTGAGAAAGG CTTTCACTGA GATTTTACCC ATTCAGTAAG TACTAATGAT ATTGTGCTGA    77700
TAGCATATAT TAAGGGAATA TATGGTATAC CACAGAGAAA GAATTAAGGA AATTTTGTGT    77760
TTTGCTTTTT GTCTGTTTGC AAAACTTACT GACTCAGCTT TCATTCTTGG GAATGTGTCA    77820
GTTTTCTGTG GGAAGATATA CATTGATGAG GAATTGATAA TGTTCTCTGT ATTTTCTTAG    77880
ATGGAGATTG TAAAAAACTT ACCTCAGAAA TATTTGCAGA GATAGAGACC TGTCTGAATG    77940
AAGTTAGAGA TGAAATTTTT ATTAGCCTTC AGCCCCAGCT TAGATGCACA TTAGGTAAGT    78000
AATTGGTAAA ACTTACTTGT ATTATACTCA TCTACCATAT AGAAATATGT ACCTCATAAG    78060
GAAATATAAT ACTGTTTGAT TACCTTGGAT GATCATATTC TTGGGAGAGA GAATCTGAGT    78120
AGTTTGACTT AGGAATCTAC CACTGGGTAA GTTATTGTAG GGCAGAGCTG TTCCATATAA    78180
ATATGTAGGC TGGTGTTCCA CCTCTTGAGA GTGGGTGCAG TTCTCAGAAC CAGGAGAATT    78240
TTAGGGGGCA TATCATTAGT TGCTTCTCTA GTACGTTTCC TAGTAGACAG ATCTAGCATT    78300
TTTAACCTCA ATTGTGCATT AAAAAGCACC GAGGGAATTT AAAAGTAAAT GCCAATGCTG    78360
GGGCATTTGA ATTAGGATCT CAGGGATGGG GCTCAGGAAA TCAGTAATTT TTAGAAACCC    78420
CACATGATTG TTATATGTAC CCAGGGTTTA GAATCTCATC TAAACCAACC ATAGTAATTC    78480
TACTTCCCTA CCAGTGATTG GTTTAGGAAT GTCCTTGTGG TAGAGTTTTG GCCAGTGGAT    78540
ATTAAGAGAA ATATGCTGAT GGCCTTTTGG GAAAGCTTCC TCGCCTTTAG AAAGGGCACA    78600
AGGATGGGAC CTCTTTGTTC TCTGTGACTT GGTTTTTGGC CTGTGGGAGT GGCGTGCAGC    78660
AAGTGAGCTA GAGAGTCTGT CCAAACCTTT CTAAATTTTT TTAGTATTGC GAAAAGGAGC    78720
TGCGGGGTTT TTTTGTTTGT TTTTGTTTTG AAAGGGCTTT TTGTTTTATT TTTCTTGTAT    78780
CCTTGTATTA ACTCTTCTAT TAATGTTATA GTAGCAGAAT ATGATACTCC CTATTAGTAA    78840
TAACCCATAT TATGTAAAAT ATCAGTGCCT TCTAGTTTTT CTCTCAATGA GTGACATTTA    78900
ACTTATATTA AAAAATGATA TTTATATTTT ATAATAAAAT CAGTTGTTGC TACTGATTTG    78960
TCTAGCATGT ACAAAAGACA CCATGCTTCC AGATCATTAT AAAAATATGAT ATTTTATAAT   79020
```

FIG. 6.30

```
ATATTTACAA TATATTTATA ACATATTTAT ATACTTAGAA TATATTTTAT AAGGCTGGGC    79080
TTGGTGGCTC ATGCTTGTAA TCCCAGCACT TTGGGAGGCC AAGGCAGGCG TATCACAAGG    79140
TCAAGAGATT GAGACCATCC TGGCCAACAT GGTGAAACCC TGTCTCTACT AAAAATACAA    79200
AAATTAGCCG GGCGTGGTAG TGTGTGCCTG TAGTTCCAGC TACTCGGGAG GCTGAGGCAG    79260
GAGAATCGCT TGAACTTGGG AGACAGAGGT TGCAGTGAGC TGAGATCACG CCATTGCATT    79320
CCAGCCTGGG GACAGAGCGA GACTCCGTCT CAAAAAATGT ATATATATAT ATATATATAT    79380
ATGTGTGTAT GTGTGTGTAT GTGCGTGTGT ATATATATAT ATCGGGAAGC ATGGCATCTT    79440
TTGTACATGC TGGACAGCTT TTGACGTACT TCTTTGACTC ATGCTTCTGC CCCCTAATTT    79500
TCACTTTTTT TCCTACATTT TATTAAAATT AATATATAAT AGTTGTATAT CTGCTTTATT    79560
TTTCATGGAC TTATACATAC ATATTTATTC TGTTCTTATA AAAGTCTGAT TTTTCGTATG    79620
CCAAATTTCT GACATTTCCT CCTCTAGGCC TGAAGAACTG TTGTAATTTA TGCATCAGAT    79680
AGGCCCTCAG ATGGAATGAA TATTCTTTTT TCTTTATATC AAGGTGTAAT TTACATATAG    79740
TAAGACCGTT TTTAAGTGTG TACAGCTCTG TAACCCTCAC TACAATCAAG ATATAGGACT    79800
CTGTCACTCT AAAACTTCTC ACCAGGTTCA TCACCCCAG CCACTGATCT GTTGAGCGAA     79860
TACTCATTTC AAAGGAGCTT TTTCCGTAAG ATCCCTAGAG TTTAGATGGA AGGGCTTTCG    79920
TGGTGCATTT AGCAGATACC ATTTCCCTTC TAGACTCCCT ACTTCAGTTC CCAGTTGAAT    79980
TAAAGAATGG TTTCTCCCCC AGCCTGAGTC ACTACCCTTC TTATCCCTGA TAATTATTTT    80040
TGGAACAAAG TTACATCTTT TGCTCCACCT CCGCCATGGG CCTGGTTTTC TATGTAACAG    80100
AAGGAATTTT TAAATTATTG TTTTGTGTAA TCATAATAAT TGGGCAAGCA TACAGCTCTT    80160
TTCAGTGCAG GAGGATTCCT CTCTTGTTTT ACTGCCCATT CAAGGATAGG TGCTATATTT    80220
TAGCTGAAGA TCTTACTAAT GAAATGCTCT GTAATCATAT AACTTATTTA AAGATGTGTT    80280
TTGAGCTCTT TCATAATATT TTAATTCATG GAGAACTTTA TGTATTTTAG ACCTGAAGAT    80340
TTTATATTGT CATTATGAAA TGTAAATTGT TTGCTTTTTC AGTTAATATA TAGTTACAAT    80400
AGAATACGGA TTTAAAGGCT GATAATGAAT TACAAAATTG TGCTATATGA CATACTGTTT    80460
ATGCATACAG TGTTGCATAT TTTCATTTCT AGGATATTGA TTTGTATTTC TACTTACAAA    80520
AAAACTTTTT AAAACTTATT TTATGGCTGG GCCCGGTGGC TCACACCTGT AATCCCAGCA    80580
CTTTGGGAGG CCGAGGCGGG TGGATCACCT GAGGTCAGGA GTTCAAGATC AGCCTGGCCA    80640
ACATGGTGAA ACCCTGTCTC TACTAAAAAT ACAAAAAATT AGCCGGACGT GGTGTAGGTG    80700
CCTGTAATCC CAGCTACTCG GGAGGCTGAG GCAGGAAAAT TGCTTGAAAC CAGGAGGCAG    80760
TGGTTGCAGC GAGCAGAGAT TGCGCCATTG CACTCCAACC TGAGCAACAA GTGCGAAACT    80820
CCTTCTCAAA AAGAAACAAA AAAACTTTTT TTAATGTTTT TGTTCAAAAG TAGCAGTGAG    80880
ACTATCCCGC AAAGGTGACT ACTAAAATAG CCTTTGTAAC TACTGATATT TATAGAATAT    80940
GCTTAGGGTT AGGGTATAAC TCGCTTGTAT TATACTCATC TACCATGTAG AAATATGTAC    81000
ATCATAAGGA AATATAATAC TGTTTGATTA CCTTGGATGA TCATATTCTT GGGAGAGAGA    81060
ATCTGAGTAG TTTGACTTAG GAATCTACCA CTGGGTAAGT TATTGTAGGG CAGAGCTGTT    81120
CCATATAAAT ATGTAGGCTG GTGTTCCACC TCTTGAGAGT GGGTGCAGTT CTCAGAACCG    81180
GGAGAATATT TAGGGGACAT ATTGTTAGTT GCTTCTCTAG TACTTTTCCC AGTAGACAGA    81240
TCTAGCATTT TTAACCTCAA TTGTGCATTA AAAAGCACCG AGGGAATTTA AAAGTAAATA    81300
CCAATCATAG GGACATTTGA ATTAGGATCT CAGGGAAGGG GCTCAGGAAA TCAGTAATTT    81360
TTAGAAACCC CACATGATTG TTATTGCTTA GGTAATAACA CCTACTGTCT ACCTTGTGGT    81420
CCTGCCAAGG TGACTGTTCC TGGCCATGTT CCAGGCAACT GTAGTTCCAG CTAGGGGGA    81480
GAACTGGACC ATGGAAGTGA GGCTCTGTCC AGGGTAGGGG AAGGGATGGA AGGTGACTGT    81540
TCCTGGCCAT GTTCCAGGCA ACTGTAGTTC CAGGCTAGGG GGAGAACTGG ACCATGGAAG    81600
TGAGGCTCTG TGCAGGGTAG GGGAAGGGAT GGAAGGACTC AGTCTCTTGG GCCAAATCGG    81660
```

FIG. 6.31

```
TAAGGCAGCA TCTAAGCTCC TCTGAGAATA GGAAGGAGAG CAACCAATTG GAAAAAGAAT    81720
GGGAAACATG TAGATTCTCC TGCTTACCTT ACTTTCCAGT CTCAAAGCTG GAAGCCAGCA    81780
TTCACTGTTC AGTTATTTTC AATGACAACA AGATTCAAAT CTTCAGTTGT AAAGTTGTTA    81840
AAGGAAAGGA TTAGACTGAA AAGTTAAGAA GAACGGTAGA TGAAGAGTCC AAAGAGTTGA    81900
GGCTGGTCAT TTAACCATTG TGTGGCCACG CCCTCTCCAC AGGTGGAACA AGATGATCAG    81960
AATAGAAATG GCCAATTCTG ATGTGTTTCT ACAGTGTTTC ACTGATTACA TTTTTTAACA    82020
TCTGTAGCAA ACCATTTCCA TAATTTTTTT TTTTTTTTTT AGAGACGAGG TCTCGCTCTG    82080
TCACCCAGGC TGGTATGCAG CGGCATGATC ATAGCTCACT GCAGCCTCAA ATTCCTGGGC    82140
TCAAATGAGC CTCCTGCCTT AGCCTCCTAA GTAGCTTGGA CTACAGGTGT GTAGCACCAC    82200
TCTCAGCTAA TTTATTTCAT TTTATTTTTT GTAGAGATAA TGCCTCGCTA TATTGGCCAG    82260
GATGGTCTCA AACGTTCATA GAAACTGGTT TTAGGTTCCT AGAGGCTGGC AGCAATTCTC    82320
AGAGGTAACG CAAGCAGTCT TCCTGCCTTG GCCTCCCAGT GTGCTGGGAT TACAAGGTGT    82380
GAGCCACCAC ACCTCATCAA TTTTTGTTTT AATATACTCT AAGGCTTATC ATAGTTCCGA    82440
GATCTTTTTT TTTTTCCTGA GAAATCTAGA AAGATGGAAG ACAGTATGGG TCTTTTGTGG    82500
ATTTTTTGTC CTAAGAAATT TTCATAAATG TCTGCCAAGG AAAAGGAAAG AGATCAAAGT    82560
GGTAATTAAA TCTTTAGGAT GGACATTTTT AGAAAAATGC TTTATAAACT TCCCCTCTCC    82620
CAACTCTGAG TGACTTATTG TGTCATACTG TATTAACACA TATTCATGCT GTAAATATAG    82680
TAAGAAAAGA CAATAGTTCA CAATTTTGGT TTAGTTTTTG CCATTATTGA TTATGAGCAG    82740
TAATTCTTCC TTTTCTTTTT GAAGGTGATA TGGAAAGCCC TGTGTTTGCA TTTCCCCTGC    82800
TCTTAAAACT AGAAACCCAC ATTGAAAAGC TCTTCCTATA TTCTTTTTCT TGGGACTTTG    82860
AATGTTCGCA GTGTGGACAC CAATATCAAA ACAGGTTAGT TTCTTTTGTT TTTTAAAATG    82920
GGTTCTTCTA GTTTCTCCAC CACTAAGGTT AAGAGAACAA TTTGAGCACC AGACACTACA    82980
GTTTGCTTGC TTCTTTAAAC TGGAAGGGTC AAAACCTCAT CGTTTGATAG ACTGCTAGTA    83040
GGATATTTCC TAAGGAGTTC TTCAGTGGGA AATAGGGACG ATGAGAGGAA TAATACACCT    83100
CCCTTCTCCA GAGTCCTTGC TGAGTAGAAT ACCTCTCAGA ATGCCATGAA ACTGTAGGCA    83160
TTTTTGTTTA TTCCTCTATT AGAAATGAGG GGTTTGCTT GTTTACTTTA GGTTTCTAAC    83220
ATTATAGACA CTAGTTTTAG GCTCTTGGAG GCTAGCAGCA ATTCTCAGAG GTAATGCAAG    83280
CTTCCCCATT TCTTCCCGTA GTCCTGTGAA AGACCAGCCA CCTCCAGAAG CCTACACATG    83340
AGTCTTCTCA GCCATACTTT CTGCTTTTCC TAATGCCTCT CAGCAGCGTA TTAGAAAGGC    83400
CATGATCGAT GTACCTGTTA CCTTCAGGCT TTGCATAAGG TGTATATGAA ACATAATGAA    83460
TTTCGTGTTT AGGCTCAGGT CCCATCCCCA GGTTACCTCT TTATCTTGGA GACACTTCTG    83520
GTCCCATACA TTTCAGATAA GAGATATTCA ACCTGTACCC ACCACGTAAG GAGAGGAATA    83580
GGTTTTAGAA GAGGAGTCAG GGAGGCAAGG TATTCCCAGA GGGATATTCT CACTTGGTCC    83640
ATACCTGAGA AAGTTGCTGG CTGGCAGTTA GGAAGATGAC CAGACTGGCT CAATTGTTCG    83700
TGTATTCAAA TTATTACAAT AGAAATAACT CTTTCCACCC CCCCCCGCCC TTTTTTTTTT    83760
TTTGAGTTGG AGTCTCGCTC CCGTCACACA GGCTGGAGTG CAGCAGCGTG ATCCCGGCTC    83820
ACTGCAGCCT CCACCTCCTG GGTTAAAGCG ATTCTCCTTC CTCAGCTTCC TGAGTAGCTG    83880
GGATTACAGG TGTGTGCCAC CACGCCCGGC TGATTTTTGT ATTTTTAGTA GAGACAGGGT    83940
TTTGCCATGT TGGCCAGGCT GGTCTTGAAC TCCTGACCTC AGGTGATCCA GCCACCTGAG    84000
CCTCCCACAG TGCTGGGATT ACAGGTGTGA GCCACCATGC CTAGCCACAC TTTTCTTTAG    84060
CTTAAGTGCT TAAGTTAGAA AACTTGAAGT CTCTCTAAGT TACTCAAGTA AAATGTGAGA    84120
TAAAAATATT ACTTTTGAAG GCCGGGCACA GTGGCTCACA TCTGTAATCC CAGCACTTTG    84180
GTAGGCCGAG GCGGGTGGAT CACGAGGTCA GGAGTTTGAG ACCAGCCTGG CCAACATGGT    84240
GAAACGCTGT CTCTACTGAA AATACAAAAA TTAGCCGGGC ATGATGGCGG ACACCTGTAG    84300
```

FIG. 6.32

```
TCCCAGCTAC TCGGGAGGCT GAGGCAGGAG AATAACTTGA AACCCGAAGG TGGAGGTTGC  84360
AGTGAGCTGA GATTGCACCA CTGCACTCCA GCCTGGTCAA CAAGAATGAC ACTCCGTCTC  84420
AAAAAAAATT AAAAAAAATT ACTTAGATAT TCATTATCTA AATATGAAAT CCTTTTTAGG  84480
TATTTAAGGA GTAGTCAAGG AGAGTTCAGT CTGGGAGGAT GCTCCAGGGA ATGCAGGCAA  84540
CAAAGGTTTT GTTTTTTTTT TAACTGGTTA ACTCAGATCT ACTAGAACAG GGTAAGGGAG  84600
GCCACAGAGT AGACACCATG AGCAAAGCTA ACCCTCCTGA GTTGAAAAAA TTATGGACGA  84660
GAAGTTATCA TTGAAATTAA CTGTTGGCAG ACATATCCAA AGAATATCGC AAGGATTTGG  84720
TCCCTTTATG CATCCTGAGA CAGATGAATG TGTGGAATGG CAGCTGGTGG GCAACAGAGC  84780
GATATTGGCA TGGTGGTGAT ACAGGGAAAT AGTTTCATCG TGTTAAAAGC CATGGAACAA  84840
AGATACATAA TGGCTGCTCT GCAGAAAAAT CCACGTCCCC TCTCCAAAGG GCCTGTTTTA  84900
CTCTGATGTA AAAATTGGGT CAGATAAATT TTCATATTAA GCTTTTTGTT GAGTAAACTT  84960
TTGTAATAGT CCCCAAAACT CCCACTAGAA CAGGGTGAGA ATTAACGTTT TATTCATACC  85020
TAGGACTTAA ATAATTTAGT GTAAGCAAGT GAGTATGAGA ACACATCTGT TTCCAGTCTT  85080
CTATCATTGC TTTATATAAA TTCTCTGGTT TTCTCCTCAC AGTAACTCAG TGAGGAAGAT  85140
CCTAGTGTCC TCATTTGGCA CGTATGGATA TGACAGCTTG AAAGGGGTTA GATTGATTCC  85200
CAAGATGACA CACTGTAAGT GGCAGAGTCA GGAGACACAC TTAGGCTCTT CTGGCCTCTA  85260
AGACTTTCTT GCTCACTGTG GTATACTCCT TAATCACTAC CTGGGTTTTA AATAATATAA  85320
ATAACCTTGC TGATTAAAAT CAGCTTAATT GTAGCTTCTC TGGAATCCAT ATCTTAGTTG  85380
TTTGACAGTT TTCGGTTGAG TGTCTTCTGT GTGTTAGGAA CTCAGGCACT GGAAATAGTG  85440
TATCTTTGCC AAATTTACTA ATTAGGTAGA GAGATAATAC ACGAACACAT AATAGAGGTC  85500
CAGTGACTTC GTAATTAATC TGATCTTTGG GCTGCTTAAC GTTAGCTTTG AATGCAAGAT  85560
GTTAAATGCG TTTTAGAGAT ATATAGCACA AACTGTGAGA GCTCAAGGGA GGGAAGCCAC  85620
TAGCCGCTTT TGTTTGCTTT TTTGTTTTTT AAAAATAATC TTACTTTGTT CTAAAAATAA  85680
AAGTAGTTAT AGAGGGAAAG CTAAAATGAA GTGACGTTTT CTTAAATATG TTTTAATATG  85740
TCATAACTTA AAACTTATTT CCACTTAATC TGAAGGAGAA CTGTCCAGCA AATTCCTTTG  85800
TTTTTGTGAA GCTGTTTTTA GTGCCAGCAT AAGGGCTTTT TACTCAACTT GGAAAGTGTA  85860
ACCCAGAGTC AGTTAAAAAC ATAGTCTTCA GAGGCAGATC TCAGGTCTGT TATTTATCAC  85920
TGTACTCTAT GTGTCACTTT CCCCATCTGT AAAATGGGGA TAAGAATAGC ACCTGCCTCT  85980
GAGAGTTGTT TGGAAGATGA GTGTCCAGTG CCATGCCCTT TGCACATAGT TAAGTGTTC    86040
AGAAATGTCA GATGTCATGT GGAGAATTAA CACTTACTTG CTGAGACAGT CTCCTTTTTA  86100
TAAACTAAAC AGTAGGAGCC TTTACATAAC AATTATCTTT GAAAATTTAA GAATTTAGCA  86160
GAAATCAGTG CATTTGTTGA TATCTTTATG TTGCTTTGCT TTTAAAATGT TAACCTCCCT  86220
GACTACTGAT GTTTTTAACA GACAGTGCTT CCTCACAAGA TTTATAAGTA TTTGCTATTG  86280
TTTAGAAAGG AAGCTTGTAT CTCTTAAGTA GCTGCTCTTT AAATTACAAA TATTTTTATT  86340
AAAGTGGATG CAGTTGAGGT TTAGTGTACA TCTTTAAAGG TCATCTTTTT AGATGGCGTT  86400
GCTCTCAAGT ATTCAGACTA AAGTGCAAAT TTAGAACTTG TGTAACCTGT GAAAACAAAA  86460
TTTGTTCACA ATTAATGCTG TGTGTGTGTG TGTTTTTTTT TTAAGGATTA AAAAAAGTTA  86520
AGTTGTATGT ATTCCTGATT TTATGTTTGG AAACATCCCC TTTTCATTTT TGGTTGTCTG  86580
TAATGGCTAG CCAGTTTGAG TTATTTGAGT AAGGGGTGAG CTCTTAATAA ATTTGACAAC  86640
CTTAGAACAG TGGTTCTTCA CTAAGGGCTA TTTTTTCCCC CTTGGGACAT TTGGCAACAT  86700
CTACAGACAA CTGGATGCCG TTACTGGCAT CTGGTGAGGA GAGGCCAGGG ATGATGCTTA  86760
ACATCCTACA GTGCACAGGA CAGTGCTTCA CAGCAAAGAC TCTCTGGTGA AAAATGCAGT  86820
GATACCATTG AGGAACCCTG TCTTTTTTTC TTGCTTCATC TCATAGTTGA AAGATATGGG  86880
AAATTAACAT GGAGCATCTT CACAGAGCTT CTTTACTAGA GGTAGGGAGG AACATTGCCA  86940
```

FIG. 6.33

```
TATTAACATG ATTTGGGGAA ATAAGAAAGT ATGAATCACG AAAAAGGGGA GGAATACTTT    87000
TAGACATTGG TTTAAATTAA TGTAAATGCA TTTAACGTTA ATGAATTTGT TATGTCATTT    87060
TTTTATAGGC ATATGAAGAG TCTGGTCACC TTTACAAATG TCATCCCTGA GTGGCACCCA    87120
CTTAATGCTG CCCATTTTGG TCCATGTAAC AATTGCAACA GTAAATCACA AATAAGAAAA    87180
ATGGTATTAG AAAAGTGAGT TAAAATTGTC TTATAATTTT TAGTACAAAA TGAAGGTGGA    87240
TTTACATTTT TCTTAATGTG TAGGATTGAA AATGGTGACA ACAACTTACC TTTCTGAAAT    87300
TTGAGTTAAC ATATATTTCT GGGTTGCCAG CTGCCTCGCT CTATCTGGCC AGTGAGCCCA    87360
CTGTCACGGT GAAGCCACTG AAAAGCCAAC TTAGGCTGAC TCTCTGGCCC CACTCTCCTA    87420
GTGTCTTTCC TTCTTTTTGC CTTTTTTCTC CCTTTAAGGA TATCAAGCTT CAGTTTTTCT    87480
CTCCTCTGCC AAGTGTATGG AGTTTCTAGA ATTCTGGGAT TTCCTTAATC AGATTTCAAG    87540
AACTAAGATG ATTCAAAGAT AAGCCACAGG CTCATCTCTC TGAATTTCCA TCTTCTCCTA    87600
GATCTCAGCA TGCTAATTCC TCATCATCTT GAAAGCTATC TAGTGGCCTT GAGCAGATAT    87660
ATTTTCATTG TATTTTGCCA GCTTTTCTGT TTGTCCTCAG TTGGGGAGGT TGGTCAGCAT    87720
TACCTTTTCC AGTATTACCA GAGAACCATC TGTTTAAACT CACAGGTCAG TTCCATCTCA    87780
GGCCGTTTCC CTCTGTCTCA TTAATGCACT CACACATGTA CACAACCTCT CTACTCTTCA    87840
TTTTCAGTCT AATCGTACAT TAAGGAAATG TTTTGAGGTC TAATTTGATG TAATAAAGAA    87900
CCGGGAACAT TAACCTTTAT GCCCTTGAAT GTGCCAGAAA CCCTTCAGAA TCTTTCCTAA    87960
AGGTTTATTC TCATTGAAGT AATAAATCCT CAGTTTATCA GTGCTTACAG GCTCAAAAGG    88020
GAAAAAGGGC AGTAGTCCCC TGTTCCCTCC TCCAGGTATC TACTTTAAAC CTTCAAATTA    88080
AGGTAGTATT TACTTTTACT TTTCAAATTG ATGTGCCTAT TCTACCGTAA TGCAGTCTGT    88140
TCTCCTTTTA TAGTAATTGA GACTAGGGTT CTCACACCAA CACCTGGGCC CCATCTCTGT    88200
TTAGCCTTTC CCTGTCCTTT CAATGCAATT GCGTATTTGG CTAACTCAGT ACTCGGTGTT    88260
TGCATTGTTA TTAATATACA TGTGTTATTC CCTCTTCAGC CAAGCAGTAT ATATAGTTAG    88320
GTTTCACTTT TACAATTCTT ATTTTTCCGG GAATTGTTAT TTGCCTTGTT TTCATTTGTT    88380
TTATTATGTA CTGTGAGTTT TTGCCAAATA CTTTAAAGAC TTATTAATAA ATTTTCAATA    88440
CTCAGATGCT TCACAGTTTT TTACTCTGTT CCTCTCCCCT TTTTTTCCTG GAACTCTTTC    88500
CTGCCACCTT TCACTCTTTG CTGCAGTCTG CGCTGGTTCC TCTCTGGGCC TGCAGCATAG    88560
GGTGCTCTTT ATTATGTACA CACTTCCAGT CACTATCGTA GTTTTTAGCC CAAGGCCTCA    88620
TCCCCACATT CTATCACATC TGTTGCCCAT AAATATCCAG TCCTTTAGGG GTTCTCTGGG    88680
AAAAATAAGC TCTTCTTTGT CATCAACATA TGCACTCCGT AGTACTCATG TCTTCACTTT    88740
GCCCGTTCTG CTGGGTAAGG TGCCACTTCT CTGTTTGCTT TCTGTCCTCT AAATATTTGA    88800
CTTCTTATTT GCTTATTTTC CTTTCTTTGT CCTTTTGGAC TCATATCTTT TTTGCCCCTC    88860
ACTATTATTT GATAGCATTT GTGTAGGAGG GCGAAGTGGG AAGGAAGAGG AGGTGTCTGT    88920
ATCTGTCTGA AGATTACAGA AGTCTGTAAT CTGTCTTGGC TGCCAGGTGT CAGTTTTGAG    88980
ATGTAAATGT TGATGATGAG GTGAGGAGAA GAGCAGCAGA GCATGGGGTC TGCCATCCTG    89040
CCTTGGACCA TGGCCTGCTT TAGGCTGCTT GGTGTATATG ATTTCATCTA GCTGTTCATA    89100
CCTGCTTTTT CCTGTGCCCC AGCACTGAAC ATAGACTCGT ACCATTGTTT TGTGTAATCT    89160
GTTAATTGGT TGCACTGCAG CATATATATT TTTTAACTAT ACAAATAAGT TGCTTCCCTT    89220
AAAGATTCAT GCTCTGATCT GGAAATGGAT TCATTAGGTA AAAGTCTTTT AATGGAAAAT    89280
GTGTTTTGAG TTCCAGTGGG CCAATTTATG AGCAGAATTT ATAATGTGGG CATTTCCTGT    89340
TTTCTTCAAA AGTAAATTGA ACTAGTGTAT GAAGTTTCAC TTAAATTTTA AATGCCAAGG    89400
TCTTTATATA AGTCCTTTGT GTTTTTTTAA TTTTGAAATT TGTATAACTT GATTTGTTTG    89460
TGTCTAATGG AATTTAGAAA TAAATTTAAT ATAGTTTTTA GGGCTAACCT AAAAGTAATT    89520
GGGTTCATCA TGGTGTCATA TGTAATTAAA ACATATAGAA TCCTAAAAAC TAATTAAGTT    89580
```

FIG. 6.34

```
CCTTGGACAC CTTATCTCAC ATAACCCACA TCTCTAATGT CTCCCCATTG GGAAAAGAGT    89640
CCATTGATAA ATCAGGTGAA TTATGCCTAG CGGGCCCAAA TCTGCTACTT TTCTTTAAGT    89700
TGTTTAGGAG TTACATTCAG ACCATGGTGA CATGGAGCAC CAAGAACTTA GAATCAGATT    89760
TCATTTTACT TGACAAACTC TTGAAAGGTC ACTGCCACAG TCTCTCTTGA GTGCAAGGCT    89820
ATGGCTATGC TTTGTAGCAC AGGGACGCGA TATTTCTCTG CTATCTTTGG GTAGCAGAGG    89880
TTAACACAGC TCCCTTGTGC TTTCTTTCTC TCTTTTCTAT TTTCTTTTCT TTTCCTAAGG    89940
ATAGATCTTT AAATAGGAGG AGTTTAACCC CATGTTAGGT GAATTCAAAT GGATCTTAGC    90000
CTGATGTCTC TTGTTCTCTT TTGGTTCCAG TTTGGTTAAT TCCTTTCATC CAATTTTCCA    90060
GTGGTTGAGG GAGAACCTAA CTTGCTCTCC TCGACTCTGA GCATCATCCT TCACTGACAG    90120
TTCAGGCATT GTGGGTAGGA AGAAGTCTGA GAACAAAACC TAGGGATAAA GTTTAGTAGA    90180
GATGGGGTTT CACCATGTTG GCCAGGTTGG TCTCGAACTC CCGACCTCAG GTAATCCACC    90240
TGCCTTGGCC TCCCAAAGTG AGGCTGGAAA TAAGACATGC TGGAATTGTA GTAGGACAC    90300
TAGAGTCTAG GGGAATCAAA GAGGAAAATG AACAGAAAAG GGAAGGGGAA GGATATTATT    90360
TGATTGACTC CAAGATGCTA CTGTTTGTAA GTTTTACCAT TTTAAAAATA TGCCATTAAG    90420
AAAGAAATGC TGGCCGGGCA TGGTGGCTTA TGCCTGTAGT CCCAGCACTT TGGGAGGCTG    90480
AAGCGGACAG ATCACCTGAG ACTAGGAATT TGAGACCATC CTGGCCAACG TGGTGAAACC    90540
GCATCTCTAC TAAAAATACA AAAATCAGCT GGATATGGTG GCACATGCCT ATTGTCCCAG    90600
CTACTCAGGA GGCTGAGACA TTAGTACTGC TTGAACTGGG GAGGCAAAGG TTTCAGTGAG    90660
CAGAGATTGT GCCACTGCAC TCCAGCCTGG GCAACAGAGT GAGACTGTCT CAAAAAAAAA    90720
AAAAAAAAGA AAGAAATGCT GCTTATTTAA CTGTGTTCTG TCAATGTTAA GGTGTATCCC    90780
GACTTCAGAG ATGTTAACAA ATGGGAAAAA ATTTGGAATT CATTAGGCAT TTGGAACTTA    90840
CAAAGTTTCG GCCGGGCATA GTGGCTCATG CCTGTAATCA CTTTGGGAGG CCAAGGCGGG    90900
TGGATTACCT AAGGTCAGGA GTTCGAGACC AATCTGGCCA ACATGGTGAA ACCCCATCTC    90960
TACTAAAAAT ACAAAAATTA GCTGGGTGTG GTGGCATGCG CCTGTAGTCC CAGCTACTCA    91020
GGAGGCTAAG GCAGGAGAAT CGCTTGAACC CAGGGGGCGG AGGTTGCAGA GAGCTGAGAT    91080
CGTGCCCTGC ACTCCAACTT GGACAACAGA GTGAGACGCC ATCTCAAAAA CAAACAAACC    91140
AAAAAAAAAA AAAAAATTTC ATAGTTACAG AAAGTAGTAT GGAGGCCATA CCGAGATTTT    91200
CGACATGGTA GTAAAACTCT GCATTATGGC TCTGTTCTGC ATCATCTCTG TTCTGCATCG    91260
TTTCACTCCA CATCAGACCC TGGATAGCTT TGGTGTACTG GTCGATCTTG TGGCAGTAAG    91320
GCTAGTGTAA TTAAGAGGAT ATTTTAAAAC TTAACATATA ATTGCTCTAG TTGTTGTCTC    91380
TTTTTTGCTG GTTAAGAAAA TCAAATTTCT ATCCTATCTG AATCTCATAG CAGACTTTGG    91440
AGATTTCTGA CAAGTCATTT CTTACTACCT AGGGGAATGT ACTTGTACTC AGCTAGAGTC    91500
TGAGTATCTT CTACATCCAG GGAATTGGGC TGAGTGTGGA TTTTGGTCTT GGCAGTTTTT    91560
ACTTTTATTA ATTTGCAAAA GAATAGAAGA CTTGGAATGT ACAAGAAGCA TAAAAATGTG    91620
TCAGGTGGTT TTACATGCGT TATTTATCAC GTTAATATGT CTTAAGATAT TTTCCACGTG    91680
TAAACTTATG TAAAGGCAGG AAACTAGTGA GATTTCATAT TCTAGGGATC AAGAGATTGT    91740
TTTAGTAACT AGCCTCAGAA AGTATCTTGA AAGGTATTAT ATAAGGTCAA GGAACTAAAT    91800
ATTAGTAAAG AGTCAGGCCA GGCGTGGTGG CTTATGCCTG TAATCCCAGC ACTTTGGGAG    91860
GCCAAGGCAG GCAGATCACT TGAAGTCAGC AGTTCGAGAC CAGCCTGGCC AACATGGTGA    91920
AACCCTGTCT TTACTAAAAA TAGTAGTGTG TGGTATGGTG GCGCATGCCT GTAATCCAGC    91980
TCCTCAGGAG GCTGTGGTGG GAGAATCACT TGAGCCCAGG AGGCGGAGAT TGCAGTAAGC    92040
TGAGATTGCA CCACTGCACT CCAACCTGGG TGACAGAGCT AGTGTCTGTC TCAAAAAAAG    92100
AAAAAAAAAA AGGTCAGATA GGTGCCTAAA GCCTGTGTGT CTCGCTATGA GAATACATCT    92160
CAAGTTTTAC TGTGGTTCAT TGATTCAGAC ATGTAGTTCA CATTTTAACC TGTCTGAAAT    92220
```

FIG. 6.35

```
GGTAATATGT GAAATTGATG TCATGATATA GTTTAATTGG CAGCATGTTT TCATAGTGGT   92280
ACATTTTATA ATTAGTGAAA TCTTAGATTT GATGAAATAG ATATGATTTT TTAAAGTGGG   92340
AAAGTTTAGT GTTATAGACA GTTTGCAGGA CTTTTTATTT TGTAGGTACT TAAATTTTGA   92400
GGACTTAATT ATTCTCTAAT AAAGTGATTG ACAAGGATTA ATGTATAAAT TATACCTTGT   92460
CAGTCTGAAC AATCTGCAGT TTGGACATTG ATTCAAATTC ATTTAGGCTG AATAAATTTT   92520
GATAAACTAA GTAAGTTTTG ACAGCTATTT AAATATTGGG AAAGGGGATA TTCAACATTT   92580
TTCTTACATC CTGAGAGCTT TGTTAAATTT AGTTATTTGA GACCCATTGG GTTCTATTTT   92640
CTGGTTCAGC ATGTTGCTGT AATGGTAAAA TACAATTTTG AAATTATAGT TGTCTTGAAG   92700
TTAATAATAA ATTGACCAAT ATGTTGTATT TTTTTCTCTA CTTAGTTACA AATTGAACTT   92760
TTCCTAAGTA GAACTTTTAA TTTGACAGGC CCCCTTTGCT TCCTGAGGTA ACTGAAATAG   92820
GCCAAATTAA TGCTTTTTTG AATATCTTAG GTTTGTTGCT TTCTTTCACA TGTTACCTAC   92880
CCCACTTAAC AAAAGCAATT AATCTCAGCA CTTGATGCCA AAGAAAATTC TAAAAGGTCT   92940
GGATTTTTTC CTTGGATTTT ACAAAGTAGC TACAATGGGA CTTTTAAGAC AAAGCTGCAT   93000
TGCTGCTTAC AGAGCAATTT TTGTTTAATG GTCTGTGTTA GAGTCATACT GCATGATGAC   93060
TTCCAACTGT CTGGGATACC ATTCTGAAAA GGGTTTAGTG TTACATACTT CTTAGAGAGA   93120
GTTCTCCATT TCTAATTAAG GCACACATCT GGAGGTGCTC AAGAAAAATT AGTGCAGTTA   93180
GCCTTGGAAG TGTTATGTGT GACTAGTTCA CTTCAGACAT CTTTTGTATA ATCAGACACA   93240
TGGCATTAAA TTTATTTAAC TTCTCTTGCT TTTCTCTCCC ACAGAGTATC TCCCATATTC   93300
ATGTTGCACT TTGTAGAAGG CTTACCACAG AATGACTTGC AGCACTATGC ATTTCATTTT   93360
GAAGGCTGTC TTTATCAGAT AACTTCTGTA ATTCAGTATC GAGCAAATAA TCATTTTATA   93420
ACATGGATTT TAGATGCTGA TGGTAAGTGT TTAGAGGTTT TCTTTTAAGA TAATTGGCAT   93480
AGAAACTAAA TTCTAGCATG TGGGGACTTT TTGGTTTTTG TTTTATAAAA AAAGACAAAC   93540
TTTGTCCTGA CTCTTTCTCT CTCCATTCTC GCCTTTGCCT TCTGCCCCTC CTCGCATCTA   93600
TTAAAAGTGA TGGTTTTAGT ATCCTGTCTC ATTTTTTCCT TTCCTTACAT CATGTATTAT   93660
AGGTAAACAC ATGCGCATGT GTGTATTTCT CTTTTAGACA AAGGATGAGA TTACTACTGT   93720
TAGCTCAGTT TTTTTTTCCC TACTTAACAT CTTTGCTTTT ATTTTTTAGA CATATTTCTA   93780
AGACTATTAA ACATTAGACT TACGTAGCCC TTCTGTCATT GTGAAATACA TAGTTTACTA   93840
ACAGCTACCA TCAAGATAAA GCCTTTATTT AAATAATTAA ACTTCTTAGT GGAAAGCTAA   93900
GTAAGCACAG TTTATGGATT TTGGGAATTT TTGCCTTGCA TTTGTCTGAT ATGGTAAAAT   93960
ATTGAGTTTG TTTTTCTCAT AATGTTCACT TTGTCTTAGA CAAGATAACT CAATCCCCTT   94020
AAAGGGTTGT ATCAAGCCAT TGATAAGGGC TCACTTTGAT ATAACCATTT CTGTTATTT    94080
AGACACTCTT TCACACTTCC TATTTTCCTC CTGGGGATGG TTTGAATGGA TGACACAATA   94140
CCATATTATA AAAGCACTTT ACAAACTGTA ACTTATGTTA TAAATGTAAT TATTACCTTA   94200
AGGTTTTACC CTGTTTCAGA TTTGAGTGGA AGTAGTTCTT TACAATACAA AACAACTTAT   94260
TTTAACTTTT TTTGCATTTC AAAGAATGAT CAATCCACTT CAGGTGCAGC ATGGTTTCCA   94320
ACCCTGACAG CATGGAAGAA TCATTTATTT AGCTTCTAAA AATGTGCAGG CTGTACCCTA   94380
GACCAGCCTT GGGGATTAGG CCCAAATATC AATGTTGGGT GTTTTTGGTA TTGGTTTTTG   94440
GCCCGCCTAC CCGCCCTTCC TTCCTTCGTT CCTCTCTCTC ATTCTCTCTC TCTCTCTCTT   94500
TCTCTCTCTC CTTCTTTGCT CCTTCATTCC TTCTCTCTCT CTCTTTTTTT TTTGAGACAG   94560
CATCTCACTA TATTGCCCAG GCTGTTCTCA AACTCCTGGG CTCAAGTGAT CCTCCTGCCT   94620
CAGCTTCCTG AGTAGCTAGG ACTACAGGCA CATGCTATGG CAATACTGTT TTAAACATTG   94680
TTTTCAAGGC TCCCCAGGTG ATTCCAGTGT GGGTCATGTG GTAGAGAACC ACTGACACAG   94740
GCAAACAAAG GATACATAAA GTTGTCTATT TAATGGGTAG GTGCAGGTAG TAGATAAGAG   94800
TGTAGCCACA TAAACCACAT GCTTAGTGAA CGGTTTTGTT TTGTGTGTAT GTGAGGGATT   94860
```

FIG. 6.36

```
AGCATCTCTG AGTATATTTT GTTTTCCCTT TTGAAACTTA TCAGAGAATT CATATGTCTG    94920
TTATGTGACT AATGCTCACA TTAAAAAAAG TTATGTGACT TTTTTTAATT CATATGTCTT    94980
TTTAATTCAT TTATTCATTC ATATGTCTGT TATGTGACTA ATGCTCTCAT AAAAAAAGTA    95040
ATGCTCAGTT TACTTTTTTT ATATCAGATC ATATATATAT GTTTTTTTTT TTGAGATGGA    95100
GTTTTGCTCT TGTTGCCCAG GCTGGAGTGT ATTGGCGCAG TCTTGTCTCA CCACCACGTC    95160
TGCCTCCCGG GTTCAAGTGA TTCTCCTGCC TCATCCTCCT GAGTAGCCGG AATACACGCA    95220
GGCGCTACCA TGCCCGGCTA ATTTTGTATT TTTAGTAGAG ACAGGGTTTC TCCATGTTGG    95280
TCAGGTTGGT CTTGAACTCC CAACCTCAGG TGACCCACCC GCCTCGGCCT CCCGAAGTGC    95340
TGGGATTACA GGCATGAGCC ACCGCACCCG GCCATATCTT ATATTTTAAT AAATATTTTA    95400
ATTTGGTCTG TAAATTTTTC TTTTTGGGGA ATGTGTTTTA AGTCTGTGTT GAGTCCTAGA    95460
CATTTGTTGT TCTCAGATAG TCACTAGTGA TACCTTAACA TTAACCAGCC TGTTGGCAAC    95520
TAAATTGGCC TGAAGTGACA ACTAAGGAAA GGTCTCTTTC TCCTTTCTTA ATCTTTGCAT    95580
TCCTTAAGAT TAGTTCTTTG TAGGAAGGCT TTGAAGTCTG GTGGCAAGTA CCCTTTATCC    95640
CTCACAATCT TAAGATAAGG TCTTTCTGAG CATTAAAAAG TGACTGTGGG AGATATGTCA    95700
AATGAGTTTT CTGTGTGTGC TCTGAGAAAT CTTTTTTTCA AAAAAGGATA GATGTACTTG    95760
TATAAGGAAA AGAGAAACTG AGCGCACTTT CAATATTTAA GTAAGTGTCT CTAACATGTT    95820
TTGCAACATA AAATGATGAC CACTGTGTTG GTCATTACTT CTCTACTGCT AAAACAATGT    95880
TTTCTAAAAT AATATACTCC TTAGAAAAAA ATATAGTGCT TGGGTGTGC ACTGTTGTAA    95940
TCCAAGGAAT AGGAAATGTT TTGTAGTAAG TGCGATGGTG TTTGACATCG TGATTTATTA    96000
ATTTATCACA TTTGGTTTCA TAGAAATAGA GTAAGCTACG TATTTGCTGT GCCGCAATTA    96060
CCATGACATT ACACTTGTAT CTATTTCTGT TTCATAGATG TGTAGATATT GATATATACA    96120
GTGGAAGTAT GGATTGTTTT GATAAGTTTC TAATGAAAGT ACAGATATTT GTTGATTATT    96180
TATTAAGAAA GGTTGTTACT CATCCAAGCC CGTGGTTAGC TTTTCCCAAA TTATCATGTG    96240
GTAGTAAGTA AAATGTAAAG AAATATACCC TCCCTTAACC CCACACCACC TGTTAGCACC    96300
TAGCCACCTT CCTTTACTTC TCAGCCGTAC TTTTTGTATT TTTTTGTTGT AGTGGTAAAA    96360
TATAAATAAC ATAAAATTTA CCATTTTAAC ATTTGTAAGT GTACAATTCA TTGGCATTGA    96420
ATACATTGTG TGCAACCACC ATCACCATCA GGACTTTTTC ATCAACCCAA ACAGAAACTA    96480
CTCATTAAAC AATAACTCCG CATCCTTCCA CCCCAAAGCC CTGGTAACCA CTATTCTACT    96540
TTCTGTCTCT GTGAATCTGT CTATTCTAGA TACCTCATAG AAGTGGAATC GTACATTATT    96600
TGTCCTTTTG TGTCTGGCTT ATTTTACTCA GCATATTTTC AAGATTCATT TGTGTTGTGG    96660
GATGTAGCAG AATGTCATTC CTTTCTAAGG CTGAGTAGCA TTGTATGTAT TATCCATTTA    96720
TCTGTTACGG ACATTTGACT ATTGTGAATA ATGCTGTTGT GAACATTGGT GGACAAGGAA    96780
CTGAAAGTCC CTGCTTTTCA TTCTTTTTGG CATAAACCTA CAAGAGGAAT GCTGGGTCT    96840
TAACGGTAAT TCTGTGTTTA ATTTTTGGAC GAACTGCCAG ACTGTTTCCA CAGCAGTTGT    96900
ACTATTTTAC ATCCCCACCA GCGTTACACA AGGATTCCAA TTTCTCTACA TCCTTGCCAA    96960
CATTTGCTAT TTTCTATTTT TTTTTAATAA TATCCATCCT AATGGGTGTC TTTTTTTTTT    97020
TTTAAAGGAA TGGTTTAAAC AGGTTACCTT CTTACTCCTC ATTCATGCTT TAGTTGACTA    97080
CATAAGGACC CCTCTCCCTA TTGGCACCAT TGAAATTGTT CAGGCAAAAA TAACTGCCAG    97140
CGACACACTG CTTTAAGTAA TGGACTTTTC CCAAGTTTTG TATTAATATT TCAGTATTTG    97200
GTAGTGCATC CTACTGCTAG TTTTTAAACT CTTCCCTTGT CATCTATCAT CTCATTCTCT    97260
CTTGACAAAT GTGAAAATGG AAGCTCAGAA ATAAAACAAG AATTAAAACG AATAGTGATC    97320
CTTCAGGTAA CAAGCTTCAT TTATCATGAA AACATATATG TATGAAACAT TCTGTTTTCT    97380
GATGTTATTG GATAAATTAG GTGATAACCA AATTCTAAGT TCCAAAAATT AAATATACTC    97440
TATCTAAGGA CTTTAACATG GCAGACAATG GTGACAAGGT CAAGAACATG TTTTAGAGTC    97500
```

FIG. 6.37

```
TTCTCCTTTG GTCGGTATTC AATGATACAA CAGTTGAAAA GGCCAGAAGA AAGTTAACCT    97560
AGGATGGTGG TTTTTGAATA TCTAACTTTC ACTTCTTTCC CATCTTCCAG GAAGTTGGCT    97620
GGAATGTGAT GACTTAAAAG GCCCATGTTC TGAAAGGCAC AAGAAATTTG AAGTTCCTGC    97680
TTCAGAGATA CATATTGTTA TTTGGGAAAG AAAAATATCC CAAGTGACAG ATAAAGAAGC    97740
TGCCTGCCTT CCACTTAAAA AGACTAATGA CCAACACGCT CTCAGTAATG AGAAACCAGT    97800
ATCTTTAACA TCGTGTTCTG TGGGTGATGC TGCCTCAGCT GAAACAGCCT CAGTAACTCA    97860
CCCTAAAGAT ATATCAGTTG CCCCTCGTAC TCTTTCACAG GACACAGCTG TAACTCATGG    97920
AGATCATTTA CTTTCAGGTC CAAAAGGTTT GGTTGACAAT ATTTTACCTC TGACACTTGA    97980
AGAAACTATC CAGAAAACAG CCTCAGTTTC ACAGTTAAAT TCTGAAGCTT TCCTGTTAGA    98040
AAATAAACCT GTAGCAGAAA ATACAGGAAT TCTCAAAACC AATACTTTGC TATCACAAGA    98100
ATCACTAATG GCTTCTTCAG TATCAGCTCC ATGTAATGAA AAGCTTATTC AAGACCAATT    98160
TGTGGACATA AGTTTTCCAT CCCAAGTTGT AAATACAAAC ATGCAGTCAG TACAGCTGAA    98220
TACAGAAGAT ACTGTAAATA CTAAATCTGT GAATAATACT GATGCTACTG GTCTTATACA    98280
GGGAGTGAAG TCAGTAGAAA TTGAGAAGGA CGCTCAGTTA AAACAATTCC TTACACCAAA    98340
AACTGAACAA TTAAAACCAG AACGTGTCAC ATCTCAGGTA TCTAATTTGA AGAAAAAAGA    98400
AACTACAGCA GATTCTCAAA CCACAACATC TAAGTCATTA CAGAATCAGT CTCTGAAAGA    98460
AAATCAGAAG AAGCCATTTG TGGGAAGTTG GGTTAAAGGC TTAATAAGCA GGGGTGCTTC    98520
TTTTATGCCA CTCTGTGTTT CAGCTCATAA TAGAAACACT ATAACTGATT TACAACCTTC    98580
AGTTAAAGGG GTAAATAATT TTGGTGGCTT TAAAACTAAA GGTATAAACC AGAAGGCCAG    98640
CCACGTATCC AAGAAAGCTC GTAAGAGTGC AAGTAAGCCT CCTCCCATCA GTAAGCCACC    98700
AGCAGGCCCT CCATCGTCTA ATGGCACAGC TGCCCACCCA CATGCTCATG CTGCTTCAGA    98760
AGTTTTGGAA AAGTCTGGAA GCACCTCATG TGGAGCTCAA CTCAACCACA GTTCTTATGG    98820
GAATGGTATT TCTTCAGCAA ACCATGAAGA CTTGGTGGAA GGTCAGATTC ATAAACTTCG    98880
TCTAAAACTT CGTAAAAAGC TAAAGGCAGA AAAGAAGAAA TTAGCTGCTC TTATGTCTTC    98940
CCCGCAAAGC AGAACAGTTC GAAGTGAAAA TCTAGAACAG GTGCCCCAGG ATGGGTCTCC    99000
AAATGATTGT GAATCAATAG AGGACTTGTT AAATGAGCTA CCATATCCAA TTGATATTGC    99060
CAGTGAGTCT GCATGCACCA CTGTTCCTGG TGTTTCCCTG TACAGTAGTC AAACTCATGA    99120
AGAAATTTTA GCGGAATTAT TGTCTCCTAC ACCTGTTTCA ACAGAGCTGT CAGAAAATGG    99180
GGAAGGTGAC TTTAGGTATT TGGGAATGGG AGATAGTCAT ATCCCACCAC CAGTACCAAG    99240
TGAATTCAAT GATGTTCCC AGAACACACA TCTGAGACAG GACCATAATT ATTGTAGCCC    99300
CACCAAGAAA AATCCATGTG AAGTTCAGCC AGACTCTCTG ACAAATAATG CCTGCGTTAG    99360
AACATTAAAC TTGGAGAGTC CGATGAAGAC TGATATTTTC GATGAGTTTT TTTCCTCCTC    99420
AGCATTAAAT GCTTTAGCAA ATGACACATT AGACCTACCT CATTTCGATG AATATCTGTT    99480
TGAGAATTAT TGAATTAATG CTTGTTAACT TTTTTCATAT AATATTTATT ATTATTAGAA    99540
GAACTTACAA TGTGTTCAGG TAGTGTTTAT ACACTGGACT TGTGTAATTA CTTGTGTAAT    99600
AACCATGAAC AAAATGCAAG GTTTAACCTT TGGTTCTGCC CATGAAGCAT GTAATCTTTC    99660
TTACACATTA AAATCACTGA ATGTGTTCTC CTTTTTGGTT TCATTTTGTT CTTGTGAGAG    99720
TATGAGGATT TCAAAATGTT AAAGATGAAA AGTGGCGTCT AGTTTCTGAC AGTTTGTACA    99780
GTTGGATGCA TTACATTTTT AGATTTGAAG TTTTGGTTAT GTTAGTGTTA TGAGTGATCT    99840
TTGTGGTGGT TTTCTTCCCC TGGAAACCTG TTGCTCGTGG CGCTTTGCCC ACGGTGCCCG    99900
AGTTCTTGTC CTGTGTCCAG ATATGCAGAC AAATGAAGGG TGAAGAAGAA GAAGAGGAGC    99960
TTTATTTAGT GTTAGAACAG CTCAGAAGGA GACCCACAGT GAGCAGCTCC CCTGTGTCGG   100020
CGGGCAGGTC GTCCCTCAAG TGTTCAGCTC TCAGCAGAGA AAAGGCCCTG GAGAGGGTGA   100080
CTCCTCTCAG CTCTCAGCAG AGAAGCAGCC CTGGAGAAGG TAGCTTCTGT TCGCAGGCAG   100140
```

FIG. 6.38

ATTGTCCAGA GGTCCTGCTG CTCTCAGACG GGGCCCTGGA GAGGATAGCT TCTATCCATA 100200
GGCAGGTTGT TCTGCCGTCT CTACAGGTCT CTGAAGCTCT TAGCAGAGAG GGTAGCTCCT 100260
CCCTGTTGCT GGTCGTCCCA CCCTCTGCTC AGTTCTGGCT GAGCCTGGGG CATTTTACGG 100320
GCCTCGGGGG AGGAAGTGCA TACTTACTGG CCTGGAAAAG GCACCAGTTC CCACTCCTAC 100380
AGGTGGGACT GGCAGCCTGG CCCTCAGCCT TCAGGCCCTC CCTGTTCATG GCTTCCAGGC 100440
TTACCCCCCT GCTTTGATCT GAGAGCTGGT GCCAATAGCA GGGAGAAGCC AAGCTGCAGA 100500
GGCAAGCACT TCCGAGCCTG CAAAAGCAGG CCCCCAAAAG TGCAGGGATG CCTGAGTCTG 100560
CACCCGCACC CAGGAGGGTG GAGATCTTGC CTGCTCCAAG GCTGCAGCCG GAATGATAGC 100620
AGGCTGACTG GAGCACCTGC CACCATCATT AGTTCAAGAG TTTATGCAGA TTTAAGTTGT 100680
ATACGGTATA TGAATGTGTG ACAGTTTTCC TTATGGTTGT GTGGCCTTCT GTAAGAGCCT 100740
ACGCCTGTTT GTTACACCGG TAGAGTGCTG TGGAATGTAA ACTTTCCCTA TGTCACTTAT 100800
CTCCTTTATC TCTCCATACA GAGGAGGGCA AGAAACCTTG TTACTTGAAC TTTAGTAATG 100860
TTAAGTGATC AATAAATCTA TAAATAAATG ATAGCAGAAA AAAGTTACCT GTTTTTGTGA 100920
TGATGTACAA ACTTTACATG TTATCACAAA TACCATCTTT CTTCCCAAGA CATTTACTTC 100980
TGTAACCAAA GTGGGACACC ATCTAACAGT TCTGTTTTGG GAGAGAGTAA TAACCAGTGC 101040
TTGTGAGGCT TGTTAGATGT TGGTTGTGAT ATATGAGATA GATGTTATTT CATTTAGACC 101100
TCAACATTCC TGTGCGTGAG ATACTTTTAT CACATCTTAC AGATAAGGAG ACTGTACTCA 101160
TTCAGTTGTG GAGCTGAGAT TGAGTAGAGT GGCTATTACA GCAGTTGAGT GCTGAGCTTA 101220
TCAATATATG TTCCACTCCT CAGGCTTCAT TTAAAGTAGG ATGCCCAAAC AGCACCACTG 101280
CCGTAGAGAT TTGAGTTAAC AGCAGTACTT ACTGAGGTTT AAGGCTGGCA GCCAGTGTCC 101340
TTGCAGTAAA ATTATTTGCT AGGGACTCAG TACTTCATAA TCTATTTGTC AGATTTACTC 101400
CTAAGCTTCT GTGTTGTTTT ATTTTTTTTC TGACAAAAGT AGTGCATATT GTCAAGGAAA 101460
AACTAGGAAA ATACCAAAAA AAAAGATTTT TGACCATGCA TTTTAATACT TAGTGACTAC 101520
AAACATTTTC CTATTTTATG CATATAGATT TTAAATAAAC GTGAGATCCT ATTGTATCTG 101580
TTTTAATGGA TAAACATTGT TTCACTGTTT TAAGATTCTG AGGTGATTTA TACTGTCTTG 101640
CCATTGTTAA TTGCAGCAGT TAGCCTTGTT GATAAATTTT TGCATGGATC CAAGTTTTGT 101700
TTTCCAGGAG TGGAGTTGCT TGGTCAAAGG AAATGCACAT TTAAGGTTTT TTGGTGATTG 101760
CATGACTGAC TTCCCTGGGC CCTCGCCAAC ACTAGGTAGT AGTATTGGGA GGAAGGGGGG 101820
AACCAATCCT GGGTGCTCCA AGATTACTAG TGAGCCTGAA CATTTTCTAT AACTATTGTC 101880
CACTTGAGTT GTTGTTTTGT TTTTTTTTTG GTGGAGGCGG GGGTGGGTTT AAGAATTGCT 101940
TATCCTTTGC TTGTACTAAT TATCTTTTCA ACAAATATTT CTAGATTACT GCTAAGGACC 102000
AAGCACTGTT ATCAGCCTGA GATAAGGCAG CACACTAGAA GGAAATCCTT GCTCCTTTTG 102060
AGTTTGCCTT CCAAACATGG AGATCAATAT ATAATGTTAG GTAGTAATAG GAGATACATG 102120
CAGTTGATTC ATGTCATTTG TAGTAGTTAT GGTCAATAAA GTTGCCTTGA ACACTGAATT 102180
AGTATAAACT GAAATACTGT TCCTAGGGGA AATAGGTTCC TGCTAGCCTG TGGTCATGAG 102240
ATTTTTGTCA AACAATCACT ATATAACCTT TTCTGTTTCT GTTTAAAGAC ATGTTATTTG 102300
ATCTATATGG TTGATTCTTT ACATTAACAT GGCCAACAGC ACTGTAACTC AGCCTGAACG 102360
AAGCTTATCT GACACATGGT GTTCTCCATA AGGCACATCA TAGCTTTCTG TGCTTAGGAA 102420
CACTAGACGG CACTTCAGCA CTGCACTTGA GGACGTTTTA AACAGTGAAA TCAACAAAAA 102480
GCACAAAAAA ATGCAACAAT AGGCTGGGCA AGGTGGCTCA CGCCTGTAAT CCCATCACTT 102540
AGGGAGGCCG AGGCGGGCGG ATCACGAGGT CAGGAGATCA AGACCATCCT GGCTAACACG 102600
GTGAAACCCC GTCTCTACTA AAAATACAAA GAATTAGCCG GGCGAGGTGG CAGGCGCCTG 102660
TAGTCCCAGC TACTCGGGAG GCTGAGGCAA GAGAATGGTG TGAACCTGGG AGGCGGAGCT 102720
TGAAGTGAGC CGAGATTGCG CCACTGCACT CCAGCCTGGG CGACAGAGCG AGACTGCGTC 102780

FIG. 6.39

```
TCAAAAAAAA AAAAAAAGGA ACAATAACAA AGACACTAGT CCCCCAAAAA TACACTTGTT   102840
TACAGTGTGA ACTGAAAGAG GAAGGTGGAG TATTGACTTG TTTGACCTCA GCTGGAAATG   102900
TGCACGTCCT GTGACTCAAA TTTTTCTCTG TTCTGTGCAT GCATGTCCAC GAATAACCAC   102960
AAGAAGCACT GAAAGCATTG ATTTTTAGGG TTACAAATTA ATTTTAGCAA GTAAATGAAT   103020
TCACAAATAC GGAATCTGTG AGTAATGAGG ACTGATTCTT TTTTTTTTTG GAGATGGAGT   103080
TTCACTCTTG TAGCCTAGGC TGGAGTGCAA TGGCATGATC TCGGCTCACT GCAACCTCCG   103140
CCTCCCGGGT TCAGCCTCCA CCTCCCGGGT TCAAGCGATT CTCCTGCCTC AGCCTCCCGA   103200
ATAGCTGGGA TTACAGGCTT GCACCACCAT GCCCGGCTAA TTTTTGTATT TTTAGTACAG   103260
ACGGGGTTTC ACCATGTTGG CCAGGCTAGC CTCGAACTCC TGACCTCAGG CAATCCACCC   103320
ACCTCAGCCT CTCAAAGTGC TGGGATTACA GGCGTGAGCC ACCGCGCCCG GCGAGGACT    103380
GATTCTTATG TCAGATGGCA CTAAATGCTA TGGAGAAGAG GAGTGGATGA GAGGGAGAAG   103440
TATTTTAGAC CAGGTAGACT TGGAAGGTTT CTTGGAGGTG GGTGATGTTT GAGAAGAGGC   103500
TTCAATAAAG TTAGGGAGCT CGCCATGTGA TTGCAGGAAG AGCGTTCCAG GAGAACAAAA   103560
GTCATGAAGA GTGAGTGCTA GGCATGTGTC TGGTCTGTTT GGGCTGCTAT AACAAAATAC   103620
CTTAGACTGG GTAAAATGTA TAAATAATAG AAGTGTATTG CTTATAGTTC TAGAAGCTGG   103680
GAAGTCCAAG ATCAAGGTAT CAGCACATTC TGGTGAAAGC TGCTCTGCTT CATGGCTGGT   103740
TCTCTCACTG TCCTCACATG GCATAAGAGG GGCACAGAGC CCTCAACCGT CTCTCCAGTG   103800
GCCCCATCTC TTAGTACTGT TGGATTGGGG ATTTAGACTT CACTAATTTT GGGGGGACAC   103860
AAACATTGAG ACCACAGCAG CATGACTGAG GATAAGCAAG AGGCCAGTGT GGTTGAGCAG   103920
AGTGATCAGT GAAGGAGAGT TAGGACATGA GTAAAGAGGC TAGCAGACAC CAGATCTCAT   103980
ATGGCTTTGT AGGCCATAGT GAGGACTTTG TTTAAGCTGA GAATAATAGA TAACCTCAGG   104040
AAAGTTTCAG GCAAGAGGGT AACATGATCT GATCTGGGTT TTAAAAGGAT CACTGAAGTG   104100
GGGAGACTGT CTACAGATGG TCTGAATAGG AGTCCTAGTC TATTACAATC TCCTTGGAGT   104160
TTAGGGTGGT AACTGGAGGT GTTCAAGAGT AGTTGGATTA CTGTTGGATT TCAAAAGTAG   104220
AGCCAACACG ATATGTGCAT TGGCTGTGAG GTAGAAGAGG AGTCAAAATG AACTCCAGGT   104280
TTTATTGACT GAGCAATTGT GCCATTTCCT GAGATGGGTC AGATTTGGGA AGGAAAGAAT   104340
TTAAAGGGGA TAAGATAATC CCATTAGGAG TGTGTTAAGT GTGAGATTCC TATTAGACTT   104400
TCGAGTGGAG ATGATTTAAT AGGAAGATAG ATCTGCAACA CTGGAGCTCA GCGGAGAGGG   104460
ACACCCTGGA GATAGCCGTT TGGGAATTAG GAATGTGTGG ATCATGTTAT AGGATGGGGT   104520
CATTTAGGGA CTTAAAACAG CTCTGAAGAA CAAAAATGGT GCCTTGATCT TGGACTTCCT   104580
GGTTTATAGA ACTGTGAGCA ATATATATAT ATTTTTTTCA AGACAGAGTC TTGCTCCGTC   104640
ATCCAGGCTG GAGTGCAGTC GCACCATCTC GGCTCACTGC AACCTCCACT TCCTGGTTCA   104700
AGCAATTCTG GTGCCTAAGC CTCCCAAGTG GTTGGGACTA TAGGTGTATG ACACCATGCC   104760
CGACTAATTT TTGTATTTTT TTGTAGAGAC AGGGTTTTGC CATGTTGGCC AGGCTGGTCT   104820
CAAACTCCTG ACCTCAAGTG ATCTGCCTGC CTTGGCCTCC CAAAGTGCTT GGATTATAGG   104880
CGTGAGCCAC CATGCCCAGA CTAAATTTCT AACATTTATA AATTATCCAG TCTAAGATAT   104940
TTTGTGATAG CAGCCCAAGC AGACCAAGGC AAAGGCCAAG CACACTTGCT CCTCCTGACT   105000
TTTGCTCTTC CTGGAATGTT CTTCCTTTAG TCACATGGTT GCCTGCCTAG CTTCATTCAA   105060
TAGGAGTGTG GTGCCCTGAA AATACAAGGA AGAATGCTTT TCTTTTTTTT AAAAGGAAGG   105120
GATGATTATC TGTCAGATGC TGCTGAAAAA GAGTAATAGA GTAATTGGCC ACTGGCTCTG   105180
GCAATAGGGA AGTTAGCTCT GCTAACTCCA CATGAACAGT TTCACATGAA CAAGTGTGAG   105240
TGGGCTCAAG AGAAGGGATG GTGAGAAAGT GGAGCTATGG ACTCACTCTT GAAACATTTT   105300
CTGGTGCCTC GTAGGGCAAT GTGAGGTCAA GGTTTTTGTT ACTGTTCTGA AGATGGGAGA   105360
GGCTGACACA TGGATGTTGT AGGTGAGAGA AGGGGCGCTT GCGGGGGCAA ACTTCTCCAG   105420
```

FIG. 6.40

```
GGATGGGATT CCAGTGTCTA AGAGGAGGCG GTGTGACCCT AAGAGCTAGA AAAATTATTT  105480
TATTAATAGG AAAGACAAAG TACTTAGGCT CAGATGCTAA GAGATTTGCT GATAAAAGAA  105540
TGAGAACGGT CTCTTCTGAT TATTTTCTTG GGGAAATAAA TAGATCATCA GCTGAGGGTG  105600
TGAGGGGAGA AGGAGTTGAA CATGGAGGAA GACAGGTGTG AAATATTGGT CTCAGAATGG  105660
AGAGCGAATT GAATAGGGAC ATGCAGTGGG CTTGCTAAGC TGTGCGGAGA GCCCGTGGGA  105720
AGTTTATGGT CATCAATTTA ATGGCGACCA GCCAAGATGG TGGTTTATTT TTCTCCAGTT  105780
GTATTTAACT GCTCAGGTGC AGGACAGAGA GACTAAGTGT GAAGTTAATT TCAGCCAACG  105840
TAGAGGAATT GTCAGGCAGA TGGGACAAGG AGATAGAGGA GAAAAGGAAT AAGGCTTCCT  105900
GCAAGGGTAA TGATTGTAGG GATGGATAAG TAAGGAACAC AGGAAGTGGC TGTCTGCTGA  105960
GTGGTGGCAG AGCTCAGTGG GTCAGAGCAA GGTTCAAAGA ATGGCAGAGA GGCACTTGTG  106020
GAGGAAGTAA GCTGGCTAGA AAGTAGTGTG CTTGAAATTA AGCTTCTGGA GATAGCAAGG  106080
TTACAGGTGA TGACAAAGTC TGAGTATGAC AAGGAAACTG CAGGGCCAGA GTTGGCAAGA  106140
ATTCATGAAA AATGAGGAGA AAGAGGCACC AAGAGGCTGG GATAGCACAT GGATTGTCTC  106200
TGTGTGAGGC AAAGTCATCT AAATGGCAGC AGTGGCCCTA GCAGAAAGAA ATATACAGTG  106260
AGCCGGAGCA AAAATCCTCA AGGACAGGCA GAACGCCATG AAAACGGCAG ATGACAGCCA  106320
AAGGAGCAGG GGCAGGGGCT CAGTCCAAAG TGTTTCAGAG TCACTGGAGG GTTGAGTGGG  106380
AAGGGGAGGG AGTGGCTGAA ATGGCAACAA GGAAGAACCT CTCTCATCTC CAGGCCCAAA  106440
AGTATGTGGA ATGCGGGAGA TAAGACAGCC ACCACTGGCC AGGGCTGTAA AGGGACATTC  106500
AGCGAATATT CAGGTTCCAT TTAGCACGAC AGCAGGGAAG GGACTGTTGG CAGAAAAAAA  106560
CTGGGGCAGT GGGATTAAAG ACAGACCACA CATTCCAAAA GGCACCGTGG GAGGGTCAGG  106620
GGGCGAGGTT AGGTCTAGGC TTCAGTGTCC TGGGAGACTC AGTCTTCACA GGGTGACAGC  106680
GATCAAGAGT GCAGCTTAGG CTGGGTGCAG TGGCTCATGC CTGTAGTCCC AGCACTTTGG  106740
GAGGCCGAGA CGGGAGGATT GCTTGAAGCC AGGAGTTTGA GACCAGTCTG ACCAACATGG  106800
CAAAACCCCA TCTCTACTAA AAATACAAAA ATCAACTGGG CATGGTGGCG TGTGCCTGTA  106860
GTCCCAGCTA CTTGAGAGGC TGAGGCAAGA GAATCACTTG AACCTGGGAA GCAGAGGTTG  106920
CAGTGAGCTG AGATCGTGCC ACTGCACTCC AACCTGGGCA ACAGAGTGAG ACCCTGTCTC  106980
AAAAACAACA ACAACAAAAA AGAAAAGAGT ACAACTTATG AAGGGGTCTC CTGGGGAGAG  107040
GGTTTTTGGG ATTCTCCTGC CTCTCAAAGT GCTGGGATTA TGGGCGTGAG CCACCACACC  107100
CAGCCGAGGG AGGCTGAGTT CTAATTGTTG TATCTCTCTT GGGATTGGCC TCCTGGGCAG  107160
TTTAAAAGAC AAGGCAAGGA ATCTTTTGGA GAAAGAGACT GGGGGCAAGG TGTGTCTGAA  107220
CAAGAAGTGT GAGAAGCTCT GTGGGCTCCC TTCAGACTTC CAGTCGTTGA ATTGGGATCT  107280
CATTTATATC AGCTCTAGGT GTAACGATAT TAAATCTTCT CTGTCATTTG GCAATTTTGG  107340
TTTATGCTTG ATCATCATTT TTAATGTTTC GACATGTAGA AGTTTAACAT TATTTTACAT  107400
TCTTTTCCTT CTGGCATCAT GTTTTAGCAA GATTGTTTCC ACCAAAAGAA TATATATATC  107460
TTCTAATGAA ACTACGTTTC TTTTTTTTTT TTCCTTTGCT TTCTCTTTTG GTATATGAAT  107520
CTTTGATTAT TTGTAATGTA TTTTGATGTG TAACACTGAA GTTTCTATTT TGTACTATTT  107580
TTTTCCCCAA ACAGTAAACT TATTGTTCAA ATACTTATTG AACAACCTTC ACTATTCTTT  107640
AACCATTTAG AATACGCCAT TCACATATCT TTCATACTAC ATTTAATAAC ATTTTTTAAT  107700
TAAAAAATAT TCTACTGATT TGTTTATTTT GAGACCAGGT TATGAAACTG GCTAATTTTT  107760
GTATTTTTGT TAAATACCGA AATTCACTGT GTTGCCAAGG CTGGTCTCGA ACTCCTGGGC  107820
TCAAGCAATC TGCCCACCTT GGCGTCTCAA AGTGCTGGGA TTACAGGTGT GAGCCGCTAC  107880
ACCCGGCCAC ACCCGGCCAA CACATATTAT TTGTTATTAC ATTTAATTCC CACAGTACAT  107940
TGAAATTATC AGGGAAAAGT TTTCAGTGAA ACATTATTGA ACGCCACATT AAAAGTGTAA  108000
ATTACAAAGA TTTAATGCCA ATTTTTCAGA AGAAAAAAGA CCAGGAGGAA GGTCTATGAA  108060
```

FIG. 6.41

```
GTTTTAGCCA GTCTCTCATC CACCTACCAT TTCACGATCA TGCACTGTGT AAGTCAGGAA   108120
AAGAGTAAGA AAAGTGAAAG ATACAATTGA TTAGAGAGTT TTGCTGGATA CTATAGATGA   108180
AAAGAACACA AAATGGAACA GCCTCTTCAA GCTTAGAGTC AACGGCTGTA GTCCCAAAGA   108240
CTGTAGTCAG AGGCGGTAGG GCCAAAAGAC ATGACTTATG GCATTGGAGG AAGAGGATGC   108300
TTTGGGAGTT CATGGTAGAA GAGGCGGAAA AAATCTGGTG GATTAAAGAA AGCATCCCAA   108360
AGTGACATTA AACTAATGAC TAAATTCTGA GCTGTTTTCA GGGGCAAAGC CTGTTGGGC    108420
ACCCCTGCCA CACTTAAAGA GTCACCTAGG TATGGTTCGT GGGCTCTGAA CAGGCCTGCT   108480
CAGTGAACAT ATTTGTGACT GTTTCTCCGG CCCTTTTAGC TGTATTGAGT AAAATTTAAA   108540
GAGACCATTG TTTTGGCCTA AGCTCCTGCC CTAGGCCCAA AGAACAGACC AAACCTGAAT   108600
GGCTTCACTT GTCCTAGGTG CTGTGTACTC AAACTGAACT TTGAAACAGG TCGGTTTTTC   108660
AAAAAAAGCA AAAGATTCAC AGCAACCAAT TAGAAGAGGC CCGGTCAACC TGAGCCAGCA   108720
TGATGAGGCT CTTCTGCTTT AATCCTACAA GGAAAGAAAC TTTGAAATGA CCAATCTGCT   108780
TTCATTCTTG GTTTCTGCTT TCTTTGGTCT ATTTCTGCCT GTAAAACCTA TCTCCTCTGC   108840
TCAGCTCATT GAAGTACCCT TCTATTTATA GATGGGATGC TGCCCGACTC ATGTATCGCT   108900
AGTAAAAGCC AATTAAATTA TTACACTCGA TTTGTTGGAA TTTTGCTATT TTGACAGCTT   108960
TTCAAAAACA CCAGTAGGTT CACATCCCTA ATTCCCCAGC CAGTGTTCCC TCAAGGAACC   109020
ATGGAAGAAG CAAAGGTGGC TGAAAGGCGC CTCAGGATGC TTCTAAGCAC GGCACATCCA   109080
TGAAAAGGCA CTTACTAATA TTTGCAGGAT AGCAAAGCAC TGCAGTGACG ATAAATCTAG   109140
TATTGGAGAA GTTCAAAATA ATCAGTAGAT TAACACAGAA GCCAGAGCTT ATAGGGAGAA   109200
AAGGAACCCT ATGAAATACT TCAAATCCGA AAACGAACAT GCATTTCCTG TTTAGTTAGT   109260
GCAGGTACGT AAAAGCTTGG TAAAGTACCC TTCTTGCCAG CTTTCTCTTT CTTACAAGCC   109320
TTTTCACTGG GCTGGGAGGC TGATATTATC TAAATATGCT GAGGAGGTTC AAGTATCTCC   109380
ACAACTCACC TCAGAGTGAA TGCTCCCCTC GGCCTTAAGG CAATATAAAC CAGCCCTGTT   109440
TAGCAGGATA GCAAAATGTT TGCGGTTGTA AACTGGTGTC CCATTGGCTG TGGCGCTTGT   109500
GGTGTAAAGA ATCCCTGTGC TTGGTAATTA ATAGAGAAAT TCTATATTTT AAACTTCAGT   109560
TGTATATTGG CTCTTATCCA TGGCAGATTT TCACGTATGT GTTATTTTTT TATTTATTCA   109620
GAGCCGGAGT CTCGCTTTGT CGCCCAGGCT GGAGTGCAGT GGCGCGATCT TGGCTCATTG   109680
CAGCCTCTGC CTCTTGGGCT CAAGCAATTC TTCTGCCTCA GCCTCCCTAG TAGCTGGGAC   109740
TACAGGTGCA TGCCACCACG CCCGGCTAAT TTTTTGTATT TTAGTAGAGA TGGGGTTTCA   109800
CCGTGTTGCT CAGGCTGGTC TTGAATTTCT GAGCTCAGGC AATCCGCCCG CCTCGGCCTC   109860
CCAAAGTGCT GGGATTATAG GTGTGAGCCA TCATGCTCGG CCCTATGTGA TATTTATTAC   109920
AATGAATTCC AATGATCAGA CCTATACTCA AGTATAAGTG AATATATCAT CAATGAAGT    109980
ATAAATGATC ATTATGTTCA TATTCACACA TACAATAATG TACTCAAGTT TATTGCTAAG   110040
GTAATTCAGA ATCTCCTTAT TTTGAAGTGT GCATTTGATA TACCTGTTTG GAATAACTA    110100
GTTTCTTATC TTTGACAGAA AATAATTTTG TTGTTTTGTT TTTACTAAAA AAGCATGGTG   110160
AAAAATGGCT CCATTTCTAA GAGAGGTAAC TAAAATATCG CAATTTGCTG GGTGTCATTA   110220
AAGTAACTCA CAAGGGAAAA AATGCAAATT GGTATCTGCT GATGGAGTAA ATCTCCGCAG   110280
AAGTGATGAC CCTGAAAGGA TCAATATATT AAAGCCCCTC CCAGCTGGTC ATTCCAGATT   110340
GCAACAATAA AGCATTAAGT GTTAAAACCT CAAGGCAGCT TTTTTTTTTT TTTTTTGTCT   110400
CAAGTCCTTT ATTATTAATT TTATAGACCT ACTTAATTAC TAAGCCAAAA AAAATCAAAC   110460
TTGTTTCTCT TTGTGACTTG TCAATAGTAT TAAACTATTC TGGTTTTTTA TTTTTGTGTT   110520
ACCTTAAAGT CTCCAGTTTA GTAATTTTTC TGTACCTAAA CACTTCGGAT TTGACATGCT   110580
TTGTGGCCTT TATCAGTAGT TAGAATGTAA ATCCAATAAA TAAAGTAAAA GCCAGGTCTT   110640
CAAAACCTGG GGGCCAAGAA CTCTGTTTTA GAGGGCCTGT GACTCTCTTG GACACTGGAC   110700
```

FIG. 6.42

```
AAAATCTCAT CTCTAAATAT GGATATTTTA GGGAGAGGGT CTTTAGGCTG TCATTTGGAT  110760
TTTCACAGGG CTCCATGTAT CCATAAGGTA GTCTCTTGGG AAGTTTGACT TCAATAAATG  110820
AAGTTTAACT TAAACCTAAA ATGAAATTTA ACTGAAAAAC AAAATCCAAT GAAAGATGCT  110880
TTCTTATGCA AAAACAAACA AACAAAAAAA AAACAAAAAA ACCCCAAAAA ACCCAAAGCC  110940
AAAGATTGTT TCTGAAATTA GGTTCTAGGT TCCAGAGCAA CTCCATGGTG GGGAATCAGC  111000
CACATGTAAA GTAAGCTAAG AGTTTGGACA ATTTGTAATA TTTATTCCTA GGTTTCTTTA  111060
AGACCCTTTC AGATTTTGAA TTCCTATTAG TAGCATCAGC CAGGTTCTAA ATGTAGGCAT  111120
CACCATAGAC ACTTCCCCAC TGCTGCAGTC CCCAACACTT GCCCAATTTT CCCTTGAATT  111180
GCACCCATGC TGCCTTCTCC AGGCCTATTT GAACCCAGAA CCTCGTTGTG CCTCGTTTGA  111240
AATATAATTT CCTCCTAACT AGTCTCTGAT CTACTATTTC CCCTACATTG CTGCCACACT  111300
AATCACCTAA AATAGATTTC ATTCTACCCT GAAACAGAAA TCTCTAATAA GTTACTCCCT  111360
TCCCTTACGG GGTAAAGTTA GCCACATCCT AGGTATTCAA GGACCTTCCA GGAGCTAAGA  111420
ACATTTCCCC TGCACCTTCT TGAAGTACAC TTGTCCTATG TACTGGTTAT GTTCATTTCT  111480
TACCCTCGCT CTCGTTTTGT CTGGAATTTT CCTTGGCCTT AAATGCCTCT CACCTGCCTG  111540
CCCACATCTC TCAGGGTTGT TTCAAATCCT CAATGAAGGC TCACAGCCCC AGTCTATGTT  111600
GGCCACTTAC TTCGTGGCCT GGGAACATTT TTCTTTGGCT GACTTGCTGA CACTCCATCA  111660
GATGCATTTT TATCTGGTTG TCCATCTGTG AACCATACCC TGAGAAGGCA GAGAGTGCCT  111720
CTGCACTGAA CATGTGCTAG GGGACAGGTC TGTGCTAGAG GGGCAAGCAC TGGGAATGAA  111780
GAACTGGTCC CTACTCCCAA GGAGTTCATA TCTCAGTGGA GGTGACAAGC AACTCACTGT  111840
TTCCGGGGGT TGTGGTGACT GCTGGGAGAA GGGGTGTCTA TATTAGATCG AAGCAGCATC  111900
AGGGGAGGTT CCCTGAGAAG GTGATGCCTC AGCGGATGTC TCCAGCTAA GTGGGGTGGA  111960
GGTGGAGAAG GGCAGAGCAG GGAGAGGATC TAGGTGGGGC GTGTAAGTCT GCATGGGTAA  112020
CTCAGGGAAC CCTTGGTAAC TGCATGTAAC TGTGTGAAGC TTTCATGAAG GAACATGGTA  112080
GGAGACTAGG GTATGGACTA TAGAAGCCCT TTTGCTAAGC TCAAGAATTT GAGGCCGGGA  112140
GCGGTGGCTC ACGCCTGAAA TCCCAGCACT TTGGGAGGCC AAGGCGGGCG GATCACGAGG  112200
TCAGGAGATC GAGACCATCC TGGCTAACAT GGTGAAACCC CGTCTCTACT AAAAAAAAAG  112260
TACAAAAAAT TAGCCGGGCG TGGTGGCGGG CGCCCGTAGT CCCAGCTACT CAGGGAGCTG  112320
AGGCAGGAGA ATGGCATGAA CCCGGGAGGC GGAGCTTGCA GTGGGCGGAG ACTGTGCCAC  112380
TGCACTCCAG CCTGGGCAAC AGTGCAAGAC TCCATCTGAA AACAACAACA ACAACAAAAA  112440
ATTTGAAGTG TATCTTGAAG GAAATCCCTT GGAGCCTAAA AATGATCATT GATAACAGAA  112500
AATGATCTCT GCTCTCGCCT AGGGTAATAT ATTCAGCTTC AAAGTGGAAG GCATGTTTT  112560
CCAAGGGCAT GTTTTCTAAG TCCCTGTAAT TGTAGTGATA GCAAATATAT GCCCTGCATC  112620
TTGAAATGTA AGACTAGGTT TGAACAGTAT ATAAATTATC TTATGATCTA ATTTCCCCTC  112680
ATTTTGTGGT TTCTACTATA AGCTACCCAG AAGTGTAGAC AGGACGTTTG GAATTTGATG  112740
GGCATCGGAA AGATTCCTAC CTAAGAACAT TTTTTTTTTT TTTTTTTTTT CTGAGAAGGA  112800
GCCTTGCTCT GTCACCCAGG CTGGAGTGCA GTGGCACGAT CTCAGCTTAC TGCAACCTCC  112860
ACCTCTCAGG TTCAAGTGAT TCTCCTGCCT CAGCCTCCTG AGTAGCTGGG ACTACAGGTG  112920
TGCACCATCA TGCCTAGTTA ATTTTTATAT TTTTAATAAA GGCAGGATTT CACTATGTTA  112980
GCCAGGCTGG TCTTGAACTC CTGACCCCAT GATCTGCCCA CCTTGGCCTC CCAAAGTGCT  113040
GGGATTACAG GTGTGAGCCA CTGCGCCCGG CCTCTAAGAA AATTTTTGAG AGCTACTTGT  113100
TCTGTTGCCT GGAATTCCAC CGTAAGTACG ACGTTGTGTC TCCTTCTCCA GGGCTACTAA  113160
CTAAACAACA GAGGGTATTG TGTTATCGAC AATTATTTGA TTGATAACTA TCAGCAAACA  113220
TTTGCCAAGG CATTCCTTTA AAGATAGCCT AGTGACTCTA TTAACTACTC CTTCTTCCAG  113280
GCTTCTAAGT TCTGTTGGAG GTAAGTAGAT CCCAGAGATA AAGCACCTAC CATAGGACCT  113340
```

FIG. 6.43

```
GAATCTTGGT AGAAATAAAT TATATCATCA TGTTATCATA TTATCATGTG TTTTTCTATC    113400
TTTAAAGTCT TATGTGAATA TTCTGCTTGA AAAATATGTG TCCTCTGTTA GACCAGAGTT    113460
GAAAATATGT TATTCAAGAA CTTGTAACAG GAACCCGCAC AATTTCTGCT GGAGTTTAAT    113520
TTCAGGGTTA ATTCTGTCAG CAATCTAAGG TAAACATTAA CATTTTTCCC TAGATTCAAG    113580
TCCGTTGTCC AAAAGCTGTA ACAGAACTTA ACTGAATAAA TAGTTTCTTA AGATGGTAAG    113640
CTTCCATATG CTTATAATGA CTCCTCTACA CGTTTTCATC TGGAAGGCTG CTCATGCTTT    113700
TGGAAGCAAA GAAGACAATC TTAAATAACT ACATTTGCTT TTTGGTGGTG CCAGATTTTT    113760
CTGAGAAACA CCAATGGAAT TTATAAATTC ACCAGTCAAT GGGCAATTGA GTTGCTGTTT    113820
TGCTATTACC ACTGCCGTTT GTGAGCATTG TTGGGAAGGT GTCTTGAAGC ACACGTGCAA    113880
GTTTCCCTTG GATAAGTAGT AGGAATAGAA TTGCCAAACC ATGGCTTCCA GTGCAGACAC    113940
AGTCTCTCCC TTGGGCCCAG CCACTAGGCA CCACACATTA AGAGGATATT GTCTGTCCAT    114000
GTCCTAGAAA CGTTGTAGCA TCATGCTCCT ATTCGATTAA AAATCTCATT ATTAAAATGA    114060
ACCATCGGGT AAATGTTGTC TCGGGAAAAG AAGCACTGAC CGTCCCTGGG TGGGCTCGAA    114120
CCACCAACCT TTCGGTTAAC AGCCGAACGC GCTAACCGAT TGCGCCACAG AGACCCAGTT    114180
ACTCAGGCCG CGCTGCGGTG TGTACAGATT CCGCGGCGC CGGCAGCCGC TCTAGCCACC    114240
CTGGGCGTCG CCACCCCAGG CGTTGCCACC CCAGGCACGG GCTGAGAAGT CGCGGGGCGC    114300
GCCGAGGAGG CAGCGGAAGC GGCCGAGGTG CCCAGCGGCC GCCGCGGGGG GAGAGGCTGT    114360
GCCCCGGCGC GCGGGAGGGG GCGGGCGAGG CCGCGTGACT CCGGGCTTCT CTGGGGACGA    114420
AGCGCGCCCC TCGTGGCGGC AGCGGCCAGT GGTCCGCAGT CGGCCCGGAC TCGGGGTAGG    114480
AAAGATCCTC TCAGCAATGG CTGCGCGCCA TGCGTGCTCT GCGGCGGGGA CCGTGCCGGC    114540
CGGGCGCGCC ACCAGTAACC AGGGACCCAG GGGAGAACCT GCCAAGGGGA ATAGGTCGCA    114600
CGGAGAGAAT ACGACACGCT TGGAGGGAAG AACCACGTGC TGTACAGGTT TAAAGGATGG    114660
AGAGTCACGT GCGCTTAGGT CCCAAACTTA AGGGACCTAA CCCTTTTTCT GGGTTGCCGC    114720
TATTGCCCCT TCTCCTTAGA CAGTTTTTCA TCTCATCACC TCTCACCCCG TAAAATGCAA    114780
CGAACATAGA TAGGCTGTGT ATCAATGTAG ACTGTATGTA TATCTGTGCT TCGTACATAA    114840
AAAGAATATG ATTTTTGCCA CCTTCTAAGA ACCAATTTGC ACCCCATTTT GAGGCATATG    114900
GCCTCTGTTG AGATTGCATA GTTTAGGGGA CATCAAAAAA GCCTTATAGA GGGACTGGCA    114960
ATTAAGATAG CCTTTCAGTT TGAAATGGCC ATTGAAGGCT TCTCCCTTTC CCTGACTTCT    115020
GAATTTTTTT TTTTTTTTT TTTTTTTTTT TTTGAGATGG AGTCTTGCCC TGTTGCTGGA    115080
GTGCAATGGC GCGATCTCGG CTCACTGCAA CCTCCGCCTC CCGGGTTCAA GCGATTCCTG    115140
CCTCAGCCTC CCGAGTAGCT GGGAATACAG GCGCCTGCCA CCACGCCCAG CTAACTTTTG    115200
TATTTTTAGT AGAGGCGGGG TTTCGCCATG CTGGCCAGGC TGGTCTGGTA CTCCTGACCT    115260
CGTGATCCGC CCGCCTCCGC CTCCCAAAGT GCTGGGATGA CATTACAGGC GTGAGCCACC    115320
GTGCCCGGCC AATTTTTTTA GGCGCACTGT TCAGTGGCAC TAAGTACATT CACATTGTTA    115380
TGCAACTATC ACCGCCATCC ATTTCCAGAA CCTTTTCATC TTCCGAAACA GAAGCTCCCT    115440
ACCCATTACA CGGTAACTCA CGATTCCCCT CCTCTAGTCG GAACAATCAC CATTCTACTT    115500
TCTGTCCCTT TGAATTTGAC TACTCTTAGA GACCTCATGT AAATGGAGTC ATACGGTGTT    115560
TGCCTGTGGC TGGCTTATTT CACTTACCAT ATGTCTTCAA GGTCCATCCA CGTTGTAGCC    115620
TGTGTCAGGA TTTCCTTCCT GGATAAGGCT GAATAAGCTG CACTGTATGC AGGTATCGCA    115680
TTTTGCTTTT CCATTCATCT CTCCGTGAAC ATTAGGGTTG CTTCCACCTG CAGCTATGAA    115740
CATGGGTCTA CAAATAACTG ATTCCCTGCT TTCAATTCTT TTGGGAATAT ACCCAGAGAT    115800
GGAGTAGCTG GATCACATGG TTTGCTATTG GCTGTACCAT TTTACATTCG CACCAACAGT    115860
GTACAAGAGT CCCTATTTCT CCTCATCTAT TTTTTTTTTA AATAATGGGC ATCCTAATGG    115920
GTATGAAGTA TCATCTCATT GTGGTTTTGC TCTGCATTTC TCTAACGATT AGTGGTGTTG    115980
```

FIG. 6.44

```
GGCATCTTTT CCAGACACCA CCAATCTGAA TTCTATGGCC CTTCGTTTAC TCACTTCCTC   116040
CCAGCAAGAG CCATTTCTGC TTCAGCAAGG AGGAAGCTGC GACTGATAGA GGGAAAGGGC   116100
CCAGGGGGCT TGCAGAGTGG GGCCTGTGCC ATGCAAGGAG AGGAGAAGAA GGTGGATCTT   116160
TGAGTAGGAC TATCTGGAGA TCCTGCTTTC ACAAGGTCCT TGCTTGTGTG CTGGGCAGCT   116220
TTTGGAGCTA GTTATCTTTA TTTTAGCCCT TGAGGGATAT TTAGGCATGT GGTGCTTGTG   116280
AGCAGCCAAT CCATGAAGAA GGAACTGATG GTCTCCACCT TGGAAATATT GGAAGAGATA   116340
ATGCCGTCCA AATTGCAGTT TTAGAAGTTA ACTTAAAATT ATGCTATTTT AATGGAATTT   116400
TGGGTGCATT TCCATTTTCT TCTTAAGAAT TGCTGGAATT TCTTAAGTGT TTAGGTGATG   116460
ATCTCTTTTT GTGATTCCTT TTTTAAAAAA CAACAACAAA ATCTTTCAAA TACATAAGAA   116520
ATAGGCCGGG CACGGTGGCG TAATCCCACC ACTTTGGGAG GCCGAGGAGG GCGGATCATG   116580
AGGTCAGGAG ATCAAGACCA TCCCGGCTAA CACGGTGAAA CCCCGTCTCT ACTAAAAAAT   116640
ACAAAAAATT AGCCGGGCGT GGTGGCGGGC GCCTGTAGTC CCAGCTACTC GGGAGGCTGA   116700
GGCAGGAGAA TGGCATGAAC CCGGGAGGCG AAGCTTGCAG TGAGCCTAGA TCGCACCACT   116760
GTACTTTAGC CTGGGCGATG GAGCAAGACT GTCTCAAAAA AAAAAAAAAG AAAAAAAAAG   116820
AAAGAAATAG ACCTTTATTT TTCTGTAACT CCACAAAATT TCTATTTTGA TTCCCTATTA   116880
TTTTGCTATT GTCAACACAG TCTCAGTCAA TTCAAGATCC TGTTTGTGCC TTTCCCTGGA   116940
GTCATTTCCA AGTGCTAAGG CTTTGGTCCA TGAGTCGCAT GTGCACACTC ATGGCTGTAG   117000
AGGGAGTTTT GCTCCCGGTG AAGGTCTTGG TGGCTCTTCT ATACCTTGAT TGAGGGAAAG   117060
GAATCTTATG TGAAGTTAGC TTTGTTGTAT CAGATATTCC ATAAAGCCAT TTCTGGGACA   117120
GTCCCCTCTG TTTATCGGAC CACAAGCTTC TCTGTCCTCA TCAAGCCCAC CTTTATACTT   117180
CATTTCTCCA GACTTCATGT CCAGACTGTG GGATGAACAA GTGGTTATAA GGTTTTAGAG   117240
GCTCCTGTAG GACTAGATGG AAGGCAAAAA AAGGAAATAA CCTTTAAGCA TGCTCTCGAT   117300
TCCTTAAATC CCATCTGAAA GTCTTAAGGA TGTCTTCTCA GTCATACTTA TTTGACAATA   117360
TTACCTAATT TTCTCCATTA GCCCAAGCTC AGGGGTCTTT CTTCTTCCAT ATTCACATGG   117420
GTGCAATGGT TTTCTGAAAG GAAAACAGCA TTACTAGGGC AGTAACATTT AATTAATCAC   117480
AGGTACTTAT CAAACTACAA AACAGGCATT CCAGGAACTG GGTGTTTCTG TTTGTAAAAT   117540
TACACTCTCG TGTACATGCT CCCACTAAAA TGTAAGTTCG CTGAGGATGG AGGTTTTGGT   117600
CTCTTTGCTC TGTGCTGTAA CCCCAACACT GCAGCAGGGC CTGGCACATA GCAGGCATGC   117660
AGGGACTATG CACTGAATCA ATGAGGAAAT GAAAACCAGG ACCATGAAGT AAACTGGACA   117720
AAATAAAATG TGATAGAAAA TCTAAATTCC TAATACATAA GGAGCACTTA TCAATTGATA   117780
TTTACAAAAT CTTTTTACAA TTCAATTAAA GACAACATAA AACAAATAAG AATGGGGACA   117840
GGAACAGAAA ATTCCCCCAA AGAAAAAAAT ATATATACAT GGTACAGCCA TTGTGGAAAG   117900
CAGTATGGAG TTCTCAAAAA TATTAAAATA GAACTATCAT ATAATCCAGC AATCCCATCC   117960
CTGGGTATAT ATCTAAAGGA AATGAAATCA GTACCCCAAA GAGGTGTCTG CACTCCCATG   118020
TTTATTGCAG CATTAGTTAC AACAGCCAAG ATATGGAATC AACCCATCAG CAGATGAAAG   118080
GATAAAGGAC ATGTGATACA TATACACAAT GGAGTAGTAT TCAGCCTTAA AAAAGAAGAA   118140
AATCCTGTCA TTTGCAACAA CATGGATGAG CCTAGAGAAC ATACTAAATG AAATAAGCCA   118200
GGCATAGAAA GACAAATGCT GCATAGTCTC ACTTAGGTGT GGAATCTAAA AAAGTCAAAT   118260
TAAAAAAAAA TGTCAAGCAG AGAATAGAAT GGTAGTTGCC AGGGACTCTG GAAGTAGCA   118320
GGGGTGGGGG TGGAGGGGAG GGGATGGGCA GAAGTTGGTC AAAAGGTACA AAGTTTCAGG   118380
TAGACAGGTG TAAGTTCTGG GGATCTATTG TACAGCGTGG TGACTGTAGT TAATACTGTA   118440
TTGTGTACTT AAAAATTGCT CACCAAAAAT GTTCTCACCA AAAAATGAT GTTTGGATAT   118500
GTTAAACAGT TTGATTTAAT CATTTTGACG TGTGTGTGTG TGTGTGTGTG TGTGTGTGTG   118560
TGTATACATC AAAACATCAC ATTATATACC ATATACAATT AATATATACA ATTTTTGTCA   118620
```

FIG. 6.45

| | |
|---|---|
| AAGAAAAAAT GCACATGACC AATATGATAA AAGTTTAGTC TCACTAGTAA TAAAAATCAA | 118680 |
| AATTAAATGA AATAAAAATT TCTTTCCCCA AATCGCAAAA GAGAAAGAAA GGTAATACTA | 118740 |
| AAACACAGTC ACGGTGTAGT GAGAGGGCTG CTCTCACACA GGACTGATGA GAATAAAATT | 118800 |
| GGAGAGCAGT GTGGTAATAT ACATATTAAA CAATGTATAT ACCCTCTCAT TTTAGAAATT | 118860 |
| CTATATTAGA AATCCATCCT AAGAAAATAA CCAGGGATGT GATCAAAATT TTGAATGCAG | 118920 |
| CAGCACAGTA TTATTTATAA TAGTTATAAA TAAGAAACAA CCTGAATGTC CAGCAACAGG | 118980 |
| CAAAAATGAT AAATAAATTG TGGCATATTT AAGCTGGTGG CTCATGCCTG TAATCCCAGC | 119040 |
| ACTTTGGGAG GCTGAGGCAG GAGGATCTCT TGAGGCCAGG AGTTTGAAAC CTGTCTGGGC | 119100 |
| AACATAACGA GACCCAGTCT CTACAACATA TTTTTTAAAA TTAGGTGGGG CATGGTAACT | 119160 |
| CATGCCTGTA ATCCCAGCAC TTTGGGAGGC TGAGGTGAGC AGATCACCTG AGGTGAGGAG | 119220 |
| TTTGAAACTA GCCTGGCCAA CATGGTGTAA CACCATCTCT ACAAAAAATA CAAAAATTAG | 119280 |
| CCAGGGTGGG GTGCGTTCCT GTAGTCCCAG CTACTCGGCA GACTGAGGTA GGAGAATCAC | 119340 |
| TTGAACCCGG GATTCGGAGG TTGCATTGAG CTGATATCAT GCCACTGCAC TCCAGCCTGG | 119400 |
| GTGAGACCCT GTCTCAAAAA AAAAAAAAAA AGAAAAAGAA AAAATTAGCT GGGCGTGGTG | 119460 |
| CTGTACGCCT GTAGTCCCAG CTATTCCGGA AGCTGAAGCG GGGGGATTGC TTGAGCCCAG | 119520 |
| GAATTTAAGG CTGCAGTGAG CTATGATTGT GCCACTCCGC TCCAGCCTGA GTGAGAAAGC | 119580 |
| AAGACTCTGT CTCTTAAAAA AAAAAAAGTG ATATATTTTT AAAATAGAGT ATATTACTTA | 119640 |
| TATAGACATC AAAAACAATA TTTTCAAGGG ATATTTAAAA ACATAGGATC ATGACAAAAT | 119700 |
| GTAAAGTTCA AAGGTAAGAT GGAGAATGGA GAACTGTGGG GAACTGTATA ATCTGACAAT | 119760 |
| TCGTAGTTGC ATACATCTTT CTGTGTGCTG GTGCTGTTAG AACACTTTGT ACGCATCACC | 119820 |
| TCATTTAAGT TCAGCATCCC TAGGTGGCAG ATACTATTAT TATATTCCAG TTTTGTTTCA | 119880 |
| CGTTGTATAT GCGGTGTGAG CCCCAATATG GGATGTGTGT GTGCACATGT GCAGTATTTG | 119940 |
| GAAAGTTCTA TGAAATATTA TTAGTGGTTA TCTCTGGGAG GTGATTTTTA TTCCTTTTCC | 120000 |
| AGTATGTTCT CAAGCATTTG CTGCAAGCAG TCTTTTGCGG GGCCAGGGTT GAGAGGCAGC | 120060 |
| AGCAGTTTCC CTAAATTACA GATAGAGGGA GGTAGGTGGT TATGCTTGGC CAGATCTCTG | 120120 |
| TCTAGGGGTA GAGGAGTGCC TGTGTGTGGG TAGGGACACC GGCGGGGGGC TTTGCCAAAC | 120180 |
| ACAGTGGAAC TGTCACGCTG GTCTCTCTTC TCAACTCTTT CACTCACCTG AGAAAAGGGT | 120240 |
| GTCTATGGAC CATGCACACT TCTGTGGGGA ATTTTACAAG ATGTGAATCA TCAGTGATGA | 120300 |
| AGATGCTTTC ATTTAAAAAG AATTGGAGTA CCTGAGATTA GAGATAACTT CTACCCTTTT | 120360 |
| AAAATATTTT TAAAAATTTC TTTGCACTGA TTTTTTTTCT TCGTTTTTAT GAGTTGTTTT | 120420 |
| CATTTGGGTG GGATAACTCA ATCTACAGGA GAATATTAAG ACTTTTTAAA TTTTAAAAAA | 120480 |
| TATACTTTCA AATACTTAAT ACATTTGTG TTAAATGACA GCCAGCAGAT ATTGACTGAA | 120540 |
| TTGGGCTAGA TGCTTCAGGG ATCTCCCTTC CATTTAAGAC TCTCCGAGAG GCCATTCCTG | 120600 |
| ACTGCAGGTC ACTGTATTAT TTTTAATTTT AAAATTTTTA CTTACTTATT TTATTTAATT | 120660 |
| TTATTTTTTG AGACAGAGTC TCACTCTGTC GCCCAGGTTG GAGTGCAGTG GCACAATCTC | 120720 |
| AGCTCACTGC AACCTCCACC TCCCGGGCTC AAGCGATTCT CCTGCCTCAG CCTCCTGACT | 120780 |
| AGCTGGGGTT ACAGGTGCAG GCCACCACAC CCCGTTAATT TTTGTATATT TAGTGGAGTC | 120840 |
| AGGGATTCGC CATGTTGGCC AGGCTAGTCT CAAACTCCTG ACCTCAAGCG ATCCTTCCAC | 120900 |
| CTCAGCCTCC CAAAATGCTG GGATTACAGG CCTGAGCCAC CCCACTCGGC CTACTTTATT | 120960 |
| AATCCACTTG CAGAAACAGG ATATACACAA AAACGTTTCA AGGCTGTAAG TGCCACTGCA | 121020 |
| TGGCACCAAT GGTAAACGTT TTACAAATTT GAGTCAGGAA CAATCATTAG TGTCACTAGC | 121080 |
| AACAAAAATC AAAATTAAAT GAAATAAAAA ATTTCTTTCC CCAAATGGCA AAGGAGAAAG | 121140 |
| AAAGGTAATA CTAACACGCA GTCAGGGTGT AGTGAGAGGG CCGCTCTCAC ACAGGACTGG | 121200 |
| TAAGTACAGA GCCATGGAGT AAGCAGGTCT TGAGCTGACA CTGGAGAGGA TCCTTTTTTT | 121260 |

FIG. 6.46

```
TTTTTATTTT TATTTTTTTA GAGTCAGGGT CTTGCTTTTT TACCCAGGCT GGAGTACAGT   121320
GGTGCCATCA TAGCTCACTG CAGCTTCAAA CTCCTGGGCT CAAGAGATCC TCCTGCCTCA   121380
GCATCCCCAG TAGCAGGGAC CACAAGTGAG AGGATCCTTT AGTGTTGTCA AGGAGAAGGA   121440
ACAGAGGTGT GGATGGGTGG GCACAGACAC AGGAGCACAG CTGAAGCAGA GGATTACAAA   121500
GGGTGGAGCC TGATGTAAAG AAACCTAATA GGTGACAGAG CATGGAGGCT CTTGAATACC   121560
AGGCTGGAAA CTGCATTAGG AACGGTGCTC ATAATTGCAG AAAATTTTAC ATGGCCTAGA   121620
TAGTCATCAA AGGATGATGT ACAAACAACT ATGGCATATT TATACAATGT GCCGACAGGA   121680
TGCACTGAAC ATTTTGAACA ACAAAGAGAC TTGATAATGG CGAGGTTTTG AGGAGGTGAA   121740
TCAGGATGCA AAAAAAGCAA ACAACTAATA AAGTTGATTG ATGACAAACA CTATCAAAAG   121800
GCAGCCAGGA GAAAAGCTAC TGGTTACCTC CAGGGAGCTG GTGAGGGAGG CTGGGTGGGA   121860
GGATCTACCC TTCTGAATTC TGAGGGCACC TCCAGTGTGG CCCTCAGAAA GCAGGAGCTT   121920
CCAGGCTAGA ATCAGATCCC GACATCCCTG TTAATTCCAC GGATTCCACA CCGAGTCAGA   121980
TTTATGATTT ACTATAGGGT TTTAAAAACC AAATTGCAGG GATGCTAGCC TATCACAGCT   122040
TATCTCAGAC ATTGTCCACT AAGGTATACA GAGTGCTGCC TGTTCCTTTG GTACCCTAAT   122100
CAGGAAACCC CATCAGATCT GCTCCTTCCT ATGGGGTAGT GAGTAACACG AAGGCTTACC   122160
ATCTCACACA GATAACTGGT CATAGGTCCA GCAGAAGTTT AAAACAGAAA ATGAGGAAAG   122220
CCATGTGATT AACTGCTGCC AGACTGTTTG TGTTACAAAC AGCAGTTCCT TAGGCATTGC   122280
CTGGGACATG CAATAATTTC TGTTACACAA TCTGTGGTAG TTAAAATGCT GCACGATGAA   122340
AGCTATCTGA TTTGGATTCA TTATTAGGTG AGCCATCTCG TCTGCAATTT GGTTCCACCA   122400
TTTTCATTTA ACAAATGTAA AAAAGTTTAT TAAGCTCTTA CAAAGTTATG CTGGGCAAAT   122460
ATGCAAAAGT CCAGATCACC TACCGCAGGA ACTAATCTAG CCTCCTCTCT GGGCACCCTG   122520
TTGTTTGGGG CTGGGCAGTT CTTTCCTGTG TAGAACCATC TAGGGCTGAA TAGGTCATTC   122580
TGACACCTGG GCACCTCTGC CTGCTCGTAA ATGGGACAAT CAGAAAGGGC CCTTATGTTT   122640
CCAAACTTTC TTTAAAGTAG CTGTTCTGAA AACATGGTCC AGGGACCCCT GATTGTCCCT   122700
GAGACCTTTG AGGGGATCTT CAAGGTTAAA ATTAATGTCA TAATAATACT AATATGTTAT   122760
CTGTCTTTTT TCACTCTCAC TTTCTCACAC GTGAACAGTG GCATTTTCCA GGTGACAGAG   122820
TGTGTGATAA TGAACCTAAC TGAATGCAGA AGCAAACATG AGAACCTAGT TTTTTCAATC   122880
AAACCAGACG TGAAAGAGAT TTGCAAAAAT GAAAAAACAA TGCTATCCTC CTCACAATAT   122940
TTTTGTTTTA GAAAATAAAG TTATTTTTCC TAGAAATGTT TTTGAGTTTA TCAGTCATAG   123000
GTTTATTATT ATAATTAAAA AATGAAATAT ACATACACAG ACATATTTTT TAAAGTTCTC   123060
AGTTTTAATC TCTTTTTTTT TTTTTTTTTT TTTGAGACGG AGTCTCGCTC TGTCGCCCAG   123120
GTTGGAGTGC AGTGGTGCGA TCTCAGCTCA CTGCAAGCTC CGCCTCCCTG GTTCGCGCCA   123180
TTCTCCTGCC TCAGCCTCCC GAGTAGCTGG GACTACAGGC ACCCGCCACC GCGCCCGGCT   123240
AATTTTTTGT ATTTTAGTA GAGACGGTGT TCACCATGT TAGCCAGGAT GGTCTCGATC   123300
TCCTGACCTC GTGATCTGCC CACCTCGGCC TCCCAAAGTG CTGGGATTAC AGGCGTGAAC   123360
CACCACGCCC GGTCTCAGTT TTAATTTCTA ATACAGTAAG TATTGATCAG TGTGCCCCAC   123420
ATTAGTAAAA GCTCTTGGGG TCCTCAGTAC TTCTTTTTAA GAGTTGTCAA GGAGTCCTGT   123480
GACCAAAAAT AGGAGAGCCA CTGCCCTAGA AGGACAGCCC CAGCCCGGGT CAGGAACAAC   123540
TGGGACAGAA CCTACTGCTC CTAGTGGATT GTAATATGAT AGGATTTAAC CTTCAAGGTT   123600
TCAACTCTTG GCAAGAGTCC ATGAGGGGCC ATGGTTTGTC CTGAGCATTG CTTACTGTTA   123660
ACAGGAGCAA GTTCCTTAGG CTGGTGAGCC AAGCCAGCCT GACGCTGGCC ATGGACATCT   123720
TAGTGGGCTG CTTGTTCTAG TGTGGGTTTT CATTTTATGG GAAATGTCAT CTGCTCTAAG   123780
GCTCTTCTCA TTTGGGGAAA TCACAAGTTC TCAGAATGTT TGTCTCTCTT GGTTGGGGCC   123840
TCTATAATTA AATTATAAAA CAGAGGTAAT GGTTAAGTAA TGCAAGATTT GACAGAAACC   123900
```

FIG. 6.47

ACAGAGGATT TAGGGTTTAA TTTGAGTGAG GCAAAGGGGG GATGAAGATG AGCGGTCCTG 123960
GAGACAAGAA AAAGATTGGA TGAAGCTGGG CACGGTGGCT CACGCCTGTA ATCCCAGTAC 124020
TTTGGGAGGC CAAGGTGGGC AGATCACTTG AGGCCAGGAG TTTGAGACCA GCCTGGCTAA 124080
CATAATGCAA CCCCGTCTCT ACTAAAAATA CAAAAATTAG CCAGGCGTGT TGGTGTGTGC 124140
CTGTAGTCAC AGCTACTTGG GAGGCTGAGG CATGAGAATC GCTTGAATCC GGGAGGCAGA 124200
GGTTGCAGTG AGCAGAGATC ATGCCACTGC ACTCCAGCCT AGGCAACAGG GTGAGACTCT 124260
GTCTTCTTTT TTTTTGAGAC GGAGTCTGTC GCCCAGGCTG GAGTGCAGTG GCATGATCTC 124320
TGCTCACTGC AAGCTCCGCC TCCCAGCTTC AAGCGAGTCT CCTGCCTCAG CCTCCCGAGT 124380
AGCTGGGATT ACAGGCATGT GCCACCACAC CCAGCTAATT TTTATATTTT TAGTAGAGAC 124440
GGGGTTTCAC CATGTTGGTC AGGCTGGTCT CAAACTCCTG ACCTCGTGAT CTGCCCGCCG 124500
CGGCCTCCCA AAGTGCTGGG ATTACAGGTG TGAGCCACCA TACCTGGCTG AGACTCTGTC 124560
TTTAAAAAAA AAAGAGAGAG AGGGAGAGAA AGATTGGATG AAACAACAGA GTGGGGAGGA 124620
CCTGTGAGCT TGGTAGCTTG GTGAAGGCAG GGCTTTATTG GGGGCCTTAG AGGGGATCCA 124680
ATAAAGGTTC CCAGTCATGG TAGTGACCTA AAGAAAATAG CATTTTAACA TCTTTCATTT 124740
CATAATAGAC AGTCACAGTT TACAAGACCC TTTCCATACA TTCCTTATGA CATCCATACT 124800
ACAGCCCAGA GGCAAGTTGT GCACTCTCTC CTCTCACAAA TACAAAAACT CAGCCTCTAG 124860
AGGCCAGCGA CCTGCTCAGG GTGATGTGCA ATTCAGGGAT GACAGAGTCG AGGCTCCCAG 124920
CCCAGTGGTT ATCCCTCACA GGCACGTTGC CTGTCAGTGT GCAGTATAAA ACTTTGTACA 124980
AGAAATCAAG TTGCATTAGT CAGTCGGATT CCCCAAATGA TCACATTGTA GATGGTGTAT 125040
GCTGTGGGCA GAGCAAGGGC TGCTGTTTCT TGGGCAAAAC AATCAGTCCC CCTCCCCCCC 125100
AAAATAAATG AATGCCAATG GTGTGACTTT ATTTTATTTA TTTTATTTTT ATTATTATTT 125160
GTGAGACAGA GTCTCACTCT TTCACCCAGG CTGGAGTGCA ATGGCATGGT CTCGGCTCAC 125220
TGCAACCTCT GCCTCCTGGG TTCAAGCGAT TCTCCCGCCT CACCCTCCCG AGTAGCTGGG 125280
ACTACAAGTG CATGCCACTG CACCCGGCTA ATTTTTGTAT TTTTTTTAAG TAGAGACAGG 125340
GTTTCACTAT GTTGGTCAGG CTGGTCTTGA ACTCCTGACC TCATGATCCA CCTGCCTCAG 125400
CCTCCCAAAG TGCTGGGATT ACAGGCATGA GCCACCGCGC CCAGCAATGT GACTTTATAA 125460
TTACAGAATG TAGGACTCAG CTCCCACTAT TGTTATGACT CAATATTCTC TTAGATAATG 125520
TTTGGGGCAC TAGCTTACAG GCAGCATTGC CCGGTGGTTA ATGTTGTAGC TTTGCAGGCA 125580
GACTGACCAT ATTAAAATTC GATCACACCA TTTGCTAAGC CTGTGGACTC GGGCACGCTT 125640
CTTTCTCTGC GTTAGTTTCC TCCTCTGTAA AACACGGATG ATGCTATAAA CACACCCAAG 125700
TCCTAGAATT GTTATATGAG TTAGAAAAGA TAGGCAAATA CAACTCTCAC AAGACAGCCT 125760
GGCCTCCAGT AAGTGCCACT GAGTGTTTGC TCTTATTGTA CAGTGGCTCC AAGTGCTTCT 125820
GTCTTGGATT ATTTCTGACC AGGTGGCTAT GTCTCCTAGT AACTTACCAA TCCTGTTGAG 125880
TCTTAATAAG CACGTCTTTG ATGCCTACAG TGCGACTGAA TTTCCAGGCC TCATTACTGG 125940
AGACACAATC ATCCTATATG CTTTTTTCCA TTTGTTTTTA ATAAAGTGGT ACATGTGTAT 126000
GGCACCAGAT CAAACAGTAC AGAACAAGTT ACAATGGAAG AGAATGGCCT CCCAGCTTTC 126060
CTGAAATCCT CAACTCAGAG ACAACTTTTT TTTTTCTGAC GGTTTCTTTA TACAGCCCTT 126120
TTTGTGGTTA CCTTCCTAAC TCTAGAAAAA CTATTCTTAC CTCTGTTTAT TTACTTAGAA 126180
ACATTAGACG TTACCTTTCA ACTCCTCAGT ATGAAGCTTT AGTTTTCAGC ACCCCAGGCC 126240
ACCACCCTCT TTCCAGGACT TACTACTTAT ACTGGTGGTA GGTGGAATTT TAAAATTCAT 126300
CAGCATTCTT TTGTGATTCT CTGTGTGTTC CAGTTTTACA GCAACCCGTA CTTGTTGCAT 126360
GAGTACAGTA GAACTGGGAG GCTCATAACT TAGCCTGCAG GACTTTCAC TTAAAGCCTG 126420
GCCCTCAGGG TGATGTCACC CACCTCATTG TGCCTGGCTC AGGAGTTTAG TCCCTCAGTT 126480
GCCTGGTTGT ATAGTTTGGA TGTTCAGCAC CTCCAAATCT CACATTGAAA TGTGATCTCC 126540

FIG. 6.48

```
AATGTTGGAT GTGGGGCCTG GTGGGAGGTG TCTGGGTCAT CAGGTGGGTC CCTCTTGAAT   126600
GGCTTGGTGC CTTCCCCATC GTAACGAGTG AGTTCTTGCT CTGGCAGTTC ACACAAGAGC   126660
TGGCTTTTTA AAGGAGCCTG GCACCTTCCG CTCTTTCTCT TGCTCTTCCT CTTCCCTTCC   126720
TTTGTCACTA AAAGCTTCCT GAGCCCTCAC CAGAAGCGGT GCAGATGCTG GTGCCATGCT   126780
TGGACCTCCT GTAGAACTGT GAGCCAAATA AACTCTTTCC TATAAATTAC CCAGTTTCAG   126840
GTATTCCTTT ATACAATGCA AAACAGACTC ACACATCTGG TAAACCCCAG TTGTTTGCTT   126900
CTAGGTAAGA CGGGAGGAGT GGGGAGCTGG TGAGGGTTTC CACTGCATTG TCTATTTTCA   126960
GGCAAGGTGT CTCCACTGAG TAGGCTTCAC ATTCAGAGCT CTGGGTAAGG TGGGCAGGAA   127020
GAGGGTTGCA GGCTGCCCAA AGGAGGGAGA GAAGAAGGCT GAATCCTTCA GTGACAACCT   127080
GTGAACCAGA GTCTTAGCTC TCTTTGAATA TTTTGTTCAG TATCTTTGGG TTTTGTTTTA   127140
TTTTGCCTAG GGTAAATGC TGACTGCCTG TTCTCTGGAC AGGAATGGAG AAGATGGTGC    127200
TAGCAGGGTT GCTGTTCATA TGTAGACATT CATGCAGTCA CTCTCTTTTC AGCACACTTC   127260
TTACTTCTGC CCTGGGTTCA GTTGCTGACT CTGAGCCCAG AAACCTTCTA GGGTTCTGTT   127320
AGGTAGATTG GCTTCCACCG TCTTTGCGAC AACCACAGAA AATTCTAGAC TGTTTTCTCT   127380
TCGGGCTTCA TTAGTCAACT TGCTTCAGTC TGTCTTGCAT CTTCTAAATA TTTATAGATC   127440
TCTCTCTTTT GTTGGAGTGG CAGAAAATGC TAGTTGACCA CCCAATATTC AAATTATCCT   127500
GCCTCCTTAA TAACAGAATA TCATTGGATG TGGTGGGTAA ATAATATACC CTAACTTTCC   127560
TTGCAGAGAG GGGTGGCCAA TGAGATGGAA ATGAAAGTCA TTGGGAAAGA CTCCCAAGAC   127620
ATCTCTTTAA ACAAGACAGA CTGAAGCAAG TTGACTAATG AAGCCCAAAG CTAGCAGTTG   127680
TTTTTGTTTA TCTTTGCCTC TTTCTTCTTC TTCCTGTGGG GACAAAGGGC AGTGATATCT   127740
GGAGCTGCAG CAGCCATTTT GGCATAATGT TGGAAAAGCC AAGAGACTCT CAGAGACCGC   127800
AGCTCCAGCA GTTTTTTATT TTTTCCAAAT ATTTGCTCCA CTGCAGGAGG ATGAGATATT   127860
CGTGTTTGTT GCCTTGTGAC TGTAGGAGGA CTGCACTTCC CTGCCTTGTT GTCAAGTTTC   127920
CCCATGTGGT CTGCTTTGGC CAGTAAAACA TGAGTGGGAG AAGCTTGGTG AACCATTGCA   127980
TGTCTACCAG CTTTTTTGCT CTCTTCCCTT TGGCATTAGA AAGGCATGTC CAGGATGGAG   128040
TTGTTCCTTC AGCCTAGATT GGGTTATGAG AAGCTAGCTG GGGGAGTCCA GTAACATATA   128100
AAGCGAGTTA GAAATAAAAC TTTGTTGTTG TAAGCTATAT ATATATATAT ATATATATAT   128160
ATATATATAT ATATATATAT AATATGTATG TAATATATAA ATACATATTA TACTTTAAGT   128220
TCTAGGGTAC ATTTGCACAA TGTGCAGGTT TATTACATAG GTATACATGT GCCATGTTGG   128280
TTTGCTGCAC CCATCAACTG CTCATTTACA TTAGGTATTT CTCCTAATGC TATCCCTCCC   128340
CAGCCCCCCA CCCCTCAACA AGCCCAGTG TGTGATGTTC CCCTTCCTGT GTCCAAGTGT    128400
TCTCATTGTT CAATTCCCAC CTATGAGTGA GAACATGTGG TGTTTGGTTT TCTGTCCTTG   128460
TGATAGTTTG CTGAGAATAA TGGTTTCCAG CTTCATTCGT GTCCCTGCAA AGGACATGAA   128520
CTCATCCTTT TTTATGGCTG CATGGTATTC CATGGTGTAT ATGTGCCACA TTTTCTTAAT   128580
CTAGTCTATC ATTGATGGAC ATTTGGGTTG GTTCCAAGTA TTTGCTATTG TGAATAGTGC   128640
CGCAATAAAC ATATGTGTGC ATGTGTCTTT ATAGTAGCAT GATTTATAAT TCTTTGGATA   128700
TATACCCAGT AATGGGATCA CTGGGTTAAG TGGTATTTCA AGTTCTAGAT CCTTGAGGAG   128760
TCGCCACACT GTCTTCCACA GTGGTTGAAC TAATTTACAC TCCCACCATC AGTGTAAAAG   128820
CATTCCTATT CCTATGTCTC CACATCCTCT CCAGAATCTG TTGTTTCCTG ACTTTTTAAT   128880
GATTGCCATT CTAATTGGCC TGAGATGGTA CCTCATTATG GTTTTGATTT GCATTTCTCT   128940
GATGACCAGT GATGATGAGC ATTTTTTCAT GTGTCTGTTG GCTGCATAAA TGTCTTCTTT   129000
TGAGTAGTGT CTGTTCATAT TGTTTGCCCA TTTTTTGATG GGGTTGTTTG TTTTTTTTCT   129060
TGTAAATTTG TTTCAGTTCT TTGTAGATTC TGGATATTAG CCCTTTGTCA GATGGGTAGG   129120
TTGCAAAAAT TATCTCCCAT TCTGTAGGTT GCCTGTTCAC TCTGATGATA GTTTCTTTTG   129180
```

FIG. 6.49

```
CTGTGCAGAA GCTCTTTAGT TTAATTAGAT CCCATTTATC TATTTTGGCT TTTGTTGCCA  129240
TTGCTTTTGG TGTTTTAGAC ATGAAGTCCT TGCCCATACC TATGTCCTGA ATGGTATCGC  129300
CTAGGTTTTC TTCTAGGGTT TTTATGGTTT TTAGGTCTAA CATTTAAGTC TTTAATCCAT  129360
CTTGAATTAA TTTTTGTATA AGGTGTAAGG ATGGTTTCCA GTTTCAGCTT TCTACATATG  129420
GCTGGCCAGT TTTCCCAGCA CCATTTATTA AATAGGGAAT CGTTTCCCCA TTTCTTGAGC  129480
TACAGATATT TTGAGTTTGG TTACCACAGT ATTATCTAGT GGAAGTTGAC TTATACAGTA  129540
TGTAATAGGA TAAATATAGG TGTGTAACAG AATATTAAGT GTTCGTGTTT CAAAGCTGAG  129600
GGGAAAATGT TAAAAGTGTT CACACACTCT AAAAAGAGAT TAGCTAAAAC TGCTTCATTA  129660
ACCACACTTT GGGGAAACCA GTTCTGAGAT TCTTCTCCAT TACTCTGACA GGTTGGACCC  129720
TCTGGGGAGC AGATCTCAAG ATCAAGTTAT GAGTGCAAGA GGTGTGTTGG GAAGCGATGG  129780
TTGTAAAAGA ATCCTGCAGT AGCACCAGGC ACAAGTCTGT CCAGGGAGAG GAGGACTTCT  129840
ACTCTCTACC AGCATCTCTC CTAAGTCCCC TTAGGGGACG GGGCAAGGA AGTGCTGGGA  129900
AGGGCAGGGC ATGGTTCCTG GCTAGGACTC CACCCCCCTG GGGCCTGTAC CCACGGACCT  129960
AGGTGAAGAC AGGCACTCCT GCCTTCTCGC CAACGGTTG CGTTTCCCAA GATCATCCTG  130020
GCCTGCCACG CCCCCATCTA CCTATTAAAC TCCCCCACCT TCCCCAAACC CTAGCAGGCA  130080
GACACACATC GGTGGAAGAA GACAGGAGCG GCTGGACATT GAAAGGACGT CGAGAGGAGC  130140
ACACCTGCAC ACCATCGACC AGCGGAACGA GGCAGAGTGT GGCTGGAGCA GTCGGAGGGA  130200
AGCCTGGGCC GCTGACTCCA GGGGAAAACC ATCTCCTTTC TGGCTCCCCC CTCTGCTGGG  130260
AGATACTTTC ACTGAATAAA ACCTTGCACT CATTCTCCAA GCCCACCTGT GATCCGATTC  130320
TTCCTGTACA CCAAGGCAAG AACCTGGGAT ACAGAAAGCC CTCTGTCCTT GTGATAAGGT  130380
AGAGGGTCTA ACTGAGCTGG TTAACACAAG CTGCCTATAG ACAGCGAAAC TGAAAGAGCA  130440
CACAATAGCA CACACTCATT GGGGCTTCAG GAGCTGTAAA TATCCACCCC TAGACGCTGC  130500
CATGGGGCGG GAGCCCCACA GCCTGCCCGT CTAGAGGTTT GAGCAGCGGG ACACTGAAGA  130560
AGAGAGCCAC ACCCTCATCG CACGTCCTGC GAGGGAGACA AGGGAACTTT TCCGGTTTCA  130620
CTTCTGCTTG GCTTGAGCTG GCACTGAAGC ACCCTTTTCC CTCCTCACTG AGGGAGCAGA  130680
GGGGAAAAGC GGTAGAACTA ACAGGCTAAC AATGCTCCTC CGAAAATATA TCGTATTTTT  130740
GGATCCCTAG AGATAGGTGA TCACGGCAGC CGCGGAGTGC ATTTGGGTCT CCTTTCAAGA  130800
AAGAACTTGC TGCTCAGCGT TGAAGAATGC AGTTGGCCAA CAGCCTCCAG CTGCTCTGTC  130860
TTCAGCATCT GCCATGGCAT CTGAGCTGAG GTCATGTTCT TCCTGGGAGG TCCCCAGCAG  130920
AAGGATCACG TGGAAGCTCC ACAAGCTCCA CAGATGTTCC AGGAGAGGAA TAGGCAGCAT  130980
TTGGAAGACA TATCCTGCCA TAACAGAGGG CATTTGCTAG TAGAGACAAC AAACAGCAAC  131040
AGCCAAGTAA ACAAACACAC AAGCACAAAG CACTTTCTCC CATTTCCCCT CATTGATCCT  131100
GTCCGGGTAG AAGCTGGGGA GGAAGTAGAA TAGGGTGAGG CGGGGTGGGG CTGGGGGGCC  131160
TACACCTTCT TCCTTCCCCC GCAGGTCCTG TCCCTGGGCC AGGCTTGAAC TAGGGGAATG  131220
GGAAAAGCTG TGAAGTGAAT GAGAATTAGG AGTTTTTATT TAGACTGGAC TTGAATTTTT  131280
TTTTTTTTTT TTTTTTTTTT GAGACAGAGC CTCGCTCTGT CACCCAGGCT GGAGTCCCGT  131340
GGCGCCATCT TGGCTCACTA CAGCCTCTGC CTCCCGGGTT CAAGCGATCC TCCCACCACA  131400
GTCTCCTGAG TAGCCGGGAT TACAGGTGCC TGCCACCATG CCCAGCTATT TTTTTTTTTT  131460
TTTGTATTTT TAGTAGAGAC AGGGCGTCAC CGTGTTGGCC AGGCTGGTCT CGAACTCCTG  131520
GCCTCAAGTG ATCTGTCCGC CTCGGCCTCC CAAGTGCTA GGATTATAGG AGTGAGCCAC  131580
CACGCCTGGC CTGGACTTGA ATTTTTAATT CCTAAAAATG AACTACCAGT TAAAATTTAA  131640
AAATGACCAA AAAAGCTATG GGATATGCTG ATGTTTTGCT TTGGGGATAA GGAAAAGATA  131700
TCTGGTTGAG CGGCATTGAA AACAGTGTAG GGAGAGAAAA ACTCATTCCT GGCTCACCCT  131760
TTTGAGTCCC ACTATCTCAA TAATCTGATG TTATATGACA CACACACACA CACGGAGG    131820
```

FIG. 6.50

AATCCTGGAA GACTCCATAT CAAGGTGGTG ATGAAGGTGA CCAGTGGGTG ATAGGATTAT 131880
AGGTGTGTGT TTATTTATTT ATTTTAATTA CCTTTTTTTA GAGACAGGGT CTCTGTCATC 131940
CAGGCTGCAG TGCAGTGGTG TGATCATGGC TCACTGCAGT CTTGCACTCC AGGGCTCAAT 132000
CCTCCTGCCT CAGTCTCCTG AGTAGCTGGA GCTGCAGTCA TGCACCAACG TGCCCAACTA 132060
ATTTACTTTA TTTTATTTTT TATTTTTTGT TAAGATGGAA TCTCACTTTA TTGCCTAGGC 132120
TGGTCTTAAA CTCCTGGTTT CAAGCATTCC TCCTACCTCA GCCTCTCAAA GTGCTGGAAT 132180
TACTGCACTT GGCCCTATTA TATTTTTAAA AAATTTCAAT AGTTTTAGGG GTAAAAGTGG 132240
CTTTGGTTAC ATAGATGAAT TGTATAGTGA TGAAGTCTGG ATTTTTAGTG TACCCATCAC 132300
CCAAATAGTG TACATTGTAC CCAATGAGTA GTTTTTCATT CCTCACCCCC ACACTGTCCC 132360
CACTTCTGAG TCTCCTGATG TCCATTATAG CACCCTGCTT TTGCGCACTT AGAGCTTACC 132420
TCCCACTTAG AAGTGAGAAC ATGTGGTAGT TGGTTTTCCC TTCCTGAGTT ACTTCACTTA 132480
GGTCAGTGGC CTCCAATTTC ATCTGAGTTG CTGCACATAA CATGATTTCA TTCTTTTTTT 132540
GACTGAGTAG TAGTCCATCT CTCTCTCTCA CACACACACA TACACACACA CACACACACA 132600
CACACACACA CACATTTATC CACTCATCCA TTGATGGGCA CTTAGGTTGC TTCTATATCT 132660
TTGCAATTGT GAATTGTGCT CCAATAAACA TACATGTGCA AGTGCTGTTT TTTCTCCCTT 132720
TTATCCTTCT TTTCTTCCCT ATGCTTCCAT AGGTACTGAG AAAGAGTCTT TTTTATATAA 132780
TTATTTCTTT TCCTTTGGGA AGATACCCAG TAGTGGGATG GCTTGATCCA ATGGTAGATC 132840
TGTTTTTAGT TCTTTGAGAA ATCTCCATAT TATCTCCATA TTGTTTTCCA TAGAGATTGT 132900
ACTAATTTAC ATTCCCACCA ACAATGTATG TGTTCCATTT TCACTGCATC GGCACCAACA 132960
ACGGTTGTTT TTTGACTTTT TAATAATGGC CATTCTGGCT GGGGTAAGGT GGTATCTCAC 133020
TGTGGTTTTA ACTTGTATTT CCCTGATAAT TAGTGATGTT GAGCATTTAA GAAATATATT 133080
TGTTGGCCAT TTGTATATCT TCTTTTAAGA AATATCTCTT GAAGTTGTTT GCCCACTTTT 133140
TAATGTGATT ATTTGTTTTT TTTTCTTGCT GATTTGTTTG AGTTCCTTGT AGCTTCTGAA 133200
TATTAGTCCT TTGTCAGAGG TATAGTTTGC AAATACTTTC TCCCATTCTG TAGGTTGTCT 133260
CTTTACTCTG TTGGTTATTT CTTTTGCTAT GCAGAAGCTT TTTAGAATAA TTAGGTCCCA 133320
TTTACTTATT TCTGTTATTT TGTTGCATTT GTTTTGGGG TGTTAGTCAC AAATTCTTTG 133380
CCTAGACCAA TGTCCAGAAG AGTTTTTCCT AGGTTTTCTT CTAGAATTTT TATGGTTTCA 133440
GGTCTTAGAT TTATGTCTTT AATCCATCTT GAATTAATTT TTGTATATGG TGAGAGATAG 133500
GAACCCGGTT TCATTCTTTT ACACTACATG TGGCTATCCA ATTTTCCCAG CACTGTTTAT 133560
TGAATAGGAT TTCCTTTCCC CAGTGTATGT TTTTGTTTGT TTGGCTGAAG ATCAGTTGGT 133620
TGTAGGTATT TGGTTTTATT TCTGGGTTCT CTATGCTATT CTACTTTTAT ACCGGTTCCA 133680
TGCTGTTTTG ATTACAATAG CCTCGTAGTA TAATTTGAAG TTGGGTAATG TGATGCCTCC 133740
AGATTTGCTC TTTTTTTGCT TAGGATTGCT TTGGCTATTT GGACCCCTCT TTGGTCTCAT 133800
ATAAATTTTA GGATTGGTTT TTCTAATTCT GTGAAAAATG ACATTGGTAT TTTGATAAGG 133860
GTTGCACTGA ATCTGTGGAT TGCTTTGGGT AGTATAGTCA TTTTTACAAT ATTGATTCTT 133920
CTAATCCATA AGCATGGTAT GTTTCTCCAT TTGCTTGTGT CATCTATTAT TTCTTTCATT 133980
AGTGTTTTGT AATTCTCCTT GTAGGGGTCT TTCACCTCCT TGGTTAAGTA TATTCCTATG 134040
TATTTTATTT TTATTTTTTG CAGCTATTGT AAATGGGATT GAGTTCTTGA TTTGATTTTG 134100
AGCTTGGCCA TCATTGGTGT ATAGCAGTGC TAGTGATTTG TGTACATTGA TTTTGTAACC 134160
TAACACTACT AAATTCACTT ATCAAATCTG GGAGATTTTT GAGGATTCCT TAGGATTTTC 134220
TAGGTATGAG ATCATATCAT TGGTAGAGGT AGTTGAGTT TCTCTTTTCC AGTTTGGATG 134280
CCCTTTATTT CTTTCTCTTG CCTGATTGCT CTGACTAGGG CTTCTAGTAC TATGTTGAAT 134340
AGAAATGGTG AAAAGTGGGC ATCCTTGTCT CATTCTAATT TTTAGGGGGA AATGCTTTCA 134400
ACTTTTCCCC ATTCATTTTG ATGTTGGCTG TGAGTTTGTC ATAGATGATT CTTACTATTT 134460

FIG. 6.51

```
TGAGATATAT TCATTTGATG CCTAGTTTGT TGAGGGATTT TATCATAAAA GGAGGCTGGA    134520
TTTTATTGAA TGCTTTTTCT GCATCTATTA AAATGATTAC GTTTTTCATT TTTAATTCTG    134580
TTTATGTCAT GAATCACATT TATTGACTTA TGTTTATTTG TTGCTTACAT CTACTTTCTA    134640
ATTTTACTAT AATAAACATG TATAATTTTG TTATCAGAAA AGTAAATGTA AAAGTGAGTT    134700
TTAATTTTAA AACTTGGGCC TAAGTCTTCC TGCCTCCCAA GCCCATTCCC TTCCTGATAT    134760
CTGGGGCTTC CCTCCTCAAG CCTGCTCTGC AGGATAAGGG GATACAGTCC ACATGCCTGC    134820
TGCTGGTTTG GCCCATGATA ACCTCCATGG GCAATGTCTG AGCCTCTGCT GTTGAGTTTT    134880
GCTTTACACA CTCCTGGCAA GGAAAGGATG GCCAACATGG CTTGGACATG GGTTGCTGAT    134940
AATTGGTGAT GTCTCATGAC TGGTTCTGCC TGGAGGGCTT GCTGTAAGTC CCTGATAGGA    135000
GGAACATGGA CCTGCACAAG AGCAGAACTT ATCTGACACT GAAGAGGACA CTTCAAGAAC    135060
AGATTATCAA AGTCTAGCTC AGGGAGAAAT ATACTTTAGA GCAGAATGAG GAATGGCGAG    135120
GCAGCTGAGC TTAGACACAA GCAGAAGGAA ATCCATGGTG AGGGCACAGG CAAGGAAAGG    135180
GGCTGAGAGA GCATTAGTGG GGGCAGTCAG GGGCAGTGGT CAGGATGCTC GGATGCCAGC    135240
GTGAACAATC GCATCAAGAT TAAACACCAT GAGGATCGTT AGACTTCCTG TCATATGTCT    135300
CCAGGTGGTG CTCCAAATAT CCTAAACCAG ATGACAGCAC CCCTCCACCC TCTGCTGTAT    135360
AAGCACATCT GCTCTCCTAT AATCATTCCC ACATAGCAAT TTATCATTTT TATTGATTTT    135420
TCTTCATTTA ATACACGTAT AAGTGTGTCT TTTATTTTTA AAAATTTGCA TTCCTTTAAT    135480
TGCTTTGGAG ATTGTGCATT TTTCTCTCTG TTGATTTACT CTGCCAATAA ACATGTAATC    135540
CTACCATAAG CATGTTTTAC TTGTGTAATC AACCAAAATA AAAAATTTAA AAAGGAATCA    135600
CTGACTATGA ATTAGACATG TGGATAGGCA CCAGGGTTGC AGACATGGCC CACGTTCTTG    135660
CATTAACTTG CACTGTGGCT GGGGCATTGG ATGGGTACAT TAAAAGGATT AAAGTAATAT    135720
AAGGCAGTAT TTATTAAGTG TTGAGTGAGC ACTACAGAAC CCAAGTGCTG AGGGAGTTTC    135780
ATGCAGGAAG AGATCAAGAG TAACACAGAG AAGAAGAATA GATCAATTTA GCGCATTCAT    135840
TTAAAAATTC ACCTTTTGCA TAAGGGGATG TGTCTTTTGT GGGGAGGAGG GGAGTTCCGA    135900
TTGGCAGTTT GTTCTCAGGG AGCTTGAAGA AGAGATCTTG GAGAGGAGAC GCAGAGAAAA    135960
CAAATGAAGA AAATGTCAAA ATGGAAGGGG TTGGCCCGGC TATGCATACC TTAGTTAGCT    136020
TAGGTAGAGT CTAAACTTTT ACAAGTGGTT TCAATAGGTG TGTTTGGTCT GGGTTCTTTG    136080
GGAGGTATCA TAGGAGAATG AAGGCAGGGA GGACGCTTCC AGCACCAAAA TTCAAAGGGA    136140
AATGTATTTT ACATGCATAG CATTGTTTTA CTCTCTTTCC ATTGGAGCA TATCTTAAAA    136200
ATTCCATTTG GAGCATATCT TAAAAACCC ATTTCTCTGA CAATGGTTCT AAAAGGGGGA    136260
AACATCCTTT GCAACAGAAT CATTCATTCT CTCATTCATC AACCACTGAT TGTGTACTAA    136320
GTGTCAGACC TGATCTCCAT CCTGCCTGGT ATGGCACTAG CTTCTGTCTT GAGACAAGCA    136380
TTGTGATAAA CCATGACCAA AAAAGGGCA GTTTATAAA CACAAGTCTG CCAGGCTTTC    136440
AGCAATTCTA AATTTCCTTT TGCAAGTCAG GCTGGAGTTA ATGGCTCTTT CCTGCAGCGG    136500
CGGAGATGAC AGGGCTCTCC CACAGTGCTG AGCAGGCAGT TTGAAAGCCC CACTTCCTGT    136560
CTCTGCATGG GCGAGTGTCC ACTGGAAGCC ACTGAGAGGA AGGAGGGAAA CCTCAGAAAC    136620
CGGCCCCTGC CTGGCTGCTT CACCCTAGAA AGCCCAGGCA GAGGAGGGAA AGGTGAAGTG    136680
CTGAAAAGA ATAAAAAAGG GGGAACATGA AAAAGAGCAA GAGCAGGAAG GAGGCAGGGA    136740
CGGGAAAGGA GGGGAAGCAC GGAAACAGCC AATGTCAAGG AGAAGAAAAG ATGGCTGGTG    136800
GAAAGGAGCT TCCAGGAATT GGGACACAGC CCTGTCTTAT TGCAAAAGAT GGAAACCCTG    136860
AAGGAGAACA GGAAGGAAAA AGAAAACAAG TCCGTCTGAG CTGGCAGGGT CCACTTTCTC    136920
ATTCTACAGA TGAGGAAACA GAGGCACAGA GAGGAAGTGG CTTGCCCAAG GGGGCAGATT    136980
CTTGAAAGGA TCATCTGCAC TCTCTCTCCC TTAATGCATT CTTACCTCTT CTTTACTCGT    137040
GAGTCAGTCC TGAAGGACAA GCTGCCTGAA GTCCCACACA GATGGGCCTG GGGCAAGCAT    137100
```

FIG. 6.52

CAAACATCCT GGGGGCCCTG GGTGAGGTTT GCTTTTAAAT TCCAGGTCAG GGAAAGGAAG 137160
GTCTTTAAGT TGTCTGCTCT AAGCTTAGTA ATCCCCCTCA GAGTTATGGG TGCGGTGTCT 137220
GGGGTAGCCG TTGCGTCTCT GGGCAAATAC CCTGGAGAAT GCAGTGTTGG TTGTCTGAGC 137280
TGGGGACAGA GTGACAGCAT AGTTGCATGC AGAGCTGGAG GCTCCTGCAG CTGTACAGGT 137340
AAGGTGCTGA AATTCTCCAC CAACCCTTCC TCTTTGCCCC CAGCACCACG AAGATAACCC 137400
TCTTTGAATA TGTGGAAGTC TGTTCTCCAA ACTTTCTAAC ATTCTCATGT CAGTCTTAAT 137460
AGATTCAGCT CAGTTACTGC CTCCTCCAGG AAGTCCTCCT TGTCTGCAAA TCGGCTGCCC 137520
ACCATGCCGG CTCACTCATA GTTTTAACTC TGTATCTTTC TAATATGCCT TAGCCCACTC 137580
TGTCAGGATT CCAGTCAGCT TCCTTCTCCT AGACTAGGAG TTGCCTCAGG CCAGGAGGAC 137640
CAGCCTTGTT CATATCTGTA CCCTGCAAAC CTGTCAATGC CCAAACCTGC TCAGTGCTTT 137700
GGAGTATGGA ACCAGCCGTC AATGCAGGAA TGTTACACTC TAAGAGTTCC CAAAGGTAGA 137760
GAGATGAGGG ATTGGTGCTG GAAGTGGGAG GTTATTCTAA GGATGGGTAT GGCAGGAAAC 137820
ACAATTATAG TTCAGGGAGT GGAGTGTCCA GGAGTGGGAG GAGAGGAACT GGGAGAAAGA 137880
GCAGAGAGTG AAAGTGAGAG CGGGCACAAA GAAAGGGAAA AAGAGTCAGG GATCAACCAA 137940
AGTGCATGCT TCCTTTTCAG CCCTGCCAGG ATGTGCAGGG CGGCTGCTGT GGACGCGTCA 138000
AGGCTCAGCC TCAAACATGT CTTCTTCCTT GACTTTTGTC TATCATTCTA AAGCTAGGTC 138060
ATTTAAAAAG TTCTTTTGTT TTCTTTCCAC CGATACTCTG ATTTCTGACA TTCGCCAAAA 138120
AGAGGTCAAG ACCCTGGCAT ACCGCCCTAC TAAGATTAAA ATAAATATTA TCCATTGAAA 138180
CTGTTATTTT TTCCTTAACT GTTATTTGTA GAGTTAAAGA TTCCCATGAT CGCGCTGGCT 138240
CTAACATCAT TTTTGGCTCT TTTGAGATCA AATTTGCAAT TGATGCAAA AATAGCTGTG 138300
ACGCATATGT GTCTGTATGT GTGTGGTTAG GAGATTTTTT ATCATTACAT CTTCTTTTGC 138360
CCTGCCTTTC TGCCTTTCTG TCCTTTTAAT TTGCGGGCTT TTGGCAACCA CAGCACGGGT 138420
CTGGTTTCCT AGGAGTTTCT TTTGTAGGAT CAAACCGCTA GTTGGCTCTT GGCCCTGTGA 138480
TAGGGCCCTG GGCTAACTTA TTGGGAAAAT GTTGCTGTAA CCCCTGCCCA GAGGTGCCTG 138540
TGACATGGGC CGCCATCTTC TCCTCTTCCC TTGGCTTCAG CCCCACCTAG AAACCTGAAC 138600
AAACATTTTC CTTGACATTT CATAAAGTGT CAGTGGCTCC TCATTTAGCA AAATACATCC 138660
CAGGGAAGTT CAAAAGTGAA AAAAGGCCGT AACTTCTTCT TCTTCTCAGG GACCTACAGA 138720
AAATATGTGG CACCTCGGCA GCCTGGCCTG CAGCACTCCC CTCCCCATCG GTGAGTCCTG 138780
CTACAGTGGG TCCAGGTGTC TGGACGCCCG GCACGCACGG CTCTCTGCAG ACCTCTGGAC 138840
AGTACCATGG GAGCCGCACA GTCCCTGCCT GTTCTGTCCG GCAGTTCTTG TTTCCCAGCA 138900
CCCTGTCTCA GGTGAGAGGT TCCCTCTTCT GCTGGGCTTC TCCTCCCTGC TGTGAACCCC 138960
AAATATCTGA GGCAGGTCAA TTTAGGAACC TTATTTGCC AAAGTTGAGG ATGTACCCAT 139020
GACACGGCCT CAGGAGGTCC TGAAGACAAG TGCCCGAGGT GATCGCGGCA CAGCTTGGTT 139080
TTATACATTT ATACAGACAT CAGTCAATAT ATGTAAGATA AACATTGGTT CGGTCCCGAA 139140
AGGCCGGACA ACTCCAAGTG GAGAGGGGGC TTCCAGTTCA CAGGTAGATA AGAGACAAAA 139200
TGTTGCATTC TTTTGAGTTT CTGATTAGCT TTTCCAAAGG AGGCAATCAG ATATGCATTT 139260
ATCTCAGTGA GCAGAGGGGT GACTTGGAAT GGAATGGAAG GCAGTTCTCA GTTTAAATTT 139320
TCCCTTTAGC TTAGTGATTT TGGGGTCCCA AGATTTATTT TCCATTCACT CTGCAGACAG 139380
GGGCTTCTGT GCATCCAGGG AGCCCCTCCT CACAGAAGGA AGCAGGCCAT TAATGAGACC 139440
CAATCCAGCT TCAACCACCT GGTAACAATT AGGACATCAC TTCTCTGAGC AAGAGCTCCT 139500
GCCTGTCCAT GAGTTATCAA GACATTCCAA TTGTTCCTCC ACATCTTTGA CATGAAGACT 139560
TGAGGGGGTC AGATTTTCCA GGGGGCTTGA TGGCATGTTC TCTTCACTGT TCCCTGCCCT 139620
GGTCATCCAA GTGACCCTTG GCAGGGAAGA GGCCCCGAGT TGCAGAATCT CTGTTCTCAC 139680
AAGCCATTGC CAACCCGGAG AGTGGCTTTG CCACTATTCC TAGCATGTTG TTGGCTATTT 139740

FIG. 6.53

CAGGAATGGG AGTATTTGAC TTTTCCCTTT GCAGTGATTG CTGCAAGGAG AGGAATTGAG 139800
AGACTCAAGT CCCTGAGATA AATATTTATC AACTATTACT GAAAGGGAGT ATGTCAAAGA 139860
AAAAATGTGG AGAAACTTCA GCTTGAACAC ATAGTTTAAA TCCAGCTTGG GTGTACTCCA 139920
GTGGGCATGG ATGTATTACT GTTTTGCAGT GCATTCTTCT ATGATCAATA CACAGAAGCA 139980
AACAGGCCAC GTGGGTAAAC AGTAATTTTC ATTACCAGG GTGAATATGG AAGTCCTCTT 140040
GTTTCCATGT CATGATGAAG GAAAGCAAGG ACCATCTTTT GCCAAGGAAC AGTGGCTGTG 140100
GGGGAACTGA GGAGATGGAA GGACAAGGCA GTCAAAAGCT TTGGAACAAC TCTTTTTTTG 140160
AGATGGAGTT TTGCTCTTGT TGTCCAGGCT GGAGTGCAAT GGCACGACCT CGGCTCACCA 140220
CAACCGCTGC CTCCCAGGTT CAAGTGATTC TCCTGCCTCA GCCTCCCGAG TAGCTGGGAT 140280
TGCAGGTATG CTCCACCATG CCTGGCTAAT TTTGTATTTT TAATAGAGAC GGGATTTCTC 140340
CACGTTGGTC AGCTGGTCTT GAACTCCCGA CCTCAGGTGA TCCACCTGCC TCGGCCTCCC 140400
AAAGTGCTGG GATTACAGGC ATGAGCCACC ATACCCGGCC CTTTTTTGGA ATAATTTTAT 140460
AGGTTTTCAA ACTATTACAC TTACCTTTTT ATATAAGAGA CAGGACATAG TCACTGAACA 140520
ATCACTCCAG ATTTTAAGTA AGTCCAGGAT GGGATGACAA TGGAACAACC ATGAAATGAA 140580
AGGAAGAATG TGTCACTGGT ATGTCCACAC GTCTCCAAAT CTCTCACCTC TGTCAGCTGC 140640
AAACAGAGCC TGAAATAAAT GTTTCCTCTG TGCACAGCCT CCACAACTTC CTCCCTCCAC 140700
GTTTCTCACT CACTCCTCTC CAGCACTTCT CTCCGGGTTC TGCTTACAAA CTTGAAACCG 140760
GCTATGCAAA AATTATAACT GTGGAAATTA TGACAGTGAA AGAGATCAGA CCTAACCGAC 140820
TCCATCTTGC TTCTAACCTT TAAGCTGTCC TTGTTCATTT TTGGGCTGAA CTAACTTTGG 140880
GAAGGAATTC AGTTCATGGT AGAACTCTGA ACAAAATTG ATAATAGCCC TTTCCTGAAA 140940
AGACCCCCTT CTTGCCTGGG GACAAGTCTG CCATTGTAGG ACTAACAAAT TAACTACAAG 141000
ATTAGAAATT AAGGTTTAGG GTTCATGCAG CCTCCAGTTC CAAGAGTCTA AACCTCCCCA 141060
AATTGCTCCT GGGGATAACA TCACTGTTGT AAAAGCTAAG ACCAGTGCTT GAGATATTTT 141120
GTAGACCCTG CTCTGGATGG ATCAGCTGAC ACCATCCAGA CTGGTAATTT GGCTCAACCA 141180
GCTCTGCCAT CCCACCCAGG AACAGAAAAA TACTCACTTC ATCACCCCAT GAGTCCATCT 141240
CTAACCTGAC CAATCAGCAC TCCCTACTTC CCAGGCCCCT ACTCGCCAAA TCTGCCTTTG 141300
GAGGCAGATA ACAACTTATC TTTAAAAACT CTGATCCCTG AATGCTCAGG AGACTGATTT 141360
GAGTAATAAT AAAACTCCGG CTCTGCATGA ATTACTCCTT TTCCATTGCA ATTCTCTTGT 141420
CTTGATAAAT TGGTTCTGTC TAGGCAGCCA GCAAGGCGAA CCCTTTGGGC GGTTACAAAC 141480
TCATCCTCTG TGGAAGAGTA GGAGTTCATG GAGAAATTGG TTGCAAATTA CAAAATTTTA 141540
TTGTAAGGTC AACTTGTCCC AGTGTCCGTC TGTGCAGCGA AGGGCCCCTG CATGGTTTAG 141600
TGATTGCAAG TTGAGCCTCT AGGGTCAGGT TGTCTAGGTT TCCATCCCAG CTCATTCACT 141660
TATTATCTGT GTGTTCTTGA GCAAGCTCCT TAATCAATTG AGGCTTTGTC CTTCTGTTTG 141720
TATAATGATG AGAATAATAA CCTCCACAAT AACCTCATCA TAAGGTTGTT GTGAAGATGG 141780
ATCAGATAAT ATATATGTAG AGTGCTTATA ACAGTGCCTG GCACATAAAA AATGCTCAAA 141840
AATCTTAAGT GTTATTAATA ATAAACTGAC ATATATTTCT TGAGCAGGGT GGTGGTAAAT 141900
GGGTGTTCTT TTTATTAAGC TTTAAAGTGT GCATAGATCA TATTAATTCT TTTTATGCAT 141960
ATGATATATT GCACATGCAT GAAAATACAT GCATTAAAAA TAAATGAGCA TTTATGAGAT 142020
TTAGTTTAGC AGTCACATGT CCCAGGATTA CAAGCCAGCA ATAATGGGTT GGAAAACATT 142080
CCAACCCATT CCAACCATTG GAAAACATTC CAACCCATCA CTGGACCCAT GTGCCAAACA 142140
ATGGAACCGC CCACAGGTTC TCATTCTTGG TTAAAAAAAT ATGATTATTA CGGGAATAAT 142200
ACTGATTCCC TAAGAATTAA TATCTGAGCA AGTTTCTTTT TTTTCCTGTC TTCTTGGAAG 142260
ATCAGCAGGT TCTAGATTCA ATGGAGTCAC TAGGATTGAG CCACCAGTAT ACGCCAGTCC 142320
TCTCCAGAAC GGCCACCTGG TGGTGGGCAC TAAGGCAGTC TCAGATGAGG ACTGATTGAC 142380

FIG. 6.54

TTTTGTGTGA ACTCAAACTG CCAAAGTCCC TCCCTCACCT TGCAAACTTC AAAGCACAAC 142440
TTTCAAAGCA CTACTTTCTT TCTTGGCTCT CAATTCTCTG CCTAGAAAAA GGGAGGTGTT 142500
GGCAAGGATG TTTGTTTAGT TCTGGGCATC AGTCAATGGT ACCCAGATCT TGCTGAACAG 142560
AAAAGACACA GATTTGTTTC TCTGAGGCAG TTGGTAGTGC TTATTGCTTA TTGCTCTCAG 142620
GGGCTTCTGC AGCAGTAGAA GGGCCCTCTT CCCCTGCCAT GCCACACTGA GAGGAGCATC 142680
CTTGGAGTCA TGGTTGGAAT CTGTTTTTGT TATGCTAGTC CTCTTCCGCA TGCTAGCTGT 142740
TGCATTGCAG GGATATGTGT ACCTGTTTAT CTTCTCCACT AGGCTCTAAG AAGCCAGGTT 142800
TCTTAAAGGA AGGAAGCTGA TCTTGTTTAT CTTGAAGTCC TCACAGTGAC ATTGCTCAGT 142860
CAATGTTGAG TGTATGAATG AATAAACGGG AACCATCACG AAAAAGCCGA AAATACAGTG 142920
GAAAGACTGG ATCATAAAAT CTTCTAAGCA AATTTTTTTT CCTCTTACAC TCCATTTCCA 142980
AATAGATAAA GTATTTTTTA AAATCCTATC AGAATATTCT AACACACTGA GTTGACAGAA 143040
TAGAGATTTT TAAATGCAGT GTCATTTGGC CAGCCATTTG TGAGAATTTA TAAATGTTTC 143100
AGTAGGTTGA AAACACTATA AAAGCAAGGA CTATGTTCAT ACCCAACAGC TGGCACTTAG 143160
TATGAATGCT AAATGAAACA TTCTCTTCTC TTTCAAGAGT CAGTCCAACC AGTGACCCTG 143220
ACAAGAAGGA AGGCACATTT AACTCAATTT AATGAACTCT TATAGAGCAT CTCCTTCTCC 143280
AAGTGCTTTG CTAAGGATGG GGTAAAAACA TGAATAAGTC TTGGATTCTG TCCTTCAGGA 143340
ATTTTCAGTC TTTGGAGGCA GATACATTTG CACCCAACTA TTATCCTAGG CAGAGTGTGA 143400
TAAGTACGAT AATAGCAGTA AAAGCTCTAA GTTAGGCAGG AGAGGAGGAG CTCGTTAAAG 143460
CTTATGGGGC CTGGGAGGCT TTCGGCGGAG TAAACTCCAG GGGACAGCT AGGCATCTGG 143520
CTGCTGGAAT TGGGAGGAGG ATCATTTTAA GTGGCTACAA CTCTGGGTGC ACAGGACTAG 143580
AGGGTGAGGG CCAAGATGGG AAATTGTGGC AGCCATCTTC CACACTGGGC GCCCGCCGAC 143640
CCTTGCTTCC TGGTATTCAT ATTATTGTGT AGTGTCCCCC AACATTGTAT CAGGGTTGGC 143700
CTGTGTGACC AATTGCATAT GGTGGGAATG ATGGTGTGTG ACTTCTAAGA CCAGTTCATA 143760
GAAGATGTGG CCAATTCCCT TACTGTCTTT TTTTTTGGCA GGGGAGTGCC GAGTTTCACC 143820
CTTGTCGCCC AGGCTGGAGT GCAATGGTGC GATCTCTGCT CACTGCAACC TCTGCCTCCC 143880
AGGTTCAAGT GATTCTCCTG CCTCAGCCTC CCAACTAGCT GTGATTACAG GTATGCGCCA 143940
CCATGCCTGG CTAATTTTGT ATTTTTAGTA GAGACGGGGT GAGATCAATG AGGCAGTCAA 144000
TTGGCCAGCC TGGTTTTGAA CTCCTGACCT CAGGTGATCC ACCCGCCTCG GCCTCCCAAA 144060
GTGCTGGGAT TACAGGCATG CGCCAACCGC GCCTGGCCCT TACTGTCCTT TGGATCAGCT 144120
GCTCTGGGGC TAGGTCAATC CTTCATGTGA CTGCAGCCCC AGCCAACATC TGGACTGAAA 144180
CCCATGAGAC ACCCTGAGCC AAAAAAGCCC AGCTAAGACT TCCTGCATTT CTGACCCACA 144240
GAAACTGAGA AAAGAAATGT TTTGTTGTTG CTTTAAGCCA CTGACTTCTG GGTCATTTG 144300
TTTTGCAGAA ATAGATAGCA GATACAGAAA AGCAGGCTGG TGGAACAGTG TGGGAAACAC 144360
CTTGATTTTC AGGGAGTTGC ACTTTGTTTA TGTGCAATGG TGCACTGTTT TTAGAAAGAC 144420
ACAAAGATGA TAATACTGGT GATGGGCATA ATACGGGTTG TCAAGAGGAG TGACTGAGGC 144480
GGGGATAATT TAAGAGGCCA CAGCAGTAGT GTGGCAAGAG GTAATGAGGG AATTGAACTT 144540
GGTGGGAATG GGTGAGATCA ACGAGGCAGT CAATATGGGC AGTGAGTGTG AAGGAGCTGC 144600
GAAGGATGAT TCTTTGGTTT TGAGCTTAGG AACATGAGAG AACCAAGATC TCATTTATCC 144660
AAAGAGGAAA CACAGAAGTG AGCCCCTGTT TGGGGCAGG GCTGGGTAGG AGGAAAAGAG 144720
TGGAGACGTC TATCTCCCCA GGAAGAGAGC CCCTGCTTC CAGATCCCAG TGGATGGCAG 144780
GGCACTCGGC TCATTCACAG ACTGGGCTCG TTGAGAAACC TTTCCCTGGA GGGCAGGGCT 144840
GCTCTGTTTC ACAGCCCATA TCCCTCATGG CCAAGTGTTC CTCGAGTGAC AGTCTCTGCC 144900
ATCAATATTT TTAGCATGTG GTCTTTCAGA GACTAAAGAG TGGCATCCAT CTCCTGAAAC 144960
TCCTTCCCCA GCTGACAGCT GGTGACCCGT GGAGGAGGGA GCTTCAGGGA GCCTGATGGG 145020

FIG. 6.55

```
CGAGAGTCTG TTCCAATGCC AATCCATTGG AAGAGATGAA GTCAGACCCG AGTTTGATAG   145080
AAAGCCTACT TCCTCCCTTG TATCCAGCTG TGGAGACCTA CCAACATCAA TGCAAACCAG   145140
AAGCTAACAC CCAGTTCATA TATCCCAAGT GGAAGGAAGC TTCTCGTGGA ATTGTCTTAC   145200
ATGACAGTAA CATAAATCCT GAAGGTAATA CTTGGCCAGG TAATGTTAGA AAAGAACCCG   145260
AACATAGGCA TTGCTATTAT AGATCCTAGG ATAGGCCTGA GCAAAAACTG TCTGGGATTC   145320
ATAACATGCT TCGTTGCAAT CTGATAGAGG GAGTGAGATC CACTCCAAAT GGAGTCTGAT   145380
TTGGGGCAAA GCAAAGAGTA TGGAAGGAAA CTTGAGAAAG GGGGACAGCT TCTCAAATGG   145440
AGTCTGGCCA CAGCTGGGGC TGGAAAAGAG ACATGACTGC GCTTGCAGAG TGGTGAGAAT   145500
TTGCTGCTAG AATTTTTAAG TTGTGTGTTT TCATTTTTAT GATAATGTAA ACTGAGATAA   145560
GCATATTCTC TGCTATCCCA ATGAGCCCCT CCTCTAGGAG GACTACCTTG CCACCTTATC   145620
CATAAATGTG TTTATAAATT ATTTTGATGC CAGCTGGTAT TTTTTAAAAA GTGGTTTTGG   145680
ACTCACAAAA AAACCATGA TGGATTTAAT ACATAACAAA GCATTTGTGT CAAGTGAAGG   145740
CCAAGTAACA TCTTAGCGTC CTGTGTGAGC GAAGGTGTCG TGGCAGTTCA AACAAGAATG   145800
CCGATGAAGC TGCCCAGGAT GGCCAAGGCC ACCTTGGTGT GTTTGAGGGG AATTAGAGTT   145860
TAGAAAAAAA AAAAAAGGCA CCTGACACTC TGAACTAATG TGGTTACCTG GAATTTTGGG   145920
GTTTTGAAGC TTTGCATTTA ATTTGCAGCT TATGGCCTGA AGGAAAAGAC AGGTGAAATG   145980
CATATCCTGG GATGAGTCAC CTGGAGGAGA GGGCTGGGAA GGGGCTGAGC TGCACATGCT   146040
CAGATCTTCT CCCAGGCTTA TCGACCCAGT GAGTCAAGTC TTCTTCCAAC GGGATAGAGT   146100
GTGAGAGAGA GCAGGGAACA GAAGCCAGAG TCTCTGTTAA ATTTCTCGGT ACATTTCTGT   146160
TAGAGAATGG AAGTTTCTCT ATCGTAGGAG ACCTTGAGAG CCTGGGATAG AAATTACCCC   146220
TTTGTCATGT ATTTTCCTCC CAGAAATAGC ATGGCCACTG TCACTGCTAA GCTGGAGTAT   146280
CATGAGCACA ATTTCTCTCA CTTTCTATAC CCATGCCTTT CTAGGAGATT GGTGGCTCCA   146340
TCAAAAAGGA GTTAAAAAGA AGCAGCACTA TTTTGTGGAA TACAATCATC ACCATTATCA   146400
CCATCAGCAC CACCAACCAG CACCACCATT ATCAAAAGCA TTCACCTGGT GTCTGCCTTA   146460
CAAACTGCAA ACTGCAGTAG GTATTTGTAA TAGAATGTTT CCTTTCCCCC TTGGGATCTG   146520
CAGAAAAGCT GGAGAATGTT TTGGTATCAA CACACTAGGT TGCATTGCTA ATCATGTGAT   146580
GGCCCCATGA CAGTCTCTGT TGGCTGGTGT AGTTCAGGTG GACGACTGCA GGATTTTGTT   146640
CTTGGAGCCT CAGTTCTGAC TGGGCTTGGG GTGTAAAAGG TTTGGGAGCC AGATGACAAG   146700
AGTATTTGAT GGGTAGAATA ATGGGTTCAT CCAAAAGATC ACCAGAATGG TTATTAAATA   146760
GTACAAAGGA GGAATTTACT GGTAATACCA GTTGCAAAC AGAGAAGAGA GTCTCCAATG    146820
TGGACTGAAA GTGCTCTCTC TTTGAAGAGG GGAAGGACAG ATTGGGTTTT ATGCCTCACA   146880
GGACTGGTAC CATACATATT CAGCAGGTTT TTGGGGAAAA TCTATACATA TTTATAAGGT   146940
GAGCTGATGC CTGCATAATA GATAAACATA TATGTAACAT ACTTTTCATA TTCATTTTGG   147000
GACTGGGTTT TGGCACTAAA ATTTGTGGAA TTTGGCTCTT TATGTTAAAA GGTGAACTAG   147060
AGGACACAAA GACGGTTTGT GTGCACCCTC TATAAACTGG CTGAAACTGG CTTAAGGTCT   147120
GCAACTGCTT ATCCAAAAAG AATGTTTGTA AGGCCAGGCC TCTGTCCAGT CAGAGTTGTA   147180
GTGGTCCAGG TTGTAAATCA AAGTTTATAG CTCTTTTTGT TAGAGAGTTC AGCTGTAGGA   147240
ATTTAGAAAT TTGCCATGCC TGCCAGGCCC TGAACCTTTG ACCCATAGGT AACTTTATTT   147300
CCTTAACCTT AGGGTCAGTC TTAGTTGATA TGGGGCATCT ATTCTGGTAT CTCAGATCCT   147360
ATGGTCAAGA GAAAAGATCC TCCACAAGAG GGTCCTATGT GGCTGCAAAA ACTGCTCTGA   147420
GCTAAATCCA CTCAAAATCA CTGCAGGATG TCACTACTAG AAAATAGGGC AGGGATAGGG   147480
ATCCCCTTCC CATGCTGCCA GAAAATGCCT GATAGCTTAC CTCCCCCGGC CCTTGAGGCT   147540
CCCTTGGAAT AGGCACATGC AATCCCATCT CCACCCAATA GAGCTTGTCC TAGAGCTCAG   147600
TTTTTTCCCA TAGTTTTCCC ACCCACTTGC ACCAGAAAAT CTAATAAAGT CATGTGATTA   147660
```

FIG. 6.56

ATACAATTCA TTTTATCACG CTTCTGAAGA TTTAAGAGAG AGCGGTCACA TTGGATTCCA 147720
CAGTACCGAC CTTCTGACGA TTCTTCATTT CACCTTTATC TATTTTTATT TTTATTTTAT 147780
TTTTTTTTCG AGACGGGGTC TCACTCTGTC ACCCAGGCTG GAGTGCAGTG GGGCAATTAC 147840
GGCTCACTGC AACCTCTGCC TTCTGTGCTC AAGCAATCCT CCCACCTCAG CCTCCCAAGT 147900
AGCTGGGATC ATAGGTGCAC ATCACCAAGC CTGGCTAATT TTTTGTATTT TTGGTAGAGA 147960
TGGGGTTTCA CCATGTTGCC CAGGCTGGTC TTGAACTTCT GAGCTCAAGT GATCTGCCCA 148020
CCATAGCCTC CCAAAGTGCT GGGATTACTC ACGTGAGCCA CCTCGCCTGG TCCCTTTCAC 148080
CTTTATTATC TTTGCCTTTA ACTCTAGTGC TTCCTCCCTG AATCAGTTAA GGATTGCATT 148140
TGGCTGCATT AACAGAAACC TGACTGCAGA AGCTTAACCA AATAGGGTAG TTTTTAAAGA 148200
GAGATTGCTT ACATCACGCA AATTGCACAA ATTTAAGTG CATAGTTCAA TGAGTTTTGA 148260
CAAATGTAGA ATAACATAGC TATATAAAAC CATTCCATCA AAAAAATTTT ATCACCATAG 148320
GAAATTGTGT CCTGTCCCTT TCTTGTCAAT CCCAACTCCT CCCCACAAGG CAACCTTCAT 148380
TCTCATTTCT CTCACCATAG CTTAGTTTTA CATGTTTCTA TAATACAGCA TCATATAAAT 148440
GGAATAATAC AGAATGCAAT CTTTTGTATG AAGCTTCCTT TGGCTCAATG TAATGTTTAT 148500
GAGATTCATC CATGTTATTG AATGTATCAG TAGTGTTTTC ATTTATATTT CCTAGTGTTC 148560
TATTGAATAA ATATACTACA ATTTGTTTAT CCACTTATTT GTTGATGAAC ATTTGGACCG 148620
TTGGCAATTT TTGCCTATTA TGCATAAAGC TGTTAAAAAA CATTCTTGTA CAAGTCTTTC 148680
ATTTCATATG TTTTTCTTTT TCTGAGGTAA ATAACTACAA GTAGAATTGT TGGGTAATAA 148740
ATAGGCATCC ATCTAATATT ATAAGCAACT GCACAACAGT TTTTCAACGT GGCTGTACTA 148800
TTTCACTCTC CCAATAGCAA CGTATGTGTT TTCCAGCTAC TCCACATGCT CACTGGCATT 148860
TCCTGTTGCC AGTTTAAACA TTTCAGCCAT TCCAGTGGAT ATGAAATCTC TCTGGCTATA 148920
ATAATTGTAT TTCTCTGATG ACTAATTATG TCAAGCCCCT TTTCAAATGC TTATCAGCCA 148980
CTTCTATACT GTCCTCTGTG ACATGTCCGT TCAATCTTTT TGCTCATTCT TTAAAAACAT 149040
TGGGTTGTTT GTCTTTTTCT TAGTTTGTCT TTTGCTTTTC ATTTATAGGA GTACATATCT 149100
TCGGAATACA AGTCCTTTGT CAGATAAATG TATTGTGAAT AATTTTCTCC TAGTTTGTGG 149160
TTTGCCTTTT CACATTCTTA ATATCTTTTG ATGAGTGGAA ACTAACTTTC AAATTATGTT 149220
CAGTAGATTA ACTTGTTTTT GTTTTGTTTT GTTTTGTTTT TTGTTTTTAA CACTGGGTCT 149280
CACTTGTTGC CCAGGCTGGA GTGTAGTGGT GCCATCATGG CTCACTGCAA CCTCTGCCTC 149340
CTGGACTCAA GGGATCCTCC TGCCTCAGCC TCCCAAGTAG CTGGGACCAC AAGCACGCAC 149400
CACTACACTT GGCTACTTTT TTATATTTTT GGTAGACACA GGATTTCGCC ATGTTGCTCA 149460
GGCTGGTCTG GAGCTCCTGA GCTCAAGCGA TTCACCCACC TCAGCCTACC AAAGTGCTGG 149520
GATTACAGGC GTGAGCCACC ACGCCCAGTC GAGTAGATCA AGTTTTAATT TTATGGCCAG 149580
TAGAGATCTA TTTCAAGGCT CTCTATTTTG TTCTGTTGCT CTATTTATCT ACCTTTATGC 149640
CAATTTTCTT CTCTTTTGAT TCAGATAGGG TTATAATAAT AATTATTTTT TCCAGGGATT 149700
AGATGGACCA GGGCTGGTGA AGTTGTTCAA GGGAGTGATC AAGAGCCTGG CTCCTTTCAT 149760
CCTTCTGTTC CATCTCCTTT GGCTCATGGA TTTTGTTTTC CAAGTGGCAA GATGGCGCCT 149820
CCACCTTTGG TATCCTATTT TAGTTCCTGG CAGAAAGAAA GGAACAGGCT AATGGCCCTG 149880
ATGAGTCTAC CCCCTTTTAA CAGGAGAAAA TTTAAAAAAC AAAAACCATG AAACCCTTTC 149940
CCAGAGGCAA CAACCAGAAT TCCATTTATC TTTCATTGAC CAGAACAGAC CACATGGTCA 150000
CTGGTGGTGG CAATGGAGAC TGGGGAGATG AATATTTTTA AGGTGGCATA TTCCAGAAGA 150060
ACACTGTGCA CTGATTGCAT TAATGAACCC ATTAATGTGC CAAGGGGAGG TTTACCTATG 150120
AGCATGGGCA AATTAGAACC CACTCTTGGA GCTGCAGGTG AGCCAATCCC ACCTAAACAG 150180
TGTGGATGCT ACAAGATGGG GAAGTAAATT GATTCTATTC CATACCCTAA CCTCTCTCCA 150240
AGATGTATTC TTAAAATAGA AGAGGGAAGA CAGAAGAAAA CATCCAGAAT ATATTTTTAT 150300

FIG. 6.57

```
TGTCTTTTAC TTCTTCAGTG CATTTTAGAT CAGTGCTTCT CAATCTGGCA AGGGGCATGC  150360
AGGAGGATGT GAGTTTTATC AGGAAAACTA CACAACCCCC CAACCACAAT GCTACCCCCA  150420
CTCCTGTGGA CCTTCTTTAA GAGAGACTCA CTATTATAGA TGGAGTTGAT ACGATTTTAA  150480
GAGAGGCCAT ATATTATTTG CTTTCTGTCT TGAAAAACTT GTGATTTTTC TGTATTGTGC  150540
TACTGCCAAA GAGAATAGAA ACCTGACTGA GGTGTCAATG TTTATGTAAC TGATTTCATG  150600
TACTTTCTGT AGTTCTACCA TTTCTGATGG TTAAAAATTT CTTGTGTGTG TGCAGTTGGG  150660
GAGTGTGTCC TCCTCCTTCT GCTCTTATAC CACACATTAG CACATCAAAA TGCTCTAATC  150720
TTTGTATGAT TATGTGGCAT GTGGTGATGC AGCCTCACAG TGGAAAAACT TCTCTTGGGC  150780
CATTGCAAAT GTAACATTTC TTTCAATCAG ATAGTGCCAT TAAGGATTTC ATTATGGCCG  150840
TCACATCCTG TGACATCTCT AAACATGCAG CATTAGGGCC TAAGTGCAGC CCTGCAGGTA  150900
GAGTTGCCAG GTTTAACAAA TAAAAATTAC ACGCTGGCCA GGCGGGGTGG CTCATGCCTG  150960
TAATCCCAGC ACTTTGGGAG GCTGAGGCAG GTGGATCATT TGAGGTCAGG AGTTCGAAAC  151020
CAGCCTGGCC AACATGGTGA AACCCCATCT CTACTAAAAA TACAAAAATT AGCTGGGCAT  151080
GGTGGCAAAT GCCTGTAATC CTAGCTACTT GCGAGGCTGA GGCAGGAGAA TCACTTGAGC  151140
CCTGGAGGCG GGGGTTGCAG TGAGCAGAGA TCACACCATT GCACTCCAGC CTGGGTGGCA  151200
GAGCGAGATT CTGTCTAAAA AACAACACCG TATTTGGGGC ATGCTGATAC TAAAAAATTA  151260
TTCATTGTTT GTCTGAAATT AAAATTTAAA TTGGGGGCCC TGTATTTTAC TGGGCAACCC  151320
ATTTGCAATA TCAGCAACAA TCTCTTATTC AGACCACTGA TTAAGTGTGC AAAATTTGAA  151380
TCTCTGAACA GTACCTATGT CCTTGATATC TTAAATTAAT GAGTGTCTTA GACACTCAAA  151440
GCAGGAGGAA GCATTATGGC AGATGTTTGA GCCCCAGAGA TGTCCATGAG CACAGCATAG  151500
AGCTCAGAGC CTTCTTTATT ATTTGCTTCA CGACAGAGCA AAGGACTGCA GCAGGTTGAC  151560
TGATATAAAA GTTTTACCAT GTCTCACAGC AGGCCTTTGC TCAAGTTTCC AGTAAGGATA  151620
TTGTATCATT TCTTGCCTGC AGTACTTGTA AATCCACTTA CACTGCCTGC TGTTGAGTCA  151680
TTTGTTTCGT CTTGAGTAGC ATGTCATCCT TGTTCCTAGA AGATAGTGAG TTTAGAGACA  151740
GTAGCCAAGC AACAGCAGAG CAGCCTCAAC CAAAACGATT TTCCATTTTG GTGGGATGAA  151800
TTGAAACACA AGCATCTTCT ATCCAGGGGA GATTTGGGGA TCATAAAGAA TCAATCTGAG  151860
CTGGTACCAC CATATTGGCT GCTGCATTTT CTAGAGTTGC CGTAACTAGT CTCACAAGCT  151920
GGGAGGCTTT ACACAACAGA CATGTATTGT CTCATAGTTC TGGATGCTAG AAATCTGGAA  151980
TCAAGGCTCC AGGGGAGAAG CTGCTCCATG GTTTTCTCTT AGCTTCTGGT GTTGCCAGCA  152040
ATCCCTGGTG TTCCTTGGCC CGCAGGCGGA TCACTCCCAT CTCTGCCTCC ATTGTCACAC  152100
GGCATTTTCC CAGTGTGCCT GACTCTGTGT TTCTTCTCAT AAGAACATCG GTCATATTGG  152160
ATTACAGGCC CGTGCTACTC CATTATGACC TCATCTTAAC TTAAACAATT ACATCTGCAG  152220
TGATCCTGTT TGCAAATAAG GTCACATTCT GAGGTTCCAG GAATTAGAAC ATAGACATAT  152280
CTTTTGGGAA CAAAATTCCA GTGATAACAG TTTCGGAGAC AGACTAGTCC TGGAGTTTGT  152340
AAGGTGAGCC AGGACCAAGG TGCCAGGATT CTCATTTTGT AAGGTCCAGG AACAAAGTGA  152400
TGTTAATAGA AAGAACATGT TTTTGTTTGT TTATTTGTTT TTGAGACAGT CTCACTCCAT  152460
CACCCAGGCT GGAATGCAGT GGTACAATCT CGGCTCACTG CCGCTGCCAT CTCCCAGGTT  152520
CAAGCGATTC TCCTGCCTCA GCCTCCTAAG TAGCTGGAAT TACAGGTGTG TCCCACCATG  152580
CCCAGCTAAT TTTTGTATAT TTGTGTGTGT GTGTGTGTGT ATATATATAC ACACACACAT  152640
ACATACATAT ATATACATAC ATATATATAT ACACACACAC ACATATATAT ATATATAAAA  152700
TATATATTTC TTTTAGTAGA GACTGGGTTT CACCATGTTG CCCAGGCTGG TCTCGAACTC  152760
CTGCGCTCAA GTGATCCACC TGTCTTGGAC TCCCTAAGTG GTGGGACTAC AGGCACAAAC  152820
CACCACGCCC AGACAGAAGG AATATGTTTC CTTCCAGTCT CACTTGACTG GCTGCTTCCC  152880
TAGATAACAA CAGAGGATGT CTGTTGCAGT TCTCATTGCT GGGGAGTCTA AACTGGAATA  152940
```

FIG. 6.58

AAACACCCAC TATCTCCATC AGGCTTGCAC TAGAGCCCAG CTCTAGCTGG AGAGAAAGAA 153000
GCTAACCCGC ACAGACACAG GACTGTAGGC AGGGAGCATC CGGGGGTATT TGGGTCCTGG 153060
CTCTGATGTG CCTAAGGCCA ACTTCTCTCT GGCCATGCTG GCGTGCATGA GCTCACTAAT 153120
CTTCCTTTTT GCCTTCCATT TTCTCCAATC CTGACTTAGC AAAGGTTGGG CAAAAGAGAC 153180
TCTGTGTGAG TTCGAGCAAA GCCTGAGATG CTGGATTTTC CAAGATACGA GAAGGGGCTG 153240
GGGGCTGGGT GAACTGGTGG TGGAGGAGGG AAGGATTAAT TTCCCAAGGA GGGGAAGGGG 153300
CCAGGACATC AGGCCCCGGG GACTTTGAAG AGAGGGTCGT GGGTAGGAGG TAGATCAAGT 153360
GGAGTGACAC AAAGGTCAGG AAAGAGGAAG TGTCCACACT GTCCTTCGAC AGACTTGAGT 153420
CTATGGGACT TCCTCCCTGC ACGGTACAAG GAAATGAGTA AGTGAGATAA TGTTGTAACT 153480
TCTGGCCCTC TGACATTGCA CTGCCCCGAT GTCACAGTTG GAAACTGTAC CTGCCCCCAT 153540
CCTTGTCTGG GGTGTGTTTG GTCTGGGGAG GGCTGGTGAA GCAAGAGGTA CTCAGAAAAA 153600
GGACAGAAAT TGCTTCCTAT TATCTGGGCA TTTGGAGGTG AAGGGGTCAC AGCTCTGGCA 153660
AAGATGGGGT TGAAAGGGCC CGGACTCCAG GGAGGGGCAG CTCTGCATGG CCTGATTCCT 153720
GCACCCCACC TTTGCCCCCT CACACCTCCT CTCATCTCCC GTTTTTGAAG AGGAGGACCC 153780
TGTCACATCT GGACAATTCT GCAAGAACTC TGTAGAACTG ACTTCACTGT GAACCAGGCT 153840
CCAGAAGTCA ACAGAAACAA AAATGCTCAC ATTTAATCAC GATGCTCCCT GGCATACACA 153900
GAAGACTCTG AAAACTTCTG AATTTGGGAA ATCCTTTGGC ACCTTGGGGC ACATTGGGAA 153960
CATAAGCCAT CAGTGCTGGT GTGTGTGTGT GTGCGCGCAC ACGCGCATGT GTGTGCATCT 154020
TCTACCATGC CTCCTACAAA TTTGACCTGG GCCCAGGGCC ATGTTCGGTG GTTTTTAAGA 154080
ACCGAGGCTC CCAGAAGCAG TATTGGGCAG CTAGAGTGGC CCCAGGATCT ATATCAAACT 154140
CTACCTGTTT CTGAACCAAA TTTCTTCTAG AATTTTATTC CATAAATCTG AATTATGGTG 154200
TCAGACTCCT AGCATACACT AAAGGAACTC TCTGCCTTGC ATTAAATAAC AGGAGTTACC 154260
CCTGGAGGTA ACTCCTAGCC CTGGCTCTTT AGAGAACAGA TGCCGAATAG GCATTAGGGG 154320
ATGTGATGGA TGTGCTAACT TTCAAAAAAA AAAAAAAAAA AAGGCCTGAG CTGAGTGCTC 154380
AGAGATTCAC AAAAAGCTGA CAGCATCTCT CTGTTCCATT GGAAGCTGGG TGATCCTTTC 154440
TACTCTTTCC TGAGAAAGGC AGTTGGGCAG GAAAAAGCTG TATCTCTGTC CTCACTGAGA 154500
GGGTTTCCCA GTCTGAGGGT GAAGGATCAG GAGAGGGAGA CCTGACGGGT CGATGTGGGG 154560
CATCATCCAC TTGAGTGAGA ACCAGAGGGA TCCCGTCATT GCCCAGGGCA GATGCTCCAT 154620
TTTGGGGGGC ATCATTCATT CTTTCCTGTT CTCCCTGCAT TCCTCTGGCT CCTGCCCAGG 154680
AGAGGTGGCC GCTGGCAAGA GAGCTTGGTG GAGGTGGGAG GTGGGAGGTG GGGGGTGGGG 154740
GGTGGGGAGT TCTTGAGCCA GGACCTAGCG CATAGTCTCC AGCCTGCTGA TGGCTGTCTT 154800
GGATGCTTCA AAGGGGAGAA GATCCTAGAT GTGGGAAACA TTGGTGGGCG TTCTGCTGGG 154860
GCATCTGTAG CCTCTGAGAA GGCTACCAGT CTCTCCTAAG CTTACGCCGT CACACCCTGG 154920
GCACTTGTTG AATGACTTTA CTTAGCTTAC AGCCTCTGGT TCCTGTTGGG AAACTTAGGG 154980
CTTGCCACAG TGTTCATTTT CCTTTGCGGG CAACTCCGTT CCTGGCACTT ATCATATTAC 155040
CCACTGTACT CCCCGCTTAG AGCTGTGTCA AGGTTCTGAG AATCTATCCC TTGGCTTGGA 155100
AGGGGTCATC TCTCTGGCCA GATCATTTCC TGATAGGTCC TGAGGCACCA CAACACATAG 155160
GAGGCTTGTC CTCTCTCTGG GGTTCACTGC CTTGCTCCTT CTCCAGGTCA ATATGTGACC 155220
TTGGACCGGT TGCTTGAGTC CCCTGGTCAT TCAGAAACAA TTGGGTTTCC CTGGCTTTGG 155280
AGCCTGGCAG CCTGGCTTTG AGAACCGGGC TTTAACTTGT CACATGACTA TGGCCAAGTT 155340
CCTGGGGCTC TCCAAGCTTC ACTTCCTCTG TAAAAAGGGC AATAATATAA TACCTGTCTT 155400
ATTGGGTTTT GTCCATGTTA GATGAGACAT TGGGTACAAA GCACTTGGTC CCGTGCCTGG 155460
CACATTTACT GCACTTAATG TATGATAGTT TTCTTATTAT TCTAATAAAC AATATGGCTT 155520
TGGGAGTATA GTTCTGCCAC ATTGCAGTGG CCAGAGTGAA GGTGGTGAGT GCCTTCTGGG 155580

FIG. 6.59

```
GCCCTGGGAG TCAAGGTTAT CCGCATGCCC TTTCTTGCTT GCTCCTCAGT GTGGCTGCCT  155640
CTATGTCCAC ACCATGCAGA TGCAACAGGT AGTTTGAACC TCTGAGGCCC ACAGTGGGAT  155700
GGGGAGGCAG GGACATCACT TATGGGGTGG GAAGTCACCC ATTCCCCAGG AAATGGCCCC  155760
AGCTGCCTTT TCCATGACTC CTCTTGAAAC CCTGTGGAGG CCACATTCGT GTTGGGGCGG  155820
TCTTTCCCAT GAGGATATGT TCAGATGCCG AGGCATTTTG AAAAGCCCTC CATAGAGTTT  155880
CCTTTCATAA CACATGATCA TCCCCTTGGG CTTCTGGTTT TTTTTCTTTC AGGACCTTAT  155940
TTTCAGGCAA GTGGCCTTTG ACCTCTAAGG CTGTCCTTTC CTAGCTACCG AATCCAGCAT  156000
TCAAAGTGAT GGAAATATGT ATATATAGTA ATAGTAAAAT ATCAGCACTT AATGGCCTGA  156060
TAAGAATGTC ACTGCAATGC TGAGTTTGGA CCAACATTTG CCTGCTCCTG CCATTGAGCC  156120
CGGGCTCCCC TCCAGAGCTG AGCTGCTGCA AGGGATCTGA GTAACTAGGG CTGTGTCAGA  156180
GTGGCGATGA CAGCCACCAC ATGCTAAGGA AGAGATCCCC AAGGACAAGG AGAATCCCAC  156240
GTGGAGCTAC TTGCTTCTTT GTCAGTCTTG TTTTTCTTAT TCACAACCT TCTAAAACAC  156300
AATCTCTCAA CCTCTATTGT TAGCTTGCAT TTTTCAATCA TGAGCACAGC TTTACCTGGC  156360
TCCATGCTTT GATTGACTCT ACCTGCCAAC ACTGCAACAA CAGGGAAAGG GACACCGGCC  156420
TCATACCATT AGATGGTGTG TAGCCTGGGC ATGAGGATAA TTAAAAACTC CAAGGGGAT  156480
TTTAACATGT AACACAGTTT GGAAACCATT GATGTAAGAT CTTCTTACTC AACATGTGCT  156540
CCAAGGAGCT GTTGTATCAG CTTATCAGAA ATGTAGATCA GGCCGCACTT GGACCTGTAG  156600
AATCAGAATC TGCATTTTAT CAGATTCCGA CATTATTTGT ATGAACATTA GCTTTTGAGA  156660
AGTGTTGCTT TAAGAGACTA AGGGGGTCAA TCTACCTCAC TTTGCAGCTC TGTGTTCCTT  156720
AGTCATTGGC TAAAATATCA GCCCCCCTGC AATGAGCCAT CCTCCCTTGT ATAGTCAGTG  156780
ATGGCCTGTG AACCTTTAGC CAACTGGAAG TGGGAGGGGA CACAGTCCAC AAAACACTAT  156840
CCTGACTTTT GACACCAACT ACAAGTCAAG GGGTTCCCCA AACCACCCTG AGTTGTGATA  156900
ATTCGCTGGG AGATCTGACA GAACTCACTG AAGGTTGTTA TACTCATGGT TGTGATCTCT  156960
TATAGGGAGG GAATACAGAT TAAAATCAGC CAAAGGAAGA AGCACACAGC ACAGAGTCCA  157020
GGACAGTGCC TGACATGGAG CCCCTACGGT CCTCTCCCGT GGAGTCACGG ACAGCGCCAC  157080
TCTCCTGGCA TTGATGTGTG ACAACACACA GGGAGTGTTC CCCACCAGGG AAGCCTTGGT  157140
GTCCAGGGTC TTTACTGTGG CTCTGTCACA TGAGCACAGC TGACTGCCCA TGCGGCCGAT  157200
CTGTTCCCAG ACTCTCCACC GCTACACATC ACTCACAGTC CCTGCTCTAA ATCACACACC  157260
ATGACCCAAT GTCCCCGGGC AAATGAAAAC ACCTCTAGCA GGCAGGACGT TCCAAAGCCT  157320
TAGAGATCAC CTCTCAGAAG CTGAGGGCAG AAGCCAGACC TCTTTTTGGG CAGGGTTAAA  157380
TTCTTTATTA CTGTTTTTGA AAAAACTCCC AAATTGAGTT TTTCCTCTTC ACTTACAGCA  157440
GCATAACAAC AATCATCAAT GCAGAAGACT TCTGCGAGCA AAGGTGTGGG GGAAAACCCC  157500
AAGCAGTGGA CACTAGCTGG TGTCCTCCAA TTTGATTCTG ATGCTGTCTA CTGGGAGATA  157560
GTGTCAGATC CTCAAGCCTA AACCCTCCTT CTCCCAGTCA GAGGGCTGGC CTTTGGAACT  157620
TCTGACCAAT CCACTTCAAG TTGAGGTTCC AACCACTCCG CTCTTTGGGT TTGGTTGATT  157680
TGCTAGAGTG GCTCACAGAA CTCAGGGAAA CACAGCTACC AGTTTATTGC GAAGGACATT  157740
TTAAAGGATA AAAGTAGGCA GATAAAGAGA TGCATAGGGC GAGGTGTGGA AAGGTCCCTA  157800
GTGCAGGAGC TTCTGTCCAT GTGGAGCGGG GGTGCACCAC CCTCTCAGTA CATGAATGAG  157860
TTCTCCTTCA CCTGCCTATC AGCCTCTACA TGTTCAGCTC CCCAACCCAG TCCTCTTGGG  157920
TTTTTATGGA AGCTTCAAGA CACCCACATT CTTTCCCCAG AGTATAGGGC AAGACCTTCT  157980
CTGGGGAGGG TTTTAAGACC CACAGTCAGA AAGGTGGGGT GGGGTCAAGA TTAGAGTCCT  158040
GCCTTGACGG GCAGGTGAAA GGGGTAGGGG GAGTAGGTGA GAAAAATTCT GTTTATTTTT  158100
TCTTTTTTTT TTTGAGACGG AGTTTCACTC TTGTTGCCCA GGGTGGAGTG CAATGGCACA  158160
ATCTCAGCTC ACTGCAACCT CCGCCTCCCA GGTTTAAGCG ATTCTCCTGC CTCAGCCTCC  158220
```

FIG. 6.60

```
CGAGTAGCTG GGATTACAGG CGTGTGCCAC CATGCCTGGC TAATTTTGTA TTTTTAATAG  158280
AGACAGGGTT TCTCCATGTT GGTCAGGCTG GTCTCAAACT CCTGACCTCA GGTGATCCAC  158340
TTGCCTCAGC CTCCCAAAGT GCTGGGATCA CAGGTGTGAG CCACTGCATC TGGCCAAAAG  158400
ATTCTGTTTT TGAGGCCTGC CTCTGAGGTC TAACACACTC AACATTATAA CAAGACTGTA  158460
GTAAGGGCTA TGGGAGTTAT GAGCCAGGAA CTGTGGATGA AAACCTATCA CAGATATGCA  158520
TATATATATA TATATATATA TATGCATATC TATAATAACT CCACAACTAC ACACTGCCTT  158580
ATTGCTCAGT TCTTCTCTCC ATGTCTCTGA CCCACCCTTG CCCCCTTCCT CCATCCTTTT  158640
CTCCATTGCA TACCCATCCA CTGTGCCCTT TGGAATGCTC ACACCATGAA CTGCAAACTC  158700
TCGTGTGGCT TCAGCCTCTT CTCTGAAAGT TCCTCTCACC TATTACTTTC TCTGGAACCT  158760
GCCATCCCTG CCACCTTCTC AAAAAAGGCC TTTTATTCTC TTCATTCCAC AAAGCTCAGT  158820
GTCAAAACAT GGGGTTTACA CTGGAAGCTG AGGTCACATC AGTAGCCGGG ATCAGGGTCG  158880
CCCTAGCTGC CCAATGCAGC TCCCAGGCCT CCTGTAAAAC CTTGACCTTT GAGGTCATGA  158940
CAGCCCTCTC CTGCTATGCT CATAGCTGAC CACTGAACTC CTGGACACTC CCTCCCCCAA  159000
GTTCACAGAG AATGTGGGCA CATGCCTTAC AGTCTTCCCT TGATCCAAAC TACTGCCTTC  159060
ATCTTGAGTG ACAGCAGCAT CTTTTGGATG TCTTGGCCTG TCTAGCTTTA TTTTTTTGTG  159120
TTCTGCCATC AAGTTGCTAC TTCTGTTGCC ATCGTGCCTG TCAGCGCAGT GCAGGCTGTG  159180
GTGAAATCCC ACGAACTCAG GCATCACACT GACCGGGTCT GAGTCCTGTC TCAGTTGTCA  159240
GCTAGTTGTG CAATGAAGGG AAAGGGACCT ACACTTTCCA AGCCTCAATT CACTCATCTA  159300
TGGCATGGTG ACAATAATGG AGGTTGATTT AAAGTCCTTT GTAAGAATTA AGAGTTATAA  159360
TAGACATAAA GTGCTGTATC TGGTATACCT AGAAAACATT CCATAAAAGT TAGTAATTGT  159420
TGGTCATGTA ATGATGACTC TCTAGGCTAG GATTTCAGCT TCATTGCATG CACATGGTGC  159480
ACTCACAGGG CGTGACCTCT CTCTGTCTCA GTAACCTCAT CTGAGGACCG GGATAATCAT  159540
ACCGCTTCAA AGGGATGTCA TAAAGATTAA ATAATATGTG TAAGGCTGCT TGCATTTAGC  159600
TGCATTCAAC AAATATTTCT GTATCTTTCT CCTCATTTCT CCTTACTTTC TTGCTTATTA  159660
TCTGCTCTAG GTATAGATTT CAGAGAACTA AGCTTGTTAC AATCCTTCAT AAAATAACCA  159720
GGTTGGTTAG GGCATTTCCA AGAGTCAATA CTGTTTAGTG ACTATTCTCT GTTTAATCTA  159780
TTTTGATTGT CCAGGGTCAT CTTTTGCTAT GTCATAGGTT GTTGGCTTCT TCTAGAGAAG  159840
TGAGACGATG GACAAGTTCC AAGTGAGTGA GGCGACTGGT CAGGATATTC CGCTGAAAAA  159900
CTCATGTCAG TTCTAATTCG TGATTGTAAT TCAATCACAG CCTGAGAACA GTAGGACTGT  159960
AGTTCAAATG CTCTGTTCCC TTTTTTTTTT CCCAGAGGAT AATTTTTTTT TTTCTTTGAG  160020
ATGGAGTCTT GCTCTGTCAC TAGGCTGGAG TGCAGTGGCG TGATCTCGGC TCACTGCAAC  160080
CTCCGCCTCC TGGGTTCAAG CAATTCTCCT GCCTCAGCCT CCCAAGTAGC TGGGACTACA  160140
GGCACATGCC ACCACGCCCA GATAATTTTC GTATTTTTAG TAGAGACGGG GTTTCCCCTT  160200
GTTGGCCAGG GTGGTCTTGA TCTCTTGACC TCATGATCCG CCCACCTCGG CCTCCCAAAG  160260
TGCTGGGATT ACAGGCGTGA GCCACCGCGC CCGGCCTCTA GAGGATAATT TTTAAATGTG  160320
CTTTTGCATT TGGAAAATGT GATTGGCATT TTTTTCTAAT TTTCTAATAT GATACGCTGT  160380
CGGATGCTAT GGATTACTTA AACCCTCTGG CTACCTAGAA AGATCTTTAA GTGGTTCTCA  160440
ACAAGCTTCA TACGCAATGT AAATTGTATT ATCTCTCAGG ATGTGTGAGA ACATCTGTTT  160500
TTCTTCTAAT GCAGTAAACA TATAAGGGTC TCTTGGGATA TCTTTTAAAT AGACTTAATA  160560
CAACATTCAG GAATGATAAC AAAATATAAT CACAGTTGTA AGGGAATGTG AGCATTTCAT  160620
ATTAATAACA TTGGAACCTT ATGTTTAATA CAGTGTTAAA AGTTGACAAA CATGTAGGAG  160680
TCAGAAAATT CAATTAAAAT TATCACAGTA ATATGAATTT AGCCACATCC TGTGTTAGTT  160740
ATGAAATCCA TTTAACACCA CAAACAGTAA TATTTTTAGC CAGTTTATTC AAAAGGAAAA  160800
CAGGAACTAA ACCACTTTCA TGCAATATAT ACTCTGTTAA TGTGGTCAGG CTAATTTTGC  160860
```

FIG. 6.61

```
TGGGGGAAGG AACTTAACTT TTGAATATTT GAATGCCCAG TCATTTAATC TGAATATCCT  160920
ATTTCCTTGC ATGTTGCAAA ATTTTTGTCA ATAAAAGGCA GAAAAAGAAA TCTCTTCTCC  160980
ATGCTCATCC CTAAGAGAAT GGGTTGTCTG TACCCTGAGA GCATTTTATG GAGGGGACAA  161040
CCACTTTTCT AATTTTCCTT CCCACTTCTC TGTGGGCACA AATGCTCTTT GGTTGAAAGA  161100
GTTGTAATTC AGTCCCAAGA TGAGGTGTGG TTACTGCATC CCTAACCTAT ATCTGGGGAC  161160
CCCACAGCCA CACACATGGG GGAAATGGAG CTTGTCATTC AGTTCTCCAG CCATTGCACA  161220
GGGTTCATGG ACTCTTCGTT GATCCCACCC CACGCTTCTT CTCTCTGCTA GCCGAACACA  161280
CTTCTCTCTT CTTTATCAGG AGGCCATAGG AGAAGGGCAT TCATTTTTAA TACACATACA  161340
TCTGCATCAA GTCTAATTTT GCCATGTCTC AATCCAACTG TCAAATGGGT TGTTTGGGGG  161400
CTATGGTGCT TATCAAACAT TTACTCAAGA ATAGCCAAAA TTAGCCAAGC AAGGAGAACT  161460
TCAGCAACGT TCCCAAATGG CCCCAACCAA GTACTGTAAG ACTGAGGATA GCTAAAGGGT  161520
CTTGAGAGGG ACTTCTCAGG CAGTGGCCCC GACATTTATC TGTTTTTTTA AGTGAGAAAT  161580
CTGAGTACCA TTCTTGACTC CTCTTCCTTA CCCCCAACCC CTCACTAAGC CTTGTGCTAC  161640
TATTTAGTAA ACAGACCCTC AATGCACAAA CTTCTGTCTA AGGCCATGGC CACCACCCTA  161700
GTCTAATCCA CCATCTCTTC TCTGGAACAG ACCCCAGCTG CTCTCCCTGT CTCTGTGCTG  161760
GTCTCTCAAT CCATGCTCCA CACTGCAGCC AGAGTGCTCT ACAATGCAAA TCCATTTGTG  161820
AGACTCCTCC TCTTAAAATC CTCAAGTGGC TTCTCTTTGC CCCCAGGATC ATTTTGAAAC  161880
TCCTTAATGG AAGAGGCATG GCCCTTTGGG ATGTGGTTCC CCAACCCCTC CCACATCATC  161940
TTTTCAATCA GATTTCCCAC TAAATGGAAA TTTTTTCAGG TCCTCAACTT TATGGTGACT  162000
TTCTCTTGCT CAGGATCTTT GAACATACTG TTTCTTCTTT CCTTTTGTAT TTGCCAAGAC  162060
AACACTTCCT CTGGTAAGAT TTTCCTGACA TCCTCTATAA AAAAAGATTG AGATAGTTGA  162120
CTACCCAAAA TGTTTCCCAT TCATTCCAAG CTCTATTCAA GGCAGTAAAG TGCCCGGCTG  162180
ACAGATTGCA TTCCTCATCT TTTCTGAAGC TAGCAATGGC CATGCAACAG CATTCTGGCC  162240
AATAAGATAG AAGTCGAAGT TGAAGGGTGG GATTTCCAAG AAAGCTCGTT GAAGACATAA  162300
TTCCTCATTT CACTTCTTAC TCTTTCTCTT TCCTGCTTCC TAAAATGCGG TGCAGATGGC  162360
AGACACTTCA AAGCTGTCTC AGGCAATCAG GTGATGTTAA GGCAGAAACC AGCTTTATGA  162420
TGGGTAGAAC AGGAAGAAAG AAGGCACCTA TGTTCTTGTT CACCTTGAAC CACACCAGCA  162480
CTGCCTTGCC TACCCCTGGA ATTCCTTTAA TGAGAGGCAA ATGAGAGCTT ACGTGTTTAA  162540
GCCATTGCTA TTTTATTTTT TTTTGTTTAT ATGCAAAAGA ACTTAATCCT AACTGATATT  162600
AACACTAACT GGGTCTATTG CTTGGTACCA AGCCAATGCA TGACACATGG TATATATGCT  162660
CAGTAAGTAT TTGTTGAATG AGTGAGGCAA TGAAAGAACA TAGAGGATAT ATATAACAGT  162720
CCTCCTGCCC AGATGTCATC TGATCCTCTT TAGGATCTGG GCCCATAAAA CTGTATCTGA  162780
TATAGTTTGA ATATTTGTTC CCTACAAATC TCATGTTGAC ATTTTATCCC TAATATTGGA  162840
GGCAGGGCCT AGTAGGAGGT GTTTTGGTCA TAGTGATAAA TGGCTTGGTG CCGTTCTCAC  162900
AGTAACGAGT GAGTTTTTAT TCTAGTGGTT CCTGCAAGAA CTGATTGTTA AAAGAGCTTG  162960
GATCCTTCCA CCCCTCTCTC ACTCTTGCTT CCTCTCTCTC ACCTTGTAAT CTCTACAAGC  163020
TCTTCACCTC CCCTTCTCCT TTTGCCATAA GTGGAAGATT TCTGAGGCCT CACCAGAAGC  163080
AGATGTTGGT TCCATGCTTC TTGTACAGCC TGCAGAACCA TGAGCCAAAT CAACTTCTTT  163140
TCTTTATAAT TATCCAGTCT CAGGTATTCC TTTATAGCAA CACAAATGGA CTAAGACAGT  163200
TTCTAATGCT ATGGTTCCTT TAGTAGGTCA GTGTAAAACC CTGGATCACT CCTGTAACAA  163260
ATTACTTGGA ACTCTTCTCA CCATACATAT TTAAAAATAG TTGCCATGTT GAAAATCCTA  163320
TAAGATCATA TTTTATTTCA AATCCAACAA CTCATTGCTA AGGAGATACA AGAAGCAGAA  163380
AATACAGAGA GACTAATGTG TTGATGATTT TTGTGAGGGA CATAAGGTCT GTGTCTAGAT  163440
TCATTTTTTT GCATGTGGAT GTCCAGTTGT TCCAGCACCA TTTGTTGAAA AGACTATCTT  163500
```

FIG. 6.62

```
TGCTCCACTG TATTGCTTTT TCTCCTTTGT CATAGATATC TGGTCACCTT ACCTTAGAGT  163560
CACAGATGAA TGGTCCTATT ACTTAACTAC TGAAAATACA GGCCAAAGCA AACAGAGGAA  163620
TAAGGGATAT ATAATAAAGT ATTTGTGTAC TTGACTTGGC TCTAAAGGAA GCATTGCGTG  163680
TCTGTGTAAA AAGAATGGGT GAGAGTTTTC CACCATTCAA TATTTCTAAT CTTTCTGAAA  163740
TACAAAGCCA GGACATCCTC TAATCCATAC ATTCCATAGT TTGGTTAATA TAAATTCCTT  163800
TATTAAATCC TTATTAAATA AAGTTATTTA TGTTTCTATG AAACTCATTT TAACTCCTAA  163860
GTGAAAAATA CTACTGAGCT AACTAAACAT CAAACATTTT TAATTTTTTA AATTTTTTTA  163920
GAGACAGGGT CTTGCTATGT TGCCCAGGCT GGCTTTGAAC TCCTGTGCTC AAGCGATCCT  163980
CCAAACTCAG CCTCCCGAGT AGCTGGGACT ACAGGTGCAT GCCACTGTGC TCAGCTAAAC  164040
ATTTTTTTGA AATGCTCTTT TAAAATCAAT TTTATTGAAG TATAAGTTAC ATACCATAAA  164100
AGTACTCATT TTGAGTGTAC AGATTGACAA GTTCTGACAA ATGTGAACAA CCATGTAACC  164160
ATCACCAAAA ATAAAGATAT GAGACATTTC CATTACCCCA AAAAGTTCCC GTGTCCCTCT  164220
CCAGTCAATA TCCAGCCCTA GCCCCAGCTC CAGGCAACCA CCAATCTGCT TTCTGTTGCT  164280
ATAAATTGTA CTTATCTTTT CTAGTGTTTC ATACAAATGG AATCATACAG CATTTACTCT  164340
TTTGTGTCTG TCTTCTTCTG CTCAGTGTAA TGTTTTTGAG ATTCATCTAT GTTCTGTGCC  164400
TCAGTAGTTT GTTCTTTTTA TTACTGGATA ATTCCATTAT AAGAATATAC CACAATTTGT  164460
TTATCCATTT ACTGCCTGAT GGGCATTTGG TTGTTTCCAG CTTTGAACTA TTTTGAATCC  164520
TAAAAGACTG CCAGTTTTGA ATGAGACCCC AGAACAATGA ATGTAGGCTC TGTATACAAG  164580
TTCAGGCTGC TGGGCAACTT AGGCCTTAAG ACACAACTCT GCCACTTAGG CCTTAAGACA  164640
CAACTGACAT GATGGTGCTT AAAGTGGCTG TGATGGAAAA GGAGGCTGTT TGGAGCCTTT  164700
GGAGTGCCTT TATAGGTGAA CCCCAGCATA GCACCTAATG ATTTGGAGCA AAGCTGTGTC  164760
ATTCCCCAAA GATAACTATT CGCCTTTTGA GAAACATCTT CTAGCTACTA TCAATAATAA  164820
ACACAGAATG CATCACCATG GGCCACCGTG TTGTCTTTTG ACCTGAGTTT CCATTGTGAA  164880
CAAGAGTCAT TTGATCCAAG GCAGAAAGTT GGGTGCACAC AGCAGTGTTC CATCATCAAA  164940
TGGAATATGA GATTGGGCCC AAGTAGGTCC TGCAGACACA ATAAGTTGC AAGAGCAAGT  165000
AGTACAGGCG CTTGGCCTGG CCAGTACTGT TGCCAAGTTG ACTGCTTCCC CTCAGTCTGC  165060
ATCTGTGGCT TCATGGGGAG TTTCCTATGA CCACTTGATG GAGGAAAAAA CAAATTGGAG  165120
CATAGTTTAT AGTGCTGGTA CTACCCAAAG TGGCTAGCTG AGGCACTACA TCTCCACTCT  165180
GGGGTGCCCG TGAAGGACAG TGCCAAAGGA AAACCCCCTC AGTGAGCAGA ACTTGGAGCA  165240
ATACAAGTGG GTGTTCATTT TACCTAGAAG AGAAGATGTC CGTGAGTTAC AGATCTACAC  165300
AAAATCACAG AGAGTGGTTA ATCGTTAGT CTGATGGTCA GGGACTTCCA AGAGACATGA  165360
TTAGAAAACT GGTGACAAGG AGTCCTGGGG AAGAGGCATA TGGATACCTC TGAACACACA  165420
CAAAACATGA GAATATGTAT CCCATATGAA TGTTAACCAA AGAGCAGCCA CAACAGAAGA  165480
GGATTTTAAA ATCAGCTGAA TAAGATGATT CATTCTGACA GCATCAGCTA GTCTCTTTCC  165540
CCAGCCACTG TTGCCCAGTG GGCTTACATA TATCATGGCC ATGGGGGCAG GGCTATGTAT  165600
GGACACAGCA ACATGAATTT CCACTCATCA AGGCCAATTT GGCTCCAGCC ATTGCTGAGT  165660
GCTCAGCCTG CCAAGATAGA AATCTACGCC AATATGGCAC CATTCCCTGG GCTAGAAAAC  165720
CAACTGGTGG AAGGTTGATT ACATTGGACC ATTTCCATCA TGGAAGGGGC AGTGCTTTGT  165780
CTTCCCTGGA ATAGACATTT ACTCTGGATA TGGATGTGCC TTCCCTGACT ACTACAATGC  165840
TCTGCCAAAC CTACCATCCA TGGGCTTAAT TTTATTTGTT ATAAAATTTC AACCACCATT  165900
GCTTCTGACC AAGGAAGTAA TCTTACAGCA AAGGAAGTAC AGATATGAGC TTCTGATCAT  165960
GGGCTTCACT GGCCTCACAG TGAAGCAGGT GGCCAGATTA GAACAGTGGA ATGGATTTTA  166020
AAGGCTCAGT TACAGCACCA GCTGGGTAGC AACACCCTGC TGGCCTGGGG TTATGTCCTG  166080
CAGGATGCTT TAAGTCAGTG ACCAATATAT GATGCTATTT CTCCCATTGT CAGGATTCAT  166140
```

FIG. 6.63

```
GGGTCCAAGA ATCATGGGGT CAAAATGGGA GTGGCTTTTC TCACTATCAC CCTGGTGTTC    166200
GGGTAGTAAT TTTTCCTTCC CATTCCTGTA ACTTTGGGCT CTGCTATTGC AGAAATCTTA    166260
GCTCCTGTGG GGGGAATGCT TCCATCAGGG AATACAATGG TGGTTCCACT AAACTGACAG    166320
CTGAGTTTGC CATCTCCTCG TGCCAGTGAA TACACAAGCA AGGAAGGGGG TTCCTTTCTC    166380
ACCTAGGGTG ACTGATCCTA ATTACCAAGG AGAAATTGGA CTGCCACTTC ACAATGAGGG    166440
TGAGGAGTAT GTACTCTATG TGTCTGTGAT TAATGTCAAT AGAAAGTGAC ACCAACCTAG    166500
TACACAGAGG ACTGATCATG GTCCAGGCCC TTCAGGAATG AAGATTTGAG TCACCAGGCA    166560
AGGAACTTGG ACTCACTGAG GAGGGCATAT TCCAAGGAGA ATATTTATC TATGTCCATC     166620
TATGTCCATC TATATTCCAT CTGTGTTCCC CTTGGAATTC CTATTCATGA ACATGGGGAA    166680
TTCCAAGGGG AATATAGAAT GAGTAGTGGA AGGTAGTTAT AAATGTAAGT CAAAACCAC    166740
ACAACCAATT TGAGAAATGA GGAAGGTAAT AGTGTTGAAT ATGTCTTCTT TATCTTGATA    166800
TAAATGTATT TGTGCATATA TTAACCAGTT TATTTATTTA TTATTATTTT TTGAGATGAG    166860
CTCTCGCCAT GTTGCCCAGG CTGGTCTTGA ACTCCTGGGC TCAACTGATT CTACCATTTA    166920
GTCCTCCGAG TAGCTGGGAC TACAGGCATG CACCACCATA CCCAGCTGAC CAGTTTTTTC    166980
CTATTCCTCT ACTTAATTTC TCTACTATAC AACATAATAT GTGTTAATGG TAGTTAACTT    167040
TATATCTCAG TATTAAGTCA CAAGATATCA AAAAGGGAAT GCGACTTAGT TACAAGCAGA    167100
ATGAATATCA CTCAAAGATG AATAAAGAGA AGAGGGTTAG TGCATTTTCT GTTGGATGAG    167160
AGAAAGTTTC ATTGTTAGGC AGAAGCATGA TTTTGCCTTT TTTTTTTTTT TCCAAGGTCT    167220
CACTCTGTGG CCCAGGCTGC AGTGCAGTGG TGCGATCTTG GCTCACTACA ACCTCTGCCT    167280
CCCGGGTTCA AGTGATTCTC CAGCCTCAGC CTCCAGAGTA GCTGGGATTA TAGGTGCGCC    167340
AGGTTAATTT TTGTATTTTT AGTAGAGAAG GTGTTTCTCC ATGTTGGCCA GGCTGGTCTT    167400
GAACTCCTGG CCTCAAGTGA CCCACCTGCT TGACCTCCC AAAGTGCTAG GATTACAGGT     167460
GTGAGCCACT GTGCACAGTC ACCACGGTCT TTTTGGGAGG CAACTTTAGC ATGGTTAAGA    167520
GGTGCGAATG GATGTTAAGC TAACACCAGG TAAGCCCTGG TAGATGTGTA TTGTGTCAGT    167580
GGGCCTACGC TGGAGCCATG TTTCCCCAAA TTCACTTTTC CTATGTACCT CTGGATTAGT    167640
GTGGGCCACT GGAGACATTT CACATGAGAT GAGGAAGGTG GGAGTGAAGG AGCAGCATCT    167700
TTTTACACTA AGCAGGTCGG GGAGGGCATG TGGCTCTGTC TCACATTGTT GGGAATCTGT    167760
CCATCATCTG GTTGGCTTAG GTCAGTGGGT GAGTTCACAG CTGTTCCAGC TTCTGCTGGA    167820
AACTCCTTCG GTTTCTCTGA CTGCTCCGTG ATGAGGGCAT CAGATTCTCC TGCAGAAAGC    167880
CCCAGTGTTG AAGTTGGGGC TTCATGTTGG TGAGTGATAG TTACGGGTTC TAGCCCAACC    167940
TGTGGTTTCT TGCAAATTTC AGTGTCAGCT CAGTCTTGCG GGTTTTGGGT TGTCCTTGCT    168000
TCCCACACTT CATGCCTTTC TTTCCCTCCT GACAGTCTGC CCTTTAGATT TTAGGATTCA    168060
GCACCAGCCA CAGAAACAGC AACCTCACTG TTAAGGGTTG AATTGTATCT CCCCAAAAGG    168120
TAGGTTGAGG CCCTACCTGC CAGGACTTCA GAATGTAACC TCATCTGGGA ATAGCATCAT    168180
TGCAAATATA ATTAATTAAG ATGAGGGCAT ACTGGCTCAG GATGGGCTCC TAATTCAATA    168240
CAACTAATGT CCTTCTATGA CAGCCACAGG AAGACAGAAA CGCCAAGGGA GAACACCATA    168300
TGCTGATGGA GGCAGTGGCA GCTGCCAGCC AAGGATTATA ACCAGAAGTC AGGAAAAAGC    168360
AAGAAGGAAT CCTCCCTTAG TGATTTTACA GGGAGCATAG CCCTGCTGAC ACCTTGATTT    168420
TGGACTTTTA TTCCCCAAAA CTGTAAAACA ATACACTTCT GTTGTTTTAA GCCACTCAGT    168480
TTGTGCTACT TTGTTATGGC AACTCCAGAA AACAAAAATA CACTCAGACT GTTTAATCAA    168540
CCTCCATAAT TGCATAAGGT CTAATCCCTA TAATAAATCC CTTAAAAATG TCTGTGTATA    168600
TATATTTAAA AATATAAAAT ATCTTCTAGT GGTTCTGCAT CTCTGGTCAA TCCCTGACTG    168660
ATACAGAATA TGTATTTTCA TTTCTAATGA TGAAATACCT GAATGAAATT TCTAGGACAT    168720
ATGGTAAGTG TATGTTTAGC TTTTAAGAAA CTGCCAACTT GGGGGAATTG CTTGAGGCCA    168780
```

FIG. 6.64

```
GGAGTTCAAA CAGCCTGGGT AACAGTGATA CCCTGTCTGT ACAAAATAAA AAATATTAGC  168840
AGCGTGTGGT GGTGTGTGTC TGTAGTCCCA GCTACTCAGG AGGCTGAGGT GGGAGATTCA  168900
CCTGAGCCCA GATCTTTGAA GTTATAGTGA GCTATGATCA CGCCACTGCA CTCTAGCCTG  168960
GGTGACAGAG TGAGAAAGCT GGTCTCTAAA AAACAAACAA ACAAAAAAGA AACTGTCAAA  169020
CTCTTCCCAA CATGTTGCCA TTTTTACATT TACCATTTTA CATTCTTACC AGCAATGATT  169080
GATAGTTCCA GTTGCTCCAT ACCCTTGCTG ACCATTCCAA TAGATGTATT GTGTTATCTC  169140
ATTGTAGTTC TAATTTGTAT TTCCCTAGTG ATTAATGATG TTTAACATCT TTTCATGCAC  169200
CTATTGGCTA TATGTATATC TTCTTTAGCA AAATATATGT TGTTATTTGA AGAGCGGAAG  169260
TTTTACATTT TGATGAAGTC TAATTTATTG ATTTTTTTTT TCTTAGATGG CTCATGCTTT  169320
TTGTGTTATC TAAAAAAAAT TTGCCTTCTT CATGGTCACA AAGACTTTCT CCTATGTTTT  169380
CTTTTGGAAG CTTTATATTT TTAGTTTTTA TGTTTATGTT TAAGACCCAT TTCTAGTTAC  169440
AATTTGTGTG ATTTTTTGGA AGGGTCAAGG TTCATTTTCT TTTCCATAAG AATGTACAGT  169500
TGTTCTAGCA CCCTTGTTAA AAAGACTTTC CTTTCCCCAT TGAACTACTT TGTCAAAAAT  169560
CAACTGAGCA TATATGGGCA TCATGAATTT TAATCCTGTT AGAACTGAAT GTTCCCAAGG  169620
CAGGCCATGC CCATGACTGA CCTCCTTTCC TTGGATTGCC TACAAAACAG ATAAAGCTAA  169680
GTCTGGAGCA AAGAAATCCA TGTCTAACCT GTATTTTTTT TTTTTTTTTT TTAGATGGGG  169740
TCTCGCTCTG TCACCCAGGC TGGAGTGCAG TGGCGTGATC CCAGCTCACT GCAATCTCTG  169800
CCTCCTGGGT TCAAGTGATT CTCCTGCCTC AGCCTCCCGA GGGGCTGGGA TTGTAGGCGT  169860
GCACCACTAT GCCCATCTAA TTTTTGTATT TTTAGTAGAG ATAGGGTTTT GCCATTTTGG  169920
CCAGACTGTC TTGAACTCCT GACCTCAGGT GATCTGCCTG CCTCGGCCTC CCACAGTTTT  169980
GTGATTATAG GCATGAGCCA CCGTGCCCGG CCTTAACCTT TGTTTTCTTA CACAACACAC  170040
TACGTGATGT TTTCCACATG CATGGGTCAT TTGCTTCATT TACGTACAAA TGCATAAGCA  170100
ATATACTGTG TGGTGTGAGT TTGTGATGGG AAAAGGAAGA AGTTTTGCGG ATACTACACT  170160
GGCTTCCTGC TATCTGTCTG TGTGAATGGC TATGGACTTT GTCTTCTATT TGTTCGCTTA  170220
GCGCAGATAT GATCAGCTTA CAACTTAAGA TTCTAGAGAA AGAGGGTCAT ATCTGTAAAG  170280
CACTCTGAGC ATGTGTGAAG TTTAATCAAT AGCATATGAG GTTACAGCAA ATTCACTATC  170340
TTTGTTTCTT CAGCTATAGA ATGGCATGAG GATTCATCTC AATTTAGTTC AATTCTGTTC  170400
AGAACCATGA GCTAGCTGTT CATGGAAGGA AAGCCCACCT GATTGTGGCC AGGGAAGGAG  170460
AAACAACACT TTAACCAGGT TGATTTGGTT CTCACAGACA CCATTGGCAT GTGACATCTG  170520
GAACAGACCA TGCCTGGTCT CTGTTCGTAT CACTTACTAT TCAGCTCAAT ATTGGTCTGA  170580
ATATTCTTTA GACTGACTGA AATGAAAAGG AACTGTTGTG TAACCATCCA TAATTCCAGC  170640
CTGTAGACCT GGGCTGTATC TCTATGCCCT GCCTGGCACA GACCCCACCT CCTGCTCCTT  170700
CTCCCTCACC ACCAGTCAAT CCTTGTCCTA ATGAACAGGG AGGGCAACCC TGAATGGGGA  170760
GTGGAGGGAA GAGATGTCAT GAGATGGCAA CGTGCACCCT GAAGTGAGGA TGAAGGCTAT  170820
GTGAATGTTG TAGGCTGACA GCCGGGCATA GTGGCCCCGT TGCCATGGCG ATGGAGGCAT  170880
GTTGATGCGA AGTGTCTGCA CAGCTCCTAG GATTTTTAAC AGCAGCTGGG CAGAGCCTCG  170940
GCGTCCCTGA ATTGTTGCCC CCCTGAGTCA CTGCTTGGCC CCAGCTGTCC TGATCTCTGT  171000
TGACAAATGG TTGTCCTTCA CAGTCAAACT ACTAACAGTA CTCTAATTAA TGAATGTGCT  171060
AATTATTCTT GCCTACTCCC AGCATATTTG TCTAACTAAC CTGTCACACA CAGATCAGTG  171120
CAGCATATGC ATAATTACGG AGAGCGCTGG GAGCAGGGGA TGGGTGGGAG AGGGGTGGGC  171180
TCGCAGCCCT GTCGCTGTGG GATATTTCTT GTAAAGTTAC CTTTGCTAAC GGTCAGATGT  171240
CGTGGGGATA TGTTATTTCC CGTGAAGTGT ATATGTCTTC CTTTCTTTCC TTTCTAAGAA  171300
TCTCTCTTCA GGGCTGAGGG GCCATTGCTC AGTGCTTTAG CCTGTGAGGG GATTGCCAGG  171360
TACAAATGCA GAAGGACCAG GGAGCCCAGG TTCTGAAGAC GATTCCGGTA GCAGCACGTA  171420
```

FIG. 6.65

```
GGGTGATTAA AACTCCAGAC TTTAAAGCCA GACCGGCCTG GGCTTGAACC CTTGTTCTGC   171480
TCCTTGCTAT GTGGGTCTTT GCCTTGACCA CATTTTTTTT TTTTTTTTAA GACAGGATCT   171540
CCCTCTCTTG CCCAGGCTGT AATGCAGTGT TGCGATCACA GCTCACTGAA GCCTCCATCT   171600
CTACAGCCTC AAGCGATCCT CCTGCCTCAG CCCCGAGTAG CTGGGACTAC AGGTCTGTGC   171660
CACCACGTCC AGCTAATTTA CTTTTGTAGA GTTGGGGGTC TTGCTATGTT GCCCAGGCTG   171720
TTCTCCAACT CCTGGACTCA AGCCATCCTC TAGCCTCGGC CTTCCAAAGT GCTGGGACTA   171780
TAGGCGTGAG CCACGGTGCC AGGCCCTTGA CCACATTTTT AACCCCTCTG AACCTCAGTT   171840
TCACTTTCTG GGCAATGGGA GGGGGGTAAT TTGTCCCTCA GAGGGTTGCA CTGAGGGCA    171900
AATGTGAGGC TCTGGGTACA ATGCCCAGTA CAGACTAGGT CCCCACGACA CAGCCGCTCA   171960
GCGGCTCCGG ATTCTGGGCT GCTCTGGACT GCGGCCAGGC GGTCTTCTGC GGGAATCCGG   172020
GCAGGCAGGG CGGGCTGCGC TCCCCTCCCC GGCTCTCCCG GTGCCCCTTG TCTTTTTGTT   172080
CTGTCTCAGC AGCTCTCTAT TAAGATGAAT GGCATTTCCA AAGGCTTCAC CTCTGATAAG   172140
TGTTCCTCTG CAGCTGCAGC CAGAATCTTA ATGTGCGCGC TGTAATTTAA TGGCCGTCTC   172200
GGCTATTAAC ACGCTCTTCT CGGGTGAAGT GGACTCCCTC CATCCCCGGG CCTCTGCACG   172260
TGCTCTGCGC GCTGGCTGGG GGTGACTCCA AGGAGCTCAG AGCGGGGTGC CCGGCACCTC   172320
TCGCCAGGCG CCTTTCGACC TTCTAAAGCG CGAATGGCTG ACTTTTCTC CCATGTGTGG    172380
GGCCCCAGAA GGTGTGGGGC CCCAGAAGGT GTGGGGTCCC TGCGTTCCAC GGAGCCCGGA   172440
AGGTTTCCAG TGATGGTGGG GGCTGACCAC GTTGGTCCCC GTGGGTGCTG TTTTCATGTG   172500
CCGGCAGATT GGGATGAGTT TAAAAGACAG AAGCGTGTAG GATAGAGAAA CTTCTTTAAA   172560
AACTGGAAAT TTTAATCTGG GGATTATAAC TATTGGACAG TCAAGTGCAA GAGTGAATAC   172620
ACTTCTCACT CCCTCCTCCC AATTTTTATT TGCGGGATTA GTCAGTCCCC CTCTGCCACA   172680
TGATAATTGT GAGAACTACC AGGGTCTTCA TTCTCCTGCC ATCTGGTTGA CCTCTCCAAG   172740
AATGGACACC CGGGCAGCCT GGGCCAATGA GGCTGTCCTA AGAGTTTAGA TGAGAGAAGT   172800
CAGTCTTTGA CAGGTGATGG AAGCTGTAAA ATGTAAAACT CCACAGTTGG TGAAGATGTC   172860
TCCAGGAAAC AGGTCTGCAG AGAGAATACG TTTGACATGC TAAGAGAAGC TGAGAGAGAG   172920
CGAGAGGAGA GATTGGAAGA AAGACAGAGA CAGAGGTAGA GAGAAGGGAA AGAGAGAGAG   172980
AAAGGGACAG AAGAGAGAGA AAAAAGAGGG GGCCGGGCGC GGTGGCTCAC GCCTGTAATC   173040
TCAGCACTTT GGGAGGCCGA GGCGGGCAGA TCACGAGGTC AGGAGATCGA GACCATCCCG   173100
GCTAACACGG TGAAACCCCC GTCTCTACTA AAAATATAA AAAAATTAG CCAGGCGTGG     173160
TGGTGGGTGC CTGTAGTCCC AGCTACTGAG GAGGCTGAGA CAGGAGAATG GCGTGAACCC   173220
GGGAGGCAGA GCTTGCAGTG AGCTGAGATC GCGCCACTGC ACTCCAGCCT GGGCAACAGA   173280
GCAAGACTCC GTCTCAAAAA AAAAAAAAAA AAAGAGAGGA AGGGCGGGAG AGAGAGAGAG   173340
AGAAAGCTCT CTAGCTCCAA GGCCTAACCA CATCTCTGTT CTTTTCAACT TCAGCTGTCA   173400
GATTTTTAGA CTCTTTGAGT GAATAAATTC TCCTTTTTGC TTAAACTAGT TTGAGCTAAG   173460
TTTCTATTGC TTGCAACTGG AATACTTTGT AAGAGGACTG GCCTTCATTT CTGATGCATT   173520
GTCACTAAGA TGTAAGTGTT AGAAGAGCTA ACGCTTTATG GGGTTCAAAC TCCTTGGCTA   173580
CCAAAACCTA AACATCCCCT GAAACTTACC AAACTGCAGG TATGAATTGG ATCTCACTAA   173640
GGTGAATATA CAAATCTTGC AAGTGCTGAG CCCTAACCAA TCTTGTAATA ACTCTGTGGT   173700
AGTTAATTTT ATGTCAAATT GATTGAGCTA AAAAATGCCC AGGTAGCTGG TAAAATGTTT   173760
TTTTCTGGGT GTGTTAGGGA GGGTGTTTCT GAAAGAGATC AGCACTGGAA TCAGCGGACT   173820
AAGTAAAGAA TTCCCACCCT CACCAATATG GTGGGTGTCA TCAATCCACT GAGGGCCTGA   173880
ATAGAACAAA AAGCGGGCAG AAGGGCAAAT TCCCTCTTCT TCTTGAGCTG GGCCATCCAT   173940
CTTCTCCTGC CCTTGGACAC TGGAGCCCCT TGTTCTCCAG CTTTGGATT CAGACTGGGT    174000
CTTGCACCAT TGCCCTCCAT CTTCTCCTGC CCTTGGACAC TGGAGCCCCT TGTTCTCCAG   174060
```

FIG. 6.66

CTTTTGGATT CAGACTGGGT CTTGCACCAT TGCCCTCCTT GATGCTCAGG CCTTTGAATG 174120
CAGACTGGTC TCCACCAGCA GCTTTTCTGA GTCCAGCT TGCAGATGGC AAACCATGAA 174180
ACTTCATGGT GTCCATGAGC ATGTGAACCA ATTTCTATTA TAAATCTGCA ATATATATAT 174240
ATGAGGAGAC TTATTTATAT ATTGGTTCAG TTTCTCTGGA GAGCCTTGGC TAATATAAAG 174300
TCTATACTCT ACAAAGTGCC CTAGGTACTC AGGGAGTACC CAAGTGTGTC ATGACCAGCC 174360
CGACAGCCCT GGCTGCTGGC TTCCCCGCAC ACAACTCTGC ACGCTGCCTT CATCAGCCTT 174420
TCTCTCTCAG CTGAACCGAG GGCATTGAAG CGGGCCTCTG GCACTGTACC TATGAGGGAG 174480
CAATATCTTC CCCTACACTG ACCTCTTCCG TGCCGAGATG CAGCCCTCCC TGCTGCCACT 174540
AGTTACAGTG GTCCATGTTC CCTTTCAAAG TGAAGTTTTG ATAAAAGCAC CTCTTAACCA 174600
ATGCCAAATA GCTAAGTCTG GACAAAGAT TGCAGGTATT TTGCATTTTC CATGTAACCT 174660
CAGAGGGATT GCCATTCACA CTGATCTGAG CTGCAGAATA CCAGGCAGCC ACCTCACCCA 174720
CCCAGCAGGT CCACTCTTAT ACTTTCTCAG AAAGCACAGC CACTCTACTC TTATTCAGTT 174780
GAAAAGAATT TCCAGGAAGG TGTTTCTGCG ATTGCCTCAG AAAAGTCAGT TCCCTTTGGG 174840
AATTTCCCTT AGGGATCATC TGTAACTCCA TTTCTGCCTT TTACCTGAAT TCTTTGGTTT 174900
GGTTTGAATT CTTTGGTTTA ATTTATGAAT TCCCTTTATT ACTTTTCTCT GAAGAAATGG 174960
AGATATCAGC TGTCCCTCCC CACTGCCATT TATTCCTTCC TTCATTCAAA CCTTATGTGG 175020
CTGCTACTTA CCGTGTGTTA AGTGTTCACT TTTTTTCTTG GAATTCAAAA AAAGAAGGAC 175080
AGTATTTGGG GCACAGATCT TTTGGTGTTC TATACATTTT TTTAAAGTTT CATTTTACAT 175140
TTGTGTGTGC GTGTGTGTGT GTGTGTGAGA CAGTCTTGCT CTGTTGCCCA GGCTGGAGTG 175200
CAGTGGCATA ATCATTGGCT CACTGTAGCC TCAAAGTCCT GGGCCCAAGC AATCTTCCCA 175260
CCTCAGCCAC CCAAAATGCT GGGGTTACAG GTTTATGCCA CTCTGTCTGA CCTGAAAGTT 175320
TTGGGTTTAC TTTCCCTTCT TTCTCTTTGC TGAAGTCAGA GATGATGGCA GCTTCCAGAT 175380
TCTCTGGTGC CTGTGCTGGG CTCGTGCTGG TCATGGTCTT GGGTCCAGGA TTCATTCTGG 175440
AGACTCTCAG GGAAGTTTCC CATGACAAGG AAATGTAGGA GAGTGTGCTG GCTTTGCGTG 175500
CTCCTCTGCC AAGCCCTGCT TCTCCTGGTG GGACACACTG AACCACAGCC AGGGCATTTT 175560
GGTGGTTAGT TAAAAAAAAA AAAAAAAAAA AAAAAAGGAA GAAGAAGGCA CTGTGTAATT 175620
GTGCCGGGGA TCTTCAGAAA TTGTAATGAT GAAAGAGTGC AAGCTCTCAC TTCCCCTTCC 175680
TGTACAGGGC AGGTTGTGCA GCTGGAGGCA GAGCAGTCCT CTCTGGGGAG CCTGAAGCAA 175740
ACATGGATCA AGAAACTGTA GGCAATGTTG TCCTGTTGGC CATCGTCACC CTCATCAGCG 175800
TGGTCCAGAA TGGTAAGGAA AGCCCTTCAC TCAGGGAAGA ACAGAAGGGG AGATTTTCTT 175860
TGATGGTTGT TTGGAAGTCA GGCTTAAACA ATTGTGTCTG TGTGTGCGCA TGCACAAACA 175920
CTTTTACCTT ATCTTTATTT TCTTCTTTTT ATTTGAATGT ATAGGGTTGT GTGTATTTCT 175980
GTGTAAATTT GGGGTTTTCC TCCTCTTAGT CTTTCACTTT TGTGGTGATT ACCAGTCCCA 176040
TTTTTAGAGC CAGGGCTGCA ACTTGAAGGT TTTGCTAAAA CCCTCACCGA AGTGTCTATG 176100
ATCAGCATTT TAACTATTAA TTAATGTGGC CAGGCAAGGG GTGGAAGGTG AGAAGACTAG 176160
AAAGGGAACA TGATATACAC ATTTACTCAG ATACTGGGCT TTTCTAACAT CTGCAGTGCA 176220
ATTGAAGTTA CCAGTCATCT GCAGTCTAAA AAGAAAGTGA TTTGGGAGG TGCGTAGAAA 176280
AAATCATCTT ATTATTTTTC CTCTATATTA CTTTTTTCTT TTTTTCTCCT GAAGAAACTT 176340
TTTTTTTTGG TGATACCTTC TTTTTCTCTA GCACGTATAA TTTTGGAAGC ATTTTTCATA 176400
TGCAGTGTAT ACTTCAGAAA GAGAGAGAGA GAGAGGAAAA TTGTCCTGTT CAGCGTTTGC 176460
ATTTCCATTA TTCCTGCTAT TAGTTAAAAA CAACAACAAC AACAAAAAAC AAGCAGGATA 176520
CCTAGATCTG GAAAAGGGAG AATTGTGTAG AGCTGTCTTC CTAAAGTTCT GAGTTAGGGC 176580
TGCCTCAGAC CACTTTCATA ACTATCTCCA GTGGCTTTGT GTTTTATATT TATTAAGATA 176640
GAGAAAAAAA GAGTAATTAC TAAGGGCAGC TGCTGTAGCT TTATGGTGAT TACTGAACAT 176700

FIG. 6.67

| | |
|---|---|
| TGACATGCTG TCACGTTTTT GGAACTTTGA GTATTTAATC ACTTTGGGAT ATTCTATTTT | 176760 |
| CCCCCATCTT GAGTGTGGAC AGATGCTGGT GATGTAGCCT TCTGGGCACA GAGCAAGCCT | 176820 |
| CCCCCTCAGC CTCTGCACCA GAAAGGCTCA GCTTCACACA CTCCAAGTAT GTTTTCTACA | 176880 |
| AGAACTACAC TTTGTGGCTT TCTGACCCAA ACATTTTTAT ACTAAATTAC ACACAACAAA | 176940 |
| GTTGTAGCTC AGAGAGGGAA CAAATGGCTT ATTTAGGCCA CCATTTTCTT GAGCCATTAT | 177000 |
| GATTTCACAC AGGGCTCCCT TGGCCCTGTA AATTGGCAAG GATTCCATTA TTCAACCCGC | 177060 |
| ATACATGTAC AGAGACCCTG CTCTGGCCCA GATAGTATTC TGGGTACAGG CGGATAGAGC | 177120 |
| AGGAAACAAA ACAGCTACAG TGATGGACAG GTCAGCCTGC AGCAATGCCT GCAGTCTCTG | 177180 |
| CAAAGGTAGC TGTATGGGTG GGCAGGTGGC TAGCACTTAT TCAGCTCTGG AAGGATCTCC | 177240 |
| CCTCTGGCCT CTCCCCTGAC ACCCATCAAT AAAACTGAGG AGCATCGGTG GACAGGGGAC | 177300 |
| CTTGTGCCCC CTCCCTGCCT GTGCAGTTGG GGCTGAACCC AGCTACGAAG TTTGAGCTCA | 177360 |
| CTCTCTCCAG CTCCCTCTCA ATTCAGAGCT GAACTGTGGG AAGCTTCAGA GCTCTCTGTT | 177420 |
| TCAAGGACAG GTTCTCCTCA CCTCTCCTAA TGGAGGTGCA CCAGGGAACT GGCCCTGCTC | 177480 |
| TGCCCAGGGC TTTCTCCTGG ACTTTGCCAT CATGGTCTAG CAAACCCTGT TCAGATTGAG | 177540 |
| GTGAGTGGTG AGATTTCGAA TTCTTTTTGA CAGATAGGAT TAAGTCTTCT TCTGTGGGAC | 177600 |
| AAGTGGGAGG TAGAGGTAAG ATTAAAGATG CCAAATGTC TGAGTCCTGA CAGCCACAAT | 177660 |
| ATGGAGATCT AGACTTTTTA CAGACCACAG GGCACAGGGG CCTCACTAAC AGAGTTCCCG | 177720 |
| GAAGTGATGA GTGTGCTGGG GGCTTCCTGG TTGAAGAGAC ACTAGAATGG ACCAGCTGGG | 177780 |
| AGCTAATTTT TTGGGCTGGA GTGTGATGGC CTGCACATCA CTGCCTCTGT CCCTCCATTG | 177840 |
| TCACAGCTGC CCCTTAGGAG CCAGCTGAGG CAATTTGTGG TCAGAGTGAC TTTGCACAGT | 177900 |
| TGTCCTGCCT GTGTTCAGGA AGGGAGTTTC TGTGGTCCCT TTGAAACCAC AGAAGAGCCC | 177960 |
| CTCGTATAGC TCTCAATGGA GGGGGCAAAA CATTCAAATA ACTCAGGAGA TAACACAACT | 178020 |
| ATTTGTTTTT AACTGTGAGT TTTTAGGCAA TCACAAAGAT CCAGATGTAT GTCCAAGCCT | 178080 |
| CTCTTTGCAA TTCTAATTAA CCTCAATGTT GCAACCATAG ACCTACCTTA CAGAGTTCAA | 178140 |
| AAAAATATGC AAAAACCCTG CCTTTCTTCT TCCTCATACC CCAAAATGCC ATTCTGAACA | 178200 |
| TTTCCTGTTA GTTAAAAAAA GATTTCCATG GTGTTACCAG GCACTGTACA CAGTCTGTGT | 178260 |
| CCCAAGACAA GGAGGTACAG TTCCACATGC GCCCATGACT GGGTTGGGCT CTGCACTCTC | 178320 |
| TCTATACTTT GAGAGCCTGA TTTTCTGTGA TTGGGCAGAG CTGGCCCACC TGGTGCAATG | 178380 |
| TCCTCCTCTG CCTTTCAAAC ATGTTTTAGT CATCAAGATC TTCAAATTTG TAACCCTTTC | 178440 |
| CAGCTTGATC CAGCAGAATG CAGATTTGGA AAAACAGAAC GAGTTTAAAA TACATGATTC | 178500 |
| TAAGAAACCT GGACCAGAAC TATCAAAACT TGGTTTCCCA GAGAATATAG CAAATGGGCT | 178560 |
| CATTGGCCAA TACTATGACA TTGGCTTTTG AGAAAAGAAA GGCTTTATTG CAAGGCTGGC | 178620 |
| CAGCAAGGAG ACAGGAGTTG GGCTCAAATC TGTCTCCCCA GTTGGGGCT TAGGGCAAGT | 178680 |
| TTTAATTACA CAGACGCATT TCTTATGAGT AGCAGGCAGA GAGCCTCCAA CTTCTTCTGC | 178740 |
| CTAGGTACCA GCAGCTTAGA CATGATGCAA ACCTGGGAAG CACATACTGT ATTTGGAGAA | 178800 |
| AGTGATTGGG AAGAAATGTG AGCTGAGGGG AGGGGCTCAG TGCCCCTGAG CTACACTTAG | 178860 |
| TGATGGCAGA GGAAGGATGT CCTCCCGCAG GAGGCTGTTC CACATCTGCT CTGGTTGTAG | 178920 |
| GGGGAGCTGG CAGGCATTAG CAGCGGCCTC TTTCCCCCAA GAGAGGCAGC CTCCTCCAAG | 178980 |
| TTTTGGCGAC ATTATGGCCC TGCAATCATA AGGGTTTGTG AGCATAGTGC TAAGGAGGGA | 179040 |
| AATGGAGCTG CTGTTACTAG TTCCACCCCA ACACACACAC ACACACTCAC AAGAAACCTC | 179100 |
| ACAAGCACCG TATTGGAAGA CTTTGCCATC CAACCTGGGA TTTGACAGGC TCTAGAAGCA | 179160 |
| GAATCATAGA CTCATGAAGT TCCCCCAAAG CAGGAATCTT CCTTACAGTA ACCCCCAACC | 179220 |
| ACCCCCCTCC ACCGCCTCCA CCGGCTGCTT CTTCCTGAAC ACTGCAGTGT TTGGAAAACT | 179280 |
| CACAAACTTC CAAGCTTGCC TTTCCTATTG TTGCATGGAT TGAAAGCTTG CGTTGTGTGA | 179340 |

FIG. 6.68

```
AGAATGGCGC TTCCTGCTGT GCTTAGTTTT ATCTCATATA ATCTTTGCAC CATTTAATCC   179400
TTGCACTCAC CCACTCATGC AACTGCCTTT GCAGAGACTG GAGGGGCCGC TGTAGGCTGA   179460
CCTTTCCTTC ACTGTACCTA TTTTGTTCCC TGCTTTATTC CCCTGCACCC AGGACACTGC   179520
CTGGCACAAA GACAGGTCTT TATAAGTGTA TGCAAGTGAA TAAAGATATA TATATTATTA   179580
TTGTTATTTT TGAGACAGTT TCACTCTGTC ACCCAGGCTG GAGTGCAGTA GCGCAATCTC   179640
AGCTGACTGC AACCTCTGCC TCCCAGGCTC AAGTGATTCT CATGTCTCAG CCTCCTGAGT   179700
AGCTAGGACT ACAAGCATGT GCCACCACGC CCAGCTAATT TTTGTATTTT TAGTAAGGAC   179760
AGGGTTTCAC CATGTTGGCC AGGTTGGCCT CCAACTCCTG ACCTCAAGTC ATCCTCCTGC   179820
CTCGACCTCC CAAAGTGCTG GGATTACAGG CATGAAACCA GCCTAGAAAT ACATACTATT   179880
ATTTATTCTT GTTTTACAGA TAAGCAAAGT GAGTCATGGA GAATTTGGTT GAAAGTCCCA   179940
AGGTCAGGAG TCGTGAAGCT GGGATTAAAA CCTAATCATC TGACTTTAGA GAGTAGACAC   180000
TTGCTCCATG CATATTGCCT CCAATTCATT CATTCAAGCA CTCCCTGCTC AAGAAGTTCT   180060
TTCTTATGTT GAGCTGAAAT CTGCAGCCCT ATGCGTTTTA CCCAGCAGTC CTGGTGCTGT   180120
TCCCTAAAAT CACTTAGACT GTGCCTGCTC TTTCTGTGTT TACAGTGTCA GCTGTAATAT   180180
CCCCCTCTTC GGCCTAACGT TTCTGAAGTC CCTTGCCACT GGGTCTCCTC TCCTCTTCCT   180240
GTGTTCTTTC TAAGAACACC TATGCAGATA GGTGTCTTCT GTACAGGGAA GCTGTTCCTG   180300
AGATCCGGGC ATCGACTCTG TTAGAATAAT CTACGTATGA GTTATTTTTT TGAGAACTAT   180360
GTGTCATTGC TGACTCATAT TAACTCTGTG GTTAACTAAA ATCTCAAGAT CTCTTTATGT   180420
TTGTTGAGAA ACTTATTTAA CTTCTCTGGC CCTCCGTTTC CTTCACTGAG CAGTGGAGTG   180480
ATTGATAACC TCCACCTGTG GTTGCTGAAG GTCTTGCACA AGATGATATA GTTAAAGTAG   180540
CTAGCAGTGC CCACGTACGG CGGATGCCTC ACAACGGTTT GCAGCCATCT CTCTATCTGT   180600
GTCTTTGTCT CTCTCTCACA CTGGTTTTGG CTTACTGTTA GCAGCTAGCC GAGATAAGTG   180660
TGTTTATGGT CTTTGCATGT ATTGTTTCTG TAGCATACTG GAGGATTACA AGAGGTTGGG   180720
GAGTGAGGGG GCGGTGAGGA GTAGACAAAG GCAGCCAACT CTTCCAAGTT TAGCTTAGAA   180780
GGAAGGAGCG GTAAACCCTA GTTGAATGTT GGACTGAAGC AGGTTTGTTT TTGTTTTGTT   180840
TAAAGGATAG GGAAGATCTG TGCGTGTTTC CAGGATAAAG AAAAGGAGAG AATATGATAT   180900
TAAAGATTCT GGAAGTGGGA GAAGGAGCAA TGAAATACAG ACTTGAAGTC AGTGGCATGG   180960
ACAGGGTCAA GATCACAGTT AGAGGATGCA GCCTTAGAGA AAAGGAAGGG GCTCGGTTCT   181020
CTGAGCAAGG AGGGAAAGAA GAGAGGCAGA TGCAGAGAAG TACGGCACAT CGTGCTGCTG   181080
GTTGTAGAAA TAACCTCTGA CTTTTAATAA AGTCATCCCT CGGTATCCCT GGGGGATTAG   181140
TTCTATGACC TCCCTCGGAT GCCAAAATTC GTGGATGCTC AAGTCCCTGA TATAAAATGG   181200
CATAGTATTT GCATTTAACC TACACACATC CTCCATATCC TTTTTTTTTT TTTTTTTTTT   181260
TTTTTTTTTT TTTTGTGAG ATGGAGTCTT GCTCTGTCGC CCTGGCTGGA GTACAGTGGC   181320
TCGATCTTGG CTCACTGCAA GCTCCGCCTC CCGGGTTCAT GCCATTCTCC TGCCTCAGCC   181380
TACAGGTGCC TGCCACCACG CCCAGCTAAT TTTTTTTTTG TATTTTTTAG TAGAGACAGG   181440
GTTTCACCAT GTTAGCCAGG ATGGTCTCGA CACATCCTCC ATATACTTTA AGTAACCTCT   181500
AGATAATCTC TAGATTACTT GTTTTGTCTT TTTTTTTTTT TTTTCTTTTT GAGATGGAGT   181560
TTCACTCTTG TCACCCAGGC TGGAGTGCAA TGGTGCAATC TCAGTTCACT GCAACCTCCG   181620
CCTCCTGGGT TCAAGCAATT CTCCTGTCTC AGCCTCCTGT GTAGCTAGGA TTACAGGCCC   181680
CTCCCCACCC CCACCCCCCA ACAACTGGCT AATTTTTGTA TTTTTAGTAG AGATGGGGTG   181740
TCACCACGTT GGCCTGGCTG GTCTTGAACT CCTGACCTCA GGTGATCTAC CCGCTTCAGC   181800
CTCCCAAAGT GATGGGATTA TAGGCATGAG CCACTGTGTG TGGCCTAGAT TACTTATAAT   181860
ACCTGATAGA ATGTAAATGC TATGTAAACA GTTGTTATAC TGTATTGTTA AAAGACAGTA   181920
ACAAGAAAAA AAATCTGTAC ATGTTCAGTC CAGACAAATG GTTTTCTGTT TTTTTTTTTT   181980
```

FIG. 6.69

TTTTTTAATA TTTTTGGTCA GTGGTTGGTT GACTCCAGGA ATGCAGAACC CGCAGATATA 182040
GAAGGTTGAT TATGCGTTCA GAGGCAGGGA ATACCATCTT GGGTTCCAGA AAGAAAATGA 182100
TCAGCATTTT CTGTCATACT CTGGTAAAAA CAGATCTTTT GAATGGACAG GTGTATTAAA 182160
CCCTGTGGAG CTGGCTGGGC CTGGCGGCTC ACGCCTGTAA TCCCAGCACT TTGGGAGGCT 182220
GAGGCAGGTG GATCACGAGG TCAGGAGTTC GAGACCAGCC TGGCCAATAT GGTGAAACCC 182280
CAACTCTACT AAAAATACAA AAATTAGCCG GGCGTGATGA CGCATGCCTG TAGTCCCAGC 182340
TACTCGGGAG GCTGAGGCAG AAGAATCGCT TGAACCCTGG AGGTGGAGGT TGCAGTGAGC 182400
CGAGATCACG CCACTGCACT CCAGCCTGGG CAACAGAGTG AGACTCCGTA TCTAAAAAAA 182460
AAAAACAAAA ACCTGTGGAG CTGATGAAAT CCTGCAGGGA GCTTCACGGT GACAGCAAGA 182520
GGAGAAACAC ATCCCCATAT GCCCCGCAGA GTTTGAAGTC CCGGCTGCAC CTCTCCCCAG 182580
CAGCAGGTTG ACTCTGGAAA GTTGCAGCGT TCTTACCTAC AGAGTGGGAA CAGTACTACC 182640
CATTGCACAG AGTGGGTGCA AAGCTCTGTG ACGGAATACA TGGCAAGTGC CCACCACATT 182700
GCCTGGGATG AGGTGGGCCC TTCCTTTACG TAAGAGAGCC CTACAGATAC ACTCAAAGTG 182760
GGCACATTCC TACAGAAGGA GTGTTATTTG TGTAGAAAAG AAAAACATGA AAGGCTTTTA 182820
TTCCTATACA CAATAAAGCA CCCCTTTAAT GTCTTTTTGA GGAGGATAAT ATGAAATTGA 182880
TGAAAAGGAA CCCTGTGGTT GGATCCCTGA CAATCACATG TATCCCTTTT TTCACTCTTG 182940
AAAAAGGAGT AAAGGAATAA AATAGAAGGG GAGAGGGGGC AGAGAGACCT TCACCGCCCC 183000
CCCCCCACCC CCCATCATCC AATCTATAGT CAAACCCTCC AGACTGTGTC TCCTTGGCAT 183060
CTCTGACACC CCCACCGCCA CCACCCCAGT CAATTCCTAT CTTATCCCCC TATCCTGGAT 183120
CTGATTCTGC TAAGTTCCTG CCACACTAAA GACAGGGTGG CTTTCTGATG ACAACATTCC 183180
TCTGCTTAAA CCTGTCAGTA ATTCCTTGTT GCTCTCAGAC GGAACTAAGT TCTGAATTTC 183240
TTCACACGGC TCTCAGCAAG GTCACAGTCA CCCTGCTAGG CCCCAGGGGC AAATCTCAAT 183300
GGTCATCTTC TTGAAGACCT GGCTCAGTTA TTTCTTTCTC ATTGAGGCTC ACGACCCCAC 183360
CTTCTTGCAT GCCTCAAACG GCCCCTTACC ATGCTCTTCT TTCGCCCATA GCTCAGCACA 183420
CCATATCATT TTAATTTATG TATTTTGCTT AATGTGGATG ATCTGTCTCC TCCTCTGCTG 183480
TCCTCACCAG AGCATCAGTT CCTCAAACCA AGGCTCTTTG TTTTGTTCTT GGATGCAAGC 183540
TAAATGTCTG GCATGTGGCA AATGGTCATA GATACATGTC ATTGAAAGAA TGATTCATCA 183600
CCTCCCTCTT TGGCCTTGTC TGTGGTTCTA CCAAATCCCA TTCCCTCCCC AGTGCCCTCC 183660
ATTCCCCCTC CTTGGCTGAA CATTCTGAAC CACAGACAGT TCTTTACCCT GAACCTTTGC 183720
ATATTTTGTT CTCTTAGCTT AGAGCGGCCC CTCTCCCTCC GTCTGCTTGG CTAAATTTCTA 183780
CTTGTTCTTC AGATTTTATC TTAGATGTCA TTCCCTCAAG GAATCCTTCT GTGACTCAAC 183840
ATGGAATTAA GTTGCCTCCT TTGACCCTGA AAGCACCATG TACTCAATCT CATCTTGGCA 183900
TGACTCACTT TGCTGTGTGG AATGTCTGCT TTCCTTGTTT GTCTATTCCT TTAGACTGTA 183960
AGATCCTAGA AAGTGGGGGC CGTGCCTTGC TCATGACTGT GTTTCTAACA CCAAACACAG 184020
TGTTCAGTAG AGAGCAGCTG CTGAGTACGT TTCTGCTAAA TGACAGTTGA TGGAGGACAT 184080
TTAGGGTTGC TTGGAGGTCA AGTCAAGGAG GCATTTAACA TTCTAGTAAA ACAAGGAAGT 184140
AACAGGCTCC TGAACATGCC CACAATGAAC CAGATGCAAA CCTTTTCCCT TGGCAGGATT 184200
CTTTGCCCAT AAAGTGGAGC ACGAAAGCAG GACCCAGAAT GGGAGGAGCT TCCAGAGGAC 184260
CGGAACACTT GCCTTTGAGC GGGTCTACAC TGCCAAGTGA GTCCTAACCC TGATGTTGCT 184320
AATAAGTGGG GGCATGGGCA GGGGGGCCTC CTTCTAGGAG TGATGACCAC CCTTAATACC 184380
ACATGTCTGT CTGAGCCAAG TTTCTGAGCG CCAGGGAGGT GAGGAAGGTT GGACTTCACC 184440
AGAGAGGCTT TGTGGACACC CTTTATCATC TTAGTGAGTG CTAGTGTCAA AACAAAGGGA 184500
GTGGGGATAT GGGGCACATT GGTGGAGGGA GGTGTGATCT CTGCAGCTTC AGAAAGATCT 184560
GAAAGAGTCA TTTGGTTAGA GAAGTTGACC TATTTCCTGT GGGGTTAGAC CAGGGTTGCT 184620

FIG. 6.70

```
ACTGTGAACA CCAGCCATGA CTCACCAGTC ACCTTCAGAA GCCACAGGCA GGACATGCTG  184680
ACGACAGCCT TCAACTCACC CACCCCTTGC TCCCCTGCGG GTGGAAGTCT GGAGGTGACA  184740
CCACTGCATT TTCTAACACG GGGGCTCCTT GAGCAACTAG AACAAGAACA GAAAGAATGG  184800
GGACATTAGC AGGTGCTTTC CCCCTCTCTC ATTCTTTTCT TTGAATAAAA AGGTTGTTTG  184860
AAAACACCTG AGCGGCTCCT AAAGATGGGT GCAATCTATT CGGGATGCAA ATCCGAATGA  184920
ATGTTATTCA AATGCTCCTC TCTTCTTTAT GCAGAGTGTA TTTCAAGGCT CAGCCAGTGG  184980
CAGGCATGCT GGGGACTATG GACTACGGAC TAGGGGCCTG TCACAGAGGA AGGCCTCATG  185040
CTAGAGAGCT AAGGGAGGAG CTGGCCTTCA GTTCCATCCC AGGAGCAACT TTGATGTTCC  185100
CAGAGATCCT TCCAAAGGGG GAGTCATGGT CACCCAAGAA AAATGTATTC AGAATGCCAA  185160
GAATGGTGCA AACTCAGGAC AAAGATTCAC ACTGCAGGGT TGGAGTCCCT GGGCTTGCTG  185220
CTGGCACCAT GGGAGGGAGG GTCCCCTTCA GGGGTACCGT TGGTTTCCTG TGAATTAAAC  185280
TGGCTTCAAG GGATCTCGAC TGAACAGGCC TATATCACAC TCACTGATAT ACTCTCTCTT  185340
CAGTCCTTCT CCTCATCTAG GTATTTTTAA TTGTTTCAGT GAGGTGTAGG CATGAGGGGA  185400
TTGGAGGGGG CATCTCCTCC ATTGCAGTTT TTCATTGGCT GCTTTGCTCC CTCAGCTCCG  185460
AAATCGCTGG GCCACTCTCG AACGCATTAG TACGGTAGTC ACAGGTTGAT TGCCTGGCCC  185520
CTTGCCCTCT GTGGGCATTT TCCCTTTCAG ACAGCCCTG AGTACTCACA GTGCTGCTAC  185580
AGTGGGCCAC CTAGATCTCC CTCTTTCTCC ATGCTCCCAC GTGCTCTGGG CTCCACTCCC  185640
TTCTCCCAAG CACTTCTGTC CAGGGCTATT CCAGCAGTCT GACCTCAAGG AAATCCTTTG  185700
CTAAACTGAT TATAGAGAGG TTTCTATTTT AACATTTAGG TCTTCCATGT ATTAATTCTC  185760
AGAATCAATT TAAGATGTTT AAAGGTGTGA TTTAAGACAT TTTAAAACCA TTTGGAGGAG  185820
AGTACAGAAA TTATGTCACT TGCTGTCAGC CTCTTTGCAC CATCTGCAGA GAAAGATACT  185880
AGAGTCCCGC CTTGGACACA TCCACATGCA AGAGGTGCAA AGAAGGTGTC TTTGATGAGG  185940
CAAGGTCAAA ACTTCTCCCC AGACGAAATC CAAAGAAAGC ATTCCTACTA TGCTATATCA  186000
GTTTGGAAAG AAAAACTTCT GCCAGGTGAC TGCATTCTCA CTGGTCACAT TGTGTTCCTA  186060
TGGACTCCTC AGCTCAACCA ATTTGGAGAA GTTATGGTGC AATTTCACCA TATCTGGTTA  186120
GAAGTTAAGT TTCCAATTTG CTGGCAATGA AGAAGAAATG GAGCAGGCCA GGCTGTGTAG  186180
TTTCTGCCAC GTGCCCCCGG GAGTGAACAG CTCTGTTTGT AAGAAGCCAT GGTGCTTAGA  186240
CCTGGGCTCG CTAGTTGCCA GCCTCCAAAT TGCAGAAGTG CCCTTTGGTT GGTGGCTATG  186300
CTGTGTCACT TGGGAAGGTC GTTTGGAAGT TCCACAGTCG TTGTGGGGTG CCAGAGATTA  186360
AAAAGCGTAA GAGGAGAGTG GAAAGTGATT GTTGCTGCTT GGGCATCCCC ACCGTGTGGG  186420
TGCTGCAGCC CAGCTCTCAA AACCCATGGG TCTGTACACT CAACCTCCAT GAGAGGGAAG  186480
GAGAAGGATG AGGGAGGGGA GAGATAGCCA TGGAAAGGTA GGAACTAAGC AGGCAGGGTG  186540
GAGAGTTTTC TGTAAGACAA AAACTGTCTG GACACTGCTG CGGTTCTGTT ACAAAGACCA  186600
CTTCCTCCCT GGGCCAGCAA CATATCTGTG TGCCTGTCTG GGTTGTAAAA AGGGTCAAAG  186660
ATCAATGCAG CAGGCAGCTA CATGCTGGCA AAAGCCAGAG GCAGCTGGTC TGTTTGCCTG  186720
TGCCAGGAAA CCACTGGGAA TGGGGTTGTG TGTTATTCTA GGAGAAAGTC GTCCCAGCAG  186780
CAGCTTCTCC AGGGGCATCC AAGAGCACTG AAAAGGGTTG CAAGATGACC CATGAGGCTG  186840
CAGGAAGAAA AGAACATGCA TTTAATCTTG CTATCTGAAA AGTAAGACAT GAAGCTTTCC  186900
TCATTTTTAA TATACACATG GACAGTAGTA TGTGTATATA GTTTATATGC AAATATACTT  186960
GTTATAAGGT TGCATGCTCA AAATTTTTGG TTCATGGGGT GTGGGATCAT AAATGTTTAG  187020
GGACCATGGC TATCAAGGAA AAACAGCATG AAGGATAAAT GATACTGGTG GATTAAAAAG  187080
ACAGATGCAT GTATTTTTAG CATAAAACAC AACTGCTGAC TGATACAGAT AGCTCAAGAT  187140
TCTGGGGCAG CTGCTGAACA GATACACTAG CCAGTGTGGC TCATCGGCTC AGACTTGGCC  187200
TTAATTAATG GGCTGTCCCT CCACCCATCT CCCATGAGGG CAGAGCTGAG CCAGGGTTTG  187260
```

FIG. 6.71

```
AGAGCTAAAA GGAATTGGAC CTGGACTCTG TTCACGTGTA TATTTTAATT CTAATTAATT    187320
CATTCTTTTG AAAGACAGAG TCACACTCTG TTGCCTAGGC TGGAGTGCAG TGGCACGATC    187380
TTGGCTCACT GCAACCTCGG CCTCCCAGGT TCAAGTTATT CTCCTGCTTC AGCCTCCTGA    187440
GTAGCTGGGA TTATAGGCAC ATGCCCCCAT GCCTGACTAA TTTTTGTATT TTTAGTAGAG    187500
ACGGGGTTTC ACCATGTCAG GCTGGTCTTG AACTCCTGAC CTCAGGTTAT CCACCCGCCT    187560
TGGCCCCTCA AAGTGTTGGA ATTACAGGTG TGAGCCACCG TGCCTGGCCT GTTCACATGT    187620
ATAAAACACA GTTTAATGTC CTATTCCCAG CCAATGAGCA TGGCTAGAGC AGCCTTGGTC    187680
AAAGTTTGGT TTTTGGAGAA AAATCCTTGT TAGCTGACCT AAGATTCCTC TTTGTGAGTG    187740
TAAGTAAGCA CAGGTTGCAG AGAGGAGAAG GGTCTCTGGA GAGGTGTAAT TTTCTAAATG    187800
GATTACAAGT TCATGGACTT TTAACAGGTG TTACAGGGGA TAACAAGTTC TTTATAGACA    187860
GACTTTTGAG GACGTTTAAG GGTATTCTGA TTCTTGGTTT TCTAAGAGGG GAATGTATTA    187920
TTTAACTACA GACACCCCTA CCGCCCACTT TTTGCAGAGT GTATCAAAAC ATGTTTTTGG    187980
AATACCACCC TCATGTCGCT TCTCCCTGCA TCTCTTATCT CTTGGTGTCC ATTCTAGACT    188040
CACTTTCTTT CTGTTTTTA TTTTTATTTT TTTTTGAGAT GGAGCTTCAC TCTGTCACCA    188100
GGCTGGAGTG CAGTGGTGCA ATCTTGGCTG ACTGCAACCT CTGCCTTCCG GGCTTAAGCA    188160
ATTTTTGTGC CTCAGCCTCC TGAGTAGCTG GGATTACAGC ATGCACCACC ATGTCCGGCT    188220
AATTTTTGTA TCTTTAGTAG AGACAGGGTT TCACTATGCT GGCCAGCCTG GTCTCAAACT    188280
CCTTACCTCA GGTGATCTGC CCGCCTCGGC CTCCCAGAGT GCTCAGATTA CAGACGTGAG    188340
CCACTGGTGC CTGGCCTAGA CTCACTTTCA AGTGGCATAG ACTTGTAAAA TTATTTAAAG    188400
GTGATAGGTC TACAATGATC CTGTCAATTA GTATTGACAC TATTATTAAT AAACTGTTAT    188460
TAATTATATT TACTTACTTT AAATTAATCC AAACTAATTA ACGGAACACT AAAGAGTTTC    188520
TATGTTTTAT TCCCAGAGGT GGAGAAAAAT GAAAGGGAAT ATAGCAACGA ATTCTTTTCT    188580
CCATAAAAAC ATGAATAGTG CAGCACATCA AGTTGAACAT ACCACAGCAA ATTGTTGCAA    188640
GATCTGCTGA GTAGCTCCTA TTTAGACCTC AAGGAATGAG ACTCAAAATG GGTTCATCAG    188700
TTCTGTTTTG CAGAAAAAAT AGCGCAAAAT TTCTCAAAAG AAAATCCAGA ATAATAATAA    188760
TTTGTCAATA GGAAAGACAT TTCCACTGGG GGTTAAGAAG GAAGACATTG AACAATGAT    188820
AGCCACCACT TATTGAATGC TTACTGTGAG CCAGGTGGCA CTTCACCTTG TTTCATTCTC    188880
ACAACAGTCT AGGGAAGTAA TTACTAATGT CTCCATCCAC CTCTTGTAGA TGAGCAAACT    188940
GAGGCTCATT GAGGCTAGGA AATGCACCCA CACTCACATA GCCCATAAGA GGCAGCCATG    189000
GCATTGGGCC CAGACCATGT GAACTTCAAA GACTACACGA GCAGCCACTG GGCAGCTGTC    189060
ATGGCTAAAG CCACTTGAAT TCAGCCCAGC AGCAACCCCC TCTCCAGGAG GGGCACATAA    189120
GCTTGCAGCT TTGGGTAGAA GCTGCACTTG AAGTCCTGGA TGGCGAGAGG GACTGGCTTG    189180
AGCCAGAGCC AGGAACAAGG CTCTGAGAAT ATTCTGGAAA TCCACAGGAG GAACCCATTT    189240
TCTTACAGCT GGGAGAATTT CATTCAACTC CAGGCTGACC ATGTTTATT AGGAACGAAG    189300
GTGACTTGAA CTAATAGTCA GGAATGGTTG AATACGGACC CAATGTCAAA TCACTAGGCA    189360
GTTCACATTT CTAATGAGCA AATCCCTTAG ACAATTAAGA ATTTTTTTCC TTTTGCATAA    189420
CCCAGACAAA ATCGCTACTT AAAAACAAAC CAAAGACCCG AAACATGAGA AAGAGAAGGA    189480
AGCAGGGGAA ATCTTTGGTA CTAATAAGTT TTTAAACAAT AAGAGCACCA GATATTTTAC    189540
CCCATCAGAC ACAGAATGTT ATTCGAATAA CCAAAAAAGG AATTTTTTCT CTAAGTTTCT    189600
TGAACTGGAA AATGAATCAT ATTTTCTCAG TCCTGAGGCT GCAATTTTGT GCCTCTAGTA    189660
ACATATAAGA ATAGATGTGA TGCCAGTGCC CAGTAGCTGC TGCAATTGTT ACTTGGGGAC    189720
CTGTTTATTC ACTAAGCACT TCACCCCAGT GATAAATTTG TAGGGGCCTC CTGCCCTTTG    189780
GAGCTCCTAC CGTGTCCATT AGATCAGTGG AAATTCTGGG ATTCAGAGCA CTTTGCAAGG    189840
TCAGCAGGGG TCTGCTCTTT CTGTCCTGTT CCTGGTTTTT GGTTGTGCCT GGATTCCAGG    189900
```

FIG. 6.72

```
GTAGGTTTCT CATCTGTTAC CTTCATAGAC TTCTCCAGAA AAGGATCTTT TGACCATCAG   189960
AGGACCACGA AGATTCCATT GGTGAGGCGC AGATAACCTG ATCTCTCTGG GTTCTCTGCA   190020
GGGCACAGAT GAAGGGCTGG CCATTCCCAA GTTCTCAGTG GTACCACTGA GGCATGAGAC   190080
CCTAATGGTT TGCATGAGCA GTTTGAAAAT TGCATCTTTG TTTTTACCTA TATAATCACA   190140
TGAAACCCGT GGTTCTCAAA CGTCAGCAGG CATCAGCATC ACATGGAGGG CTTGTTAAAA   190200
CAGATTTCTG GGCCCCAACA CAGAGTTTTA AATTCTGAAG CCTGAGGTG GGTGTGAACA    190260
TTTGCATTTC TAACATGTTC TCGATGCTGC TGCCGCCTCT GGTCCCGAGA GCATGCCTGG   190320
AGAACTGCCA CCTTCGACCA TGGACTGTGA GAATTCACAT GGACCTCAGA ATTATAATCA   190380
GTCTCTCAGT TTTACAGATA AGGAAACTAA ATCCAGAGAG ATTGTTTTGC CAATGGTGAA   190440
CAGCTGGTTA AAGTCAGGAT GGAGACTTTA ATCCTAGTCA AGTGACCTTT CCTCTGTATT   190500
TATTTCCCTC CCTTTTTATG CCTCTCAAGT CTAGTTACAC TGTTTTTCAT GGATGGGCAT   190560
ATTTATTGTC CTGATCTGGA CTGCAGACTT CTCAGGAGGA CACCTATGAT TTAATTTAGT   190620
ATAGTTGAAG AGTTAACAGA CATGGCTTTG GAGACAGACT GATTATGGTG TGAATCCCGG   190680
CTTTGCCACT CCCTAGCTGG ATGACCCTGA GCAAGTTATT CAGCTTCTCC AAGCCTGAGT   190740
TCCTTATTGG AAACATGAGA GCAATTGTGA TAGGCAGAAT AATGGCCCCC TCACCAATCA   190800
TGCCCACATC CTAATCCTAG GAACCTGTGA ATATGTTATG TTACATGGCA AGGGGAAATT   190860
CAGGCAGCTA GCCAGTTGGC CTTAAAATAA AGAGATTATC CTGGATGATC TGGGTAGGAC   190920
CTGATGTAAC CACAAGGGTC TTTTTAATGT GGAAGAAGGA GGCATAAGAG TAGATGTCAG   190980
AGTCATTCAA AATAAGAAAG ATTTGATGGG CCATCCCTGA CTTTCAGGTT GGAAGGAGGT   191040
TCTGAGTCAA GGAATACAGG TGACCTCTAG AAGCTGGAGA AGGCAAGGAA ATGGTTTCTC   191100
CCCTAGAAGT TCCAGAAGGA TTGCAGCCCT GCTAATATCT TGACTTTATA GCCCTTTGAG   191160
ATTTATTTTG GATTTCTGAC ATCCTGAACC ATAGTAAAAG GGTGTTTTTT GTTTTTTTGA   191220
GACAGAGTCT TGCTCTGTTG CCTGGGCTGG AGTGCAGTGG TGTGATCTTG GCTCGCTGCA   191280
ACCTCCGCCT CCCAGGTTCA AGTGATTCTC CTGCCTCAGC CTCCTGAGTA GCTGGGATTA   191340
CAGGTGCTTG CCACCACACC TGGCTATTTT TTGTGTTTTT AGTAGAGACA GGGTTTCACC   191400
ATGTTGGCCA GGCTGGTCTT GAACTCCTGA CCTTGTGATC TGCCTGCCTC AGCCTCCCAA   191460
ATTGCTGGGA TTACAAGGCG TGTTGTTTTA AGCCACTCAG TTTGTGGCCA CTTGTTACAG   191520
CAGCAAGAGG AAACTCATAC AGTTATCATG TGAACTCACA GGAATATGGT GAGTTAAAAA   191580
GAGAGGAAGG GTGCAAAACA TCCACGGTAG AGTGAGAACT CTCCAGGGAG TGAGGACTGT   191640
GCCCAGCATA CAGTGATCAC CCTCTTAGTA AGCTAAGTTT CTGAGCACCA GCTTTTTTGA   191700
GTTGACTTTG TTGTCTTTAA CATTTGAAGA TCACCCTTCT TTGCTCAGCC TGGCTTGCAG   191760
ACCTGGGCTG ATTTGTGGAT CTGATAGAAA AGTTTCCTTA GTTGGGCTCT TCTCCCCGAC   191820
CACCCCCATG CCAGTGTGGC CACATCCTCT GTCTGCATTG CTCACTCTTC AATTCCAAGA   191880
AGCGCAGGGG CACCGCCAGG AACAGGAACC CTGCCAGAGG AATACATCAA GAAACCAAGT   191940
CTCCCTTACG CATCACCGTA GGAACAGAGT TAATGGATTA TGAACATGTG TTTGCTTTAT   192000
ACCATTGTTT GTTTCCCAGG TGGCAGCTGG CTGCCCCATC TTATTGGGTA GATGTAAGTG   192060
GAATTACGAA TGGGATTTAT GTTTCATGCA CGATGGTGAT TATTAACTTC AACTTTCAGG   192120
TAATTTTCAG ACCACATTGC ACTAACTTGG TCTCTGATTG TTTTTCTCCT TGTTTGTTTA   192180
TTCTGCAGCC AGAACTGTGT AGATGCGTAC CCCACTTTCC TCGCTGTGCT CTGGTCTGCG   192240
GGGCTACTTT GCAGCCAAGG TAACTCAGAC TTCCCTTTGT TCATTCTCCT TCTATAAAGT   192300
GCATCTCAAG GAGGTTCAAA GGGCAGGCTT TTTGTTGAAA GGACTTTGCC TGACCTCTGG   192360
CTCCCATCTG TGAAGCCCTG GAGAGGTGAG AGCCCTCGGG AGGCCGTGTT TCAGGCATGC   192420
TCTGCACCCG TGCAGAGCGC GTGTGATAAT GCATTGCTAA TGCTTGCTCC CTGGTGGCTG   192480
GCTGAGAGCT GCTGTGCTGA CAAGGGTGGT TTAAGGCTAA ATGTGACTCA GAATCCTTAA   192540
```

FIG. 6.73

```
GCAGTGTTAG TTCAGATACA AGGGCATTAT AAATGAGAGT GCCTGAGGGA TCTATTTTGG   192600
GACCGCTGTC ACTTGGCTCT TCTGCTAATA AGCTTCCAGT GTGGTGGCCC TCCTTCAGGC   192660
ATGTTTCCAC TGAGCCACGG GCTGGATGCC ACATCCCCGG CCTTCCCACA GTTATCAGCA   192720
GCCCACAGGC TTGACTTGAG CAAGTTGGAA AGACAAATCA ACTTCCAGAG TTGATTTAAC   192780
ATTGAGTGGA AATCAGTCAT ACTTTTGGTC CCCTTTCGGG GCCACGCCTG GCACTGTGCC   192840
TGGTGGCAGA TCGGCATGAA CTGGCCAGCT TCTGTGGCCC TGGAGGGCAC AGGCAGAAAG   192900
GCCACACTCA GTCCCATGAT GAACTGTTTA AGACTTATTG TTGTCTCCCC GCTCTGTAAA   192960
GTAGATAGAG TGGATTTTAT GTCCCTTATT ACCTTTCAGG ATACTTTGAC TCAGGGAGAT   193020
AAAGTAACTT GGGTACAGCT ACTCAGCTGG TGAAGAACAC AGGCAGAATG AGTGCCTGGG   193080
TCTTTTGACT TAAAATTCTG GATTTTTCAC AAAGATCCTC TTACTTTATT CATTTACATA   193140
ATAAATATAT ATTGAAGAGC TACTCTGTGC CAAGCCCTGT GCCTAGATAT ACAGTGATAA   193200
ATAAAGAGTA GCTTCTAGAG GTCACCTGGC GGTGAGGCAC AGGCCAGCTG GCAAGATGGA   193260
CCACAGAAGT CAGTGAATGA AGACAATGAC AAGGGTGGGA AGCGCCATAT GGGAAGAGAA   193320
CCAAGTTCAG TGATAGAGAG CAGAGGTGAG GCGGCAGCAG AAACCACTTA AGGGACACCA   193380
CGTGGCACTC CTTCTGTGCT GAGAAGGCTG TCAGTAAGCT CACCATTTAT TTCCTATTTT   193440
CTCTCCTGAG TTAAATAGGA AACATGTCTC GCATTACTTG AAAAATCAAG TCAAACTATG   193500
CTCTTACTAG GAGTTATGGT TCTTTTTATG TCTTAGATGA TGCTTGATCT AGATGAATGC   193560
GGACTTGCTG TAGCTAGATA AATACAATGG GAGTTTGAAG GTGTTTCGTA GCCCTGGAAA   193620
TAGGTATTTC CTGTCAAAAC AAGCTTTGTC ATTGCCAGCA GACAAAAGCA TCAGTAACCT   193680
TGGTTGATAA TCGTCATTTC TTAGGAATAA AGTAGACTGT AGAATTTTTT TTAGCAGAAA   193740
GGAAACCCAA AGATAATTCT AGTGCAAATC CCTCACTTTA TAGAGCAGAA GCTCAAGTCC   193800
CAGAGGAACA AGTGGCTTGA ACGAACATCA GAATTTTAGG GGCTGGATTT GTACCCTCCT   193860
GGTGCCAGCA GCCCACTTCC CTGCAGGAGG CACTCACCTT CCTTGCACAG GGTATGAGT   193920
GTGGCCATTT TCCACCCATA ATCTCTGTTA GCTCATGTTC AATTGGGTTC CCATTGAAAG   193980
AAAAATGGAC CAGTAAGTTG GAGCAGAATC ATTCAGATGG TATAACATAA GGAAAAACTT   194040
TGCCCAAGGC AAATCGTGAT TGTGACAGCT TTGTGATTTT TAGAGAATAG CATGGGCCAG   194100
GCACAGTGGC TCATGCCTGT AATCCCAGCA CTTGGGAGG CCGAGGCAGG CAGGTCACTT   194160
GAGGTTGGGA GTTCGACAAC AGCCTGACCA ACATGGAGAA ACCCTGTCTC TACTAAAAAT   194220
ACAAAATTAG CTGGGCGTGG TGGTGCATGC CTGTAATGCC AGCTACTCGG GAGGCTGAGG   194280
CAGGAGAATC ACTTAAACCT GGGAGGCGGA GGTTGCGGTG AACCAAGATA GCACCATTGC   194340
ACTCCAGCCT GGGCAACAAG AGTGAAACTC CGTCTCAAAA AGAGTTCACA GTTTCTCTTT   194400
TGCTTTGATT TTCTTATCTG CCGGATAACA ATAGTATTTT GGAAGGCAGG AGGAATTGTG   194460
GAAAGAAATG GGTTTTGGGG AGTGGCTGAT TGGAGGCAAA TCCAAGGACA CTCATTGCTG   194520
GTGTGTGACT CCAGGCAGTT ACTCAGCTTT TCCAAGCCTC AGTTTCCTTA TTGTAAAACA   194580
GGACCATGGT CTAGCTAGTA GCATTCCTAT GGTGAGTGAA ATAATATGTA TAAAGCTCCT   194640
GACACAGTGC TTGGCATATA TCAGATTGAG CCATGTAAAA CTGCCAATAT CTGGCTATTT   194700
ATGACCTACA AAAATAGCAT TTCATATGAT TCCACCTAAC ATCTGAAGCG CAATAAATGT   194760
TATTATTGAT AATGCAGGTG GTGGTGATAA AGTTTTGAAA TCAGAAAGAC CTGGCTTCAA   194820
ATTCCACGCC TTCACTGGCC TGACTTATTT TCATTCATTT GACAAATATT ATTTTGAACA   194880
CCCCTATGTG CCAGGCACTA TGCCAGGCTC AGAGATGATC TAGGAAAAAG ACAGATGTCC   194940
TCATCTGTCT TAGGCTCTTG TGGCCTAAGC CTAAATTTCC TCGTCTGTCA AATGGTGACA   195000
GTAACACACT CCTTACCAGA GAGCTGGGAG GATTGGAGAC TCAAGTTCCC AAAACGCCAG   195060
GAGCACTGCG GCAGGTGAAA AGTATTCCCT CAATGGCGGA AGTGTTTAAA TTGCTTTTAT   195120
ATCTGTAGCT CTAGATAACA CTAGTTCCAG CTTAGTTAAC TCCCAGCTCC AAGCCTTCAG   195180
```

FIG. 6.74

```
GACTTCATAG AGTTATTGGG GTGCTGCTCT TGGCAGTTTC CCAAAAAGCT AGAATGCAGA   195240
GGGAATCTCC TTCCCAAAAA GCTAGAATGC AGAGGGAATC TCCTTCCCAA AAGGCTAGAA   195300
CGCAGAGGGA ATCTCCTTCC CAAAAGGCTA GAACGCAGAG GGAATCTCCT TCCCAAAAGG   195360
CTAGAATGCA GAGGGAATGT CCTTCTCTTC TAAATGGTAG CTGTTAGTTC AAGAAAGGTT   195420
AAACATTGTG CTGTGGGGAG GCTCAGGGGT GAAGGGTGTA CTTTTAAGAG AACCAGTTTC   195480
AGAGCTGGGT TTGGGGTTTA AGCCCTACCC TCTGCCCCCT TTTACGAGCT GACAGCCTTA   195540
TGCAAGCCTG GTTGACCACC TGAACCCACG TTTCCACATC TGGAAATAGA AATGTGGGTA   195600
CTAGTTATGT TGAAAGGACT CAGGTTAGAT GATAGATATG CAAATACCTT GGAAACCAGG   195660
AGTGTCCAGT CTTTTGGGTT CCCTGAGCCA CACTGGAAGA AGAGTTGTCT TGGGCCACAC   195720
ATAGAATACA CTAACCCTAT CAATAGCTGA TGAGCTAAAG AAAAAACGTT GCAAAAAAAA   195780
TCTCATATTT TTAAGAAAGT TTATGAATTT GTGTTGGGCT GTATTCAAAG CCATCCTGGG   195840
CCACGTGCGA CCCGCAGGCT CCGGGTTGGA CAAGTTTGTT GTAAACAATG CCATGATGCC   195900
GGCATAAGGT CGTTACCAGT ATTAGGAAGG TTCTCAGGTT TCCTCTAGCC CTTGGGCTCT   195960
TTTCCTGAAG TGCGTGTGTC TTCTGCTAGA TTTTGTGACC AATGTTGATT GCCTAATTGG   196020
GCTAACAGCA TGTTTTGGTG GCTACGAAAC TGACACAGGT GTTTTCATTT CTCCACTTAG   196080
TTCCTGCTGC GTTTGCTGGA CTGATGTACT TGTTTGTGAG GCAAAAGTAC TTTGTCGGTT   196140
ACCTAGGAGA GAGAACGCAG AGGTAGGTAA CTGGGACTAC TAAAGAACTG TGGAGCGATT   196200
CCTGATTTTT GAGCAGGAAG AGTGACAATT CAAAACAGTA TTTGACTAGA TTCACGGCTC   196260
CGTAGCATCC CCTTGGGTGG GAGGGGGAAG GCTGACTAGG ACCTCTGATT CTTCTTTCCC   196320
TGAGCTTTGA AGGCTCTGAA AATACAGCTG GGGGACTTG CCCAGTTTTC TTATTAAGCA    196380
ATTCCTCCGC ATGGTGCTGG CTTTCAAAGG GTGCTTCAGT GCTGTTTGCT GCACGTGCCT   196440
TGCAGCCCCA CACCCTGCAC TCCCGCCCTG CAGAGTCTGG CGCTGGAATG ACATTTTAGG   196500
TCTGGGTTCC CAGGCCTCCT GAGAGTGAAA TGTTTCATTG TTTGTCTAGA GAAATGAGAA   196560
CTAAAGCTTG CACCTTGTGA TAAGTTGTCC TGAGGAACAT ATCTTTCAGG GACCAGAAGA   196620
AAGAATGTTG GGAAAATAAG ATGCAGTAAG ATGCAGACAT GACAGCAGGG TGCAGCGGCT   196680
CACGCCTATA ATCCCAGCAC TTTGGGAGGC TGAGGTGGGT GGATCACCTG AGGTCAGGAG   196740
TTTGAGACCA GCCTGGCCAA CATGGTGAAA CCCCGTCTCT ACTAAAAAAT ATACAAAACA   196800
TTAGCCAGGC ATGGTGGTGG GCGCCTGTAA TCCCAGCTAC TCCATAGGCT GAGGCTGGAG   196860
AATCGCTTGA ACCCAGGAGG CAGAGGTTGC AGTGAGCCGA GATTGCGCCA CTGCACTCCA   196920
GCCTGGGCAA CAAAAGCAAA ACTCCATCTC AAAAAAAAAA AAAAAAAAAA AAAAAAGAT    196980
GCAGACACGA GACTGTGAAA CTGACTAGCA TCACCATTGC ATTGTTTATA GATGTTGCCA   197040
GACAGAAAGC CCCAAAGCAG CACAGTACCT TCCTGACATC TGGACTAGGA AATCTAGATT   197100
TTAGTAAAAT ACATGCTAAT ACTTACAGAA GAAATGTCGG CGTTAGAGTA TGCCGTCAGT   197160
TCCTTAGAGA TTGCAATTCC TAATGCACTA GTATGGTTTC AGGTGCCAGG AACACGTTCT   197220
GTGAGGCTGC TGCCCCAGGT GCTGACCCCA GCCTTCCACA CCATTTTCCT TCCTTGTGTT   197280
CACAGCCGCT CTGTCTTTTA CAATAGCACC CCTCTCTAGT GGCTAATGGG CTCTATGATT   197340
AGATAGCATC CTTCAGTAGT GATAAAGGCA GTGACATCCT AGGGAGGTCA GCGGGTGAAA   197400
GCGCTATATC TGGAAAACCT GAGAGCCTGT GAAGCTCAAG GACTTGACGG GGTTAGACCG   197460
TGAGCCGGGC TGCAGCTGGA AAAAGAATGA CTGTTCTTTC AGCAGATCCT TCCCTGTGCC   197520
ATCTCTTTCT TCATTCCTCT CTAGTGGCAT TCTTATTTAT CCTCTAAAAC CACAATTCCA   197580
TTATCTCTCC TATTCTTATC AACACTGCCC TAATGATAT TCTTTATTCT CTTTTGCCCT    197640
GGAAAACCTC TATCATGCCT TTTCCCATGT GATTACCTCG TTAAGAGTGG GGTGGAATG    197700
TCTAGCAATG AAATAAGAGG GTCTTCTCTT TTGCCTGGCT CCCTATGCAG CCCTATCTTA   197760
CCCCCTGCAA AGTCCCAGGG ATGTGGCTCA GTCACTGCTC CTCTCTTCAT CTGTCACCAC   197820
```

FIG. 6.75

```
TTGCTTGAGA TCCTACAGCT GCTTTAATTC CGAGACCATC TGCAGAACAT GACAAAATTT    197880
GTCCACCTAC CCACATGTCC TTTTAACTTT AAAGGCTTTA CTAACTGATT CCTATTAGGG    197940
AATGAACAGA GGTGGCAAAA ATAAACAATA GGAGATTGAT TTACAAGAAA TCTTTAAAAT    198000
AGTAGATTTC TTCGGACCTC ATTGAAATAT AAATGGCCTG CCTTCTTGTG TCCCTCCCTG    198060
GTCTCCCTCT TTAGGTGATA AGAAGAAGAT CCTGCCAGCC CCATAACCCG CCATCTGCGC    198120
GGGTTCTAGA CCCCCTTCTC CTCCCCTCTG GCCGTGGTAG GCATTACTGA TGAATCATGG    198180
TGCTCTTTCT TCCAGAGACC AAACCTGGCC TCGGAATCCT TCTTAACACA GATACTGCTT    198240
AACACAACCA CTCTGAGCAG CTGTCATAAG TAGAAGTAAT AGATACTAGA AGAAATGTCT    198300
AAGCCTAATC TAGACCAAAA TACGGCCTGA TATAGATGCA AGCCAGAGGG GCTTTATGGT    198360
TAAATGCAAG GAGATTTTCA ACCCTGCCGT CTAGAAGCTA CTTGCTGAGA TCTTCTTCAG    198420
TTGGGCCCAT CTCCTCCCCA GGCCTCTCTT CTGTTCCTGG GCTATGTCAC ACTTGGACTC    198480
TGCAGACACC TAATGCTCTT GGGACCTGCT TTAGTTCTTG ACCTCACCAA CCGAGGAGGA    198540
ATTGCTAGAT GAGATCCTTC CCCCGGAATT TCTCTCTTGA ACCCCAGATG GTCCGTTGCC    198600
CCTTTCCAGA AGTTGCTCCA GCCCTGTCCG CTTAGGAAGT TCAGTGTCAT CCTTGATCCA    198660
GTGGGTAGGG AAGACATTCC ATAATGAATG CCCCAGTCTG AGCTTCTTCC TTCAGGCTTC    198720
AGGCTGCCCT GCGAGGATTT TGCAGCTCCC TTTTTAATGC CCTCTAGAAG TTTCTGGCTC    198780
TTATTTTCAG CCCTTCATCC TACTCTCTCT GACCCCTTCC TCTATCCTGT TTAGTTCACC    198840
TGTAGCAGTT ACTACCCAGC AGTGAAGGAT GAATCTTGGT TTCGTTTCTT TTCTCTTCTT    198900
TTCTTTTTTC TCTTCTCTTT TCCCCTTCCC TTCCCTTCCC TCCCTTCACA TCACCTCATC    198960
TCACCTCACC TTACATAGTC TTGCTCTGTC ACCCAAACTG GAGTGCAGTG GCCTGATCTT    199020
GGCTCACTGC AACCTCCACC TCTTCCCAGG TTCAAGTGAT TCTTATACCT CAGCCTCTTG    199080
AGTAGCTGAG ACTACAGGTG TGCACTACCA CACCCAGCTA ATTTTTTGTA TTTTTAGTAG    199140
AGATAGGGTT TAGCTATGTT GGCCAGGCTG GTCTCGAACT GCTGAACTCA AGCAATCTGC    199200
CATCCCCGGC CTCCCAAAGT ACTGGGAGTA TAGGCATAAG CCACCCATGA TGCCCAGCCT    199260
GAATCTTGGT TTCTTCCCCA TTCATTTAAG CTATTACCTG GCCTGAACT CAATGGCACC    199320
TGGCACCAAC TGGCAACTGA CTCTTGGTCT TTTATTACCT ACCTTCCCTA GCAGGCACTG    199380
GGTTGCTCCC TCTTCCTATC CCATGGAGTC CTGTCCTCTG TTGGGGCTCC TACTGATCCT    199440
CTTGGCAATA TGAAGTTCTC AGCTCAATGG TGGGTGGGCA ATGACTGCCA ACTCTTGAGG    199500
CCAATGAACT CAGGTTACCC CACTCCTCCT CCTCCTGAGT TGCTCACTCA CTCCTCATTC    199560
ACTCAACATT GATTCAGTAG ATATTGCTA CCTGCTCTGT GCCAGGTACC AGGTCAGTTG    199620
CTGAAGGAGT AACAGTGAAC ATGACGGAGT CTTTGTCCCC AAGGAGACCC AAGGTGTCTC    199680
CTAGAGCCAG GGGCACATTG CAAGACCAAA TATATTCAAC TTACCAAAAT AATCATAGAC    199740
CTAGTTCTCA AAAAGCAAGA AGACTGATTC CTCGTTGTCA TTTCTCCTCC TCAGCATCAA    199800
TGTTTTAGAG TCTGTGGGCC CCTCCAAGTG TGGAGTATGG TGTTACTTCA CCAGAGTTTG    199860
AGGAGAAACA TTCTTCTTTT GGAAGGCCGG GGAGCATAGA TGGATATCAA GGCTGCTGTT    199920
TCTAAAAGCG AAACCCACCA AACAACAGTA TTAGAATCAT CTGTGGTGCT TATTAAAGAT    199980
ACAGATTCCT GGGCCCCATC CCAGACTTAT GAATCAGAAT CTCTGCCAGA GGAAGCCTGA    200040
GAATTTGCAT TCTCAGATGA TTCTGCATTC TCAGATAACA CATTCTTTAG GTGATTCTTA    200100
CACACACTGG AGTTTGGGAA TCGCTGAAGG CTGTTCACTT CTCTTTTCTG AGAAATGATT    200160
CATTCATTTC AGAAATATTT GCAGAGGTCC TTATTTATTG GAGATTTGTG GGTGGGCAGA    200220
GGAGAAATAT CTTGTCCTCA CAGAGCTTAC AATTTTTATT TTCTTTAGAG GTCACCAGGC    200280
TTAAAATGAC ACTTCCCTAA ATTCTGAAAA GAACAGATTT TTAAAACAAG AAGGGACTGT    200340
AATGTTTTCT GTTCCTACCT CGTATTTTGT TCACATTAAG AACCTGGGGT GGGAAGTGGA    200400
GGAGGGGGGG TGACTGGCGG GGGGCCACAG AGAGCTGAGC TGGGGTGGTC TCGAACTCCT    200460
```

FIG. 6.76

```
GAACTCAAGC AATCTGCCAG CCTCAGTCTC CCAAAGTGCT GGGATTATAG GCATGAGCCA  200520
CCCACGATGC CTGGGTGGAA CTCAGGGCTC TGGATGCCTG GGCGCCCCCA TCTCCCACAC  200580
TACGGCGCCT CATCCTAGAA GTGGTTAGCA CCTTTGAGAT GGGAATTATT TAGCAGGATG  200640
CTTTTGTGTT TTCATGTAAG TTTTATGCTG CCTGTGGAGG GCACAGCTGT TTCAAAACTA  200700
ATAACCAAAT CCTGGTCTCC GAAGTCTGAA GGCATCCTTT GCCCTGCAGT GCAAAGCACG  200760
GGATTCTGGC CTCACACAGG CAGGTCTGAA CTCCTGTGTT GCCTCTTGCT GGCTGTGGGA  200820
CCTGAGGCAA ATCATGCAAC CTCTCTTTTC TGTTTGCCTA GATGGAAAAT AGGTTTACAA  200880
TACGCCCCCA TAGGATGGCT GTGAGAATTA AAGGAAGTCA TGGGTGTACA ATACCTGGCC  200940
CCGAAAGATG CTTAATAATT TAATTCTGAC CTTCCTCACT CATTTAGGAT TATGTACCAA  201000
CTTTTAGAAA CAATGAAAGA TTAGTGAGTC TTCTGTGGTT GGTATAAAAA AAAAATAGAA  201060
ACATGAAAGA GATGTCCTCC TTGTTCAAGG GCTAATGACC CTGGTGTGCG CTGTCTAGGC  201120
CCCCAAGGTC TTCCTTCCCT GCTCACAGCA TTTCAGGTTC TCCGCAGCTT TGCTGAGCCT  201180
GGGTCAGGTT CGGTATCTGC CCACCATGCT CACTTGCCAC AGCTGTGGCC CCATTTCCAA  201240
ACTTCAGAGA CTTAAAGGTG CAGCTAATGA TGTGCCCGGC CTGGGGTCAC ATTCCCTGAG  201300
CCCTGCAGAC AAGGGAGCAG GAGGCTGAGC TCTTATCTTC CACACCCTGT GCACAGCCTG  201360
GGAAGAGTTA AAGCACCCTA GTCCTATGCT GCGAGGGCCA CATGCCCTGA GACCTTGGAA  201420
AAAATCCTAC CTGAATTGAA GAGCATCACT ATTTCATCAG GAGGCGCTGC CATTTCATTT  201480
TTCACTTCGG TTTTATCTTG AGTGTAAAAC AGCTTCGCAA ATCACTTTTT CTTGTTTCTG  201540
TAATGAGCAT ATGGTGGCCT CATTCGTGTG ATAAATCTGA GCCACCACGA TATTTGACTT  201600
TTCACAATTT AATTTATCTG AACCCTCTAT TCTCTGGCTA AAAAATATCC CTTACTTGGA  201660
CTTCTTTATT TTATTTTCAA TTCCCTTACC AGCACTAGCA GGGACTCTG TACTCATCTG  201720
CTGGCGCTGC CATAACAAAG CACTGCAGCC TGGGGGGCTC AAACCACAGA ATTTATTCTC  201780
TCACAGTCCT AGAGGCTAGA AGTCCAAGAT CAAAGTGTGG GCAGGGTCGG TTTCTCCTGC  201840
AGCCTCTCTC CTTGGCTTAT AGAGTGCCAC CTTCTACCTG TGTCTTCACA TCATCACCTC  201900
ACTGAGCATG TCTGTGTCCA AATCTCCCCT TCTTATAAGA CCCCAGTCAT ACTGGATGAG  201960
GATCCACCCA TATGAGTTCA TTTTACCTTA ATTATCTCTT TAAACACCCT GTCTCCAAAT  202020
ACAGTCCCAT TCTGAGGAAC TGAGAGTAAA GATTCAACAT ATGAATTTTG GAAGGGACCT  202080
AATTCAGCCC ACAACACCCT CTTTTGGGAT GTTTATTTTC CCCCTTAAGG AGCTAGTTAG  202140
GATGTCTTAT CTCATGAACA TGACTGTGAA CAGGAAAACA GGGAGAGAAT GAAGCTGGCC  202200
AAGGAACAGG GCTGGTGTCA GCTAGCAGTG CTTTTCTGAT GTGAGTGGGT CCCACAGGGA  202260
GCTTGTTAAA ATGCAGATTC TGATTCATTA GGTTCCAGAG GGACCTGAGA TTTCCCATTT  202320
CTGACAAGTT TCCAGTGTGG GGGCTGATGC TGCTGGTCCA CGGACCATAC TTTGAGTAGC  202380
AAGGAGCTTG ATACATAATG GCTGAGTGAC TTTCAGACTC CTGCTGTAGA AAAATTATGA  202440
GTTGGCTGGG CGTGGTGGCT CACGCCTGTA ATCCCAGCAC TTTGGGAGGC CGAGGTGGGC  202500
AGATCACCTG AGGTCAGGAG TTCGAGACCA GCCTGGCCAA CATGGTGAAA CACCATCTCT  202560
ACCAAAAATA CAAAAATTAG CCAGGTGTGG TGGCAGGTGC CTGTAATCCC AGCTACTCAG  202620
GAGGCTGAGG CAGGAGAATC GCTTGAACCC GGGAGGCAGA GGTTGCAGTG ATCTGAGATC  202680
GTGCCACTGC ACTCCAGCTG GGCAATAGAG CTTGACTCAG TCTCAAAAAA AAAAAAAGAA  202740
AAGAAAAAGA AAAATTATGA GTTATATTAT CAGCATATGG GGTGCCTTTC AAATTGATAA  202800
AATTTCTAAT ATTAAACCTG TGGATGCCAA ATGCTGCTCT CTGATTATGG CAGGAAACGG  202860
CACTTGGCAG TACGAAGTTA GCTGTTGGGC TGAGCTGGCT CATCTTGTTG TGCGGTCCTG  202920
ATTGCCTAAA GATGCCTTCC CAGGATCTTT ACTAACAATC CTCCTGAGTC ATTTGGACTT  202980
TCCCAACCTG TTATCACCTC TCAGATGGGC CAGCCATGGA GGCAGTCAGA GGAGGGCTCT  203040
GCAGAGGGAG GGCAGAAACA GGGTGGCCTC TGCATGCCAT TAGGAGGTCA CATCTCACTG  203100
```

FIG. 6.77

GGGGATGCAG TTTAGGATTT AGTGCCTTGG AGAGAAGGAT AGAGTATATT AAAACATGTC 203160
TCCGCTAGGC ATGGTGGTTT ACGCCTATAA TCCCAGCACT TTGGGAGGCC GAGGTGAGTG 203220
GATTGCCTGA GCTCAGGAGT TCAAGACCAG CCTGGCTAAC ATGACGAAAC CTCATCTCTA 203280
CTAAAATACA AAAAGTTAGC TGGGAGTGGT GGCGTGCGCC TGTAGTTGCA GCTACTTGGG 203340
AGGCTGAGGC ATGAGAATCA CTTAAGCCCA GAAGACTGAG GTTGCAGTGA GCCGAGATTG 203400
CACCACTGCA CTCCAGCTTG GCTACAGAG TGAGACTCTA TCTCAAAAAC AAAGAAACAA 203460
ACAACAACAA TAACAACAAA AACCAAGTCT CTCCCTCCAC TCAAAAATGC AAGGGCCTGT 203520
CTCCCATTGC TGGGTGCCCA GGTCTCATGA ATGTAGATAT GAATTATTCC AGTCAGCCTC 203580
AGGAGAATAG AATGAGCCCT CAGATGCCGA AGCACCTTTC AGATTCCACC GGTTTTATCG 203640
GCTCATTTAA ACTTCACTTC TAACACAGTC CTGCATTACA CACGTGTCTG TCGTTATGGG 203700
CAGCTGCAGA GAGGGTCTTA ATGGTCCTAA TGCTCAGTGA GGATGCCCAA TGGTCAACAG 203760
AACCTGCCAT CTTCAGGCCA TCAAGGAGCT CTGGAGTTAA GGAAATCATG AGAGCACAGA 203820
GGGGCGGGTA CAGCAGAGCC CTCGTGGTAA TGGGTTTTGA GGTCTAGGCT CTCTTCACTT 203880
GGGTTTGAAA TAAGTTCAAT GACTAGTAAT AGCTGAGACA CTTCTACCCT TCAAATGAAG 203940
TAAATGGGAA AATGGAGCAT TGTTGAGTCC AGGGAGCTAT AATTTAAACC CCATATATCT 204000
AAAAGGGGTA ACATTTTTGT GTGTGTGAAA TTGGTGTCAT TCGCACTGCA TCTACAGTTT 204060
TCTTTTTCCT TCTCTTCCAG CACCCCTGGC TACATATTTG GGAAACGCAT CATACTCTTC 204120
CTGTTCCTCA TGTCCGTTGC TGGCATATTC AACTATTACC TCATCTTCTT TTTCGGAAGT 204180
GACTTTGAAA ACTACATAAA GACGATCTCC ACCACCATCT CCCCTCTACT TCTCATTCCC 204240
TAACTCTCTG CTGAATATGG GGTTGGTGTT CTCATCTAAT CAATACCTAC AAGTCATCAT 204300
AATTCAGCTC TTGAGAGCAT TCTGCTCTTC TTTAGATGGC TGTAAATCTA TTGGCCATCT 204360
GGGCTTCACA GCTTGAGTTA ACCTTGCTTT TCCGGGAACA AAATGATGTC ATGTCAGCTC 204420
CGCCCCTTGA ACATGACCGT GGCCCCAAAT TTGCTATTCC CATGCATTTT GTTTGTTTCT 204480
TCACTTATCC TGTTCTCTGA AGATGTTTTG TGACCAGGTT TGTGTTTTCT TAAAATAAAA 204540
TGCAGAGACA TGTTTTAAGC TGATAGTTGA GGGGTTTTGT TAATGGCTTT TGGGGGATTT 204600
ATCTCTATAC CCACAAACGA CTAGTTTGTT TTCCTCAAAC TAAATGATAA TATTAAAAAT 204660
ACACATCCTG GCCAGGTGTG GTGGCTCATA CCTGTAATCC CAGCACTTTG GGAGGCCGAG 204720
GCAGGTGGAT CACTTGAGGT CAGGAATTAA GACCAGCCTG GCCAATATGG TGAAAGCCTG 204780
TCTGTACTAA AAATACAAAA ATTAGCCAGG TATGCTGGTG GATGCTTATA ATCCCAGCTA 204840
CTTGGGAGGT TGAGGCAGGA GAATTGCTTG AACCCGGGAG GTAGAGGTTG CAGTGAGCCA 204900
AGATCATGCC ACTGCACTCC AGCTTGGGCA ACAGAGTGAG ACTCCATCTC AAATTAAAAA 204960
AAATACACAT CTGGCTTCTG GAAAAATTAC TTGAAGATCT TTTATGACAT CCATCCCTCT 205020
TCACACAGCC ATGTGAATTA GGTTGGTATC TTCATATACT AGCATCGTGC CCAGCACTTC 205080
CATGTTATAC AGTTTAAAAT GTTCTGTAAT TCCCTGTGGG AACCTAAGAT AATGCGAGGA 205140
CCGTCATACG TGCCCCCAAA TATTGGCAAA CCAATGAATA AATGAATGAA TGAGTTTATG 205200
AATCGCTAAC TGGCTGTATT TAATGAAGTA TGTGTGTTGA GCCATTTCCC ACAGTGTGGA 205260
CAGATTTGTC CCACAATATG GGCCTCTTCC CAAAGGCCCT ACCACCTAAT GCCATCACAC 205320
TGGGGATTTG ATTTCAACAT GTGAATTTGG GGAGAGTGCA AACACTCAGA CCATAGCACC 205380
ATCTCAGTAA ATGTCCCACT GGTCACTCAG TTCATAGTGA CAGTGATCCA GCCACTGTCA 205440
TGACAGGTGC CACTTGGCAG AAACAGCACA GCTTGGAAGA TGGCGGGGTG TAGTCAAGAT 205500
TCCAGGATCC CCAACAGAGA AGCCAGCTCT TATAGGGGAG CCATTCATCA GGATTGAACT 205560
CTCAATCGAG CTGGACAGTA ATAGGTGGGT CTGTGTTATT CCCCAGATGA GTATCATGAC 205620
AGTCACAATC CTAGGAAGGA TGTGAAGCCT CCCCCAGCTC TCCTCCAGTT GCCTGCTTGG 205680
GCAGCAGAGA TGATGGAATG TGGAGTCTGG CGTGGTCTGA GGCCTGAATC CATGTGCCTC 205740

FIG. 6.78

```
ATGTATGATG CTCAGGCAAG AGGATCTCTC AATTCAAGGG AGAGGGCCTG AATGAGCCTT   205800
GCTTTCCAGG CCTGTCTGAT GGTCCAGGCT GAAGCCCCTC CTGGCTTGCA CTGCCAGACC   205860
TCATCCAGCA GGAGCTCCTT GGCATTGACT GCTTCAGGAT AGTTGCTTCT GCTCTGAGTG   205920
CTCTCTAAAG AGCAGTGCTC TACCATCCAA GCTGGGCTTT TCTTTTCTTC TTGCTGATAG   205980
GGAAGGCATG GGACATTGCA GGATGGAAGT GGCCCCCAGG CCTTCTCATG CCTGGGCTTG   206040
GTTTGGAAGG TGGTCAGGTG ATCAATAATC CTGATTGGCC TGGCATTGAG GAGTTTTCCT   206100
GGGATGTGGT CCTTTCGGTT TTTTAAAAAT TATTTTTATT GATACACATA TTTGTAGGTA   206160
TTTGTGGGGT GCATGTGATA CTTTATTATG TGTGTGGATT GTGTAATGAT GAAGTCAGGG   206220
CATTTAGGGT CTTCATCACC TTGATTATCA TTTCTATGTG TTGAGAACAT TTCAAGTTCT   206280
CAGTTCCAGC TATTTTGAAA TAGACAGTCC ATTTGTTAG CTACAGTCAC CCAACCCGGC    206340
TGTCAGACAT TGGAACTTAC TCCTATTGAA CTGTGTATTT GTACCCATTC ACCAAACTCT   206400
CTTTGGGCTT TCAGTTTTAC AACTGGGATG ATCCTGGGAA AACTAAAGTA AATCAGACAC   206460
CCGACGTGTG AGCTAGGTTA TAATATGCCC AGTGGACCCT GGGGACATCT TAGCTTTCAG   206520
AGGTCATGCT GTCCAAGCTG ACTGTGGGGC TTCCAGAAGG TGGGGAGAGG AAATGATGCA   206580
ATGGCCCATC AGAGGCACTA CTTGGGGCCT GGGGCCAGAG TGCATGTCTA AGGCATTAAG   206640
GGGAGGGGAG AGCAGCCTTC ATAATTATGA AGAGGAGTCT CAGGTGCACA GCTTCTGATG   206700
AGGGACAGCT TCTAATTGAA GACAGCATTG TGTAATGCTC AAACTCCCTG TCTTCAGAGT   206760
GCCTGCTGTA TCCCACCATC AGTTCTGTGA CTTCTCCCTA AGCCTCAATT TTGCATGTGT   206820
TACATTGGGA TAATAATAGT GCCAAACTCA TGGGGTTGTG AGGAATAATG AGGTAAAGCA   206880
ATTGAAAAGG TTTAGCACAA TATAAGTGCT CAATAAAAGC CATTATTATT ATTTTATTAC   206940
ACTAGTTTTC AATTCCTGCA TAGCAAATTC TTGCAAATGT AGGGACTCAA AACAATATAA   207000
ATTTATTATC TGACAGTTTT TCTGGGTCAG AGGTCTTACT AGGCTGTAAT CAGAGGGCAA   207060
CCAAAGCTGT GATCTCAGCT GAAGCTCAGG ATTCTCTTCC AAGCTCACTG GTTGTTGGCA   207120
GAATTCAGTT CTTTCCAGTT GGAAGACTAA AGCCTACAGT CTTCAGTCTC TAGAAGCCTT   207180
TTCTCTGGCA CAGGTTTCTC TACAACATGG CCATTTATGT CTTTAAGGCC AATAGGAGAA   207240
CATGATTAGC ATATTTTTTT TAAGTGAACT TTAGACCCTT TTTTAAAGGC CTATCTGATT   207300
AGGCCAGGCC CAAGTGAGCT TTAAGTCAAC TGATTAGAGA TCTTAATTAC ATCTGCAAAG   207360
TCCCTTCATG TTTACCGTAT AACATAACTT AGTGAAAGGA GTGAAATTGC AACCAGGTTC   207420
TGCCTGCACT CCACGGAAGG GGATTCTGCA GAAGTGTGGG TCACGGGGGG GTTATTTTGG   207480
GATTCTGCCT ACGTCACTGA GTCAAAAGAA GCTGAATGGT TGTGATGCTG AGGTTTTTGG   207540
GCAGCAGCAG TGTGTGTGTG TGAGTGAATT CATACGTATG ACCACCTGGG AAGAAAGGAG   207600
GCTGTGGTTT CCTCCACCTC CTGGCAGACA GAGAAATTTC TTTTTTTTTT TGAGACAGGG   207660
TCTGGCTCTG TTACCCAGGC TGGAGTGCAG TGGCTTGATC TCTGCTCACT GGCTCACTGC   207720
AGCCTCTGCC TCCCAGGTTC AAGTAATTCT TGTGCCTCAA CTCCAAGTAG CTGGGATTAC   207780
AGACACACAC TGCCACGCCT GGCTAATTTT TGTATTTTTA GTAGAGACGA GGTTTTGCCA   207840
TGTTGGCCAG GCTGGTCTTG AACTCCTGAC CTCAAGTGAT CCGCCCACCT CAGCCTCCCA   207900
AAGTGCTGGG ATTACAGACG TGAGCCACCA TTAACCATTT TTCTATCTCC TGTGGGAAAG   207960
GGCACAGTGA AGAACAGAT GAAGCTGAGA CATACAAGTG AACTCCTCCC TCCTCTCCAT    208020
TTAGACTAAA ATAGGATTAT TCATACTGAG ATTCTCCCTG GTTGCAAAGA GATAATCTGT   208080
GCAACTGGGT TTTTACAATT ATCCCTACCC TATGCTTTCC TCATCTGTCT TCCTCGTAGT   208140
CAGCTCAGGC TGCTATAACA AAACACCATA ACTGGGGGCT TTTGAACAAC AAAACTTTAC   208200
TTCTCACAGT TCTAGAGGCT GGAAATCCAA GATCAAGTTT CTGGCAGATT CGGTGTCTAA   208260
TGAGGTCCTG CTTTCCAGTT TATAGACAGT GCCTTATCGC TACCGCCTTA CACAGTGGAA   208320
GGAGAGGACG AGAAGCTCCT TGGGCTTTTT TTTGTTTCTT TCTTTCTCTC TCTCTCTCTT   208380
```

FIG. 6.79

```
TTTTTTTTTT TTAATAAGGT CACTATCTTA GTCCATTTTG TGTTGCTAAA AGGAACATCT    208440
GAGGTTGAGT AATTTATTTT ATTTTAAAAA GTGGCCAGGC ATGGAGGCTT ATCCTGTAAC    208500
CCTAATCCTT TAGGAGGCCA AAACAGCAGG ATTGTTTGAG GCCAGGAGTT CAAGACCAGC    208560
CTAGGCAAGA TAGTGAGACC CCATCTACCC CATCTCTACT AAAATTTTAA AAAATTAGCT    208620
GTGTGTTGTA AAGTGTGCTT GTAGTCCCGG CCACTTGAGA GGCTGAGGTG GGTGGAGTTC    208680
AAGGCTGCAG TGAGTTATGA TTGAGCCACT GCACTCCAAC CCGGGTAACG GGCAAGACC     208740
TTGTCTCTAT TTAAAAAAAA AAAATCTTTA TGTGGCTCAC TATTCTGGGT GGCTGGAAAG    208800
TTCAAGATTG GGCATCTGCA TCTGGTGACA GCCTCATGTC GCTTCCAGTC ATGGGGAAG     208860
ACGAAGGAGA GCTGGCACGT GCAGATATCA CGTGTTGAGG GCAGAAGCGA GAGAGAGAGG    208920
GGAGAGATGC CAGGCTCTTT TTAACAACCA GCACTGGGGA AACTAATAGA GTGAGAGCTC    208980
ACTGACTCCT GAGGGAGGAC ATTAATCTAT TGATGAGCGA CCTGCCTCCA TGACCCAAAC    209040
ACCTCCAACG ATACCCCACC TCCAACACTG CCACACTAGG GATTAACTTT CAACTTGAGA    209100
TTTAGAGGGG GGAAACTTAC AAACTATCGC AGGCACTAAT ACCACTCATG AGGGCTCCAC    209160
CTTCATGACC TAATCACTTC CTAAAGGCCT TACCTCTTAA TCTCATCACA TTGAGGATTC    209220
GATTTCAACT TGAATTTTGG GGGGACACCA ACATTCAGGC CATAGCATCA TCTCAATAAC    209280
TGTCCCATTG GTGGTCACTC AGGCCCCAAA CAAAGGAACC TTCCTCCATT CCTTTCCGCC    209340
CTCCCACCCA CAGTCAATCA TCCCCAAGCT CCATCAGCTC CACCTTTAAC GGCCAACCCA    209400
CCTCTGCCAC ATCTCACCAT CTCCACTGCT ATCCCTGTCA CCTGGGCCCA CCATTCTCTC    209460
TCCTGGACAG TCTCCATAGC CACCTCTGTC AGATTTATTT TATTTTTTTA TTTTTTTTTT    209520
TGAGACAGGT TCCTGCTCTG TTGCCCAGAC TGGAGTGCCA TGGCATGATC ACATCTCACT    209580
GCGGCCTCCA TCACCTGGGC TCAAGCAATC CTCCCATCTC AGCCTCCCAA GTAGCTGGGA    209640
CTACTGGCAC CACCATACCT GGCTAATTTT TTGTTGTTGT TGTTTAATTT TTAATACAGA    209700
TGAAGCCTCA CTATGTTGCC CAGGCTGCTC TTGAACTCCT GGGCTCAAGT GATCCTCCGG    209760
CCTTGGCCTC CCAAAGTGCT GGGATTACAG GCATGAGCCA CCGTGCCCAG CCCATCAGAT    209820
GTTAATGCTA CACGCACTTG CTTAAAATCC CCAGATAAT TCTCGCTGCT CTTGGAATAA     209880
TTCCCACACA CCTTGGCGTG GCCATGCAGG CTCTGTGCCA TCGGATATGT CCCTGCCCCC    209940
TCTCCCAACT CCTCCTTTCG CTTGCTCGTT CACTCAGTTC CAGCCACATT GCCCTGGGAG    210000
CTGCTCCCAC CATGGGGCTT CCTAATGCAC TGGTCTCTCT CATGCAGTGG GGCCTCTCCC    210060
TCCTTTTACT CAGTGTCTCC CAGCACCCAC CTCCTCCAGA GCCTTCCCTG ACCACCACAC    210120
CTACACCTAG GCCCTTCCTC CTCCACGCTC CCTCCTCCAC CCCGGCCTCC TACCCACGTG    210180
TCACTTCTTT ATACTCGCTG CCACCTGAAA TTAGATCATT TATTTACCCC TTTATTTGTT    210240
CAGTTTGCCT TGTCCGTTAG AATATAAGCT TCCAAAGGGC AGGAGCTTTG CCTATATTGT    210300
TAGGCCGGGC ATACAATGAG CACTCAAAAA AATATTTGAT GAGTGTATGA AGAACAGAC     210360
TGGGTTATGT AATTGTGCCT ACTTACCTAT ATGACCGTGT GGTGGGGTTT ATGGTGGGTG    210420
TGGTGGTGAT GGCTATAGGG CTATAAGCAA ATTTGGGACA GGGAGTCTAA GAAATGTTCT    210480
TAAATTTTAG TAAGCAAAGC ATCCTCTACA GAACCTGTCT TAAAACATGA AAGTTCCTTA    210540
GTGCTACCCC CAGAGGTATG ATTTGGTAGG TCAAGGATAG GGCCTGGAAA TTCACATTCT    210600
TGTTAAGATG TTCTTCATCC GGGGTTTGTT GACCACCTTT TCAGAAGATT TTGCTCTGT     210660
AGCTGTACTA CCCAATGCAG TAGTTCGTAG TCAGTGTGGC TCCTGAGCCC TTGAAGTGTA    210720
GCTCCTCTGA ACTGAGACGT GCTGTAAATG TAAATTGCAC ACCGGAGTTT GAAGAGTTAA    210780
TACAAAGAAA AAGGAATGCA AAACATCTCA TTAATAATGC TTTACACTGA TTACATATTG    210840
AAATGGTAAT CTTGTAGATA TAGTGCGTTA AATAAAAATAT ACTGTTAGGC TTAATTTCAC   210900
GTCTTTATAC TTTTAATGTG GCTACTAGAA AAATTTAAAT AACATATTCA GCTCACATTA    210960
TACTCCTATT GAACAGAGCT GATCTATAAG TTCCATGGAA GATGGCAAGT CTTCGCAGCT    211020
```

FIG. 6.80

```
GAAATAAAGG CTGGATCCCA TTCTACGGGC TCATCTTTAG CAATGATTTC TTGCAGACGA  211080
TATTGAAAAA TGTGGCAATG AAAGTTACCA CAAGCATCAA ACCAGTCCTG CCTAAATCTG  211140
GAAAATAGTT ATCTGAGGCT GTTAGCATAT GATCATGAGA GCGTTTCACC ATGGATTTCT  211200
GATCACAGAT GTGGCACATT ATTAAAATAT CACTTTTACA GTCACCCTAG AGGCTAGGGT  211260
TATCTGAATA TGGAGAAAGA AACAGCTTGT GGAGCTGTTG TATAAATGAA ATTACTAGAA  211320
AGTAATGCAC TCAATTGCAT ATTGGCTCGG GGGGTTATTC TTATTAAAAT GTTTAGAGAG  211380
GACTTTCTGT TCATTTCTGC AGAATTGCTC TTCAAATTAA GAATTTGCTT GACACGCTAA  211440
TAGACCACAG TCCCAAGAGA AGTTTATCCT TTTTTCTTCT TATCCTTGCT AAGCACTTAG  211500
ATGCTCTGCT GATAGGTAGC ATATATTGTC TATATGAAGC TTTTGTGTTA ACATTGACTA  211560
GTCCTGCAAG TTGGCACACT CTTACTTGGC CTAAAAGAAA TCAGCACCAG GCTTTAAGAA  211620
AATCAGATGA TCTACCTAAA GGAACACAAC TCTGTCTCTC TTTTGACAAT TGTTGTAAAC  211680
AAATTTTAAT GGAAATTTGC CTTAATTGTG AAGAAGTTGC TGCTAAAATG GACTTGCCAT  211740
TAATGGACTG GAACCCATTG CATAAGCAGA ATGAAATATA AGCCTTCTCA GGATTCACAC  211800
TTATAAAAAA CCATTCAGCC AATCAACAAG AGGGCAAAAG AACAAACATT TGATGTGTAA  211860
TTACTTAATT TAGTGCATAT GCATTTGGGT CCTCAATGTC AGCACTATGG CAACCAGAAC  211920
ATGGCCACAA TAACTGTCTG GAAATGTCTA TTCTTACCTG GACCCAGCAG GCCATGCCCC  211980
ACTGATTATA TAATCTCCCT CTCTCCTTGT TACGGTCTGA ATGCTTGCAT CCCTCAAAAA  212040
TTCATGTGTT GAAATCCTAA CCCCCAAGGT GATGATATTA GGAGGTCGGC CTTTTGAGAG  212100
GTAATTAGGT CATGAAGACA GCATCCTCAT GAATGGGATT AGTGTCCTTA TAAAATAGGC  212160
CCAAGGGAGC TCATTCACTT TGTCCACCAT GTGAGAACAC AGCGAGAGGG CACCATTTAT  212220
GCACCAGGAA ATGGGCCTTT TCCAGACAAT CTGTCGGTGC CTGGATCTTG GACTTCACAG  212280
CCTCTAGAAC TGTGAGAAAT TAATTTGTTT TTTATAAGCC ACCAAATCTA TGGTTTTTTT  212340
TATAGAAACC GTAATGGACT AAAACACTCC CTAATTATAT TTAAACTTAT CAGTGCACTG  212400
GGCAGTGACA TATTAAAAGA ATGCTGGCCA ACGTAATTGA CACCATAAGG CTGGATGATT  212460
CTTGTAATTT TCAGCCTCAG AAAAAGGCTG GGGAGAGGAG TCAGGGGAAA GGAGGTGGTG  212520
TGTGTGTGTG TGTGTGTGTG TGTGTGTGTG TGTGTGGTAC GGTGGATGCC TGCTGAGAGA  212580
GAAAGAGCTA TAATAACATT CTGTGGTTCA GCTGACACAT CCTTTCTGCA TCCCCTCCAA  212640
TCACCTGGGT TAATGGGGAC CTCGCTAATG TCTGAACCTC ATCTCATTTT AACCTTTTGT  212700
TTCAAAGCCT CTCTTTTCAT GACTTCCCCG CCTTCATTTT TCCCATATGG TGGGGTTATT  212760
ATTAAGACAT TAAATGAGAG TGGACAGGTA GGCAAAGGAG GTGGGTTGCA GGGGAGTTGA  212820
GGGTTGCCTG TGTACTTTTC TAGACTGTTC CACTTCACAT CAGTGAAATA TTCCCAATTG  212880
ATACTATCAT GAAACAAAGC AAATGAAATG CTGAGCACGG AGCTTCGTCT TGATGAAATG  212940
CTGAAAGAAA AGAAAGGAAA AATAAAGTAG CCATTATTTT TGCCCTTCCT CCCACCCCCA  213000
TGTTTACTAC TCTTATTTCT CTTTTGTATT GTTGTGTTGG AAGCACAGCA TCAGAAAAAC  213060
TCCCAGTTTT GAGAGATAAC TCAGTGTTTA GTTCACTTAA ACCTGAGAAA GGAGAAGAGG  213120
ATGCCACCGT GAGGTCCAGG ACGTAAAGAG GAAAAAAACA GACAAAAAAA TCCATATGAA  213180
ATGAAAATGT GAAAGAGGCG CTTTCGAGCA GATGAGTGTT GTAGATTACA GTGTTGAGAG  213240
CTGTTTGTGT CCAGAGCTGC TTGCTGCACC TGGCGGGATA AACACTGGTC TAACAGAGGA  213300
TCCTTGTTTC AAGGAGGCTG CCTTTTATTT GGGGGGACAA AATTGTTCTT GAAAGCTGCT  213360
CAGTGGTTCA AGCTACAGCA TGGTGGACTA GCAGAATGGA CTCCAGGGCC TCCGAGGAGA  213420
CAGTGACTGC TGCCAGAAAT AGTCAAGGAT AGAAAGGAAG GACTTCACTG AGGCCTGGGA  213480
GAAGATTATG GAATGGGACT GACAGCAGTG ACGGGGAGTA AAAGGGGGTG TCTGGGGGAA  213540
TTGTGCCCCA TGGTGAGAGC TAGAGGGTTC ACAAAGACTT AACCCGACGC ATCTCTCTCA  213600
CCCTGGAGAT TGGGCCCGTT CAATCTAACT GGATGGCTAT AATTTAAAAG GTTTAGGTAT  213660
```

FIG. 6.81

```
TATGACAAAC ATGGATATAT TAGGTGATAG CAATGCAAAA TGCATATGGC TTCTTGATAT    213720
AAAACACAAG ACTTGAAAGC AGCATCTTTG GCTGGGTACT ACAGCCACCC TCCTCTGTCA    213780
CTAAGGGAGG CTTTGGTGGA AAGGGCTGAG AGCCTCTAGA CTGTGAACAA AAGTAGGCAC    213840
AGAAGAACAG TTGGAGATAA TAAGTAAACC ATCTTGACAG GAATGAAGAA TTTCCTGAAA    213900
GGAAGGTCCC TGAGTTAGGT TGTTGGATGC TTTCAGTAGT GAGTTATTGA AAGTGTTTGG    213960
GGGGTGTGTG TGTGTGTGTG TATGTGCAGT ATGTGTGTGT                         214000
//
```

FIG. 6.82

SNP name     SNP amplimers

SG13S421
    GATTATATCCCACCTACCACTGCAGCTCCAGGATCCAGCTTCACAA
ACATTTGTTGAATGAATGAATAAGAAAAGAGGACACCCCCAAAGAGGCT
GCAAGGGAAAAAGCTACAAAGACAGAAGCACCAGGAAAAAGTAGGGTC
ATGTAAGTCAAAGCAGGAAAAAGTTCCATGGTGGGGTGGTCAGCAGTGT
CTAAT[A/G]CCACGAAGGCACAAAGTAGGATAAAGGTTAAAAATCAGCCT
TTGGTTTTGGCAAATATGAAGCTTATCGGTAGCCTTAGCGAGAACAATTCC
ATCAGGGAGCAGAAGCTAACTGCAGTGGGTTGAGTCATCAAGCAGGCAT
AAGGAAGTAGGGATACCCCATTATAAGCTACTCTTTCAAGAAGCTCAAAT
CTGAAG

SG13S417
    ACAAAAATTACCATCATATGCTGTCATGCATGTCTGCCAGTCTATTT
ATCATATTATTTAAGAAACAAACATTTATTGAAGATTTATCATGTGCTCAG
CACTGCCAAAGAGGAAATAAAGAGCATAATATCTATTCTTAGAAAATAAC
ATTAACACAAATAGAAAACAAGAAACCATAATGTTAAAAATATTACATAG
[C/T]AACACAGAAAGACAATGTATAATTATACATACGCACTAAAGCAAAG
ATAACATAATTTATAAATTATGAGGTACAGAATAGTTAGATTCTGAAAAT
TAAAATAATCAGGAAAAACTTCATGAAGATGAGATCTGGGCTGGATCCCA
AAGGATAGGCAGGTGGATCATGTAGAACAGGGGAAAGGAGTTCCTGATC
GG

SG13S418
    AACTAAAGAAAGCCACAAAAGTTCACCTCAATGCCAAGACATTTCT
TGATTTTTGAAAACCCAGTTGTCGAACCACCCATCTATAGAAACTTGAAA
GACTAAAAACTATCTTACTCTAAACATTTTCTAGGAAGTTGATTCTACAAC
ACATTTTGGTTTTCCAATTTGGCTTCTAATAATTATTTCAAAGTTTCTGTG[
A/G]CCTAAATTTTGTTTTACATTGATCCTTTGAATGGACTACTGTTTCCACA
TTTTAGAACATTTAAAAGATATCTACAACCCGAGTCTAATCATAAAAAA
AATCAGACAGATCCAAAATGTGGAACATTCCACTAAAAAAGGAGTGGGG
AGAGGTCTTTATTCTTCCAAAATATCAATGCCATAAAAGACAAAGACG

SG13S44
    ACCCTTCAACCCCAGCCCAGCTGCTAACTGACTACAGCCACATGAA
CAGAACCAGGTGAGACCAGAGGAAACTTCCAGTCACCTACCAGATCATGA
CAAATAATAAACGATGTTTTTTAAACCACAAAGATTTGGAGCAGCATTTG
TTACACAAAATTAGACAACTATTACAGTTCGACTAAAAACATGTTCATTTA
C[A/G]ATACTAAATTAGAAGTGTAAGAATGGGAGAAAAACTTCATACTTTA
AAAGTCATTTTTCCTCCAAAAACTTCCAACTTTGAAAAACTGATTTTTAT
AATGCATAAAAATTAAAATAACCTTAGAATTTATATGAGTAGCATAGCCA
GCTGGCTTTATTATCTGTTGTACTCAACACTTCAATAATCACTGATGTTT

SG13S45
    ATGACCTTACCTCGTTTTGTTTTCCTTGTCTGAGAGAAACACATTAG
CAGTCTCCCATCTTGTTTTCCTTTTCCTGTCACCCAGGACAGAGGGCAGT
GGTGTGATCACAGCTCTGCAGCACGACTTCCCCAGGTTCAGGTGATCCTCC
CACCTCAGCCTCCCAAGGAGCTGGGACCACAGGCACATGCCACCACGTC[
C/G]AGCTTAATTTTGTATTTTTTGGTAGAGATCAGGTTTTGCCTTATTGCC
CCAAGCTGATCTTGAATTCCTGGGCTGAAGCAATCTGCCTGCCCTGGCCTC
TCCAAGTGTTAGGATTACAGGTATAAGCCACCGTGCAGCCTTATATTTTGT
TTTAAATTTTCCTCTGTATTTTTCTCTCTGGCAAATTGTTTAGGGA

TTTTTTGGTAGAGATCAGGTTTTGCCTTATTGCCCCAAGCTGATCTT
GAATTCCTGGGCTGAAGCAATCTGCCTGCCCTGGCCTCTCCAAGTGTTAGG
ATTACAGGTATAAGCCACCGTGCAGCCTTATATTTTGTTTTAAATTTTCCTC
TGTATTTTTCTCTCTGGCAAATTGTTTAGGGAGTTTCTTTAGTTTATC[A/G]
GACTAAATTTCAAGGCTTTCCTTCCAATTTTGACATGTAAACAGTCCCTCA
TTTCTGCTTATCTAGTGATTATTCCCAAATCTGTGTTTACAGTCTAGCTGTC
TCTCCTGAGATTAAGACTTGTTTCTCTAACTACCTGACGGCAGAATCTCCT
CTTGGAAGTATCAAGGAGGCAGTTCAAAACTGAACTGGGCATT

SG13S50

GCTGATCTTGAATTCCTGGGCTGAAGCAATCTGCCTGCCCTGGCCT
CTCCAAGTGTTAGGATTACAGGTATAAGCCACCGTGCAGCCTTATATTTTG
TTTTAAATTTTCCTCTGTATTTTTCTCTCTGGCAAATTGTTTAGGGAGTTTC
TTTAGTTTATCAGACTAAATTTCAAGGCTTTCCTTCCAATTTTGACATG[C/T
]AAACAGTCCCTCATTTCTGCTTATCTAGTGATTATTCCCAAATCTGTGTTT
ACAGTCTAGCTGTCTCTCCTGAGATTAAGACTTGTTTCTCTAACTACCTGA
CGGCAGAATCTCCTCTTGGAAGTATCAAGGAGGCAGTTCAAAACTGAACT
GGGCATTGGCTCCACTCCTTCTCCTTCTCTTTACTATTAATACCC

SG13S52

TAAGTCTTATTTAGGCATCGTTTCTTCTGGGAGACCTTTGTAGAATC
TCTGAGGTTATGTTAACATGCTAAGGTTTTCTTGACATTCTCAGATTGGGT
TAGGTGAACTTTTAGCAACTTATCTTTTTACTAAAAAGTCATCCCTCAGTA
TCTGTGGGGAATTGGTTCTAGGACTCCCTAAGGATATCAAAATCTGCAT[A/
G]AGCAGCCCAGGTGAGACCAGCAGAAGCACTTTACAGTCACCTACAGGA
TCATGACAAATAATAAATCATGTTTAAGCCACAAAGTCCTTTACATAAAA
TGGTATAGTATTTGCATATAACCTACACATCTTCCTGTATCCTTTAAATCAT
CTCTAGTTTATAATACCTCATACGATGAAAATACTACGTAAATAGTT

SG13S53

AAGCAGTTCCTAATTACTGGACATTCTCAGATCTGCTAGAGCTACA
TGTCCAATTACGAGAATATACTGGAAAAAGCCCTGGATTAGAAATGAGAG
GATGTAGGTTTTAGTACCAGGTCAGCCACCTTGTTAATGCAAATTTGAGTA
AATTGTTACTTCTTTTAGGCCTTGTTTTTGCTGTTTTGTTTTTCTGACAGT[A/
C]TGGTCTCTGTGGTCCAGGCTGGAGTGCAGAGGCACAATATCAGGTCCCT
GCAGTCTCTACCTCCCAGGATCAAGCCATTTTCATGCCTCATCCTCCTGAG
TAGCTGGGATTACAGGCATGTGCCACCACACCCTCGAACTCCTGACCTCA
AGTGATCTGCTTGCCTCAGCCTCCCAAAGTGCTGGGATTAGAGGTGT

SG13S55

GAATATACTGGAAAAAGCCCTGGATTAGAAATGAGAGGATGTAGG
TTTTAGTACCAGGTCAGCCACCTTGTTAATGCAAATTTGAGTAAATTGTTA
CTTCTTTTAGGCCTTGTTTTTGCTGTTTTGTTTTTCTGACAGTATGGTCTCTG
TGGTCCAGGCTGGAGTGCAGAGGCACAATATCAGGTCCCTGCAGTCTCT[A
/G]CCTCCCAGGATCAAGCCATTTTCATGCCTCATCCTCCTGAGTAGCTGGG
ATTACAGGCATGTGCCACCACACCCTCGAACTCCTGACCTCAAGTGATCT
GCTTGCCTCAGCCTCCCAAAGTGCTGGGATTAGAGGTGTGAGCCACTGTG
CCTAGCCTTACACATTGTTTTCTTACTGGTAAAGTGGGAATATCTAGA

SG13S56

GTTTTGTTTTTCTGACAGTATGGTCTCTGTGGTCCAGGCTGGAGTGC
AGAGGCACAATATCAGGTCCCTGCAGTCTCTACCTCCCAGGATCAAGCCA
TTTTCATGCCTCATCCTCCTGAGTAGCTGGGATTACAGGCATGTGCCACCA
CACCCTCGAACTCCTGACCTCAAGTGATCTGCTTGCCTCAGCCTCCCAAA[

FIG. 8.2

G/T]TGCTGGGATTAGAGGTGTGAGCCACTGTGCCTAGCCTTACACATTGTT
TTCTTACTGGTAAAGTGGGAATATCTAGAAGTTGCATGCTACATAAATTCA
ACCATATATTATTGGCAAAAAATTTTAAAGAAAAACATCAGCTTAAGAGT
ACTAATTGAGTACATGCCTTGGAATGAGCATGAGCTGGAAAGAACAAA

SG13S57

GGCAAAAAATTTTAAAGAAAAACATCAGCTTAAGAGTACTAATTG
AGTACATGCCTTGGAATGAGCATGAGCTGGAAAGAACAAACCTGTTGTTA
CATCACTCATTGCTGTTTTCATATGCTGCTCATTGTAAATCTTGCTCAGTGG
CATGATTTTAGTGTTTAAAGATTTATTTGTTTGTTTGTTTAGGACAAAGTC[
C/T]CTACACATAATCTACTTGCTTCATATATACATACTTATGCATATTATGT
ATGTACATACATGCTCTCAGGGCTCACATGAAAAAACAGCCATTCAGGTG
ATGTGATTTATCTCATATGCTTACTTTAGAGTCAACAGGGTGTTGACTCCA
CTATACAATACTGGCATGGAGAACACATAAGTCAAAGTAGACAGGAC

SG13S58

TTTATTTGTTTGTTTGTTTAGGACAAAGTCTCTACACATAATCTACT
TGCTTCATATATACATACTTATGCATATTATGTATGTACATACATGCTCTC
AGGGCTCACATGAAAAAACAGCCATTCAGGTGATGTGATTTATCTCATAT
GCTTACTTTAGAGTCAACAGGGTGTTGACTCCACTATACAATACTGGCAT[
A/G]GAGAACACATAAGTCAAAGTAGACAGGACCCAGCCGTACCATTGGCT
AGGGCACAAATATATTCACATATGTGGAGAATGATGTACGTAGAAAGGTC
TTCATTGCACAATGCTCTTTAATAAAGATCTGGAAAAAAAAAACACCTAA
ATGTTCAAAAGGATAGGGTAGATGAAATAATGGTACATTATAAAATGGAA

SG13S59

TCTGTCACCCAGGCTGGAGTGCAGTGGCATGATCATGTCTCCTTGC
AGCCTTGACTTCCCTGGCTCAGGTGGGCCTCCCACCTCAGTCTCCCAAGTA
GCTGGAACTACAGTCGTGCACCACCATAGCCAGCTAAGATAGTGAGATGG
TGGCCCCACTGTCTTGCCCAGGCTGGACTCGATTTCCTGGGTGCAAGCACC
[C/G]TTCCCGCCTCAGCCTCCCAAAGTGCTGGGATTACAGGCATGAGTCAC
CATTCCAGCCTACTTGTCTTTAATTCTTAAAAATATTAATGTTGAGTTTTGT
CTCCCAGCATGTGGGAAAGATGTCATCCATTGCTTCTGTTTCCTGGAGGCC
TGGGAGCAAGGAGCCCAGGAACAGTATCACGAAGCTTGAGATAATAC

SG13S60

ATCATTGATGGGCATTTGGGTTGGTTCCAAGTCTTTGCTATTGTGAT
TTTTTTTTTTTTTTTTTTTTTAAGACAGAGCCTCACTCTGTTGCCCAGGC
TGGAGTGCGATGGCATGATCTCAGCTCACTGCAACCTCCGCCTCTCAGGTT
CAAGCAATTCTTCTGCCTCAGCCTCCCAAGTAGCTGGGACTACAGGC[A/G]
CCCACCACCAGGCCCAGCTAATTTTTGTATTTTTAGTAGAGACAGGGTTTC
ACCATGTTGGTCAGGCTGGTCTTGAACTCCAGACCTCATGATCTGCCTGCC
TTGGCCTCCCAAAGTGCTGAAATTACAGGTGTGAGCCACCATACCTGGCC
TAGGCAGTCTTTTTCAAAACTCAAGACTGTGCTTGTGTCTCAGG

SG13S419

TGGTATGAGGTAAGGATCCATTTTTTCCCATTTGCATAGCCAGTTT
TTGTAGCTCCACTTTATTTTCTCACTTGATCTGCCATGCCACCTCTAGCATG
TATCAACATATCATGTATGTGTGCAGCTGTTCCTTAACTCTCAATTTTATTC
TCTTGGTTACTTTGTCTAACCCAGCACTCATACTTTTTAAATTATTA[C/T]G
GCTACCTTGTAGGGCAAGAATCCTCACTTTTATTCAACTTCTTTTGAAGTG
TCTTGATGCATATTTTTTCTGATCTTACTTGGCCATATATATTTTGGGGACA
GATGTGACATCATACCAAGCTTTCTTTGCTTGACATTGTAGATATTTTCTTA
TTCATTAATGTGCTAAAAATTTTGAGTTTGGTCATACAGTC

GTTTCTAACATTATAGACACTAGTTTTAGGCTCTTGGAGGCTAGCA
GCAATTCTCAGAGGTAATGCAAGCTTCCCCATTTCTTCCCGTAGTCCTGTG
AAAGACCAGCCACCTCCAGAAGCCTACACATGAGTCTTCTCAGCCATACT
TTCTGCTTTTCCTAATGCCTCTCAGCAGCGTATTAGAAAGGCCATGATCGA
[C/T]GTACCTGTTACCTTCAGGCTTTGCATAAGGTGTATATGAAACATAAT
GAATTTCGTGTTTAGGCTCAGGTCCCATCCCCAGGTTACCTCTTTATCTTG
GAGACACTTCTGGTCCCATACATTTCAGATAAGAGATATTCAACCTGTACC
CACCACGTAAGGAGAGGAATAGGTTTTAGAAGAGGAGTCAGGGAGGCA

SG13S62

GCATCTATTAAAAGTGATGGTTTTAGTATCCTGTCTCATTTTTTCCT
TTCCTTACATCATGTATTATAGGTAAACACATGCGCATGTGTGTATTTCTC
TTTTAGACAAAGGATGAGATTACTACTGTTAGCTCAGTTTTTTTTCCCTAC
TTAACATCTTTGCTTTTATTTTTAGACATATTCTAAGACTATTAAA[C/T]A
TTAGACTTACGTAGCCCTTCTGTCATTGTGAAATACATAGTTTACTAACAG
CTACCATCAAGATAAAGCCTTTATTTAAATAATTAAACTTCTTAGTGGAAA
GCTAAGTAAGCACAGTTTATGGATTTTGGGAATTTTTGCCTTGCATTTGTC
TGATATGGTAAAATATTGAGTTTGTTTTCTCATAATGTTCAC

SG13S63

GATAACTCAATCCCCTTAAAGGGTTGTATCAAGCCATTGATAAGGG
CTCACTTTGATATAACCATTTTCTGTTATTTAGACACTCTTTCACACTTCCT
ATTTTCCTCCTGGGGATGGTTTGAATGGATGACACAATACCATATTATAAA
AGCACTTTACAAACTGTAACTTATGTTATAAATGTAATTATTACCTTAA[A/
G]GTTTTACCCTGTTTCAGATTTGAGTGGAAGTAGTTCTTTACAATACAAA
ACAACTTATTTTAACTTTTTTGCATTTCAAAGAATGATCAATCCACTTCA
GGTGCAGCATGGTTTCCAACCCTGACAGCATGGAAGAATCATTTATTTAG
CTTCTAAAAATGTGCAGGCTGTACCCTAGACCAGCCTTGGGGATTAG

SG13S64

TCCTCTCTCTCATTCTCTCTCTCTCTCTCTTTCTCTCTCTCCTTCTTTG
CTCCTTCATTCCTTCTCTCTCTCTTTTTTTTTGAGACAGCATCTCACTAT
ATTGCCCAGGCTGTTCTCAAACTCCTGGGCTCAAGTGATCCTCCTGCCTCA
GCTTCCTGAGTAGCTAGGACTACAGGCACATGCTATGGCAATACT[A/G]TT
TTAAACATTGTTTTCAAGGCTCCCCAGGTGATTCCAGTGTGGGTCATGTGG
TAGAGAACCACTGACACAGGCAAACAAGGATACATAAAGTTGTCTATTT
AATGGGTAGGTGCAGGTAGTAGATAAGAGTGTAGCCACATAAACCACAT
GCTTAGTGAACGGTTTTGTTTTGTGTGTATGTGAGGGATTAGCAT

SG13S65

TTCAGGTTCCATTTAGCACGACAGCAGGGAAGGGACTGTTGGCAG
AAAAAAACTGGGGCAGTGGGATTAAAGACAGACCACACATTCCAAAAGG
CACCGTGGGAGGGTCAGGGGGCGAGGTTAGGTCTAGGCTTCAGTGTCCTG
GGAGACTCAGTCTTCACAGGGTGACAGCGATCAAGAGTGCAGCTTAGGCT
GGGT[A/G]CAGTGGCTCATGCCTGTAGTCCCAGCACTTTGGGAGGCCGAGA
CGGGAGGATTGCTTGAAGCCAGGAGTTTGAGACCAGTCTGACCAACATGG
CAAAACCCCATCTCTACTAAAAATACAAAAATCAACTGGGCATGGTGGCG
TGTGCCTGTAGTCCCAGCTACTTGAGAGGCTGAGGCAAGAGAATCACTTG
AACC

SG13S420

TAAATGATCATTATGTTCATATTCACACATACAATAATGTACTCAA
GTTTATTGCTAAGGTAATTCAGAATCTCCTTATTTGAAGTGTGCATTTGA
TATACCTGTTTGGGAATAACTAGTTTCTTATCTTTGACAGAAAATAATTTT

FIG. 8.4

GTTGTTTTGTTTTTACTAAAAAAGCATGGTGAAAATGGCTCCATTTCTA[A
/T]GAGAGGTAACTAAAATATCGCAATTTGCTGGGTGTCATTAAAGTAACT
CACAAGGGAAAAAATGCAAATTGGTATCTGCTGATGGAGTAAATCTCCGC
AGAAGTGATGACCCTGAAGGATCAATATATTAAAGCCCCTCCCAGCTGG
TCATTCCAGATTGCAACAATAAAGCATTAAGTGTTAAAACCTCAAGGCA
SG13S66
      CTCATCAAGCCCACCTTTATACTTCATTTCTCCAGACTTCATGTCCA
GACTGTGGGATGAACAAGTGGTTATAAGGTTTAGAGGCTCCTGTAGGAC
TAGATGGAAGGCAAAAAAGGAAATAACCTTTAAGCATGCTCTCGATTCC
TTAAATCCCATCTGAAAGTCTTAAGGATGTCTTCTCAGTCATACTTATTTG[
A/G]CAATATTACCTAATTTTCTCCATTAGCCCAAGCTCAGGGGTCTTTCTT
CTTCCATATTCACATGGGTGCAATGGTTTTCTGAAAGGAAAACAGCATTA
CTAGGGCAGTAACATTTAATTAATCACAGGTACTTATCAAACTACAAAAC
AGGCATTCCAGGAACTGGGTGTTTCTGTTTGTAAAATTACACTCTCGTG
SG13S67
      TAGGACTAGATGGAAGGCAAAAAAGGAAATAACCTTTAAGCATG
CTCTCGATTCCTTAAATCCCATCTGAAAGTCTTAAGGATGTCTTCTCAGTC
ATACTTATTTGACAATATTACCTAATTTTCTCCATTAGCCCAAGCTCAGGG
GTCTTTCTTCTTCCATATTCACATGGGTGCAATGGTTTTCTGAAAGGAAAA[
C/T]AGCATTACTAGGGCAGTAACATTTAATTAATCACAGGTACTTATCAAA
CTACAAAACAGGCATTCCAGGAACTGGGTGTTTCTGTTTGTAAAATTACA
CTCTCGTGTACATGCTCCCACTAAAATGTAAGTTCGCTGAGGATGGAGGTT
TTGGTCTCTTTGCTCTGTGCTGTAACCCCAACACTGCAGCAGGGCCTG
SG13S69
      GCTGCATAGTCTCACTTAGGTGTGGAATCTAAAAAAGTCAAATTAA
AAAAAAATGTCAAGCAGAGAATAGAATGGTAGTTGCCAGGGACTCTGGG
AAGTAGCAGGGGTGGGGGTGGAGGGGAGGGGATGGGCAGAAGTTGGTCA
AAAGGTACAAAGTTTCAGGTAGACAGGTGTAAGTTCTGGGGATCTATTGT
ACAG[A/C]GTGGTGACTGTAGTTAATACTGTATTGTGTACTTAAAAATTGC
TCACCAAAAATGTTCTCACCAAAAAAATGATGTTTGGATATGTTAAACAG
TTTGATTTAATCATTTTGACGTGTGTGTGTGTGTGTGTGTGTGTGTGTGTGT
GTATACATCAAAACATCACATTATATACCATATACAATTAATATATACAAT
T
SG13S70
      GGGGTAAATGCTGACTGCCTGTTCTCTGGACAGGAATGGAGAAGA
TGGTGCTAGCAGGGTTGCTGTTCATATGTAGACATTCATGCAGTCACTCTC
TTTTCAGCACACTTCTTACTTCTGCCCTGGGTTCAGTTGCTGACTCTGAGCC
CAGAAACCTTCTAGGGTTCTGTTAGGTAGATTGGCTTCCACCGTCTTTGC[
A/G]ACAACCACAGAAAATTCTAGACTGTTTTCTCTTCGGGCTTCATTAGTC
AACTTGCTTCAGTCTGTCTTGCATCTTCTAAATATTTATAGATCTCTCTCTT
TTGTTGGAGTGGCAGAAAATGCTAGTTGACCACCCAATATTCAAATTATC
CTGCCTCCTTAATAACAGAATATCATTGGATGTGGTGGGTAAATAAT
SG13S71
      ATGGAGAAGATGGTGCTAGCAGGGTTGCTGTTCATATGTAGACATT
CATGCAGTCACTCTCTTTTCAGCACACTTCTTACTTCTGCCCTGGGTTCAGT
TGCTGACTCTGAGCCCAGAAACCTTCTAGGGTTCTGTTAGGTAGATTGGCT
TCCACCGTCTTTGCGACAACCACAGAAAATTCTAGACTGTTTTCTCTTC[A/
G]GGCTTCATTAGTCAACTTGCTTCAGTCTGTCTTGCATCTTCTAAATATTT
ATAGATCTCTCTCTTTTGTTGGAGTGGCAGAAAATGCTAGTTGACCACCCA

FIG. 8.5

ATATTCAAATTATCCTGCCTCCTTAATAACAGAATATCATTGGATGTGGTG
GGTAAATAATATACCCTAACTTTCCTTGCAGAGAGGGGTGGCCAA
SG13S72

CAGGGTTGCTGTTCATATGTAGACATTCATGCAGTCACTCTCTTTTC
AGCACACTTCTTACTTCTGCCCTGGGTTCAGTTGCTGACTCTGAGCCCAGA
AACCTTCTAGGGTTCTGTTAGGTAGATTGGCTTCCACCGTCTTTGCGACAA
CCACAGAAAATTCTAGACTGTTTTCTCTTCGGGCTTCATTAGTCAACTT[G/
T]CTTCAGTCTGTCTTGCATCTTCTAAATATTTATAGATCTCTCTCTTTTGTT
GGAGTGGCAGAAAATGCTAGTTGACCACCCAATATTCAAATTATCCTGCC
TCCTTAATAACAGAATATCATTGGATGTGGTGGGTAAATAATATACCCTA
ACTTTCCTTGCAGAGAGGGGTGGCCAATGAGATGGAAATGAAAGTC
SG13S73

TGGGATTGAGTTCTTGATTTGATTTTGAGCTTGGCCATCATTGGTGT
ATAGCAGTGCTAGTGATTTGTGTACATTGATTTGTAACCTAACACTACTA
AATTCACTTATCAAATCTGGGAGATTTTGAGGATTCCTTAGGATTTTCTA
GGTATGAGATCATATCATTGGTAGAGGTAGTTTGAGTTTCTCTTTTCCA[A/
G]TTTGGATGCCCTTTATTTCTTTCTCTTGCCTGATTGCTCTGACTAGGGCTT
CTAGTACTATGTTAATAGAAATGGTGAAAAGTGGGCATCCTTGTCTCATT
CTAATTTTTAGGGGGAAATGCTTTCAACTTTTCCCCATTCATTTTGATGTTG
GCTGTGAGTTTGTCATAGATGATTCTTACTATTTTGAGATATA
SG13S99

TCTTTTGCCCTGCCTTTCTGCCTTTCTGTCCTTTTAATTTGCGGGCTT
TTGGCAACCACAGCACGGGTCTGGTTTCCTAGGAGTTTCTTTTGTAGGATC
AAACCGCTAGTTGGCTCTTGGCCCTGTGATAGGGCCCTGGGCTAACTTATT
GGGAAAATGTTGCTGTAACCCCTGCCCAGAGGTGCCTGTGACATGGGC[C/
T]GCCATCTTCTCCTCTTCCCTTGGCTTCAGCCCCACCTAGAAACCTGAACA
AACATTTTCCTTGACATTTCATAAAGTGTCAGTGGCTCCTCATTTAGCAAA
ATACATCCCAGGGAAGTTCAAAAGTGAAAAAGGCCGTAACTTCTTCTTC
TTCTCAGGGACCTACAGAAAATATGTGGCACCTCGGCAGCCTGGCC
SG13S382

CATGGATTTTGTTTTCCAAGTGGCAAGATGGCGCCTCCACCTTTGGT
ATCCTATTTTAGTTCCTGGCAGAAAGAAAGGAACAGGCTAATGGCCCTGA
TGAGTCTACCCCCTTTTAACAGGAGAAAATTTAAAAAACAAAACCATGA
AACCCTTTCCCAGAGGCAACAACCAGAATTCCATTTATCTTTCATTGACCA
[A/G]AACAGACCACATGGTCACTGGTGGTGGCAATGGAGACTGGGGAGAT
GAATATTTTTAAGGTGGCATATTCCAGAAGAACACTGTGCACTGATTGCAT
TAATGAACCCATTAATGTGCCAAGGGGAGGTTTACCTATGAGCATGGGCA
AATTAGAACCCACTCTTGGAGCTGCAGGTGAGCCAATCCCACCTAAACAG
SG13S383

TGGTGGTGGCAATGGAGACTGGGGAGATGAATATTTTTAAGGTGGC
ATATTCCAGAAGAACACTGTGCACTGATTGCATTAATGAACCCATTAATG
TGCCAAGGGGAGGTTTACCTATGAGCATGGGCAAATTAGAACCCACTCTT
GGAGCTGCAGGTGAGCCAATCCCACCTAAACAGTGTGGATGCTACAAGAT
GG[A/G]GAAGTAAATTGATTCTATTCCATACCCTAACCTCTCTCCAAGATG
TATTCTTAAAATAGAAGAGGGAAGACAGAAGAAAACATCCAGAATATATT
TTTATTGTCTTTTACTTCTTCAGTGCATTTTAGATCAGTGCTTCTCAATCTG
GCAAGGGGCATGCAGGAGGATGTGAGTTTTATCAGGAAAACTACACAAC
C
SG13S384

TGAGCCAATCCCACCTAAACAGTGTGGATGCTACAAGATGGGGAA

FIG. 8.6

GTAAATTGATTCTATTCCATACCCTAACCTCTCTCCAAGATGTATTCTTAA
AATAGAAGAGGGAAGACAGAAGAAAACATCCAGAATATATTTTTATTGTC
TTTTACTTCTTCAGTGCATTTTAGATCAGTGCTTCTCAATCTGGCAAGGGG
C[A/G]TGCAGGAGGATGTGAGTTTTATCAGGAAAACTACACAACCCCCCA
ACCACAATGCTACCCCCACTCCTGTGGACCTTCTTTAAGAGAGACTCACTA
TTATAGATGGAGTTGATACGATTTTAAGAGAGGCCATATATTATTTGCTTT
CTGTCTTGAAAAACTTGTGATTTTCTGTATTGTGCTACTGCCAAAGAGA
SG13S381
    GGGTTGCAGTGAGCAGAGATCACACCATTGCACTCCAGCCTGGGTG
GCAGAGCGAGATTCTGTCTAAAAAACAACACCGTATTTGGGGCATGCTGA
TACTAAAAAATTATTCATTGTTTGTCTGAAATTAAAATTTAAATTGGGGGC
CCTGTATTTTACTGGGCAACCCATTTGCAATATCAGCAACAATCTCTTATT[
C/G]AGACCACTGATTAAGTGTGCAAAATTTGAATCTCTGAACAGTACCTA
TGTCCTTGATATCTTAAATTAATGAGTGTCTTAGACACTCAAAGCAGGAGG
AAGCATTATGGCAGATGTTTGAGCCCCAGAGATGTCCATGAGCACAGCAT
AGAGCTCAGAGCCTTCTTTATTATTTGCTTCACGACAGAGCAAAGGACT
SG13S366
    CATTTGCAATATCAGCAACAATCTCTTATTCAGACCACTGATTAAG
TGTGCAAAATTTGAATCTCTGAACAGTACCTATGTCCTTGATATCTTAAAT
TAATGAGTGTCTTAGACACTCAAAGCAGGAGGAAGCATTATGGCAGATGT
TTGAGCCCCAGAGATGTCCATGAGCACAGCATAGAGCTCAGAGCCTTCTT
T[A/G]TTATTTGCTTCACGACAGAGCAAAGGACTGCAGCAGGTTGACTGAT
ATAAAAGTTTTACCATGTCTCACAGCAGGCCTTTGCTCAAGTTTCCAGTAA
GGATATTGTATCATTTCTTGCCTGCAGTACTTGTAAATCCACTTACACTGC
CTGCTGTTGAGTCATTTGTTTCGTCTTGAGTAGCATGTCATCCTTGTTC
SG13S385
    TTGCAGTTCTCATTGCTGGGGAGTCTAAACTGGAATAAAACACCCA
CTATCTCCATCAGGCTTGCACTAGAGCCCAGCTCTAGCTGGAGAGAAAGA
AGCTAACCCGCACAGACACAGGACTGTAGGCAGGGAGCATCCGGGGGTA
TTTGGGTCCTGGCTCTGATGTGCCTAAGGCCAACTTCTCTCTGGCCATGCT
GG[C/T]GTGCATGAGCTCACTAATCTTCCTTTTGCCTTCCATTTTCTCCAA
TCCTGACTTAGCAAAGGTTGGGCAAAAGAGACTCTGTGTGAGTTCGAGCA
AAGCCTGAGATGCTGGATTTTCCAAGATACGAGAAGGGGCTGGGGGCTGG
GTGAACTGGTGGTGGAGGAGGGAAGGATTAATTTCCCAAGGAGGGGAAG
GG
SG13S386
    GAGAAAGAAGCTAACCCGCACAGACACAGGACTGTAGGCAGGGA
GCATCCGGGGGTATTTGGGTCCTGGCTCTGATGTGCCTAAGGCCAACTTCT
CTCTGGCCATGCTGGCGTGCATGAGCTCACTAATCTTCCTTTTGCCTTCC
ATTTTCTCCAATCCTGACTTAGCAAAGGTTGGGCAAAAGAGACTCTGTGT
GA[A/G]TTCGAGCAAAGCCTGAGATGCTGGATTTTCCAAGATACGAGAAG
GGGCTGGGGGCTGGGTGAACTGGTGGTGGAGGAGGGAAGGATTAATTTCC
CAAGGAGGGGAAGGGGCCAGGACATCAGGCCCCGGGGACTTTGAAGAGA
GGGTCGTGGGTAGGAGGTAGATCAAGTGGAGTGACACAAAGGTCAGGAA
AGAGG
SG13S1
    CATGCCTCCTACAAATTTGACCTGGGCCCAGGGCCATGTTCGGTGG
TTTTTAAGAACCGAGGCTCCCAGAAGCAGTATTGGGCAGCTAGAGTGGCC
CCAGGATCTATATCAAACTCTACCTGTTTCTGAACCAAATTTCTTCTAGAA
TTTTATTCCATAAATCTGAATTATGGTGTCAGACTCCTAGCATACACTAAA[

FIG. 8.7

[G/T]GAACTCTCTGCCTTGCATTAAATAACAGGAGTTACCCCTGGAGGTAA
CTCCTAGCCCTGGCTCTTTAGAGAACAGATGCCGAATAGGCATTAGGGGA
TGTGATGGATGTGCTAACTTTCAAAAAAAAAAAAAAAAAAAGGCCTGAG
CTGAGTGCTCAGAGATTCACAAAAAGCTGACAGCATCTCTCTGTTCCATTG

SG13S2

CTTTGGAGCCTGGCAGCCTGGCTTTGAGAACCGGGCTTTAACTTGT
CACATGACTATGGCCAAGTTCCTGGGGCTCTCCAAGCTTCACTTCCTCTGT
AAAAAGGGCAATAATATAATACCTGTCTTATTGGGTTTTGTCCATGTTAGA
TGAGACATTGGGTACAAAGCACTTGGTCCCGTGCCTGGCACATTTACTGC[
A/G]CTTAATGTATGATAGTTTTCTTATTATTCTAATAAACAATATGGCTTTG
GGAGTATAGTTCTGCCACATTGCAGTGGCCAGAGTGAAGGTGGTGAGTGC
CTTCTGGGGCCCTGGGAGTCAAGGTTATCCGCATGCCCTTTCTTGCTTGCT
CCTCAGTGTGGCTGCCTCTATGTCCACACCATGCAGATGCAACAGGT

SG13S367

ACATGATCATCCCCTTGGGCTTCTGGTTTTTTTTCTTTCAGGACCTT
ATTTTCAGGCAAGTGGCCTTTGACCTCTAAGGCTGTCCTTTCCTAGCTACC
GAATCCAGCATTCAAAGTGATGGAAATATGTATATATAGTAATAGTAAAA
TATCAGCACTTAATGGCCTGATAAGAATGTCACTGCAATGCTGAGTTTGG[
A/G]CCAACATTTGCCTGCTCCTGCCATTGAGCCCGGGCTCCCCTCCAGAGC
TGAGCTGCTGCAAGGGATCTGAGTAACTAGGGCTGTGTCAGAGTGGCGAT
GACAGCCACCACATGCTAAGGAAGAGATCCCCAAGGACAAGGAGAATCC
CACGTGGAGCTACTTGCTTCTTTGTCAGTCTTGTTTTCTTATTTCACAA

SG13S388

CCGAATCCAGCATTCAAAGTGATGGAAATATGTATATATAGTAATA
GTAAAATATCAGCACTTAATGGCCTGATAAGAATGTCACTGCAATGCTGA
GTTTGGACCAACATTTGCCTGCTCCTGCCATTGAGCCCGGGCTCCCCTCCA
GAGCTGAGCTGCTGCAAGGGATCTGAGTAACTAGGGCTGTGTCAGAGTGG
C[A/G]ATGACAGCCACCACATGCTAAGGAAGAGATCCCCAAGGACAAGGA
GAATCCCACGTGGAGCTACTTGCTTCTTTGTCAGTCTTGTTTTCTTATTTC
ACAACCTTCTAAAACACAATCTCTCAACCTCTATTGTTAGCTTGCATTTTT
CAATCATGAGCACAGCTTTACCTGGCTCCATGCTTTGATTGACTCTACC

SG13S10

TCTTATTTCACAACCTTCTAAAACACAATCTCTCAACCTCTATTGTT
AGCTTGCATTTTTCAATCATGAGCACAGCTTTACCTGGCTCCATGCTTTGA
TTGACTCTACCTGCCAACACTGCAACAACAGGGAAAGGGACACCGGCCTC
ATACCATTAGATGGTGTGTAGCCTGGGCATGAGGATAATTAAAAACTCCC[
A/T]AGGGGATTTTAACATGTAACACAGTTTGGAAACCATTGATGTAAGAT
CTTCTTACTCAACATGTGCTCCAAGGAGCTGTTGTATCAGCTTATCAGAAA
TGTAGATCAGGCCGCACTTGGACCTGTAGAATCAGAATCTGCATTTTATCA
GATTCCGACATTATTTGTATGAACATTAGCTTTTGAGAAGTGTTGCTT

SG13S3

CTTTTGACACCAACTACAAGTCAAGGGGTTCCCCAAACCACCCTGA
GTTGTGATAATTCGCTGGGAGATCTGACAGAACTCACTGAAGGTTGTTAT
ACTCATGGTTGTGATCTCTTATAGGGAGGGAATACAGATTAAAATCAGCC
AAAGGAAGAAGCACACAGCACAGAGTCCAGGACAGTGCCTGACATGGAG
CCC[C/T]TACGGTCCTCTCCCGTGGAGTCACGGACAGCGCCACTCTCCTGG
CATTGATGTGTGACAACACACAGGGAGTGTTCCCCACCAGGGAAGCCTTG
GTGTCCAGGGTCTTTACTGTGGCTCTGTCACATGAGCACAGCTGACTGCCC
ATGCGGCCGATCTGTTCCCAGACTCTCCACCGCTACACATCACTCACAGTC
C

SG13S368

GTGGCTCACAGAACTCAGGGAAACACAGCTACCAGTTTATTGCGA
AGGACATTTTAAAGGATAAAAGTAGGCAGATAAAGAGATGCATAGGGCG
AGGTGTGGAAAGGTCCCTAGTGCAGGAGCTTCTGTCCATGTGGAGCGGGG
GTGCACCACCCTCTCAGTACATGAATGAGTTCTCCTTCACCTGCCTATCAG
CCT[C/T]TACATGTTCAGCTCCCCAACCCAGTCCTCTTGGGTTTTTATGGAA
GCTTCAAGACACCCACATTCTTTCCCCAGAGTATAGGGCAAGACCTTCTCT
GGGGAGGGTTTTAAGACCCACAGTCAGAAAGGTGGGGTGGGGTCAAGAT
TAGAGTCCTGCCTTGACGGGCAGGTGAAAGGGGTAGGGGGAGTAGGTGA
GAA

SG13S369

CGGGGGTGCACCACCCTCTCAGTACATGAATGAGTTCTCCTTCACC
TGCCTATCAGCCTCTACATGTTCAGCTCCCCAACCCAGTCCTCTTGGGTTT
TTATGGAAGCTTCAAGACACCCACATTCTTTCCCCAGAGTATAGGGCAAG
ACCTTCTCTGGGGAGGGTTTTAAGACCCACAGTCAGAAAGGTGGGGTGGG
G[G/T]CAAGATTAGAGTCCTGCCTTGACGGGCAGGTGAAAGGGGTAGGGG
GAGTAGGTGAGAAAAATTCTGTTTATTTTTCTTTTTTTTTTGAGACGGAG
TTTCACTCTTGTTGCCCAGGGTGGAGTGCAATGGCACAATCTCAGCTCACT
GCAACCTCCGCCTCCCAGGTTTAAGCGATTCTCCTGCCTCAGCCTCCCG

SG13S370

ATGAGTTCTCCTTCACCTGCCTATCAGCCTCTACATGTTCAGCTCCC
CAACCCAGTCCTCTTGGGTTTTTATGGAAGCTTCAAGACACCCACATTCTT
TCCCCAGAGTATAGGGCAAGACCTTCTCTGGGGAGGGTTTTAAGACCCAC
AGTCAGAAAGGTGGGGTGGGGTCAAGATTAGAGTCCTGCCTTGACGGGCA
[A/G]GTGAAAGGGGTAGGGGGAGTAGGTGAGAAAAATTCTGTTTATTTTT
CTTTTTTTTTTGAGACGGAGTTTCACTCTTGTTGCCCAGGGTGGAGTGCA
ATGGCACAATCTCAGCTCACTGCAACCTCCGCCTCCCAGGTTTAAGCGATT
CTCCTGCCTCAGCCTCCCGAGTAGCTGGGATTACAGGCGTGTGCCACC

SG13S4

TCTTCATTCCACAAAGCTCAGTGTCAAAACATGGGGTTTACACTGG
AAGCTGAGGTCACATCAGTAGCCGGGATCAGGGTCGCCCTAGCTGCCCAA
TGCAGCTCCCAGGCCTCCTGTAAAACCTTGACCTTTGAGGTCATGACAGCC
CTCTCCTGCTATGCTCATAGCTGACCACTGAACTCCTGGACACTCCCTCCC[
G/C]CAAGTTCACAGAGAATGTGGGCACATGCCTTACAGTCTTCCCTTGATC
CAAACTACTGCCTTCATCTTGAGTGACAGCAGCATCTTTTGGATGTCTTGG
CCTGTCTAGCTTTATTTTTTGTGTTCTGCCATCAAGTTGCTACTTCTGTTG
CCATCGTGCCTGTCAGCGCAGTGCAGGCTGTGGTGAAATCCCACGA

SG13S5

TATTTTTTGTGTTCTGCCATCAAGTTGCTACTTCTGTTGCCATCGTG
CCTGTCAGCGCAGTGCAGGCTGTGGTGAAATCCCACGAACTCAGGCATCA
CACTGACCGGGTCTGAGTCCTGTCTCAGTTGTCAGCTAGTTGTGCAATGAA
GGGAAAGGGACCTACACTTTCCAAGCCTCAATTCACTCATCTATGGCAT[G
/T]GTGACAATAATGGAGGTTGATTTAAAGTCCTTTGTAAGAATTAAGAGTT
ATAATAGACATAAAGTGCTGTATCTGGTATACCTAGAAAACATTCCATAA
AAGTTAGTAATTGTTGGTCATGTAATGATGACTCTCTAGGCTAGGATTTCA
GCTTCATTGCATGCACATGGTGCACTCACAGGGCGTGACCTCTCTCT

SG13S389

GGTATACCTAGAAAACATTCCATAAAAGTTAGTAATTGTTGGTCAT
GTAATGATGACTCTCTAGGCTAGGATTTCAGCTTCATTGCATGCACATGGT
GCACTCACAGGGCGTGACCTCTCTCTGTCTCAGTAACCTCATCTGAGGACC

FIG. 8.9

GGGATAATCATACCGCTTCAAAGGGATGTCATAAAGATTAAATAATATGT[
A/G]TAAGGCTGCTTGCATTTAGCTGCATTCAACAAATATTTCTGTATCTTT
CTCCTCATTTCTCCTTACTTTCTTGCTTATTATCTGCTCTAGGTATAGATTTC
AGAGAACTAAGCTTGTTACAATCCTTCATAAAATAACCAGGTTGGTTAGG
GCATTTCCAAGAGTCAATACTGTTTAGTGACTATTCTCTGTTTAAT
SG13S90
      AAGGCTGCTTGCATTTAGCTGCATTCAACAAATATTTCTGTATCTTT
CTCCTCATTTCTCCTTACTTTCTTGCTTATTATCTGCTCTAGGTATAGATTTC
AGAGAACTAAGCTTGTTACAATCCTTCATAAAATAACCAGGTTGGTTAGG
GCATTTCCAAGAGTCAATACTGTTTAGTGACTATTCTCTGTTTAATCT[A/C]
TTTTGATTGTCCAGGGTCATCTTTTGCTATGTCATAGGTTGTTGGCTTCTTC
TAGAGAAGTGAGACGATGGACAAGTTCCAAGTGAGTGAGGCGACTGGTC
AGGATATTCCGCTGAAAAACTCATGTCAGTTCTAATTCGTGATTGTAATTC
AATCACAGCCTGAGAACAGTAGGACTGTAGTTCAAATGCTCTGTT
SG13S390
      CCTGGGTTCAAGCAATTCTCCTGCCTCAGCCTCCCAAGTAGCTGGG
ACTACAGGCACATGCCACCACGCCCAGATAATTTTCGTATTTTAGTAGAG
ACGGGGTTTCCCCTTGTTGGCCAGGGTGGTCTTGATCTCTTGACCTCATGA
TCCGCCCACCTCGGCCTCCCAAAGTGCTGGGATTACAGGCGTGAGCCACC[
A/G]CGCCCGGCCTCTAGAGGATAATTTTTAAATGTGCTTTTGCATTTGGAA
AATGTGATTGGCATTTTTTTCTAATTTTCTAATATGATACGCTGTCGGATGC
TATGGATTACTTAAACCCTCTGGCTACCTAGAAAGATCTTTAAGTGGTTCT
CAACAAGCTTCATACGCAATGTAAATTGTATTATCTCTCAGGATGT
SG13S6
      TGTGATTGGCATTTTTTTCTAATTTTCTAATATGATACGCTGTCGGA
TGCTATGGATTACTTAAACCCTCTGGCTACCTAGAAAGATCTTTAAGTGGT
TCTCAACAAGCTTCATACGCAATGTAAATTGTATTATCTCTCAGGATGTGT
GAGAACATCTGTTTTCTTCTAATGCAGTAAACATATAAGGGTCTCTTG[A/
G]GATATCTTTTAAATAGACTTAATACAACATTCAGGAATGATAACAAAAT
ATAATCACAGTTGTAAGGGAATGTGAGCATTTCATATTAATAACATTGGA
ACCTTATGTTTAATACAGTGTTAAAAGTTGACAAACATGTAGGAGTCAGA
AAATTCAATTAAAATTATCACAGTAATATGAATTTAGCCACATCCTGT
SG13S391
      ACTTAAACCCTCTGGCTACCTAGAAAGATCTTTAAGTGGTTCTCAA
CAAGCTTCATACGCAATGTAAATTGTATTATCTCTCAGGATGTGTGAGAAC
ATCTGTTTTCTTCTAATGCAGTAAACATATAAGGGTCTCTTGGGATATCT
TTTAAATAGACTTAATACAACATTCAGGAATGATAACAAAATATAATCAC[
A/G]GTTGTAAGGGAATGTGAGCATTTCATATTAATAACATTGGAACCTTAT
GTTTAATACAGTGTTAAAAGTTGACAAACATGTAGGAGTCAGAAAATTCA
ATTAAAATTATCACAGTAATATGAATTTAGCCACATCCTGTGTTAGTTATG
AAATCCATTTAACACCACAAACAGTAATATTTTAGCCAGTTTATTCA
SG13S392
      CATTTAACACCACAAACAGTAATATTTTAGCCAGTTTATTCAAAA
GGAAAACAGGAACTAAACCACTTTCATGCAATATATACTCTGTTAATGTG
GTCAGGCTAATTTTGCTGGGGGAAGGAACTTAACTTTTGAATATTTGAATG
CCCAGTCATTTAATCTGAATATCCTATTTCCTTGCATGTTGCAAAATTTTT[
G/T]TCAATAAAAGGCAGAAAAGAAATCTCTTCTCCATGCTCATCCCTAA
GAGAATGGGTTGTCTGTACCCTGAGAGCATTTTATGGAGGGGACAACCAC
TTTTCTAATTTTCCTTCCCACTTCTCTGTGGGCACAAATGCTCTTTGGTTGA
AAGAGTTGTAATTCAGTCCCAAGATGAGGTGTGGTTACTGCATCCCTA

FIG. 8.10

SG13S371
TCAATCCATGCTCCACACTGCAGCCAGAGTGCTCTACAATGCAAAT
CCATTTGTGAGACTCCTCCTCTTAAAATCCTCAAGTGGCTTCTCTTTGCCCC
CAGGATCATTTTGAAACTCCTTAATGGAAGAGGCATGGCCCTTTGGGATG
TGGTTCCCCAACCCCTCCCACATCATCTTTTCAATCAGATTTCCCACTAA[A
/G]TGGAAATTTTTTCAGGTCCTCAACTTTATGGTGACTTTCTCTTGCTCAGG
ATCTTTGAACATACTGTTTCTTCTTTCCTTTTGTATTTGCCAAGACAACACT
TCCTCTGGTAAGATTTTCCTGACATCCTCTATAAAAAAGATTGAGATAGT
TGACTACCCAAAATGTTTCCCATTCATTCCAAGCTCTATTCAAG
SG13S372
AACACTTCCTCTGGTAAGATTTTCCTGACATCCTCTATAAAAAAG
ATTGAGATAGTTGACTACCCAAAATGTTTCCCATTCATTCCAAGCTCTATT
CAAGGCAGTAAAGTGCCCGGCTGACAGATTGCATTCCTCATCTTTTCTGAA
GCTAGCAATGGCCATGCAACAGCATTCTGGCCAATAAGATAGAAGTCGAA
[A/G]TTGAAGGGTGGGATTTCCAAGAAAGCTCGTTGAAGACATAATTCCTC
ATTTCACTTCTTACTCTTTCTCTTTCCTGCTTCCTAAAATGCGGTGCAGATG
GCAGACACTTCAAAGCTGTCTCAGGCAATCAGGTGATGTTAAGGCAGAAA
CCAGCTTTATGATGGGTAGAACAGGAAGAAAGAAGGCACCTATGTTCT
SG13S393
CCTACAAATCTCATGTTGACATTTTATCCCTAATATTGGAGGCAGG
GCCTAGTAGGAGGTGTTTTGGTCATAGTGATAAATGGCTTGGTGCCGTTCT
CACAGTAACGAGTGAGTTTTTATTCTAGTGGTTCCTGCAAGAACTGATTGT
TAAAAGAGCTTGGATCCTTCCACCCCTCTCTCACTCTTGCTTCCTCTCTC[A/
T]CACCTTGTAATCTCTACAAGCTCTTCACCTCCCCTTCTCCTTTTGCCATA
AGTGGAAGATTTCTGAGGCCTCACCAGAAGCAGATGTTGGTTCCATGCTT
CTTGTACAGCCTGCAGAACCATGAGCCAAATCAACTTCTTTTCTTTATAAT
TATCCAGTCTCAGGTATTCCTTTATAGCAACACAAATGGACTAAGA
SG13S373
GTTGTTTCCAGCTTTGAACTATTTTGAATCCTAAAAGACTGCCAGTT
TTGAATGAGACCCCAGAACAATGAATGTAGGCTCTGTATACAAGTTCAGG
CTGCTGGGCAACTTAGGCCTTAAGACACAACTCTGCCACTTAGGCCTTAA
GACACAACTGACATGATGGTGCTTAAAGTGGCTGTGATGGAAAAGGAGG
CT[A/G]TTTGGAGCCTTTGGAGTGCCTTTATAGGTGAACCCCAGCATAGCA
CCTAATGATTTGGAGCAAAGCTGTGTCATTCCCCAAAGATAACTATTCGCC
TTTTGAGAAACATCTTCTAGCTACTATCAATAATAAACACAGAATGCATC
ACCATGGGCCACCGTGTTGTCTTTTGACCTGAGTTTCCATTGTGAACAAGA
SG13S374
AACTCTGCCACTTAGGCCTTAAGACACAACTGACATGATGGTGCTT
AAAGTGGCTGTGATGGAAAAGGAGGCTGTTTGGAGCCTTTGGAGTGCCTT
TATAGGTGAACCCCAGCATAGCACCTAATGATTTGGAGCAAAGCTGTGTC
ATTCCCCAAAGATAACTATTCGCCTTTTGAGAAACATCTTCTAGCTACTAT
C[A/G]ATAATAAACACAGAATGCATCACCATGGGCCACCGTGTTGTCTTTT
GACCTGAGTTTCCATTGTGAACAAGAGTCATTTGATCCAAGGCAGAAAGT
TGGGTGCACACAGCAGTGTTCCATCATCAAATGGAATATGAGATTGGGCC
CAAGTAGGTCCTGCAGACACAAATAAGTTGCAAGAGCAAGTAGTACAGG
CG
SG13S375
GAAAAGGAGGCTGTTTGGAGCCTTTGGAGTGCCTTTATAGGTGAAC
CCCAGCATAGCACCTAATGATTTGGAGCAAAGCTGTGTCATTCCCCAAAG
ATAACTATTCGCCTTTTGAGAAACATCTTCTAGCTACTATCAATAATAAAC

FIG. 8.11

ACAGAATGCATCACCATGGGCCACCGTGTTGTCTTTTGACCTGAGTTTCCA
[C/T]TGTGAACAAGAGTCATTTGATCCAAGGCAGAAAGTTGGGTGCACAC
AGCAGTGTTCCATCATCAAATGGAATATGAGATTGGGCCCAAGTAGGTCC
TGCAGACACAAATAAGTTGCAAGAGCAAGTAGTACAGGCGCTTGGCCTGG
CCAGTACTGTTGCCAAGTTGACTGCTTCCCCTCAGTCTGCATCTGTGGCTT

SG13S376

CCCCAAAGATAACTATTCGCCTTTTGAGAAACATCTTCTAGCTACT
ATCAATAATAAACACAGAATGCATCACCATGGGCCACCGTGTTGTCTTTT
GACCTGAGTTTCCATTGTGAACAAGAGTCATTTGATCCAAGGCAGAAAGT
TGGGTGCACACAGCAGTGTTCCATCATCAAATGGAATATGAGATTGGGCC
CA[A/G]GTAGGTCCTGCAGACACAAATAAGTTGCAAGAGCAAGTAGTACA
GGCGCTTGGCCTGGCCAGTACTGTTGCCAAGTTGACTGCTTCCCCTCAGTC
TGCATCTGTGGCTTCATGGGGAGTTTCCTATGACCACTTGATGGAGGAAA
AAACAAATTGGAGCATAGTTTATAGTGCTGGTACTACCCAAAGTGGCTAG
CT

SG13S394

GTCCGTGAGTTACAGATCTACACAAAATCACAGAGAGTGGTTAATC
GTTTAGTCTGATGGTCAGGGACTTCCAAGAGACATGATTAGAAAACTGGT
GACAAGGAGTCCTGGGGAAGAGGCATATGGATACCTCTGAACACACACA
AAACATGAGAATATGTATCCCATATGAATGTTAACCAAAGAGCAGCCACA
ACA[C/G]AAGAGGATTTTAAAATCAGCTGAATAAGATGATTCATTCTGACA
GCATCAGCTAGTCTCTTTCCCCAGCCACTGTTGCCCAGTGGGCTTACATAT
ATCATGGCCATGGGGGCAGGGCTATGTATGGACACAGCAACATGAATTTC
CACTCATCAAGGCCAATTTGGCTCCAGCCATTGCTGAGTGCTCAGCCTGCC
A

SG13S25

ACATGATTAGAAAACTGGTGACAAGGAGTCCTGGGGAAGAGGCAT
ATGGATACCTCTGAACACACACAAAACATGAGAATATGTATCCCATATGA
ATGTTAACCAAAGAGCAGCCACAACAGAAGAGGATTTTAAAATCAGCTG
AATAAGATGATTCATTCTGACAGCATCAGCTAGTCTCTTTCCCCAGCCACT
GTT[A/G]CCCAGTGGGCTTACATATATCATGGCCATGGGGGCAGGGCTATG
TATGGACACAGCAACATGAATTTCCACTCATCAAGGCCAATTTGGCTCCA
GCCATTGCTGAGTGCTCAGCCTGCCAAGATAGAAATCTACGCCAATATGG
CACCATTCCCTGGGCTAGAAAACCAACTGGTGGAAGGTTGATTACATTGG
ACC

SG13S395

GGGAATACAATGGTGGTTCCACTAAACTGACAGCTGAGTTTGCCAT
CTCCTCGTGCCAGTGAATACACAAGCAAGGAAGGGGGTTCCTTTCTCACC
TAGGGTGACTGATCCTAATTACCAAGGAGAAATTGGACTGCCACTTCACA
ATGAGGGTGAGGAGTATGTACTCTATGTGTCTGTGATTAATGTCAATAGA
AA[A/G]TGACACCAACCTAGTACACAGAGGACTGATCATGGTCCAGGCCC
TTCAGGAATGAAGATTTGAGTCACCAGGCAAGGAACTTGGACTCACTGAG
GAGGGCATATTCCAAGGAGAATATTTTATCTATGTCCATCTATGTCCATCT
ATATTCCATCTGTGTTCCCCTTGGAATTCCTATTCATGAACATGGGGAATT
C

SG13S396

TATAGAATGAGTAGTGGAAGGTAGTTATAAATGTAAGTCAAAAAC
CACACAACCAATTTGAGAAATGAGGAAGGTAATAGTGTTGAATATGTCTT
CTTTATCTTGATATAAATGTATTTGTGCATATATTAACCAGTTTATTTATTT
ATTATTATTTTTTGAGATGAGCTCTCGCCATGTTGCCCAGGCTGGTCTTGA[

FIG. 8.12

A/C]CTCCTGGGCTCAACTGATTCTACCATTTAGTCCTCCGAGTAGCTGGGA
CTACAGGCATGCACCACCATACCCAGCTGACCAGTTTTTCCTATTCCTCT
ACTTAATTTCTCTACTATACAACATAATATGTGTTAATGGTAGTTAACTTT
ATATCTCAGTATTAAGTCACAAGATATCAAAAAGGGAATGCGACTTA

SG13S397

ATGTCTTCTTTATCTTGATATAAATGTATTTGTGCATATATTAACCA
GTTTATTTATTTATTATTATTTTTTGAGATGAGCTCTCGCCATGTTGCCCAG
GCTGGTCTTGAACTCCTGGGCTCAACTGATTCTACCATTTAGTCCTCCGAG
TAGCTGGGACTACAGGCATGCACCACCATACCCAGCTGACCAGTTTTT[C/T
]CCTATTCCTCTACTTAATTTCTCTACTATACAACATAATATGTGTTAATGG
TAGTTAACTTTATATCTCAGTATTAAGTCACAAGATATCAAAAAGGGAAT
GCGACTTAGTTACAAGCAGAATGAATATCACTCAAAGATGAATAAAGAG
AAGAGGGTTAGTGCATTTCTGTTGGATGAGAGAAAGTTTCATTGTT

SG13S377

GCAGTGGCGTGATCCCAGCTCACTGCAATCTCTGCCTCCTGGGTTC
AAGTGATTCTCCTGCCTCAGCCTCCCGAGGGGCTGGGATTGTAGGCGTGC
ACCACTATGCCCATCTAATTTTTGTATTTTTAGTAGAGATAGGGTTTTGCC
ATTTTGGCCAGACTGTCTTGAACTCCTGACCTCAGGTGATCTGCCTGCCTC[
A/G]GCCTCCCACAGTTTTGTGATTATAGGCATGAGCCACCGTGCCCGGCCT
TAACCTTTGTTTTCTTACACAACACACTACGTGATGTTTTCCACATGCATG
GGTCATTTGCTTCATTTACGTACAAATGCATAAGCAATATACTGTGTGGTG
TGAGTTTGTGATGGGAAAAGGAAGAAGTTTTGCGGATACTACACTGG

SG13S189

GCCCAGGCTGTTCTCCAACTCCTGGACTCAAGCCATCCTCTAGCCT
CGGCCTTCCAAAGTGCTGGGACTATAGGCGTGAGCCACGGTGCCAGGCCC
TTGACCACATTTTTAACCCCTCTGAACCTCAGTTTCACTTTCTGGGCAATG
GGAGGGGGGTAATTTGTCCCTCAGAGGGTTGCACTGAGGGCAAATGTGA
G[C/G]CTCTGGGTACAATGCCCAGTACAGACTAGGTCCCCACGACACAGCC
GCTCAGCGGCTCCGGATTCTGGGCTGCTCTGGACTGCGGCCAGGCGGTCT
TCTGCGGGAATCCGGGCAGGCAGGGCGGGCTGCGCTCCCCTCCCCGGCTC
TCCCGGTGCCCCTTGTCTTTTTGTTCTGTCTCAGCAGCTCTCTATTAAGAT

SG13S100

TTTTTGTTCTGTCTCAGCAGCTCTCTATTAAGATGAATGGCATTTCC
AAAGGCTTCACCTCTGATAAGTGTTCCTCTGCAGCTGCAGCCAGAATCTTA
ATGTGCGCGCTGTAATTTAATGGCCGTCTCGGCTATTAACACGCTCTTCTC
GGGTGAAGTGGACTCCCTCCATCCCCGGGCCTCTGCACGTGCTCTGCGC[A/
G]CTGGCTGGGGGTGACTCCAAGGAGCTCAGAGCGGGGTGCCCGGCACCT
CTCGCCAGGCGCCTTTCGACCTTCTAAAGCGCGAATGGCTGGACTTTTCTC
CATGTGTGGGGCCCCAGAAGGTGTGGGGCCCCAGAAGGTGTGGGGTCCC
TGCGTTCCACGGAGCCCGGAAGGTTTCCAGTGATGGTGGGGGCTGACC

SG13S398

GGAGCCCGGAAGGTTTCCAGTGATGGTGGGGGCTGACCACGTTGG
TCCCCGTGGGTGCTGTTTTCATGTGCCGGCAGATTGGGATGAGTTAAAAG
ACAGAAGCGTGTAGGATAGAGAAACTTCTTTAAAAACTGGAAATTTTAAT
CTGGGGATTATAACTATTGGACAGTCAAGTGCAAGAGTGAATACACTTCT
CA[C/G]TCCCTCCTCCCAATTTTTATTTGCGGGATTAGTCAGTCCCCCTCTG
CCACATGATAATTGTGAGAACTACCAGGGTCTTCATTCTCCTGCCATCTGG
TTGACCTCTCCAAGAATGGACACCCGGGCAGCCTGGGCCAATGAGGCTGT
CCTAAGAGTTTAGATGAGAGAAGTCAGTCTTTGACAGGTGATGGAAGCTG

FIG. 8.13

SG13S94
CAGTGATGGTGGGGGCTGACCACGTTGGTCCCCGTGGGTGCTGTTT
TCATGTGCCGGCAGATTGGGATGAGTTTAAAAGACAGAAGCGTGTAGGAT
AGAGAAACTTCTTTAAAAACTGGAAATTTTAATCTGGGGATTATAACTATT
GGACAGTCAAGTGCAAGAGTGAATACACTTCTCACTCCCTCCTCCCAATTT
[C/T]TATTTGCGGGATTAGTCAGTCCCCCTCTGCCACATGATAATTGTGAG
AACTACCAGGGTCTTCATTCTCCTGCCATCTGGTTGACCTCTCCAAGAATG
GACACCCGGGCAGCCTGGGCCAATGAGGCTGTCCTAAGAGTTTAGATGAG
AGAAGTCAGTCTTTGACAGGTGATGGAAGCTGTAAATGTAAAACTCCA
SG13S101
TAAGAGAAGCTGAGAGAGAGCGAGAGGAGAGATTGGAAGAAAGA
CAGAGACAGAGGTAGAGAGAAGGGAAAGAGAGAGAGAAAGGGACAGAA
GAGAGAGAAAAAAGAGGGGGCCGGGCGCGGTGGCTCACGCCTGTAATCT
CAGCACTTTGGGAGGCCGAGGCGGGCAGATCACGAGGTCAGGAGATCGA
GACCATCC[C/T]GGCTAACACGGTGAAACCCCGTCTCTACTAAAAAATAT
AAAAAAAATTAGCCAGGCGTGGTGGTGGGTGCCTGTAGTCCCAGCTACTG
AGGAGGCTGAGACAGGAGAATGGCGTGAACCCGGGAGGCAGAGCTTGCA
GTGAGCTGAGATCGCGCCACTGCACTCCAGCCTGGGCAACAGAGCAAGAC
TCCGTCTCA
SG13S95
TCCACCAGCAGCTTTTCTGAGTCTCCAGCTTGCAGATGGCAAACCA
TGAAACTTCATGGTGTCCATGAGCATGTGAACCAATTTCTATTATAAATCT
GCAATATATATATGAGGAGACTTATTTATATATTGGTTCAGTTTCTCTG
GAGAGCCTTGGCTAATATAAAGTCTATACTCTACAAAGTGCCCTAGGTAC[
G/T]CAGGGAGTACCCAAGTGTGTCATGACCAGCCCGACAGCCCTGGCTGC
TGGCTTCCCCGCACACAACTCTGCACGCTGCCTTCATCAGCCTTTCTCTCT
CAGCTGAACCGAGGGCATTGAAGCGGGCCTCTGGCACTGTACCTATGAGG
GAGCAATATCTTCCCCTACACTGACCTCTTCCGTGCCGAGATGCAGCCC
SG13S102
GCCTCTGGCACTGTACCTATGAGGGAGCAATATCTTCCCCTACACT
GACCTCTTCCGTGCCGAGATGCAGCCCTCCCTGCTGCCACTAGTTACAGTG
GTCCATGTTCCCTTTCAAAGTGAAGTTTTGATAAAAGCACCTCTTAACCAA
TGCCAAATAGCTAAGTCTGGGACAAAGATTGCAGGTATTTTGCATTTTCC[
A/T]TGTAACCTCAGAGGGATTGCCATTCACACTGATCTGAGCTGCAGAAT
ACCAGGCAGCCACCTCACCCACCCAGCAGGTCCACTCTTATACTTTCTCAG
AAAGCACAGCCACTCTACTCTTATTCAGTTGAAAAGAATTTCCAGGAAGG
TGTTTCTGCGATTGCCTCAGAAAGTCAGTTCCCTTTGGGAATTTCCCT
SG13S103
TACTTTTCTCTGAAGAAATGGAGATATCAGCTGTCCCTCCCCACTG
CCATTTATTCCTTCCTTCATTCAAACCTTATGTGGCTGCTACTTACCGTGTG
TTAAGTGTTCACTTTTTTTCTTGGAATTCAAAAAAAGAAGGACAGTATTTG
GGGCACAGATCTTTTGGTGTTCTATACATTTTTTAAAGTTTCATTTTA[C/T]
ATTTGTGTGTGCGTGTGTGTGTGTGAGACAGTCTTGCTCTGTTGCCC
AGGCTGGAGTGCAGTGGCATAATCATTGGCTCACTGTAGCCTCAAAGTCC
TGGGCCCAAGCAATCTTCCCACCTCAGCCACCCAAAATGCTGGGGTTACA
GGTTTATGCCACTCTGTCTGACCTGAAAGTTTGGGTTTACTTTCC
SG13S104
GCATAATCATTGGCTCACTGTAGCCTCAAAGTCCTGGGCCCAAGCA
ATCTTCCCACCTCAGCCACCCAAAATGCTGGGGTTACAGGTTTATGCCACT
CTGTCTGACCTGAAAGTTTGGGTTTACTTTCCCTTCTTTCTCTTTGCTGAA

FIG. 8.14

GTCAGAGATGATGGCAGCTTCCAGATTCTCTGGTGCCTGTGCTGGGCTC[A/
G]TGCTGGTCATGGTCTTGGGTCCAGGATTCATTCTGGAGACTCTCAGGGA
AGTTTCCCATGACAAGGAAATGTAGGAGAGTGTGCTGGCTTTGCGTGCTC
CTCTGCCAAGCCCTGCTTCTCCTGGTGGGACACACTGAACCACAGCCAGG
GCATTTTGGTGGTTAGTTAAAAAAAAAAAAAAAAAAAAAAAAGGAAG
SG13S191

CTTCAGAAATTGTAATGATGAAGAGTGCAAGCTCTCACTTCCCCT
TCCTGTACAGGGCAGGTTGTGCAGCTGGAGGCAGAGCAGTCCTCTCTGGG
GAGCCTGAAGCAAACATGGATCAAGAAACTGTAGGCAATGTTGTCCTGTT
GGCCATCGTCACCCTCATCAGCGTGGTCCAGAATGGTAAGGAAAGCCCTT
CA[A/C]TCAGGGAAGAACAGAAGGGGAGATTTTCTTTGATGGTTGTTTGGA
AGTCAGGCTTAAACAATTGTGTCTGTGTGTGCGCATGCACAAACACTTTTA
CCTTATCTTTATTTTCTTCTTTTATTTGAATGTATAGGGTTGTGTGTATTTC
TGTGTAAATTTGGGGTTTTCCTCCTCTTAGTCTTTCACTTTGTGGTG
SG13S105

TTTTCTAACATCTGCAGTGCAATTGAAGTTACCAGTCATCTGCAGTC
TAAAAAGAAAGTGATTTTGGGAGGTGCGTAGAAAAAATCATCTTATTATT
TTTCCTCTATATTACTTTTTCTTTTTTCTCCTGAAGAAACTTTTTTTTTG
GTGATACCTTCTTTTTCTCTAGCACGTATAATTTTGGAAGCATTTTTC[A/G]
TATGCAGTGTATACTTCAGAAAGAGAGAGAGAGAGAGGAAAATTGTCCTG
TTCAGCGTTTGCATTTCCATTATTCCTGCTATTAGTTAAAAACAACAACAA
CAACAAAAAACAAGCAGGATACCTAGATCTGGAAAAGGGAGAATTGTGT
AGAGCTGTCTTCCTAAAGTTCTGAGTTAGGGCTGCCTCAGACCACTT
SG13S106

TTTTGGAAGCATTTTTCATATGCAGTGTATACTTCAGAAAGAGAGA
GAGAGAGGAAAATTGTCCTGTTCAGCGTTTGCATTTCCATTATTCCTGC
TATTAGTTAAAAACAACAACAACAACAAAAAACAAGCAGGATACCTAGA
TCTGGAAAAGGGAGAATTGTGTAGAGCTGTCTTCCTAAAGTTCTGAGTTA
GG[A/G]CTGCCTCAGACCACTTTCATAACTATCTCCAGTGGCTTTGTGTTTT
ATATTTATTAAGATAGAGAAAAAAGAGTAATTACTAAGGGCAGCTGCTG
TAGCTTTATGGTGATTACTGAACATTGACATGCTGTCACGTTTTGGAACT
TTGAGTATTTAATCACTTTGGGATATTCTATTTTCCCCCATCTTGAGTGT
SG13S107

GGAACTTTGAGTATTTAATCACTTTGGGATATTCTATTTTCCCCCAT
CTTGAGTGTGGACAGATGCTGGTGATGTAGCCTTCTGGGCACAGAGCAAG
CCTCCCCCTCAGCCTCTGCACCAGAAAGGCTCAGCTTCACACACTCCAAGT
ATGTTTCTACAAGAACTACACTTTGTGGCTTTCTGACCCAAACATTTTT[A/
G]TACTAAATTACACACAACAAAGTTGTAGCTCAGAGAGGGAACAAATGG
CTTATTTAGGCCACCATTTTCTTGAGCCATTATGATTTCACACAGGGCTCC
CTTGGCCCTGTAAATTGGCAAGGATTCCATTATTCAACCCGCATACATGTA
CAGAGACCCTGCTCTGGCCCAGATAGTATTCTGGGTACAGGCGGATA
SG13S108

TGTGGACAGATGCTGGTGATGTAGCCTTCTGGGCACAGAGCAAGCC
TCCCCCTCAGCCTCTGCACCAGAAAGGCTCAGCTTCACACACTCCAAGTAT
GTTTCTACAAGAACTACACTTTGTGGCTTTCTGACCCAAACATTTTTATA
CTAAATTACACACAACAAAGTTGTAGCTCAGAGAGGGAACAAATGGCTTA
[C/T]TTAGGCCACCATTTTCTTGAGCCATTATGATTTCACACAGGGCTCCCT
TGGCCCTGTAAATTGGCAAGGATTCCATTATTCAACCCGCATACATGTACA
GAGACCCTGCTCTGGCCCAGATAGTATTCTGGGTACAGGCGGATAGAGCA
GGAAACAAAACAGCTACAGTGATGGACAGGTCAGCCTGCAGCAATGCC

TTTTTATACTAAATTACACACAACAAAGTTGTAGCTCAGAGAGGGA
ACAAATGGCTTATTTAGGCCACCATTTTCTTGAGCCATTATGATTTCACAC
AGGGCTCCCTTGGCCCTGTAAATTGGCAAGGATTCCATTATTCAACCCGCA
TACATGTACAGAGACCCTGCTCTGGCCCAGATAGTATTCTGGGTACAGGC[
A/G]GATAGAGCAGGAAACAAAACAGCTACAGTGATGGACAGGTCAGCCT
GCAGCAATGCCTGCAGTCTCTGCAAAGGTAGCTGTATGGGTGGGCAGGTG
GCTAGCACTTATTCAGCTCTGGAAGGATCTCCCTCTGGCCTCTCCCTGA
CACCCATCAATAAAACTGAGGAGCATCGGTGGACAGGGGACCTTGTGCCC

SG13S110

TTTTCTTGAGCCATTATGATTTCACACAGGGCTCCCTTGGCCCTGTA
AATTGGCAAGGATTCCATTATTCAACCCGCATACATGTACAGAGACCCTG
CTCTGGCCCAGATAGTATTCTGGGTACAGGCGGATAGAGCAGGAAACAAA
ACAGCTACAGTGATGGACAGGTCAGCCTGCAGCAATGCCTGCAGTCTCTG
C[A/G]AAGGTAGCTGTATGGGTGGGCAGGTGGCTAGCACTTATTCAGCTCT
GGAAGGATCTCCCTCTGGCCTCTCCCTGACACCCATCAATAAAACTGA
GGAGCATCGGTGGACAGGGGACCTTGTGCCCCCTCCCTGCCTGTGCAGTT
GGGGCTGAACCCAGCTACGAAGTTTGAGCTCACTCTCTCCAGCTCCCTCTC

SG13S111

GACAGGTCAGCCTGCAGCAATGCCTGCAGTCTCTGCAAAGGTAGCT
GTATGGGTGGGCAGGTGGCTAGCACTTATTCAGCTCTGGAAGGATCTCCC
CTCTGGCCTCTCCCTGACACCCATCAATAAAACTGAGGAGCATCGGTGG
ACAGGGGACCTTGTGCCCCCTCCCTGCCTGTGCAGTTGGGGCTGAACCCA
GC[C/T]ACGAAGTTTGAGCTCACTCTCTCCAGCTCCCTCTCAATTCAGAGCT
GAACTGTGGGAAGCTTCAGAGCTCTCTGTTTCAAGGACAGGTTCTCCTCAC
CTCTCCTAATGGAGGTGCACCAGGGAACTGGCCCTGCTCTGCCCAGGGCT
TTCTCCTGGACTTTGCCATCATGGTCTAGCAAACCCTGTTCAGATTGAGG

SG13S112

CACTCTCTCCAGCTCCCTCTCAATTCAGAGCTGAACTGTGGGAAGC
TTCAGAGCTCTCTGTTTCAAGGACAGGTTCTCCTCACCTCTCCTAATGGAG
GTGCACCAGGGAACTGGCCCTGCTCTGCCCAGGGCTTTCTCCTGGACTTTG
CCATCATGGTCTAGCAAACCCTGTTCAGATTGAGGTGAGTGGTGAGATTT[
C/T]GAATTCTTTTTGACAGATAGGATTAAGTCTTCTTCTGTGGGACAAGTG
GGAGGTAGAGGTAAGATTAAAGATGGCCAAATGTCTGAGTCCTGACAGCC
ACAATATGGAGATCTAGACTTTTACAGACCACAGGGCACAGGGGCCTCA
CTAACAGAGTTCCCGGAAGTGATGAGTGTGCTGGGGGCTTCCTGGTTGA

SG13S113

TAGGATTAAGTCTTCTTCTGTGGGACAAGTGGGAGGTAGAGGTAAG
ATTAAAGATGGCCAAATGTCTGAGTCCTGACAGCCACAATATGGAGATCT
AGACTTTTACAGACCACAGGGCACAGGGGCCTCACTAACAGAGTTCCCG
GAAGTGATGAGTGTGCTGGGGGCTTCCTGGTTGAAGAGACACTAGAATGG
AC[C/G]AGCTGGGAGCTAATTTTTGGGCTGGAGTGTGATGGCCTGCACAT
CACTGCCTCTGTCCCTCCATTGTCACAGCTGCCCCTTAGGAGCCAGCTGAG
GCAATTTGTGGTCAGAGTGACTTTGCACAGTTGTCCTGCCTGTGTTCAGGA
AGGGAGTTTCTGTGGTCCCTTTGAAACCACAGAAGAGCCCCTCGTATAGC

SG13S114

AGTTGTCCTGCCTGTGTTCAGGAAGGGAGTTTCTGTGGTCCCTTTGA
AACCACAGAAGAGCCCCTCGTATAGCTCTCAATGGAGGGGCAAAACATT
CAAATAACTCAGGAGATAACACAACTATTTGTTTTTAACTGTGAGTTTTA
GGCAATCACAAAGATCCAGATGTATGTCCAAGCCTCTCTTTGCAATTCTA[

FIG. 8.16

A/T]TTAACCTCAATGTTGCAACCATAGACCTACCTTACAGAGTTCAAAAA
AATATGCAAAAACCCTGCCTTTCTTCTTCCTCATACCCCAAAATGCCATTC
TGAACATTTCCTGTTAGTTAAAAAAGATTTCCATGGTGTTACCAGGCACT
GTACACAGTCTGTGTCCCAAGACAAGGAGGTACAGTTCCACATGCGCC

SG13S115

AGGGGGCAAAACATTCAAATAACTCAGGAGATAACACAACTATTT
GTTTTTAACTGTGAGTTTTTAGGCAATCACAAAGATCCAGATGTATGTCCA
AGCCTCTCTTTGCAATTCTAATTAACCTCAATGTTGCAACCATAGACCTAC
CTTACAGAGTTCAAAAAAATATGCAAAAACCCTGCCTTTCTTCTTCCTCAT
[A/T]CCCCAAAATGCCATTCTGAACATTTCCTGTTAGTTAAAAAAGATTT
CCATGGTGTTACCAGGCACTGTACACAGTCTGTGTCCCAAGACAAGGAGG
TACAGTTCCACATGCGCCCATGACTGGGTTGGGCTCTGCACTCTCTATA
CTTTGAGAGCCTGATTTTCTGTGATTGGGCAGAGCTGGCCCACCTGGTG

SG13S116

TCTGCACTCTCTCTATACTTTGAGAGCCTGATTTTCTGTGATTGGGC
AGAGCTGGCCCACCTGGTGCAATGTCCTCCTCTGCCTTTCAAACATGTTTT
AGTCATCAAGATCTTCAAATTTGTAACCCTTCCAGCTTGATCCAGCAGAA
TGCAGATTTGGAAAAACAGAACGAGTTTAAAATACATGATTCTAAGAAA[
C/T]CTGGACCAGAACTATCAAAACTTGGTTTCCCAGAGAATATAGCAAAT
GGGCTCATTGGCCAATACTATGACATTGGCTTTTGAGAAAAGAAAGGCTT
TATTGCAAGGCTGGCCAGCAAGGAGACAGGAGTTGGGCTCAAATCTGTCT
CCCCAGTTTGGGGCTTAGGGCAAGTTTTAATTACACAGACGCATTTCTTA

SG13S117

AACCCTTTCCAGCTTGATCCAGCAGAATGCAGATTTGGAAAAACAG
AACGAGTTTAAAATACATGATTCTAAGAAACCTGGACCAGAACTATCAAA
ACTTGGTTTCCCAGAGAATATAGCAAATGGGCTCATTGGCCAATACTATG
ACATTGGCTTTTGAGAAAAGAAAGGCTTTATTGCAAGGCTGGCCAGCAAG
GA[A/G]ACAGGAGTTGGGCTCAAATCTGTCTCCCCAGTTTGGGGCTTAGGG
CAAGTTTTAATTACACAGACGCATTTCTTATGAGTAGCAGGCAGAGAGCC
TCCAACTTCTTCTGCCTAGGTACCAGCAGCTTAGACATGATGCAAACCTGG
GAAGCACATACTGTATTTGGAGAAAGTGATTGGGAAGAAATGTGAGCTGA
G

SG13S118

TACATGATTCTAAGAAACCTGGACCAGAACTATCAAAACTTGGTTT
CCCAGAGAATATAGCAAATGGGCTCATTGGCCAATACTATGACATTGGCT
TTTGAGAAAAGAAAGGCTTTATTGCAAGGCTGGCCAGCAAGGAGACAGG
AGTTGGGCTCAAATCTGTCTCCCCAGTTTGGGGCTTAGGGCAAGTTTTAAT
TA[C/T]ACAGACGCATTTCTTATGAGTAGCAGGCAGAGAGCCTCCAACTTC
TTCTGCCTAGGTACCAGCAGCTTAGACATGATGCAAACCTGGGAAGCACA
TACTGTATTTGGAGAAAGTGATTGGGAAGAAATGTGAGCTGAGGGGAGG
GGCTCAGTGCCCCTGAGCTACACTTAGTGATGGCAGAGGAAGGATGTCCT
CCC

SG13S119

TGGGGCTTAGGGCAAGTTTTAATTACACAGACGCATTTCTTATGAG
TAGCAGGCAGAGAGCCTCCAACTTCTTCTGCCTAGGTACCAGCAGCTTAG
ACATGATGCAAACCTGGGAAGCACATACTGTATTTGGAGAAAGTGATTGG
GAAGAAATGTGAGCTGAGGGGAGGGGCTCAGTGCCCCTGAGCTACACTTA
GT[A/G]ATGGCAGAGGAAGGATGTCCTCCCGCAGGAGGCTGTTCCACATCT
GCTCTGGTTGTAGGGGGAGCTGGCAGGCATTAGCAGCGGCCTCTTTCCCC
CAAGAGAGGCAGCCTCCTCCAAGTTTTGGCGACATTATGGCCCTGCAATC

FIG. 8.17

ATAAGGGTTTGTGAGCATAGTGCTAAGGAGGGAAATGGAGCTGCTGTTACTA

SG13S120

CCTCCTGAGTAGCTAGGACTACAAGCATGTGCCACCACGCCCAGCTAATTTTTGTATTTTTAGTAAGGACAGGGTTTCACCATGTTGGCCAGGTTGGCCTCCAACTCCTGACCTCAAGTCATCCTCCTGCCTCGACCTCCCAAAGTGCTGGGATTACAGGCATGAAACCAGCCTAGAAATACATACTATTATTTATTC[C/T]TGTTTTACAGATAAGCAAAGTGAGTCATGGAGAATTTGGTTGAAAGTCCCAAGGTCAGGAGTCGTGAAGCTGGGATTAAAACCTAATCATCTGACTTTAGAGAGTAGACACTTGCTCCATGCATATTGCCTCCAATTCATTCATTCAAGCACTCCTGCTCAAGAAGTTCTTTCTTATGTTGAGCTGAAATCTGCAG

SG13S121

TCATCTGACTTTAGAGAGTAGACACTTGCTCCATGCATATTGCCTCCAATTCATTCATTCAAGCACTCCTGCTCAAGAAGTTCTTTCTTATGTTGAGCTGAAATCTGCAGCCCTATGCGTTTTACCCAGCAGTCCTGGTGCTGTTCCCTAAAATCACTTAGACTGTGCCTGCTCTTTCTGTGTTTACAGTGTCAGCT[A/G]TAATATCCCCTCTTCGGCCTAACGTTTCTGAAGTCCCTTGCCACTGGGTCTCCTCTCCTCTTCCTGTGTTCTTTCTAAGAACACCTATGCAGATAGGTGTCTTCTGTACAGGGAAGCTGTTCCTGAGATCCGGGCATCGACTCTGTTAGAATAATCTACGTATGAGTTATTTTTTGAGAACTATGTGTCATTGCT

SG13S122

ATGTTGAGCTGAAATCTGCAGCCCTATGCGTTTTACCCAGCAGTCCTGGTGCTGTTCCCTAAAATCACTTAGACTGTGCCTGCTCTTTCTGTGTTTACAGTGTCAGCTGTAATATCCCCTCTTCGGCCTAACGTTTCTGAAGTCCCTTGCCACTGGGTCTCCTCTCCTCTTCCTGTGTTCTTTCTAAGAACACCTAT[A/G]CAGATAGGTGTCTTCTGTACAGGGAAGCTGTTCCTGAGATCCGGGCATCGACTCTGTTAGAATAATCTACGTATGAGTTATTTTTTGAGAACTATGTGTCATTGCTGACTCATATTAACTCTGTGGTTAACTAAAATCTCAAGATCTCTTTATGTTTGTTGAGAAACTTATTTAACTTCTCTGGCCCTCCGTTTCC

SG13S123

GTCCTGGTGCTGTTCCCTAAAATCACTTAGACTGTGCCTGCTCTTTCTGTGTTTACAGTGTCAGCTGTAATATCCCCTCTTCGGCCTAACGTTTCTGAAGTCCCTTGCCACTGGGTCTCCTCTCCTCTTCCTGTGTTCTTTCTAAGAACACCTATGCAGATAGGTGTCTTCTGTACAGGGAAGCTGTTCCTGAGATC[C/T]GGGCATCGACTCTGTTAGAATAATCTACGTATGAGTTATTTTTTGAGAACTATGTGTCATTGCTGACTCATATTAACTCTGTGGTTAACTAAAATCTCAAGATCTCTTTATGTTTGTTGAGAAACTTATTTAACTTCTCTGGCCCTCCGTTTCCTTCACTGAGCAGTGGAGTGATTGATAACCTCCACCTGTGGTT

SG13S43

CACCTATGCAGATAGGTGTCTTCTGTACAGGGAAGCTGTTCCTGAGATCCGGGCATCGACTCTGTTAGAATAATCTACGTATGAGTTATTTTTTGAGAACTATGTGTCATTGCTGACTCATATTAACTCTGTGGTTAACTAAAATCTCAAGATCTCTTTATGTTTGTTGAGAAACTTATTTAACTTCTCTGGCCCTC[A/C]GTTTCCTTCACTGAGCAGTGGAGTGATTGATAACCTCCACCTGTGGTTGCTGAAGGTCTTGCACAAGATGATATAGTTAAAGTAGCTAGCAGTGCCCACGTACGGCGGATGCCTCACAACGGTTTGCAGCCATCTCTATCTGTGTCTTTGTCTCTCTCACACTGGTTTTGGCTTACTGTTAGCAGCTAGCCGA

SG13S399

TCTGTGGTTAACTAAAATCTCAAGATCTCTTTATGTTTGTTGAGAAACTTATTTAACTTCTCTGGCCCTCCGTTTCCTTCACTGAGCAGTGGAGTGATT

FIG. 8.18

GATAACCTCCACCTGTGGTTGCTGAAGGTCTTGCACAAGATGATATAGTT
AAAGTAGCTAGCAGTGCCCACGTACGGCGGATGCCTCACAACGGTTTGC[
A/C]GCCATCTCTCTATCTGTGTCTTTGTCTCTCTCTCACACTGGTTTTGGCT
TACTGTTAGCAGCTAGCCGAGATAAGTGTGTTTATGGTCTTTGCATGTATT
GTTTCTGTAGCATACTGGAGGATTACAAGAGGTTGGGGAGTGAGGGGGCG
GTGAGGAGTAGACAAAGGCAGCCAACTCTTCCAAGTTTAGCTTAGAA

SG13S124

TTGATAACCTCCACCTGTGGTTGCTGAAGGTCTTGCACAAGATGAT
ATAGTTAAAGTAGCTAGCAGTGCCCACGTACGGCGGATGCCTCACAACGG
TTTGCAGCCATCTCTCTATCTGTGTCTTTGTCTCTCTCTCACACTGGTTTTG
GCTTACTGTTAGCAGCTAGCCGAGATAAGTGTGTTTATGGTCTTTGCATG[
C/T]ATTGTTTCTGTAGCATACTGGAGGATTACAAGAGGTTGGGGAGTGAG
GGGGCGGTGAGGAGTAGACAAAGGCAGCCAACTCTTCCAAGTTTAGCTTA
GAAGGAAGGAGCGGTAAACCCTAGTTGAATGTTGGACTGAAGCAGGTTTG
TTTTTGTTTTGTTTAAAGGATAGGGAAGATCTGTGCGTGTTTCCAGGATA

SG13S125

ACTTGAAGTCAGTGGCATGGACAGGGTCAAGATCACAGTTAGAGG
ATGCAGCCTTAGAGAAAAGGAAGGGGCTCGGTTCTCTGAGCAAGGAGGG
AAAGAAGAGAGGCAGATGCAGAGAAGTACGGCACATCGTGCTGCTGGTT
GTAGAAATAACCTCTGACTTTTAATAAAGTCATCCCTCGGTATCCCTGGGG
GATT[A/G]GTTCTATGACCTCCCTCGGATGCCAAAATTCGTGGATGCTCAA
GTCCCTGATATAAAATGGCATAGTATTTGCATTTAACCTACACACATCCTC
CATATCCTTTTTTTTTTTTTTTTTTTTTTTTTTTTTGTGAGATGGAGT
CTTGCTCTGTCGCCCTGGCTGGAGTACAGTGGCTCGATCTTGGCTCACT

SG13S400

AATACCTGATAGAATGTAAATGCTATGTAAACAGTTGTTATACTGT
ATTGTTAAAAGACAGTAACAAGAAAAAAAATCTGTACATGTTCAGTCCAG
ACAAATGGTTTTCTGTTTTTTTTTTTTTTTAATATTTTGGTCAGTGGTT
GGTTGACTCCAGGAATGCAGAACCCGCAGATATAGAAGGTTGATTATGC[
A/G]TTCAGAGGCAGGGAATACCATCTTGGGTTCCAGAAAGAAAATGATCA
GCATTTTCTGTCATACTCTGGTAAAAACAGATCTTTTGAATGGACAGGTGT
ATTAAACCCTGTGGAGCTGGCTGGGCCTGGCGGCTCACGCCTGTAATCCC
AGCACTTTGGGAGGCTGAGGCAGGTGGATCACGAGGTCAGGAGTTCGAG

SG13S126

TGCCCCGCAGAGTTTGAAGTCCCGGCTGCACCTCTCCCCAGCAGCA
GGTTGACTCTGGAAAGTTGCAGCGTTCTTACCTACAGAGTGGGAACAGTA
CTACCCATTGCACAGAGTGGGTGCAAAGCTCTGTGACGGAATACATGGCA
AGTGCCCACCACATTGCCTGGGATGAGGTGGGCCCTTCCTTTACGTAAGA
GA[A/G]CCCTACAGATACACTCAAAGTGGGCACATTCCTACAGAAGGAGT
GTTATTTGTGTAGAAAAGAAAAACATGAAAGGCTTTTATTCCTATACACA
ATAAAGCACCCCTTTAATGTCTTTTTGAGGAGGATAATATGAAATTGATGA
AAAGGAACCCTGTGGTTGGATCCCTGACAATCACATGTATCCCTTTTTCA
C

SG13S127

TACAGATACACTCAAAGTGGGCACATTCCTACAGAAGGAGTGTTAT
TTGTGTAGAAAAGAAAAACATGAAAGGCTTTTATTCCTATACACAATAAA
GCACCCCTTTAATGTCTTTTTGAGGAGGATAATATGAAATTGATGAAAAG
GAACCCTGTGGTTGGATCCCTGACAATCACATGTATCCCTTTTTCACTCT
T[A/G]AAAAAGGAGTAAAGGAATAAAATAGAANNNNNNNNNNNNNNNNN
NNNNNNNNNNNNNNNNNNNNNNNNNNNNNNNNNNNNNNNNNNNNNN

FIG. 8.19

NNNNNNNNNNNNNNNNNNNNNNNNNNNNNNNNNNATGTTTCAGTCA
CTGTATAATAACTAGCCAGATTTTTGTTGTTGTTGTTTTGTTTTGTTTTG
TTTTT

SG13S128

ACATTCTGAACCACAGACAGTTCTTTACCCTGAACCTTTGCATATTT
TGTTCTCTTAGCTTAGAGCGGCCCCTCTCCCTCCGTCTGCTTGGCTAATTTC
TACTTGTTCTTCAGATTTTATCTTAGATGTCATTCCCTCAAGGAATCCTTCT
GTGACTCAACATGGAATTAAGTTGCCTCCTTTGACCCTGAAAGCACC[A/G]
TGTACTCAATCTCATCTTGGCATGACTCACTTTGCTGTGTGGAATGTCTGC
TTTCCTTGTTTGTCTATTCCTTTAGACTGTAAGATCCTAGAAAGTGGGGGC
CGTGCCTTGCTCATGACTGTGTTTCTAACACCAAACACAGTGTTCAGTAGA
GAGCAGCTGCTGAGTACGTTCTGCTAAATGACAGTTGATGGAG

SG13S129

AATCCTTCTGTGACTCAACATGGAATTAAGTTGCCTCCTTTGACCCT
GAAAGCACCATGTACTCAATCTCATCTTGGCATGACTCACTTTGCTGTGTG
GAATGTCTGCTTTCCTTGTTTGTCTATTCCTTTAGACTGTAAGATCCTAGAA
AGTGGGGGCCGTGCCTTGCTCATGACTGTGTTTCTAACACCAAACACA[A/
G]TGTTCAGTAGAGAGCAGCTGCTGAGTACGTTCTGCTAAATGACAGTTG
ATGGAGGACATTTAGGGTTGCTTGGAGGTCAAGTCAAGGAGGCATTTAAC
ATTCTAGTAAAACAAGGAAGTAACAGGCTCCTGAACATGCCCACAATGAA
CCAGATGCAAACCTTTTCCCTTGGCAGGATTCTTTGCCCATAAAGTGG

SG13S130

AAAGCACCATGTACTCAATCTCATCTTGGCATGACTCACTTTGCTGT
GTGGAATGTCTGCTTTCCTTGTTTGTCTATTCCTTTAGACTGTAAGATCCTA
GAAAGTGGGGGCCGTGCCTTGCTCATGACTGTGTTTCTAACACCAAACAC
AGTGTTCAGTAGAGAGCAGCTGCTGAGTACGTTCTGCTAAATGACAGT[G
/T]GATGGAGGACATTTAGGGTTGCTTGGAGGTCAAGTCAAGGAGGCATTT
AACATTCTAGTAAAACAAGGAAGTAACAGGCTCCTGAACATGCCCACAAT
GAACCAGATGCAAACCTTTTCCCTTGGCAGGATTCTTTGCCCATAAAGTGG
AGCACGAAAGCAGGACCCAGAATGGGAGGAGCTTCCAGAGGACCGGAA

SG13S190

TTCTGCTAAATGACAGTTGATGGAGGACATTTAGGGTTGCTTGGAG
GTCAAGTCAAGGAGGCATTTAACATTCTAGTAAAACAAGGAAGTAACAG
GCTCCTGAACATGCCCACAATGAACCAGATGCAAACCTTTTCCCTTGGCA
GGATTCTTTGCCCATAAAGTGGAGCACGAAAGCAGGACCCAGAATGGGA
GGAG[C/T]TTCCAGAGGACCGGAACACTTGCCTTTGAGCGGGTCTACACTG
CCAAGTGAGTCCTAACCCTGATGTTGCTAATAAGTGGGGGCATGGGCAGG
GGGGCCTCCTTCTAGGAGTGATGACCACCCTTAATACCACATGTCTGTCTG
AGCCAAGTTTCTGAGCGCCAGGGAGGTGAGGAAGGTTGGACTTCACCAGA
GAG

SG13S192

GGCATTTAACATTCTAGTAAAACAAGGAAGTAACAGGCTCCTGAA
CATGCCCACAATGAACCAGATGCAAACCTTTCCCTTGGCAGGATTCTTTG
CCCATAAAGTGGAGCACGAAAGCAGGACCCAGAATGGGAGGAGCTTCCA
GAGGACCGGAACACTTGCCTTTGAGCGGGTCTACACTGCCAAGTGAGTCC
TAA[A/C]CCTGATGTTGCTAATAAGTGGGGGCATGGGCAGGGGGGCCTCCT
TCTAGGAGTGATGACCACCCTTAATACCACATGTCTGTCTGAGCCAAGTTT
CTGAGCGCCAGGGAGGTGAGGAAGGTTGGACTTCACCAGAGAGGCTTGT
GGACACCCTTTATCATCTTAGTGAGTGCTAGTGTCAAAACAAAGGGAGTG
GG

FIG. 8.20

SG13S193
GCTCCTGAACATGCCCACAATGAACCAGATGCAAACCTTTTCCCTT
GGCAGGATTCTTTGCCCATAAAGTGGAGCACGAAAGCAGGACCCAGAAT
GGGAGGAGCTTCCAGAGGACCGGAACACTTGCCTTTGAGCGGGTCTACAC
TGCCAAGTGAGTCCTAACCCTGATGTTGCTAATAAGTGGGGCATGGGCA
GGG[A/G]GGCCTCCTTCTAGGAGTGATGACCACCCTTAATACCACATGTCT
GTCTGAGCCAAGTTTCTGAGCGCCAGGGAGGTGAGGAAGGTTGGACTTCA
CCAGAGAGGCTTTGTGGACACCCTTTATCATCTTAGTGAGTGCTAGTGTCA
AAACAAAGGGAGTGGGGATATGGGGCACATTGGTGGAGGGAGGTGTGAT
CTC
SG13S88
TTGCCCATAAAGTGGAGCACGAAAGCAGGACCCAGAATGGGAGGA
GCTTCCAGAGGACCGGAACACTTGCCTTTGAGCGGGTCTACACTGCCAAG
TGAGTCCTAACCCTGATGTTGCTAATAAGTGGGGCATGGGCAGGGGGGC
CTCCTTCTAGGAGTGATGACCACCCTTAATACCACATGTCTGTCTGAGCCA
AG[C/T]TTCTGAGCGCCAGGGAGGTGAGGAAGGTTGGACTTCACCAGAGA
GGCTTTGTGGACACCCTTTATCATCTTAGTGAGTGCTAGTGTCAAAACAAA
GGGAGTGGGGATATGGGGCACATTGGTGGAGGGAGGTGTGATCTCTGCAG
CTTCAGAAAGATCTGAAAGAGTCATTTGGTTAGAGAAGTTGACCTATTTCC
T
SG13S131
AAACAAAGGGAGTGGGGATATGGGGCACATTGGTGGAGGGAGGTG
TGATCTCTGCAGCTTCAGAAAGATCTGAAAGAGTCATTTGGTTAGAGAAG
TTGACCTATTTCCTGTGGGGTTAGACCAGGGTTGCTACTGTGAACACCAGC
CATGACTCACCAGTCACCTTCAGAAGCCACAGGCAGGACATGCTGACGAC
AG[C/T]CTTCAACTCACCCACCCCTTGCTCCCCTGCGGGTGGAAGTCTGGA
GGTGACACCACTGCATTTCTAACACGGGGGCTCCTTGAGCAACTAGAAC
AAGAACAGAAAGAATGGGGACATTAGCAGGTGCTTTCCCCCTCTCTCATT
CTTTTCTTTGAATAAAAGGTTGTTTGAAAACACCTGAGCGGCTCCTAAAG
A
SG13S132
CTCCTCTCTTCTTTATGCAGAGTGTATTTCAAGGCTCAGCCAGTGGC
AGGCATGCTGGGGACTATGGACTACGGACTAGGGGCCTGTCACAGAGGA
AGGCCTCATGCTAGAGAGCTAAGGGAGGAGCTGGCCTTCAGTTCCATCCC
AGGAGCAACTTTGATGTTCCCAGAGATCCTTCCAAAGGGGGAGTCATGGT
CA[A/C]CCAAGAAAAATGTATTCAGAATGCCAAGAATGGTGCAAACTCAG
GACAAAGATTCACACTGCAGGGTTGGAGTCCCTGGGCTTGCTGCTGGCAC
CATGGGAGGGAGGGTCCCCTTCAGGGGTACCGTTGGTTTCCTGTGAATTA
AACTGGCTTCAAGGGATCTCGACTGAACAGGCCTATATCACACTCACTGA
TAT
SG13S133
TCTCCTCATCTAGGTATTTTTAATTGTTTCAGTGAGGTGTAGGCATG
AGGGGATTGGAGGGGGCATCTCCTCCATTGCAGTTTTTCATTGGCTGCTTT
GCTCCCTCAGCTCCGAAATCGCTGGGCCACTCTCGAACGCATTAGTACGG
TAGTCACAGGTTGATTGCCTGGCCCCTTGCCCTCTGTGGGCATTTTCCCT[C
/T]TCAGACAGCCCCTGAGTACTCACAGTGCTGCTACAGTGGGCCACCTAG
ATCTCCCTCTTTCTCCATGCTCCCACGTGCTCTGGGCTCCACTCCCTTCTCC
CAAGCACTTCTGTCCAGGGCTATTCCAGCAGTCTGACCTCAAGGAAATCC
TTTGCTAAACTGATTATAGAGAGGTTTCTATTTTAACATTTAGGTCT

ATCTAGGTATTTTTAATTGTTTCAGTGAGGTGTAGGCATGAGGGGA
TTGGAGGGGGCATCTCCTCCATTGCAGTTTTTCATTGGCTGCTTTGCTCCCT
CAGCTCCGAAATCGCTGGGCCACTCTCGAACGCATTAGTACGGTAGTCAC
AGGTTGATTGCCTGGCCCCTTGCCCTCTGTGGGCATTTTCCCTTTCAGAC[A
/T]GCCCCTGAGTACTCACAGTGCTGCTACAGTGGGCCACCTAGATCTCCCT
CTTTCTCCATGCTCCCACGTGCTCTGGGCTCCACTCCCTTCTCCCAAGCACT
TCTGTCCAGGGCTATTCCAGCAGTCTGACCTCAAGGAAATCCTTTGCTAAA
CTGATTATAGAGAGGTTTCTATTTTAACATTTAGGTCTTCCATGT

SG13S134

AGGTGTAGGCATGAGGGGATTGGAGGGGGCATCTCCTCCATTGCA
GTTTTTCATTGGCTGCTTTGCTCCCTCAGCTCCGAAATCGCTGGGCCACTC
TCGAACGCATTAGTACGGTAGTCACAGGTTGATTGCCTGGCCCCTTGCCCT
CTGTGGGCATTTTCCCTTTCAGACAGCCCCTGAGTACTCACAGTGCTGCTA
[C/T]AGTGGGCCACCTAGATCTCCCTCTTTCTCCATGCTCCCACGTGCTCTG
GGCTCCACTCCCTTCTCCCAAGCACTTCTGTCCAGGGCTATTCCAGCAGTC
TGACCTCAAGGAAATCCTTTGCTAAACTGATTATAGAGAGGTTTCTATTTT
AACATTTAGGTCTTCCATGTATTAATTCTCAGAATCAATTTAAGATG

SG13S135

CCTTTCAGACAGCCCCTGAGTACTCACAGTGCTGCTACAGTGGGCC
ACCTAGATCTCCCTCTTTCTCCATGCTCCCACGTGCTCTGGGCTCCACTCCC
TTCTCCCAAGCACTTCTGTCCAGGGCTATTCCAGCAGTCTGACCTCAAGGA
AATCCTTTGCTAAACTGATTATAGAGAGGTTTCTATTTTAACATTTAGG[C/
T]CTTCCATGTATTAATTCTCAGAATCAATTTAAGATGTTTAAAGGTGTGAT
TTAAGACATTTTAAAACCATTTGGAGGAGAGTACAGAAATTATGTCACTT
GCTGTCAGCCTCTTTGCACCATCTGCAGAGAAAGATACTAGAGTCCCGCC
TTGGACACATCCACATGCAAGAGGTGCAAAGAAGGTGTCTTTGATGA

SG13S136

TTCTCAGAATCAATTTAAGATGTTTAAAGGTGTGATTTAAGACATTT
TAAAACCATTTGGAGGAGAGTACAGAAATTATGTCACTTGCTGTCAGCCT
CTTTGCACCATCTGCAGAGAAAGATACTAGAGTCCCGCCTTGGACACATC
CACATGCAAGAGGTGCAAAGAAGGTGTCTTTGATGAGGCAAGGTCAAAA
CT[C/T]CTCCCCAGACGAAATCCAAAGAAAGCATTCCTACTATGCTATATC
AGTTTGGAAAGAAAAACTTCTGCCAGGTGACTGCATTCTCACTGGTCACA
TTGTGTTCCTATGGACTCCTCAGCTCAACCAATTTGGAGAAGTTATGGTGC
AATTTCACCATATCTGGTTAGAAGTTAAGTTTCCAATTTGCTGGCAATGAA

SG13S137

AAGAAGGTGTCTTTGATGAGGCAAGGTCAAAACTTCTCCCCAGACG
AAATCCAAAGAAAGCATTCCTACTATGCTATATCAGTTTGGAAAGAAAAA
CTTCTGCCAGGTGACTGCATTCTCACTGGTCACATTGTGTTCCTATGGACT
CCTCAGCTCAACCAATTTGGAGAAGTTATGGTGCAATTTCACCATATCTGG
[C/T]TAGAAGTTAAGTTTCCAATTTGCTGGCAATGAAGAAGAAATGGAGCA
GGCCAGGCTGTGTAGTTCTGCCACGTGCCCCGGGAGTGAACAGCTCTG
TTTGTAAGAAGCCATGGTGCTTAGACCTGGGCTCGCTAGTTGCCAGCCTCC
AAATTGCAGAAGTGCCCTTTGGTTGGTGGCTATGCTGTGTCACTTGGGA

SG13S86

GCAACATATCTGTGTGCCTGTCTGGGTTGTAAAAGGGTCAAAGAT
CAATGCAGCAGGCAGCTACATGCTGGCAAAAGCCAGAGGCAGCTGGTCT
GTTTGCCTGTGCCAGGAAACCACTGGGAATGGGGTTGTGTGTTATTCTAGG
AGAAAGTCGTCCCAGCAGCAGCTTCTCCAGGGGCATCCAAGAGCACTGAA

FIG. 8.22

AA[A/G]GGTTGCAAGATGACCCATGAGGCTGCAGGAAGAAAAGAACATGC
ATTTAATCTTGCTATCTGAAAAGTAAGACATGAAGCTTTCCTCATTTTTAA
TATACACATGGACAGTAGTATGTGTATATAGTTTATATGCAAATATACTTG
TTATAAGGTTGCATGCTCAAAATTTTTGGTTCATGGGGTGTGGGATCATAA

SG13S87

CAGCTACATGCTGGCAAAAGCCAGAGGCAGCTGGTCTGTTTGCCTG
TGCCAGGAAACCACTGGGAATGGGGTTGTGTGTTATTCTAGGAGAAAGTC
GTCCCAGCAGCAGCTTCTCCAGGGGCATCCAAGAGCACTGAAAAGGGTTG
CAAGATGACCCATGAGGCTGCAGGAAGAAAAGAACATGCATTTAATCTTG
CT[A/G]TCTGAAAAGTAAGACATGAAGCTTTCCTCATTTTTAATATACACA
TGGACAGTAGTATGTGTATATAGTTTATATGCAAATATACTTGTTATAAGG
TTGCATGCTCAAAATTTTTGGTTCATGGGGTGTGGGATCATAAATGTTTAG
GGACCATGGCTATCAAGGAAAAACAGCATGAAGGATAAATGATACTGGT
G

SG13S138

CTATCTGAAAAGTAAGACATGAAGCTTTCCTCATTTTTAATATACA
CATGGACAGTAGTATGTGTATATAGTTTATATGCAAATATACTTGTTATAA
GGTTGCATGCTCAAAATTTTTGGTTCATGGGGTGTGGGATCATAAATGTTT
AGGGACCATGGCTATCAAGGAAAAACAGCATGAAGGATAAATGATACTG
G[C/T]GGATTAAAAAGACAGATGCATGTATTTTAGCATAAAACACAACTG
CTGACTGATACAGATAGCTCAAGATTCTGGGGCAGCTGCTGAACAGATAC
ACTAGCCAGTGTGGCTCATCGGCTCAGACTTGGCCTTAATTAATGGGCTGT
CCCTCCACCCATCTCCCATGAGGGCAGAGCTGAGCCAGGGTTTGAGAGCT

SG13S139

AGTTTATATGCAAATATACTTGTTATAAGGTTGCATGCTCAAAATTT
TTGGTTCATGGGGTGTGGGATCATAAATGTTTAGGGACCATGGCTATCAA
GGAAAAACAGCATGAAGGATAAATGATACTGGTGGATTAAAAAGACAGA
TGCATGTATTTTAGCATAAAACACAACTGCTGACTGATACAGATAGCTC
AA[C/G]ATTCTGGGGCAGCTGCTGAACAGATACACTAGCCAGTGTGGCTCA
TCGGCTCAGACTTGGCCTTAATTAATGGGCTGTCCCTCCACCCATCTCCCA
TGAGGGCAGAGCTGAGCCAGGGTTTGAGAGCTAAAAGGAATTGGACCTG
GACTCTGTTCACGTGTATATTTTAATTCTAATTAATTCATTCTTTTGAAAGA

SG13S140

GTATTTTTAGCATAAAACACAACTGCTGACTGATACAGATAGCTCA
AGATTCTGGGGCAGCTGCTGAACAGATACACTAGCCAGTGTGGCTCATCG
GCTCAGACTTGGCCTTAATTAATGGGCTGTCCCTCCACCCATCTCCCATGA
GGGCAGAGCTGAGCCAGGGTTTGAGAGCTAAAAGGAATTGGACCTGGAC
TC[A/G/T]GTTCACGTGTATATTTTAATTCTAATTAATTCATTCTTTTGAAAG
ACAGAGTCACACTCTGTTGCCTAGGCTGGAGTGCAGTGGCACGATCTTGG
CTCACTGCAACCTCGGCCTCCCAGGTTCAAGTTATTCCTGCTTCAGCCT
CCTGAGTAGCTGGGATTATAGGCACATGCCCCATGCCTGACTAATTTT

SG13S141

GCTAAAAGGAATTGGACCTGGACTCTGTTCACGTGTATATTTTAAT
TCTAATTAATTCATTCTTTTGAAAGACAGAGTCACACTCTGTTGCCTAGGC
TGGAGTGCAGTGGCACGATCTTGGCTCACTGCAACCTCGGCCTCCCAGGT
TCAAGTTATTCCTGCTTCAGCCTCCTGAGTAGCTGGGATTATAGGCACA
[C/T]GCCCCATGCCTGACTAATTTTGTATTTTAGTAGAGACGGGGTTTC
ACCATGTCAGGCTGGTCTTGAACTCCTGACCTCAGGTTATCCACCCGCCTT
GGCCCCTCAAAGTGTTGGAATTACAGGTGTGAGCCACCGTGCCTGGCCTG
TTCACATGTATAAAACACAGTTTAATGTCCTATTCCCAGCCAATGAGC

TCAGGTTATCCACCCGCCTTGGCCCCTCAAAGTGTTGGAATTACAG
GTGTGAGCCACCGTGCCTGGCCTGTTCACATGTATAAAACACAGTTTAAT
GTCCTATTCCCAGCCAATGAGCATGGCTAGAGCAGCCTTGGTCAAAGTTT
GGTTTTTGGAGAAAAATCCTTGTTAGCTGACCTAAGATTCCTCTTTGTGAG
T[G/T]TAAGTAAGCACAGGTTGCAGAGAGGAGAAGGGTCTCTGGAGAGGT
GTAATTTTCTAAATGGATTACAAGTTCATGGACTTTTAACAGGTGTTACAG
GGGATAACAAGTTCTTTATAGACAGACTTTTGAGGACGTTTAAGGGTATTC
TGATTCTTGGTTTTCTAAGAGGGGAATGTATTATTTAACTACAGACACCC

SG13S142

AAAATCCAGAATAATAATAATTTGTCAATAGGAAAGACATTTCCAC
TGGGGGTTAAGAAGGAAGACATTGGAACAATGATAGCCACCACTTATTGA
ATGCTTACTGTGAGCCAGGTGGCACTTCACCTTGTTTCATTCTCACAACAG
TCTAGGGAAGTAATTACTAATGTCTCCATCCACCTCTTGTAGATGAGCAAA
[C/T]TGAGGCTCATTGAGGCTAGGAAATGCACCCACACTCACATAGCCCAT
AAGAGGCAGCCATGGCATTGGGCCCAGACCATGTGAACTTCAAAGACTAC
ACGAGCAGCCACTGGGCAGCTGTCATGGCTAAAGCCACTTGAATTCAGCC
CAGCAGCAACCCCCTCTCCAGGAGGGGCACATAAGCTTGCAGCTTTGGGT

SG13S143

ATAATAATAATTTGTCAATAGGAAAGACATTTCCACTGGGGGTTAA
GAAGGAAGACATTGGAACAATGATAGCCACCACTTATTGAATGCTTACTG
TGAGCCAGGTGGCACTTCACCTTGTTTCATTCTCACAACAGTCTAGGGAAG
TAATTACTAATGTCTCCATCCACCTCTTGTAGATGAGCAAACTGAGGCTCA
[C/T]TGAGGCTAGGAAATGCACCCACACTCACATAGCCCATAAGAGGCAG
CCATGGCATTGGGCCCAGACCATGTGAACTTCAAAGACTACACGAGCAGC
CACTGGGCAGCTGTCATGGCTAAAGCCACTTGAATTCAGCCCAGCAGCAA
CCCCCTCTCCAGGAGGGGCACATAAGCTTGCAGCTTTGGGTAGAAGCTGC
A

SG13S144

GCACTTGAAGTCCTGGATGGCGAGAGGGACTGGCTTGAGCCAGAG
CCAGGAACAAGGCTCTGAGAATATTCTGGAAATCCACAGGAGGAACCCAT
TTTCTTACAGCTGGGAGAATTTCATTCAACTCCAGGCTGACCATGTTTTAT
TAGGAACGAAGGTGACTTGAACTAATAGTCAGGAATGGTTGAATACGGAC
CC[A/G]ATGTCAAATCACTAGGCAGTTCACATTTCTAATGAGCAAATCCCT
TAGACAATTAAGAATTTTTTCCTTTTGCATAACCCAGACAAAATCGCTAC
TTAAAAACAAACCAAAGACCCGAAACATGAGAAAGAGAAGGAAGCAGG
GGAAATCTTTGGTACTAATAAGTTTTAAACAATAAGAGCACCAGATATTT
TA

SG13S145

ATGAGCAAATCCCTTAGACAATTAAGAATTTTTTCCTTTTGCATAA
CCCAGACAAAATCGCTACTTAAAAACAAACCAAAGACCCGAAACATGAG
AAAGAGAAGGAAGCAGGGGAAATCTTTGGTACTAATAAGTTTTAAACAA
TAAGAGCACCAGATATTTTACCCCATCAGACACAGAATGTTATTCGAATA
AC[C/G]AAAAAAGGAATTTTTTCTCTAAGTTTCTTGAACTGGAAAATGAAT
CATATTTTCTCAGTCCTGAGGCTGCAATTTGTGCCTCTAGTAACATATAA
GAATAGATGTGATGCCAGTGCCCAGTAGCTGCTGCAATTGTTACTTGGGG
ACCTGTTTATTCACTAAGCACTTCACCCCAGTGATAAATTTGTAGGGGCCT

SG13S146

CCGTGTCCATTAGATCAGTGGAAATTCTGGGATTCAGAGCACTTTG
CAAGGTCAGCAGGGGTCTGCTCTTTCTGTCCTGTTCCTGGTTTTTGGTTGTG

FIG. 8.24

CCTGGATTCCAGGGTAGGTTTCTCATCTGTTACCTTCATAGACTTCTCCAG
AAAAGGATCTTTTGACCATCAGAGGACCACGAAGATTCCATTGGTGAGG[
C/T]GCAGATAACCTGATCTCTCTGGGTTCTCTGCAGGGCACAGATGAAGG
GCTGGCCATTCCCAAGTTCTCAGTGGTACCACTGAGGCATGAGACCCTAA
TGGTTTGCATGAGCAGTTTGAAAATTGCATCTTTGTTTTACCTATATAATC
ACATGAAACCCGTGGTTCTCAAACGTCAGCAGGCATCAGCATCACATG

SG13S26

TCAGTGGTACCACTGAGGCATGAGACCCTAATGGTTTGCATGAGCA
GTTTGAAAATTGCATCTTTGTTTTACCTATATAATCACATGAAACCCGTG
GTTCTCAAACGTCAGCAGGCATCAGCATCACATGGAGGGCTTGTTAAAAC
AGATTTCTGGGCCCCAACACAGAGTTTTAAATTCTGAAGGCCTGAGGTGG
G[C/T]GTGAACATTTGCATTTCTAACATGTTCTCGATGCTGCTGCCGCCTCT
GGTCCCGAGAGCATGCCTGGAGAACTGCCACCTTCGACCATGGACTGTGA
GAATTCACATGGACCTCAGAATTATAATCAGTCTCTCAGTTTTACAGATAA
GGAAACTAAATCCAGAGAGATTGTTTTGCCAATGGTGAACAGCTGGTTA

SG13S27

ATGGTTTGCATGAGCAGTTTGAAAATTGCATCTTTGTTTTACCTAT
ATAATCACATGAAACCCGTGGTTCTCAAACGTCAGCAGGCATCAGCATCA
CATGGAGGGCTTGTTAAAACAGATTTCTGGGCCCCAACACAGAGTTTTAA
ATTCTGAAGGCCTGAGGTGGGTGTGAACATTTGCATTTCTAACATGTTCTC
[A/G]ATGCTGCTGCCGCCTCTGGTCCCGAGAGCATGCCTGGAGAACTGCCA
CCTTCGACCATGGACTGTGAGAATTCACATGGACCTCAGAATTATAATCA
GTCTCTCAGTTTTACAGATAAGGAAACTAAATCCAGAGAGATTGTTTTGCC
AATGGTGAACAGCTGGTTAAAGTCAGGATGGAGACTTTAATCCTAGTCA

SG13S147

GAGCAGTTTGAAAATTGCATCTTTGTTTTACCTATATAATCACATG
AAACCCGTGGTTCTCAAACGTCAGCAGGCATCAGCATCACATGGAGGGCT
TGTTAAAACAGATTTCTGGGCCCCAACACAGAGTTTTAAATTCTGAAGGC
CTGAGGTGGGTGTGAACATTTGCATTTCTAACATGTTCTCGATGCTGCTGC[
C/T]GCCTCTGGTCCCGAGAGCATGCCTGGAGAACTGCCACCTTCGACCAT
GGACTGTGAGAATTCACATGGACCTCAGAATTATAATCAGTCTCTCAGTTT
TACAGATAAGGAAACTAAATCCAGAGAGATTGTTTTGCCAATGGTGAACA
GCTGGTTAAAGTCAGGATGGAGACTTTAATCCTAGTCAAGTGACCTTTC

SG13S28

AGTTTGAAAATTGCATCTTTGTTTTACCTATATAATCACATGAAAC
CCGTGGTTCTCAAACGTCAGCAGGCATCAGCATCACATGGAGGGCTTGTT
AAAACAGATTTCTGGGCCCCAACACAGAGTTTTAAATTCTGAAGGCCTGA
GGTGGGTGTGAACATTTGCATTTCTAACATGTTCTCGATGCTGCTGCCGCC
[G/T]CTGGTCCCGAGAGCATGCCTGGAGAACTGCCACCTTCGACCATGGAC
TGTGAGAATTCACATGGACCTCAGAATTATAATCAGTCTCTCAGTTTTACA
GATAAGGAAACTAAATCCAGAGAGATTGTTTTGCCAATGGTGAACAGCTG
GTTAAAGTCAGGATGGAGACTTTAATCCTAGTCAAGTGACCTTTCCTCT

SG13S148

CATCTTTGTTTTACCTATATAATCACATGAAACCCGTGGTTCTCAA
ACGTCAGCAGGCATCAGCATCACATGGAGGGCTTGTTAAAACAGATTTCT
GGGCCCCAACACAGAGTTTTAAATTCTGAAGGCCTGAGGTGGGTGTGAAC
ATTTGCATTTCTAACATGTTCTCGATGCTGCTGCCGCCTCTGGTCCCGAGA[
G/T]CATGCCTGGAGAACTGCCACCTTCGACCATGGACTGTGAGAATTCAC
ATGGACCTCAGAATTATAATCAGTCTCTCAGTTTTACAGATAAGGAAACT

FIG. 8.25

AAATCCAGAGAGATTGTTTTGCCAATGGTGAACAGCTGGTTAAAGTCAGG
ATGGAGACTTTAATCCTAGTCAAGTGACCTTTCCTCTGTATTTATTTCCC
SG13S98

ATTTCTGACATCCTGAACCATAGTAAAAGGGTGTTTTTTGTTTTTTT
GAGACAGAGTCTTGCTCTGTTGCCTGGGCTGGAGTGCAGTGGTGTGATCTT
GGCTCGCTGCAACCTCCGCCTCCCAGGTTCAAGTGATTCTCCTGCCTCAGC
CTCCTGAGTAGCTGGGATTACAGGTGCTTGCCACCACACCTGGCTATTT[G/
T]TTGTGTTTTAGTAGAGACAGGGTTTCACCATGTTGGCCAGGCTGGTCTT
GAACTCCTGACCTTGTGATCTGCCTGCCTCAGCCTCCCAAATTGCTGGGAT
TACAAGGCGTGTTGTTTTAAGCCACTCAGTTTGTGGCCACTTGTTACAGCA
GCAAGAGGAAACTCATACAGTTATCATGTGAACTCACAGGAATAT
SG13S149

GATCTGCCTGCCTCAGCCTCCCAAATTGCTGGGATTACAAGGCGTG
TTGTTTTAAGCCACTCAGTTTGTGGCCACTTGTTACAGCAGCAAGAGGAA
ACTCATACAGTTATCATGTGAACTCACAGGAATATGGTGAGTTAAAAAGA
GAGGAAGGGTGCAAAACATCCACGGTAGAGTGAGAACTCTCCAGGGAGT
GAG[A/G]ACTGTGCCCAGCATACAGTGATCACCCTCTTAGTAAGCTAAGTT
TCTGAGCACCAGCTTTTTGAGTTGACTTGTTGTCTTTAACATTTGAAGAT
CACCCTTCTTTGCTCAGCCTGGCTTGCAGACCTGGGCTGATTTGTGGATCT
GATAGAAAAGTTTCCTTAGTTGGGCTCTTCTCCCCGACCACCCCCATGCC
SG13S29

TGCCTCAGCCTCCCAAATTGCTGGGATTACAAGGCGTGTTGTTTTA
AGCCACTCAGTTTGTGGCCACTTGTTACAGCAGCAAGAGGAAACTCATAC
AGTTATCATGTGAACTCACAGGAATATGGTGAGTTAAAAAGAGAGGAAG
GGTGCAAAACATCCACGGTAGAGTGAGAACTCTCCAGGGAGTGAGGACT
GTGC[A/C]CAGCATACAGTGATCACCCTCTTAGTAAGCTAAGTTTCTGAGC
ACCAGCTTTTTGAGTTGACTTTGTTGTCTTTAACATTTGAAGATCACCCTT
CTTTGCTCAGCCTGGCTTGCAGACCTGGGCTGATTTGTGGATCTGATAGAA
AAGTTTCCTTAGTTGGGCTCTTCTCCCCGACCACCCCCATGCCAGTGTGGC
SG13S89

GCTACTTTGCAGCCAAGGTAACTCAGACTTCCCTTTGTTCATTCTCC
TTCTATAAAGTGCATCTCAAGGAGGTTCAAAGGGCAGGCTTTTTGTTGAA
AGGACTTTGCCTGACCTCTGGCTCCCATCTGTGAAGCCCTGGAGAGGTGA
GAGCCCTCGGGAGGCCGTGTTTCAGGCATGCTCTGCACCCGTGCAGAGCG
C[A/G]TGTGATAATGCATTGCTAATGCTTGCTCCCTGGTGGCTGGCTGAGA
GCTGCTGTGCTGACAAGGGTGGTTTAAGGCTAAATGTGACTCAGAATCCT
TAAGCAGTGTTAGTTCAGATACAAGGGCATTATAAATGAGAGTGCCTGAG
GGATCTATTTTGGGACCGCTGTCACTTGGCTCTTCTGCTAATAAGCTTCCA
SG13S96

ACAGTTATCAGCAGCCCACAGGCTTGACTTGAGCAAGTTGGAAAG
ACAAATCAACTTCCAGAGTTGATTTAACATTGAGTGGAAATCAGTCATAC
TTTTGGTCCCCTTTCGGGGCCACGCCTGGCACTGTGCCTGGTGGCAGATCG
GCATGAACTGGCCAGCTTCTGTGGCCCTGGAGGGCACAGGCAGAAAGGCC
AC[A/G]CTCAGTCCCATGATGAACTGTTTAAGACTTATTGTTGTCTCCCGC
TCTGTAAAGTAGATAGAGTGGATTTTATGTCCCTTATTACCTTTCAGGATA
CTTTGACTCAGGGAGATAAAGTAACTTGGGTACAGCTACTCAGCTGGTGA
AGAACACAGGCAGAATGAGTGCCTGGGTCTTTTGACTTAAAATTCTGGAT
SG13S150

CTGTGCCTGGTGGCAGATCGGCATGAACTGGCCAGCTTCTGTGGCC
CTGGAGGGCACAGGCAGAAAGGCCACACTCAGTCCCATGATGAACTGTTT

FIG. 8.26

AAGACTTATTGTTGTCTCCCCGCTCTGTAAAGTAGATAGAGTGGATTTTAT
GTCCCTTATTACCTTTCAGGATACTTTGACTCAGGGAGATAAAGTAACTTG
[C/G]GTACAGCTACTCAGCTGGTGAAGAACACAGGCAGAATGAGTGCCTG
GGTCTTTTGACTTAAAATTCTGGATTTTTCACAAAGATCCTCTTACTTTATT
CATTTACATAATAAATATATATTGAAGAGCTACTCTGTGCCAAGCCCTGTG
CCTAGATATACAGTGATAAATAAAGAGTAGCTTCTAGAGGTCACCTGG
SG13S401

AAGTTCAGTGATAGAGAGCAGAGGTGAGGCGGCAGCAGAAACCAC
TTAAGGGACACCACGTGGCACTCCTTCTGTGCTGAGAAGGCTGTCAGTAA
GCTCACCATTTATTTCCTATTTTCTCTCCTGAGTTAAATAGGAAACATGTCT
CGCATTACTTGAAAAATCAAGTCAAACTATGCTCTTACTAGGAGTTATGGT
[C/T]CTTTTTATGTCTTAGATGATGCTTGATCTAGATGAATGCGGACTTGCT
GTAGCTAGATAAATACAATGGGAGTTTGAAGGTGTTTCGTAGCCCTGGAA
ATAGGTATTCCTGTCAAAACAAGCTTTGTCATTGCCAGCAGACAAAAGC
ATCAGTAACCTTGGTTGATAATCGTCATTTCTTAGGAATAAAGTAGACT
SG13S151

GTATTTCCTGTCAAAACAAGCTTTGTCATTGCCAGCAGACAAAAGC
ATCAGTAACCTTGGTTGATAATCGTCATTTCTTAGGAATAAAGTAGACTGT
AGAATTTTTTTAGCAGAAAGGAAACCCAAAGATAATTCTAGTGCAAATC
CCTCACTTTATAGAGCAGAAGCTCAAGTCCCAGAGGAACAAGTGGCTTGA
A[C/T]GAACATCAGAATTTTAGGGGCTGGATTTGTACCCTCCTGGTGCCAG
CAGCCCACTTCCCTGCAGGAGGCACTCACCTTCCTTGCACAGGGGTATGA
GTGTGGCCATTTTCCACCCATAATCTCTGTTAGCTCATGTTCAATTGGGTT
CCCATTGAAAGAAAAATGGACCAGTAAGTTGGAGCAGAATCATTCAGATG
SG13S30

AGCTTTGTCATTGCCAGCAGACAAAAGCATCAGTAACCTTGGTTGA
TAATCGTCATTTCTTAGGAATAAAGTAGACTGTAGAATTTTTTTAGCAGA
AAGGAAACCCAAAGATAATTCTAGTGCAAATCCCTCACTTTATAGAGCAG
AAGCTCAAGTCCCAGAGGAACAAGTGGCTTGAACGAACATCAGAATTTA
G[G/T]GGCTGGATTTGTACCCTCCTGGTGCCAGCAGCCCACTTCCCTGCAG
GAGGCACTCACCTTCCTTGCACAGGGGTATGAGTGTGGCCATTTTCCACCC
ATAATCTCTGTTAGCTCATGTTCAATTGGGTTCCCATTGAAAGAAAAATGG
ACCAGTAAGTTGGAGCAGAATCATTCAGATGGTATAACATAAGGAAAAA
SG13S31

TGTTTAAATTGCTTTTATATCTGTAGCTCTAGATAACACTAGTTCCA
GCTTAGTTAACTCCCAGCTCCAAGCCTTCAGGACTTCATAGAGTTATTGGG
GTGCTGCTCTTGGCAGTTTCCCAAAAAGCTAGAATGCAGAGGGAATCTCC
TTCCCAAAAAGCTAGAATGCAGAGGGAATCTCCTTCCCAAAAGGCTAGAA
[C/T]GCAGAGGGAATCTCCTTCCCAAAAAGCTAGAATGCAGAGGGAATCT
CCTTCCCAAAAGGCTAGAACGCAGAGGGAATCTCCTTCCCAAAAGGCTAG
AACGCAGAGGGAATCTCCTTCCCAAAAGGCTAGAATGCAGAGGGAATGT
CCTTCTCTTCTAAATGGTAGCTGTTAGTTCAAGAAAGGTTAAACATTGTGC
T
SG13S152

GCTGCGTTTGCTGGACTGATGTACTTGTTTGTGAGGCAAAAGTACT
TTGTCGGTTACCTAGGAGAGAGAACGCAGAGGTAGGTAACTGGGACTACT
AAAGAACTGTGGAGCGATTCCTGATTTTTGAGCAGGAAGAGTGACAATTC
AAAACAGTATTTGACTAGATTCACGGCTCCGTAGCATCCCCTTGGGTGGG
AG[C/G]GGGAAGGCTGACTAGGACCTCTGATTCTTCTTTCCCTGAGCTTTG
AAGGCTCTGAAAATACAGCTGGGGGGACTTGCCCAGTTTTCTTATTAAGC

FIG. 8.27

AATTCCTCCGCATGGTGCTGGCTTTCAAAGGGTGCTTCAGTGCTGTTTGCT
GCACGTGCCTTGCAGCCCCACACCCTGCACTCCCGCCCTGCAGAGTCTGG
C

SG13S402

GAGGCAAAAGTACTTTGTCGGTTACCTAGGAGAGAGAACGCAGAG
GTAGGTAACTGGGACTACTAAAGAACTGTGGAGCGATTCCTGATTTTTGA
GCAGGAAGAGTGACAATTCAAAACAGTATTTGACTAGATTCACGGCTCCG
TAGCATCCCCTTGGGTGGGAGGGGGAAGGCTGACTAGGACCTCTGATTCT
TCT[C/T]TCCCTGAGCTTTGAAGGCTCTGAAAATACAGCTGGGGGGACTTG
CCCAGTTTTCTTATTAAGCAATTCCTCCGCATGGTGCTGGCTTTCAAAGGG
TGCTTCAGTGCTGTTTGCTGCACGTGCCTTGCAGCCCCACACCCTGCACTC
CGCCCTGCAGAGTCTGGCGCTGGAATGACATTTTAGGTCTGGGTTCCCA
G

SG13S403

TATCTTTCAGGGACCAGAAGAAAGAATGTTGGGAAAATAAGATGC
AGTAAGATGCAGACATGACAGCAGGGTGCAGCGGCTCACGCCTATAATCC
CAGCACTTTGGGAGGCTGAGGTGGGTGGATCACCTGAGGTCAGGAGTTTG
AGACCAGCCTGGCCAACATGGTGAAACCCCGTCTCTACTAAAAAATATAC
AAA[A/G]CATTAGCCAGGCATGGTGGTGGGCGCCTGTAATCCCAGCTACTC
CATAGGCTGAGGCTGGAGAATCGCTTGAACCCAGGAGGCAGAGGTTGCA
GTGAGCCGAGATTGCGCCACTGCACTCCAGCCTGGGCAACAAAAGCAAA
ACTCCATCTCAAAAAAAAAAAAAAAAAAAAAAAAAAAAGATGCAGACACG
AGACTG

SG13S153

TGGGCGCCTGTAATCCCAGCTACTCCATAGGCTGAGGCTGGAGAAT
CGCTTGAACCCAGGAGGCAGAGGTTGCAGTGAGCCGAGATTGCGCCACTG
CACTCCAGCCTGGGCAACAAAAGCAAAACTCCATCTCAAAAAAAAAAAA
AAAAAAAAAAAAAGATGCAGACACGAGACTGTGAAACTGACTAGCAT
CACC[A/T]TTGCATTGTTTATAGATGTTGCCAGACAGAAAGCCCCAAAGCA
GCACAGTACCTTCCTGACATCTGGACTAGGAAATCTAGATTTTAGTAAAA
TACATGCTAATACTTACAGAAGAAATGTCGGCGTTAGAGTATGCCGTCAG
TTCCTTAGAGATTGCAATTCCTAATGCACTAGTATGGTTTCAGGTGCCAGG
AAC

SG13S97

ACTCCATCTCAAAAAAAAAAAAAAAAAAAAAAAAAAAAGATGCAG
ACACGAGACTGTGAAACTGACTAGCATCACCATTGCATTGTTTATAGATG
TTGCCAGACAGAAAGCCCCAAAGCAGCACAGTACCTTCCTGACATCTGGA
CTAGGAAATCTAGATTTTAGTAAAATACATGCTAATACTTACAGAAGAAA
TGTC[A/G]GCGTTAGAGTATGCCGTCAGTTCCTTAGAGATTGCAATTCCTA
ATGCACTAGTATGGTTTCAGGTGCCAGGAACACGTTCTGTGAGGCTGCTG
CCCCAGGTGCTGACCCCAGCCTTCCACACCATTTTCCTTCCTTGTGTTCAC
AGCCGCTCTGTCTTTTACAATAGCACCCCTCTCTAGTGGCTAATGGGCTCT
AT

SG13S154

AAAAAAAAAAAAAAAAAAAAAAGATGCAGACACGAGACTGTGAA
ACTGACTAGCATCACCATTGCATTGTTTATAGATGTTGCCAGACAGAAAG
CCCCAAAGCAGCACAGTACCTTCCTGACATCTGGACTAGGAAATCTAGAT
TTTAGTAAAATACATGCTAATACTTACAGAAGAAATGTCGGCGTTAGAGT
ATGC[C/T]GTCAGTTCCTTAGAGATTGCAATTCCTAATGCACTAGTATGGTT
TCAGGTGCCAGGAACACGTTCTGTGAGGCTGCTGCCCCAGGTGCTGACCC

FIG. 8.28

CAGCCTTCCACACCATTTTCCTTCCTTGTGTTCACAGCCGCTCTGTCTTTTA
CAATAGCACCCCTCTCTAGTGGCTAATGGGCTCTATGATTAGATAGCATCC
SG13S40
       TTTCAGGTGCCAGGAACACGTTCTGTGAGGCTGCTGCCCCAGGTGC
TGACCCCAGCCTTCCACACCATTTTCCTTCCTTGTGTTCACAGCCGCTCTGT
CTTTTACAATAGCACCCCTCTCTAGTGGCTAATGGGCTCTATGATTAGATA
GCATCCTTCAGTAGTGATAAAGGCAGTGACATCCTAGGGAGGTCAGCGG[
G/T]TGAAAGCGCTATATCTGGAAAACCTGAGAGCCTGTGAAGCTCAAGGA
CTTGACGGGGTTAGACCGTGAGCCGGGCTGCAGCTGGAAAAGAATGACT
GTTCTTTCAGCAGATCCTTCCCTGTGCCATCTCTTTCTTCATTCCTCTCTAG
TGGCATTCTTATTTATCCTCTAAAACCACAATTCCATTATCTCTCCTA
SG13S155
       GAGGGTCTTCTCTTTTGCCTGGCTCCCTATGCAGCCCTATCTTACCC
CCTGCAAAGTCCCAGGGATGTGGCTCAGTCACTGCTCCTCTCTTCATCTGT
CACCACTTGCTTGAGATCCTACAGCTGCTTTAATTCCGAGACCATCTGCAG
AACATGACAAAATTTGTCCACCTACCCACATGTCCTTTTAACTTTAAAG[A/
G]CTTTACTAACTGATTCCTATTAGGGAATGAACAGAGGTGGCAAAAATAA
ACAATAGGAGATTGATTTACAAGAAATCTTTAAAATAGTAGATTTCTTCG
GACCTCATTGAAATATAAATGGCCTGCCTTCTTGTGTCCCTCCCTGGTCTC
CCTCTTTAGGTGATAAGAAGAAGATCCTGCCAGCCCCATAACCCGCC
SG13S156
       TTAAAATAGTAGATTTCTTCGGACCTCATTGAAATATAAATGGCCT
GCCTTCTTGTGTCCCTCCCTGGTCTCCCTCTTTAGGTGATAAGAAGAAGAT
CCTGCCAGCCCCATAACCCGCCATCTGCGCGGGTTCTAGACCCCCTTCTCC
TCCCCTCTGGCCGTGGTAGGCATTACTGATGAATCATGGTGCTCTTTCTT[A
/C]CAGAGACCAAACCTGGCCTCGGAATCCTTCTTAACACAGATACTGCTT
AACACAACCACTCTGAGCAGCTGTCATAAGTAGAAGTAATAGATACTAGA
AGAAATGTCTAAGCCTAATCTAGACCAAAATACGGCCTGATATAGATGCA
AGCCAGAGGGGCTTTATGGTTAAATGCAAGGAGATTTTCAACCCTGCCG
SG13S157
       CTGGTCTCCCTCTTTAGGTGATAAGAAGAAGATCCTGCCAGCCCCA
TAACCCGCCATCTGCGCGGGTTCTAGACCCCCTTCTCCTCCCCTCTGGCCG
TGGTAGGCATTACTGATGAATCATGGTGCTCTTTCTTCCAGAGACCAAACC
TGGCCTCGGAATCCTTCTTAACACAGATACTGCTTAACACAACCACTCTG[
A/G]GCAGCTGTCATAAGTAGAAGTAATAGATACTAGAAGAAATGTCTAAG
CCTAATCTAGACCAAAATACGGCCTGATATAGATGCAAGCCAGAGGGGCT
TTATGGTTAAATGCAAGGAGATTTTCAACCCTGCCGTCTAGAAGCTACTTG
CTGAGATCTTCTTCAGTTGGGCCCATCTCCTCCCCAGGCCTCTCTTCTG
SG13S158
       CCATAACCCGCCATCTGCGCGGGTTCTAGACCCCCTTCTCCTCCCCT
CTGGCCGTGGTAGGCATTACTGATGAATCATGGTGCTCTTTCTTCCAGAGA
CCAAACCTGGCCTCGGAATCCTTCTTAACACAGATACTGCTTAACACAAC
CACTCTGAGCAGCTGTCATAAGTAGAAGTAATAGATACTAGAAGAAATGT
[A/C]TAAGCCTAATCTAGACCAAAATACGGCCTGATATAGATGCAAGCCA
GAGGGGCTTTATGGTTAAATGCAAGGAGATTTTCAACCCTGCCGTCTAGA
AGCTACTTGCTGAGATCTTCTTCAGTTGGGCCCATCTCCTCCCCAGGCCTC
TCTTCTGTTCCTGGGCTATGTCACACTTGGACTCTGCAGACACCTAATGC
SG13S159
       TGGTAGGCATTACTGATGAATCATGGTGCTCTTTCTTCCAGAGACC
AAACCTGGCCTCGGAATCCTTCTTAACACAGATACTGCTTAACACAACCA

FIG. 8.29

CTCTGAGCAGCTGTCATAAGTAGAAGTAATAGATACTAGAAGAAATGTCT
AAGCCTAATCTAGACCAAAATACGGCCTGATATAGATGCAAGCCAGAGG
GGC[G/T]TTATGGTTAAATGCAAGGAGATTTTCAACCCTGCCGTCTAGAAG
CTACTTGCTGAGATCTTCTTCAGTTGGGCCCATCTCCTCCCCAGGCCTCTCT
TCTGTTCCTGGGCTATGTCACACTTGGACTCTGCAGACACCTAATGCTCTT
GGGACCTGCTTTAGTTCTTGACCTCACCAACCGAGGAGGAATTGCTAGAT

SG13S160

CAGAGACCAAACCTGGCCTCGGAATCCTTCTTAACACAGATACTGC
TTAACACAACCACTCTGAGCAGCTGTCATAAGTAGAAGTAATAGATACTA
GAAGAAATGTCTAAGCCTAATCTAGACCAAAATACGGCCTGATATAGATG
CAAGCCAGAGGGGCTTTATGGTTAAATGCAAGGAGATTTTCAACCCTGCC
GT[C/T]TAGAAGCTACTTGCTGAGATCTTCTTCAGTTGGGCCCATCTCCTCC
CCAGGCCTCTCTTCTGTTCCTGGGCTATGTCACACTTGGACTCTGCAGACA
CCTAATGCTCTTGGGACCTGCTTTAGTTCTTGACCTCACCAACCGAGGAGG
AATTGCTAGATGAGATCCTTCCCCGGAATTTCTCTCTTGAACCCCAGA

SG13S32

GGGCTTTATGGTTAAATGCAAGGAGATTTTCAACCCTGCCGTCTAG
AAGCTACTTGCTGAGATCTTCTTCAGTTGGGCCCATCTCCTCCCCAGGCCT
CTCTTCTGTTCCTGGGCTATGTCACACTTGGACTCTGCAGACACCTAATGC
TCTTGGGACCTGCTTTAGTTCTTGACCTCACCAACCGAGGAGGAATTGCT[
A/C]GATGAGATCCTTCCCCGGAATTTCTCTCTTGAACCCCAGATGGTCCG
TTGCCCCTTTCCAGAAGTTGCTCCAGCCCTGTCCGCTTAGGAAGTTCAGTG
TCATCCTTGATCCAGTGGGTAGGGAAGACATTCCATAATGAATGCCCCAG
TCTGAGCTTCTTCCTTCAGGCTTCAGGCTGCCCTGCGAGGATTTTGCA

SG13S161

GTAGCTGAGACTACAGGTGTGCACTACCACACCCAGCTAATTTTTT
GTATTTTTAGTAGAGATAGGGTTTAGCTATGTTGGCCAGGCTGGTCTCGAA
CTGCTGAACTCAAGCAATCTGCCATCCCCGGCCTCCCAAAGTACTGGGAG
TATAGGCATAAGCCACCCATGATGCCCAGCCTGAATCTTGGTTTCTTCCCC
[A/G]TTCATTTAAGCTATTACCTGGGCCTGAACTCAATGGCACCTGGCACC
AACTGGCAACTGACTCTTGGTCTTTTATTACCTACCTTCCCTAGCAGGCAC
TGGGTTGCTCCCTCTTCCTATCCCATGGAGTCCTGTCCTCTGTTGGGGCTCC
TACTGATCCTCTTGGCAATATGAAGTTCTCAGCTCAATGGTGGGTGG

SG13S162

CCCGGCCTCCCAAAGTACTGGGAGTATAGGCATAAGCCACCCATG
ATGCCCAGCCTGAATCTTGGTTTCTTCCCCATTCATTTAAGCTATTACCTG
GGCCTGAACTCAATGGCACCTGGCACCAACTGGCAACTGACTCTTGGTCT
TTTATTACCTACCTTCCCTAGCAGGCACTGGGTTGCTCCCTCTTCCTATCCC
[A/G]TGGAGTCCTGTCCTCTGTTGGGGCTCCTACTGATCCTCTTGGCAATAT
GAAGTTCTCAGCTCAATGGTGGGTGGGCAATGACTGCCAACTCTTGAGGC
CAATGAACTCAGGTTACCCCACTCCTCCTCCTCCTGAGTTGCTCACTCACT
CCTCATTCACTCAACATTGATTCAGTAGATATTTGCTACCTGCTCTGT

SG13S163

CCGGCCTCCCAAAGTACTGGGAGTATAGGCATAAGCCACCCATGAT
GCCCAGCCTGAATCTTGGTTTCTTCCCCATTCATTTAAGCTATTACCTGGG
CCTGAACTCAATGGCACCTGGCACCAACTGGCAACTGACTCTTGGTCTTTT
ATTACCTACCTTCCCTAGCAGGCACTGGGTTGCTCCCTCTTCCTATCCCA[C
/T]GGAGTCCTGTCCTCTGTTGGGGCTCCTACTGATCCTCTTGGCAATATGA
AGTTCTCAGCTCAATGGTGGGTGGGCAATGACTGCCAACTCTTGAGGCCA

FIG. 8.30

ATGAACTCAGGTTACCCCACTCCTCCTCCTCCTGAGTTGCTCACTCACTCC
TCATTCACTCAACATTGATTCAGTAGATATTTGCTACCTGCTCTGTG

SG13S164

GGCATAAGCCACCCATGATGCCCAGCCTGAATCTTGGTTTCTTCCC
CATTCATTTAAGCTATTACCTGGGCCTGAACTCAATGGCACCTGGCACCAA
CTGGCAACTGACTCTTGGTCTTTTATTACCTACCTTCCCTAGCAGGCACTG
GGTTGCTCCCTCTTCCTATCCCATGGAGTCCTGTCCTCTGTTGGGGCTCC[C/
T]ACTGATCCTCTTGGCAATATGAAGTTCTAGCTCAATGGTGGGTGGGCA
ATGACTGCCAACTCTTGAGGCCAATGAACTCAGGTTACCCCACTCCTCCTC
CTCCTGAGTTGCTCACTCACTCCTCATTCACTCAACATTGATTCAGTAGAT
ATTTGCTACCTGCTCTGTGCCAGGTACCAGGTCAGTTGCTGAAGGA

SG13S165

CCTGGCACCAACTGGCAACTGACTCTTGGTCTTTTATTACCTACCTT
CCCTAGCAGGCACTGGGTTGCTCCCTCTTCCTATCCCATGGAGTCCTGTCC
TCTGTTGGGGCTCCTACTGATCCTCTTGGCAATATGAAGTTCTAGCTCAA
TGGTGGGTGGGCAATGACTGCCAACTCTTGAGGCCAATGAACTCAGGTT[A
/T]CCCCACTCCTCCTCCTCCTGAGTTGCTCACTCACTCCTCATTCACTCAAC
ATTGATTCAGTAGATATTTGCTACCTGCTCTGTGCCAGGTACCAGGTCAGT
TGCTGAAGGAGTAACAGTGAACATGACGGAGTCTTTGTCCCCAAGGAGAC
CCAAGGTGTCTCCTAGAGCCAGGGGCACATTGCAAGACCAAATATA

SG13S166

CTGGCAACTGACTCTTGGTCTTTTATTACCTACCTTCCCTAGCAGGC
ACTGGGTTGCTCCCTCTTCCTATCCCATGGAGTCCTGTCCTCTGTTGGGGC
TCCTACTGATCCTCTTGGCAATATGAAGTTCTAGCTCAATGGTGGGTGGG
CAATGACTGCCAACTCTTGAGGCCAATGAACTCAGGTTACCCCACTCCT[C/
T]CTCCTCCTGAGTTGCTCACTCACTCCTCATTCACTCAACATTGATTCAGT
AGATATTTGCTACCTGCTCTGTGCCAGGTACCAGGTCAGTTGCTGAAGGA
GTAACAGTGAACATGACGGAGTCTTTGTCCCCAAGGAGACCCAAGGTGTC
TCCTAGAGCCAGGGGCACATTGCAAGACCAAATATATTCAACTTACC

SG13S167

CCATGGAGTCCTGTCCTCTGTTGGGGCTCCTACTGATCCTCTTGGCA
ATATGAAGTTCTAGCTCAATGGTGGGTGGGCAATGACTGCCAACTCTTG
AGGCCAATGAACTCAGGTTACCCCACTCCTCCTCCTCCTGAGTTGCTCACT
CACTCCTCATTCACTCAACATTGATTCAGTAGATATTTGCTACCTGCTCT[A
/G]TGCCAGGTACCAGGTCAGTTGCTGAAGGAGTAACAGTGAACATGACGG
AGTCTTTGTCCCCAAGGAGACCCAAGGTGTCTCCTAGAGCCAGGGGCACA
TTGCAAGACCAAATATATTCAACTTACCAAAATAATCATAGACCTAGTTCT
CAAAAAGCAAGAAGACTGATTCCTCGTTGTCATTTCTCCTCCTCAGCA

SG13S168

TTAGAGTCTGTGGGCCCCTCCAAGTGTGGAGTATGGTGTTACTTCA
CCAGAGTTTGAGGAGAAACATTCTTCTTTTGGAAGGCCGGGGAGCATAGA
TGGATATCAAGGCTGCTGTTTCTAAAAGCGAAACCCACCAAACAACAGTA
TTAGAATCATCTGTGGTGCTTATTAAAGATACAGATTCCTGGGCCCCATCC
C[A/C]GACTTATGAATCAGAATCTCTGCCAGAGGAAGCCTGAGAATTTGCA
TTCTCAGATGATTCTGCATTCTCAGATAACACATTCTTTAGGTGATTCTTAC
ACACACTGGAGTTTGGGAATCGCTGAAGGCTGTTCACTTCTCTTTTCTGAG
AAATGATTCATTCATTTCAGAAATATTTGCAGAGGTCCTTATTTATTG

SG13S33

TGGCCTCATTCGTGTGATAAATCTGAGCCACCACGATATTTGACTTT
TCACAATTTAATTTATCTGAACCCTCTATTCTCTGGCTAAAAAATATCCCT

FIG. 8.31

TACTTGGACTTCTTTATTTTATTTTCAATTCCCTTACCAGCACTAGCAGGGG
ACTCTGTACTCATCTGCTGGCGCTGCCATAACAAAGCACTGCAGCCTG[G/T
]GGGGCTCAAACCACAGAATTTATTCTCTCACAGTCCTAGAGGCTAGAAGT
CCAAGATCAAAGTGTGGGCAGGGTCGGTTTCTCCTGCAGCCTCTCTCCTTG
GCTTATAGAGTGCCACCTTCTACCTGTGTCTTCACATCATCACCTCACTGA
GCATGTCTGTGTCCAAATCTCCCCTTCTTATAAGACCCCAGTCAT
SG13S41
      TCTCCTTGGCTTATAGAGTGCCACCTTCTACCTGTGTCTTCACATCA
TCACCTCACTGAGCATGTCTGTGTCCAAATCTCCCCTTCTTATAAGACCCC
AGTCATACTGGATGAGGATCCACCCATATGAGTTCATTTTACCTTAATTAT
CTCTTTAAACACCCTGTCTCCAAATACAGTCCCATTCTGAGGAACTGAG[A/
G]GTAAAGATTCAACATATGAATTTTGGAAGGGACCTAATTCAGCCCACA
ACACCCTCTTTTGGGATGTTTATTTTCCCCCTTAAGGAGCTAGTTAGGATG
TCTTATCTCATGAACATGACTGTGAACAGGAAAACAGGGAGAGAATGAA
GCTGGCCAAGGAACAGGGCTGGTGTCAGCTAGCAGTGCTTTTCTGATGT
SG13S169
      CATTTTACCTTAATTATCTCTTTAAACACCCTGTCTCCAAATACAGT
CCCATTCTGAGGAACTGAGAGTAAAGATTCAACATATGAATTTTGGAAGG
GACCTAATTCAGCCCACAACACCCTCTTTTGGGATGTTTATTTTCCCCCTT
AAGGAGCTAGTTAGGATGTCTTATCTCATGAACATGACTGTGAACAGGAA[
A/G]ACAGGGAGAGAATGAAGCTGGCCAAGGAACAGGGCTGGTGTCAGCT
AGCAGTGCTTTTCTGATGTGAGTGGGTCCCACAGGGAGCTTGTTAAAATG
CAGATTCTGATTCATTAGGTTCCAGAGGGACCTGAGATTTCCCATTTCTGA
CAAGTTTCCAGTGTGGGGGCTGATGCTGCTGGTCCACGGACCATACTTTG
SG13S404
      GGGAGAGAATGAAGCTGGCCAAGGAACAGGGCTGGTGTCAGCTAG
CAGTGCTTTTCTGATGTGAGTGGGTCCCACAGGGAGCTTGTTAAAATGCA
GATTCTGATTCATTAGGTTCCAGAGGGACCTGAGATTTCCCATTTCTGACA
AGTTTCCAGTGTGGGGCTGATGCTGCTGGTCCACGGACCATACTTTGAGT
A[G/T]CAAGGAGCTTGATACATAATGGCTGAGTGACTTTCAGACTCCTGCT
GTAGAAAAATTATGAGTTGGCTGGGCGTGGTGGCTCACGCCTGTAATCCC
AGCACTTTGGGAGGCCGAGGTGGGCAGATCACCTGAGGTCAGGAGTTCGA
GACCAGCCTGGCCAACATGGTGAAACACCATCTCTACCAAAAATACAAAA
A
SG13S170
      ACTTAAGCCCAGAAGACTGAGGTTGCAGTGAGCCGAGATTGCACC
ACTGCACTCCAGCTTGGGCTACAGAGTGAGACTCTATCTCAAAAACAAAG
AAACAAACAACAACAATAACAACAAAACCAAGTCTCTCCCTCCACTCAA
AAATGCAAGGGCCTGTCTCCCATTGCTGGGTGCCCAGGTCTCATGAATGT
AGA[C/T]ATGAATTATTCCAGTCAGCCTCAGGAGAATAGAATGAGCCCTCA
GATGCCGAAGCACCTTTCAGATTCCACCGGTTTTATCGGCTCATTTAAACT
TCACTTCTAACACAGTCCTGCATTACACACGTGTCTGTCGTTATGGGCAGC
TGCAGAGAGGGTCTTAATGGTCCTAATGCTCAGTGAGGATGCCCAATGGT
C
SG13S171
      CTCAAAAACAAAGAAACAAACAACAACAATAACAACAAAAACCA
AGTCTCTCCCTCCACTCAAAAATGCAAGGGCCTGTCTCCCATTGCTGGGTG
CCCAGGTCTCATGAATGTAGATATGAATTATTCCAGTCAGCCTCAGGAGA
ATAGAATGAGCCCTCAGATGCCGAAGCACCTTTCAGATTCCACCGGTTTT
ATC[A/G]GCTCATTTAAACTTCACTTCTAACACAGTCCTGCATTACACACGT

FIG. 8.32

GTCTGTCGTTATGGGCAGCTGCAGAGAGGGTCTTAATGGTCCTAATGCTC
AGTGAGGATGCCCAATGGTCAACAGAACCTGCCATCTTCAGGCCATCAAG
GAGCTCTGGAGTTAAGGAAATCATGAGAGCACAGAGGGGCGGGTACAGC
AGA
SG13S172
      TGTAGATATGAATTATTCCAGTCAGCCTCAGGAGAATAGAATGAGC
CCTCAGATGCCGAAGCACCTTTCAGATTCCACCGGTTTTATCGGCTCATTT
AAACTTCACTTCTAACACAGTCCTGCATTACACACGTGTCTGTCGTTATGG
GCAGCTGCAGAGAGGGTCTTAATGGTCCTAATGCTCAGTGAGGATGCCCA
[A/G]TGGTCAACAGAACCTGCCATCTTCAGGCCATCAAGGAGCTCTGGAGT
TAAGGAAATCATGAGAGCACAGAGGGGCGGGTACAGCAGAGCCCTCGTG
GTAATGGGTTTTGAGGTCTAGGCTCTCTTCACTTGGGTTTGAAATAAGTTC
AATGACTAGTAATAGCTGAGACACTTCTACCCTTCAAATGAAGTAAATGG
SG13S173
      AGCACCTTTCAGATTCCACCGGTTTTATCGGCTCATTTAAACTTCAC
TTCTAACACAGTCCTGCATTACACACGTGTCTGTCGTTATGGGCAGCTGCA
GAGAGGGTCTTAATGGTCCTAATGCTCAGTGAGGATGCCCAATGGTCAAC
AGAACCTGCCATCTTCAGGCCATCAAGGAGCTCTGGAGTTAAGGAAATCA
[A/T]GAGAGCACAGAGGGGCGGGTACAGCAGAGCCCTCGTGGTAATGGGT
TTTGAGGTCTAGGCTCTCTTCACTTGGGTTTGAAATAAGTTCAATGACTAG
TAATAGCTGAGACACTTCTACCCTTCAAATGAAGTAAATGGGAAAATGGA
GCATTGTTGAGTCCAGGGAGCTATAATTTAAACCCCATATATCTAAAAGG
SG13S42
      CACACGTGTCTGTCGTTATGGGCAGCTGCAGAGAGGGTCTTAATGG
TCCTAATGCTCAGTGAGGATGCCCAATGGTCAACAGAACCTGCCATCTTC
AGGCCATCAAGGAGCTCTGGAGTTAAGGAAATCATGAGAGCACAGAGGG
GCGGGTACAGCAGAGCCCTCGTGGTAATGGGTTTTGAGGTCTAGGCTCTC
TTC[A/G]CTTGGGTTTGAAATAAGTTCAATGACTAGTAATAGCTGAGACAC
TTCTACCCTTCAAATGAAGTAAATGGGAAAATGGAGCATTGTTGAGTCCA
GGGAGCTATAATTTAAACCCCATATATCTAAAAGGGGTAACATTTTGTGT
GTGTGAAATTGGTGTCATTCGCACTGCATCTACAGTTTTCTTTTTCCTTCTC
SG13S194
      ACATATTTGGGAAACGCATCATACTCTTCCTGTTCCTCATGTCCGTT
GCTGGCATATTCAACTATTACCTCATCTTCTTTTCGGAAGTGACTTTGAA
AACTACATAAAGACGATCTCCACCACCATCTCCCCTCTACTTCTCATTCCC
TAACTCTCTGCTGAATATGGGGTTGGTGTTCTCATCTAATCAATACCTA[C/
T]AAGTCATCATAATTCAGCTCTTGAGAGCATTCTGCTCTTCTTTAGATGGC
TGTAAATCTATTGGCCATCTGGGCTTCACAGCTTGAGTTAACCTTGCTTTT
CCGGGAACAAAATGATGTCATGTCAGCTCCGCCCCTTGAACATGACCGTG
GCCCCAAATTTGCTATTCCCATGCATTTGTTTGTTTCTTCACTTA
SG13S195
      TGGTGTTCTCATCTAATCAATACCTACAAGTCATCATAATTCAGCTC
TTGAGAGCATTCTGCTCTTCTTTAGATGGCTGTAAATCTATTGGCCATCTG
GGCTTCACAGCTTGAGTTAACCTTGCTTTTCCGGGAACAAAATGATGTCAT
GTCAGCTCCGCCCCTTGAACATGACCGTGGCCCCAAATTTGCTATTCCC[A/
G]TGCATTTGTTTGTTTCTTCACTTATCCTGTTCTCTGAAGATGTTTTGTGA
CCAGGTTTGTGTTTTCTTAAAATAAAATGCAGAGACATGTTTTAAGCTGAT
AGTTGAGGGGTTTTGTTAATGGCTTTTGGGGGATTTATCTCTATACCCACA
AACGACTAGTTTGTTTTCCTCAAACTAAATGATAATATTAAAAA

TTATCTCTATACCCACAAACGACTAGTTTGTTTTCCTCAAACTAAAT
GATAATATTAAAAATACACATCCTGGCCAGGTGTGGTGGCTCATACCTGT
AATCCCAGCACTTTGGGAGGCCGAGGCAGGTGGATCACTTGAGGTCAGGA
ATTAAGACCAGCCTGGCCAATATGGTGAAAGCCTGTCTGTACTAAAAATA
C[A/G]AAAATTAGCCAGGTATGCTGGTGGATGCTTATAATCCCAGCTACTT
GGGAGGTTGAGGCAGGAGAATTGCTTGAACCCGGGAGGTAGAGGTTGCA
GTGAGCCAAGATCATGCCACTGCACTCCAGCTTGGGCAACAGAGTGAGAC
TCCATCTCAAATTAAAAAAAATACACATCTGGCTTCTGGAAAAATTACTT
GA

SG13S34

GATCATGCCACTGCACTCCAGCTTGGGCAACAGAGTGAGACTCCAT
CTCAAATTAAAAAAAATACACATCTGGCTTCTGGAAAAATTACTTGAAGA
TCTTTTATGACATCCATCCCTCTTCACACAGCCATGTGAATTAGGTTGGTA
TCTTCATATACTAGCATCGTGCCCAGCACTTCCATGTTATACAGTTTAAAA[
G/T]GTTCTGTAATTCCCTGTGGGAACCTAAGATAATGCGAGGACCGTCAT
ACGTGCCCCCAAATATTGGCAAACCAATGAATAAATGAATGAATGAGTTT
ATGAATCGCTAACTGGCTGTATTTAATGAAGTATGTGTGTTGAGCCATTTC
CCACAGTGTGGACAGATTTGTCCCACAATATGGGCCTCTTCCCAAAGGC

SG13S175

AATTAAAAAAAATACACATCTGGCTTCTGGAAAAATTACTTGAAGA
TCTTTTATGACATCCATCCCTCTTCACACAGCCATGTGAATTAGGTTGGTA
TCTTCATATACTAGCATCGTGCCCAGCACTTCCATGTTATACAGTTTAAAA
TGTTCTGTAATTCCCTGTGGGAACCTAAGATAATGCGAGGACCGTCATAC[
A/G]TGCCCCCAAATATTGGCAAACCAATGAATAAATGAATGAATGAGTTT
ATGAATCGCTAACTGGCTGTATTTAATGAAGTATGTGTGTTGAGCCATTTC
CCACAGTGTGGACAGATTTGTCCCACAATATGGGCCTCTTCCCAAAGGCC
TACCACCTAATGCCATCACACTGGGGATTTGATTTCAACATGTGAATT

SG13S176

AGTTCATAGTGACAGTGATCCAGCCACTGTCATGACAGGTGCCACT
TGGCAGAAACAGCACAGCTTGGAAGATGGCGGGGTGTAGTCAAGATTCC
AGGATCCCCAACAGAGAAGCCAGCTCTTATAGGGGAGCCATTCATCAGGA
TTGAACTCTCAATCGAGCTGGACAGTAATAGGTGGGTCTGTGTTATTCCCC
AG[A/G]TGAGTATCATGACAGTCACAATCCTAGGAAGGATGTGAAGCCTC
CCCCAGCTCTCCTCCAGTTGCCTGCTTGGGCAGCAGAGATGATGGAATGT
GGAGTCTGGCGTGGTCTGAGGCCTGAATCCATGTGCCTCATGTATGATGCT
CAGGCAAGAGGATCTCTCAATTCAAGGGAGAGGGCCTGAATGAGCCTTGC
TT

SG13S177

CTTGGCAGAAACAGCACAGCTTGGAAGATGGCGGGGTGTAGTCAA
GATTCCAGGATCCCCAACAGAGAAGCCAGCTCTTATAGGGGAGCCATTCA
TCAGGATTGAACTCTCAATCGAGCTGGACAGTAATAGGTGGGTCTGTGTT
ATTCCCCAGATGAGTATCATGACAGTCACAATCCTAGGAAGGATGTGAAG
CCT[C/T]CCCCAGCTCTCCTCCAGTTGCCTGCTTGGGCAGCAGAGATGATG
GAATGTGGAGTCTGGCGTGGTCTGAGGCCTGAATCCATGTGCCTCATGTA
TGATGCTCAGGCAAGAGGATCTCTCAATTCAAGGGAGAGGGCCTGAATGA
GCCTTGCTTTCCAGGCCTGTCTGATGGTCCAGGCTGAAGCCCCTCCTGGCT
TG

SG13S178

CTGGCGTGGTCTGAGGCCTGAATCCATGTGCCTCATGTATGATGCT

FIG. 8.34

CAGGCAAGAGGATCTCTCAATTCAAGGGAGAGGGCCTGAATGAGCCTTGC
TTTCCAGGCCTGTCTGATGGTCCAGGCTGAAGCCCCTCCTGGCTTGCACTG
CCAGACCTCATCCAGCAGGAGCTCCTTGGCATTGACTGCTTCAGGATAGTT
[C/G]CTTCTGCTCTGAGTGCTCTCTAAAGAGCAGTGCTCTACCATCCAAGC
TGGGCTTTTCTTTTCTTCTTGCTGATAGGGAAGGCATGGGACATTGCAGGA
TGGAAGTGGCCCCCAGGCCTTCTCATGCCTGGGCTTGGTTTGGAAGGTGG
TCAGGTGATCAATAATCCTGATTGGCCTGGCATTGAGGAGTTTTCCTGG
SG13S35

TGCTCTCTAAAGAGCAGTGCTCTACCATCCAAGCTGGGCTTTTCTTT
TCTTCTTGCTGATAGGGAAGGCATGGGACATTGCAGGATGGAAGTGGCCC
CCAGGCCTTCTCATGCCTGGGCTTGGTTTGGAAGGTGGTCAGGTGATCAAT
AATCCTGATTGGCCTGGCATTGAGGAGTTTTCCTGGGATGTGGTCCTTTC[A
/G]GTTTTTAAAAATTATTTTTATTGATACACATATTTGTAGGTATTTGTGG
GGTGCATGTGATACTTTATTATGTGTGTGGATTGTGTAATGATGAAGTCAG
GGCATTTAGGGTCTTCATCACCTTGATTATCATTTCTATGTGTTGAGAACA
TTTCAAGTTCTCAGTTCCAGCTATTTTGAAATAGACAGTCCATTT
SG13S179

GATACTTTATTATGTGTGTGGATTGTGTAATGATGAAGTCAGGGCA
TTTAGGGTCTTCATCACCTTGATTATCATTTCTATGTGTTGAGAACATTTCA
AGTTCTCAGTTCCAGCTATTTTGAAATAGACAGTCCATTTTGTTAGCTACA
GTCACCCAACCCGGCTGTCAGACATTGGAACTTACTCCTATTGAACTGT[A/
G]TATTTGTACCCATTCACCAAACTCTCTTTGGGCTTTCAGTTTTACAACTG
GGATGATCCTGGGAAAACTAAAGTAAATCAGACACCCGACGTGTGAGCTA
GGTTATAATATGCCCAGTGGACCCTGGGGACATCTTAGCTTTCAGAGGTC
ATGCTGTCCAAGCTGACTGTGGGGCTTCCAGAAGGTGGGGAGAGGAA
SG13S180

TATGTGTGTGGATTGTGTAATGATGAAGTCAGGGCATTTAGGGTCT
TCATCACCTTGATTATCATTTCTATGTGTTGAGAACATTTCAAGTTCTCAGT
TCCAGCTATTTTGAAATAGACAGTCCATTTTGTTAGCTACAGTCACCCAAC
CCGGCTGTCAGACATTGGAACTTACTCCTATTGAACTGTGTATTTGTAC[C/
T]CATTCACCAAACTCTCTTTGGGCTTTCAGTTTTACAACTGGGATGATCCT
GGGAAAACTAAAGTAAATCAGACACCCGACGTGTGAGCTAGGTTATAATA
TGCCCAGTGGACCCTGGGGACATCTTAGCTTTCAGAGGTCATGCTGTCCA
AGCTGACTGTGGGGCTTCCAGAAGGTGGGGAGAGGAAATGATGCAAT
SG13S181

TGGGAAAACTAAAGTAAATCAGACACCCGACGTGTGAGCTAGGTT
ATAATATGCCCAGTGGACCCTGGGGACATCTTAGCTTTCAGAGGTCATGC
TGTCCAAGCTGACTGTGGGGCTTCCAGAAGGTGGGGAGAGGAAATGATGC
AATGGCCCATCAGAGGCACTACTTGGGGCCTGGGGCCAGAGTGCATGTCT
AAG[C/G]CATTAAGGGGAGGGGAGAGCAGCCTTCATAATTATGAAGAGGA
GTCTCAGGTGCACAGCTTCTGATGAGGGACAGCTTCTAATTGAAGACAGC
ATTGTGTAATGCTCAAACTCCCTGTCTTCAGAGTGCCTGCTGTATCCCACC
ATCAGTTCTGTGACTTCTCCCTAAGCCTCAATTTTGCATGTGTTACATTGG
GA
SG13S182

CCTGCATAGCAAATTCTTGCAAATGTAGGGACTCAAAACAATATAA
ATTTATTATCTGACAGTTTTCTGGGTCAGAGGTCTTACTAGGCTGTAATC
AGAGGGCAACCAAAGCTGTGATCTCAGCTGAAGCTCAGGATTCTCTTCCA
AGCTCACTGGTTGTTGGCAGAATTCAGTTCTTTCCAGTTGGAAGACTAAAG
[C/T]CTACAGTCTTCAGTCTCTAGAAGCCTTTTCTCTGGCACAGGTTTCTCT

FIG. 8.35

ACAACATGGCCATTTATGTCTTTAAGGCCAATAGGAGAACATGATTAGCA
TATTTTTTTAAGTGAACTTTAGACCCTTTTTAAAGGCCTATCTGATTAGG
CCAGGCCCAAGTGAGCTTTAAGTCAACTGATTAGAGATCTTAATTAC
SG13S183
     CTGAAGCTCAGGATTCTCTTCCAAGCTCACTGGTTGTTGGCAGAAT
TCAGTTCTTTCCAGTTGGAAGACTAAAGCCTACAGTCTTCAGTCTCTAGAA
GCCTTTTCTCTGGCACAGGTTTCTCTACAACATGGCCATTTATGTCTTTAA
GGCCAATAGGAGAACATGATTAGCATATTTTTTTAAGTGAACTTTAGAC[
C/T]CTTTTTTAAAGGCCTATCTGATTAGGCCAGGCCCAAGTGAGCTTTAAG
TCAACTGATTAGAGATCTTAATTACATCTGCAAAGTCCCTTCATGTTTACC
GTATAACATAACTTAGTGAAAGGAGTGAAATTGCAACCAGGTTCTGCCTG
CACTCCACGGAAGGGGATTCTGCAGAAGTGTGGGTCACGGGGGGGTTA
SG13S184
     AGAACATGATTAGCATATTTTTTTAAGTGAACTTTAGACCCTTTTT
TAAAGGCCTATCTGATTAGGCCAGGCCCAAGTGAGCTTTAAGTCAACTGA
TTAGAGATCTTAATTACATCTGCAAAGTCCCTTCATGTTTACCGTATAACA
TAACTTAGTGAAAGGAGTGAAATTGCAACCAGGTTCTGCCTGCACTCCAC[
A/G]GAAGGGGATTCTGCAGAAGTGTGGGTCACGGGGGGGTTATTTTGGGA
TTCTGCCTACGTCACTGAGTCAAAAGAAGCTGAATGGTTGTGATGCTGAG
GTTTTGGGCAGCAGCAGTGTGTGTGTGAGTGAATTCATACGTATGACC
ACCTGGGAAGAAAGGAGGCTGTGGTTTCCTCCACCTCCTGGCAGACAGA
SG13S185
     GGGATTACAGACACACACTGCCACGCCTGGCTAATTTTTGTATTTTT
AGTAGAGACGAGGTTTTGCCATGTTGGCCAGGCTGGTCTTGAACTCCTGA
CCTCAAGTGATCCGCCCACCTCAGCCTCCCAAAGTGCTGGGATTACAGAC
GTGAGCCACCATTAACCATTTTTCTATCTCCTGTGGGAAAGGGCACAGTG
A[A/G]AGAACAGATGAAGCTGAGACATACAAGTGAACTCCTCCCTCCTCTC
CATTTAGACTAAAATAGGATTATTCATACTGAGATTCTCCCTGGTTGCAAA
GAGATAATCTGTGCAACTGGGTTTTTACAATTATCCCTACCCTATGCTTTC
CTCATCTGTCTTCCTCGTAGTCAGCTCAGGCTGCTATAACAAAACACCA
SG13S405
     GGCAGATTCGGTGTCTAATGAGGTCCTGCTTTCCAGTTTATAGACA
GTGCCTTATCGCTACCGCCTTACACAGTGGAAGGAGAGGACGAGAAGCTC
CTTGGGCTTTTTTTGTTTCTTTCTTTCTCTCTCTCTCTTTTTTTTTTTT
AATAAGGTCACTATCTTAGTCCATTTGTGTTGCTAAAAGGAACATCT[A/G
]AGGTTGAGTAATTTATTTTATTTTAAAAAGTGGCCAGGCATGGAGGCTTA
TCCTGTAACCCTAATCCTTTAGGAGGCCAAAACAGCAGGATTGTTTGAGG
CCAGGAGTTCAAGACCAGCCTAGGCAAGATAGTGAGACCCCATCTACCCC
ATCTCTACTAAAATTTTAAAAAATTAGCTGTGTGTTGTAAAGTGTGC
SG13S91
     AATTTATTTTATTTTAAAAAGTGGCCAGGCATGGAGGCTTATCCTGT
AACCCTAATCCTTTAGGAGGCCAAAACAGCAGGATTGTTTGAGGCCAGGA
GTTCAAGACCAGCCTAGGCAAGATAGTGAGACCCCATCTACCCCATCTCT
ACTAAAATTTTAAAAAATTAGCTGTGTGTTGTAAAGTGTGCTTGTAGTCCC
[A/G]GCCACTTGAGAGGCTGAGGTGGGTGGAGTTCAAGGCTGCAGTGAGT
TATGATTGAGCCACTGCACTCCAACCCGGGTAACGGGGCAAGACCTTGTC
TCTATTTAAAAAAAAAAAATCTTTATGTGGCTCACTATTCTGGGTGGCTGG
AAAGTTCAAGATTGGGCATCTGCATCTGGTGACAGCCTCATGTCGCTTCC
SG13S186
     TAACCCTAATCCTTTAGGAGGCCAAAACAGCAGGATTGTTTGAGGC

FIG. 8.36

CAGGAGTTCAAGACCAGCCTAGGCAAGATAGTGAGACCCCATCTACCCCA
TCTCTACTAAAATTTTAAAAAATTAGCTGTGTGTTGTAAAGTGTGCTTGTA
GTCCCGGCCACTTGAGAGGCTGAGGTGGGTGGAGTTCAAGGCTGCAGTGA
G[A/T]TATGATTGAGCCACTGCACTCCAACCCGGGTAACGGGGCAAGACCT
TGTCTCTATTTAAAAAAAAAAAATCTTTATGTGGCTCACTATTCTGGGTGG
CTGGAAAGTTCAAGATTGGGCATCTGCATCTGGTGACAGCCTCATGTCGC
TTCCAGTCATGGGGGAAGACGAAGGAGAGCTGGCACGTGCAGATATCAC
G

SG13S187

ATCCTTTAGGAGGCCAAAACAGCAGGATTGTTTGAGGCCAGGAGTT
CAAGACCAGCCTAGGCAAGATAGTGAGACCCCATCTACCCCATCTCTACT
AAAATTTTAAAAAATTAGCTGTGTGTTGTAAAGTGTGCTTGTAGTCCCGGC
CACTTGAGAGGCTGAGGTGGGTGGAGTTCAAGGCTGCAGTGAGTTATGAT
T[A/G]AGCCACTGCACTCCAACCCGGGTAACGGGGCAAGACCTTGTCTCTA
TTTAAAAAAAAAAAATCTTTATGTGGCTCACTATTCTGGGTGGCTGGAAA
GTTCAAGATTGGGCATCTGCATCTGGTGACAGCCTCATGTCGCTTCCAGTC
ATGGGGGAAGACGAAGGAGAGCTGGCACGTGCAGATATCACGTGTTGAG
G

SG13S188

TTAAAAAATTAGCTGTGTGTTGTAAAGTGTGCTTGTAGTCCCGGCC
ACTTGAGAGGCTGAGGTGGGTGGAGTTCAAGGCTGCAGTGAGTTATGATT
GAGCCACTGCACTCCAACCCGGGTAACGGGGCAAGACCTTGTCTCTATTT
AAAAAAAAAAAATCTTTATGTGGCTCACTATTCTGGGTGGCTGGAAAGTT
CA[A/G]GATTGGGCATCTGCATCTGGTGACAGCCTCATGTCGCTTCCAGTC
ATGGGGGAAGACGAAGGAGAGCTGGCACGTGCAGATATCACGTGTTGAG
GGCAGAAGCGAGAGAGAGAGGGGAGAGATGCCAGGCTCTTTTTAACAAC
CAGCACTGGGGAAACTAATAGAGTGAGAGCTCACTGACTCCTGAGGGAG
GACAT

SG13S406

ATGGGGGAAGACGAAGGAGAGCTGGCACGTGCAGATATCACGTGT
TGAGGGCAGAAGCGAGAGAGAGAGGGGAGAGATGCCAGGCTCTTTTTAA
CAACCAGCACTGGGGAAACTAATAGAGTGAGAGCTCACTGACTCCTGAGG
GAGGACATTAATCTATTGATGAGCGACCTGCCTCCATGACCCAAACACCT
CCAA[C/T]GATACCCCACCTCCAACACTGCCACACTAGGGATTAACTTTCA
ACTTGAGATTTAGAGGGGGGAAACTTACAAACTATCGCAGGCACTAATAC
CACTCATGAGGGCTCCACCTTCATGACCTAATCACTTCCTAAAGGCCTTAC
CTCTTAATCTCATCACATTGAGGATTCGATTTCAACTTGAATTTTGGGGGG
AC

SG13S92

CTCGCTGCCACCTGAAATTAGATCATTTATTTACCCCTTTATTTGTT
CAGTTTGCCTTGTCCGTTAGAATATAAGCTTCCAAAGGGCAGGAGCTTTGC
CTATATTGTTAGGCCGGGCATACAATGAGCACTCAAAAAAATATTTGATG
AGTGTATGAAAGAACAGACTGGGTTATGTAATTGTGCCTACTTACCTATA[
C/T]GACCGTGTGGTGGGGTTTATGGTGGGTGTGGTGGTGATGGCTATAGG
GCTATAAGCAAATTTGGGACAGGGAGTCTAAGAAATGTTCTTAAATTTTA
GTAAGCAAAGCATCCTCTACAGAACCTGTCTTAAAACATGAAAGTTCCTT
AGTGCTACCCCCAGAGGTATGATTTGGTAGGTCAAGGATAGGGCCTGGAA

SG13S93

TGCCACCTGAAATTAGATCATTTATTTACCCCTTTATTTGTTCAGTT
TGCCTTGTCCGTTAGAATATAAGCTTCCAAAGGGCAGGAGCTTTGCCTATA

FIG. 8.37

TTGTTAGGCCGGGCATACAATGAGCACTCAAAAAAATATTTGATGAGTGT
ATGAAAGAACAGACTGGGTTATGTAATTGTGCCTACTTACCTATATGACC[
A/G]TGTGGTGGGGTTTATGGTGGGTGTGGTGGTGATGGCTATAGGGCTAT
AAGCAAATTTGGGACAGGGAGTCTAAGAAATGTTCTTAAATTTTAGTAAG
CAAAGCATCCTCTACAGAACCTGTCTTAAAACATGAAAGTTCCTTAGTGCT
ACCCCCAGAGGTATGATTTGGTAGGTCAAGGATAGGGCCTGGAAATTCA
SG13S36

CCTGTCTTAAAACATGAAAGTTCCTTAGTGCTACCCCCAGAGGTAT
GATTTGGTAGGTCAAGGATAGGGCCTGGAAATTCACATTCTTGTTAAGAT
GTTCTTCATCCGGGGTTTGTTGACCACCTTTTCAGAAGATTTTTGCTCTGTA
GCTGTACTACCCAATGCAGTAGTTCGTAGTCAGTGTGGCTCCTGAGCCCT[
C/T]GAAGTGTAGCTCCTCTGAACTGAGACGTGCTGTAAATGTAAATTGCA
CACCGGAGTTTGAAGAGTTAATACAAAGAAAAAGGAATGCAAAACATCT
CATTAATAATGCTTTACACTGATTACATATTGAAATGGTAATCTTGTAGAT
ATAGTGCGTTAAATAAAATATACTGTTAGGCTTAATTTCACGTCTTTATA
SG13S407

TCAGCCAATCAACAAGAGGGCAAAAGAACAAACATTTGATGTGTA
ATTACTTAATTTAGTGCATATGCATTTGGGTCCTCAATGTCAGCACTATGG
CAACCAGAACATGGCCACAATAACTGTCTGGAAATGTCTATTCTTACCTG
GACCCAGCAGGCCATGCCCCACTGATTATATAATCTCCCTCTCTCCTTGTT
A[C/T]GGTCTGAATGCTTGCATCCCTCAAAAATTCATGTGTTGAAATCCTA
ACCCCCAAGGTGATGATATTAGGAGGTCGGCCTTTTGAGAGGTAATTAGG
TCATGAAGACAGCATCCTCATGAATGGGATTAGTGTCCTTATAAAATAGG
CCCAAGGGAGCTCATTCACTTTGTCCACCATGTGAGAACACAGCGAGAGG
G
SG13S408

CCTTGTTACGGTCTGAATGCTTGCATCCCTCAAAAATTCATGTGTTG
AAATCCTAACCCCCAAGGTGATGATATTAGGAGGTCGGCCTTTTGAGAGG
TAATTAGGTCATGAAGACAGCATCCTCATGAATGGGATTAGTGTCCTTATA
AAATAGGCCCAAGGGAGCTCATTCACTTTGTCCACCATGTGAGAACACAG
[C/T]GAGAGGGCACCATTTATGCACCAGGAAATGGGCCTTTTCCAGACAAT
CTGTCGGTGCCTGGATCTTGGACTTCACAGCCTCTAGAACTGTGAGAAATT
AATTTGTTTTTTATAAGCCACCAAATCTATGGTTTTTTTATAGAAACCGTA
ATGGACTAAAACACTCCCTAATTATATTTAAACTTATCAGTGCACTG
SG13S7

CTAACCCCCAAGGTGATGATATTAGGAGGTCGGCCTTTTGAGAGGT
AATTAGGTCATGAAGACAGCATCCTCATGAATGGGATTAGTGTCCTTATA
AAATAGGCCCAAGGGAGCTCATTCACTTTGTCCACCATGTGAGAACACAG
CGAGAGGGCACCATTTATGCACCAGGAAATGGGCCTTTTCCAGACAATCT
GT[C/T]GGTGCCTGGATCTTGGACTTCACAGCCTCTAGAACTGTGAGAAAT
TAATTTGTTTTTTATAAGCCACCAAATCTATGGTTTTTTTATAGAAACCGT
AATGGACTAAAACACTCCCTAATTATATTTAAACTTATCAGTGCACTGGGC
AGTGACATATTAAAAGAATGCTGGCCAACGTAATTGACACCATAAGGCT
SG13S37

TCATCTCATTTTAACCTTTTGTTTCAAAGCCTCTCTTTTCATGACTTC
CCCGCCTTCATTTTTCCCATATGGTGGGGTTATTATTAAGACATTAAATGA
GAGTGGACAGGTAGGCAAAGGAGGTGGGTTGCAGGGGAGTTGAGGGTTG
CCTGTGTACTTTTCTAGACTGTTCCACTTCACATCAGTGAAATATTCCCA[A
/G]TTGATACTATCATGAAACAAAGCAAATGAAATGCTGAGCACGGAGCTT
CGTCTTGATGAAATGCTGAAAGAAAAGAAAGGAAAAATAAAGTAGCCAT

FIG. 8.38

TATTTTTGCCCTTCCTCCCACCCCCATGTTTACTACTCTTATTTCTCTTTTGT
ATTGTTGTGTTGGAAGCACAGCATCAGAAAAACTCCCAGTTTTGAGA

SG13S409

ACAGGTAGGCAAAGGAGGTGGGTTGCAGGGGAGTTGAGGGTTGCC
TGTGTACTTTTCTAGACTGTTCCACTTCACATCAGTGAAATATTCCCAATT
GATACTATCATGAAACAAAGCAAATGAAATGCTGAGCACGGAGCTTCGTC
TTGATGAAATGCTGAAAGAAAGAAAGGAAAAATAAAGTAGCCATTATTT
TT[A/G]CCCTTCCTCCCACCCCCATGTTTACTACTCTTATTTCTCTTTTGTAT
TGTTGTGTTGGAAGCACAGCATCAGAAAAACTCCCAGTTTTGAGAGATAA
CTCAGTGTTTAGTTCACTTAAACCTGAGAAGGAGAAGAGGATGCCACCG
TGAGGTCCAGGACGTAAAGAGGAAAAAAACAGACAAAAAAATCCATATG
A

SG13S8

CAGGTAGGCAAAGGAGGTGGGTTGCAGGGGAGTTGAGGGTTGCCT
GTGTACTTTTCTAGACTGTTCCACTTCACATCAGTGAAATATTCCCAATTG
ATACTATCATGAAACAAAGCAAATGAAATGCTGAGCACGGAGCTTCGTCT
TGATGAAATGCTGAAAGAAAGAAAGGAAAAATAAAGTAGCCATTATTTT
TG[A/C]CCTTCCTCCCACCCCCATGTTTACTACTCTTATTTCTCTTTTGTATT
GTTGTGTTGGAAGCACAGCATCAGAAAAACTCCCAGTTTTGAGAGATAAC
TCAGTGTTTAGTTCACTTAAACCTGAGAAGGAGAAGAGGATGCCACCGT
GAGGTCCAGGACGTAAAGAGGAAAAAAACAGACAAAAAAATCCATATGA
A

SG13S410

TTCGTCTTGATGAAATGCTGAAAGAAAGAAAGGAAAAATAAAGT
AGCCATTATTTTGCCCTTCCTCCCACCCCCATGTTTACTACTCTTATTTCT
CTTTTGTATTGTTGTGTTGGAAGCACAGCATCAGAAAAACTCCCAGTTTTG
AGAGATAACTCAGTGTTTAGTTCACTTAAACCTGAGAAGGAGAAGAGGA
[C/T]GCCACCGTGAGGTCCAGGACGTAAAGAGGAAAAAAACAGACAAAA
AAATCCATATGAAATGAAATGTGAAAGAGGCGCTTTCGAGCAGATGAGT
GTTGTAGATTACAGTGTTGAGAGCTGTTTGTGTCCAGAGCTGCTTGCTGCA
CCTGGCGGGATAAACACTGGTCTAACAGAGGATCCTTGTTTCAAGGAGGC
T

SG13S411

AAGAAAAGAAAGGAAAAATAAAGTAGCCATTATTTTGCCCTTCCT
CCCACCCCCATGTTTACTACTCTTATTTCTCTTTTGTATTGTTGTGTTGGAA
GCACAGCATCAGAAAAACTCCCAGTTTTGAGAGATAACTCAGTGTTTAGT
TCACTTAAACCTGAGAAGGAGAAGAGGATGCCACCGTGAGGTCCAGGA
C[A/G]TAAAGAGGAAAAAAACAGACAAAAAAATCCATATGAAATGAAAA
TGTGAAAGAGGCGCTTTCGAGCAGATGAGTGTTGTAGATTACAGTGTTGA
GAGCTGTTTGTGTCCAGAGCTGCTTGCTGCACCTGGCGGGATAAACACTG
GTCTAACAGAGGATCCTTGTTTCAAGGAGGCTGCCTTTTATTGGGGGGAC
AA

SG13S9

ATTATTTTTGCCCTTCCTCCCACCCCCATGTTTACTACTCTTATTTCT
CTTTTGTATTGTTGTGTTGGAAGCACAGCATCAGAAAAACTCCCAGTTTTG
AGAGATAACTCAGTGTTTAGTTCACTTAAACCTGAGAAGGAGAAGAGGA
TGCCACCGTGAGGTCCAGGACGTAAAGAGGAAAAAAACAGACAAAAAA
[C/T]CCATATGAAATGAAATGTGAAAGAGGCGCTTTCGAGCAGATGAGT
GTTGTAGATTACAGTGTTGAGAGCTGTTTGTGTCCAGAGCTGCTTGCTGCA

FIG. 8.39

CCTGGCGGGATAAACACTGGTCTAACAGAGGATCCTTGTTTCAAGGAGGC
TGCCTTTTATTTGGGGGGACAAAATTGTTCTTGAAAGCTGCTCAGTGGTT

SG13S412

TTTGTATTGTTGTGTTGGAAGCACAGCATCAGAAAAACTCCCAGTT
TTGAGAGATAACTCAGTGTTTAGTTCACTTAAACCTGAGAAAGGAGAAGA
GGATGCCACCGTGAGGTCCAGGACGTAAAGAGGAAAAAAACAGACAAAA
AAATCCATATGAAATGAAAATGTGAAAGAGGCGCTTTCGAGCAGATGAGT
GTT[A/G]TAGATTACAGTGTTGAGAGCTGTTTGTGTCCAGAGCTGCTTGCT
GCACCTGGCGGGATAAACACTGGTCTAACAGAGGATCCTTGTTTCAAGGA
GGCTGCCTTTTATTTGGGGGGACAAAATTGTTCTTGAAAGCTGCTCAGTGG
TTCAAGCTACAGCATGGTGGACTAGCAGAATGGACTCCAGGGCCTCCGAG
GA

SG13S413

TTTTGAGAGATAACTCAGTGTTTAGTTCACTTAAACCTGAGAAAGG
AGAAGAGGATGCCACCGTGAGGTCCAGGACGTAAAGAGGAAAAAAACAG
ACAAAAAAATCCATATGAAATGAAAATGTGAAAGAGGCGCTTTCGAGCA
GATGAGTGTTGTAGATTACAGTGTTGAGAGCTGTTTGTGTCCAGAGCTGCT
TGC[C/T]GCACCTGGCGGGATAAACACTGGTCTAACAGAGGATCCTTGTTT
CAAGGAGGCTGCCTTTTATTTGGGGGGACAAAATTGTTCTTGAAAGCTGCT
CAGTGGTTCAAGCTACAGCATGGTGGACTAGCAGAATGGACTCCAGGGCC
TCCGAGGAGACAGTGACTGCTGCCAGAAATAGTCAAGGATAGAAAGGAA
GGA

FIG. 8.40

SEQUENCE LISTING

<160> NUMBER OF SEQ ID NOS: 717

<210> SEQ ID NO 1
<211> LENGTH: 214000
<212> TYPE: DNA
<213> ORGANISM: Homo sapiens -continued

```
<400> SEQUENCE: 1
gactaagatg aatatgcatt cattcaccaa aatctcatat tcccaaaaag caggaaaggt      60
agtacagtga gatggatgat gccttcacat gactcagatg tcacgtgttt ctcaccattg     120 agaccccaa ggcaccccct cccagcattt accagaatgt gtgtgtaact atttacagtg     180
atttgtgtaa ttatttgatt gtttctcttg tatcctgtag caatgagggt agagattata     240
tcccacctac cactgcagct ccaggatcca gcttcacaaa catttgttga atgaatgaat     300
aagaaaagag gacacccca aagaggctgc aagggaaaaa gctacaaaga cagaagcacc     360
aggaaaaagt agggtcatgt aagtcaaagc aggaaaaaag ttccatggtg gggtggtcag     420
cagtgtctaa tgccacgaag gcacaaagta ggataaaggt taaaaatcag cctttggttt     480
tggcaaatat gaagcttatc ggtagcctta gcgagaacaa ttccatcagg gagcagaagc     540
taactgcagt gggttgagtc atcaagcagg cataaggaag tagggatacc ccattataag     600
ctactctttc aagaagctca aatctgaagg ttaggagaat taggtcagta gctagaagga     660
aatgtggagt cgagggctg ttttcctcc caaggagtat aaaggtgtaa cgttgcatga     720
aaccacttca gacaaaggcc gatatcaata gagaagttaa aacgcacgcc tcaagatttg     780
ggaaggcttg gggttgggct taagaggta ggagcatatt tcctatccta ggacagagaa     840 taagaagaa aggataggtt cccatggaga taaatttcta agtgttaaag aagaggctca     900
gaaaattcta gcatgatagg ctcacttttt tcttttttcca tgaaggagat ggcaaagtca     960
actgacatga gaaggtgac aatactgatg ggttgaagag cgatggacat ttgaaataac    1020
ttcttagacc agtagaggct ggagttcata aatcagaact ggctacaggt tatatatgtt    1080
tttttttttt tctccaacag cataagataa cagagcgaag tctgtagaaa tgaaagaaga    1140
gtcagatgag gatagctgga gctagtgcaa ggagggaagc accacggtgg gagccaggta    1200 cccctggat ttataattca tactgaattc caacaacaga agggctctaa gcaggagagt    1260
gacagatttc agaagactga gacacatttg gtaaaaaaaa gtaggaggaa aacctgattc    1320
tggaattagg gcagccaata gacggcagta ttttcagaaa ggagggaatg gtcaacagtg    1380
actttctagt ctggagctca ggaggaagag gcaactctac ctgatggtat taagatcatg    1440
gaggtagctg agatcaccta gcttgtgtgt gtcaaatgag aaaagaagaa agaataggag    1500
aagttcccca ggaacacaga cattaagtgg ggctgtggtg acaacacaag aagagaggct    1560
tgcaaaggag cctgagcagc tgtcatgaga gaggtaggat ggtggactcg agaagaggc    1620 agaagatgtt cttaaaggaa ggacactgct gccaagtagt cagccaattg gtgacaaaga    1680
aagaccctgt tgcgagaaaa aaagtcagtg aagtagtagg aacgatgaca gatgacactg    1740
ggttgaagac tgaggagaga gaagtgtaag agtggaagca gagggcagac cactcttctg    1800
agacactgaa gaggcatagt tagaaataaa ggggagtcgc cagaaaggaa tttgtggcta    1860
agcaagaggt tttcttttaag actgaaatac ataagcatga tttaaatgct gctgggatgg    1920
agttcacaga cctggaagac agaagacaaa gcggatcatc aagatagtgg aatttactga    1980
aatgagagag gaaaatccca tccacaggaa atgcagacat gagggagggg ccagaaggac    2040
agtgaaaaca tcagcaactg gtcccccaac ttctgagtga atgtggagat ataatcaggt    2100
aaaggactgc atcatctccc tggttaatga tggagtcaga gaaagagtg tcttatacag    2160 aagttgtgat atacttggcc gggcgcagtg gctcacgcct gtaatctaag cactttggga    2220
ggccaaggca gcggatcac ctgaggtcag gagttcatga ctggcctggt caacatggca    2280
aaatcccacc tctactaaaa acaaaagcct gtaatcccag ctactaggga ggctgaggca    2340
```

```
ggagaatcgc ttgaacccag gaggcagagg ttgcagtgag ccaaggtcgc accactgtac   2400
tccagcctgg gcaacagagc tagactcagt ctcaaaaaaa aaaaaaaaag atgtatttat   2460
tctcactgta taaatttctg tgtaagaaat actctctcat atagaagtaa atttatatat   2520
aaaattatat agaaccacta taaaatactc aggtttataa aatttatata taaacttgtt   2580
gacatataaa attccatgta aatgactata aagtactctt atatgaaaag tatatgaatt   2640
aaattatata tcaacttact tttatattac agtattttg ttatacagaa gtttatatag   2700
tgacaataaa tatttctcaa gaacgatttc acataataga agtataaatt atccatttcc   2760
aatagtgaaa aagaaaagca gttccacacc agtgacaggg ctacgaatct aagaggtaca   2820
aagacttcat tcttagagac actgaggtca gggcatggcc aacacatctg aagctgatag   2880
aattggcgct gggttggttg gagacggtac ggtattacta ttacaatggc agacgcttgg   2940
ccttgataac tagccaatca gggggaaaga ttctggtttc ctctgttatt atctgaacta   3000
gtgtgttccc aaagggttaa gatggtttat ggaaggcaca agatcagcaa accataaagg   3060
attagcacta agaaggaagg aagtagacca agtgttaatg gcgatgccat gtaagagcca   3120
ggtctgcgat gtatgttcta catggtttgg ggggtaaaaa aaatgtcagc ctccagagca   3180
cagggcttta agcctcaagt actgttaaca gtagagttta ctagtctaca gcaggaatta   3240
caaccagtaa ttctaaggcc aattactcag gcaagtttta ctagaacaag gaagctctgc   3300
ttcgaggtca aatcgatttc tgcatttata gaagcatcta gatgttctct gttcaaacaa   3360
tggggtaaaa tccccacaca ttttatttct gacagagtgt tccctatatt gcctggccag   3420
gagtgataac attgcttggc tattattaat aaaacattgc tgtggctggg cgcagtggct   3480
cacacctgta atcctggcac tttgggaggc tgaggcagga ggatcactta actccaggag   3540
tttgacagca gcctgggcaa catagcaaga tcccatctct ctaaaaaatt ttaaaattag   3600
ctgggtgtgg tggcagacac ctgtagtccc agctcctcag gaagctgagg tgggaggatc   3660
acttgagccc aagcaggttg aggctgcagc gtgctgtgac tgtgccactg cactccagcc   3720
tgcgcaacac actgagagag actctgtctc aaaaaaatac atcaaataaa aattaaaagc   3780
ccatttcttt cttttggtac attacagcca tgcacttcaa aggctagcac aattattttt   3840
ctgcagttct atatttagat tctagttaga agtaacctag gaccttcatg ttagaggtgt   3900
ctttggcaaa actgttatgt gagtgaaacg tttaatcaat tgaggataaa gatgcctcat   3960
tgctaatgaa gatgtggttt aaggatttta tgcacccagt tcatttatta acaacttgtt   4020
taagctttat tagctgggtc tctactttat aactgtgttc tttaatttac aagacaataa   4080
aaattaaaat ggtaaatggg aaacctatct tgcttttcaa taaataattt attttaataa   4140
cttcgtgggc atggtggcca aaacatttta gctgtgaaaa taatttcaat tcatattttt   4200
ttggaatcaa tattaaaagg tgatatattc tcaaatgaaa agtggacaaa tgatcagtta   4260
taggacatga ttaagaaact aaccatgagc cacgtgcagt ggctcatgcc tgtaatccca   4320
gcactctggg aggccgcggt gagcggattg cttgagccca ggagttcaag accaggctgg   4380
gcaacatggc aaaaacccgg ctctactaaa aatgcaaaaa aaaaaaaaaa aaaaaaatt   4440 tagctggggtt ttggtggctt atgcctgcag tcccagctac tcgggaggct gactcgggag   4500
gctgaggcac aagaatcatt tgaacccagg aggcagaggt tgcaatgagc tgagaataca   4560
ccactgcact ccagcctggg caacagagag agagagactc agtctcaaaa aacaaacaaa   4620
caaacaaaca aaccgctgcc ctgtgcttgg agagatctgt ttacctttac cactaaagac   4680
```

```
tgttggaagt aaattttaga aggtttataa tacctaaaag taatcacttc tgtcttatga   4740
aaggttctgc tgagattttt ctattgtggc cactagtggc aatattccag aagtcatatt   4800
taaagaatat ctttagtgga ttcagcagtt tttcaaatat gtacttttat ctctccaaca   4860
ttcatgattg caatttttca aattaacctc atgatataaa caactgtact ctatgatgcc   4920
tcatagtaca gaaactggag gcagaaagag aagttgaatg tctaagaatc ggtaattcta   4980
aaactcaaca tagaccattc agcattagtg gttctaacaa tcccactgca aaatgagttg   5040
ataatgtgta acactttagt gaactaaagc ataagaacc atggtctcct aatgcagcaa    5100
attaaaacac atgatagcta caattaatga agtacatagt cctggctggg cactatggta   5160
cgtcctttac atagattatc tcttaaatta ttaaccccgt tttagagatg agaacattcg   5220
ggctcaggaa ggttatgtaa gttatataaa aatcacaaaa taagagacag agctaagatt   5280
tgaatccaag tgtgaccagg ttcatatcaa gcttccattt ttgaatttat attagaggtc   5340
aataactcac ctttgtcctt ttaaaataat ttttggctct gtgacctaca caggcaagct   5400
gttatttaca aacaacccac acatctagat ggtcactgtc tcaccgccca cttttaccat   5460
caggactcct agtgagctgt caagggaat gctataattt tggaggttct aaatctgagg    5520
gcttaagaaa gaaagaaatt gtaaaaagca ggcattactc aggggcatag attgtcaggc   5580
agatctgtca tgcttatagg taacctccca gggccaaaaa tatatgtgcc caaactgcct   5640
aaatatttcc tgtcacttca taatactgcc tgaaatcctg ccaaattaga acttcatttg   5700
tgttgcttgt caatttttaa cgcataagca aatcacctgg agatcttgtt aaaatgcaaa   5760
ttctgattag gttaggtctg ggtctgcatg tctgatatgc ttccagaggg cactgatgct   5820
gctggtccat ggaccacact taaagaagca aaaaagatgt ctgatattta ctctctggct   5880
gcctaggagt gcttctcatt taagtgagat ctctttgtgc atcataatgg gagggatgag   5940
ctgaaaagca gcaaattaag agtgagttaa gtgtctacct cacttcccta ctatctgtaa   6000
caagcaggtt tgggcactgt ggtcaaccag aaaattcttt ccaggaccac aacccttgag   6060
attatgttgc aaagatgcaa ggacaactta gaaataattt ccagcactgg tggcactgga   6120
tgtctgtcag tggtgctggt ggcagggtcc tattcagact gtggtttacc tgcctggccc   6180
gtttggttat gggccatttt ctgagtacca tggagcatcg cccagctgac aagggcttgt   6240
actccaccct tggtgcgcag aagggaagct tggctgctac taagtttggt gcaaagtaat   6300
tgtggttttg ccattaatat ttgatacagt gagtccctac tttcctcagg tgaaactaga   6360
acttaagggg acacgctcaa gttctcatta tacagtacta agtttcaaaa atcagcaatt   6420
ttatcaaaca catgctctac agcagtggtc ggcaaacttt ttctgtaagg ggccagagag   6480
taaatgtttt agagtttctg ggccacatat ggtttctgtt ccagctataa actctgccac   6540
tgtagggcaa aagcaaccct ccacaataca tacatgaata ggtgtgttcc aaaaaaactt   6600
tatttgtgga ccctgaaatt tgaatttcat aaacttttca tgtgtcatga atattcttt    6660 tgattttttc ccaacctttt aaagatgtaa caccatttt tagcctgtag gccatataga    6720
aacaggcagt gggctgggtt tgctgaccct tgctctgaag caatgatatc tcgatccaat   6780
ttatacccac aaattttct ccttgaaacc atgcatttaa ttctcatctc ttcttaccat    6840
gacaataaga agttattcta tataacaaag agattgtacc cacccaagcc agcatttaga   6900
tcatgtcatt tgcttcctca aaatttggt ctttataaaa atcaattaaa gcaccttaaa    6960
aggtaagcag tgatgaaata tttgaaataa ttggctaatt aaacatcacc taaatagaaa   7020
ctgtgataag aaccacaaat gcgaaaagga atcatgtagt aactaatgtg gaggatatct   7080
```

```
tggtttagag atttgatgaa cacgagtttt gatttaaaaa aatttgtgca atactcactg    7140
ctttggtggg gagcttgcta tgcaagttgg tagaaaaatt tatcctaaag tcacagttct    7200
ctaccactct ggattttctc gagctaacta ccattccaaa ctattttagg cacagttact    7260
agtttcaaga atcaggcaaa ttgccctggt attagcactg ttctttctgt ggtcacaagt    7320
caaactactg tggtgaataa aattagatga tttctttagt cttccttttt tcagcccctg    7380
tagtcaattt ccagtgctcc attcaaagaa aaaccaaaaa tgtccagaat ataaccttat    7440
tttaaaactt gttaaccact gatttcactt gttaaccaaa tttttttttt ttttttttg    7500 agaatgaatc tcactctgtc accaggctgg agtgcagtgg catgatcttg gttcactgca    7560
acctccgcct cctgggtact ggttcaagca attctcctgc ctcagtctcc cgagtagctg    7620
ggattacagg tgtgcacccc cacacccagc taatttttt gtacttttag tagagatggg    7680
gtttcaccat gttggccggg ctagtcttaa actcctgacc tcgtgatccg cccgcctcgg    7740
cctcccaaag tgctgggatt gcaggcatga accactgcgc ccagcctgtt aaccaaattt    7800
ctaatcacac acacttgagg cccagtaaat gcctgctgaa aagagggtgc tggtggtgag    7860
gcaactgagg ggctaacata ctgatagctg ctgaaatctt ctacagctct ttcttgttag    7920
aacactccat cacggctccc aggcccacac cacatgaagg aacttctagc tctcttgctt    7980
gctctttacc caaatgtagt tagcaagtcc tgggaactaa acagcattga cacacttgaa    8040
gaagacaatt aggcaaatcc caactgctgt gctcctgcag ctaaagatga agactcgtcc    8100
attgggcagt tgattaattg tacctagaaa attaatttca atggtcccat gacaacatac    8160
gggcagtgaa gctctagtgt tcccctggg tggaatcttc aggatgtat agtctcccat    8220 accagctcat cctcccattt ttccagattc tggttcttct ctcttaccta gtgtgtagtg    8280
ggccaaatgg tggtccccca aaagatatg tccatgtgtt aaccctggaa actgtggatg    8340
taaccttatt tggaaaaatg gggccaggtg cagtggtgtg catgtgtagt cccagaactt    8400
tgagaagcca aggtgggaga atcgttggag cccaggagtt caagaacagc ccaggcaaca    8460
tattgagacc cccgtctcta taagcaataa aaaattagct aggtgtggtg gcatgcacct    8520
gaagttccag ctacttgaga ggctgaggca aaggactgc tcaagcccaa ggagttcaag    8580
gctgcagtga gctatgatca tgtcacccca ctccagcctg ggtgacagag tcagactccc    8640
tgtctcagga gaaaagaaaa aaaggtcttt gtaaatgtaa taaagaatct tgagataaga    8700
tcatcctgat ttaggatgga ccctaaatcc aatgacattt gtccttacaa agaaaggta    8760 gagggaactg tgagacagac acagagggga gggccttgtg aagcaggaag catagatgca    8820
gttacaagtc aaggaatgcc aaggactgtc tacaaccaga agccaggaga gatgcatggg    8880
atgatttctc cctcacagcc tccagaactt ctggcctcca ggactgtgaa gaatcaattt    8940
ctgttgtttt aagccaccaa gtttgtgtgt catttgttat ggcaatggca gtattaggac    9000
tctaatacac agtataaaaa aataaaaata gggccaggcg tggtggctca gacctataac    9060
cccagcactt tgggaggcta aggcggggag atcacttgag gtcaggagtt tgagaccaac    9120
caggccaaca tggtgaaacc ccatctctat aaaaataaa aattagttgg gcatggtggt    9180
gtgcatctgt aatcccagtt actcaggagg ctgaggcaga agaatcgctt gaacccagga    9240
agtggaggtt gtagtgaatg ccactgcact ccagcctggg tgacagagct agactccttc    9300
atcctaggac acagccaagt cttacgtagc aaaaagaagt tgttaaaggt ctgtagttct    9360
gcattaagca acacaggcat gtacctatga attatatgat tataaaagtg ctcggacagg    9420
```

```
cccatttcaa acttggcctc tttccaccaa ctgtgtactg tttctcattc cataactaga   9480
gattatgtct ttatatcctg tcaaaaaagt gaattttgt gggctaagac attatccctg    9540
tgttaaatgc accagtctta gtgtaaacaa gcctagttcc tttttcattt tggctgtcta   9600
gtatgcattt gtatatgcta ggcagtgtac taggcacctt aaatacatta ccttgtttaa   9660
cctctacagg attctgggag gtaggcatta tccccatttt atagatgaga acactgagaa   9720
gacaatgttc ataagtgcgt cacttgtctg agatgacata tttactaagt agcagaacca   9780
ggcctcgagc tactcagtct gatttccaaa gccctgctc ttaatcacat caacttcttt    9840
cctatatcac ctttcccaga gtgcgctctc atggataaag agcagaagta taagttacta   9900
ggcagcagaa aactgtagag gtgggaagat tagataaaaa atgtaaataa gaaggcttta   9960
agacaccaaa atcaaatgta aatactttat aacctgaatc agtgcttgtg ttcatgaggc  10020
tagaggtcgt gcattttatc tctaggtctg gtgatgccaa tcctgatcta cagccagcag  10080
caacagttcc ctagcctgcc tagaagtttg taaatgcatg ggctttggta ggaggaagac  10140
gagagaaagc agaacagatt attacaaacc cagtgcattc ccccttgatg ggtcaacagc  10200
gatttctttg taagtgaagg acagcacact ggttttgatg actcacgaga gagtaggagg  10260 gaaaagaag tctgaggcat tgcctggaag cctcgctctg cttaaacaag tacactaatg   10320
gctcatgcct gttactccca gcactttgga aggccaagat gggtggatca cttgaggcca  10380
ggagtttaag cccagcctgg tcaacatagc gagacctttt ctctattaaa aataaagaag  10440
aaagaaagta ataatgattc aagttctcat tctctacaaa attcacttat gactttccaa  10500
atgctagtga aaacttttag gtattgcaaa actgccttaa tgcataacgg gattctcatt   10560
ttacttagtc taagatgact ttttcacttt gaacttctgc atctttatga tcgcttagct  10620
ttctgacaag caatttcagt aagtgtttat caatttgcat ccacacgctg acacataggg  10680
gtctacttac atatccttca tgtaattgag cttttgtaaa tcatctttct acatggtaca  10740
cttctgattt tgtgtgcagc tttcttgttt aagcactgta ttaaatgctc tgcttcctac  10800
acccttagga acaatgagaa taaaagcgta atgttggtta cttcttcata tcaaaggaag  10860
ttcatctcct ggttattaaa agctattatt aaatggccat cttttgtgc ccctgtgtta   10920 agcactctac caagatacca ttaaatagat aagggccaca ctccatagag atgatggttc  10980
tatattctgt attttctggg ggagttctaa tttcatgcaa ttccttcttc ttaaataaag  11040
gcaattctct aaatatatta cctaatgtgc tttcactttc atattcttgt aagattttc   11100 acataaatca attctcaaaa aatagtatca taggccttt aaaaatagtc atgttcaaaa   11160
gtcaggctca tgaataaatg tgtgcattca ttacatatat tttcataaat tcaaatttaa  11220
aagaataaga gtagctagaa ggtggaagaa aaatcttatt ctgattagga atgcacaatc  11280
acaagaaaat ttgtgatata tatagtcatt ttattctgta ttgttttatt ttgattttgg  11340
taagacaaga aacaatgtag aaagtttgac aacttaaaaa agtaatatga gtgtgagaaa  11400
gtcctcttcc aggattagca aaaaatggt tttttttttt ttttttttccg agatggagtc   11460 tcgctctctc gcccaggctg gagtgcagtg gcgcaatctt ggctcactgc aacctccgcc  11520
tcccgggttc aagtgattct cttgcctcag cctcccaagt agctgggact acaggcatgt  11580
gccaccatgc ccggctaatt ttttttattt ttagtagaga cggggtttca ccatgctggc  11640
caggctggtc ttgaactcct gaccttgtga tctgcccgcc ttagcctccc aaagtgctgg  11700
gattacaggc gtgagccacc gtacccagcc taaatggcca agtttattta tggacaatta  11760
agctgtagaa taaaaatcta cttttaatag ctggcatagt gcctagtggt tttgaagcca  11820
```

```
caagcaggtt tacaaaaaac atttaaatcc atctgaatct acagaaaact aagattacct    11880
aagcagaaaa tgaaaatagt tcaggattaa ggaagattaa caaatgaaga gtatatgtat    11940
tttagaagta ttactttata tttttatagt ataataataa tatttacgtt cctacactta    12000
taatgagttt cgtatatata ttaaaataat ttaatggatt agtatgttta tatttgcttt    12060
tagtaaattt ggtgtatgat aaactcagtt gtctacattg tgagactaca cctgaggcaa    12120
tttctgtgtt gatatatacc tgaatagcag atattacttg ggagcaaata aaatagcttc    12180
aggcctaatt ttgcaagttc atgatgggag agtaagcatg acttcaaaga actgactttg    12240
agttaaaact tgaagaatga atgtgacaac agcaagtata aaacaatgcc aggcagaggt    12300
gggactgttc atgggtatca gggtaagtgt gttgataaat gctcaaagta ggaaatacct    12360
ttcttccccc acacatgtca gaaataact gcaatagaat gcaacgacat ctcagagata     12420
aagtgttcaa cttagctctc agagaccgtt cagttacatt ttgtaatgac attggaattg    12480
attgcatttt gaaggcaatt ctaaatgcaa agtcttcatt ttgttgatag aagctgggtt    12540
atttattatg aaatttcaaa aattaagtaa aatatctaat taggattata ccagcaaagg    12600
caaatttaga attcaagact tcatgatcca tggtaagatt attttaatgc aactctgcta    12660
attaactgaa atttcctttt actctcacat ctgccttta cttcttaaga catttttcta    12720
gtatttcacc agagcaagat atcagaaggg taaatctctt accaatgaac tttgctaatt    12780
cttagtgact ccgttgaccc tggtgtaagg atcaggaaca aagtgaatga atacatttt     12840 aatacatttc tgctttctct aattccaaag accactctaa agaataagtt atttgtgggt    12900
attatctgaa acttgggatt aaaagagacc gtgattaccc ttcagggatt ttggcaaaac    12960
ttaagccatt tcatctgaag agcaaagcaa gcctcccaca ctcttggctt attctcacaa    13020
ttatctagat atctagcaac aaaactcttg agtagtttgt taactacaga tgccaagggc    13080
tgacagtttc actttcagtt ttcagaatat cttttgtttc agtggtgtaa gcacaccatc    13140
agaatctcta ctatttaaaa taattaagtt ataattgtaa cttccattag atgtagtact    13200
taaaggaatc tagaagacac aactcattaa ttataggaat ttgactgcaa attcttctgg    13260
ggggtctgaa ttgcaaagga ggcatctttg taagtcagac tcaactcatt actctgtgat    13320
gcaggctcct ccaaatggca gcagaaacgt attactctct agaaacacta cagtagtgct    13380
acaatttcag ggttctgtag agataaggac aaattgacag aaacacattc ttagaaggac    13440
agtatcattt aaaataaaaa tactgtcata attgtacacc aggatagctt ctccataata    13500
aattctttat gattttctga tttttagaaa tcagaattga acttttaat gtgaaaaaa     13560 tgagagaatt gtttcaaaat aggaccacat ttctgtgtat aatttaaaa gtttaaaat     13620 atttgattag tagactgata aactgaaaca ttttttgataa gcttttcatt acatacaaac    13680
catataattt gtaaaaaatt ggaaattatt caaaacttca cataactaaa gtgaccaaat    13740
aaatactgga gaggaaagaa aaggagtcaa atgaatctag catttctttt ttttttttt     13800 ttttggagaa agggtctcac tgtgccaccc aggtgggagt gcaatggcac gatcatggct    13860
cactgcagcc tcaactttat gggcttaggt gatcctccca cctcggcctc ccaagtagca    13920
gggactacag gcatgcgcca acacgtccag ctaatttttt tggtattttt tgcagagacg    13980
aggtttcacc aggttgccgt ggctgatctg gaactcctgg tctcaagtga tctacccaac    14040
tcagcctccc aaagtgctgg gattacaggc gtgagccacc gcaccggcc taatctagca     14100 ttttctaaaa ggaaggaccc agcagtgaac ggcaatatca ataatcatgt tcaagactat    14160
```

-continued

```
cagacatgca agctggggat gaatgggtgg aagggggaaaa tgatgaataa atgatgaaca    14220
caagtataga cccagtggat ttgagatgcc caagatgcca gtgagatatt caaagtttaa    14280
ctcaaaagcc acttcccata tgaaatcctg acaaacactc ctacgtccaa ctggaattaa    14340
tttctcttct gggctcccac agcactctgt attttctaa tagcataaca ctattttgtt    14400
tgtagatatt tctctgatag cattactatc tttcctcttt atcacaactg tttgaagttc    14460
ttttgcctct tgcatccact gttgcccaat cccactgctg gaaggctcat cttattaagt    14520
tctgtattcc tagtgctaac acactgtcta ccatagatga tgttcaataa atggttgcta    14580
aatgaattct cttgtgataa tagcactatg gcaacataat cgacggtaaa aatttcttct    14640
caatgtttac ttttagcaga atgcattcat ttatcaactt tcattgagaa tatgctaatt    14700
tccatgaccc tgctaggaaa taggaaaata aagatgaatg taataaggtg ctcattctac    14760
tgaaagtctt gactagtgga gaattatgga tccaactttt catgaaatgc cttcagtggt    14820
aagaattctc atatttggaa taaaaatgt tatgggttgt gccaagatac ctacatactt    14880
cataattttg tagagggctg tccttactgc agaaatgtat actactatag tcatatgtgg    14940
aaattctttt tatgatgcta actgcatgct aaccagactt tttaatttaa tacttgcatt    15000
aaataaacca tgctaggaat ccaggaatct agcttggttt attttccata caatgtactc    15060
tttgtaatat gcatatacta cataaaaatt ctattaatgg cctcgtacta aagatgtgtc    15120
tgttggggaa tcagttattc tgtataattt tatcttaatt gatatattaa aatctaccaa    15180
aaatataaac tccgagtaaa agtatctgca tggtgtgcat atgttttatta tttttaagtgt   15240 cagcgtatac attttcatgc cataaagtta taaaatgaaa aatagtagc cttttatatt    15300 aagttcatgc ttatgtagtt agtaaaaaca agaaagcaat taacatacaa accatgatgg    15360
tggttaaact tgcttcagtt tgtgttttttt aaaatttgaa agtgagaaat acagctcgaa    15420
gtcagctcat attttcagta agtactgatg aggatgtact ggccctattg actacgctga    15480
ccccattaaa atatttgtga gtctaaaggt tcatatgacg ctgttccttc actctagcaa    15540
caggccatac atgtcttaca tagggactct gttcaattca ttaataccct ctgaagtgct    15600
caacatcgtg gttcatttat agtagatact caatacatac tccattaact gaattctaag    15660
ataaactgtc tgttactgac agaaattttc acttaaggga gtctccgtgg ctgaaggcaa    15720
ttttgaaatc ctgtaaaaga acccactcct ctccccaagt aatgaagttt gtcagtttca    15780
agcctgtaat aaggtactga cttaaaatta attttctaat aatacagtac tgctatgtat    15840
ctaatgtggg gttagtcaat gataggaaaa aaacataaga cagagtcaca tttaaaaatg    15900
tgtgcttagg tgcatggtga cacctgcctg tagtccagct attccagggg ctgaggcagg    15960
aagatccctt gagctcacga gtttgaggct gcagtaagcc actgcactca gcctgggcaa    16020
cagagtgaga ccctgtctct aaaaaaaatt cgttttaagt gtgctcagga cataacagga    16080
gccgctggta acatgccatt tccactgtga atatggtaag gacagaatcc ctgtctctag    16140
gccctcttcc actagtcaat ctcatcatca ccatcaaggc caacattggt attctctcct    16200
ctgagacaaa gtctttgaca ttttctatac tatactatgt cttcctctcc ccaaatgcat    16260
atacaaataa aatttgaatg cttctttctc catttagtgt aatttttttt ataacataga    16320
cccaattttc aaaccccaca atggtggatt ttatttgatg tattgtaaaa agcgctggat    16380
tgaagtcaaa tggcttggga gacctaaatt ctactcctgc ctgtaccatg aaagagacaa    16440
atcccaaggc tttgcagggc ttcagcttcc ttgtttgtag aataaagaat tataaaatca    16500
tctcttttgg tcctactggg caataaaaag ctatgattct aagcctgttc cctttttctca    16560
```

```
cctaagaata caaatttgat acaaagaggc cgcagaatgt gtcaaacact ccctgttgcc   16620
tggaattctc tcttcctttg ggttcaggga taaaggtatg ttatttctta agtctccctt   16680
tgctttcttc tgcttgcctc gtaaatattt ttccatcttg gcagtcctac atgtcttctc   16740
actctacatg ttttccctag gtgatgtgac ccagcctgtg gcttccactg ccatccacac   16800
acgtcgctgc ctctctccac atcagcatcg caactatctc ctggaagctt tccaagtgct   16860
gaactacagt aacctcaacc gaactgctgt tcattcaccc cacaggcttg ccctcctct    16920
gcatctttgt gagaacctga gagtcatcct aaactcctcc ttccacctca ctccccacat   16980
caaatcgatt accaacttgt gctgatttta tcttcaaata ctctccagaa ttgtcgctgt   17040
catggactga atatttgtgt tcccccaaat tcatatgtcc taatccctga tgtgactgta   17100
tttagagacg tgacctctaa ggagtaatta aggttcagtg aggtcaaagg tggagccctg   17160
atctgatagg atcagtgtcc ttataagaag agactagagc tgggcacagg gctcacacc    17220
tgtaatccca gtattttggg aggctgaggt gggaagatca ctcaaggaga ggagtctgag   17280
accagcctgg gcaacagagt gagactccat ctctacaaga aaataaaata gtcagacaca   17340
gtggtacaca cctgtggtcc cagctcctca ggaggctgag gcaggaggat ggcttgagcc   17400
caggaatttg aggctgcagc aagctatgat cacacctctg cactccagcc tgggtgacag   17460
catgagaccc agtctctta aaaaaaaaaa aaaaaaaggc catatatagc ccagaagagc    17520
gtcctcacca aaacccaatc ctgatagcac ctggaggact tccagcctcc agagctgtga   17580
gaaaatttct gttgcttgca ccgcccagtc tgtggtattt tgctgtggca gcccaagctg   17640
actcatcagt gaccttctct ctgttaccgc agagtagctc atcatcctct cttccctaga   17700
gtccagccac tctctcacat ctacctacct agcagtatca ctgtgggtta gagtcagatc   17760
actgcggatt aagtcctcat ctgccactg cctgtgtaaa tctgagcaag ttacttaatc    17820
tctctgtgtg tcagtaacct ccctgtgaaa tgaggctaat aatagcaggg ttgtttcaac   17880
aaggcgatac atgcataatg cttacaacac agcttggcac attataagca ttcaacgaaa   17940
agtgagctac tattatctca tccgttatca gaataaacca cctaagccac aaggctgccc   18000
acatcatcct catgttttaa aacacttcag tgggctcccc accatcaaca ggataaagtc   18060
caagcttcct tagcatttct tagaggctcc atatgaatcc ccaagttcca ctacaggaac   18120
acaggtgaac tttccactcc aacctcaggc tccttcgtgt cactcctcat ccacatggag   18180
gtaagcagca agagactccg tgcagttcct ggtggttccc tgaccctcag gcagactctc   18240
cccagccctc tgcctgcaac gtccttgccc tttgcttccc ttggccagct cccattcatt   18300
ctccttgatt ctgcttggaa gtttccctct caggaaggct ttatgaacct tagtgtaggt   18360
tatgaaccca tctttgctcc tttcatacct tttgcaagcc tttatttatt atgacactta   18420
accattatca tactgaagtg acctgttggt gtgtctttgt tccccactag acagaaaact   18480
caagatcaga gaccagttct tgttctttt tttttttttt tttttttttt ttgtatcaca    18540
gtgtttagca gcctgctata tggtaaatgt cagtaaatgt tccacaaact gaatggaatt   18600
gagctctgga atctagacca tcttttccat acccatcact cctgtcttag ttgaagtcct   18660
tatttcccat ttgaagcaat gcaaaggatt tcctaactct aatctctctt tcttccacac   18720
catcctttaa acagccgaca gaatggtcat cctaaagcac atatatccta tcttacatat   18780
cctagattcg gaacctctct gggcttctca ccatataaga agaaagtcta acctccttag   18840
caaggtgcat aggtcttcaa tgggctccac ctcacttctc tatatatacc tatactcttg   18900
```

```
ctacactaaa cttctttctt actgttgctg gaacaagttc aacgctttca aacctccctg   18960
actttgcata tgcagttcat tctgtcagga atgcccttct ctcttatgcc tgggatattc   19020
tcattcattc catatgacct atttcataag tcactcctta atgaagcctt tcttagatat   19080
ccactggggc aatcagctgc ttgctcctgt ttccacagca cattgttcac acagatagca   19140
caggacttac cacaagttat tataattttg tctgtcttgc ccatttgaat ccaagggcaa   19200
ggacggaatc attctcatct ttgtatgtcc tgggaactag aactgtacct gagacataat   19260
aaacacttga tatgtttgta attttaaat aagttaatga acggaatggc tagaaaagt    19320 gagaagaaac tctggcttac tgtatatcat actgtcatac taaaaatata tactgaagac   19380
agaatcacat tatatcatca cttttcacgc tataggccat gatccattat gaaaagagg    19440 atagtaaaaa aatcacaggg cacaattttt gtttctgtca cacacatgtg tacctgtata   19500
ttggactgga atgtaaaacg catgttccat tgtagaacgt ggttttaaaa gaggcttgga   19560
aaacactgca tatggtcatt tcttagttta gtacaattta ttattttcgt aataacctca   19620
gctataatat aagtctacca tgaagcattt tggggagatt aaatgagatg tgaaaagtaa   19680
atgtgttaga tagactgaat tcatatcata gcttgctctg atactttaca aaacatttaa   19740
ccttacccac aagttttagt ttcctcacta aagtcaccct gaggacagta atgggatctt   19800
cctcacagag tattgtgagg aatacataag agaacgtacg taaatgcctg gcacttagta   19860
tttattcaat aaatcttagc aatgatgatg ataacaacat ggtacctggc acataagaga   19920
gttaaaaatt agtttcttca gtcaaatgtg cttacattga tagttgatac taactggggt   19980
taaaaggtca ttgctggcat ctcagaaaga tagattacag tgaaataaaa aatgactact   20040
gcttaaaatg aatgaagact tatttacaaa gtcatgttca tctggtacaa taatgaagtc   20100
gctcaattgg gagaaaatga caaataatac aagtgaatat acaatcttac ttaagacgaa   20160
agaaatagga caccaggcta actatcagtc tcctaaacca caactttatt tctgatacaa   20220
agagacagtg agacaatcag ggcttccctc aaataaatta cttaatctct cttcaattca   20280
gttttgcatc tgtaaatata ataactaca atttcacagt atttccattt aaaaagttct    20340
agtgcaacat cagaaacaag aacttagtag gtgttcaaaa agaaatataa gttctgcttt   20400
gttagccagc aaatagttgc ctgtttctag ccctcacttc ttttctccta aatccctata   20460
ttgcatttat ttaacttaaa gtgctggatg tggcactacg agaaagaaaa agatatttgg   20520
taatcttgtt aaaatcatta gacatcccag gctatctgga atcaccttgg gctcacagtt   20580
agacatcagc tatggcttgt tttatttaaa aattcatcca ctgatgcatg ataatggaat   20640
tcacaggaga gcaatttacc aaaaaaaaga aatttattga tttataatgt gagatattaa   20700
tttagccaca aatatttatt gagcatctcc tacatgccag ggaatggact atatatgcca   20760
ggaaaacaga taccaatcat ttatatcagg cattttttc taatagaagg atattcgcag    20820
gagacaatgc atagcaccat gccttgcacg taacagacat ttaataacta ttagttgaat   20880
aaaattggag actagaatga tacataaaga ggcaagaaag agcaaagata agcctttctg   20940
agaatttcta tcatgttttg ctcaatagct tgtctttatc cactgcttgt atttttccat   21000
gtagctaatc ctcattggtc gttagaattg agacacccctt tccttgaaat caggagctat   21060
aggaggccat tcttcctact gggcattttc tttctgggac agggtctcac tctgtcacct   21120
aggctggagt gcatcatagc tcactataac cttgaagtcc tgggctcaag gaatcctctt   21180
gccaaagagg tgggattaca ggcatgagtc accatgccag cctatttggc atttctactg   21240
tagacaaagc agacttacag cagtaggtct acctgcctaa tacaaaaaga aaaaaaagaa   21300
```

```
ttttaacaaa caaatgaggg aatcagatcc agaaagtgat tcttataact tagattactt   21360
agagtagatc tataatctgc tctagatcca ctgcatacag tgggcccttc ttatcatatt   21420
ccataaatag cacttttctc agcccagctt ttgatgatag ctgaacagac taacagtttg   21480
tctaacaaag gctagagaag gggatagcaa ataatggccc acaggctgaa tcctgcctgc   21540
tgctcatttt tgcaaagttt tattagaata cggtcatttc cactcatttt cacactgtca   21600
atggctgctt ttgcgctaca gcagcagagc tgggtggttg gggcaggggt cacatggcta   21660
acaaagacta aaatacttat catctgacct tttacagaaa gtttgctgat ccttggagtg   21720
tacaagtatt ctatattgtt gattaagaac agaaccacaa gtattagaag ttagaccagc   21780
aggtggtaaa gctgatcatc tactaatata atggaaattg gggttcccaa tcaggactct   21840
tgctttgata gaaggccatc ttaacgagga gggagacacc tgcaggcaaa gtcagaattt   21900
tctgcaggaa aagttttgag tccatttccc cttgtgaaca agtgctcagc tatgcatttc   21960
atctttagta accatgcttc tatacctggt tctccttggc aaagatttct ttcttcagta   22020
agtctcaaga ctttctggga aggtaggag atatgggggt aaaagtgtcc caggacttac   22080
tgaaggaagt gttttatgat tatctgatag aatcactgta tcatggtaga aaggcaaac   22140
agaatataat ctgaaaatag aggtgagggt gaacaaatgg gcactaaaag tgaactcagc   22200
atcaggaagg tagcaaaaca agacatcagt caaagatatg gggtgattca gacctaagga   22260
agatttaatg tgggatgttt ccgtgtgcca ggagctggac acttaagcaa gaggagatcc   22320
aggaatgttg ctaaaaccat ggcctccata ctttattgga attagcacaa cttatccttg   22380
tttctttcat tttgcaatca aaatctttaa aaacacatta tttaaaaata cattattta   22440
aaagctagaa tgaaaattat gatatcattt aggtggttta aaaaacatcc accagccggg   22500
cgtggtggct catgcctgta atcccagcac tttgggagtc cgaggcgggc agatcacgag   22560
gtcaggagat tgagaccatc ctggctgaca cggtgaaacc ccgtctccac taaaaataca   22620
aaaaattaac cgggcgtggt ggcgggtgcc tgtggtccca gctactcggg aggctgaggc   22680
cggagaatgg catgaacccg ggaggtggag gttgcagtga gctgagatcg tgccactgca   22740
ctccagcctg ggtgacagag caagactcca tctaaaaaaa aaaacaaaa accatccacc   22800
aaaatgggaa gaagtgatga aaaattacag tccaagaaga agggccatag ctgtttaaat   22860
caattggtat atttgttatc taatataacc ccacgtaacg acaggtattt aacaaatgtt   22920
tctgctgaat ttgacgattc catttcccct acatcccata tgcaatccat cagcacccca   22980
catccaaccc atcagtacat cctgtcagca ttggctccca aatataacct aaatctaaca   23040
catatcctac tatctctgct gctacaactt tagtctgaaa tctcataatc tcccacttgt   23100
actactgtag atgactctga atgagtcttc ttgcttccat tccacacagc atccatactg   23160
atctatttt tttttcaatt ttttgtagag acggggtctt gccatgttgc ccaggctggt   23220
cttgaactcc tggcttcaag ggatcctccc acctcaacct cccaaagtga taggatttca   23280
agtatgagcc actgtgccta accctgactg atctttctaa gcataaatct aataatgccc   23340
cttccttgat taaacccttc aatgaattca cattaagcaa acaacctggc caggtgtgat   23400
ggttcatgcc tgtaatctca gcactttggg agaccaagat gggaggatca cttgaggcca   23460
ggagctcaac atcagcttag acaacatggt gaaactacat ctctacaaaa aatacaagaa   23520
ttagctgggc atggtggtgc acctatagtc ccagctactc gggcggctga gctggggaga   23580
tcacttgagc cctggaggtc aaggcagcag tgagctgtga ttatgccact acacttcagc   23640
```

```
ctggatgaag tgagacctgg tctccaaaaa aaaaaaaaaa aaaaaaaga agcagggcaa    23700 ggtggctcac acctgtaatc ccatcacttt gggaggccaa ggcaggcctc ctggatcatg    23760
aggtcaagag atcgagacca tcctggccaa catggtgaaa ccccatctct actaaaaata    23820
caaaaattag ctgggcatgg tggcatgcac ctgtagtctc aggtacttgg gaggctgagg    23880
caggagaatt gcttgaaccc gggaggcgaa ggttgcagtg agccaagatt gcctggtgac    23940
agagcgagcg agactctgtc tcaaaaaaaa aaaaaaaag aaagaaagaa agaaagaaag    24000
aaagaagaaa tccttagtcc tgtcttaact acttgagagg ctgagggagg aggatcactt    24060
gaacctagga atttgaggct ccagtgagct atgacagcac cacggtgctc tggtctggag    24120
agagtgagac cttgtctcta aagaagagaa aagaaagaa tgaatgaatg aacaaaaaga    24180
aagaaggaaa ggaaaagaag agagagagag agagaggaag aaaggaagga aggaaacaaa    24240
ataaaataaa ataataaata aataaaccca aatccaactt ctttacccta atcaacaagg    24300
ctcaaataat ctcatgccaa ctaagtctct gaacagctcc ttccattcta ttgccagatt    24360
actccatctt tcagccacaa gacctttta tcttcctttt accagccaaa cacaatccta    24420
cctcagaaca tgtgcacttt ttcttttctc tgacttgaat ctcctccacc cattatataa    24480
tcttagctca aagaggcttt tcttgacaac ttagcgaaag tatttatccc agtcattctc    24540
tgctacatta ttccaattta ttttctccat agtacatttc agcacataaa gatttcctta    24600
gtatgtgctt gttgcctttc cccaacctcc taaaatgtca gcattccttg agggcagaga    24660
ctgtttcatt cctgtatcat cagcacctaa gacagttcct ggaacatacc aagtacttaa    24720 taaaatttg tttattgact agctatgaca cattttactt atataatttc attttctcag    24780
caaaatgaac actttgaaat gtaattaatt actgatttt gcagtatttt ctaattattt    24840
aaataaaata tttactattt tggtcaacca gaattcttac attgttttag cacccagata    24900
gcttctaaaa atgcttacaa ttaacacaat tttatctagc aatatgtatt tatcactaga    24960
cagaatgcac tgaactcttc ttcattaata aaaagcaatc caggctgggt gcagtggttc    25020
acgcctgtaa tcctagcata gtggaaggcc gaggagggag gatcacttga taccaggaat    25080
tcgagaccag cctggccaac atggcaaaac cccatctcta taaaaacac aaaaattagc    25140 tgggtataat agcagacatc tatagtccca gctactcagg aggctgagag gtgggaggac    25200
tgcttgaccc caggagattg aggttgcagt gagccgtgat tgtgtcactg cactccagcc    25260
tgggctacag aatgatacct catctaaaaa aaaaaaaaaa ttagccaggc atggtggcat    25320
gcacctgtag tcccagctac tcaggaggct aaggtgggag ggtcacctga gcctggaagg    25380
tagagactgc agtgagccct gggtagcccg cgccactgca ctccagccct gagtgacaga    25440
gacccagttt caaaaaaaca caaaaaacag aaaacaaaac aaacaaacaa aaaaacccaa    25500
tgcattgctg aaatgttaaa tccattataa agaaagtac aggggtgggc atggtggttc    25560
atgcttgtaa tcccagcact tgggaggcc aaggtgggca gatcacttaa ggtcaggaat    25620
tcaagaacag cctggctaac acagtgaaaa atgcaaaata caaataagc cgggagtggt    25680 ggcgcatgcc tgtaatccca gctactcggg aggctgaggg gggagaatcg cttgaacctg    25740
ggaggtggag gttgcagtca gccaagatcg aactccagcc tgggtaacag agactccatc    25800
tcaaaaaaaa aaagtaaaaa gtatatagtt gattctgcag ggacttaaaa aagtataaat    25860
atctttttta acatcacaaa gctctgatat ctgcaggttt atgactaact actagctcac    25920
tcccatgaat acacgtatgt aaacaggctc tatacaatct acaatcccag actaagggga    25980 aaaactgtc ctgtcactgt ggtctccaac ccttggccca tttctttcct cttgaccaca    26040
```

```
aaacttctca ggagttgctt gtttcctctt gatccactta tctttagccc actccaatct    26100
ggcatcggtt ctcagtactc tccactaaaa ctgcttttat gaaggccatc aatgacgttc    26160
atgctgccaa atccagcaga cacctcctgt tttctaattt tttttattgt tattttttaa    26220
gagactgggt cttgctctgt cacccaggct ggaatgcagt gatgccatca tagctcactg    26280
cagccttaac ctccctgagt tcaagagatc cttctacctc agctgggact acaggcatgc    26340
acagctatgc ctggctaatt actcaatctt taacatagct gataattccc tccttgaaac    26400
actctcaact tttaagaaac cctgttattt tcctcctaca tttttagcca gttcttctat    26460
cagcttctcc ttatctgacc tctaaatgtt aagaacatta acaaagactg aacctagttt    26520
ttttctcccc ttactgtact gctcctgggc gatgtcaatc agtcccattg ctttagatac    26580
tatctgttga aacactgaaa tcactggttt tttttgtttt tttttttttt tttttttttt    26640
ttgagatgga gtttcgctct gttgcccagg ctggagtgca gtggtgcaat ctcggctcac    26700
tgcaagttcc acctcctggg ctcaagcaat tttcctgcct cagtctcccg agtactggga    26760
ttacaggtgt gtgccaccat acccagctaa ttttttctatt ttagtagaga tggggtttca    26820
ccatgtgtcc aggctggtct taaactcctg acctcaggtg atctgccac cttggcctcc    26880 caaaggttgg gaaagatat cccaatcttt ttcctatgat ttcttaattg atctacttga    26940
catatccact tggacttta ataggcatct caaacttaat gtgttcaaaa taaacctcgt    27000
gactttccct cccaaacctg tccctacctc cctcaataac taatattatc attcttatat    27060
tcatatattg aataaatgtt tgttccccca agtatttgtt gctataaatt tatgaagaat    27120
tcttttctca ctagttatta taattaaaat gtaatattta ttttctttaa aaactttact    27180
ttgtaggatt attattttt aaacagggac caacaataaa taacttctct acttgattaa    27240
aactagggct tcctcttgtg ctccctcagg actatttctt tgtaaaaaca ataggctaaa    27300
tcagtactgg tgtcaaagaa atcataatct cacaacttta taaatacagc atgtggcaag    27360
ggattttccc atcttatata gtaataaaat tttcagctgt gccatggcta aaagtttacc    27420
atcaaagttg gaattttaaa ttagaggtag tcatctttct ttcttttaa agaaatggag    27480 tctcactatg ttgcccaggc tggagtgcag tggctatttg caggcatgac cacagcacgc    27540
tacagcatcc tggcctcaag caattctcct gcctcagctt gccaagtagc tgggactaca    27600
ggtccctgcc accacaccca gcagaaatat ttagctttct gaatttctca agtgtgtgta    27660
tgaatgagac tagtggggtc cttaaccaag attcacagga ttttagtga tttattaaat    27720 aacttggatt tgtatctacc agcatgttct ttgaggtaca ggtatgtctt ttatatctcc    27780
taatatagtt cattacaatg ctaaatacta agatgtgatg ctcacacact acagaatagc    27840
caagcaaatg aactacttat tctcataggg ctattataat taacaaattc ttgtatcacc    27900
ccatcattat caacaacaac atgataggat ttccttttat cttgaagagt ctggaaaaag    27960
ggtaacagag agatatttct gaggaacaaa ctggtaatga gggagctact gtgtccatta    28020
caatactcct tctagaagct caatacataa tgactaatct ctggaaaaaa gcaagtgtga    28080
gaatggaagg ctcttcttca aactatgcaa aatgaatcaa tcagcagtga acaaatttat    28140
gagccaaaca aattcctaca aaaattacca tcatatgctg tcatgcatgt ctgccagtct    28200
atttatcata ttatttaaga aacaaacatt tattgaagat ttatcatgtg ctcagcactg    28260
ccaaagagga aataaagagc ataatatcta ttcttagaaa ataacattaa cacaaataga    28320
aaacaagaaa ccataatgtt aaaaatatta catagtaaca cagaaagaca atgtataatt    28380
```

```
atacatacgc actaaagcaa agataacata atttataaat tatgaggtac agaatagtta  28440
gattctgaaa attaaaataa tcaggaaaaa cttcatgaag atgagatctg ggctggatcc  28500
caaaggatag gcaggtggat catgtagaac aggggaaagg agttcctgat cggggataca  28560
atatatgtaa aaactcggag acaggactga gcgtgaaatg ttaatgggac agtaaagaaa  28620
tcttcctctg cagcgggga aaaaacagaa taatgggaaa ctgcatggtt aaaaggtttg  28680
atgttaagat agtgcttgga cacaaaagat cttaaagttg agtcaaaaga gtacaatgaa  28740
agcattagaa atagaagata aaacacaatt aggccgggtg cagcggctca tgcctgtaat  28800
cccagcactt tgggaggcca aggtgggtag atcacttgag gtcaagagtt tgagaccagc  28860
ctggccaaca tggtgaaacc ccgtctctac taaaaataca gaaattagcc gtgaatgatg  28920
gctcgtgcct gtagtcccag ctatttggga ggctgaggca ggagactcgc ttgaatctgg  28980
gaggcggagg ttgcagtgag ccgacatcgc gccactgcac tccagcctgg gtgacagagc  29040
aagcctctgt ttaaaaaaaa acggtaaaaa taaataacat ttactattgt tttctgatga  29100
tatatatggc ctctaattgt aaagctgaat gcctagttta ccactttttt ttttttttg   29160
agacggagtc ttgctcttgt tgcccaggct ggagggcaat ggcacgatct tggctcacca  29220
caacctctgt ctcccaggtt taagcgattc tccagcctca gcctcccgag tagctgggat  29280
tacaggcatg tgccatcatg ctcagctaat tttgtatttt tagtagagat ggggtttctc  29340
catgttggtc aggctggtct caaactccca acctcaggtg atccaccgc ctcagcctcc    29400
caaagggctg gattacagg cgtgaaccac cgcgcccggc ctatcattct tattttatgc    29460
attaggaaac taaggctcaa caagattaaa gctgtctagg gtcacaaaga ttgtaagtgg  29520
aggggctaga attcaaaatg agacctgctt gactcctaag cctgtaccat ttctactata  29580
tttagagtga agtagatggg ttgaagaaat atttaggagg tgaaatttca aaagtgtaca  29640
gtcagaagag aagacatata tggaaaccta aattttcaca cagtaaagtg tcaataataa  29700
aggcataatg ccaaaatgac agaggctgtg catggtggct catgcctgta atcccagcac  29760
tctgggaggc tgaggcagga agatcacttg agcccaggag tttgacacca acctggccaa  29820
cacagcgaaa ccccatctct actaaaaata caaaaaatta gctggtaatg gtggtacaca  29880
cctgtaatcc cagctactca ggaggctgag gcattagagt cacttgaacc tgggaggcag  29940
aggttgccat gagccaagat tgtgccactg cactctagcc tgggcaacag agtgagactc  30000
tgtctcaaaa aaaaaaaaag gaagactcga gggctagaac cctgaaattg ggaatgaaca  30060
ggactggctg aaaatgtttc ttgcacctga taaaaatctt gaagaagaat gctttaaata  30120
gataagaaag gagagagaga ggtgggcagt gagaggagac cacctaagt aatcagagat    30180
tacttacgtt ggttactcag gctggtctct gaatctgatt ataaatgaaa tagagattac  30240
ttaaaacaaa gggctgtaag gtagcactgt ccagcagcac tttctatgat ggaaatcttc  30300
tatatctgca ctgtccaata aggtgtagct gctagcacat gtggccactg agtacttaga  30360
atatagctac gacaaccgag aggctgaatt ttaaatttaa tttaatgaat tcaaacaaat  30420
ttattttttaa tacagcactt taaattttat ttttaaattt taatctatta tttatttaga  30480
gactgggtta tgagactggc taattttgt attttggta gagacggcgt ttcaccatgt      30540
tgcccaagtt agtctcaaac tcccgggctc aagtgatcca cctgccttgg cctcccgca    30600
aagtgctgag aatacaggtg tgagtcacca cgcccggcct aaacttaaat ttaaatagcc  30660
acgtgcgggt agtggctacc atactgcaca tgcaactgta agatgtagaa gtcagatgtg  30720
agcaaagaaa tgacaagccg ttcaatgctg ttagagaatg aaattcaagg ttccaatgat  30780
```

```
ctgaacttgt gtcccctcaa attcgtatgt tgaaatctta atcctcaatg caacagtatt   30840
aagaatttgg ggctttagga ggtaatttgg ttttgagggt ggagccctca tgaataggat   30900
gagcacctga ggtagcctct ttgacccttc caccatgtga ggacacacca cgaaggcacc   30960
atgttggaag cagagagtga gcactcccaa gacactgaat ctgccacatc ttgattttgg   31020
gcttctcagc ctacagaact gtgagcaata aatatctgct gtttataaat tatccagtgt   31080
aaagtatttt gttatagcag cctgaataga ctaagacaaa ggtggactaa ggcaggataa   31140
caggttagaa aaggaggcag ggccttttt tttttttttt tttttttgag acaaagcctc   31200
actctcaccc aggctggagt gcaatggcat gatcttggct cactgcaacc tccacctcca   31260
gggttcaagc aattctcctg tctcagcctc ccaagtagct gggattacag gtgtgcacca   31320
tcacacccag ctaatctttt gtattttag tagagacggg gtttcactat gttggccagg   31380
ctagtcttga actcttgacc ttaaatgatc cacccgcctc ggcctcccaa agtgctggga   31440
ttacaggtgt gaaccatcgc gcctggccga ggcacagtgt tttacagag aagcctgttt    31500 aaggtttaat catataaaat gtatgatatc cagtaagttt tgatataaaa aagaaacacc   31560
tggcgatttt atataatata ttgtgctaag gaattttaag cactctacat tctgctctct   31620
aagctctgta aagagcacca gggattttt tttttttt cttttgaac agggtcttgc       31680 tctgtcagcc aggctggagt gcagtggcac aatcttggct cactgcaacc tctgcctctc   31740
gggctcagcg attctcccac ctcagcctcc tgagtggttg ggaccacagg cgcatgccac   31800
tacatctggc taattttttg tagagatggg gttttgccat gttgcccagg ctggtcttta   31860
actcctgggc tcaagcgatc ctcccacctt ggcctaccac gcatgcctgg ccacaacagg   31920
gatttttaaa tgtaagacta cctagtcaac tcttattcta tattaacaat atagacaaga   31980 ataacctct aagtaatctc tatttcattt ataatcagat tcagaggttc tcttatgctt     32040
tacaatattg tcctactgtg ggtagcgcaa taactaaggt aatctgaaag accagttata   32100
ttatatacta tagttaaatg catttcaact gcatgggaga aagcaactgt gttctttcct   32160
ctcaatttta acagaaggaa aattgtcaaa attagcttat ttagaatgtc ctatcagaga   32220
attattttga ttaaaatata tttttaatca ataaaatatt tctctttggt caatacttgt   32280
caatatagaa taatatctag ccacaaaatt aaaaaaaaaa catttccccc tatattcat    32340 tcatggatct tcttgaattt ctgttatcta ggtgctttta aaagtcatat ttctgataat   32400
atgaaatcac agctccttt ctttggcata tttagttact gtattaagaa aatgtacaac    32460
acataattta gaatgggtaa ttattatatt ctctttattc ttatattgaa aatgacatga   32520
aaattaccag tcttcccagg taatataatt taagttaaag aacatctaca tactacaacc   32580
aatacccatt cccctatgtt atgtttggaa aaacatagaa gtatctttag tagtactctt   32640
agaaattatc ccaggttcag catattggta ttttatttcc aggtttaagt tacagtattt   32700
tgggcacccc aagtttaata aactattccc tgcagaaacc tgacaagtga agttgtggct   32760
gggaatatgt tagtcttcag ataaaatgaa ttgtttaaga atttgctaaa gatctcaaag   32820 catcttctt aaatctaaag aaagtcagga acaaagccac aaccaggacc atagcatcag    32880
aagatggaaa gttgctttgt cttcaaactt aaaaacatt ttccatttta aaataatttt     32940
actatttacc tgtgatactg ttgaaaatta tgaaaaaaca gataatttaa aatttagtgc   33000
ttttttttaa aaaaaaaaa aaagcgaatc cctgggacac ttcatatagt gcaaacaac      33060 aattcaagaa ttcaagcatt gaaagaaata atctcttatc ccccagtctc tgaaagggat   33120
```

```
tgcctttact actgttccca tctttatgtc catatgtacc taaggcttat ctcccactta   33180
caagtgagaa actattcagt atggcttagt cattttaat gcaagagaat aggtaaaaat    33240
gccaagcacc agccagagtt ttttctttgc agatagatgt gactcttaca ggagcagcag   33300
ggatttccca ctttgggcgg aaagcagcat ttaggtattc cccctccagt gcagttacag   33360 accaccccc cgtagaagct gctcctgtcc tctgtggcat gtcagcctct gattatcttt    33420
taataaacaa tatggcatat taagtctctt ttatgcctt ctttgtattc ccaggtacca    33480
cctccatgtc aggataacaa gaatttggta atgtttgttg aataaattta gcagaagttg   33540
aaagaaaaat cctgtttcta cagaaagata ccactggctt tggggagcc cgagttcatg    33600 atgaaactaa agaaagccac aaaagttcac ctcaatgcca agacatttct tgattttga    33660 aaacccagtt gtcgaaccac ccatctatag aaacttgaaa gactaaaaac tatcttactc   33720
taaacatttt ctaggaagtt gattctacaa cacattttgg ttttccaatt tggcttctaa   33780
taattatttc aaagtttctg tggcctaaat tttgttttac attgatcctt tgaatggact   33840
actgtttcca cattttagaa catttaaaaa gatatctaca acccgagtct aatcataaaa   33900
aaaatcagac agatccaaaa tgtggaacat tccactaaaa aaggagtggg gagaggtctt   33960
tattcttcca aaaatatcaa tgccataaaa gacaaagacg gctatggaaa tgttacagat   34020
tgaaggagac taaagttaaa tgcaagaaag gaaaaatgg catataggac agtattgaat    34080
tgactgacaa aactggatta caatagtaga gtatcaatgt taaacttgct gaagttgcta   34140
actgtatttc ttaggaatta ttcacctaag aatttaggca cacagatatg atgtatgtaa   34200 gttacctta aatggcttag aaaaaaatgt gtgtatattc atttacatac gtatctacac   34260
acacgtgtat tagcggaaga gagcaaggca cacatgtgca taagtgataa agcaaatgag   34320
atgaaatctt tatttttaaa tttaattttg taagtttcag cttttaaaa ttttagattc    34380 cggggataca cgtgcagtta ttacttgggt atattgtgtg aagctgaggt ttggacctct   34440
aatgttcctg ttgccacaac agtgaacaca gtacccagca cgcagttttt cagcccttgc   34500
cccctccctc ccgctctccc tccttgcttt tggagttccc agtgtctact gttcccatct   34560
ttatgtccat gtgtacccaa gacttatctc ccacttacaa gtgagagcat gcagtattta   34620
gttttcttgt tctgcgttag ttccgttagg ataattgcct ccagttacat tcatgtcact   34680
gcaaaggatt tgatttcatt cttttaatg gctgtgtagt attccatgtt gtataggtaa    34740
cacattttct ttatccactc atcaattaat gggcacttac attgatttca tgtgtttgct   34800
attgtgaacg gtgctgcaat gaacatctga gcgcaggtgt cttctggca gaatgattta    34860 ttttcctgtg ggtatatacc cagtaatggg attgctagct cagataagta tttctatttt   34920
tagttgctct ccacaggggt agaactaatt tgcattccca ccaacggcgt gtaagtgttc   34980
ccttttctcc acggcctcgc caacatacgt tcttttctga ttttaatag tagccatttt    35040 gaactggtaa gagatggtgt ctcattgtag tttggctttg catccaaatg agacaaaatc   35100
ttaatgacag gtgaatctag gtaaaaggca tacagacgtt ctttgtgttg tttttttaac   35160
ttacatttga agttattttc aaatgaaaaa taaaagcaag caaaaaaagg tcattcttca   35220
tctagtaaac tcttcaaaga ttaccaccc cttcaacagt ttttcctggt tctagtgagt    35280
cttctcccat ttgtttagat ctttgttgaa atgtagtctc agataaaaaa ttgtatttt    35340 atttctttta catatttcaa acaatctaaa ttctttttaa atgaaactca ttaaaaatac   35400
tgcatttgtt tctaaataaa atggtagagg taatttgcac cttccaaac agaagcaata    35460 ggagcaaccc agatgttcta gccacgatcc aagtcaacca cattcaatct aagaagtaat   35520
```

```
tgaaggctgt aacgacttct gtaaggccta caaaaatgag ttcagacaca agctctgctc  35580
agtaaaaatc tagtggcaga tgatatatac aatgatctga gaaaaaggca gaatcaacaa  35640
aggttgtatt tttatctatt gctgcgtagc atatttcctt aactttagta gcttgaaaca  35700
ataaacattt attatttcat aaagtttctg tggtcagaaa tccaggagca gcttaactgg  35760
gtggatctgg ctcagctgta gacaagatgt cggctgggac ggccatcctt tgagggctct  35820
gagggctttg agggctgcac gatccaattg caaggtggct cactcacata ctaggcaagt  35880
tactgctggg tgctgggagg agaccttagt ttcttatcac atggacctct ccacagggct  35940
gctggaatgt cctcatgacc ttccccatag tgagtattcc aagacaggaa agtggaagcc  36000
acaatgtctt tcatgaccta gcctcaaaag tgacatactg tcatttacac aatattctac  36060
tggctgtaca agttaatcct atttagtctg ggaggggact gcataagggc atgagtaaca  36120
agaggcaaga atccttgggg gccatcttgg aagctggcta cacagaagag aaaacaccag  36180
gggagtgcga agaaggtgca attaaactca attccttggt atgccaatgg taagaaatat  36240
taggtgatct ctggggtgta accttttttaa tttagttctt cactgaataa tctggccagt  36300
aattgtaata caaaatacgg cactctgaca atattctctc cctttataat caattacaca  36360
ccagaatata tataaagaaa gacttacaaa gtcacaagta attgtttggt attattttta  36420
taatcacata ctagggccct acaattagca ttcacaaaca tcactccatg ttggccagat  36480
aagtctgtct ttatagtggt ttaccatacg cgccttagca tgaagttaca tgtggttttcc  36540 ttagccatca gatgctccaa atgcaaaaaa tgtctcacca cagtcacaga atcatggaat  36600
cctaaagtta cctggggttt ctgaaaatct catgggaaca actcacgaga attaaggctt  36660
aagaaagtga tttatcaaag aacaaaacca gcaagacttg agtttagaac tcgcagcaga  36720
gttgtgacta gaacctgttg aaataggcaa tgtagaaacc cagactaagg cacattctct  36780
acaactttac tatgcaagta tgcttagata ctccttagca aacagcaggc cttgagtaaa  36840
ttctttcaga actgaataca caaaggatac agaacggaat acactaacaa tagtgcatga  36900
tgtgctcatt tctgtaatag aaatgaatta attctgatcc atctataatt tattattgct  36960
ccatgattaa cggaaggcat aggaaagatg actggaatag tgtaactagt acaaacaagt  37020
attacacttg actgaacctc attacactgc aattgcatat tatatagtat gtaggtgaac  37080
aaatactggg ttagtcagtg gacctacatt tgaatactgg ttctgctcct agacagctgt  37140
atgatttgaa tgacttcttt atactttcat agtttctctg ttcttctctg taaaacaaag  37200
gcttagaaga tattatgggt tagattatgc cccttacaaa agatgctgaa gtcctaaact  37260
acaatacctg tgaatgtgac tttatttgga aatagggtct ttgcaagtga taagaagag  37320 gtcatggagt gacctaatcc aatacgacca gtgtccttat aaaaaaaagg aaatttggat  37380
acagatacac acaaacaagg agaatatcaa atgaacatga aggcagagac cggggcggta  37440
catctacaag ccaagggaca ccaaagattt tcagcaaatc accagaagtt aggaagagtc  37500
atgggacagg ttctcacagt cctcagaaga aacccaccat gtcaatacat cattttggac  37560
ttctagtctt cagaaccgta agaaaataaa ttttttgttgt tcaagctacc caatttgtgg  37620
tactttgtta cagcagtcct agcaaactaa tacaaatgag ctcttaacac tggtctaaaa  37680
taggataatc ctatgaaatg ctacaaatgt ttgggaagat ttctcatact caactgttta  37740
cagtatacca caagcctgtc agttgaagat acaaacagac cctctataat cctctatact  37800
tatatgcaag gaacagcaca cttttctgc aaaaggtcag atagtaaaca ttttaggctt  37860
```

```
tgtgggccaa acaaggtttc tgttacattt tttttttata actccttaaa aatgtaaaaa   37920
tcaccctcat cccaacggac tacaggaaca gacctcaggt cacatttgac tcatagcctg   37980
acccctggtg tgtagggtta acaagcctcc tttccctggg ctccttttc tttcagcatt    38040 ccaagccaaa ggaaactatc tttttcaaat cattttctct cctaggtggg acatcttaca   38100
ccagcccagg catgcttccg atagccttag agtagctgtc ccttcctcag aattactgtc   38160
taattggcta gaagttagca acttttaca ttttccttc aattcctttc cattaagaag     38220
aaggcatgca ccggcaaatt acttgtgact atcaatgaca tactctcaga agcaccagta   38280
cccctgtgtt gtttctaaac ccattctaat agacacatac cccaaggtta tgctgtttgt   38340
catctcacaa aatgacttac atctagagat ttaaataatt aatgtacttt tcataactac   38400
caggtacagt agatctgata atggcagagc taagcacata tacagaaagt agggcaaggg   38460
ccagagactc attttaaagc aatgttacaa gatcgtcact gttgcttttc attttctaa    38520 atgtggccac tgctgttttc tcactaaagg aaatgttta tgtaaagtga ataacagtac    38580
ctggcataaa ataagtgctc aataaatgtt aaggccttct ctccctcttc aactggcctc   38640
ctcatttttc acaaagtgaa atagaaaaac aacatggaag ataatcctgt tgcttaggaa   38700
aaataactaa agcttgctag acaaaataca cctgaaaata taggaagtga gctatagctg   38760
gcctatatgc atgtatgttg aacaggaca agatagtgta gggtggggtg aagaggacag    38820
agaaatggaa ggaaaggggc tacagccttg gtggcaaaat aaaggataag acgactcttt   38880
taaaatggtc tatttcaaat gctgggttgt gaaacttaat ttgattactt catgagaaac   38940
agcatctata atccatccct gattttctta caacaaaat ttattattta ttttatgttt    39000
gtgtgtagat cttttatata tatacatgta cacacgtata tgtatatatt atatatgcat   39060
atgcatatat atgtgtatat acatatataa tatattgtgt gtgtatgtgt gtgtatatat   39120
aattttttta aaggaatggg gtctcactat gttgcccagg ctggacttga actcctgggc    39180
tcaagcaatc ctccacctca gcctcccaag tagcaaccaa cagttttagt tttgaaaaaa   39240
taacaaatat taaacaccca tgtgtaaggg ttggtactgg gccctgtgtt agtttgcatg   39300
ggctgtcgta acgtaacact acaggccggg cacaacggct cacgcctgta atcccagtac   39360
tttatgaggc caaggtgggc ggatcacctg aggtcaggag tttgagacca gtctgaccaa   39420
catggagaaa ccccgtctct actaaaaata caaaattagc catgtgtggt ggctcatgcc   39480
tgtaatccca gctacttggg agactgaggc aggagaatcg cttgaacctg ggaggcggag   39540
gttgtgatga gctgagatca ggccattgta ctccagcctg gcaacaaga gcaaaactct    39600 gtctcaaaaa caaaaaaaca aaacaaaaa aaccctgata acactacaga ctgggtagct   39660
ggaccaacag aaatttattt tctcacagtt ctggaggctg gaaatctaag ataaagttgt   39720
tggctggttt ggtttctgag gcctctctcc ttaacttgca gatggctgct ttcttgaaat   39780
gtcctcacat agctgtccct ctgtctgttt ctggtgtctc cccacgtatc caaatttcct   39840
cttcttataa agatactagt catattggat tagggtccac cataaagacc tcatttaaac   39900
ttaatcacct ttttacggcc ctgtgtccaa atacagtcac attccgagtt ccaggggatt   39960
agggcttcaa cctatgaatt gggggtgggg cacaattcag cccgtaacag gcctagacct   40020
taatttgtca acactacagt tagatttata gtatagtaac tgcatctgtg ctcatctaaa   40080
tgtcataccc aaatgaaata atatagcatg atgatctgaa tttattaaag gcaatttttc   40140
ctatagaaac ccaaatctat aaattatata caaactgtgg taagtactc gatacccttgc   40200 caggactcat ctatggtggt agatagacca caaagagtac cactgaaaga tcccttttcct 40260
```

```
aatcacagtt tcctcactgg cttgccacaa aacctaaaat tcttctattc tttcattggc   40320
aatttatttc ccctgaaaat gtaaataatc tctggcagag caatctatta agtgatcatc   40380
agccactaac accttagggt agaacagctc agatcacagt cttaaaataa attccatcag   40440
tatgaaattt tctttattac tgctccgcta ctggaatgtt agatcactgt ctgctttaat   40500
aataattctg gtgtaggtca ttcaaatttt gtttaagata ataagacaaa tagcaggtat   40560
aaaaacattc cgtcatctaa taaagcaacc cgagaacagt aagaagaacg tgatgaaatt   40620 aacattttg agtacctgct aggaatcaag tattctgcta gatattttag aaatcatctc   40680
aattcaatcc taaaaattat tctgtataat agtataggtt gagtattcct aatccaaaaa   40740
tctgaagctt ttttttcct gagacggagt tttgctcttg ttgaccaggc tggagtgcaa   40800
tggcgcaatc ctgactcact gcaacctccg cctcctgggt tcaagtgatt agggatactc   40860
aactggctaa atataatgca aatatttcaa aatctgaaaa acccaaatc tgaaacactt   40920 ctggtcccaa acatttcagg caagggacac tcaagttgta ttaatcccat tttacagaag   40980
aagaaacagg ctcagataaa tgaacatctc agagcttgtt gatagcaaag gagagattga   41040
aactgtcagg cctctgatcc caagccaagc catcacttcc cctgtgactt gcatgtatac   41100
atccagatgg cctgaagtaa ctgaagatcc acaaaagaag taaaaataac cttaactaat   41160
gacattctac cactgtgatt tgtttctgcc ccaccctcac tgatcaatgt actttgtaat   41220
ctccgccacc cttaagaagg ttctttataa tttcccccac ccttaagaag gttctttgta   41280
attctcccca cccttgagaa tgtaatttgt gagatccacc gctgcccgca aaacattgct   41340
cttaacttca ccacctatcc caaaacctat aagaagtaat gataatccac caccctttgc   41400
tgactctctt ttctgactca gcccgcctgc acccaggtga aataaatagc catgttgctc   41460
acacaaagcc tgtttggtgt ctcttcacat ggacacgcat gaaagaaacc ctacctggtt   41520
ctgtgtctta cctgttgggg gcctgtggtc aaactactag tacggagttt tagtgtcctc   41580
actttaaaaa tgagggttgt ggccgggcgc ggtggctcac gcctgtaatc ccagcacttt   41640
gggaggccga ggcgggcgga tcacgaggtc aagagatcga gaccatcccg gctaaaacgg   41700
tgaaaccccg tctctactaa aaatacaaaa aaattagccg ggcgtagtgg cgggcgcctg   41760
tagtcccagc tacttgggag gctgaggcag gagaatggcg tgaacccggg aggcggagct   41820
tgcagtgagc cgagatcccg ccactgcact ccagcctggg cgacagagcg agactccgtc   41880
tcaaaaaaaa aaaaaaaaa aaaaaaaaa aaaaaaaaa aaaatgagg gttgtaaggt   41940 aactacctac ttttttatagc attgtagtga agttgaaatg aattaatcca catatattat   42000
agtgtggtag aatgcagcag aactgatgat gtatgacttc taagactagt ccttaagaga   42060
cctgcagttt ttgcttttgc cctcttggaa cactcctgtt gccatgttaa gaaaaactct   42120
ggggagacta tgaaggaaga gagcatactc ggggcagggg ggtgaacagg acgtgcacat   42180
gtacgagcgt acaagccagg tgacaccagt accacagcct cagacatgtc accggggata   42240
ccagcaccac agcctcagac atgtcaccgg ggacaccagc accacagcct cagacatgtc   42300
accggggaca ccagcaccac ggcctcagac atgtcaccca gggacaccag caccagcacc   42360
acagcctcag acatgtcatc ggggacacca gccccatggt ctcagacatg tccctgaggc   42420
ccacttagac ccttcaaccc cagcccagct gctaactgac tacagccaca tgaacagaac   42480
caggtgagac cagaggaaac ttccagtcac ctaccagatc atgacaaata ataaacgatg   42540
ttttttaaac cacaaagatt tggagcagca tttgttacac aaaattagac aactattaca   42600
```

```
gttcgactaa aaacatgttc atttacaata ctaaattaga agtgtaagaa tgggagaaaa   42660
acttcatact ttaaaagtca tttttcctc caaaaacttc aactttgaa aaactgattt     42720 ttataatgca taaaaattaa aataaccta gaatttata gagtagcata gccagctggc    42780
tttattatct gttgtactca acacttcaat aatcactgat gttttagaac tcttcagatt   42840
tagaactctt gcccttgctt tagtctggtt taagctaaat aattgttctt cctcaagaac   42900
aaatgacctt acctcgtttt gttttccttg tctgagagaa acacattagc agtctcccat   42960 cttgttttc cttttcctgt cacccaggac agagggcagt ggtgtgatca cagctctgca    43020
gcacgacttc cccaggttca ggtgatcctc ccacctcagc ctcccaagga gctgggacca    43080
caggcacatg ccaccacgtc cagcttaatt ttgtattttt ttggtagaga tcaggttttg    43140
ccttattgcc ccaagctgat cttgaattcc tgggctgaag caatctgcct gccctggcct    43200
ctccaagtgt taggattaca ggtataagcc accgtgcagc cttatatttt gttttaaatt    43260
ttcctctgta tttttctctc tggcaaattg tttagggagt ttctttagtt tatcagacta    43320
aatttcaagg cttccttcc aattttgaca tgtaaacagt ccctcatttc tgcttatcta    43380
gtgattattc ccaaatctgt gtttacagtc tagctgtctc tcctgagatt aagacttgtt    43440
tctctaacta cctgacggca gaatctcctc ttggaagtat caaggaggca gttcaaaact    43500
gaactgggca ttggctccac tccttctcct tctctttact attaataccc tttctctcct    43560
tctatatgac cacactaagt cttatttagg catcgtttct tctgggagac ctttgtagaa    43620
tctctgaggt tatgttaaca tgctaaggtt ttcttgacat tctcagattg ggttaggtga    43680
acttttagca acttatcttt ttactaaaaa gtcatccctc agtatctgtg gggaattggt    43740
tctaggactc cctaaggata tcaaaatctg catgagcagc ccaggtgaga ccagcagaag    43800
cactttacag tcacctacag gatcatgaca aataataaat catgtttaag ccacaaagtc    43860
ctttacataa aatggtatag tatttgcata taacctacac atcttcctgt atcctttaaa    43920
tcatctctag tttataatac ctcatacgat gaaaatacta cgtaaatagt tgttatactg    43980
tattgtttag ggaataatga caaggaaaaa agtccacgcg tgttcagaat agatgctttt    44040
ttttctcgtc taatattatg gatccacagt tggttgaatc cacagatgtg gaatccatgg    44100
ataccaagga acgactgtat gcattttgac aattatactt ctcatcttac catgcattca    44160
acaaacagaa catgtaaagc ggtgataatg ctgtgatgaa aaataaagca ggggaagagg    44220
ctgcatccat ctagtggaaa cgatgccctt tcaatctgc acaaagagaa aaagctgctc     44280
tccaagttgg ggggtgggtg ggtcaggtat gtaaattggt caggaaggga tctgtaggca    44340
cttacagatt tgacgctaat gagatgggaa gccacaggaa ggttgtgaag aaaagacaag    44400
acatgatctg attcatgttt tgatctgata cactggttgc tagatggaga ataagctgca    44460
tggcggtgag aggaagcaga aacaatagga gggtaatgct ataatccagt ggtccataat    44520
ccaatatccc cccaaggaac agttcggcaa tgtctggtga catttctggc tgtcacaact    44580 gttgggggcgg agtgctactt gcatctagca ggtagaagct agggatgcta ctaaacatcc    44640
tacaatgcac aagacagccc ttcccccaac attgctggcc caaaacgttg atagtaccaa    44700
ggctgagaaa ctctgttata atctgtccta gaatgtagct tggattgaga tggcagtggt    44760
aagagctgga gaagtgctta gcttcccaat gtttttttgt ttgtttgttt ttgagacgga    44820
gtctcgctct gtcgcccggg ctggagtgca gtggcgtgat ctcggctcac tgcaagctct    44880
gcctcctggg ttcacgccat tctcccacct cagcctcccg agtagctggg actacgggcg    44940
cgtgccacca cacccagcta attttttgt attttagta cagacagggt ttcaccatgt    45000
```

-continued

```
tagccaggat ggtctccatc tcctgatccc gtgatccacc cacctcggcc tcccaaagtg    45060
ctgggattgc aggcgtgagc caccgcgccc ggcctgaatg ttttaaagt actggtgacc     45120 atattcgctg agggattaaa tgtaaggtat gaggggaaaa taggaatcag acaccagggt    45180
ttactgcctg agcaatgaga agaacgacgt tcctcatacg gagatgagga agaatgtgga    45240
atagcaggta aatagcatgt gcttgctttg tttggggctg tgcagaagag actgatggga    45300
ccaacgtgct cagttctgga tatattaaac ttggaatgcc tatttggcac caagtgaatg    45360
tatcaggtag gcagatggat aaatgagtct gaagttcagg ggagaggctg gggtggcaat    45420
atgaacttgg gagtctccac atctgaatag tatttaaagc tatacaacag gataaggtga    45480
tttaggaact aaacacaaat tgagacgaga tccgagccca gaggcactcc gatgtttaaa    45540
aaagaggagg aaccatcaaa agatactaag gagaagccaa gaagtaggag aactgagagt    45600
ctgagagaat cattatactc atttgatcga ctgcaacaaa tgctgcttag aggtcaagca    45660
aaatgaggac taagcaagga ccaccaggtc tggcaacatg gaggccaatg ccgacgtgga    45720
aatgagagtt ttggtgggaa gacaggaata aaagtctcac aggtctgaat tcaagagaga    45780
gaacagcaga agaagggtag aggtggtagc cataaacaat gatacattct cttgaggcct    45840
tttcttgcaa agctcagtga agaaacatgg ttccagagag ggattttttt ttctctcatt    45900
ttacatatgc aaacatataa aaaagctgaa agaattgttt gacaaccacc cttattctta    45960
ccacagattc aacatttaat gccatatgtt ttccctgtat gtactgtgta ttgtttgagg    46020
ataacttccc ctctaaatat acctcggatg tatctcctaa aataagtcca ttctcctaca    46080
tagccatagt aaccatgaac acacctagga aaattaaaaa tatattctca aatatattat    46140
atagctgggt atattacaat ttccccaata tgtgatttgc aaaccaggat caagtcaaag    46200
tccatgcaca gcatttggtt gtcatgtgtc tttggtctct attaataatg atgactgttt    46260
gaaaagacct gtcctataga ataaatttga ctgattatgt catgccattg aacttgtttt    46320
tctattctag aaggatagtt ttttagggta gtgaatacat ttattactct tggcacaata    46380
gtctaacatt tcccaatttc cttatatctc tgcccttca ttttcagaaa atcaattatt     46440
ccaagatttg ttttcattt atcatcactt attagctctg aagactcaac tgagcaactt    46500
tcagggttta tacccctat attcagaaaa aaactactac catctctcat ttaccctaag    46560
aattcatagg agagcatgtc ttaaagctga tcaataacca aaccaaacat tttattgatc    46620
atattacatt tggaaagcaa aatgaatttc ctaaaatttc ttccctgatt agcaaaatag    46680
tgcctccgaa cacttgaggg tgaaagttgt tgtcaaatat gcctacatga ctggaaatta    46740
tgacatccaa atgagttcac tgggtctgat aataatatgc tctacatgct tatgtctatg    46800
taataaacag cttacatctg gatgagaaaa ttgattatac aaatatttgg gcttctacaa    46860
ctggtcactc atctgtaagt acttaaagca acttaaaatg caaactgacc taacaatgct    46920
tatggttaga attccaaaga atgtttaggc attgtcaggt tatgttaaaa catcttctgc    46980
cacaatcttc aagtgattta tcttttctgt tgtgttgaat agctatagaa gacaaatgaa    47040
ttctgcactc ctgaattcaa tgaacatttc aagtttcctc acttacactg taagattacg    47100
tagcatattt taagaaataa attataatca ttttatttca cttattgaac ttcttttaag    47160
ctttggcatt agaattttaa tcaaagcact gccacttgct tacagtgatg gtttttaggc    47220
tctttgggcc tatggactat ttcaatgacc ttcactagcc atctagtcca ccttatccta    47280
attattacca ctgcaaaaga aaccctcact tgaataaatc agtagatggg catgaggcac    47340
```

```
ctcccaggag actataatta ttaactcata ctaaaatcaa aattgtagct attatcactc   47400
atatggtttg gctctgtgtc tccacccaaa tctcatcttg aattgtaatc cccacgtgtc   47460
aaaggagaag cctggtgcga aaggactgga tcatggggggc ggccttcccc cttgctgttc   47520
ttgtgaaaga gttctccgat ggtttaaacg catgggactt cctcctactt gctcgctctc   47580
ttctgccacc atgtaagatg tgccttgctt cccctttgcc ttctgccatg attttaagtt   47640
tcctgaggcc tccccagcca tgcagaaatg tgagtcaatt aaacctcttt tctttgtaaa   47700
ttacccagtc tcaggtagtt ctttacagca gtgtgaaaat agactaatac aatcacctta   47760
tggtaagtct gtctataaat cacctgaact ttcacagact atctagaaga acatgtaacc   47820
agagtagttc ttgatcatgc tatataaatt actgatacag aaatagagct agacaggaag   47880
gggctggtag tagagaatca tcctctggac atattctcac agcctaatct ctagctagca   47940
aattttataa tatatataaa aatacaatta tttcacaaaa ttaccatgaa acgattttat   48000
tgggatatta gacattactg aattacttgt tctgtgaggt atacagtgaa attaacatgt   48060
tataaaattg tggtagccgg cccccaagat ggcctccaat gaatccttca cctcttggta   48120
ttcatacctt tgtgtaggta ggtctgtgta acccatagaa tacagcacag tgacagtagg   48180
tcacttccga ggttaggttg tgaaagacac tgtggtttct gcctctctct cagatcacgt   48240
gctctggggg aaaagccagg tgtcattttg tgaagacact caagcagcct ttagatgact   48300
gcaaccacat aagaggctcc gaactggagc cactcagcta aaccactccc agattcctga   48360
ccatgtatca tttcatacac aatgtatgaa atgacaaatg tctgttgttt taagctgttt   48420
ggggaataat ttgttacata acaaaatata actaatacaa taatacatac tgatttaact   48480
gaagttgtaa cttcataact tatttaggta ctaaaaatca cagcaacccg atgcaaagta   48540
ctaaaaaaaa aatccattaa tacctattga gtactgttga gggcatgagg aaagctcttt   48600
catactccac ataaaacttc cttaccgtaa tattcatggc tgacctctac tcttaactcc   48660
tttctaggat aggaggggct aactgatctg acagcaagtt tgggagaaaa aattctgagg   48720
ctcggccaac ttcctctctt ctttccattt gggatttggc tgactgaaga gggtcatttg   48780
ttttggcctg ctctcttaca cagtaaatgt agtgggacaa gctctattct tgttgataga   48840
aaaactcgaa ttttaaatct gcctagttct ttgcagctcg ttgttgctcc aaatctcagc   48900
taccttttga aacaactttt ttcagtaaac ttaatttcaa tcttcatgtg atttaactgg   48960
atccaaacac aggcagataa aaaaggtggg gcattactta tcaacctcta aactaagttt   49020
aattttgtgc cctcatggag tttatagtat atttgaggtt taaactaaaa cacctggttt   49080
taaacagaaa ctataaaaaa cacgattaat aggtgaggcc gggcgcggcg gctcacgcct   49140
gtaatcccag cacttgggga ggccaaggcg ggtggatcac gaggtcagga gatcaagacc   49200
atcctggcta acacggtgtg aaaccccgtc tctactaaaa atacaaaaaa ttagcccggc   49260
gtagtggtgg gagcctgtag tcccagctac tcaggacgct gaggcaggag aatggcgtga   49320
acccggaagg cggagcttgc agtgagccat gcgccactg cactccagcc tgggtgacag   49380
agccagactc cgtctcaaaa aaacaaacaa acaaaaaaca aataggtgaa aggccgtgat   49440
cattggtaag cgtaagaaaa tctgagggag aaaaaaatat agatgcccag gccccatgcc   49500
aaactcatgg aatcatgcat gaaacccaag cagctgcagt tttaacaagt tcccaatata   49560
tagttgaccc ctgaacaatg caggtttgaa ctgcctgggt ccacttataa aatggatttg   49620
atttttttca ataaaagtta caccgagtgt gcctgcctct cctccctccc tcctacatg   49680 ctcctgctct taagcctctg ccatgaggct taagacagca agaacaaccc gtcctgttta   49740
```

```
tttcaatagt tttgggggggt gcaggtggtt tttggttaca tggataagtt ctttagtggt    49800
gatttctgag attttagtgc aactgtcacc tgagcagtgt acactgtatc caacatgtag    49860
tcttttaacc cccatccaac cttcttcccc aacccgaatc cccaaagtcc actgtatgat    49920
tcttatgcct ctgtgttttt atagcttagc tcccactttt aagtgagaac ataccatttt    49980
tggtttccca ttcctgagct acttcactta gaatactggc ctccagctcc atccaaattg    50040
ctgcaaaaga tattatttcg ttcctttgta tggatgaata gtattccacg atgtacataa    50100
acattttctt tatccactca gctcctcttc agtctactca atgtgaaggt gacaaggacg    50160
aagatcttta tgatgatcca tttccactta atgattagta aatatactta cttttcctta    50220
tgattttctt agtaactttt tttctctaac ttactttatt gtaagaatac agtatataac    50280
acatatgaca tacaaaatac gttagtcaac aatatatgct atcagtaaac ttccagtcat    50340
cagtgggcta ttagcagcta cgttttttgg gcagtcaaaa gcatggggaa ggagagggtg    50400
gtccctaacc cctgtgttgc tcaagggtca attgtaataa tacccattta agaatccatg    50460
gtatatatgg taagtgcaac aactctagaa gagagtgcta ggagttggaa aaggaaagag    50520
aaaacagaat ttaaagcaat ctgtaaagga catgcagggt ttagatgagg tggaagggtg    50580
agggaaaacc aacatctgct gtgagggcat attaactgcc agacattgtt ctatgtctta    50640
cctcatttaa gagaatttca tttcacacat ggaaaaactg aagcccagag aggttaaata    50700
atttgcctga ggccaaaatt agttaaataa cagaagtggg attagtagat gttttcattt    50760
tatcagtgaa actgagcctc agggaggtta aatattttgt atgaagtaac aaaactgaga    50820
ttaatatatg gccaagttta aatgagatct gtaaatctaa tgcctacact aaaacaaaaa    50880
aaaaaaagtg ggaagaaaag gtctatattg cttagcaaaa cagaggtagg gaagcaaaaa    50940
taaacttaca aaatcagatt agaccaccaa aaaacagtcc ccattttaac ttatgtggtg    51000
agaaccatat attaaagacc accagtggct taaaaatctt tttaaaaaat gaatctgttt    51060
tcattattca ttagttttta tctaatgaat aatgtatctt aactgataca tttactaaac    51120
aattaccagc tccaattagc actcagttac aattcaatca ttaaactgac cctcaatttta    51180
gctgtcaacc tagtcaaaac agttaagtga ttttacggtc atcctcagtt gcagaagtat    51240
aatgtttatg gctggagtca ttttattttt aactaacatt ttttaaaaag attgctttgt    51300
aacaatgtgt tatgagtcct ttgtggtaaa tactgctttt tttttgagac gcagtctcgc    51360
tttattgccc aggctggagt gcagtggtgc gatcttggat ctgaggctcc tgcctcagcc    51420
tcctgagtag ctgggactac aggcatgcgc caacgtgccc agctaatttt ttgtttttttt    51480
agtagagatg gggtttcacc atgctggcca ggctggtctc gaactcctga cctcgtgatc    51540
tgcccacctc ggccttccaa agtgctggga ttacagctat tttaaggact ttttaaaaag    51600
tgaagctaaa catttattca tccctattcc tcatctatag ggacttgtgc tctattttc    51660
tttgaagact gaagtaaaaa ttcacctttg tgagggtctt cctataatta aaattaatca    51720
ttttttcctc catagcttct acaaaacatt gcctgtacaa ctctatttag cacttatttc    51780
atcccgcctt gtatgaaaac tatttgttta caaacgtttc tacttctctt taggaataag    51840
gactatgcat tattcactgt tgtattctcc ctgcatttat ggcagtcctt tgcacattaa    51900
atacaagctt tttggctctg tgcatctctt catctggctg ttcatctgta ccctttaaaa    51960
catcctttat taaaaaaaca gtaaatgtaa aaaaaaaaaa aagccattga tgaaaaagtt    52020
aatagctttc tcaataagaa aagagtatca attatgcata cgtctgaact aacaaacatg    52080
```

```
aatgaaatag gctatttaat acattctgtt ttaaaagtag gtttggtcag ccatgtaaat    52140
tgaaaattgg gagccaccaa gataactcat caacaaatat gcactatgta ctaggcacta    52200
tatagatgat ggtgaaccaa acagatgtaa tccttgctct tacagatctc acaacctact    52260
atggggccaa aaatatatgt gtatgtgtgt gtgttataca tatatacaca cacatacatg    52320
tatatataca tatacacata cacatatata catcgcaca catacacata tatacacaca    52380
catacatatg ctatgaggaa acaaacagg  tggtgagaaa gaattagagt aggggtagag    52440
gacagagggc tcctcaaata gggtggacag cttgacacaa gacactcgag ctaagactcc    52500
aaggatgaga agacagttat gtaaagaaaa ggggactagc attgtcagca ggtagctaag    52560
gccttaaagc agacagtcat gtgctgcaat gccagcttca agcgaataca gttactaaag    52620
catatctaac cttctatgtg aatgtagtta ctaaagcata tcctccaact ttccattttt    52680
cttttgctat tgtttctacc acttctcctt ttctgttgac aattatttta aatttcctgg    52740
ctaaattaaa tgatggcatg aactctgggg aaagtaagac tacctatgtc caaataatcc    52800
taaattcctt ctagtcctta tgactgatca attcaccctg aagtgacaac tatgtcccaa    52860
ttaggaaaga gtgtttcttt atctgcactt aatttttga tttggaggct tcctgattgc    52920
taatcaacat gttgtgtgat tacttcaaca agtacttata gaacgttatt ttgtcactgg    52980
aaaaacgttc tgctgctttc tgaactttag gttgctctag agtctaggaa gagtgactgt    53040
acctaaagca gttcctaatt actggacatt ctcagatctg ctagagctac atgtccaatt    53100
acgagaatat actggaaaaa gccctggatt agaaatgaga ggatgtaggt tttagtacca    53160
ggtcagccac cttgttaatg caaatttgag taaattgtta cttcttttag gccttgtttt    53220
tgctgttttg ttttttctgac agtatggtct ctgtggtcca ggctggagtg cagaggcaca    53280
atatcaggtc cctgcagtct ctacctccca ggatcaagcc attttcatgc ctcatcctcc    53340
tgagtagctg ggattacagg catgtgccac cacaccctcg aactcctgac ctcaagtgat    53400
ctgcttgcct cagcctccca aagtgctggg attagaggtg tgagccactg tgcctagcct    53460
tacacattgt tttcttactg gtaaagtggg aatatctaga agttcatgc tacataaatt     53520 caaccatata ttattggcaa aaaatttaa agaaaaacat cagcttaaga gtactaattg     53580
agtacatgcc ttggaatgag catgagctgg aaagaacaaa cctgttgtta catcactcat    53640
tgctgttttc atatgctgct cattgtaaat cttgctcagt ggcatgattt tagtgtttaa    53700
agatttattt gtttgttgt ttaggacaaa gtctctacac ataatctact tgcttcatat     53760
atacatactt atgcatatta tgtatgtaca tacatgctct cagggctcac atgaaaaaac    53820
agccattcag gtgatgtgat ttatctcata tgcttacttt agagtcaaca gggtgttgac    53880
tccactatac aatactggca tggagaacac ataagtcaaa gtagacagga cccagccgta    53940
ccattggcta gggcacaaat atattccat  atgtggagaa tgatgtacgt agaaaggtct    54000
tcattgcaca atgctcttta ataaagatct ggaaaaaaaa aacacctaaa tgttcaaaag    54060
gatagggtag atgaaataat ggtacattat aaaatggaag attatgcagc cataaaaata    54120
aggaaatacc ttaaataata acagaacaac ttttaaggta agtgaacaaa taaggtacat    54180
aatcactatg catagtatgt accatttaca tagaaaaagg gaagaaaaat aaaatatata    54240
tagtaattta tttgttctta catgtgtaaa attttctga aaaatatacc agaaactggt      54300
agcactggtt gcttcctagg cagaaaatga ctgagtatcc ttttgtacct tttgaatttt    54360
gaaccacgtg aatgaatgtg ttacctatga acaaaatgac aagtttagat cagcaagaca    54420
gcagtttgag atgaaatggg attacaccct tagtaggaaa aactttttaa agcaggtggt    54480
```

```
acttctaaga gcaaatacct gcacatggaa tgttgaaact ataaggaact ctccttaaga   54540
gatccatcta ttccaaactt ctcattttat agatctgtaa actgagacct taaaaattca   54600
gtgacttgca taaggtcaca cagcagaaga gatgggatta gatgctagat attccaatat   54660
caagtttaga ctattaaaaa ttcagtgact tgtgtaaggt cacacagcag aagagatggg   54720
attagatgtc agatattcca gtatcaactt tagactatta tcacaccatc ttctcatttt   54780 ctggggcaa  aacagaacca agtaagtttg ggctacatta cgagttgtca tgttttttgtt  54840 tttgtttttt tgagatggag tcttgctctg tcgctcaggc tggagtgcag tggtgtaatc   54900
tcagctcatt gcaatctctg accccgggg ttcaagcaat tctccctgcc ttagcctccc    54960
gagtagctgg gttacaggc gcctcccacc gcgcccggtt aattttgta ttttttttt     55020 ttttttttag tagagacggg gtttcaccat cttggccagg ctggtcttga actcctgacc   55080
tcgtgatcca cccacctcag cctcccaaag tgctgggatt acaggtgtga gccaccacgc   55140
ccggccgagt tgtcatgttt tatctaaatt ttagagtcta atgtataaat taaccttaag   55200
ccctgaaact actaatttct tgtttggatc actatacggc tacacttaaa aatatgctgt   55260
gcatacctct atcattgcat gtatacaata tgatagatgc atgatatgac agacacacaa   55320
tatgatacac gtattttttt ctatcctaac acatctgaat ttactgaaat aactaaaatg   55380
tcttaagtta cttttttaaa tatacacatg catagcacaa gcgtgttgcc aaaaatatga   55440
atacaggttt acaattcctt aactaaaacc caagggttgg atgtgtttta gaaataagaa   55500
tttcatacaa ttttaagtg ttacagggta tataaaccat tatataacac ataccagggg    55560
ccaagggcag caccccataa tcaaacatat taatatagtt tcagcaaaac catgggata    55620 aagactatat acagcttctc aatagttcag gtcatatttt gctaccaaat gaattttgtt   55680
gccaagctta agaagttttt ggttttcacc gctttctgaa tgttagattg agatgtggga   55740
ttacagactg tactcataga gtgcttctag aaagcagtca gtcacttcaa ctctcatttt   55800
ttttttatga gactaaaaaa gaaatcatag caagtagctt ttatatccca ggtttgggcc   55860
aaagacttgt attgtggtta aggaatctaa cttagtagaa ggtgcacgag ctgacatcgt   55920
gagtggctaa aatgagagaa aaaagagaa atcctaatc atacagaagc actgaactac    55980
tgcagctgtt cgttagttat taatttaata aaagcttcct cccttttaaat catgtgagtt  56040 tataactgga aataggtcaa taaaattct gtcccacact gctgacaagc gatggacgca    56100
attagcttta atcccactgg aaggtactgc actctctctg ggaccaggat atgtagaaaa   56160
aagcatttca aatatatagg aataaccaga aatgtataca gtattctcaa cttgggaccg   56220
ttactctata atataaacga aaggggtttt ctagtcaatc tctgctgatc tcctgtacca   56280
aagttcttcc ctttataagt cttgtactac cttttacaag aggaaaaagc tctagagcga   56340
aaacacagaa cacactaaaa tcccttcctt tctctttaca actcaagccc cgcctccatt   56400
ttgtttctgt tactaatttt tcttctgaaa aaataccaaa tttacactga aagactaaaa   56460
ttcaactttg cagacaacgt tttaaaaaat acaattcagt ttggtgatgt tgttttgcag   56520
tcttacaatt ttagctacat tttaactgaa ccaattgttt tgttcaattt atgagttaat   56580
actcagcaag tttgtttttt acaaatagtg tattccattc taaaaatgga agtagcagtg   56640
gtgaacaaga aaacaaccct ctgagttttg tctatttcag gaggaagtac tactttctcc   56700
aattttaatc acaattcata aaaagaaaa acctaactag ctagatctta aatatacaaa   56760
tacattaaca atctagtaaa gcaacagaaa aaggtaaaca aactaaccag cctattttg    56820
```

```
tctggagaaa ccccaacaaa ctgctggatt ccttggccat ttgcattcag aagtaccaaa    56880
aactaaaatc cttttttacta aataatttct tctacacgag acttgtttcc tccacaccac   56940
cctatccaaa ttgtcagcat tattccagaa tataatcatt tagtttgaga ccactaaaaa    57000
accccgcagt ccaaaatacc aattgtggtt tttctgtaaa gaaatggtca gaaactacaa    57060
attgttatcc taggacacag aaccaatcga ccaaaaggac ttctggaata tgctgccccc    57120
aagatttaga atgcacaggc agaaatagca tacgcggtca cgatgtccct taagccacat    57180
gaccttccta cgaaagcaaa ggcttaaact tatcaaatga gaactccccc tttctctgaa    57240
gttaaaacaa ggcagggcag ctggaattag agcagcaggg acagatcggc tgttgactag    57300
tcagaacggg tcgtggaatg caaagtccct gcgctttcgc tgctccccctt accgtgagaa   57360 gatctggag ggaggaaagg aggagaaaca ccccagaatc ctggtagaaa agcccctggc     57420
ctcgaagatg ggctctaggg agacaggag gggcagctcc gtgtgtgatg acccttttgtg   57480 aacatgcact ctgtggcagc ttcagctcca ccgaggcttt gggagagcgg actacggatg    57540
cccggcgcgg cccagctgtg aaggccgcgc cggcggagag ggtccatggc accccccgccg   57600 gcttcggaag cccttccctc tcccacctcc gcgggtcacc ccaggaacca gcggctcccg    57660
accacgctcg cgcggaccac ggaacagcga cgcgcaagca ggtctctttc gtcagcgtaa    57720
tccctccgca gaaagccgcg cactagtttt aatcacgccc cacccctgg ccgctggcgc    57780 cacctccgcc actcgggcgc tttccagcag cttccagaaa cgtcgcctcc caaacccag     57840 ccactcacac atggcgggct cagcagccac cggccccgcc cctcctcgtc gccgcagtcg    57900
caactgcgtc tgcggccaca gggcggacag ccacgcctct gcggagggcg accggaagtg    57960
ctcacgtctt caccttcccc gccacgccac cgtcctttca ggcccagcgt gcagcaggaa    58020
ggaggactct tttgccgcgg actcaagccg gaagccgcct tcctagtgga gacgcgagtg    58080
ggggaggagc agtccgaggg gaacgtgggt tgaacgttgc aactaggggtg gagatcaagc   58140 tggaacagga gttccgatcg acccggtacc aagaagggga gtgcccgcgg caggtaaggg    58200
agaagaggga gggggtttctt tccgctctcg aaattgggaa aagagacaga gctgggatga   58260
cctatggggt agtcggcgcg ctgaaaggat gggctgggct gggacggggt tcaagtggga   58320
aaggttgatg attaaggtat agagttggac ttacagatcc gtttgggcgc agagaggtga   58380
acgctgaaga gaaaccagag tttgttttcg ttttccaagg agcgtggaga tgggcagggt   58440
taacggaccc tgcgcctcct tcggcttctt agtttgggtg ttgaaactca cctcctttgg   58500
tcctgttcgt ctctgattca agacagttgg gtttggtacc tgacagggct gggtgcagaa    58560
agctgaccct gttcctcggc ttccaggtcg gttgtggcct cgcttttgac agttcacgtg    58620
ccgagcctac tcgctctcgg agggcagct caaatgggtg ggtttaaggc cccctcttcg    58680
aacagctgtt tccctgggtt tctccatttt gcacacagga gtgtgaatta agtttaattg    58740
aatacttttt gcgattccca gggccacctt gacacgttca ttgtgctatc taactgggtt   58800
catgctgggc taataattca cattaaggct tctggagtat aagtggttca cagaagtatg    58860 aaaagggat gttagaagaa agatgctggg ggtgaagtag agttgaggaa gacagaactg    58920
gaaagctagg ttggtttcac agtacaatga gctttaggtc ataatactac ctttaggtta    58980
tattgggctg tttggacgga gtttgctgta atcaggctag agtaaataga gaattttaaa    59040
ctaagcattg acaggctcag acttgtagag gcatcatttt gacagtgata tggaagggaa   59100
agaggtagag atttgagacc tttccaaaga actgtccaca gaatttggtg acttactgtg   59160
cgaagaggga aataaagaat agggaacaac tcaagacttt ctagtctgtg tgtttggaag    59220
```

```
gatggagacg cccacattta agtgagatat gggaaggagg agcagattgt ttttgaaggg    59280
aggaagagca gttacttagg gtcaaattaa gttgtaaaat ccccccgggg attttgtatg    59340
taagtcaaag tgaattgtat ttggaagaag aactggggag cccacctctg gtatttttt    59400 tatgtccctc atatggacaa ataaacctct ggtattaaat gaattttctt ttgggggatt    59460
ctatatattc gggatttcaa ccaccaacct atctggtttt tcccgctgaa atgttggtg     59520 atggaatcag gagagcagat ttggagactc tttatatttt ataattgaga gagacaaaga    59580
gaaaaccgtt tgatttgaaa aagttttcta ggttccctca ggtagatgga aattttcatc    59640
aaaaacagtt tattcaaggt acatagccta ctagtttccc atttgagagt accgcagaat    59700
gatacgacgt gtactgcttc tctacgcaga atgaagtata aaattagcac caaatagtaa    59760 cttaattg tcaggtgcta aacttttac atgctttatc tcatttaatt cttagaagaa       59820
actaatttta caagtaagtg tctggaccaa catctgcagg tacaaagcct gaaaagcgta    59880
agtttgactc ctacatagtt ctcttttgta agtagattat aaatagaacc agccaaaggt    59940
aataagttgt ctgtgcctaa aaagaaagaa aaaagttagc atcagtagtt ctcaccagaa    60000
ggggtgattt tgcttaccag gggacatttg gcaagtcagg aaacttttgg ctgttggatc    60060
tagagggtaa aggtcagtga cgctgctaaa catcgtcagt gcatagaaca gccttcacaa    60120
acaattattt ggtcaaagat atttgtagtg ctgcagttga gaaatttctg tcttatggtt    60180
atttcttcag gaataggaaa ttaagattcg ccgatacttt cttaaaaag cagttttatt     60240 tttgaaatta ttccttggct tgaaaggttt gtgaagttta tatagccgaa ccagaatagc    60300
gtaattagat tttaaagtga attgtgagcc atcgattccc aggagatggg tgtcatagaa    60360
tcatggattc ttggatttgg gaaagactta tgcctagaat tattttacaa catttctgct    60420
aagtggtaat tctcctctgc cctaaaggtc tcctgtatt gatttcccta tcattgtgaa     60480
cccacaatta aaatgctctt aattatttt tgcttacact gagctccggt ctcttgtaat     60540
ttttactctg ttaaatgtgg ttctgcacca taggactgca ctcaaaacaa gcttgccaca    60600 tatgtaatt gtactaggac agtgtttata tttttgttca gataacaaaa taagttaaat     60660
gtggtgtaaa ttagatcatt tacaaataat aatttgttag cagcttttaa taagtagtat    60720
ttttcccaac tggtgaagta ttaatgttgg tagttgaaaa caataggaat gtatggaata    60780
tatggttcac tggttctttt gttcctgtca aatagtggca caatggatct ggggttttc     60840 tcagtataat gctggcatat ttgtttcaaa ttgtacatag actctaaaaa gttaggcttt    60900
caaattctgg tcaatatagt ttgctttaaa tagtagctgc ctctactaca agttttattt    60960
aatttgttga caaatgagtc tgctatgaaa accggtcctg ttgccagtca ctaccctctg    61020
ttcacaaatt tgctgggttt ataaatatag gtatcatttt cacttcaaga ttataatttt    61080
agaatatgtt tattctagga catatagccc tcaaaatctg cttactatat acgtcttata    61140
aaatagcatg gttctttttt atagtaaata gaatttttat ttaattgtct attgacttt    61200 tttttccagg gttcattgaa aaaatcctta gtgatattga catgtctcaa gtgacataaa    61260
ttagccaatg actcggaatg atggattctc cgaagattgg aaatggtttg ccagtgattg    61320
gaccagggac tgatataggg atatcttcac tccacatggt ggggtatttg ggaaaagtta    61380
gtgaacttat ttttgcctg agtgcaaagt tttttttttt tctctatttt tgagacttaa     61440
attcaatttt gatgttacca gttaacttct aaaaaattgt gtcttccacg gaaatcttac    61500
agtaatggcg aaagattgtt ttaatgtgtt tacctttctg tgttttattg atacatgaaa    61560
```

```
gtggaaataa aacatagacc ttatgattta ctgttctttg aaaatatggt acataaattc   61620
tcccgggtaa ttgatgttac ttttttcctt gcaaataaaa ttgatactat tcttaacaca   61680
taaaatttaa tatttaaaac tataacataa ttcttttttgg aataatagct gtatttaaag   61740
gcttatatgc atttcttttg tttgccatgt ttaaaatacc ttgtcaggat acttgtaatt   61800
gaaaattata attttttctg gttacctttc catttaactt ttaatatttt gatatattct   61860
aggaatgtct atattttaat ttgctttatt tctcttttag aattttgatt cagctaaagt   61920
tccatcagat gagtattgcc ctgcttgtag agagaaggga aagttaaaag ccttaaagac   61980
ttaccgaatt agttttcaag aatctatctt tttgtgtgag gatctgcagg taaagtatta   62040
atcttatata gtatatataa gattttctt ttttctttttg cttttttatt aattgtttta   62100
aaagtttact cattttttgt tttttagact agattttaa tatgtaatct cagttttgtaa   62160 gtctgtctgg tatacaatgt tattttttcca cctacctta cttggttgcg taaagatgtt   62220 cgttttatt gccatttgat ttgcgagagg agaaaataca tttcaaggtt tttttctttt   62280
tttttaacct tttggaggtc cttgttagct attagcatat agtagttact ctctcatctc   62340
tttggtttat ctttgcaact gatgggaaaa gttatgaatt tctaatgtac ctggaagagt   62400
attttggaaa ttggttagtc caaaaccagt atatatactc tgaactaaag agagtataga   62460
atcttgtaaa ttctaaaaga tcctttttaga agctctaaat cgcttttaga attatagtaa   62520
tttgtaccga ctggtacggc ttttatatag cagctcatta aattctgtaa tactccacat   62580
tttattgtat ttgacagttt atgagactgt ctcatacact tttaattctc agaactttgc   62640
aagatttgta ttcctatttc atgaataaga aaataaattg atttcagagg gtttgggaac   62700
ataagatcct gatacagtgg cagagctgtg gttggaatac agacttctaa tttcagatct   62760
gtttattcca gcaaaaaatt agcagttcat cagaattacc tggagtgctt ttaataaatt   62820
tctgagtatc accccagat gctgattcaa tagagttggc ccagaattct gtggttttgt   62880
aacatttgag gatgagtctg atcatcatca gccaggtttg gaaaatacta gactaaatca   62940
catggttgtt aatagatact tatgctgggt ataatttgaa gtaaagtaat cccaggcgtg   63000
tctacaaata taaatttctt tatgtttata ttcagtaatt tttttttatga gtgtcactgt   63060 ttggcactgt tgcagataca atgttaggat acaataataa aacaaaaatt tcttgccctt   63120
aaggaagtta tgtcatagag tgggaaagac agtgaacaag tatgtgttttt tctgtcaggt   63180 gataaaaagt gctgtggaga aaataaggc agtagggact ggaatgccaa agtaggggga   63240
gtttgcaatt ttaaatagga tggtgagggg aacgcttcaa tgaaaagtgc aattcgagca   63300
aaagcctgaa agaggtgaag agcagtgagc tttctaggca ggggaagcaa gttccaggaa   63360
ggccctgaga gaatggaggc tgcctgtcat gtttgtgcta ctgcaatgaa agcagcgagc   63420
cgatagaagg tggatcagaa aaataatggg ggagctggac caagtagggt cttataagcc   63480
attgtaagct ttctggcttt tactatgggt gaaaccagga accatggcag agatgttggc   63540
agaggagtga cataagttga cttcagtgtt aaaagcatta ctgtggctgc actgttgaaa   63600
atatatgtaa tgggcaagac ctgaagcagg gagattagtt atagtataat atgaattata   63660
tttggtcctt gtctatggtt tccgttacag agctaaaagt cttggaattt cctgaatgat   63720
aagagtgtcc tgttattcag aatgagcctg tttgctaaca ccggggttca tactattgtg   63780
gtgacttagg atggagccgt agatagcctc agatggggca agtagctgga aagaccacat   63840
gattagagaa ttaacgggtt agaaccttta gccccacgta caggcctcca ggaaaggagt   63900 ggagggcgctg gagatcaagc tgtataaaaa tatcaagatt tggatttaat gagtgggttg   63960
```

```
ctggggggctg gtgccgtgta ggaggtggta tgcttagagg aagtggaagc ttcatacctc    64020
ttctgtccca taccttgccc tactcatttc ttcatctata ccctttataa tatcctttag    64080
gataaaccaa taaacataag taagtgtttg tttgagttct gcgagctgtc cttgcaaact    64140
agttatgccc aagaagggg agtgggaacc tttgtagcca gtcagtcaga tgtactggtg    64200
gcctggatgt gggattggca tctgaagtgg agggagtcat gggactgagc cctcaacctg    64260
taggatctga catggtctct aggtagataa catccaaatg gaattggatt ataggatacc    64320
catttggtgt cctctggaga attgcttggt gtggggaaaa agcccccaca catctggtca    64380
caaaagtgtg ctgggaggat agaatatgtg aaaattgtca taatcaaaat ggagtcactt    64440
gtgttaaaaa agaaaaaaaa atcctgactg gccaggcaca gtggctgaca actgtaatcc    64500
caacactttg ggaggctgag gcaggaggat tgcttgatcc caggaattgg agaccagccc    64560
atgcaacata gtgtggcctt gtctctacaa aaaaaaaaat ttaaattagc tgggcatggt    64620
ggtgtgagtc tgtagcccca gctacccggg aggggggacta cgggtgcacg gcaccatgcc    64680
caggaggtcc aggctgcagt gagctgtgat tgtgccactg cattccagtc aggatgacag    64740
agtgtgagac cctgtctcta ttaaaagaaa aaaaaaagac aaatagatcc aggaaaggct    64800
atgaagagag agctttcatg cataaatacc aaaatatctc aaaagactct gcaaaaacca    64860 caccccttgca caaaggccat catgaaatac ttctgaaata cacagaaaat acatcatgaa    64920
ataaatacac agaaaatact tctgcaagga catctgccca gcaactgcct ggtccatctg    64980
tggacgggtg tcatccttgt tatttgatcct tgtagccaag ggtaattatc tcaaaacaag    65040
tatgtgatcc tccttatttt cctttaaaaa ccttttgtct tcccttacct ccctgaacac    65100
acacagttta ctatgcatg tgtattccca ttggaatact ttattcctga ataaatgtca    65160 ctttctttt agaagcttct cttttctttt tatttagatt gataagtaga aaggaaaaaa    65220 agctttttc cctttggact agttgaaggc agttgcagta ttctggggga gggggtggtg    65280
gcagaggtgt tgaggcatgg ttggagttta tttatactttt gaaggtaaag ccaacaggat    65340
ttgctgaaag attgggatat ggggttggaa agaggaatca aggatagttc caagattttt    65400
ggcttgaaaa attagaagaa tggaatcgtg aattactgag ctgggaagac ttggaagagc    65460
aaggttttgg ggagaagatc aggactgtaa gaatagagaa gtccttgtcc ccaggagtta    65520 ggttttggc tattaaagtt agatgtacta catagatttt tagttggttt tttgttttt    65580 gtttttttt tttttttt tgagacggag tctcgctctg tcacgaggct ggagtgcagt    65640
ggtgcgatct cggctcaccg caacctccga ctccctggtt caagggattc tcctgcctca    65700
gcctcctcag taggtgagat tacaggcatg tgccacccag cccagctaat ttttgtattt    65760
ttagtagaga cggggtttca ctatggccag gatgggcttg atttcctgac tcaggtgat    65820 ccacccacct cggcctccca aaatgctggg gttacaggtg tgagccacca cgcccagccc    65880
ggagttttgg ttttgaagc attctttttc aagtgataaa gcaaaaaata tataatcaag    65940
aattttaagt atatactttg gaatgttaa aaaggaacat gagtaattta ttattatttt    66000
tttaatttct agtcagcaat gagagcccag tgtactttat gaagtagatt ggtttacacc    66060
aggagtgagc agacattttg tatgatgcac aaacaaggaa tgattttttt gttttttaaa    66120
tggttaggaa aatatcaaaa taaaaatgc cagaaaaaat caaagaagg gccaggtgca    66180 gtgtttcaca cctgtaatcc cagcactttg ggaggccaag gtgggtggat tctcttgagg    66240
tcaggagttc gagaccagcc tggccaacat ggtgaaaacc tgtctctact aaaaatacaa    66300
```

```
aatagccggg tgtggtggca tatgcctgta atcccagcta cttgggaggc tgaggcagga    66360
gagtcgcttg aagccagtgg cagaagttgc agtgagccaa gatttgagcc actgcactcc    66420
agcctgggcg acagaggaga ctctatctca aaataaataa ataaataaat aaataaataa    66480
ataaatcaaa agaagaatac cctttcataa tatgtgaaaa ttaaatgaaa ttcaaatttc    66540
agtgttcata aataaagttt taccggaaca tagccatgct caatcattta tgtattgttc    66600
atggcttctt ttgcatacaa caacagagtt gggtagttgt gacagactat gtagctcata    66660
aaatctaaat atttattatc tagcccttta tcagtaaact ttgctgatcc ctgtataagt    66720
cctctgaatc aaattatttc caaagagttc cgttataaaa tttggagttt actctgctgt    66780
aaattgcaaa gaaccatttg gaaaacctct tttagtcagg tatttacatt aaaatgttcc    66840
ttgatttgta aacactaata ttcaagactg gtccaaaatt ataccaaatt gaaactctca    66900
agtgttttta aacagtagga agttttaact tttttttttt cgtggagtag tctatcattc    66960
agcgtttact ttggaacatt taattagtct tttttaaaaa cccatgaaat ttataataaa    67020
aattttaaat cattaatgtt gagtaatcaa agaaaacttt ttttgttttc tccatttgta    67080
aaatgagtac attattatta taatttgtct ttggccatac cttgttgata attacttata    67140
caagtataag aagacatggt atgttttcct ttttcctatt tcacaagaat aagtacagga    67200
atttacttaa gctgctccaa aactcagtga aagagacagg attaggtttt tttcagcatt    67260 ggatttttaaa tgatactaga tggttgcgct gggctaaaat actaatgctt tgtgtatatt    67320
tttatgactt ttttgaagac agcttaaaag ctttattcta gttataaaaa tgatacatgt    67380
tcactgtaaa tagaaacaag tcaggtatac agagatacaa atatttagaa catgtggaaa    67440
gaggcaacaa aattttataa aaagaaaaaa gataaaaatc tgaaatcatt aatttataag    67500
ggaaaaatca gggcaaggac aaattatatt acagattggc ctatggtggg agcacagatt    67560
atatagagaa aagtcagtga agacacttgc gaagagtgtg ggtggaaatc actaagtttt    67620
gcagtcccgg ggcctcttat ggtttattac tgttttgttc tttttttttt tttaatatgc    67680
attcctttgg aaccaagggt ttattatgtt ttgaataaag tagaggtgta agtaggatgc    67740 ataccatg atcttgacta cttgagattc acaaagggtt ttcgtctcag gattttttt    67800 tctcttaaaa aaatttgtat taattttaa attgtaaaaa aattcatcaa cttaaccatt    67860
tttatgtata gagttcagga gtattaggta tattcacttg tgcagcagat ctctagaact    67920 ttttcatct tgcaaaactg aaactctgta cccattaaac aaccacttcc cattttcctc    67980
tcccccagct tctggcaacc attctagttt ctgtttcttt tcttttttt tcttttgaga    68040 tggagtctct gtcgcccagg ctggagtgta gtggcatgat ctcggctcgc tgcaacttct    68100
gcctgcgggt tcaagcagtt ctcctcccte agcctcctga gtagctggga ctacaggggt    68160
gcaccaccat gcctggctaa tttttttttt tttttttttt tttgtatttt tagtagagac    68220
gggggtttca ccatgttggc caggctggtc tcgaactcct gacctcaggt gttctgcctg    68280
cctcagcctc ccaaagtgct gggattacag gcttgagcca ctgtacccgg cctctagttt    68340
atgtttctat gaatcagact cagtacctca tataaacgga atcatacagt atttgccttt    68400
tttgtgactg gcttatttca cttggcataa tggcctcaag attcatccat gttgtagcat    68460
ggatgaatat acagttagga gttccttttc ttttttaagt cttaatctcc agtttatttc    68520
tgttatttta tttatttttat tatactttaa gttctgggat acatgtgcag aacgtgcagg    68580
cttgttacat aggtatacac gtgccatggt ggtttgttgc acctgtcagc ctgtcatcta    68640
cgttaggtat ttctcctaat gctatccctc ccctagcccc ctacccgccg acaggccccg    68700
```

```
gtgtgtgatg ttccctctc tgtgtccgtg tgttctcatt gttcagctcc cacttacgag   68760
tgagaacatg cggtgtttgg ttttctgttc ctgtgttagt ttgctgagaa tgatggtttc   68820
cagcttcatc catgtctctg caaaggacat gaggagtttc ttacttttaa ggttgagtaa   68880
tattccacat tatgtgtatg ccacattttc tttatccatt cacctatctg cagatgtttg   68940
agttgctttc acttttlggg aattgtgaat aatgctgcag tgaatgtggg tgtgcaggta   69000
ccttttcaag attctgcttt tgagtttttt ttggatacgt accttttat gatgctttaa     69060
atacatatat gctatttta aaggattctc agttttctga catatgatag gacttaggaa    69120
gtaatctcaa agcatcatgt tgacaggttg ttagttgatg gtgactgcag ctagttggaa   69180
agtcagaaga atctagaact tgtccattta tactaaagaa tttcatagta agtgcagtat   69240
tatgagtgta atgttcaatt ggtagaagag gctatctgag gggatttagt gcatttcagt   69300
tatctgttgg tgtgaaacga atcaccttga aacttagtcg ctcaaaaatt ttaatggtgg   69360
ctgggcatgg tggctcacat ctggaactcc agcactttgg gaggccgagg caggcagatt   69420
gcttgaaccc aggagtttga gagcagcctg ggcaacgtgg tgaaaccttg tctctacaga   69480
aaataccgtg gcaggcgcct ttagcaccag ctacttggga ggctaaggtt gtaggatctc   69540
ttgatcccag gaggcagagg ttgcagtgag ctgggatcgt gccactatac tccagcctgg   69600
ataacagagc cagaccctgt ctcaaaaaaa aattttaatg gctccattta ttatttcaca   69660
tgattatgtg agttgactag ggaattctta cacatcacac catgtcagct gggacagctg   69720
aaatgtccac atggctggca gttggtacta gctgctagct ggaagttgag ttcaaatagt   69780
cagccagggg tctcagttat tttccatgag gttctctcca tgaggccagc tgggctcttc   69840
acagtgtgat agctgggact aagaaggagt gttccagaag aagggcttgt cctcttgagc   69900
cagtgcttat caggcctcta tgtatatcat gtgtgctaat gttccatcaa agctagtcac   69960
agggccaagc caactctgta cagtgtaggg actggctgca ggagggcatg aattaccagg   70020
aggtgtagtt ctctagttca tagggagggc catcaagata gtagtctacc atacttgtgt   70080
aaaagaaggc attaattaac tattattatt attattatta ttattttaga gacagggtct   70140
tgctctgttg cccaggctgg agcagtagag tggggcaatc atagctcatt gcagcctcca   70200
actcctgggc ttaagcaatc ctcccatctc agcctcccaa gtagctggga atacgggagt   70260
gtactgccat gcccacctga aaaagaaggc atattttaaa agcagacctt tagtgtagag   70320
ggttcttgaa tttgttattt aaaatattct ggtagttttt aaacttagga agaccccact   70380
gattctttta gtgatatgtt tacattgttg ttatttggca taaattgtgt taatgcacag   70440
taagatttca tgaagtcatt aaaattcagc cacttggact ctaaacccaa taagagatgta  70500
aaacagcagt gctatgagat gcatattcag tttcaaaata taggaaacac agaaaattact 70560
ctgtgcactt ttaatttgaa aatacttta aaatgtgtag tataatgtag tgtctgtccc   70620
aaaagagtaa cattcattat agtgtttctt tacgttgttg aaaattttaa attcacttaa   70680
cattagattt ttattaaagc aaaaatatgt tttccttatt agcttaccct tttgtaactc   70740
agattaaacc cttgattgtt caaattaacc tgaaaaaaat tattctttg gaggccaaac    70800
ttttgattaa gtagttgttt gtctctaatt ttttcaaatt tatgtgtata aatataacct   70860
gtcatcaaat caatgctaac attctataca tgtttttcat gatatgaaaa ctataaaaca   70920
tgaagttatt tgaatttgtg tagtttttat catttatttt ttactttcca gtgcatctat   70980
cctttgggct ctaaatcact taataaccta atttctcctg atttggaaga atgtcacact   71040
```

```
ccacataagc ctcagaaaag gaagagctta gaaagcagct ataaggattc acttcttttta   71100
gcaaattcca aaaagactag aaattatatt gctattgacg gtggaaaagt tttgaacagc   71160
aaacataatg gagaagtata tgacgaaacc tcgtcaaact tacctgatag tagtggtcaa   71220
cagaatccaa ttaggacagc tgattccttg gagcggaatg agattttgga agctgatact   71280
gttgacatgg ctactacaaa agatcctgct acagttgatg tctctggaac tggcagacct   71340
tccccctcaaa atgaaggatg tacatctaaa ctggaaatgc cactggagag caaatgtaca   71400
tcatttcccc aggctttatg tgtccagtgg aaaaatgctt atgctctctg ttggttagac   71460
tgtatcctgt cagctttggt gcactcggaa gagttaaaga acaccgtgac tggactgtgc   71520
tcgaaggagg aatctatatt ctggcggttg cttacaaaat ataatcaagc aaatacactt   71580
ctatatacca gtcaattgag tggtgttaaa ggttggtact aatattttat ttttatttac   71640
ttatttattc atctggagtc agggtctcat tctgtcaccc aggctggagt gcagtggcat   71700
gatcatgtct ccttgcagcc ttgacttccc tggctcaggg gggcctccca cctcagtctc   71760
ccaagtagct ggaactacag tcgtgcacca ccatagccag ctaagatagt gagatggtgg   71820
ccccactgtc ttgcccaggc tggactcgat ttcctgggtg caagcaccct tcccgcctca   71880
gcctcccaaa gtgctgggat tacaggcatg agtcaccatt ccagcctact tgtctttaat   71940
tcttaaaaat attaatgttg agttttgtct cccagcatgt gggaaagatg tcatccattg   72000
cttctgtttc ctggaggcct gggagcaagg agcccaggaa cagtatcacg aagcttgaga   72060
taataccagt tacattatcc tgactgccca aaaggcagtt ttttttgtttt ttttttttat   72120
actttaagtt ctggggtaca tgtgcagaac gtgcagtttt gttacatagg tatacgtgtg   72180
ccatggtggt ttgttgcacc catcaaccg tcacctatat taggtatttc tcctaatgct   72240
gtccttcccc aaccccctcca ttccccatca ggccccagtg tgtgatgttc ccctccctgt   72300
gtccatgtgt tctcattgtt caactgtcac ttatgagtga gaatatatgg tgtttggttt   72360
tttgttcttg tgttagtttg ctgagaatga tggtttccag ctttatccat gtccctgcaa   72420
aggacatgaa ctcatccttt tttatggctg catagtattc tatggtgtat atgtgccaca   72480
ttttctttat ccagtctatc attgatgggc atttggttg gttccaagtc tttgctattg   72540
tgattttttt ttttttttt tttttttaa gacagagcct cactctgttg cccaggctgg   72600
agtgcgatgg catgatctca gctcactgca acctccgcct ctcaggttca agcaattctt   72660
ctgcctcagc ctcccaagta gctgggacta caggcgccca ccaccaggcc cagctaattt   72720
ttgtattttt agtagagaca gggtttcacc atgttggtca ggctggtctt gaactccaga   72780
cctcatgatc tgcctgcctt ggcctcccaa agtgctgaaa ttacaggtgt gagccaccat   72840
acctggccta ggcagtcttt ttcaaaactc taagactgtg cttgtgtctc agggtgtcag   72900
gataatagtg gttagtttta agtgtttaaa ctactgaaaa gcagaatgaa gaagtgagta   72960
aaaatcaccc ataatcacac aacctcctaa gatctcttgg cacaataagg gatatgtttt   73020
tcattttatt ctctgtaaaa taggatactt atgaacccac ctcccaacac aggaagaatt   73080
aaaacattcc caataactta catttaccta tgcgtttcct cccatcccat tctctacctc   73140
cccccccataa gtaatcatta tctgaaatgt gtttcatcat tccatctttt cttagttttt   73200
cttacatgtg tttatctaaa cagtatacag tagtctcccc ttattgtagt tgtacttttc   73260
ttggtttcat ttaacccgag gtctgaaagt agatgagtat agtacagtaa tatatttga   73320
gagagaggga gaccacattc acataacttt cattacagca tattgttata attgttgtat   73380
tttattatta gttttaatct tactatgcct aattataaaa cttgatcata ggtatgtagt   73440
```

```
tataggaaaa agcataatat ataaaatgtt tagttactat ccaaggtttt aggcatccac   73500
tggggtcttg gaaggtatcc ctctcagata atggggatg gatggtactg aaccctgtat   73560
atacaatgtt tttccctata catacataat tatgatcaag tttaattaag agtaaattaa   73620
atgtgggcca ggtgcagtgg ctcacatctg taatcccagc actttaggaa gctgaagcgg   73680
gcagatctca tgaggtcaag agttcgagac cagcctggcc aacatggtga aaccccatct   73740
ctactaaaaa atacaaaaat tggctggcta tggtggcaca cgcctgtagt cacagctact   73800
ctgggaggtt gaggcaggag aattgcttga acccaggagg tggaagttga acaatcactt   73860
gaacctggga tcacgccact gcactccaac ctgcctgggt gatagaatga gactctgtct   73920
caaaaaaaaa aaaaaaaaaa aaaagtaaaa gtaaatgtgg ctcaacatgt tgctgtcagt   73980
tggaacattt gtttctgatc gtgtcttcca cccacaaatt gaatgctttt tccatcttaa   74040
cacttatcag gcactgtggc cataacttga gcagttgaga tgcaacagca aaattagcac   74100
aaatttcttt ttctttcttc gcagtttcat ggataagaga tttgttctta gatctcagca   74160
acctcagcat atgattttttt tctttaagtt gagaactttg accttttttac ttagagaagc   74220 attttacagc ttctctttgg catatctgaa ttgccagcat tactatgctc gtgctttggg   74280
gccattatta agtcaaataa gggttgcttg aacacaagca ctgcaatacc atggcaatag   74340
atcgcatcac caagatggct gctaagtgaa ccacaggcag gagtgtagac agcatggaca   74400
cattagacga agggaagatt cacgttgcca gtggaacaca gcaggacagc aagagagttc   74460
atgatgctac tcagaatggc atgaaattta aagcttataa attgtttctg gaattttccg   74520
cttaatattt tcagaccacg gttgagttca ggtaactgaa accataggaa gcaaaacacg   74580
gatgaagagg gaccacttcg tattgcctaa tttagtttgt tttgatcttc tgggacccttt   74640 ttttcttgtt gtaaaaattt atggggctgt ttatagttgt ggctcattga ttttcattg   74700 ctacataata cttccatttt gtaaatataa cagaatattc atctacctgt cagtggacag   74760
tgggtttttt ttgccattat aaatgctgct gctgtgacca tttggggggc aagtctcctg   74820
gggcacagta tgagtttccc ttctgtataa caaaggaatg gaaaattata gactttcgtg   74880
tccaaattta caagataatg acaattgttt tccaaagtgg ttgtaccaag caattctccc   74940
attaatagta tatataagag gtcttcctga tccatatatt cttcttggtt tattttcaca   75000
cttttgagat ttttgctatt tgagtggtat aaaatggtct gtgatcttga tttgccgttt   75060
ccacattttg aagaggttgt cggctctatg tgtatatatt gctcatattt gttccctctt   75120
ctgtgaaatg ccttttgtat cttatcccta tttgttctgt tctgttgatt gtcacgtttt   75180
aattgatttg tatgagtttg ttccttgtat cattgttgct agagttacat cagatgtgtt   75240
gctgaatctg ctcccagttt gcagcttgtg tttttacttt ttaaaaactg tcttgattta   75300
tagggaagtc tttatctttt catttggagc tagtaatgtt tgtggctttt taaagaaatt   75360
attactattc ccaaggtcag aaaatcattc acctatattt taactgaaaa gttataaagt   75420
tttgcttttg acattgaaat ttctcattca gttggaattc atattgatgt gtggtatgag   75480
gtaaggatcc attttttttcc catttgcata gccagttttt gtagctccac tttatttttct   75540 cacttgatct gccatgccac ctctagcatg tatcaacata tcatgtatgt gtgcagctgt   75600
tccttaactc tcaattttat tctcttggtt actttgtcta acccagcact catactttt   75660 aaattattat ggctacccttg tagggcaaga atcctcactt ttattcaact tcttttgaag   75720
tgtcttgatg catattttt ctgatcttac ttggccatat atattttggg gacagatgtg   75780
```

```
acatcatacc aagctttctt tgcttgacat tgtagatatt ttcttattca ttaatgtgct   75840
aaaaattttg agtttggtca tacagtcttt tatatggatc ttatacatcg tttccctctt   75900
gttaaccatt caggctgtta ctagtttttg ctgttgtgaa ttaacaccag gacaaatatc   75960
catatatctt ttgaattaat tactgactag tttcctagga aagatattag aatatgaata   76020
ttaaaggtct tgctgaatac agttttcaga atggttgtac caatatataa ttccattttc   76080
attatgtaga aaaaataccT cagtgttttc taaccaccTT tggttagaac attcaagacg   76140
ttatggtttt gttaggtaag aaatattttg tttcagtgta ggttttcttt gagactgaac   76200
ttttttgtgt gtgtcagtca tttacagttt tttgcaattt ttaaaattca gtttctcaca   76260
agcattttgc ctttgacttt tcttctattt ctgctttctc taattacaga aaccccagtg   76320
ttaagtaggt gacagttcag ttgtttgctg cagaagagca gcagttcaat attggaatta   76380
actttaattt tatgtttTTa atctgttact aattttttac agaataattg tagttttTat   76440
aatctggtta attatatgtt tgagctgcat tactttgcaa tgtaagtttt tttttttggc   76500
atggtcaaat aacaaaaatt ctggttaatg cttatttcat attacaggag aatccagata   76560
tttcattagg gaaacatata agcagagtgt gatcaggctg tatgaattat ttataagaga   76620
tgtgagtgaa aagatctatt tgtagcttaa gagtaagtag agtcagatgc atgtagagtc   76680
ttttattcaa aataatttTc ttattaatct tggatagttt cttgtcacag taattccatt   76740
ttgaagataa taaatattac cataaagaag tgatcaaaaa catagatatg tgtgcccaaa   76800
ggtatttatc acaatagtat ttataatagt gaaaaaagaa acaactaaaa tgtctggcaa   76860
taggagaatg attaataaag cgatgtttca gctgaatata gtggcatgcg cctgtaagcc   76920
cagctactca ggaggttgag gctgcaagat ggcttgagcc caggagttaa tgaccagccc   76980
aggcaacata gcaagaccct gtctccaaac acacaaacac acacacaagt gctatgtttc   77040
agtcactgta taataactag ccagattttt tgttgttgtt gttttgtttt tgttttTgtT   77100
ttttgagaga gcatctcact tgcccaggct ggagtgcagt agtacaatca cagctcactg   77160
cagcttgtag aaccctaacc ctcctgggct caaatgatcc tcccacctca gcctcctgag   77220
tagctgggac tacgggtggg taccaccata cccagctttt tttctaagag atagggtttt   77280
cactatgttg cccaggctgg tcagttttta atgaagcaca tttgtgtaga caaagcagga   77340
tgtggaaccg gataaacact atgttgccac tgaagacccc ttcaaacccc tcaaaaatga   77400
catagaaggg aaaatatgaga tattagtttg ggaaataatt gtaactttat taagactcct   77460
tataaatTTa tctgttccta tgacctggct aagttcaata aaagttacac agagtggaat   77520
aaatggttag acatcatttg tagtataagt aattgcacat aaggaggtaa ctttagctgt   77580
tttagagata gacatagtat ctgaaaggtt agttatttta ctagacctgt gattatttgg   77640
gtgagaaagg ctttcactga gatttTAccc attcagtaag tactaatgat attgtgctga   77700
tagcatatat taagggaata tatggtatac cacagagaaa gaattaagga aattttgtgt   77760
tttgcttttt gtctgtttgc aaaacttact gactcagctt tcattcttgg gaatgtgtca   77820
gttttctgtg ggaagatata cattgatgag gaattgataa tgttctctgt attttcttag   77880
atggagattg taaaaaactt acctcagaaa tatttgcaga gatagagacc tgtctgaatg   77940
aagttagaga tgaatttttt attagccttc agccccagct tagatgcaca ttaggtaagt   78000
aattggtaaa acttacttgt attatactca tctaccatat agaaatatgt acctcataag   78060
gaaatataat actgtttgat taccttggat gatcatattc ttgggagaga gaatctgagt   78120
agtttgactt aggaatctac cactgggtaa gttattgtag ggcagagctg ttccatataa   78180
```

```
atatgtaggc tggtgttcca cctcttgaga gtgggtgcag ttctcagaac caggagaatt      78240 ttaggggggca tatcattagt tgcttctcta gtacgtttcc tagtagacag atctagcatt      78300
tttaacctca attgtgcatt aaaaagcacc gagggaattt aaaagtaaat gccaatgctg      78360
gggcatttga attaggatct cagggatggg gctcaggaaa tcagtaattt ttagaaaccc      78420
cacatgattg ttatatgtac ccagggttta gaatctcatc taaaccaacc atagtaattc      78480
tacttcccta ccagtgattg gtttaggaat gtccttgtgg tagagttttg gccagtggat      78540
attaagagaa atatgctgat ggccttttgg gaaagcttcc tcgcctttag aaagggcaca      78600
aggatgggac ctctttgttc tctgtgactt ggttttttggc ctgtgggagt ggcgtgcagc     78660
aagtgagcta gagagtctgt ccaaacctttt ctaaattttt ttagtattgc gaaaaggagc    78720
tgcggggttt ttttgtttgt ttttgttttg aaagggcttt ttgtttttatt tttcttgtat    78780 ccttgtatta actcttctat taatgttata gtagcagaat atgatactcc ctattagtaa      78840
taacccatat tatgtaaaat atcagtgcct tctagttttt ctctcaatga gtgacattta      78900
acttatatta aaaatgata tttatatttt ataataaaat cagttgttgc tactgatttg       78960
tctagcatgt acaaaagaca ccatgcttcc agatcattat aaaatatgat attttataat      79020
atatttacaa tatatttata acatatttat atacttagaa tataattttat aaggctgggc    79080 ttggtggctc atgcttgtaa tcccagcact ttgggaggcc aaggcaggcg tatcacaagg      79140
tcaagagatt gagaccatcc tggccaacat ggtgaaaccc tgtctctact aaaaatacaa      79200
aaattagccg ggcgtggtag tgtgtgcctg tagttccagc tactcgggag gctgaggcag      79260
gagaatcgct tgaacttggg agacagaggt tgcagtgagc tgagatcacg ccattgcatt      79320
ccagcctggg gacagagcga gactccgtct caaaaaatgt atatatatat atatatatat      79380
atgtgtgtat gtgtgtgtat gtgcgtgtgt atatatatat atcgggaagc atggcatctt      79440
ttgtacatgc tggacagctt ttgacgtact tctttgactc atgcttctgc cccctaattt      79500
tcactttttt tcctacattt tattaaaatt aatatataat agttgtatat ctgctttatt      79560
tttcatggac ttatacatac atatttattc tgttcttata aaagtctgat ttttcgtatg      79620
ccaaatttct gacatttcct cctctaggcc tgaagaactg ttgtaattta tgcatcagat      79680
aggccctcag atggaatgaa tattcttttt tctttatatc aaggtgtaat ttacatatag      79740
taagaccgtt tttaagtgtg tacagctctg taaccctcac tacaatcaag atataggact     79800
ctgtcactct aaaacttctc accaggttca tcacccccag ccactgatct gttgagcgaa      79860
tactcatttc aaaggagctt tttccgtaag atccctagag tttagatgga agggctttcg      79920
tggtgcattt agcagatacc atttcccttc tagactccct acttcagttc ccagttgaat      79980
taaagaatgg tttctccccc agcctgagtc actacccttc ttatccctga taattatttt      80040
tggaacaaag ttcatctttt tgctccacct ccgccatggg cctggttttc tatgtaacag      80100
aaggaatttt taaattattg ttttgtgtaa tcataataat tgggcaagca tacagctctt      80160
ttcagtgcag gaggattcct ctcttgtttt actgcccatt caaggatagg tgctatattt      80220
tagctgaaga tcttactaat gaaatgctct gtaatcatat aacttattta aagatgtgtt      80280
ttgagctctt tcataatatt ttaattcatg gagaacttta tgtatttttag acctgaagat     80340 tttatattgt cattatgaaa tgtaaattgt ttgcttttttc agttaatata tagttacaat    80400
agaatacgga tttaaaggct gataatgaat tacaaaattg tgctatatga catactgttt     80460
atgcatacag tgttgcatat tttcatttct aggatattga tttgtatttc tacttacaaa     80520
```

```
aaaactttttt aaaacttatt ttatggctgg gcccggtggc tcacacctgt aatcccagca   80580
ctttgggagg ccgaggcggg tggatcacct gaggtcagga gttcaagatc agcctggcca   80640
acatggtgaa accctgtctc tactaaaaat acaaaaaatt agccggacgt ggtgtaggtg   80700
cctgtaatcc cagctactcg ggaggctgag gcaggaaaat tgcttgaaac caggaggcag   80760
tggttgcagc gagcagagat tgcgccattg cactccaacc tgagcaacaa gtgcgaaact   80820
ccttctcaaa aagaaacaaa aaacttttt ttaatgtttt tgttcaaaag tagcagtgag   80880
actatcccgc aaaggtgact actaaaatag cctttgtaac tactgatatt tatagaatat   80940
gcttagggtt agggtataac tcgcttgtat tatactcatc taccatgtag aaatatgtac   81000
atcataagga aatataatac tgtttgatta ccttggatga tcatattctt gggagagaga   81060
atctgagtag tttgacttag gaatctacca ctgggtaagt tattgtaggg cagagctgtt   81120
ccatataaat atgtaggctg gtgttccacc tcttgagagt gggtgcagtt ctcagaaccg   81180
ggagaatatt taggggacat attgttagtt gcttctctag tacttttccc agtagacaga   81240
tctagcattt ttaacctcaa ttgtgcatta aaaagcaccg agggaattta aaagtaaata   81300
ccaatcatag ggacatttga attaggatct cagggaaggg gctcaggaaa tcagtaattt   81360
ttagaaaccc cacatgattg ttattgctta ggtaataaca cctactgtct accttgtggt   81420
cctgccaagg tgactgttcc tggccatgtt ccaggcaact gtagttccag gctagggga   81480 gaactggacc atggaagtga ggctctgtcc agggtagggg aagggatgga aggtgactgt   81540
tcctggccat gttccaggca actgtagttc caggctaggg ggagaactgg accatggaag   81600
tgaggctctg tgcagggtag gggaagggat ggaaggactc agtctcttgg gccaaatcgg   81660
taaggcagca tctaagctcc tctgagaata ggaaggagag caaccaattg gaaaaagaat   81720
gggaaacatg tagattctcc tgcttacctt actttccagt ctcaaagctg gaagccagca   81780
ttcactgttc agttattttc aatgacaaca agattcaaat cttcagttgt aaagttgtta   81840
aaggaaagga ttagactgaa aagttaagaa gaacggtaga tgaagagtcc aaagagttga   81900
ggctggtcat ttaaccattg tgtggccacg ccctctccac aggtggaaca agatgatcag   81960
aatagaaatg gccaattctg atgtgtttct acagtgtttc actgattaca ttttttaaca   82020
tctgtagcaa accatttcca taattttttt tttttttttt agagacgagg tctcgctctg   82080
tcacccaggc tggtatgcag cggcatgatc atagctcact gcagcctcaa attcctgggc   82140
tcaaatgagc ctcctgcctt agcctcctaa gtagcttgga ctacaggtgt gtagcaccac   82200
tctcagctaa tttatttcat tttatttttt gtagagataa tgcctcgcta tattggccag   82260
gatggtctca aacgttcata gaaactggtt ttaggttcct agaggctggc agcaattctc   82320
agaggtaacg caagcagtct tcctgccttg gcctcccagt gtgctgggat tacaaggtgt   82380
gagccaccac acctcatcaa ttttgtttt aatatactct aaggcttatc atagttccga   82440
gatctttttt ttttttcctga gaatctaga aagatggaag acagtatggg tcttttgtgg   82500
attttttgtc ctaagaaatt ttcataaatg tctgccaagg aaaggaaag agatcaaagt   82560 ggtaattaaa tctttaggat ggacattttt agaaaaatgc tttataaact tcccctctcc   82620
caactctgag tgacttattg tgtcatactg tattaacaca tattcatgct gtaaatatag   82680
taagaaaaga caatagttca caattttggt ttagttttg ccattattga ttatgagcag   82740
taattcttcc ttttcttttt gaaggtgata tggaaagccc tgtgtttgca tttcccctgc   82800
tcttaaaact agaaacccac attgaaaagc tcttcctata ttcttttctt tgggactttg   82860
aatgttcgca gtgtggacac caatatcaaa acaggttagt ttctttttgt ttttaaaatg   82920
```

```
ggttcttcta gtttctccac cactaaggtt aagagaacaa tttgagcacc agacactaca   82980
gtttgcttgc ttcttaaac tggaagggtc aaaacctcat cgtttgatag actgctagta   83040
ggatatttcc taaggagttc ttcagtggga aatagggacg atgagaggaa taatacacct   83100
cccttctcca gagtccttgc tgagtagaat acctctcaga atgccatgaa actgtaggca   83160
tttttgttta ttcctctatt agaaatgagg ggttttgctt gtttactta ggtttctaac    83220
attatagaca ctagttttag gctcttggag gctagcagca attctcagag gtaatgcaag   83280
cttccccatt tcttcccgta gtcctgtgaa agaccagcca cctccagaag cctacacatg   83340
agtcttctca gccatacttt ctgctttcc taatgcctct cagcagcgta ttagaaaggc   83400
catgatcgat gtacctgtta ccttcaggct ttgcataagg tgtatatgaa acataatgaa   83460
tttcgtgttt aggctcaggt cccatcccca ggttacctct ttatcttgga gacacttctg   83520
gtcccataca tttcagataa gagatattca acctgtaccc accacgtaag gagaggaata   83580
ggttttagaa gaggagtcag ggaggcaagg tattcccaga gggatattct cacttggtcc   83640
atacctgaga aagttgctgg ctggcagtta ggaagatgac cagactggct caattgttcg   83700
tgtattcaaa ttattacaat agaaataact ctttccaccc ccccccgccc tttttttttt   83760
tttgagttgg agtctcgctc ccgtcacaca ggctggagtg cagcagcgtg atcccggctc   83820
actgcagcct ccacctcctg ggttaaagcg attctccttc ctcagcttcc tgagtagctg   83880
ggattacagg tgtgtgccac cacgcccggc tgattttgt attttagta gagacagggt   83940
tttgccatgt tggccaggct ggtcttgaac tcctgacctc aggtgatcca gccacctgag   84000
cctcccacag tgctgggatt acaggtgtga gccaccatgc ctagccacac tttcttag   84060
cttaagtgct taagttagaa aacttgaagt ctctctaagt tactcaagta aaatgtgaga   84120
taaaatatt acttttgaag gccgggcaca gtggctcaca tctgtaatcc cagcactttg   84180
gtaggccgag gcgggtggat cacgaggtca ggagtttgag accagcctgg ccaacatggt   84240
gaaacgctgt ctctactgaa aatacaaaaa ttagccgggc atgatggcgg acacctgtag   84300
tcccagctac tcgggaggct gaggcaggag aataacttga aacccgaagg tggaggttgc   84360
agtgagctga gattgcacca ctgcactcca gcctggtcaa caagaatgac actccgtctc   84420
aaaaaaaatt aaaaaaatt acttagatat tcattatcta aatatgaaat ccttttagg    84480
tatttaagga gtagtcaagg agagttcagt ctgggaggat gctccaggga atgcaggcaa   84540
caaaggtttt gtttttttt taactggtta actcagatct actagaacag ggtaagggag   84600
gccacagagt agacaccatg agcaaagcta accctcctga gttgaaaaaa ttatggacga   84660
gaagttatca ttgaaattaa ctgttggcag acatatccaa agaatatcgc aaggatttgg   84720
tcccttatg catcctgaga cagatgaatg tgtggaatgg cagctggtgg gcaacagagc   84780
gatattggca tggtggtgat acagggaaat agtttcatcg tgttaaaagc catgaacaa    84840
agatacataa tggctgctct gcagaaaaat ccacgtcccc tctccaaagg gcctgttta    84900
ctctgatgta aaaattgggt cagataaatt ttcatattaa gcttttgtt gagtaaactt    84960
ttgtaatagt ccccaaaact cccactagaa cagggtgaga attaacgttt tattcatacc   85020
taggacttaa ataatttagt gtaagcaagt gagtatgaga acacatctgt ttccagtctt   85080
ctatcattgc tttatataaa ttctctggtt ttctcctcac agtaactcag tgaggaagat   85140
cctagtgtcc tcatttggca cgtatggata tgacagcttg aaaggggtta gattgattcc   85200
caagatgaca cactgtaagt ggcagagtca ggagacacac ttaggctctt ctggcctcta   85260
```

```
agactttctt gctcactgtg gtatactcct taatcactac ctgggtttta aataatataa    85320
ataaccttgc tgattaaaat cagcttaatt gtagcttctc tggaatccat atcttagttg    85380
tttgacagtt ttcggttgag tgtcttctgt gtgttaggaa ctcaggcact ggaaatagtg    85440
tatctttgcc aaatttacta attaggtaga gagataaatac acgaacacat aatagaggtc    85500
cagtgacttc gtaattaatc tgatctttgg gctgcttaac gttagctttg aatgcaagat    85560
gttaaatgcg ttttagagat atatagcaca aactgtgaga gctcaaggga gggaagccac    85620
tagccgcttt tgtttgcttt tttgttttt aaaaataatc ttactttgtt ctaaaaataa    85680
aagtagttat agagggaaag ctaaaatgaa gtgacgtttt cttaaatatg ttttaatatg    85740
tcataactta aaacttattt ccacttaatc tgaaggagaa ctgtccagca aattcctttg    85800
tttttgtgaa gctgttttta gtgccagcat aagggcttt tactcaactt ggaaagtgta    85860
acccagagtc agttaaaaac atagtcttca gaggcagatc tcaggtctgt tatttatcac    85920
tgtactctat gtgtcacttt ccccatctgt aaaatgggga taagaatagc acctgcctct    85980
gagagttgtt tggaagatga gtgtccagtg ccatgccctt tgcacatagt ttaagtgttc    86040
agaaatgtca gatgtcatgt ggagaattaa cacttacttg ctgagacagt ctccttttta    86100
taaactaaac agtaggagcc tttacataac aattatcttt gaaaatttaa gaatttagca    86160
gaaatcagtg catttgttga tatctttatg ttgctttgct tttaaaatgt taacctccct    86220
gactactgat gtttttaaca gacagtgctt cctcacaaga tttataagta tttgctattg    86280
tttagaaagg aagcttgtat ctcttaagta gctgctcttt aaattacaaa tatttttatt    86340
aaagtggatg cagttgaggt ttagtgtaca tctttaaagg tcatcttttt agatggcgtt    86400
gctctcaagt attcagacta aagtgcaaat ttagaacttg tgtaacctgt gaaaacaaaa    86460
tttgttcaca attaatgctg tgtgtgtgtg tgtttttttt ttaaggatta aaaaaagtta    86520
agttgtatgt attcctgatt ttatgtttgg aaacatcccc ttttcatttt tggttgtctg    86580
taatggctag ccagtttgag ttatttgagt aaggggtgag ctcttaataa atttgacaac    86640
cttagaacag tggttcttca ctaagggcta ttttttcccc cttgggacat ttggcaacat    86700
ctacagacaa ctggatgccg ttactggcat ctggtgagga gaggccaggg atgatgctta    86760
acatcctaca gtgcacagga cagtgcttca cagcaaagac tctctggtga aaaatgcagt    86820
gataccattg aggaaccctg tcttttttc ttgcttcatc tcatagttga aagatatggg    86880
aaattaacat ggagcatctt cacagagctt ctttactaga ggtagggagg aacattgcca    86940
tattaacatg atttggggaa ataagaaagt atgaatcacg aaaaagggga ggaatacttt    87000
tagacattgg tttaaattaa tgtaaatgca tttaacgtta atgaatttgt tatgtcatttt   87060 ttttataggc atatgaagag tctggtcacc tttacaaatg tcatccctga gtggcaccca    87120
cttaatgctg cccatttttgg tccatgtaac aattgcaaca gtaaatcaca aataagaaaa    87180
atggtattag aaaagtgagt taaaattgtc ttataatttt tagtacaaaa tgaaggtgga    87240
tttacatttt tcttaatgtg taggattgaa aatggtgaca acaacttacc tttctgaaat    87300
ttgagttaac atatatttct gggttgccag ctgcctcgct ctatctggcc agtgagccca    87360
ctgtcacggt gaagccactg aaaagccaac ttaggctgac tctctggccc cactctccta    87420
gtgtctttcc ttcttttgc cttttttctc cctttaagga tatcaagctt cagttttct    87480 ctcctctgcc aagtgtatgg agtttctaga attctgggat ttccttaatc agatttcaag    87540
aactaagatg attcaaagat aagccacagg ctcatctctc tgaatttcca tcttctccta    87600
gatctcagca tgctaattcc tcatcatctt gaaagctatc tagtggcctt gagcagatat    87660
```

```
attttcattg tatttttgcca gcttttctgt ttgtcctcag ttggggaggt tggtcagcat  87720
tacctttttcc agtattacca gagaaccatc tgtttaaact cacaggtcag ttccatctca  87780
ggccgttttcc ctctgtctca ttaatgcact cacacatgta cacaacctct ctactcttca  87840
ttttcagtct aatcgtacat taaggaaatg ttttgaggtc taatttgatg taataaagaa  87900
ccgggaacat taacctttat gcccttgaat gtgccagaaa cccttcagaa tctttcctaa  87960
aggtttattc tcattgaagt aataaatcct cagtttatca gtgcttacag gctcaaaagg  88020
gaaaaagggc agtagtcccc tgttccctcc tccaggtatc tactttaaac cttcaaatta  88080
aggtagtatt tacttttact tttcaaattg atgtgcctat tctaccgtaa tgcagtctgt  88140
tctccttttta tagtaattga ctagggtt ctcacaccaa cacctgggcc ccatctctgt  88200
ttagccttc cctgtccttt caatgcaatt gcgtatttgg ctaactcagt actcggtgtt  88260
tgcattgtta ttaatataca tgtgttattc cctcttcagc caagcagtat atatagttag  88320
gtttcacttt tacaattctt attttttccgg gaattgttat ttgccttgtt ttcatttgtt  88380
ttattatgta ctgtgagttt tgccaaata cttttaaagac ttattaataa attttcaata  88440
ctcagatgct tcacagtttt ttactctgtt cctctcccct ttttttcctg gaactctttc  88500
ctgccaccttt tcactctttg ctgcagtctg cgctggttcc tctctgggcc tgcagcatag  88560
ggtgctcttt attatgtaca cacttccagt cactatcgta gttttttagcc caaggcctca  88620
tccccacatt ctatcacatc tgttgcccat aaatatccag tccttaggg gttctctggg  88680
aaaaataagc tcttctttgt catcaacata tgcactccgt agtactcatg tcttcacttt  88740
gcccgttctg ctgggtaagg tgccacttct ctgtttgctt tctgtcctct aaatatttga  88800
cttcttattt gcttattttc ctttctttgt ccttttggac tcatatcttt tttgccccctc  88860
actattatt gatagcattt gtgtaggagg gcgaagtggg aaggaagagg aggtgtctgt  88920
atctgtctga agattacaga agtctgtaat ctgtcttggc tgccaggtgt cagttttgag  88980
atgtaaatgt tgatgatgag gtgaggagaa gagcagcaga gcatggggtc tgccatcctg  89040
ccttggacca tggcctgctt taggctgctt ggtgtatatg atttcatcta gctgttcata  89100
cctgcttttt cctgtgcccc agcactgaac atagactcgt accattgttt tgtgtaatct  89160
gttaattggt tgcactgcag catatatatt ttttaactat acaaataagt tgcttcccctt  89220
aaagattcat gctctgatct ggaaatggat tcattaggta aaagtctttt aatggaaaat  89280
gtgttttgag ttccagtggg ccaatttatg agcagaattt ataatgtggg catttcctgt  89340
tttcttcaaa agtaaattga actagtgtat gaagtttcac ttaaatttta aatgccaagg  89400
tctttatata agtccctttgt gttttttttaa ttttgaaatt tgtataactt gatttgtttg  89460
tgtctaatgg aatttagaaa taaatttaat atagttttta gggctaaccct aaaagtaatt  89520
gggttcatca tggtgtcata tgtaattaaa acatatagaa tcctaaaaac taattaagtt  89580
ccttggacac cttatctcac ataacccaca tctctaatgt ctccccattg ggaaaagagt  89640
ccattgataa atcaggtgaa ttatgcctag cgggcccaaa tctgctactt ttctttaagt  89700
tgtttaggag ttacattcag accatggtga catggagcac caagaactta gaatcagatt  89760
tcattttact tgacaaactc ttgaaaggtc actgccacag tctctcttga gtgcaaggct  89820
atggctatgc tttgtagcac agggacgcga tatttctctg ctatctttgg gtagcagagg  89880
ttaacacagc tcccttgtgc tttctttctc tcttttctat tttcttttct tttcctaagg  89940
atagatcttt aaataggagg agtttaaccc catgttaggt gaattcaaat ggatcttagc  90000
```

```
ctgatgtctc ttgttctctt ttggttccag tttggttaat tcctttcatc caattttcca   90060
gtggttgagg gagaacctaa cttgctctcc tcgactctga gcatcatcct tcactgacag   90120
ttcaggcatt gtgggtagga agaagtctga gaacaaaacc tagggataaa gtttagtaga   90180
gatggggttt caccatgttg gccaggttgg tctcgaactc ccgacctcag gtaatccacc   90240
tgccttggcc tcccaaagtg aggctggaaa taagacatgc tggaattgta agtaggacac   90300
tagagtctag gggaatcaaa gaggaaaatg aacagaaaag ggaagggaa ggatattatt   90360 tgattgactc caagtgctac tgtttgtaa gttttaccat tttaaaaata tgccattaag   90420
aaagaaatgc tggccgggca tggtggctta tgcctgtagt cccagcactt tgggaggctg   90480
aagcggacag atcacctgag actaggaatt tgagaccatc ctggccaacg tggtgaaacc   90540
gcatctctac taaaaataca aaaatcagct ggatatggtg gcacatgcct attgtcccag   90600
ctactcagga ggctgagaca ttagtactgc ttgaactggg gaggcaaagg tttcagtgag   90660
cagagattgt gccactgcac tccagcctgg gcaacagagt gagactgtct caaaaaaaaa   90720
aaaaaaaaga aagaaatgct gcttatttaa ctgtgttctg tcaatgttaa ggtgtatccc   90780
gacttcagag atgttaacaa atgggaaaaa atttggaatt cattaggcat ttggaactta   90840
caaagtttcg gccgggcata gtggctcatg cctgtaatca ctttgggagg ccaaggcggg   90900
tggattacct aaggtcagga gttcgagacc aatctggcca acatggtgaa acccatctc   90960 tactaaaaat acaaaaatta gctgggtgtg gtggcatgcg cctgtagtcc cagctactca   91020
ggaggctaag gcaggagaat cgcttgaacc caggggcgg aggttgcaga gagctgagat   91080
cgtgccctgc actccaactt ggacaacaga gtgagacgcc atctcaaaaa caaacaaacc   91140
aaaaaaaaaa aaaaatttc atagttacag aaagtagtat ggaggccata ccgagatttt   91200
cgacatggta gtaaaactct gcattatggc tctgttctgc atcatctctg ttctgcatcg   91260
tttcactcca catcagaccc tggatagctt tggtgtactg gtcgatcttg tggcagtaag   91320
gctagtgtaa ttaagaggat attttaaaac ttaacatata attgctctag ttgttgtctc   91380
ttttttgctg gttaagaaaa tcaaatttct atcctatctg aatctcatag cagactttgg   91440
agatttctga caagtcattt cttactacct aggggaatgt acttgtactc agctagagtc   91500
tgagtatctt ctacatccag ggaattgggc tgagtgtgga ttttggtctt ggcagttttt   91560
acttttatta atttgcaaaa gaatagaaga cttggaatgt acaagaagca taaaaatgtg   91620
tcaggtggtt ttacatgcgt tatttatcac gttaatatgt cttaagatat tttccacgtg   91680
taaacttatg taaaggcagg aaactagtga gatttcatat tctagggatc aagagattgt   91740
tttagtaact agcctcagaa agtatcttga aaggtattat ataaggtcaa ggaactaaat   91800
attagtaaag agtcaggcca ggcgtggtgg cttatgcctg taatcccagc actttgggag   91860
gccaaggcag gcagatcact tgaagtcagc agttcgagac cagcctggcc aacatggtga   91920
aaccctgtct ttactaaaaa tagtagtgtg tggtatggtg gcgcatgcct gtaatccagc   91980
tcctcaggag gctgtggtgg gagaatcact tgagcccagg aggcggagat tgcagtaagc   92040
tgagattgca ccactgcact ccaacctggg tgacagagct agtgtctgtc tcaaaaaaag   92100
aaaaaaaaaa aggtcagata ggtgcctaaa gcctgtgtgt ctcgctatga gaatacatct   92160
caagttttac tgtggttcat tgattcagac atgtagttca cattttaacc tgtctgaaat   92220
ggtaatatgt gaaattgatg tcatgatata gtttaattgg cagcatgttt tcatagtggt   92280
acattttata attagtgaaa tcttagattt gatgaaatag atatgatttt ttaaagtggg   92340
aaagtttagt gttatagaca gtttgcagga ctttttattt tgtaggtact taaattttga   92400
```

```
ggacttaatt attctctaat aaagtgattg acaaggatta atgtataaat tataccttgt    92460
cagtctgaac aatctgcagt ttggacattg attcaaattc atttaggctg aataaatttt    92520
gataaactaa gtaagttttg acagctattt aaatatggg aaaggggata ttcaacattt    92580
ttcttacatc ctgagagctt tgttaaattt agttatttga acccattgg gttctatttt    92640
ctggttcagc atgttgctgt aatggtaaaa tacaattttg aaattatagt tgtcttgaag    92700
ttaataataa attgaccaat atgttgtatt tttttctcta cttagttaca aattgaactt    92760
ttcctaagta gaactttaa tttgacaggc cccctttgct tcctgaggta actgaaatag    92820
gccaaattaa tgcttttttg aatatcttag gtttgttgct ttctttcaca tgttacctac    92880
cccacttaac aaaagcaatt aatctcagca cttgatgcca agaaaaattc taaaaggtct    92940
ggatttttc cttggatttt acaaagtagc tacaatggga cttttaagac aaagctgcat    93000
tgctgcttac agagcaattt ttgtttaatg gtctgtgtta gagtcatact gcatgatgac    93060
ttccaactgt ctgggatacc attctgaaaa gggtttagtg ttacatactt cttagagaga    93120
gttctccatt tctaattaag gcacacatct ggaggtgctc aagaaaaatt agtgcagtta    93180
gccttggaag tgttatgtgt gactagttca cttcagacat cttttgtata atcagacaca    93240
tgcattaaa tttatttaac ttctcttgct tttctctccc acagagtatc tcccatattc    93300
atgttgcact ttgtagaagg cttaccacag aatgacttgc agcactatgc atttcatttt    93360
gaaggctgtc tttatcagat aacttctgta attcagtatc gagcaaataa tcattttata    93420
acatggattt tagatgctga tggtaagtgt ttagaggttt tcttttaaga taattggcat    93480
agaaactaaa ttctagcatg tggggacttt ttggttttg ttttataaaa aagacaaac     93540
tttgtcctga ctctttctct ctccattctc gcctttgcct tctgcccctc ctcgcatcta    93600
ttaaaagtga tggttttagt atcctgtctc attttttcct ttccttacat catgtattat    93660
aggtaaacac atgcgcatgt gtgtatttct cttttagaca aaggatgaga ttactactgt    93720
tagctcagtt ttttttccc tacttaacat cttttgctttt attttttaga catatttcta    93780
agactattaa acattagact tacgtagccc ttctgtcatt gtgaaataca tagttttacta   93840
acagctacca tcaagataaa gcctttattt aaataattaa acttcttagt ggaaagctaa    93900
gtaagcacag tttatggatt ttgggaattt ttgccttgca tttgtctgat atggtaaaat    93960
attgagtttg tttttctcat aatgttcact ttgtcttaga caagataact caatccccttt   94020
aaagggttgt atcaagccat tgataagggc tcacttgat ataaccattt tctgttattt     94080
agacactctt tcacacttcc tattttcctc ctggggatgg tttgaatgga tgacacaata    94140
ccatattata aaagcacttt acaaactgta acttatgtta taaatgtaat tattaccttga    94200
aggttttacc ctgtttcaga tttgagtgga agtagttctt tacaatacaa aacaacttat    94260
tttaactttt tttgcatttc aaagaatgat caatccactt caggtgcagc atggtttcca    94320
accctgacag catggaagaa tcatttattt agcttctaaa aatgtgcagg ctgtacccta    94380
gaccagcctt ggggattagg cccaaatatc aatgttgggt gttttggta ttggtttttg     94440
gcccgcctac ccgcccttcc ttccttcgtt cctctctctc attctctctc tctctctctt    94500
tctctctctc cttctttgct ccttcattcc ttctctctct ctcttttttt tttgagacag    94560
catctcacta tattgcccag gctgttctca aactcctggg ctcaagtgat cctcctgcct    94620
cagcttcctg agtagctagg actacaggca catgctatgg caatactgtt ttaaacattg    94680
ttttcaaggc tccccaggtg attccagtgt gggtcatgtg gtagagaacc actgacacag    94740
```

```
gcaaacaaag gatacataaa gttgtctatt taatgggtag gtgcaggtag tagataagag    94800
tgtagccaca taaaccacat gcttagtgaa cggttttgtt ttgtgtgtat gtgagggatt    94860
agcatctctg agtatatttt gttttccctt ttgaaactta tcagagaatt catatgtctg    94920
ttatgtgact aatgctcaca ttaaaaaaag ttatgtgact tttttttaatt catatgtctt    94980 tttaattcat ttattcattc atatgtctgt tatgtgacta atgctctcat aaaaaaagta    95040
atgctcagtt tacttttttt atatcagatc atatatatat gttttttttt ttgagatgga    95100
gttttgctct tgttgcccag gctggagtgt attggcgcag tcttgtctca ccaccacgtc    95160
tgcctcccgg gttcaagtga ttctcctgcc tcatcctcct gagtagccgg aatacacgca    95220
ggcgctacca tgcccggcta attttgtatt tttagtagag acagggtttc tccatgttgg    95280
tcaggttggt cttgaactcc caacctcagg tgacccaccc gcctcggcct cccgaagtgc    95340
tgggattaca ggcatgagcc accgcacccg gccatatctt atattttaat aaatatttta    95400
atttggtctg taaatttttc ttttttggga atgtgtttta agtctgtgtt gagtcctaga    95460
catttgttgt tctcagatag tcactagtga taccttaaca ttaaccagcc tgttggcaac    95520
taaattggcc tgaagtgaca actaaggaaa ggtctctttc tcctttctta atctttgcat    95580
tccttaagat tagttctttg taggaaggct ttgaagtctg gtggcaagta ccctttatcc    95640
ctcacaatct taagataagg tctttctgag cattaaaaag tgactgtggg agatatgtca    95700
aatgagtttt ctgtgtgtgc tctgagaaat cttttttttca aaaaggata gatgtacttg     95760 tataaggaaa agagaaactg agcgcacttt caatatttaa gtaagtgtct ctaacatgtt    95820
ttgcaacata aaatgatgac cactgtgttg gtcattactt ctctactgct aaaacaatgt    95880
tttctaaaat aatatactcc ttagaaaaaa atatagtgct ttgggtgtgc actgttgtaa    95940
tccaaggaat aggaaatgtt ttgtagtaag tgcgatggtg tttgacatcg tgatttatta    96000
atttatcaca tttggtttca tagaaataga gtaagctacg tatttgctgt gccgcaatta    96060
ccatgacatt acacttgtat ctatttctgt ttcatagatg tgtagatatt gatatataca    96120
gtggaagtat ggattgtttt gataagtttc taatgaaagt acagatattt gttgattatt    96180
tattaagaaa ggttgttact catccaagcc cgtggttagc ttttcccaaa ttatcatgtg    96240
gtagtaagta aaatgtaaag aaatataccc tcccttaacc ccacaccacc tgttagcacc    96300
tagccacctt cctttacttc tcagccgtac tttttgtatt tttttgttgt agtggtaaaa    96360
tataaataac ataaaattta ccattttaac atttgtaagt gtacaattca ttggcattga    96420
atacattgtg tgcaaccacc atcaccatca ggacttttttc atcaacccaa acagaaacta    96480
ctcattaaac aataactccg catccttcca ccccaaagcc ctggtaacca ctattctact    96540
ttctgtctct gtgaatctgt ctattctaga tacctcatag aagtggaatc gtacattatt    96600
tgtccttttg tgtctggctt attttactca gcatattttc aagattcatt tgtgttgtgg    96660
gatgtagcag aatgtcattc cttttctaagg ctgagtagca ttgtatgtat tatccattta    96720
tctgttacgg acatttgact attgtgaata atgctgttgt gaacattggt ggacaaggaa    96780
ctgaaagtcc ctgctttttca ttctttttgg cataaaccta caagaggaat tgctgggtct    96840
taacggtaat tctgtgttta attttggac gaactgccag actgtttcca cagcagttgt    96900 actatttttac atccccacca gcgttacaca aggattccaa tttctctaca tccttgccaa    96960
catttgctat tttctatttt tttttaataa tatccatcct aatgggtgtc tttttttttt    97020
tttaaaggaa tggtttaaac aggttacctt cttactcctc attcatgctt tagttgacta    97080
cataaggacc cctctcccta ttggcaccat tgaaattgtt caggcaaaaa taactgccag    97140
```

```
cgacacactg ctttaagtaa tggacttttc ccaagttttg tattaatatt tcagtatttg   97200
gtagtgcatc ctactgctag tttttaaact cttcccttgt catctatcat ctcattctct   97260
cttgacaaat gtgaaaatgg aagctcagaa ataaaacaag aattaaaacg aatagtgatc   97320
cttcaggtaa caagcttcat ttatcatgaa acatatatg tatgaaacat tctgttttct    97380
gatgttattg gataaattag gtgataacca aattctaagt tccaaaaatt aaatatactc   97440
tatctaagga ctttaacatg gcagacaatg gtgacaaggt caagaacatg ttttagagtc   97500
ttctcctttg gtcggtattc aatgatacaa cagttgaaaa ggccagaaga aagttaacct   97560
aggatggtgg ttttttgaata tctaactttc acttctttcc catcttccag gaagttggct  97620
ggaatgtgat gacttaaaag gcccatgttc tgaaaggcac aagaaatttg aagttcctgc   97680
ttcagagata catattgtta tttgggaaag aaaaatatcc caagtgacag ataaagaagc   97740
tgcctgcctt ccacttaaaa agactaatga ccaacacgct ctcagtaatg agaaaccagt   97800
atctttaaca tcgtgttctg tgggtgatgc tgcctcagct gaaacagcct cagtaactca   97860
ccctaaagat atatcagttg cccctcgtac tcttttcacag gacacagctg taactcatgg  97920
agatcattta ctttcaggtc caaaaggttt ggttgacaat attttacctc tgacacttga   97980
agaaactatc cagaaaacag cctcagtttc acagttaaat tctgaagctt tcctgttaga   98040
aaataaacct gtagcagaaa atacaggaat tctcaaaacc aatactttgc tatcacaaga   98100
atcactaatg gcttcttcag tatcagctcc atgtaatgaa aagcttattc aagaccaatt   98160
tgtggacata agttttccat cccaagttgt aaatacaaac atgcagtcag tacagctgaa   98220
tacagaagat actgtaaata ctaaatctgt gaataatact gatgctactg gtcttataca   98280
gggagtgaag tcagtagaaa ttgagaagga cgctcagtta aaacaattcc ttacaccaaa   98340
aactgaacaa ttaaaaccag aacgtgtcac atctcaggta tctaatttga agaaaaaaga   98400
aactacagca gattctcaaa ccacaacatc taagtcatta cagaatcagt ctctgaaaga   98460
aaatcagaag aagccatttg tgggaagttg ggttaaaggc ttaataagca ggggtgcttc   98520
ttttatgcca ctctgtgttt cagctcataa tagaaacact ataactgatt tacaaccttc   98580
agttaaaggg gtaaataatt ttggtggctt taaaactaaa ggtataaacc agaaggccag   98640
ccacgtatcc aagaaagctc gtaagagtgc aagtaagcct cctcccatca gtaagccacc   98700
agcaggccct ccatcgtcta atggcacagc tgcccaccca catgctcatg ctgcttcaga   98760
agttttggaa aagtctggaa gcacctcatg tggagctcaa ctcaaccaca gttcttatgg   98820
gaatggtatt tcttcagcaa accatgaaga cttggtggaa ggtcagattc ataaacttcg   98880
tctaaaactt cgtaaaaagc taaggcaga aagaagaaa ttagctgctc ttatgtcttc      98940
cccgcaaagc agaacagttc gaagtgaaaa tctagaacag gtgccccagg atgggtctcc   99000
aaatgattgt gaatcaatag aggacttgtt aaatgagcta ccatatccaa ttgatattgc   99060
cagtgagtct gcatgcacca ctgttcctgg tgtttccctg tacagtagtc aaactcatga   99120
agaaatttta gcggaattat tgtctcctac acctgtttca acagagctgt cagaaaatgg   99180
ggaaggtgac tttaggtatt tgggaatggg agatagtcat atcccaccac cagtaccaag   99240
tgaattcaat gatgtttccc agaacacaca tctgagacag gaccataatt attgtagccc   99300
caccaagaaa aatccatgtg aagttcagcc agactctctg acaaataatg cctgcgttag   99360
aacattaaac ttggagagtc cgatgaagac tgatatttc gatgagtttt tttcctcctc     99420
agcattaaat gctttagcaa atgacacatt agacctacct catttcgatg aatatctgtt   99480
```

```
tgagaattat tgaattaatg cttgttaact tttttcatat aatatttatt attattagaa   99540
gaacttacaa tgtgttcagg tagtgtttat acactggact tgtgtaatta cttgtgtaat   99600
aaccatgaac aaaatgcaag gtttaacctt tggttctgcc catgaagcat gtaatctttc   99660
ttacacatta aaatcactga atgtgttctc cttttttggtt tcattttgtt cttgtgagag   99720
tatgaggatt tcaaaatgtt aaagatgaaa agtggcgtct agtttctgac agtttgtaca   99780
gttggatgca ttacattttt agatttgaag ttttggttat gttagtgtta tgagtgatct   99840
ttgtggtggt tttcttcccc tggaaacctg ttgctcgtgg cgctttgccc acggtgcccg   99900
agttcttgtc ctgtgtccag atatgcagac aaatgaaggg tgaagaagaa gaagaggagc   99960
tttatttagt gttagaacag ctcagaagga gacccacagt gagcagctcc cctgtgtcgg  100020
cgggcaggtc gtccctcaag tgttcagctc tcagcagaga aaaggccctg gagagggtga  100080
ctcctctcag ctctcagcag agaagcagcc ctggagaagg tagcttctgt tcgcaggcag  100140
attgtccaga ggtcctgctg ctctcagacg gggccctgga gaggatagct tctatccata  100200
ggcaggttgt tctgccgtct ctacaggtct ctgaagctct tagcagagag ggtagctcct  100260
ccctgttgct ggtcgtccca ccctctgctc agttctggct gagcctgggg cattttacgg  100320
gcctcggggg aggaagtgca tacttactgg cctggaaaag gcaccagttc ccactcctac  100380
aggtgggact ggcagcctgg ccctcagcct tcaggccctc cctgttcatg gcttccaggc  100440
ttaccccct gctttgatct gagagctggt gccaatagca gggagaagcc aagctgcaga  100500
ggcaagcact tccgagcctg caaaagcagg cccccaaaag tgcagggatg cctgagtctg  100560
cacccgcacc caggagggtg gagatcttgc ctgctccaag gctgcagccg gaatgatagc  100620
aggctgactg gagcacctgc caccatcatt agttcaagag tttatgcaga tttaagttgt  100680
atacggtata tgaatgtgtg acagttttcc ttatggttgt gtggccttct gtaagagcct  100740
acgcctgttt gttacaccgg tagagtgctg tggaatgtaa actttcccta tgtcacttat  100800
ctcctttatc tctccataca gaggagggca agaaaccttg ttacttgaac tttagtaatg  100860
ttaagtgatc aataaatcta taaataaatg atagcagaaa aaagttacct gtttttgtga  100920
tgatgtacaa actttacatg ttatcacaaa taccatcttt cttcccaaga catttacttc  100980
tgtaaccaaa gtgggacacc atctaacagt tctgttttgg gagagagtaa taaccagtgc  101040
ttgtgaggct tgttagatgt tggttgtgat atatgagata gatgttattt catttagacc  101100
tcaacattcc tgtgcgtgag atactttat cacatcttac agataaggag actgtactca  101160
ttcagttgtg gagctgagat tgagtagagt ggctattaca gcagttgagt gctgagctta  101220
tcaatatatg ttccactcct caggcttcat ttaaagtagg atgcccaaac agcaccactg  101280
ccgtagagat ttgagttaac agcagtactt actgaggttt aaggctggca gccagtgtcc  101340
ttgcagtaaa attatttgct agggactcag tacttcataa tctatttgtc agatttactc  101400
ctaagcttct gtgttgtttt attttttttc tgacaaaagt agtgcatatt gtcaaggaaa  101460
aactaggaaa ataccaaaaa aaaagatttt tgaccatgca ttttaatact tagtgactac  101520
aaacattttc ctattttatg catatagatt ttaaataaac gtgagatcct attgtatctg  101580
ttttaatgga taaacattgt ttcactgttt taagattctg aggtgattta tactgtcttg  101640
ccattgttaa ttgcagcagt tagccttgtt gataaatttt tgcatggatc caagtttgt  101700
tttccaggag tggagttgct tggtcaaagg aaatgcacat ttaaggtttt tggtgattg  101760
catgactgac ttccctgggc cctgccaac actaggtagt agtattggga ggaagggggg  101820
aaccaatcct gggtgctcca agattactag tgagcctgaa cattttctat aactattgtc  101880
```

```
cacttgagtt gttgttttgt tttttttttg gtggaggcgg gggtgggttt aagaattgct  101940
tatcctttgc ttgtactaat tatcttttca acaaatattt ctagattact gctaaggacc  102000
aagcactgtt atcagcctga gataaggcag cacactagaa ggaaatcctt gctccttttg  102060
agtttgcctt ccaaacatgg agatcaatat ataatgttag gtagtaatag gagatacatg  102120
cagttgattc atgtcatttg tagtagttat ggtcaataaa gttgccttga acactgaatt  102180
agtataaact gaaatactgt tcctagggga aataggttcc tgctagcctg tggtcatgag  102240
atttttgtca acaatcact atataacctt ttctgtttct gtttaaagac atgttatttg  102300
atctatatgg ttgattcttt acattaacat ggccaacagc actgtaactc agcctgaacg  102360
aagcttatct gacacatggt gttctccata aggcacatca tagctttctg tgcttaggaa  102420
cactagacgg cacttcagca ctgcacttga ggacgtttta aacagtgaaa tcaacaaaaa  102480
gcacaaaaaa atgcaacaat aggctgggca aggtggctca cgcctgtaat cccatcactt  102540
agggaggccg aggcgggcgg atcacgaggt caggagatca agaccatcct ggctaacacg  102600
gtgaaacccc gtctctacta aaaatacaaa gaattagccg gcgaggtgg caggcgcctg  102660
tagtcccagc tactcgggag gctgaggcaa gagaatggtg tgaacctggg aggcggagct  102720
tgaagtgagc cgagattgcg ccactgcact ccagcctggg cgacagagcg agactgcgtc  102780
tcaaaaaaaa aaaaaagga acaataacaa agacactagt cccccaaaaa tacacttgtt  102840
tacagtgtga actgaaagag gaaggtggag tattgacttg tttgacctca gctggaaatg  102900
tgcacgtcct gtgactcaaa tttttctctg ttctgtgcat gcatgtccac gaataaccac  102960
aagaagcact gaaagcattg atttttaggg ttacaaatta attttagcaa gtaaatgaat  103020
tcacaaatac ggaatctgtg agtaatgagg actgattctt tttttttttg gagatggagt  103080
ttcactcttg tagcctaggc tggagtgcaa tggcatgatc tcggctcact gcaacctccg  103140
cctcccgggt tcagcctcca cctcccgggt tcaagcgatt ctcctgcctc agcctcccga  103200
atagctggga ttacaggctt gcaccaccat gcccggctaa ttttttgtatt tttagtacag  103260
acggggtttc accatgttgg ccaggctagc ctcgaactcc tgacctcagg caatccaccc  103320
acctcagcct ctcaaagtgc tgggattaca ggcgtgagcc accgcgcccg gccgaggact  103380
gattcttatg tcagatggca ctaaatgcta tggagaagag gagtggatga gagggagaag  103440
tattttagac caggtagact tggaaggttt cttggaggtg ggtgatgttt gagaagaggc  103500
ttcaataaag ttagggagct cgccatgtga ttgcaggaag agcgttccag gagaacaaaa  103560
gtcatgaaga gtgagtgcta ggcatgtgtc tggtctgttt gggctgctat aacaaaatac  103620
cttagactgg gtaaaatgta taataatag aagtgtattg cttatagttc tagaagctgg  103680
gaagtccaag atcaaggtat cagcacattc tggtgaaagc tgctctgctt catggctggt  103740
tctctcactg tcctcacatg gcataagagg ggcacagagc cctcaaccgt ctctccagtg  103800
gccccatctc ttagtactgt tggattgggg atttagactt cactaatttt gggggacac  103860
aaacattgag accacagcag catgactgag gataagcaag aggccagtgt ggttgagcag  103920
agtgatcagt gaaggagagt taggacatga gtaaagaggc tagcagacac cagatctcat  103980
atggctttgt aggccatagt gaggactttg tttaagctga gaataataga taacctcagg  104040
aaagtttcag gcaagagggt aacatgatct gatctgggtt ttaaaaggat cactgaagtg  104100
gggagactgt ctacagatgg tctgaatagg agtcctagtc tattacaatc tccttggagt  104160
ttagggtggt aactggaggt gttcaagagt agttggatta ctgttggatt tcaaaagtag  104220
```

-continued

```
agccaacacg atatgtgcat tggctgtgag gtagaagagg agtcaaaatg aactccaggt 104280
tttattgact gagcaattgt gccatttcct gagatgggtc agatttggga aggaaagaat 104340
ttaaagggga taagataatc ccattaggag tgtgttaagt gtgagattcc tattagactt 104400
tcgagtggag atgatttaat aggaagatag atctgcaaca ctggagctca gcggagaggg 104460
acaccctgga gatagccgtt tgggaattag gaatgtgtgg atcatgttat aggatggggt 104520
catttaggga cttaaaacag ctctgaagaa caaaaatggt gccttgatct tggacttcct 104580
ggtttataga actgtgagca atatatatat attttttttca agacagagtc ttgctccgtc 104640
atccaggctg gagtgcagtc gcaccatctc ggctcactgc aacctccact tcctggttca 104700
agcaattctg gtgcctaagc ctcccaagtg gttgggacta taggtgtatg acaccatgcc 104760
cgactaattt ttgtattttt ttgtagagac agggttttgc catgttggcc aggctggtct 104820
caaactcctg acctcaagtg atctgcctgc cttggcctcc caaagtgctt ggattatagg 104880
cgtgagccac catgcccaga ctaaatttct aacatttata aattatccag tctaagatat 104940
tttgtgatag cagcccaagc agaccaaggc aaaggccaag cacacttgct cctcctgact 105000
tttgctcttc ctggaatgtt cttcctttag tcacatggtt gcctgcctag cttcattcaa 105060
taggagtgtg gtgccctgaa aatacaagga agaatgcttt tcttttttt aaaaggaagg 105120 gatgattatc tgtcagatgc tgctgaaaaa gagtaataga gtaattggcc actggctctg 105180
gcaataggga agttagctct gctaactcca catgaacagt ttcacatgaa caagtgtgag 105240
tgggctcaag agaagggatg tgagaaagt ggagctatgg actcactctt gaaacatttt 105300
ctggtgcctc gtagggcaat gtgaggtcaa ggttttttgtt actgttctga agatgggaga 105360
ggctgacaca tggatgttgt aggtgagaga aggggcgctt gcgggggcaa acttctccag 105420
ggatgggatt ccagtgtcta agaggaggcg gtgtgaccct aagagctaga aaaattattt 105480
tattaatagg aaagacaaag tacttaggct cagatgctaa gagatttgct gataaaagaa 105540
tgagaacggt ctcttctgat tattttcttg gggaaataaa tagatcatca gctgagggtg 105600 tgagggaga aggagttgaa catggaggaa gacaggtgtg aaatattggt ctcagaatgg 105660
agagcgaatt gaatagggac atgcagtggg cttgctaagc tgtgcggaga gcccgtggga 105720
agtttatggt catcaattta atggcgacca gccaagatgg tggtttattt ttctccagtt 105780
gtatttaact gctcaggtgc aggacagaga gactaagtgt gaagttaatt tcagccaacg 105840
tagaggaatt gtcaggcaga tgggacaagg agatagagga gaaaggaat aaggcttcct 105900 gcaagggtaa tgattgtagg gatggataag taaggaacac aggaagtggc tgtctgctga 105960
gtggtggcag agctcagtgg gtcagagcaa ggttcaaaga atggcagaga ggcacttgtg 106020
gaggaagtaa gctggctaga aagtagtgtg cttgaaatta agcttctgga gatagcaagg 106080
ttacaggtga tgacaaagtc tgagtatgac aaggaaactg cagggccaga gttggcaaga 106140
attcatgaaa aatgaggaga aagaggcacc aagaggctgg gatagcacat ggattgtctc 106200
tgtgtgaggc aaagtcatct aaatggcagc agtggcccta gcagaaagaa atatacagtg 106260
agccggagca aaaatcctca aggacaggca gaacgccatg aaaacggcag atgacagcca 106320
aaggagcagg ggcaggggct cagtccaaag tgtttcagag tcactggagg gttgagtggg 106380
aaggggaggg agtggctgaa atggcaacaa ggaagaacct ctctcatctc caggcccaaa 106440
agtatgtgga atgcgggaga taagacagcc accactggcc agggctgtaa agggacattc 106500
agcgaatatt caggttccat ttagcacgac agcagggaag ggactgttgg cagaaaaaaa 106560
ctggggcagt gggattaaag acagaccaca cattccaaaa ggcaccgtgg gagggtcagg 106620
```

```
gggcgaggtt aggtctaggc ttcagtgtcc tgggagactc agtcttcaca gggtgacagc   106680
gatcaagagt gcagcttagg ctgggtgcag tggctcatgc ctgtagtccc agcactttgg   106740
gaggccgaga cgggaggatt gcttgaagcc aggagtttga ccagtctg accaacatgg     106800 caaaacccca tctctactaa aaatacaaaa atcaactggg catggtggcg tgtgcctgta   106860
gtcccagcta cttgagaggc tgaggcaaga gaatcacttg aacctgggaa gcagaggttg   106920
cagtgagctg agatcgtgcc actgcactcc aacctgggca acagagtgag accctgtctc   106980
aaaaacaaca acaacaaaaa agaaaagagt acaacttatg aagggg tctc ctggggagag  107040 ggttttt ggg attctcctgc ctctcaaagt gctgggatta tgggcgtgag ccaccacacc  107100
cagccgaggg aggctgagtt ctaattgttg tatctctctt gggattggcc tcctgggcag   107160
tttaaaagac aaggcaagga atcttttgga gaaagagact gggggcaagg tgtgtctgaa   107220
caagaagtgt gagaagctct gtgggctccc ttcagacttc cagtcgttga attgggatct   107280
catttatatc agctctaggt gtaacgatat taaatcttct ctgtcatttg gcaattttgg   107340
tttatgcttg atcatcattt ttaatgtttc gacatgtaga agtttaacat tattttacat   107400
tcttttcctt ctggcatcat gttttagcaa gattgtttcc accaaaagaa tatatatatc   107460
ttctaatgaa actacgtttc ttttttttt ttcctttgct ttctcttttg gtatatgaat    107520
ctttgattat ttgtaatgta ttttgatgtg taacactgaa gttctatttt tgtactattt   107580
ttttccccaa acagtaaact tattgttcaa atacttattg aacaaccttc actattcttt   107640
aaccatttag aatacgccat tcacatatct ttcatactac atttaataac attttttaat   107700
taaaaaatat tctactgatt tgtttatttt gagaccaggt tatgaaactg gctaattttt   107760
gtatttttgt taaataccga aattcactgt gttgccaagg ctggtctcga actcctgggc   107820
tcaagcaatc tgcccacctt ggcgtctcaa agtgctggga ttacaggtgt gagccgctac   107880
acccggccac acccggccaa cacatattat ttgttattac atttaattcc cacagtacat   107940
tgaaattatc agggaaaagt tttcagtgaa acattattga acgccacatt aaaagtgtaa   108000
attacaaaga tttaatgcca atttttcaga agaaaaaaga ccaggaggaa ggtctatgaa   108060
gttttagcca gtctctcatc cacctaccat ttcacgatca tgcactgtgt aagtcaggaa   108120
aagagtaaga aaagtgaaag atacaattga ttagagagtt ttgctggata ctatagatga   108180
aaagaacaca aaatggaaca gcctcttcaa gcttagagtc aacggctgta gtcccaaaga   108240
ctgtagtcag aggcggtagg gccaaaagac atgacttatg gcattggagg aagaggatgc   108300
tttgggagtt catggtagaa gaggcggaaa aaatctggtg gattaaagaa agcatcccaa   108360
agtgacatta aactaatgac taaattctga gctgttttca ggggcaaagc ctgtttgggc   108420 accctgcca cacttaaaga gtcacctagg tatggttcgt gggctctgaa caggcctgct    108480
cagtgaacat atttgtgact gtttctccgg ccctttagc tgtattgagt aaaatttaaa    108540
gagaccattg tttgccta agctcctgcc ctaggcccaa agaacagacc aaacctgaat    108600
ggcttcactt gtcctaggtg ctgtgtactc aaactgaact ttgaaacagg tcggttttc    108660 aaaaaaagca aaagattcac agcaaccaat tagaagaggc ccggtcaacc tgagccagca   108720
tgatgaggct cttctgcttt aatcctacaa ggaaagaaac tttgaaatga ccaatctgct   108780
ttcattcttg gtttctgctt tctttggtct atttctgcct gtaaaaccta tctcctctgc   108840
tcagctcatt gaagtaccct tctatttata gatgggatgc tgcccgactc atgtatcgct   108900
agtaaaagcc aattaaatta ttacactcga tttgttggaa ttttgctatt ttgacagctt   108960
```

```
ttcaaaaaca ccagtaggtt cacatcccta attccccagc cagtgttccc tcaaggaacc 109020
atggaagaag caaggtggc tgaaaggcgc ctcaggatgc ttctaagcac ggcacatcca 109080
tgaaaaggca cttactaata tttgcaggat agcaaagcac tgcagtgacg ataaatctag 109140
tattggagaa gttcaaaata atcagtagat taacacagaa gccagagctt ataggagaa 109200
aaggaaccct atgaaatact tcaaatccga aaacgaacat gcatttcctg tttagttagt 109260
gcaggtacgt aaaagcttgg taaagtaccc ttcttgccag ctttctcttt cttacaagcc 109320
ttttcactgg gctgggaggc tgatatatc taaatatgct gaggaggttc aagtatctcc 109380
acaactcacc tcagagtgaa tgctcccctc ggccttaagg caatataaac cagcccctgtt 109440
tagcaggata gcaaaatgtt tgcggttgta aactggtgtc ccattggctg tggcgcttgt 109500
ggtgtaaaga atccctgtgc ttggtaatta atagagaaat tctatatttt aaacttcagt 109560
tgtatattgg ctcttatcca tggcagattt tcacgtatgt gttatttttt tatttattca 109620
gagccggagt ctcgctttgt cgcccaggct ggagtgcagt ggcgcgatct tggctcattg 109680
cagcctctgc ctcttgggct caagcaattc ttctgcctca gcctcctag tagctgggac 109740
tacaggtgca tgccaccacg cccggctaat tttttgtatt ttagtagaga tgggggttca 109800
ccgtgttgct caggctggtc ttgaatttct gagctcaggc aatccgcccg cctcggcctc 109860
ccaaagtgct gggattatag gtgtgagcca tcatgctcgg ccctatgtga tatttattac 109920
aatgaattcc aatgatcaga cctatactca agtataagtg aatatatcat tcaatgaagt 109980
ataaatgatc attatgttca tattcacaca tacaataatg tactcaagtt tattgctaag 110040
gtaattcaga atctccttat tttgaagtgt gcatttgata tacctgtttg ggaataacta 110100
gtttcttatc tttgacagaa aataattttg ttgttttgtt tttactaaaa aagcatggtg 110160
aaaaatggct ccatttctaa gagaggtaac taaaatatcg caatttgctg ggtgtcatta 110220
aagtaactca caagggaaaa aatgcaaatt ggtatctgct gatggagtaa atctccgcag 110280
aagtgatgac cctgaaagga tcaatatatt aaagcccctc ccagctggtc attccagatt 110340
gcaacaataa agcattaagt gttaaaaacct caaggcagct tttttttttt ttttttgtct 110400
caagtccttt attattaatt ttatagacct acttaattac taagccaaaa aaaatcaaac 110460
ttgtttctct ttgtgacttg tcaatagtat taaactattc tggttttta tttttgtgtt 110520
accttaaagt ctccagtta gtaattttc tgtacctaaa cacttcggat ttgacatgct 110580
ttgtggcctt tatcagtagt tagaatgtaa atccaataaa taaagtaaaa gccaggtctt 110640
caaaacctgg gggccaagaa ctctgtttta gagggcctgt gactctcttg gacactggac 110700
aaaatctcat ctctaaatat ggatatttta gggagagggt ctttaggctg tcatttggat 110760
tttcacaggg ctccatgtat ccataaggta gtctcttggg aagtttgact tcaataaatg 110820
aagtttaact taaacctaaa atgaaattta actgaaaaac aaaatccaat gaaagatgct 110880
ttcttatgca aaaacaaaca aacaaaaaaa aaacaaaaaa accccaaaaa acccaaagcc 110940
aaagattgtt tctgaaatta ggttctaggt tccagagcaa ctccatggtg gggaatcagc 111000
cacatgtaaa gtaagctaag agtttggaca atttgtaata tttattccta ggtttcttta 111060
agaccctttc agattttgaa ttcctattag tagcatcagc caggttctaa atgtaggcat 111120
caccatagac acttccccac tgctgcagtc cccaacactt gcccaatttt cccttgaatt 111180
gcacccatgc tgccttctcc aggcctattt gaacccagaa cctcgttgtg cctcgtttga 111240
aatataattt cctcctaact agtctctgat ctactatttc ccctcacattg ctgccacact 111300
aatcacctaa aatagatttc attctaccct gaaacagaaa tctctaataa gttactccct 111360
```

```
tcccttacgg ggtaaagtta gccacatcct aggtattcaa ggaccttcca ggagctaaga   111420
acatttcccc tgcaccttct tgaagtacac ttgtcctatg tactggttat gttcatttct   111480
taccctcgct ctcgttttgt ctggaatttt ccttggcctt aaatgcctct cacctgcctg   111540
cccacatctc tcagggttgt ttcaaatcct caatgaaggc tcacagcccc agtctatgtt   111600
ggccacttac ttcgtggcct gggaacattt ttctttggct gacttgctga cactccatca   111660
gatgcatttt tatctggttg tccatctgtg aaccataccc tgagaaggca gagagtgcct   111720
ctgcactgaa catgtgctag gggacaggtc tgtgctagag gggcaagcac tgggaatgaa   111780
gaactggtcc ctactcccaa ggagttcata tctcagtgga ggtgacaagc aactcactgt   111840
ttccgggggt tgtggtgact gctgggagaa ggggtgtcta tattagatcg aagcagcatc   111900
aggggaggtt ccctgagaag gtgatgcctc agcggatgtc tcccagctaa gtgggtgga   111960 ggtggagaag ggcagagcag ggagaggatc taggtgggc gtgtaagtct gcatgggtaa   112020
ctcagggaac ccttggtaac tgcatgtaac tgtgtgaagc tttcatgaag gaacatggta   112080
ggagactagg gtatggacta tagaagcccct tttgctaagc tcaagaattt gaggccggga   112140
gcggtggctc acgcctgaaa tcccagcact ttgggaggcc aaggcgggcg gatcacgagg   112200
tcaggagatc gagaccatcc tggctaacat ggtgaaaccc cgtctctact aaaaaaaaag   112260
tacaaaaaat tagcggggcg tggtggcggg cgcccgtagt cccagctact cagggagctg   112320
aggcaggaga atggcatgaa cccgggaggc ggagcttgca gtgggcggag actgtgccac   112380
tgcactccag cctgggcaac agtgcaagac tccatctgaa acaacaaca acaacaaaaa   112440 atttgaagtg tatcttgaag gaaatccctt ggagcctaaa aatgatcatt gataacagaa   112500
aatgatctct gctctcgcct agggtaatat attcagcttc aaagtggaag ggcatgtttt   112560
ccaagggcat gttttctaag tccctgtaat tgtagtgata gcaaatatat gccctgcatc   112620
ttgaaatgta agactaggtt tgaacagtat ataaattatc ttatgatcta atttcccctc   112680
attttgtggt ttctactata agctacccag aagtgtagac aggacgtttg gaatttgatg   112740
ggcatcggaa agattcctac ctaagaacat ttttttttttt tttttttttt ctgagaagga   112800
gccttgctct gtcacccagg ctggagtgca gtggcacgat ctcagcttac tgcaacctcc   112860
acctctcagg ttcaagtgat tctcctgcct cagcctcctg agtagctggg actacaggtg   112920
tgcaccatca tgcctagtta atttttatat ttttaataaa ggcaggattt cactatgtta   112980
gccaggctgt tcttgaactc ctgacccccat gatctgccca ccttggcctc ccaaagtgct   113040
gggattacag gtgtgagcca ctgcgcccgg cctctaagaa aatttttgag agctacttgt   113100
tctgttgcct ggaattccac cgtaagtacg acgttgtgtc tccttctcca gggctactaa   113160
ctaaacaaca gagggtattg tgttatcgac aattatttga ttgataacta tcagcaaaca   113220
tttgccaagg cattccttta aagatagcct agtgactcta ttaactactc cttcttccag   113280
gcttctaagt tctgttggag gtaagtagat cccagagata aagcacctac cataggacct   113340
gaatcttggt agaaataaat tatatcatca tgttatcata ttatcatgtg tttttctatc   113400
tttaaagtct tatgtgaata ttctgcttga aaaatatgtg tcctctgtta gaccagagtt   113460
gaaaatatgt tattcaagaa cttgtaacag gaacccgcac aatttctgct ggagtttaat   113520
ttcagggtta attctgtcag caatctaagg taaacattaa cattttttccc tagattcaag   113580 tccgttgtcc aaaagctgta acagaactta actgaataaa tagttctta agatgggtaag   113640 cttccatatg cttataatga ctcctctaca cgttttcatc tggaaggctg ctcatgcttt   113700
```

```
tggaagcaaa gaagacaatc ttaaataact acatttgctt tttggtggtg ccagattttt   113760
ctgagaaaca ccaatggaat ttataaattc accagtcaat gggcaattga gttgctgttt   113820
tgctattacc actgccgttt gtgagcattg ttgggaaggt gtcttgaagc acacgtgcaa   113880
gtttcccttg gataagtagt aggaatagaa ttgccaaacc atggcttcca gtgcagacac   113940
agtctctccc ttgggcccag ccactaggca ccacacatta agaggatatt gtctgtccat   114000
gtcctagaaa cgttgtagca tcatgctcct attcgattaa aaatctcatt attaaaatga   114060
accatcgggt aaatgttgtc tcgggaaaag aagcactgac cgtccctggg tgggctcgaa   114120
ccaccaacct ttcggttaac agccgaacgc gctaaccgat tgcgccacag agacccagtt   114180
actcaggccg cgctgcggtg tgtacagatt tccgcggcgc cggcagccgc tctagccacc   114240
ctgggcgtcg ccaccccagg cgttgccacc ccaggcacgg gctgagaagt cgcggggcgc   114300
gccgaggagg cagcggaagc ggccgaggtg cccagcggcc gccgcggggg gagaggctgt   114360
gccccggcgc gcgggagggg gcgggcgagg ccgcgtgact ccgggcttct ctggggacga   114420
agcgcgcccc tcgtggcggc agcggccagt ggtccgcagt cggcccggac tcggggtagg   114480
aaagatcctc tcagcaatgg ctgcgcgcca tgcgtgctct gcggcgggga ccgtgccggc   114540
cgggcgcgcc accagtaacc agggacccag gggagaacct gccaagggga ataggtcgca   114600
cggagagaat acgacacgct tggagggaag aaccacgtgc tgtacaggtt taaaggatgg   114660
agagtcacgt gcgcttaggt cccaaactta agggacctaa ccctttttct gggttgccgc   114720
tattgccccc tctccttaga cagttttca tctcatcacc tctcacccg taaaatgcaa     114780 cgaacataga taggctgtgt atcaatgtag actgtatgta tatctgtgct tcgtacataa   114840
aaagaatatg attttgcca ccttctaaga accaatttgc accccatttt gaggcatatg    114900
gcctctgttg agattgcata gtttagggga catcaaaaaa gccttataga gggactggca   114960
attaagatag ccttttcagtt tgaaatggcc attgaaggct tctccctttc cctgacttct   115020
gaattttttt tttttttttt tttttttttt tttgagatgg agtcttgccc tgttgctgga   115080
gtgcaatggc gcgatctcgg ctcactgcaa cctccgcctc ccgggttcaa gcgattcctg   115140
cctcagcctc ccgagtagct gggaatacag gcgcctgcca ccacgcccag ctaacttttg   115200
tatttttagt agaggcgggg tttcgccatg ctggccaggc tggtctggta ctcctgacct   115260
cgtgatccgc ccgcctccgc ctcccaaagt gctgggatga cattacaggc gtgagccacc   115320
gtgcccggcc aatttttta ggcgcactgt tcagtggcac taagtacatt cacattgtta    115380
tgcaactatc accgccatcc atttccagaa ccttttcatc ttccgaaaca gaagctccct   115440
acccattaca cggtaactca cgattcccct cctctagtcg gaacaatcac cattctactt   115500
tctgtccctt tgaatttgac tactcttaga gacctcatgt aaatggagtc atacggtgtt   115560
tgcctgtggc tggcttattt cacttaccat atgtcttcaa ggtccatcca cgttgtagcc   115620
tgtgtcagga tttccttcct ggataaggct gaataagctg cactgtatgc aggtatcgca   115680
ttttgctttt ccattcatct ctccgtgaac attaggggttg cttccacctg cagctatgaa   115740
catgggtcta caaataactg attccctgct ttcaattctt ttgggaatat acccagagat   115800
ggagtagctg gatcacatgg tttgctattg gctgtaccat tttacattcg caccaacagt   115860
gtacaagagt ccctatttct cctcatctat ttttttttta aataatgggc atcctaatgg   115920
gtatgaagta tcatctcatt gtggttttgc tctgcatttc tctaacgatt agtggtgttg   115980
ggcatctttt ccagacacca ccaatctgaa ttctatggcc cttcgtttac tcacttcctc   116040
ccagcaagag ccatttctgc ttcagcaagg aggaagctgc gactgataga gggaaagggc   116100
```

```
ccaggggget tgcagagtgg ggcctgtgcc atgcaaggag aggagaagaa ggtggatctt   116160
tgagtaggac tatctggaga tcctgctttc acaaggtcct tgcttgtgtg ctggcagct    116220
tttggagcta gttatcttta ttttagccct tgagggatat ttaggcatgt ggtgcttgtg   116280
agcagccaat ccatgaagaa ggaactgatg gtctccacct tggaaatatt ggaagagata   116340
atgccgtcca aattgcagtt ttagaagtta acttaaaatt atgctatttt aatgaatttt   116400
tgggtgcatt tccatttcct tcttaagaat tgctggaatt tcttaagtgt ttaggtgatg   116460
atctctttt gtgattcctt ttttaaaaaa caacaacaaa atcttttcaaa tacataagaa   116520
ataggccggg cacggtggcg taatcccacc actttgggag gccgaggagg gcggatcatg   116580
aggtcaggag atcaagacca tcccggctaa cacggtgaaa ccccgtctct actaaaaaat   116640
acaaaaaatt agccgggcgt ggtggcgggc gcctgtagtc ccagctactc gggaggctga   116700
ggcaggagaa tggcatgaac ccgggaggcg aagcttgcag tgagcctaga tcgcaccact   116760
gtactttagc ctgggcgatg gagcaagact gtctcaaaaa aaaaaaaaag aaaaaaaaag   116820
aaagaaatag acctttattt ttctgtaact ccacaaaatt tctattttga ttccctatta   116880
ttttgctatt gtcaacacag tctcagtcaa ttcaagatcc tgtttgtgcc tttccctgga   116940
gtcatttcca agtgctaagg cttttggtcca tgagtcgcat gtgcacactc atggctgtag   117000
agggagtttt gctcccggtg aaggtcttgg tggctcttct ataccttgat tgagggaaag   117060
gaatcttatg tgaagttagc tttgttgtat cagatattcc ataaagccat ttctgggaca   117120
gtcccctctg tttatcggac cacaagcttc tctgtcctca tcaagcccac ctttatactt   117180
catttctcca gacttcatgt ccagactgtg ggatgaacaa gtggttataa ggttttagag   117240
gctcctgtag gactagatgg aaggcaaaaa aaggaaataa cctttaagca tgctctcgat   117300
tccttaaatc ccatctgaaa gtcttaagga tgtcttctca gtcatactta tttgacaata   117360
ttacctaatt ttctccatta gcccaagctc aggggtcttt cttcttccat attcacatgg   117420
gtgcaatggt tttctgaaag gaaaacagca ttactagggc agtaacattt aattaatcac   117480
aggtacttat caaactacaa aacaggcatt ccaggaactg ggtgtttctg tttgtaaaat   117540
tacactctcg tgtacatgct cccactaaaa tgtaagttcg ctgaggatgg aggttttggt   117600
ctctttgctc tgtgctgtaa ccccaacact gcagcagggc ctggcacata gcaggcatgc   117660
agggactatg cactgaatca atgaggaaat gaaaaccagg accatgaagt aaactggaca   117720
aaataaaatg tgatagaaaa tctaaattcc taatacataa ggagcactta tcaattgata   117780
tttacaaaat cttttttacaa ttcaattaaa gacaacataa aacaaataag aatggggaca   117840
ggaacagaaa attcccccaa agaaaaaaat atatatacat ggtacagcca ttgtggaaag   117900
cagtatggag ttctcaaaaa tattaaaata gaactatcat ataatccagc aatcccatcc   117960
ctgggtatat atctaaagga aatgaaatca gtaccccaaa gaggtgtctg cactcccatg   118020
tttattgcag cattagttac aacagccaag atatggaatc aacccatcag cagatgaaag   118080
gataaaggac atgtgataca tatacacaat ggagtagtat tcagccttaa aaagaagaa    118140
aatcctgtca tttgcaacaa catggatgag cctagagaac atactaaatg aaataagcca   118200
ggcatagaaa gacaaatgct gcatagtctc acttaggtgt ggaatctaaa aaagtcaaat   118260
taaaaaaaaa tgtcaagcag agaatagaat ggtagttgcc agggactctg ggaagtagca   118320
ggggtggggg tggaggggag gggatgggca gaagttggtc aaaaggtaca agtttcagg    118380
tagacaggtg taagttctgg ggatctattg tacagcgtgg tgactgtagt taatactgta   118440
```

```
ttgtgtactt aaaaattgct caccaaaaat gttctcacca aaaaaatgat gtttggatat 118500
gttaaacagt ttgatttaat cattttgacg tgtgtgtgtg tgtgtgtgtg tgtgtgtgtg 118560
tgtatacatc aaaacatcac attatatacc atatacaatt aatatataca atttttgtca 118620
aagaaaaaat gcacatgacc aatatgataa aagtttagtc tcactagtaa taaaaatcaa 118680
aattaaatga aataaaaatt tctttcccca aatcgcaaaa gagaaagaaa ggtaatacta 118740
aaacacagtc acggtgtagt gagagggctg ctctcacaca ggactgatga gaataaaatt 118800
ggagagcagt gtggtaatat acatattaaa caatgtatat accctctcat tttagaaatt 118860
ctatattaga aatccatcct aagaaaataa ccagggatgt gatcaaaatt ttgaatgcag 118920
cagcacagta ttatttataa tagttataaa taagaaacaa cctgaatgtc cagcaacagg 118980
caaaaatgat aaataaattg tggcatattt aagctggtgg ctcatgcctg taatcccagc 119040
actttgggag gctgaggcag gaggatctct tgaggccagg agtttgaaac ctgtctgggc 119100
aacataacga gacccagtct ctacaacata tttttttaaaa ttaggtgggg catggtaact 119160
catgcctgta atcccagcac tttgggaggc tgaggtgagc agatcacctg aggtgaggag 119220
tttgaaacta gcctggccaa catggtgtaa caccatctct acaaaaaata caaaaattag 119280
ccagggtggg gtgcgttcct gtagtcccag ctactcggca gactgaggta ggagaatcac 119340
ttgaacccgg gattcggagg ttgcattgag ctgatatcat gccactgcac tccagcctgg 119400
gtgagaccct gtctcaaaaa aaaaaaaaaa agaaaaagaa aaaattagct gggcgtggtg 119460
ctgtacgcct gtagtcccag ctattccgga agctgaagcg gggggattgc ttgagcccag 119520
gaatttaagg ctgcagtgag ctatgattgt gccactccgc tccagcctga gtgagaaagc 119580
aagactctgt ctcttaaaaa aaaaaaagtg atatattttt aaaatagagt atattactta 119640
tatagacatc aaaaacaata ttttcaaggg atatttaaaa acataggatc atgacaaaat 119700
gtaaagttca aagtaagat ggagaatgga gaactgtggg gaactgtata atctgacaat 119760
tcgtagttgc atacatcttt ctgtgtgctg gtgctgttag aacactttgt acgcatcacc 119820
tcatttaagt tcagcatccc taggtggcag atactattat tatattccag ttttgtttca 119880
cgttgtatat gcggtgtgag ccccaatatg ggatgtgtgt gtgcacatgt gcagtatttg 119940
gaaagttcta tgaaatatta ttagtggtta tctctgggag gtgattttta ttccttttcc 120000
agtatgttct caagcatttg ctgcaagcag tcttttgcgg ggccagggtt gagaggcagc 120060
agcagtttcc ctaaattaca gatagaggga ggtaggtggt tatgcttggc cagatctctg 120120
tctagggta gaggagtgcc tgtgtgtggg tagggacacc ggcgggggggc tttgccaaac 120180
acagtggaac tgtcacgctg gtctctcttc tcaactcttt cactcacctg agaaaggggt 120240
gtctatggac catgcacact tctgtgggga atttacaag atgtgaatca tcagtgatga 120300
agatgctttc atttaaaaag aattggagta cctgagatta gagataactt ctaccctttt 120360
aaaatatttt taaaaatttc tttgcactga ttttttttct tcgttttat gagttgtttt 120420
catttgggtg ggataactca atctacagga gaatattaag acttttttaaa ttttaaaaaa 120480
tatactttca aatacttaat acattttgtg ttaaatgaca gccagcagat attgactgaa 120540
ttgggctaga tgcttcaggg atctcccttc catttaagac tctccgagag gccattcctg 120600
actgcaggtc actgtattat ttttaatttt aaaattttta cttacttatt ttatttaatt 120660
ttattttttg agacagagtc tcactctgtc gcccaggttg gagtgcagtg gcacaatctc 120720
agctcactgc aacctccacc tcccgggctc aagcgattct cctgcctcag cctcctgact 120780
agctgggggtt acaggtgcag gccaccacac cccgttaatt tttgtatatt tagtggagtc 120840
```

```
agggattcgc catgttggcc aggctagtct caaactcctg acctcaagcg atccttccac    120900
ctcagcctcc caaaatgctg ggattacagg cctgagccac cccactcggc ctactttatt    120960
aatccacttg cagaaacagg atatacacaa aaacgtttca aggctgtaag tgccactgca    121020
tggcaccaat ggtaaacgtt ttacaaattt gagtcaggaa caatcattag tgtcactagc    121080
aacaaaaatc aaaattaaat gaaataaaaa atttctttcc ccaaatggca aaggagaaag    121140
aaaggtaata ctaacacgca gtcagggtgt agtgagaggg ccgctctcac acaggactgg    121200
taagtacaga gccatggagt aagcaggtct tgagctgaca ctggagagga tccttttttt    121260
tttttatttt tatttttta gagtcagggt cttgcttttt tacccaggct ggagtacagt    121320
ggtgccatca tagctcactg cagcttcaaa ctcctgggct caagagatcc tcctgcctca    121380
gcatccccag tagcagggac cacaagtgag aggatccttt agtgttgtca aggagaagga    121440
acagaggtgt ggatgggtgg gcacagacac aggagcacag ctgaagcaga ggattacaaa    121500
gggtggagcc tgatgtaaag aaacctaata ggtgacagag catggaggct cttgaatacc    121560
aggctggaaa ctgcattagg aacggtgctc ataattgcag aaaattttac atggcctaga    121620
tagtcatcaa aggatgatgt acaaacaact atggcatatt tatacaatgt gccgacagga    121680
tgcactgaac attttgaaca acaaagagac ttgataatgg cgaggttttg aggaggtgaa    121740
tcaggatgca aaaaagcaa acaactaata aagttgattg atgacaaaca ctatcaaaag    121800
gcagccagga gaaaagctac tggttacctc cagggagctg gtgagggagg ctgggtggga    121860
ggatctaccc ttctgaattc tgagggcacc tccagtgtgg ccctcagaaa gcaggagctt    121920
ccaggctaga atcagatccc gacatccctg ttaattccac ggattccaca ccgagtcaga    121980
tttatgattt actatagggt tttaaaaacc aaattgcagg gatgctagcc tatcacagct    122040
tatctcagac attgtccact aaggtataca gagtgctgcc tgttcctttg gtaccctaat    122100
caggaaaccc catcagatct gctccttcct atggggtagt gagtaacacg aaggcttacc    122160
atctcacaca gataactggt cataggtcca gcagaagttt aaaacagaaa atgaggaaag    122220
ccatgtgatt aactgctgcc agactgtttg tgttacaaac agcagttcct taggcattgc    122280
ctgggacatg caataatttc tgttacacaa tctgtggtag ttaaaatgct gcacgatgaa    122340
agctatctga tttggattca ttattaggtg agccatctcg tctgcaattt ggttccacca    122400
ttttcattta acaaatgtaa aaaagtttat taagctctta caagttatg ctgggcaaat     122460 atgcaaaagt ccagatcacc taccgcagga actaatctag cctcctctct gggcaccctg    122520
ttgtttgggg ctgggcagtt cttcctgtg tagaaccatc tagggctgaa taggtcattc      122580
tgacacctgg gcacctctgc ctgctcgtaa atgggacaat cagaaagggc ccttatgttt    122640
ccaaactttc tttaaagtag ctgttctgaa aacatggtcc agggaccct gattgtccct      122700 gagacctttg aggggatctt caaggttaaa attaatgtca taataatact aatatgttat    122760
ctgtcttttt tcactctcac tttctcacac gtgaacagtg gcattttcca ggtgacagag    122820
tgtgtgataa tgaacctaac tgaatgcaga agcaaacatg agaacctagt tttttcaatc    122880
aaaccagacg tgaaagagat ttgcaaaaat gaaaaaacaa tgctatcctc ctcacaatat    122940
ttttgtttta gaaaataaag ttattttttcc tagaaatgtt tttgagttta tcagtcatag   123000
gtttattatt ataattaaaa aatgaaatat acatacacag acatatttttt taaagttctc   123060 agttttaatc tcttttttttt tttttttttt tttgagacgg agtctcgctc tgtcgcccag    123120
gttggagtgc agtggtgcga tctcagctca ctgcaagctc cgcctcctg gttcgcgcca    123180
```

```
ttctcctgcc tcagcctccc gagtagctgg gactacaggc acccgccacc gcgcccggct    123240
aattttttgt attttttagta gagacggtgt ttcaccatgt tagccaggat ggtctcgatc   123300
tcctgacctc gtgatctgcc cacctcggcc tcccaaagtg ctgggattac aggcgtgaac    123360
caccacgccc ggtctcagtt ttaatttcta atacagtaag tattgatcag tgtgcccac    123420 attagtaaaa gctcttgggg tcctcagtac ttcttttttaa gagttgtcaa ggagtcctgt  123480
gaccaaaaat aggagagcca ctgccctaga aggacagccc cagcccgggt caggaacaac   123540
tgggacagaa cctactgctc ctagtggatt gtaatatgat aggatttaac cttcaaggtt   123600
tcaactcttg gcaagagtcc atgaggggcc atggtttgtc ctgagcattg cttactgtta   123660
acaggagcaa gttccttagg ctggtgagcc aagccagcct gacgctggcc atggacatct   123720
tagtgggctg cttgttctag tgtgggtttt cattttatgg gaaatgtcat ctgctctaag   123780
gctcttctca tttggggaaa tcacaagttc tcagaatgtt tgtctctctt ggttggggcc   123840
tctataatta aattataaaa cagaggtaat ggttaagtaa tgcaagattt gacagaaacc   123900
acagaggatt tagggtttaa tttgagtgag gcaaggggg gatgaagatg agcggtcctg    123960
gagacaagaa aaagattgga tgaagctggg cacggtggct cacgcctgta atcccagtac   124020
tttgggaggc caaggtgggc agatcacttg aggccaggag tttgagacca gcctggctaa   124080
cataatgcaa ccccgtctct actaaaaata caaaaattag ccaggcgtgt tggtgtgtgc   124140
ctgtagtcac agctacttgg gaggctgagg catgagaatc gcttgaatcc gggaggcaga   124200
ggttgcagtg agcagagatc atgccactgc actccagcct aggcaacagg gtgagactct   124260
gtcttctttt tttttgagac ggagtctgtc gcccaggctg gagtgcagtg gcatgatctc   124320
tgctcactgc aagctccgcc tcccagcttc aagcgagtct cctgcctcag cctcccgagt   124380
agctgggatt acaggcatgt gccaccacac ccagctaatt tttatatttt tagtagagac   124440
ggggtttcac catgttggtc aggctggtct caaactcctg acctcgtgat ctgcccgccg   124500
cggcctccca aagtgctggg attacaggtg tgagccacca tacctggctg agactctgtc   124560
tttaaaaaaa aaagagagag agggagagaa agattggatg aaacaacaga gtggggagga   124620
cctgtgagct tggtagcttg gtgaaggcag ggctttattg ggggccttag aggggatcca   124680
ataaaggttc ccagtcatgg tagtgaccta aagaaaatag cattttaaca tctttcattt   124740
cataatagac agtcacagtt tacaagaccc tttccataca ttccttatga catccatact   124800
acagcccaga ggcaagttgt gcactctctc ctctcacaaa tacaaaaact cagcctctag   124860
aggccagcga cctgctcagg gtgatgtgca attcagggat gacagagtcg aggctcccag   124920
cccagtggtt atccctcaca ggcacgttgc ctgtcagtgt gcagtataaa actttgtaca   124980
agaaatcaag ttgcattagt cagtcggatt ccccaaatga tcacattgta gatggtgtat   125040
gctgtgggca gagcaagggc tgctgttttct tgggcaaaac aatcagtccc cctcccccc    125100 aaaataaatg aatgccaatg gtgtgacttt atttattta ttttattttt attattattt    125160
gtgagacaga gtctcactct ttcacccagg ctggagtgca atggcatggt ctcggctcac   125220
tgcaacctct gcctcctggg ttcaagcgat tctcccgcct cacctcccg agtagctggg    125280 actacaagtg catgccactg cacccggcta attttttgtat ttttttaag tagagacagg   125340 gtttcactat gttggtcagg ctggtcttga actcctgacc tcatgatcca cctgcctcag   125400
cctcccaaag tgctgggatt acaggcatga gccaccgcgc ccagcaatgt gactttataa   125460
ttacagaatg taggactcag ctcccactat tgttatgact caatattctc ttagataatg   125520
tttggggcac tagcttacag gcagcattgc ccggtggtta atgttgtagc tttgcaggca   125580
```

```
gactgaccat attaaaattc gatcacacca tttgctaagc ctgtggactc gggcacgctt   125640
ctttctctgc gttagtttcc tcctctgtaa aacacggatg atgctataaa cacacccaag   125700
tcctagaatt gttatatgag ttagaaaaga taggcaaata caactctcac aagacagcct   125760
ggcctccagt aagtgccact gagtgtttgc tcttattgta cagtggctcc aagtgcttct   125820
gtcttggatt atttctgacc aggtggctat gtctcctagt aacttaccaa tcctgttgag   125880
tcttaataag cacgtctttg atgcctacag tgcgactgaa tttccaggcc tcattactgg   125940
agacacaatc atcctatatg cttttttcca tttgttttta ataaagtggt acatgtgtat   126000
ggcaccagat caaacagtac agaacaagtt acaatggaag agaatggcct cccagctttc   126060
ctgaaatcct caactcagag acaacttttt tttttctgac ggtttcttta tacagcccct   126120
tttgtggtta ccttcctaac tctagaaaaa ctattcttac ctctgtttat ttacttagaa   126180
acattagacg ttacctttca actcctcagt atgaagcttt agttttcagc accccaggcc   126240
accaccctct ttccaggact tactacttat actggtggta ggtggaattt taaaattcat   126300
cagcattctt ttgtgattct ctgtgtgttc cagttttaca gcaacccgta cttgttgcat   126360
gagtacagta gaactgggag gctcataact tagcctgcag gacttttcac ttaaagcctg   126420
gccctcaggg tgatgtcacc cacctcattg tgcctggctc aggagtttag tccctcagtt   126480
gcctggttgt atagtttgga tgttcagcac ctccaaatct cacattgaaa tgtgatctcc   126540
aatgttggat gtggggcctg gtgggaggtg tctgggtcat caggtgggtc cctcttgaat   126600
ggcttggtgc cttccccatc gtaacgagtg agttcttgct ctggcagttc acacaagagc   126660
tggcttttta aaggagcctg gcaccttccg ctctttctct tgctcttcct cttcccttcc   126720
tttgtcacta aaagcttcct gagccctcac cagaagcggt gcagatgctg gtgccatgct   126780
tggacctcct gtagaactgt gagccaaata aactctttcc tataaattac ccagtttcag   126840
gtattccttt atacaatgca aaacagactc acacatctgg taaaccccag ttgtttgctt   126900
ctaggtaaga cgggaggagt ggggagctgg tgagggtttc cactgcattg tctattttca   126960
ggcaaggtgt ctccactgag taggcttcac attcagagct ctgggtaagg tgggcaggaa   127020
gagggttgca ggctgcccaa aggagggaga gaagaaggct gaatccttca gtgacaacct   127080
gtgaaccaga gtcttagctc tctttgaata ttttgttcag tatctttggg ttttgtttta   127140
ttttgcctag gggtaaatgc tgactgcctg ttctctggac aggaatggag aagatggtgc   127200
tagcagggtt gctgttcata tgtagacatt catgcagtca ctctctttc agcacacttc   127260
ttacttctgc cctgggttca gttgctgact ctgagcccag aaaccttcta gggttctgtt   127320
aggtagattg gcttccaccg tctttgcgac aaccacagaa aattctagac tgttttctct   127380
tcgggcttca ttagtcaact tgcttcagtc tgtcttgcat cttctaaata tttatagatc   127440
tctctctttt gttggagtgg cagaaaatgc tagttgacca cccaatattc aaattatcct   127500
gcctccttaa taacagaata tcattggatg tggtgggtaa ataatatacc ctaactttcc   127560
ttgcagagag gggtggccaa tgagatgaaa atgaaagtca ttgggaaaga ctcccaagac   127620
atctctttaa acaagacaga ctgaagcaag ttgactaatg aagcccaaag ctagcagttg   127680
ttttttgttta tctttgcctc tttcttcttc ttcctgtggg acaaagggc agtgatatct   127740
ggagctgcag cagccatttt ggcataatgt tggaaaagcc aagagactct cagagaccgc   127800
agctccagca gttttttatt ttttccaaat atttgctcca ctgcaggagg atgagatatt   127860
cgtgtttgtt gccttgtgac tgtaggagga ctgcacttcc ctgccttgtt gtcaagtttc   127920
```

```
cccatgtggt ctgctttggc cagtaaaaca tgagtgggag aagcttggtg aaccattgca    127980
tgtctaccag cttttttgct ctcttccctt tggcattaga aaggcatgtc caggatggag    128040
ttgttccttc agcctagatt gggttatgag aagctagctg ggggagtcca gtaacatata    128100
aagcgagtta gaaataaaac tttgttgttg taagctatat atatatatat atatatatat    128160
atatatatat atatatatat aatatgtatg taatatataa atacatatta tactttaagt    128220
tctagggtac atttgcacaa tgtgcaggtt tattacatag gtatacatgt gccatgttgg    128280
tttgctgcac ccatcaactg ctcatttaca ttaggtattt ctcctaatgc tatccctccc    128340 cagccccccca cccctcaaca agccctagtg tgtgatgttc cccttcctgt gtccaagtgt    128400
tctcattgtt caattcccac ctatgagtga aacatgtgg tgtttggttt tctgtccttg    128460
tgatagtttc ctgagaataa tggtttccag cttcattcgt gtccctgcaa aggacatgaa    128520
ctcatccttt tttatggctg catggtattc catggtgtat atgtgccaca ttttcttaat    128580
ctagtctatc attgatggac atttggggttg gttccaagta tttgctattg tgaatagtgc    128640
cgcaataaac atatgtgtgc atgtgtcttt atagtagcat gatttataat tctttggata    128700
tatacccagt aatgggatca ctgggttaag tggtatttca agttctagat ccttgaggag    128760
tcgccacact gtcttccaca gtggttgaac taatttacac tcccaccatc agtgtaaaag    128820
cattccattt cctatgtctc cacatcctct ccagaatctg ttgtttcctg acttttaat    128880 gattgccatt ctaattggcc tgagatggta cctcattatg gttttgattt gcatttctct    128940
gatgaccagt gatgatgagc atttttcat gtgtctgttg gctgcataaa tgtcttcttt    129000
tgagtagtgt ctgttcatat tgtttgccca ttttttgatg gggttgtttg ttttttttct    129060
tgtaaatttg tttcagttct ttgtagattc tggatattag ccctttgtca gatgggtagg    129120
ttgcaaaaat tatctcccat tctgtaggtt gcctgttcac tctgatgata gtttcttttg    129180
ctgtgcagaa gctctttagt ttaattagat cccatttatc tattttggct tttgttgcca    129240
ttgcttttgg tgttttagac atgaagtcct tgcccatacc tatgtcctga atggtatcgc    129300
ctaggttttc ttctagggtt tttatggttt ttaggtctaa catttaagtc tttaatccat    129360
cttgaattaa tttttgtata aggtgtaagg atggtttcca gttcagctt tctacatatg    129420 gctggccagt tttcccagca ccatttatta aataggggaat cgtttcccca tttcttgagc    129480
tacagatatt ttgagtttgg ttaccacagt attatctagt ggaagttgac ttatacagta    129540
tgtaatagga taaatatagg tgtgtaacag aatattaagt gttcgtgttt caaagctgag    129600
gggaaaatgt taaaagtgtt cacacactct aaaaagagat tagctaaaac tgcttcatta    129660
accacacttt ggggaaacca gttctgagat tcttctccat tactctgaca ggttggaccc    129720
tctggggagc agatctcaag atcaagttat gagtgcaaga ggtgtgttgg gaagcgatgg    129780
ttgtaaaaga atcctgcagt agcaccaggc acaagtctgt ccagggagag gaggacttct    129840
actctctacc agcatctctc ctaagtcccc ttaggggacg gggcaagga agtgctggga    129900 agggcagggc atggttcctg gctaggactc caccccctg gggcctgtac ccacggacct    129960
aggtgaagac aggcactcct gccttctcgc ccaacggttg cgtttcccaa gatcatcctg    130020
gcctgccacg ccccatcta cctattaaac tcccccacct tccccaaacc ctagcaggca    130080
gacacacatc ggtggaagaa gacaggagcg gctggacatt gaaaggacgt cgagaggagc    130140
acacctgcac accatcgacc agcggaacga ggcagagtgt ggctggagca gtcggaggga    130200
agcctgggcc gctgactcca ggggaaaacc atctcctttc tggctccccc ctctgctggg    130260
agatactttc actgaataaa accttgcact cattctccaa gcccacctgt gatccgattc    130320
```

```
ttcctgtaca ccaaggcaag aacctgggat acagaaagcc ctctgtcctt gtgataaggt   130380
agagggtcta actgagctgg ttaacacaag ctgcctatag acagcgaaac tgaaagagca   130440
cacaatagca cacactcatt ggggcttcag gagctgtaaa tatccacccc tagacgctgc   130500
catgggcgg  gagccccaca gcctgcccgt ctagaggttt gagcagcggg acactgaaga   130560
agagagccac accctcatcg cacgtcctgc gaggagacaa agggaacttt tccggtttca   130620
cttctgcttg gcttgagctg gcactgaagc acccttttcc ctcctcactg agggagcaga   130680
ggggaaaagc ggtagaacta acaggctaac aatgctcctc cgaaaatata tcgtattttt   130740
ggatccctag agataggtga tcacggcagc cgcggagtgc atttgggtct cctttcaaga   130800
aagaacttgc tgctcagcgt tgaagaatgc agttggccaa cagcctccag ctgctctgtc   130860
ttcagcatct gccatggcat ctgagctgag gtcatgttct tcctgggagg tccccagcag   130920
aaggatcacg tggaagctcc acaagctcca cagatgttcc aggagaggaa taggcagcat   130980
ttggaagaca tatcctgcca taacagaggg catttgctag tagagacaac aaacagcaac   131040
agccaagtaa acaaacacac aagcacaaag cactttctcc catttcccct cattgatcct   131100
gtccgggtag aagctgggga ggaagtagaa tagggtgagg cggggtgggg ctgggggcc    131160
tacaccttct tccttccccc gcaggtcctg tccctgggcc aggcttgaac taggggaatg   131220
ggaaaagctg tgaagtgaat gagaattagg agttttatt tagactggac ttgaattttt    131280
tttttttttt tttttttttt gagacagagc ctcgctctgt cacccaggct ggagtcccgt   131340
ggcgccatct ggctcactac cagcctctgc ctcccgggtt caagcgatcc tcccaccaca   131400
gtctcctgag tagccgggat tacaggtgcc tgccaccatg cccagctatt tttttttttt   131460
tttgtatttt tagtagagac agggcgtcac cgtgttggcc aggctggtct cgaactcctg   131520
gcctcaagtg atctgtccgc ctcggcctcc ccaagtgcta ggattatagg agtgagccac   131580
cacgcctggc ctggacttga attttaatt cctaaaaatg aactaccagt taaaatttaa    131640
aaatgaccaa aaaagctatg ggatatgctg atgttttgct ttggggataa ggaaaagata   131700
tctggttgag cggcattgaa aacagtgtag ggagagaaaa actcattcct ggctcaccct   131760
tttgagtccc actatctcaa taatctgatg ttatatgaca cacacacaca cacacggagg   131820
aatcctggaa gactccatat caaggtggtg atgaaggtga ccagtgggtg ataggattat   131880
aggtgtgtgt ttatttattt attttaatta cctttttta gagacagggt ctctgtcatc    131940
caggctgcag tgcagtggtg tgatcatggc tcactgcagt cttgcactcc agggctcaat   132000
cctcctgcct cagtctcctg agtagctgga gctgcagtca tgcaccaacg tgcccaacta   132060
atttactta ttttatttt tatttttgt taagatggaa tctcacttta ttgcctaggc      132120
tggtcttaaa ctcctggttt caagcattcc tcctacctca gcctctcaaa gtgctggaat   132180
tactgcactt ggcccctatta tattttaaaa aaatttcaat agtttaggg gtaaaagtgg   132240
ctttggttac atagatgaat tgtatagtga tgaagtctgg attttagtg tacccatcac    132300
ccaaatagtg tacattgtac ccaatgagta gttttttcatt cctcaccccc acactgtccc  132360
cacttctgag tctcctgatg tccattatag caccctgctt ttgcgcactt agagcttacc   132420
tcccacttag aagtgagaac atgtggtagt tggttttccc ttcctgagtt acttcactta   132480
ggtcagtggc ctccaatttc atctgagttg ctgcacataa catgatttca ttcttttttt   132540
gactgagtag tagtccatct ctctctctca cacacacaca tacacacaca cacacacaca   132600
cacacacaca cacatttatc cactcatcca ttgatgggca cttaggttgc ttctatatct   132660
```

```
ttgcaattgt gaattgtgct ccaataaaca tacatgtgca agtgctgttt tttctcccctt   132720
ttatccttct tttcttccct atgcttccat aggtactgag aaagagtctt tttttatataa   132780
ttatttcttt tcctttggga agatacccag tagtgggatg gcttgatcca atggtagatc   132840
tgttttagt tctttgagaa atctccatat tatctccata ttgttttcca tagagattgt   132900
actaatttac attcccacca acaatgtatg tgttccattt tcactgcatc ggcaccaaca   132960
acggttgttt tttgactttt taataatggc cattctggct ggggtaaggt ggtatctcac   133020
tgtggtttta acttgtattt ccctgataat tagtgatgtt gagcatttaa gaaatatatt   133080
tgttggccat ttgtatatct tcttttaaga aatatctctt gaagttgttt gcccactttt   133140
taatgtgatt atttgttttt tttcttgct gatttgtttg agttccttgt agcttctgaa    133200
tattagtcct ttgtcagagg tatagtttgc aaatactttc tcccattctg taggttgtct   133260
ctttactctg ttggttattt cttttgctat gcagaagctt tttagaataa ttaggtccca   133320
tttacttatt tctgttattt tgttgcattt gttttttgggg tgttagtcac aaattctttg   133380
cctagaccaa tgtccagaag agtttttcct aggttttctt ctagaatttt tatggtttca   133440
ggtcttagat ttatgtcttt aatccatctt gaattaattt ttgtatatgg tgagagatag   133500
gaacccggtt tcattctttt acactacatg tggctatcca atttttccag cactgtttat   133560
tgaataggat ttccttttccc cagtgtatgt ttttgtttgt ttggctgaag atcagttggt   133620
tgtaggtatt tggttttatt tctgggttct ctatgctatt ctacttttat accggttcca   133680
tgctgttttg attacaatag cctcgtagta taatttgaag ttgggtaatg tgatgcctcc   133740
agatttgctc tttttttgct taggattgct ttggctattt ggacccctct ttggtctcat   133800
ataaatttta ggattggttt ttctaattct gtgaaaaatg acattggtat tttgataagg   133860
gttgcactga atctgtggat tgctttgggt agtatagtca tttttacaat attgattctt   133920
ctaatccata agcatggtat gtttctccat ttgcttgtgt catctattat ttctttcatt   133980
agtgttttgt aattctcctt gtaggggtct ttcacctcct tggttaagta tattcctatg   134040
tattttattt ttattttttg cagctattgt aaatgggatt gagttcttga tttgattttg   134100
agcttggcca tcattggtgt atagcagtgc tagtgatttg tgtacattga ttttgtaacc   134160
taacactact aaattcactt atcaaatctg ggagattttt gaggattcct taggattttc   134220
taggtatgag atcatatcat tggtagaggt agtttgagtt tctcttttcc agtttggatg   134280
cccttttattt ctttctcttg cctgattgct ctgactaggg cttctagtac tatgttgaat   134340
agaaatggtg aaaagtgggc atccttgtct cattctaatt tttaggggga aatgctttca   134400
acttttcccc attcattttg atgttggctg tgagtttgtc atagatgatt cttactattt   134460
tgagatatat tcatttgatg cctagtttgt tgagggattt tatcataaaa ggaggctgga   134520
ttttattgaa tgcttttttct gcatctatta aaatgattac gttttcatt tttaattctg   134580
tttatgtcat gaatcacatt tattgactta tgtttatttg ttgcttacat ctactttcta   134640
attttactat aataaacatg tataatttttg ttatcagaaa agtaaatgta aaagtgagtt   134700
ttaattttaa aacttgggcc taagtcttcc tgcctcccaa gcccattccc ttcctgatat   134760
ctggggcttc cctcctcaag cctgctctgc aggataaggg gatacagtcc acatgcctgc   134820
tgctggtttg gcccatgata acctccatgg gcaatgtctg agcctctgct gttgagtttt   134880
gctttacaca ctcctggcaa ggaaaggatg gccaacatgg cttggacatg ggttgctgat   134940
aattggtgat gtctcatgac tggttctgcc tggagggctt gctgtaagtc cctgatagga   135000
ggaacatgga cctgcacaag agcagaactt atctgacact gaagaggaca cttcaagaac   135060
```

```
agattatcaa agtctagctc agggagaaat atactttaga gcagaatgag gaatggcgag    135120
gcagctgagc ttagacacaa gcagaaggaa atccatggtg agggcacagg caaggaaagg    135180
ggctgagaga gcattagtgg gggcagtcag gggcagtggt caggatgctc ggatgccagc    135240
gtgaacaatc gcatcaagat taaacaccat gaggatcgtt agacttcctg tcatatgtct    135300
ccaggtggtg ctccaaatat cctaaaccag atgacagcac ccctccaccc tctgctgtat    135360
aagcacatct gctctcctat aatcattccc acatagcaat ttatcatttt tattgatttt    135420
tcttcattta atacacgtat aagtgtgtct tttatttta aaaatttgca ttcctttaat    135480
tgctttggag attgtgcatt tttctctctg ttgatttact ctgccaataa acatgtaatc    135540
ctaccataag catgttttac ttgtgtaatc aaccaaaata aaaaatttaa aaaggaatca    135600
ctgactatga attagacatg tggataggca ccagggttgc agacatggcc cacgttcttg    135660
cattaacttg cactgtggct ggggcattgg atgggtacat taaaaggatt aaagtaatat    135720
aaggcagtat ttattaagtg ttgagtgagc actacagaac ccaagtgctg agggagtttc    135780
atgcaggaag agatcaagag taacacagag aagaagaata gatcaattta gcgcattcat    135840
ttaaaaattc accttttgca taggggatg tgtcttttgt ggggaggagg ggagttccga    135900
ttggcagttt gttctcaggg agcttgaaga agagatcttg gagaggagac gcagagaaaa    135960
caaatgaaga aaatgtcaaa atggaagggg ttggcccggc tatgcatacc ttagttagct    136020
taggtagagt ctaaactttt acaagtggtt tcaataggtg tgtttggtct gggttctttg    136080
ggaggtatca taggagaatg aaggcaggga ggacgcttcc agcaccaaaa ttcaaaggga    136140
aatgtattt acatgcatag cattgttta ctctctttcc atttggagca tatcttaaaa    136200
attccatttg gagcatatct taaaaaaccc atttctctga caatggttct aaaaggggga    136260
aacatccttt gcaacagaat cattcattct ctcattcatc aaccactgat tgtgtactaa    136320
gtgtcagacc tgatctccat cctgcctggt atggcactag cttctgtctt gagacaagca    136380
ttgtgataaa ccatgaccaa aaaagggca gtttataaa cacaagtctg ccaggctttc    136440
agcaattcta aatttccttt tgcaagtcag gctggagtta atggctcttt cctgcagcgg    136500
cggagatgac agggctctcc cacagtgctg agcaggcagt ttgaaagccc cacttcctgt    136560
ctctgcatgg gcgagtgtcc actggaagcc actgagagga aggagggaaa cctcagaaac    136620
cggcccctgc ctggctgctt caccctagaa agcccaggca gaggagggaa aggtgaagtg    136680
ctgaaaaaga ataaaaaagg gggaacatga aaaagagcaa gagcaggaag gaggcaggga    136740
cgggaaagga ggggaagcac ggaaacagcc aatgtcaagg agaagaaaag atggctggtg    136800
gaaaggagct tccaggaatt gggacacagc cctgtcttat tgcaaaagat ggaaaccctg    136860
aaggagaaca ggaaggaaaa agaaaacaag tccgtctgag ctggcagggt ccactttctc    136920
attctacaga tgaggaaaca gaggcacaga gaggaagtgg cttgcccaag ggggcagatt    136980
cttgaaagga tcatctgcac tctctctccc ttaatgcatt cttacctctt ctttactcgt    137040
gagtcagtcc tgaaggacaa gctgcctgaa gtcccacaca gatgggcctg ggcaagcat    137100
caaacatcct gggggccctg ggtgaggttt gcttttaaat tccaggtcag ggaaaggaag    137160
gtctttaagt tgtctgctct aagcttagta atccccctca gagttatggg tgcggtgtct    137220
ggggtagccg ttgcgtctct gggcaaatac cctggagaat gcagtgttgg ttgtctgagc    137280
tggggacaga gtgacagcat agttgcatgc agagctggag gctcctgcag ctgtacaggt    137340
aaggtgctga aattctccac caacccttcc tctttgcccc cagcaccacg aagataaccc    137400
```

```
tctttgaata tgtggaagtc tgttctccaa actttctaac attctcatgt cagtcttaat    137460
agattcagct cagttactgc ctcctccagg aagtcctcct tgtctgcaaa tcggctgccc    137520
accatgccgg ctcactcata gttttaactc tgtatctttc taatatgcct tagcccactc    137580
tgtcaggatt ccagtcagct tccttctcct agactaggag ttgcctcagg ccaggaggac    137640
cagccttgtt catatctgta ccctgcaaac ctgtcaatgc ccaaacctgc tcagtgcttt    137700
ggagtatgga accagccgtc aatgcaggaa tgttacactc taagagttcc caaaggtaga    137760
gagatgaggg attggtgctg gaagtgggag gttattctaa ggatgggtat ggcaggaaac    137820
acaattatag ttcagggagt ggagtgtcca ggagtgggag gagaggaact gggagaaaga    137880
gcagagagtg aaagtgagag cgggcacaaa gaaagggaaa aagagtcagg gatcaaccaa    137940
agtgcatgct tccttttcag ccctgccagg atgtgcaggg cggctgctgt ggacgcgtca    138000
aggctcagcc tcaaacatgt cttcttcctt gacttttgtc tatcattcta aagctaggtc    138060
atttaaaaag ttcttttgtt ttctttccac cgatactctg atttctgaca ttcgccaaaa    138120
agaggtcaag accctggcat accgccctac taagattaaa ataaatatta tccattgaaa    138180
ctgttatttt ttccttaact gttatttgta gagttaaaga ttcccatgat cgcgctggct    138240
ctaacatcat ttttggctct tttgagatca aatttgcaat ttgatgcaaa aatagctgtg    138300
acgcatatgt gtctgtatgt gtgtggttag gagatttttt atcattacat cttcttttgc    138360
cctgcctttc tgcctttctg tccttttaat ttgcgggctt ttggcaacca cagcacgggt    138420
ctggtttcct aggagtttct tttgtaggat caaaccgcta gttggctctt ggccctgtga    138480
tagggccctg ggctaactta ttgggaaaat gttgctgtaa ccctgccca  gaggtgcctg    138540 tgacatgggc cgccatcttc tcctcttccc ttggcttcag ccccacctag aaacctgaac    138600
aaacattttc cttgacattt cataaagtgt cagtggctcc tcatttagca aaatacatcc    138660
cagggaagtt caaaagtgaa aaaaggccgt aacttcttct tcttctcagg gacctacaga    138720
aaatatgtgg cacctcggca gcctggcctg cagcactccc ctccccatcg gtgagtcctg    138780
ctacagtggg tccaggtgtc tggacgcccg gcacgcacgg ctctctgcag acctctggac    138840
agtaccatgg gagccgcaca gtccctgcct gttctgtccg gcagttcttg tttcccagca    138900
ccctgtctca ggtgagaggt tccctcttct gctgggcttc tcctccctgc tgtgaacccc    138960
aaatatctga ggcaggtcaa tttaggaacc ttattttgcc aaagttgagg atgtacccat    139020
gacacggcct caggaggtcc tgaagacaag tgcccgaggt gatcgcggca cagcttggtt    139080
ttatacattt atacagacat cagtcaatat atgtaagata aacattggtt cggtcccgaa    139140
aggccggaca actccaagtg gagaggggc  ttccagttca caggtagata agagacaaaa    139200
tgttgcattc ttttgagttt ctgattagct tttccaaagg aggcaatcag atatgcattt    139260
atctcagtga gcagagggt  gacttggaat ggaatggaag gcagttctca gtttaaattt    139320 tcccttttagc ttagtgattt tggggtccca agatttattt tccattcact ctgcagacag    139380
gggcttctgt gcatccaggg agccctcct  cacagaagga agcaggccat taatgagacc    139440
caatccagct tcaaccacct ggtaacaatt aggacatcac ttctctgagc aagagctcct    139500
gcctgtccat gagttatcaa gacattccaa ttgttcctcc acatctttga catgaagact    139560
tgagggggtc agattttcca gggggcttga tggcatgttc tcttcactgt tccctgccct    139620
ggtcatccaa gtgaccctt  gcagggaaga ggccccgagt tgcagaatct ctgttctcac    139680
aagccattgc caacccggag agtggctttg ccactattcc tagcatgttg ttggctattt    139740
caggaatggg agtatttgac ttttcccttt gcagtgattg ctgcaaggag aggaattgag    139800
```

```
agactcaagt ccctgagata aatatttatc aactattact gaaagggagt atgtcaaaga 139860
aaaaatgtgg agaaacttca gcttgaacac atagtttaaa tccagcttgg gtgtactcca 139920
gtgggcatgg atgtattact gttttgcagt gcattcttct atgatcaata cacagaagca 139980
aacaggccac gtgggtaaac agtaattttc atttaccagg gtgaatatgg aagtcctctt 140040
gtttccatgt catgatgaag gaaagcaagg accatctttt gccaaggaac agtggctgtg 140100
ggggaactga ggagatggaa ggacaaggca gtcaaaagct ttggaacaac tctttttttg 140160
agatggagtt ttgctcttgt tgtccaggct ggagtgcaat ggcacgacct cggctcacca 140220
caaccgctgc ctcccaggtt caagtgattc tcctgcctca gcctcccgag tagctgggat 140280
tgcaggtatg ctccaccatg cctggctaat tttgtatttt taatagagac gggatttctc 140340
cacgttggtc agctggtctt gaactcccga cctcaggtga tccacctgcc tcggcctccc 140400
aaagtgctgg gattacaggc atgagccacc atacccggcc cttttttgga ataattttat 140460
aggttttcaa actattacac ttaccttttt atataagaga caggacatag tcactgaaca 140520
atcactccag attttaagta agtccaggat gggatgacaa tggaacaacc atgaaatgaa 140580
aggaagaatg tgtcactggt atgtccacac gtctccaaat ctctcacctc tgtcagctgc 140640
aaacagagcc tgaaataaat gtttcctctg tgcacagcct ccacaacttc ctccctccac 140700
gtttctcact cactcctctc cagcacttct ctccgggttc tgcttacaaa cttgaaaccg 140760
gctatgcaaa aattataact gtggaaatta tgacagtgaa agagatcaga cctaaccgac 140820
tccatcttgc ttctaacctt taagctgtcc ttgttcattt ttgggctgaa ctaactttgg 140880
gaaggaattc agttcatggt agaactctga aacaaaattg ataatagccc tttcctgaaa 140940
agacccccctt cttgcctggg gacaagtctg ccattgtagg actaacaaat taactacaag 141000
attagaaatt aaggtttagg gttcatgcag cctccagttc caagagtcta aacctcccca 141060
aattgctcct ggggataaca tcactgttgt aaaagctaag accagtgctt gagatatttt 141120
gtagaccctg ctctggatgg atcagctgac accatccaga ctggtaattt ggctcaacca 141180
gctctgccat cccacccagg aacagaaaaa tactcacttc atcacccat gagtccatct 141240
ctaacctgac caatcagcac tccctacttc ccaggcccct actcgccaaa tctgcctttg 141300
gaggcagata acaacttatc tttaaaaact ctgatccctg aatgctcagg agactgattt 141360
gagtaataat aaaaactccgg ctctgcatga attactcctt ttccattgca attctcttgt 141420
cttgataaat tggttctgtc taggcagcca gcaaggcgaa ccctttgggc ggttacaaac 141480
tcatcctctg tggaagagta ggagttcatg gagaaattgg ttgcaaatta caaaattttta 141540
ttgtaaggtc aacttgtccc agtgtccgtc tgtgcagcga agggcccctg catggtttag 141600
tgattgcaag ttgagcctct agggtcaggt tgtctaggtt tccatcccag ctcattcact 141660
tattatctgt gtgttcttga gcaagctcct taatcaattg aggctttgtc cttctgtttt 141720
tataatgatg agaataataa cctccacaat aacctcatca taaggttgtt gtgaagatgg 141780
atcagataat atatatgtag agtgcttata acagtgcctg gcacataaaa aatgctcaaa 141840
aatcttaagt gttattaata ataaactgac atatatttct tgagcagggt ggtggtaaat 141900
gggtgttctt tttattaagc tttaaagtgt gcatagatca tattaattct ttttatgcat 141960
atgatatatt gcacatgcat gaaaatacat gcattaaaaa taaatgagca tttatgagat 142020
ttagtttagc agtcacatgt cccaggatta caagccagca ataatgggtt ggaaaacatt 142080
ccaacccatt ccaaccattg gaaaacattc caacccatca ctggaccat gtgccaaaca 142140
```

```
atggaaccgc ccacaggttc tcattcttgg ttaaaaaaat atgattatta cgggaataat   142200
actgattccc taagaattaa tatctgagca agtttctttt ttttcctgtc ttcttggaag   142260
atcagcaggt tctagattca atggagtcac taggattgag ccaccagtat acgccagtcc   142320
tctccagaac ggccacctgg tggtgggcac taaggcagtc tcagatgagg actgattgac   142380
ttttgtgtga actcaaactg ccaaagtccc tccctcacct tgcaaacttc aaagcacaac   142440
tttcaaagca ctactttctt tcttggctct caattctctg cctagaaaaa gggaggtgtt   142500
ggcaaggatg tttgtttagt tctgggcatc agtcaatggt acccagatct tgctgaacag   142560
aaaagacaca gatttgtttc tctgaggcag ttggtagtgc ttattgctta ttgctctcag   142620
gggcttctgc agcagtagaa gggccctctt ccctgccat gccacactga gaggagcatc    142680 cttgagtca tggttggaat ctgttttgt tatgctagtc ctcttccgca tgctagctgt      142740
tgcattgcag ggatatgtgt acctgtttat cttctccact aggctctaag aagccaggtt   142800
tcttaaagga aggaagctga tcttgtttat cttgaagtcc tcacagtgac attgctcagt   142860
caatgttgag tgtatgaatg aataaacggg aaccatcacg aaaaagccga aaatacagtg   142920
gaaagactgg atcataaaat cttctaagca aatttttttt cctcttacac tccatttcca   142980
aatagataaa gtattttta aaatcctatc agaatattct aacacactga gttgacagaa    143040
tagagatttt taaatgcagt gtcatttggc cagccatttg tgagaattta taatgtttc    143100 agtaggttga aaacactata aaagcaagga ctatgttcat acccaacagc tggcacttag   143160
tatgaatgct aaatgaaaca ttctcttctc tttcaagagt cagtccaacc agtgaccctg   143220
acaagaagga aggcacattt aactcaattt aatgaactct tatagagcat ctccttctcc   143280
aagtgctttg ctaaggatgg ggtaaaaaca tgaataagtc ttggattctg tccttcagga   143340
attttcagtc tttggaggca gatacatttg cacccaacta ttatcctagg cagagtgtga   143400
taagtacgat aatagcagta aaagctctaa gttaggcagg agaggaggag ctcgttaaag   143460
cttatggggc ctgggaggct ttcggcggag taaactccag ggggacagct aggcatctgg   143520
ctgctggaat tgggaggagg atcatttta gtggctacaa ctctgggtgc acaggactag    143580
agggtgaggg ccaagatggg aaattgtggc agccatcttc cacactgggc gcccgccgac   143640
ccttgcttcc tggtattcat attattgtgt agtgtccccc aacattgtat cagggttggc   143700
ctgtgtgacc aattgcatat ggtgggaatg atggtgtgtg acttctaaga ccagttcata   143760
gaagatgtgg ccaattccct tactgtcttt tttttggca ggggagtgcc gagtttcacc    143820
cttgtcgccc aggctggagt gcaatggtgc gatctctgct cactgcaacc tctgcctccc   143880
aggttcaagt gattcctg cctcagcctc ccaactagct gtgattacag gtatgcgcca    143940
ccatgcctgg ctaattttgt atttttagta gagacgggt gagatcaatg aggcagtcaa    144000
ttggccagcc tggttttgaa ctcctgacct caggtgatcc acccgcctcg gcctcccaaa   144060
gtgctgggat tacaggcatg cgccaaccgc gcctggccct tactgtcctt tggatcagct   144120
gctctggggc taggtcaatc cttcatgtga ctgcagcccc agccaacatc tggactgaaa   144180
cccatgagac accctgagcc aaaaaagccc agctaagact tcctgcattt ctgacccaca   144240
gaaactgaga aaagaaatgt tttgttgttg ctttaagcca ctgacttctg gggtcatttg   144300
ttttgcagaa atagatagca gatacagaaa agcaggctgg tggaacagtg tgggaaacac   144360
cttgattttc agggagttgc actttgttta tgtgcaatgg tgcactgttt ttagaaagac   144420
acaaagatga taatactggt gatgggcata atacggttg tcaagaggag tgactgaggc    144480
ggggataatt taagaggcca cagcagtagt gtggcaagag gtaatgaggg aattgaactt   144540
```

```
ggtgggaatg ggtgagatca acgaggcagt caatatgggc agtgagtgtg aaggagctgc   144600
gaaggatgat tctttggttt tgagcttagg aacatgagag aaccaagatc tcatttatcc   144660
aaagaggaaa cacagaagtg agccctgtt tggggcagg gctgggtagg aggaaaagag   144720
tggagacgtc tatctcccca ggaagagagc ccctgcttc cagatcccag tggatggcag   144780
ggcactcggc tcattcacag actgggctcg ttgagaaacc tttccctgga gggcagggct   144840
gctctgtttc acagcccata tccctcatgg ccaagtgttc ctcgagtgac agtctctgcc   144900
atcaatattt ttagcatgtg gtctttcaga gactaaagag tggcatccat ctcctgaaac   144960
tccttcccca gctgacagct ggtgacccgt ggaggaggga gcttcaggga gcctgatggg   145020
cgagagtctg ttccaatgcc aatccattgg aagagatgaa gtcagacccg agtttgatag   145080
aaagcctact tcctcccttg tatccagctg tggagaccta ccaacatcaa tgcaaaccag   145140
aagctaacac ccagttcata tatcccaagt ggaaggaagc ttctcgtgga attgtcttac   145200
atgacagtaa cataaatcct gaaggtaata cttggccagg taatgttaga aaagaacccg   145260
aacataggca ttgctattat agatcctagg ataggcctga gcaaaaactg tctgggattc   145320
ataacatgct tcgttgcaat ctgatagagg gagtgagatc cactccaaat ggagtctgat   145380
ttggggcaaa gcaaagagta tggaaggaaa cttgagaaag ggggacagct tctcaaatgg   145440
agtctggcca cagctggggc tggaaaagag acatgactgc gcttgcagag tggtgagaat   145500
ttgctgctag aattttttaag ttgtgtgttt tcattttttat gataatgtaa actgagataa   145560
gcatattctc tgctatccca atgagcccct cctctaggag gactaccttg ccaccttatc   145620
cataaatgtg tttataaatt attttgatgc cagctggtat tttttaaaaa gtggttttgg   145680
actcacaaaa aaaaccatga tggatttaat acataacaaa gcatttgtgt caagtgaagg   145740
ccaagtaaca tcttagcgtc ctgtgtgagc gaaggtgtcg tggcagttca aacaagaatg   145800
ccgatgaagc tgcccaggat ggccaaggcc accttggtgt gtttgagggg aattagagtt   145860
tagaaaaaaa aaaaaaggca cctgacactc tgaactaatg tggttacctg gaattttggg   145920
gttttgaagc tttgcattta atttgcagct tatggcctga aggaaaagac aggtgaaatg   145980
catatcctgg gatgagtcac ctggaggaga gggctgggaa ggggctgagc tgcacatgct   146040
cagatcttct cccaggctta tcgacccagt gagtcaagtc ttcttccaac gggatagagt   146100
gtgagagaga gcagggaaca gaagccagag tctctgttaa atttctcggt acatttctgt   146160
tagagaatgg aagtttctct atcgtaggag accttgagag cctgggatag aaattacccc   146220
tttgtcatgt attttcctcc cagaaatagc atggccactg tcactgctaa gctggagtat   146280
catgagcaca atttctctca ctttctatac ccatgccttt ctaggagatt ggtggctcca   146340 tcaaaagga gttaaaaaga agcagcacta ttttgtggaa tacaatcatc accattatca   146400
ccatcagcac caccaaccag caccaccatt atcaaaagca ttcacctggt gtctgcctta   146460
caaactgcaa actgcagtag gtatttgtaa tagaatgttt cctttccccc ttgggatctg   146520
cagaaaagct ggagaatgtt ttggtatcaa cacactaggt tgcattgcta atcatgtgat   146580
ggccccatga cagtctctgt tggctggtgt agttcaggtg gacgactgca ggattttgtt   146640
cttggagcct cagttctgac tgggcttggg gtgtaaaagg tttgggagcc agatgacaag   146700
agtatttgat gggtagaata atgggttcat ccaaaagatc accagaatgg ttattaaata   146760
gtacaaagga ggaatttact ggtaatacca gtttgcaaac agagaagaga gtctccaatg   146820
tggactgaaa gtgctctctc tttgaagagg ggaaggacag attgggtttt atgcctcaca   146880
```

```
ggactggtac catacatatt cagcaggttt ttggggaaaa tctatacata tttataaggt    146940
gagctgatgc ctgcataata gataaacata tatgtaacat acttttcata ttcattttgg    147000
gactgggttt tggcactaaa atttgtggaa tttggctctt tatgttaaaa ggtgaactag    147060
aggacacaaa gacggtttgt gtgcaccctc tataaactgg ctgaaactgg cttaaggtct    147120
gcaactgctt atccaaaaag aatgtttgta aggccaggcc tctgtccagt cagagttgta    147180
gtggtccagg ttgtaaatca aagttttatag ctcttttgt tagagagttc agctgtagga    147240
atttagaaat ttgccatgcc tgccaggccc tgaacctttg acccataggt aactttattt    147300
ccttaacctt agggtcagtc ttagttgata tggggcatct attctggtat ctcagatcct    147360
atggtcaaga gaaaagatcc tccacaagag ggtcctatgt ggctgcaaaa actgctctga    147420
gctaaatcca ctcaaaatca ctgcaggatg tcactactag aaaatagggc agggataggg    147480 atcccctttcc catgctgcca gaaaatgcct gatagcttac ctcccccggc ccttgaggct    147540
cccttggaat aggcacatgc aatcccatct ccacccaata gagcttgtcc tagagctcag    147600
ttttttccca tagttttccc acccacttgc accagaaaat ctaataaagt catgtgatta    147660
atacaattca ttttatcacg cttctgaaga tttaagagag agcggtcaca ttggattcca    147720
cagtaccgac cttctgacga ttcttcattt caccttttatc tattttttatt tttattttat    147780 tttttttcg agacggggtc tcactctgtc acccaggctg gagtgcagtg gggcaattac    147840
ggctcactgc aacctctgcc ttctgtgctc aagcaatcct cccacctcag cctcccaagt    147900
agctgggatc ataggtgcac atcaccaagc ctggctaatt ttttgtattt ttggtagaga    147960
tggggtttca ccatgttgcc caggctggtc ttgaacttct gagctcaagt gatctgccca    148020
ccatagcctc ccaaagtgct gggattactc acgtgagcca cctcgcctgg tcccttcac    148080 ctttattatc tttgcctttta actctagtgc ttcctccctg aatcagttaa ggattgcatt    148140
tggctgcatt aacagaaacc tgactgcaga agcttaacca aatagggtag ttttttaaaga    148200 gagattgctt acatcacgca aattgcacaa attttaagtg catagttcaa tgagttttga    148260
caaatgtaga ataacatagc tatataaaac cattccatca aaaaatttt atcaccatag    148320 gaaattgtgt cctgtccctt tcttgtcaat cccaactcct ccccacaagg caaccttcat    148380
tctcatttct ctcaccatag cttagttttta catgtttcta taatacagca tcatataaat    148440
ggaataatac agaatgcaat cttttgtatg aagcttcctt tggctcaatg taatgtttat    148500
gagattcatc catgttattg aatgtatcag tagtgttttc atttatattt cctagtgttc    148560
tattgaataa atatactaca atttgtttat ccacttattt gttgatgaac atttggaccg    148620
ttggcaattt ttgcctatta tgcataaagc tgttaaaaaa cattcttgta caagtctttc    148680
atttcatatg ttttttcttt tctgaggtaa ataactacaa gtagaattgt tgggtaataa    148740
ataggcatcc atctaatatt ataagcaact gcacaacagt ttttcaacgt ggctgtacta    148800
tttcactctc ccaatagcaa cgtatgtgtt ttccagctac tccacatgct cactggcatt    148860
tcctgttgcc agtttaaaca tttcagccat tccagtggat atgaaatctc tctggctata    148920
ataattgtat ttctctgatg actaattatg tcaagcccct tttcaaatgc ttatcagcca    148980
cttctatact gtcctctgtg acatgtccgt tcaatctttt tgctcattct ttaaaaacat    149040
tgggttgttt gtcttttttct tagtttgtct tttgcttttc atttatagga gtacatatct    149100
tcggaataca agtcctttgt cagataaatg tattgtgaat aattttctcc tagtttgtgg    149160
tttgcctttt cacattctta atatcttttg atgagtggaa actaactttc aaattatgtt    149220
cagtagatta acttgttttt gttttgtttt gttttgtttt ttgttttaa cactgggtct    149280
```

```
cacttgttgc caggctgga gtgtagtggt gccatcatgg ctcactgcaa cctctgcctc 149340
ctggactcaa gggatcctcc tgcctcagcc tcccaagtag ctgggaccac aagcacgcac 149400
cactacactt ggctactttt ttatatttt ggtagacaca ggatttcgcc atgttgctca 149460
ggctggtctg gagctcctga gctcaagcga ttcacccacc tcagcctacc aaagtgctgg 149520
gattacaggc gtgagccacc acgcccagtc gagtagatca agttttaatt ttatggccag 149580
tagagatcta tttcaaggct ctctattttg ttctgttgct ctatttatct acctttatgc 149640
caattttctt ctcttttgat tcagatatagg ttataataat aattatttt tccagggatt 149700
agatggacca gggctggtga agttgttcaa gggagtgatc aagagcctgg ctcctttcat 149760
ccttctgttc catctccttt ggctcatgga ttttgttttc caagtggcaa gatggcgcct 149820
ccacctttgg tatcctattt tagttcctgg cagaaagaaa ggaacaggct aatggccctg 149880
atgagtctac cccctttaa caggagaaaa tttaaaaaac aaaaaccatg aaacccttc 149940
ccagaggcaa caaccagaat tccatttatc tttcattgac cagaacagac cacatggtca 150000
ctggtggtgg caatggagac tgggagatg aatatttta aggtggcata ttccagaaga 150060
acactgtgca ctgattgcat taatgaaccc attaatgtgc caaggggagg tttacctatg 150120
agcatgggca aattagaacc cactcttgga gctgcaggtg agccaatccc acctaaacag 150180
tgtggatgct acaagatggg gaagtaaatt gattctattc catacccta cctctctcca 150240
agatgtattc ttaaaataga agagggaaga cagaagaaaa catccagaat atattttat 150300
tgtcttttac ttcttcagtg cattttagat cagtgcttct caatctggca aggggcatgc 150360
aggaggatgt gagttttatc aggaaaacta cacaaccccc caaccacaat gctaccccca 150420
ctcctgtgga ccttctttaa gagagactca ctattataga tggagttgat acgatttaa 150480
gagaggccat atattatttg ctttctgtct tgaaaaactt gtgattttc tgtattgtgc 150540
tactgccaaa gagaatagaa acctgactga ggtgtcaatg tttatgtaac tgatttcatg 150600
tactttctgt agttctacca tttctgatgg ttaaaaattt cttgtgtgtg tgcagttggg 150660
gagtgtgtcc tcctccttct gctcttatac cacacattag cacatcaaaa tgctctaatc 150720
tttgtatgat tatgtggcat gtggtgatgc agcctcacag tggaaaaact tctcttgggc 150780
cattgcaaat gtaacatttc tttcaatcag atagtgccat taaggatttc attatggccg 150840
tcacatcctg tgacatctct aaacatgcag cattagggcc taagtgcagc cctgcaggta 150900
gagttgccag gttaacaaa taaaattac acgctggcca ggcggggtgg ctcatgcctg 150960
taatcccagc actttgggag gctgaggcag gtggatcatt gaggtcagg agttcgaaac 151020
cagcctggcc aacatggtga accccatct ctactaaaaa tacaaaaatt agctgggcat 151080
ggtggcaaat gcctgtaatc ctagctactt gcgaggctga ggcaggagaa tcacttgagc 151140
cctggaggcg ggggttgcag tgagcagaga tcacaccatt gcactccagc ctgggtggca 151200
gagcgagatt ctgtctaaaa aacaacaccg tatttggggc atgctgatac taaaaaatta 151260
ttcattgttt gtctgaaatt aaaatttaaa ttggggggccc tgtatttac tgggcaaccc 151320
atttgcaata tcagcaacaa tctcttattc agaccactga ttaagtgtgc aaaatttgaa 151380
tctctgaaca gtacctatgt ccttgatatc ttaaattaat gagtgtctta gacactcaaa 151440
gcaggaggaa gcattatggc agatgtttga gccccagaga tgtccatgag cacagcatag 151500
agctcagagc cttctttatt atttgcttca cgacagagca aaggactgca gcaggttgac 151560
tgatataaaa gttttaccat gtctcacagc aggcctttgc tcaagtttcc agtaaggata 151620
```

```
ttgtatcatt tcttgcctgc agtacttgta aatccactta cactgcctgc tgttgagtca 151680
tttgtttcgt cttgagtagc atgtcatcct tgttcctaga agatagtgag tttagagaca 151740
gtagccaagc aacagcagag cagcctcaac caaaacgatt ttccattttg gtgggatgaa 151800
ttgaaacaca agcatcttct atccagggga gatttgggga tcataaagaa tcaatctgag 151860
ctggtaccac catattggct gctgcatttt ctagagttgc cgtaactagt ctcacaagct 151920
gggaggcttt acacaacaga catgtattgt ctcatagttc tggatgctag aaatctggaa 151980
tcaaggctcc aggggagaag ctgctccatg gttttctctt agcttctggt gttgccagca 152040
atccctggtg ttccttggcc cgcaggcgga tcactcccat ctctgcctcc attgtcacac 152100
ggcattttcc cagtgtgcct gactctgtgt ttcttctcat aagaacatcg gtcatattgg 152160
attacaggcc cgtgctactc cattatgacc tcatcttaac ttaaacaatt acatctgcag 152220
tgatcctgtt tgcaaataag gtcacattct gaggttccag gaattagaac atagacatat 152280
cttttgggaa caaattcca gtgataacag tttcggagac agactagtcc tggagttgt 152340
aaggtgagcc aggaccaagg tgccaggatt ctcattttgt aaggtccagg aacaaagtga 152400
tgttaataga aagaacatgt ttttgtttgt ttatttgttt ttgagacagt ctcactccat 152460
cacccaggct ggaatgcagt ggtacaatct cggctcactg ccgctgccat ctcccaggtt 152520
caagcgattc tcctgcctca gcctcctaag tagctggaat tacaggtgtg tcccaccatg 152580
cccagctaat ttttgtatat ttgtgtgtgt gtgtgtgtgt atatatatac acacacacat 152640
acatacatat atatacatac atatatatat acacacacac acatatatat atatataaaa 152700
tatatatttc ttttagtaga gactgggttt caccatgttg cccaggctgg tctcgaactc 152760
ctgcgctcaa gtgatccacc tgtcttggac tccctaagtg gtgggactac aggcacaaac 152820
caccacgccc agacagaagg aatatgtttc cttccagtct cacttgactg gctgcttccc 152880
tagataacaa cagaggatgt ctgttgcagt tctcattgct ggggagtcta aactggaata 152940
aaacacccac tatctccatc aggcttgcac tagagcccag ctctagctgg agagaaagaa 153000
gctaacccgc acagacacag gactgtaggc agggagcatc cggggtatt tgggtcctgg 153060
ctctgatgtg cctaaggcca acttctctct ggccatgctg gcgtgcatga gctcactaat 153120
cttccttttt gccttccatt ttctccaatc ctgacttagc aaaggttggg caaaagagac 153180
tctgtgtgag ttcgagcaaa gcctgagatg ctggattttc caagatacga gaaggggctg 153240
gggggctgggt gaactggtgg tggaggaggg aaggattaat ttcccaagga ggggaagggg 153300
ccaggacatc aggccccggg gactttgaag agagggtcgt gggtaggagg tagatcaagt 153360
ggagtgacac aaaggtcagg aaagaggaag tgtccacact gtccttcgac agacttgagt 153420
ctatgggact tcctccctgc acggtacaag gaaatgagta agtgagataa tgttgtaact 153480
tctggccctc tgacattgca ctgccccgat gtcacagttg gaaactgtac ctgcccccat 153540
ccttgtctgg ggtgtgtttg gtctggggag ggctggtgaa gcaagaggta ctcagaaaaa 153600
ggacagaaat tgcttcctat tatctgggca tttggaggtg aagggggtcac agctctggca 153660
aagatggggt tgaaagggcc cggactccag ggaggggcag ctctgcatgg cctgattcct 153720
gcaccccacc tttgcccccct cacacctcct ctcatctccc gttttttgaag aggaggaccc 153780
tgtcacatct ggacaattct gcaagaactc tgtagaactg acttcactgt gaaccaggct 153840
ccagaagtca acagaaacaa aaatgctcac atttaatcac gatgctccct ggcatacaca 153900
gaagactctg aaaacttctg aatttgggaa atcctttggc accttgggc acattgggaa 153960
cataagccat cagtgctggt gtgtgtgtgt gtgcgcgcac acgcgcatgt gtgtgcatct 154020
```

```
tctaccatgc ctcctacaaa tttgacctgg gcccagggcc atgttcggtg gttttttaaga    154080
accgaggctc ccagaagcag tattgggcag ctagagtggc cccaggatct atatcaaact    154140
ctacctgttt ctgaaccaaa tttcttctag aattttattc cataaatctg aattatggtg    154200
tcagactcct agcatacact aaaggaactc tctgccttgc attaaataac aggagttacc    154260
cctggaggta actcctagcc ctggctcttt agagaacaga tgccgaatag cattagggga    154320
atgtgatgga tgtgctaact ttcaaaaaaa aaaaaaaaa aaggcctgag ctgagtgctc    154380
agagattcac aaaaagctga cagcatctct ctgttccatt ggaagctggg tgatcctttc    154440
tactctttcc tgagaaaggc agttgggcag gaaaaagctg tatctctgtc ctcactgaga    154500
gggtttccca gtctgagggt gaaggatcag gagagggaga cctgacgggt cgatgtgggg    154560
catcatccac ttgagtgaga accagaggga tcccgtcatt gcccagggca gatgctccat    154620
tttgggggc atcattcatt ctttcctgtt ctccctgcat tcctctggct cctgcccagg    154680
agaggtggcc gctggcaaga gagcttggtg gaggtgggag gtgggaggtg ggggtgggg    154740
ggtggggagt tcttgagcca ggacctagcg catagtctcc agcctgctga tggctgtctt    154800
ggatgcttca aaggggagaa gatcctagat gtgggaaaca ttggtgggcg ttctgctggg    154860
gcatctgtag cctctgagaa ggctaccagt ctctcctaag cttacgccgt cacaccctgg    154920
gcacttgttg aatgacttta cttagcttac agcctctggt tcctgttggg aaacttaggg    154980
cttgccacag tgttcatttt cctttgcggg caactccgtt cctggcactt atcatattac    155040
ccactgtact cccgcttag agctgtgtca aggttctgag aatctatccc ttggcttgga    155100
aggggtcatc tctctggcca gatcatttcc tgataggtcc tgaggcacca caacacatag    155160
gaggcttgtc ctctctctgg ggttcactgc cttgctcctt ctccaggtca atatgtgacc    155220
ttggaccggt tgcttgagtc ccctggtcat tcagaaacaa ttgggtttcc ctggctttgg    155280
agcctggcag cctggctttg agaaccgggc tttaacttgt cacatgacta tggccaagtt    155340
cctggggctc tccaagcttc acttcctctg taaaagggc aataatataa tacctgtctt    155400
attgggtttt gtccatgtta gatgagacat tgggtacaaa gcacttggtc ccgtgcctgg    155460
cacatttact gcacttaatg tatgatagtt ttcttattat tctaataaac aatatggctt    155520
tgggagtata gttctgccac attgcagtgg ccagagtgaa ggtggtgagt gcttctggg    155580
gccctgggag tcaaggttat ccgcatgccc tttcttgctt gctcctcagt gtggctgcct    155640
ctatgtccac accatgcaga tgcaacaggt agtttgaacc tctgaggccc acagtgggat    155700
ggggaggcag ggacatcact tatggggtgg gaagtcaccc attccccagg aaatggcccc    155760
agctgccttt tccatgactc ctcttgaaac cctgtggagg ccacattcgt gttggggcgg    155820
tctttcccat gaggatatgt tcagatgccg aggcattttg aaaagccctc catagagttt    155880
cctttcataa cacatgatca tccccttggg cttctggttt tttttctttc aggacccttat    155940
tttcaggcaa gtggcctttg acctctaagg ctgtcctttc ctagctaccg aatccagcat    156000
tcaaagtgat ggaaatatgt atatatagta atagtaaaat atcagcactt aatggcctga    156060
taagaatgtc actgcaatgc tgagtttgga ccaacatttg cctgctcctg ccattgagcc    156120
cgggctcccc tccagagctg agctgctgca agggatctga gtaactaggg ctgtgtcaga    156180
gtggcgatga cagccaccac atgctaagga agagatcccc aaggacaagg agaatcccac    156240
gtggagctac ttgcttcttt gtcagtcttg ttttcttat ttcacaacct tctaaaacac    156300
aatctctcaa cctctattgt tagcttgcat ttttcaatca tgagcacagc tttacctggc    156360
```

```
tccatgcttt gattgactct acctgccaac actgcaacaa cagggaaagg gacaccggcc   156420
tcataccatt agatggtgtg tagcctgggc atgaggataa ttaaaaactc caagggggat   156480
tttaacatgt aacacagttt ggaaaccatt gatgtaagat cttcttactc aacatgtgct   156540
ccaaggagct gttgtatcag cttatcagaa atgtagatca ggccgcactt ggacctgtag   156600
aatcagaatc tgcattttat cagattccga cattatttgt atgaacatta gcttttgaga   156660
agtgttgctt aagagactaa aggggtcaa tctacctcac tttgcagctc tgtgttcctt   156720
agtcattggc taaaatatca gcccccctgc aatgagccat cctcccttgt atagtcagtg   156780
atggcctgtg aacctttagc caactggaag tgggagggga cacagtccac aaaacactat   156840
cctgactttt gacaccaact acaagtcaag gggttcccca aaccaccctg agttgtgata   156900
attcgctggg agatctgaca gaactcactg aaggttgtta tactcatggt tgtgatctct   156960
tatagggagg gaatacagat taaaatcagc caaaggaaga agcacacagc acagagtcca   157020
ggacagtgcc tgcatggag cccctacggt cctctcccgt ggagtcacgg acagcgccac   157080
tctcctggca ttgatgtgtg acaacacaca gggagtgttc cccaccaggg aagccttggt   157140
gtccagggtc tttactgtgg ctctgtcaca tgagcacagc tgactgccca tgcggccgat   157200
ctgttcccag actctccacc gctacacatc actcacagtc cctgctctaa atcacacacc   157260
atgacccaat gtccccgggc aaatgaaaac acctctagca ggcaggacgt tccaaagcct   157320
tagagatcac ctctcagaag ctgagggcag aagccagacc tcttttgg cagggttaaa   157380 ttctttatta ctgtttttga aaaaactccc aaattgagtt tttcctcttc acttacagca   157440
gcataacaac aatcatcaat gcagaagact tctgcgagca aaggtgtggg ggaaacccc   157500 aagcagtgga cactagctgg tgtcctccaa tttgattctg atgctgtcta ctgggagata   157560
gtgtcagatc ctcaagccta aaccctcctt ctcccagtca gagggctggc ctttggaact   157620
tctgaccaat ccacttcaag ttgaggttcc aaccactccg ctctttgggt ttggttgatt   157680
tgctagagtg gctcacagaa ctcagggaaa cacagctacc agtttattgc gaaggacatt   157740
ttaaaggata aaagtaggca gataaagaga tgcatagggc gaggtgtgga aaggtcccta   157800
gtgcaggagc ttctgtccat gtggagcggg ggtgcaccac cctctcagta catgaatgag   157860
ttctccttca cctgcctatc agcctctaca tgttcagctc cccaacccag tcctcttggg   157920
tttttatgga agcttcaaga cacccacatt cttttcccag agtataggc aagaccttct   157980 ctggggaggg tttaagacc cacagtcaga aaggtggggt ggggtcaaga ttagagtcct   158040
gccttgacgg gcaggtgaaa ggggtagggg gagtaggtga gaaaaattct gtttatttt   158100 tctttttttt tttgagacgg agtttcactc ttgttgccca gggtggagtg caatggcaca   158160
atctcagctc actgcaacct ccgcctccca ggtttaagcg attctcctgc ctcagcctcc   158220
cgagtagctg ggattacagg cgtgtgccac catgcctggc taattttgta tttttaatag   158280
agacagggtt tctccatgtt ggtcaggctg gtctcaaact cctgacctca ggtgatccac   158340
ttgcctcagc ctcccaaagt gctgggatca caggtgtgag ccactgcatc tggccaaaag   158400
attctgtttt tgaggcctgc ctctgaggtc taacacactc aacattataa caagactgta   158460
gtaagggcta tgggagttat gagccaggaa ctgtggatga aaacctatca cagatatgca   158520
tatatatata tatatatata tatgcatatc tataataact ccacaactac acactgcctt   158580
attgctcagt tcttctctcc atgtctctga cccaccttg cccccttcct ccatcctttt   158640
ctccattgca tacccatcca ctgtgcccttt ggaatgctc acaccatgaa ctgcaaactc   158700
tcgtgtggct tcagcctctt ctctgaaagt tcctctcacc tattactttc tctggaacct   158760
```

```
gccatccctg ccaccttctc aaaaaaggcc ttttattctc ttcattccac aaagctcagt 158820
gtcaaaacat ggggtttaca ctggaagctg aggtcacatc agtagccggg atcagggtcg 158880
ccctagctgc ccaatgcagc tcccaggcct cctgtaaaac cttgaccttt gaggtcatga 158940
cagccctctc ctgctatgct catagctgac cactgaactc ctggacactc cctcccccaa 159000
gttcacagag aatgtgggca catgccttac agtcttccct tgatccaaac tactgccttc 159060
atcttgagtg acagcagcat cttttggatg tcttggcctg tctagcttta ttttttgtg 159120 ttctgccatc aagttgctac ttctgttgcc atcgtgcctg tcagcgcagt gcaggctgtg 159180
gtgaaatccc acgaactcag gcatcacact gaccgggtct gagtcctgtc tcagttgtca 159240
gctagttgtg caatgaaggg aaagggacct acactttcca agcctcaatt cactcatcta 159300
tggcatggtg acaataatgg aggttgattt aaagtccttt gtaagaatta agagttataa 159360
tagacataaa gtgctgtatc tggtatacct agaaaacatt ccataaaagt tagtaattgt 159420
tggtcatgta atgatgactc tctaggctag gatttcagct tcattgcatg cacatggtgc 159480
actcacaggg cgtgacctct ctctgtctca gtaacctcat ctgaggaccg ggataatcat 159540
accgcttcaa agggatgtca taaagattaa ataatatgtg taaggctgct tgcatttagc 159600
tgcattcaac aaatatttct gtatctttct cctcatttct ccttactttc ttgcttatta 159660
tctgctctag gtatagattt cagagaacta agcttgttac aatccttcat aaaataacca 159720
ggttggttag ggcatttcca agagtcaata ctgtttagtg actattctct gtttaatcta 159780
ttttgattgt ccagggtcat cttttgctat gtcataggtt gttggcttct tctagagaag 159840
tgagacgatg gacaagttcc aagtgagtga ggcgactggt caggatattc cgctgaaaaa 159900
ctcatgtcag ttctaattcg tgattgtaat tcaatcacag cctgagaaca gtaggactgt 159960
agttcaaatg ctctgttccc tttttttttt cccagaggat aattttttt tttctttgag 160020 atggagtctt gctctgtcac taggctggag tgcagtggcg tgatctcggc tcactgcaac 160080
ctccgcctcc tgggttcaag caattctcct gcctcagcct cccaagtagc tgggactaca 160140
ggcacatgcc accacgccca gataattttc gtatttttag tagagacggg gtttcccctt 160200
gttggccagg gtggtcttga tctcttgacc tcatgatccg cccacctcgg cctcccaaag 160260
tgctgggatt acaggcgtga gccaccgcgc ccggcctcta gaggataatt tttaaatgtg 160320
cttttgcatt tggaaaatgt gattggcatt ttttctaat tttctaatat gatacgctgt 160380
cggatgctat ggattactta aaccctctgg ctacctagaa agatctttaa gtggttctca 160440
acaagcttca tacgcaatgt aaattgtatt atctctcagg atgtgtgaga acatctgttt 160500
ttcttctaat gcagtaaaca tataagggtc tcttgggata tcttttaaat agacttaata 160560
caacattcag gaatgataac aaaatataat cacagttgta agggaatgtg agcatttcat 160620
attaataaca ttggaacctt atgtttaata cagtgttaaa agttgacaaa catgtaggag 160680
tcagaaaatt caattaaaat tatcacagta atatgaattt agccacatcc tgtgttagtt 160740
atgaaatcca tttaacacca caaacagtaa tattttagc cagtttattc aaaaggaaaa 160800
caggaactaa accactttca tgcaatatat actctgttaa tgtggtcagg ctaattttgc 160860
tgggggaagg aacttaactt ttgaatattt gaatgcccag tcatttaatc tgaatatcct 160920
atttccttgc atgttgcaaa attttgtca ataaaaggca gaaaagaaa tctcttctcc 160980 atgctcatcc ctaagagaat gggttgtctg taccctgaga gcattttatg gaggggacaa 161040
ccactttcct aattttcctt cccacttctc tgtgggcaca aatgctcttt ggttgaaaga 161100
```

```
gttgtaattc agtcccaaga tgaggtgtgg ttactgcatc cctaacctat atctggggac  161160
cccacagcca cacacatggg ggaaatggag cttgtcattg agttctccag ccattgcaca  161220
gggttcatgg actcttcgtt gatcccaccc cacgcttctt ctctctgcta gccgaacaca  161280
cttctctctt ctttatcagg aggccatagg agaagggcat tcattttaa tacacataca   161340 tctgcatcaa gtctaatttt gccatgtctc aatccaactg tcaaatgggt tgtttggggg  161400
ctatggtgct tatcaaacat ttactcaaga atagccaaaa ttagccaagc aaggagaact  161460
tcagcaacgt tcccaaatgg ccccaaccaa gtactgtaag actgaggata gctaaagggt  161520
cttgagaggg acttctcagg cagtggcccc gacatttatc tgttttttta agtgagaaat  161580
ctgagtacca ttcttgactc ctcttcctta cccccaaccc ctcactaagc cttgtgctac  161640
tatttagtaa acagaccctc aatgcacaaa cttctgtcta aggccatggc caccacccta  161700
gtctaatcca ccatctcttc tctggaacag accccagctg ctctccctgt ctctgtgctg  161760
gtctctcaat ccatgctcca cactgcagcc agagtgctct acaatgcaaa tccatttgtg  161820
agactcctcc tcttaaaatc ctcaagtggc ttctctttgc ccccaggatc attttgaaac  161880
tccttaatgg aagaggcatg gccctttggg atgtggttcc caaccccctc ccacatcatc  161940
ttttcaatca gatttcccac taaatggaaa ttttttcagg tcctcaactt tatggtgact  162000
ttctcttgct caggatcttt gaacatactg tttcttcttt cctttgtat ttgccaagac   162060 aacacttcct ctggtaagat tttcctgaca tcctctataa aaaagattg agatagttga   162120 ctacccaaaa tgtttcccat tcattccaag ctctattcaa ggcagtaaag tgcccggctg  162180
acagattgca ttcctcatct tttctgaagc tagcaatggc catgcaacag cattctggcc  162240
aataagatag aagtcgaagt tgaagggtgg gatttccaag aaagctcgtt gaagacataa  162300
ttcctcattt cacttcttac tctttctctt tcctgcttcc taaaatgcgg tgcagatggc  162360
agacacttca aagctgtctc aggcaatcag gtgatgttaa ggcagaaacc agctttatga  162420
tgggtagaac aggaagaaag aaggcaccta tgttcttgtt caccttgaac cacaccagca  162480
ctgccttgcc taccctggaa attcctttaa tgagaggcaa atgagagctt acgtgtttaa  162540
gccattgcta tttttatttt ttttgtttat atgcaaaaga acttaatcct aactgatatt  162600
aacactaact gggtctattg cttggtacca agccaatgca tgacacatgg tatatatgct  162660
cagtaagtat ttgttgaatg agtgaggcaa tgaaagaaca tagaggatat atataacagt  162720
cctcctgccc agatgtcatc tgatcctctt taggatctgg gcccataaaa ctgtatctga  162780
tatagtttga atatttgttc cctacaaatc tcatgttgac attttatccc taatattgga  162840
ggcagggcct agtaggaggt gttttggtca tagtgataaa tggcttggtg ccgttctcac  162900
agtaacgagt gagtttttat tctagtggtt cctgcaagaa ctgattgtta aaagagcttg  162960
gatccttcca cccctctctc actcttgctt cctctctctc accttgtaat ctctacaagc  163020
tcttcacctc cccttctcct tttgccataa gtggaagatt tctgaggcct caccagaagc  163080
agatgttggt tccatgcttc ttgtacagcc tgcagaacca tgagccaaat caacttcttt  163140 tcttatataat tatccagtct caggtattcc tttatagcaa cacaaatgga ctaagacagt  163200
ttctaatgct atggttcctt tagtaggtca gtgtaaaacc ctggatcact cctgtaacaa  163260
attacttgga actcttctca ccatacatat ttaaaaatag ttgccatgtt gaaaatccta  163320
taagatcata tttatttca aatccaacaa ctcattgcta aggagataca agaagcagaa   163380
aatacagaga gactaatgtg ttgatgattt ttgtgaggga cataaggtct gtgtctagat  163440 tcatttttttt gcatgtggat gtccagttgt tccagcacca tttgttgaaa agactatctt  163500
```

```
tgctccactg tattgctttt tctcctttgt catagatatc tggtcacctt accttagagt 163560
cacagatgaa tggtcctatt acttaactac tgaaaataca ggccaaagca aacagaggaa 163620
taagggatat ataataaagt atttgtgtac ttgacttggc tctaaaggaa gcattgcgtg 163680
tctgtgtaaa aagaatgggt gagagttttc caccattcaa tatttctaat ctttctgaaa 163740
tacaaagcca ggacatcctc taatccatac attccatagt ttggttaata taaattcctt 163800
tattaaatcc ttattaaata aagttattta tgtttctatg aaactcattt taactcctaa 163860
gtgaaaaata ctactgagct aactaaacat caaacatttt taatttttta aattttttta 163920
gagacagggt cttgctatgt tgcccaggct ggctttgaac tcctgtgctc aagcgatcct 163980
ccaaactcag cctcccgagt agctgggact acaggtgcat gccactgtgc tcagctaaac 164040
atttttttga aatgctcttt taaaatcaat tttattgaag tataagttac ataccataaa 164100
agtactcatt ttgagtgtac agattgacaa gttctgacaa atgtgaacaa ccatgtaacc 164160
atcaccaaaa ataaagatat gagacatttc cattacccca aaagttccc gtgtccctct 164220 ccagtcaata tccagcccta gccccagctc caggcaacca ccaatctgct ttctgttgct 164280
ataaattgta cttatctttt ctagtgtttc atacaaatgg aatcatacag catttactct 164340
tttgtgtctg tcttcttctg ctcagtgtaa tgttttttgag attcatctat gttctgtgcc 164400
tcagtagttt gttctttta ttactggata attccattat aagaatatac cacaatttgt 164460
ttatccattt actgcctgat gggcatttgg ttgtttccag ctttgaacta ttttgaatcc 164520
taaaagactg ccagttttga atgagacccc agaacaatga atgtaggctc tgtatacaag 164580
ttcaggctgc tgggcaactt aggccttaag acacaactct gccacttagg ccttaagaca 164640
caactgacat gatggtgctt aaagtggctg tgatggaaaa ggaggctgtt tggagccttt 164700
ggagtgcctt tataggtgaa ccccagcata gcacctaatg atttggagca aagctgtgtc 164760 attcccaaa gataactatt cgccttttga gaaacatctt ctagctacta tcaataataa 164820
acacagaatg catcaccatg ggccaccgtg ttgtcttttg acctgagttt ccattgtgaa 164880
caagagtcat ttgatccaag gcagaaagtt gggtgcacac agcagtgttc catcatcaaa 164940
tggaatatga gattgggccc aagtaggtcc tgcagacaca aataagttgc aagagcaagt 165000
agtacaggcg cttggcctgg ccagtactgt tgccaagttg actgcttccc ctcagtctgc 165060
atctgtggct tcatggggag tttcctatga ccacttgatg gaggaaaaaa caaattggag 165120
catagtttat agtgctggta ctacccaaag tggctagctg aggcactaca tctccactct 165180
ggggtgcccg tgaaggacag tgccaaagga aaacccctc agtgagcaga acttggagca 165240
atacaagtgg gtgttcattt tacctagaag agaaagatgtc cgtgagttac agatctacac 165300
aaaatcacag agagtggtta atcgtttagt ctgatggtca gggacttcca agagacatga 165360
ttagaaaact ggtgacaagg agtcctgggg aagaggcata tggatacctc tgaacacaca 165420
caaaacatga gaatatgtat cccatatgaa tgttaaccaa agagcagcca caacagaaga 165480
ggattttaaa atcagctgaa taagatgatt cattctgaca gcatcagcta gtctctttcc 165540
ccagccactg ttgcccagtg ggcttacata tatcatggcc atggggcag ggctatgtat 165600 ggacacagca acatgaattt ccactcatca aggccaattt ggctccagcc attgctgagt 165660
gctcagcctg ccaagataga aatctacgcc aatatggcac cattccctgg gctagaaaac 165720
caactggtgg aaggttgatt acattggacc atttccatca tggaaggggc agtgctttgt 165780
cttccctgga atagacattt actctggata tggatgtgcc ttccctgact actacaatgc 165840
```

```
tctgccaaac ctaccatcca tgggcttaat tttatttgtt ataaaatttc aaccaccatt 165900
gcttctgacc aaggaagtaa tcttacagca aaggaagtac agatatgagc ttctgatcat 165960
gggcttcact ggcctcacag tgaagcaggt ggccagatta aacagtgga atggattta 166020 aaggctcagt tacagcacca gctgggtagc aacaccctgc tggcctgggg ttatgtcctg 166080
caggatgctt taagtcagtg accaatatat gatgctattt ctcccattgt caggattcat 166140
gggtccaaga atcatggggt caaaatggga gtggcttttc tcactatcac cctggtgttc 166200
gggtagtaat ttttccttcc cattcctgta actttgggct ctgctattgc agaaatctta 166260
gctcctgtgg ggggaatgct tccatcaggg aatacaatgg tggttccact aaactgacag 166320
ctgagtttgc catctcctcg tgccagtgaa tacacaagca aggaaggggg ttcctttctc 166380
acctagggtg actgatccta attaccaagg agaaattgga ctgccacttc acaatgaggg 166440
tgaggagtat gtactctatg tgtctgtgat taatgtcaat agaaagtgac accaacctag 166500
tacacagagg actgatcatg gtccaggccc ttcaggaatg aagatttgag tcaccaggca 166560
aggaacttgg actcactgag gagggcatat tccaaggaga atatttatc tatgtccatc 166620 tatgtccatc tatattccat ctgtgttccc cttggaattc ctattcatga acatgggaa 166680 ttccaagggg aatatagaat gagtagtgga aggtagttat aaatgtaagt caaaaaccac 166740
acaaccaatt tgagaaatga ggaaggtaat agtgttgaat atgtcttctt tatcttgata 166800
taaatgtatt tgtgcatata ttaaccagtt tatttattta ttattatttt ttgagatgag 166860
ctctcgccat gttgcccagg ctggtcttga actcctgggc tcaactgatt ctaccattta 166920
gtcctccgag tagctgggac tacaggcatg caccaccata cccagctgac cagtttttc 166980 ctattcctct acttaatttc tctactatac aacataaat gtgttaatgg tagttaactt 167040
tatatctcag tattaagtca caagatatca aaaagggaat gcgacttagt tacaagcaga 167100
atgaatatca ctcaaagatg aataaagaga agagggttag tgcattttct gttggatgag 167160
agaaagtttc attgttaggc agaagcatga ttttgccttt ttttttttt tccaaggtct 167220 cactctgtgg cccaggctgc agtgcagtgg tgcgatcttg gctcactaca acctctgcct 167280
cccgggttca agtgattctc cagcctcagc ctccagagta gctgggatta taggtgcgcc 167340
aggttaattt ttgtattttt agtagagaag gtgtttctcc atgttggcca ggctggtctt 167400
gaactcctgg cctcaagtga cccacctgct ttgacctccc aaagtgctag gattacaggt 167460
gtgagccact gtgcacagtc accacggtct ttttgggagg caactttagc atggttaaga 167520
ggtgcgaatg gatgttaagc taacaccagg taagccctgg tagatgtgta ttgtgtcagt 167580
gggcctacgc tggagccatg tttcccccaaa ttcactttc ctatgtacct ctggattagt 167640
gtgggccact ggagacattt cacatgagat gaggaaggtg ggagtgaagg agcagcatct 167700
ttttacacta agcaggtcgg ggagggcatg tggctctgtc tcacattgtt gggaatctgt 167760
ccatcatctg gttggcttag gtcagtgggt gagttcacag ctgttccagc ttctgctgga 167820
aactccttcg gtttctctga ctgctccgtg atgagggcat cagattctcc tgcagaaagc 167880
cccagtgttg aagttgggc ttcatgttgg tgagtgatag ttacgggttc tagcccaacc 167940
tgtggtttct tgcaaatttc agtgtcagct cagtcttgcg ggttttgggt tgtccttgct 168000
tcccacactt catgccttc tttccctcct gacagtctgc cctttagatt ttaggattca 168060
gcaccagcca cagaaacagc aacctcactg ttaagggttg aattgtatct ccccaaaagg 168120
taggttgagg ccctacctgc caggacttca gaatgtaacc tcatctggga atagcatcat 168180
tgcaaatata attaattaag atgagggcat actggctcag gatgggctcc taattcaata 168240
```

```
caactaatgt ccttctatga cagccacagg aagacagaaa cgccaaggga gaacaccata 168300
tgctgatgga ggcagtggca gctgccagcc aaggattata accagaagtc aggaaaaagc 168360
aagaaggaat cctcccttag tgattttaca gggagcatag ccctgctgac accttgattt 168420
tggactttta ttccccaaaa ctgtaaaaca atacacttct gttgttttaa gccactcagt 168480
ttgtgctact ttgttatggc aactccagaa aacaaaaata cactcagact gtttaatcaa 168540
cctccataat tgcataaggt ctaatcccta ataaaatcc cttaaaaatg tctgtgtata 168600
tatatttaaa aatataaaat atcttctagt ggttctgcat ctctggtcaa tccctgactg 168660
atacagaata tgtattttca tttctaatga tgaaatacct gaatgaaatt tctaggacat 168720
atggtaagtg tatgtttagc ttttaagaaa ctgccaactt gggggaattg cttgaggcca 168780
ggagttcaaa cagcctgggt aacagtgata ccctgtctgt acaaaataaa aaatattagc 168840
agcgtgtggt ggtgtgtgtc tgtagtccca gctactcagg aggctgaggt gggagattca 168900
cctgagccca gatctttgaa gttatagtga gctatgatca cgccactgca ctctagcctg 168960
ggtgacagag tgagaaagct ggtctctaaa aaacaaacaa acaaaaaaga aactgtcaaa 169020
ctcttcccaa catgttgcca ttttacatt taccatttta cattcttacc agcaatgatt 169080
gatagttcca gttgctccat accccttgctg accattccaa tagatgtatt gtgttatctc 169140
attgtagttc taatttgtat ttccctagtg attaatgatg tttaacatct tttcatgcac 169200
ctattggcta tatgtatatc ttcttttagca aaatatatgt tgttatttga agagcggaag 169260
ttttacattt tgatgaagtc taattattg attttttttt tcttagatgg ctcatgcttt 169320
ttgtgttatc taaaaaaaat ttgccttctt catggtcaca aagactttct cctatgtttt 169380
cttttggaag ctttatattt ttagttttta tgtttatgtt taagacccat ttctagttac 169440
aatttgtgtg attttttgga agggtcaagg ttcattttct tttccataag aatgtacagt 169500
tgttctagca cccttgttaa aaagactttc ctttccccat tgaactactt tgtcaaaaat 169560
caactgagca tatatgggca tcatgaattt taatcctgtt agaactgaat gttcccaagg 169620
caggccatgc ccatgactga cctcctttcc ttggattgcc tacaaaacag ataaagctaa 169680
gtctggagca aagaaatcca tgtctaacct gtatttttt tttttttttt ttagatgggg 169740
tctcgctctg tcacccaggc tggagtgcag tggcgtgatc ccagctcact gcaatctctg 169800
cctcctgggt tcaagtgatt ctcctgcctc agcctcccga ggggctggga ttgtaggcgt 169860
gcaccactat gcccatctaa ttttttgtatt tttagtagag atagggtttt gccattttgg 169920
ccagactgtc ttgaactcct gacctcaggt gatctgcctg cctcggcctc ccacagtttt 169980
gtgattatag gcatgagcca ccgtgcccgg ccttaacctt tgttttctta cacaacacac 170040
tacgtgatgt tttccacatg catgggtcat ttgcttcatt tacgtacaaa tgcataagca 170100
atatactgtg tggtgtgagt ttgtgatggg aaaaggaaga agttttgcgg atactacact 170160
ggcttcctgc tatctgtctg tgtgaatggc tatggacttt gtcttctatt tgttcgctta 170220
gcgcagatat gatcagctta caacttaaga ttctagagaa agagggtcat atctgtaaag 170280
cactctgagc atgtgtgaag tttaatcaat agcatatgag gttacagcaa attcactatc 170340
tttgtttctt cagctataga atggcatgag gattcatctc aatttagttc aattctgttc 170400
agaaccatga gctagctgtt catggaagga aagcccacct gattgtggcc agggaaggag 170460
aaacaacact ttaaccaggt tgatttggtt ctcacagaca ccattggcat gtgacatctg 170520
gaacagacca tgcctggtct ctgttcgtat cacttactat tcagctcaat attggtctga 170580
```

```
atattcttta gactgactga aatgaaaagg aactgttgtg taaccatcca taattccagc   170640
ctgtagacct gggctgtatc tctatgccct gcctggcaca gaccccacct cctgctcctt   170700
ctccctcacc accagtcaat ccttgtccta atgaacaggg agggcaaccc tgaatgggga   170760
gtggagggaa gagatgtcat gagatggcaa cgtgcaccct gaagtgagga tgaaggctat   170820
gtgaatgttg taggctgaca gccgggcata gtggccccgt tgccatggcg atggaggcat   170880
gttgatgcga agtgtctgca cagctcctag gattttaac agcagctggg cagagcctcg    170940
gcgtccctga attgttgccc ccctgagtca ctgcttggcc ccagctgtcc tgatctctgt   171000
tgacaaatgg ttgtccttca cagtcaaact actaacagta ctctaattaa tgaatgtgct   171060
aattattctt gcctactccc agcatatttg tctaactaac ctgtcacaca cagatcagtg   171120
cagcatatgc ataattacgg agagcgctgg gagcagggga tgggtgggag aggggtgggc   171180
tcgcagccct gtcgctgtgg gatatttctt gtaaagttac ctttgctaac ggtcagatgt   171240
cgtggggata tgttatttcc cgtgaagtgt atatgtcttc ctttctttcc tttctaagaa   171300
tctctcttca gggctgaggg gccattgctc agtgctttag cctgtgaggg gattgccagg   171360
tacaaatgca gaaggaccag ggagcccagg ttctgaagac gattccggta gcagcacgta   171420
gggtgattaa aactccagac tttaaagcca gaccggcctg ggcttgaacc cttgttctgc   171480
tccttgctat gtgggtcttt gccttgacca cattttttt ttttttttaa gacaggatct    171540
ccctctcttg cccaggctgt aatgcagtgt tgcgatcaca gctcactgaa gcctccatct   171600
ctacagcctc aagcgatcct cctgcctcag ccccgagtag ctgggactac aggtctgtgc   171660
caccacgtcc agctaattta cttttgtaga gttggggtc ttgctatgtt gcccaggctg    171720
ttctccaact cctggactca agccatcctc tagcctcggc cttccaaagt gctgggacta   171780
taggcgtgag ccacggtgcc aggcccttga ccacattttt aacccctctg aacctcagtt   171840
tcactttctg ggcaatggga gggggtaat ttgtccctca gagggttgca ctgaggggca    171900
aatgtgaggc tctgggtaca atgcccagta cagactaggt ccccacgaca cagccgctca   171960
gcggctccgg attctgggct gctctggact gcggccaggc ggtcttctgc gggaatccgg   172020
gcaggcaggg cgggctgcgc tcccctcccc ggctctcccg gtgcccttg tcttttgtt     172080
ctgtctcagc agctctctat taagatgaat ggcatttcca aaggcttcac ctctgataag   172140
tgttcctctg cagctgcagc cagaatctta atgtgcgcgc tgtaatttaa tggccgtctc   172200
ggctattaac acgctcttct cgggtgaagt ggactccctc catccccggg cctctgcacg   172260
tgctctgcgc gctggctggg ggtgactcca aggagctcag agcggggtgc ccggcacctc   172320
tcgccaggcg cctttcgacc ttctaaagcg cgaatggctg acttttctc ccatgtgtgg    172380
ggccccagaa ggtgtgggc cccagaaggt gtggggtccc tgcgttccac ggagcccgga    172440
aggtttccag tgatggtggg ggctgaccac gttggtcccc gtgggtgctg ttttcatgtg   172500
ccggcagatt gggatgagtt taaaagacag aagcgtgtag gatagagaaa cttctttaaa   172560
aactggaaat tttaatctgg ggattataac tattggacag tcaagtgcaa gagtgaatac   172620
acttctcact ccctcctccc aatttttatt tgcgggatta gtcagtcccc ctctgccaca   172680
tgataattgt gagaactacc agggtcttca ttctcctgcc atctggttga cctctccaag   172740
aatggacacc cggcagcct gggccaatga ggctgtccta agagtttaga tgagagaagt    172800
cagtctttga caggtgatgg aagctgtaaa atgtaaaact ccacagttgg tgaagatgtc   172860
tccaggaaac aggtctgcag agagaatacg tttgacatgc taagaaagc tgagagagag    172920
cgagaggaga gattggaaga aagacagaga cagaggtaga gagaagggaa agagagagag   172980
```

-continued

```
aagggacag aagagagaga aaaagagg  ggccgggcgc ggtggctcac gcctgtaatc  173040
tcagcacttt gggaggccga ggcgggcaga tcacgaggtc aggagatcga gaccatcccg  173100
gctaacacgg tgaaacccccc gtctctacta aaaatataa  aaaaaattag ccaggcgtgg  173160
tggtgggtgc ctgtagtccc agctactgag gaggctgaga caggagaatg gcgtgaaccc  173220
gggaggcaga gcttgcagtg agctgagatc gcgccactgc actccagcct gggcaacaga  173280
gcaagactcc gtctcaaaaa aaaaaaaaaa aagagagga  agggcgggag agagagagag  173340
agaaagctct ctagctccaa ggcctaacca catctctgtt cttttcaact tcagctgtca  173400
gattttaga  ctctttgagt gaataaattc tccttttgc  ttaaactagt ttgagctaag  173460
tttctattgc ttgcaactgg aatactttgt aagaggactg gccttcattt ctgatgcatt  173520
gtcactaaga tgtaagtgtt agaagagcta acgctttatg gggttcaaac tccttggcta  173580
ccaaaaccta aacatcccct gaaacttacc aaactgcagg tatgaattgg atctcactaa  173640
ggtgaatata caaatcttgc aagtgctgag ccctaaccaa tcttgtaata actctgtggt  173700
agttaatttt atgtcaaatt gattgagcta aaaaatgccc aggtagctgg taaaatgttt  173760
ttttctgggt gtgttaggga gggtgtttct gaaagagatc agcactggaa tcagcggact  173820
aagtaaagaa ttcccaccct caccaatatg gtgggtgtca tcaatccact gagggcctga  173880
atagaacaaa agcgggcag  aagggcaaat tccctcttct tcttgagctg gccatccat   173940
cttctcctgc ccttggacac tggagccct  tgttctccag cttttggatt cagactgggt  174000
cttgcaccat tgccctccat cttctcctgc ccttggacac tggagcccct tgttctccag  174060
cttttggatt cagactgggt cttgcaccat tgccctcctt gatgctcagg cctttgaatg  174120
cagactggtc tccaccagca gctttctga  gtctccagct tgcagatggc aaaccatgaa  174180
acttcatggt gtccatgagc atgtgaacca atttctatta taaatctgca atatatatat  174240
atgaggagac ttatttatat attggttcag tttctctgga gagccttggc taatataaag  174300
tctatactct acaaagtgcc ctaggtactc agggagtacc caagtgtgtc atgaccagcc  174360
cgacagccct ggctgctggc ttcccgcac  acaactctgc acgctgcctt catcagcctt  174420
tctctctcag ctgaaccgag ggcattgaag cgggcctctg gcactgtacc tatgagggag  174480
caatatcttc ccctacactg acctcttccg tgccgagatg cagccctccc tgctgccact  174540
agttacagtg gtccatgttc cctttcaaag tgaagttttg ataaaagcac ctcttaacca  174600
atgccaaata gctaagtctg ggacaaagat tgcaggtatt ttgcatttc  catgtaacct  174660
cagagggatt gccattcaca ctgatctgag ctgcagaata ccaggcagcc acctcaccca  174720
cccagcaggt ccactcttat actttctcag aaagcacagc cactctactc ttattcagtt  174780
gaaaagaatt tccaggaagg tgtttctgcg attgcctcag aaaagtcagt tccctttggg  174840
aatttccctt agggatcatc tgtaactcca tttctgcctt ttacctgaat tctttggttt  174900
ggtttgaatt ctttggttta atttatgaat tcccttttatt acttttctct gaagaaatgg  174960
agatatcagc tgtccctccc cactgccatt tattccttcc ttcattcaaa ccttatgtgg  175020
ctgctactta ccgtgtgtta agtgttcact ttttttcttg gaattcaaaa aagaaggac   175080
agtatttggg gcacagatct tttggtgttc tatacatttt tttaaagttt cattttacat  175140
ttgtgtgtgc gtgtgtgtgt gtgtgtgaga cagtcttgct ctgttgccca ggctggagtg  175200
cagtggcata atcattggct cactgtagcc tcaaagtcct gggcccaagc aatcttccca  175260
cctcagccac ccaaaatgct ggggttacag gtttatgcca ctctgtctga cctgaaagtt  175320
```

```
ttgggtttac tttcccttct ttctctttgc tgaagtcaga gatgatggca gcttccagat  175380
tctctggtgc ctgtgctggg ctcgtgctgg tcatggtctt gggtccagga ttcattctgg  175440
agactctcag ggaagtttcc catgacaagg aaatgtagga gagtgtgctg gctttgcgtg  175500
ctcctctgcc aagccctgct tctcctggtg ggacacactg aaccacagcc agggcatttt  175560
ggtggttagt taaaaaaaaa aaaaaaaaa aaaaaggaa gaagaaggca ctgtgtaatt  175620
gtgccgggga tcttcagaaa ttgtaatgat gaaagagtgc aagctctcac ttcccttcc  175680 tgtacagggc aggttgtgca gctggaggca gagcagtcct ctctgggag cctgaagcaa  175740 acatggatca agaaactgta ggcaatgttg tcctgttggc catcgtcacc ctcatcagcg  175800
tggtccagaa tggtaaggaa agcccttcac tcagggaaga acagaagggg agattttctt  175860
tgatggttgt ttggaagtca ggcttaaaca attgtgtctg tgtgtgcgca tgcacaaaca  175920
cttttacctt atctttattt tcttcttttt atttgaatgt atagggttgt gtgtatttct  175980
gtgtaaattt ggggttttcc tcctcttagt cttcactt tgtggtgatt accagtccca  176040
tttttagagc cagggctgca acttgaaggt tttgctaaaa ccctcaccga agtgtctatg  176100
atcagcattt taactattaa ttaatgtggc caggcaaggg gtggaaggtg agaagactag  176160
aaagggaaca tgatatacac atttactcag atactgggct tttctaacat ctgcagtgca  176220
attgaagtta ccagtcatct gcagtctaaa agaaagtga ttttgggagg tgcgtagaaa  176280
aaatcatctt attatttttc ctctatatta ctttttttctt tttttctcct gaagaaactt  176340 tttttttttgg tgataccttc tttttctcta gcacgtataa ttttgaaagc atttttcata  176400
tgcagtgtat acttcagaaa gagagagaga gagaggaaaa ttgtcctgtt cagcgtttgc  176460
atttccatta ttcctgctat tagttaaaaa caacaacaac aacaaaaaac aagcaggata  176520
cctagatctg gaaaagggag aattgtgtag agctgtcttc ctaaagttct gagttagggc  176580
tgcctcagac cactttcata actatctcca gtggctttgt gttttatatt tattaagata  176640
gagaaaaaaa gagtaattac taagggcagc tgctgtagct ttatggtgat tactgaacat  176700
tgacatgctg tcacgttttt ggaactttga gtatttaatc actttgggat attctatttt  176760
cccccatctt gagtgtggac agatgctggt gatgtagcct tctgggcaca gagcaagcct  176820 cccctcagc ctctgcacca gaaaggctca gcttcacaca ctccaagtat gttttctaca  176880
agaactacac tttgtggctt tctgacccaa acatttttat actaaattac acacaacaaa  176940
gttgtagctc agagagggaa caaatggctt atttaggcca ccatttttctt gagccattat  177000 gatttcacac agggctccct tggccctgta aattggcaag gattccatta ttcaacccgc  177060
atacatgtac agagaccctg ctctggccca gatagtattc tgggtacagg cggatagagc  177120
aggaaacaaa acagctacag tgatggacag gtcagcctgc agcaatgcct gcagtctctg  177180
caaaggtagc tgtatgggtg ggcaggtggc tagcacttat tcagctctgg aaggatctcc  177240
cctctggcct ctcccctgac acccatcaat aaaactgagg agcatcggtg gacagggggac  177300 cttgtgccc ctccctgcct gtgcagttgg ggctgaaccc agctacgaag tttgagctca  177360
ctctctccag ctccctctca attcagagct gaactgtggg aagcttcaga gctctctgtt  177420
tcaaggacag gttctcctca cctctcctaa tggaggtgca ccagggaact ggccctgctc  177480
tgcccagggc tttctcctgg actttgccat catggtctag caaaccctgt tcagattgag  177540
gtgagtggtg agatttcgaa ttctttttga cagataggat taagtcttct tctgtgggac  177600
aagtgggagg tagaggtaag attaaagatg gccaaatgtc tgagtcctga cagccacaat  177660
atggagatct agactttta cagaccacag ggcacagggg cctcactaac agagttcccg  177720
```

```
gaagtgatga gtgtgctggg ggcttcctgg ttgaagagac actagaatgg accagctggg    177780
agctaattt ttgggctgga gtgtgatggc ctgcacatca ctgcctctgt ccctccattg     177840
tcacagctgc cccttaggag ccagctgagg caatttgtgg tcagagtgac tttgcacagt    177900
tgtcctgcct gtgttcagga agggagtttc tgtggtccct ttgaaaccac agaagagccc    177960
ctcgtatagc tctcaatgga gggggcaaaa cattcaaata actcaggaga taacacaact    178020
atttgttttt aactgtgagt ttttaggcaa tcacaaagat ccagatgtat gtccaagcct    178080
ctctttgcaa ttctaattaa cctcaatgtt gcaaccatag acctacctta cagagttcaa    178140
aaaaatatgc aaaaaccctg cctttcttct tcctcatacc ccaaaatgcc attctgaaca    178200
tttcctgtta gttaaaaaaa gatttccatg gtgttaccag gcactgtaca cagtctgtgt    178260
cccaagacaa ggaggtacag ttccacatgc gcccatgact gggttgggct ctgcactctc    178320
tctatacttt gagagcctga ttttctgtga ttgggcagag ctggcccacc tggtgcaatg    178380
tcctcctctg cctttcaaac atgttttagt catcaagatc ttcaaatttg taaccctttc    178440
cagcttgatc cagcagaatg cagatttgga aaaacagaac gagtttaaaa tacatgattc    178500
taagaaacct ggaccagaac tatcaaaact tggtttccca gagaatatag caaatgggct    178560
cattggccaa tactatgaca ttggcttttg agaaaagaaa ggcttattg caaggctggc     178620
cagcaaggag acaggagttg ggctcaaatc tgtctcccca gtttgggct tagggcaagt     178680
tttaattaca cagacgcatt tcttatgagt agcaggcaga gagcctccaa cttcttctgc    178740
ctaggtacca gcagcttaga catgatgcaa acctgggaag cacatactgt atttggagaa    178800
agtgattggg aagaaatgtg agctgagggg aggggctcag tgcccctgag ctacacttag    178860
tgatggcaga ggaaggatgt cctcccgcag gaggctgttc cacatctgct ctggttgtag    178920
ggggagctgg caggcattag cagcggcctc tttcccccaa gagaggcagc ctcctccaag    178980
ttttggcgac attatggccc tgcaatcata agggtttgtg agcatagtgc taaggaggga    179040
aatggagctg ctgttactag ttccacccca acacacacac acacactcac aagaaacctc    179100
acaagcaccg tattgaagag ctttgccatc caacctggga tttgacaggc tctagaagca    179160
gaatcataga ctcatgaagt tcccccaaag caggaatctt ccttacagta accccaacc     179220
accccctcc accgcctcca ccggctgctt cttcctgaac actgcagtgt ttggaaaact     179280
cacaaacttc caagcttgcc tttcctattg ttgcatggat tgaaagcttg cgttgtgtga    179340
agaatggcgc ttcctgctgt gcttagtttt atctcatata atctttgcac catttaatcc    179400
ttgcactcac ccactcatgc aactgccttt gcagagactg gagggccgc tgtaggctga     179460
cctttccttc actgtaccta ttttgttccc tgctttattc ccctgcaccc aggacactgc    179520
ctggcacaaa gacaggtctt tataagtgta tgcaagtgaa taaagatata tatattatta    179580
ttgttatttt tgagacagtt tcactctgtc acccaggctg gagtgcagta gcgcaatctc    179640
agctgactgc aacctctgcc tcccaggctc aagtgattct catgtctcag cctcctgagt    179700
agctaggact acaagcatgt gccaccacgc ccagctaatt tttgtatttt tagtaaggac    179760
agggtttcac catgttggcc aggttggcct ccaactcctg acctcaagtc atcctcctgc    179820
ctcgacctcc caaagtgctg ggattacagg catgaaacca gcctagaaat acatactatt    179880
atttattctt gttttacaga taagcaaagt gagtcatgga gaatttggtt gaaagtccca    179940
aggtcaggag tcgtgaagct gggattaaaa cctaatcatc tgactttaga gagtagacac    180000
ttgctccatg catattgcct ccaattcatt cattcaagca ctccctgctc aagaagttct    180060
```

```
ttcttatgtt gagctgaaat ctgcagccct atgcgtttta cccagcagtc ctggtgctgt  180120
tccctaaaat cacttagact gtgcctgctc tttctgtgtt tacagtgtca gctgtaatat  180180
cccctcttc ggcctaacgt ttctgaagtc ccttgccact gggtctcctc tcctcttcct   180240
gtgttctttc taagaacacc tatgcagata ggtgtcttct gtacagggaa gctgttcctg  180300
agatccgggc atcgactctg ttagaataat ctacgtatga gttatttttt tgagaactat  180360
gtgtcattgc tgactcatat taactctgtg gttaactaaa atctcaagat ctctttatgt  180420
ttgttgagaa acttatttaa cttctctggc cctccgtttc cttcactgag cagtggagtg  180480
attgataacc tccacctgtg gttgctgaag gtcttgcaca agatgatata gttaaagtag  180540
ctagcagtgc ccacgtacgg cggatgcctc acaacggttt gcagccatct ctctatctgt  180600
gtctttgtct ctctctcaca ctggttttgg cttactgtta gcagctagcc gagataagtg  180660
tgtttatggt ctttgcatgt attgtttctg tagcatactg gaggattaca agaggttggg  180720
gagtgagggg gcggtgagga gtagacaaag gcagccaact cttccaagtt tagcttagaa  180780
ggaaggagcg gtaaacccta gttgaatgtt ggactgaagc aggtttgttt ttgttttgtt  180840
taaaggatag ggaagatctg tgcgtgtttc caggataaag aaaaggagag aatatgatat  180900
taaagattct ggaagtggga gaaggagcaa tgaaatacag acttgaagtc agtggcatgg  180960
acagggtcaa gatcacagtt agaggatgca gccttagaga aaaggaaggg gctcggttct  181020
ctgagcaagg agggaaagaa gagaggcaga tgcagagaag tacggcacat cgtgctgctg  181080
gttgtagaaa taacctctga cttttaataa agtcatccct cggtatccct gggggattag  181140
ttctatgacc tccctcggat gccaaaattc gtggatgctc aagtccctga tataaaatgg  181200
catagtattt gcatttaacc tacacacatc ctccatatcc tttttttttt ttttttttt   181260
tttttttttt ttttgtgag atggagtctt gctctgtcgc cctggctgga gtacagtggc   181320
tcgatcttgg ctcactgcaa gctccgcctc ccgggttcat gccattctcc tgcctcagcc  181380
tacaggtgcc tgccaccacg cccagctaat ttttttttg tatttttag tagagacagg    181440
gtttcaccat gttagccagg atggtctcga cacatcctcc atatacttta agtaaacctct 181500
agataatctc tagattactt gttttgtctt tttttttttt tttctttttt gagatggagt  181560
ttcactcttg tcacccaggc tggagtgcaa tggtgcaatc tcagttcact gcaacctccg  181620
cctcctgggt tcaagcaatt ctcctgtctc agcctcctgt gtagctagga ttacaggccc  181680
ctccccaccc ccacccccca caactggct aatttttgta ttttagtag agatggggtg    181740
tcaccacgtt ggcctggctg gtcttgaact cctgacctca ggtgatctac ccgcttcagc  181800
ctcccaaagt gatgggatta taggcatgag ccactgtgtg tggcctagat tacttataat  181860
acctgataga atgtaaatgc tatgtaaaca gttgttatac tgtattgtta aaagacagta  181920
acaagaaaaa aaatctgtac atgttcagtc cagacaaatg gttttctgtt tttttttttt  181980
tttttaata tttttggtca gtggttggtt gactccagga atgcagaacc cgcagatata   182040
gaaggttgat tatgcgttca gaggcaggga ataccatctt gggttccaga agaaaatga   182100
tcagcatttt ctgtcatact ctggtaaaaa cagatctttt gaatgacag gtgtattaaa   182160
ccctgtggag ctggctgggc ctggcggctc acgcctgtaa tcccagcact ttgggaggct  182220
gaggcaggtg gatcacgagg tcaggagttc gagaccagcc tggccaatat ggtgaaaccc  182280
caactctact aaaaatacaa aaattagccg ggcgtgatga cgcatgcctg tagtcccagc  182340
tactcgggag gctgaggcag aagaatcgct tgaaccctgg aggtgaggt tgcagtgagc   182400
cgagatcacg ccactgcact ccagcctggg caacagagtg agactccgta tctaaaaaaa  182460
```

```
aaaaacaaaa acctgtggag ctgatgaaat cctgcaggga gcttcacggt gacagcaaga   182520
ggagaaacac atccccatat gccccgcaga gtttgaagtc ccggctgcac ctctccccag   182580
cagcaggttg actctggaaa gttgcagcgt tcttacctac agagtgggaa cagtactacc   182640
cattgcacag agtgggtgca aagctctgtg acggaataca tggcaagtgc ccaccacatt   182700
gcctgggatg aggtgggccc ttcctttacg taagagagcc ctacagatac actcaaagtg   182760
ggcacattcc tacagaagga gtgttatttg tgtagaaaag aaaaacatga aaggctttta   182820
ttcctataca caataaagca ccccttttaat gtcttttttga ggaggataat atgaaattga   182880
tgaaaaggaa ccctgtggtt ggatccctga caatcacatg tatccctttt ttcactcttg   182940
aaaaaggagt aaaggaataa aatagaaggg gagaggggc agagagacct tcaccgcccc   183000 cccccaccc cccatcatcc aatctatagt caaaccctcc agactgtgtc tccttggcat   183060
ctctgacacc cccaccgcca ccaccccagt caattcctat cttatccccc tatcctggat   183120
ctgattctgc taagttcctg ccacactaaa gacagggtgg ctttctgatg acaacattcc   183180
tctgcttaaa cctgtcagta attccttgtt gctctcagac ggaactaagt tctgaatttc   183240
ttcacacggc tctcagcaag gtcacagtca ccctgctagg ccccaggggc aaatctcaat   183300
ggtcatcttc ttgaagacct ggctcagtta tttctttctc attgaggctc acgaccccac   183360
cttcttgcat gcctcaaacg gcccttacc atgctcttct ttcgcccata gctcagcaca   183420
ccatatcatt ttaatttatg tattttgctt aatgtggatg atctgtctcc tcctctgctg   183480
tcctcaccag agcatcagtt cctcaaacca aggctctttg ttttgttctt ggatgcaagc   183540
taaatgtctg gcatgtggca aatggtcata gatacatgtc attgaaagaa tgattcatca   183600
cctccctctt tggccttgtc tgtggttcta ccaaatccca ttccctcccc agtgccctcc   183660 attcccctc cttggctgaa cattctgaac cacagacagt tctttaccct gaacctttgc   183720
atattttgtt ctcttagctt agagcggccc ctctccctcc gtctgcttgg ctaatttcta   183780
cttgttcttc agattttatc ttagatgtca ttccctcaag gaatccttct gtgactcaac   183840
atggaattaa gttgcctcct ttgaccctga agcaccatg tactcaatct catcttgca    183900 tgactcactt tgctgtgtgg aatgtctgct ttccttgttt gtctattcct ttagactgta   183960
agatcctaga aagtggggc cgtgccttgc tcatgactgt gtttctaaca ccaaacacag   184020
tgttcagtag agagcagctg ctgagtacgt ttctgctaaa tgacagttga tggaggacat   184080
ttagggttgc ttggaggtca agtcaaggag gcatttaaca ttctagtaaa acaaggaagt   184140
aacaggctcc tgaacatgcc cacaatgaac cagatgcaaa ccttttccct tggcaggatt   184200
ctttgcccat aaagtggagc acgaaagcag gacccgaat gggaggagct tccagaggac    184260
cggaacactt gcctttgagc gggtctacac tgccaagtga gtcctaaccc tgatgttgct   184320
aataagtggg ggcatgggca ggggggcctc cttctaggag tgatgaccac ccttaatacc   184380
acatgtctgt ctgagccaag tttctgagcg ccagggaggt gaggaaggtt ggacttcacc   184440
agagaggctt tgtggacacc ctttatcatc ttagtgagtg ctagtgtcaa acaaaggga    184500 gtggggatat ggggcacatt ggtggaggga ggtgtgatct ctgcagcttc agaaagatct   184560
gaaagagtca tttggttaga gaagttgacc tatttcctgt ggggttagac cagggttgct   184620
actgtgaaca ccagccatga ctcaccagtc accttcagaa gccacaggca ggacatgctg   184680
acgacagcct tcaactcacc caccccttgc tccctgcgg gtggaagtct ggaggtgaca    184740
ccactgcatt ttctaacacg ggggctcctt gagcaactag aacaagaaca gaaagaatgg   184800
```

```
ggacattagc aggtgctttc cccctctctc attcttttct ttgaataaaa aggttgtttg 184860
aaaacacctg agcggctcct aaagatgggt gcaatctatt cgggatgcaa atccgaatga 184920
atgttattca aatgctcctc tcttctttat gcagagtgta tttcaaggct cagccagtgg 184980
caggcatgct ggggactatg gactacgac  taggggcctg tcacagagga aggcctcatg 185040
ctagagagct aagggaggag ctggccttca gttccatccc aggagcaact ttgatgttcc 185100
cagagatcct tccaaagggg gagtcatggt cacccaagaa aaatgtattc agaatgccaa 185160
gaatggtgca aactcaggac aaagattcac actgcagggt tggagtccct gggcttgctg 185220
ctggcaccat ggggagggagg gtccccttca ggggtaccgt tggtttcctg tgaattaaac 185280
tggcttcaag ggatctcgac tgaacaggcc tatatcacac tcactgatat actctctctt 185340
cagtccttct cctcatctag gtatttttaa ttgtttcagt gaggtgtagg catgagggga 185400
ttggagggg  catctcctcc attgcagttt tcattggct  gctttgctcc ctcagctccg 185460
aaatcgctgg gccactctcg aacgcattag tacggtagtc acaggttgat tgcctggccc 185520
cttgccctct gtgggcattt tccctttcag acagcccctg agtactcaca gtgctgctac 185580
agtgggccac ctagatctcc ctctttctcc atgctcccac gtgctctggg ctccactccc 185640
ttctcccaag cacttctgtc cagggctatt ccagcagtct gacctcaagg aaatcctttg 185700
ctaaactgat tatagagagg tttctatttt aacatttagg tcttccatgt attaattctc 185760
agaatcaatt taagatgttt aaaggtgtga tttaagacat tttaaaacca tttggaggag 185820
agtacagaaa ttatgtcact tgctgtcagc ctctttgcac catctgcaga gaaagatact 185880
agagtcccgc cttggacaca tccacatgca agaggtgcaa agaaggtgtc tttgatgagg 185940
caaggtcaaa acttctcccc agacgaaatc caaagaaagc attcctacta tgctatatca 186000
gtttggaaag aaaaacttct gccaggtgac tgcattctca ctggtcacat tgtgttccta 186060
tggactcctc agctcaacca atttggagaa gttatggtgc aatttcacca tatctggtta 186120
gaagttaagt ttccaatttg ctggcaatga agaagaaatg gagcaggcca ggctgtgtag 186180
tttctgccac gtgccccccgg gagtgaacag ctctgtttgt aagaagccat ggtgcttaga 186240
cctgggctcg ctagttgcca gcctccaaat tgcagaagtg ccctttggtt ggtggctatg 186300
ctgtgtcact tgggaaggtc gtttggaagt tccacagtcg ttgtggggtg ccagagatta 186360
aaaagcgtaa gaggagagtg gaaagtgatt gttgctgctt gggcatcccc accgtgtggg 186420
tgctgcagcc cagctctcaa aacccatggg tctgtacact caacctccat gagagggaag 186480
gagaaggatg agggagggga gagatagcca tggaaaggta ggaactaagc aggcagggtg 186540
gagagttttc tgtaagacaa aaactgtctg gacactgctg cggttctgtt acaaagacca 186600
cttcctccct gggccagcaa catatctgtg tgcctgtctg ggttgtaaaa agggtcaaag 186660
atcaatgcag caggcagcta catgctggca aaagccagag gcagctggtc tgtttgcctg 186720
tgccaggaaa ccactgggaa tggggttgtg tgttattcta ggagaaagtc gtcccagcag 186780
cagcttctcc aggggcatcc aagagcactg aaaagggttg caagatgacc catgaggctg 186840
caggaagaaa agaacatgca tttaatcttg ctatctgaaa agtaagacat gaagctttcc 186900
tcattttttaa tatacacatg gacagtagta tgtgtatata gtttatatgc aaatatactt 186960
gttataaggt tgcatgctca aaatttttgg ttcatgggt  gtgggatcat aaatgtttag 187020
ggaccatggc tatcaaggaa aaacagcatg aaggataaat gatactggtg gattaaaaag 187080
acagatgcat gtatttttag cataaaaacac aactgctgac tgatacagat agctcaagat 187140
tctggggcag ctgctgaaca gatacactag ccagtgtggc tcatcggctc agacttggcc 187200
```

```
ttaattaatg ggctgtccct ccacccatct cccatgaggg cagagctgag ccagggtttg   187260
agagctaaaa ggaattggac ctggactctg ttcacgtgta tattttaatt ctaattaatt   187320
cattcttttg aaagacagag tcacactctg ttgcctaggc tggagtgcag tggcacgatc   187380
ttggctcact gcaacctcgg cctcccaggt tcaagttatt ctcctgcttc agcctcctga   187440
gtagctggga ttataggcac atgccccat gcctgactaa ttttttgtatt tttagtagag   187500 acggggtttc accatgtcag gctggtcttg aactcctgac ctcaggttat ccacccgcct   187560
tggcccctca aagtgttgga attacaggtg tgagccaccg tgcctggcct gttcacatgt   187620
ataaaacaca gtttaatgtc ctattcccag ccaatgagca tggctagagc agccttggtc   187680
aaagtttggt ttttggagaa aaatccttgt tagctgacct aagattcctc tttgtgagtg   187740
taagtaagca caggttgcag agaggagaag ggtctctgga gaggtgtaat tttctaaatg   187800
gattacaagt tcatggactt ttaacaggtg ttacagggga taacaagttc tttatagaca   187860 gactttttgag gacgtttaag ggtattctga ttcttggttt tctaagaggg gaatgtatta   187920
tttaactaca gacaccccta ccgcccactt tttgcagagt gtatcaaaac atgttttttgg   187980 aataccaccc tcatgtcgct tctccctgca tctcttatct cttggtgtcc attctagact   188040
cactttcttt ctgttttta ttttatttt ttttgagat ggagcttcac tctgtcacca   188100
ggctggagtg cagtggtgca atcttggctg actgcaacct ctgccttccg ggcttaagca   188160 attttttgtgc ctcagcctcc tgagtagctg ggattacagc atgcaccacc atgtccggct   188220 aatttttttgta tctttagtag agacagggtt tcactatgct ggccagcctg gtctcaaact   188280
ccttacctca ggtgatctgc ccgcctcggc ctcccagagt gctcagatta cagacgtgag   188340
ccactggtgc ctggcctaga ctcactttca agtggcatag acttgtaaaa ttatttaaag   188400
gtgataggtc tacaatgatc ctgtcaatta gtattgacac tattattaat aaactgttat   188460
taattatatt tacttacttt aaattaatcc aaactaatta acggaacact aaagagtttc   188520
tatgttttat tcccagaggt ggagaaaaat gaaagggaat atagcaacga attctttttct   188580 ccataaaaac atgaatagtg cagcacatca agttgaacat accacagcaa attgttgcaa   188640
gatctgctga gtagctccta tttagacctc aaggaatgag actcaaaatg ggttcatcag   188700
ttctgttttg cagaaaaaat agcgcaaaat ttctcaaaag aaaatccaga ataataataa   188760
tttgtcaata ggaaagacat ttccactggg ggttaagaag gaagacattg gaacaatgat   188820
agccaccact tattgaatgc ttactgtgag ccaggtggca cttcacccttg tttcattctc   188880 acaacagtct agggaagtaa ttactaatgt ctccatccac ctcttgtaga tgagcaaact   188940
gaggctcatt gaggctagga aatgcaccca cactcacata gcccataaga ggcagccatg   189000
gcattgggcc cagaccatgt gaacttcaaa gactacacga gcagccactg ggcagctgtc   189060
atggctaaag ccacttgaat tcagcccagc agcaacccccc tctccaggag gggcacataa   189120
gcttgcagct ttgggtagaa gctgcacttg aagtcctgga tggcgagagg gactggcttg   189180
agccagagcc aggaacaagg ctctgagaat attctggaaa tccacaggag gaaccccattt   189240 tcttacagct gggagaattt cattcaactc caggctgacc atgttttatt aggaacgaag   189300
gtgacttgaa ctaatagtca ggaatggttg aatacggacc caatgtcaaa tcactaggca   189360 gttcacatttt ctaatgagca aatcccttag acaattaaga attttttttcc ttttgcataa   189420 cccagacaaa atcgctactt aaaaacaaac caaagacccg aaacatgaga aagaaagga   189480 agcagggaa atctttggta ctaataagtt tttaaacaat aagagcacca gatattttac   189540
```

```
cccatcagac acagaatgtt attcgaataa ccaaaaaagg aatttttcct ctaagtttct 189600
tgaactggaa aatgaatcat attttctcag tcctgaggct gcaattttgt gcctctagta 189660
acatataaga atagatgtga tgccagtgcc cagtagctgc tgcaattgtt acttggggac 189720
ctgtttattc actaagcact tcaccccagt gataaatttg taggggcctc ctgcccttg 189780
gagctcctac cgtgtccatt agatcagtgg aaattctggg attcagagca ctttgcaagg 189840
tcagcagggg tctgctcttt ctgtcctgtt cctggttttt ggttgtgcct ggattccagg 189900
gtaggtttct catctgttac cttcatagac ttctccagaa aaggatcttt tgaccatcag 189960
aggaccacga agattccatt ggtgaggcgc agataacctg atctctctgg ttctctgca 190020
gggcacagat gaagggctgg ccattcccaa gttctcagtg gtaccactga ggcatgagac 190080
cctaatggtt tgcatgagca gtttgaaaat tgcatctttg tttttaccta tataatcaca 190140
tgaaacccgt ggttctcaaa cgtcagcagg catcagcatc acatggaggg cttgttaaaa 190200
cagatttctg ggccccaaca cagagtttta aattctgaag gcctgaggtg ggtgtgaaca 190260
tttgcatttc taacatgttc tcgatgctgc tgccgcctct ggtcccgaga gcatgcctgg 190320
agaactgcca ccttcgacca tggactgtga gaattcacat ggacctcaga attataatca 190380
gtctctcagt tttacagata aggaaactaa atccagagag attgttttgc caatggtgaa 190440
cagctggtta aagtcaggat ggagactttta atcctagtca agtgaccttt cctctgtatt 190500
tatttccctc ccttttttatg cctctcaagt ctagttacac tgtttttcat ggatgggcat 190560
atttattgtc ctgatctgga ctgcagactt tcaggagga cacctatgat ttaatttagt 190620
atagttgaag agttaacaga catggctttg gagacagact gattatggtg tgaatcccgg 190680
cttttgccact ccctagctgg atgaccctga gcaagttatt cagcttctcc aagcctgagt 190740
tccttattgg aaacatgaga gcaattgtga taggcagaat aatggccccc tcaccaatca 190800
tgcccacatc ctaatcctag gaacctgtga atatgttatg ttacatggca aggggaaatt 190860
caggcagcta gccagttggc cttaaaataa agagattatc ctggatgatc tgggtaggac 190920
ctgatgtaac cacaagggtc tttttaatgt ggaagaagga ggcataagag tagatgtcag 190980
agtcattcaa aataagaaag atttgatggg ccatccctga ctttcaggtt ggaaggaggt 191040
tctgagtcaa ggaatacagg tgacctctag aagctggaga aggcaaggaa atggtttctc 191100
ccctagaagt tccagaagga ttgcagccct gctaatatct tgactttata gcccttgag 191160
atttattttg gatttctgac atcctgaacc atagtaaaag ggtgttttt gtttttttga 191220
gacagagtct tgctctgttg cctgggctgg agtgcagtgg tgtgatcttg gctcgctgca 191280
acctccgcct cccaggttca agtgattctc ctgcctcagc ctcctgagta gctgggatta 191340
caggtgcttg ccaccacacc tggctatttt ttgtgttttt agtagagaca gggtttcacc 191400
atgttggcca ggctggtctt gaactcctga ccttgtgatc tgcctgcctc agcctcccaa 191460
attgctggga ttacaaggcg tgttgtttta agccactcag tttgtggcca cttgttacag 191520
cagcaagagg aaactcatac agttatcatg tgaactcaca ggaatatggt gagttaaaaa 191580
gagaggaagg gtgcaaaaca tccacggtag agtgagaact ctccagggag tgaggactgt 191640
gcccagcata cagtgatcac cctcttagta agctaagttt ctgagcacca gctttttga 191700
gttgactttg ttgtctttaa catttgaaga tcacccttct ttgctcagcc tggcttgcag 191760
acctgggctg atttgtggat ctgatagaaa agtttcctta gttgggctct tctccccgac 191820
cacccccatg ccagtgtggc cacatcctct gtctgcattg ctcactcttc aattccaaga 191880
agcgcagggg caccgccagg aacaggaacc ctgccagagg aatacatcaa gaaaccaagt 191940
```

```
ctcccttacg catcaccgta ggaacagagt taatggatta tgaacatgtg tttgctttat    192000
accattgttt gtttcccagg tggcagctgg ctgccccatc ttattgggta gatgtaagtg    192060
gaattacgaa tgggatttat gtttcatgca cgatggtgat tattaacttc aactttcagg    192120
taattttcag accacattgc actaacttgg tctctgattg ttttctcct tgtttgttta     192180
ttctgcagcc agaactgtgt agatgcgtac cccactttcc tcgctgtgct ctggtctgcg    192240
gggctacttt gcagccaagg taactcagac ttccctttgt tcattctcct tctataaagt    192300
gcatctcaag gaggttcaaa gggcaggctt tttgttgaaa ggactttgcc tgacctctgg    192360
ctcccatctg tgaagccctg gagaggtgag agccctcggg aggccgtgtt tcaggcatgc    192420
tctgcacccg tgcagagcgc gtgtgataat gcattgctaa tgcttgctcc ctggtggctg    192480
gctgagagct gctgtgctga caagggtggt ttaaggctaa atgtgactca gaatccttaa    192540
gcagtgttag ttcagataca agggcattat aaatgagagt gcctgaggga tctatttggg    192600
gaccgctgtc acttggctct tctgctaata agcttccagt gtggtggccc tccttcaggc    192660
atgtttccac tgagccacgg gctggatgcc acatccccgg ccttcccaca gttatcagca    192720
gcccacaggc ttgacttgag caagttggaa agacaaatca acttccagag ttgatttaac    192780
attgagtgga aatcagtcat acttttggtc ccctttcggg gccacgcctg gcactgtgcc    192840
tggtggcaga tcggcatgaa ctggccagct tctgtggccc tggagggcac aggcagaaag    192900
gcccacactca gtcccatgat gaactgttta agacttattg ttgtctcccc gctctgtaaa    192960
gtagatagag tggattttat gtcccttatt acctttcagg atactttgac tcagggagat    193020
aaagtaactt gggtacagct actcagctgg tgaagaacac aggcagaatg agtgcctggg    193080
tcttttgact taaaattctg gattttcac aaagatcctc ttactttatt catttacata     193140
ataaatatat attgaagagc tactctgtgc caagccctgt gcctagatat acagtgataa    193200
ataaagagta gcttctagag gtcacctggc ggtgaggcac aggccagctg gcaagatgga    193260
ccacagaagt cagtgaatga agacaatgac aagggtggga agcgccatat gggaagagaa    193320
ccaagttcag tgatagagag cagaggtgag gcggcagcag aaaccactta agggacacca    193380
cgtggcactc cttctgtgct gagaaggctg tcagtaagct caccatttat ttcctatttt    193440
ctctcctgag ttaaatagga aacatgtctc gcattacttg aaaaatcaag tcaaactatg    193500
ctcttactag gagttatggt tcttttatg tcttagatga tgcttgatct agatgaatgc     193560
ggacttgctg tagctagata aatacaatgg gagtttgaag gtgtttcgta gccctggaaa    193620
taggtatttc ctgtcaaaac aagctttgtc attgccagca gacaaaagca tcagtaacct    193680
tggttgataa tcgtcatttc ttaggaataa agtagactgt agaattttt ttagcagaaa     193740
ggaaacccaa agataattct agtgcaaatc cctcacttta tagagcagaa gctcaagtcc    193800
cagaggaaca agtggcttga acgaacatca gaattttagg ggctggattt gtaccctcct    193860
ggtgccagca gcccacttcc ctgcaggagg cactcaccct ccttgcacag gggtatgagt    193920
gtggccattt tccacccata atctctgtta gctcatgttc aattgggttc ccattgaaag    193980
aaaaatggac cagtaagttg gagcagaatc attcagatgg tataacataa ggaaaaactt    194040
tgcccaaggc aaatcgtgat tgtgacagct ttgtgatttt tagagaatag catgggccag    194100
gcacagtggc tcatgcctgt aatcccagca ctttgggagg ccgaggcagg caggtcactt    194160
gaggttggga gttcgacaac agcctgacca acatggagaa accctgtctc tactaaaaat    194220
acaaaattag ctgggcgtgg tggtgcatgc ctgtaatgcc agctactcgg gaggctgagg    194280
```

```
caggagaatc acttaaacct gggaggcgga ggttgcggtg aaccaagata gcaccattgc   194340
actccagcct gggcaacaag agtgaaactc cgtctcaaaa agagttcaca gtttctcttt   194400
tgctttgatt ttcttatctg ccggataaca atagtatttt ggaaggcagg aggaattgtg   194460
gaaagaaatg ggttttgggg agtggctgat tggaggcaaa tccaaggaca ctcattgctg   194520
gtgtgtgact ccaggcagtt actcagcttt tccaagcctc agtttcctta ttgtaaaaca   194580
ggaccatggt ctagctagta gcattcctat ggtgagtgaa ataatatgta taaagctcct   194640
gacacagtgc ttggcatata tcagattgag ccatgtaaaa ctgccaatat ctggctattt   194700
atgacctaca aaaatagcat ttcatatgat tccacctaac atctgaagcg caataaatgt   194760
tattattgat aatgcaggtg gtggtgataa agttttgaaa tcagaaagac ctggcttcaa   194820
attccacgcc ttcactggcc tgacttattt tcattcattt gacaaatatt attttgaaca   194880
cccctatgtg ccaggcacta tgccaggctc agagatgatc taggaaaaag acagatgtcc   194940
tcatctgtct taggctcttg tggcctaagc ctaaatttcc tcgtctgtca aatggtgaca   195000
gtaacacact ccttaccaga gagctgggag gattggagac tcaagttccc aaaacgccag   195060
gagcactgcg gcaggtgaaa agtattccct caatggcgga agtgtttaaa ttgcttttat   195120
atctgtagct ctagataaca ctagttccag cttagttaac tcccagctcc aagccttcag   195180
gacttcatag agttattggg gtgctgctct tggcagtttc ccaaaaagct agaatgcaga   195240
gggaatctcc ttcccaaaaa gctagaatgc agagggaatc tccttcccaa aaggctagaa   195300
cgcagaggga atctccttcc caaaaggcta aacgcagag ggaatctcct tcccaaaagg   195360
ctagaatgca gagggaatgt ccttctcttc taaatggtag ctgttagttc aagaaaggtt   195420
aaacattgtg ctgtggggag gctcagggg gaagggtgta cttttaagag aaccagtttc   195480
agagctgggt ttggggttta agccctaccc tctgcccct tttacgagct gacagcctta   195540
tgcaagcctg gttgaccacc tgaacccacg tttccacatc tggaaataga aatgtgggta   195600
ctagttatgt tgaaaggact caggttagat gatagatatg caaataccct ggaaaccagg   195660
agtgtccagt ctttttgggtt ccctgagcca cactggaaga agagttgtct tgggccacac   195720
atagaataca ctaaccctat caatagctga tgagctaaag aaaaaacgtt gcaaaaaaaa   195780
tctcatattt ttaagaaagt ttatgaattt gtgttgggct gtattcaaag ccatcctggg   195840
ccacgtgcga cccgcaggct ccgggttgga caagtttgtt gtaaacaatg ccatgatgcc   195900
ggcataaggt cgttaccagt attaggaagg ttctcaggtt tcctctagcc cttgggctct   195960
tttcctgaag tgcgtgtgtc ttctgctaga ttttgtgacc aatgttgatt gcctaattgg   196020
gctaacagca tgttttggtg gctacgaaac tgacacaggt gttttcattt ctccacttag   196080
ttcctgctgc gtttgctgga ctgatgtact tgtttgtgag gcaaaagtac tttgtcggtt   196140
acctaggaga gagaacgcag aggtaggtaa ctgggactac taaagaactg tggagcgatt   196200
cctgattttt gagcaggaag agtgacaatt caaaacagta tttgactaga ttcacggctc   196260
cgtagcatcc ccttgggtgg gaggggaag gctgactagg acctctgatt cttctttccc   196320
tgagctttga aggctctgaa aatacagctg ggggacttg cccagttttc ttattaagca   196380
attcctccgc atggtgctgg ctttcaaagg gtgcttcagt gctgtttgct gcacgtgcct   196440
tgcagcccca caccctgcac tcccgccctg cagagtctgg cgctggaatg acattttagg   196500
tctgggttcc caggcctcct gagagtgaaa tgtttcattg tttgtctaga gaaatgagaa   196560
ctaaagcttg caccttgtga taagttgtcc tgaggaacat atctttcagg gaccagaaga   196620
aagaatgttg ggaaaataag atgcagtaag atgcagacat gacagcaggg tgcagcggct   196680
```

```
cacgcctata atcccagcac tttgggaggc tgaggtgggt ggatcacctg aggtcaggag   196740
tttgagacca gcctggccaa catggtgaaa ccccgtctct actaaaaaat atacaaaaca   196800
ttagccaggc atggtggtgg gcgcctgtaa tcccagctac tccataggct gaggctggag   196860
aatcgcttga acccaggagg cagaggttgc agtgagccga gattgcgcca ctgcactcca   196920
gcctgggcaa caaagcaaa actccatctc aaaaaaaaa aaaaaaaaa aaaaaagat   196980 gcagacacga gactgtgaaa ctgactagca tcaccattgc attgtttata gatgttgcca   197040
gacagaaagc cccaaagcag cacagtacct tcctgacatc tggactagga aatctagatt   197100
ttagtaaaat acatgctaat acttacagaa gaaatgtcgg cgttagagta tgccgtcagt   197160
tccttagaga ttgcaattcc taatgcacta gtatggtttc aggtgccagg aacacgttct   197220
gtgaggctgc tgcccaggt gctgacccca gccttccaca ccattttcct tccttgtgtt   197280
cacagccgct ctgtctttta caatagcacc cctctctagt ggctaatggg ctctatgatt   197340
agatagcatc cttcagtagt gataaaggca gtgacatcct agggaggtca gcgggtgaaa   197400
gcgctatatc tggaaaacct gagagcctgt gaagctcaag gacttgacgg ggttagaccg   197460
tgagccgggc tgcagctgga aaaagaatga ctgttctttc agcagatcct tccctgtgcc   197520
atctctttct tcattcctct ctagtggcat tcttatttat cctctaaaac cacaattcca   197580
ttatctctcc tattcttatc aacactgccc taaatgatat tctttattct cttttgccct   197640
ggaaaacctc tatcatgcct tttcccatgt gattacctcg ttaagagtgg gggtggaatg   197700
tctagcaatg aaataagagg gtcttctctt ttgcctggct ccctatgcag ccctatctta   197760 cccctgcaa agtcccaggg atgtggctca gtcactgctc ctctcttcat ctgtcaccac   197820
ttgcttgaga tcctacagct gctttaattc cgagaccatc tgcagaacat gacaaaattt   197880
gtccacctac ccacatgtcc ttttaacttt aaaggcttta ctaactgatt cctattaggg   197940
aatgaacaga ggtggcaaaa ataaacaata ggagattgat ttacaagaaa tctttaaaat   198000
agtagatttc ttcggacctc attgaaatat aaatggcctg ccttcttgtg tccctccctg   198060
gtctccctct ttaggtgata agaagaagat cctgccagcc cataacccg ccatctgcgc   198120 gggttctaga cccccttctc ctcccctctg gccgtggtag gcattactga tgaatcatgg   198180 tgctcttct tccagagacc aaacctggcc tcggaatcct tcttaacaca gatactgctt   198240
aacacaacca ctctgagcag ctgtcataag tagaagtaat agatactaga agaaatgtct   198300
aagcctaatc tagaccaaaa tacggcctga tatagatgca agccgagggg gctttatggt   198360
taaatgcaag gagatttttca accctgccgt ctagaagcta cttgctgaga tcttcttcag   198420
ttgggcccat ctcctcccca ggcctctctt ctgttcctgg gctatgtcac acttggactc   198480
tgcagacacc taatgctctt gggacctgct ttagttcttg acctcaccaa ccgaggagga   198540
attgctagat gagatccttc ccccggaatt tctctcttga accccagatg gtccgttgcc   198600
cctttccaga agttgctcca gccctgtccg cttaggaagt tcagtgtcat ccttgatcca   198660
gtgggtaggg aagacattcc ataatgaatg ccccagtctg agcttcttcc ttcaggcttc   198720
aggctgccct gcgaggattt tgcagctccc tttttaatgc cctctagaag tttctggctc   198780
ttattttcag cccttcatcc tactctctct gaccccttcc tctatcctgt ttagttcacc   198840
tgtagcagtt actacccagc agtgaaggat gaatcttggt ttcgtttctt ttctcttctt   198900 ttctttttc tcttctcttt tccccttccc ttccctccc tccctcaca tcacctcatc   198960 tcacctcacc ttacatagtc ttgctctgtc acccaaactg gagtgcagtg gcctgatctt   199020
```

```
ggctcactgc aacctccacc tcttcccagg ttcaagtgat tcttatacct cagcctcttg 199080
agtagctgag actacaggtg tgcactacca cacccagcta attttttgta tttttagtag 199140
agatagggtt tagctatgtt ggccaggctg gtctcgaact gctgaactca agcaatctgc 199200
catccccggc ctcccaaagt actgggagta taggcataag ccacccatga tgcccagcct 199260
gaatcttggt ttcttcccca ttcatttaag ctattacctg ggcctgaact caatggcacc 199320
tggcaccaac tggcaactga ctcttggtct tttattacct accttcccta gcaggcactg 199380
ggttgctccc tcttcctatc ccatggagtc ctgtcctctg ttggggctcc tactgatcct 199440
cttggcaata tgaagttctc agctcaatgg tgggtgggca atgactgcca actcttgagg 199500
ccaatgaact caggttaccc cactcctcct cctcctgagt tgctcactca ctcctcattc 199560
actcaacatt gattcagtag atatttgcta cctgctctgt gccaggtacc aggtcagttg 199620
ctgaaggagt aacagtgaac atgacggagt ctttgtcccc aaggagaccc aaggtgtctc 199680
ctagagccag gggcacattg caagaccaaa tatattcaac ttaccaaaat aatcatagac 199740
ctagttctca aaaagcaaga agactgattc ctcgttgtca tttctcctcc tcagcatcaa 199800
tgttttagag tctgtgggcc cctccaagtg tggagtatgg tgttacttca ccagagtttg 199860
aggagaaaca ttcttctttt ggaaggccgg ggagcataga tggatatcaa ggctgctgtt 199920
tctaaaagcg aaacccacca aacaacagta ttagaatcat ctgtggtgct tattaaagat 199980
acagattcct gggccccatc ccagacttat gaatcagaat ctctgccaga ggaagcctga 200040
gaatttgcat tctcagatga ttctgcattc tcagataaca cattctttag gtgattctta 200100
cacacactgg agtttgggaa tcgctgaagg ctgttcactt ctcttttctg agaaatgatt 200160
cattcatttc agaaatattt gcagaggtcc ttatttattg gagatttgtg ggtgggcaga 200220
ggagaaatat cttgtcctca cagagcttac aattttttatt tctttagag gtcaccaggc 200280
ttaaaatgac acttccctaa attctgaaaa gaacagattt ttaaaacaag aagggactgt 200340
aatgttttct gttcctacct cgtatttttgt tcacattaag aacctggggt gggaagtgga 200400
ggagggggg tgactggcgg ggggccacag agagctgagc tggggtggtc tcgaactcct 200460
gaactcaagc aatctgccag cctcagtctc ccaaagtgct gggattatag gcatgagcca 200520
cccacgatgc ctgggtggaa ctcagggctc tggatgcctg ggcgccccca tctcccacac 200580
tacggcgcct catcctagaa gtggttagca cctttgagat gggaattatt tagcaggatg 200640
cttttgtgtt ttcatgtaag ttttatgctg cctgtggagg gcacagctgt ttcaaaacta 200700
ataaccaaat cctggtctcc gaagtctgaa ggcatccttt gccctgcagt gcaaagcacg 200760
ggattctggc ctcacacagg caggtctgaa ctcctgtgtt gcctcttgct ggctgtggga 200820
cctgaggcaa atcatgcaac ctctcttttc tgtttgccta gatggaaaat aggtttacaa 200880
tacgccccca taggatggct gtgagaatta aggaagtca tgggtgtaca atacctggcc 200940
ccgaaagatg cttaataatt taattctgac cttcctcact catttaggat tatgtaccaa 201000
cttttagaaa caatgaaaga ttagtgagtc ttctgtggtt ggtataaaaa aaaaatagaa 201060
acatgaaaga gatgtcctcc ttgttcaagg gctaatgacc ctggtgtgcg ctgtctaggc 201120
ccccaaggtc ttccttccct gctcacagca tttcaggttc tccgcagctt tgctgagcct 201180
gggtcaggtt cggtatctgc ccaccatgct cacttgccac agctgtggcc ccatttccaa 201240
acttcagaga cttaaaggtg cagctaatga tgtgcccggc ctggggtcac attccctgag 201300
ccctgcagac aagggagcag gaggctgagc tcttatcttc cacaccctgt gcacagcctg 201360
ggaagagtta aagcacccta gtcctatgct gcgagggcca catgccctga gaccttggaa 201420
```

```
aaaatcctac ctgaattgaa gagcatcact atttcatcag gaggcgctgc catttcattt   201480
ttcacttcgg ttttatcttg agtgtaaaac agcttcgcaa atcacttttt cttgtttctg   201540
taatgagcat atggtggcct cattcgtgtg ataaatctga gccaccacga tatttgactt   201600
ttcacaattt aatttatctg aaccctctat tctctggcta aaaaatatcc cttacttgga   201660
cttctttatt ttattttcaa ttcccttacc agcactagca ggggactctg tactcatctg   201720
ctggcgctgc cataacaaag cactgcagcc tgggggctc aaaccacaga atttattctc    201780
tcacagtcct agaggctaga agtccaagat caaagtgtgg gcagggtcgg tttctcctgc   201840
agcctctctc cttggcttat agagtgccac cttctacctg tgtcttcaca tcatcacctc   201900
actgagcatg tctgtgtcca aatctcccct tcttataaga ccccagtcat actggatgag   201960
gatccaccca tatgagttca ttttaccttta attatctctt taaacaccct gtctccaaat   202020
acagtcccat tctgaggaac tgagagtaaa gattcaacat atgaattttg aagggacct    202080
aattcagccc acaacaccct cttttgggat gtttattttc cccttaagg agctagttag    202140
gatgtcttat ctcatgaaca tgactgtgaa caggaaaaca gggagagaat gaagctggcc   202200
aaggaacagg gctggtgtca gctagcagtg cttttctgat gtgagtgggt cccacaggga   202260
gcttgttaaa atgcagattc tgattcatta ggttccagag ggacctgaga tttcccattt   202320
ctgacaagtt tccagtgtgg gggctgatgc tgctggtcca cggaccatac tttgagtagc   202380
aaggagcttg atacataatg gctgagtgac tttcagactc ctgctgtaga aaaattatga   202440
gttggctggg cgtggtggct cacgcctgta atcccagcac tttgggaggc cgaggtgggc   202500
agatcacctg aggtcaggag ttcgagacca gcctggccaa catggtgaaa caccatctct   202560
accaaaaata caaaaattag ccaggtgtgg tggcaggtgc ctgtaatccc agctactcag   202620
gaggctgagg caggagaatc gcttgaaccc gggaggcaga ggttgcagtg atctgagatc   202680
gtgccactgc actccagctg ggcaatagag cttgactcag tctcaaaaaa aaaaaagaa    202740
aagaaaaaga aaattatga gttatattat cagcatatgg ggtgcctttc aaattgataa    202800
aatttctaat attaaacctg tggatgccaa atgctgctct ctgattatgg caggaaacgg   202860
cacttggcag tacgaagtta gctgttgggc tgagctggct catcttgttg tgcggtcctg   202920
attgcctaaa gatgccttcc caggatcttt actaacaatc ctcctgagtc atttggactt   202980
tcccaacctg ttatcacctc tcagatgggc cagccatgga ggcagtcaga ggagggctct   203040
gcagagggag ggcagaaaca gggtggcctc tgcatgccat taggaggtca catctccactg  203100
ggggatgcag tttaggattt agtgccttgg agagaaggat agagtatatt aaaacatgtc   203160
tccgctaggc atggtggttt acgcctataa tcccagcact tgggaggcc gaggtgagtg    203220
gattgcctga gctcaggagt tcaagaccag cctggctaac atgacgaaac ctcatctcta   203280
ctaaaataca aaagttagc tgggagtggt ggcgtgcgcc tgtagttgca gctacttggg    203340
aggctgaggc atgagaatca cttaagccca gaagactgag gttgcagtga gccgagattg   203400
caccactgca ctccagcttg ggctacagag tgagactcta tctcaaaaac aaagaaacaa   203460
acaacaacaa taacaacaaa aaccaagtct ctccctccac tcaaaaatgc aagggcctgt   203520
ctcccattgc tgggtgccca ggtctcatga atgtagatat gaattattcc agtcagcctc   203580
aggagaatag aatgagccct cagatgccga agcaccttc agattccacc ggttttatcg    203640
gctcatttaa acttcacttc taacacagtc ctgcattaca cacgtgtctg tcgttatggg   203700
cagctgcaga gagggtctta atggtcctaa tgctcagtga ggatgcccaa tggtcaacag   203760
```

```
aacctgccat cttcaggcca tcaaggagct ctggagttaa ggaaatcatg agagcacaga 203820
ggggcgggta cagcagagcc ctcgtggtaa tgggttttga ggtctaggct ctcttcactt 203880
gggtttgaaa taagttcaat gactagtaat agctgagaca cttctaccct tcaaatgaag 203940
taaatgggaa aatggagcat tgttgagtcc agggagctat aatttaaacc ccatatatct 204000
aaaaggggta acatttttgt gtgtgtgaaa ttggtgtcat tcgcactgca tctacagttt 204060
tcttttttcct tctcttccag cacccctggc tacatatttg ggaaacgcat catactcttc 204120
ctgttcctca tgtccgttgc tggcatattc aactattacc tcatcttctt tttcggaagt 204180
gactttgaaa actacataaa gacgatctcc accaccatct cccctctact tctcattccc 204240
taactctctg ctgaatatgg ggttggtgtt ctcatctaat caatacctac aagtcatcat 204300
aattcagctc ttgagagcat tctgctcttc tttagatggc tgtaaatcta ttggccatct 204360
gggcttcaca gcttgagtta accttgcttt tccgggaaca aaatgatgtc atgtcagctc 204420
cgccccttga acatgaccgt ggccccaaat ttgctattcc catgcatttt gtttgtttct 204480
tcacttatcc tgttctctga agatgttttg tgaccaggtt tgtgttttct taaaataaaa 204540
tgcagagaca tgttttaagc tgatagttga gggttttgt taatggcttt tgggggatttt 204600
atctctatac ccacaaacga ctagtttgtt ttcctcaaac taaatgataa tattaaaaat 204660
acacatcctg gccaggtgtg gtggctcata cctgtaatcc cagcactttg ggaggccgag 204720
gcaggtggat cacttgaggt caggaattaa gaccagcctg gccaatatgg tgaaagcctg 204780
tctgtactaa aaatacaaaa attagccagg tatgctggtg gatgcttata atcccagcta 204840
cttgggaggt tgaggcagga gaattgcttg aacccgggag gtagaggttg cagtgagcca 204900
agatcatgcc actgcactcc agcttgggca acagagtgag actccatctc aaattaaaaa 204960
aaatacacat ctggcttctg gaaaaattac ttgaagatct tttatgacat ccatccctct 205020
tcacacagcc atgtgaatta ggttggtatc ttcatatact agcatcgtgc ccagcacttc 205080
catgttatac agtttaaaat gttctgtaat tccctgtggg aacctaagat aatgcgagga 205140
ccgtcatacg tgcccccaaa tattggcaaa ccaatgaata aatgaatgaa tgagtttatg 205200
aatcgctaac tggctgtatt taatgaagta tgtgtgttga gccatttccc acagtgtgga 205260
cagatttgtc ccacaatatg ggcctcttcc caaaggccct accacctaat gccatcacac 205320
tggggatttg atttcaacat gtgaatttgg ggagagtgca aacactcaga ccatagcacc 205380
atctcagtaa atgtcccact ggtcactcag ttcatagtga cagtgatcca gccactgtca 205440
tgacaggtgc cacttggcag aaacagcaca gcttggaaga tggcggggtg tagtcaagat 205500
tccaggatcc ccaacagaga agccagctct tataggggag ccattcatca ggattgaact 205560
ctcaatcgag ctggacagta ataggtgggt ctgtgttatt ccccagatga gtatcatgac 205620
agtcacaatc ctaggaagga tgtgaagcct cccccagctc tcctccagtt gcctgcttgg 205680
gcagcagaga tgatgaatg tggagtctgg cgtggtctga ggcctgaatc catgtgcctc 205740
atgtatgatg ctcaggcaag aggatctctc aattcaaggg agagggcctg aatgagcctt 205800
gctttccagg cctgtctgat ggtccaggct gaagcccctc ctggcttgca ctgccagacc 205860
tcatccagca ggagctcctt ggcattgact gcttcaggat agttgcttct gctctgagtg 205920
ctctctaaag agcagtgctc taccatccaa gctgggcttt tcttttcttc ttgctgatag 205980
ggaaggcatg ggacattgca ggatggaagt ggcccccagg ccttctcatg cctgggcttg 206040
gtttggaagg tggtcaggtg atcaataatc ctgattggcc tggcattgag gagttttcct 206100
gggatgtggt cctttcggtt ttttaaaaat tatttttatt gatacacata tttgtaggta 206160
```

```
tttgtggggt gcatgtgata ctttattatg tgtgtggatt gtgtaatgat gaagtcaggg  206220
catttagggt cttcatcacc ttgattatca tttctatgtg ttgagaacat ttcaagttct  206280
cagttccagc tattttgaaa tagacagtcc attttgttag ctacagtcac ccaacccggc  206340
tgtcagacat tggaacttac tcctattgaa ctgtgtattt gtacccattc accaaactct  206400
ctttgggctt tcagttttac aactgggatg atcctgggaa aactaaagta aatcagacac  206460
ccgacgtgtg agctaggtta taatatgccc agtggaccct ggggacatct tagctttcag  206520
aggtcatgct gtccaagctg actgtggggc ttccagaagg tggggagagg aaatgatgca  206580
atggcccatc agaggcacta cttggggcct ggggccagag tgcatgtcta aggcattaag  206640
gggaggggag agcagccttc ataattatga agaggagtct caggtgcaca gcttctgatg  206700
agggacagct tctaattgaa gacagcattg tgtaatgctc aaactccctg tcttcagagt  206760
gcctgctgta tcccaccatc agttctgtga cttctcccta agcctcaatt ttgcatgtgt  206820
tacattggga taataatagt gccaaactca tgggggttgtg aggaataatg aggtaaagca  206880
attgaaaagg tttagcacaa tataagtgct caataaaagc cattattatt attttattac  206940
actagttttc aattcctgca tagcaaattc ttgcaaatgt agggactcaa aacaatataa  207000
atttattatc tgacagtttt tctgggtcag aggtcttact aggctgtaat cagagggcaa  207060
ccaaagctgt gatctcagct gaagctcagg attctcttcc aagctcactg gttgttggca  207120
gaattcagtt ctttccagtt ggaagactaa agcctacagt cttcagtctc tagaagcctt  207180
ttctctggca caggtttctc tacaacatgg ccatttatgt ctttaaggcc aataggagaa  207240
catgattagc atattttttt taagtgaact ttagacccctt tttttaaaggc ctatctgatt  207300
aggccaggcc caagtgagct ttaagtcaac tgattagaga tcttaattac atctgcaaag  207360
tcccttcatg tttaccgtat aacataactt agtgaaagga gtgaaattgc aaccaggttc  207420
tgcctgcact ccacggaagg ggattctgca gaagtgtggg tcacgggggg gttattttgg  207480
gattctgcct acgtcactga gtcaaaagaa gctgaatggt tgtgatgctg aggttttgg  207540
gcagcagcag tgtgtgtgtg tgagtgaatt catacgtatg accacctggg aagaaaggag  207600
gctgtggttt cctccaccctc ctggcagaca gagaaatttc ttttttttt tgagacaggg  207660
tctggctctg ttacccaggc tggagtgcag tggcttgatc tctgctcact ggctcactgc  207720
agcctctgcc tcccaggttc aagtaattct tgtgcctcaa ctccaagtag ctgggattac  207780
agacacacac tgccacgcct ggctaatttt tgtatttta gtagagacga ggttttgcca  207840
tgttggccag gctggtcttg aactcctgac ctcaagtgat ccgcccacct cagcctccca  207900
aagtgctggg attacagacg tgagccacca ttaaccattt ttctatctcc tgtgggaaag  207960
ggcacagtga agaacagat gaagctgaga catacaagtg aactcctccc tcctctccat  208020
ttagactaaa ataggattat tcatactgag attctccctg gttgcaaaga gataatctgt  208080
gcaactgggt ttttacaatt atccctaccc tatgctttcc tcatctgtct tcctcgtagt  208140
cagctcaggc tgctataaca aaacaccata actgggggct tttgaacaac aaaacttttac  208200
ttctcacagt tctagaggct ggaaatccaa gatcaagttt ctggcagatt cggtgtctaa  208260
tgaggtcctg ctttccagtt tatagacagt gccttatcgc taccgcctta cacagtggaa  208320
ggagaggacg agaagctcct tgggcttttt tttgtttctt tctttctctc tctctctctt  208380
ttttttttttt ttaataaggt cactatctta gtccattttg tgttgctaaa aggaacatct  208440
gaggttgagt aatttatttt attttaaaaa gtggccaggc atggaggctt atcctgtaac  208500
```

```
cctaatcctt taggaggcca aaacagcagg attgtttgag gccaggagtt caagaccagc  208560
ctaggcaaga tagtgagacc ccatctaccc catctctact aaaattttaa aaaattagct  208620
gtgtgttgta aagtgtgctt gtagtcccgg ccacttgaga ggctgaggtg ggtggagttc  208680
aaggctgcag tgagttatga ttgagccact gcactccaac ccgggtaacg gggcaagacc  208740
ttgtctctat ttaaaaaaaa aaaatcttta tgtggctcac tattctgggt ggctggaaag  208800
ttcaagattg ggcatctgca tctggtgaca gcctcatgtc gcttccagtc atggggaag  208860 acgaaggaga gctggcacgt gcagatatca cgtgttgagg gcagaagcga gagagagagg  208920
ggagagatgc caggctcttt ttaacaacca gcactgggga aactaataga gtgagagctc  208980
actgactcct gagggaggac attaatctat tgatgagcga cctgcctcca tgacccaaac  209040
acctccaacg ataccccacc tccaacactg ccacactagg gattaacttt caacttgaga  209100
tttagagggg ggaaacttac aaactatcgc aggcactaat accactcatg agggctccac  209160
cttcatgacc taatcacttc ctaaaggcct tacctcttaa tctcatcaca ttgaggattc  209220
gatttcaact tgaattttgg ggggacacca acattcaggc catagcatca tctcaataac  209280
tgtcccattg gtggtcactc aggccccaaa caaaggaacc ttcctccatt cctttccgcc  209340
ctcccaccca cagtcaatca tccccaagct ccatcagctc cacctttaac ggccaaccca  209400
cctctgccac atctcaccat ctccactgct atccctgtca cctgggccca ccattctctc  209460
tcctggacag tctccatagc cacctctgtc agatttattt tattttttta ttttttttt  209520 tgagacaggt tcctgctctg ttgcccagac tggagtgcca tggcatgatc acatctcact  209580
gcggcctcca tcacctgggc tcaagcaatc ctcccatctc agcctcccaa gtagctggga  209640
ctactggcac caccatacct ggctaatttt ttgttgttgt tgtttaattt ttaatacaga  209700
tgaagcctca ctatgttgcc caggctgctc ttgaactcct gggctcaagt gatcctccgg  209760
ccttggcctc ccaaagtgct gggattacag gcatgagcca ccgtgcccag cccatcagat  209820
gttaatgcta cacgcacttg cttaaaatcc cccagataat tctcgctgct cttggaataa  209880
ttcccacaca ccttggcgtg gccatgcagg ctctgtgcca tcggatatgt ccctgccccc  209940
tctcccaact cctcctttcg cttgctcgtt cactcagttc cagccacatt gccctgggag  210000
ctgctcccac catggggctt cctaatgcac tggtctctct catgcagtgg ggcctctccc  210060
tccttttact cagtgtctcc cagcacccac ctcctccaga gccttccctg accaccacac  210120
ctacacctag gcccttcctc ctccacgctc cctcctccac cccggcctcc tacccacgtg  210180
tcacttcttt atactcgctg ccacctgaaa ttagatcatt tatttacccc tttatttgtt  210240
cagtttgcct tgtccgttag aatataagct tccaaagggc aggagctttg cctatattgt  210300
taggccgggc atacaatgag cactcaaaaa aatatttgat gagtgtatga aagaacagac  210360
tgggttatgt aattgtgcct acttacctat atgaccgtgt ggtggggttt atggtgggtg  210420
tggtggtgat ggctataggg ctataagcaa atttgggaca gggagtctaa gaaatgttct  210480
taaattttag taagcaaagc atcctctaca gaacctgtct aaaacatga aagttcctta  210540 gtgctacccc cagaggtatg atttggtagg tcaaggatag ggcctggaaa ttcacattct  210600
tgttaagatg ttcttcatcc ggggtttgtt gaccaccttt tcagaagatt tttgctctgt  210660
agctgtacta cccaatgcag tagttcgtag tcagtgtggc tcctgagccc ttgaagtgta  210720
gctcctctga actgagacgt gctgtaaatg taaattgcac accggagttt gaagagttaa  210780
tacaaagaaa aaggaatgca aaacatctca ttaataatgc tttacactga ttacatattg  210840
aaatggtaat cttgtagata tagtgcgtta aataaaatat actgttaggc ttaatttcac  210900
```

```
gtctttatac ttttaatgtg gctactagaa aaatttaaat aacatattca gctcacatta 210960
tactcctatt gaacagagct gatctataag ttccatggaa gatggcaagt cttcgcagct 211020
gaaataaagg ctggatccca ttctacgggc tcatctttag caatgatttc ttgcagacga 211080
tattgaaaaa tgtggcaatg aaagttacca caagcatcaa accagtcctg cctaaatctg 211140
gaaaatagtt atctgaggct gttagcatat gatcatgaga gcgtttcacc atggatttct 211200
gatcacagat gtggcacatt attaaaatat cacttttaca gtcaccctag aggctagggt 211260
tatctgaata tggagaaaga aacagcttgt ggagctgttg tataaatgaa attactagaa 211320
agtaatgcac tcaattgcat attggctcgg ggggttattc ttattaaaat gtttagagag 211380
gactttctgt tcatttctgc agaattgctc ttcaaattaa gaatttgctt gacacgctaa 211440
tagaccacag tcccaagaga agtttatcct ttttcttct tatccttgct aagcacttag 211500
atgctctgct gataggtagc atatattgtc tatatgaagc ttttgtgtta acattgacta 211560
gtcctgcaag ttggcacact cttacttggc ctaaagaaa tcagcaccag gctttaagaa 211620
aatcagatga tctacctaaa ggaacacaac tctgtctctc ttttgacaat tgttgtaaac 211680
aaattttaat ggaaatttgc cttaattgtg aagaagttgc tgctaaaatg gacttgccat 211740
taatggactg gaacccattg cataagcaga atgaaatata agccttctca ggattcacac 211800
ttataaaaaa ccattcagcc aatcaacaag agggcaaaag aacaaacatt tgatgtgtaa 211860
ttacttaatt tagtgcatat gcatttgggt cctcaatgtc agcactatgg caaccagaac 211920
atggccacaa taactgtctg gaaatgtcta ttcttacctg gacccagcag gccatgcccc 211980
actgattata taatctccct ctctccttgt tacggtctga atgcttgcat ccctcaaaaa 212040
ttcatgtgtt gaaatcctaa ccccaaggt gatgatatta ggaggtcggc cttttgagag 212100
gtaattaggt catgaagaca gcatcctcat gaatgggatt agtgtcctta taaaataggc 212160
ccaagggagc tcattcactt tgtccaccat gtgagaacac agcgagaggg caccatttat 212220
gcaccaggaa atgggccttt tccagacaat ctgtcggtgc ctggatcttg gacttcacag 212280
cctctagaac tgtgagaaat taatttgttt tttataagcc accaaatcta tggtttttt 212340
tatagaaacc gtaatggact aaaacactcc ctaattatat ttaaacttat cagtgcactg 212400
ggcagtgaca tattaaaaga atgctggcca acgtaattga caccataagg ctggatgatt 212460
cttgtaattt tcagcctcag aaaaaggctg gggagaggag tcaggggaaa ggaggtggtg 212520
tgtgtgtgtg tgtgtgtgtg tgtgtgtgtg tgtgtggtac ggtggatgcc tgctgagaga 212580
gaaagagcta taataacatt ctgtggttca gctgacacat cctttctgca tcccctccaa 212640
tcacctgggt taatggggac ctcgctaatg tctgaacctc atctcatttt aaccttttgt 212700
ttcaaagcct ctctttttcat gacttccccg ccttcatttt tcccatatgg tggggttatt 212760
attaagacat taaatgagag tggacaggta ggcaaaggag gtgggttgca ggggagttga 212820
gggttgcctg tgtactttc tagactgttc cacttcacat cagtgaaata ttcccaattg 212880
atactatcat gaaacaaagc aaatgaaatg ctgagcacgg agcttcgtct tgatgaaatg 212940
ctgaaagaaa agaaaggaaa aataaagtag ccattatttt tgcccttcct cccacccca 213000
tgtttactac tcttatttct cttttgtatt gttgtgttgg aagcacagca tcagaaaaac 213060
tcccagtttt gagagataac tcagtgttta gttcacttaa acctgagaaa ggagaagagg 213120
atgccaccgt gaggtccagg acgtaaagag gaaaaaaaca gacaaaaaaa tccatatgaa 213180
atgaaaatgt gaaagaggcg ctttcgagca gatgagtgtt gtagattaca gtgttgagag 213240
```

```
ctgtttgtgt ccagagctgc ttgctgcacc tggcgggata aacactggtc taacagagga  213300
tccttgtttc aaggaggctg ccttttattt gggggggacaa aattgttctt gaaagctgct  213360
cagtggttca agctacagca tggtggacta gcagaatgga ctccagggcc tccgaggaga  213420
cagtgactgc tgccagaaat agtcaaggat agaaggaag gacttcactg aggcctggga   213480
gaagattatg gaatgggact gacagcagtg acgggagta aaaggggtg tctggggaa    213540 ttgtgcccca tggtgagagc tagagggttc acaaagactt aacccgacgc atctctctca  213600
ccctggagat tgggcccgtt caatctaact ggatggctat aatttaaaag gtttaggtat  213660
tatgacaaac atggatatat taggtgatag caatgcaaaa tgcatatggc ttcttgatat  213720
aaaacacaag acttgaaagc agcatctttg ctgggtact acagccaccc tcctctgtca   213780
ctaagggagg ctttggtgga aagggctgag agcctctaga ctgtgaacaa agtaggcac   213840 agaagaacag ttggagataa taagtaaacc atcttgacag gaatgaagaa tttcctgaaa  213900
ggaaggtccc tgagttaggt tgttggatgc tttcagtagt gagttattga aagtgtttgg  213960
ggggtgtgtg tgtgtgtgtg tatgtgcagt atgtgtgtgt                        214000

<210> SEQ ID NO 2
<211> LENGTH: 161
<212> TYPE: PRT
<213> ORGANISM: Homo sapiens

<400> SEQUENCE: 2

Met Asp Gln Glu Thr Val Gly Asn Val Val Leu Leu Ala Ile Val Thr
1               5                   10                  15

Leu Ile Ser Val Val Gln Asn Gly Phe Phe Ala His Lys Val Glu His
                20                  25                  30

Glu Ser Arg Thr Gln Asn Gly Arg Ser Phe Gln Arg Thr Gly Thr Leu
            35                  40                  45

Ala Phe Glu Arg Val Tyr Thr Ala Asn Gln Asn Cys Val Asp Ala Tyr
        50                  55                  60

Pro Thr Phe Leu Ala Val Leu Trp Ser Ala Gly Leu Leu Cys Ser Gln
65                  70                  75                  80

Val Pro Ala Ala Phe Ala Gly Leu Met Tyr Leu Phe Val Arg Gln Lys
                85                  90                  95

Tyr Phe Val Gly Tyr Leu Gly Glu Arg Thr Gln Ser Thr Pro Gly Tyr
            100                 105                 110

Ile Phe Gly Lys Arg Ile Ile Leu Phe Leu Phe Leu Met Ser Val Ala
        115                 120                 125

Gly Ile Phe Asn Tyr Tyr Leu Ile Phe Phe Phe Gly Ser Asp Phe Glu
    130                 135                 140

Asn Tyr Ile Lys Thr Ile Ser Thr Thr Ile Ser Pro Leu Leu Leu Ile
145                 150                 155                 160

Pro

<210> SEQ ID NO 3
<211> LENGTH: 873
<212> TYPE: DNA/RNA
<213> ORGANISM: Homo sapiens

<400> SEQUENCE: 3
acttcccctt cctgtacagg gcaggttgtg cagctggagg cagagcagtc ctctctgggg    60
agcctgaagc aaacatggat caagaaactg taggcaatgt tgtcctgttg gccatcgtca   120
ccctcatcag cgtggtccag aatggattct ttgcccataa agtggagcac gaaagcagga   180
```

```
cccagaatgg gaggagcttc cagaggaccg gaacacttgc ctttgagcgg gtctacactg      240
ccaaccagaa ctgtgtagat gcgtaccca ctttcctcgc tgtgctctgg tctgcgggc       300 tactttgcag ccaagttcct gctgcgtttg ctggactgat gtacttgttt gtgaggcaaa      360
agtactttgt cggttaccta ggagagagaa cgcagagcac ccctggctac atatttggga      420
aacgcatcat actcttcctg ttcctcatgt ccgttgctgg catattcaac tattacctca      480
tcttcttttt cggaagtgac tttgaaaact acataaagac gatctccacc accatctccc      540
ctctacttct cattccctaa ctctctgctg aatatggggt tggtgttctc atctaatcaa      600
tacctacaag tcatcataat tcagctcttg agagcattct gctcttcttt agatggctgt      660
aaatctattg gccatctggg cttcacagct tgagttaacc ttgcttttcc gggaacaaaa      720
tgatgtcatg tcagctccgc cccttgaaca tgaccgtggc cccaaatttg ctattcccat      780
gcattttgtt tgtttcttca cttatcctgt tctctgaaga tgttttgtga ccaggtttgt      840
gttttcttaa aataaaatgc agagacatgt ttt                                   873
```

```
<210> SEQ ID NO 4
<211> LENGTH: 24
<212> TYPE: DNA
<213> ORGANISM: Homo sapiens

<400> SEQUENCE: 4
cctttgcttt gttcctattt cttt                                              24

<210> SEQ ID NO 5
<211> LENGTH: 20
<212> TYPE: DNA
<213> ORGANISM: Homo sapiens

<400> SEQUENCE: 5
tcccattgcc cagagttaat                                                   20

<210> SEQ ID NO 6
<211> LENGTH: 23
<212> TYPE: DNA
<213> ORGANISM: Homo sapiens

<400> SEQUENCE: 6
tcctcatgtc ttcacctaga agc                                               23

<210> SEQ ID NO 7
<211> LENGTH: 20
<212> TYPE: DNA
<213> ORGANISM: Homo sapiens

<400> SEQUENCE: 7
ccactcatga gggagctgtt                                                   20

<210> SEQ ID NO 8
<211> LENGTH: 21
<212> TYPE: DNA
<213> ORGANISM: Homo sapiens

<400> SEQUENCE: 8
tgtcacaggc acacactctc t                                                 21

<210> SEQ ID NO 9
<211> LENGTH: 20
<212> TYPE: DNA
```

```
<213> ORGANISM: Homo sapiens

<400> SEQUENCE: 9
gagtatggct gctgctcctc                                              20

<210> SEQ ID NO 10
<211> LENGTH: 20
<212> TYPE: DNA
<213> ORGANISM: Homo sapiens

<400> SEQUENCE: 10
atggctcaca ctggcctaaa                                              20

<210> SEQ ID NO 11
<211> LENGTH: 23
<212> TYPE: DNA
<213> ORGANISM: Homo sapiens

<400> SEQUENCE: 11
tgaacagacc aataatagtg cag                                          23

<210> SEQ ID NO 12
<211> LENGTH: 20
<212> TYPE: DNA
<213> ORGANISM: Homo sapiens

<400> SEQUENCE: 12
aagccaccct ttaaacagca                                              20

<210> SEQ ID NO 13
<211> LENGTH: 20
<212> TYPE: DNA
<213> ORGANISM: Homo sapiens

<400> SEQUENCE: 13
gctgaggaag caactccact                                              20

<210> SEQ ID NO 14
<211> LENGTH: 20
<212> TYPE: DNA
<213> ORGANISM: Homo sapiens

<400> SEQUENCE: 14
gctctgaatt ccctggcata                                              20

<210> SEQ ID NO 15
<211> LENGTH: 21
<212> TYPE: DNA
<213> ORGANISM: Homo sapiens

<400> SEQUENCE: 15
ttagccctag tcccactctc c                                            21

<210> SEQ ID NO 16
<211> LENGTH: 20
<212> TYPE: DNA
<213> ORGANISM: Homo sapiens

<400> SEQUENCE: 16
caagaggcct gcataaggaa                                              20

<210> SEQ ID NO 17
<211> LENGTH: 20
```

```
<212> TYPE: DNA
<213> ORGANISM: Homo sapiens

<400> SEQUENCE: 17
agattgccgg tggcttaaat                                            20

<210> SEQ ID NO 18
<211> LENGTH: 20
<212> TYPE: DNA
<213> ORGANISM: Homo sapiens

<400> SEQUENCE: 18
tgtctgttcc cgtctgtctg                                            20

<210> SEQ ID NO 19
<211> LENGTH: 20
<212> TYPE: DNA
<213> ORGANISM: Homo sapiens

<400> SEQUENCE: 19
ttcatcctct gccaaattcc                                            20

<210> SEQ ID NO 20
<211> LENGTH: 20
<212> TYPE: DNA
<213> ORGANISM: Homo sapiens

<400> SEQUENCE: 20
ggcatgtatt cactgcctga                                            20

<210> SEQ ID NO 21
<211> LENGTH: 23
<212> TYPE: DNA
<213> ORGANISM: Homo sapiens

<400> SEQUENCE: 21
aaacccattc ttcttcctct tac                                        23

<210> SEQ ID NO 22
<211> LENGTH: 21
<212> TYPE: DNA
<213> ORGANISM: Homo sapiens

<400> SEQUENCE: 22
tatgtgttca gcccagacct c                                          21

<210> SEQ ID NO 23
<211> LENGTH: 19
<212> TYPE: DNA
<213> ORGANISM: Homo sapiens

<400> SEQUENCE: 23
ccctgccatg tgcatttac                                             19

<210> SEQ ID NO 24
<211> LENGTH: 20
<212> TYPE: DNA
<213> ORGANISM: Homo sapiens

<400> SEQUENCE: 24
catttcggaa ggcaaagaaa                                            20

<210> SEQ ID NO 25
```

-continued

```
<211> LENGTH: 20
<212> TYPE: DNA
<213> ORGANISM: Homo sapiens

<400> SEQUENCE: 25
ttgcaatgag gaatgaagca                                              20

<210> SEQ ID NO 26
<211> LENGTH: 23
<212> TYPE: DNA
<213> ORGANISM: Homo sapiens

<400> SEQUENCE: 26
tccattatcc atctgttcat tca                                          23

<210> SEQ ID NO 27
<211> LENGTH: 25
<212> TYPE: DNA
<213> ORGANISM: Homo sapiens

<400> SEQUENCE: 27
gaagaattaa ttgtaggagg caaga                                        25

<210> SEQ ID NO 28
<211> LENGTH: 21
<212> TYPE: DNA
<213> ORGANISM: Homo sapiens

<400> SEQUENCE: 28
ctgacatcac cacattgatc g                                            21

<210> SEQ ID NO 29
<211> LENGTH: 22
<212> TYPE: DNA
<213> ORGANISM: Homo sapiens

<400> SEQUENCE: 29
catacacagc catgtggaat ta                                           22

<210> SEQ ID NO 30
<211> LENGTH: 20
<212> TYPE: DNA
<213> ORGANISM: Homo sapiens

<400> SEQUENCE: 30
acggtgatga cgcctacatt                                              20

<210> SEQ ID NO 31
<211> LENGTH: 23
<212> TYPE: DNA
<213> ORGANISM: Homo sapiens

<400> SEQUENCE: 31
tcacatggac caattaccta gaa                                          23

<210> SEQ ID NO 32
<211> LENGTH: 25
<212> TYPE: DNA
<213> ORGANISM: Homo sapiens

<400> SEQUENCE: 32
aaattacttc atcttgacga taaca                                        25
```

```
<210> SEQ ID NO 33
<211> LENGTH: 20
<212> TYPE: DNA
<213> ORGANISM: Homo sapiens

<400> SEQUENCE: 33
ctattgggga ctgcagagag                                              20

<210> SEQ ID NO 34
<211> LENGTH: 20
<212> TYPE: DNA
<213> ORGANISM: Homo sapiens

<400> SEQUENCE: 34
agccagtgtc cacaaggaag                                              20

<210> SEQ ID NO 35
<211> LENGTH: 21
<212> TYPE: DNA
<213> ORGANISM: Homo sapiens

<400> SEQUENCE: 35
gagggtgaga cacatctctg g                                            21

<210> SEQ ID NO 36
<211> LENGTH: 20
<212> TYPE: DNA
<213> ORGANISM: Homo sapiens

<400> SEQUENCE: 36
aatcgtgcct cagttccatc                                              20

<210> SEQ ID NO 37
<211> LENGTH: 20
<212> TYPE: DNA
<213> ORGANISM: Homo sapiens

<400> SEQUENCE: 37
ccaccaggaa caacacacac                                              20

<210> SEQ ID NO 38
<211> LENGTH: 18
<212> TYPE: DNA
<213> ORGANISM: Homo sapiens

<400> SEQUENCE: 38
ttgctctcca gcctgggc                                                18

<210> SEQ ID NO 39
<211> LENGTH: 18
<212> TYPE: DNA
<213> ORGANISM: Homo sapiens

<400> SEQUENCE: 39
ttcctctggc tgcctgcg                                                18

<210> SEQ ID NO 40
<211> LENGTH: 20
<212> TYPE: DNA
<213> ORGANISM: Homo sapiens

<400> SEQUENCE: 40
tcctgcatga gaaggaactg                                              20
```

```
<210> SEQ ID NO 41
<211> LENGTH: 20
<212> TYPE: DNA
<213> ORGANISM: Homo sapiens

<400> SEQUENCE: 41
cgacattcac tgtggctctt                                              20

<210> SEQ ID NO 42
<211> LENGTH: 20
<212> TYPE: DNA
<213> ORGANISM: Homo sapiens

<400> SEQUENCE: 42
tttgattccg tggtccatta                                              20

<210> SEQ ID NO 43
<211> LENGTH: 21
<212> TYPE: DNA
<213> ORGANISM: Homo sapiens

<400> SEQUENCE: 43
ttatttggtc ggtgcacctt t                                            21

<210> SEQ ID NO 44
<211> LENGTH: 20
<212> TYPE: DNA
<213> ORGANISM: Homo sapiens

<400> SEQUENCE: 44
ggtgcaccga ccaaataagt                                              20

<210> SEQ ID NO 45
<211> LENGTH: 22
<212> TYPE: DNA
<213> ORGANISM: Homo sapiens

<400> SEQUENCE: 45
ccagcttatt ctctctgcct tc                                           22

<210> SEQ ID NO 46
<211> LENGTH: 22
<212> TYPE: DNA
<213> ORGANISM: Homo sapiens

<400> SEQUENCE: 46
ggtaggttga aatgggctaa ca                                           22

<210> SEQ ID NO 47
<211> LENGTH: 21
<212> TYPE: DNA
<213> ORGANISM: Homo sapiens

<400> SEQUENCE: 47
tcatgacaag gtgttggatt t                                            21

<210> SEQ ID NO 48
<211> LENGTH: 20
<212> TYPE: DNA
<213> ORGANISM: Homo sapiens

<400> SEQUENCE: 48
cctcctctgc catgaagcta                                              20
```

```
<210> SEQ ID NO 49
<211> LENGTH: 20
<212> TYPE: DNA
<213> ORGANISM: Homo sapiens

<400> SEQUENCE: 49
ctatttggtc tgcgggttgt                                              20

<210> SEQ ID NO 50
<211> LENGTH: 20
<212> TYPE: DNA
<213> ORGANISM: Homo sapiens

<400> SEQUENCE: 50
tactgggtta tcgcctgacc                                              20

<210> SEQ ID NO 51
<211> LENGTH: 20
<212> TYPE: DNA
<213> ORGANISM: Homo sapiens

<400> SEQUENCE: 51
ccaatggacc tcttggacat                                              20

<210> SEQ ID NO 52
<211> LENGTH: 20
<212> TYPE: DNA
<213> ORGANISM: Homo sapiens

<400> SEQUENCE: 52
tttcggcaca gtcctcaata                                              20

<210> SEQ ID NO 53
<211> LENGTH: 19
<212> TYPE: DNA
<213> ORGANISM: Homo sapiens

<400> SEQUENCE: 53
cagctgggtg tggtgacat                                               19

<210> SEQ ID NO 54
<211> LENGTH: 20
<212> TYPE: DNA
<213> ORGANISM: Homo sapiens

<400> SEQUENCE: 54
cagagaggaa caggcagagg                                              20

<210> SEQ ID NO 55
<211> LENGTH: 20
<212> TYPE: DNA
<213> ORGANISM: Homo sapiens

<400> SEQUENCE: 55
agtggctggg aagccttatt                                              20

<210> SEQ ID NO 56
<211> LENGTH: 23
<212> TYPE: DNA
<213> ORGANISM: Homo sapiens

<400> SEQUENCE: 56
```
aggtgagaga acaaacctgt ctt                                            23

<210> SEQ ID NO 57
<211> LENGTH: 20
<212> TYPE: DNA
<213> ORGANISM: Homo sapiens

<400> SEQUENCE: 57
gccttccttc taaggccaac                                                20

<210> SEQ ID NO 58
<211> LENGTH: 26
<212> TYPE: DNA
<213> ORGANISM: Homo sapiens

<400> SEQUENCE: 58
ctgtagactt tatccctgac ttactg                                         26

<210> SEQ ID NO 59
<211> LENGTH: 24
<212> TYPE: DNA
<213> ORGANISM: Homo sapiens

<400> SEQUENCE: 59
caatgaatga tgaagattcc actc                                           24

<210> SEQ ID NO 60
<211> LENGTH: 23
<212> TYPE: DNA
<213> ORGANISM: Homo sapiens

<400> SEQUENCE: 60
tgacaccatg tcttactgtt tgc                                            23

<210> SEQ ID NO 61
<211> LENGTH: 25
<212> TYPE: DNA
<213> ORGANISM: Homo sapiens

<400> SEQUENCE: 61
gaggatacaa tgagaaccaa atctc                                          25

<210> SEQ ID NO 62
<211> LENGTH: 20
<212> TYPE: DNA
<213> ORGANISM: Homo sapiens

<400> SEQUENCE: 62
caggatcatc agccaggttt                                                20

<210> SEQ ID NO 63
<211> LENGTH: 20
<212> TYPE: DNA
<213> ORGANISM: Homo sapiens

<400> SEQUENCE: 63
gctgcatgtc actaggcatt                                                20

<210> SEQ ID NO 64
<211> LENGTH: 20
<212> TYPE: DNA
<213> ORGANISM: Homo sapiens

<400> SEQUENCE: 64
ccacagaatg ctccaaaggt                                               20

<210> SEQ ID NO 65
<211> LENGTH: 22
<212> TYPE: DNA
<213> ORGANISM: Homo sapiens

<400> SEQUENCE: 65
gagttcaagt gatggatgac ga                                            22

<210> SEQ ID NO 66
<211> LENGTH: 24
<212> TYPE: DNA
<213> ORGANISM: Homo sapiens

<400> SEQUENCE: 66
cagatagatg aataggtgga tgga                                          24

<210> SEQ ID NO 67
<211> LENGTH: 20
<212> TYPE: DNA
<213> ORGANISM: Homo sapiens

<400> SEQUENCE: 67
cactgttcca agtgctttgc                                               20

<210> SEQ ID NO 68
<211> LENGTH: 20
<212> TYPE: DNA
<213> ORGANISM: Homo sapiens

<400> SEQUENCE: 68
tatgcgttgt gtgtgctgtg                                               20

<210> SEQ ID NO 69
<211> LENGTH: 22
<212> TYPE: DNA
<213> ORGANISM: Homo sapiens

<400> SEQUENCE: 69
gggccttaga ttcttgtagt gg                                            22

<210> SEQ ID NO 70
<211> LENGTH: 20
<212> TYPE: DNA
<213> ORGANISM: Homo sapiens

<400> SEQUENCE: 70
tgtccagact gcctcctaca                                               20

<210> SEQ ID NO 71
<211> LENGTH: 20
<212> TYPE: DNA
<213> ORGANISM: Homo sapiens

<400> SEQUENCE: 71
tgcaacacct ggttcacaat                                               20

<210> SEQ ID NO 72
<211> LENGTH: 20
<212> TYPE: DNA
<213> ORGANISM: Homo sapiens

```
<400> SEQUENCE: 72
tttgcgagtc cttgtggagt                                                   20

<210> SEQ ID NO 73
<211> LENGTH: 20
<212> TYPE: DNA
<213> ORGANISM: Homo sapiens

<400> SEQUENCE: 73
acagtccgct ccctcctaat                                                   20

<210> SEQ ID NO 74
<211> LENGTH: 18
<212> TYPE: DNA
<213> ORGANISM: Homo sapiens

<400> SEQUENCE: 74
atgcttggcc ctcagttt                                                     18

<210> SEQ ID NO 75
<211> LENGTH: 21
<212> TYPE: DNA
<213> ORGANISM: Homo sapiens

<400> SEQUENCE: 75
ttggcaaccc aagctaatat g                                                 21

<210> SEQ ID NO 76
<211> LENGTH: 19
<212> TYPE: DNA
<213> ORGANISM: Homo sapiens

<400> SEQUENCE: 76
ctccacagtg acagtgagg                                                    19

<210> SEQ ID NO 77
<211> LENGTH: 17
<212> TYPE: DNA
<213> ORGANISM: Homo sapiens

<400> SEQUENCE: 77
gagaggttcc caatccc                                                      17

<210> SEQ ID NO 78
<211> LENGTH: 20
<212> TYPE: DNA
<213> ORGANISM: Homo sapiens

<400> SEQUENCE: 78
cagctcctgg ccatatttct                                                   20

<210> SEQ ID NO 79
<211> LENGTH: 20
<212> TYPE: DNA
<213> ORGANISM: Homo sapiens

<400> SEQUENCE: 79
gagccatttc tctgggtctg                                                   20

<210> SEQ ID NO 80
<211> LENGTH: 20
<212> TYPE: DNA
<213> ORGANISM: Homo sapiens
```

-continued

<400> SEQUENCE: 80
ggtccgtgtc aaccctaga                                        20

<210> SEQ ID NO 81
<211> LENGTH: 19
<212> TYPE: DNA
<213> ORGANISM: Homo sapiens

<400> SEQUENCE: 81
caggttgatg ggagggaaa                                        19

<210> SEQ ID NO 82
<211> LENGTH: 20
<212> TYPE: DNA
<213> ORGANISM: Homo sapiens

<400> SEQUENCE: 82
cgggaaatga cagtgagacc                                       20

<210> SEQ ID NO 83
<211> LENGTH: 20
<212> TYPE: DNA
<213> ORGANISM: Homo sapiens

<400> SEQUENCE: 83
tgcctagatt ctcccgtaag                                       20

<210> SEQ ID NO 84
<211> LENGTH: 16
<212> TYPE: DNA
<213> ORGANISM: Homo sapiens

<400> SEQUENCE: 84
gtgcccagcc agattc                                           16

<210> SEQ ID NO 85
<211> LENGTH: 16
<212> TYPE: DNA
<213> ORGANISM: Homo sapiens

<400> SEQUENCE: 85
gcccccagtc aggttt                                           16

<210> SEQ ID NO 86
<211> LENGTH: 21
<212> TYPE: DNA
<213> ORGANISM: Homo sapiens

<400> SEQUENCE: 86
tttctctctc cacggaatga a                                     21

<210> SEQ ID NO 87
<211> LENGTH: 21
<212> TYPE: DNA
<213> ORGANISM: Homo sapiens

<400> SEQUENCE: 87
aacccattct cacagggtgt a                                     21

<210> SEQ ID NO 88
<211> LENGTH: 20
<212> TYPE: DNA

<213> ORGANISM: Homo sapiens

<400> SEQUENCE: 88
aggagtgtgg cagctttgag                                              20

<210> SEQ ID NO 89
<211> LENGTH: 20
<212> TYPE: DNA
<213> ORGANISM: Homo sapiens

<400> SEQUENCE: 89
tggattcccg tgagtaccag                                              20

<210> SEQ ID NO 90
<211> LENGTH: 17
<212> TYPE: DNA
<213> ORGANISM: Homo sapiens

<400> SEQUENCE: 90
atgctgggat cacaggc                                                 17

<210> SEQ ID NO 91
<211> LENGTH: 19
<212> TYPE: DNA
<213> ORGANISM: Homo sapiens

<400> SEQUENCE: 91
aacctggtgg acttttgct                                               19

<210> SEQ ID NO 92
<211> LENGTH: 20
<212> TYPE: DNA
<213> ORGANISM: Homo sapiens

<400> SEQUENCE: 92
agcatttcca atggtgcttt                                              20

<210> SEQ ID NO 93
<211> LENGTH: 21
<212> TYPE: DNA
<213> ORGANISM: Homo sapiens

<400> SEQUENCE: 93
catgttgata tgcctgaagg a                                            21

<210> SEQ ID NO 94
<211> LENGTH: 20
<212> TYPE: DNA
<213> ORGANISM: Homo sapiens

<400> SEQUENCE: 94
cactgtctgc tgccactcat                                              20

<210> SEQ ID NO 95
<211> LENGTH: 27
<212> TYPE: DNA
<213> ORGANISM: Homo sapiens

<400> SEQUENCE: 95
agagattatg tgatgtaccc tctctat                                      27

<210> SEQ ID NO 96
<211> LENGTH: 20

```
<212> TYPE: DNA
<213> ORGANISM: Homo sapiens

<400> SEQUENCE: 96
tgatgaagat ctgggcgtta                                              20

<210> SEQ ID NO 97
<211> LENGTH: 20
<212> TYPE: DNA
<213> ORGANISM: Homo sapiens

<400> SEQUENCE: 97
tgcctgtgct cactcactct                                              20

<210> SEQ ID NO 98
<211> LENGTH: 22
<212> TYPE: DNA
<213> ORGANISM: Homo sapiens

<400> SEQUENCE: 98
atgacctaga aatgatactg gc                                           22

<210> SEQ ID NO 99
<211> LENGTH: 20
<212> TYPE: DNA
<213> ORGANISM: Homo sapiens

<400> SEQUENCE: 99
cagacaccac aacacacatt                                              20

<210> SEQ ID NO 100
<211> LENGTH: 20
<212> TYPE: DNA
<213> ORGANISM: Homo sapiens

<400> SEQUENCE: 100
tggtttaaaa acctcatgcc                                              20

<210> SEQ ID NO 101
<211> LENGTH: 25
<212> TYPE: DNA
<213> ORGANISM: Homo sapiens

<400> SEQUENCE: 101
atcccaaact ctgtacttat gtagg                                        25

<210> SEQ ID NO 102
<211> LENGTH: 20
<212> TYPE: DNA
<213> ORGANISM: Homo sapiens

<400> SEQUENCE: 102
ccttggctgt tgtgactggt                                              20

<210> SEQ ID NO 103
<211> LENGTH: 20
<212> TYPE: DNA
<213> ORGANISM: Homo sapiens

<400> SEQUENCE: 103
cactcaggtg ggaggatcac                                              20

<210> SEQ ID NO 104
```

```
<211> LENGTH: 20
<212> TYPE: DNA
<213> ORGANISM: Homo sapiens

<400> SEQUENCE: 104
cactttgcca gtagccttga                                              20

<210> SEQ ID NO 105
<211> LENGTH: 21
<212> TYPE: DNA
<213> ORGANISM: Homo sapiens

<400> SEQUENCE: 105
ttgggaaagt aacccagag a                                             21

<210> SEQ ID NO 106
<211> LENGTH: 20
<212> TYPE: DNA
<213> ORGANISM: Homo sapiens

<400> SEQUENCE: 106
tttgggaaga gccatgagac                                              20

<210> SEQ ID NO 107
<211> LENGTH: 20
<212> TYPE: DNA
<213> ORGANISM: Homo sapiens

<400> SEQUENCE: 107
ctctgggcat tggaggatta                                              20

<210> SEQ ID NO 108
<211> LENGTH: 20
<212> TYPE: DNA
<213> ORGANISM: Homo sapiens

<400> SEQUENCE: 108
gggagacaag tcaggtgagg                                              20

<210> SEQ ID NO 109
<211> LENGTH: 26
<212> TYPE: DNA
<213> ORGANISM: Homo sapiens

<400> SEQUENCE: 109
ctgagtatgg agtcttcatc attatc                                       26

<210> SEQ ID NO 110
<211> LENGTH: 22
<212> TYPE: DNA
<213> ORGANISM: Homo sapiens

<400> SEQUENCE: 110
tgctactaga tttgaccaac ca                                           22

<210> SEQ ID NO 111
<211> LENGTH: 26
<212> TYPE: DNA
<213> ORGANISM: Homo sapiens

<400> SEQUENCE: 111
gacttgtaaa ggatttagtg atttcg                                       26
```

```
<210> SEQ ID NO 112
<211> LENGTH: 20
<212> TYPE: DNA
<213> ORGANISM: Homo sapiens

<400> SEQUENCE: 112
gtggaaggcc tctctctgtg                                              20

<210> SEQ ID NO 113
<211> LENGTH: 20
<212> TYPE: DNA
<213> ORGANISM: Homo sapiens

<400> SEQUENCE: 113
tgcttcttga gggaaagcat                                              20

<210> SEQ ID NO 114
<211> LENGTH: 21
<212> TYPE: DNA
<213> ORGANISM: Homo sapiens

<400> SEQUENCE: 114
ccttcagagg atttcccttt c                                            21

<210> SEQ ID NO 115
<211> LENGTH: 20
<212> TYPE: DNA
<213> ORGANISM: Homo sapiens

<400> SEQUENCE: 115
ctggtttgac tccagcttca                                              20

<210> SEQ ID NO 116
<211> LENGTH: 20
<212> TYPE: DNA
<213> ORGANISM: Homo sapiens

<400> SEQUENCE: 116
cctggcacgg aatagacact                                              20

<210> SEQ ID NO 117
<211> LENGTH: 19
<212> TYPE: DNA
<213> ORGANISM: Homo sapiens

<400> SEQUENCE: 117
ggcctccttt gctctgaag                                               19

<210> SEQ ID NO 118
<211> LENGTH: 21
<212> TYPE: DNA
<213> ORGANISM: Homo sapiens

<400> SEQUENCE: 118
catccctgtg gctgattaag a                                            21

<210> SEQ ID NO 119
<211> LENGTH: 20
<212> TYPE: DNA
<213> ORGANISM: Homo sapiens

<400> SEQUENCE: 119
aacagttcca gcccgttcta                                              20
```

```
<210> SEQ ID NO 120
<211> LENGTH: 22
<212> TYPE: DNA
<213> ORGANISM: Homo sapiens

<400> SEQUENCE: 120
tttcaaagga atatccaagt gc                                              22

<210> SEQ ID NO 121
<211> LENGTH: 24
<212> TYPE: DNA
<213> ORGANISM: Homo sapiens

<400> SEQUENCE: 121
tggcgtacca tataaacagt tctc                                            24

<210> SEQ ID NO 122
<211> LENGTH: 20
<212> TYPE: DNA
<213> ORGANISM: Homo sapiens

<400> SEQUENCE: 122
ttcaatgaag gtgccgaagt                                                 20

<210> SEQ ID NO 123
<211> LENGTH: 20
<212> TYPE: DNA
<213> ORGANISM: Homo sapiens

<400> SEQUENCE: 123
tgtctatccc aaagctgcaa                                                 20

<210> SEQ ID NO 124
<211> LENGTH: 21
<212> TYPE: DNA
<213> ORGANISM: Homo sapiens

<400> SEQUENCE: 124
gctcagtcca agttcatgct c                                               21

<210> SEQ ID NO 125
<211> LENGTH: 20
<212> TYPE: DNA
<213> ORGANISM: Homo sapiens

<400> SEQUENCE: 125
tgggattggg ttctggatac                                                 20

<210> SEQ ID NO 126
<211> LENGTH: 22
<212> TYPE: DNA
<213> ORGANISM: Homo sapiens

<400> SEQUENCE: 126
cctactttcc atctcctcct tg                                              22

<210> SEQ ID NO 127
<211> LENGTH: 24
<212> TYPE: DNA
<213> ORGANISM: Homo sapiens

<400> SEQUENCE: 127
tggagtaagt tggagaattg ttga                                            24
```

<210> SEQ ID NO 128
<211> LENGTH: 24
<212> TYPE: DNA
<213> ORGANISM: Homo sapiens

<400> SEQUENCE: 128
gcaagactct gttgaagaag aaga                                         24

<210> SEQ ID NO 129
<211> LENGTH: 21
<212> TYPE: DNA
<213> ORGANISM: Homo sapiens

<400> SEQUENCE: 129
tccctctgtt tgagtttctc g                                            21

<210> SEQ ID NO 130
<211> LENGTH: 20
<212> TYPE: DNA
<213> ORGANISM: Homo sapiens

<400> SEQUENCE: 130
ccttgggcag tcagagaaac                                              20

<210> SEQ ID NO 131
<211> LENGTH: 20
<212> TYPE: DNA
<213> ORGANISM: Homo sapiens

<400> SEQUENCE: 131
cccgtgaagt ctgagaggtg                                              20

<210> SEQ ID NO 132
<211> LENGTH: 19
<212> TYPE: DNA
<213> ORGANISM: Homo sapiens

<400> SEQUENCE: 132
aggcacagtc gctcatgtc                                               19

<210> SEQ ID NO 133
<211> LENGTH: 24
<212> TYPE: DNA
<213> ORGANISM: Homo sapiens

<400> SEQUENCE: 133
aaactttagc taatggtggt caaa                                         24

<210> SEQ ID NO 134
<211> LENGTH: 25
<212> TYPE: DNA
<213> ORGANISM: Homo sapiens

<400> SEQUENCE: 134
gagcatgtgt gactttcata ttcag                                        25

<210> SEQ ID NO 135
<211> LENGTH: 22
<212> TYPE: DNA
<213> ORGANISM: Homo sapiens

<400> SEQUENCE: 135

```
agtggctatt cattgctaca gg                                        22

<210> SEQ ID NO 136
<211> LENGTH: 20
<212> TYPE: DNA
<213> ORGANISM: Homo sapiens

<400> SEQUENCE: 136
ttgctggatg ctggtttcta                                           20

<210> SEQ ID NO 137
<211> LENGTH: 27
<212> TYPE: DNA
<213> ORGANISM: Homo sapiens

<400> SEQUENCE: 137
aaagagagag agaaagagaa agaaaga                                   27

<210> SEQ ID NO 138
<211> LENGTH: 22
<212> TYPE: DNA
<213> ORGANISM: Homo sapiens

<400> SEQUENCE: 138
aaagtggatg cagttgaggt tt                                        22

<210> SEQ ID NO 139
<211> LENGTH: 22
<212> TYPE: DNA
<213> ORGANISM: Homo sapiens

<400> SEQUENCE: 139
gctagccatt acagacaacc aa                                        22

<210> SEQ ID NO 140
<211> LENGTH: 21
<212> TYPE: DNA
<213> ORGANISM: Homo sapiens

<400> SEQUENCE: 140
cagggctcca tgtatccata a                                         21

<210> SEQ ID NO 141
<211> LENGTH: 20
<212> TYPE: DNA
<213> ORGANISM: Homo sapiens

<400> SEQUENCE: 141
caatctttgg ctttgggttt                                           20

<210> SEQ ID NO 142
<211> LENGTH: 16
<212> TYPE: DNA
<213> ORGANISM: Homo sapiens

<400> SEQUENCE: 142
ctggttgagc ggcatt                                               16

<210> SEQ ID NO 143
<211> LENGTH: 16
<212> TYPE: DNA
<213> ORGANISM: Homo sapiens

<400> SEQUENCE: 143
```

-continued tgcagcctgg atgaca                                                    16

<210> SEQ ID NO 144
<211> LENGTH: 22
<212> TYPE: DNA
<213> ORGANISM: Homo sapiens

<400> SEQUENCE: 144
cctatggaag catagggaag aa                                             22

<210> SEQ ID NO 145
<211> LENGTH: 21
<212> TYPE: DNA
<213> ORGANISM: Homo sapiens

<400> SEQUENCE: 145
cccacttctg agtctcctga t                                              21

<210> SEQ ID NO 146
<211> LENGTH: 20
<212> TYPE: DNA
<213> ORGANISM: Homo sapiens

<400> SEQUENCE: 146
gggaaatgga gctgctgtta                                                20

<210> SEQ ID NO 147
<211> LENGTH: 20
<212> TYPE: DNA
<213> ORGANISM: Homo sapiens

<400> SEQUENCE: 147
gagtgggtga gtgcaaggat                                                20

<210> SEQ ID NO 148
<211> LENGTH: 17
<212> TYPE: DNA
<213> ORGANISM: Homo sapiens

<400> SEQUENCE: 148
ctctcagcag gcatcca                                                   17

<210> SEQ ID NO 149
<211> LENGTH: 19
<212> TYPE: DNA
<213> ORGANISM: Homo sapiens

<400> SEQUENCE: 149
gccaacgtaa ttgacacca                                                 19

<210> SEQ ID NO 150
<211> LENGTH: 21
<212> TYPE: DNA
<213> ORGANISM: Homo sapiens

<400> SEQUENCE: 150
tgaaaggaag gtccctgagt t                                              21

<210> SEQ ID NO 151
<211> LENGTH: 21
<212> TYPE: DNA
<213> ORGANISM: Homo sapiens

<400> SEQUENCE: 151
ccctgctttg cacaagttat c                                          21

<210> SEQ ID NO 152
<211> LENGTH: 20
<212> TYPE: DNA
<213> ORGANISM: Homo sapiens

<400> SEQUENCE: 152
cacatgaggc tgtatgtgga                                            20

<210> SEQ ID NO 153
<211> LENGTH: 20
<212> TYPE: DNA
<213> ORGANISM: Homo sapiens

<400> SEQUENCE: 153
tgtgcaggaa tgagaagtcg                                            20

<210> SEQ ID NO 154
<211> LENGTH: 18
<212> TYPE: DNA
<213> ORGANISM: Homo sapiens

<400> SEQUENCE: 154
ccttaggccc cataatct                                              18

<210> SEQ ID NO 155
<211> LENGTH: 21
<212> TYPE: DNA
<213> ORGANISM: Homo sapiens

<400> SEQUENCE: 155
caaattcctc aattgcaaaa t                                          21

<210> SEQ ID NO 156
<211> LENGTH: 20
<212> TYPE: DNA
<213> ORGANISM: Homo sapiens

<400> SEQUENCE: 156
ggtcattcag ggagccattc                                            20

<210> SEQ ID NO 157
<211> LENGTH: 25
<212> TYPE: DNA
<213> ORGANISM: Homo sapiens

<400> SEQUENCE: 157
ccattatatt tcaccaagag gctgc                                      25

<210> SEQ ID NO 158
<211> LENGTH: 20
<212> TYPE: DNA
<213> ORGANISM: Homo sapiens

<400> SEQUENCE: 158
agtcaaggct gacagggaag                                            20

<210> SEQ ID NO 159
<211> LENGTH: 20
<212> TYPE: DNA
<213> ORGANISM: Homo sapiens -continued

```
<400> SEQUENCE: 159
gctctcagcc ctcaatgtgt                                              20

<210> SEQ ID NO 160
<211> LENGTH: 20
<212> TYPE: DNA
<213> ORGANISM: Homo sapiens

<400> SEQUENCE: 160
atttgggttc ctctcccaat                                              20

<210> SEQ ID NO 161
<211> LENGTH: 20
<212> TYPE: DNA
<213> ORGANISM: Homo sapiens

<400> SEQUENCE: 161
acaaactctt gctgctggtg                                              20

<210> SEQ ID NO 162
<211> LENGTH: 20
<212> TYPE: DNA
<213> ORGANISM: Homo sapiens

<400> SEQUENCE: 162
tgcctggtca tctacccatt                                              20

<210> SEQ ID NO 163
<211> LENGTH: 20
<212> TYPE: DNA
<213> ORGANISM: Homo sapiens

<400> SEQUENCE: 163
tctactgcag cgctgatctt                                              20

<210> SEQ ID NO 164
<211> LENGTH: 20
<212> TYPE: DNA
<213> ORGANISM: Homo sapiens

<400> SEQUENCE: 164
tccttccaga aggtttgcat                                              20

<210> SEQ ID NO 165
<211> LENGTH: 23
<212> TYPE: DNA
<213> ORGANISM: Homo sapiens

<400> SEQUENCE: 165
tgcaaagttg ttcaagagag aca                                          23

<210> SEQ ID NO 166
<211> LENGTH: 20
<212> TYPE: DNA
<213> ORGANISM: Homo sapiens

<400> SEQUENCE: 166
cagcaggaag atggacaggt                                              20

<210> SEQ ID NO 167
<211> LENGTH: 21
<212> TYPE: DNA
```

```
<213> ORGANISM: Homo sapiens

<400> SEQUENCE: 167
cacactgcat cacacatacc c                                        21

<210> SEQ ID NO 168
<211> LENGTH: 18
<212> TYPE: DNA
<213> ORGANISM: Homo sapiens

<400> SEQUENCE: 168
tatgccagta tgcctgct                                            18

<210> SEQ ID NO 169
<211> LENGTH: 19
<212> TYPE: DNA
<213> ORGANISM: Homo sapiens

<400> SEQUENCE: 169
gtcacatcag tccatttgc                                           19

<210> SEQ ID NO 170
<211> LENGTH: 23
<212> TYPE: DNA
<213> ORGANISM: Homo sapiens

<400> SEQUENCE: 170
ggtttatgtc tgtgtgtgtg tgc                                      23

<210> SEQ ID NO 171
<211> LENGTH: 23
<212> TYPE: DNA
<213> ORGANISM: Homo sapiens

<400> SEQUENCE: 171
tgagggatgt cagagaaata tgc                                      23

<210> SEQ ID NO 172
<211> LENGTH: 22
<212> TYPE: DNA
<213> ORGANISM: Homo sapiens

<400> SEQUENCE: 172
tgatgaaatt gcctagtgat gc                                       22

<210> SEQ ID NO 173
<211> LENGTH: 20
<212> TYPE: DNA
<213> ORGANISM: Homo sapiens

<400> SEQUENCE: 173
ggatccaatc gtacgctacc                                          20

<210> SEQ ID NO 174
<211> LENGTH: 20
<212> TYPE: DNA
<213> ORGANISM: Homo sapiens

<400> SEQUENCE: 174
acctaaacac cacggactgg                                          20

<210> SEQ ID NO 175
<211> LENGTH: 22
```

```
<212> TYPE: DNA
<213> ORGANISM: Homo sapiens

<400> SEQUENCE: 175
caggtatcga cattcttcca aa                                              22

<210> SEQ ID NO 176
<211> LENGTH: 26
<212> TYPE: DNA
<213> ORGANISM: Homo sapiens

<400> SEQUENCE: 176
ggtgatctag ggaattattt gtcttc                                          26

<210> SEQ ID NO 177
<211> LENGTH: 20
<212> TYPE: DNA
<213> ORGANISM: Homo sapiens

<400> SEQUENCE: 177
ttggccacta aggtccagat                                                 20

<210> SEQ ID NO 178
<211> LENGTH: 20
<212> TYPE: DNA
<213> ORGANISM: Homo sapiens

<400> SEQUENCE: 178
cctttgaggc tggatctgtt                                                 20

<210> SEQ ID NO 179
<211> LENGTH: 23
<212> TYPE: DNA
<213> ORGANISM: Homo sapiens

<400> SEQUENCE: 179
tttccttatc attcattccc tca                                             23

<210> SEQ ID NO 180
<211> LENGTH: 22
<212> TYPE: DNA
<213> ORGANISM: Homo sapiens

<400> SEQUENCE: 180
agatattgtc tccgttccat ga                                              22

<210> SEQ ID NO 181
<211> LENGTH: 22
<212> TYPE: DNA
<213> ORGANISM: Homo sapiens

<400> SEQUENCE: 181
cccagatata aggacctggc ta                                              22

<210> SEQ ID NO 182
<211> LENGTH: 23
<212> TYPE: DNA
<213> ORGANISM: Homo sapiens

<400> SEQUENCE: 182
tttaagccct gtggaatgta ttt                                             23

<210> SEQ ID NO 183
```

```
<211> LENGTH: 21
<212> TYPE: DNA
<213> ORGANISM: Homo sapiens

<400> SEQUENCE: 183
gacattgcag gtcaagtagg g                                              21

<210> SEQ ID NO 184
<211> LENGTH: 20
<212> TYPE: DNA
<213> ORGANISM: Homo sapiens

<400> SEQUENCE: 184
tgcataaggc tggagacaga                                                20

<210> SEQ ID NO 185
<211> LENGTH: 19
<212> TYPE: DNA
<213> ORGANISM: Homo sapiens

<400> SEQUENCE: 185
cacagcagat gggagcaaa                                                 19

<210> SEQ ID NO 186
<211> LENGTH: 21
<212> TYPE: DNA
<213> ORGANISM: Homo sapiens

<400> SEQUENCE: 186
agccagttgt ctttcatcct g                                              21

<210> SEQ ID NO 187
<211> LENGTH: 23
<212> TYPE: DNA
<213> ORGANISM: Homo sapiens

<400> SEQUENCE: 187
tgcctgtgct tgtatattct gtg                                            23

<210> SEQ ID NO 188
<211> LENGTH: 20
<212> TYPE: DNA
<213> ORGANISM: Homo sapiens

<400> SEQUENCE: 188
gtgcatgtgc ataccagacc                                                20

<210> SEQ ID NO 189
<211> LENGTH: 20
<212> TYPE: DNA
<213> ORGANISM: Homo sapiens

<400> SEQUENCE: 189
ggcaagatga cctctggaaa                                                20

<210> SEQ ID NO 190
<211> LENGTH: 22
<212> TYPE: DNA
<213> ORGANISM: Homo sapiens

<400> SEQUENCE: 190
tttgtgttcc aggtgagaat tg                                             22
```

```
<210> SEQ ID NO 191
<211> LENGTH: 20
<212> TYPE: DNA
<213> ORGANISM: Homo sapiens

<400> SEQUENCE: 191
gaaccatatc ccaaggcact                                              20

<210> SEQ ID NO 192
<211> LENGTH: 22
<212> TYPE: DNA
<213> ORGANISM: Homo sapiens

<400> SEQUENCE: 192
ttgttcccac attcattcta ca                                           22

<210> SEQ ID NO 193
<211> LENGTH: 20
<212> TYPE: DNA
<213> ORGANISM: Homo sapiens

<400> SEQUENCE: 193
ttaaactcgt ggcaaagacg                                              20

<210> SEQ ID NO 194
<211> LENGTH: 18
<212> TYPE: DNA
<213> ORGANISM: Homo sapiens

<400> SEQUENCE: 194
caccatgcct ggctctttt                                                18

<210> SEQ ID NO 195
<211> LENGTH: 22
<212> TYPE: DNA
<213> ORGANISM: Homo sapiens

<400> SEQUENCE: 195
aacttctcca gttgtgtggt tg                                           22

<210> SEQ ID NO 196
<211> LENGTH: 20
<212> TYPE: DNA
<213> ORGANISM: Homo sapiens

<400> SEQUENCE: 196
cctaccattg acactctcag                                              20

<210> SEQ ID NO 197
<211> LENGTH: 16
<212> TYPE: DNA
<213> ORGANISM: Homo sapiens

<400> SEQUENCE: 197
tagggccatc cattct                                                  16

<210> SEQ ID NO 198
<211> LENGTH: 25
<212> TYPE: DNA
<213> ORGANISM: Homo sapiens

<400> SEQUENCE: 198
tctgtgtgta ttgtgtactc ctctg                                        25
```

```
<210> SEQ ID NO 199
<211> LENGTH: 22
<212> TYPE: DNA
<213> ORGANISM: Homo sapiens

<400> SEQUENCE: 199
tcacacaatt tgaaccaatc ct                                              22

<210> SEQ ID NO 200
<211> LENGTH: 20
<212> TYPE: DNA
<213> ORGANISM: Homo sapiens

<400> SEQUENCE: 200
accaagatat gaaggccaaa                                                 20

<210> SEQ ID NO 201
<211> LENGTH: 22
<212> TYPE: DNA
<213> ORGANISM: Homo sapiens

<400> SEQUENCE: 201
cctccagcta gaacaatgtg aa                                              22

<210> SEQ ID NO 202
<211> LENGTH: 21
<212> TYPE: DNA
<213> ORGANISM: Homo sapiens

<400> SEQUENCE: 202
tgatcatgtc agcagcagaa g                                               21

<210> SEQ ID NO 203
<211> LENGTH: 20
<212> TYPE: DNA
<213> ORGANISM: Homo sapiens

<400> SEQUENCE: 203
agtaacaggt gagggcatgg                                                 20

<210> SEQ ID NO 204
<211> LENGTH: 21
<212> TYPE: DNA
<213> ORGANISM: Homo sapiens

<400> SEQUENCE: 204
tgtccatagc tgtagccctg t                                               21

<210> SEQ ID NO 205
<211> LENGTH: 20
<212> TYPE: DNA
<213> ORGANISM: Homo sapiens

<400> SEQUENCE: 205
ctcaatgggc atctttaggc                                                 20

<210> SEQ ID NO 206
<211> LENGTH: 22
<212> TYPE: DNA
<213> ORGANISM: Homo sapiens

<400> SEQUENCE: 206
caaacaaaca aacaagcaaa cc                                              22
```

```
<210> SEQ ID NO 207
<211> LENGTH: 21
<212> TYPE: DNA
<213> ORGANISM: Homo sapiens

<400> SEQUENCE: 207
tggacgtttc tttcagtgag g                                         21

<210> SEQ ID NO 208
<211> LENGTH: 23
<212> TYPE: DNA
<213> ORGANISM: Homo sapiens

<400> SEQUENCE: 208
tgataactta ccagcatgtg agc                                       23

<210> SEQ ID NO 209
<211> LENGTH: 21
<212> TYPE: DNA
<213> ORGANISM: Homo sapiens

<400> SEQUENCE: 209
tcacctcacc taaggatctg c                                         21

<210> SEQ ID NO 210
<211> LENGTH: 23
<212> TYPE: DNA
<213> ORGANISM: Homo sapiens

<400> SEQUENCE: 210
gctagcaaat ctctcaactt cca                                       23

<210> SEQ ID NO 211
<211> LENGTH: 20
<212> TYPE: DNA
<213> ORGANISM: Homo sapiens

<400> SEQUENCE: 211
tcttctccat gctgcttcct                                           20

<210> SEQ ID NO 212
<211> LENGTH: 20
<212> TYPE: DNA
<213> ORGANISM: Homo sapiens

<400> SEQUENCE: 212
catgcaattg cccaatagag                                           20

<210> SEQ ID NO 213
<211> LENGTH: 22
<212> TYPE: DNA
<213> ORGANISM: Homo sapiens

<400> SEQUENCE: 213
ttgggcttgt ctacctagtt ca                                        22

<210> SEQ ID NO 214
<211> LENGTH: 20
<212> TYPE: DNA
<213> ORGANISM: Homo sapiens

<400> SEQUENCE: 214
```

| | |
|---|---|
| gctgcacgta tttgttggtg | 20 |

<210> SEQ ID NO 215
<211> LENGTH: 20
<212> TYPE: DNA
<213> ORGANISM: Homo sapiens

<400> SEQUENCE: 215

| | |
|---|---|
| aaacagcaga aatgggaacc | 20 |

<210> SEQ ID NO 216
<211> LENGTH: 20
<212> TYPE: DNA
<213> ORGANISM: Homo sapiens

<400> SEQUENCE: 216

| | |
|---|---|
| ccgtgggcta tcaatttctg | 20 |

<210> SEQ ID NO 217
<211> LENGTH: 21
<212> TYPE: DNA
<213> ORGANISM: Homo sapiens

<400> SEQUENCE: 217

| | |
|---|---|
| aagatgcaat ctggtttcca a | 21 |

<210> SEQ ID NO 218
<211> LENGTH: 20
<212> TYPE: DNA
<213> ORGANISM: Homo sapiens

<400> SEQUENCE: 218

| | |
|---|---|
| cccaagactg aggaggtcaa | 20 |

<210> SEQ ID NO 219
<211> LENGTH: 20
<212> TYPE: DNA
<213> ORGANISM: Homo sapiens

<400> SEQUENCE: 219

| | |
|---|---|
| gctgacggag aggaaagaga | 20 |

<210> SEQ ID NO 220
<211> LENGTH: 20
<212> TYPE: DNA
<213> ORGANISM: Homo sapiens

<400> SEQUENCE: 220

| | |
|---|---|
| tcacaaagca agcaatcaca | 20 |

<210> SEQ ID NO 221
<211> LENGTH: 20
<212> TYPE: DNA
<213> ORGANISM: Homo sapiens

<400> SEQUENCE: 221

| | |
|---|---|
| tgatggatgc accatgttta | 20 |

<210> SEQ ID NO 222
<211> LENGTH: 20
<212> TYPE: DNA
<213> ORGANISM: Homo sapiens

<400> SEQUENCE: 222
tgagaagcct gggcattaag                                             20

<210> SEQ ID NO 223
<211> LENGTH: 20
<212> TYPE: DNA
<213> ORGANISM: Homo sapiens

<400> SEQUENCE: 223
acaagctcat ccagggaaag                                             20

<210> SEQ ID NO 224
<211> LENGTH: 19
<212> TYPE: DNA
<213> ORGANISM: Homo sapiens

<400> SEQUENCE: 224
agagctgatc tggccgaag                                              19

<210> SEQ ID NO 225
<211> LENGTH: 21
<212> TYPE: DNA
<213> ORGANISM: Homo sapiens

<400> SEQUENCE: 225
ggtggacaca gaatccacac t                                           21

<210> SEQ ID NO 226
<211> LENGTH: 18
<212> TYPE: DNA
<213> ORGANISM: Homo sapiens

<400> SEQUENCE: 226
ggcctgaaag gtatcctc                                               18

<210> SEQ ID NO 227
<211> LENGTH: 18
<212> TYPE: DNA
<213> ORGANISM: Homo sapiens

<400> SEQUENCE: 227
tcccaccata agcacaag                                               18

<210> SEQ ID NO 228
<211> LENGTH: 22
<212> TYPE: DNA
<213> ORGANISM: Homo sapiens

<400> SEQUENCE: 228
tcaacctagg attggcatta ca                                          22

<210> SEQ ID NO 229
<211> LENGTH: 21
<212> TYPE: DNA
<213> ORGANISM: Homo sapiens

<400> SEQUENCE: 229
tctaggattt gtgcctttcc a                                           21

<210> SEQ ID NO 230
<211> LENGTH: 20
<212> TYPE: DNA
<213> ORGANISM: Homo sapiens

```
<400> SEQUENCE: 230
attcgtgcag ctgtttctgc                                              20

<210> SEQ ID NO 231
<211> LENGTH: 22
<212> TYPE: DNA
<213> ORGANISM: Homo sapiens

<400> SEQUENCE: 231
gcatgacatt gtaaatggag ga                                           22

<210> SEQ ID NO 232
<211> LENGTH: 20
<212> TYPE: DNA
<213> ORGANISM: Homo sapiens

<400> SEQUENCE: 232
ggtgggaatg tgtgactgaa                                              20

<210> SEQ ID NO 233
<211> LENGTH: 22
<212> TYPE: DNA
<213> ORGANISM: Homo sapiens

<400> SEQUENCE: 233
ccaggtacaa cattctcctg at                                           22

<210> SEQ ID NO 234
<211> LENGTH: 16
<212> TYPE: DNA
<213> ORGANISM: Homo sapiens

<400> SEQUENCE: 234
tgcaggtggg agtcaa                                                  16

<210> SEQ ID NO 235
<211> LENGTH: 24
<212> TYPE: DNA
<213> ORGANISM: Homo sapiens

<400> SEQUENCE: 235
aaataacaag aagtgacctt ccta                                         24

<210> SEQ ID NO 236
<211> LENGTH: 21
<212> TYPE: DNA
<213> ORGANISM: Homo sapiens

<400> SEQUENCE: 236
aaaggatgca ttcggttaga g                                            21

<210> SEQ ID NO 237
<211> LENGTH: 20
<212> TYPE: DNA
<213> ORGANISM: Homo sapiens

<400> SEQUENCE: 237
actgtcctgt gcctgtgctt                                              20

<210> SEQ ID NO 238
<211> LENGTH: 20
<212> TYPE: DNA
<213> ORGANISM: Homo sapiens
```

<400> SEQUENCE: 238
gtccacctaa tggctcattc                                              20

<210> SEQ ID NO 239
<211> LENGTH: 21
<212> TYPE: DNA
<213> ORGANISM: Homo sapiens

<400> SEQUENCE: 239
caagaagcac tcatgtttgt g                                            21

<210> SEQ ID NO 240
<211> LENGTH: 19
<212> TYPE: DNA
<213> ORGANISM: Homo sapiens

<400> SEQUENCE: 240
agcctgtgat tggctgaga                                               19

<210> SEQ ID NO 241
<211> LENGTH: 20
<212> TYPE: DNA
<213> ORGANISM: Homo sapiens

<400> SEQUENCE: 241
ggcttacagc tgcctccttt                                              20

<210> SEQ ID NO 242
<211> LENGTH: 21
<212> TYPE: DNA
<213> ORGANISM: Homo sapiens

<400> SEQUENCE: 242
cccacagagc actttgttag a                                            21

<210> SEQ ID NO 243
<211> LENGTH: 21
<212> TYPE: DNA
<213> ORGANISM: Homo sapiens

<400> SEQUENCE: 243
gcctccctta agctgttatg c                                            21

<210> SEQ ID NO 244
<211> LENGTH: 23
<212> TYPE: DNA
<213> ORGANISM: Homo sapiens

<400> SEQUENCE: 244
cactctttac tgccaatcac tcc                                          23

<210> SEQ ID NO 245
<211> LENGTH: 19
<212> TYPE: DNA
<213> ORGANISM: Homo sapiens

<400> SEQUENCE: 245
gccgtgtggg tgtatgaat                                               19

<210> SEQ ID NO 246
<211> LENGTH: 22
<212> TYPE: DNA

<213> ORGANISM: Homo sapiens

<400> SEQUENCE: 246
ttgtaccagg aaccaaagac aa                         22

<210> SEQ ID NO 247
<211> LENGTH: 20
<212> TYPE: DNA
<213> ORGANISM: Homo sapiens

<400> SEQUENCE: 247
cacagacaga ggcacattga                            20

<210> SEQ ID NO 248
<211> LENGTH: 20
<212> TYPE: DNA
<213> ORGANISM: Homo sapiens

<400> SEQUENCE: 248
gctctggtca ctcctgctgt                            20

<210> SEQ ID NO 249
<211> LENGTH: 19
<212> TYPE: DNA
<213> ORGANISM: Homo sapiens

<400> SEQUENCE: 249
catgcctggc tgattgttt                             19

<210> SEQ ID NO 250
<211> LENGTH: 16
<212> TYPE: DNA
<213> ORGANISM: Homo sapiens

<400> SEQUENCE: 250
ccaacatcgg gaactg                                16

<210> SEQ ID NO 251
<211> LENGTH: 21
<212> TYPE: DNA
<213> ORGANISM: Homo sapiens

<400> SEQUENCE: 251
tgcattcttt aagtccatgt c                          21

<210> SEQ ID NO 252
<211> LENGTH: 21
<212> TYPE: DNA
<213> ORGANISM: Homo sapiens

<400> SEQUENCE: 252
cagcaactga caactcatcc a                          21

<210> SEQ ID NO 253
<211> LENGTH: 20
<212> TYPE: DNA
<213> ORGANISM: Homo sapiens

<400> SEQUENCE: 253
cctcaatcct cagctccaac                            20

<210> SEQ ID NO 254
<211> LENGTH: 21

<210> SEQ ID NO 254
<211> LENGTH: 21
<212> TYPE: DNA
<213> ORGANISM: Homo sapiens

<400> SEQUENCE: 254
tgattggttc tgttgttgct g                                              21

<210> SEQ ID NO 255
<211> LENGTH: 19
<212> TYPE: DNA
<213> ORGANISM: Homo sapiens

<400> SEQUENCE: 255
agcccaaggc tcttgtgag                                                 19

<210> SEQ ID NO 256
<211> LENGTH: 21
<212> TYPE: DNA
<213> ORGANISM: Homo sapiens

<400> SEQUENCE: 256
tccttcacag cttcaaactc a                                              21

<210> SEQ ID NO 257
<211> LENGTH: 22
<212> TYPE: DNA
<213> ORGANISM: Homo sapiens

<400> SEQUENCE: 257
agtgagaagc ttccatactg gt                                             22

<210> SEQ ID NO 258
<211> LENGTH: 20
<212> TYPE: DNA
<213> ORGANISM: Homo sapiens

<400> SEQUENCE: 258
gccaaccgtt agacaaatga                                                20

<210> SEQ ID NO 259
<211> LENGTH: 21
<212> TYPE: DNA
<213> ORGANISM: Homo sapiens

<400> SEQUENCE: 259
ctacatgtgc accacaacac c                                              21

<210> SEQ ID NO 260
<211> LENGTH: 19
<212> TYPE: DNA
<213> ORGANISM: Homo sapiens

<400> SEQUENCE: 260
agtttattgc cgccgagag                                                 19

<210> SEQ ID NO 261
<211> LENGTH: 19
<212> TYPE: DNA
<213> ORGANISM: Homo sapiens

<400> SEQUENCE: 261
acccaccaca ttcacaagc                                                 19

<210> SEQ ID NO 262

```
<211> LENGTH: 20
<212> TYPE: DNA
<213> ORGANISM: Homo sapiens

<400> SEQUENCE: 262
cgattgccat gtctctttga                                               20

<210> SEQ ID NO 263
<211> LENGTH: 20
<212> TYPE: DNA
<213> ORGANISM: Homo sapiens

<400> SEQUENCE: 263
gagatctggc ctggatttgt                                               20

<210> SEQ ID NO 264
<211> LENGTH: 23
<212> TYPE: DNA
<213> ORGANISM: Homo sapiens

<400> SEQUENCE: 264
tcattgtcag cacagaatga act                                           23

<210> SEQ ID NO 265
<211> LENGTH: 20
<212> TYPE: DNA
<213> ORGANISM: Homo sapiens

<400> SEQUENCE: 265
ggagggaggg aagaaagaga                                               20

<210> SEQ ID NO 266
<211> LENGTH: 22
<212> TYPE: DNA
<213> ORGANISM: Homo sapiens

<400> SEQUENCE: 266
gggaagagga gattgacttg tt                                            22

<210> SEQ ID NO 267
<211> LENGTH: 20
<212> TYPE: DNA
<213> ORGANISM: Homo sapiens

<400> SEQUENCE: 267
ggaacaccat cattccaacc                                               20

<210> SEQ ID NO 268
<211> LENGTH: 20
<212> TYPE: DNA
<213> ORGANISM: Homo sapiens

<400> SEQUENCE: 268
tacaagctcc accgtccttc                                               20

<210> SEQ ID NO 269
<211> LENGTH: 20
<212> TYPE: DNA
<213> ORGANISM: Homo sapiens

<400> SEQUENCE: 269
tgagttgctg cctcttcaaa                                               20
```

```
<210> SEQ ID NO 270
<211> LENGTH: 20
<212> TYPE: DNA
<213> ORGANISM: Homo sapiens

<400> SEQUENCE: 270
tgctaatggg ccaaggaata                                              20

<210> SEQ ID NO 271
<211> LENGTH: 23
<212> TYPE: DNA
<213> ORGANISM: Homo sapiens

<400> SEQUENCE: 271
gctaaatgtc ctcatgaata gcc                                          23

<210> SEQ ID NO 272
<211> LENGTH: 20
<212> TYPE: DNA
<213> ORGANISM: Homo sapiens

<400> SEQUENCE: 272
tgtcctgcag acagatggtc                                              20

<210> SEQ ID NO 273
<211> LENGTH: 20
<212> TYPE: DNA
<213> ORGANISM: Homo sapiens

<400> SEQUENCE: 273
cctccggagt agctggatta                                              20

<210> SEQ ID NO 274
<211> LENGTH: 20
<212> TYPE: DNA
<213> ORGANISM: Homo sapiens

<400> SEQUENCE: 274
gagactggcc ctcattcttg                                              20

<210> SEQ ID NO 275
<211> LENGTH: 25
<212> TYPE: DNA
<213> ORGANISM: Homo sapiens

<400> SEQUENCE: 275
aagaagccag agacaaagaa ataca                                        25

<210> SEQ ID NO 276
<211> LENGTH: 24
<212> TYPE: DNA
<213> ORGANISM: Homo sapiens

<400> SEQUENCE: 276
catctatctt tggattcagt ggtg                                         24

<210> SEQ ID NO 277
<211> LENGTH: 20
<212> TYPE: DNA
<213> ORGANISM: Homo sapiens

<400> SEQUENCE: 277
tgctcccaac atcttaccag                                              20
```

```
<210> SEQ ID NO 278
<211> LENGTH: 23
<212> TYPE: DNA
<213> ORGANISM: Homo sapiens

<400> SEQUENCE: 278
tgtcctctgg tcatttctat ggt                                        23

<210> SEQ ID NO 279
<211> LENGTH: 23
<212> TYPE: DNA
<213> ORGANISM: Homo sapiens

<400> SEQUENCE: 279
catgaatgag aagtgatgaa tgg                                        23

<210> SEQ ID NO 280
<211> LENGTH: 22
<212> TYPE: DNA
<213> ORGANISM: Homo sapiens

<400> SEQUENCE: 280
cagacactgt aaactggctt cg                                         22

<210> SEQ ID NO 281
<211> LENGTH: 20
<212> TYPE: DNA
<213> ORGANISM: Homo sapiens

<400> SEQUENCE: 281
gccacattgc tatcagcgta                                            20

<210> SEQ ID NO 282
<211> LENGTH: 20
<212> TYPE: DNA
<213> ORGANISM: Homo sapiens

<400> SEQUENCE: 282
atgtgctgtg gtccagattt                                            20

<210> SEQ ID NO 283
<211> LENGTH: 25
<212> TYPE: DNA
<213> ORGANISM: Homo sapiens

<400> SEQUENCE: 283
cctactactg caattactcc ctacc                                      25

<210> SEQ ID NO 284
<211> LENGTH: 21
<212> TYPE: DNA
<213> ORGANISM: Homo sapiens

<400> SEQUENCE: 284
tgtcataggc ttgcggtatt t                                          21

<210> SEQ ID NO 285
<211> LENGTH: 20
<212> TYPE: DNA
<213> ORGANISM: Homo sapiens

<400> SEQUENCE: 285
ttggtagggt cctttccttt                                            20
```

<210> SEQ ID NO 286
<211> LENGTH: 20
<212> TYPE: DNA
<213> ORGANISM: Homo sapiens

<400> SEQUENCE: 286
gcctgctcac tgttgtttga                                                    20

<210> SEQ ID NO 287
<211> LENGTH: 21
<212> TYPE: DNA
<213> ORGANISM: Homo sapiens

<400> SEQUENCE: 287
cggttatcag agactggtgg t                                                  21

<210> SEQ ID NO 288
<211> LENGTH: 21
<212> TYPE: DNA
<213> ORGANISM: Homo sapiens

<400> SEQUENCE: 288
ggcttatttc atgtacggct a                                                  21

<210> SEQ ID NO 289
<211> LENGTH: 26
<212> TYPE: DNA
<213> ORGANISM: Homo sapiens

<400> SEQUENCE: 289
ggttaaactc tacttagtcc tgatgc                                             26

<210> SEQ ID NO 290
<211> LENGTH: 20
<212> TYPE: DNA
<213> ORGANISM: Homo sapiens

<400> SEQUENCE: 290
gaactctgca ggcacctctt                                                    20

<210> SEQ ID NO 291
<211> LENGTH: 20
<212> TYPE: DNA
<213> ORGANISM: Homo sapiens

<400> SEQUENCE: 291
cctgaagcgc ttgtactgaa                                                    20

<210> SEQ ID NO 292
<211> LENGTH: 20
<212> TYPE: DNA
<213> ORGANISM: Homo sapiens

<400> SEQUENCE: 292
ttggcttctc gctctttctt                                                    20

<210> SEQ ID NO 293
<211> LENGTH: 20
<212> TYPE: DNA
<213> ORGANISM: Homo sapiens

<400> SEQUENCE: 293

-continued

| | |
|---|---|
| agccatcagt cacatgcaaa | 20 |

<210> SEQ ID NO 294
<211> LENGTH: 20
<212> TYPE: DNA
<213> ORGANISM: Homo sapiens

<400> SEQUENCE: 294

| | |
|---|---|
| agatctccag ggcagaggac | 20 |

<210> SEQ ID NO 295
<211> LENGTH: 20
<212> TYPE: DNA
<213> ORGANISM: Homo sapiens

<400> SEQUENCE: 295

| | |
|---|---|
| ccttcctccc tccttctctc | 20 |

<210> SEQ ID NO 296
<211> LENGTH: 22
<212> TYPE: DNA
<213> ORGANISM: Homo sapiens

<400> SEQUENCE: 296

| | |
|---|---|
| cagtcaaatg tctcaacctt cc | 22 |

<210> SEQ ID NO 297
<211> LENGTH: 20
<212> TYPE: DNA
<213> ORGANISM: Homo sapiens

<400> SEQUENCE: 297

| | |
|---|---|
| ctagcaacat ggccaagaaa | 20 |

<210> SEQ ID NO 298
<211> LENGTH: 21
<212> TYPE: DNA
<213> ORGANISM: Homo sapiens

<400> SEQUENCE: 298

| | |
|---|---|
| cgtcattgat cccaatcatc t | 21 |

<210> SEQ ID NO 299
<211> LENGTH: 20
<212> TYPE: DNA
<213> ORGANISM: Homo sapiens

<400> SEQUENCE: 299

| | |
|---|---|
| ggctgatagc ctcccttgta | 20 |

<210> SEQ ID NO 300
<211> LENGTH: 20
<212> TYPE: DNA
<213> ORGANISM: Homo sapiens

<400> SEQUENCE: 300

| | |
|---|---|
| acctttcaag cttccggttt | 20 |

<210> SEQ ID NO 301
<211> LENGTH: 20
<212> TYPE: DNA
<213> ORGANISM: Homo sapiens

<400> SEQUENCE: 301

```
ttccatccgt ccatctatcc                                          20

<210> SEQ ID NO 302
<211> LENGTH: 23
<212> TYPE: DNA
<213> ORGANISM: Homo sapiens

<400> SEQUENCE: 302
ttaaagtcac ttgtctgtgg tca                                      23

<210> SEQ ID NO 303
<211> LENGTH: 27
<212> TYPE: DNA
<213> ORGANISM: Homo sapiens

<400> SEQUENCE: 303
tttgtaggaa tcaagtcaaa taatgta                                  27

<210> SEQ ID NO 304
<211> LENGTH: 20
<212> TYPE: DNA
<213> ORGANISM: Homo sapiens

<400> SEQUENCE: 304
ctttcggaag cttgagccta                                          20

<210> SEQ ID NO 305
<211> LENGTH: 20
<212> TYPE: DNA
<213> ORGANISM: Homo sapiens

<400> SEQUENCE: 305
cccaagacca ctgccatatt                                          20

<210> SEQ ID NO 306
<211> LENGTH: 22
<212> TYPE: DNA
<213> ORGANISM: Homo sapiens

<400> SEQUENCE: 306
tgacaggttt gggtatattg ga                                       22

<210> SEQ ID NO 307
<211> LENGTH: 20
<212> TYPE: DNA
<213> ORGANISM: Homo sapiens

<400> SEQUENCE: 307
tgcttaatgt agtggcagca                                          20

<210> SEQ ID NO 308
<211> LENGTH: 20
<212> TYPE: DNA
<213> ORGANISM: Homo sapiens

<400> SEQUENCE: 308
tcctgccttt gtgaattcct                                          20

<210> SEQ ID NO 309
<211> LENGTH: 20
<212> TYPE: DNA
<213> ORGANISM: Homo sapiens
```

-continued

<400> SEQUENCE: 309
gttgaatgag gtgggcatta                                           20

<210> SEQ ID NO 310
<211> LENGTH: 22
<212> TYPE: DNA
<213> ORGANISM: Homo sapiens

<400> SEQUENCE: 310
ttgggaataa atcaggtgtt ga                                        22

<210> SEQ ID NO 311
<211> LENGTH: 20
<212> TYPE: DNA
<213> ORGANISM: Homo sapiens

<400> SEQUENCE: 311
gcagcagctc agcatttctc                                           20

<210> SEQ ID NO 312
<211> LENGTH: 21
<212> TYPE: DNA
<213> ORGANISM: Homo sapiens

<400> SEQUENCE: 312
ccatttaatc ctccagccat t                                         21

<210> SEQ ID NO 313
<211> LENGTH: 20
<212> TYPE: DNA
<213> ORGANISM: Homo sapiens

<400> SEQUENCE: 313
gctccacctt gttaccctga                                           20

<210> SEQ ID NO 314
<211> LENGTH: 20
<212> TYPE: DNA
<213> ORGANISM: Homo sapiens

<400> SEQUENCE: 314
acaaccctgg aatctggact                                           20

<210> SEQ ID NO 315
<211> LENGTH: 22
<212> TYPE: DNA
<213> ORGANISM: Homo sapiens

<400> SEQUENCE: 315
gaaggaaagg aaaggaaaga aa                                        22

<210> SEQ ID NO 316
<211> LENGTH: 23
<212> TYPE: DNA
<213> ORGANISM: Homo sapiens

<400> SEQUENCE: 316
tgacaagact gaaacttcat cag                                       23

<210> SEQ ID NO 317
<211> LENGTH: 20
<212> TYPE: DNA
<213> ORGANISM: Homo sapiens

```
<400> SEQUENCE: 317
gatgcttgct ttgggaggta                                          20

<210> SEQ ID NO 318
<211> LENGTH: 20
<212> TYPE: DNA
<213> ORGANISM: Homo sapiens

<400> SEQUENCE: 318
caggttagag cccatccaag                                          20

<210> SEQ ID NO 319
<211> LENGTH: 20
<212> TYPE: DNA
<213> ORGANISM: Homo sapiens

<400> SEQUENCE: 319
aggctcagct tcatccacat                                          20

<210> SEQ ID NO 320
<211> LENGTH: 20
<212> TYPE: DNA
<213> ORGANISM: Homo sapiens

<400> SEQUENCE: 320
aagcaaatat gcaaaattgc                                          20

<210> SEQ ID NO 321
<211> LENGTH: 23
<212> TYPE: DNA
<213> ORGANISM: Homo sapiens

<400> SEQUENCE: 321
tccttctgtt tcttgactta aca                                      23

<210> SEQ ID NO 322
<211> LENGTH: 20
<212> TYPE: DNA
<213> ORGANISM: Homo sapiens

<400> SEQUENCE: 322
gggaacaggt cacaggtcat                                          20

<210> SEQ ID NO 323
<211> LENGTH: 20
<212> TYPE: DNA
<213> ORGANISM: Homo sapiens

<400> SEQUENCE: 323
ggaagactgg gtggtcacag                                          20

<210> SEQ ID NO 324
<211> LENGTH: 20
<212> TYPE: DNA
<213> ORGANISM: Homo sapiens

<400> SEQUENCE: 324
ttccttctgc ttgtgagctg                                          20

<210> SEQ ID NO 325
<211> LENGTH: 20
<212> TYPE: DNA
```

```
<213> ORGANISM: Homo sapiens

<400> SEQUENCE: 325
taccctcacc ttcctcatgc                                              20

<210> SEQ ID NO 326
<211> LENGTH: 20
<212> TYPE: DNA
<213> ORGANISM: Homo sapiens

<400> SEQUENCE: 326
gaagacattg gcaggtctgg                                              20

<210> SEQ ID NO 327
<211> LENGTH: 20
<212> TYPE: DNA
<213> ORGANISM: Homo sapiens

<400> SEQUENCE: 327
gagccctcat gttgggataa                                              20

<210> SEQ ID NO 328
<211> LENGTH: 22
<212> TYPE: DNA
<213> ORGANISM: Homo sapiens

<400> SEQUENCE: 328
ttgttgattc tcccattctg tg                                           22

<210> SEQ ID NO 329
<211> LENGTH: 25
<212> TYPE: DNA
<213> ORGANISM: Homo sapiens

<400> SEQUENCE: 329
tcacctacct catctcatac tcaaa                                        25

<210> SEQ ID NO 330
<211> LENGTH: 20
<212> TYPE: DNA
<213> ORGANISM: Homo sapiens

<400> SEQUENCE: 330
tcttccggac aagtttccaa                                              20

<210> SEQ ID NO 331
<211> LENGTH: 20
<212> TYPE: DNA
<213> ORGANISM: Homo sapiens

<400> SEQUENCE: 331
tgggtcattc tggacattca                                              20

<210> SEQ ID NO 332
<211> LENGTH: 20
<212> TYPE: DNA
<213> ORGANISM: Homo sapiens

<400> SEQUENCE: 332
gcaaatgagg ctggtaaggt                                              20

<210> SEQ ID NO 333
<211> LENGTH: 20
```

```
<212> TYPE: DNA
<213> ORGANISM: Homo sapiens

<400> SEQUENCE: 333
tgcactgtgg tagagggaaa                                              20

<210> SEQ ID NO 334
<211> LENGTH: 27
<212> TYPE: DNA
<213> ORGANISM: Homo sapiens

<400> SEQUENCE: 334
caacatactc ctatgcctag aaagaaa                                      27

<210> SEQ ID NO 335
<211> LENGTH: 20
<212> TYPE: DNA
<213> ORGANISM: Homo sapiens

<400> SEQUENCE: 335
ctcaccaggc agaaacaggt                                              20

<210> SEQ ID NO 336
<211> LENGTH: 19
<212> TYPE: DNA
<213> ORGANISM: Homo sapiens

<400> SEQUENCE: 336
cccaatggca tgcttcact                                               19

<210> SEQ ID NO 337
<211> LENGTH: 19
<212> TYPE: DNA
<213> ORGANISM: Homo sapiens

<400> SEQUENCE: 337
ggttctccca gcattggtt                                               19

<210> SEQ ID NO 338
<211> LENGTH: 20
<212> TYPE: DNA
<213> ORGANISM: Homo sapiens

<400> SEQUENCE: 338
aaggcctctg ggtaggtagg                                              20

<210> SEQ ID NO 339
<211> LENGTH: 20
<212> TYPE: DNA
<213> ORGANISM: Homo sapiens

<400> SEQUENCE: 339
aagcaatcct tatgggctct                                              20

<210> SEQ ID NO 340
<211> LENGTH: 20
<212> TYPE: DNA
<213> ORGANISM: Homo sapiens

<400> SEQUENCE: 340
ccaggtaatc agaagcctca                                              20

<210> SEQ ID NO 341
```

```
<211> LENGTH: 20
<212> TYPE: DNA
<213> ORGANISM: Homo sapiens

<400> SEQUENCE: 341
ttccgttaaa tccagccatc                                              20

<210> SEQ ID NO 342
<211> LENGTH: 20
<212> TYPE: DNA
<213> ORGANISM: Homo sapiens

<400> SEQUENCE: 342
cagggactgc agtgtctcaa                                              20

<210> SEQ ID NO 343
<211> LENGTH: 20
<212> TYPE: DNA
<213> ORGANISM: Homo sapiens

<400> SEQUENCE: 343
atgccacatt tgcctctctc                                              20

<210> SEQ ID NO 344
<211> LENGTH: 25
<212> TYPE: DNA
<213> ORGANISM: Homo sapiens

<400> SEQUENCE: 344
ccaccttcca cttaatacaa acttc                                        25

<210> SEQ ID NO 345
<211> LENGTH: 21
<212> TYPE: DNA
<213> ORGANISM: Homo sapiens

<400> SEQUENCE: 345
gaagcaatcc attccaagaa a                                            21

<210> SEQ ID NO 346
<211> LENGTH: 20
<212> TYPE: DNA
<213> ORGANISM: Homo sapiens

<400> SEQUENCE: 346
gtcctgaggg tgtccaggta                                              20

<210> SEQ ID NO 347
<211> LENGTH: 22
<212> TYPE: DNA
<213> ORGANISM: Homo sapiens

<400> SEQUENCE: 347
gctggagaac tcctattctg ct                                           22

<210> SEQ ID NO 348
<211> LENGTH: 20
<212> TYPE: DNA
<213> ORGANISM: Homo sapiens

<400> SEQUENCE: 348
tggagctatt gcggttctct                                              20
```

```
<210> SEQ ID NO 349
<211> LENGTH: 23
<212> TYPE: DNA
<213> ORGANISM: Homo sapiens

<400> SEQUENCE: 349
tcaaatctct ctttcctcct cct                                        23

<210> SEQ ID NO 350
<211> LENGTH: 20
<212> TYPE: DNA
<213> ORGANISM: Homo sapiens

<400> SEQUENCE: 350
cagttccagc tacgggagaa                                            20

<210> SEQ ID NO 351
<211> LENGTH: 20
<212> TYPE: DNA
<213> ORGANISM: Homo sapiens

<400> SEQUENCE: 351
ccgcatttag gcaagtctca                                            20

<210> SEQ ID NO 352
<211> LENGTH: 20
<212> TYPE: DNA
<213> ORGANISM: Homo sapiens

<400> SEQUENCE: 352
aagcacacac agatgctagg                                            20

<210> SEQ ID NO 353
<211> LENGTH: 20
<212> TYPE: DNA
<213> ORGANISM: Homo sapiens

<400> SEQUENCE: 353
cctcagcctc cataatctca                                            20

<210> SEQ ID NO 354
<211> LENGTH: 20
<212> TYPE: DNA
<213> ORGANISM: Homo sapiens

<400> SEQUENCE: 354
gtacagagcc caccttctgg                                            20

<210> SEQ ID NO 355
<211> LENGTH: 20
<212> TYPE: DNA
<213> ORGANISM: Homo sapiens

<400> SEQUENCE: 355
tcactatgct gcaaggcaag                                            20

<210> SEQ ID NO 356
<211> LENGTH: 23
<212> TYPE: DNA
<213> ORGANISM: Homo sapiens

<400> SEQUENCE: 356
ggtgcttgct gtaaatataa ttg                                        23
```

```
<210> SEQ ID NO 357
<211> LENGTH: 20
<212> TYPE: DNA
<213> ORGANISM: Homo sapiens

<400> SEQUENCE: 357
cactacagca gattgcacca                                               20

<210> SEQ ID NO 358
<211> LENGTH: 20
<212> TYPE: DNA
<213> ORGANISM: Homo sapiens

<400> SEQUENCE: 358
gatttgaaaa tgagcagtcc                                               20

<210> SEQ ID NO 359
<211> LENGTH: 20
<212> TYPE: DNA
<213> ORGANISM: Homo sapiens

<400> SEQUENCE: 359
gtcgggcact acgtttatct                                               20

<210> SEQ ID NO 360
<211> LENGTH: 20
<212> TYPE: DNA
<213> ORGANISM: Homo sapiens

<400> SEQUENCE: 360
tgggtgaaga tgctacctga                                               20

<210> SEQ ID NO 361
<211> LENGTH: 20
<212> TYPE: DNA
<213> ORGANISM: Homo sapiens

<400> SEQUENCE: 361
cccttcttcc tttccctctc                                               20

<210> SEQ ID NO 362
<211> LENGTH: 21
<212> TYPE: DNA
<213> ORGANISM: Homo sapiens

<400> SEQUENCE: 362
tgccaggtct gagttgtaag c                                             21

<210> SEQ ID NO 363
<211> LENGTH: 20
<212> TYPE: DNA
<213> ORGANISM: Homo sapiens

<400> SEQUENCE: 363
cagcatgaga ccctgtcaaa                                               20

<210> SEQ ID NO 364
<211> LENGTH: 27
<212> TYPE: DNA
<213> ORGANISM: Homo sapiens

<400> SEQUENCE: 364
gaaagaaaga aagaaagaag aaagaaa                                       27
```

```
<210> SEQ ID NO 365
<211> LENGTH: 20
<212> TYPE: DNA
<213> ORGANISM: Homo sapiens

<400> SEQUENCE: 365
aatcaccaaa cctggaagca                                              20

<210> SEQ ID NO 366
<211> LENGTH: 27
<212> TYPE: DNA
<213> ORGANISM: Homo sapiens

<400> SEQUENCE: 366
gaaagaaaga aagaaagaag aaagaaa                                      27

<210> SEQ ID NO 367
<211> LENGTH: 20
<212> TYPE: DNA
<213> ORGANISM: Homo sapiens

<400> SEQUENCE: 367
aatcaccaaa cctggaagca                                              20

<210> SEQ ID NO 368
<211> LENGTH: 25
<212> TYPE: DNA
<213> ORGANISM: Homo sapiens

<400> SEQUENCE: 368
tctgagttaa acacttgagt tgctg                                        25

<210> SEQ ID NO 369
<211> LENGTH: 21
<212> TYPE: DNA
<213> ORGANISM: Homo sapiens

<400> SEQUENCE: 369
ccagtaaatg gcagtgtggt t                                            21

<210> SEQ ID NO 370
<211> LENGTH: 27
<212> TYPE: DNA
<213> ORGANISM: Homo sapiens

<400> SEQUENCE: 370
tgtcatggat atttctacat aaaccaa                                      27

<210> SEQ ID NO 371
<211> LENGTH: 23
<212> TYPE: DNA
<213> ORGANISM: Homo sapiens

<400> SEQUENCE: 371
tgaagatggt tattgcttcc ttc                                          23

<210> SEQ ID NO 372
<211> LENGTH: 20
<212> TYPE: DNA
<213> ORGANISM: Homo sapiens

<400> SEQUENCE: 372
```
cgctttgttt ggtttggttt                    20

<210> SEQ ID NO 373
<211> LENGTH: 20
<212> TYPE: DNA
<213> ORGANISM: Homo sapiens

<400> SEQUENCE: 373
atgcagttgt cccacatgct                    20

<210> SEQ ID NO 374
<211> LENGTH: 20
<212> TYPE: DNA
<213> ORGANISM: Homo sapiens

<400> SEQUENCE: 374
tcctgcactc caaaggaaac                    20

<210> SEQ ID NO 375
<211> LENGTH: 25
<212> TYPE: DNA
<213> ORGANISM: Homo sapiens

<400> SEQUENCE: 375
aactctggtt taattcagct ttgtc              25

<210> SEQ ID NO 376
<211> LENGTH: 21
<212> TYPE: DNA
<213> ORGANISM: Homo sapiens

<400> SEQUENCE: 376
ttcttgaggg cataaagctg a                  21

<210> SEQ ID NO 377
<211> LENGTH: 20
<212> TYPE: DNA
<213> ORGANISM: Homo sapiens

<400> SEQUENCE: 377
cacactcacc aggcactctg                    20

<210> SEQ ID NO 378
<211> LENGTH: 23
<212> TYPE: DNA
<213> ORGANISM: Homo sapiens

<400> SEQUENCE: 378
caggtttgat gaaggaaata tgc                23

<210> SEQ ID NO 379
<211> LENGTH: 22
<212> TYPE: DNA
<213> ORGANISM: Homo sapiens

<400> SEQUENCE: 379
gggatcctct gcatttctct aa                 22

<210> SEQ ID NO 380
<211> LENGTH: 20
<212> TYPE: DNA
<213> ORGANISM: Homo sapiens

<400> SEQUENCE: 380

```
tttgccaaat caaccttcag                                               20

<210> SEQ ID NO 381
<211> LENGTH: 20
<212> TYPE: DNA
<213> ORGANISM: Homo sapiens

<400> SEQUENCE: 381
cctgcttcac acctctgacc                                               20

<210> SEQ ID NO 382
<211> LENGTH: 20
<212> TYPE: DNA
<213> ORGANISM: Homo sapiens

<400> SEQUENCE: 382
actcacacac aaccaccaca                                               20

<210> SEQ ID NO 383
<211> LENGTH: 20
<212> TYPE: DNA
<213> ORGANISM: Homo sapiens

<400> SEQUENCE: 383
gctactggtg ggtcgtaagc                                               20

<210> SEQ ID NO 384
<211> LENGTH: 18
<212> TYPE: DNA
<213> ORGANISM: Homo sapiens

<400> SEQUENCE: 384
ttcagagacc atcacggc                                                 18

<210> SEQ ID NO 385
<211> LENGTH: 25
<212> TYPE: DNA
<213> ORGANISM: Homo sapiens

<400> SEQUENCE: 385
ctggaaaaat cagttgaatc ctagc                                         25

<210> SEQ ID NO 386
<211> LENGTH: 20
<212> TYPE: DNA
<213> ORGANISM: Homo sapiens

<400> SEQUENCE: 386
aggaaagccg agaaagcata                                               20

<210> SEQ ID NO 387
<211> LENGTH: 20
<212> TYPE: DNA
<213> ORGANISM: Homo sapiens

<400> SEQUENCE: 387
catgtatcca catgcccaga                                               20

<210> SEQ ID NO 388
<211> LENGTH: 20
<212> TYPE: DNA
<213> ORGANISM: Homo sapiens
```

```
<400> SEQUENCE: 388
ccttcagcgc agctacatct                                              20

<210> SEQ ID NO 389
<211> LENGTH: 20
<212> TYPE: DNA
<213> ORGANISM: Homo sapiens

<400> SEQUENCE: 389
agaactgcga ggtccaagtg                                              20

<210> SEQ ID NO 390
<211> LENGTH: 22
<212> TYPE: DNA
<213> ORGANISM: Homo sapiens

<400> SEQUENCE: 390
gggagaaaga gaggtaggaa gg                                           22

<210> SEQ ID NO 391
<211> LENGTH: 20
<212> TYPE: DNA
<213> ORGANISM: Homo sapiens

<400> SEQUENCE: 391
ttcccaagtt agcagcatcc                                              20

<210> SEQ ID NO 392
<211> LENGTH: 27
<212> TYPE: DNA
<213> ORGANISM: Homo sapiens

<400> SEQUENCE: 392
ttctagagga gtctatttct ttactgg                                      27

<210> SEQ ID NO 393
<211> LENGTH: 21
<212> TYPE: DNA
<213> ORGANISM: Homo sapiens

<400> SEQUENCE: 393
ggagctgtca cttgagcttt g                                            21

<210> SEQ ID NO 394
<211> LENGTH: 20
<212> TYPE: DNA
<213> ORGANISM: Homo sapiens

<400> SEQUENCE: 394
ccgtgaccta cagggaacat                                              20

<210> SEQ ID NO 395
<211> LENGTH: 20
<212> TYPE: DNA
<213> ORGANISM: Homo sapiens

<400> SEQUENCE: 395
ggcatcgggt gtttctattc                                              20

<210> SEQ ID NO 396
<211> LENGTH: 20
<212> TYPE: DNA
<213> ORGANISM: Homo sapiens
```

```
<400> SEQUENCE: 396
agacctgcct gtgttctggt                                              20

<210> SEQ ID NO 397
<211> LENGTH: 23
<212> TYPE: DNA
<213> ORGANISM: Homo sapiens

<400> SEQUENCE: 397
ggagtgaaat aagtggaact gga                                          23

<210> SEQ ID NO 398
<211> LENGTH: 26
<212> TYPE: DNA
<213> ORGANISM: Homo sapiens

<400> SEQUENCE: 398
cattaaatga gtcataaagg tcatgg                                       26

<210> SEQ ID NO 399
<211> LENGTH: 20
<212> TYPE: DNA
<213> ORGANISM: Homo sapiens

<400> SEQUENCE: 399
aacattgttg ctttgctgga                                              20

<210> SEQ ID NO 400
<211> LENGTH: 20
<212> TYPE: DNA
<213> ORGANISM: Homo sapiens

<400> SEQUENCE: 400
ggccttagct cagtttctgg                                              20

<210> SEQ ID NO 401
<211> LENGTH: 20
<212> TYPE: DNA
<213> ORGANISM: Homo sapiens

<400> SEQUENCE: 401
tgcaaagaca tttgcggata                                              20

<210> SEQ ID NO 402
<211> LENGTH: 19
<212> TYPE: DNA
<213> ORGANISM: Homo sapiens

<400> SEQUENCE: 402
cctgcatttg tgtacgtgt                                               19

<210> SEQ ID NO 403
<211> LENGTH: 23
<212> TYPE: DNA
<213> ORGANISM: Homo sapiens

<400> SEQUENCE: 403
cagagccgtg gtagtatatt ttt                                          23

<210> SEQ ID NO 404
<211> LENGTH: 20
<212> TYPE: DNA
```

<213> ORGANISM: Homo sapiens

<400> SEQUENCE: 404
ggaaccagtc atttgggtgt                                           20

<210> SEQ ID NO 405
<211> LENGTH: 20
<212> TYPE: DNA
<213> ORGANISM: Homo sapiens

<400> SEQUENCE: 405
ttattgctcc ctcgtccaag                                           20

<210> SEQ ID NO 406
<211> LENGTH: 26
<212> TYPE: DNA
<213> ORGANISM: Homo sapiens

<400> SEQUENCE: 406
tgccttaagg tctattattt cctttc                                    26

<210> SEQ ID NO 407
<211> LENGTH: 20
<212> TYPE: DNA
<213> ORGANISM: Homo sapiens

<400> SEQUENCE: 407
accaatgcag gaagactcaa                                           20

<210> SEQ ID NO 408
<211> LENGTH: 21
<212> TYPE: DNA
<213> ORGANISM: Homo sapiens

<400> SEQUENCE: 408
ctgatgaaag gacacacatg c                                         21

<210> SEQ ID NO 409
<211> LENGTH: 23
<212> TYPE: DNA
<213> ORGANISM: Homo sapiens

<400> SEQUENCE: 409
tgcattaact atgcagcttg aaa                                       23

<210> SEQ ID NO 410
<211> LENGTH: 18
<212> TYPE: DNA
<213> ORGANISM: Homo sapiens

<400> SEQUENCE: 410
gtcgtgcaat cccgagag                                             18

<210> SEQ ID NO 411
<211> LENGTH: 20
<212> TYPE: DNA
<213> ORGANISM: Homo sapiens

<400> SEQUENCE: 411
ggattcctgc tggctcttct                                           20

<210> SEQ ID NO 412
<211> LENGTH: 20

```
<212> TYPE: DNA
<213> ORGANISM: Homo sapiens

<400> SEQUENCE: 412
ctggtgtggt caggaaatga                                          20

<210> SEQ ID NO 413
<211> LENGTH: 24
<212> TYPE: DNA
<213> ORGANISM: Homo sapiens

<400> SEQUENCE: 413
gtgctaaaca catgtgagtg agag                                     24

<210> SEQ ID NO 414
<211> LENGTH: 22
<212> TYPE: DNA
<213> ORGANISM: Homo sapiens

<400> SEQUENCE: 414
tttgaccatg ctttctcttt ga                                       22

<210> SEQ ID NO 415
<211> LENGTH: 20
<212> TYPE: DNA
<213> ORGANISM: Homo sapiens

<400> SEQUENCE: 415
gcttgatgac tccctgctgt                                          20

<210> SEQ ID NO 416
<211> LENGTH: 20
<212> TYPE: DNA
<213> ORGANISM: Homo sapiens

<400> SEQUENCE: 416
aagccattga aaggcaggta                                          20

<210> SEQ ID NO 417
<211> LENGTH: 20
<212> TYPE: DNA
<213> ORGANISM: Homo sapiens

<400> SEQUENCE: 417
gggactttcc ggcttctatt                                          20

<210> SEQ ID NO 418
<211> LENGTH: 20
<212> TYPE: DNA
<213> ORGANISM: Homo sapiens

<400> SEQUENCE: 418
ggtttgggaa ccattctcct                                          20

<210> SEQ ID NO 419
<211> LENGTH: 22
<212> TYPE: DNA
<213> ORGANISM: Homo sapiens

<400> SEQUENCE: 419
gcagagaagg gatttactcc ag                                       22

<210> SEQ ID NO 420
```

```
<211> LENGTH: 20
<212> TYPE: DNA
<213> ORGANISM: Homo sapiens

<400> SEQUENCE: 420
acttgacatg gagcaagctg                                              20

<210> SEQ ID NO 421
<211> LENGTH: 21
<212> TYPE: DNA
<213> ORGANISM: Homo sapiens

<400> SEQUENCE: 421
agctcatcat gctgtaagga g                                            21

<210> SEQ ID NO 422
<211> LENGTH: 20
<212> TYPE: DNA
<213> ORGANISM: Homo sapiens

<400> SEQUENCE: 422
cacaggctct cacattctcg                                              20

<210> SEQ ID NO 423
<211> LENGTH: 20
<212> TYPE: DNA
<213> ORGANISM: Homo sapiens

<400> SEQUENCE: 423
tgacactcat ccctctgctg                                              20

<210> SEQ ID NO 424
<211> LENGTH: 27
<212> TYPE: DNA
<213> ORGANISM: Homo sapiens

<400> SEQUENCE: 424
tgagtttcat aagtttacta cctgctg                                      27

<210> SEQ ID NO 425
<211> LENGTH: 20
<212> TYPE: DNA
<213> ORGANISM: Homo sapiens

<400> SEQUENCE: 425
ggcagggaga aaggacaaat                                              20

<210> SEQ ID NO 426
<211> LENGTH: 22
<212> TYPE: DNA
<213> ORGANISM: Homo sapiens

<400> SEQUENCE: 426
tcccttatgt gggattagtt ga                                           22

<210> SEQ ID NO 427
<211> LENGTH: 23
<212> TYPE: DNA
<213> ORGANISM: Homo sapiens

<400> SEQUENCE: 427
cagacatgga actgagattt ttt                                          23
```

```
<210> SEQ ID NO 428
<211> LENGTH: 22
<212> TYPE: DNA
<213> ORGANISM: Homo sapiens

<400> SEQUENCE: 428
tgttccatct ctctacccat gt                                              22

<210> SEQ ID NO 429
<211> LENGTH: 24
<212> TYPE: DNA
<213> ORGANISM: Homo sapiens

<400> SEQUENCE: 429
tcaatgttct tattgagtgg gaaa                                            24

<210> SEQ ID NO 430
<211> LENGTH: 20
<212> TYPE: DNA
<213> ORGANISM: Homo sapiens

<400> SEQUENCE: 430
atatccaccc acccacacat                                                 20

<210> SEQ ID NO 431
<211> LENGTH: 20
<212> TYPE: DNA
<213> ORGANISM: Homo sapiens

<400> SEQUENCE: 431
tagctctgag ggcagagacc                                                 20

<210> SEQ ID NO 432
<211> LENGTH: 19
<212> TYPE: DNA
<213> ORGANISM: Homo sapiens

<400> SEQUENCE: 432
ccgtccttcc tccactgat                                                  19

<210> SEQ ID NO 433
<211> LENGTH: 20
<212> TYPE: DNA
<213> ORGANISM: Homo sapiens

<400> SEQUENCE: 433
agagcactga gggagcaaat                                                 20

<210> SEQ ID NO 434
<211> LENGTH: 20
<212> TYPE: DNA
<213> ORGANISM: Homo sapiens

<400> SEQUENCE: 434
agctacagca cgaggcagtt                                                 20

<210> SEQ ID NO 435
<211> LENGTH: 21
<212> TYPE: DNA
<213> ORGANISM: Homo sapiens

<400> SEQUENCE: 435
tttgaattga gttgctgttc g                                               21
```

```
<210> SEQ ID NO 436
<211> LENGTH: 21
<212> TYPE: DNA
<213> ORGANISM: Homo sapiens

<400> SEQUENCE: 436
tgtacaccac caaccattct g                                              21

<210> SEQ ID NO 437
<211> LENGTH: 20
<212> TYPE: DNA
<213> ORGANISM: Homo sapiens

<400> SEQUENCE: 437
gggaagaaag gcaaatagca                                                20

<210> SEQ ID NO 438
<211> LENGTH: 20
<212> TYPE: DNA
<213> ORGANISM: Homo sapiens

<400> SEQUENCE: 438
ggattggcaa ttagcaggtc                                                20

<210> SEQ ID NO 439
<211> LENGTH: 22
<212> TYPE: DNA
<213> ORGANISM: Homo sapiens

<400> SEQUENCE: 439
gcctggtcaa agataacaga cg                                             22

<210> SEQ ID NO 440
<211> LENGTH: 20
<212> TYPE: DNA
<213> ORGANISM: Homo sapiens

<400> SEQUENCE: 440
cctgattaag ctggcctttg                                                20

<210> SEQ ID NO 441
<211> LENGTH: 20
<212> TYPE: DNA
<213> ORGANISM: Homo sapiens

<400> SEQUENCE: 441
atccttctgg gaccctcatc                                                20

<210> SEQ ID NO 442
<211> LENGTH: 20
<212> TYPE: DNA
<213> ORGANISM: Homo sapiens

<400> SEQUENCE: 442
gctttgcttc cttcttggtg                                                20

<210> SEQ ID NO 443
<211> LENGTH: 20
<212> TYPE: DNA
<213> ORGANISM: Homo sapiens

<400> SEQUENCE: 443
caacattacg gccagtctca                                                20
```

<210> SEQ ID NO 444
<211> LENGTH: 20
<212> TYPE: DNA
<213> ORGANISM: Homo sapiens

<400> SEQUENCE: 444
ggtgcatctg ataagccaaa                                              20

<210> SEQ ID NO 445
<211> LENGTH: 20
<212> TYPE: DNA
<213> ORGANISM: Homo sapiens

<400> SEQUENCE: 445
gctgtcttgg acacagtgga                                              20

<210> SEQ ID NO 446
<211> LENGTH: 20
<212> TYPE: DNA
<213> ORGANISM: Homo sapiens

<400> SEQUENCE: 446
caccatcatc atctggttgg                                              20

<210> SEQ ID NO 447
<211> LENGTH: 20
<212> TYPE: DNA
<213> ORGANISM: Homo sapiens

<400> SEQUENCE: 447
gagctcattg aaaggcagga                                              20

<210> SEQ ID NO 448
<211> LENGTH: 25
<212> TYPE: DNA
<213> ORGANISM: Homo sapiens

<400> SEQUENCE: 448
ccatccatct atccatttat ctctg                                        25

<210> SEQ ID NO 449
<211> LENGTH: 20
<212> TYPE: DNA
<213> ORGANISM: Homo sapiens

<400> SEQUENCE: 449
ggatttatcc ttgccctgct                                              20

<210> SEQ ID NO 450
<211> LENGTH: 23
<212> TYPE: DNA
<213> ORGANISM: Homo sapiens

<400> SEQUENCE: 450
ctatcatcca tccatcctat ttg                                          23

<210> SEQ ID NO 451
<211> LENGTH: 20
<212> TYPE: DNA
<213> ORGANISM: Homo sapiens

<400> SEQUENCE: 451
ttagggcagc tacctggaaa                                              20

<210> SEQ ID NO 452
<211> LENGTH: 20
<212> TYPE: DNA
<213> ORGANISM: Homo sapiens
<220> FEATURE:
<221> NAME/KEY: misc_feature
<222> LOCATION: 8
<223> OTHER INFORMATION: n = A,T,C or G

<400> SEQUENCE: 452
aggactanag atgaatgctc                                              20

<210> SEQ ID NO 453
<211> LENGTH: 20
<212> TYPE: DNA
<213> ORGANISM: Homo sapiens

<400> SEQUENCE: 453
gacatgactc catgtttggt                                              20

<210> SEQ ID NO 454
<211> LENGTH: 20
<212> TYPE: DNA
<213> ORGANISM: Homo sapiens

<400> SEQUENCE: 454
cctcaccttg caatttcctg                                              20

<210> SEQ ID NO 455
<211> LENGTH: 20
<212> TYPE: DNA
<213> ORGANISM: Homo sapiens

<400> SEQUENCE: 455
ctgacttgcc tgttggcata                                              20

<210> SEQ ID NO 456
<211> LENGTH: 21
<212> TYPE: DNA
<213> ORGANISM: Homo sapiens

<400> SEQUENCE: 456
tttgggatct tgaagacctt t                                            21

<210> SEQ ID NO 457
<211> LENGTH: 19
<212> TYPE: DNA
<213> ORGANISM: Homo sapiens

<400> SEQUENCE: 457
ttgtggcatg tccttggtt                                               19

<210> SEQ ID NO 458
<211> LENGTH: 23
<212> TYPE: DNA
<213> ORGANISM: Homo sapiens

<400> SEQUENCE: 458
tgtacactgc aaacattgct aaa                                          23

<210> SEQ ID NO 459
<211> LENGTH: 24

<212> TYPE: DNA
<213> ORGANISM: Homo sapiens

<400> SEQUENCE: 459
ttgtcctttc attatgacgt gtct                                          24

<210> SEQ ID NO 460
<211> LENGTH: 23
<212> TYPE: DNA
<213> ORGANISM: Homo sapiens

<400> SEQUENCE: 460
aagcctgaaa ggatacacac aaa                                           23

<210> SEQ ID NO 461
<211> LENGTH: 20
<212> TYPE: DNA
<213> ORGANISM: Homo sapiens

<400> SEQUENCE: 461
caggatccca gactttccag                                               20

<210> SEQ ID NO 462
<211> LENGTH: 20
<212> TYPE: DNA
<213> ORGANISM: Homo sapiens

<400> SEQUENCE: 462
ggtgaatccc accctcatac                                               20

<210> SEQ ID NO 463
<211> LENGTH: 24
<212> TYPE: DNA
<213> ORGANISM: Homo sapiens

<400> SEQUENCE: 463
ttggtatgtt tcctattgtt gcat                                          24

<210> SEQ ID NO 464
<211> LENGTH: 21
<212> TYPE: DNA
<213> ORGANISM: Homo sapiens

<400> SEQUENCE: 464
gaaccagtga gttttattta c                                             21

<210> SEQ ID NO 465
<211> LENGTH: 21
<212> TYPE: DNA
<213> ORGANISM: Homo sapiens

<400> SEQUENCE: 465
agacacagca tataatacat g                                             21

<210> SEQ ID NO 466
<211> LENGTH: 20
<212> TYPE: DNA
<213> ORGANISM: Homo sapiens

<400> SEQUENCE: 466
tgaagctttg tggcttgttg                                               20

<210> SEQ ID NO 467

```
<211> LENGTH: 20
<212> TYPE: DNA
<213> ORGANISM: Homo sapiens

<400> SEQUENCE: 467
gactgagtcc acagcccatt                                              20

<210> SEQ ID NO 468
<211> LENGTH: 25
<212> TYPE: DNA
<213> ORGANISM: Homo sapiens

<400> SEQUENCE: 468
cctggcctgt tagttttat tgtta                                         25

<210> SEQ ID NO 469
<211> LENGTH: 22
<212> TYPE: DNA
<213> ORGANISM: Homo sapiens

<400> SEQUENCE: 469
cccagtcttg ggtatgtttt ta                                           22

<210> SEQ ID NO 470
<211> LENGTH: 20
<212> TYPE: DNA
<213> ORGANISM: Homo sapiens

<400> SEQUENCE: 470
ccaccatgca agaacagatg                                              20

<210> SEQ ID NO 471
<211> LENGTH: 20
<212> TYPE: DNA
<213> ORGANISM: Homo sapiens

<400> SEQUENCE: 471
gctttgcact tggctgtctt                                              20

<210> SEQ ID NO 472
<211> LENGTH: 24
<212> TYPE: DNA
<213> ORGANISM: Homo sapiens

<400> SEQUENCE: 472
ttgcatgaag taaagtatcc ctgt                                         24

<210> SEQ ID NO 473
<211> LENGTH: 21
<212> TYPE: DNA
<213> ORGANISM: Homo sapiens

<400> SEQUENCE: 473
cacaaaccac aagatgattg g                                            21

<210> SEQ ID NO 474
<211> LENGTH: 21
<212> TYPE: DNA
<213> ORGANISM: Homo sapiens

<400> SEQUENCE: 474
gggcatcatg tctacaactc a                                            21
```

```
<210> SEQ ID NO 475
<211> LENGTH: 20
<212> TYPE: DNA
<213> ORGANISM: Homo sapiens

<400> SEQUENCE: 475
accaagggca cttgctgata                                               20

<210> SEQ ID NO 476
<211> LENGTH: 20
<212> TYPE: DNA
<213> ORGANISM: Homo sapiens

<400> SEQUENCE: 476
aggatgaaga gggaggaagg                                               20

<210> SEQ ID NO 477
<211> LENGTH: 26
<212> TYPE: DNA
<213> ORGANISM: Homo sapiens

<400> SEQUENCE: 477
ccagactgat cttccttaat tagttg                                        26

<210> SEQ ID NO 478
<211> LENGTH: 20
<212> TYPE: DNA
<213> ORGANISM: Homo sapiens

<400> SEQUENCE: 478
cctcctcttt ctgctgctgt                                               20

<210> SEQ ID NO 479
<211> LENGTH: 21
<212> TYPE: DNA
<213> ORGANISM: Homo sapiens

<400> SEQUENCE: 479
agccaaagaa cccaaagaaa c                                             21

<210> SEQ ID NO 480
<211> LENGTH: 20
<212> TYPE: DNA
<213> ORGANISM: Homo sapiens

<400> SEQUENCE: 480
gccctacttt gcctcagaaa                                               20

<210> SEQ ID NO 481
<211> LENGTH: 20
<212> TYPE: DNA
<213> ORGANISM: Homo sapiens

<400> SEQUENCE: 481
gcaactcatg ccagcctcta                                               20

<210> SEQ ID NO 482
<211> LENGTH: 22
<212> TYPE: DNA
<213> ORGANISM: Homo sapiens

<400> SEQUENCE: 482
aactgtgtta atgatgggca aa                                            22
```

```
<210> SEQ ID NO 483
<211> LENGTH: 20
<212> TYPE: DNA
<213> ORGANISM: Homo sapiens

<400> SEQUENCE: 483
aacgagcgca tgaaacctat                                               20

<210> SEQ ID NO 484
<211> LENGTH: 20
<212> TYPE: DNA
<213> ORGANISM: Homo sapiens

<400> SEQUENCE: 484
cctggtcaat tgaacccaaa                                               20

<210> SEQ ID NO 485
<211> LENGTH: 23
<212> TYPE: DNA
<213> ORGANISM: Homo sapiens

<400> SEQUENCE: 485
tgaaggaaga taaagcaggg taa                                           23

<210> SEQ ID NO 486
<211> LENGTH: 20
<212> TYPE: DNA
<213> ORGANISM: Homo sapiens

<400> SEQUENCE: 486
ctctctctgg ccctctcttg                                               20

<210> SEQ ID NO 487
<211> LENGTH: 23
<212> TYPE: DNA
<213> ORGANISM: Homo sapiens

<400> SEQUENCE: 487
ggtaacttgc cattcttcta cca                                           23

<210> SEQ ID NO 488
<211> LENGTH: 20
<212> TYPE: DNA
<213> ORGANISM: Homo sapiens

<400> SEQUENCE: 488
actccacctg aagggagaaa                                               20

<210> SEQ ID NO 489
<211> LENGTH: 21
<212> TYPE: DNA
<213> ORGANISM: Homo sapiens

<400> SEQUENCE: 489
tggaagccac taattggaga a                                             21

<210> SEQ ID NO 490
<211> LENGTH: 23
<212> TYPE: DNA
<213> ORGANISM: Homo sapiens

<400> SEQUENCE: 490
aatggatgga tacctcctta tca                                           23
```

```
<210> SEQ ID NO 491
<211> LENGTH: 20
<212> TYPE: DNA
<213> ORGANISM: Homo sapiens

<400> SEQUENCE: 491
ctcattgtgg ctttctgtgc                                                  20

<210> SEQ ID NO 492
<211> LENGTH: 20
<212> TYPE: DNA
<213> ORGANISM: Homo sapiens

<400> SEQUENCE: 492
gtacccacac ctcaccaagc                                                  20

<210> SEQ ID NO 493
<211> LENGTH: 20
<212> TYPE: DNA
<213> ORGANISM: Homo sapiens

<400> SEQUENCE: 493
cgtagctcac attcccaaca                                                  20

<210> SEQ ID NO 494
<211> LENGTH: 20
<212> TYPE: DNA
<213> ORGANISM: Homo sapiens

<400> SEQUENCE: 494
ggcgagtgaa agagaggaca                                                  20

<210> SEQ ID NO 495
<211> LENGTH: 20
<212> TYPE: DNA
<213> ORGANISM: Homo sapiens

<400> SEQUENCE: 495
gggtggtaat tcccagatga                                                  20

<210> SEQ ID NO 496
<211> LENGTH: 20
<212> TYPE: DNA
<213> ORGANISM: Homo sapiens

<400> SEQUENCE: 496
tctgcaacag ccagaatcaa                                                  20

<210> SEQ ID NO 497
<211> LENGTH: 22
<212> TYPE: DNA
<213> ORGANISM: Homo sapiens

<400> SEQUENCE: 497
tgtctgttgg caactttctg tc                                               22

<210> SEQ ID NO 498
<211> LENGTH: 20
<212> TYPE: DNA
<213> ORGANISM: Homo sapiens

<400> SEQUENCE: 498
```
aggtgaaccc agtccagcta                                         20

<210> SEQ ID NO 499
<211> LENGTH: 20
<212> TYPE: DNA
<213> ORGANISM: Homo sapiens

<400> SEQUENCE: 499
tcttaggcaa aggagccagt                                         20

<210> SEQ ID NO 500
<211> LENGTH: 19
<212> TYPE: DNA
<213> ORGANISM: Homo sapiens

<400> SEQUENCE: 500
acatgagcac tggtgactg                                          19

<210> SEQ ID NO 501
<211> LENGTH: 20
<212> TYPE: DNA
<213> ORGANISM: Homo sapiens

<400> SEQUENCE: 501
ggcctcaaat gttttaagca                                         20

<210> SEQ ID NO 502
<211> LENGTH: 20
<212> TYPE: DNA
<213> ORGANISM: Homo sapiens

<400> SEQUENCE: 502
ttctgggtgt tcgctattcc                                         20

<210> SEQ ID NO 503
<211> LENGTH: 20
<212> TYPE: DNA
<213> ORGANISM: Homo sapiens

<400> SEQUENCE: 503
tttcctgtcc agtcctgacc                                         20

<210> SEQ ID NO 504
<211> LENGTH: 22
<212> TYPE: DNA
<213> ORGANISM: Homo sapiens

<400> SEQUENCE: 504
gttttgcagg tctaggtcac ac                                      22

<210> SEQ ID NO 505
<211> LENGTH: 17
<212> TYPE: DNA
<213> ORGANISM: Homo sapiens

<400> SEQUENCE: 505
aggatagctt gagcccg                                            17

<210> SEQ ID NO 506
<211> LENGTH: 396
<212> TYPE: DNA
<213> ORGANISM: Homo sapiens

<400> SEQUENCE: 506

```
gattatatcc cacctaccac tgcagctcca ggatccagct tcacaaacat ttgttgaatg      60
aatgaataag aaaagaggac accccaaag aggctgcaag ggaaaaagct acaagacag      120 aagcaccagg aaaagtagg gtcatgtaag tcaaagcagg aaaaaagttc catggtgggg      180
tggtcagcag tgtctaatrc cacgaaggca caaagtagga taaggttaa aaatcagcct      240 ttggttttgg caaatatgaa gcttatcggt agccttagcg agaacaattc catcagggag      300
cagaagctaa ctgcagtggg ttgagtcatc aagcaggcat aaggaagtag ggatacccca      360
ttataagcta ctctttcaag aagctcaaat ctgaag                              396

<210> SEQ ID NO 507
<211> LENGTH: 396
<212> TYPE: DNA
<213> ORGANISM: Homo sapiens

<400> SEQUENCE: 507
acaaaaatta ccatcatatg ctgtcatgca tgtctgccag tctatttatc atattattta      60
agaaacaaac atttattgaa gatttatcat gtgctcagca ctgccaaaga ggaaataaag      120
agcataatat ctattcttag aaaataacat taacacaaat agaaacaag aaaccataat       180 gttaaaaata ttcatagya acacagaaag acaatgtata attatacata cgcactaaag       240
caaagataac ataatttata aattatgagg tacagaatag ttagattctg aaaattaaaa      300
taatcaggaa aaacttcatg aagatgagat ctgggctgga tcccaaagga taggcaggtg      360
gatcatgtag aacaggggaa aggagttcct gatcgg                              396

<210> SEQ ID NO 508
<211> LENGTH: 396
<212> TYPE: DNA
<213> ORGANISM: Homo sapiens

<400> SEQUENCE: 508
aactaaagaa agccacaaaa gttcacctca atgccaagac atttcttgat ttttgaaaac      60
ccagttgtcg aaccacccat ctatagaaac ttgaaagact aaaaactatc ttactctaaa      120
cattttctag gaagttgatt ctacaacaca ttttggtttt ccatttggc ttctaataat       180 tatttcaaag tttctgtgrc ctaaattttg ttttacattg atcctttgaa tggactactg      240
tttccacatt ttagaacatt taaaaagata tctacaaccc gagtctaatc ataaaaaaaa      300
tcagacagat ccaaaatgtg gaacattcca ctaaaaagg agtggggaga ggtctttatt       360
cttccaaaaa tatcaatgcc ataaaagaca aagacg                              396

<210> SEQ ID NO 509
<211> LENGTH: 396
<212> TYPE: DNA
<213> ORGANISM: Homo sapiens

<400> SEQUENCE: 509
acccttcaac cccagcccag ctgctaactg actacagcca catgaacaga accaggtgag      60
accagaggaa acttccagtc acctaccaga tcatgacaaa taataaacga tgttttttaa      120
accacaaaga tttggagcag catttgttac acaaaattag acaactatta cagttcgact      180
aaaaacatgt tcatttacra tactaaatta gaagtgtaag aatgggagaa aaacttcata      240
ctttaaaagt cattttttcc tccaaaaact tccaactttg aaaaactgat ttttataatg      300
cataaaaatt aaaataaccct tagaatttat atgagtagca tagccagctg gctttattat      360
```

```
ctgttgtact caacacttca ataatcactg atgttt                             396
```

<210> SEQ ID NO 510
<211> LENGTH: 396
<212> TYPE: DNA
<213> ORGANISM: Homo sapiens

<400> SEQUENCE: 510

```
atgaccttac ctcgttttgt tttccttgtc tgagagaaac acattagcag tctcccatct    60
tgttttttcct tttcctgtca cccaggacag agggcagtgg tgtgatcaca gctctgcagc   120
acgacttccc caggttcagg tgatcctccc acctcagcct cccaaggagc tgggaccaca   180
ggcacatgcc accacgtcsa gcttaatttt gtattttttt ggtagagatc aggttttgcc   240
ttattgcccc aagctgatct tgaattcctg gctgaagca atctgcctgc cctgcctct    300
ccaagtgtta ggattacagg tataagccac cgtgcagcct tatattttgt tttaaatttt   360
cctctgtatt tttctctctg gcaaattgtt taggga                              396
```

<210> SEQ ID NO 511
<211> LENGTH: 396
<212> TYPE: DNA
<213> ORGANISM: Homo sapiens

<400> SEQUENCE: 511

```
tttttttggta gagatcaggt tttgccttat tgccccaagc tgatcttgaa ttcctgggct    60
gaagcaatct gcctgccctg gcctctccaa gtgttaggat tacaggtata agccaccgtg   120
cagccttata ttttgtttta aattttcctc tgtattttc tctctggcaa attgtttagg   180
gagtttcttt agtttatcrg actaaatttc aaggctttcc ttccaatttt gacatgtaaa   240
cagtccctca tttctgctta tctagtgatt attcccaaat ctgtgtttac agtctagctg   300
tctctcctga gattaagact tgtttctcta actacctgac ggcagaatct cctcttggaa   360
gtatcaagga ggcagttcaa aactgaactg ggcatt                              396
```

<210> SEQ ID NO 512
<211> LENGTH: 396
<212> TYPE: DNA
<213> ORGANISM: Homo sapiens

<400> SEQUENCE: 512

```
gctgatcttg aattcctggg ctgaagcaat ctgcctgccc tggcctctcc aagtgttagg    60
attacaggta taagccaccg tgcagcctta tattttgttt taaattttcc tctgtatttt   120
tctctctggc aaattgttta gggagtttct tagtttatc agactaaatt tcaaggcttt   180
ccttccaatt ttgacatgya aacagtccct catttctgct tatctagtga ttattcccaa   240
atctgtgttt acagtctagc tgtctctcct gagattaaga cttgtttctc taactacctg   300
acggcagaat ctcctcttgg aagtatcaag gaggcagttc aaaactgaac tgggcattgg   360
ctccactcct tctccttctc tttactatta ataccc                              396
```

<210> SEQ ID NO 513
<211> LENGTH: 396
<212> TYPE: DNA
<213> ORGANISM: Homo sapiens

<400> SEQUENCE: 513

```
taagtcttat ttaggcatcg tttcttctgg gagacctttg tagaatctct gaggttatgt    60
taacatgcta aggttttctt gacattctca gattgggtta ggtgaacttt tagcaactta   120
```

```
tctttttact aaaaagtcat ccctcagtat ctgtggggaa ttggttctag gactccctaa    180
ggatatcaaa atctgcatra gcagcccagg tgagaccagc agaagcactt tacagtcacc    240
tacaggatca tgacaaataa taaatcatgt ttaagccaca aagtccttta cataaaatgg    300
tatagtattt gcatataacc tacacatctt cctgtatcct ttaaatcatc tctagtttat    360
aatacctcat acgatgaaaa tactacgtaa atagtt                              396
```

<210> SEQ ID NO 514
<211> LENGTH: 396
<212> TYPE: DNA
<213> ORGANISM: Homo sapiens

<400> SEQUENCE: 514

```
aagcagttcc taattactgg acattctcag atctgctaga gctacatgtc caattacgag    60
aatatactgg aaaaagccct ggattagaaa tgagaggatg taggttttag taccaggtca    120
gccaccttgt taatgcaaat ttgagtaaat tgttacttct tttaggcctt gttttgctg    180 ttttgttttt ctgacagtmt ggtctctgtg gtccaggctg gagtgcagag gcacaatatc    240
aggtccctgc agtctctacc tcccaggatc aagccatttt catgcctcat cctcctgagt    300
agctgggatt acaggcatgt gccaccacac cctcgaactc ctgacctcaa gtgatctgct    360
tgcctcagcc tcccaaagtg ctgggattag aggtgt                              396
```

<210> SEQ ID NO 515
<211> LENGTH: 396
<212> TYPE: DNA
<213> ORGANISM: Homo sapiens

<400> SEQUENCE: 515

```
gaatatactg gaaaaagccc tggattagaa atgagaggat gtaggtttta gtaccaggtc    60
agccaccttg ttaatgcaaa tttgagtaaa ttgttacttc ttttaggcct tgttttgct    120 gttttgtttt tctgacagta tggtctctgt ggtccaggct ggagtgcaga ggcacaatat    180
caggtccctg cagtctctrc ctcccaggat caagccattt tcatgcctca tcctcctgag    240
tagctgggat tacaggcatg tgccaccaca ccctcgaact cctgacctca agtgatctgc    300
ttgcctcagc tcccaaagt gctgggatta gaggtgtgag ccactgtgcc tagccttaca    360 cattgtttc ttactggtaa agtgggaata tctaga                              396
```

<210> SEQ ID NO 516
<211> LENGTH: 396
<212> TYPE: DNA
<213> ORGANISM: Homo sapiens

<400> SEQUENCE: 516

```
gttttgtttt tctgacagta tggtctctgt ggtccaggct ggagtgcaga ggcacaatat    60
caggtccctg cagtctctac ctcccaggat caagccattt tcatgcctca tcctcctgag    120
tagctgggat tacaggcatg tgccaccaca ccctcgaact cctgacctca agtgatctgc    180
ttgcctcagc tcccaaakt gctgggatta gaggtgtgag ccactgtgcc tagccttaca    240 cattgtttc ttactggtaa agtgggaata tctagaagtt gcatgctaca taaattcaac    300
catatattat tggcaaaaaa ttttaaagaa aaacatcagc ttaagagtac taattgagta    360
catgccttgg aatgagcatg agctggaaag aacaaa                              396
```

<210> SEQ ID NO 517

<211> LENGTH: 396
<212> TYPE: DNA
<213> ORGANISM: Homo sapiens

<400> SEQUENCE: 517

| | | | | | |
|---|---|---|---|---|---|
| ggcaaaaaat | tttaaagaaa | aacatcagct | taagagtact | aattgagtac | atgccttgga | 60 |
| atgagcatga | gctggaaaga | acaaacctgt | tgttacatca | ctcattgctg | ttttcatatg | 120 |
| ctgctcattg | taaatcttgc | tcagtggcat | gattttagtg | tttaaagatt | tatttgtttg | 180 |
| tttgtttagg | acaaagtcyc | tacacataat | ctacttgctt | catatataca | tacttatgca | 240 |
| tattatgtat | gtacatacat | gctctcaggg | ctcacatgaa | aaaacagcca | ttcaggtgat | 300 |
| gtgatttatc | tcatatgctt | actttagagt | caacagggtg | ttgactccac | tatacaatac | 360 |
| tggcatggag | aacacataag | tcaaagtaga | caggac | | | 396 |

<210> SEQ ID NO 518
<211> LENGTH: 396
<212> TYPE: DNA
<213> ORGANISM: Homo sapiens

<400> SEQUENCE: 518

| | | | | | |
|---|---|---|---|---|---|
| tttatttgtt | tgtttgttta | ggacaaagtc | tctacacata | atctacttgc | ttcatatata | 60 |
| catacttatg | catattatgt | atgtacatac | atgctctcag | ggctcacatg | aaaaaacagc | 120 |
| cattcaggtg | atgtgattta | tctcatatgc | ttactttaga | gtcaacaggg | tgttgactcc | 180 |
| actatacaat | actggcatrg | agaacacata | agtcaaagta | gacaggaccc | agccgtacca | 240 |
| ttggctaggg | cacaaatata | ttcacatatg | tggagaatga | tgtacgtaga | aaggtcttca | 300 |
| ttgcacaatg | ctctttaata | aagatctgga | aaaaaaaaac | acctaaatgt | tcaaaggat | 360 |
| agggtagatg | aaataatggt | acattataaa | atggaa | | | 396 |

<210> SEQ ID NO 519
<211> LENGTH: 396
<212> TYPE: DNA
<213> ORGANISM: Homo sapiens

<400> SEQUENCE: 519

| | | | | | |
|---|---|---|---|---|---|
| tctgtcaccc | aggctggagt | gcagtggcat | gatcatgtct | ccttgcagcc | ttgacttccc | 60 |
| tggctcaggt | gggcctccca | cctcagtctc | ccaagtagct | ggaactacag | tcgtgcacca | 120 |
| ccatagccag | ctaagatagt | gagatggtgg | cccactgtc | ttgcccaggc | tggactcgat | 180 |
| ttcctgggtg | caagcaccst | tcccgcctca | gcctcccaaa | gtgctggat | tacaggcatg | 240 |
| agtcaccatt | ccagcctact | tgtctttaat | tcttaaaaat | attaatgttg | agttttgtct | 300 |
| cccagcatgt | gggaaagatg | tcatccattg | cttctgtttc | ctggaggcct | gggagcaagg | 360 |
| agcccaggaa | cagtatcacg | aagcttgaga | taatac | | | 396 |

<210> SEQ ID NO 520
<211> LENGTH: 396
<212> TYPE: DNA
<213> ORGANISM: Homo sapiens

<400> SEQUENCE: 520

| | | | | | |
|---|---|---|---|---|---|
| atcattgatg | gcatttggg | ttggttccaa | gtctttgcta | ttgtgatttt | tttttttttt | 60 |
| tttttttttt | taagacagag | cctcactctg | ttgcccaggc | tggagtgcga | tggcatgatc | 120 |
| tcagctcact | gcaacctccg | cctctcaggt | tcaagcaatt | cttctgcctc | agcctcccaa | 180 |
| gtagctggga | ctacaggcrc | ccaccaccag | gcccagctaa | ttttttgtatt | tttagtagag | 240 |

```
acagggtttc accatgttgg tcaggctggt cttgaactcc agacctcatg atctgcctgc      300
cttggcctcc caaagtgctg aaattacagg tgtgagccac catacctggc ctaggcagtc      360
tttttcaaaa ctctaagact gtgcttgtgt ctcagg                                396
```

<210> SEQ ID NO 521
<211> LENGTH: 395
<212> TYPE: DNA
<213> ORGANISM: Homo sapiens

<400> SEQUENCE: 521

```
ggtatgaggt aaggatccat ttttttccca tttgcatagc cagttttttgt agctccactt     60 tattttctca cttgatctgc catgccacct ctagcatgta tcaacatatc atgtatgtgt     120
gcagctgttc cttaactctc aatttttattc tcttggttac tttgtctaac ccagcactca    180
tactttttaa attattaygg ctaccttgta gggcaagaat cctcactttt attcaacttc     240
ttttgaagtg tcttgatgca tattttttct gatcttactt ggccatatat attttgggga    300
cagatgtgac atcataccaa gctttctttg cttgacattg tagatatttt cttattcatt    360
aatgtgctaa aaattttgag tttggtcata cagtc                                395
```

<210> SEQ ID NO 522
<211> LENGTH: 396
<212> TYPE: DNA
<213> ORGANISM: Homo sapiens

<400> SEQUENCE: 522

```
gtttctaaca ttatagacac tagttttagg ctcttggagg ctagcagcaa ttctcagagg     60
taatgcaagc ttccccattt cttcccgtag tcctgtgaaa gaccagccac ctccagaagc    120
ctacacatga gtcttctcag ccatactttc tgcttttcct aatgcctctc agcagcgtat    180
tagaaaggcc atgatcgayg tacctgttac cttcaggctt tgcataaggt gtatatgaaa    240
cataatgaat ttcgtgttta ggctcaggtc ccatccccag gttacctctt tatcttggag    300
acacttctgg tcccatacat ttcagataag agatattcaa cctgtaccca ccacgtaagg    360
agaggaatag gttttagaag aggagtcagg gaggca                                396
```

<210> SEQ ID NO 523
<211> LENGTH: 396
<212> TYPE: DNA
<213> ORGANISM: Homo sapiens

<400> SEQUENCE: 523

```
gcatctatta aaagtgatgg ttttagtatc ctgtctcatt ttttcctttc cttacatcat     60
gtattatagg taaacacatg cgcatgtgtg tatttctctt ttagacaaag gatgagatta    120
ctactgttag ctcagttttt ttttccctac ttaacatctt tgcttttatt ttttagacat    180
atttctaaga ctattaaaya ttagacttac gtagcccttc tgtcattgtg aaatacatag    240
tttactaaca gctaccatca agataaagcc tttatttaaa taattaaaact tcttagtgga    300 aagctaagta agcacagttt atggattttg ggaattttttg ccttgcattt gtctgatatg    360
gtaaaatatt gagtttgttt ttctcataat gttcac                                396
```

<210> SEQ ID NO 524
<211> LENGTH: 396
<212> TYPE: DNA
<213> ORGANISM: Homo sapiens

<400> SEQUENCE: 524

```
gataactcaa tccccttaaa gggttgtatc aagccattga taagggctca ctttgatata        60
accattttct gttatttaga cactctttca cacttcctat tttcctcctg gggatggttt       120
gaatggatga cacaatacca tattataaaa gcactttaca aactgtaact tatgttataa       180
atgtaattat taccttaarg ttttaccctg tttcagattt gagtggaagt agttctttac       240
aatacaaaac aacttatttt aactttttt gcatttcaaa gaatgatcaa tccacttcag       300
gtgcagcatg gtttccaacc ctgacagcat ggaagaatca tttatttagc ttctaaaaat       360
gtgcaggctg taccctagac cagccttggg gattag                                 396
```

<210> SEQ ID NO 525
<211> LENGTH: 396
<212> TYPE: DNA
<213> ORGANISM: Homo sapiens

<400> SEQUENCE: 525

```
tcctctctct cattctctct ctctctctct ttctctctct ccttctttgc tccttcattc        60
cttctctctc tctctttttt ttttgagaca gcatctcact atattgccca ggctgttctc       120
aaactcctgg gctcaagtga tcctcctgcc tcagcttcct gagtagctag gactacaggc       180
acatgctatg caatactrt tttaaacatt gttttcaagg ctccccaggt gattccagtg       240
tgggtcatgt ggtagagaac cactgacaca ggcaaacaaa ggatacataa agttgtctat       300
ttaatgggta ggtgcaggta gtagataaga gtgtagccac ataaaccaca tgcttagtga       360
acggttttgt tttgtgtgta tgtgagggat tagcat                                 396
```

<210> SEQ ID NO 526
<211> LENGTH: 396
<212> TYPE: DNA
<213> ORGANISM: Homo sapiens

<400> SEQUENCE: 526

```
ttcaggttcc atttagcacg acagcaggga agggactgtt ggcagaaaaa aactggggca        60
gtgggattaa agacagacca cacattccaa aaggcaccgt gggagggtca gggggcgagg       120
ttaggtctag gcttcagtgt cctgggagac tcagtcttca cagggtgaca gcgatcaaga       180
gtgcagctta ggctgggtrc agtggctcat gcctgtagtc ccagcacttt gggaggccga       240
gacgggagga ttgcttgaag ccaggagttt gagaccagtc tgaccaacat ggcaaaaccc       300
catctctact aaaaatacaa aaatcaactg gcatggtgg cgtgtgcctg tagtcccagc       360
tacttgagag gctgaggcaa gagaatcact tgaacc                                 396
```

<210> SEQ ID NO 527
<211> LENGTH: 396
<212> TYPE: DNA
<213> ORGANISM: Homo sapiens

<400> SEQUENCE: 527

```
taaatgatca ttatgttcat attcacacat acaataatgt actcaagttt attgctaagg        60
taattcagaa tctccttatt ttgaagtgtg catttgatat acctgtttgg gaataactag       120
tttcttatct ttgacagaaa ataatttgt tgttttgttt ttactaaaaa agcatggtga       180
aaaatggctc catttctawg agaggtaact aaaatatcgc aatttgctgg gtgtcattaa       240
agtaactcac aagggaaaaa atgcaaattg gtatctgctg atggagtaaa tctccgcaga       300
agtgatgacc ctgaaaggat caatatatta aagcccctcc cagctggtca ttccagattg       360
```

```
caacaataaa gcattaagtg ttaaaacctc aaggca                              396

<210> SEQ ID NO 528
<211> LENGTH: 396
<212> TYPE: DNA
<213> ORGANISM: Homo sapiens

<400> SEQUENCE: 528
ctcatcaagc ccacctttat acttcatttc tccagacttc atgtccagac tgtgggatga    60
acaagtggtt ataaggtttt agaggctcct gtaggactag atggaaggca aaaaaaggaa   120 ataacctttta agcatgctct cgattcctta aatcccatct gaaagtctta aggatgtctt   180
ctcagtcata cttatttgrc aatattacct aattttctcc attagcccaa gctcaggggt   240
cttctcttct tccatattcac atgggtgcaa tggttttctg aaaggaaaac agcattacta   300
gggcagtaac atttaattaa tcacaggtac ttatcaaact acaaacagg cattccagga    360 actgggtgtt tctgtttgta aaattacact ctcgtg                             396

<210> SEQ ID NO 529
<211> LENGTH: 396
<212> TYPE: DNA
<213> ORGANISM: Homo sapiens

<400> SEQUENCE: 529
taggactaga tggaaggcaa aaaaggaaa taacctttaa gcatgctctc gattccttaa    60
atcccatctg aaagtcttaa ggatgtcttc tcagtcatac ttatttgaca atattaccta   120
attttctcca ttagcccaag ctcaggggtc tttcttcttc catattcaca tgggtgcaat   180
ggttttctga aggaaaaya gcattactag ggcagtaaca tttaattaat cacaggtact   240
tatcaaacta caaacaggc attccaggaa ctgggtgttt ctgtttgtaa aattacactc   300
tcgtgtacat gctcccacta aatgtaagt tcgctgagga tggaggtttt ggtctctttg    360
ctctgtgctg taaccccaac actgcagcag ggcctg                             396

<210> SEQ ID NO 530
<211> LENGTH: 396
<212> TYPE: DNA
<213> ORGANISM: Homo sapiens

<400> SEQUENCE: 530
gctgcatagt ctcacttagg tgtggaatct aaaaaagtca aattaaaaaa aaatgtcaag    60
cagagaatag aatggtagtt gccagggact ctggaagta gcaggggtgg gggtggaggg   120
gaggggatgg gcagaagttg gtcaaaaggt acaaagtttc aggtagacag gtgtaagttc   180
tggggatcta ttgtacagmg tggtgactgt agttaatact gtattgtgta cttaaaaatt   240
gctcaccaaa aatgttctca ccaaaaaaat gatgtttgga tatgttaaac agtttgatttt   300 aatcattttg acgtgtgtgt gtgtgtgtgt gtgtgtgtgt gtgtatatac atcaaaacat    360
cacattatat accatataca attaatatat acaatt                             396

<210> SEQ ID NO 531
<211> LENGTH: 396
<212> TYPE: DNA
<213> ORGANISM: Homo sapiens

<400> SEQUENCE: 531
ggggtaaatg ctgactgcct gttctctgga caggaatgga gaagatggtg ctagcagggt    60
```

| | |
|---|---|
| tgctgttcat atgtagacat tcatgcagtc actctctttt cagcacactt cttacttctg | 120 |
| ccctgggttc agttgctgac tctgagccca gaaaccttct agggttctgt taggtagatt | 180 |
| ggcttccacc gtctttgcra caaccacaga aaattctaga ctgttttctc ttcgggcttc | 240 |
| attagtcaac ttgcttcagt ctgtcttgca tcttctaaat atttatagat ctctctcttt | 300 |
| tgttggagtg cagaaaatg ctagttgacc acccaatatt caaattatcc tgcctcctta | 360 |
| ataacagaat atcattggat gtggtgggta ataat | 396 |

<210> SEQ ID NO 532
<211> LENGTH: 396
<212> TYPE: DNA
<213> ORGANISM: Homo sapiens

<400> SEQUENCE: 532

| | |
|---|---|
| atggagaaga tggtgctagc agggttgctg ttcatatgta gacattcatg cagtcactct | 60 |
| cttttcagca cacttcttac ttctgccctg ggttcagttg ctgactctga gcccagaaac | 120 |
| cttctagggt tctgttaggt agattggctt ccaccgtctt tgcgacaacc acagaaaatt | 180 |
| ctagactgtt ttctcttcrg gcttcattag tcaacttgct tcagtctgtc ttgcatcttc | 240 |
| taaatattta tagatctctc tcttttgttg gagtggcaga aaatgctagt tgaccaccca | 300 |
| atattcaaat atcctgcct ccttaataac agaatatcat tggatgtggt gggtaaataa | 360 |
| tatacccta ctttccttgc agagagggt ggccaa | 396 |

<210> SEQ ID NO 533
<211> LENGTH: 396
<212> TYPE: DNA
<213> ORGANISM: Homo sapiens

<400> SEQUENCE: 533

| | |
|---|---|
| cagggttgct gttcatatgt agacattcat gcagtcactc tcttttcagc acacttctta | 60 |
| cttctgccct gggttcagtt gctgactctg agcccagaaa ccttctaggg ttctgttagg | 120 |
| tagattggct tccaccgtct tgcgacaac cacagaaaat tctagactgt tttctcttcg | 180 |
| gcttcatta gtcaacttkc ttcagtctgt cttgcatctt ctaaatattt atagatctct | 240 |
| ctcttttgtt ggagtggcag aaaatgctag ttgaccaccc aatattcaaa ttatcctgcc | 300 |
| tccttaataa cagaatatca ttggatgtgg tgggtaaata atatacccta actttccttg | 360 |
| cagagagggg tggccaatga gatggaaatg aaagtc | 396 |

<210> SEQ ID NO 534
<211> LENGTH: 396
<212> TYPE: DNA
<213> ORGANISM: Homo sapiens

<400> SEQUENCE: 534

| | |
|---|---|
| tgggattgag ttcttgattt gatttgagc ttggccatca ttggtgtata gcagtgctag | 60 |
| tgatttgtgt acattgattt tgtaacctaa cactactaaa ttcacttatc aaatctggga | 120 |
| gatttttgag gattccttag gatttctag gtatgagatc atatcattgg tagaggtagt | 180 |
| ttgagtttct cttttccart tggatgccc tttatttctt tctcttgcct gattgctctg | 240 |
| actagggctt ctagtactat gttgaataga aatggtgaaa agtgggcatc cttgtctcat | 300 |
| tctaattttt aggggaaat gctttcaact ttccccatt catttgatg ttggctgtga | 360 |
| gtttgtcata gatgattctt actattttga gatata | 396 |

<210> SEQ ID NO 535
<211> LENGTH: 396
<212> TYPE: DNA
<213> ORGANISM: Homo sapiens

<400> SEQUENCE: 535

```
tcttttgccc tgcctttctg cctttctgtc cttttaattt gcgggctttt ggcaaccaca      60
gcacgggtct ggtttcctag gagtttcttt tgtaggatca aaccgctagt tggctcttgg     120
ccctgtgata gggccctggg ctaacttatt gggaaaatgt tgctgtaacc cctgcccaga     180
ggtgcctgtg acatgggcyg ccatcttctc ctcttcccctt ggcttcagcc ccacctagaa     240
acctgaacaa acattttcct tgacatttca taaagtgtca gtggctcctc atttagcaaa     300
atacatccca gggaagttca aaagtgaaaa aaggccgtaa cttcttcttc ttctcaggga     360
cctacagaaa atatgtggca cctcggcagc ctggcc                              396
```

<210> SEQ ID NO 536
<211> LENGTH: 396
<212> TYPE: DNA
<213> ORGANISM: Homo sapiens

<400> SEQUENCE: 536

```
catggatttt gttttccaag tggcaagatg gcgcctccac ctttggtatc ctattttagt      60
tcctggcaga agaaaggaa caggctaatg gccctgatga gtctacccccc ttttaacagg     120
agaaaattta aaaacaaaa accatgaaac cctttcccag aggcaacaac cagaattcca     180
tttatctttc attgaccara acagaccaca tggtcactgg tggtggcaat ggagactggg     240
gagatgaata ttttttaaggt ggcatattcc agaagaacac tgtgcactga ttgcattaat     300
gaacccatta atgtgccaag gggaggttta cctatgagca tgggcaaatt agaacccact     360
cttggagctg caggtgagcc aatcccacct aaacag                              396
```

<210> SEQ ID NO 537
<211> LENGTH: 396
<212> TYPE: DNA
<213> ORGANISM: Homo sapiens

<400> SEQUENCE: 537

```
tggtggtggc aatggagact ggggagatga atatttttaa ggtggcatat tccagaagaa      60
cactgtgcac tgattgcatt aatgaaccca ttaatgtgcc aaggggaggt ttacctatga     120
gcatgggcaa attagaaccc actcttggag ctgcaggtga gccaatccca cctaaacagt     180
gtggatgcta caagatggrg aagtaaattg attctattcc atacctaac ctctctccaa     240
gatgtattct taaatagaa gagggaagac agaagaaaac atccagaata tatttttatt     300
gtcttttact tcttcagtgc attttagatc agtgcttctc aatctggcaa ggggcatgca     360
ggaggatgtg agttttatca ggaaaactac acaacc                              396
```

<210> SEQ ID NO 538
<211> LENGTH: 396
<212> TYPE: DNA
<213> ORGANISM: Homo sapiens

<400> SEQUENCE: 538

```
tgagccaatc ccacctaaac agtgtggatg ctacaagatg gggaagtaaa ttgattctat      60
tccatacccct aacctctctc caagatgtat tcttaaaata gaagagggaa gacagaagaa     120
aacatccaga atatattttt attgtctttt acttcttcag tgcattttag atcagtgctt     180
```

```
ctcaatctgg caaggggcrt gcaggaggat gtgagtttta tcaggaaaac tacacaaccc      240
cccaaccaca atgctacccc cactcctgtg gaccttcttt aagagagact cactattata      300
gatggagttg atacgatttt aagagaggcc atatattatt tgctttctgt cttgaaaaac      360
ttgtgatttt tctgtattgt gctactgcca aagaga                                396
```

<210> SEQ ID NO 539
<211> LENGTH: 396
<212> TYPE: DNA
<213> ORGANISM: Homo sapiens

<400> SEQUENCE: 539

```
gggttgcagt gagcagagat cacaccattg cactccagcc tgggtggcag agcgagattc      60
tgtctaaaaa acaacaccgt atttggggca tgctgatact aaaaaattat tcattgtttg      120
tctgaaatta aaatttaaat tgggggccct gtattttact gggcaaccca tttgcaatat      180
cagcaacaat ctcttattsa gaccactgat taagtgtgca aaatttgaat ctctgaacag      240
tacctatgtc cttgatatct aaattaatg agtgtcttag acactcaaag caggaggaag       300
cattatggca gatgtttgag ccccagagat gtccatgagc acagcataga gctcagagcc      360
ttctttatta tttgcttcac gacagagcaa aggact                                396
```

<210> SEQ ID NO 540
<211> LENGTH: 396
<212> TYPE: DNA
<213> ORGANISM: Homo sapiens

<400> SEQUENCE: 540

```
catttgcaat atcagcaaca atctcttatt cagaccactg attaagtgtg caaaatttga      60
atctctgaac agtacctatg tccttgatat cttaaattaa tgagtgtctt agacactcaa      120
agcaggagga agcattatgg cagatgtttg agccccagag atgtccatga gcacagcata      180
gagctcagag ccttctttrt tatttgcttc acgacagagc aaaggactgc agcaggttga      240
ctgatataaa agttttacca tgtctcacag caggcctttg ctcaagtttc cagtaaggat      300
attgtatcat ttcttgcctg cagtacttgt aaatccactt acactgcctg ctgttgagtc      360
atttgtttcg tcttgagtag catgtcatcc ttgttc                                396
```

<210> SEQ ID NO 541
<211> LENGTH: 396
<212> TYPE: DNA
<213> ORGANISM: Homo sapiens

<400> SEQUENCE: 541

```
ttgcagttct cattgctggg gagtctaaac tggaataaaa cacccactat ctccatcagg      60
cttgcactag agcccagctc tagctggaga gaaagaagct aacccgcaca gacacaggac      120
tgtaggcagg gagcatccgg gggtatttgg gtcctggctc tgatgtgcct aaggccaact      180
tctctctggc catgctggyg tgcatgagct cactaatctt ccttttttgcc ttccattttc      240 tccaatcctg acttagcaaa ggttgggcaa aagagactct gtgtgagttc gagcaaagcc      300
tgagatgctg gattttccaa gatacgagaa ggggctgggg gctgggtgaa ctggtggtgg      360
aggagggaag gattaatttc ccaaggaggg gaaggg                                396
```

<210> SEQ ID NO 542
<211> LENGTH: 396
<212> TYPE: DNA
<213> ORGANISM: Homo sapiens

<400> SEQUENCE: 542

```
gagaaagaag ctaacccgca cagacacagg actgtaggca gggagcatcc gggggtattt      60
gggtcctggc tctgatgtgc ctaaggccaa cttctctctg gccatgctgg cgtgcatgag     120
ctcactaatc ttccttttg ccttccattt tctccaatcc tgacttagca aaggttgggc      180
aaaagagact ctgtgtgart tcgagcaaag cctgagatgc tggattttcc aagatacgag     240
aaggggctgg gggctgggtg aactggtggt ggaggaggga aggattaatt tcccaaggag     300
gggaaggggc caggacatca ggccccgggg actttgaaga gagggtcgtg ggtaggaggt     360
agatcaagtg gagtgacaca aaggtcagga aagagg                               396
```

<210> SEQ ID NO 543
<211> LENGTH: 396
<212> TYPE: DNA
<213> ORGANISM: Homo sapiens

<400> SEQUENCE: 543

```
catgcctcct acaaatttga cctgggccca gggccatgtt cggtggtttt taagaaccga      60
ggctcccaga agcagtattg ggcagctaga gtggccccag gatctatatc aaactctacc     120
tgtttctgaa ccaaatttct tctagaattt tattccataa atctgaatta tggtgtcaga     180
ctcctagcat acactaaakg aactctctgc cttgcattaa ataacaggag ttacccctgg     240
aggtaactcc tagccctggc tctttagaga acagatgccg aataggcatt aggggatgtg     300
atggatgtgc taactttcaa aaaaaaaaaa aaaaaaggc ctgagctgag tgctcagaga     360
ttcacaaaaa gctgacagca tctctctgtt ccattg                               396
```

<210> SEQ ID NO 544
<211> LENGTH: 396
<212> TYPE: DNA
<213> ORGANISM: Homo sapiens

<400> SEQUENCE: 544

```
ctttggagcc tggcagcctg gctttgagaa ccgggcttta acttgtcaca tgactatggc      60
caagttcctg gggctctcca agcttcactt cctctgtaaa aagggcaata atataatacc     120
tgtcttattg ggttttgtcc atgttagatg agacattggg tacaaagcac ttggtcccgt     180
gcctggcaca tttactgcrc ttaatgtatg atagttttct tattattcta ataaacaata     240
tggctttggg agtatagttc tgccacattg cagtggccag agtgaaggtg gtgagtgcct     300
tctgggccc tgggagtcaa ggttatccgc atgccctttc ttgcttgctc ctcagtgtgg     360
ctgcctctat gtccacacca tgcagatgca acaggt                               396
```

<210> SEQ ID NO 545
<211> LENGTH: 396
<212> TYPE: DNA
<213> ORGANISM: Homo sapiens

<400> SEQUENCE: 545

```
acatgatcat ccccttgggc ttctggtttt ttttctttca ggaccttatt ttcaggcaag      60
tggcctttga cctctaaggc tgtcctttcc tagctaccga atccagcatt caaagtgatg     120
gaaatatgta tatatagtaa tagtaaaata tcagcactta atggcctgat aagaatgtca     180
ctgcaatgct gagtttggrc caacatttgc ctgctcctgc cattgagccc gggctcccct     240
ccagagctga gctgctgcaa gggatctgag taactagggc tgtgtcagag tggcgatgac     300
```

```
agccaccaca tgctaaggaa gagatcccca aggacaagga gaatcccacg tggagctact    360
tgcttctttg tcagtcttgt ttttcttatt tcacaa                              396

<210> SEQ ID NO 546
<211> LENGTH: 396
<212> TYPE: DNA
<213> ORGANISM: Homo sapiens

<400> SEQUENCE: 546
ccgaatccag cattcaaagt gatggaaata tgtatatata gtaatagtaa aatatcagca     60
cttaatggcc tgataagaat gtcactgcaa tgctgagttt ggaccaacat ttgcctgctc    120
ctgccattga gcccgggctc ccctccagag ctgagctgct gcagggatc tgagtaacta    180 gggctgtgtc agagtggcra tgacagccac cacatgctaa ggaagagatc cccaaggaca    240
aggagaatcc cacgtggagc tacttgcttc tttgtcagtc ttgttttttct tatttcacaa  300 ccttctaaaa cacaatctct caacctctat tgttagcttg cattttcaa tcatgagcac    360 agctttacct ggctccatgc tttgattgac tctacc                              396

<210> SEQ ID NO 547
<211> LENGTH: 396
<212> TYPE: DNA
<213> ORGANISM: Homo sapiens

<400> SEQUENCE: 547
tcttatttca caaccttcta aaacacaatc tctcaacctc tattgttagc ttgcattttt     60
caatcatgag cacagcttta cctggctcca tgctttgatt gactctacct gccaacactg    120
caacaacagg gaaagggaca ccggcctcat accattagat ggtgtgtagc ctgggcatga    180
ggataattaa aaactcccwa ggggatttta acatgtaaca cagtttggaa accattgatg    240
taagatcttc ttactcaaca tgtgctccaa ggagctgttg tatcagctta tcagaaatgt    300
agatcaggcc gcacttggac ctgtagaatc agaatctgca ttttatcaga ttccgacatt    360
atttgtatga acattagctt ttgagaagtg ttgctt                              396

<210> SEQ ID NO 548
<211> LENGTH: 396
<212> TYPE: DNA
<213> ORGANISM: Homo sapiens

<400> SEQUENCE: 548
cttttgacac caactacaag tcaaggggtt ccccaaacca ccctgagttg tgataattcg     60
ctgggagatc tgacagaact cactgaaggt tgttatactc atggttgtga tctcttatag    120
ggagggaata cagattaaaa tcagccaaag gaagaagcac acagcacaga gtccaggaca    180
gtgcctgaca tggagcccyt acggtcctct cccgtggagt cacggacagc gccactctcc    240
tggcattgat gtgtgacaac acacaggag tgttccccac cagggaagcc ttggtgtcca    300
gggtctttac tgtggctctg tcacatgagc acagctgact gcccatgcgg ccgatctgtt   360
cccagactct ccaccgctac acatcactca cagtcc                              396

<210> SEQ ID NO 549
<211> LENGTH: 396
<212> TYPE: DNA
<213> ORGANISM: Homo sapiens

<400> SEQUENCE: 549
gtggctcaca gaactcaggg aaacacagct accagtttat tgcgaaggac attttaaagg     60
```

```
ataaaagtag gcagataaag agatgcatag ggcgaggtgt ggaaaggtcc ctagtgcagg      120
agcttctgtc catgtggagc gggggtgcac caccctctca gtacatgaat gagttctcct      180
tcacctgcct atcagcctyt acatgttcag ctccccaacc cagtcctctt gggtttttat      240
ggaagcttca agacacccac attctttccc cagagtatag ggcaagacct tctctgggga      300
gggttttaag acccacagtc agaaaggtgg ggtggggtca agattagagt cctgccttga      360
cgggcaggtg aaaggggtag ggggagtagg tgagaa                               396
```

\<210\> SEQ ID NO 550
\<211\> LENGTH: 396
\<212\> TYPE: DNA
\<213\> ORGANISM: Homo sapiens

\<400\> SEQUENCE: 550

```
cgggggtgca ccaccctctc agtacatgaa tgagttctcc ttcacctgcc tatcagcctc       60
tacatgttca gctccccaac ccagtcctct tgggttttta tggaagcttc aagacaccca      120
cattctttcc ccagagtata gggcaagacc ttctctgggg agggttttaa gacccacagt      180
cagaaaggtg gggtggggkc aagattagag tcctgccttg acgggcaggt gaaagggta       240 gggggagtag gtgagaaaaa ttctgtttat tttttctttt ttttttgag acggagtttc       300 actcttgttg cccagggtgg agtgcaatgg cacaatctca gctcactgca acctccgcct      360
cccaggttta agcgattctc ctgcctcagc ctcccg                                396
```

\<210\> SEQ ID NO 551
\<211\> LENGTH: 396
\<212\> TYPE: DNA
\<213\> ORGANISM: Homo sapiens

\<400\> SEQUENCE: 551

```
atgagttctc cttcacctgc ctatcagcct ctacatgttc agctccccaa cccagtcctc       60
ttgggttttt atggaagctt caagacaccc acattctttc cccagagtat agggcaagac      120
cttctctggg gagggtttta agacccacag tcagaaaggt ggggtggggt caagattaga      180
gtcctgcctt gacgggcarg tgaaagggt aggggagta ggtgagaaaa attctgttta      240
ttttttcttt ttttttttga acggagttt cactcttgtt gcccagggtg gagtgcaatg       300
gcacaatctc agctcactgc aacctccgcc tcccaggttt aagcgattct cctgcctcag      360
cctcccgagt agctgggatt acaggcgtgt gccacc                                396
```

\<210\> SEQ ID NO 552
\<211\> LENGTH: 396
\<212\> TYPE: DNA
\<213\> ORGANISM: Homo sapiens

\<400\> SEQUENCE: 552

```
tcttcattcc acaaagctca gtgtcaaaac atggggttta cactggaagc tgaggtcaca       60
tcagtagccg ggatcagggt cgccctagct gcccaatgca gctcccaggc ctcctgtaaa      120
accttgacct ttgaggtcat gacagccctc tcctgctatg ctcatagctg accactgaac      180
tcctggacac tccctcccsc aagttcacag agaatgtggg cacatgcctt acagtcttcc      240
cttgatccaa actactgcct tcatcttgag tgacagcagc atcttttgga tgtcttggcc      300
tgtctagctt tattttttg tgttctgcca tcaagttgct acttctgttg ccatcgtgcc      360
tgtcagcgca gtgcaggctg tggtgaaatc ccacga                                396
```

<210> SEQ ID NO 553
<211> LENGTH: 396
<212> TYPE: DNA
<213> ORGANISM: Homo sapiens

<400> SEQUENCE: 553

```
tatttttttg tgttctgcca tcaagttgct acttctgttg ccatcgtgcc tgtcagcgca      60
gtgcaggctg tggtgaaatc ccacgaactc aggcatcaca ctgaccgggt ctgagtcctg     120
tctcagttgt cagctagttg tgcaatgaag ggaaagggac ctacactttc caagcctcaa     180
ttcactcatc tatggcatkg tgacaataat ggaggttgat ttaaagtcct ttgtaagaat     240
taagagttat aatagacata aagtgctgta tctggtatac ctagaaaaca ttccataaaa     300
gttagtaatt gttggtcatg taatgatgac tctctaggct aggatttcag cttcattgca     360
tgcacatggt gcactcacag ggcgtgacct ctctct                               396
```

<210> SEQ ID NO 554
<211> LENGTH: 396
<212> TYPE: DNA
<213> ORGANISM: Homo sapiens

<400> SEQUENCE: 554

```
ggtataccta gaaacattc cataaaagtt agtaattgtt ggtcatgtaa tgatgactct       60
ctaggctagg atttcagctt cattgcatgc acatggtgca ctcacagggc gtgacctctc     120
tctgtctcag taacctcatc tgaggaccgg gataatcata ccgcttcaaa gggatgtcat     180
aaagattaaa taatatgtrt aaggctgctt gcatttagct gcattcaaca aatatttctg     240
tatctttctc ctcatttctc cttactttct tgcttattat ctgctctagg tatagatttc     300
agagaactaa gcttgttaca atccttcata aaataaccag gttggttagg gcatttccaa     360
gagtcaatac tgtttagtga ctattctctg tttaat                               396
```

<210> SEQ ID NO 555
<211> LENGTH: 396
<212> TYPE: DNA
<213> ORGANISM: Homo sapiens

<400> SEQUENCE: 555

```
aaggctgctt gcatttagct gcattcaaca aatatttctg tatctttctc ctcatttctc      60
cttactttct tgcttattat ctgctctagg tatagatttc agagaactaa gcttgttaca     120
atccttcata aaataaccag gttggttagg gcatttccaa gagtcaatac tgtttagtga     180
ctattctctg tttaatctmt tttgattgtc cagggtcatc ttttgctatg tcataggttg     240
ttggcttctt ctagagaagt gagacgatgg acaagttcca agtgagtgag gcgactggtc     300
aggatattcc gctgaaaaac tcatgtcagt tctaattcgt gattgtaatt caatcacagc     360
ctgagaacag taggactgta gttcaaatgc tctgtt                               396
```

<210> SEQ ID NO 556
<211> LENGTH: 396
<212> TYPE: DNA
<213> ORGANISM: Homo sapiens

<400> SEQUENCE: 556

```
cctgggttca agcaattctc ctgcctcagc ctcccaagta gctgggacta caggcacatg      60
ccaccacgcc cagataattt tcgtattttt agtagacg gggtttcccc ttgttggcca       120
gggtggtctt gatctcttga cctcatgatc cgcccacctc ggcctcccaa agtgctggga     180
```

```
ttacaggcgt gagccaccrc gcccggcctc tagaggataa ttttaaaatg tgcttttgca    240
tttggaaaat gtgattggca ttttttttcta attttctaat atgatacgct gtcggatgct    300
atggattact taaaccctct ggctacctag aaagatcttt aagtggttct caacaagctt    360
catacgcaat gtaaattgta ttatctctca ggatgt                              396
```

<210> SEQ ID NO 557
<211> LENGTH: 396
<212> TYPE: DNA
<213> ORGANISM: Homo sapiens

<400> SEQUENCE: 557

```
tgtgattggc atttttttct aattttctaa tatgatacgc tgtcggatgc tatggattac    60
ttaaaccctc tggctaccta gaaagatctt taagtggttc tcaacaagct tcatacgcaa    120
tgtaaattgt attatctctc aggatgtgtg agaacatctg ttttcttct aatgcagtaa    180 acatataagg gtctcttgrg atatctttta aatagactta atacaacatt caggaatgat    240
aacaaaatat aatcacagtt gtaagggaat gtgagcattt catattaata acattggaac    300
cttatgttta atacagtgtt aaaagttgac aaacatgtag gagtcagaaa attcaattaa    360
aattatcaca gtaatatgaa tttagccaca tcctgt                              396
```

<210> SEQ ID NO 558
<211> LENGTH: 396
<212> TYPE: DNA
<213> ORGANISM: Homo sapiens

<400> SEQUENCE: 558

```
acttaaaccc tctggctacc tagaaagatc tttaagtggt tctcaacaag cttcatacgc    60
aatgtaaatt gtattatctc tcaggatgtg tgagaacatc tgttttcttct ctaatgcagt    120 aaacatataa gggtctcttg ggatatcttt taaatagact taatacaaca ttcaggaatg    180
ataacaaaat ataatcacrg ttgtaaggga atgtgagcat ttcatattaa taacattgga    240
accttatgtt taatacagtg ttaaaagttg acaaacatgt aggagtcaga aaattcaatt    300
aaaattatca gtaatatatg aatttagcca catcctgtgt tagttatgaa atccatttaa    360
caccacaaac agtaatattt ttagccagtt tattca                              396
```

<210> SEQ ID NO 559
<211> LENGTH: 396
<212> TYPE: DNA
<213> ORGANISM: Homo sapiens

<400> SEQUENCE: 559

```
catttaacac cacaaacagt aatattttta gccagtttat tcaaaaggaa acaggaact     60 aaaccacttt catgcaatat atactctgtt aatgtggtca ggctaatttt gctgggggaa    120
ggaacttaac ttttgaatat ttgaatgccc agtcatttaa tctgaatatc ctatttcctt    180
gcatgttgca aaattttttkt caataaaagg cagaaaaaga atctcttcct ccatgctcat    240
ccctaagaga atgggttgtc tgtaccctga gagcatttta tggaggggac aaccacttt     300 ctaatttcc ttcccacttc tctgtgggca caaatgctct tggttgaaaa gagttgtaat     360
tcagtcccaa gatgaggtgt ggttactgca tcccta                              396
```

<210> SEQ ID NO 560
<211> LENGTH: 396
<212> TYPE: DNA

<213> ORGANISM: Homo sapiens

<400> SEQUENCE: 560

| tcaatccatg ctccacactg cagccagagt gctctacaat gcaaatccat ttgtgagact | 60 |
| cctcctctta aaatcctcaa gtggcttctc tttgccccca ggatcatttt gaaactcctt | 120 |
| aatggaagag gcatggccct tgggatgtg gttcccaac ccctcccaca tcatcttttc | 180 |
| aatcagattt cccactaart ggaaattttt tcaggtcctc aactttatgg tgactttctc | 240 |
| ttgctcagga tctttgaaca tactgtttct tctttccttt tgtatttgcc aagacaacac | 300 |
| ttcctctggt aagattttcc tgacatcctc tataaaaaaa gattgagata gttgactacc | 360 |
| caaaatgttt cccattcatt ccaagctcta ttcaag | 396 |

<210> SEQ ID NO 561
<211> LENGTH: 396
<212> TYPE: DNA
<213> ORGANISM: Homo sapiens

<400> SEQUENCE: 561

| aacacttcct ctggtaagat tttcctgaca tcctctataa aaaagattg agatagttga | 60 |
| ctacccaaaa tgtttcccat tcattccaag ctctattcaa ggcagtaaag tgcccggctg | 120 |
| acagattgca ttcctcatct tttctgaagc tagcaatggc catgcaacag cattctggcc | 180 |
| aataagatag aagtcgaart tgaagggtgg gatttccaag aaagctcgtt gaagacataa | 240 |
| ttcctcattt cacttcttac tcttttctctt tcctgcttcc taaaatgcgg tgcagatggc | 300 |
| agacacttca agctgtctc aggcaatcag gtgatgttaa ggcagaaacc agctttatga | 360 |
| tgggtagaac aggaagaaag aaggcaccta tgttct | 396 |

<210> SEQ ID NO 562
<211> LENGTH: 396
<212> TYPE: DNA
<213> ORGANISM: Homo sapiens

<400> SEQUENCE: 562

| cctacaaatc tcatgttgac attttatccc taatattgga ggcagggcct agtaggaggt | 60 |
| gttttggtca tagtgataaa tggcttggtg ccgttctcac agtaacgagt gagttttat | 120 |
| tctagtggtt cctgcaagaa ctgattgtta aaagagcttg gatccttcca ccctctctc | 180 |
| actcttgctt cctctctcwc accttgtaat ctctacaagc tcttcacctc cccttctcct | 240 |
| tttgccataa gtggaagatt tctgaggcct caccagaagc agatgttggt tccatgcttc | 300 |
| ttgtacagcc tgcagaacca tgagccaaat caacttcttt tctttataat tatccagtct | 360 |
| caggtattcc tttatagcaa cacaaatgga ctaaga | 396 |

<210> SEQ ID NO 563
<211> LENGTH: 396
<212> TYPE: DNA
<213> ORGANISM: Homo sapiens

<400> SEQUENCE: 563

| gttgtttcca gctttgaact attttgaatc ctaaaagact gccagttttg aatgagaccc | 60 |
| cagaacaatg aatgtaggct ctgtatacaa gttcaggctg ctgggcaact taggccttaa | 120 |
| gacacaactc tgccacttag gccttaagac acaactgaca tgatggtgct taaagtggct | 180 |
| gtgatggaaa aggaggctrt ttggagcctt tggagtgcct ttataggtga acccagcat | 240 |
| agcacctaat gatttggagc aaagctgtgt cattccccaa agataactat tcgccttttg | 300 |

```
agaaacatct tctagctact atcaataata aacacagaat gcatcaccat gggccaccgt    360
gttgtctttt gacctgagtt tccattgtga acaaga                              396

<210> SEQ ID NO 564
<211> LENGTH: 396
<212> TYPE: DNA
<213> ORGANISM: Homo sapiens

<400> SEQUENCE: 564
aactctgcca cttaggcctt aagacacaac tgacatgatg gtgcttaaag tggctgtgat     60
ggaaaaggag gctgtttgga gcctttggag tgcctttata ggtgaacccc agcatagcac    120
ctaatgattt ggagcaaagc tgtgtcattc cccaaagata actattcgcc ttttgagaaa    180
catcttctag ctactatcra ataaaacac agaatgcatc accatgggcc accgtgttgt    240
cttttgacct gagtttccat tgtgaacaag agtcatttga tccaaggcag aaagttgggt    300
gcacacagca gtgttccatc atcaaatgga atatgagatt gggcccaagt aggtcctgca    360
gacacaaata agttgcaaga gcaagtagta caggcg                              396

<210> SEQ ID NO 565
<211> LENGTH: 396
<212> TYPE: DNA
<213> ORGANISM: Homo sapiens

<400> SEQUENCE: 565
gaaaaggagg ctgtttggag cctttggagt gcctttatag gtgaacccca gcatagcacc     60
taatgatttg gagcaaagct gtgtcattcc ccaaagataa ctattcgcct tttgagaaac    120
atcttctagc tactatcaat aaaacaca gaatgcatca ccatgggcca ccgtgttgtc    180
ttttgacctg agtttccayt gtgaacaaga gtcatttgat ccaaggcaga aagttgggtg    240
cacacagcag tgttccatca tcaaatgaa tatgagattg gcccaagta ggtcctgcag    300 acacaaataa gttgcaagag caagtagtac aggcgcttgg cctggccagt actgttgcca    360
agttgactgc ttcccctcag tctgcatctg tggctt                              396

<210> SEQ ID NO 566
<211> LENGTH: 396
<212> TYPE: DNA
<213> ORGANISM: Homo sapiens

<400> SEQUENCE: 566
ccccaaagat aactattcgc cttttgagaa acatcttcta gctactatca ataaaaaca      60 cagaatgcat caccatgggc caccgtgttg tcttttgacc tgagtttcca ttgtgaacaa    120
gagtcatttg atccaaggca gaaagttggg tgcacacagc agtgttccat catcaaatgg    180
aatatgagat tgggcccarg taggtcctgc agacacaaat aagttgcaag agcaagtagt    240
acaggcgctt ggcctggcca gtactgttgc caagttgact gcttcccctc agtctgcatc    300
tgtggcttca tggggagttt cctatgacca cttgatggag gaaaaaacaa attggagcat    360
agtttatagt gctggtacta cccaaagtgg ctagct                              396

<210> SEQ ID NO 567
<211> LENGTH: 396
<212> TYPE: DNA
<213> ORGANISM: Homo sapiens

<400> SEQUENCE: 567
```

-continued

```
gtccgtgagt tacagatcta cacaaaatca cagagagtgg ttaatcgttt agtctgatgg      60
tcagggactt ccaagagaca tgattagaaa actggtgaca aggagtcctg gggaagaggc     120
atatggatac ctctgaacac acacaaaaca tgagaatatg tatcccatat gaatgttaac     180
caaagagcag ccacaacasa agaggatttt aaaatcagct gaataagatg attcattctg     240
acagcatcag ctagtctctt tccccagcca ctgttgccca gtgggcttac atatatcatg     300
gccatggggg cagggctatg tatggacaca gcaacatgaa tttccactca tcaaggccaa     360
tttggctcca gccattgctg agtgctcagc ctgcca                               396
```

<210> SEQ ID NO 568
<211> LENGTH: 396
<212> TYPE: DNA
<213> ORGANISM: Homo sapiens

<400> SEQUENCE: 568

```
acatgattag aaaactggtg acaaggagtc ctggggaaga ggcatatgga tacctctgaa      60
cacacacaaa acatgagaat atgtatccca tatgaatgtt aaccaaagag cagccacaac     120
agaagaggat tttaaaatca gctgaataag atgattcatt ctgacagcat cagctagtct     180
ctttccccag ccactgttrc ccagtgggct acatatatc atggccatgg ggcagggct       240 atgtatggac acagcaacat gaatttccac tcatcaaggc caatttggct ccagccattg     300
ctgagtgctc agcctgccaa gatagaaatc tacgccaata tggcaccatt ccctgggcta     360
gaaaaccaac tggtggaagg ttgattacat tggacc                               396
```

<210> SEQ ID NO 569
<211> LENGTH: 396
<212> TYPE: DNA
<213> ORGANISM: Homo sapiens

<400> SEQUENCE: 569

```
gggaatacaa tggtggttcc actaaactga cagctgagtt tgccatctcc tcgtgccagt      60
gaatacacaa gcaaggaagg gggttccttt ctcacctagg gtgactgatc ctaattacca     120
aggagaaatt ggactgccac ttcacaatga gggtgaggag tatgtactct atgtgtctgt     180
gattaatgtc aatagaaart gacaccaacc tagtacacag aggactgatc atggtccagg     240
cccttcagga atgaagattt gagtcaccag gcaaggaact tggactcact gaggagggca     300
tattccaagg agaatatttt atctatgtcc atctatgtcc atctatattc catctgtgtt     360
ccccttggaa ttcctattca tgaacatggg gaattc                               396
```

<210> SEQ ID NO 570
<211> LENGTH: 396
<212> TYPE: DNA
<213> ORGANISM: Homo sapiens

<400> SEQUENCE: 570

```
tatagaatga gtagtggaag gtagttataa atgtaagtca aaaccacac aaccaatttg       60 agaaatgagg aaggtaatag tgttgaatat gtcttcttta tcttgatata aatgtatttg     120
tgcatatatt aaccagttta tttatttatt attattttttt gagatgagct ctcgccatgt     180
tgcccaggct ggtcttgamc tcctgggctc aactgattct accatttagt cctccgagta     240
gctgggacta caggcatgca ccaccatacc cagctgacca gttttttcct attcctctac     300
ttaatttctc tactatacaa cataatatgt gttaatggta gttaacttta tatctcagta     360
ttaagtcaca agatatcaaa aagggaatgc gactta                               396
```

<210> SEQ ID NO 571
<211> LENGTH: 396
<212> TYPE: DNA
<213> ORGANISM: Homo sapiens

<400> SEQUENCE: 571

```
atgtcttctt tatcttgata taaatgtatt tgtgcatata ttaaccagtt tatttattta      60
ttattatttt ttgagatgag ctctcgccat gttgcccagg ctggtcttga actcctgggc     120
tcaactgatt ctaccattta gtcctccgag tagctgggac tacaggcatg caccaccata     180
cccagctgac cagtttttyc ctattcctct acttaatttc tctactatac aacataatat     240
gtgttaatgg tagttaactt tatatctcag tattaagtca caagatatca aaaagggaat     300
gcgacttagt tacaagcaga atgaatatca ctcaaagatg aataaagaga agagggttag     360
tgcattttct gttggatgag agaaagtttc attgtt                               396
```

<210> SEQ ID NO 572
<211> LENGTH: 396
<212> TYPE: DNA
<213> ORGANISM: Homo sapiens

<400> SEQUENCE: 572

```
gcagtggcgt gatcccagct cactgcaatc tctgcctcct gggttcaagt gattctcctg      60
cctcagcctc ccgaggggct gggattgtag gcgtgcacca ctatgcccat ctaattttg      120
tattttagt agagataggg ttttgccatt ttggccagac tgtcttgaac tcctgacctc      180
aggtgatctg cctgcctcrg cctcccacag ttttgtgatt ataggcatga gccaccgtgc      240
ccggccttaa cctttgtttt cttacacaac acactacgtg atgttttcca catgcatggg      300
tcatttgctt catttacgta caaatgcata agcaatatac tgtgtggtgt gagtttgtga      360
tgggaaaagg aagaagtttt gcggatacta cactgg                                396
```

<210> SEQ ID NO 573
<211> LENGTH: 396
<212> TYPE: DNA
<213> ORGANISM: Homo sapiens

<400> SEQUENCE: 573

```
gcccaggctg ttctccaact cctggactca agccatcctc tagcctcggc cttccaaagt      60
gctgggacta taggcgtgag ccacggtgcc aggcccttga ccacatttt aaccctctg      120
aacctcagtt tcactttctg ggcaatggga gggggtaat ttgtccctca gagggttgca      180
ctgaggggca aatgtgagsc tctgggtaca atgcccagta cagactaggt ccccacgaca      240
cagccgctca gcggctccgg attctgggct gctctggact gcggccaggc ggtcttctgc      300
gggaatccgg gcaggcaggg cgggctgcgc tcccctcccc ggctctcccg gtgccccttg      360
tcttttgtt ctgtctcagc agctctctat taagat                                 396
```

<210> SEQ ID NO 574
<211> LENGTH: 396
<212> TYPE: DNA
<213> ORGANISM: Homo sapiens

<400> SEQUENCE: 574

```
tttttgttct gtctcagcag ctctctatta agatgaatgg catttccaaa ggcttcacct      60
ctgataagtg ttcctctgca gctgcagcca gaatcttaat gtgcgcgctg taatttaatg     120
```

```
gccgtctcgg ctattaacac gctcttctcg ggtgaagtgg actccctcca tccccgggcc      180
tctgcacgtg ctctgcgcrc tggctggggg tgactccaag gagctcagag cggggtgccc      240
ggcacctctc gccaggcgcc tttcgacctt ctaaagcgcg aatggctgga cttttctccc      300
atgtgtgggg ccccagaagg tgtggggccc cagaaggtgt ggggtccctg cgttccacgg      360
agcccggaag gtttccagtg atggtggggg ctgacc                                396
```

<210> SEQ ID NO 575
<211> LENGTH: 396
<212> TYPE: DNA
<213> ORGANISM: Homo sapiens

<400> SEQUENCE: 575

```
ggagcccgga aggtttccag tgatggtggg ggctgaccac gttggtcccc gtgggtgctg       60 tttttcatgtg ccggcagatt gggatgagtt aaaagacag aagcgtgtag gatagagaaa      120
cttctttaaa aactggaaat tttaatctgg ggattataac tattggacag tcaagtgcaa      180
gagtgaatac acttctcast ccctcctccc aattttatt tgcgggatta gtcagtcccc       240
ctctgccaca tgataattgt gagaactacc agggtcttca ttctcctgcc atctggttga      300
cctctccaag aatggacacc cgggcagcct gggccaatga ggctgtccta agagtttaga      360
tgagagaagt cagtctttga caggtgatgg aagctg                                396
```

<210> SEQ ID NO 576
<211> LENGTH: 396
<212> TYPE: DNA
<213> ORGANISM: Homo sapiens

<400> SEQUENCE: 576

```
cagtgatggt gggggctgac cacgttggtc cccgtgggtg ctgttttcat gtgccggcag       60
attgggatga gtttaaaaga cagaagcgtg taggatagag aaacttcttt aaaaactgga      120
aattttaatc tggggattat aactattgga cagtcaagtg caagagtgaa tacacttctc      180
actccctcct cccaatttyt atttgcggga ttagtcagtc cccctctgcc acatgataat      240
tgtgagaact accagggtct tcattctcct gccatctggt tgacctctcc aagaatggac      300
acccgggcag cctgggccaa tgaggctgtc ctaagagttt agatgagaga agtcagtctt      360
tgacaggtga tggaagctgt aaaatgtaaa actcca                                396
```

<210> SEQ ID NO 577
<211> LENGTH: 396
<212> TYPE: DNA
<213> ORGANISM: Homo sapiens

<400> SEQUENCE: 577

```
taagagaagc tgagagagag cgagaggaga gattggaaga agacagaga cagaggtaga       60 gagaagggaa agagagagag aaagggacag aagagagaga aaaagagggg ggccgggcgc      120
ggtggctcac gcctgtaatc tcagcacttt gggaggccga gcgggcaga tcacgaggtc      180 aggagatcga gaccatccyg gctaacacgg tgaaaccccc gtctctacta aaaaatataa      240
aaaaaattag ccaggcgtgg tggtgggtgc ctgtagtccc agctactgag gaggctgaga      300
caggagaatg gcgtgaaccc gggaggcaga gcttgcagtg agctgagatc gcgccactgc      360
actccagcct gggcaacaga gcaagactcc gtctca                                396
```

<210> SEQ ID NO 578
<211> LENGTH: 396

```
<212> TYPE: DNA
<213> ORGANISM: Homo sapiens

<400> SEQUENCE: 578
tccaccagca gcttttctga gtctccagct tgcagatggc aaaccatgaa acttcatggt    60
gtccatgagc atgtgaacca atttctatta taaatctgca atatatatat atgaggagac   120
ttatttatat attggttcag tttctctgga gagccttggc taatataaag tctatactct   180
acaaagtgcc ctaggtackc agggagtacc caagtgtgtc atgaccagcc cgacagccct   240
ggctgctggc ttccccgcac acaactctgc acgctgcctt catcagcctt tctctctcag   300
ctgaaccgag ggcattgaag cgggcctctg gcactgtacc tatgagggag caatatcttc   360
ccctacactg acctcttccg tgccgagatg cagccc                             396

<210> SEQ ID NO 579
<211> LENGTH: 396
<212> TYPE: DNA
<213> ORGANISM: Homo sapiens

<400> SEQUENCE: 579
gcctctggca ctgtacctat gagggagcaa tatcttcccc tacactgacc tcttccgtgc    60
cgagatgcag ccctccctgc tgccactagt tacagtggtc catgttccct ttcaaagtga   120
agttttgata aaagcacctc ttaaccaatg ccaaatagct aagtctggga caaagattgc   180
aggtattttg cattttccwt gtaacctcag agggattgcc attcacactg atctgagctg   240
cagaatacca ggcagccacc tcacccaccc agcaggtcca ctcttatact ttctcagaaa   300
gcacagccac tctactctta ttcagttgaa aagaatttcc aggaaggtgt ttctgcgatt   360
gcctcagaaa agtcagttcc ctttgggaat ttccct                             396

<210> SEQ ID NO 580
<211> LENGTH: 396
<212> TYPE: DNA
<213> ORGANISM: Homo sapiens

<400> SEQUENCE: 580
tactttctct tgaagaaatg gagatatcag ctgtccctcc ccactgccat ttattccttc    60
cttcattcaa accttatgtg gctgctactt accgtgtgtt aagtgttcac ttttttttctt   120
ggaattcaaa aaagaagga cagtatttgg ggcacagatc ttttggtgtt ctatacattt   180
ttttaaagtt tcattttaya tttgtgtgtg cgtgtgtgtg tgtgtgtgag acagtcttgc   240
tctgttgccc aggctggagt gcagtggcat aatcattggc tcactgtagc ctcaaagtcc   300
tgggcccaag caatcttccc acctcagcca cccaaaatgc tggggttaca ggtttatgcc   360
actctgtctg acctgaaagt tttgggttta cttttcc                            396

<210> SEQ ID NO 581
<211> LENGTH: 396
<212> TYPE: DNA
<213> ORGANISM: Homo sapiens

<400> SEQUENCE: 581
gcataatcat tggctcactg tagcctcaaa gtcctgggcc caagcaatct tcccacctca    60
gccacccaaa atgctggggt tacaggttta tgccactctg tctgacctga aagttttggg   120
tttactttcc cttctttctc tttgctgaag tcagagatga tggcagcttc cagattctct   180
ggtgcctgtg ctgggctcrt gctggtcatg gtcttgggtc caggattcat tctggagact   240
```

```
ctcagggaag tttcccatga caaggaaatg taggagagtg tgctggcttt gcgtgctcct    300
ctgccaagcc ctgcttctcc tggtgggaca cactgaacca cagccagggc attttggtgg    360
ttagttaaaa aaaaaaaaaa aaaaaaaaaa aggaag                             396
```

```
<210> SEQ ID NO 582
<211> LENGTH: 396
<212> TYPE: DNA
<213> ORGANISM: Homo sapiens

<400> SEQUENCE: 582
cttcagaaat tgtaatgatg aaagagtgca agctctcact tccccttcct gtacagggca    60
ggttgtgcag ctggaggcag agcagtcctc tctgggagc ctgaagcaaa catggatcaa    120
gaaactgtag gcaatgttgt cctgttggcc atcgtcaccc tcatcagcgt ggtccagaat    180
ggtaaggaaa gcccttcamt cagggaagaa cagaagggga attttctttt gatggttgtt    240
tggaagtcag gctaaacaa ttgtgtctgt gtgtgcgcat gcacaaacac ttttaccttg    300
tctttatttt cttcttttta tttgaatgta tagggttgtg tgtatttctg tgtaaatttg    360
gggttttcct cctcttagtc tttcacttt gtggtg                              396
```

```
<210> SEQ ID NO 583
<211> LENGTH: 396
<212> TYPE: DNA
<213> ORGANISM: Homo sapiens

<400> SEQUENCE: 583
ttttctaaca tctgcagtgc aattgaagtt accagtcatc tgcagtctaa aagaaagtg    60 attttgggag gtgcgtagaa aaaatcatct tattattttt cctctatatt acttttttct    120
ttttttctcc tgaagaaact tttttttttg gtgataccttt cttttttctct agcacgtata    180 attttggaag catttttcrt atgcagtgta tacttcagaa agagagagag agagaggaaa    240
attgtcctgt tcagcgtttg catttccatt attcctgcta ttagttaaaa acaacaacaa    300
caacaaaaaa caagcaggat acctagatct ggaaaaggga aattgtgta gagctgtctt    360 cctaaagttc tgagttaggg ctgcctcaga ccactt                             396
```

```
<210> SEQ ID NO 584
<211> LENGTH: 396
<212> TYPE: DNA
<213> ORGANISM: Homo sapiens

<400> SEQUENCE: 584
ttttggaagc attttcata tgcagtgtat acttcagaaa gagagagaga gagaggaaaa    60
ttgtcctgtt cagcgtttgc atttccatta ttcctgctat tagttaaaaa caacaacaac    120
aacaaaaaac aagcaggata cctagatctg gaaagggag aattgtgtag agctgtcttc    180
ctaaagttct gagttaggrc tgcctcagac cactttcata actatctcca gtggctttgt    240
gttttatatt tattaagata gagaaaaaaa gagtaattac taagggcagc tgctgtagct    300
ttatggtgat tactgaacat tgacatgctg tcacgttttt ggaactttga gtatttaatc    360
actttgggat attctatttt cccccatctt gagtgt                             396
```

```
<210> SEQ ID NO 585
<211> LENGTH: 396
<212> TYPE: DNA
<213> ORGANISM: Homo sapiens

<400> SEQUENCE: 585
```

```
ggaactttga gtatttaatc actttgggat attctatttt ccccatcttt gagtgtggac      60
agatgctggt gatgtagcct tctgggcaca gagcaagcct ccccctcagc tctgcacca     120 gaaaggctca gcttcacaca ctccaagtat gttttctaca agaactacac tttgtggctt     180
tctgacccaa acatttttrt actaaattac acacaacaaa gttgtagctc agagagggaa     240
caaatggctt atttaggcca ccattttctt gagccattat gatttcacac agggctccct     300
tggccctgta aattggcaag gattccatta ttcaacccgc atacatgtac agagaccctg     360
ctctggccca gatagtattc tgggtacagg cggata                               396
```

<210> SEQ ID NO 586
<211> LENGTH: 396
<212> TYPE: DNA
<213> ORGANISM: Homo sapiens

<400> SEQUENCE: 586

```
tgtggacaga tgctggtgat gtagccttct gggcacagag caagcctccc cctcagcctc      60
tgcaccagaa aggctcagct tcacacactc caagtatgtt ttctacaaga actcactttt     120
gtggctttct gacccaaaca tttttatact aaattacaca caacaaagtt gtagctcaga     180
gagggaacaa atggcttayt taggccacca ttttcttgag ccattatgat ttcacacagg     240
gctcccttgg ccctgtaaat tggcaaggat tccattattc aacccgcata catgtacaga     300
gaccctgctc tggcccagat agtattctgg gtacaggcgg atagagcagg aaacaaaaca     360
gctacagtga tggacaggtc agcctgcagc aatgcc                               396
```

<210> SEQ ID NO 587
<211> LENGTH: 396
<212> TYPE: DNA
<213> ORGANISM: Homo sapiens

<400> SEQUENCE: 587

```
ttttatact aaattacaca caacaaagtt gtagctcaga gagggaacaa atggcttatt      60
taggccacca ttttcttgag ccattatgat ttcacacagg gctcccttgg ccctgtaaat     120
tggcaaggat tccattattc aacccgcata catgtacaga gaccctgctc tggcccagat     180
agtattctgg gtacaggcrg atagagcagg aaacaaaaca gctacagtga tggacaggtc     240
agcctgcagc aatgcctgca gtctctgcaa aggtagctgt atgggtgggc aggtggctag     300
cacttattca gctctggaag gatctcccct ctggcctctc ccctgacacc catcaataaa     360
actgaggagc atcggtggac aggggacctt gtgccc                               396
```

<210> SEQ ID NO 588
<211> LENGTH: 396
<212> TYPE: DNA
<213> ORGANISM: Homo sapiens

<400> SEQUENCE: 588

```
ttttcttgag ccattatgat ttcacacagg gctcccttgg ccctgtaaat tggcaaggat      60
tccattattc aacccgcata catgtacaga gaccctgctc tggcccagat agtattctgg     120
gtacaggcgg atagagcagg aaacaaaaca gctacagtga tggacaggtc agcctgcagc     180
aatgcctgca gtctctgcra aggtagctgt atgggtgggc aggtggctag cacttattca     240
gctctggaag gatctcccct ctggcctctc ccctgacacc catcaataaa actgaggagc     300
atcggtggac aggggacctt gtgccccctc cctgcctgtg cagttgggc tgaacccagc     360
```

```
tacgaagttt gagctcactc tctccagctc cctctc                              396

<210> SEQ ID NO 589
<211> LENGTH: 396
<212> TYPE: DNA
<213> ORGANISM: Homo sapiens

<400> SEQUENCE: 589
gacaggtcag cctgcagcaa tgcctgcagt ctctgcaaag gtagctgtat gggtgggcag    60
gtggctagca cttattcagc tctggaagga tctcccctct ggcctctccc ctgacaccca   120
tcaataaaac tgaggagcat cggtggacag gggaccttgt gccccctccc tgcctgtgca   180
gttggggctg aacccagcya cgaagtttga gctcactctc tccagctccc tctcaattca   240
gagctgaact gtgggaagct tcagagctct ctgtttcaag gacaggttct cctcacctct   300
cctaatggag gtgcaccagg gaactggccc tgctctgccc agggctttct cctggacttt   360
gccatcatgg tctagcaaac cctgttcaga ttgagg                             396

<210> SEQ ID NO 590
<211> LENGTH: 396
<212> TYPE: DNA
<213> ORGANISM: Homo sapiens

<400> SEQUENCE: 590
cactctctcc agctccctct caattcagag ctgaactgtg ggaagcttca gagctctctg    60
tttcaaggac aggttctcct cacctctcct aatggaggtg caccagggaa ctggccctgc   120
tctgcccagg gctttctcct ggactttgcc atcatggtct agcaaaccct gttcagattg   180
aggtgagtgg tgagatttyg aattcttttt gacagatagg attaagtctt cttctgtggg   240
acaagtggga ggtagaggta agattaaaga tggccaaatg tctgagtcct gacagccaca   300
atatggagat ctagcttttt tacagaccac agggcacagg ggcctcacta acagagttcc   360
cggaagtgat gagtgtgctg ggggcttcct ggttga                             396

<210> SEQ ID NO 591
<211> LENGTH: 396
<212> TYPE: DNA
<213> ORGANISM: Homo sapiens

<400> SEQUENCE: 591
taggattaag tcttcttctg tgggacaagt gggaggtaga ggtaagatta aagatggcca    60
aatgtctgag tcctgacagc cacaatatgg agatctagac tttttacaga ccacagggca   120
caggggcctc actaacagag ttcccggaag tgatgagtgt gctgggggct tcctggttga   180
agagacacta gaatgacsa gctggagct aattttttgg gctggagtgt gatggcctgc    240
acatcactgc ctctgtccct ccattgtcac agctgcccct taggagccag ctgaggcaat   300
ttgtggtcag agtgactttg cacagttgtc ctgcctgtgt tcaggaaggg agtttctgtg   360
gtccctttga aaccacagaa gagcccctcg tatagc                             396

<210> SEQ ID NO 592
<211> LENGTH: 396
<212> TYPE: DNA
<213> ORGANISM: Homo sapiens

<400> SEQUENCE: 592
agttgtcctg cctgtgttca ggaagggagt ttctgtggtc cctttgaaac cacagaagag    60
cccctcgtat agctctcaat ggagggggca aaacattcaa ataactcagg agataacaca   120
```

```
actatttgtt tttaactgtg agttttaggg caatcacaaa gatccagatg tatgtccaag    180
cctctctttg caattctawt taacctcaat gttgcaacca tagacctacc ttacagagtt    240
caaaaaaata tgcaaaaacc ctgcctttct tcttcctcat accccaaaat gccattctga    300
acatttcctg ttagttaaaa aaagatttcc atggtgttac caggcactgt acacagtctg    360
tgtcccaaga caaggaggta cagttccaca tgcgcc                              396
```

<210> SEQ ID NO 593
<211> LENGTH: 396
<212> TYPE: DNA
<213> ORGANISM: Homo sapiens

<400> SEQUENCE: 593

```
aggggggcaaa acattcaaat aactcaggag ataacacaac tatttgtttt taactgtgag    60 ttttaggca atcacaaaga tccagatgta tgtccaagcc tctctttgca attctaatta    120
acctcaatgt tgcaaccata gacctacctt acagagttca aaaaatatg caaaaaccct    180 gcctttcttc ttcctcatwc cccaaaatgc cattctgaac atttcctgtt agttaaaaaa    240
agatttccat ggtgttacca ggcactgtac acagtctgtg tcccaagaca aggaggtaca    300
gttccacatg cgcccatgac tgggttgggc tctgcactct ctctatactt tgagagcctg    360
attttctgtg attgggcaga gctggcccac ctggtg                             396
```

<210> SEQ ID NO 594
<211> LENGTH: 396
<212> TYPE: DNA
<213> ORGANISM: Homo sapiens

<400> SEQUENCE: 594

```
tctgcactct ctctatactt tgagagcctg attttctgtg attgggcaga gctggcccac    60
ctggtgcaat gtcctcctct gcctttcaaa catgttttag tcatcaagat cttcaaattt    120
gtaacccttt ccagcttgat ccagcagaat gcagatttgg aaaaacagaa cgagtttaaa    180
atacatgatt ctaagaaayc tggaccagaa ctatcaaaac ttggtttccc agagaatata    240
gcaaatgggc tcattggcca atactatgac attggctttt gagaaaagaa aggctttatt    300
gcaaggctgg ccagcaagga cagggagtt gggctcaaat ctgtctcccc agtttggggc    360
ttagggcaag ttttaattac acagacgcat ttctta                             396
```

<210> SEQ ID NO 595
<211> LENGTH: 396
<212> TYPE: DNA
<213> ORGANISM: Homo sapiens

<400> SEQUENCE: 595

```
aaccctttcc agcttgatcc agcagaatgc agatttggaa aaacagaacg agtttaaaat    60
acatgattct aagaaacctg gaccagaact atcaaaactt ggtttcccag agaatatagc    120
aaatgggctc attggccaat actatgacat tggcttttga gaaaagaaag ctttattgc    180 aaggctggcc agcaaggara caggagttgg gctcaaatct gtctcccag tttggggctt    240 agggcaagtt ttaattacac agacgcattt cttatgagta gcaggcagag agcctccaac    300
ttcttctgcc taggtaccag cagcttagac atgatgcaaa cctgggaagc acatactgta    360
tttggagaaa gtgattggga agaaatgtga gctgag                             396
```

<210> SEQ ID NO 596

```
<211> LENGTH: 396
<212> TYPE: DNA
<213> ORGANISM: Homo sapiens

<400> SEQUENCE: 596
tacatgattc taagaaacct ggaccagaac tatcaaaact tggtttccca gagaatatag      60
caaatgggct cattggccaa tactatgaca ttggcttttg agaaaagaaa ggctttattg     120
caaggctggc cagcaaggag acaggagttg ggctcaaatc tgtctcccca gtttgggact     180
tagggcaagt tttaattaya cagacgcatt tcttatgagt agcaggcaga gagcctccaa     240
cttcttctgc ctaggtacca gcagcttaga catgatgcaa acctgggaag cacatactgt     300
atttggagaa agtgattggg aagaaatgtg agctgagggg aggggctcag tgcccctgag     360
ctacacttag tgatggcaga ggaaggatgt cctccc                               396

<210> SEQ ID NO 597
<211> LENGTH: 396
<212> TYPE: DNA
<213> ORGANISM: Homo sapiens

<400> SEQUENCE: 597
tggggcttag ggcaagtttt aattacacag acgcatttct tatgagtagc aggcagagag      60
cctccaactt cttctgccta ggtaccagca gcttagacat gatgcaaacc tgggaagcac     120
atactgtatt tggagaaagt gattgggaag aaatgtgagc tgaggggagg ggctcagtgc     180
ccctgagcta cacttagtra tggcagagga aggatgtcct cccgcaggag ctgttccac     240 atctgctctg gttgtagggg gagctggcag gcattagcag cggcctcttt cccccaagag     300
aggcagcctc ctccaagttt tggcgacatt atggccctgc aatcataagg gtttgtgagc     360
atagtgctaa ggagggaaat ggagctgctg ttacta                                396

<210> SEQ ID NO 598
<211> LENGTH: 396
<212> TYPE: DNA
<213> ORGANISM: Homo sapiens

<400> SEQUENCE: 598
cctcctgagt agctaggact acaagcatgt gccaccacgc ccagctaatt tttgtatttt      60
tagtaaggac agggtttcac catgttggcc aggttggcct ccaactcctg acctcaagtc     120
atcctcctgc ctcgacctcc caaagtgctg ggattacagg catgaaacca gcctagaaat     180
acatactatt atttattcyt gttttacaga taagcaaagt gagtcatgga gaatttggtt     240
gaaagtccca aggtcaggag tcgtgaagct gggattaaaa cctaatcatc tgactttaga     300
gagtagacac ttgctccatg catattgcct ccaattcatt cattcaagca ctccctgctc     360
aagaagttct ttcttatgtt gagctgaaat ctgcag                                396

<210> SEQ ID NO 599
<211> LENGTH: 396
<212> TYPE: DNA
<213> ORGANISM: Homo sapiens

<400> SEQUENCE: 599
tcatctgact ttagagagta gacacttgct ccatgcatat tgcctccaat tcattcattc      60
aagcactccc tgctcaagaa gttctttctt atgttgagct gaaatctgca gccctatgcg     120
ttttacccag cagtcctggt gctgttccct aaaatcactt agactgtgcc tgctcttcct     180
gtgtttacag tgtcagctrt aatatccccc tcttcggcct aacgtttctg aagtcccttg     240
```

```
ccactgggtc tcctctcctc ttcctgtgtt ctttctaaga acacctatgc agataggtgt    300
cttctgtaca gggaagctgt tcctgagatc cgggcatcga ctctgttaga ataatctacg    360
tatgagttat ttttttgaga actatgtgtc attgct                              396

<210> SEQ ID NO 600
<211> LENGTH: 396
<212> TYPE: DNA
<213> ORGANISM: Homo sapiens

<400> SEQUENCE: 600
atgttgagct gaaatctgca gcoctatgcg ttttacccag cagtcctggt gctgttccct    60
aaaatcactt agactgtgcc tgctctttct gtgtttacag tgtcagctgt aatatccccc    120
tcttcggcct aacgtttctg aagtcccttg ccactgggtc tcctctcctc ttcctgtgtt    180
ctttctaaga acacctatrc agataggtgt cttctgtaca gggaagctgt tcctgagatc    240
cgggcatcga ctctgttaga ataatctacg tatgagttat ttttttgaga actatgtgtc    300
attgctgact catattaact ctgtggttaa ctaaaatctc aagatctctt tatgtttgtt    360
gagaaactta tttaacttct ctggccctcc gtttcc                              396

<210> SEQ ID NO 601
<211> LENGTH: 396
<212> TYPE: DNA
<213> ORGANISM: Homo sapiens

<400> SEQUENCE: 601
gtcctggtgc tgttccctaa aatcacttag actgtgcctg ctctttctgt gtttacagtg    60
tcagctgtaa tatccccctc ttcggcctaa cgtttctgaa gtcccttgcc actgggtctc    120
ctctcctctt cctgtgttct ttctaagaac acctatgcag ataggtgtct tctgtacagg    180
gaagctgttc ctgagatcyg ggcatcgact ctgttagaat aatctacgta tgagttattt    240
ttttgagaac tatgtgtcat tgctgactca tattaactct gtggttaact aaaatctcaa    300
gatctcttta tgtttgttga gaaacttatt taacttctct ggccctccgt ttccttcact    360
gagcagtgga gtgattgata acctccacct gtggtt                              396

<210> SEQ ID NO 602
<211> LENGTH: 396
<212> TYPE: DNA
<213> ORGANISM: Homo sapiens

<400> SEQUENCE: 602
cacctatgca gataggtgtc ttctgtacag ggaagctgtt cctgagatcc gggcatcgac    60
tctgttagaa taatctacgt atgagttatt ttttgagaa ctatgtgtca ttgctgactc    120
atattaactc tgtggttaac taaaatctca agatctcttt atgtttgttg agaaacttat    180
ttaacttctc tggccctcmg tttccttcac tgagcagtgg agtgattgat aacctccacc    240
tgtggttgct gaaggtcttg cacaagatga tatagttaaa gtagctagca gtgcccacgt    300
acggcggatg cctcacaacg gtttgcagcc atctctctat ctgtgtcttt gtctctctct    360
cacactggtt ttggcttact gttagcagct agccga                              396

<210> SEQ ID NO 603
<211> LENGTH: 396
<212> TYPE: DNA
<213> ORGANISM: Homo sapiens
```

```
<400> SEQUENCE: 603
tctgtggtta actaaaatct caagatctct ttatgtttgt tgagaaactt atttaacttc      60
tctggccctc cgtttccttc actgagcagt ggagtgattg ataacctcca cctgtggttg     120
ctgaaggtct tgcacaagat gatatagtta aagtagctag cagtgcccac gtacggcgga     180
tgcctcacaa cggtttgcmg ccatctctct atctgtgtct ttgtctctct ctcacactgg     240
ttttggctta ctgttagcag ctagccgaga taagtgtgtt tatggtcttt gcatgtattg     300
tttctgtagc atactggagg attacaagag gttggggagt gaggggcgg tgaggagtag      360 acaaaggcag ccaactcttc caagtttagc ttagaa                               396

<210> SEQ ID NO 604
<211> LENGTH: 396
<212> TYPE: DNA
<213> ORGANISM: Homo sapiens

<400> SEQUENCE: 604
ttgataacct ccacctgtgg ttgctgaagg tcttgcacaa gatgatatag ttaaagtagc      60
tagcagtgcc cacgtacggc ggatgcctca caacggtttg cagccatctc tctatctgtg    120
tctttgtctc tctctcacac tggttttggc ttactgttag cagctagccg agataagtgt    180
gtttatggtc tttgcatgya ttgtttctgt agcatactgg aggattacaa gaggttgggg    240
agtgaggggg cggtgaggag tagacaaagg cagccaactc ttccaagttt agcttagaag    300
gaaggagcgg taaaccctag ttgaatgttg gactgaagca ggtttgtttt tgttttgttt    360
aaaggatagg gaagatctgt gcgtgtttcc aggata                              396

<210> SEQ ID NO 605
<211> LENGTH: 396
<212> TYPE: DNA
<213> ORGANISM: Homo sapiens

<400> SEQUENCE: 605
acttgaagtc agtggcatgg acagggtcaa gatcacagtt agaggatgca gccttagaga      60
aaaggaaggg gctcggttct ctgagcaagg agggaaagaa gagaggcaga tgcagagaag    120
tacggcacat cgtgctgctg gttgtagaaa taacctctga cttttaataa agtcatccct    180
cggtatccct gggggattrg ttctatgacc tccctcggat gccaaaattc gtggatgctc    240
aagtccctga tataaaatgg catagtattt gcatttaacc tacacacatc ctccatatcc    300
tttttttttt ttttttttt tttttttttt ttttgtgag atggagtctt gctctgtcgc      360
cctggctgga gtacagtggc tcgatcttgg ctcact                              396

<210> SEQ ID NO 606
<211> LENGTH: 396
<212> TYPE: DNA
<213> ORGANISM: Homo sapiens

<400> SEQUENCE: 606
aatacctgat agaatgtaaa tgctatgtaa acagttgtta tactgtattg ttaaaagaca      60
gtaacaagaa aaaaatctg tacatgttca gtccagacaa atggttttct gtttttttt      120 tttttttta atatttttgg tcagtggttg gttgactcca ggaatgcaga acccgcagat    180
atagaaggtt gattatgcrt tcagaggcag ggaataccat cttgggttcc agaaagaaaa    240
tgatcagcat tttctgtcat actctggtaa aaacagatct tttgaatgga caggtgtatt    300
aaaccctgtg gagctggctg ggcctggcgg ctcacgcctg taatcccagc actttgggag    360
```

```
<210> SEQ ID NO 607
<211> LENGTH: 396
<212> TYPE: DNA
<213> ORGANISM: Homo sapiens

<400> SEQUENCE: 607
tgccccgcag agtttgaagt cccggctgca cctctcccca gcagcaggtt gactctggaa      60
agttgcagcg ttcttaccta cagagtggga acagtactac ccattgcaca gagtgggtgc     120
aaagctctgt gacggaatac atggcaagtg cccaccacat tgcctgggat gaggtgggcc     180
cttcctttac gtaagagarc cctacagata cactcaaagt gggcacattc ctacagaagg     240
agtgttattt gtgtagaaaa gaaaaacatg aaaggctttt attcctatac acaataaagc     300
accccttaa tgtcttttg aggaggataa tatgaaattg atgaaaagga accctgtggt      360
tggatccctg acaatcacat gtatcccttt tttcac                               396

<210> SEQ ID NO 608
<211> LENGTH: 396
<212> TYPE: DNA
<213> ORGANISM: Homo sapiens
<220> FEATURE:
<221> NAME/KEY: misc_feature
<222> LOCATION: (227)..(326)
<223> OTHER INFORMATION: n = A,T,C or G

<400> SEQUENCE: 608
tacagataca ctcaaagtgg gcacattcct acagaaggag tgttatttgt gtagaaaaga     60
aaaacatgaa aggcttttat tcctatacac aataaagcac ccctttaatg tcttttttgag    120
gaggataata tgaaattgat gaaaaggaac cctgtggttg atccctgac aatcacatgt     180
atcccttttt tcactcttra aaaggagta aaggaataaa atagaannnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnatgt tcagtcact gtataataac tagccagatt     360
ttttgttgtt gttgttttgt ttttgttttt gttttt                               396

<210> SEQ ID NO 609
<211> LENGTH: 396
<212> TYPE: DNA
<213> ORGANISM: Homo sapiens

<400> SEQUENCE: 609
acattctgaa ccacagacag ttctttaccc tgaacctttg catattttgt tctcttagct     60
tagagcggcc cctctccctc cgtctgcttg gctaatttct acttgttctt cagattttat    120
cttagatgtc attccctcaa ggaatccttc tgtgactcaa catggaatta agttgcctcc    180
tttgaccctg aaagcaccrt gtactcaatc tcatcttggc atgactcact ttgctgtgtg    240
gaatgtctgc tttccttgtt tgtctattcc tttagactgt aagatcctag aaagtggggg    300
ccgtgccttg ctcatgactg tgtttctaac accaaacaca gtgttcagta gagagcagct    360
gctgagtacg tttctgctaa atgacagttg atggag                               396

<210> SEQ ID NO 610
<211> LENGTH: 396
<212> TYPE: DNA
<213> ORGANISM: Homo sapiens
```

<400> SEQUENCE: 610

```
aatccttctg tgactcaaca tggaattaag ttgcctcctt tgaccctgaa agcaccatgt      60
actcaatctc atcttggcat gactcacttt gctgtgtgga atgtctgctt tccttgtttg     120
tctattcctt tagactgtaa gatcctagaa agtgggggcc gtgccttgct catgactgtg     180
tttctaacac caaacacart gttcagtaga gagcagctgc tgagtacgtt tctgctaaat     240
gacagttgat ggaggacatt tagggttgct tggaggtcaa gtcaaggagg catttaacat     300
tctagtaaaa caaggaagta acaggctcct gaacatgccc acaatgaacc agatgcaaac     360 cttttcccctt ggcaggattc tttgcccata aagtgg                              396
```

<210> SEQ ID NO 611
<211> LENGTH: 396
<212> TYPE: DNA
<213> ORGANISM: Homo sapiens

<400> SEQUENCE: 611

```
aaagcaccat gtactcaatc tcatcttggc atgactcact tgctgtgtg aatgtctgc       60 tttccttgtt tgtctattcc tttagactgt aagatcctag aaagtggggg ccgtgccttg    120
ctcatgactg tgtttctaac accaaacaca gtgttcagta gagagcagct gctgagtacg    180
tttctgctaa atgacagtkg atggaggaca tttaggttg cttggaggtc aagtcaagga     240
ggcatttaac attctagtaa aacaaggaag taacaggctc ctgaacatgc cacaatgaa     300 ccagatgcaa accttttccc ttggcaggat tctttgccca taaagtggag cacgaaagca    360
ggacccagaa tgggaggagc ttccagagga ccggaa                              396
```

<210> SEQ ID NO 612
<211> LENGTH: 396
<212> TYPE: DNA
<213> ORGANISM: Homo sapiens

<400> SEQUENCE: 612

```
ttctgctaaa tgacagttga tggaggacat ttagggttgc ttggaggtca agtcaaggag     60
gcatttaaca ttctagtaaa acaaggaagt aacaggctcc tgaacatgcc acaatgaac    120 cagatgcaaa ccttttccct tggcaggatt ctttgcccat aaagtggagc acgaaagcag    180
gacccagaat gggaggagyt tccagaggac cggaacactt gcctttgagc gggtctacac    240
tgccaagtga gtcctaaccc tgatgttgct aataagtggg gcatgggca ggggggcctc     300 cttctaggag tgatgaccac ccttaatacc acatgtctgt ctgagccaag tttctgagcg    360
ccagggaggt gaggaaggtt ggacttcacc agagag                               396
```

<210> SEQ ID NO 613
<211> LENGTH: 396
<212> TYPE: DNA
<213> ORGANISM: Homo sapiens

<400> SEQUENCE: 613

```
ggcatttaac attctagtaa aacaaggaag taacaggctc ctgaacatgc cacaatgaa      60 ccagatgcaa accttttccc ttggcaggat tctttgccca taaagtggag cacgaaagca    120
ggacccagaa tgggaggagc ttccagagga ccggaacact tgcctttgag cgggtctaca    180
ctgccaagtg agtcctaamc tgatgttgc taataagtgg gggcatgggc agggggggcct    240 ccttctagga gtgatgacca cccttaatac acatgtctg tctgagccaa gtttctgagc     300
gccagggagg tgaggaaggt tggacttcac cagagaggct tgtggacac cctttatcat    360
```
cttagtgagt gctagtgtca aaacaaaggg agtggg 396

<210> SEQ ID NO 614
<211> LENGTH: 396
<212> TYPE: DNA
<213> ORGANISM: Homo sapiens

<400> SEQUENCE: 614
gctcctgaac atgcccacaa tgaaccagat gcaaaccttt tcccttggca ggattctttg    60
cccataaagt ggagcacgaa agcaggaccc agaatgggag gagcttccag aggaccggaa   120
cacttgcctt tgagcgggtc tacactgcca agtgagtcct aaccctgatg ttgctaataa   180
gtggggcat gggcagggrg gcctccttct aggagtgatg accacccta ataccacatg     240
tctgtctgag ccaagtttct gagcgccagg gaggtgagga aggttggact tcaccagaga   300
ggctttgtgg acacccttta tcatcttagt gagtgctagt gtcaaaacaa agggagtggg   360
gatatggggc acattggtgg agggaggtgt gatctc                             396

<210> SEQ ID NO 615
<211> LENGTH: 396
<212> TYPE: DNA
<213> ORGANISM: Homo sapiens

<400> SEQUENCE: 615
ttgcccataa agtggagcac gaaagcagga cccagaatgg gaggagcttc cagaggaccg    60
gaacacttgc ctttgagcgg gtctacactg ccaagtgagt cctaaccctg atgttgctaa   120
taagtggggg catgggcagg ggggcctcct tctaggagtg atgaccaccc ttaataccac   180
atgtctgtct gagccaagyt tctgagcgcc agggaggtga ggaaggttgg acttcaccag   240
agaggctttg tggacaccct ttatcatctt agtgagtgct agtgtcaaaa caaagggagt   300
ggggatatgg ggcacattgg tgagggagg tgtgatctct gcagcttcag aaagatctga   360
aagagtcatt tggttagaga agttgaccta tttcct                             396

<210> SEQ ID NO 616
<211> LENGTH: 396
<212> TYPE: DNA
<213> ORGANISM: Homo sapiens

<400> SEQUENCE: 616
aaacaaaggg agtggggata tggggcacat tggtggaggg aggtgtgatc tctgcagctt    60
cagaaagatc tgaaagagtc atttggttag agaagttgac ctatttcctg tggggttaga   120
ccagggttgc tactgtgaac accagccatg actcaccagt caccttcaga gccacaggc    180
aggacatgct gacgacagyc ttcaactcac ccaccccttg ctccctgcg ggtggaagtc    240
tggaggtgac accactgcat tttctaacac ggggctcct tgagcaacta gaacaagaac   300
agaaagaatg gggacattag caggtgcttt ccccctctct cattctttc tttgaataaa    360
aaggttgttt gaaacaccct gagcggctcc taaaga                             396

<210> SEQ ID NO 617
<211> LENGTH: 396
<212> TYPE: DNA
<213> ORGANISM: Homo sapiens

<400> SEQUENCE: 617
ctcctctctt ctttatgcag agtgtatttc aaggctcagc cagtggcagg catgctgggg    60

```
actatggact acggactagg ggcctgtcac agaggaaggc ctcatgctag agagctaagg    120
gaggagctgg ccttcagttc catcccagga gcaactttga tgttcccaga gatccttcca    180 aaggggagt catggtcamc caagaaaaat gtattcagaa tgccaagaat ggtgcaaact    240
caggacaaag attcacactg cagggttgga gtccctgggc ttgctgctgg caccatggga    300
gggagggtcc ccttcagggg taccgttggt ttcctgtgaa ttaaactggc ttcaagggat    360
ctcgactgaa caggcctata tcacactcac tgatat                              396

<210> SEQ ID NO 618
<211> LENGTH: 396
<212> TYPE: DNA
<213> ORGANISM: Homo sapiens

<400> SEQUENCE: 618
tctcctcatc taggtatttt taattgtttc agtgaggtgt aggcatgagg ggattggagg     60
gggcatctcc tccattgcag tttttcattg gctgctttgc tccctcagct ccgaaatcgc    120
tgggccactc tcgaacgcat tagtacggta gtcacaggtt gattgcctgg ccccttgccc    180
tctgtgggca ttttccctyt cagacagccc ctgagtactc acagtgctgc tacagtgggc    240
cacctagatc tccctctttc tccatgctcc cacgtgctct gggctccact cccttctccc    300
aagcacttct gtccagggct attccagcag tctgacctca aggaaatcct ttgctaaact    360
gattatagag aggtttctat tttaacattt aggtct                              396

<210> SEQ ID NO 619
<211> LENGTH: 396
<212> TYPE: DNA
<213> ORGANISM: Homo sapiens

<400> SEQUENCE: 619
atctaggtat ttttaattgt ttcagtgagg tgtaggcatg aggggattgg aggggggcatc    60 tcctccattg cagtttttca ttggctgctt tgctccctca gctccgaaat cgctgggcca   120
ctctcgaacg cattagtacg gtagtcacag gttgattgcc tggccccttg ccctctgtgg   180
gcattttccc tttcagacwg ccctgagta ctcacagtgc tgctacagtg ggccacctag    240
atctccctct ttctccatgc tcccacgtgc tctgggctcc actcccttct cccaagcact   300
tctgtccagg gctattccag cagtctgacc tcaaggaaat cctttgctaa actgattata   360
gagaggtttc tattttaaca tttaggtctt ccatgt                              396

<210> SEQ ID NO 620
<211> LENGTH: 396
<212> TYPE: DNA
<213> ORGANISM: Homo sapiens

<400> SEQUENCE: 620
aggtgtaggc atgaggggat tgaggggggc atctcctcca ttgcagtttt tcattggctg     60
ctttgctccc tcagctccga aatcgctggg ccactctcga acgcattagt acggtagtca   120
caggttgatt gcctggcccc ttgccctctg tgggcatttt cccttcaga cagcccctga    180 gtactcacag tgctgctaya gtgggccacc tagatctccc tctttctcca tgctcccacg   240
tgctctgggc tccactccct tctcccaagc acttctgtcc aggctattc cagcagtctg    300 acctcaagga aatcctttgc taaactgatt atagagaggt ttctatttta acatttaggt   360
cttccatgta ttaattctca gaatcaattt aagatg                              396
```

<210> SEQ ID NO 621
<211> LENGTH: 396
<212> TYPE: DNA
<213> ORGANISM: Homo sapiens

<400> SEQUENCE: 621

```
cctttcagac agcccctgag tactcacagt gctgctacag tgggccacct agatctccct      60
ctttctccat gctcccacgt gctctgggct ccactcccct ctcccaagca cttctgtcca     120
gggctattcc agcagtctga cctcaaggaa atcctttgct aaactgatta tagagaggtt     180
tctattttaa catttaggyc ttccatgtat taattctcag aatcaattta agatgtttaa     240
aggtgtgatt taagacattt taaaaccatt tggaggagag tacagaaatt atgtcacttg     300
ctgtcagcct ctttgcacca tctgcagaga aagatactag agtcccgcct tggacacatc     360
cacatgcaag aggtgcaaag aaggtgtctt tgatga                               396
```

<210> SEQ ID NO 622
<211> LENGTH: 396
<212> TYPE: DNA
<213> ORGANISM: Homo sapiens

<400> SEQUENCE: 622

```
ttctcagaat caatttaaga tgtttaaagg tgtgatttaa gacattttaa aaccatttgg      60
aggagagtac agaaattatg tcacttgctg tcagcctctt tgcaccatct gcagagaaag     120
atactagagt cccgccttgg acacatccac atgcaagagg tgcaaagaag gtgtctttga     180
tgaggcaagg tcaaaactyc tccccagacg aaatccaaag aaagcattcc tactatgcta     240
tatcagtttg gaaagaaaaa cttctgccag gtgactgcat tctcactggt cacattgtgt     300
tcctatggac tcctcagctc aaccaatttg gagaagttat ggtgcaattt caccatatct     360
ggttagaagt taagtttcca atttgctggc aatgaa                               396
```

<210> SEQ ID NO 623
<211> LENGTH: 396
<212> TYPE: DNA
<213> ORGANISM: Homo sapiens

<400> SEQUENCE: 623

```
aagaaggtgt ctttgatgag gcaaggtcaa aacttctccc cagacgaaat ccaaagaaag      60
cattcctact atgctatatc agtttggaaa gaaaaacttc tgccaggtga ctgcattctc     120
actggtcaca ttgtgttcct atggactcct cagctcaacc aatttggaga agttatggtg     180
caatttcacc atatctggyt agaagttaag tttccaattt gctggcaatg aagaagaaat     240
ggagcaggcc aggctgtgta gtttctgcca cgtgccccccg ggagtgaaca gctctgtttg     300
taagaagcca tggtgcttag acctgggctc gctagttgcc agcctccaaa ttgcagaagt     360
gccctttggt tggtggctat gctgtgtcac ttggga                               396
```

<210> SEQ ID NO 624
<211> LENGTH: 396
<212> TYPE: DNA
<213> ORGANISM: Homo sapiens

<400> SEQUENCE: 624

```
gcaacatatc tgtgtgcctg tctgggttgt aaaaagggtc aaagatcaat gcagcaggca      60
gctacatgct ggcaaaagcc agaggcagct ggtctgtttg cctgtgccag gaaaccactg     120
ggaatggggt tgtgtgttat tctaggagaa agtcgtccca gcagcagctt ctccaggggc     180
```

-continued

| | |
|---|---|
| atccaagagc actgaaaarg gttgcaagat gacccatgag gctgcaggaa gaaaagaaca | 240 |
| tgcatttaat cttgctatct gaaaagtaag acatgaagct ttcctcattt ttaatataca | 300 |
| catggacagt agtatgtgta tatagtttat atgcaaatat acttgttata aggttgcatg | 360 |
| ctcaaaattt ttggttcatg gggtgtggga tcataa | 396 |

<210> SEQ ID NO 625
<211> LENGTH: 396
<212> TYPE: DNA
<213> ORGANISM: Homo sapiens

<400> SEQUENCE: 625

| | |
|---|---|
| cagctacatg ctggcaaaag ccagaggcag ctggtctgtt tgcctgtgcc aggaaaccac | 60 |
| tgggaatggg gttgtgtgtt attctaggag aaagtcgtcc cagcagcagc ttctccaggg | 120 |
| gcatccaaga gcactgaaaa gggttgcaag atgacccatg aggctgcagg aagaaaagaa | 180 |
| catgcattta atcttgctrt ctgaaaagta agacatgaag ctttcctcat ttttaatata | 240 |
| cacatggaca gtagtatgtg tatatagttt atatgcaaat atacttgtta taaggttgca | 300 |
| tgctcaaaat ttttggttca tggggtgtgg gatcataaat gtttagggac catggctatc | 360 |
| aaggaaaaac agcatgaagg ataaatgata ctggtg | 396 |

<210> SEQ ID NO 626
<211> LENGTH: 396
<212> TYPE: DNA
<213> ORGANISM: Homo sapiens

<400> SEQUENCE: 626

| | |
|---|---|
| ctatctgaaa agtaagacat gaagctttcc tcattttttaa tatacacatg gacagtagta | 60 |
| tgtgtatata gtttatatgc aaatatactt gttataaggt tgcatgctca aaattttttgg | 120 |
| ttcatggggt gtgggatcat aaatgtttag ggaccatggc tatcaaggaa aaacagcatg | 180 |
| aaggataaat gatactggyg gattaaaaag acagatgcat gtattttttag cataaaacac | 240 |
| aactgctgac tgatacagat agctcaagat tctggggcag ctgctgaaca gatacactag | 300 |
| ccagtgtggc tcatcggctc agacttggcc ttaattaatg ggctgtccct ccacccatct | 360 |
| cccatgaggg cagagctgag ccagggtttg agagct | 396 |

<210> SEQ ID NO 627
<211> LENGTH: 396
<212> TYPE: DNA
<213> ORGANISM: Homo sapiens

<400> SEQUENCE: 627

| | |
|---|---|
| agtttatatg caaatatact tgttataagg ttgcatgctc aaaattttttg gttcatgggg | 60 |
| tgtgggatca taaatgttta ggaccatgg ctatcaagga aaaacagcat gaaggataaa | 120 |
| tgatactggt ggattaaaaa gacagatgca tgtatttttta gcataaaaca caactgctga | 180 |
| ctgatacaga tagctcaasa ttctggggca gctgctgaac agatacacta gccagtgtgg | 240 |
| ctcatcggct cagacttggc cttaattaat gggctgtccc tccacccatc tcccatgagg | 300 |
| gcagagctga gccagggttt gagagctaaa aggaattgga cctggactct gttcacgtgt | 360 |
| atatttttaat tctaattaat tcattctttt gaaaga | 396 |

<210> SEQ ID NO 628
<211> LENGTH: 394
<212> TYPE: DNA
<213> ORGANISM: Homo sapiens

<400> SEQUENCE: 628

```
gtattttag cataaaacac aactgctgac tgatacagat agctcaagat tctggggcag    60
ctgctgaaca gatacactag ccagtgtggc tcatcggctc agacttggcc ttaattaatg   120
ggctgtccct ccacccatct cccatgaggg cagagctgag ccagggtttg agagctaaaa   180
ggaattggac ctggactcdg ttcacgtgta tattttaatt ctaattaatt cattcttttg   240
aaagacagag tcacactctg ttgcctaggc tggagtgcag tggcacgatc ttggctcact   300
gcaacctcgg cctcccaggt tcaagttatt ctcctgcttc agcctcctga gtagctggga   360
ttataggcac atgcccccat gcctgactaa tttt                               394
```

<210> SEQ ID NO 629
<211> LENGTH: 396
<212> TYPE: DNA
<213> ORGANISM: Homo sapiens

<400> SEQUENCE: 629

```
gctaaaagga attggacctg gactctgttc acgtgtatat tttaattcta attaattcat    60
tcttttgaaa gacagagtca cactctgttg cctaggctgg agtgcagtgg cacgatcttg   120
gctcactgca acctcggcct cccaggttca agttattctc ctgcttcagc ctcctgagta   180
gctgggatta taggcacayg cccccatgcc tgactaattt ttgtattttt agtagagacg   240
gggtttcacc atgtcaggct ggtcttgaac tcctgacctc aggttatcca cccgccttgg   300
cccctcaaag tgttggaatt acaggtgtga gccaccgtgc ctggcctgtt cacatgtata   360
aaacacagtt taatgtccta ttcccagcca atgagc                             396
```

<210> SEQ ID NO 630
<211> LENGTH: 396
<212> TYPE: DNA
<213> ORGANISM: Homo sapiens

<400> SEQUENCE: 630

```
tcaggttatc cacccgcctt ggcccctcaa agtgttggaa ttacaggtgt gagccaccgt    60
gcctggcctg ttcacatgta taaaacacag tttaatgtcc tattcccagc caatgagcat   120
ggctagagca gccttggtca agtttggtt tttggagaaa atccttgtt agctgaccta    180
agattcctct ttgtgagtkt aagtaagcac aggttgcaga gaggagaagg gtctctggag   240
aggtgtaatt ttctaaatgg attacaagtt catggacttt taacaggtgt tacagggggat   300
aacaagttct ttatagacag acttttgagg acgtttaagg gtattctgat tcttggtttt   360
ctaagagggg aatgtattat ttaactacag acaccc                             396
```

<210> SEQ ID NO 631
<211> LENGTH: 396
<212> TYPE: DNA
<213> ORGANISM: Homo sapiens

<400> SEQUENCE: 631

```
aaaatccaga ataataataa tttgtcaata ggaaagacat ttccactggg ggttaagaag    60
gaagacattg gaacaatgat agccaccact tattgaatgc ttactgtgag ccaggtggca   120
cttcaccttg tttcattctc acaacagtct agggaagtaa ttactaatgt ctccatccac   180
ctcttgtaga tgagcaaayt gaggctcatt gaggctagga aatgcaccca cactcacata   240
gcccataaga ggcagccatg gcattgggcc cagaccatgt gaacttcaaa gactacacga   300
```

```
gcagccactg ggcagctgtc atggctaaag ccacttgaat tcagcccagc agcaacccc       360
tctccaggag gggcacataa gcttgcagct ttgggt                                 396

<210> SEQ ID NO 632
<211> LENGTH: 396
<212> TYPE: DNA
<213> ORGANISM: Homo sapiens

<400> SEQUENCE: 632
ataataataa tttgtcaata ggaaagacat ttccactggg ggttaagaag gaagacattg       60
gaacaatgat agccaccact tattgaatgc ttactgtgag ccaggtggca cttcaccttg      120
tttcattctc acaacagtct agggaagtaa ttactaatgt ctccatccac ctcttgtaga      180
tgagcaaact gaggctcayt gaggctagga aatgcaccca cactcacata gcccataaga      240
ggcagccatg gcattgggcc cagaccatgt gaacttcaaa gactacacga gcagccactg      300
ggcagctgtc atggctaaag ccacttgaat tcagcccagc agcaacccc tctccaggag       360
gggcacataa gcttgcagct ttgggtagaa gctgca                                 396

<210> SEQ ID NO 633
<211> LENGTH: 396
<212> TYPE: DNA
<213> ORGANISM: Homo sapiens

<400> SEQUENCE: 633
gcacttgaag tcctggatgg cgagagggac tggcttgagc cagagccagg aacaaggctc       60
tgagaatatt ctggaaatcc acaggaggaa cccattttct tacagctggg agaatttcat      120
tcaactccag gctgaccatg ttttattagg aacgaaggtg acttgaacta atagtcagga      180
atggttgaat acggacccra tgtcaaatca ctaggcagtt cacatttcta atgagcaaat      240
cccttagaca attaagaatt ttttccttt tgcataaccc agacaaaatc gctacttaaa       300
aacaaaccaa agacccgaaa catgagaaag agaaggaagc aggggaaatc tttggtacta      360
ataagttttt aaacaataag agcaccagat atttta                                 396

<210> SEQ ID NO 634
<211> LENGTH: 396
<212> TYPE: DNA
<213> ORGANISM: Homo sapiens

<400> SEQUENCE: 634
atgagcaaat cccttagaca attaagaatt ttttccttt tgcataaccc agacaaaatc        60
gctacttaaa aacaaaccaa agacccgaaa catgagaaag agaaggaagc agggaaatc      120
tttggtacta ataagttttt aaacaataag agcaccagat attttacccc atcagacaca      180
gaatgttatt cgaataacsa aaaaggaat ttttctcta agtttcttga actggaaaat       240
gaatcatatt ttctcagtcc tgaggctgca attttgtgcc tctagtaaca tataagaata      300
gatgtgatgc cagtgcccag tagctgctgc aattgttact tggggacctg tttattcact      360
aagcacttca ccccagtgat aaatttgtag gggcct                                 396

<210> SEQ ID NO 635
<211> LENGTH: 396
<212> TYPE: DNA
<213> ORGANISM: Homo sapiens

<400> SEQUENCE: 635
ccgtgtccat tagatcagtg gaaattctgg gattcagagc actttgcaag gtcagcaggg       60
```

```
gtctgctctt tctgtcctgt tcctggtttt tggttgtgcc tggattccag ggtaggtttc      120
tcatctgtta ccttcataga cttctccaga aaaggatctt ttgaccatca gaggaccacg      180
aagattccat tggtgaggyg cagataacct gatctctctg ggttctctgc agggcacaga      240
tgaagggctg gccattccca agttctcagt ggtaccactg aggcatgaga ccctaatggt      300
ttgcatgagc agtttgaaaa ttgcatcttt gtttttacct atataatcac atgaaacccg      360
tggttctcaa acgtcagcag gcatcagcat cacatg                               396

<210> SEQ ID NO 636
<211> LENGTH: 396
<212> TYPE: DNA
<213> ORGANISM: Homo sapiens

<400> SEQUENCE: 636
tcagtggtac cactgaggca tgagacccta atggtttgca tgagcagttt gaaaattgca       60
tctttgtttt tacctatata atcacatgaa acccgtggtt ctcaaacgtc agcaggcatc      120
agcatcacat ggagggcttg ttaaaacaga tttctgggcc ccaacacaga gttttaaatt      180
ctgaaggcct gaggtgggyg tgaacatttg catttctaac atgttctcga tgctgctgcc      240
gcctctggtc ccgagagcat gcctggagaa ctgccacctt cgaccatgga ctgtgagaat      300
tcacatggac ctcagaatta taatcagtct ctcagtttta cagataagga aactaaatcc      360
agagagattg ttttgccaat ggtgaacagc tggtta                               396

<210> SEQ ID NO 637
<211> LENGTH: 396
<212> TYPE: DNA
<213> ORGANISM: Homo sapiens

<400> SEQUENCE: 637
atggtttgca tgagcagttt gaaaattgca tctttgtttt tacctatata atcacatgaa       60
acccgtggtt ctcaaacgtc agcaggcatc agcatcacat ggagggcttg ttaaaacaga      120
tttctgggcc ccaacacaga gttttaaatt ctgaaggcct gaggtgggtg tgaacatttg      180
catttctaac atgttctcra tgctgctgcc gcctctggtc ccgagagcat gcctggagaa      240
ctgccacctt cgaccatgga ctgtgagaat tcacatggac ctcagaatta taatcagtct      300
ctcagtttta cagataagga aactaaatcc agagagattg ttttgccaat ggtgaacagc      360
tggttaaagt caggatggag actttaatcc tagtca                               396

<210> SEQ ID NO 638
<211> LENGTH: 396
<212> TYPE: DNA
<213> ORGANISM: Homo sapiens

<400> SEQUENCE: 638
gagcagtttg aaaattgcat ctttgttttt acctatataa tcacatgaaa cccgtggttc       60
tcaaacgtca gcaggcatca gcatcacatg gagggcttgt aaaacagat ttctgggccc      120 caacacagag ttttaaattc tgaaggcctg aggtgggtgt gaacatttgc atttctaaca      180
tgttctcgat gctgctgcyg cctctggtcc cgagagcatg cctggagaac tgccaccttc      240
gaccatggac tgtgagaatt cacatggacc tcagaattat aatcagtctc tcagttttac      300
agataaggaa actaaatcca gagagattgt tttgccaatg gtgaacagct ggttaaagtc      360
aggatggaga ctttaatcct agtcaagtga cctttc                               396
```

<210> SEQ ID NO 639
<211> LENGTH: 396
<212> TYPE: DNA
<213> ORGANISM: Homo sapiens

<400> SEQUENCE: 639

| | | | | | | |
|---|---|---|---|---|---|---|
| agtttgaaaa | ttgcatcttt | gttttttacct | atataatcac | atgaaacccg | tggttctcaa | 60 |
| acgtcagcag | gcatcagcat | cacatggagg | gcttgttaaa | acagatttct | gggcccccaac | 120 |
| acagagtttt | aaattctgaa | ggcctgaggt | gggtgtgaac | atttgcattt | ctaacatgtt | 180 |
| ctcgatgctg | ctgccgcckc | tggtcccgag | agcatgcctg | agaactgcc | accttcgacc | 240 |
| atggactgtg | agaattcaca | tggacctcag | aattataatc | agtctctcag | ttttacagat | 300 |
| aaggaaacta | atccagaga | gattgttttg | ccaatggtga | acagctggtt | aaagtcagga | 360 |
| tggagacttt | aatcctagtc | aagtgacctt | tcctct | | | 396 |

<210> SEQ ID NO 640
<211> LENGTH: 396
<212> TYPE: DNA
<213> ORGANISM: Homo sapiens

<400> SEQUENCE: 640

| | | | | | | |
|---|---|---|---|---|---|---|
| catctttgtt | tttacctata | taatcacatg | aaacccgtgg | ttctcaaacg | tcagcaggca | 60 |
| tcagcatcac | atggagggct | tgttaaaaca | gatttctggg | ccccaacaca | gagttttaaa | 120 |
| ttctgaaggc | ctgaggtggg | tgtgaacatt | tgcatttcta | acatgttctc | gatgctgctg | 180 |
| ccgcctctgg | tcccgagakc | atgcctggag | aactgccacc | ttcgaccatg | gactgtgaga | 240 |
| attcacatgg | acctcagaat | tataatcagt | ctctcagttt | tacagataag | gaaactaaat | 300 |
| ccagagagat | tgttttgcca | atggtgaaca | gctggtaaaa | gtcaggatgg | agactttaat | 360 |
| cctagtcaag | tgacctttcc | tctgtattta | tttccc | | | 396 |

<210> SEQ ID NO 641
<211> LENGTH: 396
<212> TYPE: DNA
<213> ORGANISM: Homo sapiens

<400> SEQUENCE: 641

| | | | | | | |
|---|---|---|---|---|---|---|
| atttctgaca | tcctgaacca | tagtaaaagg | gtgttttttg | tttttttgag | acagagtctt | 60 |
| gctctgttgc | ctgggctgga | gtgcagtggt | gtgatcttgg | ctcgctgcaa | cctccgcctc | 120 |
| ccaggttcaa | gtgattctcc | tgcctcagcc | tcctgagtag | ctgggattac | aggtgcttgc | 180 |
| caccacacct | ggctatttkt | tgtgttttta | gtagagacag | ggtttcacca | tgttggccag | 240 |
| gctggtcttg | aactcctgac | cttgtgatct | gcctgcctca | gcctcccaaa | ttgctgggat | 300 |
| tacaaggcgt | gttgttttaa | gccactcagt | ttgtggccac | ttgttacagc | agcaagagga | 360 |
| aactcataca | gttatcatgt | gaactcacag | gaatat | | | 396 |

<210> SEQ ID NO 642
<211> LENGTH: 396
<212> TYPE: DNA
<213> ORGANISM: Homo sapiens

<400> SEQUENCE: 642

| | | | | | | |
|---|---|---|---|---|---|---|
| gatctgcctg | cctcagcctc | ccaaattgct | gggattacaa | ggcgtgttgt | tttaagccac | 60 |
| tcagtttgtg | gccacttgtt | acagcagcaa | gaggaaactc | atacagttat | catgtgaact | 120 |
| cacaggaata | tggtgagtta | aaaagagagg | aagggtgcaa | acatccacg | gtagagtgag | 180 |

```
aactctccag ggagtgagra ctgtgcccag catacagtga tcaccctctt agtaagctaa      240
gtttctgagc accagctttt ttgagttgac tttgttgtct ttaacatttg aagatcaccc      300
ttctttgctc agcctggctt gcagacctgg gctgatttgt ggatctgata gaaaagtttc      360
cttagttggg ctcttctccc cgaccacccc catgcc                                396
```

<210> SEQ ID NO 643
<211> LENGTH: 396
<212> TYPE: DNA
<213> ORGANISM: Homo sapiens

<400> SEQUENCE: 643

```
tgcctcagcc tcccaaattg ctgggattac aaggcgtgtt gttttaagcc actcagtttg       60
tggccacttg ttacagcagc aagaggaaac tcatacagtt atcatgtgaa ctcacaggaa      120
tatggtgagt taaaaagaga ggaagggtgc aaaacatcca cggtagagtg agaactctcc      180
agggagtgag gactgtgcmc agcatacagt gatcaccctc ttagtaagct aagtttctga      240
gcaccagctt ttttgagttg actttgttgt ctttaacatt tgaagatcac ccttcttttgc     300 tcagcctggc ttgcagacct gggctgattt gtggatctga tagaaaagtt tccttagttg      360
ggctcttctc cccgaccacc cccatgccag tgtggc                                396
```

<210> SEQ ID NO 644
<211> LENGTH: 396
<212> TYPE: DNA
<213> ORGANISM: Homo sapiens

<400> SEQUENCE: 644

```
gctactttgc agccaaggta actcagactt ccctttgttc attctccttc tataaagtgc       60
atctcaagga ggttcaaagg gcaggctttt tgttgaaagg actttgcctg acctctggct      120
cccatctgtg aagccctgga gaggtgagag ccctcgggag gccgtgtttc aggcatgctc      180
tgcacccgtg cagagcgcrt gtgataatgc attgctaatg cttgctccct ggtggctggc      240
tgagagctgc tgtgctgaca agggtggttt aaggctaaat gtgactcaga atccttaagc      300
agtgttagtt cagatacaag ggcattataa atgagagtgc ctgagggatc tattttggga      360
ccgctgtcac ttggctcttc tgctaataag cttcca                                396
```

<210> SEQ ID NO 645
<211> LENGTH: 396
<212> TYPE: DNA
<213> ORGANISM: Homo sapiens

<400> SEQUENCE: 645

```
acagttatca gcagcccaca ggcttgactt gagcaagttg gaaagacaaa tcaacttcca       60
gagttgattt aacattgagt ggaaatcagt catactttttg gtccccttttc ggggccacgc     120 ctggcactgt gcctggtggc agatcggcat gaactggcca gcttctgtgg ccctggaggg      180
cacaggcaga aaggccacrc tcagtcccat gatgaactgt ttaagactta ttgttgtctc      240
cccgctctgt aaagtagata gagtggattt tatgtcccctt attacctttc aggatacttt     300
gactcaggga gataaagtaa cttgggtaca gctactcagc tggtgaagaa cacaggcaga      360
atgagtgcct gggtcttttg acttaaaatt ctggat                                396
```

<210> SEQ ID NO 646
<211> LENGTH: 396
<212> TYPE: DNA

<213> ORGANISM: Homo sapiens

<400> SEQUENCE: 646

```
ctgtgcctgg tggcagatcg gcatgaactg gccagcttct gtggccctgg agggcacagg    60
cagaaaggcc acactcagtc ccatgatgaa ctgtttaaga cttattgttg tctccccgct   120
ctgtaaagta gatagagtgg attttatgtc ccttattacc tttcaggata ctttgactca   180
gggagataaa gtaacttgsg tacagctact cagctggtga agaacacagg cagaatgagt   240
gcctgggtct tttgacttaa aattctggat ttttcacaaa gatcctctta ctttattcat   300
ttacataata aatatatatt gaagagctac tctgtgccaa gccctgtgcc tagatataca   360
gtgataaata aagagtagct tctagaggtc acctgg                             396
```

<210> SEQ ID NO 647
<211> LENGTH: 396
<212> TYPE: DNA
<213> ORGANISM: Homo sapiens

<400> SEQUENCE: 647

```
aagttcagtg atagagagca gaggtgaggc ggcagcagaa accacttaag ggacaccacg    60
tggcactcct tctgtgctga gaaggctgtc agtaagctca ccatttattt cctattttct   120
ctcctgagtt aaataggaaa catgtctcgc attacttgaa aaatcaagtc aaactatgct   180
cttactagga gttatggtyc tttttatgtc ttagatgatg cttgatctag atgaatgcgg   240
acttgctgta gctagataaa tacaatggga gtttgaaggt gtttcgtagc cctggaaata   300
ggtatttcct gtcaaaacaa gctttgtcat tgccagcaga caaaagcatc agtaaccttg   360
gttgataatc gtcatttctt aggaataaag tagact                             396
```

<210> SEQ ID NO 648
<211> LENGTH: 396
<212> TYPE: DNA
<213> ORGANISM: Homo sapiens

<400> SEQUENCE: 648

```
gtatttcctg tcaaaacaag ctttgtcatt gccagcagac aaaagcatca gtaaccttgg    60
ttgataatcg tcatttctta ggaataaagt agactgtaga attttttta gcagaaagga   120
aacccaaaga taattctagt gcaaatccct cactttatag agcagaagct caagtcccag   180
aggaacaagt ggcttgaayg aacatcagaa ttttaggggc tggatttgta ccctcctggt   240
gccagcagcc cacttccctg caggaggcac tcaccttcct tgcacagggg tatgagtgtg   300
gccattttcc acccataatc tctgttagct catgttcaat tgggttccca ttgaaagaaa   360
aatggaccag taagttggag cagaatcatt cagatg                             396
```

<210> SEQ ID NO 649
<211> LENGTH: 396
<212> TYPE: DNA
<213> ORGANISM: Homo sapiens

<400> SEQUENCE: 649

```
agctttgtca ttgccagcag acaaaagcat cagtaacctt ggttgataat cgtcatttct    60
taggaataaa gtagactgta gaattttttt tagcagaaag gaaacccaaa gataattcta   120
gtgcaaatcc ctcactttat agagcagaag ctcaagtccc agaggaacaa gtggcttgaa   180
cgaacatcag aattttagkg gctggatttg taccctcctg gtgccagcag cccacttccc   240
tgcaggaggc actcaccttc cttgcacagg ggtatgagtg tggccatttt ccacccataa   300
```
tctctgttag ctcatgttca attgggttcc cattgaaaga aaaatggacc agtaagttgg    360
agcagaatca ttcagatggt ataacataag gaaaaa                              396

<210> SEQ ID NO 650
<211> LENGTH: 396
<212> TYPE: DNA
<213> ORGANISM: Homo sapiens

<400> SEQUENCE: 650
tgtttaaatt gcttttatat ctgtagctct agataacact agttccagct tagttaactc    60
ccagctccaa gccttcagga cttcatagag ttattggggt gctgctcttg gcagtttccc    120
aaaaagctag aatgcagagg gaatctcctt cccaaaaagc tagaatgcag agggaatctc    180
cttcccaaaa ggctagaayg cagagggaat ctccttccca aaaagctaga atgcagaggg    240
aatctccttc ccaaaaggct agaacgcaga gggaatctcc ttcccaaaag ctagaacgc     300 agagggaatc tccttcccaa aaggctagaa tgcagaggga atgtccttct cttctaaatg    360
gtagctgtta gttcaagaaa ggttaaacat tgtgct                              396

<210> SEQ ID NO 651
<211> LENGTH: 396
<212> TYPE: DNA
<213> ORGANISM: Homo sapiens

<400> SEQUENCE: 651
gctgcgtttg ctggactgat gtacttgttt gtgaggcaaa agtactttgt cggttaccta    60
ggagagagaa cgcagaggta ggtaactggg actactaaag aactgtggag cgattcctga    120
tttttgagca ggaagagtga caattcaaaa cagtatttga ctagattcac ggctccgtag    180
catccccttg ggtgggagsg ggaaggctga ctaggacctc tgattcttct ttccctgagc    240
tttgaaggct ctgaaaatac agctgggggg acttgcccag ttttcttatt aagcaattcc    300
tccgcatggt gctggctttc aaagggtgct tcagtgctgt ttgctgcacg tgccttgcag    360
ccccacaccc tgcactcccg ccctgcagag tctggc                              396

<210> SEQ ID NO 652
<211> LENGTH: 396
<212> TYPE: DNA
<213> ORGANISM: Homo sapiens

<400> SEQUENCE: 652
gaggcaaaag tactttgtcg gttacctagg agagagaacg cagaggtagg taactgggac    60
tactaaagaa ctgtggagcg attcctgatt tttgagcagg aagagtgaca attcaaaaca    120
gtatttgact agattcacgg ctccgtagca tccccttggg tgggaggggg aaggctgact    180
aggacctctg attcttctyt ccctgagctt tgaaggctct gaaaatacag ctgggggac    240 ttgcccagtt ttcttattaa gcaattcctc cgcatggtgc tggctttcaa agggtgcttc    300
agtgctgttt gctgcacgtg ccttgcagcc ccacaccctg cactcccgcc ctgcagagtc    360
tggcgctgga atgacatttt aggtctgggt tcccag                              396

<210> SEQ ID NO 653
<211> LENGTH: 396
<212> TYPE: DNA
<213> ORGANISM: Homo sapiens

<400> SEQUENCE: 653

| | |
|---|---:|
| tatctttcag ggaccagaag aaagaatgtt gggaaaataa gatgcagtaa gatgcagaca | 60 |
| tgacagcagg gtgcagcggc tcacgcctat aatcccagca ctttgggagg ctgaggtggg | 120 |
| tggatcacct gaggtcagga gtttgagacc agcctggcca acatggtgaa accccgtctc | 180 |
| tactaaaaaa tatacaaarc attagccagg catggtggtg ggcgcctgta atcccagcta | 240 |
| ctccataggc tgaggctgga gaatcgcttg aacccaggag gcagaggttg cagtgagccg | 300 |
| agattgcgcc actgcactcc agcctgggca acaaaagcaa aactccatct caaaaaaaaa | 360 |
| aaaaaaaaaa aaaaaaaaga tgcagacacg agactg | 396 |

<210> SEQ ID NO 654
<211> LENGTH: 396
<212> TYPE: DNA
<213> ORGANISM: Homo sapiens

<400> SEQUENCE: 654

| | |
|---|---:|
| tgggcgcctg taatcccagc tactccatag gctgaggctg gagaatcgct tgaacccagg | 60 |
| aggcagaggt tgcagtgagc cgagattgcg ccactgcact ccagcctggg caacaaaagc | 120 |
| aaaactccat ctcaaaaaaa aaaaaaaaaa aaaaaaaaaa gatgcagaca cgagactgtg | 180 |
| aaactgacta gcatcaccwt tgcattgttt atagatgttg ccagacagaa agccccaaag | 240 |
| cagcacagta ccttcctgac atctggacta ggaaatctag attttagtaa aatacatgct | 300 |
| aatacttaca gaagaaatgt cggcgttaga gtatgccgtc agttccttag agattgcaat | 360 |
| tcctaatgca ctagtatggt ttcaggtgcc aggaac | 396 |

<210> SEQ ID NO 655
<211> LENGTH: 396
<212> TYPE: DNA
<213> ORGANISM: Homo sapiens

<400> SEQUENCE: 655

| | |
|---|---:|
| actccatctc aaaaaaaaaa aaaaaaaaaa aaaaaagat gcagacacga gactgtgaaa | 60 |
| ctgactagca tcaccattgc attgtttata gatgttgcca gacagaaagc cccaaagcag | 120 |
| cacagtacct tcctgacatc tggactagga aatctagatt ttagtaaaat acatgctaat | 180 |
| acttacagaa gaaatgtcrg cgttagagta tgccgtcagt tccttagaga ttgcaattcc | 240 |
| taatgcacta gtatggtttc aggtgccagg aacacgttct gtgaggctgc tgccccaggt | 300 |
| gctgacccca gccttccaca ccatttttcct tccttgtgtt cacagccgct ctgtctttta | 360 |
| caatagcacc cctctctagt ggctaatggg ctctat | 396 |

<210> SEQ ID NO 656
<211> LENGTH: 396
<212> TYPE: DNA
<213> ORGANISM: Homo sapiens

<400> SEQUENCE: 656

| | |
|---|---:|
| aaaaaaaaaa aaaaaaaaaa aagatgcaga cacgagactg tgaaactgac tagcatcacc | 60 |
| attgcattgt ttatagatgt tgccagacag aaagccccaa agcagcacag taccttcctg | 120 |
| acatctggac taggaaatct agattttagt aaaatacatg ctaatactta cagaagaaat | 180 |
| gtcggcgtta gagtatgcyg tcagttcctt agagattgca attcctaatg cactagtatg | 240 |
| gtttcaggtg ccaggaacac gttctgtgag gctgctgccc caggtgctga ccccagcctt | 300 |
| ccacaccatt ttccttcctt gtgttcacag ccgctctgtc ttttacaata gcacccctct | 360 |
| ctagtggcta atgggctcta tgattagata gcatcc | 396 |

<210> SEQ ID NO 657
<211> LENGTH: 396
<212> TYPE: DNA
<213> ORGANISM: Homo sapiens

<400> SEQUENCE: 657

```
tttcaggtgc caggaacacg ttctgtgagg ctgctgcccc aggtgctgac cccagccttc    60
cacaccattt tccttccttg tgttcacagc cgctctgtct tttacaatag caccectctc   120
tagtggctaa tgggctctat gattagatag catccttcag tagtgataaa ggcagtgaca   180
tcctagggag gtcagcggkt gaaagcgcta tatctggaaa acctgagagc ctgtgaagct   240
caaggacttg acggggttag accgtgagcc gggctgcagc tggaaaaaga atgactgttc   300
tttcagcaga tccttccctg tgccatctct ttcttcattc ctctctagtg gcattcttat   360
ttatcctcta aaaccacaat tccattatct ctccta                             396
```

<210> SEQ ID NO 658
<211> LENGTH: 396
<212> TYPE: DNA
<213> ORGANISM: Homo sapiens

<400> SEQUENCE: 658

```
gagggtcttc tcttttgcct ggctccctat gcagccctat cttacccct gcaaagtccc    60
agggatgtgg ctcagtcact gctcctctct tcatctgtca ccacttgctt gagatcctac   120
agctgcttta attccgagac catctgcaga acatgacaaa atttgtccac ctacccacat   180
gtccttttaa ctttaaagrc tttactaact gattcctatt agggaatgaa cagaggtggc   240
aaaaataaac aataggagat tgatttacaa gaaatctttta aaatagtaga tttcttcgga   300
cctcattgaa atataaatgg cctgccttct tgtgtccctc cctggtctcc ctctttaggt   360
gataagaaga agatcctgcc agccccataa cccgcc                             396
```

<210> SEQ ID NO 659
<211> LENGTH: 396
<212> TYPE: DNA
<213> ORGANISM: Homo sapiens

<400> SEQUENCE: 659

```
ttaaaatagt agatttcttc ggacctcatt gaaatataaa tggcctgcct tcttgtgtcc    60
ctccctggtc tccctctttta ggtgataaga agaagatcct gccagcccca taacccgcca   120
tctgcgcggg ttctagaccc ccttctcctc ccctctggcc gtggtaggca ttactgatga   180
atcatggtgc tctttcttmc agagaccaaa cctggcctcg gaatccttct taacacagat   240
actgcttaac acaaccactc tgagcagctg tcataagtag aagtaataga tactagaaga   300
aatgtctaag cctaatctag accaaaatac ggcctgatat agatgcaagc cagaggggct   360
ttatggttaa atgcaaggag attttcaacc ctgccg                             396
```

<210> SEQ ID NO 660
<211> LENGTH: 396
<212> TYPE: DNA
<213> ORGANISM: Homo sapiens

<400> SEQUENCE: 660

```
ctggtctccc tctttaggtg ataagaagaa gatcctgcca gccccataac ccgccatctg    60
cgcgggttct agaccccctt ctcctcccct ctggccgtgg taggcattac tgatgaatca   120
```

```
tggtgctctt tcttccagag accaaacctg gcctcggaat ccttcttaac acagatactg    180
cttaacacaa ccactctgrg cagctgtcat aagtagaagt aatagatact agaagaaatg    240
tctaagccta atctagacca aaatacggcc tgatatagat gcaagccaga ggggctttat    300
ggttaaatgc aaggagattt caaccctgc cgtctagaag ctacttgctg agatcttctt     360
cagttgggcc catctcctcc ccaggcctct cttctg                              396
```

<210> SEQ ID NO 661
<211> LENGTH: 396
<212> TYPE: DNA
<213> ORGANISM: Homo sapiens

<400> SEQUENCE: 661

```
ccataacccg ccatctgcgc gggttctaga ccccttctc ctccctctg gccgtggtag       60 gcattactga tgaatcatgg tgctcttct tccagagacc aaacctggcc tcggaatcct     120
tcttaacaca gatactgctt aacacaacca ctctgagcag ctgtcataag tagaagtaat    180
agatactaga agaaatgtmt aagcctaatc tagaccaaaa tacggcctga tatagatgca    240
agccagaggg gctttatggt taaatgcaag gagattttca accctgccgt ctagaagcta    300
cttgctgaga tcttcttcag ttgggcccat ctcctcccca ggcctctctt ctgttcctgg    360
gctatgtcac acttggactc tgcagacacc taatgc                              396
```

<210> SEQ ID NO 662
<211> LENGTH: 396
<212> TYPE: DNA
<213> ORGANISM: Homo sapiens

<400> SEQUENCE: 662

```
tggtaggcat tactgatgaa tcatggtgct ctttcttcca gagaccaaac ctggcctcgg     60
aatccttctt aacacagata ctgcttaaca caaccactct gagcagctgt cataagtaga    120
agtaatagat actagaagaa atgtctaagc ctaatctaga ccaaaatacg gcctgatata    180
gatgcaagcc agaggggckt tatggttaaa tgcaaggaga ttttcaaccc tgccgtctag    240
aagctacttg ctgagatctt cttcagttgg gcccatctcc tccccaggcc tctcttctgt    300
tcctgggcta tgtcacactt ggactctgca gacacctaat gctcttggga cctgctttag    360
ttcttgacct caccaaccga ggaggaattg ctagat                              396
```

<210> SEQ ID NO 663
<211> LENGTH: 396
<212> TYPE: DNA
<213> ORGANISM: Homo sapiens

<400> SEQUENCE: 663

```
cagagaccaa acctggcctc ggaatccttc ttaacacaga tactgcttaa cacaaccact     60
ctgagcagct gtcataagta gaagtaatag atactagaag aaatgtctaa gcctaatcta    120
gaccaaaata cggcctgata tagatgcaag ccagaggggc tttatggtta aatgcaagga    180
gattttcaac cctgccgtyt agaagctact tgctgagatc ttcttcagtt gggcccatct    240
cctccccagg cctctcttct gttcctgggc tatgtcacac ttggactctg cagacaccta    300
atgctcttgg gacctgcttt agttcttgac ctcaccaacc gaggaggaat tgctagatga    360
gatccttccc ccggaatttc tctcttgaac cccaga                              396
```

<210> SEQ ID NO 664
<211> LENGTH: 396

<210> SEQ ID NO 664
<211> LENGTH: 396
<212> TYPE: DNA
<213> ORGANISM: Homo sapiens

<400> SEQUENCE: 664

| | | | | | | |
|---|---|---|---|---|---|---|
| gggctttatg | gttaaatgca | aggagatttt | caaccctgcc | gtctagaagc | tacttgctga | 60 |
| gatcttcttc | agttgggccc | atctcctccc | caggcctctc | ttctgttcct | gggctatgtc | 120 |
| acacttggac | tctgcagaca | cctaatgctc | ttgggacctg | ctttagttct | tgacctcacc | 180 |
| aaccgaggag | gaattgctmg | atgagatcct | tcccccggaa | tttctctctt | gaaccccaga | 240 |
| tggtccgttg | ccccttttcca | gaagttgctc | cagccctgtc | cgcttaggaa | gttcagtgtc | 300 |
| atccttgatc | cagtgggtag | ggaagacatt | ccataatgaa | tgccccagtc | tgagcttctt | 360 |
| ccttcaggct | tcaggctgcc | ctgcgaggat | tttgca | | | 396 |

<210> SEQ ID NO 665
<211> LENGTH: 396
<212> TYPE: DNA
<213> ORGANISM: Homo sapiens

<400> SEQUENCE: 665

| | | | | | | |
|---|---|---|---|---|---|---|
| gtagctgaga | ctacaggtgt | gcactaccac | acccagctaa | ttttttgtat | ttttagtaga | 60 |
| gatagggttt | agctatgttg | gccaggctgg | tctcgaactg | ctgaactcaa | gcaatctgcc | 120 |
| atccccggcc | tcccaaagta | ctgggagtat | aggcataagc | cacccatgat | gcccagcctg | 180 |
| aatcttggtt | tcttccccrt | tcatttaagc | tattacctgg | gcctgaactc | aatggcacct | 240 |
| ggcaccaact | ggcaactgac | tcttggtctt | ttattaccta | ccttccctag | caggcactgg | 300 |
| gttgctccct | cttcctatcc | catggagtcc | tgtcctctgt | tggggctcct | actgatcctc | 360 |
| ttggcaatat | gaagttctca | gctcaatggt | gggtgg | | | 396 |

<210> SEQ ID NO 666
<211> LENGTH: 396
<212> TYPE: DNA
<213> ORGANISM: Homo sapiens

<400> SEQUENCE: 666

| | | | | | | |
|---|---|---|---|---|---|---|
| cccggcctcc | caaagtactg | ggagtatagg | cataagccac | ccatgatgcc | cagcctgaat | 60 |
| cttggtttct | tccccattca | tttaagctat | tacctgggcc | tgaactcaat | ggcacctggc | 120 |
| accaactggc | aactgactct | tggtctttta | ttacctacct | tccctagcag | gcactgggtt | 180 |
| gctccctctt | cctatcccrt | ggagtcctgt | cctctgttgg | ggctcctact | gatcctcttg | 240 |
| gcaatatgaa | gttctcagct | caatggtggg | tgggcaatga | ctgccaactc | ttgaggccaa | 300 |
| tgaactcagg | ttaccccact | cctcctcctc | ctgagttgct | cactcactcc | tcattcactc | 360 |
| aacattgatt | cagtagatat | ttgctacctg | ctctgt | | | 396 |

<210> SEQ ID NO 667
<211> LENGTH: 396
<212> TYPE: DNA
<213> ORGANISM: Homo sapiens

<400> SEQUENCE: 667

| | | | | | | |
|---|---|---|---|---|---|---|
| ccggcctccc | aaagtactgg | gagtataggc | ataagccacc | catgatgccc | agcctgaatc | 60 |
| ttggtttctt | ccccattcat | ttaagctatt | acctgggcct | gaactcaatg | gcacctggca | 120 |
| ccaactggca | actgactctt | ggtcttttat | acctacctt | ccctagcagg | cactgggttg | 180 |
| ctccctcttc | ctatcccayg | gagtcctgtc | ctctgttggg | gctcctactg | atcctcttgg | 240 |

```
caatatgaag ttctcagctc aatggtgggt gggcaatgac tgccaactct tgaggccaat        300
gaactcaggt taccccactc ctcctcctcc tgagttgctc actcactcct cattcactca        360
acattgattc agtagatatt tgctacctgc tctgtg                                   396
```

<210> SEQ ID NO 668
<211> LENGTH: 396
<212> TYPE: DNA
<213> ORGANISM: Homo sapiens

<400> SEQUENCE: 668

```
ggcataagcc acccatgatg cccagcctga atcttggttt cttccccatt catttaagct         60
attacctggg cctgaactca atggcacctg gcaccaactg gcaactgact cttggtcttt        120
tattacctac cttccctagc aggcactggg ttgctccctc ttcctatccc atggagtcct        180
gtcctctgtt ggggctccya ctgatcctct tggcaatatg aagttctcag ctcaatggtg        240
ggtgggcaat gactgccaac tcttgaggcc aatgaactca ggttacccca ctcctcctcc        300
tcctgagttg ctcactcact cctcattcac tcaacattga ttcagtagat atttgctacc        360
tgctctgtgc caggtaccag gtcagttgct gaagga                                   396
```

<210> SEQ ID NO 669
<211> LENGTH: 396
<212> TYPE: DNA
<213> ORGANISM: Homo sapiens

<400> SEQUENCE: 669

```
cctggcacca actggcaact gactcttggt cttttattac ctaccttccc tagcaggcac         60
tgggttgctc cctcttccta tcccatggag tcctgtcctc tgttggggct cctactgatc        120
ctcttggcaa tatgaagttc tcagctcaat ggtgggtggg caatgactgc caactcttga        180
ggccaatgaa ctcaggttwc cccactcctc ctcctcctga ttgctcact cactcctcat        240 tcactcaaca ttgattcagt agatatttgc tacctgctct gtgccaggta ccaggtcagt        300
tgctgaagga gtaacagtga acatgacgga gtctttgtcc caaggagac caaggtgtc         360 tcctagagcc aggggcacat tgcaagacca aatata                                   396
```

<210> SEQ ID NO 670
<211> LENGTH: 396
<212> TYPE: DNA
<213> ORGANISM: Homo sapiens

<400> SEQUENCE: 670

```
ctggcaactg actcttggtc ttttattacc taccttccct agcaggcact gggttgctcc         60
ctcttcctat cccatggagt cctgtcctct gttggggctc ctactgatcc tcttggcaat        120
atgaagttct cagctcaatg gtgggtgggc aatgactgcc aactcttgag gccaatgaac        180
tcaggttacc ccactcctyc tcctcctgag ttgctcactc actcctcatt cactcaacat        240
tgattcagta gatatttgct acctgctctg tgccaggtac caggtcagtt gctgaaggag        300
taacagtgaa catgacggag tctttgtccc aaggagacc caaggtgtct cctagagcca        360
ggggcacatt gcaagaccaa atatattcaa cttacc                                   396
```

<210> SEQ ID NO 671
<211> LENGTH: 396
<212> TYPE: DNA
<213> ORGANISM: Homo sapiens

<400> SEQUENCE: 671

```
ccatggagtc ctgtcctctg ttggggctcc tactgatcct cttggcaata tgaagttctc    60
agctcaatgg tgggtgggca atgactgcca actcttgagg ccaatgaact caggttaccc   120
cactcctcct cctcctgagt tgctcactca ctcctcattc actcaacatt gattcagtag   180
atatttgcta cctgctctrt gccaggtacc aggtcagttg ctgaaggagt aacagtgaac   240
atgacggagt ctttgtcccc aaggagaccc aaggtgtctc ctagagccag ggcacattg    300 caagaccaaa tatattcaac ttaccaaaat aatcatagac ctagttctca aaaagcaaga   360
agactgattc ctcgttgtca tttctcctcc tcagca                             396
```

<210> SEQ ID NO 672
<211> LENGTH: 396
<212> TYPE: DNA
<213> ORGANISM: Homo sapiens

<400> SEQUENCE: 672

```
ttagagtctg tgggcccctc caagtgtgga gtatggtgtt acttcaccag agtttgagga    60
gaaacattct tcttttggaa ggccggggag catagatgga tatcaaggct gctgtttcta   120
aaagcgaaac ccaccaaaca acagtattag aatcatctgt ggtgcttatt aaagatacag   180
attcctgggc ccatcccmg acttatgaat cagaatctct gccagaggaa gcctgagaat    240
ttgcattctc agatgattct gcattctcag ataacacatt ctttaggtga ttcttacaca   300
cactggagtt tgggaatcgc tgaaggctgt tcacttctct tttctgagaa atgattcatt   360
catttcagaa atatttgcag aggtccttat ttattg                             396
```

<210> SEQ ID NO 673
<211> LENGTH: 396
<212> TYPE: DNA
<213> ORGANISM: Homo sapiens

<400> SEQUENCE: 673

```
tggcctcatt cgtgtgataa atctgagcca ccacgatatt tgacttttca caatttaatt    60
tatctgaacc ctctattctc tggctaaaaa atatccctta cttggacttc tttattttat   120
tttcaattcc cttaccagca ctagcagggg actctgtact catctgctgg cgctgccata   180
acaaagcact gcagcctgkg gggctcaaac cacagaattt attctctcac agtcctagag   240
gctagaagtc caagatcaaa gtgtgggcag ggtcggtttc tcctgcagcc tctctccttg   300
gcttatagag tgccaccttc tacctgtgtc ttcacatcat cacctcactg agcatgtctg   360
tgtccaaatc tccccttctt ataagacccc agtcat                             396
```

<210> SEQ ID NO 674
<211> LENGTH: 396
<212> TYPE: DNA
<213> ORGANISM: Homo sapiens

<400> SEQUENCE: 674

```
tctccttggc ttatagagtg ccaccttcta cctgtgtctt cacatcatca cctcactgag    60
catgtctgtg tccaaatctc cccttcttat aagaccccag tcatactgga tgaggatcca   120
cccatatgag ttcattttac cttaattatc tcttttaaaca ccctgtctcc aaatacagtc   180
ccattctgag gaactgagrg taaagattca acatatgaat tttggaaggg acctaattca   240
gcccacaaca ccctcttttg ggatgtttat tttcccccctt aaggagctag ttaggatgtc   300
ttatctcatg aacatgactg tgaacaggaa aacagggaga gaatgaagct ggccaaggaa   360
```

```
cagggctggt gtcagctagc agtgcttttc tgatgt                               396
```

<210> SEQ ID NO 675
<211> LENGTH: 396
<212> TYPE: DNA
<213> ORGANISM: Homo sapiens

<400> SEQUENCE: 675

```
cattttacct taattatctc tttaaacacc ctgtctccaa atacagtccc attctgagga     60
actgagagta aagattcaac atatgaattt tggaagggac ctaattcagc ccacaacacc    120
ctcttttggg atgtttattt tccccttaa ggagctagtt aggatgtctt atctcatgaa    180
catgactgtg aacaggaara cagggagaga atgaagctgg ccaaggaaca gggctggtgt    240
cagctagcag tgcttttctg atgtgagtgg gtcccacagg gagcttgtta aaatgcagat    300
tctgattcat taggttccag agggacctga gatttcccat ttctgacaag tttccagtgt    360
gggggctgat gctgctggtc cacggaccat actttg                              396
```

<210> SEQ ID NO 676
<211> LENGTH: 396
<212> TYPE: DNA
<213> ORGANISM: Homo sapiens

<400> SEQUENCE: 676

```
gggagagaat gaagctggcc aaggaacagg gctggtgtca gctagcagtg cttttctgat     60
gtgagtgggt cccacaggga gcttgttaaa atgcagattc tgattcatta ggttccagag    120
ggacctgaga tttcccattt ctgacaagtt ccagtgtgg gggctgatgc tgctggtcca    180
cggaccatac tttgagtakc aaggagcttg atacataatg gctgagtgac tttcagactc    240
ctgctgtaga aaattatga gttggctggg cgtggtggct cacgcctgta atcccagcac    300
tttgggaggc cgaggtgggc agatcacctg aggtcaggag ttcgagacca gcctggccaa    360
catggtgaaa caccatctct accaaaaata caaaaa                              396
```

<210> SEQ ID NO 677
<211> LENGTH: 396
<212> TYPE: DNA
<213> ORGANISM: Homo sapiens

<400> SEQUENCE: 677

```
acttaagccc agaagactga ggttgcagtg agccgagatt gcaccactgc actccagctt     60
gggctacaga gtgagactct atctcaaaaa caaagaaaca acaacaaca ataacaacaa    120
aaaccaagtc tctccctcca ctcaaaaatg caagggcctg tctcccattg ctgggtgccc    180
aggtctcatg aatgtagaya tgaattattc cagtcagcct caggagaata gaatgagccc    240
tcagatgccg aagcaccttt cagattccac cggttttatc ggctcattta aacttcactt    300
ctaacacagt cctgcattac acacgtgtct gtcgttatgg gcagctgcag agagggtctt    360
aatggtccta atgctcagtg aggatgccca atggtc                              396
```

<210> SEQ ID NO 678
<211> LENGTH: 396
<212> TYPE: DNA
<213> ORGANISM: Homo sapiens

<400> SEQUENCE: 678

```
ctcaaaaaca aagaaacaaa caacaacaat aacaacaaaa accaagtctc tccctccact     60
caaaaatgca agggcctgtc tcccattgct gggtgcccag gtctcatgaa tgtagatatg    120
```

```
aattattcca gtcagcctca ggagaataga atgagccctc agatgccgaa gcacctttca    180
gattccaccg gttttatcrg ctcatttaaa cttcacttct aacacagtcc tgcattacac    240
acgtgtctgt cgttatgggc agctgcagag agggtcttaa tggtcctaat gctcagtgag    300
gatgcccaat ggtcaacaga acctgccatc ttcaggccat caaggagctc tggagttaag    360
gaaatcatga gagcacagag gggcgggtac agcaga                              396
```

<210> SEQ ID NO 679
<211> LENGTH: 396
<212> TYPE: DNA
<213> ORGANISM: Homo sapiens

<400> SEQUENCE: 679

```
tgtagatatg aattattcca gtcagcctca ggagaataga atgagccctc agatgccgaa    60
gcacctttca gattccaccg gttttatcgg ctcatttaaa cttcacttct aacacagtcc    120
tgcattacac acgtgtctgt cgttatgggc agctgcagag agggtcttaa tggtcctaat    180
gctcagtgag gatgcccart ggtcaacaga acctgccatc ttcaggccat caaggagctc    240
tggagttaag gaaatcatga gagcacagag gggcgggtac agcagagccc tcgtggtaat    300
gggttttgag gtctaggctc tcttcacttg ggttttgaaat aagttcaatg actagtaata    360
gctgagacac ttctacccctt caaatgaagt aaatgg                              396
```

<210> SEQ ID NO 680
<211> LENGTH: 396
<212> TYPE: DNA
<213> ORGANISM: Homo sapiens

<400> SEQUENCE: 680

```
agcaccttc agattccacc ggttttatcg gctcatttaa acttcacttc taacacagtc     60
ctgcattaca cacgtgtctg tcgttatggg cagctgcaga gagggtctta atggtcctaa    120
tgctcagtga ggatgcccaa tggtcaacag aacctgccat cttcaggcca tcaaggagct    180
ctggagttaa ggaaatcawg agagcacaga ggggcgggta cagcagagcc ctcgtggtaa    240
tgggttttga ggtctaggct ctcttcactt gggtttgaaa taagttcaat gactagtaat    300
agctgagaca cttctacccct tcaaatgaag taaatgggaa aatggagcat tgttgagtcc    360
agggagctat aatttaaacc ccatatatct aaaagg                               396
```

<210> SEQ ID NO 681
<211> LENGTH: 396
<212> TYPE: DNA
<213> ORGANISM: Homo sapiens

<400> SEQUENCE: 681

```
cacacgtgtc tgtcgttatg gcagctgca gagagggtct taatggtcct aatgctcagt     60
gaggatgccc aatggtcaac agaacctgcc atcttcaggc catcaaggag ctctggagtt    120
aaggaaatca tgagagcaca gaggggcggg tacagcagag ccctcgtggt aatgggtttt    180
gaggtctagg ctctcttcrc ttgggtttga aataagttca atgactagta atagctgaga    240
cacttctacc cttcaaatga agtaaatggg aaaatggagc attgttgagt ccagggagct    300
ataatttaaa ccccatatat ctaaaagggg taacattttt gtgtgtgtga aattggtgtc    360
attcgcactg catctacagt tttcttttc cttctc                                396
```

<210> SEQ ID NO 682

<211> LENGTH: 396
<212> TYPE: DNA
<213> ORGANISM: Homo sapiens

<400> SEQUENCE: 682

```
acatatttgg gaaacgcatc atactcttcc tgttcctcat gtccgttgct ggcatattca      60
actattacct catcttcttt ttcggaagtg actttgaaaa ctacataaag acgatctcca     120
ccaccatctc ccctctactt ctcattccct aactctctgc tgaatatggg gttggtgttc     180
tcatctaatc aatacctaya agtcatcata attcagctct tgagagcatt ctgctcttct     240
ttagatggct gtaaatctat tggccatctg gcttcacag cttgagttaa ccttgctttt      300
ccgggaacaa aatgatgtca tgtcagctcc gcccttgaa catgaccgtg gccccaaatt      360
tgctattccc atgcattttg tttgtttctt cactta                               396
```

<210> SEQ ID NO 683
<211> LENGTH: 396
<212> TYPE: DNA
<213> ORGANISM: Homo sapiens

<400> SEQUENCE: 683

```
tggtgttctc atctaatcaa tacctacaag tcatcataat tcagctcttg agagcattct      60
gctcttcttt agatggctgt aaatctattg ccatctggg cttcacagct tgagttaacc     120
ttgctttttcc gggaacaaaa tgatgtcatg tcagctccgc ccttgaaca tgaccgtggc      180
cccaaatttg ctattcccrt gcattttgtt tgtttcttca cttatcctgt tctctgaaga     240
tgttttgtga ccaggtttgt gttttcttaa aataaaatgc agagacatgt tttaagctga     300
tagttgaggg gttttgttaa tggcttttgg gggatttatc tctataccca caaacgacta     360
gtttgttttc ctcaaactaa atgataatat taaaaa                               396
```

<210> SEQ ID NO 684
<211> LENGTH: 396
<212> TYPE: DNA
<213> ORGANISM: Homo sapiens

<400> SEQUENCE: 684

```
ttatctctat acccacaaac gactagtttg ttttcctcaa actaaatgat aatattaaaa      60
atacacatcc tggccaggtg tggtggctca tacctgtaat cccagcactt tgggaggccg     120
aggcaggtgg atcacttgag gtcaggaatt aagaccagcc tggccaatat ggtgaaagcc     180
tgtctgtact aaaaatacra aaattagcca ggtatgctgg tggatgctta taatcccagc     240
tacttgggag gttgaggcag gagaattgct tgaacccggg aggtagaggt tgcagtgagc     300
caagatcatg ccactgcact ccagcttggg caacagagtg agactccatc tcaaattaaa     360
aaaaatacac atctggcttc tggaaaaatt acttga                               396
```

<210> SEQ ID NO 685
<211> LENGTH: 396
<212> TYPE: DNA
<213> ORGANISM: Homo sapiens

<400> SEQUENCE: 685

```
gatcatgcca ctgcactcca gcttgggcaa cagagtgaga ctccatctca aattaaaaaa      60
aatacacatc tggcttctgg aaaaattact tgaagatctt ttatgacatc catccctctt     120
cacacagcca tgtgaattag gttggtatct tcatatacta gcatcgtgcc cagcacttcc     180
atgttataca gtttaaaakg ttctgtaatt ccctgtggga acctaagata atgcgaggac     240
```

```
cgtcatacgt gcccccaaat attggcaaac caatgaataa atgaatgaat gagtttatga     300
atcgctaact ggctgtattt aatgaagtat gtgtgttgag ccatttccca cagtgtggac     360
agatttgtcc cacaatatgg gcctcttccc aaaggc                               396

<210> SEQ ID NO 686
<211> LENGTH: 396
<212> TYPE: DNA
<213> ORGANISM: Homo sapiens

<400> SEQUENCE: 686
aattaaaaaa aatacacatc tggcttctgg aaaaattact tgaagatctt ttatgacatc     60
catccctctt cacacagcca tgtgaattag gttggtatct tcatatacta gcatcgtgcc     120
cagcacttcc atgttataca gtttaaaatg ttctgtaatt ccctgtggga acctaagata     180
atgcgaggac cgtcatacrt gcccccaaat attggcaaac caatgaataa atgaatgaat     240
gagtttatga atcgctaact ggctgtattt aatgaagtat gtgtgttgag ccatttccca     300
cagtgtggac agatttgtcc cacaatatgg gcctcttccc aaaggcccta ccacctaatg     360
ccatcacact ggggatttga tttcaacatg tgaatt                               396

<210> SEQ ID NO 687
<211> LENGTH: 396
<212> TYPE: DNA
<213> ORGANISM: Homo sapiens

<400> SEQUENCE: 687
agttcatagt gacagtgatc cagccactgt catgacaggt gccacttggc agaaacagca     60
cagcttggaa gatggcgggg tgtagtcaag attccaggat ccccaacaga gaagccagct     120
cttatagggg agccattcat caggattgaa ctctcaatcg agctggacag taataggtgg     180
gtctgtgtta ttccccagrt gagtatcatg acagtcacaa tcctaggaag gatgtgaagc     240
ctcccccagc tctcctccag ttgcctgctt gggcagcaga gatgatggaa tgtggagtct     300
ggcgtggtct gaggcctgaa tccatgtgcc tcatgtatga tgctcaggca agaggatctc     360
tcaattcaag ggagagggcc tgaatgagcc ttgctt                               396

<210> SEQ ID NO 688
<211> LENGTH: 396
<212> TYPE: DNA
<213> ORGANISM: Homo sapiens

<400> SEQUENCE: 688
cttggcagaa acagcacagc ttggaagatg gcggggtgta gtcaagattc aggatcccc      60 aacagagaag ccagctctta tagggagcc attcatcagg attgaactct caatcgagct      120
ggacagtaat aggtgggtct gtgttattcc ccagatgagt atcatgacag tcacaatcct      180
aggaaggatg tgaagcctyc cccagctctc ctccagttgc ctgcttgggc agcagagatg     240
atggaatgtg gagtctggcg tggtctgagg cctgaatcca tgtgcctcat gtatgatgct     300
caggcaagag gatctctcaa ttcaagggag agggcctgaa tgagccttgc tttccaggcc     360
tgtctgatgg tccaggctga agcccctcct ggcttg                               396

<210> SEQ ID NO 689
<211> LENGTH: 396
<212> TYPE: DNA
<213> ORGANISM: Homo sapiens
```

<400> SEQUENCE: 689

```
ctggcgtggt ctgaggcctg aatccatgtg cctcatgtat gatgctcagg caagaggatc      60
tctcaattca agggagaggg cctgaatgag ccttgctttc caggcctgtc tgatggtcca     120
ggctgaagcc cctcctggct tgcactgcca gacctcatcc agcaggagct ccttggcatt     180
gactgcttca ggatagttsc ttctgctctg agtgctctct aaagagcagt gctctaccat     240
ccaagctggg ctttctcttt cttcttgctg atagggaagg catgggacat tgcaggatgg     300
aagtggcccc caggccttct catgcctggg cttggtttgg aaggtggtca ggtgatcaat     360
aatcctgatt ggcctggcat tgaggagttt tcctgg                               396
```

<210> SEQ ID NO 690
<211> LENGTH: 396
<212> TYPE: DNA
<213> ORGANISM: Homo sapiens

<400> SEQUENCE: 690

```
tgctctctaa agagcagtgc tctaccatcc aagctgggct tttcttttct tcttgctgat      60
agggaaggca tggacattg caggatggaa gtggccccca ggccttctca tgcctgggct     120
tggtttggaa ggtggtcagg tgatcaataa tcctgattgg cctggcattg aggagttttc     180
ctgggatgtg gtcctttcrg ttttttaaaa attattttta ttgatacaca tatttgtagg     240
tatttgtggg gtgcatgtga tactttatta tgtgtgtgga ttgtgtaatg atgaagtcag     300
ggcatttagg gtcttcatca ccttgattat catttctatg tgttgagaac atttcaagtt     360
ctcagttcca gctatttga aatagacagt ccattt                                396
```

<210> SEQ ID NO 691
<211> LENGTH: 396
<212> TYPE: DNA
<213> ORGANISM: Homo sapiens

<400> SEQUENCE: 691

```
gatactttat tatgtgtgtg gattgtgtaa tgatgaagtc agggcattta gggtcttcat      60
caccttgatt atcatttcta tgtgttgaga catttcaag ttctcagttc cagctatttt     120
gaaatagaca gtccattttg ttagctacag tcacccaacc cggctgtcag acattggaac     180
ttactcctat tgaactgtrt atttgtaccc attccaaaa ctctctttgg gctttcagtt     240
ttacaactgg gatgatcctg ggaaaactaa agtaaatcag acacccgacg tgtgagctag     300
gttataatat gcccagtgga ccctggggac atcttagctt tcagaggtca tgctgtccaa     360
gctgactgtg gggcttccag aaggtgggga gaggaa                               396
```

<210> SEQ ID NO 692
<211> LENGTH: 396
<212> TYPE: DNA
<213> ORGANISM: Homo sapiens

<400> SEQUENCE: 692

```
tatgtgtgtg gattgtgtaa tgatgaagtc agggcattta gggtcttcat caccttgatt      60
atcatttcta tgtgttgaga catttcaag ttctcagttc cagctatttt gaaatagaca     120
gtccattttg ttagctacag tcacccaacc cggctgtcag acattggaac ttactcctat     180
tgaactgtgt atttgtacyc attccaaaa ctctctttgg gctttcagtt ttacaactgg     240
gatgatcctg ggaaaactaa agtaaatcag acacccgacg tgtgagctag gttataatat     300
gcccagtgga ccctggggac atcttagctt tcagaggtca tgctgtccaa gctgactgtg     360
```

```
gggcttccag aaggtgggga gaggaaatga tgcaat                                  396
```

<210> SEQ ID NO 693
<211> LENGTH: 396
<212> TYPE: DNA
<213> ORGANISM: Homo sapiens

<400> SEQUENCE: 693

```
tgggaaaact aaagtaaatc agacacccga cgtgtgagct aggttataat atgcccagtg         60
gaccctgggg acatcttagc tttcagaggt catgctgtcc aagctgactg tggggcttcc        120
agaaggtggg gagaggaaat gatgcaatgg cccatcagag gcactacttg gggcctgggg        180
ccagagtgca tgtctaagsc attaagggga ggggagagca gccttcataa ttatgaagag        240
gagtctcagg tgcacagctt ctgatgaggg acagcttcta attgaagaca gcattgtgta        300
atgctcaaac tccctgtctt cagagtgcct gctgtatccc accatcagtt ctgtgacttc        360
tccctaagcc tcaattttgc atgtgttaca ttggga                                  396
```

<210> SEQ ID NO 694
<211> LENGTH: 396
<212> TYPE: DNA
<213> ORGANISM: Homo sapiens

<400> SEQUENCE: 694

```
cctgcatagc aaattcttgc aaatgtaggg actcaaaaca atataaattt attatctgac         60
agttttctg ggtcagaggt cttactaggc tgtaatcaga gggcaaccaa agctgtgatc        120
tcagctgaag ctcaggattc tcttccaagc tcactggttg ttggcagaat tcagttcttt        180
ccagttggaa gactaaagyc tacagtcttc agtctctaga agccttttct ctggcacagg        240
tttctctaca acatggccat ttatgtcttt aaggccaata ggagaacatg attagcatat        300
tttttttaag tgaactttag acccttttt aaaggcctat ctgattaggc caggcccaag        360
tgagctttaa gtcaactgat tagagatctt aattac                                  396
```

<210> SEQ ID NO 695
<211> LENGTH: 396
<212> TYPE: DNA
<213> ORGANISM: Homo sapiens

<400> SEQUENCE: 695

```
ctgaagctca ggattctctt ccaagctcac tggttgttgg cagaattcag ttctttccag         60
ttggaagact aaagcctaca gtcttcagtc tctagaagcc ttttctctgg cacaggtttc        120
tctacaacat ggccatttat gtctttaagg ccaataggag aacatgatta gcatattttt        180
tttaagtgaa ctttagacyc tttttaaag gcctatctga ttaggccagg cccaagtgag        240
ctttaagtca actgattaga gatcttaatt acatctgcaa agtcccttca tgtttaccgt        300
ataacataac ttagtgaaag gagtgaaatt gcaaccaggt tctgcctgca ctccacggaa        360
ggggattctg cagaagtgtg ggtcacgggg gggtta                                  396
```

<210> SEQ ID NO 696
<211> LENGTH: 396
<212> TYPE: DNA
<213> ORGANISM: Homo sapiens

<400> SEQUENCE: 696

```
agaacatgat tagcatattt tttttaagtg aactttagac ccttttttaa aggcctatct         60
```

```
gattaggcca ggcccaagtg agctttaagt caactgatta gagatcttaa ttacatctgc        120
aaagtccctt catgtttacc gtataacata acttagtgaa aggagtgaaa ttgcaaccag        180
gttctgcctg cactccacrg aaggggattc tgcagaagtg tgggtcacgg ggggttatt         240 ttgggattct gcctacgtca ctgagtcaaa agaagctgaa tggttgtgat gctgaggttt        300
ttgggcagca gcagtgtgtg tgtgtgagtg aattcatacg tatgaccacc tgggaagaaa        360
ggaggctgtg gtttcctcca cctcctggca gacaga                                  396

<210> SEQ ID NO 697
<211> LENGTH: 396
<212> TYPE: DNA
<213> ORGANISM: Homo sapiens

<400> SEQUENCE: 697
gggattacag acacacactg ccacgcctgg ctaattttg tattttagt agagacgagg            60 ttttgccatg ttggccaggc tggtcttgaa ctcctgacct caagtgatcc gcccacctca        120
gcctcccaaa gtgctgggat tacagacgtg agccaccatt aaccatttt ctatctcctg         180 tgggaaaggg cacagtgara gaacagatga agctgagaca tacaagtgaa ctcctccctc        240
ctctccattt agactaaaat aggattattc atactgagat tctccctggt tgcaaagaga        300
taatctgtgc aactgggttt ttacaattat ccctaccctat gctttcctc atctgtcttc        360 ctcgtagtca gctcaggctg ctataacaaa acacca                                  396

<210> SEQ ID NO 698
<211> LENGTH: 396
<212> TYPE: DNA
<213> ORGANISM: Homo sapiens

<400> SEQUENCE: 698
ggcagattcg gtgtctaatg aggtcctgct ttccagttta tagacagtgc cttatcgcta         60
ccgccttaca cagtggaagg agaggacgag aagctccttg ggcttttttt tgtttctttc        120
tttctctctc tctctctttt tttttttttt aataaggtca ctatcttagt ccattttgtg        180
ttgctaaaag gaacatctra ggttgagtaa tttatttat tttaaaagt ggccaggcat          240 ggaggcttat cctgtaaccc taatccttta ggaggccaaa acagcaggat tgtttgaggc        300
caggagttca agaccagcct aggcaagata gtgagacccc atctacccca tctctactaa        360
aattttaaaa aattagctgt gtgttgtaaa gtgtgc                                  396

<210> SEQ ID NO 699
<211> LENGTH: 396
<212> TYPE: DNA
<213> ORGANISM: Homo sapiens

<400> SEQUENCE: 699
aatttatttt attttaaaaa gtggccaggc atggaggctt atcctgtaac cctaatcctt         60
taggaggcca aaacagcagg attgtttgag gccaggagtt caagaccagc ctaggcaaga        120
tagtgagacc ccatctaccc catctctact aaaattttaa aaaattagct gtgtgttgta        180
aagtgtgctt gtagtcccrg ccacttgaga ggctgaggtg ggtggagttc aaggctgcag        240
tgagttatga ttgagccact gcactccaac ccgggtaacg gggcaagacc ttgtctctat        300
ttaaaaaaaa aaaatcttta tgtggctcac tattctgggt ggctggaaag ttcaagattg        360
ggcatctgca tctggtgaca gcctcatgtc gcttcc                                  396
```

<210> SEQ ID NO 700
<211> LENGTH: 396
<212> TYPE: DNA
<213> ORGANISM: Homo sapiens

<400> SEQUENCE: 700

```
taaccctaat cctttaggag gccaaaacag caggattgtt tgaggccagg agttcaagac      60
cagcctaggc aagatagtga accccatct accccatctc tactaaaatt ttaaaaaatt     120
agctgtgtgt tgtaaagtgt gcttgtagtc ccggccactt gagaggctga ggtgggtgga    180
gttcaaggct gcagtgagwt atgattgagc cactgcactc caacccgggt aacgggcaa     240
gaccttgtct ctatttaaaa aaaaaaaatc tttatgtggc tcactattct gggtggctgg    300
aaagttcaag attgggcatc tgcatctggt gacagcctca tgtcgcttcc agtcatgggg    360
gaagacgaag gagagctggc acgtgcagat atcacg                              396
```

<210> SEQ ID NO 701
<211> LENGTH: 396
<212> TYPE: DNA
<213> ORGANISM: Homo sapiens

<400> SEQUENCE: 701

```
atcctttagg aggccaaaac agcaggattg tttgaggcca ggagttcaag accagcctag     60
gcaagatagt gagaccccat ctaccccatc tctactaaaa ttttaaaaaa ttagctgtgt    120
gttgtaaagt gtgcttgtag tcccggccac ttgagaggct gaggtgggtg gagttcaagg    180
ctgcagtgag ttatgattra gccactgcac tccaacccgg gtaacggggc aagaccttgt    240
ctctatttaa aaaaaaaaaa tctttatgtg gctcactatt ctgggtggct ggaaagttca    300
agattgggca tctgcatctg gtgacagcct catgtcgctt ccagtcatgg gggaagacga    360
aggagagctg gcacgtgcag atatcacgtg ttgagg                              396
```

<210> SEQ ID NO 702
<211> LENGTH: 396
<212> TYPE: DNA
<213> ORGANISM: Homo sapiens

<400> SEQUENCE: 702

```
ttaaaaaatt agctgtgtgt tgtaaagtgt gcttgtagtc ccggccactt gagaggctga     60
ggtgggtgga gttcaaggct gcagtgagtt atgattgagc cactgcactc caacccgggt    120
aacgggcaa gaccttgtct ctatttaaaa aaaaaaatc tttatgtggc tcactattct     180
gggtggctgg aaagttcarg attgggcatc tgcatctggt gacagcctca tgtcgcttcc    240
agtcatgggg gaagacgaag gagagctggc acgtgcagat atcacgtgtt gagggcagaa    300
gcgagagaga gagggggagag atgccaggct cttttttaaca accagcactg gggaaactaa    360
tagagtgaga gctcactgac tcctgaggga ggacat                              396
```

<210> SEQ ID NO 703
<211> LENGTH: 396
<212> TYPE: DNA
<213> ORGANISM: Homo sapiens

<400> SEQUENCE: 703

```
atgggggaag acgaaggaga gctggcacgt gcagatatca cgtgttgagg gcagaagcga     60
gagagagagg ggagagatgc caggctcttt ttaacaacca gcactgggga aactaataga    120
gtgagagctc actgactcct gagggaggac attaatctat tgatgagcga cctgcctcca    180
```

```
tgacccaaac acctccaayg ataccccacc tccaacactg ccacactagg gattaacttt      240
caacttgaga tttagagggg ggaaacttac aaactatcgc aggcactaat accactcatg      300
agggctccac cttcatgacc taatcacttc ctaaaggcct tacctcttaa tctcatcaca      360
ttgaggattc gatttcaact tgaattttgg ggggac                                396

<210> SEQ ID NO 704
<211> LENGTH: 396
<212> TYPE: DNA
<213> ORGANISM: Homo sapiens

<400> SEQUENCE: 704
ctcgctgcca cctgaaatta gatcatttat ttaccccttt atttgttcag tttgccttgt      60
ccgttagaat ataagcttcc aaagggcagg agctttgcct atattgttag gccgggcata     120
caatgagcac tcaaaaaaat atttgatgag tgtatgaaag aacagactgg gttatgtaat     180
tgtgcctact tacctatayg accgtgtggt ggggtttatg gtgggtgtgg tggtgatggc     240
tatagggcta taagcaaatt tgggacaggg agtctaagaa atgttcttaa attttagtaa     300
gcaaagcatc tctacagaaa cctgtcttaa aacatgaaag ttccttagtg ctaccccag      360 aggtatgatt tggtaggtca aggatagggc ctggaa                               396

<210> SEQ ID NO 705
<211> LENGTH: 396
<212> TYPE: DNA
<213> ORGANISM: Homo sapiens

<400> SEQUENCE: 705
tgccacctga aattagatca tttatttacc cctttatttg ttcagtttgc cttgtccgtt      60
agaatataag cttccaaagg gcaggagctt tgcctatatt gttaggccgg gcatacaatg     120
agcactcaaa aaatatttg atgagtgtat gaaagaacag actgggttat gtaattgtgc      180
ctacttacct atatgaccrt gtggtggggt ttatggtggg tgtggtggtg atggctatag     240
ggctataagc aaatttggga cagggagtct aagaaatgtt cttaaatttt agtaagcaaa     300
gcatcctcta cagaacctgt cttaaaacat gaaagttcct tagtgctacc cccagaggta     360
tgatttggta ggtcaaggat agggcctgga aattca                               396

<210> SEQ ID NO 706
<211> LENGTH: 396
<212> TYPE: DNA
<213> ORGANISM: Homo sapiens

<400> SEQUENCE: 706
cctgtcttaa aacatgaaag ttccttagtg ctaccccag aggtatgatt tggtaggtca       60
aggatagggc ctggaaattc acattcttgt taagatgttc ttcatccggg gtttgttgac     120 cacctttttca gaagattttt gctctgtagc tgtactaccc aatgcagtag ttcgtagtca    180
gtgtggctcc tgagccctyg aagtgtagct cctctgaact gagacgtgct gtaaatgtaa    240
attgcacacc ggagtttgaa gagttaatac aaagaaaaag gaatgcaaaa catctcatta    300
ataatgcttt acactgatta catattgaaa tggtaatctt gtagatatag tgcgttaaat    360
aaaatatact gttaggctta atttcacgtc tttata                               396

<210> SEQ ID NO 707
<211> LENGTH: 396
<212> TYPE: DNA
<213> ORGANISM: Homo sapiens
```

<400> SEQUENCE: 707

```
tcagccaatc aacaagaggg caaaagaaca aacatttgat gtgtaattac ttaatttagt      60
gcatatgcat ttgggtcctc aatgtcagca ctatggcaac cagaacatgg ccacaataac     120
tgtctggaaa tgtctattct tacctggacc cagcaggcca tgccccactg attatataat     180
ctccctctct ccttgttayg gtctgaatgc ttgcatccct caaaaattca tgtgttgaaa     240
tcctaacccc caaggtgatg atattaggag gtcggccttt tgagaggtaa ttaggtcatg     300
aagacagcat cctcatgaat gggattagtg tccttataaa ataggcccaa gggagctcat     360
tcactttgtc caccatgtga gaacacagcg agaggg                               396
```

<210> SEQ ID NO 708
<211> LENGTH: 396
<212> TYPE: DNA
<213> ORGANISM: Homo sapiens

<400> SEQUENCE: 708

```
ccttgttacg gtctgaatgc ttgcatccct caaaaattca tgtgttgaaa tcctaacccc      60
caaggtgatg atattaggag gtcggccttt tgagaggtaa ttaggtcatg aagacagcat     120
cctcatgaat gggattagtg tccttataaa ataggcccaa gggagctcat tcactttgtc     180
caccatgtga gaacacagyg agaggcacc atttatgcac caggaaatgg ccttttcca       240
gacaatctgt cggtgcctgg atcttggact tcacagcctc tagaactgtg agaaattaat     300
ttgttttta taagccacca aatctatggt ttttttata gaaaccgtaa tggactaaaa       360
cactccctaa ttatatttaa acttatcagt gcactg                               396
```

<210> SEQ ID NO 709
<211> LENGTH: 396
<212> TYPE: DNA
<213> ORGANISM: Homo sapiens

<400> SEQUENCE: 709

```
ctaaccccca aggtgatgat attaggaggt cggccttttg agaggtaatt aggtcatgaa      60
gacagcatcc tcatgaatgg gattagtgtc cttataaaat aggcccaagg gagctcattc     120
actttgtcca ccatgtgaga acacagcgag agggcaccat ttatgcacca ggaaatgggc     180
cttttccaga caatctgtyg gtgcctggat cttggacttc acagcctcta gaactgtgag     240
aaattaattt gttttttata agccaccaaa tctatggttt ttttataga aaccgtaatg      300
gactaaaaca ctccctaatt atatttaaac ttatcagtgc actgggcagt gacatattaa     360
aagaatgctg gccaacgtaa ttgacaccat aaggct                               396
```

<210> SEQ ID NO 710
<211> LENGTH: 396
<212> TYPE: DNA
<213> ORGANISM: Homo sapiens

<400> SEQUENCE: 710

```
tcatctcatt ttaacctttt gtttcaaagc ctctcttttc atgacttccc cgccttcatt      60
tttcccatat ggtggggtta ttattaagac attaaatgag agtggacagg taggcaaagg     120
aggtgggttg caggggagtt gagggttgcc tgtgtacttt tctagactgt tccacttcac     180
atcagtgaaa tattcccart tgatactatc atgaaacaaa gcaatgaaa tgctgagcac      240
ggagcttcgt cttgatgaaa tgctgaaaga aagaaagga aaaataaagt agccattatt      300
```

```
tttgcccttc ctcccacccc catgtttact actcttattt ctcttttgta ttgttgtgtt    360
ggaagcacag catcagaaaa actcccagtt ttgaga                              396
```

<210> SEQ ID NO 711
<211> LENGTH: 396
<212> TYPE: DNA
<213> ORGANISM: Homo sapiens

<400> SEQUENCE: 711

```
acaggtaggc aaaggaggtg ggttgcaggg gagttgaggg ttgcctgtgt acttttctag     60
actgttccac ttcacatcag tgaaatattc ccaattgata ctatcatgaa acaaagcaaa    120
tgaaatgctg agcacggagc ttcgtcttga tgaaatgctg aaagaaaaga aggaaaaat    180
aaagtagcca ttattttrc ccttcctccc accccatgt ttactactct tatttctctt    240
ttgtattgtt gtgttggaag cacagcatca gaaaaactcc cagttttgag agataactca    300
gtgtttagtt cacttaaacc tgagaaagga gaagaggatg ccaccgtgag gtccaggacg    360
taaagaggaa aaaacagac aaaaaaatcc atatga                              396
```

<210> SEQ ID NO 712
<211> LENGTH: 396
<212> TYPE: DNA
<213> ORGANISM: Homo sapiens

<400> SEQUENCE: 712

```
caggtaggca aaggaggtgg gttgcagggg agttgagggt tgcctgtgta cttttctaga     60
ctgttccact tcacatcagt gaaatattcc caattgatac tatcatgaaa caaagcaaat    120
gaaatgctga gcacggagct tcgtcttgat gaaatgctga aagaaagaa aggaaaata    180
aagtagccat tattttgmc cttcctccca ccccatgtt tactactctt atttctcttt    240
tgtattgttg tgttggaagc acagcatcag aaaaactccc agttttgaga gataactcag    300
tgtttagttc acttaaacct gagaaggag aagaggatgc caccgtgagg tccaggacgt    360
aaagaggaaa aaacagaca aaaaaatcca tatgaa                              396
```

<210> SEQ ID NO 713
<211> LENGTH: 396
<212> TYPE: DNA
<213> ORGANISM: Homo sapiens

<400> SEQUENCE: 713

```
ttcgtcttga tgaaatgctg aaagaaaaga aggaaaaat aaagtagcca ttattttgc     60
ccttcctccc accccatgt ttactactct tatttctctt ttgtattgtt gtgttggaag    120
cacagcatca gaaaaactcc cagttttgag agataactca gtgtttagtt cacttaaacc    180
tgagaaagga gaagaggayg ccaccgtgag gtccaggacg taaagaggaa aaaacagac    240
aaaaaaatcc atatgaaatg aaaatgtgaa agaggcgctt tcgagcagat gagtgttgta    300
gattacagtg ttgagagctg tttgtgtcca gagctgcttg ctgcacctgg cgggataaac    360
actggtctaa cagaggatcc ttgtttcaag gaggct                              396
```

<210> SEQ ID NO 714
<211> LENGTH: 396
<212> TYPE: DNA
<213> ORGANISM: Homo sapiens

<400> SEQUENCE: 714

```
aagaaaagaa aggaaaaata agtagccat tattttgcc cttcctccca ccccatgtt     60
```

```
tactactctt atttctcttt tgtattgttg tgttggaagc acagcatcag aaaaactccc    120
agttttgaga gataactcag tgtttagttc acttaaacct gagaaaggag aagaggatgc    180
caccgtgagg tccaggacrt aaagaggaaa aaaacagaca aaaaaatcca tatgaaatga    240
aaatgtgaaa gaggcgcttt cgagcagatg agtgttgtag attacagtgt tgagagctgt    300
ttgtgtccag agctgcttgc tgcacctggc gggataaaca ctggtctaac agaggatcct    360
tgtttcaagg aggctgcctt ttatttgggg ggacaa                              396
```

<210> SEQ ID NO 715
<211> LENGTH: 396
<212> TYPE: DNA
<213> ORGANISM: Homo sapiens

<400> SEQUENCE: 715

```
attattttg cccttcctcc caccccatg tttactactc ttatttctct tttgtattgt       60
tgtgttggaa gcacagcatc agaaaaactc ccagttttga gagataactc agtgtttagt    120
tcacttaaac ctgagaaagg agaagaggat gccaccgtga ggtccaggac gtaaagagga    180
aaaaaacaga caaaaaaayc catatgaaat gaaaatgtga agaggcgct ttcgagcaga     240 tgagtgttgt agattacagt gttgagagct gtttgtgtcc agagctgctt gctgcacctg    300
gcgggataaa cactggtcta acagaggatc cttgtttcaa ggaggctgcc ttttatttgg    360
ggggacaaaa ttgttcttga agctgctca gtggtt                               396
```

<210> SEQ ID NO 716
<211> LENGTH: 396
<212> TYPE: DNA
<213> ORGANISM: Homo sapiens

<400> SEQUENCE: 716

```
tttgtattgt tgtgttggaa gcacagcatc agaaaaactc ccagttttga gagataactc     60
agtgtttagt tcacttaaac ctgagaaagg agaagaggat gccaccgtga ggtccaggac    120
gtaaagagga aaaaaacaga caaaaaaatc catatgaaat gaaaatgtga agaggcgct     180 ttcgagcaga tgagtgttrt agattacagt gttgagagct gtttgtgtcc agagctgctt    240
gctgcacctg gcgggataaa cactggtcta acagaggatc cttgtttcaa ggaggctgcc    300
ttttatttgg ggggacaaaa ttgttcttga agctgctca gtggttcaag ctacagcatg     360
gtggactagc agaatggact ccagggcctc cgagga                              396
```

<210> SEQ ID NO 717
<211> LENGTH: 396
<212> TYPE: DNA
<213> ORGANISM: Homo sapiens

<400> SEQUENCE: 717

```
ttttgagaga taactcagtg tttagttcac ttaaacctga gaaggagaa gaggatgcca      60 ccgtgaggtc caggacgtaa agaggaaaaa acagacaaa aaaatccata tgaaatgaaa    120
atgtgaaaga ggcgctttcg agcagatgag tgttgtagat tacagtgttg agagctgttt    180
gtgtccagag ctgcttgcyg cacctggcgg ataaacact ggtctaacag aggatccttg     240
tttcaaggag gctgcctttt atttgggggg acaaaattgt tcttgaaagc tgctcagtgg    300
ttcaagctac agcatggtgg actagcagaa tggactccag gcctccgag gagacagtga     360 ctgctgccag aaatagtcaa ggatagaaag gaagga                              396
```

USE OF 5-LIPOXYGENASE ACTIVATING PROTEIN (FLAP) GENE TO ASSESS SUSCEPTIBILITY FOR MYOCARDIAL INFARCTION

RELATED APPLICATION

This application is a continuation-in-part of U.S. application Ser. No. 10/769,542, filed on Jan. 30, 2004 now abandoned, which is a continuation-in-part of International Application No. PCT/US03/32805, which designated the United States and was filed on Oct. 16, 2003, published in English, which claims the benefit of U.S. Provisional Application No. 60/419,432, filed on Oct. 17, 2002. The entire teachings of the above applications are incorporated herein by reference.

BACKGROUND OF THE INVENTION

Myocardial infarction (MI) is one of the most common diagnoses in hospitalized patients in industrialized countries. Myocardial Infarction generally occurs when there is an abrupt decrease in coronary blood flow following a thrombotic occlusion of a coronary artery previously narrowed by atherosclerosis. Infarction occurs when a coronary artery thrombus develops rapidly at a site a vascular injury, which is produced or facilitated by factors such as cigarette smoking, hypertension and lipid accumulation. In most cases, infarction occurs when an atherosclerotic plaque fissures, ruptures or ulcerates and when conditions favor thrombogenesis. In rare cases, infarction may be due to coronary artery occlusion caused by coronary emboli, congenital abnormalities, coronary spasm, and a wide variety of systemic, particularly inflammatory diseases.

Although classical risk factors such as smoking, hyperlipidemia, hypertension, and diabetes are associated with many cases of coronary heart disease (CHD) and MI, many patients do not have involvement of these risk factors. In fact, many patients who exhibit one or more of these risk factors do not develop MI. Family history has long been recognized as one of the major risk factors. Although some of the familial clustering of MI reflects the genetic contribution to the other conventional risk factors, a large number of studies have suggested that there are significant genetic susceptibility factors, beyond those of the known risk factors (Friedlander Y, et al., Br Heart J. 1985; 53:382-7, Shea S. et al., J. Am. Coll. Cardiol. 1984; 4:793-801, and Hopkins P. N., et al., Am. J. Cardiol. 1988; 62:703-7). Major genetic susceptibility factors have not yet been identified.

SUMMARY OF THE INVENTION

As described herein, a locus on chromosome 13q12-13 has been identified as playing a major role in Myocardial Infarction (MI). The locus, herein after referred to as the MI locus, comprises nucleic acid that encodes 5-lipoxygenase activating protein (ALOX5AP or FLAP), herein after referred to as FLAP. The gene has also been shown to play a role in stroke.

The present invention relates to isolated nucleic acid molecules comprising a portion or the entire human FLAP nucleic acid or a variant thereof. In one embodiment, the nucleic acid molecule has at least one polymorphism that is correlated with the incidence of myocardial infarction or stroke. Identification of nucleic acids and polymorphisms in this locus can pave the way for a better understanding of the disease process, which in turn can lead to improved diagnostic and therapeutic methods.

The invention further pertains to methods of diagnosing a susceptibility to myocardial infarction or stroke, comprising detecting an alteration in the expression or composition of a polypeptide encoded by a FLAP nucleic acid in a test sample, in comparison with the expression or composition of a polypeptide encoded by FLAP in a control sample, wherein the presence of an alteration in expression or composition of the polypeptide in the test sample is indicative of a susceptibility to myocardial infarction or stroke.

The invention also relates to an isolated nucleic acid molecule comprising a FLAP nucleic acid, wherein the FLAP nucleic acid has a nucleic acid sequence of SEQ ID NO: 1 or SEQ ID NO: 3, or the complement of SEQ ID NO: 1 or SEQ ID NO: 3, wherein the nucleic acid molecule comprises a polymorphism as indicated in Table 13.

In another embodiment, the invention relates to an isolated nucleic acid molecule having a polymorphism as indicated in Table 13, which hybridizes under high stringency conditions to a nucleic acid sequence of SEQ ID NO: 1 or SEQ ID NO: 3, or the complement of SEQ ID NO: 1 or SEQ ID NO: 3.

In yet another embodiment, a method for assaying for the presence of a first nucleic acid molecule in a sample is described, comprising contacting said sample with a second nucleic acid molecule, where the second nucleic acid molecule comprises a nucleic acid sequence of SEQ ID NO: 1 or SEQ ID NO: 3, and hybridizes to the first nucleic acid under high stringency conditions.

The invention also relates to a vector comprising an isolated nucleic acid molecule of the invention operably linked to a regulatory sequence, as well as to a recombinant host cell comprising the vector. The invention also provides a method for preparing a polypeptide encoded by an isolated nucleic acid molecule comprising culturing the recombinant host cell under conditions suitable for expression of said nucleic acid molecule.

Also contemplated by the invention is a method of assaying a sample for the presence of a polypeptide encoded by an isolated nucleic acid molecule of the invention, comprising contacting the sample with an antibody that specifically binds to the polypeptide.

The invention further provides a method of identifying an agent that alters expression of a FLAP nucleic acid, comprising: contacting a solution containing a nucleic acid comprising the promoter region of the FLAP nucleic acid operably linked to a reporter gene with an agent to be tested; assessing the level of expression of the reporter gene; and comparing the level of expression with a level of expression of the reporter gene in the absence of the agent; wherein if the level of expression of the reporter gene in the presence of the agent differs, by an amount that is statistically significant, from the level of expression in the absence of the agent, then the agent is an agent that alters expression of the FLAP nucleic acid. An agent identified by this method is also contemplated.

The invention additionally comprises a method of identifying an agent that alters expression of a FLAP nucleic acid, in which a solution containing a nucleic acid described herein or a derivative or fragment thereof is contacted with an agent to be tested, and expression of the nucleic acid, derivative or fragment in the presence of the agent is assessed and compared with expression of the nucleic acid, derivative or fragment in the absence of the agent. If expression of the nucleic acid, derivative or fragment in the presence of the agent differs, by an amount that is statistically significant, from the expression in the absence of the agent, then the agent is an agent that alters expression of the FLAP nucleic acid. In certain embodiments, the expression of the nucleic acid, derivative or fragment in the presence of the agent comprises expression of one or more splicing variant(s) that differ in kind or in quantity from the expression of one or more splicing variant(s) the absence of the agent. Agents identified by this method are also contemplated. Representative agents include antisense nucleic acid to a FLAP nucleic acid; a FLAP polypeptide; a FLAP nucleic acid receptor; a FLAP nucleic acid binding agent; a peptidomimetic; a fusion protein; a prodrug thereof; an antibody; and a ribozyme. A method of altering expression of a FLAP nucleic acid comprising contacting a cell containing a FLAP nucleic acid with such an agent is also contemplated.

The invention further pertains to a method of identifying a polypeptide which interacts with a FLAP polypeptide, employing a yeast two-hybrid system that uses a first vector which comprises a nucleic acid encoding a DNA binding domain and a FLAP polypeptide, splicing variant, or a fragment or derivative thereof, and a second vector which comprises a nucleic acid encoding a transcription activation domain and a nucleic acid encoding a test polypeptide. If transcriptional activation occurs in the yeast two-hybrid system, the test polypeptide is a polypeptide which interacts with a FLAP polypeptide.

A transgenic animal comprising a nucleic acid of the invention such as an exogenous FLAP nucleic acid or a nucleic acid encoding a FLAP polypeptide is also contemplated.

In yet another embodiment, the invention relates to a method for assaying a sample for the presence of a FLAP nucleic acid, by contacting the sample with a nucleic acid comprising a contiguous nucleic acid sequence which is at least partially complementary to a part of the sequence of said FLAP nucleic acid, under conditions appropriate for hybridization, and assessing whether hybridization has occurred between a FLAP nucleic acid and said nucleic acid, wherein if hybridization has occurred, a FLAP nucleic acid is present in the nucleic acid. In certain embodiments, the contiguous nucleic acid sequence is completely complementary to a part of the sequence of said FLAP nucleic acid and in other embodiments; amplification is of at least part of said FLAP nucleic acid.

In certain embodiments, the contiguous nucleic acid sequence is 100 or fewer nucleotides in length and is either: a) at least 80% identical to a contiguous sequence of nucleotides of SEQ ID NO: 1 or SEQ ID NO: 3; b) at least 80% identical to the complement of a contiguous sequence of nucleotides in of SEQ ID NO: 1 or SEQ ID NO: 3; or c) capable of selectively hybridizing to said FLAP nucleic acid.

The invention also pertains to a reagent for assaying a sample for the presence of a FLAP nucleic acid, the reagent comprising a nucleic acid comprising a contiguous nucleic acid sequence which is at least partially complementary to a part of the nucleic acid sequence of said FLAP nucleic acid. The reagent can comprise a contiguous nucleotide sequence which is completely complementary to a part of the nucleic acid sequence of said FLAP nucleic acid. A reagent kit for assaying a sample for the presence of a FLAP nucleic acid is also described, including (e.g., in separate containers), one or more labeled nucleic acids comprising a contiguous nucleic acid sequence which is at least partially complementary to a part of the nucleic acid sequence of said FLAP nucleic acid; and reagents for detection of said label. The labeled nucleic acid can comprise a contiguous nucleotide sequence which is completely complementary to a part of the nucleic acid sequence of said FLAP nucleic acid. Also described herein is a reagent kit for assaying a sample for the presence of a FLAP nucleic acid, comprising one or more nucleic acids comprising a contiguous nucleic acid sequence which is at least partially complementary to a part of the nucleic acid sequence of said FLAP nucleic acid, and which is capable of acting as a primer for said FLAP nucleic acid when maintained under conditions for primer extension.

The invention also provides for the use of a nucleic acid for assaying a sample for the presence of a FLAP nucleic acid, in which the nucleic acid is 100 or fewer nucleotides in length and is either: at least 80% identical to a contiguous sequence of nucleotides of SEQ ID NO: 1 or SEQ ID NO: 3; at least 80% identical to the complement of a contiguous sequence of nucleotides of SEQ ID NO: 1 or SEQ ID NO: 3; or capable of selectively hybridizing to said FLAP nucleic acid.

In yet another embodiment, the use of a first nucleic acid for assaying a sample for the presence of a FLAP nucleic acid that has at least one nucleotide difference from the first nucleic acid is described, in which the first nucleic acid is 100 or fewer nucleotides in length and which is either: at least 80% identical to a contiguous sequence of nucleotides of SEQ ID NO: 1 or SEQ ID NO: 3 or one of the sequences shown in Table 13; at least 80% identical to the complement of a contiguous sequence of nucleotides of SEQ ID NO: 1 or SEQ ID NO: 3 one of the sequences shown in Table 13; or capable of selectively hybridizing to said FLAP nucleic acid.

The invention also relates to a method of diagnosing a susceptibility to myocardial infarction or stroke in an individual, comprising determining the presence or absence in the individual of certain single nucleotide polymorphisms (SNPs) or of certain "haplotypes" (combinations of genetic markers); the presence of the SNP or the haplotype is diagnostic of susceptibility to myocardial infarction or stroke. In one embodiment, a haplotype associated with a susceptibility to myocardial infarction or stroke comprises markers SG13S99, SG13S25, SG13S377, SG13S106, SG13S32 and SG13S35 at the 13q12-13 locus. In one particular embodiment, the presence of the alleles T, G, G, G, A and G at SG13S99, SG13S25, SG13S377, SG13S106, SG13S32 and SG13S35, respectively (the B6 haplotype), is diagnostic of susceptibility to myocardial infarction or stroke. In another embodiment, a haplotype associated with a susceptibility to myocardial infarction or stroke comprises markers SG13S99, SG13S25, SG13S106, SG13S30 and SG13S42 at the 13q12-13 locus. In one particular embodiment, the presence of the alleles T, G, G, G and A at SG13S99, SG13S25, SG13S106, SG13S30 and SG13S42, respectively (the B5 haplotype), is diagnostic of susceptibility to myocardial infarction or stroke. In a third embodiment, a haplotype associated with a susceptibility to myocardial infarction or stroke comprises markers SG13S25, SG13S106, SG13S30 and SG13S42 at the 13q12-13 locus. In one particular embodiment, the presence of the alleles G, G, G and A at SG13S25, SG13S106, SG13S30 and SG13S42, respectively (the B4 haplotype), is diagnostic of susceptibility to myocardial infarction or stroke. In a fourth embodiment, a haplotype associated with a susceptibility to myocardial infarction or stroke comprises markers SG13S25, SG13S106, SG13S30 and SG13S32 at the 13q 12-13 locus. In one particular embodiment, the presence of the alleles G, G, G and A at SG13S25, SG13S106, SG13S30 and SG13S32, respectively (the Bs4 haplotype), is diagnostic of susceptibility to myocardial infarction or stroke.

In a fifth embodiment, a haplotype associated with a susceptibility to myocardial infarction or stroke comprises markers SG13S99, SG13S25, SG13S114, SG13S89 and SG13S32 at the 13q12-13 locus. In one particular embodiment, the presence of the alleles T, G, T, G and A at SG13S99, SG13S25, SG13S114, SG13S89 and SG13S32, respectively (the A5 haplotype), is diagnostic of susceptibility to myocardial infarction or stroke. In a sixth embodiment, a haplotype associated with a susceptibility to myocardial infarction or stroke comprises markers SG13S25, SG13S114, SG13S89 and SG13S32 at the 13q12-13 locus. In one particular embodiment, the presence of the alleles G, T, G and A at SG13S25, SG13S114, SG13S89 and SG13S32, respectively (the A4 haplotype), is diagnostic of susceptibility to myocardial infarction or stroke. The presence or absence of the haplotype can be determined by various methods, including, for example, using enzymatic amplification, restriction fragment length polymorphism analysis, sequence analysis or electrophoretic analysis of nucleic acid from the individual.

A further embodiment of the invention is a method for identification of susceptibility to myocardial infarction or stroke, by identifying haplotypes and/or SNPs that can be used to identify individuals at risk of developing MI or stroke. In certain embodiments, haplotypes can comprise, for example, at least one of the polymorphisms as indicated in Table 13, or as shown in the haplotypes in Table 5, Table 7, Table 9, Table 14, and/or Table 15. In certain additional embodiments, the haplotype can be one of haplotypes B4, BS4, B5, B6, A4, A5 or Hap B.

A method for the diagnosis and identification of susceptibility to myocardial infarction or stroke in an individual is also described, comprising: screening for a SNP or an at-risk haplotype in the FLAP nucleic acid that is more frequently present in an individual susceptible to myocardial infarction or stroke compared to an individual who is not susceptible to myocardial infarction or stroke, wherein the SNP or the at-risk haplotype increases the risk significantly. In certain embodiments, the significant increase is at least about 20%, and in other embodiments, the significant increase is identified as an odds ratio of at least about 1.2.

An additional embodiment comprises methods for the diagnosis of increased risk of susceptibility to myocardial infarction or stroke in an individual, by screening for a SNP or an at-risk haplotype in the FLAP nucleic acid that is more frequently present in an individual susceptible to myocardial infarction or stroke (affected), compared to the frequency of its presence in a healthy individual (control). The presence of the SNP or at-risk haplotype is indicative of a susceptibility to myocardial infarction or stroke. In one embodiment, an at-risk haplotype has a p value <0.05. In certain other embodiments, the screening for the presence of an at-risk haplotype comprises screening for an at-risk haplotype within or near FLAP that significantly correlates with a haplotype such as a halotype shown in Table 5; a haplotype shown in Table 7; a haplotype shown in Table 9; a haplotype shown in Table 14; a haplotype shown in Table 15; haplotype B4; haplotype Bs4; haplotype B5; haplotype B6; haplotype A4; haplotype A5; or haplotype HapB. In other embodiments, screening for the presence of an at-risk haplotype comprises screening for an at-risk haplotype within or near FLAP that significantly correlates with susceptibility to myocardial infarction or stroke.

A further embodiment comprises methods of diagnosing FLAP-associated myocardial infarction or stroke in an individual who has had a myocardial infarction and/or a stroke, by detecting a polymorphism in a FLAP nucleic acid, or an alteration in the expression or composition of a polypeptide encoded by a flap nucleic acid, wherein the presence of the polymorphism in the nucleic acid or the alteration in expression or composition is indicative of FLAP-associated myocardial infarction or stroke. Additional embodiments of the invention include methods for identification of FLAP-associated myocardial infarction or stroke, by identifying haplotypes and/or SNPs associated with MI or stroke. The haplotypes can comprise, for example, at least one of the polymorphisms as indicated in Table 13, or as shown in the haplotypes in Table 5, Table 7, Table 9, Table 14, and/or Table 15. In certain additional embodiments, the haplotype can one of haplotypes B4, BS4, B5, B6, A4, A5 or Hap B.

BRIEF DESCRIPTION OF THE DRAWINGS

The foregoing and other objects, features and advantages of the invention will be apparent from the following more particular description of preferred embodiments of the invention.

FIG. 4 shows the amino acid sequence of FLAP (SEQ ID NO: 2) and the mRNA of FLAP (SEQ ID NO: 3).

FIGS. 6.1-6.82 shows the genomic sequence of the FLAP gene (SEQ ID NO: 1).

FIGS. 8.1-8.40 show the sequences of the FLAP nucleic acid flanking the SNPs that were identified by sequencing samples from patients (SEQ ID NOs: 506-717).

DETAILED DESCRIPTION OF THE INVENTION

Extensive genealogical information has been combined with powerful gene sharing methods to map a susceptibility gene for myocardial infarction on chromosome 13q 12-13. A genome wide scan of 296 multiplex Icelandic families with 713 MI patients was performed. Through a suggestive linkage to a locus on chromosome 13q12-13 for female MI patients and early onset MI patients, and a microsatellite marker association analysis, the gene encoding the 5-lipoxygenase activating protein (FLAP) was identified.

Figure 1:
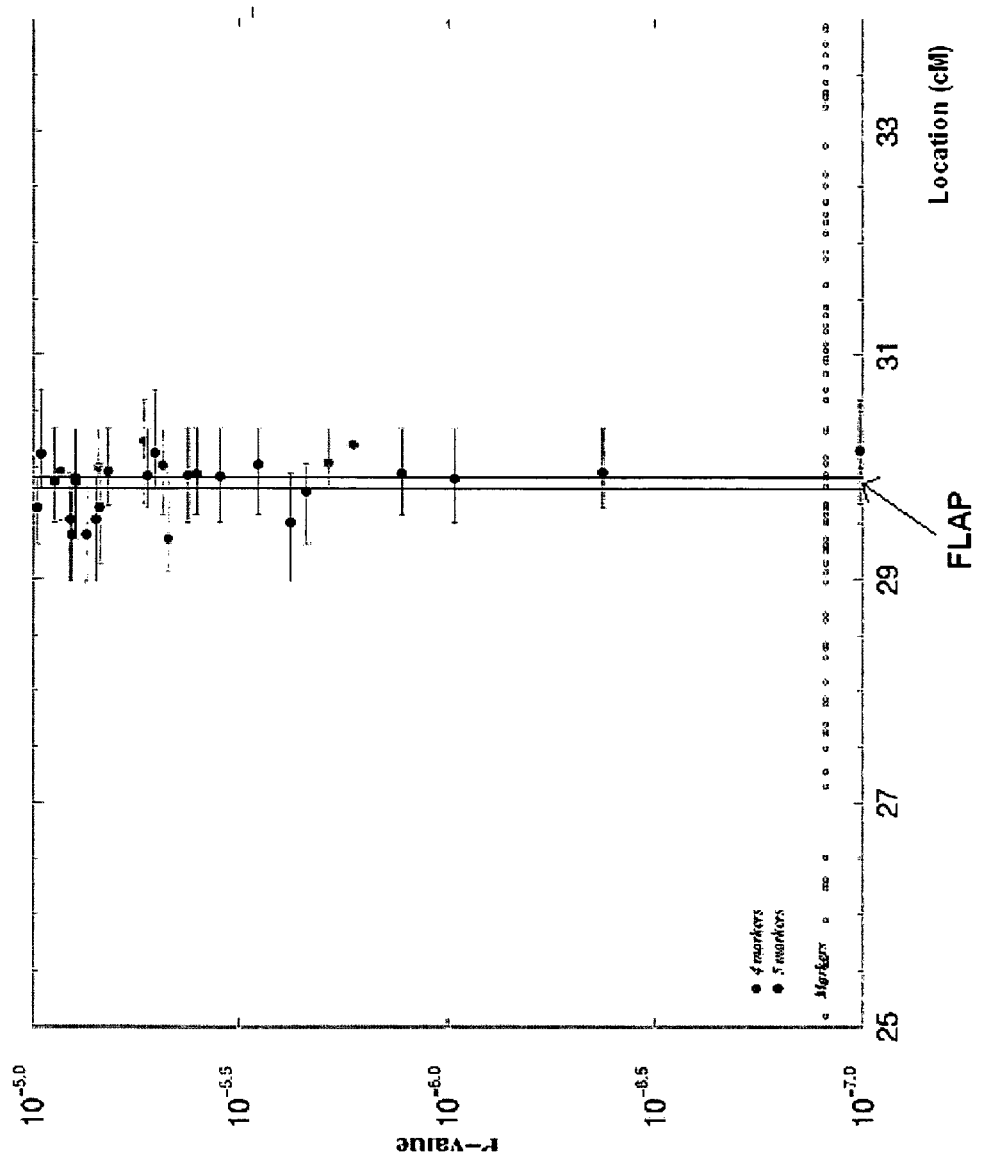
FIG. 1 shows the results from a haplotype association analysis using 4 and 5 microsatellite markers. The p-value of the association is plotted on the y-axis and position of markers on the x-axis. Only haplotypes that show association with a p-value $<10^{-5}$ are shown in the figure. The most significant microsatellite marker haplotype association is found using markers DG13S1103, DG13S166, DG13S1287, DG13S1061 and DG13S301, with alleles 4, 0, 2, 14 and 3, respectively (p-value of $1.02 \times 10^{-7}$). Carrier frequency of the haplotype is 7.3% in affected individuals and 0.3% in controls. These results are based on 437 patients and 721 controls. The area that is common to all the haploytypes shown in the figure includes only one gene, FLAP.
Figure 2:
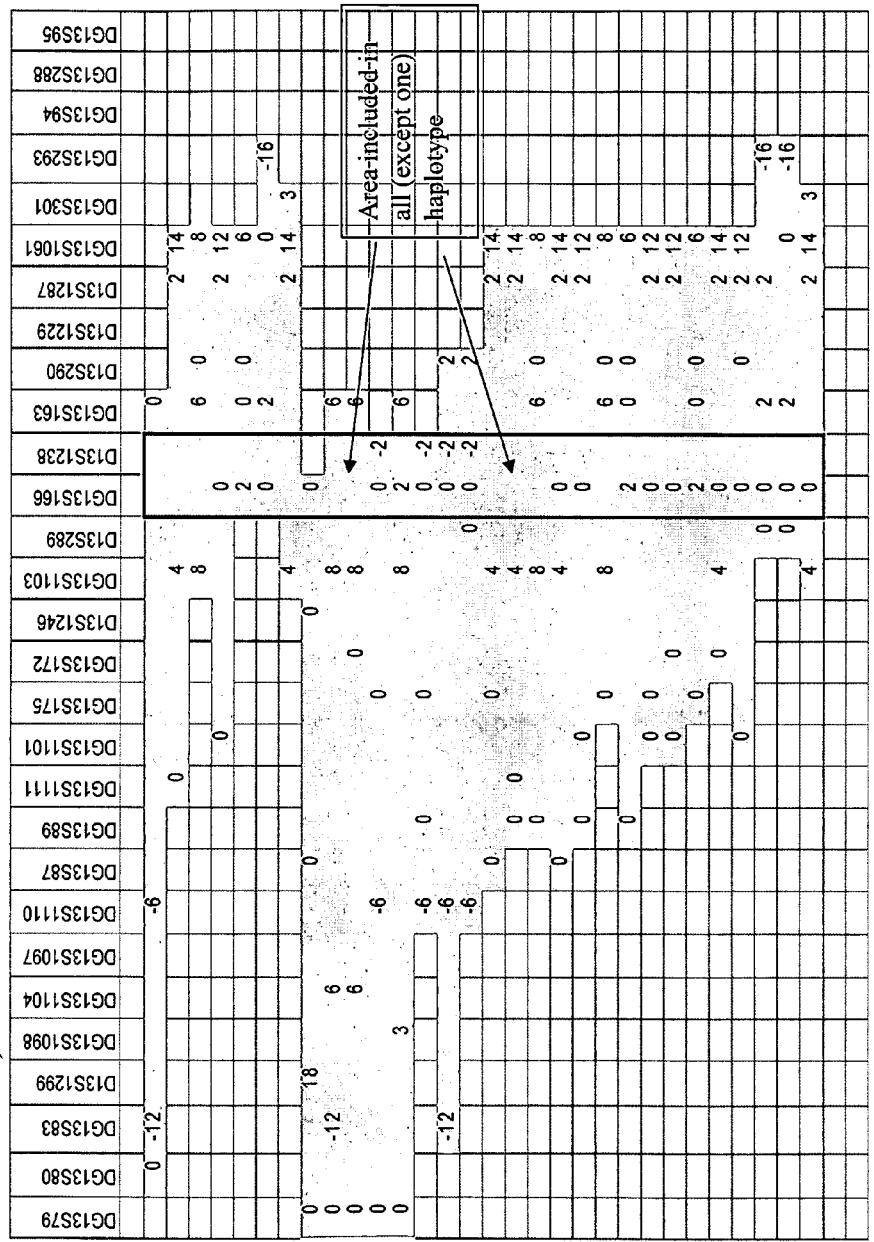
FIG. 2 shows the alleles of the markers defining the most significant microsatellite marker haplotypes. The area defined with a black square is a common area to all the most significantly associated haplotypes. The FLAP nucleic acid is located between markers DG13S166 and D13S1238. Two marker haplotype involving alleles 0 and –2 for markers DG13S166 and S13S1238, respectively, is found in excess in patients. Carrier frequency of this haploype is 27% in patients and 15.4% in controls p-value $1 \times 10^{-3}$).
Figure 3:
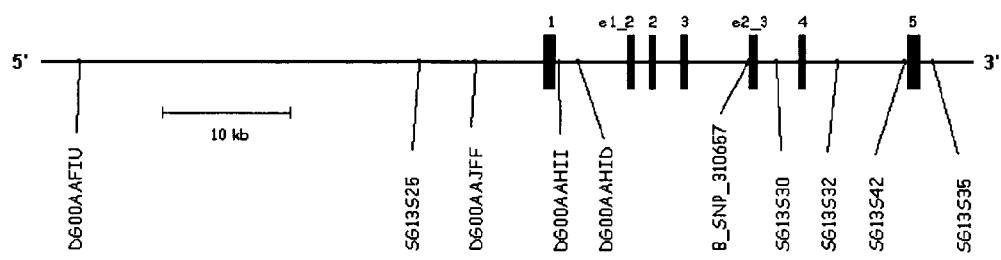
FIG. 3 shows the relative location of key SNPs and exons of the ALOX5AP/FLAP gene. Haplotype length varies between 33 to 68 kb.

Subsequent to the mapping of the MI susceptibility gene to chromosome 13q12-13 the candidate locus was finely mapped with microsatellite markers. Patients with myocardial infarction and controls were initially genotyped with microsatellite markers with an average spacing between markers of less than 100 kb over a 7.6 Mb candidate region. Initial haplotype association analysis that included these microsatellite markers revealed several extended haplotypes composed of 4 and 5 microsatellite markers that were significantly associated with female MI (see FIGS. 1 and 2). A region common to all these extended haplotypes, is defined by markers DG13S166 and D13S1238. This region included only one gene, the FLAP nucleic acid sequence. The two marker haplotype involving alleles 0 and −2 for markers DG13S166 and D13S1238, respectively, was found in excess in patients.

This was the first evidence that the FLAP gene might be involved in the pathogenesis of myocardial infarction.

Subsequent haplotype analysis that included more microsatellite markers in the candidate region on chromosome 13q12-13, now with a marker density of 1 microsatellite marker per 60 kb, showed decreased significance of the original haplotype association. However, the haplotype association analysis using increased density of markers again pointed towards the FLAP gene. This analysis strongly suggested that a 300 kb region was involved in the susceptibility of myocardial infarction. This 300 kb region included only two genes, the gene encoding highly charged protein (D13S106E) and the gene encoding 5-lipoxygenase activating protein (FLAP).

In view of the association results described above and because of the known role of the 5-lipoxygenease pathway in inflammatory processes, FLAP was an attractive candidate and therefore further efforts were focused on this gene.

SNP Haplotype Association to MI, and Subsequently to Stroke

In an effort to identify haplotypes involving only SNP markers that associate with MI, additional SNPs were identified by sequencing the FLAP gene and the region flanking the gene. A total of 48 SNPs in 1343 patients and 624 unrelated controls were genotyped. Haplotype association analysis involving only these SNPs revealed two correlated series of SNP haplotypes that were in significant excess in patients, denoted as A and B in Table 7. The length of the haplotypes varied between 33 and 69 kb, and the haplotypes covered one or two blocks of linkage disequilibrium. Both series of haplotypes contained the common allele G of the SNP SG13S25. All haplotypes in the A series contain the SNP SG13S114, while all haplotypes in the B series contain the SNP SG13S106. In the B series, the haplotypes B4, B5, and B6 have a relative risk (RR) greater than 2 and with allelic frequencies above 10%. The haplotypes in the A series have slightly lower RR and lower p-values, but higher frequency (15-16%). The haplotypes in series B and A are strongly correlated, i.e., the haplotypes in B define a subset of the haplotypes in A. Hence, haplotypes in series B are more specific than A. However, haplotypes in series A are more sensitive, i.e. they capture more individuals with the putative mutation, as is observed in the population attributable risk which is less for B than for A. Furthermore, these haplotypes showed similar risk ratios and allelic frequencies for early-onset patients (defined as onset of first MI before the age of 55) and for both genders. In addition, analyzing various groups of patients with known risk factors, such as hypertension, high cholesterol, smoking and diabetes, did not reveal any significant correlation with these haplotypes, suggesting that the haplotypes in the FLAP gene represent an independent genetic susceptibility factor for MI.

The product of the FLAP gene is involved in an important inflammatory pathway, and could thus be a predisposing factor for plaque rupture in MI. Since MI and stroke are both considered to be atherothrombotic diseases the MI at-risk haplotypes were assessed to determine whether they also were associated with stroke. Nineteen of the SNPs that defined the MI at-risk haplotypes (A and B series) were evaluated in stroke patients and unrelated controls. In the analysis, a subset of patients that did not have MI and were unrelated within 4 meiosis was used. The results from the haplotype association analysis are summarized in Table 9. The frequency of the at-risk haplotypes in all stroke patients was very similar to that of the MI patients and the haplotype conferred a similar relative risk. The B4 haplotype, previously described for MI, is carried by 19% of all stroke patients and 11% of controls. Carriers of this haplotype have nearly twofold risk (RR=1.95, P=1.6 10-4) of having a stroke. Adding the fifth SNP (SG13S35) to the B4 haplotype increases the relative risk to 2.04 (p-value 5.8 10-5). The allelic frequency of this haplotype is 10.2% in stroke patients and 5.3% in controls. Also shown in Table 9 is a 4 SNP haplotype defined as Bs4 that is highly correlated with the B4 haplotype (r2=0.93). Bs4 haplotype has a RR of 2.01, carrier frequency in patients of 19% and population attributable risk of 10%. This haplotype was tested with different subtypes of stroke (Table 9). Of interest is that all stroke subtypes have a considerably higher frequency of the 'at-risk' haplotype than controls resulting in the increased relative risk.

The FLAP nucleic acid encodes a 5-lipoxygenase activating protein, which, in combination with 5-lipoxygenase (5-LO), is required for leukotriene synthesis. FLAP acts coordinately with 5-LO to catalyze the first step in the synthesis of leukotrienes from arachidonic acid. It catalyzes the conversion of arachidonic acid to 5(S)-hydroperoxy-6-trans-8,11, 14-cis-eicosatetraenoic acid (5-HPETE), and further to the allylic epoxide 5 (S)-trans7,9 trans 11,14-cis-eicosatetraenoic acid (leukotriene A4, LTA4).

The leukotrienes are a family of highly potent biological mediators of inflammatory processes produced primarily by bone marrow derived leukocytes such as monocytes, macrophages, and neurophils. Both FLAP and 5-LO are detected within atherosclerosis lesions (Proc Natl Acad Sci USA. 2003 Feb. 4; 100(3):1238-43.), indicating that the vessel itself can be a source of leukotrienes. Inhibitors of FLAP function impede translocation of 5-LO from the cytoplasm to the cell membrane and inhibit activation of 5-LO and thereby decrease leukotriene synthesis.

Independent confirmation of FLAP association to MI was obtained in a British cohort of patients with sporadic MI. These findings support FLAP as the first specific gene isolated that confers substantial risk of the complex traits of MI and stroke.

As a result of these discoveries, genetic tests can now be developed to identify those that are at increased risk of developing myocardial infarction (MI) or stroke.

NUCLEIC ACIDS OF THE INVENTION

FLAP Nucleic Acids, Portions and Variants

Accordingly, the invention pertains to isolated nucleic acid molecules comprising a human FLAP nucleic acid. The term, "FLAP nucleic acid," as used herein, refers to an isolated nucleic acid molecule encoding FLAP polypeptide. The FLAP nucleic acid molecules of the present invention can be RNA, for example, mRNA, or DNA, such as cDNA and genomic DNA. DNA molecules can be double-stranded or single-stranded; single stranded RNA or DNA can be either the coding, or sense strand or the non-coding, or antisense strand. The nucleic acid molecule can include all or a portion of the coding sequence of the gene or nucleic acid and can further comprise additional non-coding sequences such as introns and non-coding 3' and 5' sequences (including regulatory sequences, for example).

For example, a FLAP nucleic acid can consist of SEQ ID NOs: 1 or 3 or the complement thereof, or to a portion or fragment of such an isolated nucleic acid molecule (e.g., cDNA or the nucleic acid) that encodes FLAP polypeptide (e.g., a polypeptide such as SEQ ID NO: 2). In a preferred embodiment, the isolated nucleic acid molecule comprises a nucleic acid molecule selected from the group consisting of SEQ ID NOs: 1 or 3, or their complement thereof.

Additionally, the nucleic acid molecules of the invention can be fused to a marker sequence, for example, a sequence that encodes a polypeptide to assist in isolation or purification of the polypeptide. Such sequences include, but are not limited to, those that encode a glutathione-S-transferase (GST) fusion protein and those that encode a hemagglutinin A (HA) polypeptide marker from influenza.

An "isolated" nucleic acid molecule, as used herein, is one that is separated from nucleic acids that normally flank the gene or nucleic acid sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material may be purified to essential homogeneity, for example as determined by PAGE or column chromatography such as HPLC. In certain embodiments, an isolated nucleic acid molecule comprises at least about 50, 80 or 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 5 kb, including but not limited to 4 kb, 3 kb, 2 kb, 1 kb, 0.5 kb or 0.1 kb of nucleotides which flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule or nucleic acid sequence can include a nucleic acid molecule or nucleic acid sequence that is synthesized chemically or by recombinant means. Therefore, recombinant DNA contained in a vector is included in the definition of "isolated" as used herein. Also, isolated nucleotide sequences include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded polypeptide, as probes for isolating homologous sequences (e.g., from other mammalian species), for gene mapping (e.g., by in situ hybridization with chromosomes), or for detecting expression of the nucleic acid in tissue (e.g., human tissue), such as by Northern blot analysis.

The present invention also pertains to nucleic acid molecules which are not necessarily found in nature but which encode a FLAP polypeptide (e.g., a polypeptide having an amino acid sequence comprising an amino acid sequence of SEQ ID NOs: 2), or another splicing variant of a FLAP polypeptide or polymorphic variant thereof. Thus, for example, DNA molecules that comprise a sequence that is different from the naturally occurring nucleic acid sequence but which, due to the degeneracy of the genetic code, encode a FLAP polypeptide of the present invention are also the subjects of this invention. The invention also encompasses nucleotide sequences encoding portions (fragments), or encoding variant polypeptides such as analogues or derivatives of a FLAP polypeptide. Such variants can be naturally occurring, such as in the case of allelic variation or single nucleotide polymorphisms, or non-naturally-occurring, such as those induced by various mutagens and mutagenic processes. Intended variations include, but are not limited to, addition, deletion and substitution of one or more nucleotides that can result in conservative or non-conservative amino acid changes, including additions and deletions. Preferably, the nucleotide (and/or resultant amino acid) changes are silent or conserved; that is, they do not alter the characteristics or activity of a FLAP polypeptide. In one preferred embodiment, the nucleotide sequences are fragments that comprise one or more polymorphic microsatellite markers. In another preferred embodiment, the nucleotide sequences are fragments that comprise one or more single nucleotide polymorphisms in a FLAP nucleic acid (e.g., the single nucleotide polymorphisms set forth in Table 13, below).

Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequence via hydrogen bonding and other chemical interactions. Such molecules include, for example, those in which peptide linkages substitute for phosphate linkages in the backbone of the molecule.

The invention also pertains to nucleic acid molecules that hybridize under high stringency hybridization conditions, such as for selective hybridization, to a nucleic acid sequence described herein (e.g., nucleic acid molecules which specifically hybridize to a nucleic acid sequence encoding polypeptides described herein, and, optionally, have an activity of the polypeptide). In one embodiment, the invention includes variants described herein which hybridize under high stringency hybridization conditions (e.g., for selective hybridization) to a nucleic acid sequence comprising a nucleic acid sequence selected from the group consisting of SEQ ID NOs: 1 or 3 or the complement thereof. In another embodiment, the invention includes variants described herein which hybridize under high stringency hybridization conditions (e.g., for selective hybridization) to a nucleic acid sequence encoding an amino acid sequence of SEQ ID NO: 2 or a polymorphic variant thereof. In a preferred embodiment, the variant that hybridizes under high stringency hybridizations has an activity of a FLAP.

Such nucleic acid molecules can be detected and/or isolated by specific hybridization (e.g., under high stringency conditions). "Specific hybridization," as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity that is less than perfect (e.g., 70%, 75%, 85%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in *Current Protocols in Molecular Biology* (Ausubel, F. M. et al., "*Current Protocols in Molecular Biology*", John Wiley & Sons, (1998), the entire teachings of which are incorporated by reference herein). The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules. Typically, conditions are used such that sequences at least about 60%, at least about 70%, at least about 80%, at least about 90% or at least about 95% or more identical to each other remain hybridized to one another. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology* 200: 546-556 (1991), and in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of −17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 minutes at room temperature; a moderate stringency wash can comprise washing in a prewarmed solution (42° C.) solution containing 0.2×SSC/0.1% SDS for 15 minutes at 42° C.; and a high stringency wash can comprise washing in prewarmed (68° C.) solution containing 0.1×SSC/0.1% SDS for 15 minutes at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

The percent homology or identity of two nucleotide or amino acid sequences can be determined by aligning the sequences for optimal comparison purposes (e.g., gaps can be introduced in the sequence of a first sequence for optimal alignment). The nucleotides or amino acids at corresponding positions are then compared, and the percent identity between the two sequences is a function of the number of identical positions shared by the sequences (i.e., % identity=# of identical positions/total # of positions×100). When a position in one sequence is occupied by the same nucleotide or amino acid residue as the corresponding position in the other sequence, then the molecules are homologous at that position. As used herein, nucleic acid or amino acid "homology" is equivalent to nucleic acid or amino acid "identity". In certain embodiments, the length of a sequence aligned for comparison purposes is at least 30%, for example, at least 40%, in certain embodiments at least 60%, and in other embodiments at least 70%, 80%, 90% or 95% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA* 90:5873-5877 (1993). Such an algorithm is incorporated into the NBLAST and XBLAST programs (version 2.0) as described in Altschul et al., *Nucleic Acids Res.* 25:389-3402 (1997). When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

Another preferred non-limiting example of a mathematical algorithm utilized for the comparison of sequences is the algorithm of Myers and Miller, *CABIOS* 4(1): 11-17 (1988). Such an algorithm is incorporated into the ALIGN program (version 2.0) which is part of the GCG sequence alignment software package (Accelrys, Cambridge, UK). When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, *Comput. Appl. Biosci.* 10:3-5 (1994); and FASTA described in Pearson and Lipman, *Proc. Natl. Acad. Sci. USA* 85:2444-8 (1988).

In another embodiment, the percent identity between two amino acid sequences can be accomplished using the GAP program in the GCG software package using either a BLOSUM63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package using a gap weight of 50 and a length weight of 3.

The present invention also provides isolated nucleic acid molecules that contain a fragment or portion that hybridizes under highly stringent conditions to a nucleic acid sequence comprising SEQ ID NO: 1 or 3 or the complement of SEQ ID NO: 1 or 3, and also provides isolated nucleic acid molecules that contain a fragment or portion that hybridizes under highly stringent conditions to a nucleic acid sequence encoding an amino acid sequence of the invention or polymorphic variant thereof. The nucleic acid fragments of the invention are at least about 15, for example, at least about 18, 20, 23 or 25 nucleotides, and can be 30, 40, 50, 100, 200 or more nucleotides in length. Longer fragments, for example, 30 or more nucleotides in length, encoding antigenic polypeptides described herein are particularly useful, such as for the generation of antibodies as described below.

Probes and Primers

In a related aspect, the nucleic acid fragments of the invention are used as probes or primers in assays such as those described herein. "Probes" or "primers" are oligonucleotides that hybridize in a base-specific manner to a complementary strand of nucleic acid molecules. Such probes and primers include polypeptide nucleic acids, as described in Nielsen et al. (*Science* 254:1497-1500 (1991)).

A probe or primer comprises a region of nucleic acid that hybridizes to at least about 15, for example about 20-25, and in certain embodiments about 40, 50 or 75, consecutive nucleotides of a nucleic acid of the invention, such as a nucleic acid comprising a contiguous nucleic acid sequence of SEQ ID NOs: 1 or 3 or the complement of SEQ ID NOs: 1 or 3, or a nucleic acid sequence encoding an amino acid sequence of SEQ ID NO: 2 or polymorphic variant thereof. In preferred embodiments, a probe or primer comprises 100 or fewer nucleotides, in certain embodiments, from 6 to 50 nucleotides, for example, from 12 to 30 nucleotides. In other embodiments, the probe or primer is at least 70% identical to the contiguous nucleic acid sequence or to the complement of the contiguous nucleotide sequence, for example, at least 80% identical, in certain embodiments at least 90% identical, and in other embodiments at least 95% identical, or even capable of selectively hybridizing to the contiguous nucleic acid sequence or to the complement of the contiguous nucleotide sequence. Often, the probe or primer further comprises a label, e.g., radioisotope, fluorescent compound, enzyme, or enzyme co-factor.

The nucleic acid molecules of the invention such as those described above can be identified and isolated using standard molecular biology techniques and the sequence information provided herein. For example, nucleic acid molecules can be amplified and isolated using the polymerase chain reaction and synthetic oligonucleotide primers based on one or more of SEQ ID NOs: 1 or 3, or the complement thereof, or designed based on nucleotides based on sequences encoding one or more of the amino acid sequences provided herein. See generally *PCR Technology: Principles and Applications for DNA Amplification* (ed. H. A. Erlich, Freeman Press, NY, N.Y., 1992); *PCR Protocols: A Guide to Methods and Applications* (Eds. Innis et al., Academic Press, San Diego, Calif., 1990); Mattila et al., *Nucl. Acids Res.* 19:4967 (1991); Eckert et al., *PCR Methods and Applications* 1:17 (1991); PCR (eds. McPherson et al., IRL Press, Oxford); and U.S. Pat. No. 4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), and self-sustained sequence replication (Guatelli et al., *Proc. Nat. Acad. Sci. USA* 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be labeled, for example, radiolabeled, and used as a probe for screening a cDNA library derived from human cells, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a polypeptide of the appropriate molecular weight. For example, the direct analysis of the nucleic acid molecules of the present invention can be accomplished using well-known methods that are commercially available. See, for example, Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the polypeptide and the DNA encoding the polypeptide can be isolated, sequenced and further characterized.

Antisense nucleic acid molecules of the invention can be designed using the nucleotide sequences of SEQ ID NOs: 1 or 3 and/or the complement of one or more of SEQ ID NOs: 1 or 3 and/or a portion of one or more of SEQ ID NOs: 1 or 3 or the complement of one or more of SEQ ID NOs: 1 or 3 and/or a sequence encoding the amino acid sequences of SEQ ID NOs: 2 or encoding a portion of one or more of SEQ ID NOs: 1 or 3 or their complement. They can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

The nucleic acid sequences can also be used to compare with endogenous DNA sequences in patients to identify one or more of the disorders related to FLAP, and as probes, such as to hybridize and discover related DNA sequences or to subtract out known sequences from a sample. The nucleic acid sequences can further be used to derive primers for genetic fingerprinting, to raise anti-polypeptide antibodies using DNA immunization techniques, and as an antigen to raise anti-DNA antibodies or elicit immune responses. Portions or fragments of the nucleotide sequences identified herein (and the corresponding complete gene sequences) can be used in numerous ways as polynucleotide reagents. For example, these sequences can be used to: (i) map their respective genes on a chromosome; and, thus, locate gene regions or nucleic acid regions associated with genetic disease; (ii) identify an individual from a minute biological sample (tissue typing); and (iii) aid in forensic identification of a biological sample. Additionally, the nucleotide sequences of the invention can be used to identify and express recombinant polypeptides for analysis, characterization or therapeutic use, or as markers for tissues in which the corresponding polypeptide is expressed, either constitutively, during tissue differentiation, or in diseased states. The nucleic acid sequences can additionally be used as reagents in the screening and/or diagnostic assays described herein, and can also be included as components of kits (e.g., reagent kits) for use in the screening and/or diagnostic assays described herein.

Vectors

Another aspect of the invention pertains to nucleic acid constructs containing a nucleic acid molecule of SEQ ID NOs: 1 or 3 or the complement thereof (or a portion thereof). Yet another aspect of the invention pertains to nucleic acid constructs containing a nucleic acid molecule encoding an amino acid of SEQ ID NO: 2 or polymorphic variant thereof. The constructs comprise a vector (e.g., an expression vector) into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, such as expression vectors, are capable of directing the expression of genes or nucleic acids to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" or "operatively linked" is intended to mean that the nucleic acid sequence of interest is linked to the regulatory sequence(s) in a manner which allows for expression of the nucleic acid sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, "Gene Expression Technology", Methods in Enzymology 185, Academic Press, San Diego, Calif. (1990). Regulatory sequences include those which direct constitutive expression of a nucleic acid sequence in many types of host cell and those which direct expression of the nucleic acid sequence only in certain host cells (e.g., tissue-specific regulatory sequences). It will be appreciated by those skilled in the art that the design of the expression vector can depend on such factors as the choice of the host cell to be transformed and the level of expression of polypeptide desired. The expression vectors of the invention can be introduced into host cells to thereby produce polypeptides, including fusion polypeptides, encoded by nucleic acid molecules as described herein.

The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a nucleic acid molecule of the invention can be expressed in bacterial cells (e.g., *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene or nucleic acid that encodes a selectable marker (e.g., for resistance to antibiotics) is generally introduced into the host cells along with the gene or nucleic acid of interest. Preferred selectable markers include those that confer resistance to drugs, such as G418, hygromycin and methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene or nucleic acid will survive, while the other cells die).

A host cell of the invention, such as a prokaryotic host cell or eukaryotic host cell in culture can be used to produce (i.e., express) a polypeptide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a nucleic acid molecule of the invention has been introduced (e.g., an exogenous FLAP nucleic acid, or an exogenous nucleic acid encoding a FLAP polypeptide). Such host cells can then be used to create non-human transgenic animals in which exogenous nucleotide sequences have been introduced into the genome or homologous recombinant animals in which endogenous nucleotide sequences have been altered. Such animals are useful for studying the function and/or activity of the nucleic acid sequence and polypeptide encoded by the sequence and for identifying and/or evaluating modulators of their activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens and amphibians. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo* (Cold Spring Harbor Laboratory Press, Cold Spring Harbor, N.Y., 1986). Methods for constructing homologous recombination vectors and homologous recombinant animals are described further in Bradley, *Current Opinion in BioTechnology* 2:823-829 (1991) and in PCT Publication Nos. WO 90/11354, WO 91/01140, WO 92/0968, and WO 93/04169. Clones of the non-human transgenic animals described herein can also be produced according to the methods described in Wilmut et al., *Nature* 385:810-813 (1997) and PCT Publication Nos. WO 97/07668 and WO 97/07669.

POLYPEPTIDES OF THE INVENTION

The present invention also pertains to isolated polypeptides encoded by FLAP nucleic acids ("FLAP polypeptides"), and fragments and variants thereof, as well as polypeptides encoded by nucleotide sequences described herein (e.g., other splicing variants). The term "polypeptide" refers to a polymer of amino acids, and not to a specific length; thus, peptides, oligopeptides and proteins are included within the definition of a polypeptide. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell (e.g., in a "fusion protein") and still be "isolated" or "purified."

The polypeptides of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

When a polypeptide is recombinantly produced, it can also be substantially free of culture medium, i.e., culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, a polypeptide of the invention comprises an amino acid sequence encoded by a nucleic acid molecule comprising a nucleic acid sequence selected from the group consisting of SEQ ID NO: 1 or 3, or the complement of SEQ ID NO: 1 or 3, or portions thereof, or a portion or polymorphic variant thereof. However, the polypeptides of the invention also encompass fragment and sequence variants. Variants include a substantially homologous polypeptide encoded by the same genetic locus in an organism, i.e., an allelic variant, as well as other splicing variants. Variants also encompass polypeptides derived from other genetic loci in an organism, but having substantial homology to a polypeptide encoded by a nucleic acid molecule comprising a nucleic acid sequence selected from the group consisting of SEQ ID NOs: 1 or 3 or their complement, or portions thereof, or having substantial homology to a polypeptide encoded by a nucleic acid molecule comprising a nucleic acid sequence selected from the group consisting of nucleotide sequences encoding SEQ ID NO: 2 or polymorphic variants thereof. Variants also include polypeptides substantially homologous or identical to these polypeptides but derived from another organism, i.e., an ortholog. Variants also include polypeptides that are substantially homologous or identical to these polypeptides that are produced by chemical synthesis. Variants also include polypeptides that are substantially homologous or identical to these polypeptides that are produced by recombinant methods.

As used herein, two polypeptides (or a region of the polypeptides) are substantially homologous or identical when the amino acid sequences are at least about 45-55%, in certain embodiments at least about 70-75%, and in other embodiments at least about 80-85%, and in others greater than about 90% or more homologous or identical. A substantially homologous amino acid sequence, according to the present invention, will be encoded by a nucleic acid molecule hybridizing to SEQ ID NO: 1 or 3 or portion thereof, under stringent conditions as more particularly described above, or will be encoded by a nucleic acid molecule hybridizing to a nucleic acid sequence encoding SEQ ID NO: 2 or a portion thereof or polymorphic variant thereof, under stringent conditions as more particularly described thereof.

The invention also encompasses polypeptides having a lower degree of identity but having sufficient similarity so as to perform one or more of the same functions performed by a polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found in Bowie et al., *Science* 247:1306-1310 (1990).

A variant polypeptide can differ in amino acid sequence by one or more substitutions, deletions, insertions, inversions, fusions, and truncations or a combination of any of these. Further, variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity in vitro, or in vitro proliferative activity. Sites that are critical for polypeptide activity can also be determined by structural analysis such as crystallization, nuclear magnetic resonance or photoaffinity labeling (Smith et al., *J. Mol. Biol.* 224:899-904 (1992); de Vos et al., *Science* 255:306-312 (1992)).

The invention also includes fragments of the polypeptides of the invention. Fragments can be derived from a polypeptide encoded by a nucleic acid molecule comprising SEQ ID NO: 1 or 3, or the complement of SEQ ID NO: 1 or 3 (or other variants). However, the invention also encompasses fragments of the variants of the polypeptides described herein. As used herein, a fragment comprises at least 6 contiguous amino acids. Useful fragments include those that retain one or more of the biological activities of the polypeptide as well as fragments that can be used as an immunogen to generate polypeptide-specific antibodies.

Biologically active fragments (peptides which are, for example, 6, 9, 12, 15, 16, 20, 30, 35, 36, 37, 38, 39, 40, 50, 100 or more amino acids in length) can comprise a domain, segment, or motif that has been identified by analysis of the polypeptide sequence using well-known methods, e.g., signal peptides, extracellular domains, one or more transmembrane segments or loops, ligand binding regions, zinc finger domains, DNA binding domains, acylation sites, glycosylation sites, or phosphorylation sites.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and propolypeptide regions fused to the amino terminus of the polypeptide fragment and an additional region fused to the carboxyl terminus of the fragment.

The invention thus provides chimeric or fusion polypeptides. These comprise a polypeptide of the invention operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment the fusion polypeptide does not affect function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example beta-galactosidase fusions, yeast two-hybrid GAL fusions, poly-His fusions and Ig fusions. Such fusion polypeptides, particularly poly-His fusions, can facilitate the purification of recombinant polypeptide. In certain host cells (e.g., mammalian host cells), expression and/or secretion of a polypeptide can be increased using a heterologous signal sequence. Therefore, in another embodiment, the fusion polypeptide contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al., *Journal of Molecular Recognition*, 8:52-58 (1995) and Johanson et al., *The Journal of Biological Chemistry*, 270,16: 9459-9471 (1995). Thus, this invention also encompasses soluble fusion polypeptides containing a polypeptide of the invention and various portions of the constant regions of heavy or light chains of immunoglobulins of various subclasses (IgG, IgM, IgA, IgE).

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed and re-amplified to generate a chimeric nucleic acid sequence (see Ausubel et al., *Current Protocols in Molecular Biology*, 1992). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

The isolated polypeptide can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector introduced into a host cell and the polypeptide expressed in the host cell. The polypeptide can then be isolated from the cells by an appropriate purification scheme using standard protein purification techniques.

The polypeptides of the present invention can be used to raise antibodies or to elicit an immune response. The polypeptides can also be used as a reagent, e.g., a labeled reagent, in assays to quantitatively determine levels of the polypeptide or a molecule to which it binds (e.g., a ligand) in biological fluids. The polypeptides can also be used as markers for cells or tissues in which the corresponding polypeptide is preferentially expressed, either constitutively, during tissue differentiation, or in diseased states. The polypeptides can be used to isolate a corresponding binding agent, e.g., ligand, such as, for example, in an interaction trap assay, and to screen for peptide or small molecule antagonists or agonists of the binding interaction. For example, because members of the leukotriene pathway including FLAP bind to receptors, the leukotriene pathway polypeptides can be used to isolate such receptors.

ANTIBODIES OF THE INVENTION

Polyclonal and/or monoclonal antibodies that specifically bind one form of the polypeptide or nucleic acid product (e.g., a polypeptide encoded by a nucleic acid having a SNP as set forth in Table 13), but not to another form of the polypeptide or nucleic acid product, are also provided. Antibodies are also provided which bind a portion of either polypeptide encoded by nucleic acids of the invention (e.g., SEQ ID NO: 1 or SEQ ID NO: 3, or the complement of SEQ ID NO: 1 or SEQ ID NO: 3), or to a polypeptide encoded by nucleic acids of the invention that contain a polymorphic site or sites. The invention also provides antibodies to the polypeptides and polypeptide fragments of the invention, or a portion thereof, or having an amino acid sequence encoded by a nucleic acid molecule comprising all or a portion of SEQ ID NOs: 1 or 3, or the complement thereof, or another variant or portion thereof. The term "antibody" as used herein refers to immunoglobulin molecules and immunologically active portions of immunoglobulin molecules, i.e., molecules that contain an antigen binding site that specifically binds an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4:72 (1983)); the EBV-hybridoma technique (Cole et al., *Monoclonal Antibodies and Cancer Therapy*, Alan R. Liss, 1985, Inc., pp. 77-96); or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.* 54:387-402 (1981). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Anti-* bod. *Hybridomas* 3:81-85 (1992); Huse et al., *Science* 246: 1275-1281 (1989); Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin and aequorin, and examples of suitable radioactive material include $^{125}I$, $^{131}I$, $^{35}S$ or $^{3}H$.

DIAGNOSTIC ASSAYS

Diagnosis Using Probes, Primers, Polypeptides, and Antibodies

The nucleic acids, probes, primers, polypeptides and antibodies described herein can be used in methods of diagnosis of a susceptibility to MI or stroke, or to a disease or condition associated with a gene such as FLAP, as well as in kits useful for diagnosis of a susceptibility to MI or stroke, or to a disease or condition associated with FLAP. In one embodiment, the kit useful for diagnosis of susceptibility to MI or stroke, or to a disease or condition associated with FLAP comprises primers as described herein, wherein the primers contain one or more of the SNPs identified in Table 13.

In one embodiment of the invention, diagnosis of susceptibility to MI or stroke (or diagnosis of or susceptibility to a disease or condition associated with FLAP), is made by detecting a polymorphism in a FLAP nucleic acid as described herein. The polymorphism can be an alteration in a FLAP nucleic acid, such as the insertion or deletion of a single nucleotide, or of more than one nucleotide, resulting in a frame shift alteration; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene or nucleic acid; duplication of all or a part of the gene or nucleic acid; transposition of all or a part of the gene or nucleic acid; or rearrangement of all or a part of the gene or nucleic acid. More than one such alteration may be present in a single gene or nucleic acid. Such sequence changes cause an alteration in the polypeptide encoded by a FLAP nucleic acid. For example, if the alteration is a frame shift alteration, the frame shift can result in a change in the encoded amino acids, and/or can result in the generation of a premature stop codon, causing generation of a truncated polypeptide. Alternatively, a polymorphism associated with a disease or condition associated with a FLAP nucleic acid or a susceptibility to a disease or condition associated with a FLAP nucleic acid can be a synonymous alteration in one or more nucleotides (i.e., an alteration that does not result in a change in the polypeptide encoded by a FLAP nucleic acid). Such a polymorphism may alter splicing sites, affect the stability or transport of mRNA, or otherwise affect the transcription or translation of the nucleic acid. A FLAP nucleic acid that has any of the alteration described above is referred to herein as an "altered nucleic acid."

In a first method of diagnosing a susceptibility to MI or stroke, hybridization methods, such as Southern analysis, Northern analysis, or in situ hybridizations, can be used (see *Current Protocols in Molecular Biology*, Ausubel, F. et al., eds., John Wiley & Sons, including all supplements through 1999). For example, a biological sample from a test subject (a "test sample") of genomic DNA, RNA, or cDNA, is obtained from an individual suspected of having, being susceptible to or predisposed for, or carrying a defect for, a susceptibility to a disease or condition associated with a FLAP nucleic acid (the "test individual"). The individual can be an adult, child, or fetus. The test sample can be from any source which contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined to determine whether a polymorphism in a nucleic acid is present, and/or to determine which splicing variant(s) encoded by the FLAP is present. The presence of the polymorphism or splicing variant(s) can be indicated by hybridization of the nucleic acid in the genomic DNA, RNA, or cDNA to a nucleic acid probe. A "nucleic acid probe", as used herein, can be a DNA probe or an RNA probe; the nucleic acid probe can contain at least one polymorphism in a FLAP nucleic acid or contains a nucleic acid encoding a particular splicing variant of a FLAP nucleic acid. The probe can be any of the nucleic acid molecules described above (e.g., the nucleic acid, a fragment, a vector comprising the nucleic acid, a probe or primer, etc.).

To diagnose a susceptibility to MI or stroke (or a disease or condition associated with FLAP), the test sample containing a FLAP nucleic acid is contacted with at least one nucleic acid probe to form a hybridization sample. A preferred probe for detecting mRNA or genomic DNA is a labeled nucleic acid probe capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA or genomic DNA. For example, the nucleic acid probe can be all or a portion of one of SEQ ID NOs: 1 and 3, or the complement thereof; or a portion thereof; or can be a nucleic acid encoding all or a portion of one of SEQ ID NO: 2. Other suitable probes for use in the diagnostic assays of the invention are described above (see e.g., probes and primers discussed under the heading, "Nucleic Acids of the Invention").

The hybridization sample is maintained under conditions that are sufficient to allow specific hybridization of the nucleic acid probe to a FLAP nucleic acid. "Specific hybridization", as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and FLAP nucleic acid in the test sample, then the FLAP has the polymorphism, or is the splicing variant, that is present in the nucleic acid probe. More than one nucleic acid probe can also be used concurrently in this method. Specific hybridization of any one of the nucleic acid probes is indicative of a polymorphism in the FLAP nucleic acid, or of the presence of a particular splicing variant encoding the FLAP nucleic acid, and is therefore diagnostic for a susceptibility to a disease or condition associated with FLAP (e.g., MI or stroke).

In Northern analysis (see *Current Protocols in Molecular Biology*, Ausubel, F. et al., eds., John Wiley & Sons, supra) the hybridization methods described above are used to identify the presence of a polymorphism or a particular splicing variant, associated with a disease or condition associated with or a susceptibility to a disease or condition associated with FLAP (e.g., MI or stroke). For Northern analysis, a test sample of RNA is obtained from the individual by appropriate means. Specific hybridization of a nucleic acid probe, as described above, to RNA from the individual is indicative of a polymorphism in a FLAP nucleic acid, or of the presence of a particular splicing variant encoded by a FLAP nucleic acid, and is therefore diagnostic for susceptibility to a disease or condition associated with FLAP (e.g., MI or stroke).

For representative examples of use of nucleic acid probes, see, for example, U.S. Pat. Nos. 5,288,611 and 4,851,330. Alternatively, a peptide nucleic acid (PNA) probe can be used instead of a nucleic acid probe in the hybridization methods described above. PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P. E. et al., *Bioconjugate Chemistry* 5, American Chemical Society, p. 1 (1994). The PNA probe can be designed to specifically hybridize to a nucleic acid having a polymorphism associated with a susceptibility to a disease or condition associated with FLAP (e.g., MI or stroke). Hybridization of the PNA probe to a FLAP nucleic acid as described herein is diagnostic for the disease or condition or the susceptibility to the disease or condition.

In another method of the invention, mutation analysis by restriction digestion can be used to detect an altered nucleic acid, or nucleic acids containing a polymorphism(s), if the mutation or polymorphism in the nucleic acid results in the creation or elimination of a restriction site. A test sample containing genomic DNA is obtained from the individual. Polymerase chain reaction (PCR) can be used to amplify a FLAP nucleic acid (and, if necessary, the flanking sequences) in the test sample of genomic DNA from the test individual. RFLP analysis is conducted as described (see *Current Protocols in Molecular Biology*, supra). The digestion pattern of the relevant DNA fragment indicates the presence or absence of the alteration or polymorphism in the FLAP nucleic acid, and therefore indicates the presence or absence of the susceptibility to a disease or condition associated with FLAP (e.g., MI or stroke).

Sequence analysis can also be used to detect specific polymorphisms in the FLAP nucleic acid. A test sample of DNA or RNA is obtained from the test individual. PCR or other appropriate methods can be used to amplify the nucleic acid, and/or its flanking sequences, if desired. The sequence of a FLAP nucleic acid, or a fragment of the nucleic acid, or cDNA, or fragment of the cDNA, or mRNA, or fragment of the mRNA, is determined, using standard methods. The sequence of the nucleic acid, nucleic acid fragment, cDNA, cDNA fragment, mRNA, or mRNA fragment is compared with the known nucleic acid sequence of the nucleic acid, cDNA (e.g., one or more of SEQ ID NOs: 1 or 3, and/or the complement of SEQ ID NO: 1 or 3), or a nucleic acid sequence encoding SEQ ID NO: 2 or a fragment thereof) or mRNA, as appropriate. The presence of a polymorphism in the FLAP nucleic acid indicates that the individual has disease or a susceptibility to a disease associated with FLAP (e.g., MI or stroke).

Allele-specific oligonucleotides can also be used to detect the presence of polymorphism(s) in the FLAP nucleic acid, through the use of dot-blot hybridization of amplified oligonucleotides with allele-specific oligonucleotide (ASO) probes (see, for example, Saiki, R. et al., *Nature* 324:163-166 (1986)). An "allele-specific oligonucleotide" (also referred to herein as an "allele-specific oligonucleotide probe") is an oligonucleotide of approximately 10-50 base pairs, for example, approximately 15-30 base pairs, that specifically hybridizes to a FLAP nucleic acid, and that contains a polymorphism associated with a susceptibility to a disease or condition associated with FLAP (e.g., MI or stroke). An allele-specific oligonucleotide probe that is specific for particular polymorphisms in a FLAP nucleic acid can be prepared, using standard methods (see *Current Protocols in Molecular Biology*, supra). To identify polymorphisms in the nucleic acid associated with disease or susceptibility to disease, a test sample of DNA is obtained from the individual. PCR can be used to amplify all or a fragment of a FLAP nucleic acid, and its flanking sequences. The DNA containing the amplified FLAP nucleic acid (or fragment of the nucleic acid) is dot-blotted, using standard methods (see *Current Protocols in Molecular Biology*, supra), and the blot is contacted with the oligonucleotide probe. The presence of specific hybridization of the probe to the amplified FLAP is then detected. Specific hybridization of an allele-specific oligonucleotide probe to DNA from the individual is indicative of a polymorphism in the FLAP, and is therefore indicative of a susceptibility to a disease or condition associated with FLAP (e.g., MI or stroke).

An allele-specific primer hybridizes to a site on target DNA overlapping a polymorphism and only primes amplification of an allelic form to which the primer exhibits perfect complementarity. See Gibbs, *Nucleic Acid Res.* 17, 2427-2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

With the addition of such analogs as locked nucleic acids (LNAs), the size of primers and probes can be reduced to as few as 8 bases. LNAs are a novel class of bicyclic DNA analogs in which the 2' and 4' positions in the furanose ring are joined via an O-methylene (oxy-LNA), S-methylene (thio-LNA), or amino methylene (amino-LNA) moiety. Common to all of these LNA variants is an affinity toward complementary nucleic acids, which is by far the highest reported for a DNA analog. For example, particular all oxy-LNA nonamers have been shown to have melting temperatures of 64° C. and 74° C. when in complex with complementary DNA or RNA, respectively, as oposed to 28° C. for both DNA and RNA for the corresponding DNA nonamer. Substantial increases in $T_m$ are also obtained when LNA monomers are used in combination with standard DNA or RNA monomers. For primers and probes, depending on where the LNA monomers are included (e.g., the 3' end, the 5' end, or in the middle), the $T_m$ could be increased considerably.

In another embodiment, arrays of oligonucleotide probes that are complementary to target nucleic acid sequence segments from an individual, can be used to identify polymorphisms in a FLAP nucleic acid. For example, in one embodiment, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and WO 92/10092. These arrays can generally be produced using mechanical synthesis methods or light directed synthesis methods that incorporate a combination of photolithographic methods and solid phase oligonucleotide synthesis methods. See Fodor et al., *Science* 251:767-777 (1991); Pirrung et al., U.S. Pat. No. 5,143,854; (see also PCT Application WO 90/15070); Fodor et al., PCT Publication WO 92/10092; and U.S. Pat. No. 5,424,186, the entire teachings of each of which are incorporated by reference herein. Techniques for the synthesis of these arrays using mechanical synthesis methods are described in, e.g., U.S. Pat. No. 5,384,261, the entire teachings of which are incorporated by reference herein. In another example, linear arrays can be utilized.

Once an oligonucleotide array is prepared, a nucleic acid of interest is hybridized with the array and scanned for polymorphisms. Hybridization and scanning are generally carried out by methods described herein and also in, e.g., published PCT Application Nos. WO 92/10092 and WO 95/11995, and U.S. Pat. No. 5,424,186, the entire teachings of which are incorporated by reference herein. In brief, a target nucleic acid sequence that includes one or more previously identified polymorphic markers is amplified using well-known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

In a reverse method, a probe, containing a polymorphism, can be coupled to a solid surface and PCR amplicons are then added to hybridize to these probes.

Although primarily described in terms of a single detection block, e.g., detection of a single polymorphism arrays can include multiple detection blocks, and thus be capable of analyzing multiple, specific polymorphisms. It will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional uses of oligonucleotide arrays for detection of polymorphisms can be found, for example, in U.S. Pat. Nos. 5,858,659 and 5,837,832, the entire teachings of which are incorporated by reference herein. Other methods of nucleic acid analysis can be used to detect polymorphisms in a nucleic acid described herein, or variants encoded by a nucleic acid described herein. Representative methods include direct manual sequencing (Church and Gilbert, *Proc. Natl. Acad. Sci. USA* 81:1991-1995 (1988); Sanger, F. et al., *Proc. Natl. Acad. Sci., USA* 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V. C. et al., *Proc. Natl. Acad. Sci. USA* 86:232-236 (1989)), mobility shift analysis (Orita, M. et al., *Proc. Natl. Acad. Sci. USA* 86:2766-2770 (1989)), restriction enzyme analysis (Flavell et al., *Cell* 15:25 (1978); Geever, et al., *Proc. Natl. Acad. Sci. USA* 78:5081 (1981)); heteroduplex analysis; chemical mismatch cleavage (CMC) (Cotton et al., *Proc. Natl. Acad. Sci. USA* 85:4397-4401 (1985)); RNase protection assays (Myers, R. M. et al., *Science* 230:1242 (1985)); use of polypeptides which recognize nucleotide mismatches, such as *E. coli* mutS protein; allele-specific PCR, for example.

In one embodiment of the invention, diagnosis of a susceptibility to a disease or condition associated with FLAP (e.g., MI or stroke) can also be made by expression analysis by quantitative PCR (kinetic thermal cycling). Techniques utilizing TaqMan® can also be used to allow the identification of polymorphisms and whether a patient is homozygous or heterozygous. Techniques can assess the presence of an alteration in the expression or composition of the polypeptide encoded by a FLAP nucleic acid or splicing variants encoded by a FLAP nucleic acid. Further, the expression of the variants can be quantified as physically or functionally different.

In another embodiment of the invention, diagnosis of a susceptibility to MI or stroke (or of another disease or condition associated with FLAP) can also be made by examining expression and/or composition of a FLAP polypeptide, by a variety of methods, including enzyme linked immunosorbent assays (ELISAs), Western blots, immunoprecipitations and immunofluorescence. A test sample from an individual is assessed for the presence of an alteration in the expression and/or an alteration in composition of the polypeptide encoded by a FLAP nucleic acid, or for the presence of a particular variant encoded by a FLAP nucleic acid. An alteration in expression of a polypeptide encoded by a FLAP nucleic acid can be, for example, an alteration in the quantitative polypeptide expression (i.e., the amount of polypeptide produced); an alteration in the composition of a polypeptide encoded by a FLAP nucleic acid is an alteration in the qualitative polypeptide expression (e.g., expression of an altered FLAP polypeptide or of a different splicing variant). In a preferred embodiment, diagnosis of a susceptibility to a disease or condition associated with FLAP is made by detecting a particular splicing variant encoded by that FLAP variant, or a particular pattern of splicing variants.

Both such alterations (quantitative and qualitative) can also be present. An "alteration" in the polypeptide expression or composition, refers to an alteration in expression or composition in a test sample, as compared with the expression or composition of polypeptide by a FLAP nucleic acid in a control sample. A control sample is a sample that corresponds to the test sample (e.g., is from the same type of cells), and is from an individual who is not affected by the disease or a susceptibility to a disease or condition associated with a FLAP nucleic acid. An alteration in the expression or composition of the polypeptide in the test sample, as compared with the control sample, is indicative of a susceptibility to a disease or condition associated with FLAP (e.g., MI or stroke). Similarly, the presence of one or more different splicing variants in the test sample, or the presence of significantly different amounts of different splicing variants in the test sample, as compared with the control sample, is indicative of a susceptibility to a disease or condition associated with a FLAP nucleic acid. Various means of examining expression or composition of the polypeptide encoded by a FLAP nucleic acid can be used, including: spectroscopy, colorimetry, electrophoresis, isoelectric focusing and immunoassays (e.g., David et al., U.S. Pat. No. 4,376,110) such as immunoblotting (see also *Current Protocols in Molecular Biology*, particularly Chapter 10). For example, in one embodiment, an antibody capable of binding to the polypeptide (e.g., as described above), preferably an antibody with a detectable label, can be used. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. Western blotting analysis, using an antibody as described above that specifically binds to a polypeptide encoded by an altered FLAP (e.g., by a FLAP having a SNP as shown in Table 13), or an antibody that specifically binds to a polypeptide encoded by a non-altered nucleic acid, or an antibody that specifically binds to a particular splicing variant encoded by a nucleic acid, can be used to identify the presence in a test sample of a particular splicing variant or of a polypeptide encoded by a polymorphic or altered FLAP, or the absence in a test sample of a particular splicing variant or of a polypeptide encoded by a non-polymorphic or non-altered nucleic acid. The presence of a polypeptide encoded by a polymorphic or altered nucleic acid, or the absence of a polypeptide encoded by a non-polymorphic or non-altered nucleic acid, is diagnostic for a susceptibility to a disease or condition associated with FLAP, as is the presence (or absence) of particular splicing variants encoded by the FLAP nucleic acid.

In one embodiment of this method, the level or amount of polypeptide encoded by a FLAP nucleic acid in a test sample is compared with the level or amount of the polypeptide encoded by the FLAP in a control sample. A level or amount of the polypeptide in the test sample that is higher or lower than the level or amount of the polypeptide in the control sample, such that the difference is statistically significant, is indicative of an alteration in the expression of the polypeptide encoded by the FLAP, and is diagnostic for disease or condition, or for a susceptibility to a disease or condition, associated with that FLAP. Alternatively, the composition of the polypeptide encoded by a FLAP nucleic acid in a test sample is compared with the composition of the polypeptide encoded by the FLAP in a control sample (e.g., the presence of different splicing variants). A difference in the composition of the polypeptide in the test sample, as compared with the composition of the polypeptide in the control sample, is diagnostic for a susceptibility to a disease or condition associated with that FLAP. In another embodiment, both the level or amount and the composition of the polypeptide can be assessed in the test sample and in the control sample. A difference in the amount or level of the polypeptide in the test sample, compared to the control sample; a difference in composition in the test sample, compared to the control sample; or both a difference in the amount or level, and a difference in the composition, is indicative of a susceptibility to a disease or condition, associated with FLAP (e.g., MI or stroke).

Diagnosis Utilizing at-Risk Haplotypes

The invention further pertains to a method for the diagnosis and identification of susceptibility to myocardial infarction or stroke in an individual, by identifying an at-risk haplotype in FLAP. As used herein, combinations of genetic markers are referred to herein as "haplotypes," and the present invention describes methods whereby detection of particular haplotypes is indicative of a susceptibility to myocardial infarction or stroke. In certain embodiments, the "haplotype" identified in the methods of diagnosis can be a single marker, such as a single nucleotide polymorphism (SNP). In certain other embodiments, the "haplotype" can include more than one marker. The detection of the particular genetic markers that make up the particular haplotypes can be performed by a variety of methods described herein and known in the art. For example, genetic markers can be detected at the nucleic acid level, e.g., by direct sequencing or at the amino acid level if the genetic marker affects the coding sequence of FLAP, e.g., by immunoassays based on antibodies that recognize the FLAP protein or a particular FLAP variant protein.

In one embodiment of the invention, diagnosis of a susceptibility to MI or stroke is made by detecting a haplotype associated with FLAP as described herein. The FLAP-associated haplotypes (e.g., those described in Tables 5, 7, 9, 14 or 15), describe a set of genetic markers ("alleles") associated with FLAP. In a certain embodiment, the haplotype can comprise one or more alleles, two or more alleles, three or more alleles, four or more alleles, or five or more alleles. The genetic markers are particular "alleles" at "polymorphic sites" associated with FLAP. A nucleotide position at which more than one sequence is possible in a population (either a natural population or a synthetic population, e.g., a library of synthetic molecules), is referred to herein as a "polymorphic site". Where a polymorphic site is a single nucleotide in length, the site is referred to as a single nucleotide polymorphism ("SNP"). For example, if at a particular chromosomal location, one member of a population has an adenine and another member of the population has a thymine at the same position, then this position is a polymorphic site, and, more specifically, the polymorphic site is a SNP. Polymorphic sites can allow for differences in sequences based on substitutions, insertions or deletions. Each version of the sequence with respect to the polymorphic site is referred to herein as an "allele" of the polymorphic site. Thus, in the previous example, the SNP allows for both an adenine allele and a thymine allele.

Typically, a reference sequence is referred to for a particular sequence. Alleles that differ from the reference are referred to as "variant" alleles. For example, the reference FLAP sequence is described herein by SEQ ID NO: 1 (genomic) or SEQ ID NO: 3 (mRNA). The term, "variant FLAP", as used herein, refers to a FLAP sequence that differs from SEQ ID NO: 1 or SEQ ID NO: 3, but is otherwise substantially similar. The genetic markers that make up the haplotypes described herein include FLAP variants. The variants of FLAP that are used to determine the haplotypes disclosed herein of the present invention are associated with a susceptibility to MI or stroke. Additional variants can include changes that affect a FLAP polypeptide, as described above.

Haplotypes are a combination of genetic markers, e.g., particular alleles at polymorphic sites. The haplotypes described herein (e.g., in Tables 5, 7, 9, 14 or 15; haplotypes B4, Bs4, B5, B6, A4, A5; HapB) are found more frequently in individuals having MI and/or stroke than in individuals not affected by these diseases. Therefore, these haplotypes have predictive value for detecting susceptibility to MI or stroke in an individual.

In one embodiment, the at-risk haplotype is one which confers a significant risk of MI or stroke. In one embodiment, significance associated with a haplotype is measured by an odds ratio. In a further embodiment, the significance is measured by a percentage. In one embodiment, a significant risk is measured as an odds ratio of at least about 1.2, including by not limited to: 1.2, 1.3, 1.4, 1.5, 1.6, 1.7, 1.8 and 1.9. In a further embodiment, an odds ratio of at least 1.2 is significant. In a further embodiment, an odds ratio of at least about 1.5 is significant. In a further embodiment, a significant increase in risk is at least about 1.7 is significant. In a further embodiment, a significant increase in risk is at least about 20%, including but not limited to about 25%, 30%, 35%, 40%, 45%, 50%, 55%, 60%, 65%, 70%, 75%, 80%, 85%, 90%, 95%, and 98%. In a further embodiment, a significant increase in risk is at least about 50%. It is understood however, that identifying whether a risk is medically significant may also depend on a variety of factors, including the specific disease, the haplotype, and often, environmental factors.

The invention also pertains to methods of diagnosing a susceptibility to myocardial infarction or stroke in an individual, comprising screening for an at-risk haplotype in the FLAP nucleic acid that is more frequently present in an individual susceptible to myocardial infarction or stroke (affected), compared to the frequency of its presence in a healthy individual (control), wherein the presence of the haplotype is indicative of susceptibility to myocardial infarction or stroke. As an example of a simple test for correlation would be a Fisher-exact test on a two by two table. Given a cohort of chromosomes the two by two table is constructed out of the number of chromosomes that include both of the haplotypes, one of the haplotype but not the other and neither of the haplotypes.

In certain embodiments, the screening for the presence of an at-risk haplotype comprises screening for an at-risk haplotype within or near FLAP that significantly correlates with a haplotype such as a haplotype shown in Table 5; a haplotype shown in Table 7; a haplotype shown in Table 9; a haplotype shown in Table 14; a haplotype shown in Table 15; haplotype B4; haplotype Bs4; haplotype B5; haplotype B6; haplotype A4; haplotype A5; or haplotype HapB. In other embodiments, screening for the presence of an at-risk haplotype comprises screening for an at-risk haplotype within or near FLAP that significantly correlates with susceptibility to myocardial infarction or stroke.

In one particular embodiment, the at-risk haplotype is characterized by the presence of polymorphism(s) represented in Table 13. For example, SG13S99, where the SNP can be a "C" or a "T"; SG13S25, where the SNP can be a "G" or an "A"; SG13S377, where the SNP can be a "G" or an "A"; SG13S106, where the SNP can be a "G" or an "A"; SG13S114, where the SNP can be a "T" or an "A"; SG13S89, where the SNP can be a "G" or an "A"; SG13S30, where the SNP can be a "G" or a "T"; SG13S32, where the SNP can be a "C" or an "A"; SG13S42, where the SNP can be a "G" or an "A"; and SG13S35, where the SNP can be a "G" or an "A". In another embodiment, the at-risk haplotype is selected from the group consisting of: haplotype B4, Bs4, B5, B6, A4 and A5. The at-risk haplotype can also comprise a combination of the markers in the haplotypes B4, BS4, B5, B6, A4 and/or A5. In further embodiments, the at-risk haplotype can be haplotype HapB. In other embodiments, the at-risk haplotype comprises a polymorphism shown in any one of Tables 5, 7, 9, 14 or 15.

Standard techniques for genotyping for the presence of SNPs and/or microsatellite markers that are associated with myocardial infarctionor stroke can be used, such as fluorescent based techniques (Chen, et al., *Genome Res.* 9, 492 (1999), PCR, LCR, Nested PCR and other techniques for nucleic acid amplification. In a preferred embodiment, the method comprises assessing in an individual the presence or frequency of SNPs and/or microsatellites in the FLAP nucleic acid that are associated with myocardial infarction or stroke, wherein an excess or higher frequency of the SNPs and/or microsatellites compared to a healthy control individual is indicative that the individual is susceptible to myocardial infarction or stroke.

Haplotype analysis involves defining a candidate susceptibility locus using LOD scores. The defined regions are then ultra-fine mapped with microsatellite markers with an average spacing between markers of less than 100 kb. All usable microsatellite markers that found in public databases and mapped within that region can be used. In addition, microsatellite markers identified within the deCODE genetics sequence assembly of the human genome can be used.

The frequencies of haplotypes in the patient and the control groups using an expectation-maximization algorithm can be estimated (Dempster A. et al., 1977. *J. R. Stat. Soc. B*, 39:1-389). An implementation of this algorithm that can handle missing genotypes and uncertainty with the phase can be used. Under the null hypothesis, the patients and the controls are assumed to have identical frequencies. Using a likelihood approach, an alternative hypothesis where a candidate at-risk-haplotype, which can include the FLAP SNPs, is allowed to have a higher frequency in patients than controls, while the ratios of the frequencies of other haplotypes are assumed to be the same in both groups is tested. Likelihoods are maximized separately under both hypotheses and a corresponding 1-df likelihood ratio statistic is used to evaluate the statistic significance.

To look for at-risk-haplotypes in the 1-lod drop, for example, association of all possible combinations of genotyped markers is studied, provided those markers span a practical region. The combined patient and control groups can be randomly divided into two sets, equal in size to the original group of patients and controls. The haplotype analysis is then repeated and the most significant p-value registered is determined. This randomization scheme can be repeated, for example, over 100 times to construct an empirical distribution of p-values. In a preferred embodiment, a p-value of <0.05 is indicative of an at-risk haplotype.

A detailed discussion of haplotype analysis follows.

Haplotype Analysis

Our general approach to haplotype analysis involves using likelihood-based inference applied to NEsted MOdels. The method is implemented in our program NEMO, which allows for many polymorphic markers, SNPs and microsatellites. The method and software are specifically designed for case-control studies where the purpose is to identify haplotype groups that confer different risks. It is also a tool for studying LD structures.

When investigating haplotypes constructed from many markers, apart from looking at each haplotype individually, meaningful summaries often require putting haplotypes into groups. A particular partition of the haplotype space is a model that assumes haplotypes within a group have the same risk, while haplotypes in different groups can have different risks. Two models/partitions are nested when one, the alternative model, is a finer partition compared to the other, the null model, i.e, the alternative model allows some haplotypes assumed to have the same risk in the null model to have different risks. The models are nested in the classical sense that the null model is a special case of the alternative model. Hence traditional generalized likelihood ratio tests can be used to test the null model against the alternative model. Note that, with a multiplicative model, if haplotypes $h_i$ and $h_j$ are assumed to have the same risk, it corresponds to assuming that $f_i/p_i = f_j/p_j$ where f and p denote haplotype frequencies in the affected population and the control population respectively.

One common way to handle uncertainty in phase and missing genotypes is a two-step method of first estimating haplotype counts and then treating the estimated counts as the exact counts, a method that can sometimes be problematic (e.g., see the information measure section below) and may require randomization to properly evaluate statistical significance. In NEMO, maximum likelihood estimates, likelihood ratios and p-values are calculated directly, with the aid of the EM algorithm, for the observed data treating it as a missing-data problem.

NEMO allows complete flexibility for partitions. For example, the first haplotype problem described in the Methods section on Statistical analysis considers testing whether $h_1$ has the same risk as the other haplotypes $h_2, \ldots, h_k$. Here the alternative grouping is $[h_1]$, $[h_2, \ldots, h_k]$ and the null grouping is $[h_1, \ldots, h_k]$. The second haplotype problem in the same section involves three haplotypes $h_1=G0$, $h_2=GX$ and $h_3=AX$, and the focus is on comparing $h_1$ and $h_2$. The alternative grouping is $[h_1]$, $[h_2]$, $[h_3]$ and the null grouping is $[h_1, h_2]$, $[h_3]$. If composite alleles exist, one could collapse these alleles into one at the data processing stage, and performed the test as described. This is a perfectly valid approach, and indeed, whether we collapse or not makes no difference if there were no missing information regarding phase. But, with the actual data, if each of the alleles making up a composite correlates differently with the SNP alleles, this will provide some partial information on phase. Collapsing at the data processing stage will unnecessarily increase the amount of missing information. A nested-models/partition framework can be used in this scenario. Let $h_2$ be split into $h_{2a}, h_{2b}, \ldots, h_{2e}$, and $h_3$ be split into $h_{3a}, h_{3b}, \ldots, h_{3e}$. Then the alternative grouping is $[h_1]$, $[h_{2a}, h_{2b}, \ldots, h_{2e}]$, $[h_{3a}, h_{3b}, \ldots, h_{3e}]$ and the null grouping is $[h_1, h_{2a}, h_{2b}, \ldots, h_{2e}]$, $[h_{3a}, h_{3b}, \ldots, h_{3e}]$. The same method can be used to handle composite where collapsing at the data processing stage is not even an option since $L_C$ represents multiple haplotypes constructed from multiple SNPs. Alternatively, a 3-way test with the alternative grouping of $[h_1]$, $[h_{2a}, h_{2b}, \ldots, h_{2e}]$, $[h_{3a}, h_{3b}, \ldots, h_{3e}]$ versus the null grouping of $[h_1, h_{2a}, h_2b \ldots, h_{2e}, h_{3a}, h_{3b}, \ldots, h_{3e}]$ could also be performed. Note that the generalized likelihood ratio test-statistic would have two degrees of freedom instead of one.

Measuring Information

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. Interestingly, one can measure information loss by considering a two-step procedure to evaluating statistical significance that appears natural but happens to be systematically anti-conservative. Suppose we calculate the maximum likelihood estimates for the population haplotype frequencies calculated under the alternative hypothesis that there are differences between the affected population and control population, and use these frequency estimates as estimates of the observed frequencies of haplotype counts in the affected sample and in the control sample. Suppose we then perform a likelihood ratio test treating these estimated haplotype counts as though they are the actual counts. We could also perform a Fisher's exact test, but we would then need to round off these estimated counts since they are in general non-integers. This test will in general be anti-conservative because treating the estimated counts as if they were exact counts ignores the uncertainty with the counts, overestimates the effective sample size and underestimates the sampling variation. It means that the chi-square likelihood-ratio test statistic calculated this way, denoted by $\Lambda^*$, will in general be bigger than $\Lambda$, the likelihood-ratio test-statistic calculated directly from the observed data as described in methods. But $\Lambda^*$ is useful because the ratio $\Lambda/\Lambda^*$ happens to be a good measure of information, or $1-(\Lambda/\Lambda^*)$ is a measure of the fraction of information lost due to missing information. This information measure for haplotype analysis is described in Nicolae and Kong, Technical Report 537, Department of Statistics, University of Statistics, University of Chicago, Revised for *Biometrics* (2003) as a natural extension of information measures defined for linkage analysis, and is implemented in NEMO.

Statistical Analysis.

For single marker association to the disease, the Fisher exact test can be used to calculate two-sided p-values for each individual allele. All p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families for the linkage analysis, first and second-degree relatives can be eliminated from the patient list. Furthermore, the test can be repeated for association correcting for any remaining relatedness among the patients, by extending a variance adjustment procedure (e.g., as described in Risch, N. & Teng, J., "The relative power of family-based and case-control designs for linkage disequilibrium studies of complex human diseases I. DNA pooling," *Genome Res.* 8:1278-1288 (1998)) for sibships so that it can be applied to general familial relationships, and present both adjusted and unadjusted p-values for comparison. The differences are in general very small as expected. To assess the significance of single-marker association corrected for multiple testing we carried out a randomisation test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model), (Terwilliger, J. D. & Ott, J., *Hum Hered*, 42, 337-46 (1992) and Falk, C. T. & Rubinstein, P, *Ann Hum Genet* 51 (Pt 3), 227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes $h_i$ and $h_j$, risk($h_i$)/risk($h_j$)=($f_i/p_i$)/($f_j/p_j$), where f and p denote respectively frequencies in the affected population and in the control population. While there is some power loss if the true model is not multiplicative, the loss tends to be mild except for extreme cases. Most importantly, p-values are always valid since they are computed with respect to null hypothesis.

In general, haplotype frequencies are estimated by maximum likelihood and tests of differences between cases and controls are performed using a generalized likelihood ratio test (Rice, J. A. *Mathematical Statistics and Data Analysis*, 602 (International Thomson Publishing, (1995)). deCODE's haplotype analysis program called NEMO, which stands for NEsted MOdels, can be used to calculate all the haplotype results. To handle uncertainties with phase and missing genotypes, it is emphasized that we do not use a common two-step approach to association tests, where haplotype counts are first estimated, possibly with the use of the EM algorithm, Dempster, (A. P., Laird, N. M. & Rubin, D. B., *Journal of the Royal Statistical Society B*, 39, 1-38 (1971)) and then tests are performed treating the estimated counts as though they are true counts, a method that can sometimes be problematic and may require randomisation to properly evaluate statistical significance. Instead, with NEMO, maximum likelihood estimates, likelihood ratios and p-values are computed with the aid of the EM-algorithm directly for the observed data, and hence the loss of information due to uncertainty with phase and missing genotypes is automatically captured by the likelihood ratios. Even so, it is of interest to know how much information is retained, or lost, due to incomplete information. Described herein is such a measure that is natural under the likelihood framework. For a fixed set of markers, the simplest tests performed compare one selected haplotype against all the others. Call the selected haplotype $h_1$ and the others $h_2, \ldots, h_k$. Let $p_1, \ldots, p_k$ denote the population frequencies of the haplotypes in the controls, and $f_1, \ldots, f_k$ denote the population frequencies of the haplotypes in the affecteds. Under the null hypothesis, $f_i = p_i$ for all i. The alternative model we use for the test assumes $h_2, \ldots, h_k$ to have the same risk while $h_1$ is allowed to have a different risk. This implies that while $p_1$ can be different from $f_1$, $f_i/(f_2+\ldots+f_k)=p_i/(p_2+\ldots+p_k)=\beta_i$ for i=2, ..., k. Denoting $f_1/p_1$ by r, and noting that $\beta_2+\ldots+\beta_k=1$, the test statistic based on generalized likelihood ratios is $$\Lambda = 2[l(\hat{r}, \hat{p}_1, \hat{\beta}_2, \ldots, \hat{\beta}_{k-1}) - l(1, \tilde{p}_1, \tilde{\beta}_2, \ldots, \tilde{\beta}_{k-1})]$$

where l denotes $\log_e$ likelihood and and ^ denote maximum likelihood estimates under the null hypothesis and alternative hypothesis respectively. $\Lambda$ has asymptotically a chi-square distribution with 1-df, under the null hypothesis. Slightly more complicated null and alternative hypotheses can also be used. For example, let $h_1$ be G0, $h_2$ be GX and $h_3$ be AX. When comparing G0 against GX, i.e., this is the test which gives estimated RR of 1.46 and p-value=0.0002, the null assumes G0 and GX have the same risk but AX is allowed to have a different risk. The alternative hypothesis allows, for example, three haplotype groups to have different risks. This implies that, under the null hypothesis, there is a constraint that $f_1/p_1 = f_2/p_2$, or $w=[f_1/p_1]/[f_2/p_2]=1$. The test statistic based on generalized likelihood ratios is $$\Lambda = 2[l(\hat{p}_1, \hat{f}_1, \hat{p}_2, \hat{w}) - l(\tilde{p}_1, \tilde{f}_1, \tilde{p}_2, 1)]$$

that again has asymptotically a chi-square distribution with 1-df under the null hypothesis. If there are composite haplotypes (for example, $h_2$ and $h_3$), that is handled in a natural manner under the nested models framework.

LD between pairs of SNPs can be calculated using the standard definition of D' and $R^2$ (Lewontin, R., *Genetics* 49, 49-67 (1964) and Hill, W. G. & Robertson, A. *Theor. Appl. Genet.* 22, 226-231 (1968)). Using NEMO, frequencies of the two marker allele combinations are estimated by maximum likelihood and deviation from linkage equilibrium is evaluated by a likelihood ratio test. The definitions of D' and $R^2$ are extended to include microsatellites by averaging over the values for all possible allele combination of the two markers weighted by the marginal allele probabilities. When plotting all marker combination to elucidate the LD structure in a particular region, we plot D' in the upper left corner and the p-value in the lower right corner. In the LD plots the markers can be plotted equidistant rather than according to their physical location, if desired.

Statistical Methods for Linkage Analysis

Multipoint, affected-only allele-sharing methods can be used in the analyses to assess evidence for linkage. Results, both the LOD-score and the non-parametric linkage (NPL) score, can be obtained using the program Allegro (Gudbjartsson et al., *Nat. Genet.* 25:12-3, 2000). Our baseline linkage analysis uses the $S_{pairs}$ scoring function (Whittemore, A. S., Halpern, J. (1994), *Biometrics* 50:118-27; Kruglyak L, et al. (1996), *Am J Hum Genet* 58:1347-63), the exponential allele-sharing model (Kong, A. and Cox, N. J. (1997), *Am J Hum Genet* 61:1179-88) and a family weighting scheme that is halfway, on the log-scale, between weighting each affected pair equally and weighting each family equally. The information measure we use is part of the Allegro program output and the information value equals zero if the marker genotypes are completely uninformative and equals one if the genotypes determine the exact amount of allele sharing by decent among the affected relatives (Gretarsdottir et al., *Am. J. Hom. Genet,* 70:593-603, (2002)). We computed the P-values two different ways and here report the less significant result. The first P-value can be computed on the basis of large sample theory; the distribution of $Z_{lr} = \sqrt{(2[\log_e(10)\text{LOD}])}$ approximates a standard normal variable under the null hypothesis of no linkage (Kong, A. and Cox, N. J. (1997), *Am J Hum Genet* 61:1179-88). The second P-value can be calculated by comparing the observed LOD-score with its complete data sampling distribution under the null hypothesis (e.g., Gudbjartsson et al., *Nat. Genet.* 25:12-3, 2000). When the data consist of more than a few families, these two P-values tend to be very similar.

Kits

Kits (e.g., reagent kits) useful in the methods of diagnosis comprise components useful in any of the methods described herein, including for example, hybridization probes or primers as described herein (e.g., labeled probes or primers), reagents for detection of labeled molecules, restriction enzymes (e.g., for RFLP analysis), allele-specific oligonucleotides, antibodies which bind to altered or to non-altered (native) FLAP polypeptide, means for amplification of nucleic acids comprising a FLAP, or means for analyzing the nucleic acid sequence of a nucleic acid described herein, or for analyzing the amino acid sequence of a polypeptide as described herein, etc. In one embodiment, a kit for diagnosing susceptibility to MI or stroke can comprise primers for nucleic acid amplification of a region in the FLAP nucleic acid comprising an at-risk haplotype that is more frequently present in an individual having MI or stroke or susceptible to MI or stroke. The primers can be designed using portions of the nucleic acids flanking SNPs that are indicative of MI or stroke. In a particularly preferred embodiment, the primers are designed to amplify regions of the FLAP nucleic acid associated with an at-risk haplotype for MI or stroke, or more particularly the haplotypes defined by the following SNPs: SG13S99, SG13S25, SG13S377, SG13S106, SG13S114, SG13S89, SG13S30, SG13S32, SG13S42, and SG13S35, at the locus on chromosome 13q12-13. In other preferred embodiments, the primers are designed to amplify regions of the FLAP nucleic acid associated with a haplotype such as haplotype B4, Bs4, B5, B6, A4, A5, HapB, a haplotype shown in Table 5, and/or a haplotype shown in Table 7, and/or a haplotype shown in Table 9, and/or a haplotype shown in Table 14, and/or a haplotype shown in Table 15.

Diagnosis of Flap-Related Disease

Although the methods of diagnosis above have been described in the context of diagnosing susceptibility to MI or stroke, the methods can also be used to identify FLAP-associated MI and/or stroke. For example, individuals who have experienced MI and/or stroke can be assessed to determine whether the presence in'the individual of a polymorphism in a FLAP nucleic acid, or the presence of an at-risk haplotype in the individual, as described above, could have been a contributing factor to the MI and/or stroke. As used herein, the terms, "FLAP-associated MI" and "FLAP-associated stroke," refer to the occurrence of an MI or stroke in an individual who has a polymorphism in a FLAP nucleic acid or an at-risk FLAP haplotype. Identification of FLAP-associated MI or stroke facilitates treatment planning, as treatment can be designed and therapeutics selected to target components of the FLAP pathway.

In one embodiment of the invention, diagnosis of FLAP-associated MI or stroke, is made by detecting a polymorphism in a FLAP nucleic acid as described herein. A polymorphism in a FLAP nucleic acid is described above. A test sample of genomic DNA, RNA, or cDNA, is obtained from an individual who has had at least one MI and/or stroke, to determine whether the MI or stroke is FLAP-associated. The DNA, RNA, or cDNA sample is then examined to determine whether a polymorphism in a nucleic acid is present, and/or to determine which splicing variant(s) encoded by the FLAP is present. If the FLAP nucleic acid has the polymorphism, or is the splicing variant associated with disease, then the presence of the polymorphism or the splicing variant is indicative of FLAP-associated MI or stroke.

For example, in one embodiment, hybridization methods, such as Southern analysis, Northern analysis, or in situ hybridizations, can be used to detect the polymorphism. In other embodiments, mutation analysis by restriction digestion or sequence analysis can also be used, as can allele-specific oligonucleotides, or quantitative PCR (kinetic thermal cycling). Diagnosis of FLAP-associated MI or stroke can also be made by examining expression and/or composition of a FLAP polypeptide, by a variety of methods, including enzyme linked immunosorbent assays (ELISAs), Western blots, immunoprecipitations and immunofluorescence. A test sample from an individual is assessed for the presence of an alteration in the expression and/or an alteration in composition of the polypeptide encoded by a FLAP nucleic acid, or for the presence of a particular variant encoded by a FLAP nucleic acid. An alteration in expression of a polypeptide encoded by a FLAP nucleic acid can be, for example, an alteration in the quantitative polypeptide expression (i.e., the amount of polypeptide produced); an alteration in the composition of a polypeptide encoded by a FLAP nucleic acid is an alteration in the qualitative polypeptide expression (e.g., expression of an altered FLAP polypeptide or of a different splicing variant).

In other embodiments, the invention pertains to a method for the diagnosis and identification of FLAP-associated myocardial infarction or stroke in an individual, by identifying the presence of an at-risk haplotype in FLAP as described in detail herein. For example, the haplotypes described herein in Tables 14 and 15, are found more frequently in individuals having MI, or stroke than in individuals not affected by these diseases. Therefore, these haplotypes have predictive value for detecting FLAP-associated MI or stroke in an individual. In certain embodiments, an at-risk haplotype is characterized by the presence of polymorphism(s) shown in Table 13. In other embodiments, the at-risk haplotype is selected from the group consisting of: haplotype B4, Bs4, B5, B6, A4 and A5. The at-risk haplotype can also comprise a combination of the markers in the haplotypes B4, Bs4, B5, B6, A4 and/or A5. In further embodiments, the at-risk haplotype can be haplotype HapB. The methods described herein can be used to assess a sample from an individual for the presence or absence of an at-risk haplotype; the presence of an at-risk haplotype is indicative of FLAP-associated MI or stroke.

In representative embodiments of the invention, a method of diagnosing FLAP-associated myocardial infarction or stroke in an individual who has had a myocardial infarction and/or a stroke, comprises detecting a polymorphism in a FLAP nucleic acid, wherein the presence of the polymorphism in the nucleic acid is indicative of FLAP-associated myocardial infarction or stroke. Alternatively, a method of diagnosing FLAP-associated myocardial infarction or stroke in an individual who has had a myocardial infarction and/or a stroke, comprises detecting an alteration in the expression or composition of a polypeptide encoded by a FLAP nucleic acid in a test sample, in comparison with the expression or composition of a polypeptide encoded by a FLAP nucleic acid in a control sample, wherein the presence of an alteration in expression or composition of the polypeptide in the test sample is indicative of FLAP-associated myocardial infarction or stroke. In addition, a method of diagnosing FLAP-associated myocardial infarction or stroke in an individual who has had a myocardial infarction and/or a stroke, comprises determining the presence or absence in the individual of a haplotype selected from haplotypes shown in Table 5, haplotypes shown in Table 7, haplotypes shown in Table 9, haplotypes shown in Table 14, and haplotypes shown in Table 15, wherein the presence of the haplotype is diagnostic of FLAP-associated myocardial infarction or stroke. Also, a method of diagnosing FLAP-associated myocardial infarction or stroke in an individual who has had a myocardial infarction and/or a stroke, comprises determining the presence or absence in the individual of haplotype B4, Bs4, B5, B6, A4, A5, or HapB, wherein the presence of the haplotype is diagnostic of FLAP-associated myocardial infarction or stroke.

SCREENING ASSAYS AND AGENTS IDENTIFIED THEREBY

The invention provides methods (also referred to herein as "screening assays") for identifying the presence of a nucleotide that hybridizes to a nucleic acid of the invention, as well as for identifying the presence of a polypeptide encoded by a nucleic acid of the invention. In one embodiment, the presence (or absence) of a nucleic acid molecule of interest (e.g., a nucleic acid that has significant homology with a nucleic acid of the invention) in a sample can be assessed by contacting the sample with a nucleic acid comprising a nucleic acid of the invention (e.g., a nucleic acid having the sequence of one of SEQ ID NOs: 1 or 3 or the complement thereof, or a nucleic acid encoding an amino acid having the sequence of SEQ ID NO: 2, or a fragment or variant of such nucleic acids), under stringent conditions as described above, and then assessing the sample for the presence (or absence) of hybridization. In a preferred embodiment, high stringency conditions are conditions appropriate for selective hybridization. In another embodiment, a sample containing a nucleic acid molecule of interest is contacted with a nucleic acid containing a contiguous nucleic acid sequence (e.g., a primer or a probe as described above) that is at least partially complementary to a part of the nucleic acid molecule of interest (e.g., a FLAP nucleic acid), and the contacted sample is assessed for the presence or absence of hybridization. In a preferred embodiment, the nucleic acid containing a contiguous nucleic acid sequence is completely complementary to a part of the nucleic acid molecule of interest.

In any of these embodiments, all or a portion of the nucleic acid of interest can be subjected to amplification prior to performing the hybridization.

In another embodiment, the presence (or absence) of a polypeptide of interest, such as a polypeptide of the invention or a fragment or variant thereof, in a sample can be assessed by contacting the sample with an antibody that specifically hybridizes to the polypeptide of interest (e.g., an antibody such as those described above), and assessing the sample for the presence (or absence) of binding of the antibody to the polypeptide of interest.

In another embodiment, the invention provides methods for identifying agents (e.g., fusion proteins, polypeptides, peptidomimetics, prodrugs, receptors, binding agents, antibodies, small molecules or other drugs, or ribozymes which alter (e.g., increase or decrease) the activity of the polypeptides described herein, or which otherwise interact with the polypeptides herein. For example, such agents can be agents which bind to polypeptides described herein (e.g., binding agent for members of the leukotriene pathway, such as FLAP binding agents); which have a stimulatory or inhibitory effect on, for example, activity of polypeptides of the invention; or which change (e.g., enhance or inhibit) the ability of the polypeptides of the invention to interact with members of the leukotriene pathway binding agents (e.g., receptors or other binding agents); or which alter posttranslational processing of the leukotriene pathway member polypeptide, such as a FLAP polypeptide (e.g., agents that alter proteolytic processing to direct the polypeptide from where it is normally synthesized to another location in the cell, such as the cell surface; agents that alter proteolytic processing such that more polypeptide is released from the cell, etc.)

In one embodiment, the invention provides assays for screening candidate or test agents that bind to or modulate the activity of polypeptides described herein (or biologically active portion(s) thereof), as well as agents identifiable by the assays. Test agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S., *Anticancer Drug Des.* 12:145 (1997)).

In one embodiment, to identify agents which alter the activity of a FLAP polypeptide, a cell, cell lysate, or solution containing or expressing a FLAP polypeptide (e.g., SEQ ID NO: 2 or another splicing variant encoded by a FLAP nucleic acid, such as a nucleic acid comprising a SNP as shown in Table 13), or a fragment or derivative thereof (as described above), can be contacted with an agent to be tested; alternatively, the polypeptide can be contacted directly with the agent to be tested. The level (amount) of FLAP activity is assessed (e.g., the level (amount) of FLAP activity is measured, either directly or indirectly), and is compared with the level of activity in a control (i.e., the level of activity of the FLAP polypeptide or active fragment or derivative thereof in the absence of the agent to be tested). If the level of the activity in the presence of the agent differs, by an amount that is statistically significant, from the level of the activity in the absence of the agent, then the agent is an agent that alters the activity of a FLAP polypeptide. An increase in the level of FLAP activity in the presence of the agent relative to the activity in the absence of the agent, indicates that the agent is an agent that enhances (is an agonist of) FLAP activity. Similarly, a decrease in the level of FLAP activity in the presence of the agent, relative to the activity in the absence of the agent, indicates that the agent is an agent that inhibits (is an antagonist of) FLAP activity. In another embodiment, the level of activity of a FLAP polypeptide or derivative or fragment thereof in the presence of the agent to be tested, is compared with a control level that has previously been established. A statistically significant difference in the level of the activity in the presence of the agent from the control level indicates that the agent alters FLAP activity.

The present invention also relates to an assay for identifying agents which alter the expression of a FLAP nucleic acid (e.g., antisense nucleic acids, fusion proteins, polypeptides, peptidomimetics, prodrugs, receptors, binding agents, antibodies, small molecules or other drugs, or ribozymes; which alter (e.g., increase or decrease) expression (e.g., transcription or translation) of the nucleic acid or which otherwise interact with the nucleic acids described herein, as well as agents identifiable by the assays. For example, a solution containing a nucleic acid encoding a FLAP polypeptide (e.g., a FLAP nucleic acid) can be contacted with an agent to be tested. The solution can comprise, for example, cells containing the nucleic acid or cell lysate containing the nucleic acid;

alternatively, the solution can be another solution that comprises elements necessary for transcription/translation of the nucleic acid. Cells not suspended in solution can also be employed, if desired. The level and/or pattern of FLAP expression (e.g., the level and/or pattern of mRNA or of protein expressed, such as the level and/or pattern of different splicing variants) is assessed, and is compared with the level and/or pattern of expression in a control (i.e., the level and/or pattern of the FLAP expression in the absence of the agent to be tested). If the level and/or pattern in the presence of the agent differ, by an amount or in a manner that is statistically significant, from the level and/or pattern in the absence of the agent, then the agent is an agent that alters the expression of the FLAP nucleic acid. Enhancement of FLAP expression indicates that the agent is an agonist of FLAP activity. Similarly, inhibition of FLAP expression indicates that the agent is an antagonist of FLAP activity.

In another embodiment, the level and/or pattern of FLAP polypeptide(s) (e.g., different splicing variants) in the presence of the agent to be tested, is compared with a control level and/or pattern that have previously been established. A level and/or pattern in the presence of the agent that differs from the control level and/or pattern by an amount or in a manner that is statistically significant indicates that the agent alters FLAP expression.

In another embodiment of the invention, agents which alter the expression of a FLAP nucleic acid or which otherwise interact with the nucleic acids described herein, can be identified using a cell, cell lysate, or solution containing a nucleic acid encoding the promoter region of the FLAP nucleic acid operably linked to a reporter gene. After contact with an agent to be tested, the level of expression of the reporter gene (e.g., the level of mRNA or of protein expressed) is assessed, and is compared with the level of expression in a control (i.e., the level of the expression of the reporter gene in the absence of the agent to be tested). If the level in the presence of the agent differs, by an amount or in a manner that is statistically significant, from the level in the absence of the agent, then the agent is an agent that alters the expression of the FLAP nucleic acid, as indicated by its ability to alter expression of a nucleic acid that is operably linked to the FLAP nucleic acid promoter.

Enhancement of the expression of the reporter indicates that the agent is an agonist of FLAP activity. Similarly, inhibition of the expression of the reporter indicates that the agent is an antagonist of FLAP activity. In another embodiment, the level of expression of the reporter in the presence of the test agent, is compared with a control level that has previously been established. A level in the presence of the agent that differs from the control level by an amount or in a manner that is statistically significant indicates that the agent alters expression.

Agents which alter the amounts of different splicing variants encoded by a FLAP nucleic acid (e.g., an agent which enhances activity of a first splicing variant, and which inhibits activity of a second splicing variant), as well as agents which are agonists of activity of a first splicing variant and antagonists of activity of a second splicing variant, can easily be identified using these methods described above.

In other embodiments of the invention, assays can be used to assess the impact of a test agent on the activity of a polypeptide relative to a FLAP binding agent. For example, a cell that expresses a compound that interacts with a FLAP nucleic acid (herein referred to as a "FLAP binding agent", which can be a polypeptide or other molecule that interacts with a FLAP nucleic acid, such as a receptor, or another molecule, such as 5-LO) is contacted with a FLAP in the presence of a test agent, and the ability of the test agent to alter the interaction between the FLAP and the FLAP binding agent is determined. Alternatively, a cell lysate or a solution containing the FLAP binding agent can be used. An agent which binds to the FLAP or the FLAP binding agent can alter the interaction by interfering with, or enhancing the ability of the FLAP to bind to, associate with, or otherwise interact with the FLAP binding agent. Determining the ability of the test agent to bind to a FLAP nucleic acid or a FLAP nucleic acid binding agent can be accomplished, for example, by coupling the test agent with a radioisotope or enzymatic label such that binding of the test agent to the polypeptide can be determined by detecting the labeled with $^{125}I$, $^{35}S$, $^{14}C$ or $^{3}H$, either directly or indirectly, and the radioisotope detected by direct counting of radioemmission or by scintillation counting. Alternatively, test agents can be enzymatically labeled with, for example, horseradish peroxidase, alkaline phosphatase, or luciferase, and the enzymatic label detected by determination of conversion of an appropriate substrate to product. It is also within the scope of this invention to determine the ability of a test agent to interact with the polypeptide without the labeling of any of the interactants. For example, a microphysiometer can be used to detect the interaction of a test agent with a FLAP or a FLAP binding agent without the labeling of either the test agent, FLAP, or the FLAP binding agent. McConnell, H. M. et al., Science 257:1906-1912 (1992). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between ligand and polypeptide.

Thus, these receptors can be used to screen for compounds that are agonists for use in treating a disease or condition associated with FLAP or a susceptibility to a disease or condition associated with FLAP, or antagonists for studying a susceptibility to a disease or condition associated with FLAP (e.g., MI or stroke). Drugs can be designed to regulate FLAP activation, that in turn can be used to regulate signaling pathways and transcription events of genes downstream or of proteins or polypeptides interacting with FLAP (e.g., 5-LO).

In another embodiment of the invention, assays can be used to identify polypeptides that interact with one or more FLAP polypeptides, as described herein. For example, a yeast two-hybrid system such as that described by Fields and Song (Fields, S. and Song, O., Nature 340:245-246 (1989)) can be used to identify polypeptides that interact with one or more FLAP polypeptides. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used which includes a nucleic acid encoding a DNA binding domain and also a FLAP polypeptide, splicing variant, or fragment or derivative thereof, and a second vector is used which includes a nucleic acid encoding a transcription activation domain and also a nucleic acid encoding a polypeptide which potentially may interact with the FLAP polypeptide, splicing variant, or fragment or derivative thereof (e.g., a FLAP polypeptide binding agent or receptor). Incubation of yeast containing the first vector and the second vector under appropriate conditions (e.g., mating conditions such as used in the Matchmaker™ system from Clontech (Palo Alto, Calif., USA)) allows identification of colonies that express the markers of interest. These colonies can be examined to identify the polypeptide(s) that interact with the FLAP polypeptide or fragment or derivative thereof. Such polypeptides may be useful as agents that alter the activity of expression of a FLAP polypeptide, as described above.

In more than one embodiment of the above assay methods of the present invention, it may be desirable to immobilize either the FLAP, the FLAP binding agent, or other components of the assay on a solid support, in order to facilitate separation of complexed from uncomplexed forms of one or both of the polypeptides, as well as to accommodate automation of the assay. Binding of a test agent to the polypeptide, or interaction of the polypeptide with a binding agent in the presence and absence of a test agent, can be accomplished in any vessel suitable for containing the reactants. Examples of such vessels include microtitre plates, test tubes, and microcentrifuge tubes. In one embodiment, a fusion protein (e.g., a glutathione-S-transferase fusion protein) can be provided which adds a domain that allows a FLAP nucleic acid or a FLAP binding agent to be bound to a matrix or other solid support.

In another embodiment, modulators of expression of nucleic acid molecules of the invention are identified in a method wherein a cell, cell lysate, or solution containing a nucleic acid encoding a FLAP nucleic acid is contacted with a test agent and the expression of appropriate mRNA or polypeptide (e.g., splicing variant(s)) in the cell, cell lysate, or solution, is determined. The level of expression of appropriate mRNA or polypeptide(s) in the presence of the test agent is compared to the level of expression of mRNA or polypeptide(s) in the absence of the test agent. The test agent can then be identified as a modulator of expression based on this comparison. For example, when expression of mRNA or polypeptide is greater (statistically significantly greater) in the presence of the test agent than in its absence, the test agent is identified as a stimulator or enhancer of the mRNA or polypeptide expression. Alternatively, when expression of the mRNA or polypeptide is less (statistically significantly less) in the presence of the test agent than in its absence, the test agent is identified as an inhibitor of the mRNA or polypeptide expression. The level of mRNA or polypeptide expression in the cells can be determined by methods described herein for detecting mRNA or polypeptide.

In yet another embodiment, the invention provides methods for identifying agents (e.g., fusion proteins, polypeptides, peptidomimetics, prodrugs, receptors, binding agents, antibodies, small molecules or other drugs, or ribozymes) which alter (e.g., increase or decrease) the activity of a member of leukotriene pathway binding agent, such as a FLAP binding agent (e.g., 5-LO), as described herein. For example, such agents can be agents which have a stimulatory or inhibitory effect on, for example, the activity of a member of leukotriene pathway binding agent, such as a FLAP binding agent; which change (e.g., enhance or inhibit) the ability a member of leukotriene pathway binding agents, (e.g., receptors or other binding agents) to interact with the polypeptides of the invention; or which alter posttranslational processing of the member of leukotriene pathway binding agent, (e.g., agents that alter proteolytic processing to direct the member of the leukotriene pathway binding agent from where it is normally synthesized to another location in the cell, such as the cell surface; agents that alter proteolytic processing such that more active binding agent is released from the cell, etc.).

For example, the invention provides assays for screening candidate or test agents that bind to or modulate the activity of a member of the leukotriene pathway (or enzymatically active portion(s) thereof), as well as agents identifiable by the assays. As described above, test agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. *Anticancer Drug Des.*, 12:145 (1997)). In one embodiment, to identify agents which alter the activity of a member of the leukotriene pathway (such as a FLAP binding agent), a cell, cell lysate, or solution containing or expressing a binding agent (e.g., 5-LO, or a leukotriene pathway member receptor), or a fragment (e.g., an enzymatically active fragment) or derivative thereof, can be contacted with an agent to be tested; alternatively, the binding agent (or fragment or derivative thereof) can be contacted directly with the agent to be tested. The level (amount) of binding agent activity is assessed (either directly or indirectly), and is compared with the level of activity in a control (i.e., the level of activity in the absence of the agent to be tested). If the level of the activity in the presence of the agent differs, by an amount that is statistically significant, from the level of the activity in the absence of the agent, then the agent is an agent that alters the activity of the member of the leukotriene pathway. An increase in the level of the activity relative to a control, indicates that the agent is an agent that enhances (is an agonist of) the activity. Similarly, a decrease in the level of activity relative to a control, indicates that the agent is an agent that inhibits (is an antagonist of) the activity. In another embodiment, the level of activity in the presence of the agent to be tested, is compared with a control level that has previously been established. A level of the activity in the presence of the agent that differs from the control level by an amount that is statistically significant indicates that the agent alters the activity.

This invention further pertains to novel agents identified by the above-described screening assays. Accordingly, it is within the scope of this invention to further use an agent identified as described herein in an appropriate animal model. For example, an agent identified as described herein (e.g., a test agent that is a modulating agent, an antisense nucleic acid molecule, a specific antibody, or a polypeptide-binding agent) can be used in an animal model to determine the efficacy, toxicity, or side effects of treatment with such an agent. Alternatively, an agent identified as described herein can be used in an animal model to determine the mechanism of action of such an agent.

Furthermore, this invention pertains to uses of novel agents identified by the above-described screening assays for treatments as described herein. In addition, an agent identified as described herein can be used to alter activity of a polypeptide encoded by a FLAP nucleic acid, or to alter expression of a FLAP nucleic acid, by contacting the polypeptide or the nucleic acid (or contacting a cell comprising the polypeptide or the nucleic acid) with the agent identified as described herein.

The present invention is now illustrated by the following Examples, which are not intended to be limiting in any way.

EXAMPLE 1

MI Susceptibility Gene Mapped to Chromosome 13 and Association Between MI and FLAP Subjects and Methods A genome wide scan of 296 multiplex Icelandic families with 713 MI patients was performed. Through the suggestive linkage to a locus on chromosome 13q12-13, the gene encoding the 5-lipoxygenase activating protein (FLAP) was identified, and a 4-SNP haplotype within the gene was determined to confer a near 2-fold risk of MI and stroke. Male patients showed strongest association to the at-risk haplotype. Independent confirmation of FLAP association to MI was obtained in, a British cohort of patients with sporadic MI. These findings support FLAP as the first specific gene isolated that confers substantial risk of the complex traits of both MI and stroke.

Methods

Study Population

Patients entering the study were recruited from a registry that includes all MIs that occurred before the age of 75 (over 8,000 patients) in Iceland from 1981 to 2000. This registry is a part of the World Health Organization MONICA Project (The World Health Organization MONICA Project, WHO MONICA Project Principal Investigators, *J Clin Epidemiol* 41, 105-14 (1988)). Diagnoses of all patients in the registry followed strict diagnostic rules based on signs, symptoms, electrocardiograms, cardiac enzymes, and necropsy findings.

Genotypes from 713 MI patients and 1741 of their first-degree relatives were used in the linkage analysis. For the microsatellite association study of the MI locus, 802 unrelated MI patients (n=233 females, n=624 males and n=302 early onset) and 837 population-based controls were used. For the SNP association study in and around the FLAP gene 779 unrelated MI patients were genotyped (n=293 females, n=486 males and n=358 early onset). The control group for the SNP association study was population based and comprised of 628 unrelated males and females in the age range of 30-85 years whose medical history was unknown. The stroke cohort used in this study has previously been described (Gretarsdottir, S. et al. *Nat Genet* 35, 131-8 (2003); Gretarsdottir, S. et al., *Am J Hum Genet* 70, 593-603 (2002)). For the stroke linkage analysis, genotypes from 342 male patients with ischemic stroke or TIA that were linked to at least one other male patient within and including 6 meioses in 164 families were used. For the association studies, 702 patients with all forms of stroke (n=329 females and n=373 males) were analysed. Patients with stroke that also had MI were excluded. Controls used for the stroke association studies were the same as used in the MI SNP association study (n=628).

The study was approved by the Data Protection Commission of Iceland and the National Bioethics Committee of Iceland. Informed consent was obtained from all study participants. Personal identifiers associated with medical information and blood samples were encrypted with a third party encryption system as previously described (Gulcher, J. R., Kristjansson, K., Gudbjartsson, H. & Stefansson, K., *Eur J Hum Genet* 8, 739-42 (2000)).

Statistical Analysis

A genome-wide scan was performed as previously described (Gretarsdottir, S. et al. *Am J Hum Genet* 70, 593-603 (2002)), using a set of approximately 1000 microsatellite markers. Multipoint, affected-only allele-sharing methods (Kong, A. & Cox, N. J., *Am J Hum Genet* 61, 1179-88 (1997)) were used to assess the evidence for linkage. All results were obtained using the program Allegro (Gudbjartsson, D. F., Jonasson, K., Frigge, M. L. & Kong, A. Allegro, *Nat Genet* 25, 12-3 (2000)) and the deCODE genetic map (Kong, A. et al., *Nat Genet* 31, 241-7 (2002)). The $S_{pairs}$ scoring function (Whittemore, A. S. & Halpern, J., *Biometrics* 50, 118-27 (1994); Kruglyak, L., Daly, M. J., Reeve-Daly, M. P. & Lander, E. S., *Am J Hum Genet* 58, 1347-63 (1996)) was used, as was the exponential allele-sharing model (Kong, A. & Cox, N. J. *Am J Hum Genet* 61, 1179-88 (1997)) to generate the relevant 1-df (degree of freedom) statistics. When combining the family scores to obtain an overall score, a weighting scheme was used that is halfway on a log scale between weighting each affected pair equally and weighting each family equally. In the analysis, all genotyped individuals who are not affected are treated as "unknown". Because of concern with small sample behaviour, corresponding P values were usually computed in two different ways for comparison, and the less significant one was reported. The first P value is computed based on large sample theory; $Z_{lr}=\sqrt{(2 \log_e(10) \text{LOD})}$ and is distributed approximately as a standard normal distribution under the null hypothesis of no linkage (Kong, A. & Cox, N. J. *Am J Hum Genet* 61, 1179-88 (1997)). A second P value is computed by comparing the observed LOD score to its complete data sampling distribution under the null hypothesis (Gudbjartsson, D. F., Jonasson, K., Frigge, M. L. & Kong, A. Allegro, *Nat Genet* 25, 12-3 (2000)). When a data set consists of more than a handful of families, these two P values tend to be very similar. The information measure that was used (Nicolae, D. University of Chicago (1999)), and is implemented in Allegro, is closely related to a classical measure of information (Dempster, A., Laird, N M, Rubin, D B., *J R Stat Soc B* 39, 1-38 (1977) and has a property that is between 0, if the marker genotypes are completely uninformative, and 1, if the genotypes determine the exact amount of allele sharing by descent among the affected relatives.

For single-marker association studies, Fisher's exact test was used to calculate two-sided P values for each allele. All P values were unadjusted for multiple comparisons unless specifically indicated. Allelic rather than carrier frequencies were presented for microsatellites, SNPs and haplotypes. To minimize any bias due to the relatedness of the patients that were recruited as families for the linkage analysis, first and second-degree relatives were eliminated from the patient list. For the haplotype analysis, the program NEMO was used (Gretarsdottir, S. et al., *Nat Genet* 35, 131-8 (2003)), which handles missing genotypes and uncertainty with phase through a likelihood procedure, using the expectation-maximization algorithm as a computational tool to estimate haplotype frequencies. Under the null hypothesis, the affected individuals and controls are assumed to have identical haplotype frequencies. Under the alternative hypotheses, the candidate at-risk haplotype is allowed to have a higher frequency in the affected individuals than in controls, while the ratios of frequencies of all other haplotypes are assumed to be the same in both groups. Likelihoods are maximized separately under both hypotheses, and a corresponding 1-df likelihood ratio statistic is used to evaluate statistical significance (id). Even though searches were only performed for haplotypes that increase the risk, all reported P values are two-sided unless otherwise stated. To assess the significance of the haplotype association corrected for multiple testing, a randomisation test was carried out using the same genotype data. The cohorts of affected individuals and controls were randomized, and the analysis was repeated. This procedure was repeated up to 1,000 times and the P value presented is the fraction of replications that produced a P value for a haplotype tested that is lower than or equal to the P value observed using the original patient and control cohorts.

For both single-marker and haplotype analysis, relative risk (RR) and population attributable risk was calculated assuming a multiplicative model (Terwilliger, J. D. & Ott, J. A., *Hum Hered* 42, 337-46 (1992); Falk, C. T. & Rubinstein, P., *Ann Hum Genet* 51 (Pt 3), 227-33 (1987)) in which the risk of the two alleles of haplotypes a person carries multiply. We calculated LD between pairs of SNPs using the standard definition of D' (Lewontin, R. C., *Genetics* 50, 757-82 (1964)) and $R^2$ (Hill, W. G. & Robertson, A., *Genetics* 60, 615-28 (1968)). Using NEMO, frequencies of the two marker allele combinations are estimated by maximum likelihood, and deviation from linkage equilibrium is evaluated by a likelihood ratio test. When plotting all SNP combinations to elucidate the LD structure in a particular region, D' was plotted in the upper left corner and the P value in the lower right corner. In the LD plots presented, the markers are plotted equidistantly rather than according to their physical positions.

Identification of DNA Polymorphisms.

New polymorphic repeats (i.e., dinucleotide or trinucleotide repeats) were identified with the Sputnik program. For microsatellite alleles: the CEPH sample 1347-02 (Centre d'Etudes du Polymorphisme Humain, genomics repository) is used as a reference. The lower allele of each microsatellite in this sample is set at 0 and all other alleles in other samples are numbered according in relation to this reference. Thus allele 1 is 1 bp longer than the lower allele in the CEPH sample, allele 2 is 2 bp longer than the lower allele in the CEPH sample, allele 3 is 3 bp longer than the lower allele in the CEPH sample, allele 4 is 4 bp longer than the lower allele in the CEPH sample, allele −1 is 1 bp shorter than the lower allele in the CEPH sample, allele −2 is 2 bp shorter than the lower allele in the CEPH sample, and so on. Single nucleotide polymorphisms in the gene were detected by PCR sequencing exonic and intronic regions from patients and controls. Public single nucleotide polymorphisms were obtained from the NCBI SNP database. SNPs were genotyped using a method for detecting SNPs with fluorescent polarization template-directed dye-terminator incorporation (SNP-FP-TDI assay) (Chen, X., Zehnbauer, B., Gnirke, A. & Kwok, P. Y., *Proc Natl Acad Sci USA* 94, 10756-61. (1997)) and TaqMan assays (Applied Biosystems).

British Study Population

The method of recruitment of 3 separate cohorts of British subjects has been described previously (Steeds, R., Adams, M., Smith, P., Channer, K. & Samani, N. J., *Thromb Haemost* 79, 980-4 (1998); Brouilette, S., Singh, R. K., Thompson, J. R., Goodall, A. H. & Samani, N. J., *Arterioscler Thromb Vasc Biol* 23, 842-6 (2003)). In brief, in the first two cohorts, a total of 547 patients included those who were admitted to the coronary care units (CCU) of the Leicester Royal Infirmary, Leicester (July 1993-April 1994) and the Royal Hallamshire Hospital, Sheffield (November 1995-March 1997) and satisfied the World Health Organisation criteria for acute MI in terms of symptoms, elevations in cardiac enzymes or electrocardiographic changes (Nomenclature and criteria for diagnosis of ischemic heart disease. Report of the Joint International Society and Federation of Cardiology/World Health Organization task force on standardization of clinical nomenclature. *Circulation* 59, 607-9 (1979)). A total of 530 control subjects were recruited in each hospital from adult visitors to patients with non-cardiovascular disease on general medical, surgical, orthopaedic and obstetric wards to provide subjects likely to be representative of the source population from which the subjects originated. Subjects who reported a history of coronary heart disease were excluded.

In the third cohort, 203 subjects were recruited retrospectively from the registries of 3 coronary care units in Leicester. All had suffered an MI according to WHO criteria before the age of 50 years. At the time of participation, patients were at least 3 months from the acute event. The control cohort comprised 180 subjects with no personal or family history of premature coronary heart disease, matched for age, sex, and current smoking status with the cases. Control subjects were recruited from 3 primary care practices located within the same geographical area. In all cohorts subjects were white of Northern European origin.

Results

Linkage Analysis

A genome wide scan was performed in search of MI susceptibility genes using a framework set of approximately 1000 microsatellite markers. The initial linkage analysis included 713 MI patients who fulfilled the WHO MONICA research criteria (The World Health Organization MONICA Project, WHO MONICA Project Principal Investigators, *J Clin Epidemiol* 41, 105-14 (1988)) and were clustered in 296 extended families. The linkage analysis was also repeated for early onset, male and female patients separately. Description of the number of patients and families in each analysis are provided in Table 1.

TABLE 1

Number of patients that cluster into families and the corresponding number of families used in the linkage analysis

| Phenotype | Number of patients | Number of families | Number of pairs | Genotyped relatives[a] |
|---|---|---|---|---|
| All MI patients | 713 | 296 | 863 | 1741 |
| Males | 575 | 248 | 724 | 1385 |
| Females | 140 | 56 | 108 | 366 |
| Early onset | 194 | 93 | 156 | 739 |

[a]Genotyped relatives were used to increase the information on IBD sharing among the patients in the linkage analysis.

Figure 5:
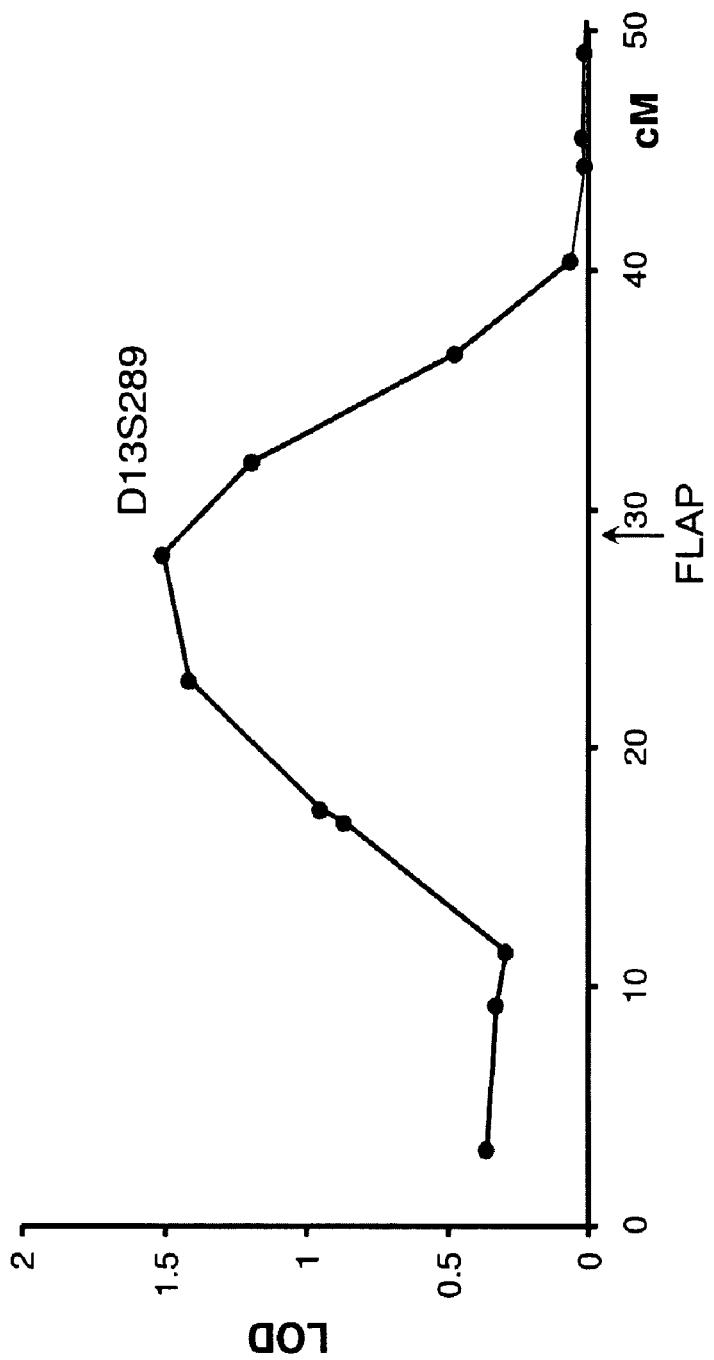
FIG. 5 shows linkage scan using framework microsatellite markers on chromosome 13 for male patients with ischemic stroke or TIA (n=342 in 164 families at 6 meiosis). The LOD score is expressed on the y axis and the distance from the pter in Kosambi cM on the x axis.
Figure 7:
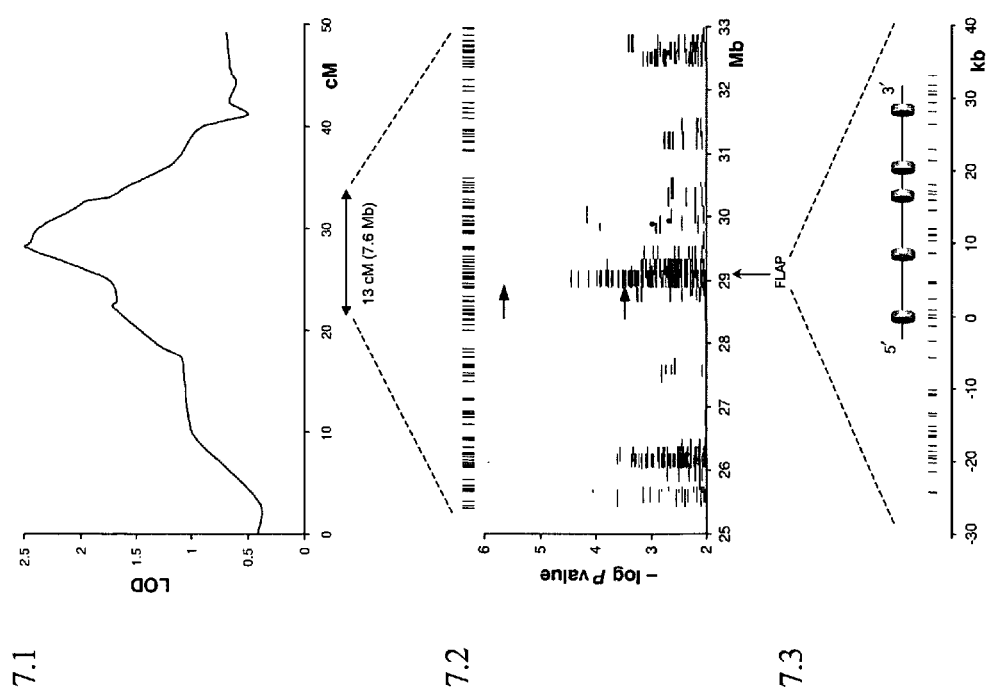
FIG. 7 shows a schematic view of the chromosome 13 linkage region showing the FLAP gene. (7.1) The linkage scan for female MI patients and the one LOD drop region that includes the FLAP gene; (7.2) Microsatellite association for all MI patients: single marker association (black dots) and two, three, four and five marker haplotype association. The arrows indicate the location of the most significant haplotype association across the FLAP gene in males and females. (7.3) The FLAP gene structure, with exons shown as cylinders, and the location of all the SNPs typed in the region (vertical lines). The vertical lines indicate the position of the microsatellites (shown in 9.2) and SNPs (shown in 10.3) used in the analysis.

None of these analyses yielded a locus of genome-wide significance. However, the most promising LOD score (LOD=2.86) was observed on chromosome 13q12-13 for female MI patients at the peak marker D13S289 (data not shown). This locus also had the most promising LOD score (LOD=2.03) for patients with early onset MI. After increasing the information on identity-by-descent sharing to over 90% by typing 14 additional microsatellite markers in a 30 centiMorgan (cM) region around D13S289, the LOD score from the female analysis dropped to 2.48 (P value=0.00036), while the highest LOD score remained at D13S289 (FIG. 7.1). In addition, in an independent linkage study of male patients with ischemic stroke or transient ischemic attack we observed linkage to the same locus with a LOD score of 1.51 at the same peak marker (FIG. 5), further suggesting that a cardiovascular susceptibility factor might reside at this locus.

Microsatellite Association Study

The 7.6 Mb region that corresponds to a drop of one in LOD score in the female MI analysis, contains 40 known genes (Table 2).

TABLE 2

Genes residing within the one LOD drop region of the chromosome 13q12-13 linkage peak.

| LL_Symbol | LL_gene_name |
|---|---|
| USP12L1 | ubiquitin specific protease 12 like 1 |
| RPL21 | ribosomal protein L21 |
| GTF3A | general transcription factor IIIA |
| MTIF3 | mitochondrial translational initiation factor 3 |
| PDZRN1 | PDZ domain containing ring finger 1 |
| MGC9850 | hypothetical protein MGC9850 |
| POLR1D | polymerase (RNA) I polypeptide D, 16 kDa |
| GSH1 | GS homeobox 1 |
| IPF1 | insulin promoter factor 1, homeodomain transcription factor |
| CDX2 | caudal type homeo box transcription factor 2 |
| FLT3 | fms-related tyrosine kinase 3 |
| LOC255967 | hypothetical protein LOC255967 |
| FLT1 | fms-related tyrosine kinase 1 (vascular endothelial growth factor/vascular permeability factor receptor) |
| C13orf12 | chromosome 13 open reading frame 12 |
| LOC283537 | hypothetical protein LOC283537 |
| KIAA0774 | KIAA0774 protein |
| SLC7A1 | solute carrier family 7 (cationic amino acid transporter, y+ system), member 1 |
| UBL3 | ubiquitin-like 3 |
| MGC2599 | hypothetical protein MGC2599 similar to katanin p60 subunit A 1 2599 |
| HMGB1 | high-mobility group box 1 |
| D13S106E | highly charged protein |
| ALOX5AP | arachidonate 5-lipoxygenase-activating protein |
| FLJ14834 | hypothetical protein FLJ14834 |
| MGC40178 | hypothetical protein MGC40178 |
| HSPH1 | heat shock 105 kDa/110 kDa protein 1 |
| B3GTL | beta 3-glycosyltransferase-like |
| GREAT | similar to G protein coupled receptor affecting testicular descent (*H. sapiens*) |
| LOC196549 | similar to hypothetical protein FLJ20897 |
| 13CDNA73 | hypothetical protein CG003 |
| BRCA2 | breast cancer 2, early onset |
| CG018 | hypothetical gene CG018 |
| PRO0297 | PRO0297 protein |
| LOC88523 | CG016 |
| CG012 | hypothetical gene CG012 |
| CG030 | hypothetical gene CG030 |
| CG005 | hypothetical protein from BCRA2 region |
| APRIN | androgen-induced proliferation inhibitor |
| KL | Klotho |
| STARD13 | START domain containing 13 |
| RFC3 | replication factor C (activator 1) 3, 38 kDa |

To determine which gene in this region most likely contributes to MI, 120 microsatellite markers were typed within this region, and a case-control association study was performed using 802 unrelated MI patients and 837 population-based controls. The association study was also repeated for each of the three phenotypes that were used in the linkage study, i.e. early onset, male and female MI patients. In addition to testing each marker individually, haplotypes constructed out of those markers for association were also tested. All usable microsatellite markers that were found in public databases and mapped within that region were used. In addition, microsatellite markers identified within the deCODE genetics sequence assembly of the human genome were used (see Table 6).

The initial association analysis was performed when the average spacing between microsatellite markers was approximately 100 kb. This analysis revealed several extended haplotypes composed of 4 and 5 microsatellite markers that were significantly associated with female MI (see FIGS. 1 and 2 and Tables 13 and 14). A region common to all these extended haplotypes, is defined by markers DG13S166 and D13S1238. This region included only one gene, the FLAP nucleic acid sequence. The two marker haplotype involving alleles 0 and −2 for markers DG13S166 and D13S1238, respectively, was found in excess in patients.

This was the first evidence that the FLAP gene might be involved in the pathogenesis of myocardial infarction.

Subsequent haplotype analysis that included more microsatellite markers in the candidate region on chromosome 13q12-13, now with a marker density of 1 microsatellite marker per 60 kb, showed decreased significance of the original haplotype association. However, the haplotype association analysis using increased density of markers again pointed towards the FLAP gene. This analysis strongly suggested that a 300 kb region was involved in the susceptibility of myocardial infarction. As shown in FIG. 7.2, the haplotype that showed association to all MI with the lowest P value (0.00009) covered a region that contains 2 known genes, including the gene encoding arachidonate 5-lipoxygenase-activating protein (FLAP) and a gene with an unknown function called highly charged protein. However, the haplotype association to female MI in this region was less significant (P value=0.005) than for all MI patients and to our surprise, the most significant haplotype association was observed for male MI patients (P value=0.000002). This male MI haplotype was the only haplotype that remained significant after adjusting for all haplotypes tested.

In view of the association results described above, FLAP was an attractive candidate and therefore efforts were focused on this gene.

Screening for Polymorphisms in FLAP and Linkage Disequilibrium Mapping

To determine whether variations within the FLAP gene significantly associate with M, I and to search for causal variations, the FLAP gene was sequenced in 93 patients and 93 controls. The sequenced region covers 60 kb containing the FLAP gene, including the 5 known exons and introns and the 26 kb region 5' to the first exon and 7 kb region 3' to the fifth exon. In all, 144 SNPs were identified, of those 96 were excluded from further analysis either because of low minor allele frequency or they were completely correlated with other SNPs and thus redundant. FIG. 7 shows the distribution of the 48 SNPs, used for genotyping, relative to exons, introns and the 5' and 3' flanking regions of the FLAP gene. Only one SNP was identified within a coding sequence (exon 2). This SNP did not lead to amino acid substitution. The locations of these SNPs in the NCBI human genome assembly, build 34, are listed in Table 3.

TABLE 3

Locations of all genotyped SNPs in NCBI build 34 of the human genome assembly

| SNP name | Build34 start |
|---|---|
| SG13S381 | 29083350 |
| SG13S366 | 29083518 |
| SG13S1 | 29086224 |
| SG13S2 | 29087473 |
| SG13S367 | 29088090 |
| SG13S10 | 29088473 |
| SG13S3 | 29089044 |
| SG13S368 | 29089886 |
| SG13S4 | 29090997 |
| SG13S5 | 29091307 |
| SG13S90 | 29091780 |
| SG13S6 | 29092536 |
| SG13S371 | 29093964 |
| SG13S372 | 29094259 |
| SG13S373 | 29096688 |
| SG13S375 | 29096874 |
| SG13S376 | 29096962 |
| SG13S25 | 29097553 |
| SG13S377 | 29101965 |

TABLE 3-continued

Locations of all genotyped SNPs in NCBI build 34 of the human genome assembly

| SNP name | Build34 start |
| --- | --- |
| SG13S100 | 29104271 |
| SG13S95 | 29106329 |
| SG13S191 | 29107830 |
| SG13S106 | 29108579 |
| SG13S114 | 29110096 |
| SG13S121 | 29112174 |
| SG13S122 | 29112264 |
| SG13S43 | 29112455 |
| SG13S192 | 29116308 |
| SG13S88 | 29116401 |
| SG13S137 | 29118118 |
| SG13S86 | 29118815 |
| SG13S87 | 29118873 |
| SG13S39 | 29119740 |
| SG13S26 | 29122253 |
| SG13S27 | 29122283 |
| SG13S29 | 29123643 |
| SG13S89 | 29124441 |
| SG13S96 | 29124906 |
| SG13S30 | 29125840 |
| SG13S97 | 29129139 |
| SG13S32 | 29130547 |
| SG13S41 | 29134045 |
| SG13S42 | 29135877 |
| SG13S34 | 29137100 |
| SG13S35 | 29138117 |
| SG13S181 | 29138633 |
| SG13S184 | 29139435 |
| SG13S188 | 29140805 |

In addition to the SNPs, a polymorphism consisting of a monopolymer A repeat that has been described in the FLAP promoter region was typed (Koshino, T. et al., *Mol Cell Biol Res Commun* 2, 32-5 (1999)).

Figure 9:
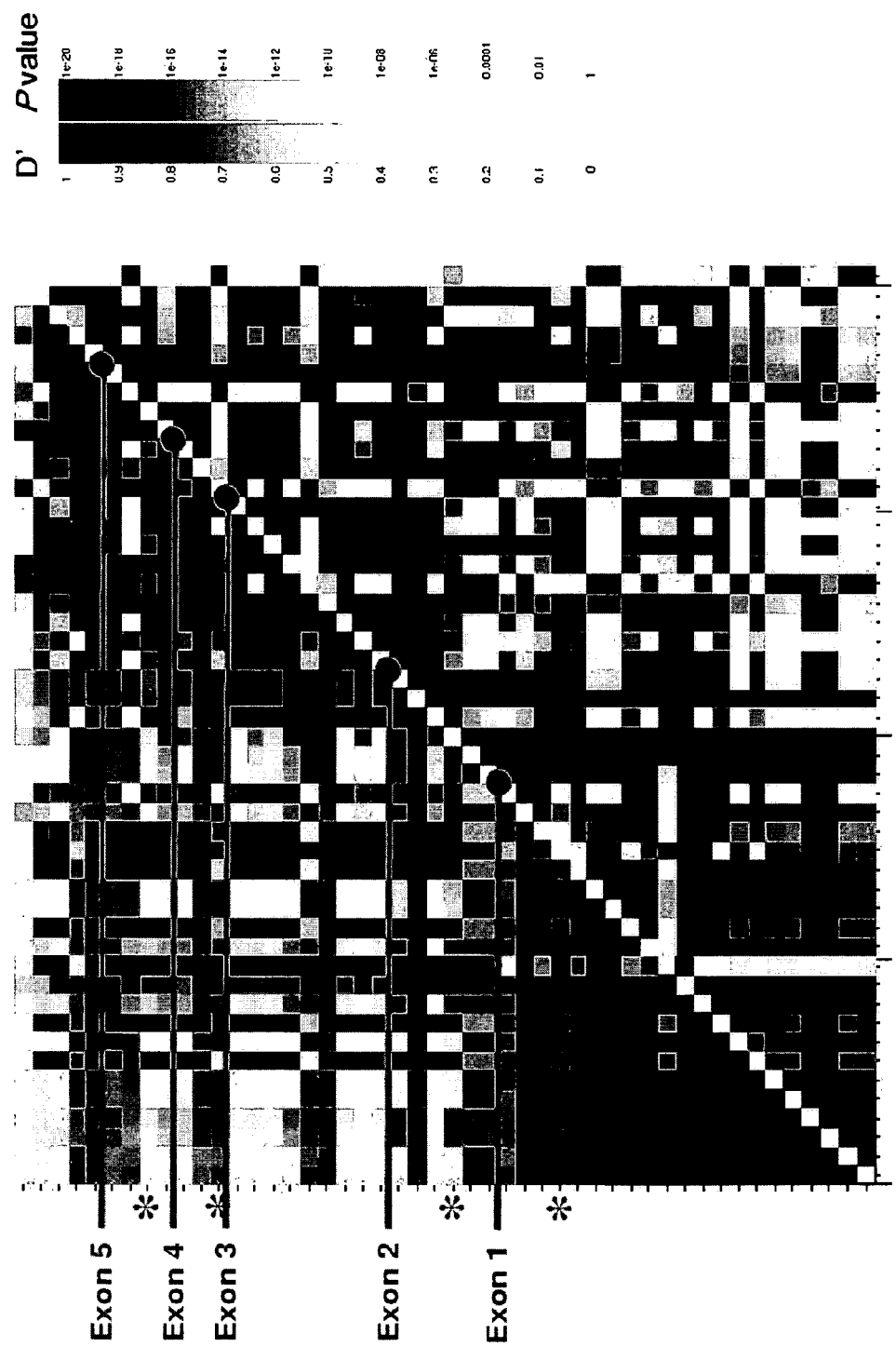
FIG. 9 shows pairwise linkage disequilibrium (LD) between SNPs in a 60 kb region encompassing FLAP. The markers are plotted equidistantly. Two measures of LD are shown: D' in the upper left triangle and P values in the lower right triangle. Lines indicate the positions of the exons of FLAP and stars indicate the location of the markers of the at-risk haplotype A4. Scales for the LD strength are provided for both measures to the right.

The linkage disequilibrium (LD) block structure defined by the 48 SNPs that were selected for further genotyping is shown in FIG. 9. A strong LD was detected across the FLAP region, although it appears that at least one recombination may have occurred dividing the region into two strongly correlated LD blocks.

Haplotype Association to MI

To perform a case-control association study the 48 selected SNPs and the monopolymer A repeat marker were genotyped in a set of 779 unrelated MI patients and 628 population-based controls. Each of the 49 markers was tested individually for association to the disease. Three SNPs, one located 3 kb upstream of the first exon and the other two 1 and 3 kb downstream of the first exon, showed nominally significant association to MI (Table 4).

TABLE 4

SNP allelic association in the MI cohort

| Pheno-type | Marker | Allele | P value | RR | # Pat. | % Pat. | # Ctrl | % Ctrl |
| --- | --- | --- | --- | --- | --- | --- | --- | --- |
| All patients | SG13S106 | G | 0.0044 | 1.29 | 681 | 72.0 | 530 | 66.6 |
|  | SG13S100 | A | 0.020 | 1.29 | 388 | 69.6 | 377 | 63.9 |
|  | SG13S114 | T | 0.021 | 1.21 | 764 | 70.0 | 602 | 65.8 |
| Males | SG13S106 | G | 0.0037 | 1.35 | 422 | 72.9 | 530 | 66.6 |
|  | SG13S100 | A | 0.0099 | 1.36 | 292 | 70.7 | 377 | 63.9 |
|  | SG13S114 | T | 0.026 | 1.24 | 477 | 70.4 | 602 | 65.8 |
| Early onset | SG13S100 | A | 0.0440 | 1.43 | 99 | 71.7 | 377 | 63.9 |

Nominally significant SNP association with corresponding number of patients (# Pat.) and controls (#Ctrl). RR refers to relative risk.

However, after adjusting for the number of markers tested, these results were not significant. A search was then conducted for haplotypes that show association to the disease using the same cohorts. The result of haplotype association analysis limited to haplotype combinations constructed out of two, three or four SNPs are shown in Table 5. The resulting P values were adjusted for all the haplotypes we tested by randomizing the patients and controls (see Methods). Several haplotypes were found that were significantly associated to the disease with an adjusted P value less that 0.05 (Table 5).

TABLE 5

SNP haplotypes that significantly associate with Icelandic MI patients

| SG13S4 | SG13S6 | SG13S372 | SG13S25 | SG13S377 | SG13S100 | SG13S95 | SG13S114 | SG13S192 | SG13S137 | SG13S86 | SG13S87 | SG13S39 |
| --- | --- | --- | --- | --- | --- | --- | --- | --- | --- | --- | --- | --- |
|  |  |  |  |  | G |  | T |  |  |  |  |  |
|  |  |  |  |  | G |  | T |  |  |  | A |  |
|  |  |  |  |  | G |  | T |  |  |  |  |  |
|  |  |  |  |  | G | A |  |  |  |  | A |  |
|  |  |  |  |  | G |  | T |  |  |  |  |  |
|  |  |  |  |  | G |  | T |  |  | G |  |  |
|  |  |  |  |  | G | A |  |  |  |  |  |  |
|  |  |  |  |  | G | A |  |  |  |  |  |  |
|  |  |  |  |  | G |  | T |  |  |  |  |  |
|  |  |  |  |  | G |  | T |  |  |  |  |  |
|  | G |  |  |  |  | T | T |  |  |  |  |  |
|  |  |  |  |  | G | A |  |  |  | G |  |  |
|  |  |  |  |  | G |  | T | A |  |  |  |  |
|  |  |  |  |  | G |  | T |  |  |  |  |  |
|  | G |  |  |  |  |  | T |  |  |  |  |  |
|  | G |  | G |  |  |  | T |  |  |  |  |  |
|  | G |  |  |  | A |  |  |  |  |  |  |  |
|  |  |  |  |  | G | A |  |  |  |  |  |  |
|  | G |  |  |  | A |  |  |  |  |  | A |  |
|  |  |  |  |  | G | A |  |  |  |  |  |  |
|  | G |  |  |  |  |  | T | A |  |  | A |  |
|  |  |  |  |  | G | A |  |  |  |  |  | G |
|  | G |  |  |  | A |  |  |  |  |  |  |  |
|  | G |  |  |  |  |  | T |  |  |  |  |  |
|  |  |  |  |  | G | A |  |  |  |  |  |  |

TABLE 5-continued

SNP haplotypes that significantly associate with Icelandic MI patients

| SG13S27 | SG13S89 | SG13S96 | SG13S32 | SG13S41 | SG13S42 | SG13S34 | SG13S188 | P value[a] | P value[b] | Pat.frq | Ctrl.frq | RR | D'[c] |
|---|---|---|---|---|---|---|---|---|---|---|---|---|---|
|  | G |  |  |  |  | T |  |  |  |  |  |  |  |
|  | G |  |  |  |  |  |  |  |  |  |  |  |  |
|  |  | G | A |  |  |  |  |  |  |  |  |  |  |
|  |  | G | A |  |  |  |  |  |  |  |  |  |  |
|  |  | G |  |  |  | T | A |  |  |  |  |  |  |
|  |  | G | A |  |  |  | A |  |  |  |  |  |  |
|  |  | G |  |  |  | T | C |  |  |  |  |  |  |
|  |  | G |  |  |  | T |  |  |  |  |  |  |  |
|  |  | G |  |  |  | T | C |  |  |  |  |  |  |
|  |  | G | G | A |  |  |  |  |  |  |  |  |  |
|  | G |  |  |  |  | T |  |  |  |  |  |  |  |
|  | G |  |  |  |  | T | G |  |  |  |  |  |  |
|  | G |  | A |  |  |  |  |  |  |  |  |  |  |
|  |  | G | A |  |  |  | G |  |  |  |  |  |  |
| C | G |  | A |  |  |  |  |  |  |  |  |  |  |
|  | G |  |  |  |  | T | A |  |  |  |  |  |  |
|  | G |  | A |  |  |  |  |  |  |  |  |  |  |
|  | G |  |  |  |  | T |  |  |  |  |  |  |  |
|  |  | G |  |  |  | T |  |  |  |  |  |  |  |
|  | G | G | A |  |  |  |  |  |  |  |  |  |  |
|  | G |  | G | A |  |  | A |  |  |  |  |  |  |
|  | G |  | A |  |  |  |  | 0.0000023 | 0.005 | 0.158 | 0.095 | 1.80 | 1.00 |
|  |  |  | A |  |  |  |  | 0.0000030 | 0.006 | 0.158 | 0.095 | 1.78 | 1.00 |
|  |  |  | A |  |  | T |  | 0.0000032 | 0.007 | 0.157 | 0.094 | 1.79 | 1.00 |
|  |  |  | A |  |  |  |  | 0.0000046 | 0.012 | 0.158 | 0.083 | 2.07 | 0.89 |
|  |  |  | A |  |  |  |  | 0.0000047 | 0.012 | 0.154 | 0.093 | 1.78 | 1.00 |
|  |  |  | A |  |  |  |  | 0.0000055 | 0.015 | 0.147 | 0.087 | 1.81 | 1.00 |
|  |  |  | A |  |  | T |  | 0.0000061 | 0.017 | 0.157 | 0.083 | 2.07 | 0.89 |
|  | G |  | A |  |  |  |  | 0.0000063 | 0.017 | 0.157 | 0.084 | 2.04 | 0.89 |
|  |  |  | A |  |  |  |  | 0.0000070 | 0.021 | 0.157 | 0.096 | 1.76 | 1.00 |
|  |  | A | A |  |  |  |  | 0.0000075 | 0.022 | 0.149 | 0.089 | 1.78 | 1.00 |
|  |  |  | A |  |  |  |  | 0.0000083 | 0.024 | 0.208 | 0.139 | 1.62 | 0.99 |
|  |  |  | A |  |  |  |  | 0.0000084 | 0.026 | 0.145 | 0.074 | 2.14 | 0.88 |
|  |  |  | A |  |  |  |  | 0.0000084 | 0.026 | 0.139 | 0.082 | 1.82 | 1.00 |
| G |  |  | A |  |  |  |  | 0.0000091 | 0.028 | 0.156 | 0.096 | 1.75 | 1.00 |
|  |  |  | A |  |  | T |  | 0.0000094 | 0.028 | 0.210 | 0.141 | 1.61 | 0.99 |
|  |  |  | A |  |  |  |  | 0.0000100 | 0.028 | 0.156 | 0.096 | 1.74 | 1.00 |
|  |  |  | A |  |  |  | A | 0.0000101 | 0.028 | 0.215 | 0.133 | 1.80 | 0.81 |
|  |  |  | A |  |  |  |  | 0.0000105 | 0.028 | 0.157 | 0.084 | 2.03 | 0.89 |
|  |  |  | A |  |  |  |  | 0.0000108 | 0.029 | 0.214 | 0.133 | 1.78 | 0.81 |
|  |  | A | A |  |  |  |  | 0.0000110 | 0.030 | 0.146 | 0.075 | 2.10 | 0.88 |
|  |  |  | A |  |  |  |  | 0.0000112 | 0.030 | 0.212 | 0.144 | 1.60 | 1.00 |
|  |  |  |  |  |  | T |  | 0.0000113 | 0.030 | 0.151 | 0.081 | 2.03 | 0.78 |
|  |  |  | A |  |  |  |  | 0.0000118 | 0.031 | 0.156 | 0.096 | 1.73 | 1.00 |
|  |  |  | A |  |  | T |  | 0.0000126 | 0.034 | 0.212 | 0.131 | 1.79 | 0.79 |
|  | G |  | A |  |  |  |  | 0.0000129 | 0.035 | 0.211 | 0.144 | 1.59 | 1.00 |
| G |  |  | A |  |  |  |  | 0.0000134 | 0.035 | 0.156 | 0.084 | 2.01 | 0.89 |
|  |  |  | A |  |  |  |  | 0.0000136 | 0.036 | 0.211 | 0.143 | 1.60 | 1.00 |
|  |  |  | A |  |  |  |  | 0.0000137 | 0.036 | 0.156 | 0.085 | 2.00 | 0.89 |
|  |  |  |  | A |  |  |  | 0.0000148 | 0.037 | 0.151 | 0.081 | 2.01 | 0.78 |
|  |  |  |  |  |  | T |  | 0.0000150 | 0.037 | 0.160 | 0.099 | 1.73 | 0.87 |
|  |  |  | A |  |  |  |  | 0.0000150 | 0.037 | 0.130 | 0.066 | 2.13 | 0.90 |
|  |  |  |  |  |  | T |  | 0.0000154 | 0.039 | 0.152 | 0.094 | 1.73 | 0.93 |
|  |  |  | A | A |  |  |  | 0.0000154 | 0.040 | 0.155 | 0.097 | 1.70 | 1.00 |
|  |  |  | A |  |  |  |  | 0.0000157 | 0.040 | 0.141 | 0.085 | 1.76 | 1.00 |
|  |  |  | A |  |  |  |  | 0.0000158 | 0.040 | 0.152 | 0.084 | 1.94 | 0.90 |
| G |  |  | A |  |  |  |  | 0.0000163 | 0.040 | 0.210 | 0.143 | 1.59 | 0.99 |
|  |  |  | A |  |  |  |  | 0.0000166 | 0.041 | 0.200 | 0.134 | 1.61 | 0.92 |
|  | G |  | A |  |  |  |  | 0.0000168 | 0.042 | 0.213 | 0.133 | 1.76 | 0.81 |
|  |  |  | A |  |  |  |  | 0.0000168 | 0.042 | 0.156 | 0.084 | 2.00 | 0.89 |
|  |  |  | A |  |  |  |  | 0.0000171 | 0.042 | 0.211 | 0.136 | 1.70 | 0.81 |
|  |  |  | A |  |  |  |  | 0.0000183 | 0.043 | 0.192 | 0.128 | 1.62 | 0.85 |
|  |  |  | A |  |  |  |  | 0.0000184 | 0.043 | 0.212 | 0.132 | 1.77 | 0.81 |
|  |  |  |  | A |  | T |  | 0.0000193 | 0.046 | 0.328 | 0.251 | 1.46 | 0.99 |
| G |  |  |  |  |  | T |  | 0.0000194 | 0.046 | 0.175 | 0.115 | 1.64 | 0.98 |
|  |  |  | A |  |  |  |  | 0.0000202 | 0.048 | 0.210 | 0.136 | 1.70 | 0.81 |
|  |  |  |  |  |  |  |  | 0.0000209 | 0.049 | 0.151 | 0.082 | 2.00 | 0.76 |

[a]Single test P values.
[b]P values adjusted for all the SNP haplotypes tested.
[c]Measure of correlation with haplotype A4.

The most significant association was observed for a four SNP haplotype spanning 33 kb, including the first four exons of the gene (FIG. 7.3), with a nominal P value of 0.0000023 and an adjusted P value of 0.005. This haplotype, labelled haplotype A4, has haplotype frequency of 15.8% (carrier frequency 30.3%) in patients versus 9.5% (carrier frequency 17.9%) in controls (Table 6). The relative risk conferred by haplotype A4 compared to other haplotypes constructed out of the same SNPs, assuming a multiplicative model, was 1.8 and the corresponding population attributable risk (PAR) was 13.5%. As shown in Table 6, haplotype A4 was observed in higher frequency in male patients (carrier frequency 30.9%) than in female patients (carrier frequency 25.7%). All the other haplotypes that were significantly associated with an adjusted P value less than 0.05, were highly correlated with haplotype A4 and should be considered variants of that haplotype (Table 5).

TABLE 6

Association of the A4 haplotype to MI and Stroke

| Phenotype (n) | Frq. Pat. | RR | PAR | P-value | P-value[a] |
|---|---|---|---|---|---|
| MI (779) | 0.158 | 1.80 | 0.135 | 0.0000023 | 0.005 |
| Males (486) | 0.169 | 1.95 | 0.158 | 0.00000091 | ND[b] |
| Females (293) | 0.138 | 1.53 | 0.094 | 0.0098 | ND |
| Early onset (358) | 0.138 | 1.53 | 0.094 | 0.0058 | ND |
| Stroke (702)[c] | 0.149 | 1.67 | 0.116 | 0.000095 | ND |
| Males (373) | 0.156 | 1.76 | 0.131 | 0.00018 | ND |
| Females (329) | 0.141 | 1.55 | 0.098 | 0.0074 | ND |

[a] P value adjusted for the number of haplotypes tested.
[b] Not done.
[c] Excluding known cases of MI.
Shown is the FLAP A4 haplotype and corresponding number of patients (n), haplotype frequency in patients (Frq. pat.), relative risk (RR), population attributed risk (PAR) and P values. The A4 haplotype is defined by the following SNPs: SG13S25, SG13S114, SG13S89 and SG13S32 (Table 5). The same controls (n = 628) are used for the association analysis in MI and stroke, as well as for the male, female and early onset analysis. The A4 frequency in the control cohort is 0.095.

Additional SNP Haplotype Association to MI

Two correlated series of SNP haplotypes were observed in excess in patients, denoted as A and B in Table 7. The length of the haplotypes varies between 33 and 69 kb and cover one or two blocks of linkage disequilibrium. Both series of haplotypes contain the common allele G of the SNP SG13S25. All haplotypes in the A series (e.g., A4 haplotype) contain the SNP SG13S114, while all haplotypes in the B series contain the SNP SG13S106. In the B series, the haplotypes B4, BS4, B5, and B6 have a relative risk (RR) greater than 2 and allelic frequencies above 10% (Table 7). The haplotypes in the A series have slightly lower RR and p-values, but higher allelic frequency (15-16%), and as such we also consider them interesting. The haplotypes in series B and A are strongly correlated, i.e. the B haplotypes define a subset of the A haplotypes. Hence, B haplotypes are more specific than A haplotypes. However, A haplotypes are more sensitive, i.e. they capture more individuals with the putative mutation, as is observed in the population attributable risk which is less for B than for A. Furthermore, these haplotypes show similar risk ratios and allelic frequency for early-onset patients (defined as onset of first MI before the age of 55). In addition, analyzing various groups of patients with known risk factors, such as hypertension, high cholesterol, smoking and diabetes, did not reveal any significant correlation with these haplotypes.

In conclusion, a series of correlated MI disease risk haplotypes has been identified, consisting of 4-6 SNPs, with relative risk greater than 2 and allelic frequency in MI patients greater than 10%. The length of the haplotypes varies between 39-68 kb. These haplotypes are carried by 19% (B5) to 29% (A4) of MI patients. The results suggest that the 'at risk' haplotypes in the FLAP gene represent a new major independent risk factor for MI.

TABLE 7

SNP haplotypes and the corresponding p-values

| | p-val | RR | #aff | aff.frq. | carr.frq. | #con | con.frq. | PAR | SG13S99 | SG13S25 | SG13S377 |
|---|---|---|---|---|---|---|---|---|---|---|---|
| B4 | 4.80E−05 | 2.08 | 903 | 0.106 | 0.2 | 619 | 0.054 | 0.11 | | G | |
| B5 | 2.40E−05 | 2.2 | 910 | 0.101 | 0.19 | 623 | 0.049 | 0.11 | T | G | |
| B6 | 1.80E−06 | 2.22 | 913 | 0.131 | 0.24 | 623 | 0.063 | 0.14 | T | G | G |
| A4 | 5.10E−06 | 1.81 | 919 | 0.159 | 0.29 | 623 | 0.095 | 0.14 | | G | |
| A5 | 2.60E−06 | 1.91 | 920 | 0.15 | 0.28 | 624 | 0.085 | 0.14 | T | G | |

| | SG13S106 | SG13S114 | SG13S89 | SG13S30 | SG13S32 | SG13S42 | SG13S35 |
|---|---|---|---|---|---|---|---|
| B4 | G | | | | G | A | |
| B5 | G | | | | G | A | |
| B6 | G | | | | | A | G |
| A4 | | T | G | | | A | |
| A5 | | T | G | | | A | |

Relative risk (RR), number of patients (#aff), allelic frequency in patients (aff.frq.), carrier frequency in patients (carr.frq.), number of controls (#con), allelic frequency in controls (con.frq.), population attributable risk (PAR). The patients used for this analysis were all unrelated within 4 meioses.

Association of the A4 Haplotype to Stroke

In view of the linkage observed for stroke in male patients to the FLAP locus and since there is a high degree of co-morbidity among MI and stroke, with most of these cases occurring on the basis of an atherosclerotic disease, it was evaluated whether haplotype A4 also conferred risk of stroke. The SNPs defining haplotype A4 were typed on the Icelandic stroke patient cohort. First and second degree relatives and all known cases of MI were removed, and 702 stroke patients were tested for association. The results are also listed in Table 6, above. A significant association of haplotype A4 to stroke was observed, with a relative risk of 1.67 (P value=0.000095). In addition, it was determined whether haplotype A4 was primarily associated with a particular sub-phenotype of stroke, and found that both ischemic and hemorrhagic stroke were significantly associated with haplotype A4 (Table 8).

TABLE 8

Association of the A4 haplotype to subgroups of stroke

| Phenotype (n) | Pat. Frq. | RR | PAR | P-value |
|---|---|---|---|---|
| Stroke[a] (702) | 0.149 | 1.67 | 0.116 | 0.000095 |
| Ischemic (484) | 0.148 | 1.65 | 0.113 | 0.00053 |
| TIA (148) | 0.137 | 1.51 | 0.090 | 0.058 |
| Hemorrhagic (68) | 0.167 | 1.91 | 0.153 | 0.024 |

[a]Excluding known cases of MI.

It should be noted that similar to the stronger association of Haplotype A4 to male MI compared to female MI, it also shows stronger association to male stroke (Table 6).

Table 9 shows that the haplotype A4 increases the risk of having a stroke to a similar extent as it increases the risk of having an MI. The 'at risk' haplotype is carried by 28% of stroke patients and 17% of controls, meaning that the relative risk of having stroke for the carriers of this haplotype is 1.7 (p-value=$5.8 \cdot 10^{-06}$). Also shown in Table 9 are the haplotype B series (B4 and Bs4). The Bs4 haplotype has 10% allelic frequency in stroke patients. Relative risk of having stroke for carriers of Bs4 is estimated to be around 2.

TABLE 9

| | | | | | | | Haplotype relation to MI and Stroke | | | | | | | | |
|---|---|---|---|---|---|---|---|---|---|---|---|---|---|---|---|
| | p-val | r | #aff | Aff.frq. | #con | con.frq. | info | SG13S25 | SG13S106 | SG13S114 | SG13S89 | SG13S30 | SG13S32 | SG13S41 | SG13S42 | SG13S35 |
| MI haplotypes | | | | | | | | | | | | | | | | |
| All MI patients | | | | | | | | | | | | | | | | |
| A4 | 5.3E-07 | 1.80 | 1407 | 0.16 | 614 | 0.09 | 0.82 | G | | T | G | | A | | | |
| B4 | 1.0E-04 | 1.87 | 1388 | 0.10 | 612 | 0.06 | 0.67 | G | G | | G | G | | | A | |
| Males MI | | | | | | | | | | | | | | | | |
| A4 | 2.5E-08 | 2.00 | 864 | 0.17 | 614 | 0.09 | 0.82 | G | | T | G | | A | | | |
| B4 | 1.1E-05 | 2.12 | 852 | 0.11 | 612 | 0.06 | 0.67 | G | G | | G | G | | | A | |
| Females MI | | | | | | | | | | | | | | | | |
| A4 | 1.9E-02 | 1.44 | 543 | 0.13 | 614 | 0.09 | 0.73 | G | | T | G | | A | | | |
| B4 | 7.9E-02 | 1.45 | 536 | 0.08 | 612 | 0.06 | 0.60 | G | G | | G | G | | | A | |
| Replication in stroke | | | | | | | | | | | | | | | | |
| All stroke patients | | | | | | | | | | | | | | | | |
| A4 | 5.8E-06 | 1.73 | 1238 | 0.15 | 614 | 0.09 | 0.80 | G | | T | G | | A | | | |
| B4 | 2.3E-04 | 1.83 | 1000 | 0.10 | 612 | 0.06 | 0.71 | G | G | | G | G | | | A | |
| Males stroke | | | | | | | | | | | | | | | | |
| A4 | 1.1E-06 | 1.91 | 710 | 0.17 | 614 | 0.09 | 0.79 | G | | T | G | | A | | | |
| B4 | 3.1E-05 | 2.11 | 574 | 0.11 | 612 | 0.06 | 0.72 | G | G | | G | G | | | A | |
| Females stroke | | | | | | | | | | | | | | | | |
| A4 | 9.9E-03 | 1.49 | 528 | 0.13 | 614 | 0.10 | 0.74 | G | | T | G | | A | | | |
| B4 | 6.3E-02 | 1.47 | 426 | 0.08 | 612 | 0.06 | 0.70 | G | G | | G | G | | | A | |
| All stroke excluding MI | 8.4E-05 | 1.65 | 1054 | 0.15 | 614 | 0.09 | 0.78 | G | | T | G | | A | | | |
| Males stroke excluding MI | 6.4E-05 | 1.78 | 573 | 0.16 | 614 | 0.09 | 0.75 | G | | T | G | | A | | | |
| Females stroke excluding MI | 1.2E-02 | 1.49 | 481 | 0.14 | 614 | 0.10 | 0.72 | G | | T | G | | A | | | |
| Cardioembolic stroke | 6.6E-04 | 1.87 | 248 | 0.16 | 614 | 0.10 | 0.74 | G | | T | G | | A | | | |
| Cardioembolic stroke excluding MI | 3.8E-02 | 1.56 | 191 | 0.14 | 614 | 0.10 | 0.70 | G | | T | G | | A | | | |
| Large vessel stroke | 8.0E-02 | 1.47 | 150 | 0.13 | 614 | 0.09 | 0.83 | G | | T | G | | A | | | |
| Large vessel stroke excluding MI | 2.9E-01 | 1.31 | 114 | 0.12 | 614 | 0.09 | 0.80 | G | | T | G | | A | | | |
| Small vessel stroke | 7.2E-04 | 2.05 | 166 | 0.18 | 614 | 0.09 | 0.71 | G | | T | G | | A | | | |
| Small vessel stroke excluding MI | 1.0E-04 | 2.31 | 152 | 0.20 | 614 | 0.10 | 0.71 | G | | T | G | | A | | | |
| Hemorrhagic stroke | 4.4E-02 | 1.73 | 97 | 0.15 | 614 | 0.09 | 0.72 | G | | T | G | | A | | | |
| Hemorrhagic stroke excluding MI | 3.9E-02 | 1.78 | 92 | 0.16 | 614 | 0.09 | 0.71 | G | | T | G | | A | | | |
| Unknown cause stroke | 1.3E-04 | 1.88 | 335 | 0.16 | 614 | 0.09 | 0.75 | G | | T | G | | A | | | |
| Unknown cause stroke excluding MI | 6.5E-04 | 1.82 | 297 | 0.16 | 614 | 0.09 | 0.72 | G | | T | G | | A | | | |
| MI and stroke together | | | | | | | | | | | | | | | | |
| All patients with either MI or stroke | | | | | | | | | | | | | | | | |
| Best haplo A4 | 4.1E-07 | 1.75 | 2659 | 0.15 | 614 | 0.09 | 0.82 | G | | T | G | | A | | | |
| B4 | 4.1E-05 | 1.85 | 2205 | 0.10 | 612 | 0.06 | 0.70 | G | G | | G | G | | | A | |
| Males | | | | | | | | | | | | | | | | |

TABLE 9-continued

Haplotype relation to MI and Stroke

| | p-val | r | #aff | Aff.frq | #con | con.frq. | info | SG13S25 | SG13S106 | SG13S114 | SG13S89 | SG13S30 | SG13S32 | SG13S41 | SG13S42 | SG13S35 |
|---|---|---|---|---|---|---|---|---|---|---|---|---|---|---|---|---|
| A4 | 1.4E-08 | 1.93 | 1437 | 0.17 | 614 | 0.09 | 0.82 | G | | T | G | G | A | | | |
| B4 | 2.0E-06 | 2.11 | 1290 | 0.11 | 612 | 0.06 | 0.70 | G | G | | | G | | | | A | G |
| Females | | | | | | | | | | | | | | | | |
| A4 | 3.6E-03 | 1.47 | 1024 | 0.13 | 614 | 0.09 | 0.77 | G | | T | G | G | A | | | |
| B4 | 2.8E-02 | 1.48 | 915 | 0.08 | 612 | 0.06 | 0.66 | G | G | | | G | | | | A | |
| Patients with both MI and stroke | | | | | | | | | | | | | | | | |
| A4 | 6.1E-05 | 2.10 | 184 | 0.18 | 614 | 0.09 | 0.86 | G | | T | G | G | A | | | |
| Patients and controls unrelated in 4 meloses | | | | | | | | | | | | | | | | |
| Stroke patients excluding MI B4 | 1.6E-04 | 1.95 | 624 | 0.102 | 612 | 0.055 | 0.74 | G | G | | | G | | | | A | |
| | 5.8E-05 | 2.04 | 624 | 0.102 | 612 | 0.053 | 0.76 | G | G | | | G | | | | A | |
| BS4 | 1.1E-04 | 2.01 | 624 | 0.103 | 611 | 0.054 | 0.72 | G | G | | | G | A | | | |
| | 6.6E-05 | 2.03 | 624 | 0.102 | 611 | 0.053 | 0.75 | G | G | | | G | A | | | |
| | 4.3E-05 | 2.08 | 625 | 0.101 | 611 | 0.051 | 0.76 | G | G | | | G | A | | | |
| Patients with both stroke and MI | 1.3E-02 | 1.99 | 183 | 0.099 | 611 | 0.052 | 0.65 | G | | | | G | | | | | |
| Stroke Males | 2.2E-05 | 2.18 | 574 | 0.108 | 611 | 0.053 | 0.71 | | | | | | | A | A | | |
| Stroke Females | 1.1E-02 | 1.71 | 426 | 0.089 | 611 | 0.054 | 0.69 | | | | | | | | | | |
| Large vessel stroke | 2.0E-01 | 1.50 | 137 | 0.078 | 611 | 0.053 | 0.71 | G | G | | | G | A | | | |
| Cardoembolic stroke | 7.9E-03 | 1.96 | 207 | 0.099 | 611 | 0/053 | 0.71 | | | | | | | | | | |
| Small vessel stroke | 1.2E-04 | 2.78 | 139 | 0.137 | 611 | 0.054 | 0.72 | G | G | | | G | A | | | |
| Hemorrhagic stroke | 1.6E-03 | 2.9 | 83 | 0.143 | 611 | 0.053 | 0.63 | G | G | | | G | A | | | |
| Unknown cause stroke | 9.0E-04 | 2.10 | 280 | 0.109 | 611 | 0.055 | 0.70 | | | | | | | | | | |

Haplotype Association to FLAP in a British Cohort

In an independent study, it was determined whether variants in the FLAP gene also have impact on risk of MI in a population outside Iceland. The four SNPs, defining Haplotype A4, were typed in a cohort of 750 patients from the United Kingdom who had sporadic MI, and in 728 British population controls. The patients and controls come from 3 separate study cohorts recruited in Leicester and Sheffield. No significant differences were found in the frequency of the haplotype between patients and controls (16.9% versus 15.3%, respectively). However, when 9 additional SNPs, distributed across the FLAP gene, were typed in the British cohort and a search was performed for other haplotypes that might be associated with MI, two SNPs showed association to MI with a nominally significant P value (data not shown). Moreover, three and four SNP haplotype combinations increased the risk of MI in the British cohort further and the most significant association was observed for a four SNP haplotype with a nominal P value=0.00037 (Table 10).

TABLE 10

Association of the HapB haplotype to British MI patients

| Phenotype (n) | Frq. Pat. | RR | PAR | P-value | P-value[a] |
|---|---|---|---|---|---|
| MI (750) | 0.075 | 1.95 | 0.072 | 0.00037 | 0.046 |
| Males (546) | 0.075 | 1.97 | 0.072 | 0.00093 | ND |
| Females (204) | 0.073 | 1.90 | 0.068 | 0.021 | ND |

[a] P value adjusted for the number of haplotypes tested using 1,000 randomization tests.
Shown are the results for HapB that shows the strongest association in British MI cohort. HapB is defined by the following SNPs: SG13S377, SG13S114, SG13S41 and SG13S35 (that have the following alleles A, A, A and G, respectively. In all three phenotypes shown the same set of n = 728 British controls is used and the frequency of HapB in the control cohort is 0.040. Number of patients (n), haplotype frequency in patients (Frq. pat.), relative risk (RR) and population attributed risk (PAR).

This was called haplotype HapB. The haplotype frequency of HapB is 7.5% in the MI patient cohort (carrier frequency 14.4%), compared to 4.0% (carrier frequency 7.8%) in controls, conferring a relative risk of 1.95 (Table 10). This haplotype remained significant after adjusting for all haplotypes tested, using 1000 randomisation steps, with an adjusted P value=0.046. No other SNP haplotype had an adjusted P value less than 0.05. The two at-risk haplotypes haplotype A4 and HapB appear to be mutually exclusive with no instance where the same chromosome carries both haplotypes.

Discussion

These results show that variants of the gene encoding FLAP associate with increased risk of MI and stroke. In the Icelandic cohort, a haplotype that spans the FLAP gene is carried by 30% of all MI patients and almost doubles the risk of MI. These findings were subsequently replicated in an independent cohort of stroke patients. In addition, another haplotype that spans the FLAP gene is associated with MI in a British cohort. Suggestive linkage to chromosome 13q 12-13 was observed with several different phenotypes, including female MI, early onset MI of both sexes, and ischemic stroke or TIA in males. However, surprisingly, the strongest haplotype association was observed to males with MI or stroke. Therefore, there may be other variants or haplotypes within the FLAP gene, or in other genes within the linkage region, that also may confer risk to these cardiovascular phenotypes.

These data also show that the at-risk haplotype of the FLAP gene has increased frequency in all subgroups of stroke, including ischemic, TIA, and hemorrhagic stroke.

Association was not found between Haplotype A4 and MI in a British cohort. However, significant association to MI was found with a different variant over the FLAP gene. The fact that different haplotypes of the gene are found conferring risk to MI in a second population is not surprising. A common disease like MI associates with many different mutations or sequence variations, and the frequencies of these disease associated variants may differ between populations. Furthermore, the same mutations may be seen arising on different haplotypic backgrounds.

TABLE 11

The marker map for chromosome 13 used in the linkage analysis.

| Location (cM) | Marker |
|---|---|
| 6 | D13S175 |
| 9.8 | D13S1243 |
| 13.5 | D13S1304 |
| 17.2 | D13S217 |
| 21.5 | D13S289 |
| 25.1 | D13S171 |
| 28.9 | D13S219 |
| 32.9 | D13S218 |
| 38.3 | D13S263 |
| 42.8 | D13S326 |
| 45.6 | D13S153 |
| 49.4 | D13S1320 |
| 52.6 | D13S1296 |
| 55.9 | D13S156 |
| 59.8 | D13S1306 |
| 63.9 | D13S170 |
| 68.7 | D13S265 |
| 73 | D13S167 |
| 76.3 | D13S1241 |
| 79.5 | D13S1298 |
| 81.6 | D13S1267 |
| 84.7 | D13S1256 |
| 85.1 | D13S158 |
| 87 | D13S274 |
| 93.5 | D13S173 |
| 96.7 | D13S778 |
| 102.7 | D13S1315 |
| 110.6 | D13S285 |
| 115 | D13S293 |

A LOD score suggestive of linkage of 2.5 was found at marker D13S289.

TABLE 12

Marker Map for the second step of Linkage Analysis

| Location (cM) | Marker |
|---|---|
| 1.758 | D13S175 |
| 9.235 | D13S787 |
| 11.565 | D13S1243 |
| 16.898 | D13S221 |
| 17.454 | D13S1304 |
| 18.011 | D13S1254 |
| 18.59 | D13S625 |
| 19.308 | D13S1244 |
| 19.768 | D13S243 |
| 22.234 | D13S1250 |
| 22.642 | D13S1242 |
| 22.879 | D13S217 |
| 25.013 | D13S1299 |
| 28.136 | D13S289 |
| 28.678 | D13S290 |
| 29.134 | D13S1287 |
| 30.073 | D13S260 |
| 31.98 | D13S171 |
| 32.859 | D13S267 |

TABLE 12-continued

Marker Map for the second step of Linkage Analysis

| Location (cM) | Marker |
|---|---|
| 33.069 | D13S1293 |
| 33.07 | D13S620 |
| 34.131 | D13S220 |
| 36.427 | D13S219 |
| 39.458 | D13S1808 |
| 40.441 | D13S218 |
| 41.113 | D13S1288 |
| 41.996 | D13S1253 |
| 42.585 | D13S1248 |
| 44.288 | D13S1233 |
| 44.377 | D13S263 |
| 45.535 | D13S325 |
| 45.536 | D13S1270 |
| 45.537 | D13S1276 |
| 49.149 | D13S326 |
| 49.532 | D13S1272 |
| 52.421 | D13S168 |
| 52.674 | D13S287 |
| 60.536 | D13S1320 |
| 64.272 | D13S1296 |
| 71.287 | D13S156 |
| 76.828 | D13S1306 |
| 77.86 | D13S170 |
| 82.828 | D13S265 |
| 91.199 | D13S1241 |
| 93.863 | D13S1298 |
| 97.735 | D13S779 |
| 100.547 | D13S1256 |
| 102.277 | D13S274 |
| 111.885 | D13S173 |
| 112.198 | D13S796 |
| 115.619 | D13S778 |
| 119.036 | D13S1315 |
| 126.898 | D13S285 |
| 131.962 | D13S293 |

The inclusion of additional microsatellite markers increased the information on sharing by descent from 0.7 to 0.8, around the markers that gave the highest LOD scores.

Table 13 shows the exons with positions that encode the FLAP protein, markers and SNPs identified within the genomic sequence by the methods described herein.

| NCBI build34; start on chr. 13 (bp) | NCBI build34; stop on chr. 13 (bp) | SNP/marker/ exon name | alias1 | alias2 | public SNP | Variation |
|---|---|---|---|---|---|---|
| 28932432 | 28932432 | SG13S421 | | DG00AAFQR | rs1556428 | A/G |
| 28960356 | 28960356 | SG13S417 | | SNP13B_R1028729 | rs1028729 | C/T |
| 28965803 | 28965803 | SG13S418 | | SNP13B_Y1323898 | rs1323898 | A/G |
| 28974627 | 28974627 | SG13S44 | | | | A/G |
| 28975101 | 28975101 | SG13S45 | | | | C/G |
| 28975315 | 28975315 | SG13S46 | | | | A/G |
| 28975353 | 28975353 | SG13S50 | | | | C/T |
| 28975774 | 28975774 | SG13S52 | | | | A/G |
| 28985244 | 28985244 | SG13S53 | | | rs1408167 | A/C |
| 28985303 | 28985303 | SG13S55 | | | rs1408169 | A/G |
| 28985423 | 28985423 | SG13S56 | | | | G/T |
| 28985734 | 28985734 | SG13S57 | | | rs6490471 | C/T |
| 28985902 | 28985902 | SG13S58 | | | rs6490472 | A/G |
| 29003869 | 29003869 | SG13S59 | | | | C/G |
| 29004696 | 29004696 | SG13S60 | | | | A/G |
| 29007670 | 29007670 | SG13S419 | | SNP13B_K912392 | rs912392 | C/T |
| 29015410 | 29015410 | SG13S61 | | | | C/T |
| 29025792 | 29025792 | SG13S62 | | | | C/T |
| 29026202 | 29026202 | SG13S63 | | | rs7997114 | A/G |
| 29026668 | 29026668 | SG13S64 | | | | A/G |
| 29038707 | 29038707 | SG13S65 | | | | A/G |
| 29042180 | 29042180 | SG13S420 | | DG00AAFIV | rs2248564 | A/T |
| 29049355 | 29049355 | SG13S66 | | | | A/G |
| 29049446 | 29049446 | SG13S67 | | | | C/T |
| 29050416 | 29050416 | SG13S69 | | | | A/C |
| 29059348 | 29059348 | SG13S70 | | | | A/G |
| 29059383 | 29059383 | SG13S71 | | | | A/G |
| 29059402 | 29059402 | SG13S72 | | | | G/T |
| 29063702 | 29063949 | D13S289 | | | | |
| 29064359 | 29064753 | DG13S166 | | | | |
| 29066272 | 29066272 | SG13S73 | | | | A/G |
| 29070551 | 29070551 | SG13S99 | SNP_13_Y1323892 | DG00AAFIU | rs1323892 | C/T |
| 29081983 | 29081983 | SG13S382 | FLA267479 | | | A/G |
| 29082200 | 29082200 | SG13S383 | FLA267696 | | | A/G |
| 29082357 | 29082357 | SG13S384 | FLA267853 | | | A/G |
| 29083350 | 29083350 | SG13S381 | FLA268846 | DG00AAJER | | C/G |
| 29083518 | 29083518 | SG13S366 | FLA269014 | DG00AAJES | rs4312166 | A/G |
| 29085102 | 29085102 | SG13S385 | FLA270742 | | | C/T |
| 29085190 | 29085190 | SG13S386 | FLA270830 | | | A/G |
| 29086224 | 29086224 | SG13S1 | FLA271864 | | | C/T |
| 29087473 | 29087473 | SG13S2 | FLA273371 | | | A/G |

| | | | | | | |
|---|---|---|---|---|---|---|
| 29088090 | 29088090 | SG13S367 | FLA273988 | DG00AAJEU | rs4474551 | A/G |
| 29088186 | 29088186 | SG13S388 | FLA274084 | | | A/G |
| 29088473 | 29088473 | SG13S10 | FLA274371 | | | A/T |
| 29089044 | 29089044 | SG13S3 | FLA274942 | | | C/T |
| 29089886 | 29089886 | SG13S368 | FLA275784 | DG00AAJEV | | C/T |
| 29090025 | 29090025 | SG13S369 | FLA275923 | DG00AAJEW | | G/T |
| 29090054 | 29090054 | SG13S370 | FLA275952 | DG00AAJEX | | A/G |
| 29090997 | 29090997 | SG13S4 | FLA276895 | | | G/C |
| 29091307 | 29091307 | SG13S5 | FLA277205 | | rs4238133 | G/T |
| 29091580 | 29091580 | SG13S389 | FLA277478 | | | A/G |
| 29091780 | 29091780 | SG13S90 | FLA277678 | | | A/C |
| 29092287 | 29092287 | SG13S390 | FLA278185 | | rs5004913 | A/G |
| 29092536 | 29092536 | SG13S6 | FLA278434 | | | A/G |
| 29092594 | 29092594 | SG13S391 | FLA278492 | | | A/G |
| 29092947 | 29092947 | SG13S392 | FLA278845 | | | G/T |
| 29093964 | 29093964 | SG13S371 | FLA279888 | | rs4409939 | A/G |
| 29094259 | 29094259 | SG13S372 | FLA280183 | DG00AAJEZ | | A/G |
| 29094999 | 29094999 | SG13S393 | FLA280923 | | | A/T |
| 29096688 | 29096688 | SG13S373 | FLA282612 | DG00AAJFA | | A/G |
| 29096813 | 29096813 | SG13S374 | FLA282737 | DG00AAJFB | | A/G |
| 29096874 | 29096874 | SG13S375 | FLA282798 | DG00AAJFC | | C/T |
| 29096962 | 29096962 | SG13S376 | FLA282886 | DG00AAJFD | | A/G |
| 29097476 | 29097476 | SG13S394 | FLA283400 | | | C/G |
| 29097553 | 29097553 | SG13S25 | FLA283477 | | | A/G |
| 29098486 | 29098486 | SG13S395 | FLA284410 | | | A/G |
| 29098891 | 29098891 | SG13S396 | FLA284815 | | | A/C |
| 29098979 | 29098979 | SG13S397 | FLA284903 | | | C/T |
| 29101965 | 29101965 | SG13S377 | FLA287889 | DG00AAJFF | | A/G |
| 29103909 | 29103909 | SG13S189 | FLA289833 | | | C/G |
| 29104271 | 29104271 | SG13S100 | FLA290195 | DG00AAHIK | rs4073259 | A/G |
| 29104629 | 29104629 | SG13S398 | FLA290553 | | | C/G |
| 29104646 | 29104646 | SG13S94 | FLA290570 | | rs4073261 | C/T |
| 29105099 | 29105099 | SG13S101 | FLA291023 | | rs4075474 | C/T |
| 29106329 | 29106329 | SG13S95 | FLA292253 | | | G/T |
| 29106652 | 29106652 | SG13S102 | FLA292576 | | | A/T |
| 29107138 | 29107138 | SG13S103 | FLA293062 | | | C/T |
| 29107404 | 29107404 | SG13S104 | FLA293328 | | | A/G |
| 29107668 | 29107812 | EXON1 | | | | |
| 29107830 | 29107830 | SG13S191 | FLA293754 | DG00AAFJT | rs4769055 | A/C |
| 29108398 | 29108398 | SG13S105 | FLA294322 | | | A/G |
| 29108579 | 29108579 | SG13S106 | FLA294503 | DG00AAHII | | A/G |
| 29108919 | 29108919 | SG13S107 | FLA294843 | | rs4075131 | A/G |
| 29108972 | 29108972 | SG13S108 | FLA294896 | | rs4075132 | C/T |
| 29109112 | 29109112 | SG13S109 | FLA295036 | | | A/G |
| 29109182 | 29109182 | SG13S110 | FLA295106 | | | A/G |
| 29109344 | 29109344 | SG13S111 | FLA295268 | | rs4597169 | C/T |
| 29109557 | 29109557 | SG13S112 | FLA295481 | | | C/T |
| 29109773 | 29109773 | SG13S113 | FLA295697 | | rs4293222 | C/G |
| 29110096 | 29110096 | SG13S114 | FLA296020 | DG00AAHID | | A/T |
| 29110178 | 29110178 | SG13S115 | FLA296102 | | | A/T |
| 29110508 | 29110508 | SG13S116 | FLA296432 | | rs4769871 | C/T |
| 29110630 | 29110630 | SG13S117 | FLA296554 | | rs4769872 | A/G |
| 29110689 | 29110689 | SG13S118 | FLA296613 | | rs4769873 | C/T |
| 29110862 | 29110862 | SG13S119 | FLA296786 | | | A/G |
| 29111889 | 29111889 | SG13S120 | FLA297813 | | | C/T |
| 29112174 | 29112174 | SG13S121 | FLA298098 | DG00AAHIJ | rs4503649 | A/G |
| 29112264 | 29112264 | SG13S122 | FLA298188 | DG00AAHIH | | A/G |
| 29112306 | 29112306 | SG13S123 | FLA298230 | | | C/T |
| 29112455 | 29112455 | SG13S43 | FLA298379 | | rs3885907 | A/C |
| 29112583 | 29112583 | SG13S399 | FLA298507 | | | A/C |
| 29112680 | 29112680 | SG13S124 | FLA298604 | | rs3922435 | C/T |
| 29113139 | 29113139 | SG13S125 | FLA299063 | | | A/G |
| 29114056 | 29114056 | SG13S400 | FLA299980 | | | A/G |
| 29114738 | 29114738 | SG13S126 | FLA300662 | | | A/G |
| 29114940 | 29114940 | SG13S127 | FLA300864 | | | A/G |
| 29115878 | 29115878 | SG13S128 | FLA302094 | | rs4254165 | A/G |
| 29116020 | 29116020 | SG13S129 | FLA302236 | | rs4360791 | A/G |
| 29116068 | 29116068 | SG13S130 | FLA302284 | | | G/T |
| 29116196 | 29116296 | EXON2 | | | | |
| 29116249 | 29116249 | SG13S190 | FLA302465 | | | C/T |
| 29116308 | 29116308 | SG13S192 | FLA302524 | B_SNP_302524 | rs3803277 | A/C |
| 29116344 | 29116344 | SG13S193 | FLA302560 | | | A/G |
| 29116401 | 29116401 | SG13S88 | FLA302617 | B_SNP_302617 | rs3803278 | C/T |
| 29116688 | 29116688 | SG13S131 | FLA302904 | | | C/T |
| 29117133 | 29117133 | SG13S132 | FLA303349 | | | A/C |
| 29117546 | 29117546 | SG13S133 | FLA303762 | | rs4356336 | C/T |
| 29117553 | 29117553 | SG13S38 | FLA303769 | | rs4584668 | A/T |
| 29117580 | 29117580 | SG13S134 | FLA303796 | | | C/T |
| 29117741 | 29117741 | SG13S135 | FLA303957 | | rs4238137 | C/T |

-continued

| | | | | | | |
|---|---|---|---|---|---|---|
| 29117954 | 29117954 SG13S136 | FLA304170 | | rs4147063 | C/T |
| 29118118 | 29118118 SG13S137 | FLA304334 | DG00AAHIG | rs4147064 | C/T |
| 29118815 | 29118815 SG13S86 | FLA305031 | | | A/G |
| 29118873 | 29118873 SG13S87 | FLA305089 | DG00AAHOJ | | A/G |
| 29119069 | 29119069 SG13S138 | FLA305285 | | | C/T |
| 29119138 | 29119138 SG13S139 | FLA305354 | | | C/G |
| 29119289 | 29119289 SG13S140 | FLA305505 | | | A/G/T |
| 29119462 | 29119462 SG13S141 | FLA305678 | | | C/T |
| 29119740 | 29119740 SG13S39 | FLA305956 | | | G/T |
| 29120939 | 29120939 SG13S142 | FLA307155 | | rs4387455 | C/T |
| 29120949 | 29120949 SG13S143 | FLA307165 | | rs4254166 | C/T |
| 29121342 | 29121342 SG13S144 | FLA307558 | | rs4075692 | A/G |
| 29121572 | 29121572 SG13S145 | FLA307788 | | | C/G |
| 29121988 | 29121988 SG13S146 | FLA308204 | | | C/T |
| 29122253 | 29122253 SG13S26 | FLA308469 | | | C/T |
| 29122283 | 29122283 SG13S27 | FLA308499 | | | A/G |
| 29122294 | 29122294 SG13S147 | FLA308510 | | | C/T |
| 29122298 | 29122298 SG13S28 | FLA308514 | | | G/T |
| 29122311 | 29122311 SG13S148 | FLA308527 | | | G/T |
| 29123370 | 29123370 SG13S98 | FLA309586 | | | G/T |
| 29123635 | 29123635 SG13S149 | FLA309851 | | | A/G |
| 29123643 | 29123643 SG13S29 | FLA309859 | | | A/C |
| 29124188 | 29124259 EXON3 | | | | |
| 29124441 | 29124441 SG13S89 | FLA310657 | B_SNP_310657 | rs4769874 | A/G |
| 29124906 | 29124906 SG13S96 | FLA311122 | | rs4072653 | A/G |
| 29125032 | 29125032 SG13S150 | FLA311248 | | | C/G |
| 29125521 | 29125521 SG13S401 | FLA311737 | | | C/T |
| 29125822 | 29125822 SG13S151 | FLA312038 | | | C/T |
| 29125840 | 29125840 SG13S30 | FLA312056 | | | G/T |
| 29127301 | 29127301 SG13S31 | FLA313550 | | | C/T |
| 29128080 | 29128162 EXON4 | | | | |
| 29128284 | 29128284 SG13S152 | FLA314500 | | | C/G |
| 29128316 | 29128316 SG13S402 | FLA314532 | | rs4468448 | C/T |
| 29128798 | 29128798 SG13S403 | FLA315014 | | rs4399410 | A/G |
| 29129016 | 29129016 SG13S153 | FLA315232 | | | A/T |
| 29129139 | 29129139 SG13S97 | FLA315355 | | | A/G |
| 29129154 | 29129154 SG13S154 | FLA315370 | | | C/T |
| 29129395 | 29129395 SG13S40 | FLA315611 | | | G/T |
| 29129915 | 29129915 SG13S155 | FLA316131 | | rs4769875 | A/G |
| 29130192 | 29130192 SG13S156 | FLA316408 | | | A/C |
| 29130256 | 29130256 SG13S157 | FLA316472 | | | A/G |
| 29130299 | 29130299 SG13S158 | FLA316515 | | | A/C |
| 29130353 | 29130353 SG13S159 | FLA316569 | | | G/T |
| 29130391 | 29130391 SG13S160 | FLA316607 | | | C/T |
| 29130547 | 29130547 SG13S32 | FLA316763 | | | A/C |
| 29131280 | 29131280 SG13S161 | FLA317496 | | | A/G |
| 29131403 | 29131403 SG13S162 | FLA317619 | | | A/G |
| 29131404 | 29131404 SG13S163 | FLA317620 | | | C/T |
| 29131431 | 29131431 SG13S164 | FLA317647 | | rs4769058 | C/T |
| 29131517 | 29131517 SG13S165 | FLA317733 | | | A/T |
| 29131528 | 29131528 SG13S166 | FLA317744 | | rs4769059 | C/T |
| 29131599 | 29131599 SG13S167 | FLA317815 | | rs4769876 | A/G |
| 29132003 | 29132003 SG13S168 | FLA318219 | | | A/C |
| 29133753 | 29133753 SG13S33 | FLA319969 | | | G/T |
| 29134045 | 29134045 SG13S41 | FLA320261 | | | A/G |
| 29134177 | 29134177 SG13S169 | FLA320393 | | | A/G |
| 29134379 | 29134379 SG13S404 | FLA320595 | | rs4427651 | G/T |
| 29135558 | 29135558 SG13S170 | FLA321774 | | rs3935645 | C/T |
| 29135640 | 29135640 SG13S171 | FLA321856 | | rs3935644 | A/G |
| 29135750 | 29135750 SG13S172 | FLA321966 | | | A/G |
| 29135809 | 29135809 SG13S173 | FLA322025 | | | A/T |
| 29135877 | 29135877 SG13S42 | FLA322093 | | rs4769060 | A/G |
| 29136080 | 29136556 EXON5 | | | | |
| 29136290 | 29136290 SG13S194 | FLA322506 | | | C/T |
| 29136462 | 29136462 SG13S195 | FLA322678 | | rs1132340 | A/G |
| 29136797 | 29136797 SG13S174 | FLA323013 | | | A/G |
| 29137100 | 29137100 SG13S34 | FLA323316 | | | G/T |
| 29137150 | 29137150 SG13S175 | FLA323366 | | | A/G |
| 29137607 | 29137607 SG13S176 | FLA323823 | | | A/G |
| 29137651 | 29137651 SG13S177 | FLA323867 | | | C/T |
| 29137905 | 29137905 SG13S178 | FLA324121 | | | C/G |
| 29138117 | 29138117 SG13S35 | FLA324333 | | | A/G |
| 29138375 | 29138375 SG13S179 | FLA324591 | | | A/G |
| 29138385 | 29138385 SG13S180 | FLA324601 | | | C/T |
| 29138633 | 29138633 SG13S181 | FLA324849 | DG00AAHIF | rs4420371 | C/G |
| 29139153 | 29139153 SG13S182 | FLA325369 | | | C/T |
| 29139277 | 29139277 SG13S183 | FLA325493 | | rs4466940 | C/T |
| 29139435 | 29139435 SG13S184 | FLA325651 | DG00AAHOI | rs4445746 | A/G |
| 29139971 | 29139971 SG13S185 | FLA326187 | | | A/G |

-continued

| | | | | | | |
|---|---|---|---|---|---|---|
| 29140441 | 29140441 | SG13S405 | FLA326657 | | | A/G |
| 29140649 | 29140649 | SG13S91 | FLA326865 | | | A/G |
| 29140695 | 29140695 | SG13S186 | FLA326911 | | rs4769877 | A/T |
| 29140703 | 29140703 | SG13S187 | FLA326919 | | | A/G |
| 29140805 | 29140805 | SG13S188 | FLA327021 | DG00AAJFE | | A/G |
| 29141049 | 29141049 | SG13S406 | FLA327265 | | | C/T |
| 29142392 | 29142392 | SG13S92 | FLA328644 | | rs4429158 | C/T |
| 29142397 | 29142397 | SG13S93 | FLA328649 | | | A/G |
| 29142712 | 29142712 | SG13S36 | FLA328964 | | | C/T |
| 29144013 | 29144013 | SG13S407 | FLA330265 | | | C/T |
| 29144203 | 29144203 | SG13S408 | FLA330455 | | | C/T |
| 29144234 | 29144589 | D13S1238 | | | | |
| 29144255 | 29144255 | SG13S7 | FLA330507 | | | C/T |
| 29144877 | 29144877 | SG13S37 | FLA331129 | | | A/G |
| 29144982 | 29144982 | SG13S409 | FLA331234 | | | A/G |
| 29144983 | 29144983 | SG13S8 | FLA331235 | | rs4491352 | A/C |
| 29145122 | 29145122 | SG13S410 | FLA331374 | | rs4319601 | C/T |
| 29145143 | 29145143 | SG13S411 | FLA331395 | | | A/G |
| 29145171 | 29145171 | SG13S9 | FLA331423 | | | C/T |
| 29145221 | 29145221 | SG13S412 | FLA331473 | | rs4769062 | A/G |
| 29145265 | 29145265 | SG13S413 | FLA331517 | | rs4238138 | C/T |

| minor allele | minor allele frequency (%) | start position in SEQ ID NO: 1 | end position in SEQ ID NO: 1 |
|---|---|---|---|
| G | 10.32 | 432 | 432 |
| G | 30.46 | 28356 | 28356 |
| T | 37.38 | 33803 | 33803 |
| G | 0.545 | 42627 | 42627 |
| G | 1.111 | 43101 | 43101 |
| G | 0.328 | 43315 | 43315 |
| C | 0.495 | 43353 | 43353 |
| A | 6.993 | 43774 | 43774 |
| C | 30.876 | 53244 | 53244 |
| G | 6.731 | 53303 | 53303 |
| T | 0.353 | 53423 | 53423 |
| C | 31.356 | 53734 | 53734 |
| A | 30.935 | 53902 | 53902 |
| G | 5.492 | 71869 | 71869 |
| A | 1.812 | 72696 | 72696 |
| G | 35.00 | 75670 | 75670 |
| C | 1.314 | 83410 | 83410 |
| T | 3.521 | 93792 | 93792 |
| A | 30.031 | 94202 | 94202 |
| A | 1.724 | 94668 | 94668 |
| A | 0.369 | 106707 | 106707 |
| A | 13.66 | 110180 | 110180 |
| A | 20.779 | 117355 | 117355 |
| T | 5.965 | 117446 | 117446 |
| A | 16.923 | 118416 | 118416 |
| A | 34.364 | 127348 | 127348 |
| A | 8.537 | 127383 | 127383 |
| T | 25.536 | 127402 | 127402 |
| | | 131702 | 131949 |
| | | 132359 | 132753 |
| A | 37.302 | 134272 | 134272 |
| C | 6.25 | 138551 | 138551 |
| A | 0.49 | 149983 | 149983 |
| A | 14.08 | 150200 | 150200 |
| G | 0.62 | 150357 | 150357 |
| G | 14.01 | 151350 | 151350 |
| T | 0.58 | 151518 | 151518 |
| C | 30.21 | 153102 | 153102 |
| A | 10.95 | 153190 | 153190 |
| G | 30.00 | 154224 | 154224 |
| A | 27.95 | 155473 | 155473 |
| G | 2.41 | 156090 | 156090 |
| A | 0.39 | 156186 | 156186 |
| T | 10.23 | 156473 | 156473 |
| T | 15.17 | 157044 | 157044 |
| T | 13.60 | 157886 | 157886 |
| G | 12.44 | 158025 | 158025 |
| A | 13.45 | 158054 | 158054 |
| G | 14.59 | 158997 | 158997 |
| T | 26.84 | 159307 | 159307 |
| A | 12.73 | 159580 | 159580 |
| C | 43.67 | 159780 | 159780 |
| A | 12.18 | 160287 | 160287 |
| A | 8.38 | 160536 | 160536 |

| | | | |
|---|---|---|---|
| G | 0.62 | 160594 | 160594 |
| T | 12.34 | 160947 | 160947 |
| G | 25.34 | 161964 | 161964 |
| C | 0.24 | 162259 | 162259 |
| T | 25.66 | 162999 | 162999 |
| A | 14.84 | 164688 | 164688 |
| G | 12.37 | 164813 | 164813 |
| C | 14.55 | 164874 | 164874 |
| G | 11.99 | 164962 | 164962 |
| C | 14.66 | 165476 | 165476 |
| A | 12.21 | 165553 | 165553 |
| A | 0.79 | 166486 | 166486 |
| C | 10.15 | 166891 | 166891 |
| C | 3.53 | 166979 | 166979 |
| A | 12.45 | 169965 | 169965 |
| C | 0.62 | 171909 | 171909 |
| G | 31.55 | 172271 | 172271 |
| G | 4.94 | 172629 | 172629 |
| C | 15.51 | 172646 | 172646 |
| T | 27.91 | 173099 | 173099 |
| G | 14.74 | 174329 | 174329 |
| T | 1.17 | 174652 | 174652 |
| T | 1.28 | 175138 | 175138 |
| A | 2.17 | 175404 | 175404 |
| | | 175668 | 175812 |
| A | 30.11 | 175830 | 175830 |
| G | 0.66 | 176398 | 176398 |
| A | 28.31 | 176579 | 176579 |
| G | 14.85 | 176919 | 176919 |
| C | 1.21 | 176972 | 176972 |
| A | 1.04 | 177112 | 177112 |
| G | 0.88 | 177182 | 177182 |
| C | 1.14 | 177344 | 177344 |
| T | 7.10 | 177557 | 177557 |
| C | 22.52 | 177773 | 177773 |
| A | 20.86 | 178096 | 178096 |
| T | 13.83 | 178178 | 178178 |
| T | 4.05 | 178508 | 178508 |
| A | 4.07 | 178630 | 178630 |
| T | 4.07 | 178689 | 178689 |
| A | 1.06 | 178862 | 178862 |
| C | 16.00 | 179889 | 179889 |
| G | 49.36 | 180174 | 180174 |
| A | 29.75 | 180264 | 180264 |
| T | 5.06 | 180306 | 180306 |
| C | 46.23 | 180455 | 180455 |
| C | 1.59 | 180583 | 180583 |
| T | 1.45 | 180680 | 180680 |
| G | 11.32 | 181139 | 181139 |
| A | 3.25 | 182056 | 182056 |
| A | 34.12 | 182738 | 182738 |
| G | 29.63 | 182940 | 182940 |
| A | 45.68 | 183878 | 183878 |
| G | 36.65 | 184020 | 184020 |
| G | 8.07 | 184068 | 184068 |
| | | 184196 | 184296 |
| T | 1.02 | 184249 | 184249 |
| A | 49.57 | 184308 | 184308 |
| A | 0.58 | 184344 | 184344 |
| C | 24.71 | 184401 | 184401 |
| T | 7.19 | 184688 | 184688 |
| A | 1.10 | 185133 | 185133 |
| T | 37.65 | 185546 | 185546 |
| A | 45.50 | 185553 | 185553 |
| T | 1.22 | 185580 | 185580 |
| T | 0.89 | 185741 | 185741 |
| T | 36.69 | 185954 | 185954 |
| T | 29.11 | 186118 | 186118 |
| A | 30.19 | 186815 | 186815 |
| G | 3.29 | 186873 | 186873 |
| T | 36.96 | 187069 | 187069 |
| G | 36.63 | 187138 | 187138 |
| T | 37.34 | 187289 | 187289 |
| C | 1.15 | 187462 | 187462 |
| T | 9.91 | 187740 | 187740 |
| C | 3.36 | 188939 | 188939 |
| T | 36.24 | 188949 | 188949 |
| A | 31.58 | 189342 | 189342 |
| G | 0.45 | 189572 | 189572 |

-continued

| | | | |
|---|---|---|---|
| T | 1.14 | 189988 | 189988 |
| T | 46.57 | 190253 | 190253 |
| A | 10.34 | 190283 | 190283 |
| T | 8.00 | 190294 | 190294 |
| T | 33.71 | 190298 | 190298 |
| T | 2.29 | 190311 | 190311 |
| G | 1.19 | 191370 | 191370 |
| A | 1.01 | 191635 | 191635 |
| A | 47.88 | 191643 | 191643 |
| | | 192188 | 192259 |
| A | 4.68 | 192441 | 192441 |
| G | 29.72 | 192906 | 192906 |
| C | 8.22 | 193032 | 193032 |
| C | 21.10 | 193521 | 193521 |
| T | 8.57 | 193822 | 193822 |
| T | 23.23 | 193840 | 193840 |
| T | 24.20 | 195301 | 195301 |
| | | 196080 | 196162 |
| C | 23.89 | 196284 | 196284 |
| T | 19.33 | 196316 | 196316 |
| G | 11.50 | 196798 | 196798 |
| T | 3.08 | 197016 | 197016 |
| A | 9.72 | 197139 | 197139 |
| T | 0.98 | 197154 | 197154 |
| T | 2.24 | 197395 | 197395 |
| A | 1.43 | 197915 | 197915 |
| A | 1.80 | 198192 | 198192 |
| G | 2.38 | 198256 | 198256 |
| A | 0.61 | 198299 | 198299 |
| G | 2.55 | 198353 | 198353 |
| T | 0.83 | 198391 | 198391 |
| C | 48.50 | 198547 | 198547 |
| G | 2.44 | 199280 | 199280 |
| G | 2.45 | 199403 | 199403 |
| C | 2.45 | 199404 | 199404 |
| C | 2.55 | 199431 | 199431 |
| T | 20.00 | 199517 | 199517 |
| T | 2.46 | 199528 | 199528 |
| A | 3.50 | 199599 | 199599 |
| C | 8.39 | 200003 | 200003 |
| T | 8.99 | 201753 | 201753 |
| G | 5.41 | 202045 | 202045 |
| G | 4.12 | 202177 | 202177 |
| G | 38.33 | 202379 | 202379 |
| C | 32.77 | 203558 | 203558 |
| G | 48.03 | 203640 | 203640 |
| G | 1.67 | 203750 | 203750 |
| A | 0.68 | 203809 | 203809 |
| G | 42.44 | 203877 | 203877 |
| | | 204080 | 204556 |
| T | 0.30 | 204290 | 204290 |
| G | 2.46 | 204462 | 204462 |
| G | 0.56 | 204797 | 204797 |
| G | 30.23 | 205100 | 205100 |
| A | 2.40 | 205150 | 205150 |
| A | 2.24 | 205607 | 205607 |
| T | 1.64 | 205651 | 205651 |
| C | 1.40 | 205905 | 205905 |
| A | 9.52 | 206117 | 206117 |
| A | 48.14 | 206375 | 206375 |
| T | 2.50 | 206385 | 206385 |
| C | 49.41 | 206633 | 206633 |
| T | 2.36 | 207153 | 207153 |
| T | 12.07 | 207277 | 207277 |
| A | 16.67 | 207435 | 207435 |
| G | 7.66 | 207971 | 207971 |
| A | 9.66 | 208441 | 208441 |
| A | 7.78 | 208649 | 208649 |
| A | 25.71 | 208695 | 208695 |
| A | 1.43 | 208703 | 208703 |
| G | 4.71 | 208805 | 208805 |
| T | 0.56 | 209049 | 209049 |
| T | 8.33 | 210392 | 210392 |
| A | 7.23 | 210397 | 210397 |
| C | 15.88 | 210712 | 210712 |
| T | 3.29 | 212013 | 212013 |
| T | 0.30 | 212203 | 212203 |
| | | 212234 | 212589 |
| T | 16.28 | 212255 | 212255 |

-continued

| | | | |
|---|---|---|---|
| G | 16.70 | 212877 | 212877 |
| A | 1.93 | 212982 | 212982 |
| C | 30.64 | 212983 | 212983 |
| T | 20.57 | 213122 | 213122 |
| A | 1.54 | 213143 | 213143 |
| C | 16.37 | 213171 | 213171 |
| A | 7.42 | 213221 | 213221 |
| T | 1.91 | 213265 | 213265 |

TABLE 14

Extended 4 microsatellite marker haplotypes in the initial haplotype analysis.

| 4 markers: Length | p-val | RR | N_af | P_al | P_ca | N_ct | P_al | P_ca | Alleles | | | | Markers |
|---|---|---|---|---|---|---|---|---|---|---|---|---|---|
| 0.88 | 4.71E−06 | 6.23 | 428 | 0.065 | 0.125 | 721 | 0.011 | 0.022 | 0 | −12 | −6 | 0 | DG13S80 DG13S83 DG13S1110 DG13S163 |
| 0.82 | 8.60E−06 | INF | 438 | 0.032 | 0.062 | 720 | 0 | 0 | 0 | 4 | 2 | 14 | DG13S1111 DG13S1103 D13S1287 DG13S1061 |
| 0.67 | 6.98E−06 | 19.91 | 435 | 0.03 | 0.059 | 721 | 0.002 | 0.003 | 8 | 6 | 0 | 8 | DG13S1103 DG13S163 D13S290 DG13S1061 |
| 0.767 | 4.85E−06 | 26.72 | 436 | 0.048 | 0.094 | 721 | 0.002 | 0.004 | 0 | 0 | 2 | 12 | DG13S1101 DG13S166 D13S1287 DG13S1061 |
| 0.515 | 1.93E−06 | INF | 422 | 0.048 | 0.094 | 721 | 0 | 0 | 2 | 0 | 0 | 6 | DG13S166 DG13S163 D13S290 DG13S1061 |
| 0.864 | 1.68E−06 | INF | 424 | 0.024 | 0.048 | 717 | 0 | 0 | 0 | 2 | 0 | −16 | DG13S166 DG13S163 DG13S1061 DG13S293 |
| 0.927 | 5.38E−06 | INF | 435 | 0.034 | 0.067 | 720 | 0 | 0 | 4 | 2 | 14 | 3 | DG13S1103 D13S1287 DG13S1061 DG13S301 |

Length=length of haplotype in Mb. P-val=p-value. RR=Relative risk. N af=Number of patients. P al=allelic frequency of haplotype. P ca=carrier frequency of haplotype. N ct=number of controls. Alleles=alleles in the haplotype. Markers=markers in the haplotype.

TABLE 15

Extended 5 microsatellite marker haplotypes in the initial haplotype analysis.

| 5markers: Length | p-val | RR | N_af | P_al | P_ca | N_ct | P_al | P_ca | Alleles | | | | | Markers |
|---|---|---|---|---|---|---|---|---|---|---|---|---|---|---|
| 0.851 | 7.45E−06 | 15.43 | 413 | 0.034 | 0.067 | 715 | 0.002 | 0.005 | 0 | 18 | 0 | 0 | 0 | DG13S79 D13S1299 DG13S87 D13S1246 DG13S166 |
| 0.964 | 8.07E−06 | INF | 437 | 0.023 | 0.045 | 721 | 0 | 0 | 0 | −12 | 6 | 8 | 6 | DG13S79 DG13S83 DG13S1104 |

TABLE 15-continued

Extended 5 microsatellite marker haplotypes in the initial haplotype analysis.

| 5markers: | | pos.rr-frqgt1perc | | | | | | Alleles | | | | | Markers |
|---|---|---|---|---|---|---|---|---|---|---|---|---|---|
| Length | p-val | RR | N_af | P_al | P_ca | N_ct | P_al | P_ca | | | | | |
| 0.964 | 2.38E−06 | INF | 437 | 0.026 | 0.052 | 720 | 0 | 0 | 0 | 6 | 0 | 8 | 6 | DG13S1103 DG13S163 DG13S79 DG13S1104 DG13S172 |
| 0.931 | 7.05E−06 | 5.8 | 429 | 0.068 | 0.131 | 721 | 0.012 | 0.025 | 0 | −6 | 0 | 0 | −2 | DG13S1103 DG13S163 DG13S79 DG13S1110 DG13S175 |
| 0.964 | 8.13E−06 | INF | 434 | 0.021 | 0.041 | 721 | 0 | 0 | 0 | 3 | 8 | 2 | 6 | DG13S166 D13S1238 DG13S79 DG13S1098 DG13S1103 |
| 0.597 | 9.78E−06 | 4.58 | 428 | 0.074 | 0.143 | 717 | 0.017 | 0.034 | −6 | 0 | 0 | 0 | −2 | DG13S166 DG13S163 DG13S1110 DG13S89 DG13S175 |
| 0.896 | 6.92E−06 | INF | 428 | 0.026 | 0.051 | 721 | 0 | 0 | −12 | −6 | 0 | −2 | 2 | DG13S166 D13S1238 DG13S83 DG13S1110 DG13S166 |
| 0.722 | 2.18E−06 | INF | 453 | 0.026 | 0.051 | 738 | 0 | 0 | −6 | 0 | 0 | −2 | 2 | D13S1238 D13S290 DG13S1110 D13S289 DG13S166 |
| 0.982 | 7.88E−06 | INF | 437 | 0.028 | 0.055 | 721 | 0 | 0 | 0 | 0 | 4 | 2 | 14 | D13S1238 D13S290 DG13S87 DG13S175 DG13S1103 |
| 0.841 | 8.88E−06 | INF | 438 | 0.032 | 0.062 | 720 | 0 | 0 | 0 | 0 | 4 | 2 | 14 | D13S1287 DG13S1061 DG13S89 DG13S1111 DG13S1103 |
| 0.841 | 9.67E−07 | INF | 435 | 0.029 | 0.057 | 721 | 0 | 0 | 0 | 8 | 6 | 0 | 8 | D13S1287 DG13S1061 DG13S89 DG13S1103 DG13S163 |
| 0.982 | 7.90E−06 | 18.63 | 437 | 0.026 | 0.052 | 721 | 0.001 | 0.003 | 0 | 4 | 0 | 2 | 14 | D13S290 DG13S1061 DG13S87 DG13S1103 DG13S166 |
| 0.841 | 3.52E−06 | 28.52 | 436 | 0.048 | 0.094 | 721 | 0.002 | 0.004 | 0 | 0 | 0 | 2 | 12 | D13S1287 DG13S1061 DG13S89 DG13S1101 DG13S166 |
| 0.705 | 5.28E−06 | INF | 435 | 0.027 | 0.053 | 721 | 0 | 0 | 0 | 8 | 6 | 0 | 8 | D13S1287 DG13S1061 DG13S175 DG13S1103 DG13S163 |
| 0.841 | 4.21E−06 | INF | 422 | 0.048 | 0.093 | 721 | 0 | 0 | 0 | 2 | 0 | 0 | 6 | D13S290 DG13S1061 DG13S89 DG13S166 DG13S163 |
| 0.767 | 4.02E−06 | 28.11 | 436 | 0.049 | 0.095 | 721 | 0.002 | 0.004 | 0 | 0 | 0 | 2 | 12 | D13S290 DG13S1061 DG13S1101 DG13S175 DG13S166 D13S1287 DG13S1061 |

TABLE 15-continued

Extended 5 microsatellite marker haplotypes in the initial haplotype analysis.

5markers: pos.rr-frqgt1perc

| Length | p-val | RR | N_af | P_al | P_ca | N_ct | P_al | P_ca | Alleles | | | | | Markers |
|---|---|---|---|---|---|---|---|---|---|---|---|---|---|---|
| 0.767 | 1.29E−06 | 31.07 | 436 | 0.047 | 0.092 | 721 | 0.002 | 0.003 | 0 | 0 | 0 | 2 | 12 | DG13S1101 DG13S172 DG13S166 D13S1287 DG13S1061 |
| 0.705 | 4.25E−07 | INF | 422 | 0.048 | 0.093 | 721 | 0 | 0 | 0 | 2 | 0 | 0 | 6 | DG13S175 DG13S166 DG13S163 D13S290 DG13S1061 |
| 0.683 | 6.58E−06 | INF | 437 | 0.029 | 0.056 | 721 | 0 | 0 | 0 | 4 | 0 | 2 | 14 | DG13S172 DG13S1103 DG13S166 D13S1287 DG13S1061 |
| 0.767 | 2.85E−06 | 32.43 | 436 | 0.044 | 0.087 | 721 | 0.001 | 0.003 | 0 | 0 | 0 | 2 | 12 | DG13S1101 DG13S166 D13S290 D13S1287 DG13S1061 |
| 0.865 | 9.58E−06 | 18.39 | 451 | 0.023 | 0.045 | 739 | 0.001 | 0.003 | 0 | 0 | 2 | 2 | −16 | D13S289 DG13S166 DG13S163 D13S1287 DG13S293 |
| 0.865 | 5.08E−06 | INF | 453 | 0.019 | 0.038 | 739 | 0 | 0 | 0 | 0 | 2 | 0 | −16 | D13S289 DG13S166 DG13S163 DG13S1061 DG13S293 |
| 0.927 | 1.02E−07 | 27.65 | 437 | 0.037 | 0.073 | 721 | 0.001 | 0.003 | 4 | 0 | 2 | 14 | 3 | DG13S1103 DG13S166 D13S1287 DG13S1061 DG13S301 |

Length = length of haplotype in Mb. P-val = p-value. RR = Relative risk. N af = Number of patients. P al = allelic frequency of haplotype. P ca = carrier frequency of haplotype. N ct = number of controls. Alleles = alleles in the haplotype. Markers = markers in the haplotype

TABLE 16

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S2393 | CCTTTGCTTTGTTCCTATTTCTTT (SEQ ID NO. 4) | TCCCATTGCCCAGAGTTAAT (SEQ ID NO. 5) | 22831401 | 22831787 |
| DG13S2070 | TCCTCATGTCTTCACCTAGAAGC (SEQ ID NO. 6) | CCACTCATGAGGGAGCTGTT (SEQ ID NO. 7) | 23020439 | 23020651 |
| DG13S2071 | TGTCACAGGCACACACTCTCT (SEQ ID NO. 8) | GAGTATGGCTGCTGCTCCTC (SEQ ID NO. 9) | 23066973 | 23067076 |
| DG13S2072 | ATGGCTCACACTGGCCTAAA (SEQ ID NO. 10) | TGAACAGACCAATAATAGTGCAG (SEQ ID NO. 11) | 23136964 | 23137114 |
| DG13S2078 | AAGCCACCCTTTAAACAGCA (SEQ ID NO. 12) | GCTGAGGAAGCAACTCCACT (SEQ ID NO. 13) | 23591927 | 23592081 |
| DG13S2079 | GCTCTGAATTCCCTGGCATA (SEQ ID NO. 14) | TTAGCCCTAGTCCCACTCTCC (SEQ ID NO. 15) | 23646974 | 23647183 |

TABLE 16-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S2082 | CAAGAGGCCTGCATAAGGAA (SEQ ID NO. 16) | AGATTGCCGGTGGCTTAAAT (SEQ ID NO. 17) | 23807898 | 23808174 |
| DG13S2083 | TGTCTGTTCCCGTCTGTCTG (SEQ ID NO. 18) | TTCATCCTCTGCCAAATTCC (SEQ ID NO. 19) | 23882291 | 23882532 |
| DG13S2086 | GGCATGTATTCACTGCCTGA (SEQ ID NO. 20) | AAACCCATTCTTCTTCCTCTTAC (SEQ ID NO. 21) | 24069346 | 24069771 |
| DG13S2089 | TATGTGTTCAGCCCAGACCTC (SEQ ID NO. 22) | CCCTGCCATGTGCATTTAC (SEQ ID NO. 23) | 24274920 | 24275129 |
| DG13S44 | CATTTCGGAAGGCAAAGAAA (SEQ ID NO. 24) | TTGCAATGAGGAATGAAGCA (SEQ ID NO. 25) | 24413148 | 24413382 |
| DG13S2095 | TCCATTATCCATCTGTTCATTCA (SEQ ID NO. 26) | GAAGAATTAATTGTAGGAGGCAAGA (SEQ ID NO. 27) | 24621830 | 24622121 |
| DG13S46 | CTGACATCACCACATTGATCG (SEQ ID NO. 28) | CATACACAGCCATGTGGAATTA (SEQ ID NO. 29) | 24652046 | 24652291 |
| DG13S2101 | ACGGTGATGACGCCTACATT (SEQ ID NO. 30) | TCACATGGACCAATTACCTAGAA (SEQ ID NO. 31) | 24863557 | 24863744 |
| D13S1254 | AAATTACTTCATCTTGACGATAACA (SEQ ID NO. 32) | CTATTGGGGACTGCAGAGAG (SEQ ID NO. 33) | 25316434 | 25316657 |
| DG13S55 | AGCCAGTGTCCACAAGGAAG (SEQ ID NO. 34) | GAGGGTGAGACACATCTCTGG (SEQ ID NO. 35) | 25337471 | 25337753 |
| DG13S54 | AATCGTGCCTCAGTTCCATC (SEQ ID NO. 36) | CCACCAGGAACAACACACAC (SEQ ID NO. 37) | 25377308 | 25377463 |
| D13S625 | TTGCTCTCCAGCCTGGGC (SEQ ID NO. 38) | TTCCTCTGGCTGCCTGCG (SEQ ID NO. 39) | 25391207 | 25391395 |
| DG13S2695 | TCCTGCATGAGAAGGAACTG (SEQ ID NO. 40) | CGACATTCACTGTGGCTCTT (SEQ ID NO. 41) | 25415551 | 25415807 |
| DG13S1479 | TTTGATTCCGTGGTCCATTA (SEQ ID NO. 42) | TTATTTGGTCGGTGCACCTTT (SEQ ID NO. 43) | 25459039 | 25459368 |
| DG13S2696 | GGTGCACCGACCAAATAAGT (SEQ ID NO. 44) | CCAGCTTATTCTCTCTGCCTTC (SEQ ID NO. 45) | 25459351 | 25459478 |
| DG13S1440 | GGTAGGTTGAAATGGGCTAACA (SEQ ID NO. 46) | TCATGACAAGGTGTTGGATTT (SEQ ID NO. 47) | 25520858 | 25520987 |
| DG13S1890 | CCTCCTCTGCCATGAAGCTA (SEQ ID NO. 48) | CTATTTGGTCTGCGGGTTGT (SEQ ID NO. 49) | 25672727 | 25673140 |
| DG13S1540 | TACTGGGTTATCGCCTGACC (SEQ ID NO. 50) | CCAATGGACCTCTTGGACAT (SEQ ID NO. 51) | 25704358 | 25704504 |
| DG13S59 | TTTCGGCACAGTCCTCAATA (SEQ ID NO. 52) | CAGCTGGGTGTGGTGACAT (SEQ ID NO. 53) | 25720194 | 25720421 |
| DG13S1545 | CAGAGAGGAACAGGCAGAGG (SEQ ID NO. 54) | AGTGGCTGGGAAGCCTTATT (SEQ ID NO. 55) | 25760018 | 25760404 |
| DG13S1524 | AGGTGAGAGAACAAACCTGTCTT (SEQ ID NO. 56) | GCCTTCCTTCTAAGGCCAAC (SEQ ID NO. 57) | 25843657 | 25843768 |
| DG13S1529 | CTGTAGACTTTATCCCTGACTTACTG (SEQ ID NO. 58) | CAATGAATGATGAAGATTCCACTC (SEQ ID NO. 59) | 26098943 | 26099063 |
| DG13S1908 | TGACACCATGTCTTACTGTTTGC (SEQ ID NO. 60) | GAGGATACAATGAGAACCAAATCTC (SEQ ID NO. 61) | 26110282 | 26110493 |

TABLE 16-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S2525 | CAGGATCATCAGCCAGGTTT (SEQ ID NO. 62) | GCTGCATGTCACTAGGCATT (SEQ ID NO. 63) | 26123233 | 26123381 |
| DG13S1546 | CCACAGAATGCTCCAAAGGT (SEQ ID NO. 64) | GAGTTCAAGTGATGGATGACGA (SEQ ID NO. 65) | 26159644 | 26159995 |
| DG13S1444 | CAGATAGATGAATAGGTGGATGGA (SEQ ID NO. 66) | CACTGTTCCAAGTGCTTTGC (SEQ ID NO. 67) | 26207544 | 26207727 |
| DG13S66 | TATGCGTTGTGTGCTGTG (SEQ ID NO. 68) | GGGCCTTAGATTCTTGTAGTGG (SEQ ID NO. 69) | 26279746 | 26279962 |
| DG13S1907 | TGTCCAGACTGCCTCCTACA (SEQ ID NO. 70) | TGCAACACCTGGTTCACAAT (SEQ ID NO. 71) | 26378401 | 26378521 |
| DG13S68 | TTTGCGAGTCCTTGTGGAGT (SEQ ID NO. 72) | ACAGTCCGCTCCCTCCTAAT (SEQ ID NO. 73) | 26511587 | 26511825 |
| DG13S69 | ATGCTTGGCCCTCAGTTT (SEQ ID NO. 74) | TTGGCAACCCAAGCTAATATG (SEQ ID NO. 75) | 26518188 | 26518483 |
| D13S1250 | CTCCACAGTGACAGTGAGG (SEQ ID NO. 76) | GAGAGGTTCCCAATCCC (SEQ ID NO. 77) | 26721525 | 26721686 |
| DG13S574 | CAGCTCCTGGCCATATTTCT (SEQ ID NO. 78) | GAGCCATTTCTCTGGGTCTG (SEQ ID NO. 79) | 26853541 | 26853693 |
| DG13S73 | GGTCCGTGTCAACCCTTAGA (SEQ ID NO. 80) | CAGGTTGATGGGAGGGAAA (SEQ ID NO. 81) | 26878938 | 26879133 |
| DG13S1532 | CGGGAAATGACAGTGAGACC (SEQ ID NO. 82) | TGCCTAGATTCTCCCGTAAG (SEQ ID NO. 83) | 26899505 | 26899652 |
| D13S1242 | GTGCCCAGCCAGATTC (SEQ ID NO. 84) | GCCCCCAGTCAGGTTT (SEQ ID NO. 85) | 26943073 | 26943316 |
| DG13S576 | TTTCTCTCTCCACGGAATGAA (SEQ ID NO. 86) | AACCCATTCTCACAGGGTGTA (SEQ ID NO. 87) | 27121599 | 27121797 |
| DG13S1917 | AGGAGTGTGGCAGCTTTGAG (SEQ ID NO. 88) | TGGATTCCCGTGAGTACCAG (SEQ ID NO. 89) | 27135092 | 27135232 |
| D13S217 | ATGCTGGGATCACAGGC (SEQ ID NO. 90) | AACCTGGTGGACTTTTGCT (SEQ ID NO. 91) | 27169880 | 27170051 |
| DG13S581 | AGCATTTCCAATGGTGCTTT (SEQ ID NO. 92) | CATGTTGATATGCCTGAAGGA (SEQ ID NO. 93) | 27318359 | 27318725 |
| DG13S1471 | CACTGTCTGCTGCCACTCAT (SEQ ID NO. 94) | AGAGATTATGTGATGTACCCTCTCTAT (SEQ ID NO. 95) | 27403303 | 27403544 |
| DG13S2505 | TGATGAAGATCTGGGCGTTA (SEQ ID NO. 96) | TGCCTGTGCTCACTCACTCT (SEQ ID NO. 97) | 27493479 | 27493626 |
| D13S120 | ATGACCTAGAAATGATACTGGC (SEQ ID NO. 98) | CAGACACCACAACACACATT (SEQ ID NO. 99) | 27540983 | 27541093 |
| D13S1486 | TGGTTTAAAAACCTCATGCC (SEQ ID NO. 100) | ATCCCAAACTCTGTACTTATGTAGG (SEQ ID NO. 101) | 27623349 | 27623496 |
| DG13S1495 | CCTTGGCTGTTGTGACTGGT (SEQ ID NO. 102) | CACTCAGGTGGGAGGATCAC (SEQ ID NO. 103) | 27668199 | 27668471 |
| DG13S1845 | CACTTTGCCAGTAGCCTTGA (SEQ ID NO. 104) | TTGGGAAAGTTAACCCAGAGA (SEQ ID NO. 105) | 27788787 | 27789056 |
| DG13S1030 | TTTGGGAAGAGCCATGAGAC (SEQ ID NO. 106) | CTCTGGGCATTGGAGGATTA (SEQ ID NO. 107) | 27872811 | 27873164 |

TABLE 16-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S584 | GGGAGACAAGTCAGGTGAGG (SEQ ID NO. 108) | CTGAGTATGGAGTCTTCATCATTATC (SEQ ID NO. 109) | 27924334 | 27924484 |
| DG13S79 | TGCTACTAGATTTGACCAACCA (SEQ ID NO. 110) | GACTTGTAAAGGATTTAGTGATTTCG (SEQ ID NO. 111) | 28213368 | 28213495 |
| DG13S80 | GTGGAAGGCCTCTCTCTGTG (SEQ ID NO. 112) | TGCTTCTTGAGGGAAAGCAT (SEQ ID NO. 113) | 28297121 | 28297353 |
| DG13S1934 | CCTTCAGAGGATTTCCCTTTC (SEQ ID NO. 114) | CTGGTTTGACTCCAGCTTCA (SEQ ID NO. 115) | 28461787 | 28462194 |
| DG13S1104 | CCTGGCACGGAATAGACACT (SEQ ID NO. 116) | GGCCTCCTTTGCTCTGAAG (SEQ ID NO. 117) | 28497694 | 28498071 |
| DG13S1097 | CATCCCTGTGGCTGATTAAGA (SEQ ID NO. 118) | AACAGTTCCAGCCCGTTCTA (SEQ ID NO. 119) | 28532382 | 28532543 |
| DG13S1110 | TTTCAAAGGAATATCCAAGTGC (SEQ ID NO. 120) | TGGCGTACCATATAAACAGTTCTC (SEQ ID NO. 121) | 28547636 | 28547900 |
| DG13S87 | TTCAATGAAGGTGCCGAAGT (SEQ ID NO. 122) | TGTCTATCCCAAAGCTGCAA (SEQ ID NO. 123) | 28597688 | 28597905 |
| DG13S2400 | GCTCAGTCCAAGTTCATGCTC (SEQ ID NO. 124) | TGGGATTGGGTTCTGGATAC (SEQ ID NO. 125) | 28671947 | 28672231 |
| DG13S3114 | CCTACTTTCCATCTCCTCCTTG (SEQ ID NO. 126) | TGGAGTAAGTTGGAGAATTGTTGA (SEQ ID NO. 127) | 28678081 | 28678248 |
| DG13S1111 | GCAAGACTCTGTTGAAGAAGAA (SEQ ID NO. 128) | TCCCTCTGTTTGAGTTTCTCG (SEQ ID NO. 129) | 28760422 | 28760531 |
| DG13S3122 | CCTTGGGCAGTCAGAGAAAC (SEQ ID NO. 130) | CCCGTGAAGTCTGAGAGGTG (SEQ ID NO. 131) | 28778662 | 28778906 |
| DG13S1101 | AGGCACAGTCGCTCATGTC (SEQ ID NO. 132) | AAACTTTAGCTAATGGTGGTCAAA (SEQ ID NO. 133) | 28812542 | 28812874 |
| D13S1246 | GAGCATGTGTGACTTTCATATTCAG (SEQ ID NO. 134) | AGTGGCTATTCATTGCTACAGG (SEQ ID NO. 135) | 28903534 | 28903738 |
| DG13S1103 | TTGCTGGATGCTGGTTTCTA (SEQ ID NO. 136) | AAAGAGAGAGAGAAAGAGAAAGAAAGA (SEQ ID NO. 137) | 28910502 | 28910765 |
| DG13S3147 | AAAGTGGATGCAGTTGAGGTTT (SEQ ID NO. 138) | GCTAGCCATTACAGACAACCAA (SEQ ID NO. 139) | 29018341 | 29018591 |
| DG13S3150 | CAGGGCTCCATGTATCCATAA (SEQ ID NO. 140) | CAATCTTTGGCTTTGGGTTT (SEQ ID NO. 141) | 29042766 | 29042948 |
| D13S289 | CTGGTTGAGCGGCATT (SEQ ID NO. 142) | TGCAGCCTGGATGACA (SEQ ID NO. 143) | 29063702 | 29063949 |
| DG13S166 | CCTATGGAAGCATAGGGAAGAA (SEQ ID NO. 144) | CCCACTTCTGAGTCTCCTGAT (SEQ ID NO. 145) | 29064359 | 29064753 |
| DG13S3156 | GGGAAATGGAGCTGCTGTTA (SEQ ID NO. 146) | GAGTGGGTGAGTGCAAGGAT (SEQ ID NO. 147) | 29111037 | 29111416 |
| D13S1238 | CTCTCAGCAGGCATCCA (SEQ ID NO. 148) | GCCAACGTAATTGACACCA (SEQ ID NO. 149) | 29144427 | 29144579 |
| DG13S2605 | TGAAAGGAAGGTCCCTGAGTT (SEQ ID NO. 150) | CCCTGCTTTGCACAAGTTATC (SEQ ID NO. 151) | 29145896 | 29146055 |
| DG13S163 | CACATGAGGCTGTATGTGGA (SEQ ID NO. 152) | TGTGCAGGAATGAGAAGTCG (SEQ ID NO. 153) | 29177152 | 29177313 |

TABLE 16-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| D13S290 | CCTTAGGCCCCATAATCT (SEQ ID NO. 154) | CAAATTCCTCAATTGCAAAAT (SEQ ID NO. 155) | 29227323 | 29227512 |
| D13S1229 | GGTCATTCAGGGAGCCATTC (SEQ ID NO. 156) | CCATTATATTTCACCAAGAGGCTGC (SEQ ID NO. 157) | 29282262 | 29282396 |
| DG13S2358 | AGTCAAGGCTGACAGGGAAG (SEQ ID NO. 158) | GCTCTCAGCCCTCAATGTGT (SEQ ID NO. 159) | 29342275 | 29342399 |
| DG13S2658 | ATTTGGGTTCCTCTCCCAAT (SEQ ID NO. 160) | ACAAACTCTTGCTGCTGGTG (SEQ ID NO. 161) | 29348162 | 29348426 |
| DG13S1460 | TGCCTGGTCATCTACCCATT (SEQ ID NO. 162) | TCTACTGCAGCGCTGATCTT (SEQ ID NO. 163) | 29389048 | 29389297 |
| DG13S2434 | TCCTTCCAGAAGGTTTGCAT (SEQ ID NO. 164) | TGCAAAGTTGTTCAAGAGAGACA (SEQ ID NO. 165) | 29485254 | 29485392 |
| DG13S1448 | CAGCAGGAAGATGGACAGGT (SEQ ID NO. 166) | CACACTGCATCACACATACCC (SEQ ID NO. 167) | 29499404 | 29499531 |
| D13S1287 | TATGCCAGTATGCCTGCT (SEQ ID NO. 168) | GTCACATCAGTCCATTTGC (SEQ ID NO. 169) | 29513830 | 29514063 |
| DG13S2665 | GGTTTATGTCTGTGTGTGTGC (SEQ ID NO. 170) | TGAGGGATGTCAGAGAAATATGC (SEQ ID NO. 171) | 29747845 | 29747984 |
| DG13S1904 | TGATGAAATTGCCTAGTGATGC (SEQ ID NO. 172) | GGATCCAATCGTACGCTACC (SEQ ID NO. 173) | 29767797 | 29767922 |
| DG13S1490 | ACCTAAACACCACGGACTGG (SEQ ID NO. 174) | CAGGTATCGACATTCTTCCAAA (SEQ ID NO. 175) | 29908555 | 29908958 |
| DG13S2637 | GGTGATCTAGGGAATTATTTGTCTTC (SEQ ID NO. 176) | TTGGCCACTAAGGTCCAGAT (SEQ ID NO. 177) | 29941956 | 29942120 |
| DG13S96 | CCTTTGAGGCTGGATCTGTT (SEQ ID NO. 178) | TTTCCTTATCATTCATTCCCTCA (SEQ ID NO. 179) | 30166433 | 30166650 |
| D13S260 | AGATATTGTCTCCGTTCCATGA (SEQ ID NO. 180) | CCCAGATATAAGGACCTGGCTA (SEQ ID NO. 181) | 30234833 | 30234997 |
| DG13S17 | TTTAAGCCCTGTGGAATGTATTT (SEQ ID NO. 182) | GACATTGCAGGTCAAGTAGGG (SEQ ID NO. 183) | 30288392 | 30288544 |
| DG13S306 | TGCATAAGGCTGGAGACAGA (SEQ ID NO. 184) | CACAGCAGATGGGAGCAAA (SEQ ID NO. 185) | 30404049 | 30404203 |
| DG13S2486 | AGCCAGTTGTCTTTCATCCTG (SEQ ID NO. 186) | TGCCTGTGCTTGTATATTCTGTG (SEQ ID NO. 187) | 30411508 | 30411755 |
| DG13S18 | GTGCATGTGCATACCAGACC (SEQ ID NO. 188) | GGCAAGATGACCTCTGGAAA (SEQ ID NO. 189) | 30456875 | 30457193 |
| DG13S1062 | TTTGTGTTCCAGGTGAGAATTG (SEQ ID NO. 190) | GAACCATATCCCAAGGCACT (SEQ ID NO. 191) | 30551596 | 30551715 |
| DG13S1093 | TTGTTCCCACATTCATTCTACA (SEQ ID NO. 192) | TTAAACTCGTGGCAAAGACG (SEQ ID NO. 193) | 30625918 | 30626190 |
| DG13S1059 | CACCATGCCTGGCTCTTT (SEQ ID NO. 194) | AACTTCTCCAGTTGTGTGGTTG (SEQ ID NO. 195) | 30822917 | 30823246 |
| D13S171 | CCTACCATTGACACTCTCAG (SEQ ID NO. 196) | TAGGGCCATCCATTCT (SEQ ID NO. 197) | 31051937 | 31052167 |
| DG13S2359 | TCTGTGTGTATTGTGTACTCCTCTG (SEQ ID NO. 198) | TCACACAATTTGAACCAATCCT (SEQ ID NO. 199) | 31073673 | 31073849 |

TABLE 16-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S1092 | ACCAAGATATGAAGGCCAAA (SEQ ID NO. 200) | CCTCCAGCTAGAACAATGTGAA (SEQ ID NO. 201) | 31113759 | 31113934 |
| DG13S2629 | TGATCATGTCAGCAGCAGAAG (SEQ ID NO. 202) | AGTAACAGGTGAGGGCATGG (SEQ ID NO. 203) | 31179791 | 31179953 |
| DG13S1449 | TGTCCATAGCTGTAGCCCTGT (SEQ ID NO. 204) | CTCAATCGGGCATCTTTAGGC (SEQ ID NO. 205) | 31199228 | 31199498 |
| DG13S312 | CAAACAAACAAACAAGCAAACC (SEQ ID NO. 206) | TGGACGTTTCTTTCAGTGAGG (SEQ ID NO. 207) | 31280202 | 31280550 |
| DG13S1511 | TGATAACTTACCAGCATGTGAGC (SEQ ID NO. 208) | TCACCTCACCTAAGGATCTGC (SEQ ID NO. 209) | 31321562 | 31321854 |
| DG13S2454 | GCTAGCAAATCTCTCAACTTCCA (SEQ ID NO. 210) | TCTTCTCCATGCTGCTTCCT (SEQ ID NO. 211) | 31352662 | 31352803 |
| DG13S314 | CATGCAATTGCCCAATAGAG (SEQ ID NO. 212) | TTGGGCTTGTCTACCTAGTTCA (SEQ ID NO. 213) | 31379760 | 31380086 |
| DG13S1071 | GCTGCACGTATTTGTTGGTG (SEQ ID NO. 214) | AAACAGCAGAAATGGGAACC (SEQ ID NO. 215) | 31447431 | 31447669 |
| DG13S1068 | CCGTGGGCTATCAATTTCTG (SEQ ID NO. 216) | AAGATGCAATCTGGTTTCCAA (SEQ ID NO. 217) | 31553333 | 31553570 |
| DG13S1077 | CCCAAGACTGAGGAGGTCAA (SEQ ID NO. 218) | GCTGACGGAGAGGAAAGAGA (SEQ ID NO. 219) | 31569360 | 31569733 |
| DG13S2343 | TCACAAAGCAAGCAATCACA (SEQ ID NO. 220) | TGATGGATGCACCATGTTTA (SEQ ID NO. 221) | 31653489 | 31653608 |
| DG13S316 | TGAGAAGCCTGGGCATTAAG (SEQ ID NO. 222) | ACAAGCTCATCCAGGGAAAG (SEQ ID NO. 223) | 31708002 | 31708244 |
| DG13S1558 | AGAGCTGATCTGGCCGAAG (SEQ ID NO. 224) | GGTGGACACAGAATCCACACT (SEQ ID NO. 225) | 31986248 | 31986627 |
| D13S267 | GGCCTGAAAGGTATCCTC (SEQ ID NO. 226) | TCCCACCATAAGCACAAG (SEQ ID NO. 227) | 32062233 | 32062380 |
| DG13S1478 | TCAACCTAGGATTGGCATTACA (SEQ ID NO. 228) | TCTAGGATTTGTGCCTTTCCA (SEQ ID NO. 229) | 32157761 | 32158137 |
| DG13S1551 | ATTCGTGCAGCTGTTTCTGC (SEQ ID NO. 230) | GCATGACATTGTAAATGGAGGA (SEQ ID NO. 231) | 32364898 | 32365153 |
| DG13S1884 | GGTGGGAATGTGTGACTGAA (SEQ ID NO. 232) | CCAGGTACAACATTCTCCTGAT (SEQ ID NO. 233) | 32451203 | 32451315 |
| D13S1293 | TGCAGGTGGGAGTCAA (SEQ ID NO. 234) | AAATAACAAGAAGTGACCTTCCTA (SEQ ID NO. 235) | 32536337 | 32536467 |
| DG13S1518 | AAAGGATGCATTCGGTTAGAG (SEQ ID NO. 236) | ACTGTCCTGTGCCTGTGCTT (SEQ ID NO. 237) | 32588965 | 32589321 |
| D13S620 | GTCCACCTAATGGCTCATTC (SEQ ID NO. 238) | CAAGAAGCACTCATGTTTGTG (SEQ ID NO. 239) | 32627749 | 32627947 |
| DG13S1866 | AGCCTGTGATTGGCTGAGA (SEQ ID NO. 240) | GGCTTACAGCTGCCTCCTTT (SEQ ID NO. 241) | 32633306 | 32633709 |
| DG13S1927 | CCCACAGAGCACTTTGTTAGA (SEQ ID NO. 242) | GCCTCCCTTAAGCTGTTATGC (SEQ ID NO. 243) | 32691932 | 32692304 |
| DG13S1503 | CACTCTTTACTGCCAATCACTCC (SEQ ID NO. 244) | GCCGTGTGGGTGTATGAAT (SEQ ID NO. 245) | 32699827 | 32700058 |

TABLE 16-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S332 | TTGTACCAGGAACCAAAGACAA (SEQ ID NO. 246) | CACAGACAGAGGCACATTGA (SEQ ID NO. 247) | 32764576 | 32764751 |
| DG13S333 | GCTCTGGTCACTCCTGCTGT (SEQ ID NO. 248) | CATGCCTGGCTGATTGTTT (SEQ ID NO. 249) | 32872275 | 32872720 |
| D13S220 | CCAACATCGGGAACTG (SEQ ID NO. 250) | TGCATTCTTTAAGTCCATGTC (SEQ ID NO. 251) | 32967602 | 32967793 |
| DG13S1919 | CAGCAACTGACAACTCATCCA (SEQ ID NO. 252) | CCTCAATCCTCAGCTCCAAC (SEQ ID NO. 253) | 33014255 | 33014477 |
| DG13S2383 | TGATTGGTTCTGTTGTTGCTG (SEQ ID NO. 254) | AGCCCAAGGCTCTTGTGAG (SEQ ID NO. 255) | 33053369 | 33053553 |
| DG13S1439 | TCCTTCACAGCTTCAAACTCA (SEQ ID NO. 256) | AGTGAGAAGCTTCCATACTGGT (SEQ ID NO. 257) | 33070030 | 33070264 |
| DG13S335 | GCCAACCGTTAGACAAATGA (SEQ ID NO. 258) | CTACATGTGCACCACAACACC (SEQ ID NO. 259) | 33102278 | 33102478 |
| DG13S340 | AGTTTATTGCCGCCGAGAG (SEQ ID NO. 260) | ACCCACCACATTCACAAGC (SEQ ID NO. 261) | 33124866 | 33125238 |
| DG13S1496 | CGATTGCCATGTCTCTTTGA (SEQ ID NO. 262) | GAGATCTGGCCTGGATTTGT (SEQ ID NO. 263) | 33215915 | 33216066 |
| DG13S347 | TCATTGTCAGCACAGAATGAACT (SEQ ID NO. 264) | GGAGGGAGGGAAGAAAGAGA (SEQ ID NO. 265) | 33280351 | 33280688 |
| DG13S339 | GGGAAGAGGAGATTTGACTTGTT (SEQ ID NO. 266) | GGAACACCATCATTCCAACC (SEQ ID NO. 267) | 33352425 | 33352656 |
| DG13S1926 | TACAAGCTCCACCGTCCTTC (SEQ ID NO. 268) | TGAGTTGCTGCCTCTTCAAA (SEQ ID NO. 269) | 33388692 | 33388919 |
| DG13S1469 | TGCTAATGGGCCAAGGAATA (SEQ ID NO. 270) | GCTAAATGTCCTCATGAATAGCC (SEQ ID NO. 271) | 33416571 | 33416940 |
| DG13S351 | TGTCCTGCAGACAGATGGTC (SEQ ID NO. 272) | CCTCCGGAGTAGCTGGATTA (SEQ ID NO. 273) | 33497762 | 33498055 |
| DG13S26 | GAGACTGGCCCTCATTCTTG (SEQ ID NO. 274) | AAGAAGCCAGAGACAAAGAAATACA (SEQ ID NO. 275) | 33584096 | 33584425 |
| DG13S30 | CATCTATCTTTGGATTCAGTGGTG (SEQ ID NO. 276) | TGCTCCCAACATCTTACCAG (SEQ ID NO. 277) | 33731684 | 33732071 |
| DG13S1435 | TGTCCTCTGGTCATTTCTATGGT (SEQ ID NO. 278) | CATGAATGAGAAGTGATGAATGG (SEQ ID NO. 279) | 33762069 | 33762285 |
| DG13S356 | CAGACACTGTAAACTGGCTTCG (SEQ ID NO. 280) | GCCACATTGCTATCAGCGTA (SEQ ID NO. 281) | 33908746 | 33908957 |
| DG13S2316 | ATGTGCTGTGGTCCAGATTT (SEQ ID NO. 282) | CCTACTACTGCAATTACTCCCTACC (SEQ ID NO. 283) | 33913787 | 33913954 |
| DG13S357 | TGTCATAGGCTTGCGGTATTT (SEQ ID NO. 284) | TTGGTAGGGTCCTTTCCTTT (SEQ ID NO. 285) | 33935177 | 33935378 |
| DG13S1032 | GCCTGCTCACTGTTGTTTGA (SEQ ID NO. 286) | CGGTTATCAGAGACTGGTGGT (SEQ ID NO. 287) | 33967059 | 33967269 |
| DG13S1557 | GGCTTATTTCATGTACGGCTA (SEQ ID NO. 288) | GGTTAAACTCTACTTAGTCCTGATGC (SEQ ID NO. 289) | 33996100 | 33996249 |
| DG13S1925 | GAACTCTGCAGGCACCTCTT (SEQ ID NO. 290) | CCTGAAGCGCTTGTACTGAA (SEQ ID NO. 291) | 34079148 | 34079570 |

TABLE 16-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S360 | TTGGCTTCTCGCTCTTTCTT (SEQ ID NO. 292) | AGCCATCAGTCACATGCAAA (SEQ ID NO. 293) | 34138872 | 34139221 |
| DG13S1522 | AGATCTCCAGGGCAGAGGAC (SEQ ID NO. 294) | CCTTCCTCCCTCCTTCTCTC (SEQ ID NO. 295) | 34195314 | 34195659 |
| DG13S2324 | CAGTCAAATGTCTCAACCTTCC (SEQ ID NO. 296) | CTAGCAACATGGCCAAGAAA (SEQ ID NO. 297) | 34224040 | 34224206 |
| DG13S1517 | CGTCATTGATCCCAATCATCT (SEQ ID NO. 298) | GGCTGATAGCCTCCCTTGTA (SEQ ID NO. 299) | 34271358 | 34271587 |
| DG13S364 | ACCTTTCAAGCTTCCGGTTT (SEQ ID NO. 300) | TTCCATCCGTCCATCTATCC (SEQ ID NO. 301) | 34323307 | 34323478 |
| DG13S1036 | TTAAAGTCACTTGTCTGTGGTCA (SEQ ID NO. 302) | TTTGTAGGAATCAAGTCAAATAATGTA (SEQ ID NO. 303) | 34525065 | 34525280 |
| DG13S1037 | CTTTCGGAAGCTTGAGCCTA (SEQ ID NO. 304) | CCCAAGACCACTGCCATATT (SEQ ID NO. 305) | 34616658 | 34616926 |
| DG13S1854 | TGACAGGTTTGGGTATATTGGA (SEQ ID NO. 306) | TGCTTAATGTAGTGGCAGCA (SEQ ID NO. 307) | 34622055 | 34622151 |
| DG13S1038 | TCCTGCCTTTGTGAATTCCT (SEQ ID NO. 308) | GTTGAATGAGGTGGGCATTA (SEQ ID NO. 309) | 34702405 | 34702738 |
| DG13S2366 | TTGGGAATAAATCAGGTGTTGA (SEQ ID NO. 310) | GCAGCAGCTCAGCATTTCTC (SEQ ID NO. 311) | 34735455 | 34735583 |
| DG13S1039 | CCATTTAATCCTCCAGCCATT (SEQ ID NO. 312) | GCTCCACCTTGTTACCCTGA (SEQ ID NO. 313) | 34743651 | 34743817 |
| DG13S1840 | ACAACCCTGGAATCTGGACT (SEQ ID NO. 314) | GAAGGAAAGGAAAGGAAAGAAA (SEQ ID NO. 315) | 34805466 | 34805682 |
| DG13S369 | TGACAAGACTGAAACTTCATCAG (SEQ ID NO. 316) | GATGCTTGCTTTGGGAGGTA (SEQ ID NO. 317) | 34815499 | 34815755 |
| DG13S2481 | CAGGTTAGAGCCCATCCAAG (SEQ ID NO. 318) | AGGCTCAGCTTCATCCACAT (SEQ ID NO. 319) | 34867728 | 34867872 |
| D13S219 | AAGCAAATATGCAAAATTGC (SEQ ID NO. 320) | TCCTTCTGTTTCTTGACTTAACA (SEQ ID NO. 321) | 34956581 | 34956707 |
| DG13S2351 | GGGAACAGGTCACAGGTCAT (SEQ ID NO. 322) | GGAAGACTGGGTGGTCACAG (SEQ ID NO. 323) | 35099146 | 35099320 |
| DG13S384 | TTCCTTCTGCTTGTGAGCTG (SEQ ID NO. 324) | TACCCTCACCTTCCTCATGC (SEQ ID NO. 325) | 35499548 | 35499763 |
| DG13S1507 | GAAGACATTGGCAGGTCTGG (SEQ ID NO. 326) | GAGCCCTCATGTTGGGATAA (SEQ ID NO. 327) | 35557977 | 35558206 |
| DG13S1512 | TTGTTGATTCTCCCATTCTGTG (SEQ ID NO. 328) | TCACCTACCTCATCTCATACTCAAA (SEQ ID NO. 329) | 35668964 | 35669201 |
| DG13S1556 | TCTTCCGGACAAGTTTCCAA (SEQ ID NO. 330) | TGGGTCATTCTGGACATTCA (SEQ ID NO. 331) | 35791215 | 35791467 |
| DG13S388 | GCAAATGAGGCTGGTAAGGT (SEQ ID NO. 332) | TGCACTGTGGTAGAGGGAAA (SEQ ID NO. 333) | 35817061 | 35817320 |
| DG13S1442 | CAACATACTCCTATGCCTAGAAAGAAA (SEQ ID NO. 334) | CTCACCAGGCAGAAACAGGT (SEQ ID NO. 335) | 35842967 | 35843335 |
| DG13S1045 | CCCAATGGCATGCTTCACT (SEQ ID NO. 336) | GGTTCTCCCAGCATTGGTT (SEQ ID NO. 337) | 35928180 | 35928324 |

TABLE 16-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S2452 | AAGGCCTCTGGGTAGGTAGG (SEQ ID NO. 338) | AAGCAATCCTTATGGGCTCT (SEQ ID NO. 339) | 35948528 | 35948826 |
| DG13S2350 | CCAGGTAATCAGAAGCCTCA (SEQ ID NO. 340) | TTCCGTTAAATCCAGCCATC (SEQ ID NO. 341) | 36011840 | 36011961 |
| DG13S2483 | CAGGGACTGCAGTGTCTCAA (SEQ ID NO. 342) | ATGCCACATTTGCCTCTCTC (SEQ ID NO. 343) | 36027396 | 36027703 |
| DG13S1100 | CCACCTTCCACTTAATACAAACTTC (SEQ ID NO. 344) | GAAGCAATCCATTCCAAGAAA (SEQ ID NO. 345) | 36056838 | 36057115 |
| DG13S1501 | GTCCTGAGGGTGTCCAGGTA (SEQ ID NO. 346) | GCTGGAGAACTCCTATTCTGCT (SEQ ID NO. 347) | 36215761 | 36215909 |
| DG13S1868 | TGGAGCTATTGCGGTTCTCT (SEQ ID NO. 348) | TCAAATCTCTCTTTCCTCCTCCT (SEQ ID NO. 349) | 36313203 | 36313417 |
| DG13S395 | CAGTTCCAGCTACGGGAGAA (SEQ ID NO. 350) | CCGCATTTAGGCAAGTCTCA (SEQ ID NO. 351) | 36317151 | 36317507 |
| D13S1491 | AAGCACACACAGATGCTAGG (SEQ ID NO. 352) | CCTCAGCCTCCATAATCTCA (SEQ ID NO. 353) | 36361442 | 36361571 |
| DG13S400 | GTACAGAGCCCACCTTCTGG (SEQ ID NO. 354) | TCACTATGCTGCAAGGCAAG (SEQ ID NO. 355) | 36369862 | 36370134 |
| D13S894 | GGTGCTTGCTGTAAATATAATTG (SEQ ID NO. 356) | CACTACAGCAGATTGCACCA (SEQ ID NO. 357) | 36536509 | 36536706 |
| D13S218 | GATTTGAAAATGAGCAGTCC (SEQ ID NO. 358) | GTCGGGCACTACGTTTATCT (SEQ ID NO. 359) | 36830331 | 36830519 |
| DG13S1553 | TGGGTGAAGATGCTACCTGA (SEQ ID NO. 360) | CCCTTCTTCCTTTCCCTCTC (SEQ ID NO. 361) | 36898814 | 36899040 |
| DG13S411 | TGCCAGGTCTGAGTTGTAAGC (SEQ ID NO. 362) | CAGCATGAGACCCTGTCAAA (SEQ ID NO. 363) | 36908058 | 36908265 |
| DG13S1870 | GAAAGAAAGAAAGAAAGAAGAAAGAAA (SEQ ID NO. 364) | AATCACCAAACCTGGAAGCA (SEQ ID NO. 365) | 36927423 | 36927632 |
| DG13S1870 | GAAAGAAAGAAAGAAAGAAGAAAGAAA (SEQ ID NO. 366) | AATCACCAAACCTGGAAGCA (SEQ ID NO. 367) | 36927485 | 36927632 |
| DG13S39 | TCTGAGTTAAACACTTGAGTTGCTG (SEQ ID NO. 368) | CCAGTAAATGGCAGTGTGGTT (SEQ ID NO. 369 | 36957292 | 36957640 |
| DG13S2415 | TGTCATGGATATTTCTACATAAACCAA (SEQ ID NO. 370) | TGAAGATGGTTATTGCTTCCTTC (SEQ ID NO. 371) | 36984719 | 36984955 |
| DG13S412 | CGCTTTGTTTGGTTTGGTTT (SEQ ID NO. 372) | ATGCAGTTGTCCCACATGCT (SEQ ID NO. 373) | 37036929 | 37037137 |
| DG13S414 | TCCTGCACTCCAAAGGAAAC (SEQ ID NO. 374) | AACTCTGGTTTAATTCAGCTTTGTC (SEQ ID NO. 375) | 37047489 | 37047713 |
| DG13S1872 | TTCTTGAGGGCATAAAGCTGA (SEQ ID NO. 376) | CACACTCACCAGGCACTCTG (SEQ ID NO. 377) | 37119505 | 37119608 |
| DG13S416 | CAGGTTTGATGAAGGAAATATGC (SEQ ID NO. 378) | GGGATCCTCTGCATTTCTCTAA (SEQ ID NO. 379) | 37125983 | 37126184 |
| DG13S2607 | TTTGCCAAATCAACCTTCAG (SEQ ID NO. 380) | CCTGCTTCACACCTCTGACC (SEQ ID NO. 381) | 37317455 | 37317831 |
| DG13S1898 | ACTCACACACAACCACCACA (SEQ ID NO. 382) | GCTACTGGTGGGTCGTAAGC (SEQ ID NO. 383) | 37318932 | 37319055 |

TABLE 16-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| D13S1288 | TTCAGAGACCATCACGGC (SEQ ID NO. 384) | CTGGAAAAATCAGTTGAATCCTACG (SEQ ID NO. 385) | 37321295 | 37321486 |
| DG13S2567 | AGGAAAGCCGAGAAAGCATA (SEQ ID NO. 386) | CATGTATCCACATGCCCAGA (SEQ ID NO. 387) | 37416093 | 37416462 |
| DG13S418 | CCTTCAGCGCAGCTACATCT (SEQ ID NO. 388) | AGAACTGCGAGGTCCAAGTG (SEQ ID NO. 389) | 37473016 | 37473380 |
| DG13S419 | GGGAGAAAGAGAGGTAGGAAGG (SEQ ID NO. 390) | TTCCCAAGTTAGCAGCATCC (SEQ ID NO. 391) | 37532947 | 37533123 |
| DG13S1051 | TTCTAGAGGAGTCTATTTCTTTACTGG (SEQ ID NO. 392) | GGAGCTGTCACTTGAGCTTTG (SEQ ID NO. 393) | 37694432 | 37694579 |
| DG13S1841 | CCGTGACCTACAGGGAACAT (SEQ ID NO. 394) | GGCATCGGGTGTTTCTATTC (SEQ ID NO. 395) | 37715601 | 37715829 |
| DG13S1052 | AGACCTGCCTGTGTTCTGGT (SEQ ID NO. 396) | GGAGTGAAATAAGTGGAACTGGA (SEQ ID NO. 397) | 37831275 | 37831438 |
| DG13S1053 | CATTAAATGAGTCATAAAGGTCATGG (SEQ ID NO. 398) | AACATTGTTGCTTTGCTGGA (SEQ ID NO. 399) | 37935190 | 37935311 |
| DG13S423 | GGCCTTAGCTCAGTTTCTGG (SEQ ID NO. 400) | TGCAAAGACATTTGCGGATA (SEQ ID NO. 401) | 37941221 | 37941411 |
| D13S1253 | CCTGCATTTGTGTACGTGT (SEQ ID NO. 402) | CAGAGCCGTGGTAGTATATTTTT (SEQ ID NO. 403) | 37944396 | 37944533 |
| DG13S2539 | GGAACCAGTCATTTGGGTGT (SEQ ID NO. 404) | TTATTGCTCCCTCGTCCAAG (SEQ ID NO. 405) | 38050898 | 38051253 |
| DG13S2509 | TGCCTTAAGGTCTATTATTTCCTTTC (SEQ ID NO. 406) | ACCAATGCAGGAAGACTCAA (SEQ ID NO. 407) | 38067039 | 38067186 |
| DG13S1863 | CTGATGAAAGGACACACATGC (SEQ ID NO. 408) | TGCATTAACTATGCAGCTTGAAA (SEQ ID NO. 409) | 38092085 | 38092353 |
| DG13S2510 | GTCGTGCAATCCCGAGAG (SEQ ID NO. 410) | GGATTCCTGCTGGCTCTTCT (SEQ ID NO. 411) | 38197807 | 38198059 |
| DG13S1909 | CTGGTGTGGTCAGGAAATGA (SEQ ID NO. 412) | GTGCTAAACACATGTGAGTGAGAG (SEQ ID NO. 413) | 38309328 | 38309442 |
| DG13S428 | TTTGACCATGCTTTCTCTTTGA (SEQ ID NO. 414) | GCTTGATGACTCCCTGCTGT (SEQ ID NO. 415) | 38346716 | 38347069 |
| DG13S1858 | AAGCCATTGAAAGGCAGGTA (SEQ ID NO. 416) | GGGACTTTCCGGCTTCTATT (SEQ ID NO. 417) | 38371574 | 38371742 |
| DG13S1911 | GGTTTGGGAACCATTCTCCT (SEQ ID NO. 418) | GCAGAGAAGGGATTTACTCCAG (SEQ ID NO. 419) | 38475656 | 38475877 |
| DG13S433 | ACTTGACATGGAGCAAGCTG (SEQ ID NO. 420) | AGCTCATCATGCTGTAAGGAG (SEQ ID NO. 421) | 38516056 | 38516191 |
| DG13S2421 | CACAGGCTCTCACATTCTCG (SEQ ID NO. 422) | TGACACTCATCCCTCTGCTG (SEQ ID NO. 423) | 38534972 | 38535357 |
| DG13S2375 | TGAGTTTCATAAGTTTACTACCTGCTG (SEQ ID NO. 424) | GGCAGGGAGAAAGGACAAAT (SEQ ID NO. 425) | 38548257 | 38548440 |
| D13S1248 | TCCCTTATGTGGGATTAGTTGA (SEQ ID NO. 426) | CAGACATGGAACTGAGATTTTTT (SEQ ID NO. 427) | 38558005 | 38558267 |
| DG13S1856 | TGTTCCATCTCTCTACCCATGT (SEQ ID NO. 428) | TCAATGTTCTTATTGAGTGGGAAA (SEQ ID NO. 429) | 38577323 | 38577506 |

TABLE 16-continued

Basepair position of microsatellite markers (start and stop of the amplimersin NCBI sequence assembly build 34 and primer sequences (forward and reverse).

| Marker name | forward primer | reverse primer | basepair start position | basepair stop position |
|---|---|---|---|---|
| DG13S435 | ATATCCACCCACCCACACAT (SEQ ID NO. 430) | TAGCTCTGAGGGCAGAGACC (SEQ ID NO. 431) | 38591043 | 38591261 |
| DG13S2459 | CCGTCCTTCCTCCACTGAT (SEQ ID NO. 432) | AGAGCACTGAGGGAGCAAAT (SEQ ID NO. 433) | 38596056 | 38596299 |
| DG13S438 | AGCTACAGCACGAGGCAGTT (SEQ ID NO. 434) | TTTGAATTGAGTTGCTGTTCG (SEQ ID NO. 435) | 38676957 | 38677248 |
| DG13S1865 | TGTACACCACCAACCATTCTG (SEQ ID NO. 436) | GGGAAGAAAGGCAAATAGCA (SEQ ID NO. 437) | 38684800 | 38684904 |
| DG13S2354 | GGATTGGCAATTAGCAGGTC (SEQ ID NO. 438) | GCCTGGTCAAAGATAACAGACG (SEQ ID NO. 439) | 38773862 | 38774026 |
| DG13S2534 | CCTGATTAAGCTGGCCTTTG (SEQ ID NO. 440) | ATCCTTCTGGGACCCTCATC (SEQ ID NO. 441) | 38801698 | 38801951 |
| DG13S1903 | GCTTTGCTTCCTTCTTGGTG (SEQ ID NO. 442) | CAACATTACGGCCAGTCTCA (SEQ ID NO. 443) | 38802843 | 38803052 |
| DG13S1896 | GGTGCATCTGATAAGCCAAA (SEQ ID NO. 444) | GCTGTCTTGGACACAGTGGA (SEQ ID NO. 445) | 38815291 | 38815405 |
| DG13S443 | CACCATCATCATCTGGTTGG (SEQ ID NO. 446) | GAGCTCATTGAAAGGCAGGA (SEQ ID NO. 447) | 38838839 | 38839093 |
| DG13S445 | CCATCCATCTATCCATTTATCTCTG (SEQ ID NO. 448) | GGATTTATCCTTGCCCTGCT (SEQ ID NO. 449) | 38840399 | 38840584 |
| DG13S447 | CTATCATCCATCCATCCTATTTG (SEQ ID NO. 450) | TTAGGGCAGCTACCTGGAAA (SEQ ID NO. 451) | 38840751 | 38840928 |
| D13S1233 | AGGACTANAGATGAATGCTC (SEQ ID NO. 452) | GACATGACTCCATGTTTGGT (SEQ ID NO. 453) | 38875108 | 38875292 |
| DG13S2320 | CCTCACCTTGCAATTTCCTG (SEQ ID NO. 454) | CTGACTTGCCTGTTGGCATA (SEQ ID NO. 455) | 38957405 | 38957570 |
| DG13S451 | TTTGGGATCTTGAAGACCTTT (SEQ ID NO. 456) | TTGTGGCATGTCCTTGGTT (SEQ ID NO. 457) | 39032835 | 39033191 |
| DG13S180 | TGTACACTGCAAACATTGCTAAA (SEQ ID NO. 458) | TTGTCCTTTCATTATGACGTGTCT (SEQ ID NO. 459) | 39233968 | 39234350 |
| DG13S458 | AAGCCTGAAAGGATACACACAAA (SEQ ID NO. 460) | CAGGATCCCAGACTTTCCAG (SEQ ID NO. 461) | 39475899 | 39476187 |
| DG13S2547 | GGTGAATCCCACCCTCATAC (SEQ ID NO. 462) | TTGGTATGTTTCCTATTGTTGCAT (SEQ ID NO. 463) | 39612492 | 39612849 |
| D13S244 | GAACCAGTGAGTTTTTATTAC (SEQ ID NO. 464) | AGACACAGCATATAATACATG (SEQ ID NO. 465) | 39665226 | 39665353 |
| DG13S2435 | TGAAGCTTTGTGGCTTGTTG (SEQ ID NO. 466) | GACTGAGTCCACAGCCCATT (SEQ ID NO. 467) | 39863067 | 39863301 |
| D13S263 | CCTGGCCTGTTAGTTTTTATTGTTA (SEQ ID NO. 468) | CCCAGTCTTGGGTATGTTTTTA (SEQ ID NO. 469) | 39878976 | 39879126 |
| DG13S188 | CCACCATGCAAGAACAGATG (SEQ ID NO. 470) | GCTTTGCACTTGGCTGTCTT (SEQ ID NO. 471) | 39935769 | 39936103 |
| DG13S189 | TTGCATGAAGTAAAGTATCCCTGT (SEQ ID NO. 472) | CACAAACCACAAGATGATTGG (SEQ ID NO. 473) | 39968676 | 39969030 |
| DG13S190 | GGGCATCATGTCTACAACTCA (SEQ ID NO. 474) | ACCAAGGGCACTTGCTGATA (SEQ ID NO. 475) | 40027542 | 40027801 |

TABLE 16-continued

Basepair position of microsatellite markers (start and stop of the amplimers in NCBI sequence assembly build 34 and primer sequences (forward and reverse).

| Marker name | forward primer | reverse primer | basepair start position | basepair stop position |
|---|---|---|---|---|
| DG13S2370 | AGGATGAAGAGGGAGGAAGG (SEQ ID NO. 476) | CCAGACTGATCTTCCTTAATTAGTTG (SEQ ID NO. 477) | 40159684 | 40159812 |
| DG13S196 | CCTCCTCTTTCTGCTGCTGT (SEQ ID NO. 478) | AGCCAAAGAACCCAAAGAAAC (SEQ ID NO. 479) | 40251445 | 40251793 |
| DG13S2457 | GCCCTACTTTGCCTCAGAAA (SEQ ID NO. 480) | GCAACTCATGCCAGCCTCTA (SEQ ID NO. 481) | 40376042 | 40376447 |
| DG13S2445 | AACTGTGTTAATGATGGGCAAA (SEQ ID NO. 482) | AACGAGCGCATGAAACCTAT (SEQ ID NO. 483) | 40422793 | 40423200 |
| DG13S211 | CCTGGTCAATTGAACCCAAA (SEQ ID NO. 484) | TGAAGGAAGATAAAGCAGGGTAA (SEQ ID NO. 485) | 40434073 | 40434172 |
| DG13S472 | CTCTCTCTGGCCCTCTCTTG (SEQ ID NO. 486) | GGTAACTTGCCATTCTTCTACCA (SEQ ID NO. 487) | 40476985 | 40477395 |
| DG13S207 | ACTCCACCTGAAGGGAGAAA (SEQ ID NO. 488) | TGGAAGCCACTAATTGGAGAA (SEQ ID NO. 489) | 40545942 | 40546202 |
| DG13S200 | AATGGATGGATACCTCCTTATCA (SEQ ID NO. 490) | CTCATTGTGGCTTTCTGTGC (SEQ ID NO. 491) | 40737337 | 40737570 |
| DG13S198 | GTACCCACACCTCACCAAGC (SEQ ID NO. 492) | CGTAGCTCACATTCCCAACA (SEQ ID NO. 493) | 40811813 | 40812059 |
| DG13S215 | GGCGAGTGAAAGAGAGGACA (SEQ ID NO. 494) | GGGTGGTAATTCCCAGATGA (SEQ ID NO. 495) | 40871695 | 40871992 |
| DG13S221 | TCTGCAACAGCCAGAATCAA (SEQ ID NO. 496) | TGTCTGTTGGCAACTTTCTGTC (SEQ ID NO. 497) | 41107773 | 41108117 |
| DG13S219 | AGGTGAACCCAGTCCAGCTA (SEQ ID NO. 498) | TCTTAGGCAAAGGAGCCAGT (SEQ ID NO. 499) | 41127591 | 41127734 |
| D13S1270 | ACATGAGCACTGGTGACTG (SEQ ID NO. 500) | GGCCTCAAATGTTTTAAGCA (SEQ ID NO. 501) | 41161654 | 41161831 |
| DG13S225 | TTCTGGGTGTTCGCTATTCC (SEQ ID NO. 502) | TTTCCTGTCCAGTCCTGACC (SEQ ID NO. 503) | 41212951 | 41213310 |
| D13S1276 | GTTTTGCAGGTCTAGGTCACAC (SEQ ID NO. 504) | AGGATAGCTTGAGCCCG (SEQ ID NO. 505) | 41213917 | 41214090 |

All references cited herein are incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of assessing susceptibility to myocardial infarction (MI) in a human individual, the method comprising:
screening nucleic acid of the individual to determine whether the nucleic acid comprises a 5-lipoxygenase activating protein (FLAP) haplotype that comprises polymorphisms SG13S114, allele T; SG13S32, allele A; SG13S25, allele G; and SG13S89, allele G;
wherein the presence of the haplotype in the nucleic acid of the individual identifies the individual as having elevated susceptibility to MI, and wherein the absence of the haplotype in the nucleic acid of the individual identifies the individual as not having the elevated susceptibility to MI due to the haplotype.

2. The method of claim 1, wherein the haplotype further comprises polymorphism SG13S99, allele T.

3. The method of claim 1 or 2, comprising obtaining a biological sample from the individual that comprises the nucleic acid, and screening the nucleic acid from the biological sample.

4. The method of claim 1 or 2, wherein the screening step comprises subjecting said nucleic acid to at least one procedure selected from the group consisting of: (a) enzymatic amplification of nucleic acid from the individual; (b) electrophoretic analysis; (c) restriction fragment length polymorphism analysis; and (d) nucleotide sequence analysis.

* * * * *

UNITED STATES PATENT AND TRADEMARK OFFICE
CERTIFICATE OF CORRECTION

| | |
|---|---|
| PATENT NO. | : 7,507,531 B2 |
| APPLICATION NO. | : 10/829674 |
| DATED | : March 24, 2009 |
| INVENTOR(S) | : Anna Helgadottir |

It is certified that error appears in the above-identified patent and that said Letters Patent is hereby corrected as shown below:

On the Title Page:

At field (73), "chf." should be -- ehf. --.

Signed and Sealed this

Fifteenth Day of September, 2009

David J. Kappos
*Director of the United States Patent and Trademark Office*